United States Patent
Chen et al.

(10) Patent No.: US 12,037,583 B2
(45) Date of Patent: Jul. 16, 2024

(54) COMPOSITIONS AND METHODS FOR IMMUNOONCOLOGY

(71) Applicants: Novartis AG, Basel (CH); Intellia Therapeutics, Inc., Cambridge, MA (US)

(72) Inventors: Ming-Wei Chen, Winchester, MA (US); Melissa Deck, Acton, MA (US); Glenn Dranoff, Lexington, MA (US); Craig Stephen Mickanin, Hopkinton, MA (US); Reynald Lescarbeau, Dracut, MA (US); Celeste Richardson, Brookline, MA (US); Morag Helen Stewart, Boston, MA (US); Yi Yang, Belmont, MA (US)

(73) Assignees: Novartis AG, Basel (CH); Intellia Therapeutics, Inc., Cambridge, MA (US)

( * ) Notice: Subject to any disclaimer, the term of this patent is extended or adjusted under 35 U.S.C. 154(b) by 980 days.

(21) Appl. No.: 15/780,751

(22) PCT Filed: Dec. 2, 2016

(86) PCT No.: PCT/IB2016/057318
§ 371 (c)(1),
(2) Date: Jun. 1, 2018

(87) PCT Pub. No.: WO2017/093969
PCT Pub. Date: Jun. 8, 2017

(65) Prior Publication Data
US 2018/0362975 A1    Dec. 20, 2018

Related U.S. Application Data

(60) Provisional application No. 62/394,290, filed on Sep. 14, 2016, provisional application No. 62/316,784, filed on Apr. 1, 2016, provisional application No. 62/263,169, filed on Dec. 4, 2015.

(51) Int. Cl.
| | |
|---|---|
| *C12N 15/113* | (2010.01) |
| *A61K 9/00* | (2006.01) |
| *A61K 31/7088* | (2006.01) |
| *A61K 35/17* | (2015.01) |
| *A61K 38/17* | (2006.01) |
| *A61K 38/46* | (2006.01) |
| *A61K 45/06* | (2006.01) |
| *C12N 15/09* | (2006.01) |
| *C12N 15/10* | (2006.01) |

(52) U.S. Cl.
CPC .......... *C12N 15/113* (2013.01); *A61K 9/0009* (2013.01); *A61K 31/7088* (2013.01); *A61K 35/17* (2013.01); *A61K 38/177* (2013.01); *A61K 38/1774* (2013.01); *A61K 38/465* (2013.01); *A61K 45/06* (2013.01); *C12N 15/09* (2013.01); *C12N 15/102* (2013.01); *C12N 15/1135* (2013.01); *C12N 15/1138* (2013.01); *C12N 2310/10* (2013.01); *C12N 2310/20* (2017.05); *C12N 2310/315* (2013.01); *C12N 2310/321* (2013.01); *C12N 2320/32* (2013.01); *C12N 2320/35* (2013.01); *C12N 2510/00* (2013.01); *Y02A 50/30* (2018.01)

(58) Field of Classification Search
None
See application file for complete search history.

(56) References Cited

U.S. PATENT DOCUMENTS

| | | |
|---|---|---|
| 5,359,046 A | 10/1994 | Capon et al. |
| 5,686,281 A | 11/1997 | Roberts |
| 5,712,149 A | 1/1998 | Roberts |
| 5,874,240 A | 2/1999 | Ni et al. |
| 5,906,936 A | 5/1999 | Eshhar et al. |
| 6,103,521 A | 8/2000 | Capon et al. |
| 6,319,494 B1 | 11/2001 | Capon et al. |
| 6,355,779 B1 | 3/2002 | Goodwin et al. |
| 6,410,319 B1 | 6/2002 | Raubitschek et al. |
| 6,475,481 B2 | 11/2002 | Talmadge |
| 6,569,997 B1 | 5/2003 | Kwon |
| 7,049,136 B2 | 5/2006 | Seed et al. |
| 7,052,906 B1 | 5/2006 | Lawson et al. |
| 7,070,995 B2 | 7/2006 | Jensen |
| 7,265,209 B2 | 9/2007 | Jensen |
| 7,319,143 B2 | 1/2008 | Gross et al. |
| 7,320,787 B2 | 1/2008 | Seed et al. |
| 7,446,190 B2 | 11/2008 | Sadelain et al. |
| 7,446,191 B2 | 11/2008 | Jensen |
| 7,514,537 B2 | 4/2009 | Jensen |
| 7,638,326 B2 | 12/2009 | June et al. |
| 7,741,465 B1 | 6/2010 | Eshhar et al. |
| 7,745,140 B2 | 6/2010 | June et al. |

(Continued)

FOREIGN PATENT DOCUMENTS

| | | |
|---|---|---|
| CN | 104611370 A | 5/2015 |
| CN | 105051188 A | 11/2015 |

(Continued)

OTHER PUBLICATIONS

Sato T, Akatsuka H, Yamaguchi Y, Miyashita K, Tanaka M, et al. (2015) Establishment of β-2 microglobulin deficient human iPS cells using CRISPR/Cas9 system. Integr Mol Med 2: (Year: 2015).*

Sato T, Akatsuka H, Yamaguchi Y, Miyashita K, Tanaka M, et al. (2015) Establishment of β-2 microglobulin deficient human iPS cells using CRISPR/Cas9 system. Integr Mol Med 2015;2(6):373-7. Cited in prior action. (Year: 2015).*

(Continued)

*Primary Examiner* — Robert M Kelly
(74) *Attorney, Agent, or Firm* — Finnegan, Henderson, Farabow, Garrett & Dunner, LLP

(57) ABSTRACT

The present invention is directed to genome editing systems, reagents and methods for immunooncology.

55 Claims, 85 Drawing Sheets
Specification includes a Sequence Listing.

(56) References Cited

U.S. PATENT DOCUMENTS

| | | |
|---|---|---|
| 7,754,482 B2 | 7/2010 | Riley et al. |
| 7,994,298 B2 | 8/2011 | Zhang et al. |
| 8,211,422 B2 | 7/2012 | Eshhar et al. |
| 8,252,914 B2 | 8/2012 | Zhang et al. |
| 8,389,282 B2 | 3/2013 | Sadelain et al. |
| 8,399,645 B2 | 3/2013 | Campana et al. |
| 8,465,743 B2 | 6/2013 | Rosenberg et al. |
| 8,637,307 B2 | 1/2014 | June et al. |
| 8,722,400 B2 | 5/2014 | Riley et al. |
| 8,906,682 B2 | 12/2014 | June et al. |
| 8,911,993 B2 | 12/2014 | June et al. |
| 8,916,381 B1 | 12/2014 | June et al. |
| 8,975,071 B1 | 3/2015 | June et al. |
| 9,101,584 B2 | 8/2015 | June et al. |
| 9,102,760 B2 | 8/2015 | June et al. |
| 9,102,761 B2 | 8/2015 | June et al. |
| 9,272,002 B2 | 3/2016 | Powell, Jr. et al. |
| 9,328,156 B2 | 5/2016 | June et al. |
| 9,365,641 B2 | 6/2016 | June et al. |
| 9,394,368 B2 | 7/2016 | Brogdon et al. |
| 9,402,865 B2 | 8/2016 | Powell et al. |
| 9,422,351 B2 | 8/2016 | Scholler et al. |
| 9,446,105 B2 | 9/2016 | Powell, Jr. |
| 9,464,140 B2 | 10/2016 | June et al. |
| 9,481,728 B2 | 11/2016 | June et al. |
| 9,499,629 B2 | 11/2016 | June et al. |
| 9,518,123 B2 | 12/2016 | June et al. |
| 9,540,445 B2 | 1/2017 | June et al. |
| 9,572,836 B2 | 2/2017 | June et al. |
| 9,573,988 B2 | 2/2017 | Brogdon et al. |
| 9,598,489 B2 | 3/2017 | Powell, Jr. |
| 9,708,384 B2 | 7/2017 | Scholler et al. |
| 9,714,278 B2 | 7/2017 | June et al. |
| 9,745,368 B2 | 8/2017 | Milone et al. |
| 9,765,156 B2 | 9/2017 | June et al. |
| 9,777,061 B2 | 10/2017 | Ebersbach et al. |
| 9,815,901 B2 | 11/2017 | Brogdon et al. |
| 9,999,671 B2 | 6/2018 | Liu et al. |
| 10,689,438 B2 | 6/2020 | Zhang et al. |
| 2003/0060444 A1 | 3/2003 | Finney et al. |
| 2003/0077249 A1 | 4/2003 | Bebbington et al. |
| 2003/0105000 A1 | 6/2003 | Pero et al. |
| 2003/0148982 A1 | 8/2003 | Brenner et al. |
| 2003/0224520 A1 | 12/2003 | June et al. |
| 2004/0038886 A1 | 2/2004 | Finney et al. |
| 2004/0043401 A1 | 3/2004 | Sadelain et al. |
| 2005/0113564 A1 | 5/2005 | Campana et al. |
| 2005/0129671 A1 | 6/2005 | Cooper et al. |
| 2007/0036773 A1 | 2/2007 | Cooper et al. |
| 2008/0131415 A1 | 6/2008 | Riddell et al. |
| 2008/0160090 A1 | 7/2008 | Oraevsky et al. |
| 2008/0254513 A1 | 10/2008 | Cayli |
| 2009/0257994 A1 | 10/2009 | Jensen |
| 2011/0052554 A1 | 3/2011 | Zakrzewski et al. |
| 2011/0158957 A1 | 6/2011 | Bonini et al. |
| 2012/0027802 A1 | 2/2012 | Bonini et al. |
| 2012/0148552 A1 | 6/2012 | Jensen |
| 2012/0302466 A1 | 11/2012 | Sentman |
| 2012/0321667 A1 | 12/2012 | Sentman |
| 2013/0071409 A1 | 3/2013 | Riley et al. |
| 2013/0071414 A1 | 3/2013 | Dotti et al. |
| 2013/0149337 A1 | 6/2013 | Cooper et al. |
| 2013/0155909 A1 | 6/2013 | Jackson et al. |
| 2013/0287748 A1 | 10/2013 | June et al. |
| 2014/0050708 A1 | 2/2014 | Powell et al. |
| 2014/0099309 A1 | 4/2014 | Powell, Jr. et al. |
| 2014/0099340 A1 | 4/2014 | June et al. |
| 2014/0106449 A1 | 4/2014 | June et al. |
| 2014/0186947 A1 | 7/2014 | June et al. |
| 2014/0212446 A1 | 7/2014 | Riley et al. |
| 2014/0219975 A1 | 8/2014 | June et al. |
| 2014/0227237 A1 | 8/2014 | June et al. |
| 2014/0271635 A1 | 9/2014 | Brogdon et al. |
| 2014/0273226 A1* | 9/2014 | Wu .................. C12N 15/102 435/455 |
| 2014/0322169 A1 | 10/2014 | Harper et al. |
| 2014/0322183 A1 | 10/2014 | Milone et al. |
| 2014/0322212 A1 | 10/2014 | Brogdon et al. |
| 2014/0322275 A1 | 10/2014 | Brogdon et al. |
| 2014/0349402 A1 | 11/2014 | Cooper et al. |
| 2014/0370045 A1 | 12/2014 | June et al. |
| 2015/0017136 A1 | 1/2015 | Galetto et al. |
| 2015/0017141 A1 | 1/2015 | June et al. |
| 2015/0140019 A1 | 5/2015 | June et al. |
| 2015/0190428 A1 | 7/2015 | June et al. |
| 2015/0202286 A1 | 7/2015 | June et al. |
| 2015/0283178 A1 | 10/2015 | June et al. |
| 2015/0290244 A1 | 10/2015 | June et al. |
| 2015/0342994 A1 | 12/2015 | Riley et al. |
| 2016/0046724 A1 | 2/2016 | Brogdon et al. |
| 2016/0051651 A1 | 2/2016 | Brogdon et al. |
| 2016/0068601 A1 | 3/2016 | Brogdon et al. |
| 2016/0096892 A1 | 4/2016 | Brogdon et al. |
| 2016/0185861 A1 | 6/2016 | Bedoya et al. |
| 2016/0186208 A1 | 6/2016 | Jaenisch et al. |
| 2016/0311907 A1 | 10/2016 | Brogdon et al. |
| 2016/0311917 A1 | 10/2016 | Beatty et al. |
| 2016/0340406 A1 | 11/2016 | Zhao et al. |
| 2016/0348073 A1* | 12/2016 | Meissner .............. C12N 5/0636 |
| 2016/0362472 A1 | 12/2016 | Bitter et al. |
| 2017/0008963 A1 | 1/2017 | Brogdon et al. |
| 2017/0081411 A1 | 3/2017 | Engels et al. |
| 2017/0137783 A1 | 5/2017 | Bedoya et al. |
| 2017/0183415 A1 | 6/2017 | Brogdon et al. |
| 2017/0209492 A1 | 7/2017 | June et al. |
| 2017/0211055 A1 | 7/2017 | Brogdon et al. |
| 2017/0226495 A1 | 8/2017 | Guimaraes |
| 2017/0239294 A1 | 8/2017 | Thomas-Tikhonenko et al. |
| 2017/0260268 A1 | 9/2017 | Beatty et al. |
| 2017/0274014 A1 | 9/2017 | Brogdon et al. |
| 2017/0306416 A1 | 10/2017 | Bedoya et al. |
| 2017/0335281 A1 | 11/2017 | Loew et al. |
| 2018/0022795 A1 | 1/2018 | Milone et al. |
| 2018/0044423 A1 | 2/2018 | Ebersbach et al. |
| 2018/0044424 A1 | 2/2018 | June et al. |
| 2018/0118834 A1 | 5/2018 | Brogdon et al. |
| 2018/0125892 A1 | 5/2018 | Brannetti et al. |
| 2018/0133296 A1 | 5/2018 | Barrett et al. |
| 2018/0140602 A1 | 5/2018 | Angst et al. |
| 2018/0230193 A1 | 8/2018 | Loew et al. |
| 2018/0252727 A1 | 9/2018 | Garfall et al. |
| 2018/0258149 A1 | 9/2018 | Motz et al. |
| 2018/0298068 A1 | 10/2018 | Albelda |
| 2018/0312595 A1 | 11/2018 | Brogdon et al. |
| 2018/0344738 A1 | 12/2018 | Behnke et al. |
| 2019/0000880 A1 | 1/2019 | Motz et al. |
| 2019/0000944 A1 | 1/2019 | Brogdon et al. |
| 2019/0135940 A1 | 5/2019 | Brogdon et al. |
| 2019/0151365 A1 | 5/2019 | Anak et al. |
| 2019/0153061 A1 | 5/2019 | Brogdon et al. |
| 2019/0161542 A1 | 5/2019 | Gill et al. |
| 2019/0263914 A1 | 8/2019 | Brogdon et al. |
| 2019/0269727 A1 | 9/2019 | Fachin et al. |
| 2019/0292238 A1 | 9/2019 | Bitter et al. |
| 2019/0292257 A1 | 9/2019 | Bedoya et al. |
| 2019/0298715 A1 | 10/2019 | Motz et al. |
| 2019/0330356 A1 | 10/2019 | Brogdon et al. |
| 2019/0336504 A1 | 11/2019 | Gill et al. |
| 2019/0375815 A1 | 12/2019 | Engels et al. |
| 2019/0382500 A1 | 12/2019 | Abujoub et al. |
| 2019/0388471 A1 | 12/2019 | June et al. |
| 2019/0389928 A1 | 12/2019 | Posey et al. |
| 2020/0048359 A1 | 2/2020 | Albelda et al. |
| 2020/0055948 A1 | 2/2020 | Daley et al. |
| 2020/0061113 A1 | 2/2020 | Kassim et al. |
| 2020/0087376 A1 | 3/2020 | Fraietta et al. |
| 2020/0131474 A1 | 4/2020 | Berenshteyn et al. |
| 2021/0017266 A1 | 1/2021 | Racine et al. |
| 2021/0071182 A1 | 3/2021 | Brogdon et al. |

FOREIGN PATENT DOCUMENTS

| | | |
|---|---|---|
| CN | 105158466 A | 12/2015 |
| EP | 0574512 A1 | 12/1993 |

(56) References Cited

FOREIGN PATENT DOCUMENTS

| | | |
|---|---|---|
| EP | 0871495 A1 | 10/1998 |
| EP | 1226244 A2 | 7/2002 |
| EP | 1955708 A1 | 8/2008 |
| JP | 2016501531 A | 1/2016 |
| RU | 2560701 | 8/2015 |
| WO | WO 1992/015322 A1 | 9/1992 |
| WO | WO 1995/007268 A1 | 3/1995 |
| WO | WO 1995/030014 A1 | 11/1995 |
| WO | WO 1996/023814 A1 | 8/1996 |
| WO | WO 1996/024671 A1 | 8/1996 |
| WO | WO 1997/015669 A1 | 5/1997 |
| WO | WO 1997/023613 A2 | 7/1997 |
| WO | WO 1998/018809 A1 | 5/1998 |
| WO | WO 1999/000494 A2 | 1/1999 |
| WO | WO 2000/014257 A1 | 3/2000 |
| WO | WO 2002/033101 A1 | 4/2002 |
| WO | WO 2002/077029 A2 | 10/2002 |
| WO | WO 2002/088334 A1 | 11/2002 |
| WO | WO 2003/057171 A2 | 7/2003 |
| WO | WO 2005/019429 A2 | 3/2005 |
| WO | WO 2005/044996 A2 | 5/2005 |
| WO | WO 2005/118788 A2 | 12/2005 |
| WO | WO 2006/060878 A1 | 6/2006 |
| WO | WO 2008/045437 A2 | 4/2008 |
| WO | WO 2009/150229 A1 | 12/2009 |
| WO | WO 2010/085660 A2 | 7/2010 |
| WO | WO 2010/129469 A1 | 11/2010 |
| WO | WO 2011/059836 A2 | 5/2011 |
| WO | WO 2011/097477 A1 | 8/2011 |
| WO | WO 2011/156430 A2 | 12/2011 |
| WO | WO 2012/004299 A1 | 1/2012 |
| WO | WO 2012/012667 A2 | 1/2012 |
| WO | WO 2012/058460 A2 | 5/2012 |
| WO | WO 2012/079000 A1 | 6/2012 |
| WO | WO 2012/079000 A1 | 6/2012 |
| WO | WO 2012/082841 A2 | 6/2012 |
| WO | WO 2012/099973 A2 | 7/2012 |
| WO | WO 2012/127464 A2 | 9/2012 |
| WO | WO 2012/129514 A1 | 9/2012 |
| WO | WO 2012/135854 A2 | 10/2012 |
| WO | WO 2012/138858 A1 | 10/2012 |
| WO | WO 2013/019615 A2 | 2/2013 |
| WO | WO 2013/033626 A2 | 3/2013 |
| WO | WO 2013/040371 A2 | 3/2013 |
| WO | WO 2013/040557 A2 | 3/2013 |
| WO | WO 2013/059593 A1 | 4/2013 |
| WO | WO 2013/074916 A1 | 5/2013 |
| WO | WO 2013/126712 A1 | 8/2013 |
| WO | WO 2013/126729 A1 | 8/2013 |
| WO | WO 2013/126733 A1 | 8/2013 |
| WO | WO 2013/176915 A1 | 11/2013 |
| WO | WO 2013/176916 A1 | 11/2013 |
| WO | WO 2014/011984 A1 | 1/2014 |
| WO | WO 2014/011987 A1 | 1/2014 |
| WO | WO 2014/011988 A2 | 1/2014 |
| WO | WO 2014/011993 A2 | 1/2014 |
| WO | WO 2014/011996 A1 | 1/2014 |
| WO | WO 2014/012001 A2 | 1/2014 |
| WO | WO 2014/031687 A1 | 2/2014 |
| WO | WO 2014/039513 A2 | 3/2014 |
| WO | WO 2014/055442 A2 | 4/2014 |
| WO | WO 2014/055657 A1 | 4/2014 |
| WO | WO 2014/055668 A1 | 4/2014 |
| WO | WO 2014/055771 A1 | 4/2014 |
| WO | WO 2014/059173 A2 | 4/2014 |
| WO | WO 2014/124134 A1 | 8/2014 |
| WO | WO 2014/130635 A1 | 8/2014 |
| WO | WO 2014/138704 A1 | 9/2014 |
| WO | WO 2014/145252 A2 | 9/2014 |
| WO | WO 2014/153270 A1 | 9/2014 |
| WO | WO 2014/165177 A1 | 10/2014 |
| WO | WO 2014/165707 A2 | 10/2014 |
| WO | WO 2014/165825 A2 | 10/2014 |
| WO | WO 2014/184741 A1 | 11/2014 |
| WO | WO 2014/184744 A1 | 11/2014 |
| WO | WO 2014/186585 A2 | 11/2014 |
| WO | WO 2014/190273 A1 | 11/2014 |
| WO | WO 2014/191128 A1 | 12/2014 |
| WO | WO 2014/191521 A2 | 12/2014 |
| WO | WO 2014/191527 A1 | 12/2014 |
| WO | WO 2014/204723 A1 | 12/2014 |
| WO | WO 2015/048577 A2 | 4/2015 |
| WO | WO 2015/073683 A2 | 5/2015 |
| WO | WO 2015/075195 A1 | 5/2015 |
| WO | WO 2015/090229 A1 | 6/2015 |
| WO | WO 2015/090230 A1 | 6/2015 |
| WO | WO 2015/112626 A1 | 7/2015 |
| WO | WO 2015/136001 A1 | 9/2015 |
| WO | WO 2015/142661 A1 | 9/2015 |
| WO | WO 2015/142675 A2 | 9/2015 |
| WO | WO-2015136001 A1 * 9/2015 ........... C12N 5/0636 |
| WO | WO 2015/148860 A1 | 10/2015 |
| WO | WO 2015/157252 A1 | 10/2015 |
| WO | WO 2015/161276 A2 | 10/2015 |
| WO | WO 2015/164740 A1 | 10/2015 |
| WO | WO 2015/164745 A1 | 10/2015 |
| WO | WO 2015/200920 A1 | 12/2015 |
| WO | WO 2016/009326 A1 | 1/2016 |
| WO | WO 2016/011080 A2 | 1/2016 |
| WO | WO 2016/011210 A2 | 1/2016 |
| WO | WO 2016/014501 A1 | 1/2016 |
| WO | WO 2016/014530 A1 | 1/2016 |
| WO | WO 2016/014535 A1 | 1/2016 |
| WO | WO 2016/014553 A1 | 1/2016 |
| WO | WO 2016/014565 A2 | 1/2016 |
| WO | WO 2016/014576 A1 | 1/2016 |
| WO | WO 2016/019300 A1 | 2/2016 |
| WO | WO 2016/021972 A1 | 2/2016 |
| WO | WO 2016/025880 A1 | 2/2016 |
| WO | WO 2016/028896 A1 | 2/2016 |
| WO | WO 2016/044605 A1 | 3/2016 |
| WO | WO 2016/049024 A2 | 3/2016 |
| WO | WO 2016/054032 A1 | 4/2016 |
| WO | WO 2016/057705 A1 | 4/2016 |
| WO | WO 2016/063264 A1 | 4/2016 |
| WO | WO 2016/065329 A1 | 4/2016 |
| WO | WO 2016/069282 A1 | 5/2016 |
| WO | WO 2016/069283 A1 | 5/2016 |
| WO | WO 2016/073955 A2 | 5/2016 |
| WO | WO 2016/109410 A2 | 7/2016 |
| WO | WO 2016/120217 A1 | 8/2016 |
| WO | WO 2016/142532 A1 | 9/2016 |
| WO | WO 2016/146542 A1 | 9/2016 |
| WO | WO 2016/154596 A1 | 9/2016 |
| WO | WO 2016/160721 A1 | 10/2016 |
| WO | WO 2016/164731 A2 | 10/2016 |
| WO | WO 2016/168595 A1 | 10/2016 |
| WO | WO 2016/183041 A2 | 11/2016 |
| WO | WO 2017/015427 A1 | 1/2017 |
| WO | WO 2017/049166 A1 | 3/2017 |
| WO | WO 2017/093969 A1 | 6/2017 |
| WO | WO 2017/117112 A1 | 7/2017 |
| WO | WO 2018/132783 A1 | 7/2018 |
| WO | WO 2018/175733 A1 | 9/2018 |
| WO | WO 2018/198077 A2 | 11/2018 |
| WO | WO 2019/097305 A2 | 5/2019 |
| WO | WO 2019/126574 A1 | 6/2019 |
| WO | WO 2019/237035 A1 | 12/2019 |
| WO | WO 2020/084580 A1 | 4/2020 |
| WO | WO 2021/220132 A1 | 11/2021 |

OTHER PUBLICATIONS

Montague TG, Cruz JM, Gagnon JA, Church GM, Valen E. CHOPCHOP: a CRISPR/Cas9 and TALEN web tool for genome editing. Nucleic acids research. Jul. 1, 2014;42(W1):W401-7. (Year: 2014).*

CHOPCHOP; http://chopchop.cbu.uib.no/; retrieved Dec. 9, 2021 (Year: 2021).*

Hendel A, Bak RO, Clark JT, Kennedy AB, Ryan DE, Roy S, Steinfeld I, Lunstad BD, Kaiser RJ, Wilkens AB, Bacchetta R. Chemically modified guide RNAs enhance CRISPR-Cas genome

(56) References Cited

OTHER PUBLICATIONS editing in human primary cells. Nature biotechnology. Sep. 2015; 33(9):985-9. (Year: 2015).*
ABSS Alignments of Seq ID No. 7858 and US20140273226A1, Seq IDs 16 and 20; alignment Dec. 2021. (Year: 2021).*
Zhang, et al. (2017) "Engineering CAR-T cells", Biomarker Research, 5:22, 6 pages. (Year: 2017).*
Gilham, et al. (2012) "CAR-T cells and solid tumors: tuning T cells to challenge an inveterate foe", Trends in Molecular Medicine, 18(7): 377-84. (Year: 2012).*
Marofi, et al. (2021) "CAR T cells in solid tumors: challenges and opportunities", Stem Cell Research & Therapy, 12:81, 16 pages. (Year: 2021).*
Li, et al. (2014) "Stem Cell Treatment for Alzheimer's Disease", International Journal of Molecule Sciences, 15(10): 19226-38. (Year: 2014).*
Davies, et al. (2014) "Opportunities and limitations of natural killer cells as adoptive therapy for malignant disease", Cytotherapy, 16: 1453-66. (Year: 2014).*
Abaza et al., "Effects of Amino Acid Substitutions Outside an Antigenic Site on Protein Binding to Monoclonal Antibodies of Predetermined Specificity Obtained by Peptide Immunization: Demonstration with Region 94-100 (Antigenic Site 3) of Myoglobin," Journal of Protein Chemistry (1992), vol. 11, No. 5, pp. 433-444.
Almagro et al., "Humanization of Antibodies," Frontiers in Bioscience (2008), vol. 13, pp. 1619-1633.
Attianese et al., "In vitro and in vivo model of a novel immunotherapy approach for chronic lymphocytic leukemia by anti-CD23 chimeric antigen receptor," Blood (2011), vol. 117, No. 18, pp. 4736-4745.
Baeksgaard et al., "Acute tumor lysis syndrome in solid tumors—a case report and review of the literature," Cancer Chemotherapy Pharmacology (2003), vol. 51, pp. 187-192.
Barrett et al., "Relation of clinical culture method to T-cell memory status and efficacy in xenograft models of adoptive immunotherapy," Cytotherapy (2014), vol. 16, No. 5, pp. 619-630.
Barsov "Telomerase and primary T cells: biology and immortalization for adoptive immunotherapy," Immunotherapy (2011), vol. 3, No. 3, pp. 407-421.
Berry al., "Selection of Target Sites for Mobile DNA Integration in the Human Genome," PLoS Comput Biol (2006), vol. 2, No. 11, e157, pp. 1450-1462.
Berry et al., "Comparing DNA integration site clusters with scan statistics," Bioinformatics (2014), vol. 30, pp. 1493-1500.
Berry et al., "Estimating abundances of retroviral insertion sites from DNA fragment length data," Bioinformatics (2012), 28, No. 6, pp. 755-762.
Bondanza et al., "Suicide gene therapy of graft-versus-host disease induced by central memory human T lymphocytes," Blood (2006), vol. 107, No. 5, pp. 1828-1836.
Brady et al., "A method to sequence and quantify DNA integration for monitoring outcome in gene therapy," Nucleic Acids Res (2011), vol. 39, No. 11, e72, pp. 1-8.
Brady et al., "Integration target site selection by a resurrected human endogenous retrovirus," Genes Dev (2009), vol. 23, pp. 633-642.
Brentjens et al., "Treatment of Chronic Lymphocytic Leukemia With Genetically Targeted Autologous T Cells: Case Report of an Unforeseen Adverse Event in a Phase I Clinical Trial," The American Society of Gene Therapy (2010), vol. 18, No. 4, pp. 666-668.
Brentjens et al., "A Phase I Trial for the Treatment of chemo-Refractory Chronic Lymphocytic Leukemia with CD19-Targeted Autologous T Cells," Molecular Therapy (2008), vol. 16, Suppl. 1, p. S15.
Brentjens et al., "CD19-Targeted T Cells Rapidly Induce Molecular Remissions in Adults with Chemotherapy-Refractory Acute Lymphoblastic Leukemia," Sci. Transl. Med. 5:177ra138 (2013).
Brentjens et al., "Eradication of systemic B-cell tumors by genetically targeted human T lymphocytes co-stimulated by CD80 and interleukin-15," Nature Medicine (2003), vol. 9, No. 3, pp. 279-286.
Brentjens et al., "Genetically Targeted T Cells Eradicate Systemic Acute Lymphoblastic Leukemia Xenografts," Clinical Cancer Research (2007), vol. 13, No. 18, pp. 5426-5435.a.
Brentjens et al., "Safety and persistence of adoptively transferred autologous CD19-targeted T cells in patients with relapsed or chemotherapy refractory B-cell leukemias," Blood (2011). vol. 118, No. 18, pp. 4817-4828.
Brocker et al., "Signals through T Cell Receptor—Chain alone are Insufficient to Prime Resting T Lymphocytes," J. Exp. Med. (1995), vol. 181, pp. 1653-1659.
Buenrostro et al., "Transposition of native chromatin for multimodal regulatory analysis and personal epigenomics," Nat Methods (2013), vol. 10, No. 12, pp. 1213-1218.
Busque et al., "Recurrent Somatic TET2 Mutations in Normal Elderly Individuals With Clonal Hematopoiesis," Nature Genetics (2012), vol. 44, pp. 1179-1181.
Call "The T Cell Receptor: Critical Role of the Membrane Environment in Receptor Assembly and Function," Annu. Rev. Immunol. (2005), vol. 23, pp. 101-125.
Carpenito et al., "Control of large, established tumor xenografts with genetically retargeted human T cells containing CD28 and CD137 domains," Proc Natl Acad Sci USA (2009), vol. 106, pp. 3360-3365.
Carty et al., "The loss of TET2 promotes CD8+ T cell memory differentiation," J Immunol (2017), vol. 200, No. 1, pp. 82-91.
Cha et al., "IL-7 + IL-15 are superior to IL-2 for the ex vivo expansion of 4T1 mammary carcinoma-specific T cells with greater efficacy against tumors in vivo," Breast Cancer Research and Treatment, Kluwer Academic Publishers (2009), vol. 122, No. 2, pp. 359-369.
Cheadle et al., "CAR T cells: driving the road from the laboratory to the clinic," Immunological Reviews (2013), vol. 257, No. 1, pp. 91-106.
Colman et al., "Effects of amino acid sequence changes on antibody-antigen interactions," Research in Immunology (1994), vol. 145, No. 1, pp. 33-36.
Couper et al., "Anti-CD25 antibody-mediated depletion of effector T cell populations enhances susceptibility of mice to acute but not chronic Toxoplasma gondii infection," The Journal of Immunology (2009), vol. 182, No. 7, pp. 3985-3994.
Daber et al., "Understanding the limitations of next generation sequencing informatics, an approach to clinical pipeline validation using artificial data sets," Cancer Genet (2013), vol. 206, No. 12, pp. 441-448.
Database Biosis [Online], Database accession No. PREV201700298608 dated Dec. 2, 2016.
Davila et al., "B Cell Aplasia In a Patient with Relapsed B Cell Acute Lymphoblastic Leukemia Following Re-Induction and Consolidation with Autologous T Cells Genetically Targeted to the CD19 Antigen," 53rd ASH Annual Meeting and Exposition (2010) Oral and Poster Abstract.
Döhner et al., "p53 Gene Deletion Predicts for Poor Survival and Non-Response to Therapy With Purine Analogs in Chronic B-Cell Leukemias," Blood (1995), vol. 85, No. 6, pp. 1580-1589.
Dotti et al., "Design and development of therapies using chimeric antigen receptor-expressing T cells," Immunological Reviews (2013), vol. 257, No. 1, pp. 107-126.
Dropulic et al., "Gene-Based Immunotherapy for Human Immunodeficiency Virus Infection and Acquired Immunodeficiency Syndrome," Human Gene Therapy (2006), vol. 17, pp. 577-588.
Dull et al, "A Third-Generation Lentivirus Vector with a Conditional Packaging System," Journal of Virology (1998), vol. 72, No. 11, pp. 8463-8471.
Efimova et al., "The hydroxyl form of 5-methylcytosine-5-hydroxymethylcytosine: a new look at the biological role in the mammalian genome," Ekologicheskaya genetika, Ecological Genetics. (2014), vol. 12, No. 1, pp. 3-13.
Eshhar et al., "Specific activation and targeting of cytotoxic lymphocytes through chimeric single chains consisting of antibody-binding domains and the γ or ζsubunits of the immunoglobulin and T-cell receptors," PNAS USA (1993) 90: 720-724.
Finney et al., "Activation of resting human primary T cells with chimeric receptors: costimulation from CD28, inducible costimula-

(56) References Cited

OTHER PUBLICATIONS tor, CD134, and CD137 (4-1BB) in series with signals from the TCR zeta chain," J. Immunol. (2004) 172: 104-113.
Finney et al., "Chimeric receptors providing both primary and costimulatory signaling in T cells from a single gene product," J. Immunol. (1998) 161: 2791-2797.
Flynn et al., "Stem memory T cells (TSCM)-their role in cancer and HIV immunotherapies," Clinical & Translational Immunology (2014), vol. 3, No. 7, pp. 1-7.
Fraietta et al, "Disruption of TET2 promotes the therapeutic efficacy of CD19-targeted T cells, " Nature (2018), vol. 558, No. 7709, pp. 307-312.
Fraietta et al., "Ibrutinib enhances chimeric antigen receptor T-cell engraftment and efficacy in leukemia," Blood (2016), vol. 127, No. 9, pp. 1117-1127.
Frey, "Genetically Engineered Lymphocyte Therapy in Treating Patients With B-Cell Leukemia or Lymphoma That is Resistant or Refractory to Chemotherapy," (2015) Clinical Trial NCT01029366.
Friedmann-Morvinski et al., "Redirected primary T cells harboring a chimeric receptor require costimulation for their antigen-specific activation," Blood (2005) 105: 3087-3093.
Fujiwara et al., "Profiles of De Novo CD25-Positive Mature B-Cell Lymphomas," Blood (2013), vol. 122, No. 21, pp. 4308 (1-6).
Geiger et al., "Development and Application of Receptor-Modified T Lymphocytes for Adoptive Immunotherapy," Transfusion Medicine Reviews (2001), vol. 15, No. 1, pp. 21-34.
Geiger et al., "Integrated src kinase and constimulatory activity enhances signal transduction through single-chain chimeric receptors in T lymphocytes," Blood 98(8): 2364-2371 (2001).
GenBank Accession No. NP_000725.1 accessed on Jan. 7, 2016 from http://www.ncbi.nlm.nih.gov/protein/NP_000725.
GenBank Accession No. NP_932170.1 accessed Jan. 7, 2016 from http://www.ncbi.nlm.nih.gov/protein/NP_932170.
Gerriets et al., "Metabolic programming and PDHK1 control CD4+ T cell subsets and inflammation," The Journal of Clinical Investigation (2015), vol. 125, No. 1, pp. 194-207.
Gilham et al., "Primary Polyclonal Human T Lymphocytes Targeted to Carcino-Embryonic Antigens and Neural Cell Adhesion Molecule Tumor Antigens by CD3-Based Chimeric Immune Receptors," Journal of Immunotherapy (2002), vol. 25, No. 2, pp. 139-151.
Gong et al., "Cancer Patient T Cells Genetically Targeted to Prostate-Specific Membrane Antigen Specifically Lyse Prostate Cancer Cells and Release Cytokines in Response to Prostate-Specific Membrane Antigen," Neoplasia (1999), vol. 1, No. 2, pp. 123-127.
Gribben et al., "Stem cell transplantation for indolent lymphoma and chronic lymphocytic leukemia," Biol Blood Marrow Transplant (2011), vol. 17, (1 Suppl): S63-S70.
Griffin et al., "Development and applications of surface-linked single chain antibodies against T-cell antigens," Journal of Immunological Methods (2001), vol. 248, pp. 77-90.
Gross et al, "Expression of immunoglobulin-T-cell receptor chimeric molecules as functional receptors with antibody-type specificity," PNAS (1989), vol. 86, pp. 10024-10028.
Gross et al., "Endowing T cells with antibody specificity using chimeric T cell receptors," The FASEB Journal (1992) 6:3370-3378.
Grupp et al., "Chimeric Antigen Receptor-Modified T Cells for Acute Lymphoid Leukemia," New England Journal of Medicine (2013), vol. 368, No. 16, pp. 1509-1518.
Hallek et al., "Guidelines for the diagnosis and treatment of chronic lymphocytic leukemia: a report from the International Workshop on Chronic Lymphocytic Leukemia updating the National Cancer Institute Working Group 1996 guidelines," Blood (2008), vol. 111, No. 12, pp. 5446-5456.
Han et al., "Malignant B Cells Induce the Conversion of CD4+ CD25-T Cells to Regulatory T Cells in B-Cell Non-Hodgkin Lymphoma," PLoS One (2011), vol. 6, No. 12, e28649.
Hekele et al., "Growth Retardation of Tumors by Adoptive Transfer of Cytotoxic T Lymphocytes Reprogrammed by CD44V6-Specific SCFV:ζ-Chimera," Int J. Cancer (1996), vol. 68, pp. 232-238.
Hernandez-Sanchez et al., "TET2 Overexpression in Chronic Lymphocytic Leukemia Is Unrelated to the Presence of TET2 Variations," BioMed Research International (2014) Article ID 814294, pp. 1-6.
Ho et al., "Adoptive immunotherapy: Engineering T cell responses as biological weapons for tumor mass destruction," Cancer Cell (2003), vol. 3, pp. 431-437.
Hollyman et al., "Manufacturing validation of biologically functional T cells targeted to CD19 antigen for autologous adoptive cell therapy," J Immunother (2009), vol. 32, No. 2, pp. 169-180.
Hombach et al., "The Recombinant T Cell Receptor Strategy: Insights into Structure and Function of Recombinant Immunoreceptors on the Way Towards an Optimal Receptor Design for Cellular Immunotherapy," Current Gene Therapy (2002) 2: 211-226.
Horii et al., "Genome Engineering of Mammalian Haploid Embryonic Stem Cells Using the Cas9/RNA System," PeerJ, © 2013 Horii et al., 14 pages.
Hosing et al., "CARs in Chronic Lymphocytic Leukemia—Ready to Drive," Current Hematologic Malignancy Reports (2012), vol. 8, No. 1, pp. 60-70.
Husebekk et al., "Selection and expansion of T cells from untreated patients with CLL: source of cells for immune reconstitution?," Cytotherapy (2000), vol. 2, No. 3, pp. 187-193.
Ikeda et al., "Recurrent HIV-1 Integration at the BACH2 Locus in Resting CD4+ T Cell Populations during Effective Highly Active Antiretroviral Therapy," The Journal of Infectious Diseases (2007), vol. 195, pp. 716-725.
Imai et al., "Chimeric receptors with 4-1BB signaling capacity provoke potent cytotoxicity against acute lymphoblastic leukemia," Leukemia, 18: 676-684 (2004).
Imai et al., "Genetic modification of primary natural killer cells overcomes inhibitory signals and induces specific killing of leukemic cells," Blood (2005), vol. 106, No. 1, pp. 376-383.
International Search Report and Written Opinion for International Application No. PCT/US2015/067635 dated Jun. 28, 2016.
International Search Report and Written Opinion for International Application No. PCT/US2016/043255 dated Dec. 16, 2016.
International Search Report and Written Opinion for International Application No. PCT/US2016/052260 dated Jan. 16, 2017.
International Search Report and Written Opinion for International Application No. PCT/US2016/068683 dated Jun. 1, 2017.
International Search Report and Written Opinion for International Application No. PCT/US2018/023785 dated Sep. 6, 2018.
International Search Report and Written Opinion from International Application No. PCT/US2011/064191 dated May 1, 2012.
International Search Report and Written Opinion from International Application No. PCT/US2016/027751 dated Jul. 1, 2016.
Irving et al., "The cytoplasmic domain of the T cell receptor zeta chain is sufficient to couple to receptor-associated signal transduction pathways," Cell (1991) 64: 891-901.
Iyer et al., "Prediction of novel families of enzymes involved in oxidative and other complex modifications of bases in nucleic acids," Cell Cycle (2009), vol. 8, No. 11, pp. 1698-1710.
Jena et al., "Chimeric Antigen Receptor (CAR)-Specific Monoclonal Antibody to Detect CD19-Specific T Cells in Clinical Trials," PLoS One (2013), vol. 8, No. 3, e57838, pp. 1-12.
Jena et al., "Redirecting T-cell specificity by introducing a tumor-specific chimeric antigen receptor," Blood, May 3, 2010, vol. 116, No. 7, pp. 1035-1044.
Jensen. et al., "Anti-Transgene Rejection Responses Contribute to Attenuated Persistence of Adoptively Transferred CD20/CD19-Specific Chimeric Antigen Receptor Re-directed T Cells in Humans," Biol Blood Marrow Transplant (2010), vol. 16, No. 9, pp. 1245-1256.
Jin et al., "Simplified Method of the Growth of Human Tumor Infiltrating Lymphocytes (TIL) in Gas-Permeable Flasks to Numbers Needed for Patient Treatment," J Immunother (2012), vol. 35, No. 3, pp. 283-292.

(56) References Cited

OTHER PUBLICATIONS

Johnson et al., "Gene therapy with human and mouse T-cell receptors mediates cancer regression and targets normal tissues expressing cognate antigen," Blood (2009), vol. 114, No. 3, pp. 535-545.
Jones et al., "Circulating clonotypic B cells in classic Hodgkin lymphoma," Blood (2009), vol. 113, No. 23, pp. 5920-5926.
Joo et al., "Targeted cancer therapy—are the days of systemic chemotherapy numbered?," Maturitas (2013), vol. 76, No. 4, pp. 308-314.
June et al., "Engineering lymphocyte subsets: tools, trials and tribulations," Nat Rev Immunol, (2009), vol. 9, No. 10, pp. 704-716.
Kalos et al., "T Cells with Chimeric Antigen Receptors Have Potent Antitumor Effects and Can Establish Memory in Patients with Advanced Leukemia," Science Translation Medicine (2011), vol. 3, No. 95, 95ra73.
Kershaw et al., "A Phase I Study on Adoptive Immunotherapy Using Gene-Modified T Cells for Ovarian Cancer," Clin. Cancer Res. (2006) 12(20 Pt 1): 6106-6115.
Kim et al., "Human 4-1BB regulates CD28 co-stimulation to promote Th1 cell responses," Eur. J. Immunol. (1998), vol. 28, pp. 881-890.
Kmieciak et al., "Ex vivo Expansion of Tumor-reactive T Cells by Means of Byrostatin 1/Ionomycin and the Common Gamma Chain Cytokines Formulation," Journal of Visualized Experiments (2011) vol. 47, doi: 10.3791/2381, pp. 1-4.
Kochenderfer et al, "A Phase I Clinical Trial of Treatment of B-Cell Malignancies with Autologous Anti-Cd19-CAR-Transduced T Cells," Blood (2010) vol. 116 No. 21 pp. 1179-1180 & 52nd Annual Meeting of the American-Society-of-Hematology (ASH); Orlando, FL, USA; Dec. 4-7, 2010 abstract.
Kochenderfer et al., "Construction and Pre-clinical Evaluation of an Anti-CD19 Chimeric Antigen Receptor," J Immunother (2009), vol. 32, No. 7, pp. 689-702.
Kochenderfer et al., "Eradication of B-lineage cells and regression of lymphoma in a patient treated with autologous T cells genetically-engineered to recognize CD19," Blood 116: 4099-4102 (2010).
Koehler et al., "Engineered T Cells for the Adoptive Therapy of B-Cell Chronic Lymphocytic Leukaemia," Advances in Hematology (2012), vol. 180, No. 9, pp. 6365-13.
Kohn et al., "CARs on Track in the Clinic," Molecular Therapy (2011), vol. 19, No. 3, pp. 432-438.
Krause et al., "Antigen-dependent CD28 Signaling Selectively Enhances Survival and Proliferation in Genetically Modified Activated Human Primary T Lymphocytes," J. Exp. Med. (1998), vol. 188, Np. 4, pp. 619-626.
Kunimoto et al., "Tet2 disruption leads to enhanced self-renewal and altered differentiation of fetal liver hematopoietic stem cells," s.Scentific Reports 2(273) 10 pgs. (2012) DOI 1038/srep00273.
Kwon et al., "cDNA sequences of two inducible T-cell genes," Proc. Natl. Acad. Sci. U.S.A., (1989) 86(6): 1963-1967.
Lamanna et al., "Pentostatin, Cyclophosphamide, and Rutuximab Is an Active, Well-Tolerated Regimen for Patients With Previously Treated Chronic Lymphocytic Leukemia," Journal of Clinical Oncology (2008), vol. 24, No. 10, pp. 1575-1581.
Lamers et al., "Treatment of Metastatic Renal Cell Carcinoma With Autologous T-Lymphocytes Genetically Retargeted Against Carbonic Anhydrase IX: First Clinical Experience," J. Clin. Oncol. (2006) 24(13): e20-e22.
Laport et al., "Adoptive transfer of costimulated T cells induces lymphocytosis in patients with relapsed/refractory non-Hodgkin lymphoma following CD34 +-selected hematopoietic cell transplantation," Blood (2003), vol. 102, No. 6, pp. 2004-2013.
Laukka et al., "Fumarate and Succinate Regulate Expression of Hypoxia-inducible Genes via TET Enzymes," The Journal of Biological Chemistry (2016), vol. 291, No. 8, pp. 4256-4265.
Lee et al., "T cells expressing CD19 chimeric antigen receptors for acute lymphoblastic leukaemia in children and young adults: a phase 1 dose escalation trial," Lancet (2014), vol. 385, No. 9967, pp. 517-528.

Lee et al., "The Future is Now: Chimeric Antigen Receptors as New Targeted Therapies for Childhood Cancer," Clin. Cancer Res.(2012) 18: 2780-2790.
Lee et al., "In vivo Inhibition of Human CD19-Targeted Effector T Cells by Natural T Regulatory Cells in a Xenotransplant Murine Model of B Cell Malignancy," Cancer Research (2011), vol. 71, No. 8, pp. 2871-2881.
Letourneur et al., "T-cell and basophil activation through the cytoplasmic tail of T-cell-receptor zeta family proteins," Proc. Natl. Acad. Sci. U.S.A (1991) 88: 8905-8909.
Levine et al., "Gene transfer in humans using a conditionally replicating lentiviral vector," PNAS (2006), vol. 103, No. 46, pp. 17372-17377.
Lipowska-Bhalla et al., "Targeted immunotherapy of cancer with CAR T cells: achievements and challenges," Cancer Immunology Immunotherapy (2012), vol. 61, pp. 953-962.
Macallan et al., "Measurement and modeling of human T cell kinetics, " European Journal of Immunology (2003), vol. 33, pp. 2316-2326.
Maher et al., "Human T lymphocyte cytotoxicity and proliferation directed by a single chimeric TCRzeta/CD28 receptor," Nat. Biotechnol. (2002) 20: 70-75.
Maude et al., "Chimeric Antigen Receptor T Cells for Sustained Remissions in Leukemia," The New England Journal of Medicine (2014), vol. 371, No. 16, pp. 1507-1517.
McGuinness et al., "Anti-tumor activity of human T cells expressing the CC49-ζ chimeric immune receptor," Hum. Gene Ther.(1999) 10: 165-173.
Milone et al, "Chimeric Receptors Containing CD137 Signal Transduction Domains Mediate Enhanced Survival of T Cells and Increased Antileukemic Efficacy In Vivo," Molecular Therapy (2009), vol. 17, No. 8, pp. 1453-1464.
Molina, "A Decade of Rituximab: Improving Survival Outcomes in Non-Hodgkin's Lymphoma," Annu. Rev. Med. (2008), vol. 59, pp. 237-250.
Moran-Crusio et al., "Tet2 Loss Leads to Increased Hematopoietic Stem Cell Self-Renewal and Myeloid Transformation," Cancer Cell, Cell Press Article, vol. 20, No. 1, Jun. 6, 2011, 14 pages.
Morgan et al., "Case Report of a Serious Adverse Event Following the Administration of T Cells Transduced With a Chimeric Anitgen Receptor Recognizing ErbB2," Mol. Ther. 18(4): 843-851 (2010).
Moritz et al., "A spacer region between the single chain antibody- and the CD3 zeta-chain domain of chimeric T cell receptor components is required for efficient ligand binding and signaling activity," Gene Therapy 2(8): 539-546 (1995).
Moritz et al., "Cytotoxic T lymphocytes with a grafted recognition specificity for ERBB2-expressing tumor cells," Proc. Natl. Acad. Sci (1994), vol. 91, pp. 4318-4322.
Muthusamy et al., "Defective activation and survival of T cells lacking the Ets-1 transcription factor," Nature (1995), vol. 377, pp. 639-642.
Naldini et al., "In Vivo Gene Delivery and Stable Transduction of Nondividing Cells by a Lentiviral Vector," Science (1996), vol. 272, pp. 263-267.
NCBI accession HM_852952 accessed Sep. 29, 2015 from http://www.ncbi.nlm.nih.gov/nuccore/hm852952.
Nicholson et al., "Construction and Characterisation of a Function CD19 Specific Single Chain Fv Fragment for Immunotherapy of B Lineage Leukaemia and Lymphoma," Molecular Immunology 34(16-17): 1157-1165 (1997).
Ninomiya et al, "Tumor indoleamine 2,3-dioxygenase (IDO) inhibits CD19-CAR T cells and is downregulated by lymphodepleting drugs," Blood (2015), vol. 125, No. 25, pp. 3905-3916.
Ocwieja et al., "HIV Integration Targeting: A Pathway Involving Transportin-3 and the Nuclear Pore Protein RanBP2," PLoS Pathog (2011), vol. 7, No. 3, e1001313, pp. 1-14.
Park et al., "Adoptive Immunotherapy for B-cell Malignancies with Autologous Chimeric Antigen Receptor Modified Tumor Targeted T Cells," Discovery Medicine (2010), vol. 9, No. 47, pp. 277-288.
Park et al., "Adoptive Transfer of Chimeric Antigen Receptor Re-directed Cytolytic T Lymphocyte Clones in Patients with Neuroblastoma," Molecular Therapy (2007), vol. 15, No. 4, pp. 825-833.

(56) References Cited

OTHER PUBLICATIONS

Partial Search Report and Invitation to Pay Additional Fees for International Application No. PCT/US2016/052260 dated Nov. 16, 2016.
Patel et al., "Impact of chimeric immune receptor extracellular protein domains on T cell function," Gene Therapy (1999), vol. 6, pp. 412-419.
Pauken et al., "Epigenetic stability of exhausted T cells limits durability of reinvigoration by PD-1 blockade," Science (2016), vol. 354, No. 6316, pp. 1160-1165.
PCT International Preliminary Report on Patentability Chapter I issued in International Application No. PCT/US2018/023631 dated Sep. 24, 2019, 11 pages.
PCT International Preliminary Report on Patentability issued in PCT/US2019/036111, dated Dec. 8, 2020, 12 pgs.
PCT International Search Report issued in International Application No. PCT/US2018/023631 dated Oct. 25, 2018, 7 pages.
PCT International Search Report issued in PCT/US2019/036111, dated Nov. 7, 2019, 7 pgs.
PCT Written Opinion of the International Searching Authority issued in International Application No. PCT/US2018/023631 dated Oct. 22, 2018, 10 pages.
PCT Written Opinion of the International Searching Authority issued in PCT/US2019/036111, dated Nov. 7, 2019, 11 pgs.
Piper et al., "Chronic lymphocytic leukemia cells drive the global CD4+ T cell repertoire towards a regulatory phenotype and leads to the accumulation of CD4+ forkhead box P3+ T cells," Clinical and Experimental Immunology (2011), vol. 166, No. 2, pp. 154-163.
Porter et al., "Chimeric antigen receptor T cells persist and induce sustained remissions in relapsed refractory chronic lymphocytic leukemia," Science Translational Medicine (2015), vol. 7, No. 303, ra139, pp. 1-25.
Porter et al., "A phase 1 trial of donor lymphocyte infusions expanded and activated ex vivo via CD3/CD28 costimulation," Blood (2006), vol. 107, No. 4, pp. 1325-1331.
Porter et al., "Chimeric Antigen Receptor-Modified T Cells in Chronic Lymphoid Leukemia," The New England Journal of Medicine (2011), vol. 365, No. 8, pp. 725-733.
Porter et al., "Chimeric Antigen Receptor Therapy for B-cell Malignancies," Journal of Cancer (2011), vol. 2, pp. 331-332.
Powell et al., "Large-Scale Depletion of CD25+ Regulatory T Cells from Patient Leukapheresis Samples," Journal of Immunotherapy (2005), vol. 28, No. 4, pp. 403-411.
Powell et al., "Partial Reduction of Human FOXP3+ CD4 T Cells In Vivo After CD25-directed Recombinant Immunotoxin Administration," J Immunother (2008), vol. 31, pp. 189-198.
Priceman et al., "Smart CARs Engineered for Cancer Immunotherapy," Curr Opin Oncol (2015), vol. 27, No. 6, pp. 466-474.
Pronier et al., "Inhibition of TET2-mediated conversion of 5-methylcytosine to 5-hydroxymethylcytosine disturbs erythroid and granulomonocytic differentiation of human hematopoietic progenitors," Blood (2011), vol. 118, No. 9, pp. 2551-2555.
Pule, M. A. et al., "Virus-specific T cells engineered to coexpress tumor-specific receptors: persistence and antitumor activity in individuals with neuroblastoma," Nat. Med. (2008). Vol. 14, No. 11, pp. 1264-1270.
Rapoport et al., "Restoration of immunity in lymphopenic individuals with cancer by vaccination and adoptive T-cell transfer," Nature Medicine (2005), vol. 11, No. 11, pp. 1230-1237.
Roederer, "T-cell dynamics of immunodeficiency," Nature Medicine (1995), vol. 1, No. 7, pp. 621-622.
Romeo et al., "Cellular immunity to HIV activated by CD4 fused to T cell or Fc receptor polypeptides," Cell (1991) 64:1037-1046.
Rudikoff et al., "Single amino acid substitution altering antigen-binding specificity," PNAS (1982), vol. 79, pp. 1979-1983.
Rufer et al., "Transfer of the human telomerase reverse transcriptase (TERT) gene into T lymphocytes results in extension of replicative potential," Blood (2001), pp. 597-603.
Sabbagh et al., "TNF family ligands define niches for T cell memory," Trends in Immunology (2007), vol. 28, No. 8, pp. 333-339.
Sadelain et al., "The promise and potential pitfalls of chimeric antigen receptors," Current Opinion Immunology (2009), vol. 21, No. 2, pp. 215-223.
Sadelain et al., "Targeting Tumours with Genetically Enhanced T Lymphocytes," Nature Reviews: Cancer (2003) 3: 35-45.
Savoldo et al., "CD28 costimulation improves expansion and persistence of chimeric antigen receptor-modified T cells in lymphoma patients," The Journal of Clinical Investigation (2011), vol. 121, No. 5, pp. 1822-1826.
Scholler et al., "Decade-Long Safety and Function of Retroviral-Modified Chimeric Antigen Receptor T-cells," Science Translational Medicine (2012) vol. 4, No. 132, ra153, pp. 1-16.
Scourzic et al., "TET Proteins and the Control of Cytosine Demethylation in Cancer," Genome Medicine (2015), vol. 7, No. 1, © Scourzic et al, licensee BioMed Central, 16 pages.
Sebestyén et al., "Human TCR That Incorporate CD3Z Induce Highly Preferred Pairing between TCR α and β Chains following Gene Transfer," Journal of Immunology (2008), vol. 180, pp. 7736-7746.
Shide et al., "TET2 is Essential for Survival and Hematopoietic Stem Cell Homeostasis," Leukemia (2012) 26, © 2012 Macmillan Publishers Limited, www.nature.com/leu, pp. 2216-2223.
Shirasun. et al., "Functional Design of Chimeric T-Cell Antigen Receptors for Adoptive Immunotherapy of Cancer: Architecture and Outcomes," AntiCancer Res. (2012) 32: 2377-2384.
Shvidel et al., "Cell surface expression of CD25 antigen (surface IL-2 receptor alpha-chain) is not a prognostic marker in chronic lymphocytic leukemia: results of a retrospective study of 281 patients," Ann Hematol (2012), vol. 91, pp. 1597-1602.
Singapore Search Report and Written Opinion for Singapore Application No. 11201705293W dated Mar. 22, 2018.
Singapore Search Report and Written Opinion for Singapore Application No. 11201708516Y dated Sep. 25, 2018.
Singh et al., "Early memory phenotypes drive T cell proliferation in patients with pediatric malignancies," Science Translational Medicine (2012), vol. 8, No. 320, pp. 320ra3-320ra3.
Slaney et al., "Dual-specific Chimeric Antigen Receptor T Cells and an Indirect Vaccine Eradicate a Variety of Large Solid Tumors in an Immunocompetent Self-antigen Setting," Clinical Cancer Research (2017), vol. 23, No. 10, pp. 2478-2490.
Sorror et al., "Outcomes after allogeneic hematopoietic cell transplantation with nonmyeloablative or myeloablative conditioning regimens for treatment of lymphoma and chronic lymphocytic leukemia," Blood (2008), vol. 111, No. 1, pp. 446-452.
Stroncek et al., "Highlights of the society for immunotherapy of cancer (SITC) 27th annual meeting," Journal for ImmunoTherapy of Cancer (2013), vol. 1, No. 4, pp. 1-11.
Tahiliani et al., "Conversion of 5-Methylcytosine to 5-Hydroxymethylcytosine in Mammalian DNA by MLL Partner TET1," Science (2009), vol. 324, pp. 930-935.
Taylor et al., "IL-10 suppresses CD2-mediated T cell activation via SHP-1," Molecular Immunology (2009), vol. 46, pp. 622-629.
Terakura et al., "Generation of CD19-chimeric antigen receptor modified CD8+ T cells derived from virus-specific central memory T cells," Blood (2012), vol. 119, No. 1, pp. 72-82.
Till et al., "Adoptive immunotherapy for indolent non-Hodgkin lymphoma and mantle cell lymphoma using genetically modified autologous CD20-specific T cells," Blood (2008), vol. 112, No. 6, pp. 2261-2271.
Tretter et al., "Succinate, an intermediate in metabolism, signal transduction, ROS, hypoxia, and tumorigenesis," Biochimica et Biophysica Acta (2016), vol. 1857, pp. 1086-1101.
Tsukumo et al., "Bach2 maintains T cells in a naive state by suppressing effector memory-related genes," PNAS (2013), vol. 110, No. 26, pp. 10735-10740.
Uckun et al., "Detailed studies on expression and function of CD19 surface determinant by using B43 monoclonal antibody and the clinical potential of anti-CD19 immunotoxins," Blood (1988), vol. 71, pp. 13-29.

(56) References Cited

OTHER PUBLICATIONS

Urak et al., "Ex vivo Akt inhibition promotes the generation of potent CD19CAR T cells for adoptive immunotherapy," Journal for Immunotherapy of Cancer (2017), vol. 5, No. 1, pp. 7-13.
Verbinnen et al., "Contribution of Regulatory T Cells and Effector T Cell Deletion in Tolerance Induction by Costimulation Blockade1," Journal of Immunology (2008), vol. 181, pp. 1034-1042.
Vinay et al., "Role of 4-1BB in immune responses," Immunology (1998), vol. 10, pp. 481-489.
Wang et al., "CS-1 Re-Directed Central Memory T Cell Therapy for Multiple Myeloma," Blood (2014), vol. 124, No. 21, Meeting Abstract 1114.
Wang et al., "Phenotypic and Functional Attributes of Lentivirus Modified CD19-specific Human $CD8^+$ Central Memory T Cells Manufactured at Clinical Scale," J. Immunother (2012), vol. 35, No. 9, pp. 689-701.
Wilkie et al., "Dual Targeting of ErbB2 and MUC1 in Breast Cancer Using Chimeric Antigen Receptors Engineered to Provide Complementary Signaling," J Clin Immunol (2012), vol. 32, pp. 1059-1070.
Willemsen et al., "Genetic Engineering of T Cell Specificity for Immunotherapy of Cancer," Human Immunology (2003), vol. 64, pp. 56-68.
Wu et al., "Suppression of TET1-Dependent DNA Demethylation Is Essential for KRAS-Mediated Transformation," Cell Reports (2014), vol. 9, pp. 1827-1840.
Xu et al., "Oncometabolite 2-Hydroxyglutarate Is a Comparative Inhibitor of alpha-Ketoglutarate-Dependent Dioxygenases," Cancer Cell (2011), vol. 19, No. 1, pp. 17-30.
Yeh et al., "Mutation of epigenetic regulators TET2 and MLL3 in patients with HTLV-I-induced acute adult T-cell leukemia," Molecular Cancer (2016), vol. 15, No. 15, pp. 1-7.
Zang et al., "Mutations in 5-methylcytosine oxidase TET2 and RhoA cooperatively disrupt T cell homeostasis," The Journal of Clinical Investigation (2017), vol. 127, pp. 2998-3012.
Zhang et al., "Efficiency of CD19 chimeric antigen receptor-modified T cells for treatment of B cell malignancies in phase I clinical trials: a meta analysis," Oncotarget (2015), vol. 6, No. 32, pp. 33961-33971.
Zhang et al., "Down-regulation of TET2 in $CD3^+$ and $CD34^+$ cells of myelodysplastic syndromes and enhances $CD34^+$ cells proliferation," Int J Clin Exp Pathol (2015), vol. 8, No. 9, pp. 10840-10846.
Zhao et al., "A Herceptin-Based Chimeric Antigen Receptor with Modified Signaling Domains Leads to Enhanced Survival of Transduced T Lymphocytes and Antitumor Activity," The Journal of Immunology (2009), vol. 183, pp. 5563-5574.
Zufferey et al., "Multiply attenuated lentiviral vector achieves efficient gene delivery in vivo," Nature Biotechnology (1997), vol. 15, pp. 871-876.
Nemudryi, A.A. et al., "TALEN and CRISPR/Cas Genome Editing Systems: Tools of Discovery," Acta Naturae, Jul. 2014, vol. 6, No. 3, Copyright © 2014 Park-media, Ltd., pp. 19-40.
Database WPI Week 201572, Derwent World Patents Index, AN 2015-42037B, XP002767532,.
Gilbert, Luke A. et al., "Genome-Scale CRISPR-Mediated Control of Gene Repression and Activation," Cell, vol. 159, No. 3, Oct. 9, 2014, pp. 647-661, © 2014 Elsevier Inc.
Mandal, Pankaj K. et al., "Efficient Ablation of Genes in Human Hematopoietic Stem and Effector Cells Using CRISPR/Cas9," Cell Stem Cell, Nov. 6, 2014, 15(5):643-52, vol. 15, No. 5., © 2014 Elsevier Inc.
PCT International Search Report issued in International Application No. PCT/IB2016/057318 dated May 9, 2017, 9 pages.
PCT Written Opinion of the International Searching Authority issued in International Application No. PCT/IB2016/057318 dated Jun. 8, 2017, 14 pages.
Ren, Jiangtao et al., "Multiplex Cripsr/Cas9 Genome Editing to Generate Potent Universal CART and PD1—Deficient Cells Against Leukemia," Blood 2015 126:4280; © 2015 by The American Society of Hematology.

Sato, Takehito et al., "Establishment of β2-microglobulin deficient human iPS cells using CRISPR/Cas9 system," Integrative Molecular Medicine, vol. 2(6), pp. 373-377.
Torikai, Hiroki et al., "A Foundation for Universal T-Cell Based Immunotherapy: T Cells Engineered to Express a CD-Specific Chimeric-Antigen-Receptor and Eliminate Expression of Endogenous TCR," Blood, Jun. 14, 2012, vol. 1192, No. 24, pp. 5697-5705, 10 pgs., from www.bloodjournal.org by guest on Dec. 11, 2018, © 2012 by The American Society of Hematology.
Appel et al. "Nucleic Acids: from A to Z" pp. 221, 2013, edited by S. Muller translated from English,—Moscow: BINOM, Laboratoriya znanii, 2013 backbone (p. 221).
Amescua et al., "Limbal stem cell transplantation: current perspectives", Clin Opthalmol., Apr. 1, 2016;10:593-602.
Appel et al. "Nucleic Acids: from A to Z" p. 221, 2013, edited by S. Muller translated from English,—Moscow: BINOM, Laboratoriya znanii, 2013 backbone (p. 221).
Bernal et al. "Implication of the β2-microglobulin gene in the generation of tumor escape phenotypes," Cancer Immunol. Immunother., 2012, v.61, p. 1359-1371.
Carty et al. (2014) "TET2 Regulates CD8+ T Cell Differentiation," Blood 124, Abstract 203.
CHOPCHOP, chopchop.cbu.uib.no/results/1642721720510.5486/ last accessed Jan. 20, 2022.
Dang et al. "Optimizing sgRNA structure to improve CRISPR-Cas9 knockout efficiency," Genome Biol. 2015, 16:280 (10 pages).
Edit-R predesigned crRNA; product description downloaded from the internet on Mar. 30, 2022.
Gen Bank NC_000004.12, Homo sapiens Chromosome 4, GRCh38. p13, region 105269700 to 10527600; 2021.
Hendel et al. "Chemically modified guide RNAs enhance CRISPR-Cas genome editing in human primary cells," Nat Biotechnol. 2015, 33(9):985-989.
Ibarra et al. "Targeted Killing of HIV Infected Cells Using CCR5-Disrupted Anti-HIV-CAR T Cells," Molecular Therapy, 2016, 24(Suppl 1): S301, Abstract 761.
Jinek et al. "A programmable dual-RNA-guided DNA endonuclease in adaptive bacterial immunity," Science. 2012 , 337(6096):816-21.
Ko et al., (2011) "Ten-Eleven-Translocation 2 (TET2) negatively regulates homeostasis and differentiation of hematopoietic stem cells in mice," PNAS 108(35): 14566-14571.
Lin et al. "Topical administration of orbital fat-derived stem cells promotes corneal tissue regeneration," Stem Cell Res Ther. 2013; 4(3):72.
Montague et al. "CHOPCHOP: a CRISPR/Cas9 and TALEN web tool for genome editing," Nucleic Acids Res. 2014, 42(Web Server issue):W401-7.
Myadelets "Part 1. Cytology, embryology and general histology" Histology, cytology and human embryology, textbook, Vitebsk:VSMU, 2014, p. 197.
Office Action issued in Russian Patent Application No. 2019133280/ 10(065730) dated Sep. 24, 2021, 10 pgs.
PCT International Search Report and Written Opinion of the International Searching Authority received in PCT/IB2019/059162, dated Jan. 21, 2020 (12 pgs.).
Perrin "Make Mouse Studies Work," Nature, Mar. 27, 2014;507(7493):423-5 Preclinical research: Make mouse studies work.
Qin et al. "Efficient CRISPR/Cas9-Mediated Genome Editing in Mice by Zygote Electroporation of Nuclease," Genetics, 2015, 200: 423-430.
Shaw et al. "Novel ROCK inhibitors for the treatment of pulmonary arterial hypertension," Bioorg Med Chem Lett. Oct. 15, 2014;24(20):4812-7. doi: 10.1016/j.bmcl.2014.09.002. Epub Sep. 6, 2014. PMID: 25248678.
Shrikant et al. "Regulating functional cell fates in CD8 T cells," Immunol. Res., 2010, 46: 12-22.
Tang et al. "A nanobody-based system using fluorescent proteins as scaffolds for cell-specific gene manipulation," Cell. 2013, 154: 1370-1379.
Wang et al. "One-step generation of mice carrying mutations in multiple genes by CRISPR/Cas-mediated genome engineering." Cell. May 9, 2013;153(4):910-8.

(56) References Cited

OTHER PUBLICATIONS

Wang et al., "Highly efficient homology-driven genome editing in human T cells by combining zinc-finger nuclease mRNA and AAV6 donor delivery," *Nucleic Acids Research*, 2016, 44(3): e30, 9 pages, available online Nov. 2, 2015.

Yang et al. "One-Step Generation of Mice Carrying Reporter and Conditional Alleles by CRISPR/Cas-Mediated Genome Engineering," *Cell*, 2013, 154: 1370-1379.

Yang et al., "Universal Corneal Epithelial-Like Cells Derived from Human Embryonic Stem Cells for Cellularization of a Corneal Scaffold", Transl Vis Sci Technol. Oct. 10, 2018;7(5):23 (16 pgs.).

Derksen et al. "Illegitimate WNT signaling promotes proliferation of multiple myeloma cells," PNAS, 2004, vol. 101 No. 16 p. 6122-6127.

Dirks. "Brain tumor stem cells: bringing order to the chaos of brain cancer," J Clin Oncol. Jun. 10, 2008;26(17):2916-24.

Internet Archive Wayback Machine, ChopChop, https://web.archive.org/web/20220000000000*/https://chopchop.rc.fas.harvard.edu, Feb. 5, 2015.

Kozhucharova "New Human Embryonic Stem Cell Lines C612 and C910," Cytology, 2009; 51(7):551-558, p. 551 [in Russian].

Labun et al. "CHOPCHOP v2: a web tool for the next generation of CRISPR genome engineering," Nucleic Acids Res. Jul. 8, 2016;44(W1):W272-6. doi: 10.1093/nar/gkw398. Epub May 16, 2016. PMID: 27185894; PMCID: PMC4987937.

Liang et al. "Rapid and highly efficient mammalian cell engineering via Cas9 protein transfection", J Biotechnol. Aug. 20, 2015;208:44-53.

Lopez-Lazaro "The migration ability of stem cells can explain the existence of cancer of unknown primary site. Rethinking metastasis," Oncoscience. May 1, 2015;2(5):467-75.

Menzorov et al. "What Collections of Cell Lines Are for," Vavilov Journal of Genetics and Selection, 2016; 20(6): 945-948; p. 947 [in Russian].

Menzorov, A.G.. "Murine and Human Embryonic Stem Cells," Vavilov Journal of Genetics and Selection, 2013; 17(2): 234-245 [in Russian].

Office Action issued in Russian Patent Application No. 2019133280/10(065730) dated Mar. 14, 2023, 26 pgs.

Office Action issued in Russian Patent Application No. 2019133280/10(065730) dated May 2, 2023, 15 pgs.

PCT International Search Report and Written Opinion of the International Searching Authority issued in PCT/IB2021/053413, dated Sep. 7, 2021, 13.

Tran et al. "Survival comparison between glioblastoma multiforme and other incurable cancers," J Clin Neurosci. Apr. 2010;17(4):417-21.

Vechkanov et al. "Foundations of Cell Engineering: a textbook"—Rostov-na-Donu, 2012; pp. 15, 16. [in Russian].

Wiles et al. "CRISPR-Cas9-mediated genome editing and guide RNA design. Mamm Genome," Oct. 2015;26(9-10):501-10. doi: 10.1007/s00335-015-9565-z. Epub May 20, 2015. PMID: 25991564; PMCID: PMC4602062.

Yangulov et al. "The Effect of Various Cryoprotective Media on the Viability of Cryopreserved Lymphoblastic Cell Lines H-9 and U-937," Problems of Cryobiology. 1991; 3: 46-49 [in Russian].

Zhdanov et al. "The Mystery of the Third Kingdom," Moscow, "Znanie", 1975-176 pages; pp. 124, 125 [in Russian].

\* cited by examiner

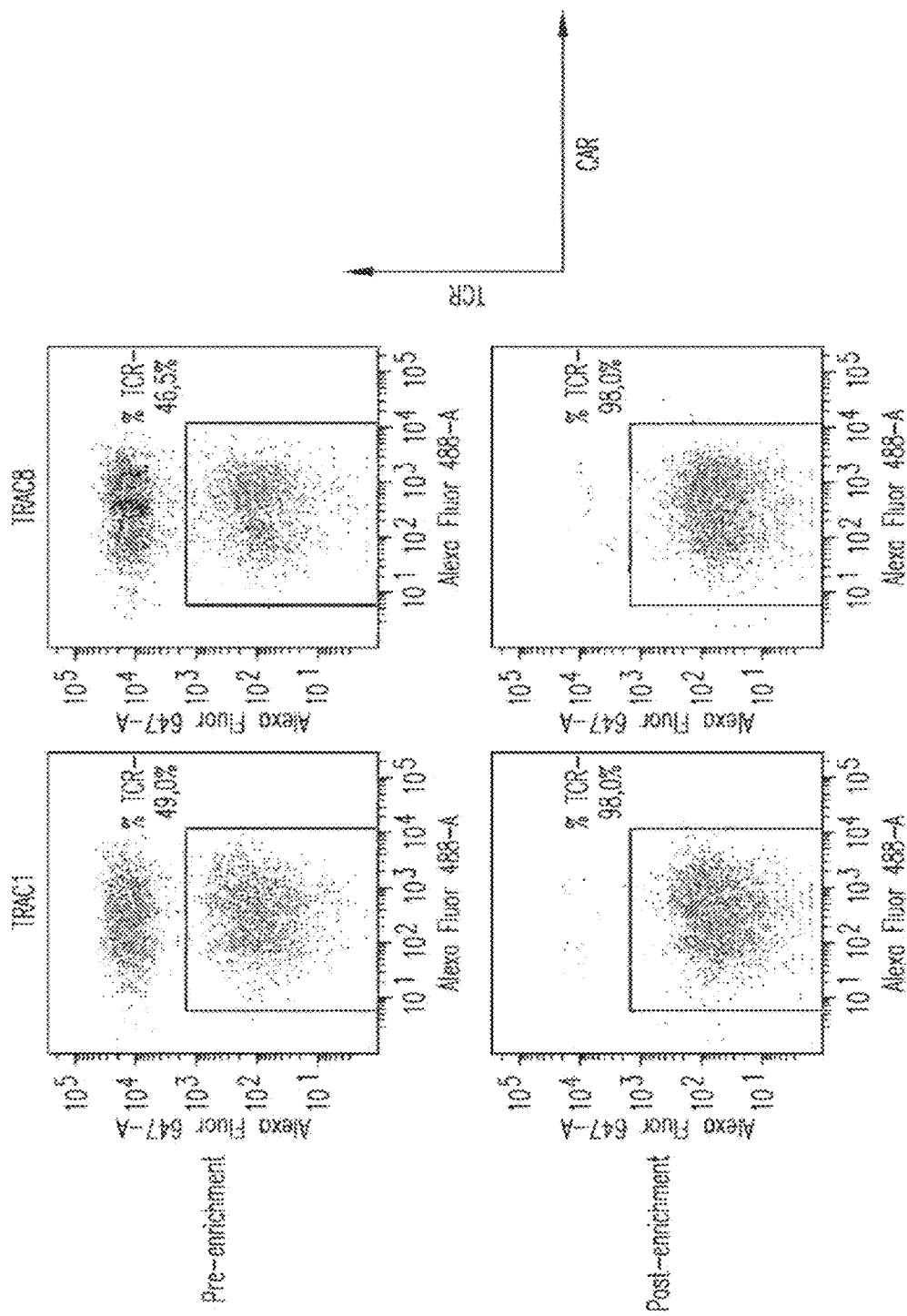

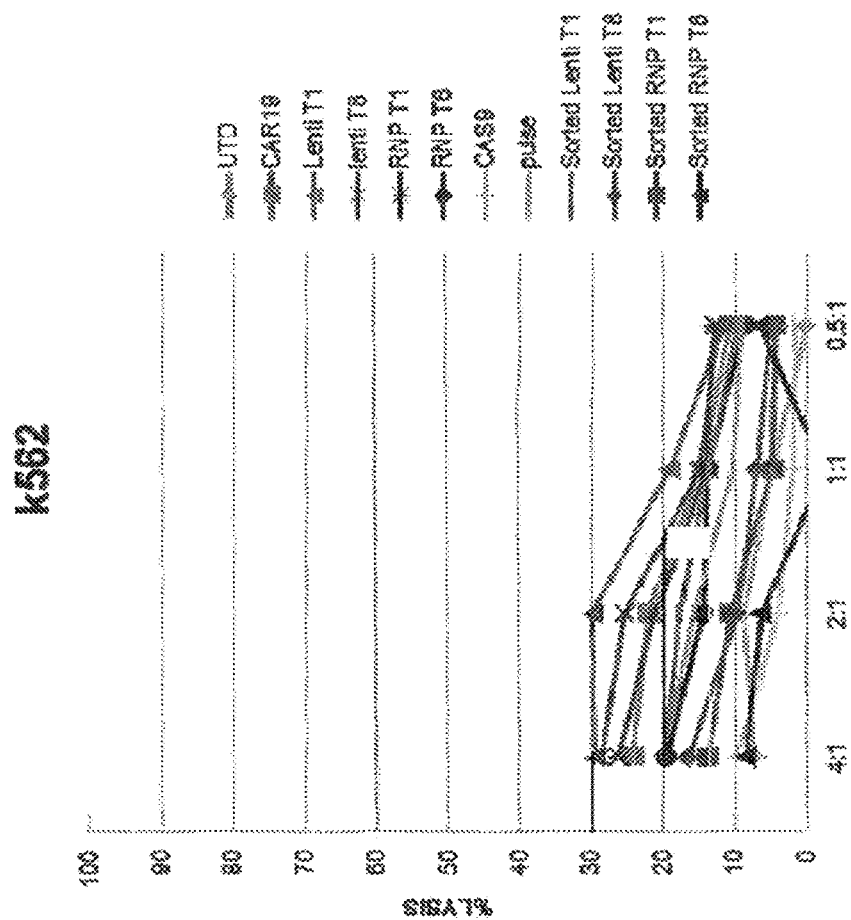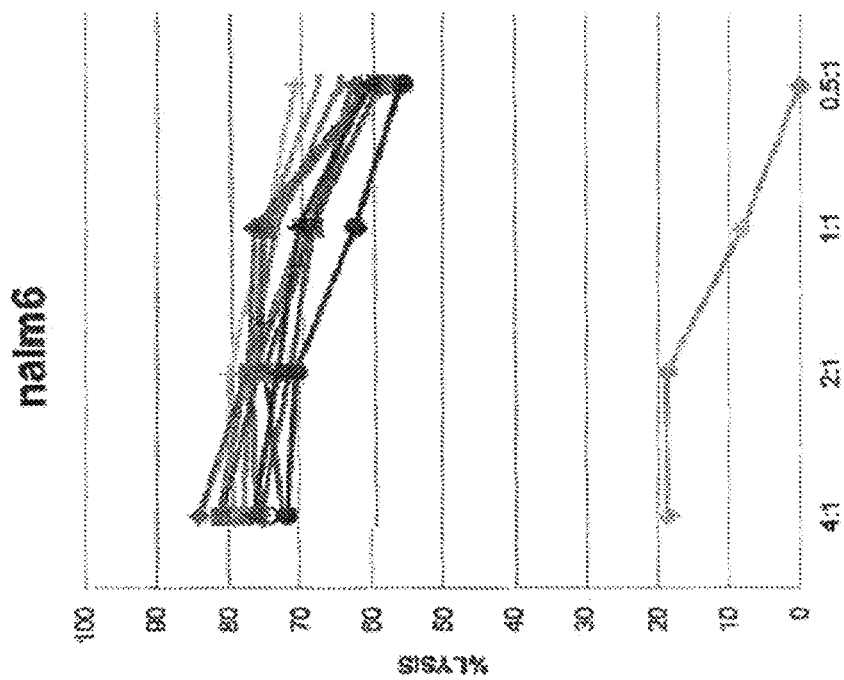
FIG. 7

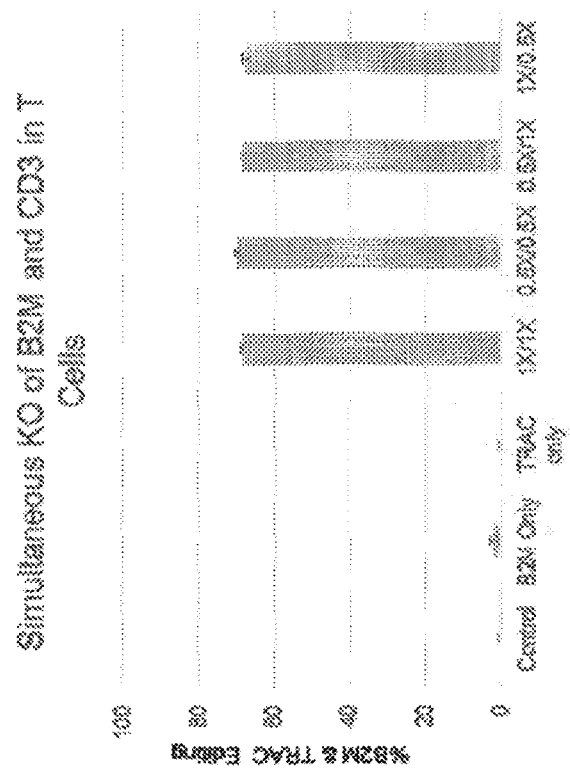

| gRNA ID | Species | Strand | Location | Avg % Edit | SD Edit | Editing Rank | Ave % PS | SD PS | PS rank |
|---|---|---|---|---|---|---|---|---|---|
| CR002077 | h | + | Chr20:1392999-1393020 | 82.22 | 5.96 | 1 | 76.13 | 4.34 | 1 |
| CR002097 | h | - | Chr20:1392846-1392868 | 74.27 | 3.87 | 4 | 67.97 | 3.89 | 2 |
| CR002096 | h | + | Chr20:1392847-1392869 | 63.30 | 3.03 | 8 | 58.53 | 2.29 | 3 |
| CR002064 | h | + | Chr20:1393053-1393075 | 64.65 | 7.97 | 7 | 56.80 | 6.85 | 4 |
| CR002091 | h | - | Chr20:1392880-1392902 | 78.42 | 2.47 | 2 | 56.20 | 2.70 | 5 |
| CR002057 | h | + | Chr20:1393117-1393139 | 61.01 | 2.06 | 9 | 51.13 | 2.00 | 6 |
| CR002100 | h | + | Chr20:1392814-1392836 | 56.42 | 0.99 | 11 | 49.20 | 0.96 | 7 |
| CR002113 | h | - | Chr20:1375513-1375535 | 50.51 | 5.97 | 17 | 46.47 | 5.85 | 8 |
| CR002056 | h | + | Chr20:1393118-1393140 | 51.26 | 0.23 | 16 | 45.73 | 0.89 | 9 |
| CR002078 | h | + | Chr20:1392995-1393017 | 56.06 | 5.91 | 13 | 45.70 | 4.44 | 10 |
| CR002068 | h | + | Chr20:1393039-1393061 | 60.55 | 7.79 | 5 | 44.70 | 4.09 | 11 |
| CR002104 | h | - | Chr20:1375565-1375587 | 55.58 | 4.38 | 14 | 43.87 | 5.22 | 12 |
| CR002070 | h | + | Chr20:1393018-1393040 | 59.50 | 8.10 | 10 | 43.17 | 4.19 | 13 |
| CR002086 | h | - | Chr20:1392907-1392929 | 52.13 | 4.69 | 15 | 42.63 | 2.94 | 14 |
| CR002063 | h | - | Chr20:1393057-1393079 | 77.18 | 3.99 | 3 | 42.43 | 1.37 | 15 |

FIG. 23

| gRNA ID | CD3+ T cells (NGS) | | | |
|---|---|---|---|---|
| | % Edit | Stdev | % FS edit | StDev |
| CR002100 | 50.3 | 2.3 | 46.1 | 2.3 |
| CR002097 | 46.0 | 4.5 | 38.7 | 4.5 |
| CR002091 | 51.2 | 7.9 | 35.7 | 7.9 |
| CR002085 | 39.5 | 7.1 | 30.4 | 7.1 |
| CR002086 | 33.6 | 1.9 | 29.3 | 1.9 |
| CR002089 | 40.2 | 1.9 | 28.3 | 1.9 |
| CR002088 | 33.8 | 2.4 | 26.2 | 2.4 |
| CR002096 | 23.8 | 3.0 | 22.3 | 3.0 |
| CR002095 | 29.1 | 4.0 | 20.1 | 4.0 |
| CR002080 | 29.7 | 7.5 | 18.9 | 1.5 |
| CR002109 | 25.2 | 3.4 | 16.4 | 3.4 |
| CR002112 | 21.8 | 0.7 | 15.7 | 0.7 |
| CR002110 | 15.3 | 1.4 | 13.6 | 1.4 |
| CR002108 | 19.2 | 1.4 | 13.7 | 1.4 |
| CR002104 | 18.2 | 0.7 | 13.1 | 0.7 |
| CR002115 | 16.3 | 1.8 | 12.4 | 1.8 |
| CR002116 | 10.2 | 0.2 | 8.6 | 0.2 |
| CR002087 | 12.5 | 0.6 | 8.3 | 0.6 |
| CR002107 | 8.7 | 0.6 | 5.9 | 0.6 |
| CR002113 | 6.3 | 0.7 | 5.3 | 0.7 |

FIG. 24

| Guide RNA | % indels (avg) Expt. 1 | % indels (avg) Expt. 2 | % frameshift edits (avg) Expt. 2 |
|---|---|---|---|
| CR000961 | 96.95 | 96.54 | 77.27 |
| CR000978 | 86.31 | 93.97 | 46.86 |
| CR000984 | 96.96 | | |
| CR000992 | 14.97 | 95.57 | 65.73 |
| CR000960 | 95.12 | | |
| CR000979 | 91.03 | | |
| CR000991 | | 96.65 | 52.14 |
| CR000993 | | 97.14 | 37.88 |

| Guide RNA | % indels (avg) | % frameshift edits (avg) |
|---|---|---|
| CR002961 | 91.38 | 86.88 |
| CR002965 | 92.49 | 75.36 |
| CR002967 | 99.24 | 87.58 |
| CR002972 | 88.41 | 84.76 |
| CR002976 | 90.40 | 81.85 |
| CR002980 | 88.81 | 27.07 |

| Guide RNA | % indels (avg) | % frameshift edits (avg) |
|---|---|---|
| CR002967 | 95.35 | 84.59 |
| CR002992 | 94.82 | 60.91 |
| CR002993 | 96.09 | 65.11 |
| CR003007 | 96.16 | 82.93 |

FIG. 43

| Guide-Treatment | Variant Read | Frequency (avg) | Avg (Indel Length) | Unique Concatenate (Call) |
|---|---|---|---|---|
| CR002967 | GCAGCTCACAGTGTGCCACCATGGAGTTGGGGCCCCTAGAAGGATGGCTACCTGGAGCTTCTTAACAGCGATGCTGACCCC | 38.70% | 1 | Frameshift |
| CR002967 | GCAGCTCACAGTGTGCCACCATGGAGTTGGAGTTGGGG---TAGAAGGTGGCTACCTGGAGCTTCTTAACAGCGATGCTGACCCC | 4.83% | -4 | Frameshift |
| CR002967 | GCAGCTCACAGTGTGCCACCATGGAGTTGGGGCCCCAGAAGGTGGCTACCTGGAGCTTCTTAACAGCGATGCTGACCCC | 2.66% | -1 | Frameshift |
| CR002967 | GCAGCTCACAGTGTGCCACCATGGAG------------------------------CTTCTTAACAGCGATGCTGACCC | 2.50% | -30 | In Frame |
| CR002967 | GCAGCTCACAGTGTGCCACCATGGAGTTGGGGC--------------TACCTGGAGCTTCTTAACAGCGATGCTGACCCC | 2.30% | -14 | Frameshift |
| CR002967 | GCAGCTCACAGTGTGCCACCATGGAGTTGGG-----TAGAAGGTGGCTACCTGGAGCTTCTTAACAGCGATGCTGACCCC | 2.01% | -5 | Frameshift |
| CR002967 | GCAGCTCACAGTGTGCCACCATGGAGTTGG----------------CTACCTGGAGCTTCTTAACAGGGATGCTGACCCC | 1.90% | -16 | Frameshift |
| CR002967 | GCAGCTCACAGTGTGCCACC-------------------------------TGGAGCTTCTTAACAGGGATGCTGACCCC | 1.85% | -31 | Frameshift |
| CR002967 | GCAGCTCACAGTGTGCCACCATGGAGTTGGGCACC-TAGAAGGCCC-TAGAAGGTGGCTACCTGGAGCTTCTTAACAGCGATGCTGACCCC | 1.82% | -1 | Frameshift |
| CR002992 | GCAGCAGGCTGTGTGTGTGACATGGAAGGTGATGAAGA-------AGAAGGTGGCTACCTGGGG | 1.81% | -5 | Frameshift |
| CR002992 | CAGCAGGCTGTGTGTGTGACATGGAAGGTGATGAAGA-ACCAGGGAGGCTTATGCCAATATCGGTGAGGAAGCACCTGAGC | 6.68% | -2 | Frameshift |
| CR002992 | CAGCAGGCTGTGTGTGTGACATGGAAGGTGATGAAGA--GAGGCTTATGCCAATATCGGTGAGGAAGCACCTGAGC | 4.03% | -1 | Frameshift |
| CR002992 | CAGCAGGCTGTGTTGTGTGACATGGAAGG------------GAGGCTTATGCCAATATCGGTGAGGAAGCACCTGAGC | 3.82% | -16 | Frameshift |
| CR002992 | CAGCAGGCTGTGTGTGTGACATGGACATGGAAGG--------GCTTATGCCAATATCGGTGAGGAAGCACCTGAGC | 3.36% | -9 | In Frame |
| CR002992 | CAGCAGGCTGTGTGTGTGACATGGAAGG-------------------CTTATGCCAATATCGGTGAGGAAGCACCTGAGC | 3.06% | -20 | Frameshift |
| CR002992 | CAGCAGGCTGTGTGTGTGACATGGAAGG-CAGGGAGGAG-CAGGGAGGCTTATGCCAATATCGGTGAGGAAGCACCTGAGC | 2.59% | -2 | Frameshift |
| CR002992 | CAGCAGGCTGTGTGTGTGACATGGAAGG-------GGAAGGCTTATGCCAATATCGGTGAGGAAGCACCTGAGC | 2.19% | -7 | Frameshift |
| CR002992 | CAGCAGGCTGTGTGTGTGACA-----------------------GGAAGCACCTGAGC | 2.04% | -21 | Frameshift |
| CR002993 | CAGCAGGCTGTGTGTGTGACATGGAAGGTGA--------------------CCAGGGAGGCTTATGCCAATATCGGTGAGGAAGCACCTGAGC | 2.02% | -38 | Frameshift |
| CR002993 | AGCAGGCTGTTGTGTGTGACATGGAAGGTGATGAATGAA----CCAGGGAGGCTTATGCCAATATCGGTGAGGAAGCACCTGAGC | 2.01% | -4 | Frameshift |
| CR002993 | AGCAGGCTGTTGTGTGTGACATGGAAGGTGATGAAGAGTGATGAAGA-ACCAGGGAGGCTTATGCCAATATCGGTGAGGAAGCACCTGAGCC | 16.80% | -1 | Frameshift |
| CR002993 | AGCAGGCTGTTGTGTGTGACATGGAAGGTGATGAAGAaCCAGGGAGGCTTATGCCAATATCGGTGAGGAAGCACCTGAGCC | 8.07% | 1 | Frameshift |
| CR002993 | AGCAGGCTGTTGTGTGTGACATGGAAGGTGA--------------------GGAAGCACCTGAGC | 4.44% | -38 | Frameshift |
| CR002993 | AGCAGGCTGTTGTGTGTGACATGGAAGGTGATG-------CCAATATCGGTGAGGAAGCACCTGAGCC | 3.00% | -20 | In Frame |
| CR002993 | AGCAGGCTGTTGTGTGTGACATGGAAGGTGATGAAGAG-------GCTTATGCCAATATCGGTGAGGAAGCACCTGAGCC | 2.77% | -21 | In Frame |
| CR002993 | AGCAGGCTGTTGTGTGTGACATGGAAGGTGATGAAGG-------GAGGCTTATGCCAATATCGGTGAGGAAGCACCTGAGCC | 2.71% | -9 | In Frame |
| CR002993 | AGCAGGCTGTTGTGTGTGACATGGAAGGTGAAGG----------GAGGCTTATGCCAATATCGGTGAGGAAGCACCTGAGCC | 2.48% | -10 | Frameshift |
| CR002993 | AGCAGGCTGTGTGTGTGACATGGAAGGTGATGAAGG--CCAGGGAGGCTTATGCCAATATCGGTGAGGAAGCACCTGAGCC | 2.15% | -2 | Frameshift |
| CR002993 | AGCAGGCTGTGTGTGTGACATGGAAGATGAAG---GGAGGCTTATGCCAATATCGGTGAGGAAGCACCTGAGCC | 1.97% | -7 | Frameshift |
| CR002993 | AGCAGGCTGTGTTGTGTGACATGGAAGGTGATGAAG------GGAGGCTTATGCCAATATCGGTGAGGAAGCACCTGAGCC | 1.77% | -7 | Frameshift |
| CR003007 | TTTTTCTCAAAGTAGAGCACATAGGACCAGATGA--GAGTATGGAGATGGAGTATCGGTGAGAGTGAGAGTATGGAGCAGAAGAAGTTGGGCAGAAA | 46.65% | 1 | Frameshift |
| CR003007 | TTTTTCTCAAAGTAGAGCACATAGGACCAGATGA-TGATCGGTGAGAGTGA-TGATCGGTGAGAGTGAGAGTATGCCAGCAGAAGAAGTTGGGCAGAAA | 4.85% | 6 | In Frame |
| CR003007 | TTTTTCTCAAAGTAGAGCACATAGGACCAGATGA--CGGTGAGAGTGAGAGTATGCCAGCAGAAGAAGTTGGGCAGAAA | 2.52% | -2 | Frameshift |
| CR003007 | TTTTTCTCAAAGTAGAGCACATAGGACCAGATGA--TCGGTGAGAGTATGGAGAGTGAGAGTATGCCAGCAGAAGAAGTTGGGCAGAAA | 2.28% | -5 | Frameshift |
| CR003007 | TTTTTCTCAAAGTAGAGCACATAGGACCAGATGA-------GAGTATGGAGATGGAGTATCGGTGAGAGTGAGAGTATGCCAGCAGAAGAAGTTGGGCAGAAA | 2.18% | -12 | In Frame |
| CR003007 | TTTTTCTCAAAGTAGAGCACATAGGACCAGATGA--ATCGGTGAGAGTATGCCAGCAGAAGAAGTTGGGCAGAAA | 1.64% | -2 | Frameshift |
| CR003007 | TTTTTCTCAAAGTAGAGCACATAGGACCAGATGA--GATGATCGGTGAGAGTATCGGAGAGTATGCCAGCAGAAGAAGTTGGGCAGAAA | 1.42% | -1 | Frameshift |
| CR003007 | TTTTTCTCAAAGTAGAGCACATAGGACCAGATG---TGATCGGTGAGAGTATGCCAGCAGAAGAAGTTGGGCAGAAA | 1.38% | -3 | In Frame |
| CR003007 | TTTTTCTCAAAGTAGAGCACATAGGACCAGATGA----TGATCGGTGAGAGTATGCCAGCAGAAGAAGTTGGGCAGAAA | 1.09% | -4 | Frameshift |
| CR003007 | TTTTTCTCAAAGTAGAGCACATAGGACCAGATGA---GATCGGTGAGAGTATGGAGAGTATGCCAGCAGAAGAAGTTGGGCAGAAA | 0.99% | -3 | In Frame |

FIG. 44

%indels (frameshifts)

| | Triple 1 | Triple 2 | Triple 3 | Triple 4 |
|---|---|---|---|---|
| B2M locus * | 92.71 (39.46) | 84.51 (38.33) | 84.75 (39.20) | 94.94 (39.16) |
| TRAC locus | 83.11 (74.95) | 83.89 (77.08) | 94.82 (78.85) | 96.08 (77.97) |
| CIITA locus | 80.59 (80.87) | 96.44 (83.63) | 90.78 (80.79) | 58.89 (40.69) |

FIG. 47

*Frameshift calculation for this guide does not include edits that alter or remove the start codon, so is an underestimate of disruptions of the coding sequence

| Guide RNA | % indels (avg) | % frameshift edits (avg) |
|---|---|---|
| CR002100 | 91.11 | 73.28 |
| CR002097 | 90.89 | 81.82 |
| CR002091 | 89.72 | 68.92 |
| CR002086 | 81.52 | 67.04 |
| CR002085 | 85.33 | 64.22 |

| Guide-Treatment | Variant Read | Indel frequency (avg) | Indel length (avg) | Unique Concatenate (Call) |
|---|---|---|---|---|
| CR002100 | CCCCTCCCGCTGGCCCCGACTCACCGGTGAGTGCACCACGCAGGTCTGGCGCGCT | 27.04% | 1 | Frameshift |
| CR002100 | CCCCTCCCCGCTGGGCCCCGGA-TCACGGTGAGTGCACCACGCAGGTCTGGCGCGCT | 5.77% | -1 | Frameshift |
| CR002100 | CCCCTCCCCGCTGGGCCCCGAC--ACCGGTGAGTGCACCACGCAGGTCTGGCGCGCT | 3.92% | -2 | Frameshift |
| CR002100 | CCCCTCCCCGCTGGGCCCCG--TCACGGTGAGTGCACCACGCAGGTCTGGCGCGCT | 3.59% | -2 | Frameshift |
| CR002100 | CCCCTCCCCG-------------GTGTAGTGCACCACGCAGGTCTGGCGCGCT | 3.31% | -19 | Frameshift |
| CR002097 | CTGGGCCCCGACTCACGGGTGTAGTGCACCACGCAAGGTCTGGCGCGCTTGGGGAAGGT | 59.62% | 1 | Frameshift |
| CR002097 | CTGGGCCCCGACTCACGGTGTAGTGCACCACGCA--CTGGCGCGCTTGGGGAAGGT | 2.24% | -3 | In Frame |
| CR002097 | CTGGGCCCCGACTCACGGTGTAGTGCACCACGCA----TGGCGCGCTTGGGGAAGGT | 1.94% | -4 | Frameshift |
| CR002097 | CTGGGCCCCGACTCACGGTGTAGTGCACCACGCA-TCTGGCGCGCTTGGGGAAGGT | 1.86% | -2 | Frameshift |
| CR002097 | CTGGGCCCCGACTCACGGTGTAGTGCACCACGC--------------TTGGGAAGGT | 1.47% | -14 | Frameshift |
| CR002091 | CAGGTCTGGCGCGCTTGGGGAAGGTGGGCCCTGAG-AGACAGAGAAGGGCATGCTGAGC | 40.37% | -1 | Frameshift |
| CR002091 | CAGGTCTGGCGCGCTTGGGGAAGGTGCGGCCCTGAGGAGGACAGAGAAGAGACGGGCATGCTGAGC | 9.41% | 1 | Frameshift |
| CR002091 | CTGGTCTGGCGCGCTTGGCGCGCTTGGGGAAGGTGCGCCCTGAG--ACAGAGACAGGGCATGCTGAGC | 7.55% | -3 | In Frame |
| CR002091 | CAGGTCTGGCGCGCTTGGGGAAGGTGCGCCCTG-GGAGACAGAGAAGGGCATGCTGAGC | 4.87% | -1 | Frameshift |
| CR002091 | CAGGTCTGGCGCGCTTGGGGAAGGTGGGCCCTGA--CAGAGACAGGGCATGCTGAGC | 1.61% | -5 | Frameshift |
| CR002086 | GAGCCGGCGCGGCGCACTACTCACGGTCTCCTGGG-AGATGGTTTCCACCTGCACTCCCA | 28.55% | -1 | Frameshift |
| CR002086 | GAGCCGGCGCGGCGCACTACTCACGGTCTCACGGTCTCCTGGG--ATGGTTTCCACCTGCACTCCCA | 5.26% | -3 | In Frame |
| CR002086 | GAGCCGGCGCGGCGCACTACTCACGGTCTCCTGGG--AGATGGTTTCCACCTGCACTCCCA | 4.68% | -2 | Frameshift |
| CR002086 | GAGCCGGCGCGGCGCACTACTCACGGTCTCCTG-------------TGCACTCCCA | 4.21% | -25 | Frameshift |
| CR002085 | GAGCCGGCGCGGCGCACTACTCACGGTCTCCTG-------CACTCCCA | 3.91% | -19 | Frameshift |
| CR002085 | GGGAGATGGTTTCCACCTGCACTC-ATGCGCGGGGGACGCTGAGCGGCGGGGCGGGGCG | 31.48% | -1 | Frameshift |
| CR002085 | GGGAGATGGTTTCCACCTGCACTC--ATGCGCGGGGGACGCTGAGCGGCGGGGCGGGCG | 6.10% | -2 | Frameshift |
| CR002085 | GGGAGATGGTTTCCACCTGCACTCCATGCGCGGGGGACGCTGAGCGGCGGGGCGGGCG | 4.66% | 0 | In Frame |
| CR002085 | GGGAGATGGTTTCCACCTGCAC--CCATGGCGCGGGGGACGCTGAGCGGCGGGGCGGGCG | 4.62% | -2 | Frameshift |
| CR002085 | GGGAGATGGTTTCCACCTGCAC---CATGCGCGGGCGCCGACGCTGAGCGGCGGGGCGGGCG | 1.70% | -3 | In Frame |

| gRNA Targeting Domain ID | Target | Species | % CD3-negative cells (Mean) | SD |
|---|---|---|---|---|
| CR005334 | CD3 delta | Human | 98.8 | 0.4 |
| CR005335 | CD3 delta | Human | 3.2 | 0.3 |
| CR005336 | CD3 delta | Human | 4.3 | 0.4 |
| CR005337 | CD3 delta | Human | 13.1 | 0.7 |
| CR005338 | CD3 delta | Human | 2.8 | 0.3 |
| CR005339 | CD3 delta | Human | 19.4 | 2.1 |
| CR005340 | CD3 delta | Human | 1.9 | 0.1 |
| CR005341 | CD3 delta | Human | 5.0 | 0.6 |
| CR005342 | CD3 delta | Human | 6.5 | 1.0 |
| CR005343 | CD3 delta | Human | 2.5 | 0.5 |
| CR005344 | CD3 delta | Human | 23.2 | 1.0 |
| CR005345 | CD3 delta | Human | 71.9 | 2.1 |
| CR005346 | CD3 delta | Human | 3.1 | 0.6 |
| CR005347 | CD3 delta | Human | 30.6 | 2.2 |
| CR005348 | CD3 delta | Human | 6.3 | 0.8 |

FIG. 65

| gRNA Targeting Domain ID | Target | Species | % CD3-negative cells (Mean) | SD |
|---|---|---|---|---|
| CR005349 | CD3 gamma | Human | 3.1 | 0.4 |
| CR005350 | CD3 gamma | Human | 2.6 | 0.6 |
| CR005351 | CD3 gamma | Human | 9.8 | 0.3 |
| CR005352 | CD3 gamma | Human | 3.6 | 0.6 |
| CR005353 | CD3 gamma | Human | 2.3 | 0.1 |
| CR005354 | CD3 gamma | Human | 8.8 | 0.2 |
| CR005355 | CD3 gamma | Human | 2.7 | 0.6 |
| CR005356 | CD3 gamma | Human | 27.9 | 2.9 |
| CR005357 | CD3 gamma | Human | 2.6 | 0.5 |
| CR005358 | CD3 gamma | Human | 2.2 | 0.2 |
| CR005359 | CD3 gamma | Human | 3.0 | 0.4 |
| CR005360 | CD3 gamma | Human | 2.5 | 0.7 |
| CR005361 | CD3 gamma | Human | 2.5 | 0.5 |
| CR005362 | CD3 gamma | Human | 17.7 | 0.8 |
| CR005363 | CD3 gamma | Human | 11.9 | 0.7 |

FIG. 66

COMPOSITIONS AND METHODS FOR IMMUNOONCOLOGY

RELATED APPLICATIONS

This application is a U.S. National Phase filing of the International Application Serial No. PCT/IB2016/057318 filed Dec. 2, 2016, which claims priority to U.S. Provisional patent application No. 62/263,169, filed Dec. 4, 2015, U.S. Provisional patent application No. 62/316,784, filed Apr. 1, 2016, and U.S. Provisional patent application No. 62/394,290, filed Sep. 14, 2016. The entire contents of these applications are incorporated herein by reference.

BACKGROUND

CRISPRs (Clustered Regularly Interspaced Short Palindromic Repeats) evolved in bacteria as an adaptive immune system to defend against viral attack. Upon exposure to a virus, short segments of viral DNA are integrated into the CRISPR locus of the bacterial genome. RNA is transcribed from a portion of the CRISPR locus that includes the viral sequence. That RNA, which contains sequence complimentary to the viral genome, mediates targeting of a Cas9 protein to the sequence in the viral genome. The Cas9 protein cleaves and thereby silences the viral target.

Recently, the CRISPR/Cas system has been adapted for genome editing in eukaryotic cells. The introduction of site-specific single (SSBs) or double strand breaks (DSBs) allows for target sequence alteration through, for example, non-homologous end-joining (NHEJ) or homology-directed repair (HDR).

SUMMARY OF THE INVENTION

The inventions described herein relate to compositions and methods for immunooncology, for example, cells modified at specific target sequences in their genome, including as modified by introduction of CRISPR systems that include gRNA molecules which target said target sequences, and methods of making and using therefore. For example, the present disclosure relates to gRNA molecules, CRISPR systems, cells, and methods useful for genome editing of cells, e.g., T cells, e.g., T-cells further engineered to express a chimeric antigen receptor, and useful for treating diseases such as cancers.

In a first aspect, the invention provides a gRNA molecule including a tracr and crRNA, wherein the crRNA includes a targeting domain that is complementary with a target sequence of an allogeneic T-cell target selected from B2M, CD247, CD3D, CD3E, CD3G, TRAC, TRBC1, TRBC2, HLA-A, HLA-B, HLA-C, DCK, CD52, FKBP1A, CIITA, NLRC5, RFXANK, RFX5, RFXAP, or NR3C1.

In embodiments of the gRNA molecule:
2(a) the allogeneic T-cell target is B2M, and the targeting domain includes any one of SEQ ID NO: 1 to SEQ ID NO: 83 or SEQ ID NO: 5492 to SEQ ID NO: 5527;
2(b) the allogeneic T-cell target is TRAC, and the targeting domain includes any one of SEQ ID NO: 5528 to SEQ ID NO: 5623 or SEQ ID NO: 5816 to SEQ ID NO: 5965;
2(c) the allogeneic T-cell target is TRBC1, and the targeting domain includes any one of SEQ ID NO: 5624 to SEQ ID NO: 5643 or SEQ ID NO: 5966 to SEQ ID NO: 6097;
2(d) the allogeneic T-cell target is TRBC2, and the targeting domain includes any one of SEQ ID NO: 5644 to SEQ ID NO: 5719 or SEQ ID NO: 6098 to SEQ ID NO: 6226;
2(e) the allogeneic T-cell target is CD247, and the targeting domain includes any one of SEQ ID NO: 84 to SEQ ID NO: 392;
2(f) the allogeneic T-cell target is CD3D, and the targeting domain includes any one of SEQ ID NO: 393 to SEQ ID NO: 532 or SEQ ID NO: 10780 to SEQ ID NO: 10794;
2(g) the allogeneic T-cell target is CD3E, and the targeting domain includes any one of SEQ ID NO: 533 to SEQ ID NO: 839 or SEQ ID NO: 10677 to SEQ ID NO: 10764;
2(h) the allogeneic T-cell target is CD3G, and the targeting domain includes any one of SEQ ID NO: 840 to SEQ ID NO: 968 or SEQ ID NO: 10765 to SEQ ID NO: 10779;
2(i) the allogeneic T-cell target is HLA-A, and the targeting domain includes any one of SEQ ID NO: 969 to SEQ ID NO: 1345;
2(j) the allogeneic T-cell target is MLA-B, and the targeting domain includes any one of SEQ ID NO: 1346 to SEQ ID NO: 1698;
2(k) the allogeneic T-cell target is HLA-C, and the targeting domain includes any one of SEQ ID NO: 1699 to SEQ ID NO: 2068;
2(l) the allogeneic T-cell target is DCK, and the targeting domain includes any one of SEQ ID NO: 5278 to SEQ ID NO: 5491;
2(m) the allogeneic T-cell target is CD52, and the targeting domain includes any one of SEQ ID NO: 6227 to SEQ ID NO: 6324;
2(n) the allogeneic T-cell target is FKBP1A, and the targeting domain includes any one of SEQ ID NO: 6325 to SEQ ID NO: 6583 or SEQ ID NO: 6662 to SEQ ID NO: 6749;
2(o) the allogeneic T-cell target is NR3C1, and the targeting domain includes any one of SEQ ID NO: 2069 to SEQ ID NO: 2941;
2(p) the allogeneic T-cell target is CIITA, and the targeting domain includes any one of SEQ ID NO: 6750 to SEQ ID NO: 7716 or SEQ ID NO: 7717 to SEQ ID NO: 7804; or
2(q) the allogeneic T-cell target is NLRC5, and the targeting domain includes any one of SEQ ID NO: 8622 to SEQ ID NO: 10089.

In embodiments of the gRNA molecule, the allogeneic T-cell target is TRAC, and the targeting domain includes SEQ ID NO: 5569, SEQ ID NO: 5585, SEQ ID NO: 5587, SEQ ID NO: 5592, SEQ ID NO: 5601, SEQ ID NO: 5589, SEQ ID NO: 5600, SEQ ID NO: 5594, SEQ ID NO: 5571, SEQ ID NO: 5593, SEQ ID NO: 5574, SEQ ID NO: 5598, SEQ ID NO: 5586, SEQ ID NO: 5599, SEQ ID NO: 5591, SEQ ID NO: 5610, SEQ ID NO: 5608, SEQ ID NO: 5617, SEQ ID NO: 5619, or SEQ ID NO: 5620, for example, the targeting domain includes SEQ ID NO: 5569, SEQ ID NO: 5586, SEQ ID NO: 5587, SEQ ID NO: 5592, SEQ ID NO: 5599, or SEQ ID NO: 5600, for example, targeting domain includes SEQ ID NO: 5569, SEQ ID NO: 5587, SEQ ID NO: 5592 or SEQ ID NO: 5586, for example, the targeting domain includes SEQ ID NO: 5569.

In embodiments of the gRNA molecule, the allogeneic T-cell target is TRBC2, and the targeting domain includes SEQ ID NO: 5719, SEQ ID NO: 5694, SEQ ID NO: 5706, SEQ ID NO: 5696, SEQ ID NO: 5711, SEQ ID NO: 5708, SEQ ID NO: 5709, SEQ ID NO: 5712, SEQ ID NO: 5703, SEQ ID NO: 5707, SEQ ID NO: 5687, SEQ ID NO: 5705, SEQ ID NO: 5713, SEQ ID NO: 5715, or SEQ ID NO: 5710.

In embodiments of the gRNA molecule, the allogeneic T-cell target is B2M, and the targeting domain includes SEQ ID NO: 5519, SEQ ID NO: 5497, SEQ ID NO: 5499, SEQ ID NO: 5498, SEQ ID NO: 5503, SEQ ID NO: 5496, SEQ ID NO: 5507, SEQ ID NO: 5515, SEQ ID NO: 5493, SEQ ID NO: 5506, SEQ ID NO: 5509, SEQ ID NO: 5517, SEQ ID NO: 5521, SEQ ID NO: 5520, SEQ ID NO: 5500, SEQ ID NO: 5494, SEQ ID NO: 5508, SEQ ID NO: 5514, or SEQ ID NO: 5492, for example, the targeting domain includes SEQ ID NO: 5496, SEQ ID NO: 5498, or SEQ ID NO: 5509.

In embodiments of the gRNA molecule, the allogeneic T-cell target is CIITA, and the targeting domain includes SEQ ID NO: 7771, SEQ ID NO: 7769, SEQ ID NO: 7773, SEQ ID NO: 7726, SEQ ID NO: 7758, SEQ ID NO: 7739, SEQ ID NO: 7779, SEQ ID NO: 7770, SEQ ID NO: 7749, SEQ ID NO: 7754, SEQ ID NO: 7745, SEQ ID NO: 7785, SEQ ID NO: 7731, SEQ ID NO: 7772, SEQ ID NO: 7743, or SEQ ID NO: 7750, for example, the targeting domain includes SEQ ID NO: 7769, SEQ ID NO: 7771, SEQ ID NO: 7739, or SEQ ID NO: 7785.

In embodiments of the gRNA molecule, the allogeneic T-cell target is CD3E, and the targeting domain includes SEQ ID NO: 10729, SEQ ID NO: 10719, SEQ ID NO: 10764, SEQ ID NO: 10789, SEQ ID NO: 10701, SEQ ID NO: 10700, or SEQ ID NO: 10722.

In embodiments of the gRNA molecule, the allogeneic T-cell target is FKBP1A, and the targeting domain includes SEQ ID NO: 6693, SEQ ID NO: 6705, SEQ ID NO: 6694, SEQ ID NO: 6708, or SEQ ID NO: 6699.

In a second aspect, the invention provides a gRNA molecule including a tracr and crRNA, wherein the crRNA includes a targeting domain that is complementary with a target sequence of an inhibitory molecule or downstream effector of signaling through an inhibitory molecule selected from CD274, HAVCR2, LAG3, PDCD1, PD-L2, CTLA4, CEACAM (e.g., CEACAM-1, CEACAM-3 and/or CEACAM-5), VISTA, BTLA, TIGIT, LAIR1, CD160, 2B4, CD80, CD86, B7-H3 (CD113), B7-H4 (VTCN1), HVEM (TNERSF14 or CD107), K1R, A2aR, MHC class I, MHC class II, GAL9, adenosine, and TGF beta, or PTPN11.

In embodiments of the gRNA molecule:
15(a) the inhibitory molecule is CD274 (PD-L1), and the targeting domain includes any one of SEQ ID NO: 2942 to SEQ ID NO: 3270;
15(b) the inhibitory molecule is HAVCR2 (TIM3), and the targeting domain includes any one of SEQ ID NO: 3271 to SEQ ID NO: 3541;
15(c) the inhibitory molecule is LAG3, and the targeting domain includes any one of SEQ ID NO: 3542 to SEQ ID NO: 4032;
15(d) the inhibitory molecule is PDCD1 (PD-1), and the targeting domain includes any one of SEQ ID NO: 4033 to SEQ ID NO: 4589 or SEQ ID NO: 5720 to SEQ ID NO: 5815; or
15(e) the downstream effector of signaling through an inhibitory molecule is PTPN1, and the targeting domain includes any one of SEQ ID NO: 4590 to SEQ ID NO: 5277.

In embodiments of the gRNA molecule, the inhibitory molecule is PDCD1, and the targeting domain includes SEQ ID NO: 5743, SEQ ID NO: 5798, SEQ ID NO: 5748, SEQ ID NO: 5722, SEQ ID NO: 5800, SEQ ID NO: 5735, SEQ ID NO: 5724, SEQ ID NO: 5731, SEQ ID NO: 5725, SEQ ID NO: 5775, SEQ ID NO: 5766, SEQ ID NO: 5727, SEQ ID NO: 5744, SEQ ID NO: 5751, or SEQ ID NO: 5734, for example, the targeting domain includes SEQ ID NO: 5775.

In embodiments of the gRNA molecule, including in any of the aforementioned aspects and embodiments, the targeting domain includes 17, 18, 19, 20, 21 (if present in the reference sequence), 22 (if present in the reference sequence), 23 (if present in the reference sequence), 24 (if present in the reference sequence), or 25 (if present in the reference sequence) consecutive nucleic acids of any one of the recited targeting domain sequences. In other embodiments of the gRNA molecule, including in any of the aforementioned aspects and embodiments, the targeting domain consists of 17, 18, 19, 20, 21 (if present in the reference sequence), 22 (if present in the reference sequence), 23 (if present in the reference sequence), or 24 (if present in the reference sequence), or 25 (if present in the reference sequence) consecutive nucleic acids of any one of the recited targeting domain sequences. In embodiments of the gRNA molecule, including in any of the aforementioned aspects and embodiments, the 17, 18, 19, 20, 21 (if present in the reference sequence), 22 (if present in the reference sequence), 23 (if present in the reference sequence), or 24 (if present in the reference sequence), or 25 (if present in the reference sequence) consecutive nucleic acids of any one of the recited targeting domain sequences are the 17, 18, 19, 20, 21 (if present in the reference sequence), 22 (if present in the reference sequence), 23 (if present in the reference sequence), or 24 (if present in the reference sequence), or 25 (if present in the reference sequence) consecutive nucleic acids disposed at the 3' end of the recited targeting domain sequence. In other embodiments of the gRNA molecule, including in any of the aforementioned aspects and embodiments, the 17, 18, 19, 20, 21 (if present in the reference sequence), 22 (if present in the reference sequence), 23 (if present in the reference sequence), or 24 (if present in the reference sequence), or 25 (if present in the reference sequence) consecutive nucleic acids of any one of the recited targeting domain sequences are the 17, 18, 19, 20, 21 (if present in the reference sequence), 22 (if present in the reference sequence), 23 (if present in the reference sequence), or 24 (if present in the reference sequence), or 25 (if present in the reference sequence) consecutive nucleic acids disposed at the 5' end of the recited targeting domain sequence. In other embodiments of the gRNA molecule, including in any of the aforementioned aspects and embodiments, the 17, 18, 19, 20, 21 (if present in the reference sequence), 22 (if present in the reference sequence), 23 (if present in the reference sequence), or 24 (if present in the reference sequence), or 25 (if present in the reference sequence) consecutive nucleic acids of any one of the recited targeting domain sequences do not include either the 5' or 3' nucleic acid of the recited targeting domain sequence.

In embodiments of the gRNA molecule, including in any of the aforementioned aspects and embodiments, the targeting domain consists of the recited targeting domain sequence.

The following general aspects of the gRNA molecule may be combined, alone or in combination, with any of the gRNAs comprising a targeting domain described herein, for example, a targeting domain recited in any of the aforementioned aspects and embodiments.

In embodiments of the gRNA molecule, including in any of the aforementioned aspects and embodiments, a portion of the crRNA and a portion of the tracr hybridize to form a flagpole including SEQ ID NO: 6584 or SEQ ID NO: 6585. In other embodiments, the flagpole further includes a first flagpole extension, located 3' to the crRNA portion of the flagpole, wherein said first flagpole extension includes SEQ ID NO: 6586. In other embodiments, the flagpole further includes a second flagpole extension located 3' to the crRNA portion of the flagpole and, if present, the first flagpole extension, wherein said second flagpole extension includes SEQ ID NO: 6587.

In embodiments of the gRNA molecule, including in any of the aforementioned aspects and embodiments, the tracr includes, for example, consists of:
  (a) SEQ ID NO: 7820, optionally further including, at the 3' end, an additional 1, 2, 3, 4, 5, 6, or 7 uracil (U) nucleotides;
  (b) SEQ ID NO: 6660; or
  (c) SEQ ID NO: 6661. In such embodiments, the crRNA portion of the flagpole includes SEQ ID NO: 6607 or SEQ ID NO: 6608.

In embodiments of the gRNA molecule, including in any of the aforementioned aspects and embodiments, the tracr includes SEQ ID NO: 6589 or SEQ ID NO: 6590, and optionally, if a first flagpole extension is present, a first tracr extension, disposed 5' to SEQ ID NO: 6589 or SEQ ID NO: 6590, said first tracr extension including SEQ ID NO: 6591.

In embodiments of the gRNA molecule, including in any of the aforementioned aspects and embodiments, the targeting domain and the tracr are disposed on separate nucleic acid molecules.

In embodiments of the gRNA molecule, including in any of the aforementioned aspects and embodiments, the crRNA includes (for example, consists of), from 5' to 3', [targeting domain]—:
  a) SEQ ID NO: 6584;
  b) SEQ ID NO: 6585;
  c) SEQ ID NO: 6605;
  d) SEQ ID NO: 6606;
  e) SEQ ID NO: 6607;
  f) SEQ ID NO: 6608; or
  g) SEQ ID NO: 7806.

In embodiments of the gRNA molecule, including in any of the aforementioned aspects and embodiments, the tracr includes (for example, consists of), from 5' to 3':
  a) SEQ ID NO: 6589;
  b) SEQ ID NO: 6590;
  c) SEQ ID NO: 6609;
  d) SEQ ID NO: 6610;
  e) SEQ ID NO: 6660;
  f) SEQ ID NO: 6661;
  g) SEQ ID NO: 7820;
  h) SEQ ID NO: 7807;
  i) SEQ ID NO: 7808;
  j) SEQ ID NO: 7809;
  k) any of a) to j), above, further including, at the 3' end, at least 1, 2, 3, 4, 5, 6 or 7 uracil (U) nucleotides, e.g., 1, 2, 3, 4, 5, 6, or 7 uracil (U) nucleotides;
  l) any of a) to k), above, further including, at the 3' end, at least 1, 2, 3, 4, 5, 6 or 7 adenine (A) nucleotides, e.g., 1, 2, 3, 4, 5, 6, or 7 adenine (A) nucleotides; or
  m) any of a) to l), above, further including, at the 5' end (e.g., at the 5' terminus), at least 1, 2, 3, 4, 5, 6 or 7 adenine (A) nucleotides, e.g., 1, 2, 3, 4, 5, 6, or 7 adenine (A) nucleotides.

In preferred embodiments of the gRNA molecule, including in any of the aforementioned aspects and embodiments, the targeting domain and the tracr are disposed on separate nucleic acid molecules, and the nucleic acid molecule including the targeting domain includes SEQ ID NO: 6607, optionally disposed immediately 3' to the targeting domain, and the nucleic acid molecule including the tracr includes, e.g., consists of, SEQ ID NO: 6660.

In other embodiments of the gRNA molecule, including in any of the aforementioned aspects and embodiments, the targeting domain and the tracr are disposed on a single nucleic acid molecule, and wherein the tracr is disposed 3' to the targeting domain. In such embodiments of the gRNA molecule, including in any of the aforementioned aspects and embodiments, the gRNA molecule further includes a loop, disposed 3' to the targeting domain and 5' to the tracr, for example, a loop that includes (for example, consists of) SEQ ID NO: 6588.

In embodiments of the gRNA molecule, including in any of the aforementioned aspects and embodiments, the gRNA molecule includes (for example, consists of), from 5' to 3', [targeting domain]—:
  (a) SEQ ID NO: 6601;
  (b) SEQ ID NO: 6602;
  (c) SEQ ID NO: 6603;
  (d) SEQ ID NO: 6604;
  (e) SEQ ID NO: 7811; or
  (f) any of (a) to (e), above, further including, at the 3' end, 1, 2, 3, 4, 5, 6 or 7 uracil (U) nucleotides.

In preferred embodiments of the gRNA molecule, including in any of the aforementioned aspects and embodiments, the targeting domain and the tracr are disposed on a single nucleic acid molecule, and wherein said nucleic acid molecule includes, e.g., consists of, said targeting domain and SEQ ID NO: 6601, optionally disposed immediately 3' to said targeting domain.

In preferred embodiments of the gRNA molecule, including in any of the aforementioned aspects and embodiments, the targeting domain and the tracr are disposed on a single nucleic acid molecule, and wherein said nucleic acid molecule includes, e.g., consists of, said targeting domain and SEQ ID NO: 7811, optionally disposed immediately 3' to said targeting domain.

In embodiments, the gRNA molecule consists of unmodified RNA nucleotides and nucleic acid bonds. In other embodiments, the gRNA molecule contains one or more modifications, for example as described herein. In embodiments of the gRNA molecule, including in any of the aforementioned aspects and embodiments, one, or optionally more than one, of the nucleic acid molecules of the gRNA molecule includes:
  a) a, e.g., three, phosphorothioate modification(s) at the 3' end of said nucleic acid molecule or molecules;
  b) a, e.g., three, phosphorothioate modification(s) at the 5' end of said nucleic acid molecule or molecules;
  c) a, e.g., three, 2'-O-methyl modification(s) at the 3' end of said nucleic acid molecule or molecules;
  d) a, e.g., three, 2'-O-methyl modification(s) at the 5' end of said nucleic acid molecule or molecules;
  e) a 2' O-methyl modification at each of the $4^{th}$-to-terminal, $3^{rd}$-to-terminal, and $2^{nd}$-to-terminal 3' residues of said nucleic acid molecule or molecules; or
  f) any combination thereof.

In embodiments of the gRNA molecule, including in any of the aforementioned aspects and embodiments, when a CRISPR system (e.g., an RNP as described herein, e.g., an RNP that includes a Cas9 molecule, for example as described herein) including the gRNA molecule (e.g., as described herein) is introduced into a cell, an indel is formed at or near the target sequence complementary to the targeting domain of the gRNA molecule. In embodiments, the indel is a frameshift mutation. In embodiments, the indel is an indel listed in any of FIG. 34A, FIG. 34B, FIG. 36, FIG. 38, FIG. 41, FIG. 44, FIG. 48, FIG. 49, FIG. 50 or FIG. 53.

In embodiments of the gRNA molecule, including in any of the aforementioned aspects and embodiments, when a CRISPR system (e.g., an RNP as described herein, e.g., an RNP that includes a Cas9 molecule, for example as described herein) including the gRNA molecule (e.g., as described herein) is introduced into a population of cells, an indel is formed at or near the target sequence complementary to the targeting domain of the gRNA molecule in at least about 40%, e.g., at least about 50%, e.g., at least about 60%, e.g., at least about 70%, e.g., at least about 80%, e.g., at least about 90%, e.g., at least about 95%, e.g., at least about 96%, e.g., at least about 97%, e.g., at least about 98%, e.g., at least about 99%, of the cells of the population. In embodiments, an indel that is a frameshift mutation is formed at or near the target sequence complementary to the targeting domain of the gRNA molecule in at least about 20%, e.g., at least about 30%, e.g., at least about 35%, e.g., at least about 40%, e.g., at least about 45%, e.g., at least about 50%, e.g., at least about 55%, e.g., at least about 60%, e.g., at least about 65%, e.g., at least about 70%, e.g., at least about 75%, e.g., at least about 80%, e.g., at least about 85%, e.g., at least about 90%, e.g., at least about 95%, e.g., at least about 99%, of the cells of the population. In embodiments, in at least about 30%, e.g., least about 40%, e.g., at least about 50%, e.g., at least about 60%, e.g., at least about 70%, e.g., at least about 80%, e.g., at least about 90%, e.g., at least about 95%, e.g., at least about 96%, e.g., at least about 97%, e.g., at least about 98%, e.g., at least about 99%, of the cells of the population, the indel is an indel listed in any of FIG. 34A, FIG. 34B, FIG. 36, FIG. 38, FIG. 41, FIG. 44, FIG. 48, FIG. 49, FIG. 50 or FIG. 53. In embodiments, the five most frequently detected indels in said population of cells include three or more, e.g., four, e.g., five, of the indels associated with any gRNA listed in any of FIG. 34A, FIG. 34B, FIG. 36, FIG. 38, FIG. 41, FIG. 44, FIG. 48, FIG. 49, FIG. 50 or FIG. 53. The indel or indel pattern is as measured and/or quantitated by, for example, next generation sequencing (NGS).

In embodiments of the gRNA molecule, including in any of the aforementioned aspects and embodiments, when a CRISPR system (e.g., an RNP as described herein, e.g., an RNP that includes a Cas9 molecule, for example as described herein) including the gRNA molecule (e.g., as described herein) is introduced into a cell (or population of cells) as described herein, expression of the gene including the target sequence complementary to the targeting domain of the gRNA molecule is reduced or eliminated in said cell. In embodiments, expression of said gene is reduced or eliminated in at least about 40%, e.g., at least about 50%, e.g., at least about 60%, e.g., at least about 70%, e.g., at least about 80%, e.g., at least about 90%, e.g., at least about 95%, e.g., at least about 96%, e.g., at least about 97%, e.g., at least about 98%, e.g., at least about 99%, of the cells of the population. In embodiments, the reduced or eliminated expression is measured by flow cytometry. In other embodiments, for example, in the case of FKBP1A, reduced or eliminated expression is measured by a functional assay, for example as described herein.

In embodiments of the gRNA molecule, including in any of the aforementioned aspects and embodiments, when a CRISPR system (e.g., an RNP as described herein, e.g., an RNP that includes a Cas9 molecule, for example as described herein) including the gRNA molecule (e.g., as described herein) is introduced into a cell as described herein, no off-target indels are formed in said cell, e.g., as detectable by next generation sequencing and/or a nucleotide insertional assay, for example as described herein.

In embodiments of the gRNA molecule, including in any of the aforementioned aspects and embodiments, when a CRISPR system (e.g., an RNP as described herein, e.g., an RNP that includes a Cas9 molecule, for example as described herein) including the gRNA molecule (e.g., as described herein) is introduced into a population of cells as described herein, an off-target indel is detected in no more than about 5%, e.g., no more than about 1%, e.g., no more than about 0.1%, e.g., no more than about 0.01%, of the cells of the population of cells e.g., as detectable by next generation sequencing and/or a nucleotide insertional assay.

In any of the aforementioned aspects and embodiments reciting a cell, the cell is (or population of cells includes) a mammalian, primate, or human cell, e.g., is a human cell. In any of the aforementioned aspects and embodiments reciting a cell, the cell is (or population of cells includes) an immune effector cell, for example, a T cell or NK cell, e.g., is a T cell, for example, a CD4+ T cell, a CD8+ T cell, or a combination thereof.

In any of the aforementioned aspects and embodiments reciting a cell, the cell (or population of cells) has been, or will be, engineered to express a chimeric antigen receptor (CAR). In embodiments, the CAR is:
(a) a CD19 CAR; or
(b) a BCMA CAR. In embodiments:
(a) the CAR is a CD19 CAR including an antigen binding domain including any one of SEQ ID NO: 7883 to SEQ ID NO: 7898;
(b) the CAR is a CD19 CAR including SEQ ID NO: 7909 or SEQ ID NO: 7920;
(c) the CAR is a BCMA CAR including an antigen binding domain including any one of SEQ ID NO: 7939 to SEQ ID NO: 8112, e.g., including an antigen binding domain of SEQ ID NO: 7949; or
(d) the CAR is a BCMA CAR including any one of SEQ ID NO: 8549 to SEQ ID NO: 8621, e.g., including SEQ ID NO: 8559.

In any of the aforementioned aspects and embodiments reciting a cell, the cell is allogeneic with respect to a patient to be administered said cell. In other embodiments, the cell is autologous with respect to a patient to be administered said cell.

In another aspect, the invention provides a composition including a first gRNA molecule of any of the previous aspects and embodiments, further including a Cas9 molecule. In embodiments, the Cas9 molecule includes, e.g., consists of, any one of SEQ ID NO: 6611 or SEQ ID NO: 7821 to SEQ ID NO: 7831. In embodiments, the Cas9 molecule is an active or inactive *S. pyogenes* Cas9. In preferred embodiments, the first gRNA molecule and Cas9 molecule are present in a ribonuclear protein complex (RNP).

In aspects, the composition may include more than one gRNA molecule, for example, more than one gRNA molecule, each of which is complexed with a Cas9 molecule described herein. For example, in embodiments, the composition further includes a second gRNA molecule; a second gRNA molecule and a third gRNA molecule; or a second gRNA molecule, a third gRNA molecule, and a fourth gRNA molecule, wherein the second gRNA molecule, the third gRNA molecule (if present), and the fourth gRNA molecule (if present) are a gRNA molecule as described herein, for example, a gRNA molecule of any of the previous aspects and embodiments, and wherein each gRNA molecule of the composition is complementary to a different target sequence (i.e., comprises a different targeting domain). In embodiments, the first gRNA molecule, the second gRNA molecule, the third gRNA molecule (if present), and the fourth gRNA molecule (if present) are complementary to target sequences within the same gene. In such embodiments, the first gRNA molecule, the second gRNA molecule, the third gRNA molecule (if present), and the fourth gRNA molecule (if present) are complementary to target sequences not more than 20000 nucleotides, not more than 10000 nucleotides, not more than 6000, not more than 5000 nucleotides, not more than 4000, not more than 1000 nucleotides, not more than 500 nucleotides, not more than 400 nucleotides, not more than 300 nucleotides, not more than 200 nucleotides, not more than 100 nucleotides, not more than 90 nucleotides, not more than 80 nucleotides, not more than 70 nucleotides, not more than 60 nucleotides, not more than 50 nucleotides, not more than 40 nucleotides, not more than 30 nucleotides, not more than 20 nucleotides or not more than 10 nucleotides apart. In other embodiments the first gRNA molecule, the second gRNA molecule, the third gRNA molecule (if present), and the fourth gRNA molecule (if present) are complementary to target sequence within different genes or loci, for example, different genes as described herein.

In embodiments, the first gRNA molecule is the gRNA molecule of any of 2(b), 2(c), 2(d), 2(d), 2(e), 2(f), 2(g) or 2(h); and the second gRNA molecule is the gRNA molecule of any of 2(a), 2(i), 2(j), 2(k) or 2(q); and the third gRNA molecule is the gRNA molecule of any of 15(a), 15(b), 15(c), 15(d), or 15(e). In other embodiments, the first gRNA molecule is the gRNA molecule of any of 2(b), 2(c), 2(d), 2(d), 2(e), 2(f), 2(g) or 2(h); and the second gRNA molecule is the gRNA molecule of any of 2(l), 2(m), 2(n), or 2(o); and the third gRNA molecule is the gRNA molecule of any of 15(a), 15(b), 15(c), 15(d), or 15(e). In other embodiments, the first gRNA molecule is the gRNA molecule of any of 2(b), 2(c), 2(d), 2(d), 2(e), 2(f), 2(g) or 2(h); and the second gRNA molecule is the gRNA molecule of any of 2(l), 2(m), 2(n), or 2(o). In other embodiments, the first gRNA molecule is the gRNA molecule of any of 2(b), 2(c), 2(d), 2(d), 2(e), 2(f), 2(g) or 2(h); and the second gRNA molecule is the gRNA molecule of any of 2(a), 2(i), 2(j), or 2(k). In other embodiments, the first gRNA molecule is the gRNA molecule of any of 2(b), 2(c), 2(d), 2(d), 2(e), 2(f), 2(g) or 2(h); and the second gRNA molecule is the gRNA molecule of any of 15(a), 15(b), 15(c), 15(d), or 15(e). In other embodiments, first gRNA molecule is the gRNA molecule of any of 15(a), 15(b), 15(c), 15(d), or 7(e); and the second gRNA molecule is the gRNA molecule of any of 15(a), 15(b), 15(c), 15(d), or 15(e). In embodiments of any of the aforementioned embodiments, a third gRNA is present, and the third gRNA molecule is a gRNA molecule of any of 15(a), 15(b), 15(c), 15(d), or 15(e). In embodiments, the composition consists of two gRNA molecules of any of the aforementioned gRNA molecule aspects and embodiments. In embodiments, the composition consists of three gRNA molecules of any of the aforementioned gRNA molecule aspects and embodiments. In embodiments, the composition consists of a first gRNA molecule of any of the aforementioned aspects and embodiments, wherein the targeting domain of said first gRNA molecule is a targeting domain of any of 2(a), 2(i), 2(j), or 2(k); and a second gRNA molecule of any of the aforementioned gRNA molecule aspects and embodiments, wherein the targeting domain of said second gRNA molecule is a targeting domain of any of 2(b), 2(c), 2(d), 2(f), 2(g), 2(h), or 2(i).

In embodiments, the composition includes two gRNA molecules, and the targeting domain of said first gRNA molecule includes, for example, consists of, SEQ ID NO: 5519, SEQ ID NO: 5497, SEQ ID NO: 5499, SEQ ID NO: 5498, SEQ ID NO: 5503, SEQ ID NO: 5496, SEQ ID NO: 5507, SEQ ID NO: 5515, SEQ ID NO: 5493, SEQ ID NO: 5506, SEQ ID NO: 5509, SEQ ID NO: 5517, SEQ ID NO: 5521, SEQ ID NO: 5520, SEQ ID NO: 5500, SEQ ID NO: 5494, SEQ ID NO: 5508, SEQ ID NO: 5514, or SEQ ID NO: 5492; and the targeting domain of said second gRNA molecule includes, for example, consists of, SEQ ID NO: 5569, SEQ ID NO: 5585, SEQ ID NO: 5587, SEQ ID NO: 5592, SEQ ID NO: 5601, SEQ ID NO: 5589, SEQ ID NO: 5600, SEQ ID NO: 5594, SEQ ID NO: 5571, SEQ ID NO: 5593, SEQ ID NO: 5574, SEQ ID NO: 5598, SEQ ID NO: 5586, SEQ ID NO: 5599, SEQ ID NO: 5591, SEQ ID NO: 5610, SEQ ID NO: 5608, SEQ ID NO: 5617, SEQ ID NO: 5619, or SEQ ID NO: 5620.

In embodiments, the composition includes two gRNA molecules, and the targeting domain of said first gRNA molecule includes, for example, consists of, SEQ ID NO: 5496, SEQ ID NO: 5498, or SEQ ID NO: 5509; and the targeting domain of said second gRNA molecule includes, for example, consists of, SEQ ID NO: 5569, SEQ ID NO: 5586, SEQ ID NO: 5587, SEQ ID NO: 5592, SEQ ID NO: 5599, or SEQ ID NO: 5600.

In embodiments, the composition includes two gRNA molecules, and the targeting domain of said first gRNA molecule includes, for example, consists of, SEQ ID NO: 5496, SEQ ID NO: 5498, or SEQ ID NO: 5509; and the targeting domain of said second gRNA molecule includes, for example, consists of, SEQ ID NO: 5569.

In embodiments, the composition includes two gRNA molecules, and the targeting domain of said first gRNA molecule includes, for example, consists of, SEQ ID NO: 5496, SEQ ID NO: 5498, or SEQ ID NO: 5509; and the targeting domain of said second gRNA molecule includes, for example, consists of, SEQ ID NO: 10729, SEQ ID NO: 10719, SEQ ID NO: 10764, SEQ ID NO: 10789, SEQ ID NO: 10701, SEQ ID NO: 10700, or SEQ ID NO: 10722.

In embodiments, including in any of the aforementioned aspects and embodiments, the composition further includes a third gRNA molecule described herein, for example, in any of the aforementioned gRNA molecule aspects and embodiments, wherein the targeting domain of said third gRNA molecule is a targeting domain of any of 2(n) or 2(q). In embodiments, the targeting domain of said third gRNA molecule includes, for example, consists of, SEQ ID NO: 7771, SEQ ID NO: 7769, SEQ ID NO: 7773, SEQ ID NO: 7726, SEQ ID NO: 7758, SEQ ID NO: 7739, SEQ ID NO: 7779, SEQ ID NO: 7770, SEQ ID NO: 7749, SEQ ID NO: 7754, SEQ ID NO: 7745, SEQ ID NO: 7785, SEQ ID NO: 7731, SEQ ID NO: 7772, SEQ ID NO: 7743, or SEQ ID NO: 7750; for example, includes (for example consists of) SEQ ID NO: 7769, SEQ ID NO: 7771, SEQ ID NO: 7739, or SEQ ID NO: 7785.

In embodiments, including in any of the aforementioned aspects and embodiments, the composition further includes a fourth gRNA molecule described herein, for example, in any of the aforementioned gRNA molecule aspects and embodiments, wherein the targeting domain of said fourth gRNA molecule is complementary to a target sequence of a target of an NK inhibitory molecule, for example, LILRB1. In embodiments, the targeting domain of said fourth gRNA molecule includes, e.g., consists of:

a) any one of SEQ ID NO: 10090 to SEQ ID NO: 10673;
b) 17, 18, 19, 20, 21, 22, 23, or 24 consecutive nucleotides, preferably 20 consecutive nucleotides, of any one of SEQ ID NO: 10090 to SEQ ID NO: 10673.
c) The 5' 17, 18, 19, 20, 21, 22, 23 or 24 nucleotides, preferably 20 nucleotides, of any one of SEQ ID NO: 10090 to SEQ ID NO: 10673; or
d) The 3' 17, 18, 19, 20, 21, 22, 23 or 24 nucleotides, preferably 20 nucleotides, of any one of SEQ ID NO: 10090 to SEQ ID NO: 10673.

In embodiments of the composition (including in any of the aforementioned aspects and embodiments), the targeting domain of the first gRNA molecule (as described herein), the targeting domain of the second gRNA molecule (as described herein), and, if present, the targeting domain of the third gRNA molecule (as described herein), include, e.g., consist of, the sequences of any of:
  a) Combination A1 to combination A72 of Table 33;
  b) Combination B1 to combination B84 of Table 34;
  c) Combination C1 to combination C42 of Table 35;
  d) Combination D1 to combination D36 of Table 36;
  e) Combination E1 to combination E30 of Table 37; or
  f) Combination F1 to combination F60 of Table 38.

In any of the aforementioned aspects and embodiments, each of said gRNA molecules is in a ribonuclear protein complex (RNP) with a Cas9 molecule described herein.

In embodiments, the gRNA molecule or composition is formulated in a medium suitable for electroporation.

In embodiments wherein each of said gRNA molecules is in a RNP with a Cas9 molecule described herein, each of said RNP complexes is at a concentration of less than about 10 uM, e.g., less than about 3 uM, e.g., less than about 1 uM, e.g., less than about 0.5 uM, e.g., less than about 0.3 uM, e.g., less than about 0.1 uM.

In embodiments, the composition further includes a cell, e.g., a population of cells, e.g., an immune effector cell, e.g., a CAR-expressing immune effector cell, e.g., described herein.

In another aspect, the invention provides a nucleic acid that encodes a gRNA molecule of any of the previous gRNA molecule aspects or embodiments, or a (for example, all) component(s) of a composition of any of the aforementioned composition aspects and embodiments. In embodiments, the nucleic acid includes a promoter operably linked to the sequence that encodes the gRNA molecule. In embodiments, the promoter is a promoter recognized by an RNA polymerase II or RNA polymerase III. In other embodiments, the promoter is a U6 promoter or an H1 promoter. In embodiments, the nucleic acid further encodes a Cas9 molecule. In embodiments, the nucleic acid includes a promoter operably linked to the sequence that encodes a Cas9 molecule, for example, an EF-1 promoter, a CMV IE gene promoter, an EF-1α promoter, an ubiquitin C promoter, or a phosphoglycerate kinase (PGK) promoter.

In another aspect, the invention provides a vector that includes the nucleic acid of any of any of the aforementioned nucleic acid aspects and embodiments. In embodiments, the vector is selected from the group consisting of a lentiviral vector, an adenoviral vector, an adeno-associated viral (AAV) vector, a herpes simplex virus (HSV) vector, a plasmid, a minicircle, a nanoplasmid, and an RNA vector.

In another aspect, the invention provides a composition that includes a gRNA molecule of any the aforementioned gRNA molecule aspects and embodiments, and nucleic acid encoding a Cas9 molecule, for example, as described herein.

In another aspect, the invention provides a composition that includes a nucleic acid encoding a gRNA molecule of any the aforementioned gRNA molecule aspects and embodiments, and a Cas9 molecule, for example, as described herein.

In embodiments of any of the compositions of the invention, the composition further includes a template nucleic acid. In embodiments, the template nucleic acid includes a nucleotide that corresponds to a nucleotide of a target sequence of the gRNA molecule. In embodiments, the template nucleic acid includes nucleic acid encoding a chimeric antigen receptor (CAR), for example, as described herein. In embodiments, the CAR is (a) a CD19 CAR, e.g., as described in WO2012/079000 or WO2014/153270; or (b) a BCMA CAR, e.g., as described herein, e.g., a BCMA CAR including SEQ ID NO: 8559. In embodiments, the template nucleic acid includes nucleic acid encoding an NK inhibitory molecule, for example, as described herein.

In another aspect, the invention provides a method of altering e.g., altering the structure, e.g., sequence of, a target sequence of a cell, including contacting said cell with a) a gRNA molecule, e.g., more than one gRNA molecule, of any of the previous gRNA molecule aspects and embodiments, and a Cas9 molecule, for example, as described herein; b) a gRNA molecule, e.g., more than one gRNA molecule, of any of the previous gRNA molecule aspects and embodiments and nucleic acid encoding a Cas9 molecule, for example, as described herein; c) nucleic acid encoding a gRNA molecule, e.g., more than one gRNA molecule, of any of the previous gRNA molecule aspects and embodiments and a Cas9 molecule, for example, as described herein; d) nucleic acid encoding a gRNA molecule, e.g., more than one gRNA molecule, of any of the previous gRNA molecule aspects and embodiments and nucleic acid encoding a Cas9 molecule, for example, as described herein; e) any of a) to d), above, and a template nucleic acid; f) any of a) to d) above, and nucleic acid including sequence encoding a template nucleic acid; g) a composition of any of the previous composition aspects and embodiments; or h) a vector of any of the previous vector aspects and embodiments. In embodiments, the gRNA molecule or nucleic acid encoding the gRNA molecule, and the Cas9 molecule or nucleic acid encoding the Cas9 molecule, are formulated in a single composition. In other embodiments, the gRNA molecule or nucleic acid encoding the gRNA molecule, and the Cas9 molecule or nucleic acid encoding the Cas9 molecule, are formulated in more than one composition. In embodiments, the more than one composition are delivered, for example, delivered to a cell described herein, simultaneously or sequentially. In embodiments, the cell is an animal cell, for example, a mammalian, primate, or human cell. In embodiments, the cell is an immune effector cell (e.g., a population of immune effector cells), for example, a T cell or NK cell, for example, T cell, for example, a CD4+ T cell, a CD8+ T cell, or a combination thereof. In embodiments, the cell has been, or will be, engineered to express a chimeric antigen receptor (CAR), for example, as described herein. In embodiments, the cell includes, or will include a chimeric antigen receptor (CAR), for example, as described herein. In embodiments, the cell includes, or will include nucleic acid encoding a chimeric antigen receptor (CAR), for example, as described herein. In embodiments, the CAR is (a) a CD19 CAR; or (b) a BCMA CAR. In embodiments, the CAR is a CD19 CAR including an antigen binding domain including any one of SEQ ID NO: 7883 to SEQ ID NO: 7898. In embodiments, the CAR is a CD19 CAR and includes any one of SEQ ID NO: 7908 to SEQ ID NO: 7920. In embodiments, the CAR is a BCMA CAR including an antigen binding domain including any one of SEQ ID NO:

7939 to SEQ ID NO: 8112. In embodiments, the CAR is a BCMA CAR and includes any one of SEQ ID NO: 8549 to SEQ ID NO: 8621, e.g., includes SEQ ID NO: 8559. In embodiments the cell is allogeneic with respect to a patient to be administered said cell. In embodiments, the cell is isolated from a healthy human donor. In embodiments the cell is autologous with respect to a patient to be administered said cell.

In another aspect, the invention provides a cell, altered by a method of any of the aforementioned method aspects and embodiments, for example, altered by a method described herein. In another aspect, the invention provides a cell that includes a first gRNA molecule of any of the aforementioned gRNA molecule aspects and embodiments, or a composition of any of the aforementioned composition aspects and embodiments, a nucleic acid of any of the aforementioned nucleic acid aspects and embodiments, or a vector of any of the aforementioned vector aspects and embodiments. In embodiments, the gRNA molecule, composition, nucleic acid or vector is introduced into said cell ex vivo. In other embodiments, the gRNA molecule, composition, nucleic acid or vector is introduced into said cell in vivo. In embodiments, the cell is an animal cell, for example, a mammalian, primate, or human cell. In embodiments, the cell is an immune effector cell (e.g., a population of immune effector cells), for example, a T cell or NK cell, for example, T cell, for example, a CD4+ T cell, a CD8+ T cell, or a combination thereof. In embodiments, the cell has been, or will be, engineered to express a chimeric antigen receptor (CAR), for example, as described herein. In embodiments, the cell includes, or will include a chimeric antigen receptor (CAR), for example, as described herein. In embodiments, the cell includes, or will include nucleic acid encoding a chimeric antigen receptor (CAR), for example, as described herein. In embodiments, the CAR is (a) a CD19 CAR; or (b) a BCMA CAR. In embodiments, the CAR is a CD19 CAR including an antigen binding domain including any one of SEQ ID NO: 7883 to SEQ ID NO: 7898. In embodiments, the CAR is a CD19 CAR and includes any one of SEQ ID NO: 7908 to SEQ ID NO: 7920. In embodiments, the CAR is a BCMA CAR including an antigen binding domain including any one of SEQ ID NO: 7939 to SEQ ID NO: 8112. In embodiments, the CAR is a BCMA CAR and includes any one of SEQ ID NO: 8549 to SEQ ID NO: 8621, e.g., includes SEQ ID NO: 8559. In embodiments the cell is allogeneic with respect to a patient to be administered said cell. In embodiments, the cell is isolated from a healthy human donor. In embodiments the cell is autologous with respect to a patient to be administered said cell. In embodiments, the cell includes, has included, or will include a second gRNA molecule, or a nucleic acid encoding the second gRNA molecule of any of the aforementioned gRNA molecule aspects and embodiments, wherein the first gRNA molecule and second gRNA molecule include nonidentical targeting domains. In embodiments, the first gRNA molecule includes a targeting domain complementary with a target sequence of an allogeneic T-cell target (e.g., a targeting domain described in Tables 1, 3, 4 or 5), and the second gRNA molecule includes a targeting domain complementary with a target sequence of an inhibitory molecule or downstream effector of signaling through an inhibitory molecule (e.g., includes a targeting domain described in Table 2 or Table 6). In embodiments, the inhibitory molecule or downstream effector of signaling through an inhibitory molecule is CD274, HAVCR2, LAG3, PDCD1, PD-L2, CTLA4, CEACAM (e.g., CEACAM-1, CEACAM-3 and/or CEACAM-5), VISTA, BTLA, TIGIT, LAIR1, CD160, 2B4, CD80, CD86, B7-H14 (CD113), B7-H4 (VTCN1), HVEM (TNFRSF14 or CD107), KIR, A2aR, MHC class I, MHC class II, GAL9, adenosine, and TGF beta, or PTPN11. In embodiments, the first gRNA molecule includes a targeting domain complementary with a target sequence of TRAC, TRBC1, TRBC2, CD247, CD3D, CD3E, or CD3G, and the second gRNA molecule includes a targeting domain complementary with a target sequence of NLRC5, e.g., includes a targeting domain including (e.g., consisting of) any one of SEQ ID NO: 8622 to SEQ ID NO: 10089. In embodiments, the first gRNA molecule includes a targeting domain complementary with a target sequence of TRAC, TRBC1, TRBC2, CD247, CD3D, CD3E, or CD3G, and the second gRNA molecule includes a targeting domain complementary with a target sequence of B2M, HLA-A, HLA-B or HLA-C. In embodiments, the cell further includes, has included, or will include a third gRNA molecule of any of the aforementioned gRNA molecule aspects and embodiments, or a nucleic acid encoding the third gRNA molecule of any of the aforementioned gRNA molecule aspects and embodiments, wherein the first gRNA molecule, the second gRNA molecule and the third gRNA molecule include nonidentical targeting domains. In embodiments, the third gRNA molecule includes a targeting domain complementary with a target sequence of CIITA, RFXANK, RFX5, or RFXAP, e.g., CIITA, e.g., includes a targeting domain including, e.g., consisting of, any one of SEQ ID NO: 7717 to SEQ ID NO: 7804, e.g., includes a targeting domain including, e.g., consisting of, any one of SEQ ID NO: 7769, SEQ ID NO: 7771, or SEQ ID NO: 7785. In embodiments, the cell includes three gRNA molecules, and the first gRNA molecule includes a targeting domain complementary with a target sequence of TRAC; the second gRNA molecule includes a targeting domain complementary with a target sequence of B2M; and the third gRNA molecule includes a targeting domain complementary with a target sequence of CIITA. In embodiments, the cell includes three gRNA molecules, and the first gRNA molecule includes a targeting domain complementary with a target sequence of TRAC; the second gRNA molecule includes a targeting domain complementary with a target sequence of NLRC5; and the third gRNA molecule includes a targeting domain complementary with a target sequence of CIITA. In embodiments, the cell includes two gRNA molecules, and the first gRNA molecule includes a targeting domain complementary with a target sequence of TRAC, TRBC1, TRBC2, CD247, CD3D, CD3E, or CD3G, and the second gRNA molecule includes a targeting domain complementary with a target sequence of NR3C1, DCK, CD52 or FKBP1A.

In embodiments of the cell which includes a gRNA molecule (e.g., more than one gRNA molecule described herein):
(1) the first gRNA molecule includes a targeting domain selected from the group consisting of SEQ ID NO: 5528 to SEQ ID NO: 5623 or SEQ ID NO: 5816 to SEQ ID NO: 5965, and the second guide RNA molecule includes a targeting domain selected from the group consisting of SEQ ID NO: 1 to SEQ ID NO: 83 and SEQ ID NO: 5492 to SEQ ID NO: 5527;
(2) the first gRNA molecule includes a targeting domain selected from the group consisting of SEQ ID NO: 5528 to SEQ ID NO: 5623 or SEQ ID NO: 5816 to SEQ ID NO: 5965, and the second guide RNA molecule includes a targeting domain selected from the group consisting of SEQ ID NO: 969 to SEQ ID NO: 1345;

(3) the first gRNA molecule includes a targeting domain selected from the group consisting of SEQ ID NO: 5528 to SEQ ID NO: 5623 or SEQ ID NO: 5816 to SEQ ID NO: 5965, and the second guide RNA molecule includes a targeting domain selected from the group consisting of SEQ ID NO: 1346 to SEQ ID NO: 1698;

(4) the first gRNA molecule includes a targeting domain selected from the group consisting of SEQ ID NO: 5528 to SEQ ID NO: 5623 or SEQ ID NO: 5816 to SEQ ID NO: 5965, and the second guide RNA molecule includes a targeting domain selected from the group consisting of SEQ ID NO: 1699 to SEQ ID NO: 2068;

(5) the first gRNA molecule includes a targeting domain selected from the group consisting of SEQ ID NO: 5528 to SEQ ID NO: 5623 or SEQ ID NO: 5816 to SEQ ID NO: 5965, and the second guide RNA molecule includes a targeting domain selected from the group consisting of SEQ ID NO: 2069 to SEQ ID NO: 2941;

(6) the first gRNA molecule includes a targeting domain selected from the group consisting of SEQ ID NO: 5528 to SEQ ID NO: 5623 or SEQ ID NO: 5816 to SEQ ID NO: 5965, and the second guide RNA molecule includes a targeting domain selected from the group consisting of SEQ ID NO: 5278 to SEQ ID NO: 5491;

(7) the first gRNA molecule includes a targeting domain selected from the group consisting of SEQ ID NO: 5528 to SEQ ID NO: 5623 or SEQ ID NO: 5816 to SEQ ID NO: 5965, and the second guide RNA molecule includes a targeting domain selected from the group consisting of SEQ ID NO: 6227 to SEQ ID NO: 6324;

(8) the first gRNA molecule includes a targeting domain selected from the group consisting of SEQ ID NO: 5528 to SEQ ID NO: 5623 or SEQ ID NO: 5816 to SEQ ID NO: 5965, and the second guide RNA molecule includes a targeting domain selected from the group consisting of SEQ ID NO: 6325 to SEQ ID NO: 6583;

(9) the first gRNA molecule includes a targeting domain selected from the group consisting of SEQ ID NO: 5624 to SEQ ID NO: 5643 or SEQ ID NO: 5966 to SEQ ID NO: 6097, and the second guide RNA molecule includes a targeting domain selected from the group consisting of SEQ ID NO: 1 to SEQ ID NO: 83 and SEQ ID NO: 5492 to SEQ ID NO: 5527;

(10) the first gRNA molecule includes a targeting domain selected from the group consisting of SEQ ID NO: 5624 to SEQ ID NO: 5643 or SEQ ID NO: 5966 to SEQ ID NO: 6097, and the second guide RNA molecule includes a targeting domain selected from the group consisting of SEQ ID NO: 969 to SEQ ID NO: 1345;

(11) the first gRNA molecule includes a targeting domain selected from the group consisting of SEQ ID NO: 5624 to SEQ ID NO: 5643 or SEQ ID NO: 5966 to SEQ ID NO: 6097, and the second guide RNA molecule includes a targeting domain selected from the group consisting of SEQ ID NO: 1346 to SEQ ID NO: 1698;

(12) the first gRNA molecule includes a targeting domain selected from the group consisting of SEQ ID NO: 5624 to SEQ ID NO: 5643 or SEQ ID NO: 5966 to SEQ ID NO: 6097, and the second guide RNA molecule includes a targeting domain selected from the group consisting of SEQ ID NO: 1699 to SEQ ID NO: 2068;

(13) the first gRNA molecule includes a targeting domain selected from the group consisting of SEQ ID NO: 5624 to SEQ ID NO: 5643 or SEQ ID NO: 5966 to SEQ ID NO: 6097, and the second guide RNA molecule includes a targeting domain selected from the group consisting of SEQ ID NO: 2069 to SEQ ID NO: 2941;

(14) the first gRNA molecule includes a targeting domain selected from the group consisting of SEQ ID NO: 5624 to SEQ ID NO: 5643 or SEQ ID NO: 5966 to SEQ ID NO: 6097, and the second guide RNA molecule includes a targeting domain selected from the group consisting of SEQ ID NO: 5278 to SEQ ID NO: 5491;

(15) the first gRNA molecule includes a targeting domain selected from the group consisting of SEQ ID NO: 5624 to SEQ ID NO: 5643 or SEQ ID NO: 5966 to SEQ ID NO: 6097, and the second guide RNA molecule includes a targeting domain selected from the group consisting of SEQ ID NO: 6227 to SEQ ID NO: 6324;

(16) the first gRNA molecule includes a targeting domain selected from the group consisting of SEQ ID NO: 5624 to SEQ ID NO: 5643 or SEQ ID NO: 5966 to SEQ ID NO: 6097, and the second guide RNA molecule includes a targeting domain selected from the group consisting of SEQ ID NO: 6325 to SEQ ID NO: 6583;

(17) the first gRNA molecule includes a targeting domain selected from the group consisting of SEQ ID NO: 5644 to SEQ ID NO: 5719 or SEQ ID NO: 6098 to SEQ ID NO: 6226, and the second guide RNA molecule includes a targeting domain selected from the group consisting of SEQ ID NO: 1 to SEQ ID NO: 83 and SEQ ID NO: 5492 to SEQ ID NO: 5527;

(18) the first gRNA molecule includes a targeting domain selected from the group consisting of SEQ ID NO: 5644 to SEQ ID NO: 5719 or SEQ ID NO: 6098 to SEQ ID NO: 6226, and the second guide RNA molecule includes a targeting domain selected from the group consisting of SEQ ID NO: 969 to SEQ ID NO: 1345;

(19) the first gRNA molecule includes a targeting domain selected from the group consisting of SEQ ID NO: 5644 to SEQ ID NO: 5719 or SEQ ID NO: 6098 to SEQ ID NO: 6226, and the second guide RNA molecule includes a targeting domain selected from the group consisting of SEQ ID NO: 1346 to SEQ ID NO: 1698;

(20) the first gRNA molecule includes a targeting domain selected from the group consisting of SEQ ID NO: 5644 to SEQ ID NO: 5719 or SEQ ID NO: 6098 to SEQ ID NO: 6226, and the second guide RNA molecule includes a targeting domain selected from the group consisting of SEQ ID NO: 1699 to SEQ ID NO: 2068;

(21) the first gRNA molecule includes a targeting domain selected from the group consisting of SEQ ID NO: 5644 to SEQ ID NO: 5719 or SEQ ID NO: 6098 to SEQ ID NO: 6226, and the second guide RNA molecule includes a targeting domain selected from the group consisting of SEQ ID NO: 2069 to SEQ ID NO: 2941;

(22) the first gRNA molecule includes a targeting domain selected from the group consisting of SEQ ID NO: 5644 to SEQ ID NO: 5719 or SEQ ID NO: 6098 to SEQ ID NO: 6226, and the second guide RNA molecule includes a targeting domain selected from the group consisting of SEQ ID NO: 5278 to SEQ ID NO: 5491;

(23) the first gRNA molecule includes a targeting domain selected from the group consisting of SEQ ID NO: 5644 to SEQ ID NO: 5719 or SEQ ID NO: 6098 to SEQ ID NO: 6226, and the second guide RNA molecule includes a targeting domain selected from the group consisting of SEQ ID NO: 6227 to SEQ ID NO: 6324;

(24) the first gRNA molecule includes a targeting domain selected from the group consisting of SEQ ID NO: 5644 to SEQ ID NO: 5719 or SEQ ID NO: 6098 to SEQ ID NO: 6226, and the second guide RNA molecule includes a targeting domain selected from the group consisting of SEQ ID NO: 6325 to SEQ ID NO: 6583;

(25) the first gRNA molecule includes a targeting domain selected from the group consisting of SEQ ID NO: 84 to SEQ ID NO: 392, and the second guide RNA molecule includes a targeting domain selected from the group consisting of SEQ ID NO: 1 to SEQ ID NO: 83 and SEQ ID NO: 5492 to SEQ ID NO: 5527;

(26) the first gRNA molecule includes a targeting domain selected from the group consisting of SEQ ID NO: 84 to SEQ ID NO: 392, and the second guide RNA molecule includes a targeting domain selected from the group consisting of SEQ ID NO: 969 to SEQ ID NO: 1345;

(27) the first gRNA molecule includes a targeting domain selected from the group consisting of SEQ ID NO: 84 to SEQ ID NO: 392, and the second guide RNA molecule includes a targeting domain selected from the group consisting of SEQ ID NO: 1346 to SEQ ID NO: 1698;

(28) the first gRNA molecule includes a targeting domain selected from the group consisting of SEQ ID NO: 84 to SEQ ID NO: 392, and the second guide RNA molecule includes a targeting domain selected from the group consisting of SEQ ID NO: 1699 to SEQ ID NO: 2068;

(29) the first gRNA molecule includes a targeting domain selected from the group consisting of SEQ ID NO: 84 to SEQ ID NO: 392, and the second guide RNA molecule includes a targeting domain selected from the group consisting of SEQ ID NO: 2069 to SEQ ID NO: 2941;

(30) the first gRNA molecule includes a targeting domain selected from the group consisting of SEQ ID NO: 84 to SEQ ID NO: 392, and the second guide RNA molecule includes a targeting domain selected from the group consisting of SEQ ID NO: 5278 to SEQ ID NO: 5491;

(31) the first gRNA molecule includes a targeting domain selected from the group consisting of SEQ ID NO: 84 to SEQ ID NO: 392, and the second guide RNA molecule includes a targeting domain selected from the group consisting of SEQ ID NO: 6227 to SEQ ID NO: 6324;

(32) the first gRNA molecule includes a targeting domain selected from the group consisting of SEQ ID NO: 84 to SEQ ID NO: 392, and the second guide RNA molecule includes a targeting domain selected from the group consisting of SEQ ID NO: 6325 to SEQ ID NO: 6583;

(33) the first gRNA molecule includes a targeting domain selected from the group consisting of SEQ ID NO: 393 to SEQ ID NO: 532, and the second guide RNA molecule includes a targeting domain selected from the group consisting of SEQ ID NO: 1 to SEQ ID NO: 83 and SEQ ID NO: 5492 to SEQ ID NO: 5527;

(34) the first gRNA molecule includes a targeting domain selected from the group consisting of SEQ ID NO: 393 to SEQ ID NO: 532, and the second guide RNA molecule includes a targeting domain selected from the group consisting of SEQ ID NO: 969 to SEQ ID NO: 1345;

(35) the first gRNA molecule includes a targeting domain selected from the group consisting of SEQ ID NO: 393 to SEQ ID NO: 532, and the second guide RNA molecule includes a targeting domain selected from the group consisting of SEQ ID NO: 1346 to SEQ ID NO: 1698;

(36) the first gRNA molecule includes a targeting domain selected from the group consisting of SEQ ID NO: 393 to SEQ ID NO: 532, and the second guide RNA molecule includes a targeting domain selected from the group consisting of SEQ ID NO: 1699 to SEQ ID NO: 2068;

(37) the first gRNA molecule includes a targeting domain selected from the group consisting of SEQ ID NO: 393 to SEQ ID NO: 532, and the second guide RNA molecule includes a targeting domain selected from the group consisting of SEQ ID NO: 2069 to SEQ ID NO: 2941;

(38) the first gRNA molecule includes a targeting domain selected from the group consisting of SEQ ID NO: 393 to SEQ ID NO: 532, and the second guide RNA molecule includes a targeting domain selected from the group consisting of SEQ ID NO: 5278 to SEQ ID NO: 5491;

(39) the first gRNA molecule includes a targeting domain selected from the group consisting of SEQ ID NO: 393 to SEQ ID NO: 532, and the second guide RNA molecule includes a targeting domain selected from the group consisting of SEQ ID NO: 6227 to SEQ ID NO: 6324;

(40) the first gRNA molecule includes a targeting domain selected from the group consisting of SEQ ID NO: 393 to SEQ ID NO: 532, and the second guide RNA molecule includes a targeting domain selected from the group consisting of SEQ ID NO: 6325 to SEQ ID NO: 6583;

(41) the first gRNA molecule includes a targeting domain selected from the group consisting of SEQ ID NO: 533 to SEQ ID NO: 839, and the second guide RNA molecule includes a targeting domain selected from the group consisting of SEQ ID NO: 1 to SEQ ID NO: 83 and SEQ ID NO: 5492 to SEQ ID NO: 5527;

(42) the first gRNA molecule includes a targeting domain selected from the group consisting of SEQ ID NO: 533 to SEQ ID NO: 839, and the second guide RNA molecule includes a targeting domain selected from the group consisting of SEQ ID NO: 969 to SEQ ID NO: 1345;

(43) the first gRNA molecule includes a targeting domain selected from the group consisting of SEQ ID NO: 533 to SEQ ID NO: 839, and the second guide RNA molecule includes a targeting domain selected from the group consisting of SEQ ID NO: 1346 to SEQ ID NO: 1698;

(44) the first gRNA molecule includes a targeting domain selected from the group consisting of SEQ ID NO: 533 to SEQ ID NO: 839, and the second guide RNA molecule includes a targeting domain selected from the group consisting of SEQ ID NO: 1699 to SEQ ID NO: 2068;

(45) the first gRNA molecule includes a targeting domain selected from the group consisting of SEQ ID NO: 533 to SEQ ID NO: 839, and the second guide RNA molecule includes a targeting domain selected from the group consisting of SEQ ID NO: 2069 to SEQ ID NO: 2941;

(46) the first gRNA molecule includes a targeting domain selected from the group consisting of SEQ ID NO: 533 to SEQ ID NO: 839, and the second guide RNA molecule includes a targeting domain selected from the group consisting of SEQ ID NO: 5278 to SEQ ID NO: 5491;

(47) the first gRNA molecule includes a targeting domain selected from the group consisting of SEQ ID NO: 533 to SEQ ID NO: 839, and the second guide RNA molecule includes a targeting domain selected from the group consisting of SEQ ID NO: 6227 to SEQ ID NO: 6324;

(48) the first gRNA molecule includes a targeting domain selected from the group consisting of SEQ ID NO: 533 to SEQ ID NO: 839, and the second guide RNA molecule includes a targeting domain selected from the group consisting of SEQ ID NO: 6325 to SEQ ID NO: 6583;

(49) the first gRNA molecule includes a targeting domain selected from the group consisting of SEQ ID NO: 840 to SEQ ID NO: 968, and the second guide RNA molecule includes a targeting domain selected from the group consisting of SEQ ID NO: 1 to SEQ ID NO: 83 and SEQ ID NO: 5492 to SEQ ID NO: 5527;

(50) the first gRNA molecule includes a targeting domain selected from the group consisting of SEQ ID NO: 840 to SEQ ID NO: 968, and the second guide RNA molecule includes a targeting domain selected from the group consisting of SEQ ID NO: 969 to SEQ ID NO: 1345;

(51) the first gRNA molecule includes a targeting domain selected from the group consisting of SEQ ID NO: 840 to SEQ ID NO: 968, and the second guide RNA molecule includes a targeting domain selected from the group consisting of SEQ ID NO: 1346 to SEQ ID NO: 1698;

(52) the first gRNA molecule includes a targeting domain selected from the group consisting of SEQ ID NO: 840 to SEQ ID NO: 968, and the second guide RNA molecule includes a targeting domain selected from the group consisting of SEQ ID NO: 1699 to SEQ ID NO: 2068;

(53) the first gRNA molecule includes a targeting domain selected from the group consisting of SEQ ID NO: 840 to SEQ ID NO: 968, and the second guide RNA molecule includes a targeting domain selected from the group consisting of SEQ ID NO: 2069 to SEQ ID NO: 2941;

(54) the first gRNA molecule includes a targeting domain selected from the group consisting of SEQ ID NO: 840 to SEQ ID NO: 968, and the second guide RNA molecule includes a targeting domain selected from the group consisting of SEQ ID NO: 5278 to SEQ ID NO: 5491;

(55) the first gRNA molecule includes a targeting domain selected from the group consisting of SEQ ID NO: 840 to SEQ ID NO: 968, and the second guide RNA molecule includes a targeting domain selected from the group consisting of SEQ ID NO: 6227 to SEQ ID NO: 6324; or

(56) the first gRNA molecule includes a targeting domain selected from the group consisting of SEQ ID NO: 840 to SEQ ID NO: 968, and the second guide RNA molecule includes a targeting domain selected from the group consisting of SEQ ID NO: 6325 to SEQ ID NO: 6583.

In embodiments, including in any of the aforementioned cell aspects and embodiments, the cell further includes a third gRNA molecule including a targeting domain complementary with a target sequence of an inhibitory molecule or downstream effector of signaling through an inhibitory molecule, wherein the inhibitory molecule or downstream effector of signaling through an inhibitory molecule is CD274, HAVCR2, LAG3, PDCD1, PD-L2, CTLA4, CEACAM (e.g., CEACAM-1, CEACAM-3 and/or CEACAM-5), VISTA, BTLA, TIGIT, LAIR1, CD160, 2B4, CD80, CD86, B7-H3 (CD113), B7-H4 (VTCN1), HVEM (TNFRSF14 or CD107), KIR, A2aR, MHC class I, MHC class II, GAL9, adenosine, and TGF beta, or PTPN11, for example, the third gRNA molecule is comprises a targeting domain of any of 15(a) to 15(e).

In embodiments of the cell which includes a gRNA molecule (e.g., more than one gRNA molecule described herein):

(1) the first gRNA molecule includes a targeting domain selected from the group consisting of SEQ ID NO: 5528 to SEQ ID NO: 5623 or SEQ ID NO: 5816 to SEQ ID NO: 5965, and the second guide RNA molecule includes a targeting domain selected from the group consisting of SEQ ID NO: 2942 to SEQ ID NO: 3270;

(2) the first gRNA molecule includes a targeting domain selected from the group consisting of SEQ ID NO: 5528 to SEQ ID NO: 5623 or SEQ ID NO: 5816 to SEQ ID NO: 5965, and the second guide RNA molecule includes a targeting domain selected from the group consisting of SEQ ID NO: 3271 to SEQ ID NO: 3541;

(3) the first gRNA molecule includes a targeting domain selected from the group consisting of SEQ ID NO: 5528 to SEQ ID NO: 5623 or SEQ ID NO: 5816 to SEQ ID NO: 5965, and the second guide RNA molecule includes a targeting domain selected from the group consisting of SEQ ID NO: 3542 to SEQ ID NO: 4032;

(4) the first gRNA molecule includes a targeting domain selected from the group consisting of SEQ ID NO: 5528 to SEQ ID NO: 5623 or SEQ ID NO: 5816 to SEQ ID NO: 5965, and the second guide RNA molecule includes a targeting domain selected from the group consisting of SEQ ID NO: 4033 to SEQ ID NO: 4589 and SEQ ID NO: 5720 to SEQ ID NO: 5815;

(5) the first gRNA molecule includes a targeting domain selected from the group consisting of SEQ ID NO: 5528 to SEQ ID NO: 5623 or SEQ ID NO: 5816 to SEQ ID NO: 5965, and the second guide RNA molecule includes a targeting domain selected from the group consisting of SEQ ID NO: 4590 to SEQ ID NO: 5277;

(6) the first gRNA molecule includes a targeting domain selected from the group consisting of SEQ ID NO: 5624 to SEQ ID NO: 5643 or SEQ ID NO: 5966 to SEQ ID NO: 6097, and the second guide RNA molecule includes a targeting domain selected from the group consisting of SEQ ID NO: 2942 to SEQ ID NO: 3270;

(7) the first gRNA molecule includes a targeting domain selected from the group consisting of SEQ ID NO: 5624 to SEQ ID NO: 5643 or SEQ ID NO: 5966 to SEQ ID NO: 6097, and the second guide RNA molecule includes a targeting domain selected from the group consisting of SEQ ID NO: 3271 to SEQ ID NO: 3541;

(8) the first gRNA molecule includes a targeting domain selected from the group consisting of SEQ ID NO: 5624 to SEQ ID NO: 5643 or SEQ ID NO: 5966 to SEQ ID NO: 6097, and the second guide RNA molecule includes a targeting domain selected from the group consisting of SEQ ID NO: 3542 to SEQ ID NO: 4032;

(9) the first gRNA molecule includes a targeting domain selected from the group consisting of SEQ ID NO: 5624 to SEQ ID NO: 5643 or SEQ ID NO: 5966 to SEQ ID NO: 6097, and the second guide RNA molecule includes a targeting domain selected from the group consisting of SEQ ID NO: 4033 to SEQ ID NO: 4589 and SEQ ID NO: 5720 to SEQ ID NO: 5815;

(10) the first gRNA molecule includes a targeting domain selected from the group consisting of SEQ ID NO: 5624 to SEQ ID NO: 5643 or SEQ ID NO: 5966 to SEQ ID NO: 6097, and the second guide RNA molecule includes a targeting domain selected from the group consisting of SEQ ID NO: 4590 to SEQ ID NO: 5277;

(11) the first gRNA molecule includes a targeting domain selected from the group consisting of SEQ ID NO: 5644 to SEQ ID NO: 5719 or SEQ ID NO: 6098 to SEQ ID NO: 6226, and the second guide RNA molecule includes a targeting domain selected from the group consisting of SEQ ID NO: 2942 to SEQ ID NO: 3270;

(12) the first gRNA molecule includes a targeting domain selected from the group consisting of SEQ ID NO: 5644 to SEQ ID NO: 5719 or SEQ ID NO: 6098 to SEQ ID NO: 6226, and the second guide RNA molecule includes a targeting domain selected from the group consisting of SEQ ID NO: 3271 to SEQ ID NO: 3541;

(13) the first gRNA molecule includes a targeting domain selected from the group consisting of SEQ ID NO: 5644 to SEQ ID NO: 5719 or SEQ ID NO: 6098 to SEQ ID NO: 6226, and the second guide RNA molecule includes a targeting domain selected from the group consisting of SEQ ID NO: 3542 to SEQ ID NO: 4032;

(14) the first gRNA molecule includes a targeting domain selected from the group consisting of SEQ ID NO: 5644 to SEQ ID NO: 5719 or SEQ ID NO: 6098 to SEQ ID NO: 6226, and the second guide RNA molecule includes a targeting domain selected from the group consisting of SEQ ID NO: 4033 to SEQ ID NO: 4589 and SEQ ID NO: 5720 to SEQ ID NO: 5815;

(15) the first gRNA molecule includes a targeting domain selected from the group consisting of SEQ ID NO: 5644 to SEQ ID NO: 5719 or SEQ ID NO: 6098 to SEQ ID NO: 6226, and the second guide RNA molecule includes a targeting domain selected from the group consisting of SEQ ID NO: 4590 to SEQ ID NO: 5277;

(16) the first gRNA molecule includes a targeting domain selected from the group consisting of SEQ ID NO: 84 to SEQ ID NO: 392, and the second guide RNA molecule includes a targeting domain selected from the group consisting of SEQ ID NO: 2942 to SEQ ID NO: 3270;

(17) the first gRNA molecule includes a targeting domain selected from the group consisting of SEQ ID NO: 84 to SEQ ID NO: 392, and the second guide RNA molecule includes a targeting domain selected from the group consisting of SEQ ID NO: 3271 to SEQ ID NO: 3541;

(18) the first gRNA molecule includes a targeting domain selected from the group consisting of SEQ ID NO: 84 to SEQ ID NO: 392, and the second guide RNA molecule includes a targeting domain selected from the group consisting of SEQ ID NO: 3542 to SEQ ID NO: 4032;

(19) the first gRNA molecule includes a targeting domain selected from the group consisting of SEQ ID NO: 84 to SEQ ID NO: 392, and the second guide RNA molecule includes a targeting domain selected from the group consisting of SEQ ID NO: 4033 to SEQ ID NO: 4589 and SEQ ID NO: 5720 to SEQ ID NO: 5815;

(20) the first gRNA molecule includes a targeting domain selected from the group consisting of SEQ ID NO: 84 to SEQ ID NO: 392, and the second guide RNA molecule includes a targeting domain selected from the group consisting of SEQ ID NO: 4590 to SEQ ID NO: 5277;

(21) the first gRNA molecule includes a targeting domain selected from the group consisting of SEQ ID NO: 393 to SEQ ID NO: 532, and the second guide RNA molecule includes a targeting domain selected from the group consisting of SEQ ID NO: 2942 to SEQ ID NO: 3270;

(22) the first gRNA molecule includes a targeting domain selected from the group consisting of SEQ ID NO: 393 to SEQ ID NO: 532, and the second guide RNA molecule includes a targeting domain selected from the group consisting of SEQ ID NO: 3271 to SEQ ID NO: 3541;

(23) the first gRNA molecule includes a targeting domain selected from the group consisting of SEQ ID NO: 393 to SEQ ID NO: 532, and the second guide RNA molecule includes a targeting domain selected from the group consisting of SEQ ID NO: 3542 to SEQ ID NO: 4032;

(24) the first gRNA molecule includes a targeting domain selected from the group consisting of SEQ ID NO: 393 to SEQ ID NO: 532, and the second guide RNA molecule includes a targeting domain selected from the group consisting of SEQ ID NO: 4033 to SEQ ID NO: 4589 and SEQ ID NO: 5720 to SEQ ID NO: 5815;

(25) the first gRNA molecule includes a targeting domain selected from the group consisting of SEQ ID NO: 393 to SEQ ID NO: 532, and the second guide RNA molecule includes a targeting domain selected from the group consisting of SEQ ID NO: 4590 to SEQ ID NO: 5277;

(26) the first gRNA molecule includes a targeting domain selected from the group consisting of SEQ ID NO: 533 to SEQ ID NO: 839, and the second guide RNA molecule includes a targeting domain selected from the group consisting of SEQ ID NO: 2942 to SEQ ID NO: 3270;

(27) the first gRNA molecule includes a targeting domain selected from the group consisting of SEQ ID NO: 533 to SEQ ID NO: 839, and the second guide RNA molecule includes a targeting domain selected from the group consisting of SEQ ID NO: 3271 to SEQ ID NO: 3541;

(28) the first gRNA molecule includes a targeting domain selected from the group consisting of SEQ ID NO: 533 to SEQ ID NO: 839, and the second guide RNA molecule includes a targeting domain selected from the group consisting of SEQ ID NO: 3542 to SEQ ID NO: 4032;

(29) the first gRNA molecule includes a targeting domain selected from the group consisting of SEQ ID NO: 533 to SEQ ID NO: 839, and the second guide RNA molecule includes a targeting domain selected from the group consisting of SEQ ID NO: 4033 to SEQ ID NO: 4589 and SEQ ID NO: 5720 to SEQ ID NO: 5815;

(30) the first gRNA molecule includes a targeting domain selected from the group consisting of SEQ ID NO: 533 to SEQ ID NO: 839, and the second guide RNA molecule includes a targeting domain selected from the group consisting of SEQ ID NO: 4590 to SEQ ID NO: 5277;

(31) the first gRNA molecule includes a targeting domain selected from the group consisting of SEQ ID NO: 840 to SEQ ID NO: 968, and the second guide RNA molecule includes a targeting domain selected from the group consisting of SEQ ID NO: 2942 to SEQ ID NO: 3270;

(32) the first gRNA molecule includes a targeting domain selected from the group consisting of SEQ ID NO: 840 to SEQ ID NO: 968, and the second guide RNA molecule includes a targeting domain selected from the group consisting of SEQ ID NO: 3271 to SEQ ID NO: 3541;

(33) the first gRNA molecule includes a targeting domain selected from the group consisting of SEQ ID NO: 840 to SEQ ID NO: 968, and the second guide RNA molecule includes a targeting domain selected from the group consisting of SEQ ID NO: 3542 to SEQ ID NO: 4032;

(34) the first gRNA molecule includes a targeting domain selected from the group consisting of SEQ ID NO: 840 to SEQ ID NO: 968, and the second guide RNA molecule includes a targeting domain selected from the group consisting of SEQ ID NO: 4033 to SEQ ID NO: 4589 and SEQ ID NO: 5720 to SEQ ID NO: 5815; or

(35) the first gRNA molecule includes a targeting domain selected from the group consisting of SEQ ID NO: 840 to SEQ ID NO: 968, and the second guide RNA molecule includes a targeting domain selected from the group consisting of SEQ ID NO: 4590 to SEQ ID NO: 5277.

In embodiments of the cell, the targeting domain of the first gRNA molecule, the targeting domain of the second gRNA molecule, and, if present, the targeting domain of the third gRNA molecule, include, e.g., consist of, the sequences of any of:

g) Combination A1 to combination A72 of Table 33;
h) Combination B1 to combination B84 of Table 34;
i) Combination C1 to combination C42 of Table 35;
j) Combination D1 to combination D36 of Table 36;
k) Combination E1 to combination E30 of Table 37; or
l) Combination F1 to combination F60 of Table 38.

In embodiments of the cell, the first gRNA molecule includes a targeting domain including SEQ ID NO: 5569, SEQ ID NO: 5592, or SEQ ID NO: 5586, and the second gRNA molecule includes a targeting domain including SEQ ID NO: 5775.

In any of the aforementioned cell aspects and embodiments, a gene including a target sequence complementary to the targeting domain of the first gRNA molecule, and, optionally, a gene including a target sequence complementary to the targeting domain of the second gRNA molecule and/or a gene including a target sequence complementary to the targeting domain of the third gRNA molecule, has been altered such that expression of a functional product of the gene including a target sequence complementary to the targeting domain of the first gRNA molecule, and, optionally, the gene including a target sequence complementary to the targeting domain of the second gRNA molecule and/or a functional product of a gene including a target sequence complementary to the targeting domain of the third gRNA molecule, has been reduced or eliminated.

In another aspect, the invention provides a method of providing an anti-tumor immunity in a subject, the method including administering to the subject an effective amount of a cell as described herein, for example, a cell of any of the aforementioned cell aspects and embodiments.

In another aspect, the invention provides a method of treating cancer in a subject, the method including administering to the subject an effective amount of a cell as described herein, for example, a cell of any of the aforementioned cell aspects and embodiments.

In another aspect, the invention provides a method of treating a subject having a disease associated with expression of a tumor antigen, e.g., a proliferative disease, a precancerous condition, a cancer, and a non-cancer related indication associated with expression of the tumor antigen, the method including administering to the subject an effective amount of a cell as described herein, for example, a cell of any of the aforementioned cell aspects and embodiments. In embodiments, the disease associated with expression of a tumor antigen is cancer or a non-cancer related indication. In embodiments, The disease is cancer selected from colon cancer, rectal cancer, renal-cell carcinoma, liver cancer, non-small cell carcinoma of the lung, cancer of the small intestine, cancer of the esophagus, melanoma, bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, carcinoma of the fallopian tubes, carcinoma of the endometrium, carcinoma of the cervix, carcinoma of the vagina, carcinoma of the vulva, Hodgkin's Disease, non-Hodgkin's lymphoma, cancer of the endocrine system, cancer of the thyroid gland, cancer of the parathyroid gland, cancer of the adrenal gland, sarcoma of soft tissue, cancer of the urethra, cancer of the penis, solid tumors of childhood, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers, combinations of said cancers, and metastatic lesions of said cancers. In embodiments, the cancer is a hematologic cancer selected from the group consisting of chronic lymphocytic leukemia (CLL), acute leukemias, acute lymphoid leukemia (ALL), B-cell acute lymphoid leukemia (B-ALL), T-cell acute lymphoid leukemia (T-ALL), chronic myelogenous leukemia (CML), acute myeloid leukemia (AML), B cell prolymphocytic leukemia, blastic plasmacytoid dendritic cell neoplasm, Burkitt's lymphoma, diffuse large B cell lymphoma, follicular lymphoma, hairy cell leukemia, small cell- or a large cell-follicular lymphoma, malignant lymphoproliferative conditions, MALT lymphoma, mantle cell lymphoma, marginal zone lymphoma, multiple myeloma, myelodysplasia and myelodysplastic syndrome, non-Hodgkin's lymphoma, Hodgkin's lymphoma, plasmablastic lymphoma, plasmacytoid dendritic cell neoplasm, Waldenstrom macroglobulinemia, and pre-leukemia.

In embodiments of any of the aforementioned methods, the method further includes administering a chemotherapeutic agent, for example, cyclophosphamide, fludarabine, or cyclophosphamide and fludarabine. In embodiments of the methods, the method includes administering a lymphodepleting agent or immunosuppressant prior to administering to the subject an effective amount of the cell as described herein, for example, a cell of any of the aforementioned cell aspects and embodiments.

In another aspect, the invention provides a method of preparing cells (e.g., a population of cells) for immunotherapy, the method including: (a) modifying cells by reducing or eliminating expression of a component of a T-cell receptor (TCR), for example, by introducing into said cells a gRNA molecule (as described herein), e.g., more than one gRNA molecule; (b) modifying cells by reducing or eliminating expression of an FILA (e.g., HLA-A, HLA-B, and/or HLA-C) or B2M, for example, by introducing into said cells a gRNA molecule (as described herein), e.g., more than one gRNA molecule; and (c) expanding said cells. In embodiments, the method further includes modifying said cells by reducing or eliminating expression of CIITA, for example, by introducing into said cells a gRNA molecule (as described herein), e.g., more than one gRNA molecule, wherein said modifying optionally takes place before the step of expanding said cells.

In another aspect, the invention provides a method of preparing cells (e.g., a population of cells) for immunotherapy including: (a) modifying cells by reducing or eliminating expression of a component of a T-cell receptor (TCR), for example, by introducing into said cells a gRNA molecule (as described herein), e.g., more than one gRNA molecule; (b) modifying cells by reducing or eliminating expression of a target for an immunosuppressant, for example, by introducing into said cells a gRNA molecule (as described herein), e.g., more than one gRNA molecule (as described herein); and (c) expanding said cells.

In embodiments of any of the aforementioned methods of preparing cells, the method further includes (d) modifying cells by reducing or eliminating expression of a first inhibitory molecule or downstream effector of signaling through an inhibitory molecule, for example, introducing into said cells a gRNA molecule (as described herein), e.g., more than one gRNA molecule; wherein said modifying optionally takes place before the step of expanding said cells.

In another aspect, the invention provides a method of preparing cells (e.g., a population of cells) for immunotherapy including: (a) modifying cells by reducing or eliminating expression of a first inhibitory molecule or downstream effector of signaling through an inhibitory molecule, for example, by introducing into said cells a gRNA molecule (as described herein), e.g., more than one gRNA molecule; and (c) expanding said cells.

In embodiments of any of the aforementioned methods of preparing cells, the method further includes (e) modifying cells by reducing or eliminating expression of a second inhibitory molecule or downstream effector of signaling through an inhibitory molecule, for example, by introducing into said cells a gRNA molecule, e.g., more than one gRNA molecule, wherein the first inhibitory molecule or downstream effector of signaling through an inhibitory molecule and second inhibitory molecule or downstream effector of signaling through an inhibitory molecule are different.

In embodiments of any of the aforementioned methods of preparing cells, the introduction of each of the gRNA molecules is simultaneous or sequential. In embodiments, the introduction of each of the gRNA molecules is sequential, and separated by a period of at least 24 hours, 2 days, 3 days, 4 days, 5 days, 6 days, 7 days, 8 days, 9 days or 10 days.

In embodiments of any of the aforementioned methods of preparing cells, the method further includes introducing into the cells nucleic acid encoding a chimeric antigen receptor (CAR), e.g., described herein. In embodiments, the nucleic acid encoding a CAR is disposed on a template nucleic acid. In embodiments, the nucleic acid encoding a CAR is disposed on a RNA vector. In embodiments, the nucleic acid encoding a CAR is disposed on a lentiviral vector.

In embodiments of any of the aforementioned methods of preparing cells, the method further includes isolating cells which are negative for TCR expression. In embodiments, the isolating results in a population of cells in which greater than about 75%, for example, greater than about 80%, 85%, 90%, 91%, 92%, 93, 94%, 95%, 96%, 97%, 98%, 99% or 99.5% of the cells are negative for TCR expression. In embodiments, the step of isolating cells which are negative for TCR expression includes contacting the cell population with a composition including an antibody specific for a component of a T cell receptor (TCR), optionally bound to a solid support or detectable label, and isolating the cells which do not bind to said antibody. In embodiments, the cells are immune effector cells, for example, T cells or NK cells, for example, T cells. In embodiments, the cells are allogeneic with respect to a subject to which they are to be administered, for example, the cells are isolated from a healthy donor, e.g., a donor which does not suffer from a condition associated with expression of a tumor antigen. In embodiments, the cells are autologous with respect to a subject to which they are to be administered. In embodiments of any of the aforementioned methods of preparing cells, steps (a) and/or (b) are performed ex vivo. In embodiments, step (c) is performed ex vivo. In embodiments, the expansion of step (c) is performed for a period of at least 2, 3, 4, 5, 6, 7, 8, 9, 10, 11, 12, 13, 14, or 15 days, or for a period of 2-15, 2-14, 2-13, 2-12, 2-11, 2-10, 3-10, 2-9, 3-9, 2-8, 3-8, 2-7, 3-7, 2-6, 3-6, 2-5, or 3-5 days.

In embodiments of any of the aforementioned methods of preparing cells, the gRNA molecules are gRNA molecules described herein, and the targeting domains of each of the gRNA molecules (for example, used in combination) include, for example, consist of, the sequences of any of the combinations listed in Table 33, Table 34, Table 35, Table 36, Table 37 or Table 38. In embodiments the targeting domains of each of the gRNA molecules include, for example, consist, of the sequences of any of:

a) Combination A1 to combination A72 of Table 33, for example, combination A1 to A4, combination A5 to A8, combination A37 to A40, or combination A41 to A44;
b) Combination B1 to combination B84 of Table 34;
c) Combination C1 to combination C42 of Table 35;
d) Combination D1 to combination D36 of Table 36, for example, combination D2, combination D4, combination D20, or combination D22;
e) Combination E1 to combination E30 of Table 37, for example, combination E2, combination E4, combination E8, or combination E10; or
f) Combination F1 to combination F60 of Table 38, for example, any of combination F1 to F4, combination F5 to F8, combination F13 to F16, or combination F17 to F20.

In another aspect, the invention provides a method of treating a subject in need thereof that includes administering cells (e.g., population of cells) prepared by a method of preparing cells described herein, for example, a method of any of the aforementioned aspects and embodiments of methods of preparing cells. In embodiments, particularly in embodiments that include a gRNA molecule which binds to a target sequence of a target for an immunosuppressant, the method further includes administering an immunosuppressive agent, for example, rapamycin, a rapalog or mTor inhibitor, e.g., RAD001. In embodiments, the subject has a disease associated with expression of a tumor antigen, e.g., a proliferative disease, a precancerous condition, a cancer, and a non-cancer related indication associated with expression of the tumor antigen, wherein said administration treats said disease associated with expression of a tumor antigen. In embodiments, the disease associated with expression of a tumor antigen is cancer or a non-cancer related indication. In embodiments, the disease is cancer selected from colon cancer, rectal cancer, renal-cell carcinoma, liver cancer, non-small cell carcinoma of the lung, cancer of the small intestine, cancer of the esophagus, melanoma, bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, carcinoma of the fallopian tubes, carcinoma of the endometrium, carcinoma of the cervix, carcinoma of the vagina, carcinoma of the vulva, Hodgkin's Disease, non-Hodgkin's lymphoma, cancer of the endocrine system, cancer of the thyroid gland, cancer of the parathyroid gland, cancer of the adrenal gland, sarcoma of soft tissue, cancer of the urethra, cancer of the penis, solid tumors of childhood, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers, combinations of said cancers, and metastatic lesions of said cancers. In embodiments, the cancer is a hematologic cancer selected from the group consisting of chronic lymphocytic leukemia (CLL), acute leukemias, acute lymphoid leukemia (ALL), B-cell acute lymphoid leukemia (B-ALL), T-cell acute lymphoid leukemia (T-ALL), chronic myelogenous leukemia (CML), acute myeloid leukemia (AML), B cell prolymphocytic leukemia, blastic plasmacytoid dendritic cell neoplasm, Burkitt's lymphoma, diffuse large B cell lymphoma, follicular lymphoma, hairy cell leukemia, small cell- or a large cell-follicular lymphoma, malignant lymphoproliferative conditions, MALT lymphoma, mantle cell lymphoma, marginal zone lymphoma, multiple myeloma, myelodysplasia and myelodysplastic syndrome, non-Hodgkin's lymphoma, Hodgkin's lymphoma, plasmablastic lymphoma, plasmacytoid dendritic cell neoplasm, Waldenstrom macroglobulinemia, and pre-leukemia.

In another aspect, the invention provides method of treating a patient suffering from a disease including:
(a) providing a population of cells from an allogeneic donor;
(b) introducing into the cells a CRISPR System (e.g., an S. pyogenes Cas9 CRISPR system) including a first gRNA molecule (or nucleic acid encoding said gRNA molecule) including a targeting domain complementary to a target sequence in a gene selected from CD247, CD3D, CD3E, CD3G, TRAC, TRBC1, and TRBC2;
(c) optionally, selecting those cells in which expression of functional TCR has been reduced or eliminated;
(d) transducing the cells with nucleic acid encoding a CAR; and
(e) administering the cells to a patient in need thereof, e.g., a patient who has a disease associated with expression of an antigen recognized by the CAR. In embodiments, the first gRNA molecule is to CD247, CD3D, CD3E, CD3G, TRAC, TRBC1, or TRBC2.

In embodiments, the method of treating a patient suffering from a disease further includes introducing into the cells a CRISPR System (e.g., an S. pyogenes Cas9 CRISPR system) including a second gRNA molecule (or nucleic acid encoding said gRNA molecule) including a targeting domain complementary to a target sequence in a gene selected from B2M, HLA-A, HLA-B or HLA-C. In embodiments, the second gRNA is to B2M, HLA-A, HLA-B or HLA-C. In embodiments, the method further includes introducing into the cells a CRISPR System (e.g., an S. pyogenes Cas9 CRISPR system) including a third gRNA molecule (or nucleic acid encoding said gRNA molecule) including a targeting domain complementary to a target sequence in a gene selected from CIITA, RFXANK, RFXAP, RFX5, HLA-DM, HLA-DO, HLA-DR, HLA-DQ and HLA-DP.

In other embodiments, the method of treating a patient suffering from a disease further includes introducing into the cells a CRISPR System (e.g., an S. pyogenes Cas9 CRISPR system) including a second gRNA molecule (or nucleic acid encoding said gRNA molecule) including a targeting domain complementary to a target sequence in a gene selected from DCK, CD52, FKBP1A or NR3C1. In embodiments where the second gRNA is to DCK, the method further including administering a nucleoside analog-based drug to said patient, for example, the nucleoside analog-based drug is cytarabine or gemcitabine. In embodiments, where the second gRNA is to CD52, the method further including administering an anti-CD52 antibody or antigen-binding fragment thereof to said patient, for example, the anti-CD52 antibody or antigen-binding fragment thereof is alemtuzumab (CAMPATH®). In embodiments where the second gRNA is to FKBP1A, the method further including administering FK506, cyclosporine, rapamycin or rapalog, or mTor inhibitor such as RAD001, to said patient. In embodiments where the second gRNA is to NR3C1, the method further including administering a corticosteroid to said patient, for example, the corticosteroid is dexamethasone.

In embodiments of any of the aforementioned methods of treating a patient suffering from a disease, the gRNA molecules are gRNA molecules described herein, and the targeting domains of each of the gRNA molecules (for example, used in combination) include, for example, consist of, the sequences of any of the combinations listed in Table 33, Table 34, Table 35, Table 36, Table 37 or Table 38. In embodiments the targeting domains of each of the gRNA molecules include, for example, consist, of the sequences of any of:
a) Combination A1 to combination A72 of Table 33, for example, combination A1 to A4, combination A5 to A8, combination A37 to A40, or combination A41 to A44;
b) Combination B1 to combination B84 of Table 34;
c) Combination C1 to combination C42 of Table 35;
d) Combination D1 to combination D36 of Table 36, for example, combination D2, combination D4, combination D20, or combination D22;
e) Combination E1 to combination E30 of Table 37, for example, combination E2, combination E4, combination E8, or combination E10; or
f) Combination F1 to combination F60 of Table 38, for example, any of combination F1 to F4, combination F5 to F8, combination F13 to F16, or combination F17 to F20.

In embodiments of any of the aforementioned methods of treating a patient suffering from a disease, the method further includes introducing into the cells a CRISPR System (e.g., an *S. pyogenes* Cas9 CRISPR system) including a fourth gRNA molecule (or nucleic acid encoding said gRNA molecule) including a targeting domain complementary to a target sequence in a gene selected from CD274, HAVCR2, LAG3, PDCD1, PD-L2, CTLA4, CEACAM (e.g., CEACAM-1, CEACAM-3 and/or CEACAM-5), VISTA, BTLA, TIGIT, LAIR1, CD160, 2B4, CD80, CD86, B7-H3 (CD113), B7-H4 (VTCN1), HVEM (TNFRSF14 or CD107), KIR, A2aR, MHC class I, MHC class II, GAL9, adenosine, and TGF beta, or PTPN11, for example, a fourth gRNA molecule is to CD274, HAVCR2, LAG3, PDCD1 or PTPN11.

In another aspect, the invention provides a method of treating a patient suffering from a disease including:
(a) providing a population of cells (as described herein), for example, immune effector cells;
(b) introducing into the population of cells a CRISPR System (e.g., an *S. pyogenes* Cas9 CRISPR system) including a first gRNA molecule (or nucleic acid encoding said gRNA molecule) including a targeting domain complementary to a target sequence in a gene selected from CD247, CD3D, CD3E, CD3G, TRAC, TRBC1, and TRBC2;
(c) introducing into the population of cells a CRISPR System (e.g., an *S. pyogenes* Cas9 CRISPR system) including a second gRNA molecule (or nucleic acid encoding said gRNA molecule) including a targeting domain complementary to a target sequence in a gene selected from B2M, HLA-A, HLA-B and HLA-C;
(d) optionally, selecting those cells in which expression of functional TCR, functional B2M, or both functional TCR and B2M has been reduced or eliminated;
(d) introducing into the population of cells a nucleic acid encoding a CAR; and
(e) administering the population of cells to a patient in need thereof, e.g., a patient who has a disease associated with expression of an antigen recognized by the CAR. In embodiments of the method, the method further comprises (f) introducing into the population of cells a CRISPR System (e.g., an *S. pyogenes* Cas9 CRISPR system) including a third gRNA molecule (or nucleic acid encoding said gRNA molecule) including a targeting domain complementary to a target sequence in a gene selected from CIITA, RFXANK, RFX5, and RFXAP. In embodiments, the first gRNA molecule includes a targeting domain complementary to a target sequence in a gene selected from TRAC, TRBC1 and TRBC2, for example, as described herein, for example, TRAC, for example, includes (for example consists of) a targeting domain selected from SEQ ID NO: 5569, SEQ ID NO: 5585, SEQ ID NO: 5592, SEQ ID NO: 5601, SEQ ID NO: 5589, SEQ ID NO: 5600, SEQ ID NO: 5594, SEQ ID NO: 5571, SEQ ID NO: 5593, SEQ ID NO: 5574, SEQ ID NO: 5598, SEQ ID NO: 5586, SEQ ID NO: 5599, SEQ ID NO: 5591, SEQ ID NO: 5610, SEQ ID NO: 5608, SEQ ID NO: 5617, SEQ ID NO: 5619, and SEQ ID NO: 5620, for example, selected from SEQ ID NO: 5569, SEQ ID NO: 5592, SEQ ID NO: 5587, SEQ ID NO: 5599, SEQ ID NO: 5600, and SEQ ID NO: 5586, e.g., selected from SEQ ID NO: 5569, SEQ ID NO: 5586, and SEQ ID NO: 5592. In other embodiments, the first gRNA molecule includes a targeting domain complementary to a target sequence in a gene selected from CD3E, CD3G and CD3D, for example, as described herein. In embodiments, the second gRNA molecule includes a targeting domain complementary to a target sequence in a B2M gene, for example, as described herein, for example, including (for example consisting of) a targeting domain selected from SEQ ID NO: 5519, SEQ ID NO: 5497, SEQ ID NO: 5499, SEQ ID NO: 5498, SEQ ID NO: 5503, SEQ ID NO: 5496, SEQ ID NO: 5507, SEQ ID NO: 5515, SEQ ID NO: 5493, SEQ ID NO: 5506, SEQ ID NO: 5509, SEQ ID NO: 5517, SEQ ID NO: 5521, SEQ ID NO: 5520, SEQ ID NO: 5500, SEQ ID NO: 5494, SEQ ID NO: 5508, SEQ ID NO: 5514, and SEQ ID NO: 5492, for example, selected from SEQ ID NO: 5496, SEQ ID NO: 5498 and SEQ ID NO: 5509. In embodiments, the third gRNA molecule includes a targeting domain complementary to a target sequence in a CIITA gene, for example, as described herein, for example, including (for example consisting of) a targeting domain selected from SEQ ID NO: 7771, SEQ ID NO: 7769, SEQ ID NO: 7773, SEQ ID NO: 7726, SEQ ID NO: 7758, SEQ ID NO: 7739, SEQ ID NO: 7779, SEQ ID NO: 7770, SEQ ID NO: 7749, SEQ ID NO: 7754, SEQ ID NO: 7745, SEQ ID NO: 7785, SEQ ID NO: 7731, SEQ ID NO: 7772, SEQ ID NO: 7743, or SEQ ID NO: 7750, for example, selected from SEQ ID NO: 7769, SEQ ID NO: 7771, SEQ ID NO: 7739 or SEQ ID NO: 7785. In preferred embodiments, the targeting domains of each of the gRNA molecules (for example, used in combination) include, for example, consist of, the sequences of any of the combinations listed in Table 33, Table 34, or Table 38. In embodiments the targeting domains of each of the gRNA molecules include, for example, consist, of the sequences of any of:
a) Combination A1 to combination A72 of Table 33, for example, combination A1 to A4, combination A5 to A8, combination A37 to A40, or combination A41 to A44;
b) Combination B1 to combination B84 of Table 34; or
c) Combination F1 to combination F60 of Table 38, for example, any of combination F1 to F4, combination F5 to F8, combination F13 to F16, or combination F17 to F20.

In embodiments of the method of treating a patient suffering from a disease, the method further includes introducing into said cells a nucleic acid molecule encoding an NK inhibitory molecule (e.g., as described herein), e.g., a nucleic acid molecule encoding an HLA-G:B2M fusion, e.g., a nucleic acid molecule encoding SEQ ID NO: 10674. In embodiments of the method of treating a patient suffering from a disease the cell (or population of cells) is an immune effector cell (or population of immune effector cells), for example, a T cell (or population of T cells). In embodiments, the cell (or population of cells) is allogeneic relative to the patient, for example, is isolated from a healthy human donor. In other embodiments, the cell (or population of cells) is autologous relative to the patient. In embodiments, the CAR is a CD19 CAR (for example, described herein), for example, a CD19 CAR including an antigen binding domain including any one of SEQ ID NO: 7883 to SEQ ID NO: 7898. In other embodiments, the CAR is a BCMA CAR, for example, including an antigen recognition domain including any one of SEQ ID NO: 7939 to SEQ ID NO: 8112 or SEQ ID NO: 8155 to SEQ ID NO: 8166, e.g., includes an antigen recognition domain including, e.g., consisting of, SEQ ID NO: 7949, for example, including any one of SEQ ID NO: 8549 to SEQ ID NO: 8621, e.g., including, e.g., consisting of, SEQ ID NO: 8559.

In another aspect, the invention provides a modified cell, which has reduced or eliminated expression of: a) a component of the T cell receptor; b) B2M; and/or c) CIITA, relative to an unmodified cell of the same type. In embodiments, the component of the T cell receptor is a TCR alpha chain or a TCR beta chain, for example, the TCR alpha chain. In other embodiments, the component of the TCR is CD3 delta, CD3 epsilon, or CD3 gamma, e.g., is CD3 epsilon. In embodiments, the modified cell (or population of cells) has reduced or eliminated expression of a component of the T cell receptor, B2M and CIITA.

In another aspect, the invention provides a modified cell, including an insertion or deletion of a base pair, e.g., more than one base pair, at or near: a) a gene encoding a component of the T cell receptor; b) B2M; and/or c) CIITA; relative to an unmodified cell of the same type. In embodiments, each of said insertions or deletions is an indel. In embodiments, each of said insertion or deletion is a frameshift mutation. In embodiments, the modified cell (or population of cells) an insertion or deletion of a base pair, e.g., more than one base pair, at or near a gene encoding a component of the T cell receptor, B2M and CIITA.

In another aspect, the invention provides a population of cells including the modified cell of any the aforementioned cell (e.g., modified cell) aspects and embodiments, wherein in at least about 30% of the cells, at least one said insertion or deletion is a frameshift mutation, e.g., as measured by NGS.

In another aspect, the invention provides a cell including (e.g., a population of cells including a cell, e.g., more than one cell, including):
  (a) Nucleic acid sequence encoding a CAR, e.g., as described herein;
  (b) Optionally, nucleic acid sequence encoding an NK inhibitory molecule, e.g., as described herein, e.g., nucleic acid encoding an HLA-G or HLA-G:B2M fusion as described herein;
  (c) An indel at or near a sequence of a gene encoding a component of a TCR (e.g., TRAC, TRBC1 TRBC2, CD3E, CD3D or CD3G, e.g. TRAC) or its regulatory elements, e.g., an indel at or near a target sequence of a gRNA including a targeting domain to a component of a TCR (e.g., TRAC, TRBC1, TRBC2, CD3E, CD3D, or CD3G e.g. TRAC), e.g., including a targeting domain listed in Table 1, Table 4, Table 5, Table 6e, Table 6f, or Table 6g;
  (d) An indel at or near a sequence of the gene encoding B2M or its regulatory elements, e.g., an indel at or near a target sequence of a gRNA including a targeting domain to B2M, e.g., including a targeting domain listed in Table 1 or Table 3;
  (e) Optionally, an indel at or near a sequence of the gene encoding CIITA or its regulatory elements, e.g., an indel at or near a target sequence of a gRNA including a targeting domain to CIITA, e.g., including a targeting domain listed in Table 1 or Table 6c; and
  (f) Optionally, an indel at or near a sequence of the gene encoding LILRB1 or its regulatory elements, e.g., an indel at or near a target sequence of a gRNA including a targeting domain to LILRB1, e.g., including a targeting domain listed in Table 6d;

Wherein the cell (or population of cells including said cell) expresses the CAR and, optionally, the NK inhibitory molecule, and exhibits reduced or eliminated expression and/or function of one or more of: i) a component of a TCR (e.g., TRAC, TRBC1 TRBC2, CD3D, CD3E or CD3G, e.g. TRAC), ii) B2M, iii) CIITA, and/or iv) LILRB1. In embodiments the targeting domain sequences of the gRNA molecules (as described herein) to a component of a TCR, B2M and CIITA include, for example, consist of the targeting domains listed in any combination listed in Table 33, Table 34 or Table 38, for example,
  a) Combination A1 to combination A72 of Table 33, for example, combination A1 to A4, combination A5 to A8, combination A37 to A40, or combination A41 to A44;
  b) Combination B1 to combination B84 of Table 34; or
  c) Combination F1 to combination F60 of Table 38, for example, any of combination F1 to F4, combination F5 to F8, combination F13 to F16, or combination F17 to F20.

In another aspect, the invention provides a cell including (e.g., a population of cells including a cell, e.g., more than one cell, including):
  (a) Nucleic acid sequence encoding a CAR, e.g., as described herein;
  (b) Optionally, nucleic acid sequence encoding an NK inhibitory molecule, e.g., as described herein, e.g., nucleic acid encoding an HLA-G as described herein;
  (c) An indel at or near a sequence of a gene encoding a component of a TCR (e.g., TRAC, TRBC1 TRBC2, CD3D, CD3E or CD3G, e.g. TRAC) or its regulatory elements, e.g., an indel at or near a target sequence of a gRNA including a targeting domain to a component of a TCR (e.g., TRAC, TRBC1 TRBC2, CD3D, CD3E or CD3G, e.g. TRAC), e.g., including a targeting domain listed in Table 1, Table 4, Table 5, Table 6e, Table 6f, or Table 6g;
  (d) An indel at or near a sequence of the gene encoding NLRC5 or its regulatory elements, e.g., an indel at or near a target sequence of a gRNA including a targeting domain to NLRC5, e.g., including a targeting domain listed in Table 1;
  (e) Optionally, an indel at or near a sequence of the gene encoding CIITA or its regulatory elements, e.g., an indel at or near a target sequence of a gRNA including a targeting domain to CIITA, e.g., including a targeting domain listed in Table 1 or Table 6c; and
  (f) Optionally, an indel at or near a sequence of the gene encoding LILRB1 or its regulatory elements, e.g., an indel at or near a target sequence of a gRNA including a targeting domain to LILRB1, e.g., including a targeting domain listed in Table 6d;

Wherein the cell (or population of cells including one or more of said cells) expresses the CAR and, optionally, the NK inhibitory molecule, and exhibits reduced or eliminated expression and/or function of one or more of: i) a component of a TCR (e.g., TRAC, TRBC1 TRBC2, CD3D, CD3E or CD3G, e.g. TRAC), ii) B2M, iii) NLRC5, and/or iv) LILRB1.

In another aspect, the invention provides a cell including (e.g., a population of cells including a cell, e.g., more than one cell, including):
  (a) Nucleic acid sequence encoding a CAR, e.g., as described herein;
  (b) An indel at or near a sequence of a gene encoding a component of a TCR (e.g., TRAC, TRBC1 TRBC2, CD3D, CD3E or CD3G, e.g. TRAC) or its regulatory elements, e.g., an indel at or near a target sequence of a gRNA including a targeting domain to a component of a TCR (e.g., TRAC, TRBC1 TRBC2, CD3D, CD3E or CD3G, e.g. TRAC), e.g., including a targeting domain listed in Table 1, Table 4, Table 5, Table 6e, Table 6f, or Table 6g; and
  (c) An indel at or near a sequence of the gene encoding FKBP1A or its regulatory elements, e.g., an indel at or near a target sequence of a gRNA including a targeting domain to FKBP1A, e.g., including a targeting domain listed in Table 1 or Table 6b;
Wherein the cell (or population of cells including a cell, e.g., more than one cell, including) expresses the CAR, and exhibits reduced or eliminated expression and/or function of one or more of: i) a component of a TCR (e.g., TRAC, TRBC1 TRBC2, CD3D, CD3E or CD3G, e.g. TRAC), and/or ii) FKBP12. In embodiments the targeting domain sequences of the gRNA molecules (as described herein) to a component of a TCR and FKBP1A include, for example, consist of the targeting domains listed in any combination listed in Table 35, Table 36 or Table 37, for example
  a) Combination C1 to combination C42 of Table 35;
  b) Combination D1 to combination D36 of Table 36, for example, combination D2, combination D4, combination D20, or combination D22; or
  c) Combination E1 to combination E30 of Table 37, for example, combination E2, combination E4, combination E8, or combination E10.

In another aspect, the invention provides a cell including (e.g., a population of cells including a cell, e.g., more than one cell, including):
  (a) Nucleic acid sequence encoding a CAR, e.g., as described herein;
  (b) Nucleic acid sequence encoding a rapamycin-resistant mTor, e.g., as described herein, e.g., nucleic acid sequence encoding an mTor including a S2035 mutation, e.g., an S20351 mutation; and;
  (c) An indel at or near a sequence of a gene encoding a component of a TCR (e.g., TRAC, TRBC1 TRBC2, CD3D, CD3E or CD3G, e.g. TRAC) or its regulatory elements, e.g., an indel at or near a target sequence of a gRNA including a targeting domain to a component of a TCR (e.g., TRAC, TRBC1 TRBC2, CD3D, CD3E or CD3G, e.g. TRAC), e.g., including a targeting domain listed in Table 1, Table 4, Table 5, Table 6e, Table 6f, or Table 6g;
Wherein the cell (or population of cells including said cell, e.g., more than one of said cell) expresses the CAR and the rapamycin-resistant mTor, and exhibits reduced or eliminated expression and/or function of a component of a TCR (e.g., TRAC, TRBC1 TRBC2, CD3D, CD3E or CD3G, e.g. TRAC).

In embodiments, that include an indel at or near a gene encoding a component of the TCR, B2M and CIITA, the targeting domain of the gRNA molecule to a component of the TCR, the targeting domain of the gRNA molecule to B2M, and the targeting domain of the gRNA molecule to CIIRA comprise, e.g., consists of, respectively: a) the targeting domain sequences for said gRNA molecules listed in any combination of A1 to A72 in Table 33; b) the targeting domain sequences for said gRNA molecules listed in any combination of F1 to F60 in Table 38; or c) the targeting domain sequence for each gRNA molecule listed in any combination of B1 to B84 in Table 34.

In embodiments, that include an indel at or near a gene encoding a component of the TCR and FKBP1A, the targeting domain of the gRNA molecule to a component of the TCR, and the targeting domain of the gRNA molecule(s) to FKBP1A comprise, e.g., consists of, respectively, a) the targeting domain sequences for said gRNA molecules listed in any combination of C1 to C42 in Table 35; b) the targeting domain sequences for said gRNA molecules listed in any combination of D1 to D36 in Table 36; or c) the targeting domain sequences for said gRNA molecules listed in any combination of E1 to E30 in Table 37.

In embodiments of any of the cell aspects and embodiments described above, each of said indels in said cell is made by introducing into said cell a gRNA molecule, e.g., more than one gRNA molecule, (e.g., a CRISPR system, e.g., more than one CRISPR system, including said gRNA molecule, e.g., each of said more than one gRNA molecules), each including a targeting domain which is complementary to a target sequence at or near each of said indels.

In another aspect, the invention provides a population of cells, wherein at least about 30%, for example, at least about 50%, for example, at least about 75%, for example, at least about 90% of the cells of the population are a cell of any of the aforementioned cell aspects or embodiments. In embodiments, in at least about 30% of said cells (e.g., in at least about 40%, e.g., in at least about 50%, e.g., in at least about 60%, e.g., in at least about 70%, e.g., in at least about 80%, e.g., in at least about 90%, e.g., in at least about 95%, e.g., in at least about 99% of said cells), each of said indels is a frameshift mutation. In embodiments, including in any of the aforementioned cell aspects and embodiments, the invention provides a cell (or population of cells) that includes an indel listed in FIG. 34A, FIG. 34B or FIG. 49. In embodiments, including in any of the aforementioned cell aspects and embodiments, the invention provides a cell (or population of cells) that includes an indel listed in FIG. 36 or FIG. 48. In embodiments, including in any of the aforementioned cell aspects and embodiments, the invention provides a cell (or population of cells) that includes an indel listed in FIG. 38, FIG. 41, FIG. 44 or FIG. 50. In embodiments, including in any of the aforementioned cell aspects and embodiments, the invention provides a cell (or population of cells) that includes an indel listed in FIG. 53.

In another aspect, the invention provides a population of cells that include a cell of any of the aforementioned cell aspects and embodiments. In embodiments, at least about 20% of the cells of the population of cells is a cell of any of the aforementioned cell aspects and embodiments. In embodiments, at least about 50% of the cells of the population of cells is a cell of any of the aforementioned cell aspects and embodiments. In embodiments, less than about 5%, e.g., less than about 1%, e.g., less than about of the cells of the population of cells includes an off-target indel. In embodiments, the cell of the population of cells is engineered to express a chimeric antigen receptor (CAR). In embodiments, the CAR is a CD19 CAR (for example, described herein), for example, a CD19 CAR including an antigen binding domain including any one of SEQ ID NO: 7883 to SEQ ID NO: 7898, or includes the sequence of SEQ ID NO: 7909 or SEQ ID NO: 7920. In other embodiments, the CAR is a BCMA CAR, for example, including an antigen recognition domain including any one of SEQ ID NO: 7939 to SEQ ID NO: 8112 or SEQ ID NO: 8155 to SEQ ID NO: 8166, e.g., including an antigen recognition domain including, e.g., consisting of, SEQ ID NO: 7949, for example, including any one of SEQ ID NO: 8549 to SEQ ID NO: 8621, e.g., including, e.g., consisting of, SEQ ID NO: 8559. In embodiments, the cell is an animal cell, for example, a mammalian, primate, or human cell, e.g., a human cell. In embodiments, the cell is an immune effector cell (e.g., a population of immune effector cells), for example, a T cell or NK cell, for example, a T cell, for example, a CD4+ T cell, a CD8+ T cell, or a combination thereof. In embodiments, the cell is allogeneic relative to a patient to be administered said cell, for example, the cell is isolated from a healthy human subject. In other embodiments, the cell is autologous relative to a patient to be administered said cell.

In another aspect, the invention provides a method of treating a disease, e.g., a cancer, in a patient in need thereof, including administering the cell of any of the aforementioned cell aspects and embodiments. In embodiments, particularly in embodiments in which expression or function of a target for an immunosuppressant has been reduced or eliminated, the method further includes administering an immunosuppressant, e.g., RAD001.

In another aspect, the invention provides a gRNA molecule as described herein (for example in any of the aforementioned gRNA molecule aspects and embodiments), a composition as described herein (for example in any of the aforementioned composition aspects and embodiments), a nucleic acid as described herein (for example in any of the aforementioned nucleic acid aspects and embodiments), a vector as described herein (for example in any of the aforementioned vector aspects and embodiments), or a cell (or population of cells) as described herein (for example in any of the aforementioned cell (e.g., modified cell) or population of cells aspects and embodiments), for use as a medicament.

In another aspect, the invention provides a gRNA molecule as described herein (for example in any of the aforementioned gRNA molecule aspects and embodiments), a composition as described herein (for example in any of the aforementioned composition aspects and embodiments), a nucleic acid as described herein (for example in any of the aforementioned nucleic acid aspects and embodiments), a vector as described herein (for example in any of the aforementioned vector aspects and embodiments), or a cell (or population of cells) as described herein (for example in any of the aforementioned cell (e.g., modified cell) or population of cells aspects and embodiments), for use in the manufacture of a medicament.

In another aspect, the invention provides a gRNA molecule as described herein (for example in any of the aforementioned gRNA molecule aspects and embodiments), a composition as described herein (for example in any of the aforementioned composition aspects and embodiments), a nucleic acid as described herein (for example in any of the aforementioned nucleic acid aspects and embodiments), a vector as described herein (for example in any of the aforementioned vector aspects and embodiments), or a cell (or population of cells) as described herein (for example in any of the aforementioned cell (e.g., modified cell) or population of cells aspects and embodiments), for use in the treatment of a disease.

In another aspect, the invention provides a gRNA molecule as described herein (for example in any of the aforementioned gRNA molecule aspects and embodiments), a composition as described herein (for example in any of the aforementioned composition aspects and embodiments), a nucleic acid as described herein (for example in any of the aforementioned nucleic acid aspects and embodiments), a vector as described herein (for example in any of the aforementioned vector aspects and embodiments), or a cell (or population of cells) as described herein (for example in any of the aforementioned cell (e.g., modified cell) or population of cells aspects and embodiments), for use in the treatment of a disease, wherein the disease is a disease associated with expression of a tumor antigen, e.g., a proliferative disease, a precancerous condition, a cancer, and a non-cancer related indication associated with expression of the tumor antigen.

In another aspect, the invention provides a gRNA molecule as described herein (for example in any of the aforementioned gRNA molecule aspects and embodiments), a composition as described herein (for example in any of the aforementioned composition aspects and embodiments), a nucleic acid as described herein (for example in any of the aforementioned nucleic acid aspects and embodiments), a vector as described herein (for example in any of the aforementioned vector aspects and embodiments), or a cell (or population of cells) as described herein (for example in any of the aforementioned cell (e.g., modified cell) or population of cells aspects and embodiments), for use in the treatment of a cancer, wherein the cancer is a hematologic cancer selected from the group consisting of chronic lymphocytic leukemia (CLL), acute leukemias, acute lymphoid leukemia (ALL), B-cell acute lymphoid leukemia (B-ALL), T-cell acute lymphoid leukemia (T-ALL), chronic myelogenous leukemia (CML), acute myeloid leukemia (AML), B cell prolymphocytic leukemia, blastic plasmacytoid dendritic cell neoplasm, Burkitt's lymphoma, diffuse large B cell lymphoma, follicular lymphoma, hairy cell leukemia, small cell- or a large cell-follicular lymphoma, malignant lymphoproliferative conditions, MALT lymphoma, mantle cell lymphoma, marginal zone lymphoma, multiple myeloma, myelodysplasia and myelodysplastic syndrome, non-Hodgkin's lymphoma, Hodgkin's lymphoma, plasmablastic lymphoma, plasmacytoid dendritic cell neoplasm, Waldenstrom macroglobulinemia, and pre-leukemia.

In another aspect, the invention provides a gRNA molecule as described herein (for example in any of the aforementioned gRNA molecule aspects and embodiments), a composition as described herein (for example in any of the aforementioned composition aspects and embodiments), a nucleic acid as described herein (for example in any of the aforementioned nucleic acid aspects and embodiments), a vector as described herein (for example in any of the aforementioned vector aspects and embodiments), or a cell (or population of cells) as described herein (for example in any of the aforementioned cell (e.g., modified cell) or population of cells aspects and embodiments), for use in the treatment of a cancer, e.g., wherein the cancer is selected from the group consisting of mesothelioma, adenocarcinoma, glioblastoma, colon cancer, rectal cancer, renal-cell carcinoma, liver cancer, non-small cell carcinoma of the lung, cancer of the small intestine, cancer of the esophagus, melanoma, bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, carcinoma of the fallopian tubes, carcinoma of the endometrium, carcinoma of the cervix, carcinoma of the vagina, carcinoma of the vulva, Hodgkin's Disease, non-Hodgkin's lymphoma, cancer of the endocrine system, cancer of the thyroid gland, cancer of the parathyroid gland, cancer of the adrenal gland, sarcoma of soft tissue, cancer of the urethra, cancer of the penis, solid tumors of childhood, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers, combinations of said cancers, and metastatic lesions of said cancers.

In addition to the specific features of the invention described above, it is contemplated that the following general features of gRNA molecules, Cas9 molecules and cells are applicable to any aspect and embodiment of the invention described herein, including those aspects and embodiments described above.

In any of the aspects and embodiments disclosed herein, the gRNA molecule (e.g., the gRNA molecule, or combination of gRNA molecules, including a targeting domain described herein) may include one or more of the following features:

In certain embodiments, the gRNA molecule (e.g., the gRNA molecule, or one or more gRNA molecules of a combination of gRNA molecules, including a targeting domain described herein) is a dgRNA molecule, wherein the targeting domain and the tracr are disposed on separate nucleic acid molecules. In embodiments, the crRNA includes, from 5' to 3', [targeting domain]—:

a) SEQ ID NO: 6584;
b) SEQ ID NO: 6585;
c) SEQ ID NO: 6605;
d) SEQ ID NO: 6606;
e) SEQ ID NO: 6607;
f) SEQ ID NO: 6608; or
g) SEQ ID NO: 7806. In a preferred embodiment, the crRNA includes, from 5' to 3', [targeting domain]-[SEQ ID NO: 6607]. In embodiments, the tracr includes more than 15, e.g., 20 or more, 30 or more, 40 or more, 50 or more, 60 or more, 70 or more, or 80 or more, nucleotides of the *S. Pyogenes* tracr sequence (GUUG-GAACCAUUCAAAACAG-CAUAGCAAGUUAAAAUAAGGCUAGU-CCGUUAUCAACUUG AAAAAGUGGCACCGAGUCGGUGC). In embodiments, the tracr additionally includes 1 or more, e.g., 1, 2, 3, 4, 5, 6, or 7, e.g., preferably 4 or 7, U nucleotides at the 3' end. In preferred dgRNA embodiments, the tracr includes SEQ ID NO: 7820. In embodiments, the tracr additionally includes 1 or more, e.g., 1, 2, 3, 4, 5, 6, or 7, e.g., preferably 4 or 7, U nucleotides at the 3' end. In preferred dgRNA embodiments, the tracr includes, e.g., consists of, SEQ ID NO: 6660. In preferred dgRNA embodiments, the crRNA includes, e.g., consists of, [targeting domain]-SEQ ID NO: 6607, and the tracr includes SEQ ID NO: 7820, e.g., includes, e.g., consists of, SEQ ID NO: 6660.

In other embodiments, the gRNA molecule (e.g., the gRNA molecule, or one or more gRNA molecules of a combination of gRNA molecules, including a targeting domain described herein) is a sgRNA molecule, wherein the targeting domain and the tracr are disposed a single nucleic acid molecule. In embodiments, the sgRNA molecule includes, e.g., consists of: [targeting domain]—

(a) SEQ ID NO: 6601;
(b) SEQ ID NO: 6602;
(c) SEQ ID NO: 6603;
(d) SEQ ID NO: 6604; or
(e) any of (a) to (d), above, further including, at the 3' end, 1, 2, 3, 4, 5, 6 or 7 uracil (U) nucleotides. In a preferred embodiment, the sgRNA molecule includes [targeting domain]-SEQ ID NO: 6601. In a preferred embodiment, the sgRNA molecule includes, e.g., consists of, [targeting domain]-SEQ ID NO: 7811.

In embodiments, including in any of the aforementioned aspects and embodiments, one or more of the nucleic acid molecules of the gRNA molecule described herein, e.g., all of the nucleic acid molecules of the gRNA molecule described herein, do not include a modification to a nucleotide or internucleotide bond. In other embodiments, including in any of the aforementioned aspects and embodiments, one or more of the nucleic acid molecules of the gRNA molecule described herein include one or more modifications to a nucleotide or internucleotide bond, e.g. as described herein. In embodiments, said modification includes a 2' O-methyl modification. In embodiments, said modification includes a phosphorothioate modification. In embodiments, said modification includes a 2' O-methyl modification at each of the 1, 2, 3 or more, e.g., 3, 3' nucleotides of the nucleic acid of the gRNA molecule. In embodiments, said modification includes a 2' O-methyl modification at each of the $4^{th}$-to-terminal, $3^{rd}$-to-terminal, and $2^{nd}$-to-terminal 3' nucleotides of the nucleic acid of the gRNA molecule. In embodiments, said modification includes a 2' O-methyl modification at each of the 1, 2, 3 or more, e.g., 3, 5' nucleotides of the nucleic acid of the gRNA molecule. In embodiments, said modification includes a 2' O-methyl modification at each of the $4^{th}$-to-terminal, $3^{rd}$-to-terminal, and $2^{nd}$-to-terminal 3' nucleotides of the nucleic acid of the gRNA molecule, and a 2' O-methyl modification at each of the 1, 2, 3 or more, e.g., 3, 5' nucleotides of the nucleic acid of the gRNA molecule. In embodiments, said modification includes one or more, e.g., 1, 2, 3, or more, e.g., 3, phosphorothioate bonds at the 3' end of the nucleic acid molecule of the gRNA. In embodiments, said modification includes one or more, e.g., 1, 2, 3, or more, e.g., 3, phosphorothioate bonds at the 5' end of the nucleic acid molecule of the gRNA. In embodiments, said modification includes one or more, e.g., 1, 2, 3, or more, e.g., 3, phosphorothioate bonds at the 3' end and at the 5' end of the nucleic acid molecule of the gRNA. In embodiments involving a dgRNA molecule, both the molecule including the tracr and the molecule including the crRNA are modified as described herein. In other embodiments involving a dgRNA molecule, the molecule including the tracr is unmodified, and the molecule including the crRNA is modified as described herein. In other embodiments involving a dgRNA molecule, the molecule including the crRNA is unmodified, and the molecule including the tracr is modified as described herein.

In aspects of the invention that include more than one gRNA molecule, each gRNA molecule can independently be a dgRNA molecule or a sgRNA molecule, e.g., as described herein. In embodiments, all of the gRNA molecules of a combination described herein are dgRNA molecules. In embodiments, all of the gRNA molecules of a combination described herein are sgRNA molecules. In embodiments, one or more of the gRNA molecules of a combination described herein are dgRNA molecules, and one or more of the other gRNA molecules of a combination described herein are sgRNA molecules.

In embodiments, the gRNA molecule of the invention is a gRNA molecule that produces an indel at or near the target sequence of the gRNA when introduced into a cell described herein. In embodiments, the gRNA molecule of the invention is a gRNA molecule that produces an indel in at least about 70%, e.g., at least about 80%, e.g., at least about 90%, e.g., at least about 95%, e.g., at least about 96%, e.g., at least about 97%, e.g., at least about 98%, e.g., at least about 99%, or more, of the cells, e.g., as described herein, of a population of cells to which the gRNA molecule is introduced. In embodiments, the indel frequency is measured by NGS, e.g., as described herein. In embodiments, said indel or indels are or include frameshift mutations. In embodiments, the gRNA molecule of the invention is a gRNA molecule that produces a frameshift mutation in at least about 30%, e.g., at least about 40%, e.g., at least about 50%, e.g., at least about 60%, e.g., at least about 70%, e.g., at least about 75%, e.g., at least about 80%, e.g., at least about 85%, e.g., at least about 90%, e.g., at least about 95%, or more, of the cells, e.g., as described herein, of a population of cells to which the gRNA molecule is introduced. In embodiments, the frameshift mutation frequency is measured by NGS, e.g., as described herein. In embodiments, said indel, indel frequency, frameshift mutation and/or frameshift mutation frequency is measured in the cell (or population or cells) after introduction of the gRNA molecule as an RNP with a Cas9 molecule described herein. In embodiments, said indel, indel frequency, frameshift mutation and/or frameshift mutation frequency is measured in the cell (or population or cells) after introduction of the gRNA molecule by electroporation.

In embodiments, the gRNA molecule of the invention is a gRNA molecule that produces an indel at an off-target site with at least a 50-fold, e.g., at least 100-fold, e.g., at least 1000-fold, lower frequency than at or near the target sequence of the gRNA, when introduced into a cell or population of cells described herein. In preferred embodiments, the gRNA does not produce a detectable indel at any off-target site when introduced into a cell or population of cells described herein. In embodiments, the off-target indel analysis is measured by targeted off-target sequencing of predicted off-target binding sites, e.g., as described herein. In embodiments, off-target indel analysis is measured by nucleotide insertional analysis, e.g., as described herein. In embodiments, the off-target analysis is measured in the cell (or population or cells) after introduction of the gRNA molecule as an RNP with a Cas9 molecule described herein. In embodiments, the off-target analysis is measured in the cell (or population or cells) after introduction of the gRNA molecule by electroporation.

In embodiments, the RNP or combination of RNPs is delivered to the cells by a single electroporation. In embodiments the cells of the invention are subjected to only a single electroporation step.

In aspects and embodiments of the invention that include a combination of gRNA molecules, each of the gRNA molecules of the combination can independently include any of the aforementioned features.

In any of the aspects and embodiments disclosed herein, the Cas9 molecule may include one or more of the following features:

In aspects the Cas9 molecule is an *S. Pyogenes* Cas9, e.g., a modified or unmodified *S. Pyogenes* Cas9 molecule as described herein. In embodiments, the Cas9 molecule includes SEQ ID NO: 6611. In other embodiments, the Cas9 molecule includes, e.g., consists of, SEQ ID NO: 7821. In other embodiments, the Cas9 molecule includes, e.g., consists of, SEQ ID NO: 7822. In other embodiments, the Cas9 molecule includes, e.g., consists of, SEQ ID NO: 7823. In other embodiments, the Cas9 molecule includes, e.g., consists of, SEQ ID NO: 7824. In other embodiments, the Cas9 molecule includes, e.g., consists of, SEQ ID NO: 7825. In other embodiments, the Cas9 molecule includes, e.g., consists of, SEQ ID NO: 7826. In other embodiments, the Cas9 molecule includes, e.g., consists of, SEQ ID NO: 7827. In other embodiments, the Cas9 molecule includes, e.g., consists of, SEQ ID NO: 7828. In other embodiments, the Cas9 molecule includes, e.g., consists of, SEQ ID NO: 7829. In other embodiments, the Cas9 molecule includes, e.g., consists of, SEQ ID NO: 7830. In other embodiments, the Cas9 molecule includes, e.g., consists of, SEQ ID NO: 7831. Preferred Cas9 molecules are Cas9 molecules that include, e.g., consist of, SEQ ID NO: 7821, SEQ ID NO: 7822, SEQ ID NO: 7825 and SEQ ID NO: 7828.

In aspects and embodiments that include one or more RNP complexes, e.g., one or more RNP complexes that include a Cas9 molecule described herein, each of said RNP complexes is at a concentration of less than about 10 uM, e.g., less than about 3 uM, e.g., less than about 1 uM, e.g., less than about 0.5 uM, e.g., less than about 0.3 uM, e.g., less than about 0.1 uM. In embodiments, said concentration is the concentration of the RNP complex in the composition including the cell (e.g., population of cells), e.g., as described herein, to which the RNP is to be introduced, e.g., as described herein, e.g., by electroporation. In embodiments, the media of the composition is suitable for electroporation.

In aspects and embodiments of the invention that include a combination of gRNA molecules, for example a combination of RNPs that include different gRNA molecules, each of the Cas9 molecules of the combination can independently include any of the aforementioned features.

In any of the aspects and embodiments disclosed herein, the cell (e.g., population of cells) may include one or more of the following features:

In aspects, the cell (e.g., population of cells) includes one or more cells that have reduced or eliminated expression of a component of the T-cell receptor (TCR). In embodiments, the reduced or eliminated expression of a component of the T-cell receptor (TCR) includes reduced or eliminated expression of TRAC. In embodiments, the reduced or eliminated expression of a component of the T-cell receptor (TCR) includes reduced or eliminated expression of TRBC1. In embodiments, the reduced or eliminated expression of a component of the T-cell receptor (TCR) includes reduced or eliminated expression of TRBC2. In embodiments, the reduced or eliminated expression of a component of the T-cell receptor (TCR) includes reduced or eliminated expression of CD3G. In embodiments, the reduced or eliminated expression of a component of the T-cell receptor (TCR) includes reduced or eliminated expression of CD3D. In embodiments, the reduced or eliminated expression of a component of the T-cell receptor (TCR) includes reduced or eliminated expression of CD3E. In embodiments, said reduced or eliminated expression of said component of the TCR is the result of introduction of one or more, e.g., one or two, e.g., one gRNA molecule described herein to said component of the TCR into said cell. In embodiments, the cell includes an indel, e.g., a frameshift mutation, e.g., as described herein, at or near the target sequence of a targeting domain of a gRNA molecule to said component of the TCR. In embodiments, the population of cells includes at least about 50%, e.g., at least about 60%, e.g., at least about 70%, e.g., at least about 80%, e.g., at least about 90% or more cells (as described herein) which exhibit reduced or eliminated expression of a component of the TCR. In embodiments, said reduced or eliminated expression of a component of the TCR is as measured by flow cytometry, e.g., as described herein.

In aspects, (including either alternatively, or in addition to, the reduced or eliminated expression of a component of the TCR) the cell (e.g., population of cells) includes one or more cells that have reduced or eliminated expression of beta-2 microglobulin (B2M). In embodiments, said reduced or eliminated expression of said B2M is the result of introduction of one or more, e.g., one or two, e.g., one gRNA molecule described herein to B2M into said cell. In embodiments, the cell includes an indel, e.g., a frameshift mutation, e.g., as described herein, at or near the target sequence of a targeting domain of a gRNA molecule to said B2M. In embodiments, the population of cells includes at least about 50%, e.g., at least about 60%, e.g., at least about 70%, e.g., at least about 80%, e.g., at least about 90% or more cells (as described herein) which exhibit reduced or eliminated expression of B2M. In embodiments, said reduced or eliminated expression of B2M is as measured by flow cytometry, e.g., as described herein.

In aspects, (including either alternatively, or in addition to, the reduced or eliminated expression of a component of the TCR and/or B2M) the cell (e.g., population of cells) includes one or more cells that have reduced or eliminated expression of CIITA. In embodiments, said reduced or eliminated expression of said CIITA is the result of introduction of one or more, e.g., one or two, e.g., one gRNA molecule to said CIITA described herein into said cell. In embodiments, the cell includes an indel, e.g., a frameshift mutation, e.g., as described herein, at or near the target sequence of a targeting domain of a gRNA molecule to said CIITA. In embodiments, the population of cells includes at least about 50%, e.g., at least about 60%, e.g., at least about 70%, e.g., at least about 80%, e.g., at least about 90% or more cells (as described herein) which exhibit reduced or eliminated expression of CIITA. In embodiments, said reduced or eliminated expression of B2M is as measured by flow cytometry, e.g., as described herein.

In aspects, (including either alternatively, or in addition to, the reduced or eliminated expression of a component of the TCR) the cell (e.g., population of cells) includes one or more cells that have reduced or eliminated expression of a target of an immunosuppressant, e.g., FKBP1A. In embodiments, said reduced or eliminated expression of said FKBP1A is the result of introduction of one or more, e.g., one or two, e.g., one, gRNA molecule described herein to said FKBP1A into said cell. In embodiments, the cell includes an indel, e.g., a frameshift mutation, e.g., as described herein, at or near the target sequence of a targeting domain of a gRNA molecule to said FKBP1A. In embodiments, the population of cells includes at least about 50%, e.g., at least about 60%, e.g., at least about 70%, e.g., at least about 80%, e.g., at least about 90% or more cells (as described herein) which exhibit reduced or eliminated expression of FKBP1A. In embodiments, said reduced or eliminated expression of FKBP1A is as measured by flow cytometry, e.g., as described herein.

In some aspects, it is desired that the cell exhibits reduced or eliminated expression of more than one gene. In an aspect, the cell exhibits reduced or eliminated expression of a component of the TCR (e.g., TRAC, TRBC1, TRBC2, CD3E, CD3G, and/or CD3D), reduced or eliminated expression of B2M, and reduced or eliminated expression of CIITA. In embodiments, the reduced or eliminated expression results from introduction into the cell a combination of gRNA molecules, wherein the gRNA molecules of the combination include the targeting domain sequences listed in any of combinations A1 to A72. In embodiments, the reduced or eliminated expression results from introduction into the cell a combination of gRNA molecules, wherein the gRNA molecules of the combination include the targeting domain sequences listed in any of combinations B1 to B84. In embodiments, said cell includes an indel, e.g., a frameshift mutation, at or near the target sequences of each of the gRNA molecule targeting domains listed in Table 33, Table 34 or Table 38 (e.g., the gRNA molecules in any of combinations A1 to A72, B1 to B84, or F1 to F60).

In some aspects, it is desired that the cell exhibits reduced or eliminated expression of more than one gene. In an aspect, the cell exhibits reduced or eliminated expression of a component of the TCR (e.g., TRAC, TRBC1, TRBC2, CD3E, CD3G, and/or CD3D), and reduced or eliminated expression of a target of an immunosuppressant, e.g., FKBP1A. In embodiments, the reduced or eliminated expression results from introduction into the cell a combination of gRNA molecules, wherein the gRNA molecules of the combination include the targeting domain sequences listed in any of combinations C1 to C42. In embodiments, the reduced or eliminated expression results from introduction into the cell a combination of gRNA molecules, wherein the gRNA molecules of the combination include the targeting domain sequences listed in any of combinations D1 to D36. In embodiments, said cell includes an indel, e.g., a frameshift mutation, at or near the target sequences of each of the gRNA molecule targeting domains listed in Table 35, Table 36 or Table 37 (e.g., the gRNA molecules in any of combinations C1 to C42, D1 to D36, or E1 to E30).

In preferred embodiments in which it is intended to reduce or eliminate expression of both a component of the T cell receptor, e.g., TRAC, and B2M (including embodiments when expression or function of an additional target, e.g., more than one additional target, e.g., CIITA, is also reduced or eliminated), the gRNA molecule which targets TRAC is selected from SEQ ID NO: 7833, SEQ ID NO: 7834, SEQ ID NO: 7835, a dgRNA comprising, e.g., consisting of, SEQ ID NO: 7836 and SEQ ID NO: 6660, a dgRNA comprising, e.g., consisting of, SEQ ID NO: 7837 and SEQ ID NO: 6660, a dgRNA comprising, e.g., consisting of, SEQ ID NO: 7836 and SEQ ID NO: 10798, and a dgRNA comprising, e.g., consisting of, SEQ ID NO: 7837 and SEQ ID NO: 10798, and the gRNA molecule which targets B2M is selected from SEQ ID NO: 7853, SEQ ID NO: 7854, SEQ ID NO: 7855, a dgRNA comprising, e.g., consisting of, SEQ ID NO: 7856 and SEQ ID NO: 6660, a dgRNA comprising, e.g., consisting of, SEQ ID NO: 7857 and SEQ ID NO: 6660, a dgRNA comprising, e.g., consisting of, SEQ ID NO: 7856 and SEQ ID NO: 10798, and a dgRNA comprising, e.g., consisting of, SEQ ID NO: 7857 and SEQ ID NO: 10798. As described herein, in embodiments of any of the combinations, each of said gRNA molecules is provided as an RNP with a Cas9 molecule, e.g., a Cas9 molecule described herein.

In preferred embodiments in which it is intended to reduce or eliminate expression of both a component of the T cell receptor, e.g., TRAC, and B2M (including embodiments when expression or function of an additional target, e.g., more than one additional target, e.g., CIITA, is also reduced or eliminated), the gRNA molecule which targets TRAC is selected from SEQ ID NO: 7833, SEQ ID NO: 7834, SEQ ID NO: 7835, a dgRNA comprising, e.g., consisting of, SEQ ID NO: 7836 and SEQ ID NO: 6660, a dgRNA comprising, e.g., consisting of, SEQ ID NO: 7837 and SEQ ID NO: 6660, a dgRNA comprising, e.g., consisting of, SEQ ID NO: 7836 and SEQ ID NO: 10798, and a dgRNA comprising, e.g., consisting of, SEQ ID NO: 7837 and SEQ ID NO: 10798, and the gRNA molecule which targets B2M is selected from SEQ ID NO: 7858, SEQ ID NO: 7859, SEQ ID NO: 7860, a dgRNA comprising, e.g., consisting of, SEQ ID NO: 7861 and SEQ ID NO: 6660, a dgRNA comprising, e.g., consisting of, SEQ ID NO: 7862 and SEQ ID NO: 6660, a dgRNA comprising, e.g., consisting of, SEQ ID NO: 7861 and SEQ ID NO: 10798, and a dgRNA comprising, e.g., consisting of, SEQ ID NO: 7862 and SEQ ID NO: 10798. As described herein, in embodiments of any of the combinations, each of said gRNA molecules is provided as an RNP with a Cas9 molecule, e.g., a Cas9 molecule described herein.

In preferred embodiments in which it is intended to reduce or eliminate expression of both a component of the T cell receptor, e.g., TRAC, and B2M (including embodiments when expression or function of an additional target, e.g., more than one additional target, e.g., CIITA, is also reduced or eliminated), the gRNA molecule which targets TRAC is selected from SEQ ID NO: 7838, SEQ ID NO: 7839, SEQ ID NO: 7840, a dgRNA comprising, e.g., consisting of, SEQ ID NO: 7841 and SEQ ID NO: 6660, a dgRNA comprising, e.g., consisting of, SEQ ID NO: 7842 and SEQ ID NO: 6660, a dgRNA comprising, e.g., consisting of, SEQ ID NO: 7841 and SEQ ID NO: 10798, and a dgRNA comprising, e.g., consisting of, SEQ ID NO: 7842 and SEQ ID NO: 10798, and the gRNA molecule which targets B2M is selected from SEQ ID NO: 7853, SEQ ID NO: 7854, SEQ ID NO: 7855, a dgRNA comprising, e.g., consisting of, SEQ ID NO: 7856 and SEQ ID NO: 6660, a dgRNA comprising, e.g., consisting of, SEQ ID NO: 7857 and SEQ ID NO: 6660, a dgRNA comprising, e.g., consisting of, SEQ ID NO: 7856 and SEQ ID NO: 10798, and a dgRNA comprising, e.g., consisting of, SEQ ID NO: 7857 and SEQ ID NO: 10798. As described herein, in embodiments of any of the combinations, each of said gRNA molecules is provided as an RNP with a Cas9 molecule, e.g., a Cas9 molecule described herein.

In preferred embodiments in which it is intended to reduce or eliminate expression of both a component of the T cell receptor, e.g., TRAC, and B2M (including embodiments when expression or function of an additional target, e.g., more than one additional target, e.g., CIITA, is also reduced or eliminated), the gRNA molecule which targets TRAC is selected from SEQ ID NO: 7838, SEQ ID NO: 7839, SEQ ID NO: 7840, a dgRNA comprising, e.g., consisting of, SEQ ID NO: 7841 and SEQ ID NO: 6660, a dgRNA comprising, e.g., consisting of, SEQ ID NO: 7842 and SEQ ID NO: 6660, a dgRNA comprising, e.g., consisting of, SEQ ID NO: 7841 and SEQ ID NO: 10798, and a dgRNA comprising, e.g., consisting of, SEQ ID NO: 7842 and SEQ ID NO: 10798, and the gRNA molecule which targets B2M is selected from SEQ ID NO: 7858, SEQ ID NO: 7859, SEQ ID NO: 7860, a dgRNA comprising, e.g., consisting of, SEQ ID NO: 7861 and SEQ ID NO: 6660, a dgRNA comprising, e.g., consisting of, SEQ ID NO: 7862 and SEQ ID NO: 6660, a dgRNA comprising, e.g., consisting of, SEQ ID NO: 7861 and SEQ ID NO: 10798, and a dgRNA comprising, e.g., consisting of, SEQ ID NO: 7862 and SEQ ID NO: 10798. As described herein, in embodiments of any of the combinations, each of said gRNA molecules is provided as an RNP with a Cas9 molecule, e.g., a Cas9 molecule described herein.

In preferred embodiments in which it is intended to reduce or eliminate expression of both a component of the T cell receptor, e.g., TRBC, and B2M (including embodiments when expression or function of an additional target, e.g., more than one additional target, e.g., CIITA, is also reduced or eliminated), the gRNA molecule which targets TRBC is selected from SEQ ID NO: 7843, SEQ ID NO: 7844, SEQ ID NO: 7845, a dgRNA comprising, e.g., consisting of, SEQ ID NO: 7846 and SEQ ID NO: 6660, a dgRNA comprising, e.g., consisting of, SEQ ID NO: 7847 and SEQ ID NO: 6660, a dgRNA comprising, e.g., consisting of, SEQ ID NO: 7846 and SEQ ID NO: 10798, and a dgRNA comprising, e.g., consisting of, SEQ ID NO: 7847 and SEQ ID NO: 10798, and the gRNA molecule which targets B2M is selected from SEQ ID NO: 7853, SEQ ID NO: 7854, SEQ ID NO: 7855, a dgRNA comprising, e.g., consisting of, SEQ ID NO: 7856 and SEQ ID NO: 6660, a dgRNA comprising, e.g., consisting of, SEQ ID NO: 7857 and SEQ ID NO: 6660, a dgRNA comprising, e.g., consisting of, SEQ ID NO: 7856 and SEQ ID NO: 10798, and a dgRNA comprising, e.g., consisting of, SEQ ID NO: 7857 and SEQ ID NO: 10798. As described herein, in embodiments of any of the combinations, each of said gRNA molecules is provided as an RNP with a Cas9 molecule, e.g., a Cas9 molecule described herein.

In preferred embodiments in which it is intended to reduce or eliminate expression of both a component of the T cell receptor, e.g., TRBC, and B2M (including embodiments when expression or function of an additional target, e.g., more than one additional target, e.g., CIITA, is also reduced or eliminated), the gRNA molecule which targets TRBC is selected from SEQ ID NO: 7843, SEQ ID NO: 7844, SEQ ID NO: 7845, a dgRNA comprising, e.g., consisting of, SEQ ID NO: 7846 and SEQ ID NO: 6660, a dgRNA comprising, e.g., consisting of, SEQ ID NO: 7847 and SEQ ID NO: 6660, a dgRNA comprising, e.g., consisting of, SEQ ID NO: 7846 and SEQ ID NO: 10798, and a dgRNA comprising, e.g., consisting of, SEQ ID NO: 7847 and SEQ ID NO: 10798, and the gRNA molecule which targets B2M is selected from SEQ ID NO: 7858, SEQ ID NO: 7859, SEQ ID NO: 7860, a dgRNA comprising, e.g., consisting of, SEQ ID NO: 7861 and SEQ ID NO: 6660, a dgRNA comprising, e.g., consisting of, SEQ ID NO: 7862 and SEQ ID NO: 6660, a dgRNA comprising, e.g., consisting of, SEQ ID NO: 7861 and SEQ ID NO: 10798, and a dgRNA comprising, e.g., consisting of, SEQ ID NO: 7862 and SEQ ID NO: 10798. As described herein, in embodiments of any of the combinations, each of said gRNA molecules is provided as an RNP with a Cas9 molecule, e.g., a Cas9 molecule described herein.

In preferred embodiments in which it is intended to reduce or eliminate expression of both a component of the T cell receptor, e.g., TRBC, and B2M (including embodiments when expression or function of an additional target, e.g., more than one additional target, e.g., CIITA, is also reduced or eliminated), the gRNA molecule which targets TRBC is selected from SEQ ID NO: 7848, SEQ ID NO: 7849, SEQ ID NO: 7850, a dgRNA comprising, e.g., consisting of, SEQ ID NO: 7851 and SEQ ID NO: 6660, a dgRNA comprising, e.g., consisting of, SEQ ID NO: 7852 and SEQ ID NO: 6660, a dgRNA comprising, e.g., consisting of, SEQ ID NO: 7851 and SEQ ID NO: 10798, and a dgRNA comprising, e.g., consisting of, SEQ ID NO: 7852 and SEQ ID NO: 10798, and the gRNA molecule which targets B2M is selected from SEQ ID NO: 7853, SEQ ID NO: 7854, SEQ ID NO: 7855, a dgRNA comprising, e.g., consisting of, SEQ ID NO: 7856 and SEQ ID NO: 6660, a dgRNA comprising, e.g., consisting of, SEQ ID NO: 7857 and SEQ ID NO: 6660, a dgRNA comprising, e.g., consisting of, SEQ ID NO: 7856 and SEQ ID NO: 10798, and a dgRNA comprising, e.g., consisting of, SEQ ID NO: 7857 and SEQ ID NO: 10798. As described herein, in embodiments of any of the combinations, each of said gRNA molecules is provided as an RNP with a Cas9 molecule, e.g., a Cas9 molecule described herein.

In preferred embodiments in which it is intended to reduce or eliminate expression of both a component of the T cell receptor, e.g., TRBC, and B2M (including embodiments when expression or function of an additional target, e.g., more than one additional target, e.g., CIITA, is also reduced or eliminated), the gRNA molecule which targets TRBC is selected from SEQ ID NO: 7848, SEQ ID NO: 7849, SEQ ID NO: 7850, a dgRNA comprising, e.g., consisting of, SEQ ID NO: 7851 and SEQ ID NO: 6660, a dgRNA comprising, e.g., consisting of, SEQ ID NO: 7852 and SEQ ID NO: 6660, a dgRNA comprising, e.g., consisting of, SEQ ID NO: 7851 and SEQ ID NO: 10798, and a dgRNA comprising, e.g., consisting of, SEQ ID NO: 7852 and SEQ ID NO: 10798, and the gRNA molecule which targets B2M is selected from SEQ ID NO: 7858, SEQ ID NO: 7859, SEQ ID NO: 7860, a dgRNA comprising, e.g., consisting of, SEQ ID NO: 7861 and SEQ ID NO: 6660, a dgRNA comprising, e.g., consisting of, SEQ ID NO: 7862 and SEQ ID NO: 6660, a dgRNA comprising, e.g., consisting of, SEQ ID NO: 7861 and SEQ ID NO: 10798, and a dgRNA comprising, e.g., consisting of, SEQ ID NO: 7862 and SEQ ID NO: 10798. As described herein, in embodiments of any of the combinations, each of said gRNA molecules is provided as an RNP with a Cas9 molecule, e.g., a Cas9 molecule described herein.

In preferred embodiments in which it is intended to reduce or eliminate expression of both a component of the T cell receptor, e.g., TRAC, and FKBP1A (including embodiments when expression or function of an additional target, e.g., more than one additional target, is also reduced or eliminated), the gRNA molecule which targets TRAC is selected from SEQ ID NO: 7833, SEQ ID NO: 7834, SEQ ID NO: 7835, a dgRNA comprising, e.g., consisting of, SEQ ID NO: 7836 and SEQ ID NO: 6660, a dgRNA comprising, e.g., consisting of, SEQ ID NO: 7837 and SEQ ID NO: 6660, a dgRNA comprising, e.g., consisting of, SEQ ID NO: 7836 and SEQ ID NO: 10798, and a dgRNA comprising, e.g., consisting of, SEQ ID NO: 7837 and SEQ ID NO: 10798, and the gRNA molecule which targets FKBP1A is selected from SEQ ID NO: 7863, SEQ ID NO: 7864, SEQ ID NO: 7865, a dgRNA comprising, e.g., consisting of, SEQ ID NO: 7866 and SEQ ID NO: 6660, a dgRNA comprising, e.g., consisting of, SEQ ID NO: 7867 and SEQ ID NO: 6660, a dgRNA comprising, e.g., consisting of, SEQ ID NO: 7866 and SEQ ID NO: 10798, and a dgRNA comprising, e.g., consisting of, SEQ ID NO: 7867 and SEQ ID NO: 10798. As described herein, in embodiments of any of the combinations, each of said gRNA molecules is provided as an RNP with a Cas9 molecule, e.g., a Cas9 molecule described herein.

In preferred embodiments in which it is intended to reduce or eliminate expression of both a component of the T cell receptor, e.g., TRAC, and FKBP1A (including embodiments when expression or function of an additional target, e.g., more than one additional target, is also reduced or eliminated), the gRNA molecule which targets TRAC is selected from SEQ ID NO: 7833, SEQ ID NO: 7834, SEQ ID NO: 7835, a dgRNA comprising, e.g., consisting of, SEQ ID NO: 7836 and SEQ ID NO: 6660, a dgRNA comprising, e.g., consisting of, SEQ ID NO: 7837 and SEQ ID NO: 6660, a dgRNA comprising, e.g., consisting of, SEQ ID NO: 7836 and SEQ ID NO: 10798, and a dgRNA comprising, e.g., consisting of, SEQ ID NO: 7837 and SEQ ID NO: 10798, and the gRNA molecule which targets FKBP1A is selected from SEQ ID NO: 7868, SEQ ID NO: 7869, SEQ ID NO: 7870, a dgRNA comprising, e.g., consisting of, SEQ ID NO: 7871 and SEQ ID NO: 6660, a dgRNA comprising, e.g., consisting of, SEQ ID NO: 7872 and SEQ ID NO: 6660, a dgRNA comprising, e.g., consisting of, SEQ ID NO: 7871 and SEQ ID NO: 10798, and a dgRNA comprising, e.g., consisting of, SEQ ID NO: 7872 and SEQ ID NO: 10798. As described herein, in embodiments of any of the combinations, each of said gRNA molecules is provided as an RNP with a Cas9 molecule, e.g., a Cas9 molecule described herein.

In preferred embodiments in which it is intended to reduce or eliminate expression of both a component of the T cell receptor, e.g., TRAC, and FKBP1A (including embodiments when expression or function of an additional target, e.g., more than one additional target, is also reduced or eliminated), the gRNA molecule which targets TRAC is selected from SEQ ID NO: 7838, SEQ ID NO: 7839, SEQ ID NO: 7840, a dgRNA comprising, e.g., consisting of, SEQ ID NO: 7841 and SEQ ID NO: 6660, a dgRNA comprising, e.g., consisting of, SEQ ID NO: 7842 and SEQ ID NO: 6660, a dgRNA comprising, e.g., consisting of, SEQ ID NO: 7841 and SEQ ID NO: 10798, and a dgRNA comprising, e.g., consisting of, SEQ ID NO: 7842 and SEQ ID NO: 10798, and the gRNA molecule which targets FKBP1A is selected from SEQ ID NO: 7863, SEQ ID NO: 7864, SEQ ID NO: 7865, a dgRNA comprising, e.g., consisting of, SEQ ID NO: 7866 and SEQ ID NO: 6660, a dgRNA comprising, e.g., consisting of, SEQ ID NO: 7867 and SEQ ID NO: 6660, a dgRNA comprising, e.g., consisting of, SEQ ID NO: 7866 and SEQ ID NO: 10798, and a dgRNA comprising, e.g., consisting of, SEQ ID NO: 7867 and SEQ ID NO: 10798. As described herein, in embodiments of any of the combinations, each of said gRNA molecules is provided as an RNP with a Cas9 molecule, e.g., a Cas9 molecule described herein.

In preferred embodiments in which it is intended to reduce or eliminate expression of both a component of the T cell receptor, e.g., TRAC, and FKBP1A (including embodiments when expression or function of an additional target, e.g., more than one additional target, is also reduced or eliminated), the gRNA molecule which targets TRAC is selected from SEQ ID NO: 7838, SEQ ID NO: 7839, SEQ ID NO: 7840, a dgRNA comprising, e.g., consisting of, SEQ ID NO: 7841 and SEQ ID NO: 6660, a dgRNA comprising, e.g., consisting of, SEQ ID NO: 7842 and SEQ ID NO: 6660, a dgRNA comprising, e.g., consisting of, SEQ ID NO: 7841 and SEQ ID NO: 10798, and a dgRNA comprising, e.g., consisting of, SEQ ID NO: 7842 and SEQ ID NO: 10798, and the gRNA molecule which targets FKBP1A is selected from SEQ ID NO: 7868, SEQ ID NO: 7869, SEQ ID NO: 7870, a dgRNA comprising, e.g., consisting of, SEQ ID NO: 7871 and SEQ ID NO: 6660, a dgRNA comprising, e.g., consisting of, SEQ ID NO: 7872 and SEQ ID NO: 6660, a dgRNA comprising, e.g., consisting of, SEQ ID NO: 7871 and SEQ ID NO: 10798, and a dgRNA comprising, e.g., consisting of, SEQ ID NO: 7872 and SEQ ID NO: 10798. As described herein, in embodiments of any of the combinations, each of said gRNA molecules is provided as an RNP with a Cas9 molecule, e.g., a Cas9 molecule described herein.

In preferred embodiments in which it is intended to reduce or eliminate expression of both a component of the T cell receptor, e.g., TRBC, and FKBP1A (including embodiments when expression or function of an additional target, e.g., more than one additional target, is also reduced or eliminated), the gRNA molecule which targets TRBC is selected from SEQ ID NO: 7843, SEQ ID NO: 7844, SEQ ID NO: 7845, a dgRNA comprising, e.g., consisting of, SEQ ID NO: 7846 and SEQ ID NO: 6660, a dgRNA comprising, e.g., consisting of, SEQ ID NO: 7847 and SEQ ID NO: 6660, a dgRNA comprising, e.g., consisting of, SEQ ID NO: 7846 and SEQ ID NO: 10798, and a dgRNA comprising, e.g., consisting of, SEQ ID NO: 7847 and SEQ ID NO: 10798, and the gRNA molecule which targets FKBP1A is selected from SEQ ID NO: 7863, SEQ ID NO: 7864, SEQ ID NO: 7865, a dgRNA comprising, e.g., consisting of, SEQ ID NO: 7866 and SEQ ID NO: 6660, a dgRNA comprising, e.g., consisting of, SEQ ID NO: 7867 and SEQ ID NO: 6660, a dgRNA comprising, e.g., consisting of, SEQ ID NO: 7866 and SEQ ID NO: 10798, and a dgRNA comprising, e.g., consisting of, SEQ ID NO: 7867 and SEQ ID NO: 10798. As described herein, in embodiments of any of the combinations, each of said gRNA molecules is provided as an RNP with a Cas9 molecule, e.g., a Cas9 molecule described herein.

In preferred embodiments in which it is intended to reduce or eliminate expression of both a component of the T cell receptor, e.g., TRBC, and FKBP1A (including embodiments when expression or function of an additional target, e.g., more than one additional target, is also reduced or eliminated), the gRNA molecule which targets TRBC is selected from SEQ ID NO: 7843, SEQ ID NO: 7844, SEQ ID NO: 7845, a dgRNA comprising, e.g., consisting of, SEQ ID NO: 7846 and SEQ ID NO: 6660, a dgRNA comprising, e.g., consisting of, SEQ ID NO: 7847 and SEQ ID NO: 6660, a dgRNA comprising, e.g., consisting of, SEQ ID NO: 7846 and SEQ ID NO: 10798, and a dgRNA comprising, e.g., consisting of, SEQ ID NO: 7847 and SEQ ID NO: 10798, and the gRNA molecule which targets FKBP1A is selected from SEQ ID NO: 7868, SEQ ID NO: 7869, SEQ ID NO: 7870, a dgRNA comprising, e.g., consisting of, SEQ ID NO: 7871 and SEQ ID NO: 6660, a dgRNA comprising, e.g., consisting of, SEQ ID NO: 7872 and SEQ ID NO: 6660, a dgRNA comprising, e.g., consisting of, SEQ ID NO: 7871 and SEQ ID NO: 10798, and a dgRNA comprising, e.g., consisting of, SEQ ID NO: 7872 and SEQ ID NO: 10798. As described herein, in embodiments of any of the combinations, each of said gRNA molecules is provided as an RNP with a Cas9 molecule, e.g., a Cas9 molecule described herein.

In preferred embodiments in which it is intended to reduce or eliminate expression of both a component of the T cell receptor, e.g., TRBC, and FKBP1A (including embodiments when expression or function of an additional target, e.g., more than one additional target, is also reduced or eliminated), the gRNA molecule which targets TRBC is selected from SEQ ID NO: 7848, SEQ ID NO: 7849, SEQ ID NO: 7850, a dgRNA comprising, e.g., consisting of, SEQ ID NO: 7851 and SEQ ID NO: 6660, a dgRNA comprising, e.g., consisting of, SEQ ID NO: 7852 and SEQ ID NO: 6660, a dgRNA comprising, e.g., consisting of, SEQ ID NO: 7851 and SEQ ID NO: 10798, and a dgRNA comprising, e.g., consisting of, SEQ ID NO: 7852 and SEQ ID NO: 10798, and the gRNA molecule which targets FKBP1A is selected from SEQ ID NO: 7863, SEQ ID NO: 7864, SEQ ID NO: 7865, a dgRNA comprising, e.g., consisting of, SEQ ID NO: 7866 and SEQ ID NO: 6660, a dgRNA comprising, e.g., consisting of, SEQ ID NO: 7867 and SEQ ID NO: 6660, a dgRNA comprising, e.g., consisting of, SEQ ID NO: 7866 and SEQ ID NO: 10798, and a dgRNA comprising, e.g., consisting of, SEQ ID NO: 7867 and SEQ ID NO: 10798. As described herein, in embodiments of any of the combinations, each of said gRNA molecules is provided as an RNP with a Cas9 molecule, e.g., a Cas9 molecule described herein.

In preferred embodiments in which it is intended to reduce or eliminate expression of both a component of the T cell receptor, e.g., TRBC, and FKBP1A (including embodiments when expression or function of an additional target, e.g., more than one additional target, is also reduced or eliminated), the gRNA molecule which targets TRBC is selected from SEQ ID NO: 7848, SEQ ID NO: 7849, SEQ ID NO: 7850, a dgRNA comprising, e.g., consisting of, SEQ ID NO: 7851 and SEQ ID NO: 6660, a dgRNA comprising, e.g., consisting of, SEQ ID NO: 7852 and SEQ ID NO: 6660, a dgRNA comprising, e.g., consisting of, SEQ ID NO: 7851 and SEQ ID NO: 10798, and a dgRNA comprising, e.g., consisting of, SEQ ID NO: 7852 and SEQ ID NO: 10798, and the gRNA molecule which targets FKBP1A is selected from SEQ ID NO: 7868, SEQ ID NO: 7869, SEQ ID NO: 7870, a dgRNA comprising, e.g., consisting of, SEQ ID NO: 7871 and SEQ ID NO: 6660, a dgRNA comprising, e.g., consisting of, SEQ ID NO: 7872 and SEQ ID NO: 6660, a dgRNA comprising, e.g., consisting of, SEQ ID NO: 7871 and SEQ ID NO: 10798, and a dgRNA comprising, e.g., consisting of, SEQ ID NO: 7872 and SEQ ID NO: 10798. As described herein, in embodiments of any of the combinations, each of said gRNA molecules is provided as an RNP with a Cas9 molecule, e.g., a Cas9 molecule described herein.

In one aspect, the cell exhibits reduced or eliminated expression of only one component of the TCR (though it may exhibit reduced or eliminated expression of one or more other targets which are not a component of the TCR). In embodiments, the cell comprises an indel at or near a target sequence within only a single gene (or its regulatory elements) that is a component of the TCR (though the cell may comprise an indel at or near a target sequence within one or more additional genes (or its regulatory elements) which are not a component of the TCR). Thus, in embodiments, the cell does not comprise an indel within more than one gene that is a component of a TCR. In embodiments, the cell does not comprise an indel within TRAC and within a gene encoding a second component of the TCR, e.g., TRBC1 or TRBC2.

In one aspect, the cell does not exhibit reduced or eliminated expression of a gene comprising a target sequence of an inhibitory molecule or downstream effector of signaling through an inhibitory molecule (though it may exhibit reduced or eliminated expression of one or more other genes). In embodiments, the cell does not include an indel at or near a target sequence in a gene (or its regulatory elements) of an inhibitory molecule or downstream effector of signaling through an inhibitory molecule (though it may include an indel at one or more other genes (or its regulatory elements)). In embodiments, the cell does not comprise an indel within PDCD1 or its regulatory elements.

In aspects, the cell is an animal cell, for example, a mammalian, primate, or human cell, e.g., a human cell. In aspects, the cell is an immune effector cell (e.g., a population of cells including one or more immune effector cells), for example, a T cell or NK cell, for example a T cell, for example a CD4+ T cell, a CD8+ T cell, or a combination thereof.

In aspects, the cell the cell is autologous with respect to a patient to be administered said cell. In other aspects, the cell is allogeneic with respect to a patient to be administered said cell. In embodiments, the cell is allogeneic with respect to a patient to be administered said cell, and is an induced pluripotent stem cell or is a cell derived therefrom. In embodiments, the cell is allogeneic with respect to a patient to be administered said cell, and is an immune effector cell, e.g., a T cell, isolated from a healthy human donor.

In aspects, a cell (or population of cells), e.g., as described herein, e.g., a CAR-expressing cell as described herein, is modified and/or altered, e.g., by the methods described herein, ex vivo. In other aspects, a cell (or population of cells), e.g., as described herein, e.g., a CAR-expressing cell as described herein, is modified and/or altered, e.g., by the methods described herein, in vivo. In aspects, the CRISPR systems, gRNA molecules (including in an RNP complex with a Cas9 molecule as described herein) and/or compositions (e.g., compositions comprising more than one gRNA molecule of the invention) of the invention are introduced into a cell, e.g., as described herein, e.g., a CAR-expressing cell as described herein, ex vivo. In other aspects, the CRISPR systems, gRNA molecules (including in an RNP complex with a Cas9 molecule as described herein) and/or compositions (e.g., compositions comprising more than one gRNA molecule of the invention) of the invention are introduced into a cell, e.g., as described herein, e.g., a CAR-expressing cell as described herein, in vivo.

In aspects, the cell has been, is, or will be, engineered to express a chimeric antigen receptor (CAR), as described herein (for example, the cell includes, or will include, nucleic acid sequence encoding a CAR). In embodiments, the CAR recognizes an antigen selected from: CD19; CD123; CD22; CD30; CD171; CS-1 (also referred to as CD2 subset 1, CRACC, SLAMF7, CD319, and 19A24); C-type lectin-like molecule-1 (CLL-1 or CLECL1); CD33; epidermal growth factor receptor variant III (EGFRvIII); ganglioside G2 (GD2); ganglioside GD3 (aNeu5Ac(2-8) aNeu5Ac(2-3)bDGalp(1-4)bDGlcp(1-1)Cer); TNF receptor family member B cell maturation (BCMA); Tn antigen ((Tn Ag) or (GalNAcα-Ser/Thr)); prostate-specific membrane antigen (PSMA); Receptor tyrosine kinase-like orphan receptor 1 (ROR1); Fms-Like Tyrosine Kinase 3 (FLT3); Tumor-associated glycoprotein 72 (TAG72); CD38; CD44v6; Carcinoembryonic antigen (CEA); Epithelial cell adhesion molecule (EPCAM); B7H3 (CD276); KIT (CD117); Interleukin-13 receptor subunit alpha-2 (IL-13Ra2 or CD213A2); Mesothelin; Interleukin 11 receptor alpha (IL-11Ra); prostate stem cell antigen (PSCA); Protease Serine 21 (Testisin or PRSS21); vascular endothelial growth factor receptor 2 (VEGFR2); Lewis(Y) antigen; CD24; Platelet-derived growth factor receptor beta (PDGFR-beta); Stage-specific embryonic antigen-4 (SSEA-4); CD20; Folate receptor alpha; Receptor tyrosine-protein kinase ERBB2 (Her2/neu); Mucin 1, cell surface associated (MUC1); epidermal growth factor receptor (EGFR); neural cell adhesion molecule (NCAM); Prostase; prostatic acid phosphatase (PAP); elongation factor 2 mutated (ELF2M); Ephrin B2; fibroblast activation protein alpha (FAP); insulin-like growth factor 1 receptor (IGF-I receptor), carbonic anhydrase IX (CAIX); Proteasome (Prosome, Macropain) Subunit, Beta Type, 9 (LMP2); glycoprotein 100 (gp100); oncogene fusion protein consisting of breakpoint cluster region (BCR) and Abelson murine leukemia viral oncogene homolog 1 (Abl) (bcr-abl); tyrosinase; ephrin type-A receptor 2 (EphA2); Fucosyl GM1; sialyl Lewis adhesion molecule (sLe); ganglioside GM3 (aNeu5Ac(2-3)bDGalp(1-4) bDGlcp(1-1)Cer); transglutaminase 5 (TGS5); high molecular weight-melanoma-associated antigen (HMW-MAA); o-acetyl-GD2 ganglioside (OAcGD2); Folate receptor beta; tumor endothelial marker 1 (TEM1/CD248); tumor endothelial marker 7-related (TEM7R); claudin 6 (CLDN6); thyroid stimulating hormone receptor (TSHR); G protein-coupled receptor class C group 5, member D (GPRC5D); chromosome X open reading frame 61 (CXORF61); CD97; CD179a; anaplastic lymphoma kinase (ALK); Polysialic acid; placenta-specific 1 (PLAC1); hexasaccharide portion of globoH glycoceramide (GloboH); mammary gland differentiation antigen (NY-BR-1); uroplakin 2 (UPK2); Hepatitis A virus cellular receptor 1 (HAVCR1); adrenoceptor beta 3 (ADRB3); pannexin 3 (PANX3); G protein-coupled receptor 20 (GPR20); lymphocyte antigen 6 complex, locus K9 (LY6K); Olfactory receptor 51E2 (OR51E2); TCR Gamma Alternate Reading Frame Protein (TARP); Wilms tumor protein (WT1); Cancer/testis antigen 1 (NY-ESO-1); Cancer/testis antigen 2 (LAGE-1a); Melanoma-associated antigen 1 (MAGE-A1); ETS translocation-variant gene 6, located on chromosome 12p (ETV6-AML); sperm protein 17 (SPA17); X Antigen Family, Member 1A (XAGE1); angiopoietin-binding cell surface receptor 2 (Tie 2); melanoma cancer testis antigen-1 (MAD-CT-1); melanoma cancer testis antigen-2 (MAD-CT-2); Fos-related antigen 1; tumor protein p53 (p53); p53 mutant; prostein; surviving; telomerase; prostate carcinoma tumor antigen-1 (PCTA-1 or Galectin 8), melanoma antigen recognized by T cells 1 (MelanA or MART1); Rat sarcoma (Ras) mutant; human Telomerase reverse transcriptase (hTERT); sarcoma translocation breakpoints; melanoma inhibitor of apoptosis (ML-IAP); ERG (transmembrane protease, serine 2 (TMPRSS2) ETS fusion gene); N-Acetyl glucosaminyl-transferase V (NA17); paired box protein Pax-3 (PAX3); Androgen receptor; Cyclin B1; v-myc avian myelocytomatosis viral oncogene neuroblastoma derived homolog (MYCN); Ras Homolog Family Member C (RhoC); Tyrosinase-related protein 2 (TRP-2); Cytochrome P450 1B1 (CYP1B1); CCCTC-Binding Factor (Zinc Finger Protein)-Like (BORIS or Brother of the Regulator of Imprinted Sites), Squamous Cell Carcinoma Antigen Recognized By T Cells 3 (SART3); Paired box protein Pax-5 (PAX5); proacrosin binding protein sp32 (OY-TES1); lymphocyte-specific protein tyrosine kinase (LCK); A kinase anchor protein 4 (AKAP-4); synovial sarcoma, X breakpoint 2 (SSX2); Receptor for Advanced Glycation Endproducts (RAGE-1); renal ubiquitous 1 (RU1); renal ubiquitous 2 (RU2); legumain; human papilloma virus E6 (HPV E6); human papilloma virus E7 (HPV E7); intestinal carboxyl esterase; heat shock protein 70-2 mutated (mut hsp70-2); CD79a; CD79b; CD72; Leukocyte-associated immunoglobulin-like receptor 1 (LAIR1); Fc fragment of IgA receptor (FCAR or CD89); Leukocyte immunoglobulin-like receptor subfamily A member 2 (LILRA2); CD300 molecule-like family member f (CD300LF); C-type lectin domain family 12 member A (CLEC12A); bone marrow stromal cell antigen 2 (BST2); EGF-like module-containing mucin-like hormone receptor-like 2 (EMR2); lymphocyte antigen 75 (LY75); Glypican-3 (GPC3); Fc receptor-like 5 (FCRL5); and immunoglobulin lambda-like polypeptide 1 (IGLL1), e.g., as described herein.

In embodiments, the CAR includes an antigen recognition domain that binds CD19, e.g., as described herein. In embodiments, the CAR includes an anti-CD19 binding domain that includes, e.g., consists of, SEQ ID NO: 7895. In embodiments, the CAR includes an anti-CD19 binding domain that includes, e.g., consists of, SEQ ID NO: 7884.

In embodiments, the CAR includes an antigen recognition domain that binds BCMA, e.g., as described herein. In embodiments, the CAR includes an anti-BCMA binding domain that includes, e.g., consists of, SEQ ID NO: 7949.

In embodiments, the CAR includes an antigen binding domain, a transmembrane domain, and an intracellular signaling domain. In embodiments the transmembrane domain includes the sequence of SEQ ID NO: 6644. In embodiments, the intracellular signaling domain includes a primary signaling domain and/or a costimulatory signaling domain. In embodiments, the primary signaling domain includes, e.g., consists of, the sequence of SEQ ID NO: 6648 or SEQ ID NO: 6650. In embodiments, the costimulatory signaling domain includes, e.g., consists of, the sequence of SEQ ID NO: 6646 or SEQ ID NO: 6636, e.g., includes, e.g., consists of, the sequence of SEQ ID NO: 6646. In other embodiments, the costimulatory signaling domain includes sequence from the intracellular signaling domain of CD28.

In embodiments, the CAR is a CD19 CAR, and includes, e.g., consists of, the sequence of SEQ ID NO: 7920. In embodiments, the CAR is a CD19 CAR, and includes, e.g., consists of, the sequence of SEQ ID NO: 7909. In embodiments, the cell, e.g., described herein, includes nucleic acid sequence encoding a CD19 CAR described herein, e.g., a CD19 CAR that includes the sequence of SEQ ID NO: 7920 or SEQ ID NO: 7909.

In embodiments, the CAR is a BCMA CAR, and includes, e.g., consists of, the sequence of SEQ ID NO: 8559. In embodiments, the cell, e.g., described herein, includes nucleic acid sequence encoding a BCMA CAR described herein, e.g., a BCMA CAR that includes SEQ ID NO: 8559. In embodiments, the nucleic acid sequence encoding the BCMA CAR includes, e.g., consists of, SEQ ID NO: 8574.

In aspects, the cell of the invention (e.g., the population of the cells of the invention), e.g., described herein, further include nucleic acid sequence encoding an NK inhibitory molecule. Such cells are preferred when the cells exhibit reduced or eliminated expression of one or more major histocompatibility class I (MHC I) molecules (e.g., via reduced or eliminated expression of B2M, e.g., achieved by the methods described herein) and/or reduced or eliminated expression of one or more major histocompatibility class II (MMC II) molecules (e.g., via reduced or eliminated expression of CIITA, e.g., achieved by the methods described herein). In embodiments, the NK inhibitory molecule is an HLA-G molecule, e.g., an HLA-G molecule that does not require B2M, e.g., HLA-G2, HLA-G3, HLA-G4. In other embodiments, the NK inhibitory molecule is an HLA-G:B2M fusion molecule. An exemplary HLA-G:B2M fusion molecule is SEQ ID NO: 10674. An exemplary nucleic acid sequence encoding said HLA-G:B2M fusion is SEQ ID NO: 10675.

In embodiments, the cell (e.g., population of cells), exhibits reduced or eliminated expression of a target of an NK inhibitory molecule, e.g., reduced or eliminated expression of LILRB1.

In embodiments, a CAR-expressing cell of the invention (e.g., the cell wherein expression or function of one or more proteins has been reduced or eliminated, e.g., by the methods described herein), maintains the ability to proliferate in response to stimulation, for example, binding of the CAR to its target antigen. In embodiments, the proliferation occurs ex vivo. In embodiments, the proliferation occurs in vivo. In embodiments, the proliferation occurs both ex vivo and in vivo. In embodiments, the level of proliferation is substantially the same as the level of proliferation exhibited by the same cell type (e.g., a CAR-expressing cell of the same type) but which has not had expression or function of one or more proteins reduced or eliminated, e.g., by the methods described herein. In embodiments, the level of proliferation is at least 80%, at least 85%, at least 90%, at least 95%, at least 98% or more of the level of proliferation exhibited by the same cell type (e.g., a CAR-expressing cell of the same type) but which has not had expression or function of one or more proteins reduced or eliminated, e.g., by the methods described herein.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In addition, the materials, methods, and examples are illustrative only and not intended to be limiting. Headings, sub-headings or numbered or lettered elements, e.g., (a), (b), (i) etc, are presented merely for ease of reading. The use of headings or numbered or lettered elements in this document does not require the steps or elements be performed in alphabetical order or that the steps or elements are necessarily discrete from one another. Other features, objects, and advantages of the invention will be apparent from the description and drawings, and from the claims.

BRIEF DESCRIPTION OF THE DRAWINGS

FIG. 6: Expression profiles of primary T cells engineered to express a CD19 CAR and treated with RNP comprising gRNA targeting TCR alpha. Pre-enrichment shows the cell populations that are CAR+/− and TCR+/− following 11 days in culture. Post-enrichment shows >98% TCR− T cells after isolation using a CD3 microbead negative selection step.

FIG. 7: Shown is the cytotoxic activity of CD19 CAR transduced T-cells against a target positive (Nalm6-luc) and target negative (K562-luc) cell line. "T1" and "T8" refer to gRNA TRAC-1 and TRAC-8 respectively. Shown are lentivirus or RNP-introduced Cas9/gRNA, and the results for both unsorted and TCR− sorted ("sorted") T cell populations

FIG. 12: Mean (n≥3) editing of CRISPR systems with dgRNAs as indicated to TRAC in HEK cells (stably expressing Cas9) or primary human CD3+ T cells (delivery of dgRNA:Cas9 RNP by electroporation). Also shown is % of cells exhibiting loss of TCR as determined by flow cytometry using an anti-TCRa/b antibody.

FIG. 14: Mean (n≥3) editing of CRISPR systems with dgRNAs as indicated to B2M in HEK cells (stably expressing Cas9), in CD34+ primary human hematopoietic stem cells, and % loss of B2M in primary CD3+ T cells as measured by flow cytometry. NGS assays were run 24 hours after introduction of the CRISPR systems to the indicated cells; Flow cytometry assay was run 3-5 days after introduction of the CRISPR systems to the CD3+ T cells.

FIG. 17B: % of cells negative for both B2M and TCR at the indicated gRNA ratios.

FIG. 23: % editing (N=3) and % Frameshift edit (FS) as measured by NGS in HEK293 cells stably expressing Cas9 using dgRNAs that include the targeting domain to FKBP1A as indicated.

FIG. 24: % editing (N=3) and % Frameshift edit (FS edit) as measured by NGS in CD3+ T cells using RNPs that include dgRNAs that include the targeting domain to FKBP1A indicated.

FIG. 33C: Genomic editing of the TRAC locus resulting from human primary T cell electroporation with RNP containing the indicated gRNA targeting the TRAC locus is shown. The frequency of insertions or deletions is indicated (% indels) and the percentage of these edits that result in frameshifting of the coding sequence is shown (% frameshift edits).

FIGS. 34A and 34B: The top 5 most frequently observed sequence changes are shown in detail for each TRAC targeting gRNA used for primary human T cell editing. FIGS. 34A and 34B are the outcome from 2 independently performed electroporation experiments. Wild type (wt) unmodified bases are shown in uppercase letters. Deletions relative to wt sequence are shown by "–"; insertions relative to wt sequence are shown by lowercase letters. Data for each experiment are the average from triplicate PCR products. FIG. 34A to 34B disclose SEQ ID NOS 10845-10899, respectively, in order of appearance.

FIG. 36: Genomic editing of the B2M locus resulting from human primary T cell electroporation with RNP containing the indicated gRNA targeting the B2M locus. The frequency of insertions or deletions is indicated (% indels) and the percentage of these edits that result in frameshifting of the coding sequence is shown (% frameshift edits) in the top panel. The top 10 most frequently observed sequence changes are shown in the bottom panel in detail for each B2M targeting gRNA used for primary human T cell editing. Wild type (wt) unmodified bases are shown in uppercase letters. Deletions relative to wt sequence are shown by "–"; insertions relative to wt sequence are shown by lowercase letters. Data are the average from triplicate PCR products. FIG. 36 discloses SEQ ID NOS 10900-10919, respectively, in order of appearance.

FIG. 38: Genomic editing of the CIITA locus resulting from human primary T cell electroporation with RNP containing the indicated gRNA targeting the CIITA locus is shown. The frequency of insertions or deletions is indicated (% indels) and the percentage of these edits that result in frameshifting of the coding sequence is shown (% frameshift edits). The top 5 most frequently observed sequence changes are shown in detail in the bottom panel. Wild type (wt) unmodified bases are shown in uppercase letters. Deletions relative to wt sequence are shown by "–"; insertions relative to wt sequence are shown by lowercase letters. Data are the average from triplicate PCR products. FIG. 38 discloses SEQ ID NOS 10920-10939, respectively, in order of appearance.

FIG. 40: Genomic editing of the CIITA locus resulting from human primary T cell electroporation with RNP containing the indicated gRNA targeting the CIITA locus is shown. The frequency of insertions or deletions is indicated (% indels) and the percentage of these edits that result in frameshifting of the coding sequence is shown (% frameshift edits).

FIG. 41: The top 5 most frequently observed sequence changes (indels) for each CIITA targeting gRNA used for primary human T cell editing. Data are the average from triplicate PCR products. Wild type (wt) unmodified bases are shown in uppercase letters. Deletions relative to wt sequence are shown by "–"; insertions relative to wt sequence are shown by lowercase letters. FIG. 41 discloses SEQ ID NOS 10940-10974, respectively, in order of appearance.

FIG. 43: Genomic editing of the CIITA locus resulting from human primary T cell electroporation with RNP containing the indicated gRNA targeting the CIITA locus is shown. The frequency of insertions or deletions is indicated (% indels) and the percentage of these edits that result in frameshifting of the coding sequence is shown (% frameshift edits).

FIG. 44. The top 5 most frequently observed sequence changes for each CIITA targeting gRNA used for primary human T cell editing. Data are the average from triplicate PCR products. Wild type (wt) unmodified bases are shown in uppercase letters. Deletions relative to wt sequence are shown by "–"; insertions relative to wt sequence are shown by lowercase letters. FIG. 44 discloses SEQ ID NOS 10975-11014, respectively, in order of appearance.

FIG. 47: Genomic editing of the B2M, TRAC, and CIITA loci resulting from human primary T cell simultaneous electroporation with 3 RNPs containing gRNAs targeting the B2M, TRAC, and CIITA loci. The frequency of insertions or deletions is indicated (% indels) and the percentage of these edits that result in frameshifting of the coding sequence is shown in parentheses.

FIG. 48: The top 10 most frequently observed sequence changes at the B2M locus in primary human T cells for the B2M targeting gRNA CR00442 in the context of simultaneous editing of 3 loci (triple editing) with different concentrations of each RNP as shown in the schematic in FIG. 45. Wild type (wt) unmodified bases are shown in uppercase letters. Deletions relative to wt sequence are shown by "–"; insertions relative to wt sequence are shown by lowercase letters. Data are the average from triplicate PCR products. FIG. 48 discloses SEQ ID NOS 11015-11054, respectively, in order of appearance.

FIG. 49: The top 10 most frequently observed sequence changes at the TRAC locus in primary human T cells for the TRAC targeting gRNA CR000961 in the context of simultaneous editing of 3 loci (triple editing) with different concentrations of each RNP as shown in the schematic in FIG. 45. Wild type (wt) unmodified bases are shown in uppercase letters. Deletions relative to wt sequence are shown by "–"; insertions relative to wt sequence are shown by lowercase letters. Data are the average from triplicate PCR products. FIG. 49 discloses SEQ ID NOS 11055-11094, respectively, in order of appearance.

FIG. 50: The top 10 most frequently observed sequence changes at the CIITA locus in primary human T cells for the CIITA targeting gRNA CR002991 in the context of simultaneous editing of 3 loci (triple editing) with different concentrations of each RNP as shown in the schematic in FIG. 45. Wild type (wt) unmodified bases are shown in uppercase letters. Deletions relative to wt sequence are shown by "–"; insertions relative to wt sequence are shown by lowercase letters. Data are the average from triplicate PCR products. FIG. 50 discloses SEQ ID NOS 11095-11134, respectively, in order of appearance.

FIG. 52: Genomic editing of the FKBP1A locus resulting from human primary T cell electroporation with RNPs containing the indicated gRNAs targeting FKBP1A. The frequency of insertions or deletions is indicated (% indels) and the percentage of these edits that result in frameshifting of the coding sequence is shown.

FIG. 53: The top 5 most frequently observed sequence changes for each FKBP1A targeting gRNA used for primary human T cell editing are shown. Wild type (wt) unmodified bases are shown in uppercase letters. Deletions relative to wt sequence are shown by "–"; insertions relative to wt sequence are shown by lowercase letters. Data are the average from triplicate PCR products. FIG. 53 discloses SEQ ID NOS 11135-11159, respectively, in order of appearance.

FIG. 58: Sensitivity to gene edited (TRAC and/or FKBP1A) CART cells to RAD001. CART cells were prepared expressing the BCMA10 CAR (FIG. 58A-1, FIG. 58A-2, and FIG. 58A-3), the CD19 CAR (FIG. 58B-1. FIG. 58B-2, and FIG. 58B-3), or no CAR (FIG. 59C-1, FIG. 58C-2, and FIG. 58C-3; UTD). Gene editing was performed on CART cells or UTD cells using the CR000961 guide to target the TRAC locus and/or the CR002097 and CR002086 guides to target the FKBP1A locus (as indicated by 961, 2097, and 2086, respectively). CART cells electroporated with an RNP containing no guide RNA were prepared as a negative control. After RNP electroporation cells were treated with 2.5 nM RAD001 (upper panel, indicated at +RAD001) or left untreated (lower panel, indicated as— RAD001) and the impact on mTOR pathway inhibition was evaluated by analyzing S6 phosphorylation (pS6) by flow cytometry. The Y-axis indicates side scatter (SSC) and the X-axis indicates the level of phosphorylated S6 protein (pS6). Positive staining for pS6, shown in the lower right quadrant of the FACS plots, was determined by gating above the fluorescence level seen in a control stained with isotype antibody (not shown). The percentage of cells with phosphorylation of S6 is shown with histograms (upper panels) and graphically (lower panel).

FIG. 65: % editing in primary human CD3+ T cells as measured by loss of surface expression of CD3 (as measured by flow cytometry) 72 hours after introduction of CRISPR systems targeting CD3 delta (dgRNA comprising the indicated targeting domain). Each % CD3-negative cells is the average of three independent experiments (SD=standard deviation).

FIG. 66: % editing in primary human CD3+ T cells as measured by loss of surface expression of CD3 (as measured by flow cytometry) 72 hours after introduction of CRISPR systems targeting CD3 gamma (dgRNA comprising the indicated targeting domain). Each % CD3-negative cells mean value is the average of three independent experiments (SD=standard deviation).

DEFINITIONS

Figure 1:
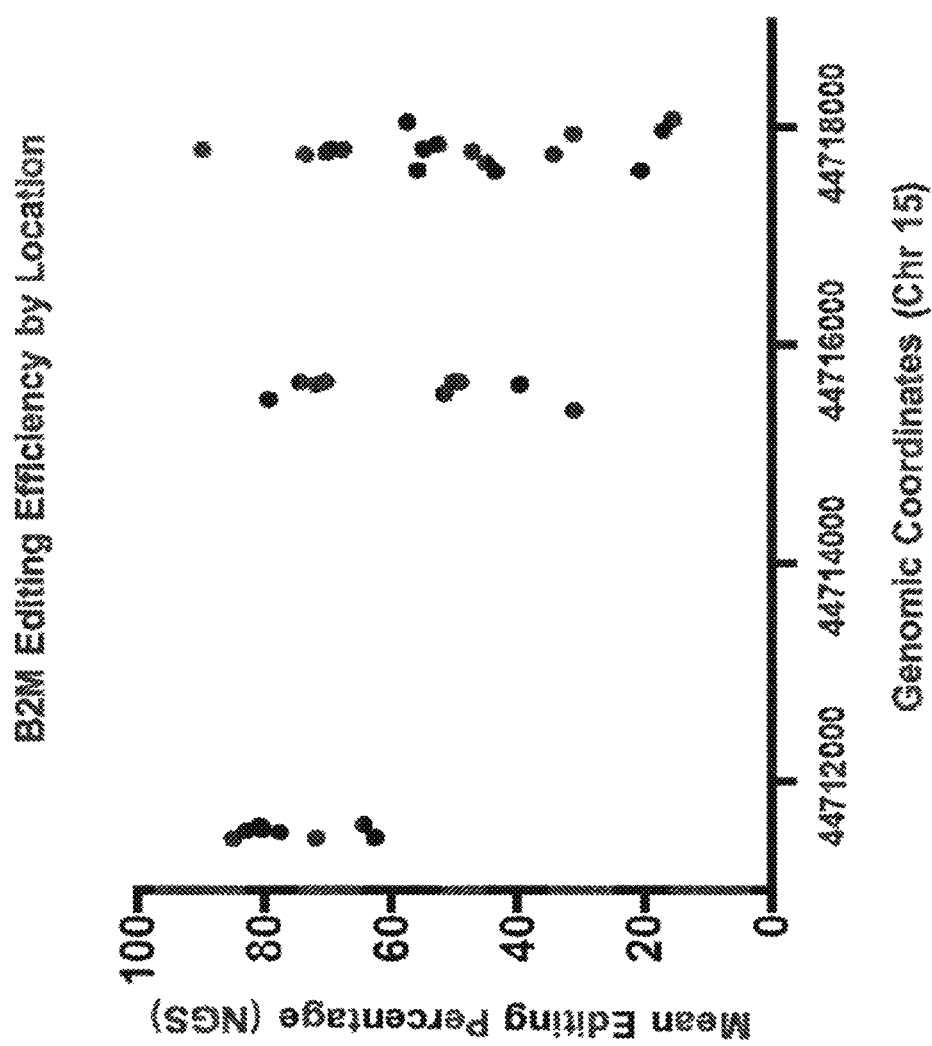
FIG. 1: Cas9 editing of the B2M locus. Fraction of editing detected by NGS in HEK-293 Cas9GFP 24 h post-delivery of crRNA targeting the B2M locus and trRNA by lipofection. Each dot indicates a different crRNA, the trRNA was held constant. Genomic coordinates indicate location on Chromosome 15. (n=3).

The terms "CRISPR system," "Cas system" or "CRISPR/Cas system" refer to a set of molecules comprising an RNA-guided nuclease or other effector molecule and a gRNA molecule that together are necessary and sufficient to direct and effect modification of nucleic acid at a target sequence by the RNA-guided nuclease or other effector molecule. In one embodiment, a CRISPR system comprises a gRNA and a Cas protein, e.g., a Cas9 protein. Such systems comprising a Cas9 or modified Cas9 molecule are referred to herein as "Cas9 systems" or "CRISPR/Cas9 systems." In one example, the gRNA molecule and Cas molecule may be complexed, to form a ribonuclear protein (RNP) complex.

The terms "guide RNA," "guide RNA molecule," "gRNA molecule" or "gRNA" are used interchangeably, and refer to a set of nucleic acid molecules that promote the specific directing of a RNA-guided nuclease or other effector molecule (typically in complex with the gRNA molecule) to a target sequence. In some embodiments, said directing is accomplished through hybridization of a portion of the gRNA to DNA (e.g., through the gRNA targeting domain), and by binding of a portion of the gRNA molecule to the RNA-guided nuclease or other effector molecule (e.g., through at least the gRNA tracr). In embodiments, a gRNA molecule consists of a single contiguous polynucleotide molecule, referred to herein as a "single guide RNA" or "sgRNA" and the like. In other embodiments, a gRNA molecule consists of a plurality, usually two, polynucleotide molecules, which are themselves capable of association, usually through hybridization, referred to herein as a "dual guide RNA" or "dgRNA," and the like. gRNA molecules are described in more detail below, but generally include a targeting domain and a tracr. In embodiments the targeting domain and tracr are disposed on a single polynucleotide. In other embodiments, the targeting domain and tracr are disposed on separate polynucleotides.

The term "targeting domain" as the term is used in connection with a gRNA, is the portion of the gRNA molecule that recognizes, e.g., is complementary to, a target sequence, e.g., a target sequence within the nucleic acid of a cell, e.g., within a gene.

The term "crRNA" as the term is used in connection with a gRNA molecule, is a portion of the gRNA molecule that comprises a targeting domain and a region that interacts with a tracr to form a flagpole region.

The term "target sequence" refers to a sequence of nucleic acids complimentary, for example fully complementary, to a gRNA targeting domain. In embodiments, the target sequence is disposed on genomic DNA. In an embodiment the target sequence is adjacent to (either on the same strand or on the complementary strand of DNA) a protospacer adjacent motif (PAM) sequence recognized by a protein having nuclease or other effector activity, e.g., a PAM sequence recognized by Cas9. In embodiments, the target sequence is a target sequence of an allogeneic T cell target. In embodiments, the target sequence is a target sequence of an inhibitory molecule. In embodiments, the target sequence is a target sequence of a downstream effector of an inhibitory molecule.

The term "flagpole" as used herein in connection with a gRNA molecule, refers to the portion of the gRNA where the crRNA and the tracr bind to, or hybridize to, one another.

The term "tracr" as used herein in connection with a gRNA molecule, refers to the portion of the gRNA that binds to a nuclease or other effector molecule. In embodiments, the tracr comprises nucleic acid sequence that binds specifically to Cas9. In embodiments, the tracr comprises nucleic acid sequence that forms part of the flagpole.

The terms "Cas9" or "Cas9 molecule" refer to an enzyme from bacterial Type II CRISPR/Cas system responsible for DNA cleavage. Cas9 also includes wild-type protein as well as functional and non-functional mutants thereof.

The term "complementary" as used in connection with nucleic acid, refers to the pairing of bases, A with T or U, and G with C. The term complementary refers to nucleic acid molecules that are completely complementary, that is, form A to T or U pairs and G to C pairs across the entire reference sequence, as well as molecules that are at least 80%, 85%, 90%, 95%, 99% complementary.

"Template Nucleic Acid" as used in connection with homology-directed repair or homologous recombination, refers to nucleic acid to be inserted at the site of modification by the CRISPR system donor sequence for gene repair (insertion) at site of cutting. In one aspect, the template nucleic acid comprises nucleic acid sequence encoding a chimeric antigen receptor (CAR), e.g., as described herein. In one aspect, the template nucleic acid comprises a vector comprising nucleic acid sequence encoding a chimeric antigen receptor (CAR), e.g., as described herein.

An "indel," as the term is used herein, refers to a nucleic acid comprising one or more insertions of nucleotides, one or more deletions of nucleotides, or a combination of insertions and defections of nucleotides, relative to a reference nucleic acid, that results after being exposed to a composition comprising a gRNA molecule, for example a CRISPR system. Indels can be determined by sequencing nucleic acid after being exposed to a composition comprising a gRNA molecule, for example, by NGS. With respect to the site of an indel, an indel is said to be "at or near" a reference site (e.g., a site complementary to a targeting domain of a gRNA molecule) if it comprises at least one insertion or deletion within about 10, 9, 8, 7, 6, 5, 4, 3, 2, or 1 nucleotide(s) of the reference site, or is overlapping with part or all of said reference site (e.g., comprises at least one insertion or deletion overlapping with, or within 10, 9, 8, 7, 6, 5, 4, 3, 2, or 1 nucleotides of a site complementary to the targeting domain of a gRNA molecule, e.g., a gRNA molecule described herein).

An "indel pattern," as the term is used herein, refers to a set of indels that results after exposure to a composition comprising a gRNA molecule. In an embodiment, the indel pattern consists of the top three indels, by frequency of appearance. In an embodiment, the indel pattern consists of the top five indels, by frequency of appearance. In an embodiment, the indel pattern consists of the indels which are present at greater than about 5% frequency relative to all sequencing reads. In an embodiment, the indel pattern consists of the indels which are present at greater than about 10% frequency relative to total number of indel sequencing reads (i.e., those reads that do not consist of the unmodified reference nucleic acid sequence). In an embodiment, the indel pattern includes of any 3 of the top five most frequently observed indels. The indel pattern may be determined, for example, by sequencing cells of a population of cells which were exposed to the gRNA molecule.

An "off-target indel," as the term I used herein, refers to an indel at or near a site other than the target sequence of the targeting domain of the gRNA molecule. Such sites may comprise, for example, 1, 2, 3, 4, 5 or more mismatch nucleotides relative to the sequence of the targeting domain of the gRNA. In exemplary embodiments, such sites are detected using targeted sequencing of in silico predicted off-target sites, or by an insertional method known in the art.

The term "inhibitory molecule" refers to a molecule, which when activated, causes or contributes to an inhibition of cell survival, activation, proliferation and/or function; and the gene encoding said molecule and its associated regulatory elements, e.g., promoters. In embodiments, an inhibitory molecule is a molecule expressed on an immune effector cell, e.g., on a T cell. Non-limiting examples of inhibitory molecules are PD-1, PD-L1, PD-L2, CTLA4, TIM3, LAG3, CEACAM (e.g., CEACAM-1, CEACAM-3 and/or CEACAM-5), VISTA, BTLA, TIGIT, LAIR1, CD160, 2B4, CD80, CD86, B7-H3 (CD276), B7-H4 (VTCN1), HVEM (TNFRSF14 or CD107), KIR, A2aR, MHC class I, MHC class II, GAL9, adenosine, and TGF beta. It will be understood that the term inhibitory molecule refers to the gene (and its associated regulatory elements) encoding an inhibitory molecule protein when it is used in connection with a target sequence or gRNA molecule. In an embodiment, gene encoding the inhibitory molecule is CD274. In an embodiment, the gene encoding the inhibitory molecule is HAVCR2. In an embodiment, the gene encoding the inhibitory molecule is LAG3. In an embodiment, the gene encoding the inhibitory molecule is PDCD1.

The term "downstream effector of signaling through an inhibitory molecule" refers to a molecule that mediates the inhibitory effect of an inhibitory molecule; and the gene encoding said molecule and its associated regulatory elements, e.g., promoters. It will be understood that the term downstream effector of signaling through an inhibitory molecule refers to the gene (and its associated regulatory elements) encoding a downstream effector of signaling through an inhibitory molecule protein when it is used in connection with a target sequence or gRNA molecule. In an embodiment, the gene encoding the downstream effector of signaling through an inhibitory molecule is PTPN11.

The terms "allogeneic T cell target" and "allogeneic T-cell target" are used interchangeably herein, and refer to a protein that mediates or contributes to a host versus graft response, mediates or contributes to a graft versus host response, or is a target for an immunosuppressant; and the gene encoding said molecule and its associated regulatory elements, e.g., promoters. It will be understood that the term allogeneic T cell target refers to the gene (and its associated regulatory elements) encoding an allogeneic T cell target protein when it is used in connection with a target sequence or gRNA molecule. Without being bound by theory, inhibition or elimination of one or more allogeneic cell targets, e.g., by the methods and compositions disclosed herein, may improve the efficacy, survival, function and/or viability of an allogeneic cell, e.g., an allogeneic T cell, for example, by reducing or eliminating undesirable immunogenicity (such as a host versus graft response or a graft versus host response).

In a non-limiting example, the protein that mediates or contributes to a graft versus host response or host versus graft response is one or more components of the T cell receptor. In an embodiment, the component of the T cell receptor is the T cell receptor alpha, for example the constant domain of the TCR alpha. In an embodiment, the component of the T cell receptor is the T cell receptor beta chain, for example the constant domain 1 or constant domain 2 of the TCR beta. In an embodiment, the component of the T cell receptor is the T cell receptor delta chain. In an embodiment, the component of the T cell receptor is the T cell receptor epsilon chain. In an embodiment, the component of the T cell receptor is the T cell receptor zeta chain. In an embodiment, the component of the T cell receptor is the T cell receptor gamma chain. Thus, in embodiments where the protein encoded by the allogeneic T cell target is a component of the TCR, the gene encoding the allogeneic T cell target may be, for example, TRAC, TRBC1, TRBC2, CD3D, CD3E, CD3G or CD247, and combinations thereof.

In a non-limiting example, the protein that mediates or contributes to a graft versus host response or host versus graft response is an HLA protein or B2M. Examples of HLA proteins include HLA-A, HLA-B and HLA-C. Thus, in embodiments where the allogeneic T cell target protein is a HLA or B2M protein, the gene encoding the allogeneic T cell target may be, for example, HLA-A, HLA-B, HLA-C or B2M, and combinations thereof. In other embodiments, the allogeneic T cell target protein is NLRC5, and the gene encoding the allogeneic T cell target may be, for example, NLRC5.

In a non-limiting example, the protein that mediates or contributes to a graft versus host response or host versus graft response is a major histocompatibility complex class II (MHC II) molecule (e.g., HLA-Dx (where x refers to a letter of a MHC II protein, e.g., HLA-DM, HLA-DO, HLA-DR, HLA-DQ and/or HLA-DP)), or a regulatory factor for expression of a MHC II, and combinations thereof. A non-limiting example is CIITA (also referred to herein as C2TA). Thus, in embodiments where the allogeneic T cell target protein is a CIITA, the gene encoding the allogeneic T cell target may be, for example, CIITA. In another non-limiting example, the protein that mediates or contributes to a graft versus host response or host versus graft response is RFXANK. In another non-limiting example, the protein that mediates or contributes to a graft versus host response or host versus graft response is RFXAP. In another non-limiting example, the protein that mediates or contributes to a graft versus host response or host versus graft response is RFX5.

The term "target for an immunosuppressant" as used herein refers to a molecular target, for example a receptor or other protein, for an immunosuppressant agent (the terms, "immunosuppressant" and "immunosuppressive" are used interchangeably herein in connection with an agent, or target for an agent). An immunosuppressant agent is an agent that suppresses immune function by one of several mechanisms of action. In other words, an immunosuppressive agent is a role played by a compound which is exhibited by a capability to diminish the extent and/or voracity of an immune response. One example of a type of activity exhibited by an immunosuppressant agent is the activity of eliminating T-cells, for example, activated T-cells. Another example of a type of activity exhibited by an immunosuppressant agent is the activity of reducing the activity or activation level of T-cells. As a non-limiting example, an immunosuppressive agent can be a calcineurin inhibitor, a target of rapamycin, an interleukin-2 a-chain blocker, an inhibitor of inosine monophosphate dehydrogenase, an inhibitor of dihydrofolic acid reductase, a corticosteroid, cyclosporine, or an immunosuppressive antimetabolite. Classical cytotoxic immunosuppressants act by inhibiting DNA synthesis. Others may act through activation of T-cells or by inhibiting the activation of helper cells. As non limiting examples, targets for immunosuppressive agent can be a receptor for an immunosuppressive agent such as: Deoxycytidine kinase, CD52, glucocorticoid receptor (GR), a FKBP family gene member, e.g., FKBP12, and a cyclophilin family gene member. In an embodiment, the target for an immunosuppressant is deoxycytidine kinase (DCK), and the immunosuppressant is a nucleoside analog-based drug such as cytarabine (cytosine arabinoside) or gemcitabine. In an embodiment, the target for an immunosuppressant is GR, and the immunosuppressant is a corticosteroid such as dexamethasone. In an embodiment, the target for an immunosuppressant is CD52, and the immunosuppressant is an anti-CD52 antibody or antigen-binding fragment thereof such as alemtuzumab (CAMPATH®). In an embodiment, the target for an immunosuppressant is FKBP12, and the immunosuppressant is FK506 (or analog or FKBP12-binding fragment thereof), cyclosporine, rapamycin or rapalog, or mTor inhibitor such as RAD001. Thus, in embodiments where the allogeneic T cell target is a target for an immunosuppressant protein, the gene encoding the allogeneic T cell target may be, for example, NR3C1, FKBP1A, CD52, or DCK, and combinations thereof.

The term "rapamycin-resistant mTor" refers to an mTor protein (and the gene encoding said mTor protein) which has reduced or eliminated binding to FKBP12 (including in the presence of rapamycin, FK506, a rapalog, cyclosporin and/or other mTor inhibitor such as RAD001). In exemplary embodiments, the rapamycin-resistant mTor comprises one or more mutations to the FRB domain. In an exemplary embodiment, the rapamycin resistant mTor comprises, e.g., consists of, a mutation to S2035, e.g., comprises, e.g., consists of, an S2035I mutation.

The term "a" and "an" refers to one or to more than one (i.e., to at least one) of the grammatical object of the article. By way of example, "an element" means one element or more than one element.

The term "about" when referring to a measurable value such as an amount, a temporal duration, and the like, is meant to encompass variations of ±20% or in some instances ±10%, or in some instances ±5%, or in some instances ±1%, or in some instances ±0.1% from the specified value, as such variations are appropriate to perform the disclosed methods.

The term "Chimeric Antigen Receptor" or alternatively a "CAR" refers to a set of polypeptides, typically two in the simplest embodiments, which when in an immune effector cell, provides the cell with specificity for a target cell, typically a cancer cell, and with intracellular signal generation. In some embodiments, a CAR comprises at least an extracellular antigen binding domain, a transmembrane domain and a cytoplasmic signaling domain (also referred to herein as "an intracellular signaling domain") comprising a functional signaling domain derived from a stimulatory molecule and/or costimulatory molecule as defined below. In some aspects, the set of polypeptides are contiguous with each other. In some embodiments, the set of polypeptides include a dimerization switch that, upon the presence of a dimerization molecule, can couple the polypeptides to one another, e.g., can couple an antigen binding domain to an intracellular signaling domain. In one aspect, the stimulatory molecule is the zeta chain associated with the T cell receptor complex. In one aspect, the cytoplasmic signaling domain further comprises one or more functional signaling domains derived from at least one costimulatory molecule as defined below. In one aspect, the costimulatory molecule is chosen from the costimulatory molecules described herein, e.g., 4 1BB (i.e., CD137), CD27 and/or CD28. In one aspect, the CAR comprises a chimeric fusion protein comprising an extracellular antigen binding domain, a transmembrane domain and an intracellular signaling domain comprising a functional signaling domain derived from a stimulatory molecule. In one aspect, the CAR comprises a chimeric fusion protein comprising an extracellular antigen binding domain, a transmembrane domain and an intracellular signaling domain comprising a functional signaling domain derived from a costimulatory molecule and a functional signaling domain derived from a stimulatory molecule. In one aspect, the CAR comprises a chimeric fusion protein comprising an extracellular antigen binding domain, a transmembrane domain and an intracellular signaling domain comprising two functional signaling domains derived from one or more costimulatory molecule(s) and a functional signaling domain derived from a stimulatory molecule. In one aspect, the CAR comprises a chimeric fusion protein comprising an extracellular antigen binding domain, a transmembrane domain and an intracellular signaling domain comprising at least two functional signaling domains derived from one or more costimulatory molecule(s) and a functional signaling domain derived from a stimulatory molecule. In one aspect the CAR comprises an optional leader sequence at the amino-terminus (N-ter) of the CAR fusion protein. In one aspect, the CAR further comprises a leader sequence at the N-terminus of the extracellular antigen binding domain, wherein the leader sequence is optionally cleaved from the antigen binding domain (e.g., a scFv) during cellular processing and localization of the CAR to the cellular membrane.

A CAR that comprises an antigen binding domain (e.g., a scFv, or TCR) that targets a specific tumor marker X, such as those described herein, is also referred to as XCAR. For example, a CAR that comprises an antigen binding domain that targets CD19 is referred to as CD19CAR. As another example, a CAR that comprises an antigen binding domain that targets BCMA is referred to as a BCMA CAR.

The term "signaling domain" refers to the functional portion of a protein which acts by transmitting information within the cell to regulate cellular activity via defined signaling pathways by generating second messengers or functioning as effectors by responding to such messengers.

The term "antibody," as used herein, refers to a protein, or polypeptide sequence derived from an immunoglobulin molecule which specifically binds with an antigen. Antibodies can be polyclonal or monoclonal, multiple or single chain, or intact immunoglobulins, and may be derived from natural sources or from recombinant sources. Antibodies can be tetramers of immunoglobulin molecules.

The term "antibody fragment" refers to at least one portion of an antibody, that retains the ability to specifically interact with (e.g., by binding, steric hinderance, stabilizing/destabilizing, spatial distribution) an epitope of an antigen. Examples of antibody fragments include, but are not limited to, Fab, Fab', F(ab')2, Fv fragments, scFv antibody fragments, disulfide-linked Fvs (sdFv), a Fd fragment consisting of the VH and CH1 domains, linear antibodies, single domain antibodies such as sdAb (either VL or VH), camelid domains, multi-specific antibodies formed from antibody fragments such as a bivalent fragment comprising two Fab fragments linked by a disulfide brudge at the hinge region, and an isolated CDR or other epitope binding fragments of an antibody. An antigen binding fragment can also be incorporated into single domain antibodies, maxibodies, minibodies, nanobodies, intrabodies, diabodies, triabodies, tetrabodies, v-NAR and bis-scFv (see, e.g., Hollinger and Hudson, Nature Biotechnology 23:1126-1136, 2005). Antigen binding fragments can also be grafted into scaffolds based on polypeptides such as a fibronectin type III (Fn3) (see U.S. Pat. No. 6,703,199, which describes fibronectin polypeptide minibodies).

The term "scFv" refers to a fusion protein comprising at least one antibody fragment comprising a variable region of a light chain and at least one antibody fragment comprising a variable region of a heavy chain, wherein the light and heavy chain variable regions are contiguously linked, e.g., via a synthetic linker, e.g., a short flexible polypeptide linker, and capable of being expressed as a single chain polypeptide, and wherein the scFv retains the specificity of the intact antibody from which it is derived. Unless specified, as used herein an scFv may have the VL and VH variable regions in either order, e.g., with respect to the N-terminal and C-terminal ends of the polypeptide, the scFv may comprise VL-linker-VH or may comprise VH-linker-VL.

The portion of the CAR of the invention comprising an antibody or antibody fragment thereof may exist in a variety of forms where the antigen binding domain is expressed as part of a contiguous polypeptide chain including, for example, a single domain antibody fragment (sdAb), a single chain antibody (scFv), a humanized antibody or bispecific antibody (Harlow et al., 1999, In: Using Antibodies: A Laboratory Manual, Cold Spring Harbor Laboratory Press, NY; Harlow et al., 1989, In: Antibodies: A Laboratory Manual, Cold Spring Harbor, New York; Houston et al., 1988, Proc. Natl. Acad. Sci. USA 85:5879-5883; Bird et al., 1988, Science 242:423-426). In one aspect, the antigen binding domain of a CAR composition of the invention comprises an antibody fragment. In a further aspect, the CAR comprises an antibody fragment that comprises a scFv. The precise amino acid sequence boundaries of a given CDR can be determined using any of a number of well-known schemes, including those described by Kabat et al. (1991), "Sequences of Proteins of Immunological Interest," 5th Ed. Public Health Service, National Institutes of Health, Bethesda, MD ("Kabat" numbering scheme), Al-Lazikani et al., (1997) JMB 273, 927-948 ("Chothia" numbering scheme), or a combination thereof.

As used herein, the term "binding domain" or "antibody molecule" refers to a protein, e.g., an immunoglobulin chain or fragment thereof, comprising at least one immunoglobulin variable domain sequence. The term "binding domain" or "antibody molecule" encompasses antibodies and antibody fragments. In an embodiment, an antibody molecule is a multispecific antibody molecule, e.g., it comprises a plurality of immunoglobulin variable domain sequences, wherein a first immunoglobulin variable domain sequence of the plurality has binding specificity for a first epitope and a second immunoglobulin variable domain sequence of the plurality has binding specificity for a second epitope. In an embodiment, a multispecific antibody molecule is a bispecific antibody molecule. A bispecific antibody has specificity for no more than two antigens. A bispecific antibody molecule is characterized by a first immunoglobulin variable domain sequence which has binding specificity for a first epitope and a second immunoglobulin variable domain sequence that has binding specificity for a second epitope.

The portion of the CAR of the invention comprising an antibody or antibody fragment thereof may exist in a variety of forms where the antigen binding domain is expressed as part of a contiguous polypeptide chain including, for example, a single domain antibody fragment (sdAb), a single chain antibody (scFv), a humanized antibody, or bispecific antibody (Harlow et al., 1999, In: Using Antibodies: A Laboratory Manual, Cold Spring Harbor Laboratory Press, NY; Harlow et al., 1989, In: Antibodies: A Laboratory Manual, Cold Spring Harbor, New York; Houston et al., 1988, Proc. Natl. Acad. Sci. USA 85:5879-5883; Bird et al., 1988, Science 242:423-426). In one aspect, the antigen binding domain of a CAR composition of the invention comprises an antibody fragment. In a further aspect, the CAR comprises an antibody fragment that comprises a scFv.

The term "antibody heavy chain," refers to the larger of the two types of polypeptide chains present in antibody molecules in their naturally occurring conformations, and which normally determines the class to which the antibody belongs.

The term "antibody light chain," refers to the smaller of the two types of polypeptide chains present in antibody molecules in their naturally occurring conformations. Kappa (κ) and lambda (λ) light chains refer to the two major antibody light chain isotypes.

The term "recombinant antibody" refers to an antibody which is generated using recombinant DNA technology, such as, for example, an antibody expressed by a bacteriophage or yeast expression system. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using recombinant DNA or amino acid sequence technology which is available and well known in the art.

The term "antigen" or "Ag" refers to a molecule that provokes an immune response. This immune response may involve either antibody production, or the activation of specific immunologically-competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded solely by a full length nucleotide sequence of a gene. It is readily apparent that the present invention includes, but is not limited to, the use of partial nucleotide sequences of more than one gene and that these nucleotide sequences are arranged in various combinations to encode polypeptides that elicit the desired immune response. Moreover, a skilled artisan will understand that an antigen need not be encoded by a "gene" at all. It is readily apparent that an antigen can be generated synthesized or can be derived from a biological sample, or might be macromolecule besides a polypeptide. Such a biological sample can include, but is not limited to a tissue sample, a tumor sample, a cell or a fluid with other biological components.

The term "anti-cancer effect" refers to a biological effect which can be manifested by various means, including but not limited to, e.g., a decrease in tumor volume, a decrease in the number of cancer cells, a decrease in the number of metastases, an increase in life expectancy, decrease in cancer cell proliferation, decrease in cancer cell survival, or amelioration of various physiological symptoms associated with the cancerous condition. An "anti-cancer effect" can also be manifested by the ability of the peptides, polynucleotides, cells and antibodies in prevention of the occurrence of cancer in the first place. The term "anti-tumor effect" refers to a biological effect which can be manifested by various means, including but not limited to, e.g., a decrease in tumor volume, a decrease in the number of tumor cells, a decrease in tumor cell proliferation, or a decrease in tumor cell survival.

The term "autologous" refers to any material derived from the same individual into whom it is later to be re-introduced.

The term "allogeneic" refers to any material derived from a different animal of the same species as the individual to whom the material is introduced. Two or more individuals are said to be allogeneic to one another when the genes at one or more loci are not identical. In some aspects, allogeneic material from individuals of the same species may be sufficiently unlike genetically to interact antigenically The term "xenogeneic" refers to a graft derived from an animal of a different species.

The term "cancer" refers to a disease characterized by the uncontrolled growth of aberrant cells. Cancer cells can spread locally or through the bloodstream and lymphatic system to other parts of the body. Examples of various cancers are described herein and include but are not limited to, breast cancer, prostate cancer, ovarian cancer, cervical cancer, skin cancer, pancreatic cancer, colorectal cancer, renal cancer, liver cancer, brain cancer, lymphoma, leukemia, lung cancer and the like. The terms "tumor" and "cancer" are used interchangeably herein, e.g., both terms encompass solid and liquid, e.g., diffuse or circulating, tumors. As used herein, the term "cancer" or "tumor" includes premalignant, as well as malignant cancers and tumors.

"Derived from" as that term is used herein, indicates a relationship between a first and a second molecule. It generally refers to structural similarity between the first molecule and a second molecule and does not connotate or include a process or source limitation on a first molecule that is derived from a second molecule. For example, in the case of an intracellular signaling domain that is derived from a CD3zeta molecule, the intracellular signaling domain retains sufficient CD3zeta structure such that is has the required function, namely, the ability to generate a signal under the appropriate conditions. It does not connotate or include a limitation to a particular process of producing the intracellular signaling domain, e.g., it does not mean that, to provide the intracellular signaling domain, one must start with a CD3zeta sequence and delete unwanted sequence, or impose mutations, to arrive at the intracellular signaling domain.

The phrase "disease associated with expression of a tumor antigen as described herein" includes, but is not limited to, a disease associated with expression of a tumor antigen as described herein or condition associated with cells which express a tumor antigen as described herein including, e.g., proliferative diseases such as a cancer or malignancy or a precancerous condition such as a myelodysplasia, a myelodysplastic syndrome or a preleukemia; or a noncancer related indication associated with cells which express a tumor antigen as described herein. In one aspect, a cancer associated with expression of a tumor antigen as described herein is a hematological cancer. In one aspect, a cancer associated with expression of a tumor antigen as described herein is a solid cancer. Further diseases associated with expression of a tumor antigen described herein include, but not limited to, e.g., atypical and/or non-classical cancers, malignancies, precancerous conditions or proliferative diseases associated with expression of a tumor antigen as described herein. Non-cancer related indications associated with expression of a tumor antigen as described herein include, but are not limited to, e.g., autoimmune disease, (e.g., lupus), inflammatory disorders (allergy and asthma) and transplantation. In some embodiments, the tumor antigen-expressing cells express, or at any time expressed, mRNA encoding the tumor antigen. In an embodiment, the tumor antigen-expressing cells produce the tumor antigen protein (e.g., wild-type or mutant), and the tumor antigen protein may be present at normal levels or reduced levels. In an embodiment, the tumor antigen-expressing cells produced detectable levels of a tumor antigen protein at one point, and subsequently produced substantially no detectable tumor antigen protein.

The term "conservative sequence modifications" refers to amino acid modifications that do not significantly affect or alter the binding characteristics of the antibody or antibody fragment containing the amino acid sequence. Such conservative modifications include amino acid substitutions, additions and deletions. Modifications can be introduced into an antibody or antibody fragment of the invention by standard techniques known in the art, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within a CAR of the invention can be replaced with other amino acid residues from the same side chain family and the altered CAR can be tested using the functional assays described herein.

The term "stimulation," refers to a primary response induced by binding of a stimulatory molecule (e.g., a TCR/CD3 complex or CAR) with its cognate ligand (or tumor antigen in the case of a CAR) thereby mediating a signal transduction event, such as, but not limited to, signal transduction via the TCR/CD3 complex or signal transduction via the appropriate NK receptor or signaling domains of the CAR. Stimulation can mediate altered expression of certain molecules.

The term "stimulatory molecule," refers to a molecule expressed by an immune cell (e.g., T cell, NK cell, B cell) that provides the cytoplasmic signaling sequence(s) that regulate activation of the immune cell in a stimulatory way for at least some aspect of the immune cell signaling pathway. In one aspect, the signal is a primary signal that is initiated by, for instance, binding of a TCR/CD3 complex with an MHC molecule loaded with peptide, and which leads to mediation of a T cell response, including, but not limited to, proliferation, activation, differentiation, and the like. A primary cytoplasmic signaling sequence (also referred to as a "primary signaling domain") that acts in a stimulatory manner may contain a signaling motif which is known as immunoreceptor tyrosine-based activation motif or ITAM. Examples of an ITAM containing cytoplasmic signaling sequence that is of particular use in the invention includes, but is not limited to, those derived from CD3 zeta, common FcR gamma (FCER1G), Fc gamma RIIa, FcR beta (Fc Epsilon R1b), CD3 gamma, CD3 delta, CD3 epsilon, CD79a, CD79b, DAP10, and DAP12. In a specific CAR of the invention, the intracellular signaling domain in any one or more CARS of the invention comprises an intracellular signaling sequence, e.g., a primary signaling sequence of CD3-zeta. In a specific CAR of the invention, the primary signaling sequence of CD3-zeta is the sequence provided as SEQ ID NO:18, or the equivalent residues from a non-human species, e.g., mouse, rodent, monkey, ape and the like. In a specific CAR of the invention, the primary signaling sequence of CD3-zeta is the sequence as provided in SEQ ID NO:20, or the equivalent residues from a non-human species, e.g., mouse, rodent, monkey, ape and the like.

The term "antigen presenting cell" or "APC" refers to an immune system cell such as an accessory cell (e.g., a B-cell, a dendritic cell, and the like) that displays a foreign antigen complexed with major histocompatibility complexes (MHC's) on its surface. T-cells may recognize these complexes using their T-cell receptors (TCRs). APCs process antigens and present them to T-cells.

An "intracellular signaling domain," as the term is used herein, refers to an intracellular portion of a molecule. The intracellular signaling domain generates a signal that promotes an immune effector function of the CAR containing cell, e.g., a CART cell. Examples of immune effector function, e.g., in a CART cell, include cytolytic activity and helper activity, including the secretion of cytokines.

In an embodiment, the intracellular signaling domain can comprise a primary intracellular signaling domain. Exemplary primary intracellular signaling domains include those derived from the molecules responsible for primary stimulation, or antigen dependent simulation. In an embodiment, the intracellular signaling domain can comprise a costimulatory intracellular domain. Exemplary costimulatory intracellular signaling domains include those derived from molecules responsible for costimulatory signals, or antigen independent stimulation. For example, in the case of a CART, a primary intracellular signaling domain can comprise a cytoplasmic sequence of a T cell receptor, and a costimulatory intracellular signaling domain can comprise cytoplasmic sequence from co-receptor or costimulatory molecule.

A primary intracellular signaling domain can comprise a signaling motif which is known as an immunoreceptor tyrosine-based activation motif or ITAM. Examples of ITAM containing primary cytoplasmic signaling sequences include, but are not limited to, those derived from CD3 zeta, common FcR gamma (FCER1G), Fc gamma RIIa, FcR beta (Fc Epsilon R1b), CD3 gamma, CD3 delta, CD3 epsilon, CD79a, CD79b, DAP10, and DAP12.

The term "zeta" or alternatively "zeta chain", "CD3-zeta" or "TCR–zeta" is defined as the protein provided as GenBan Acc. No. BAG36664.1, or the equivalent residues from a non-human species, e.g., mouse, rodent, monkey, ape and the like, and a "zeta stimulatory domain" or alternatively a "CD3-zeta stimulatory domain" or a "TCR-zeta stimulatory domain" is defined as the amino acid residues from the cytoplasmic domain of the zeta chain, or functional derivatives thereof, that are sufficient to functionally transmit an initial signal necessary for T cell activation. In one aspect the cytoplasmic domain of zeta comprises residues 52 through 164 of GenBank Acc. No. BAG36664.1 or the equivalent residues from a non-human species, e.g., mouse, rodent, monkey, ape and the like, that are functional orthologs thereof. In one aspect, the "zeta stimulatory domain" or a "CD3-zeta stimulatory domain" is the sequence provided as SEQ ID NO:18. In one aspect, the "zeta stimulatory domain" or a "CD3-zeta stimulatory domain" is the sequence provided as SEQ ID NO:20.

The term a "costimulatory molecule" refers to a cognate binding partner on a T cell that specifically binds with a costimulatory ligand, thereby mediating a costimulatory response by the T cell, such as, but not limited to, proliferation. Costimulatory molecules are cell surface molecules other than antigen receptors or their ligands that are contribute to an efficient immune response. Costimulatory molecules include, but are not limited to an MHC class I molecule, BTLA and a Toll ligand receptor, as well as OX40, CD27, CD28, CDS, ICAM-1, LFA-1 (CD11a/CD18), ICOS (CD278), and 4-1BB (CD137). Further examples of such costimulatory molecules include CDS, ICAM-1, GITR, BAFFR, HVEM (LIGHTR), SLAMF7, NKp80 (KLRF1), NKp44, NKp30, NKp46, CD160, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, NKG2D, NKG2C, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, CD19a, and a ligand that specifically binds with CD83.

A costimulatory intracellular signaling domain can be the intracellular portion of a costimulatory molecule. A costimulatory molecule can be represented in the following protein families: TNF receptor proteins, Immunoglobulin-like proteins, cytokine receptors, integrins, signaling lymphocytic activation molecules (SLAM proteins), and activating NK cell receptors. Examples of such molecules include CD27, CD28, 4-1BB (CD137), OX40, GITR, CD30, CD40, ICOS, BAFFR, HVEM, ICAM-1, lymphocyte function-associated antigen-1 (LFA-1), CD2, CDS, CD7, CD287, LIGHT, NKG2C, NKG2D, SLAMF7, NKp80, NKp30, NKp44, NKp46, CD160, B7-113, and a ligand that specifically binds with CD83, and the like.

The intracellular signaling domain can comprise the entire intracellular portion, or the entire native intracellular signaling domain, of the molecule from which it is derived, or a functional fragment or derivative thereof.

The term "4-1BB" refers to a member of the TNFR superfamily with an amino acid sequence provided as GenBank Ace. No. AAA62478.2, or the equivalent residues from a non-human species, e.g., mouse, rodent, monkey, ape and the like; and a "4-1BB costimulatory domain" is defined as amino acid residues 214-255 of GenBank Acc. No. AAA62478.2, or the equivalent residues from a non-human species, e.g., mouse, rodent, monkey, ape and the like. In one aspect, the "4-1BB costimulatory domain" is the sequence provided as SEQ ID NO:14 or the equivalent residues from a non-human species, e.g., mouse, rodent, monkey, ape and the like.

"Immune effector cell," as that term is used herein, refers to a cell that is involved in an immune response, e.g., in the promotion of an immune effector response. Examples of immune effector cells include T cells, e.g., alpha/beta T cells and gamma/delta T cells, B cells, natural killer (NK) cells, natural killer T (NKT) cells, mast cells, and myeloic-derived phagocytes.

"Immune effector function or immune effector response," as that term is used herein, refers to function or response, e.g., of an immune effector cell, that enhances or promotes an immune attack of a target cell. E.g., an immune effector function or response refers a property of a T or NK cell that promotes killing or the inhibition of growth or proliferation, of a target cell. In the case of a T cell, primary stimulation and co-stimulation are examples of immune effector function or response.

The term "encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (e.g., rRNA, tRNA and mRNA) or a defined sequence of amino acids and the biological properties resulting therefrom. Thus, a gene, cDNA, or RNA, encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or a RNA may also include introns to the extent that the nucleotide sequence encoding the protein may in some version contain an intron(s).

The term "effective amount" or "therapeutically effective amount" are used interchangeably herein, and refer to an amount of a compound, formulation, material, or composition, as described herein effective to achieve a particular biological result.

The term "endogenous" refers to any material from or produced inside an organism, cell, tissue or system.

The term "exogenous" refers to any material introduced from or produced outside an organism, cell, tissue or system.

The term "expression" refers to the transcription and/or translation of a particular nucleotide sequence driven by a promoter.

The term "transfer vector" refers to a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "transfer vector" includes an autonomously replicating plasmid or a virus. The term should also be construed to further include non-plasmid and non-viral compounds which facilitate transfer of nucleic acid into cells, such as, for example, a polylysine compound, liposome, and the like. Examples of viral transfer vectors include, but are not limited to, adenoviral vectors, adeno-associated virus vectors, retroviral vectors, lentiviral vectors, and the like.

The term "expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, including cosmids, plasmids (e.g., naked or contained in liposomes) and viruses (e.g., lentiviruses, retroviruses, adenoviruses, and adeno-associated viruses) that incorporate the recombinant polynucleotide.

The term "homologous" or "identity" refers to the subunit sequence identity between two polymeric molecules, e.g., between two nucleic acid molecules, such as, two DNA molecules or two RNA molecules, or between two polypeptide molecules. When a subunit position in both of the two molecules is occupied by the same monomeric subunit; e.g., if a position in each of two DNA molecules is occupied by adenine, then they are homologous or identical at that position. The homology between two sequences is a direct function of the number of matching or homologous positions; e.g., if half (e.g., five positions in a polymer ten subunits in length) of the positions in two sequences are homologous, the two sequences are 50% homologous; if 90% of the positions (e.g., 9 of 10), are matched or homologous, the two sequences are 90% homologous.

"Humanized" forms of non-human (e.g., murine) antibodies are chimeric immunoglobulins, immunoglobulin chains or fragments thereof (such as Fv, Fab, Fab', F(ab')2 or other antigen-binding subsequences of antibodies) which contain minimal sequence derived from non-human immunoglobulin. For the most part, humanized antibodies and antibody fragments thereof are human immunoglobulins (recipient antibody or antibody fragment) in which residues from a complementary-determining region (CDR) of the recipient are replaced by residues from a CDR of a non-human species (donor antibody) such as mouse, rat or rabbit having the desired specificity, affinity, and capacity. In some instances, Fv framework region (FR) residues of the human immunoglobulin are replaced by corresponding non-human residues. Furthermore, a humanized antibody/antibody fragment can comprise residues which are found neither in the recipient antibody nor in the imported CDR or framework sequences. These modifications can further refine and optimize antibody or antibody fragment performance. In general, the humanized antibody or antibody fragment thereof will comprise substantially all of at least one, and typically two, variable domains, in which all or substantially all of the CDR regions correspond to those of a non-human immunoglobulin and all or a significant portion of the FR regions are those of a human immunoglobulin sequence. The humanized antibody or antibody fragment can also comprise at least a portion of an immunoglobulin constant region (Fc), typically that of a human immunoglobulin. For further details, see Jones et al., Nature, 321: 522-525, 1986; Reichmann et al., Nature, 332: 323-329, 1988; Presta, Curr. Op. Struct. Biol., 2: 593-596, 1992.

"Fully human" refers to an immunoglobulin, such as an antibody or antibody fragment, where the whole molecule is of human origin or consists of an amino acid sequence identical to a human form of the antibody or immunoglobulin.

The term "isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

The term "operably linked" or "transcriptional control" refers to functional linkage between a regulatory sequence and a heterologous nucleic acid sequence resulting in expression of the latter. For example, a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Operably linked DNA sequences can be contiguous with each other and, e.g., where necessary to join two protein coding regions, are in the same reading frame.

The term "parenteral" administration of an immunogenic composition includes, e.g., subcutaneous (s.c.), intravenous (i.v.), intramuscular (i.m.), or intrasternal injection, intratumoral, or infusion techniques.

The term "nucleic acid" or "polynucleotide" refers to deoxyribonucleic acids (DNA) or ribonucleic acids (RNA) and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260:2605-2608 (1985); and Rossolini et al., Mol. Cell. Probes 8:91-98 (1994)).

The terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. A polypeptide includes a natural peptide, a recombinant peptide, or a combination thereof.

The term "promoter" refers to a DNA sequence recognized by the synthetic machinery of the cell, or introduced synthetic machinery, required to initiate the specific transcription of a polynucleotide sequence.

The term "promoter/regulatory sequence" refers to a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

The term "constitutive" promoter refers to a nucleotide sequence which, when operably linked with a polynucleotide which encodes or specifies a gene product, causes the gene product to be produced in a cell under most or all physiological conditions of the cell.

The term "inducible" promoter refers to a nucleotide sequence which, when operably linked with a polynucleotide which encodes or specifies a gene product, causes the gene product to be produced in a cell substantially only when an inducer which corresponds to the promoter is present in the cell.

The term "tissue-specific" promoter refers to a nucleotide sequence which, when operably linked with a polynucleotide encodes or specified by a gene, causes the gene product to be produced in a cell substantially only if the cell is a cell of the tissue type corresponding to the promoter.

The terms "cancer associated antigen" or "tumor antigen" interchangeably refers to a molecule (typically a protein, carbohydrate or lipid) that is expressed on the surface of a cancer cell, either entirely or as a fragment (e.g., MHC/peptide), and which is useful for the preferential targeting of a pharmacological agent to the cancer cell. In some embodiments, a tumor antigen is a marker expressed by both normal cells and cancer cells, e.g., a lineage marker, e.g., CD19 on B cells. In some embodiments, a tumor antigen is a cell surface molecule that is overexpressed in a cancer cell in comparison to a normal cell, for instance, 1-fold over expression, 2-fold overexpression, 3-fold overexpression or more in comparison to a normal cell. In some embodiments, a tumor antigen is a cell surface molecule that is inappropriately synthesized in the cancer cell, for instance, a molecule that contains deletions, additions or mutations in comparison to the molecule expressed on a normal cell. In some embodiments, a tumor antigen will be expressed exclusively on the cell surface of a cancer cell, entirely or as a fragment (e.g., MHC/peptide), and not synthesized or expressed on the surface of a normal cell. In some embodiments, the CARs of the present invention includes CARs comprising an antigen binding domain (e.g., antibody or antibody fragment) that binds to a MHC presented peptide. Normally, peptides derived from endogenous proteins fill the pockets of Major histocompatibility complex (MHC) class I molecules, and are recognized by T cell receptors (TCRs) on CD8+ T lymphocytes. The MHC class I complexes are constitutively expressed by all nucleated cells. In cancer, virus-specific and/or tumor-specific peptide/MHC complexes represent a unique class of cell surface targets for immunotherapy. TCR-like antibodies targeting peptides derived from viral or tumor antigens in the context of human leukocyte antigen (HLA)-A1 or HLA-A2 have been described (see, e.g., Sastry et al., J Virol. 2011 85(5):1935-1942; Sergeeva et al., Blood, 2011 117(16):4262-4272; Verma et al., J Immunol 2010 184(4):2156-2165; Willemsen et al., Gene Ther 2001 8(21):1601-1608; Dao et al., Sci Transl Med 2013 5(176):176ra33; Tassev et al., Cancer Gene Ther 2012 19(2):84-100). For example, TCR-like antibody can be identified from screening a library, such as a human say phage displayed library.

The term "tumor-supporting antigen" or "cancer-supporting antigen" interchangeably refer to a molecule (typically a protein, carbohydrate or lipid) that is expressed on the surface of a cell that is, itself, not cancerous, but supports the cancer cells, e.g., by promoting their growth or survival e.g., resistance to immune cells. Exemplary cells of this type include stromal cells and myeloid-derived suppressor cells (MDSCs). The tumor-supporting antigen itself need not play a role in supporting the tumor cells so long as the antigen is present on a cell that supports cancer cells.

The term "flexible polypeptide linker" or "linker" as used in the context of a scFv refers to a peptide linker that consists of amino acids such as glycine and/or serine residues used alone or in combination, to link variable heavy and variable light chain regions together. In one embodiment, the flexible polypeptide linker is a Gly/Ser linker and comprises the amino acid sequence (Gly-Gly-Gly-Ser)n, where n is a positive integer equal to or greater than 1. For example, n=1, n=2, n=3. n=4, n=5 and n=6, n=7, n=8, n=9 and n=10 (SEQ ID NO:6592). In one embodiment, the flexible polypeptide linkers include, but are not limited to, (Gly4 Ser)4 (SEQ ID NO:6593) or (Gly4 Ser)3 (SEQ ID NO:6594). In another embodiment, the linkers include multiple repeats of (Gly2Ser), (GlySer) or (Gly3Ser) (SEQ ID NO:6595). Also included within the scope of the invention are linkers described in WO2012/138475, incorporated herein by reference).

As used herein in connection with a messenger RNA (mRNA), a 5' cap (also termed an RNA cap, an RNA 7-methylguanosine cap or an RNA m7G cap) is a modified guanine nucleotide that has been added to the "front" or 5' end of a eukaryotic messenger RNA shortly after the start of transcription. The 5' cap consists of a terminal group which is linked to the first transcribed nucleotide. Its presence is critical for recognition by the ribosome and protection from RNases. Cap addition is coupled to transcription, and occurs co-transcriptionally, such that each influences the other. Shortly after the start of transcription, the end of the mRNA being synthesized is bound by a cap-synthesizing complex associated with RNA polymerase. This enzymatic complex catalyzes the chemical reactions that are required for mRNA capping. Synthesis proceeds as a multi-step biochemical reaction. The capping moiety can be modified to modulate functionality of mRNA such as its stability or efficiency of translation.

As used herein, "in vitro transcribed RNA" refers to RNA, preferably mRNA, that has been synthesized in vitro. Generally, the in vitro transcribed RNA is generated from an in vitro transcription vector. The in vitro transcription vector comprises a template that is used to generate the in vitro transcribed RNA.

As used herein, a "poly(A)" is a series of adenosines attached by polyadenylation to the mRNA. In the preferred embodiment of a construct for transient expression, the polyA is between 50 and 5000 (SEQ ID NO: 6596), preferably greater than 64, more preferably greater than 100, most preferably greater than 300 or 400. poly(A) sequences can be modified chemically or enzymatically to modulate mRNA functionality such as localization, stability or efficiency of translation.

As used herein, "polyadenylation" refers to the covalent linkage of a polyadenylyl moiety, or its modified variant, to a messenger RNA molecule. In eukaryotic organisms, most messenger RNA (mRNA) molecules are polyadenylated at the 3' end. The 3' poly(A) tail is a long sequence of adenine nucleotides (often several hundred) added to the pre-mRNA through the action of an enzyme, polyadenylate polymerase.

In higher eukaryotes, the poly(A) tail is added onto transcripts that contain a specific sequence, the polyadenylation signal. The poly(A) tail and the protein bound to it aid in protecting mRNA from degradation by exonucleases. Polyadenylation is also important for transcription termination, export of the mRNA from the nucleus, and translation. Polyadenylation occurs in the nucleus immediately after transcription of DNA into RNA, but additionally can also occur later in the cytoplasm. After transcription has been terminated, the mRNA chain is cleaved through the action of an endonuclease complex associated with RNA polymerase. The cleavage site is usually characterized by the presence of the base sequence AAUAAA near the cleavage site. After the mRNA has been cleaved, adenosine residues are added to the free 3' end at the cleavage site.

As used herein, "transient" refers to expression of a non-integrated transgene for a period of hours, days or weeks, wherein the period of time of expression is less than the period of time for expression of the gene if integrated into the genome or contained within a stable plasmid replicon in the host cell.

As used herein, the terms "treat", "treatment" and "treating" refer to the reduction or amelioration of the progression, severity and/or duration of a proliferative disorder, or the amelioration of one or more symptoms (preferably, one or more discernible symptoms) of a proliferative disorder resulting from the administration of one or more therapies (e.g., one or more therapeutic agents such as a CAR of the invention). In specific embodiments, the terms "treat", "treatment" and "treating" refer to the amelioration of at least one measurable physical parameter of a proliferative disorder, such as growth of a tumor, not necessarily discernible by the patient. In other embodiments the terms "treat", "treatment" and "treating"-refer to the inhibition of the progression of a proliferative disorder, either physically by, e.g., stabilization of a discernible symptom, physiologically by, e.g., stabilization of a physical parameter, or both. In other embodiments the terms "treat", "treatment" and "treating" refer to the reduction or stabilization of tumor size or cancerous cell count.

The term "signal transduction pathway" refers to the biochemical relationship between a variety of signal transduction molecules that play a role in the transmission of a signal from one portion of a cell to another portion of a cell. The phrase "cell surface receptor" includes molecules and complexes of molecules capable of receiving a signal and transmitting signal across the membrane of a cell.

The term "subject" is intended to include living organisms in which an immune response can be elicited (e.g., mammals, human).

The term, a "substantially purified" cell refers to a cell that is essentially free of other cell types. A substantially purified cell also refers to a cell which has been separated from other cell types with which it is normally associated in its naturally occurring state. In some instances, a population of substantially purified cells refers to a homogenous population of cells. In other instances, this term refers simply to cell that have been separated from the cells with which they are naturally associated in their natural state. In some aspects, the cells are cultured in vitro. In other aspects, the cells are not cultured in vitro.

The term "therapeutic" as used herein means a treatment. A therapeutic effect is obtained by reduction, suppression, remission, or eradication of a disease state.

The term "prophylaxis" as used herein means the prevention of or protective treatment for a disease or disease state.

In the context of the present invention, "tumor antigen" or "hyperproliferative disorder antigen" or "antigen associated with a hyperproliferative disorder" refers to antigens that are common to specific hyperproliferative disorders. In certain aspects, the hyperproliferative disorder antigens of the present invention are derived from, cancers including but not limited to primary or metastatic melanoma, thymoma, lymphoma, sarcoma, lung cancer, liver cancer, non-Hodgkin lymphoma, Hodgkin lymphoma, leukemias, uterine cancer, cervical cancer, bladder cancer, kidney cancer and adenocarcinomas such as breast cancer, prostate cancer, ovarian cancer, pancreatic cancer, and the like.

The term "transfected" or "transformed" or "transduced" refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

The term "specifically binds," refers to a molecule recognizing and binding with a binding partner (e.g., a protein or nucleic acid) present in a sample, but which molecule does not substantially recognize or bind other molecules in the sample.

"Membrane anchor" or "membrane tethering domain", as that term is used herein, refers to a polypeptide or moiety, e.g., a myristoyl group, sufficient to anchor an extracellular or intracellular domain to the plasma membrane.

The term "bioequivalent" refers to an amount of an agent other than the reference compound (e.g., RAD001), required to produce an effect equivalent to the effect produced by the reference dose or reference amount of the reference compound (e.g., RAD001). In an embodiment the effect is the level of mTOR inhibition, e.g., as measured by P70 S6 kinase inhibition, e.g., as evaluated in an in vivo or in vitro assay, e.g., as measured by an assay described herein, e.g., the Boulay assay. In an embodiment, the effect is alteration of the ratio of PD-1 positive/PD-1 negative T cells, as measured by cell sorting. In an embodiment a bioequivalent amount or dose of an mTOR inhibitor is the amount or dose that achieves the same level of P70 S6 kinase inhibition as does the reference dose or reference amount of a reference compound. In an embodiment, a bioequivalent amount or dose of an mTOR inhibitor is the amount or dose that achieves the same level of alteration in the ratio of PD-1 positive/PD-1 negative T cells as does the reference dose or reference amount of a reference compound.

The term "low, immune enhancing, dose" when used in conjunction with an mTOR inhibitor, e.g., an allosteric mTOR inhibitor, e.g., RAD001 or rapamycin, or a catalytic mTOR inhibitor, refers to a dose of mTOR inhibitor that partially, but not fully, inhibits mTOR activity, e.g., as measured by the inhibition of P70 S6 kinase activity. Methods for evaluating mTOR activity, e.g., by inhibition of P70 S6 kinase, are discussed herein. The dose is insufficient to result in complete immune suppression but is sufficient to enhance the immune response. In an embodiment, the low, immune enhancing, dose of mTOR inhibitor results in a decrease in the number of PD-1 positive T cells and/or an increase in the number of PD-1 negative T cells, or an increase in the ratio of PD-1 negative T cells/PD-1 positive T cells. In an embodiment, the low, immune enhancing, dose of mTOR inhibitor results in an increase in the number of naive T cells. In an embodiment, the low, immune enhancing, dose of mTOR inhibitor results in one or more of the following:

an increase in the expression of one or more of the following markers: CD62Lhigh, CD127high, CD27+, and BCL2, e.g., on memory T cells, e.g., memory T cell precursors;

a decrease in the expression of KLRG1, e.g., on memory T cells, e.g., memory T cell precursors; and an increase in the number of memory T cell precursors, e.g., cells with any one or combination of the following characteristics: increased CD62Lhigh, increased CD127high, increased CD27+, decreased KLRG1, and increased BCL2;

wherein any of the changes described above occurs, e.g., at least transiently, e.g., as compared to a non-treated subject.

"Refractory" as used herein refers to a disease, e.g., cancer, that does not respond to a treatment. In embodiments, a refractory cancer can be resistant to a treatment before or at the beginning of the treatment. In other embodiments, the refractory cancer can become resistant during a treatment. A refractory cancer is also called a resistant cancer.

"Relapsed" as used herein refers to the return of a disease (e.g., cancer) or the signs and symptoms of a disease such as cancer after a period of improvement, e.g., after prior treatment of a therapy, e.g., cancer therapy.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. As another example, a range such as 95-99% identity, includes something with 95%, 96%, 97%, 98% or 99% identity, and includes subranges such as 96-99%, 96-98%, 96-97%, 97-99%, 97-98% and 98-99% identity. This applies regardless of the breadth of the range.

The gRNA molecules, compositions and methods described herein relate to genome editing in eukaryotic cells using a CRISPR/Cas system, e.g., a Cas9 system. In particular, the gRNA molecules, compositions and methods described herein relate to regulation of expression of (or expression of functional versions of) target molecules that have an effect on the function of a transplanted cell, for example a cell for cancer immunotherapy. In an aspect, the transplanted cell is an immune effector cell, e.g., an NK cell or T cell. In an aspect, the cell is an allogeneic cell. In an aspect, the cell has been, is or will be engineered to express a chimeric antigen receptor. Thus, provided herein are compositions and methods for altering, e.g., inhibiting or reducing, the expression and/or function (e.g., the level of expression of a functional version) of a gene product which may improve the efficacy (for example, by reducing or eliminating undesirable immunogenicity (such as a host versus graft response or a graft versus host response)), function, proliferation, stimulation or survival of a transplanted cell, for example a transplanted immune effector cell, for example a NK cell or T cell, for example a T cell engineered to express a chimeric antigen receptor (CAR), for example an allogeneic CAR-expressing T cell for immunotherapy.

In aspects, the gene products are allogeneic T cell targets such as a component of the T cell receptor, e.g., CD3zeta, CD3 epsilon, CD3 gamma, CD3 delta, T cell receptor (TCR) alpha or TCR beta; an FILA molecule or beta-2 micoglobulin (B2M), e.g., an HLA-A, an HLA-B, an HLA-C or B2M; a CIITA molecule; or a target for an immunosuppressant, e.g., glucocorticoid receptor, deoxycytidine kinase, an FKBP, CD52 or a cyclophilin family member; and combinations thereof. Without being bound by theory it is believed that inhibition or elimination of the level of an allogeneic T cell target or level of expression of an allogeneic T cell target gene product (e.g., via alteration of the gene) may improve the function of a cell, e.g., a transplanted cell, e.g., a transplanted immune effector cell, e.g., a CART cell, e.g., an allogeneic CART cell, by reducing or eliminating a graft vs. host response, a host vs. graft response, or will render said transplanted cell resistant to immunosuppressant therapy.

In an aspect, compositions and methods described herein can be used to improve cell, e.g., T cell, e.g., CAR-engineered T cell, e.g., allogeneic CAR-engineered T cell function (for example, by reducing or eliminating undesirable immunogenicity (such as a host versus graft response or a graft versus host response)), survival, proliferation and/or efficacy by altering the gene of a component of the T cell receptor (TCR), e.g., CD3zeta, CD3 epsilon, CD3 gamma, CD3 delta, T cell receptor (TCR) alpha, e.g., constant region of TCR alpha, or TCR beta, e.g., constant region 1 or constant region 2 of TCR beta gene. While not wishing to be bound by theory, it is considered that reduced or absent expression of functional T-cell receptor components reduces or eliminates the presence of TCR on the surface of said cell, thereby reducing or preventing graft vs. host disease by eliminating T cell receptor recognition of and response to host tissues. This approach, therefore, could be used to generate "off the shelf" T cells (Torikai et al., 2012 Blood 119, 5697-5705).

In an aspect, compositions and methods described herein can be used to improve cell, e.g., T cell, e.g., CAR-engineered T cell, e.g., allogeneic CAR-engineered T cell function (for example, by reducing or eliminating undesirable immunogenicity (such as a host versus graft response or a graft versus host response)), survival, proliferation and/or efficacy by altering the gene of a component of the major histocompatibility complex, e.g., an HLA protein or B2M, e.g., HLA-A, HLA-B, HLA-C or B2M (encoded by the B2M gene), or protein which regulates expression of one or more components of the major histocompatibility complex, e.g., NLRC5. While not wishing to be bound by theory, it is considered that reduced or absent expression of a mismatch (e.g., one that does not match the type of the subject receiving the cell therapy) HLA protein (or component) reduces or eliminate host vs. graft disease by eliminating host T cell receptor recognition of and response to mismatched (e.g., allogeneic) graft tissue. This approach, therefore, could be used to generate "off the shelf" T cells.

In an aspect, compositions and methods described herein can be used to improve cell, e.g., T cell, e.g., CAR-engineered T cell, e.g., allogeneic CAR-engineered T cell function (for example, by reducing or eliminating undesirable immunogenicity (such as a host versus graft response or a graft versus host response)), survival, proliferation and/or efficacy by altering a gene of a component of the major histocompatibility complex class II or a regulator of MHC class II expression, e.g., CIITA (encoded by the CIITA gene), RFXANK, RFX5, or RFXAP, and combinations thereof, e.g., CIITA. While not wishing to be bound by theory, it is believed that reducing or eliminating the expression of a regulator of MHC class II expression, e.g., CIITA, will reduce or eliminate the expression of MHC class II molecules on the allogeneic cell, thereby reducing or eliminating expression of a mismatch (e.g., one that does not match the type of the subject receiving the cell therapy) MHC class II protein (or component), thereby reducing or eliminating host vs. graft disease by, e.g., eliminating host T cell receptor recognition of and response to mismatched (e.g., allogeneic) graft tissue, e.g., allogeneic T cell, e.g., allogeneic CART cell, as described herein. This approach, therefore, could be used to generate "off the shelf" T cells.

In an aspect, it may be beneficial to reduce or eliminate expression of both one or more MHC class I molecules and one or more MHC II molecules, e.g., in a T cell, e.g., in an allogeneic T cell, e.g., in an allogeneic CART cell, e.g., as described herein, to further reduce or eliminate the host versus graft disease response upon administration of the cell. Thus, in embodiments of the cells and methods of the invention, cells may be contacted with a composition of the invention (e.g., a composition comprising a gRNA and a Cas9 molecule) comprising a gRNA molecule, e.g., as described herein, to B2M (e.g., such that expression of one or more MHC class I molecules is reduced or eliminated in said cell) and a composition of the invention (e.g., a composition comprising a gRNA and a Cas9 molecule) comprising a gRNA molecule, e.g., as described herein, to CIITA (e.g., such that expression of one or more MHC class II molecules is reduced or eliminated). In embodiments of the cells and methods of the invention, the cell may also be contacted with a composition of the invention (e.g., a composition comprising a gRNA and a Cas9 molecule) comprising a gRNA molecule, e.g., as described herein, to a component of the TCR, e.g., to TRAC and/or TRBC (e.g., such that expression of the T cell receptor, e.g., one or more components of the TCR is reduced or eliminated). In an embodiment, a cell of the invention has reduced or eliminated expression of TCR (e.g., as detected by flow cytometry), reduced or eliminated expression of one or more MHC class I molecules (e.g., as detected by flow cytometry), and reduced or eliminated expression of one or more MHC class II molecules (e.g., as detected by flow cytometry). In an embodiment, a cell of the invention has reduced or eliminated expression of TRAC, reduced or eliminated expression of B2M, and reduced or eliminated expression of CIITA. In an embodiment, a cell of the invention has reduced or eliminated expression of TRAC, reduced or eliminated expression of NLRC5, and reduced or eliminated expression of CIITA. In embodiments, the reduced or eliminated expression is measured relative to a similar cell that has not been treated with a composition or CRISPR system of the invention. In embodiments, the cell is an immune effector cell, e.g., a T cell or NK cell, e.g., a T cell, e.g., as described herein. In embodiments the cell is a T cell which is engineered to express a chimeric antigen receptor (CAR), e.g., as described herein. In embodiments, the CAR is a BCMA CAR, e.g., as described herein. In an embodiment, the invention provides a cell, e.g., an immune effector cell, e.g., a T cell or NK cell, e.g., a T cell, engineered to express a BCMA CAR which is TCR−/B2M−/CIITA− or TCR−/NLRC5−/CIITA−. In embodiments, the cell is a human cell. In embodiments, the cell is allogeneic relative to a subject to be administered said cell. In embodiments, the reduced or eliminated expression of TCR, B2M, NLRC5 and/or CIITA is accomplished by introducing into said cell a composition, CRISPR system, or gRNA of the invention, e.g., as described herein, or by a method as described herein.

In an aspect, compositions and methods described herein can be used to improve cell, e.g., T cell, e.g., CAR-engineered T cell, e.g., allogeneic CAR-engineered T cell function (for example, by reducing or eliminating undesirable immunogenicity (such as a host versus graft response or a graft versus host response)), survival, proliferation and/or efficacy by altering the gene of a target for an immunosuppressant, e.g., glucocorticoid receptor (GR) (encoded by NR3C1). Without being bound by theory, it is considered that absent or reduced expression of functional GR on a cell therapy product allows that cell therapy product to function in the presence of an immunosuppressive such as a corticosteroid such as dexamethasone, said immunosuppressive being administered to, for example, reduce or eliminate host vs. graft disease. This approach, therefore, could be used to generate "off the shelf" T cells.

In an aspect, compositions and methods described herein can be used to improve cell, e.g., T cell, e.g., CAR-engineered T cell, e.g., allogeneic CAR-engineered T cell function (for example, by reducing or eliminating undesirable immunogenicity (such as a host versus graft response or a graft versus host response)), survival, proliferation and/or efficacy by altering the gene of a target for an immunosuppressant, e.g., CD52 (encoded by CD52). Without being bound by theory, it is considered that absent or reduced expression of functional CD52 on a cell therapy product allows that cell therapy product to function in the presence of an immunosuppressive such as an anti-CD52 antibody or antigen-binding fragment thereof such as alemtuzumab (CAMPATH®), said immunosuppressive being administered to, for example, reduce or eliminate host vs. graft disease. This approach, therefore, could be used to generate "off the shelf" T cells.

In an aspect, compositions and methods described herein can be used to improve cell, e.g., T cell, e.g., CAR-engineered T cell, e.g., allogeneic CAR-engineered T cell function (for example, by reducing or eliminating undesirable immunogenicity (such as a host versus graft response or a graft versus host response)), survival, proliferation and/or efficacy by altering the gene of a target for an immunosuppressant, e.g., an FKBP family member, e.g., FKBP12 (encoded by FKBP1A). Without being bound by theory, it is considered that absent or reduced expression of functional FKBP12 on a cell therapy product allows that cell therapy product to function in the presence of an immunosuppressive such as FK506 (or FKBP12-binding fragment or analog thereof), cyclosporine, rapamycin or rapalog, or mTor inhibitor such as RAD001, said immunosuppressive being administered to, for example, reduce or eliminate host vs. graft disease. This approach, therefore, could be used to generate "off the shelf" T cells.

In an aspect, compositions and methods described herein can be used to improve cell, e.g., T cell, e.g., CAR-engineered T cell, e.g., allogeneic CAR-engineered T cell function (for example, by reducing or eliminating undesirable immunogenicity (such as a host versus graft response or a graft versus host response)), survival, proliferation and/or efficacy by altering the gene of a target for an immunosuppressant, e.g., deoxycytidine kinase (encoded by DCK). Without being bound by theory, it is considered that absent or reduced expression of functional deoxycytidine kinase on a cell therapy product allows that cell therapy product to function in the presence of an immunosuppressive a nucleoside analog-based drug such as cytarabine (cytosine arabinoside) or gemcitabine], said immunosuppressive being administered to, for example, reduce or eliminate host vs.

graft disease or treat a cancer. This approach, therefore, could be used to generate "off the shelf" T cells.

In aspects, the gene products are inhibitory molecules, e.g., immune checkpoint proteins, e.g., PD-1, PD-L1, PD-L2, CTLA4, TIM3, LAG3, CEACAM (e.g., CEACAM-1, CEACAM-3 and/or CEACAM-5), VISTA, BTLA, TIGIT, LAIR1, CD160, 2B4, CD80, CD86, B7-H3 (CD276), B7-H4 (VTCN1), HVEM (TNFRSF14 or CD107), KIR, A2aR, MHC class I, MHC class II, GAL9, adenosine, and TGF beta. Without being bound by theory, it is believed that inhibition or elimination of the level of an inhibitory molecule or level of expression of inhibitory molecule gene product (e.g., via alteration of the gene) may improve the function of a cell, e.g., a transplanted cell, e.g., a transplanted immune effector cell, e.g., a CART cell, e.g., an allogeneic CART cell, by reducing or eliminating the inhibitory effects mediated by said inhibitory molecule.

In one aspect, the compositions and methods described herein can be used to decrease the effect of immune suppressive factors on cells, e.g., CAR engineered T cells, by altering the gene of an inhibitory molecule, e.g., PD1. While not wishing to be bound by theory, it is considered that reduced or absent expression of Programed Cell Death 1 (PD-1) (encoded by PDCD1) abrogates the induction of a suppressed or non-responsive state ("anergy").

In one aspect, the compositions and methods described herein can be used to decrease the effect of immune suppressive factors on cells, e.g., CAR engineered T cells, by altering the gene of an inhibitory molecule, e.g., Tim3. While not wishing to be bound by theory, it is considered that reduced or absent expression of Tim3 (encoded by HAVCR2) abrogates the induction of a suppressed or non-responsive state ("anergy").

In one aspect, the compositions and methods described herein can be used to decrease the effect of immune suppressive factors on cells, e.g., CAR engineered T cells, by altering the gene of an inhibitory molecule, e.g., CTLA4 gene. While not wishing to be bound by theory, it is considered that reduced or absent expression of cytotoxic T-lymphocyte associated antigen 4 (encoded by CTLA4) abrogates the induction of a suppressed or non-responsive state ("anergy").

In one aspect, the compositions and methods described herein can be used to decrease the effect of immune suppressive factors on cells, e.g., CAR engineered T cells, by altering the gene of an inhibitory molecule, e.g., Lag3 gene. While not wishing to be bound by theory, it is considered that reduced or absent expression of Lymphocyte-activation gene 3 (Lag3) (encoded by LAG3) abrogates the induction of a suppressed or non-responsive state ("anergy").

In one aspect, the compositions and methods described herein can be used to decrease the effect of immune suppressive factors on cells, e.g., CAR engineered T cells, by altering the gene of an inhibitory molecule, e.g., PD-L1 gene. While not wishing to be bound by theory, it is considered that reduced or absent expression of Programmed Death Ligand 1 (PD-L1, also known as CD274 and B7-H1) (encoded by CD274) abrogates the induction of a suppressed or non-responsive state ("anergy").

In one aspect, the compositions and methods described herein can be used to decrease the effect of immune suppressive factors on cells, e.g., CAR engineered T cells, by altering the gene of a downstream effector molecule of an inhibitory molecule, e.g., Tyrosine-protein phosphatase non-receptor type 1 gene. While not wishing to be bound by theory, it is considered that reduced or absent expression of functional tyrosine-protein phosphatase non-receptor type 1, also known as protein-tyrosine phosphatase 1B, (encoded by PTPN1) abrogates the induction of a suppressed or non-responsive state ("anergy") by affecting signaling through an inhibitory molecule.

In aspects, the compositions and methods described herein may be used in combination to generate cells, e.g., transplanted cells, e.g., allogeneic cells, e.g., immune effector cells, e.g., NK cells or T cells, e.g., CAR-engineered T cells with enhanced efficacy (for example, by reducing or eliminating undesirable immunogenicity (such as a host versus graft response or a graft versus host response)), survival, proliferation and/or stimulation relative to unmodified cells.

In one approach, the compositions and methods described herein may be used to generate cells in which levels or expression levels of a functional component of TCR have been reduced or eliminated and in which levels or expression levels of a functional MHC have been reduced or eliminated. In one embodiment, cells have reduced or eliminated levels or expression levels of TCR alpha and HLA-A. In one embodiment, cells have reduced or eliminated levels or expression levels of TCR alpha and HLA-B. In one embodiment, cells have reduced or eliminated levels or expression levels of TCR alpha and HLA-C. In one embodiment, cells have reduced or eliminated levels or expression levels of TCR alpha and B2M. In one embodiment, cells have reduced or eliminated levels or expression levels of TCR alpha and NLRC5. In one embodiment, cells have reduced or eliminated levels or expression levels of TCR beta and HLA-A. In one embodiment, cells have reduced or eliminated levels or expression levels of TCR beta and HLA-B. In one embodiment, cells have reduced or eliminated levels or expression levels of TCR beta and HLA-C. In one embodiment, cells have reduced or eliminated levels or expression levels of TCR beta and B2M. In one embodiment, cells have reduced or eliminated levels or expression levels of TCR beta and NLRC5. In one embodiment, cells have reduced or eliminated levels or expression levels of CD3zeta and HLA-A. In one embodiment, cells have reduced or eliminated levels or expression levels of CD3zeta and HLA-B. In one embodiment, cells have reduced or eliminated levels or expression levels of CD3zeta and HLA-C. In one embodiment, cells have reduced or eliminated levels or expression levels of CD3zeta and B2M. In one embodiment, cells have reduced or eliminated levels or expression levels of CD3zeta and NLRC5. In one embodiment, cells have reduced or eliminated levels or expression levels of CD3 epsilon and HLA-A. In one embodiment, cells have reduced or eliminated levels or expression levels of CD3 epsilon and HLA-B. In one embodiment, cells have reduced or eliminated levels or expression levels of CD3 epsilon and HLA-C. In one embodiment, cells have reduced or eliminated levels or expression levels of CD3 epsilon and B2M. In one embodiment, cells have reduced or eliminated levels or expression levels of CD3 epsilon and NLRC5. In one embodiment, cells have reduced or eliminated levels or expression levels of CD3 gamma and HLA-A. In one embodiment, cells have reduced or eliminated levels or expression levels of CD3 gamma and HLA-B. In one embodiment, cells have reduced or eliminated levels or expression levels of CD3 gamma and HLA-C. In one embodiment, cells have reduced or eliminated levels or expression levels of CD3 gamma and B2M. In one embodiment, cells have reduced or eliminated levels or expression levels of CD3 gamma and NLRC5. In one embodiment, cells have reduced or eliminated levels or expression levels of CD3 delta and HLA-A. In one embodiment, cells have reduced or eliminated levels or expression levels of CD3 delta and HLA-B. In one embodiment, cells have reduced or eliminated levels or expression levels of CD3 delta and HLA-C. In one embodiment, cells have reduced or eliminated levels or expression levels of CD3 delta and B2M. In one embodiment, cells have reduced or eliminated levels or expression levels of CD3 delta and NLRC5. In any of the aforementioned embodiments, the cells may have reduced or eliminated levels or expression levels of CIITA. In an embodiment, the cells have reduced or eliminated levels or expression levels of TRAC, B2M and CIITA. In an embodiment, the cells have reduced or eliminated levels or expression levels of TRBC, B2M and CIITA. In an embodiment, the cells have reduced or eliminated levels or expression levels of TRAC, TRBC, B2M and CIITA. In an embodiment, the cells have reduced or eliminated levels or expression levels of TRAC, NLRC5 and CIITA. In an embodiment, the cells have reduced or eliminated levels or expression levels of TRBC, NLRC5 and CIITA. In an embodiment, the cells have reduced or eliminated levels or expression levels of TRAC, TRBC, NLRC5 and CIITA. In any of the aforementioned embodiments, the cells may additionally have reduced or eliminated levels or expression levels of one or more inhibitory molecules or downstream effectors of an inhibitory molecule. In one aspect, the one or more inhibitory molecules comprises PD-1. In one aspect, the one or more inhibitory molecules comprises PD-L1. In one aspect, the one or more inhibitory molecules comprises Lag3. In one aspect, the one or more inhibitory molecules comprises Tim3. In one aspect, the one or more inhibitory molecules comprises CTLA4. In one aspect, the one or more inhibitory molecules comprises PTPN1. In one aspect, the one or more inhibitory molecules comprises PD-1 and PD-L1. In one aspect, the one or more inhibitory molecules comprises PD-1 and Lag3. In one aspect, the one or more inhibitory molecules comprises PD-1 and Tim3. In one aspect, the one or more inhibitory molecules comprises PD-1 and CTLA4. In one aspect, the one or more inhibitory molecules comprises PD-L1 and Lag3. In one aspect, the one or more inhibitory molecules comprises PD-L1 and Tim3. In one aspect, the one or more inhibitory molecules comprises PD-L1 and CTLA4. In one aspect, the one or more inhibitory molecules comprises Tim3 and Lag3. In one aspect, the one or more inhibitory molecules comprises Tim3 and CTLA4. In one aspect, the one or more inhibitory molecules comprises Lag3 and CTLA4. In one aspect, the one or more inhibitory molecules comprises, PD-1, PD-L1 and Lag3. In one aspect, the one or more inhibitory molecules comprises, PD-1, PD-L1 and Tim3. In one aspect, the one or more inhibitory molecules comprises, PD-1, PD-L1 and CTLA-4. In one aspect, the one or more inhibitory molecules comprises, PD-1, Tim3 and Lag3. In one aspect, the one or more inhibitory molecules comprises, PD-L1, Tim3 and Lag3. In one aspect, the one or more inhibitory molecules comprises, CTLA4, Tim3 and Lag3.

In one aspect, the compositions and methods described herein may be used to generate cells, e.g., T cells, e.g., CAR-engineered T cells, in which levels or expression levels of two or more, e.g., 2, e.g., 3, e.g., 4, inhibitory molecules have been reduced or eliminated. In one aspect, the two or more, e.g., 2, e.g., 3, e.g., 4, inhibitory molecules comprises PD-1 and PD-L1. In one aspect, the two or more, e.g., 2, e.g., 3, e.g., 4, inhibitory molecules comprises PD-1 and Lag3. In one aspect, the two or more, e.g., 2, e.g., 3, e.g., 4, inhibitory molecules comprises PD-1 and Tim3. In one aspect, the two or more, e.g., 2, e.g., 3, e.g., 4, inhibitory molecules comprises PD-1 and CTLA4. In one aspect, the two or more, e.g., 2, e.g., 3, e.g., 4, inhibitory molecules comprises PD-L1 and Lag3. In one aspect, the two or more, e.g., 2, e.g., 3, e.g., 4, inhibitory molecules comprises PD-L1 and Tim3. In one aspect, the two or more, e.g., 2, e.g., 3, e.g., 4, inhibitory molecules comprises PD-L1 and CTLA4. In one aspect, the two or more, e.g., 2, e.g., 3, e.g., 4, inhibitory molecules comprises Tim3 and Lag3. In one aspect, the two or more, e.g., 2, e.g., 3, e.g., 4, inhibitory molecules comprises Tim3 and CTLA4. In one aspect, the two or more, e.g., 2, e.g., 3, e.g., 4, inhibitory molecules comprises Lag3 and CTLA4. In one aspect, the two or more, e.g., 2, e.g., 3, e.g., 4, inhibitory molecules comprises, PD-1, PD-L1 and Lag3. In one aspect, the two or more, e.g., 2, e.g., 3, e.g., 4, inhibitory molecules comprises, PD-1, PD-L1 and Tim3. In one aspect, the two or more, e.g., 2, e.g., 3, e.g., 4, inhibitory molecules comprises, PD-1, PD-L1 and CTLA-4. In one aspect, the two or more, e.g., 2, e.g., 3, e.g., 4, inhibitory molecules comprises, PD-1, Tim3 and Lag3. In one aspect, the two or more, e.g., 2, e.g., 3, e.g., 4, inhibitory molecules comprises, PD-L1, Tim3 and Lag3. In one aspect, the two or more, e.g., 2, e.g., 3, e.g., 4, inhibitory molecules comprises, CTLA4, Tim3 and Lag3.

In embodiments in which the cells have reduced or eliminated levels or expression levels of TCR alpha, the cells preferably comprise, or at one time comprised, a gRNA molecule comprising a targeting domain comprising SEQ ID NO: SEQ ID NO: 5816 to SEQ ID NO: 5965 or SEQ ID NO: 5528 to SEQ ID NO: 5623, for example, SEQ ID NO: 5569, SEQ ID NO: 5587, SEQ ID NO: 5592 or SEQ ID NO: 5586, or a gRNA molecule comprising a targeting domain consisting of 17, 18, 19, 20, 21, 22, 23, 24 or 25 consecutive nucleotides, preferably 20 consecutive nucleotides, of SEQ ID NO: SEQ ID NO: 5816 to SEQ ID NO: 5965 or SEQ ID NO: 5528 to SEQ ID NO: 5623.

In embodiments in which the cells have reduced or eliminated levels or expression levels of TCR beta, the cells preferably comprise, or at one time comprised, a gRNA molecule comprising a targeting domain comprising SEQ ID NO: 5966 to SEQ ID NO: 6097 or SEQ ID NO: 5624 to SEQ ID NO: 5643, or a gRNA molecule comprising a targeting domain consisting of 17, 18, 19, 20, 21, 22, 23, 24 or 25 consecutive nucleotides, preferably 20 consecutive nucleotides, of SEQ ID NO: 5966 to SEQ ID NO: 6097 or SEQ ID NO: 5624 to SEQ ID NO: 5643. In embodiments in which the cells have reduced or eliminated levels or expression levels of TCR beta, the cells preferably comprise, or at one time comprised, a gRNA molecule comprising a targeting domain comprising SEQ ID NO: 6098 to SEQ ID NO: 6226 or SEQ ID NO: 5644 to SEQ ID NO: 5719, or a gRNA molecule comprising a targeting domain consisting of 17, 18, 19, 20, 21, 22, 23, 24 or 25 consecutive nucleotides, preferably 20 consecutive nucleotides, of SEQ ID NO: 6098 to SEQ ID NO: 6226 or SEQ ID NO: 5644 to SEQ ID NO: 5719.

In embodiments in which the cells have reduced or eliminated levels or expression levels of CD3zeta (encoded by CD247 gene), the cells preferably comprise, or at one time comprised, a gRNA molecule comprising a targeting domain comprising SEQ ID NO: 84 to SEQ ID NO: 392, or a gRNA molecule comprising a targeting domain consisting of 17, 18, 19, 20, 21, 22, 23, 24 or 25 consecutive nucleotides, preferably 20 consecutive nucleotides, of SEQ ID NO: 84 to SEQ ID NO: 392.

In embodiments in which the cells have reduced or eliminated levels or expression levels of CD3 epsilon (encoded by CD3E gene), the cells preferably comprise, or at one time comprised, a gRNA molecule comprising a targeting domain comprising SEQ ID NO: 533 to SEQ ID NO: 839, or a gRNA molecule comprising a targeting domain consisting of 17, 18, 19, 20, 21, 22, 23, 24 or 25 consecutive nucleotides, preferably 20 consecutive nucleotides, of SEQ ID NO: 533 to SEQ ID NO: 839.

In embodiments in which the cells have reduced or eliminated levels or expression levels of CD3 delta (encoded by CD3D gene), the cells preferably comprise, or at one time comprised, a gRNA molecule comprising a targeting domain comprising SEQ ID NO: 393 to SEQ ID NO: 532, or a gRNA molecule comprising a targeting domain consisting of 17, 18, 19, 20, 21, 22, 23, 24 or 25 consecutive nucleotides, preferably 20 consecutive nucleotides, of SEQ ID NO: 393 to SEQ ID NO: 532.

In embodiments in which the cells have reduced or eliminated levels or expression levels of CD3 gamma (encoded by CD3G gene), the cells preferably comprise, or at one time comprised, a gRNA molecule comprising a targeting domain comprising SEQ ID NO: 840 to SEQ ID NO: 968, or a gRNA molecule comprising a targeting domain consisting of 17, 18, 19, 20, 21, 22, 23, 24 or 25 consecutive nucleotides, preferably 20 consecutive nucleotides, of SEQ ID NO: 840 to SEQ ID NO: 968.

In embodiments in which the cells have reduced or eliminated levels or expression levels of B2M (encoded by B2M gene), the cells preferably comprise, or at one time comprised, a gRNA molecule comprising a targeting domain comprising SEQ ID NO: 1 to SEQ ID NO: 83 or SEQ ID NO: 5492 to SEQ ID NO: 5527, or a gRNA molecule comprising a targeting domain consisting of 17, 18, 19, 20, 21, 22, 23, 24 or 25 consecutive nucleotides, preferably 20 consecutive nucleotides, of SEQ ID NO: 1 to SEQ ID NO: 83 or SEQ ID NO: 5492 to SEQ ID NO: 5527.

In embodiments in which the cells have reduced or eliminated levels or expression levels of NLRC5 (encoded by NLRC5 gene), the cells preferably comprise, or at one time comprised, a gRNA molecule comprising a targeting domain comprising SEQ ID NO: 8622 to SEQ ID NO: 10089, or a gRNA molecule comprising a targeting domain consisting of 17, 18, 19, or 20 consecutive nucleotides, preferably 20 consecutive nucleotides, of SEQ ID NO: 8622 to SEQ ID NO: 10089.

In embodiments in which the cells have reduced or eliminated levels or expression levels of HLA-A (encoded by HLA-A gene), the cells preferably comprise, or at one time comprised, a gRNA molecule comprising a targeting domain comprising SEQ ID NO: 969 to SEQ ID NO: 1345, or a gRNA molecule comprising a targeting domain consisting of 17, 18, 19, 20, 21, 22, 23, 24 or 25 consecutive nucleotides, preferably 20 consecutive nucleotides, of SEQ ID NO: 969 to SEQ ID NO: 1345.

In embodiments in which the cells have reduced or eliminated levels or expression levels of HLA-B (encoded by HLA-B gene), the cells preferably comprise, or at one time comprised, a gRNA molecule comprising a targeting domain comprising SEQ ID NO: 1346 to SEQ ID NO: 1698, or a gRNA molecule comprising a targeting domain consisting of 17, 18, 19, 20, 21, 22, 23, 24 or 25 consecutive nucleotides, preferably 20 consecutive nucleotides, of SEQ ID NO: 1346 to SEQ ID NO: 1698.

In embodiments in which the cells have reduced or eliminated levels or expression levels of HLA-C (encoded by HLA-C gene), the cells preferably comprise, or at one time comprised, a gRNA molecule comprising a targeting domain comprising SEQ ID NO: 1699 to SEQ ID NO: 2068, or a gRNA molecule comprising a targeting domain consisting of 17, 18, 19, 20, 21, 22, 23, 24 or 25 consecutive nucleotides, preferably 20 consecutive nucleotides, of SEQ ID NO: 1699 to SEQ ID NO: 2068.

In embodiments in which the cells have reduced or eliminated levels or expression levels of CIITA (encoded by CTIIA gene), the cells preferably comprise, or at one time comprised, a gRNA molecule comprising a targeting domain comprising any one of SEQ ID NO: 6750 to SEQ ID NO: 7716, or a gRNA molecule comprising a targeting domain consisting of 17, 18, 19, 20, 21, 22, 23, 24 or 25 consecutive nucleotides, preferably 20 consecutive nucleotides, of SEQ ID NO: 6750 to SEQ ID NO: 7716. In embodiments, the gRNA molecule comprises a targeting domain comprises any one of SEQ ID NO: 7717 to SEQ ID NO: 7804.

In embodiments in which the cells have reduced or eliminated levels or expression levels of GR (encoded by NR3C1 gene), the cells preferably comprise, or at one time comprised, a gRNA molecule comprising a targeting domain comprising SEQ ID NO: 2069 to SEQ ID NO: 2941, or a gRNA molecule comprising a targeting domain consisting of 17, 18, 19, 20, 21, 22, 23, 24 or 25 consecutive nucleotides, preferably 20 consecutive nucleotides, of SEQ ID NO: 2069 to SEQ ID NO: 2941.

In embodiments in which the cells have reduced or eliminated levels or expression levels of FKBP12 (encoded by FKBP1A gene), the cells preferably comprise, or at one time comprised, a gRNA molecule comprising a targeting domain comprising SEQ ID NO: 6325 to SEQ ID NO: 6583, or a gRNA molecule comprising a targeting domain consisting of 17, 18, 19, 20, 21, 22, 23, 24 or 25 consecutive nucleotides, preferably 20 consecutive nucleotides, of SEQ ID NO: 6325 to SEQ ID NO: 6583.

In embodiments in which the cells have reduced or eliminated levels or expression levels of CD52 (encoded by CD52 gene), the cells preferably comprise, or at one time comprised, a gRNA molecule comprising a targeting domain comprising SEQ ID NO: 6227 to SEQ ID NO: 6324, or a gRNA molecule comprising a targeting domain consisting of 17, 18, 19, 20, 21, 22, 23, 24 or 25 consecutive nucleotides, preferably 20 consecutive nucleotides, of SEQ ID NO: 6227 to SEQ ID NO: 6324.

In embodiments in which the cells have reduced or eliminated levels or expression levels of DCK (encoded by DCK gene), the cells preferably comprise, or at one time comprised, a gRNA molecule comprising a targeting domain comprising SEQ ID NO: 5278 to SEQ ID NO: 5491, or a gRNA molecule comprising a targeting domain consisting of 17, 18, 19, 20, 21, 22, 23, 24 or 25 consecutive nucleotides, preferably 20 consecutive nucleotides, of SEQ ID NO: 5278 to SEQ ID NO: 5491.

In embodiments in which the cells have reduced or eliminated levels or expression levels of PD-L1 (encoded by CD274 gene), the cells preferably comprise, or at one time comprised, a gRNA molecule comprising a targeting domain comprising SEQ ID NO: 2942 to SEQ ID NO: 3270, or a gRNA molecule comprising a targeting domain consisting of 17, 18, 19, 20, 21, 22, 23, 24 or 25 consecutive nucleotides, preferably 20 consecutive nucleotides, of SEQ ID NO: 2942 to SEQ ID NO: 3270.

In embodiments in which the cells have reduced or eliminated levels or expression levels of Tim3 (encoded by HAVCR2 gene), the cells preferably comprise, or at one time comprised, a gRNA molecule comprising a targeting domain comprising SEQ ID NO: 3271 to SEQ ID NO: 3541, or a gRNA molecule comprising a targeting domain consisting of 17, 18, 19, 20, 21, 22, 23, 24 or 25 consecutive nucleotides, preferably 20 consecutive nucleotides, of SEQ ID NO: 3271 to SEQ ID NO: 3541.

In embodiments in which the cells have reduced or eliminated levels or expression levels of Lag3 (encoded by LAG3 gene), the cells preferably comprise, or at one time comprised, a gRNA molecule comprising a targeting domain comprising SEQ ID NO: 3542 to SEQ ID NO: 4032, or a gRNA molecule comprising a targeting domain consisting of 17, 18, 19, 20, 21, 22, 23, 24 or 25 consecutive nucleotides, preferably 20 consecutive nucleotides, of SEQ ID NO: 3542 to SEQ ID NO: 4032.

In embodiments in which the cells have reduced or eliminated levels or expression levels of PD-1 (encoded by PDCD1 gene), the cells preferably comprise, or at one time comprised, a gRNA molecule comprising a targeting domain comprising SEQ ID NO: 4033 to SEQ ID NO: 4589 or SEQ ID NO: 5720 to SEQ ID NO: 5815, or a gRNA molecule comprising a targeting domain consisting of 17, 18, 19, 20, 21, 22, 23, 24 or 25 consecutive nucleotides, preferably 20 consecutive nucleotides, of SEQ ID NO: 4033 to SEQ ID NO: 4589 or SEQ ID NO: 5720 to SEQ ID NO: 5815. In one embodiment, the gRNA molecule comprises a targeting domain comprising SEQ ID NO: 5775, or comprises a targeting domain comprising or consisting of 17, 18, or 19 consecutive nucleotides of SEQ ID NO: 5775.

In embodiments in which the cells have reduced or eliminated levels or expression levels of Tyrosine-protein phosphatase non-receptor type 1 (encoded by PTPN1 gene), the cells preferably comprise, or at one time comprised, a gRNA molecule comprising a targeting domain comprising SEQ ID NO: 4590 to SEQ ID NO: 5277, or a gRNA molecule comprising a targeting domain consisting of 17, 18, 19, 20, 21, 22, 23, 24 or 25 consecutive nucleotides, preferably 20 consecutive nucleotides, of SEQ ID NO: 4590 to SEQ ID NO: 5277.

In any of the aforementioned aspects and embodiments the cell is an autologous cell. In any of the aforementioned aspects and embodiments, the cell is an allogeneic cell. In any of the aforementioned embodiments and aspects, the cell is or will be engineered to express a chimeric antigen receptor (CAR), e.g., as described herein. In any of the aforementioned aspects and embodiments, the cell is a T cell.

Additional features of the gRNA molecule, the CRISPR systems, Cas9 molecules, cells, CAR molecules, and methods of the invention are described in detail below.

I. gRNA Molecules

A gRNA molecule may have a number of domains, as described more fully below, however, a gRNA molecule typically comprises at least a crRNA domain (comprising a targeting domain) and a tracr. The gRNA molecules of the invention, used as a component of a CRISPR system, are useful for modifying (e.g., modifying the sequence) DNA at or near a target site. Such modifications include deletions and or insertions that result in, for example, reduced or eliminated expression of a functional product of the gene comprising the target site. These uses, and additional uses, are described more fully below.

In an embodiment, a unimolecular, or sgRNA comprises, preferably from 5' to 3': a crRNA (which contains a targeting domain complementary to a target sequence and a region that forms part of a flagpole (i.e., a crRNA flagpole region)); a loop; and a tracr (which contains a domain complementary to the crRNA flagpole region, and a domain which additionally binds a nuclease or other effector molecule, e.g., a Cas molecule, e.g., aCas9 molecule), and may take the following format (from 5' to 3'):

[targeting domain]-[crRNA flagpole region]-[optional first flagpole extension]-[loop]-[optional first tracr extension]-[tracr flagpole region]-[tracr nuclease binding domain].

In embodiments, the tracr nuclease binding domain binds to a Cas protein, e.g., a Cas9 protein.

In an embodiment, a bimolecular, or dgRNA comprises two polynucleotides; the first, preferably from 5' to 3': a crRNA (which contains a targeting domain complementary to a target sequence and a region that forms part of a flagpole; and the second, preferably from 5' to 3': a tracr (which contains a domain complementary to the crRNA flagpole region, and a domain which additionally binds a nuclease or other effector molecule, e.g., a Cas molecule, e.g., Cas9 molecule), and may take the following format (from 5' to 3'):

Polynucleotide 1 (crRNA): [targeting domain]-[crRNA flagpole region]-[optional first flagpole extension]-[optional second flagpole extension]

Polynucleotide 2 (tracr): [optional first tracr extension]-[tracr flagpole region]-[tracr nuclease binding domain]

In embodiments, the tracr nuclease binding domain binds to a Cas protein, e.g., a Cas9 protein.

In some aspects, the targeting domain comprises or consists of a targeting domain sequence described herein, e.g., a targeting domain described in Table 1, 2, 3, 4, 5, 6, 6b, or 6c, or a targeting domain comprising or consisting of 17, 18, 19, 20, 21, 22, 23, 24, or 25 (preferably 20) consecutive nucleotides of a targeting domain sequence described in Table 1, 2, 3, 4, 5, 6, 6b, or 6c.

In some aspects, the flagpole, e.g., the crRNA flagpole region, comprises, from 5' to 3': GUUUUAGAGCUA (SEQ ID NO: 6584).

In some aspects, the flagpole, e.g., the crRNA flagpole region, comprises, from 5' to 3': GUUUAAGAGCUA (SEQ ID NO: 6585).

In some aspects the loop comprises, from 5' to 3': GAAA (SEQ ID NO: 6588).

In some aspects the tracr comprises, from 5' to 3': UAGCAAGUUAAAAUAAGGCUAGUCCGUUAU-CAACUUGAAAAAGUGGCACCGAGUCGGUG C (SEQ ID NO: 6589) and is preferably used in a gRNA molecule comprising SEQ ID NO: 6584.

In some aspects the tracr comprises, from 5' to 3': UAGCAAGUUUAAAUAAGGCUAGUCCGUUAU-CAACUUGAAAAAGUGGCACCGAGUCGGUG C (SEQ ID NO: 6590) and is preferably used in a gRNA molecule comprising SEQ ID NO: 6585.

In some aspects, the gRNA may also comprise, at the 3' end, additional U nucleic acids. For example the gRNA may comprise an additional 1, 2, 3, 4, 5, 6, 7, 8, 9, or 10 U nucleic acids at the 3' end (SEQ ID NO: 10806). In an embodiment, the gRNA comprises an additional 4 U nucleic acids at the 3' end. In the case of dgRNA, one or more of the polynucleotides of the dgRNA (e.g., the polynucleotide comprising the targeting domain and the polynucleotide comprising the tracr) may comprise, at the 3' end, additional U nucleic acids. For example, the case of dgRNA, one or more of the polynucleotides of the dgRNA (e.g., the polynucleotide comprising the targeting domain and the polynucleotide comprising the tracr) may comprise an additional 1, 2, 3, 4, 5, 6, 7, 8, 9, or 10 U nucleic acids at the 3' end (SEQ ID NO: 10806). In an embodiment, in the case of dgRNA, one or more of the polynucleotides of the dgRNA (e.g., the polynucleotide comprising the targeting domain and the polynucleotide comprising the tracr) comprises an additional 4 U nucleic acids at the 3' end. In an embodiment of a dgRNA, only the polynucleotide comprising the tracr comprises the additional U nucleic acid(s), e.g., 4 U nucleic acids. In an embodiment of a dgRNA, only the polynucleotide comprising the targeting domain comprises the additional U nucleic acid(s). In an embodiment of a dgRNA, both the polynucleotide comprising the targeting domain and the polynucleotide comprising the tracr comprise the additional U nucleic acids, e.g., 4 U nucleic acids.

In some aspects, the gRNA may also comprise, at the 3' end, additional A nucleic acids. For example the gRNA may comprise an additional 1, 2, 3, 4, 5, 6, 7, 8, 9, or 10 A nucleic acids at the 3' end (SEQ ID NO: 10809). In an embodiment, the gRNA comprises an additional 4 A nucleic acids at the 3' end. In the case of dgRNA, one or more of the polynucleotides of the dgRNA (e.g., the polynucleotide comprising the targeting domain and the polynucleotide comprising the tracr) may comprise, at the 3' end, additional A nucleic acids. For example, the case of dgRNA, one or more of the polynucleotides of the dgRNA (e.g., the polynucleotide comprising the targeting domain and the polynucleotide comprising the tracr) may comprise an additional 1, 2, 3, 4, 5, 6, 7, 8, 9, or 10 A nucleic acids at the 3' end (SEQ ID NO: 10809). In an embodiment, in the case of dgRNA, one or more of the polynucleotides of the dgRNA (e.g., the polynucleotide comprising the targeting domain and the polynucleotide comprising the tracr) comprises an additional 4 A nucleic acids at the 3' end. In an embodiment of a dgRNA, only the polynucleotide comprising the tracr comprises the additional A nucleic acid(s), e.g., 4 A nucleic acids. In an embodiment of a dgRNA, only the polynucleotide comprising the targeting domain comprises the additional A nucleic acid(s). In an embodiment of a dgRNA, both the polynucleotide comprising the targeting domain and the polynucleotide comprising the tracr comprise the additional U nucleic acids, e.g., 4 A nucleic acids.

In embodiments, one or more of the polynucleotides of the gRNA molecule may comprise a cap at the 5' end.

In an embodiment, a unimolecular, or sgRNA comprises, preferably from 5' to 3': a crRNA (which contains a targeting domain complementary to a target sequence; a crRNA flagpole region; first flagpole extension; a loop; a first tracr extension (which contains a domain complementary to at least a portion of the first flagpole extension); and a tracr (which contains a domain complementary to the crRNA flagpole region, and a domain which additionally binds a Cas9 molecule). In some aspects, the targeting domain comprises a targeting domain sequence described herein, e.g., a targeting domain described in Table 1, 2, 3, 4, 5, 6, 6b, or 6c, or a targeting domain comprising or consisting of 17, 18, 19, 20, 21, 22, 23, 24, or 25 (preferably 20) consecutive nucleotides of a targeting domain sequence described in Table 1, 2, 3, 4, 5, 6, 6b, or 6c, for example the 3' 17, 18, 19, 20, 21, 22, 23, 24 or 25 (preferably 20) consecutive nucleotides of a targeting domain sequence described in Table 1, 2, 3, 4, 5, 6, 6b, or 6c.

In aspects comprising a first flagpole extension and/or a first tracr extension, the flagpole, loop and tracr sequences may be as described above. In general any first flagpole extension and first tracr extension may be employed, provided that they are complementary. In embodiments, the first flagpole extension and first tracr extension consist of 3, 4, 5, 6, 7, 8, 9, 10 or more complementary nucleotides.

In some aspects, the first flagpole extension comprises, from 5' to 3': UGCUG (SEQ ID NO: 6586). In some aspects, the first flagpole extension consists of SEQ ID NO: 6586.

In some aspects, the first tracr extension comprises, from 5' to 3': CAGCA (SEQ ID NO: 6591). In some aspects, the first tracr extension consists of SEQ ID NO: 6591.

In an embodiment, a dgRNA comprises two nucleic acid molecules. In some aspects, the dgRNA comprises a first nucleic acid which contains, preferably from 5' to 3': a targeting domain complementary to a target sequence; a crRNA flagpole region; optionally a first flagpole extension; and, optionally, a second flagpole extension; and a second nucleic acid (which may be referred to herein as a tracr), and comprises at least a domain which binds a Cas molecule, e.g., a Cas9 molecule) comprising preferably from 5' to 3': optionally a first tracr extension; and a tracr (which contains a domain complementary to the crRNA flagpole region, and a domain which additionally binds a Cas, e.g., Cas9, molecule). The second nucleic acid may additionally comprise, at the 3' end (e.g., 3' to the tracr) additional U nucleic acids. For example the tracr may comprise an additional 1, 2, 3, 4, 5, 6, 7, 8, 9, or 10 U nucleic acids at the 3' end (e.g., 3' to the tracr) (SEQ ID NO: 10806). The second nucleic acid may additionally or alternately comprise, at the 3' end (e.g., 3' to the tracr) additional A nucleic acids. For example the tracr may comprise an additional 1, 2, 3, 4, 5, 6, 7, 8, 9, or 10 A nucleic acids at the 3' end (e.g., 3' to the tracr) (SEQ ID NO: 10809). In some aspects, the targeting domain comprises a targeting domain sequence described herein, e.g., a targeting domain described in Table 1, 2, 3, 4, 5, 6, 6b, or 6c, or a targeting domain comprising or consisting of 17, 18, 19, 20, 21, 22, 23, 24, or 25 (preferably 20) consecutive nucleotides of a targeting domain sequence described in Table 1, 2, 3, 4, 5, 6, 6b, or 6c.

In aspects involving a dgRNA, the crRNA flagpole region, optional first flagpole extension, optional first tracr extension and tracr sequences may be as described above.

In some aspects, the optional second flagpole extension comprises, from 5' to 3': UUUUG (SEQ ID NO: 6587).

In embodiments, the 3' 1, 2, 3, 4, or 5 nucleotides, the 5' 1, 2, 3, 4, or 5 nucleotides, or both the 3' and 5' 1, 2, 3, 4, or 5 nucleotides of the gRNA molecule (and in the case of a dgRNA molecule, the polynucleotide comprising the targeting domain and/or the polynucleotide comprising the tracr) are modified nucleic acids, as described more fully in section XIII, below.

The domains are discussed briefly below:

1) The Targeting Domain:

Guidance on the selection of targeting domains can be found, e.g., in Fu Y el al. NAT BIOTECHNOL 2014 (doi: 10.1038/nbt.2808) and Sternberg S H el al. NATURE 2014 (doi: 10.1038/nature13011).

The targeting domain comprises a nucleotide sequence that is complementary, e.g., at least 80, 85, 90, 95, or 99% complementary, e.g., fully complementary, to the target sequence on the target nucleic acid. The targeting domain is part of an RNA molecule and will therefore comprise the base uracil (U), while any DNA encoding the gRNA molecule will comprise the base thymine (T). While not wishing to be bound by theory, it is believed that the complementarity of the targeting domain with the target sequence contributes to specificity of the interaction of the gRNA molecule/Cas9 molecule complex with a target nucleic acid. It is understood that in a targeting domain and target sequence pair, the uracil bases in the targeting domain will pair with the adenine bases in the target sequence.

In an embodiment, the targeting domain is 5 to 50, e.g., 10 to 40, e.g., 10 to 30, e.g., 15 to 30, e.g., 15 to 25 nucleotides in length. In an embodiment, the targeting domain is 15, 16, 17, 18, 19, 20, 21, 22, 23, 24 or 25 nucleotides in length. In an embodiment, the targeting domain is 16 nucleotides in length. In an embodiment, the targeting domain is 17 nucleotides in length. In an embodiment, the targeting domain is 18 nucleotides in length. In an embodiment, the targeting domain is 19 nucleotides in length. In an embodiment, the targeting domain is 20 nucleotides in length. In an embodiment, the targeting domain is 21 nucleotides in length. In an embodiment, the targeting domain is 22 nucleotides in length. In an embodiment, the targeting domain is 23 nucleotides in length. In an embodiment, the targeting domain is 24 nucleotides in length. In an embodiment, the targeting domain is 25 nucleotides in length. In embodiments, the aforementioned 16, 17, 18, 19, 20, 21, 22, 23, 24, or 25 nucleotides comprise the 5'-16, 17, 18, 19, 20, 21, 22, 23, 24, or 25 nucleotides from a targeting domain described in Table 1, 2, 3, 4, 5, 6, 6b, or 6c. In embodiments, the aforementioned 16, 17, 18, 19, 20, 21, 22, 23, 24, or 25 nucleotides comprise the 3'-16, 17, 18, 19, 20, 21, 22, 23, 24, or 25 nucleotides from a targeting domain described in Table 1, 2, 3, 4, 5, 6, 6b, or 6c.

Without being bound by theory, it is believed that the 8, 9 or 10 nucleic acids of the targeting domain disposed at the 3' end of the targeting domain is important for targeting the target sequence, and may thus be referred to as the "core" region of the targeting domain. In an embodiment, the core domain is fully complementary with the target sequence.

The strand of the target nucleic acid with which the targeting domain is complementary is referred to herein as the target sequence. In some aspects, the target sequence is disposed on a chromosome, e.g., is a target within a gene. In some aspects the target sequence is disposed within an exon of a gene. In some aspects the target sequence is disposed within an intron of a gene. In some aspects, the target sequence comprises, or is proximal (e.g., within 10, 20, 30, 40, 50, 100, 200, 300, 400, 500, or 1000 nucleic acids) to a binding site of a regulatory element, e.g., a promoter or transcription factor binding site, of a gene of interest. Some or all of the nucleotides of the domain can have a modification, e.g., modification found in Section XIII herein.

2) crRNA Flagpole Region:

The flagpole contains portions from both the crRNA and the tracr. The crRNA flagpole region is complementary with a portion of the tracr, and in an embodiment, has sufficient complementarity to a portion of the tracr to form a duplexed region under at least some physiological conditions, for example, normal physiological conditions. In an embodiment, the crRNA flagpole region is 5 to 30 nucleotides in length. In an embodiment, the crRNA flagpole region is 5 to 25 nucleotides in length. The crRNA flagpole region can share homology with, or be derived from, a naturally occurring portion of the repeat sequence from a bacterial CRISPR array. In an embodiment, it has at least 50% homology with a crRNA flagpole region disclosed herein, e.g., an S. pyogenes, or S. thermophilus, crRNA flagpole region.

In an embodiment, the flagpole, e.g., the crRNA flagpole region, comprises SEQ ID NO: 6584. In an embodiment, the flagpole, e.g., the crRNA flagpole region, comprises sequence having at least 50%, 60%, 70%, 80%, 85%, 90%, 95% or 99% homology with SEQ ID NO: 6584. In an embodiment, the flagpole, e.g., the crRNA flagpole region, comprises at least 5, 6, 7, 8, 9, 10, or 11 nucleotides of SEQ ID NO: 6584. In an embodiment, the flagpole, e.g., the crRNA flagpole region, comprises SEQ ID NO: 6585. In an embodiment, the flagpole comprises sequence having at least 50%, 60%, 70%, 80%, 85%, 90%, 95% or 99% homology with SEQ ID NO: 6585. In an embodiment, the flagpole, e.g., the crRNA flagpole region, comprises at least 5, 6, 7, 8, 9, 10, or 11 nucleotides of SEQ ID NO: 6585.

Some or all of the nucleotides of the domain can have a modification, e.g., modification described in Section XIII herein.

3) First Flagpole Extension

When a tracr comprising a first tracr extension is used, the crRNA may comprise a first flagpole extension. In general any first flagpole extension and first tracr extension may be employed, provided that they are complementary. In embodiments, the first flagpole extension and first tracr extension consist of 3, 4, 5, 6, 7, 8, 9, 10 or more complementary nucleotides.

The first flagpole extension may comprise nucleotides that are complementary, e.g., 80%, 85%, 90%, 95% or 99%, e.g., fully complementary, with nucleotides of the first tracr extension. In some aspects, the first flagpole extension nucleotides that hybridize with complementary nucleotides of the first tracr extension are contiguous. In some aspects, the first flagpole extension nucleotides that hybridize with complementary nucleotides of the first tracr extension are discontinuous, e.g., comprises two or more regions of hybridization separated by nucleotides that do not base pair with nucleotides of the first tracr extension. In some aspects, the first flagpole extension comprises at least 2, 3, 4, 5, 6, 7, 8, 9, 10, 11, 12, 13, 14, 15, 16, 17, 18, 19, 20 or more nucleotides. In some aspects, the first flagpole extension comprises, from 5' to 3': UGCUG (SEQ ID NO: 6586). In some aspects, the first flagpole extension consists of SEQ ID NO: 6586. In some aspects the first flagpole extension comprises nucleic acid that is at least 80%, 85%, 90%, 95% or 99% homology to SEQ ID NO: 6586.

Some or all of the nucleotides of the first tracr extension can have a modification, e.g., modification found in Section XIII herein.

3) The Loop

A loop serves to link the crRNA flagpole region (or optionally the first flagpole extension, when present) with the tracr (or optionally the first tracr extension, when present) of a sgRNA. The loop can link the crRNA flagpole region and tracr covalently or non-covalently. In an embodiment, the linkage is covalent. In an embodiment, the loop covalently couples the crRNA flagpole region and tracr. In an embodiment, the loop covalently couples the first flagpole extension and the first tracr extension. In an embodiment, the loop is, or comprises, a covalent bond interposed between the crRNA flagpole region and the domain of the tracr which hybridizes to the crRNA flagpole region. Typically, the loop comprises one or more, e.g., 2, 3, 4, 5, 6, 7, 8, 9, or 10 nucleotides.

In dgRNA molecules the two molecules can be associated by virtue of the hybridization between at least a portion of the crRNA (e.g., the crRNA flagpole region) and at least a portion of the tracr (e.g., the domain of the tracr which is complementary to the crRNA flagpole region).

A wide variety of loops are suitable for use in sgRNAs. Loops can consist of a covalent bond, or be as short as one or a few nucleotides, e.g., 1, 2, 3, 4, or 5 nucleotides in length. In an embodiment, a loop is 2, 3, 4, 5, 6, 7, 8, 9, 10, 15, 20, or 25 or more nucleotides in length. In an embodiment, a loop is 2 to 50, 2 to 40, 2 to 30, 2 to 20, 2 to 10, or 2 to 5 nucleotides in length. In an embodiment, a loop shares homology with, or is derived from, a naturally occurring sequence. In an embodiment, the loop has at least 50% homology with a loop disclosed herein. In an embodiment, the loop comprises SEQ ID NO: 6588.

Some or all of the nucleotides of the domain can have a modification, e.g., modification described in Section XIII herein.

4) The Second Flagpole Extension

In an embodiment, a dgRNA can comprise additional sequence, 3' to the crRNA flagpole region or, when present, the first flagpole extension, referred to herein as the second flagpole extension. In an embodiment, the second flagpole extension is, 2-10, 2-9, 2-8, 2-7, 2-6, 2-5, or 2-4 nucleotides in length. In an embodiment, the second flagpole extension is 2, 3, 4, 5, 6, 7, 8, 9, or 10 or more nucleotides in length. In an embodiment, the second flagpole extension comprises SEQ ID NO: 6587.

5) The Tracr:

The tracr is the nucleic acid sequence required for nuclease, e.g., Cas9, binding. Without being bound by theory, it is believed that each Cas9 species is associated with a particular tracr sequence. Tracr sequences are utilized in both sgRNA and in dgRNA systems. In an embodiment, the tracr comprises sequence from, or derived from, an S. pyogenes tracr. In some aspects, the tracr has a portion that hybridizes to the flagpole portion of the crRNA, e.g., has sufficient complementarity to the crRNA flagpole region to form a duplexed region under at least some physiological conditions (sometimes referred to herein as the tracr flagpole region or a tracr domain complementary to the crRNA flagpole region). In embodiments, the domain of the tracr that hybridizes with the crRNA flagpole region comprises at least 5, 6, 7, 8, 9, 10, 11, 12, 13, 14, 15, 16, 17, 18, 19, or 20 nucleotides that hybridize with complementary nucleotides of the crRNA flagpole region. In some aspects, the tracr nucleotides that hybridize with complementary nucleotides of the crRNA flagpole region are contiguous. In some aspects, the tracr nucleotides that hybridize with complementary nucleotides of the crRNA flagpole region are discontinuous, e.g., comprises two or more regions of hybridization separated by nucleotides that do not base pair with nucleotides of the crRNA flagpole region. In some aspects, the portion of the tracr that hybridizes to the crRNA flagpole region comprises, from 5' to 3': UAGCAAGUUAAAA (SEQ ID NO: 6597). In some aspects, the portion of the tracr that hybridizes to the crRNA flagpole region comprises, from 5' to 3': UAGCAAGUUUAAA (SEQ ID NO: 6598). In embodiments, the sequence that hybridizes with the crRNA flagpole region is disposed on the tracr 5'- to the sequence of the tracr that additionally binds a nuclease, e.g., a Cas molecule, e.g., a Cas9 molecule.

The tracr further comprises a domain that additionally binds to a nuclease, e.g., a Cas molecule, e.g., a Cas9 molecule. Without being bound by theory, it is believed that Cas9 from different species bind to different tracr sequences. In some aspects, the tracr comprises sequence that binds to a S. pyogenes Cas9 molecule. In some aspects, the tracr comprises sequence that binds to a Cas9 molecule disclosed herein. In some aspects, the domain that additionally binds a Cas9 molecule comprises, from 5' to 3':

```
                                    (SEQ ID NO: 6599)
UAAGGCUAGUCCGUUAUCAACUUGAAAAAGUGGCACCGAGUCGGUGC.
```

In some aspects the domain that additionally binds a Cas9 molecule comprises, from 5' to 3':

```
                                    (SEQ ID NO: 6600)
UAAGGCUAGUCCGUUAUCAACUUGAAAAAGUGGCACCGAGUCGGUGC
UUUU.
```

In some embodiments, the tracr comprises SEQ ID NO: 6589. In some embodiments, the tracr comprises SEQ ID NO: 6590.

Some or all of the nucleotides of the tracr can have a modification, e.g., modification found in Section XIII herein. In embodiments, the gRNA (e.g., the sgRNA or the tracr and/or crRNA of a dgRNA), e.g., any of the gRNA or gRNA components described above, comprises an inverted abasic residue at the 5' end, the 3' end or both the 5' and 3' end of the gRNA. In embodiments, the gRNA (e.g., the sgRNA or the tracr and/or crRNA of a dgRNA), e.g., any of the gRNA or gRNA components described above, comprises one or more phosphorothioate bonds between residues at the 5' end of the polynucleotide, for example, a phosphorthioate bond between the first two 5' residues, between each of the first three 5' residues, between each of the first four 5' residues, or between each of the first five 5' residues. In embodiments, the gRNA or gRNA component may alternatively or additionally comprise one or more phosphorothioate bonds between residues at the 3' end of the polynucleotide, for example, a phosphorthioate bond between the first two 3' residues, between each of the first three 3' residues, between each of the first four 3' residues, or between each of the first five 3' residues. In an embodiment, the gRNA (e.g., the sgRNA or the tracr and/or crRNA of a dgRNA), e.g., any of the gRNA or gRNA components described above, comprises a phosphorothioate bond between each of the first four 5' residues (e.g., comprises, e.g., consists of, three phosphorothioate bonds at the 5' end(s)), and a phosphorothioate bond between each of the first four 3' residues (e.g., comprises, e.g., consists of, three phosphorothioate bonds at the 3' end(s)). In an embodiment, any of the phosphorothioate modifications described above are combined with an inverted abasic residue at the 5' end, the 3' end, or both the 5' and 3' ends of the polynucleotide. In such embodiments, the inverted abasic nucleotide may be linked to the 5' and/or 3' nucleotide by a phosphate bond or a phosphorothioate bond. In embodiments, the gRNA (e.g., the sgRNA or the tracr and/or crRNA of a dgRNA), e.g., any of the gRNA or gRNA components described above, comprises one or more nucleotides that include a 2' O-methyl modification. In embodiments, each of the first 1, 2, 3, or more of the 5' residues comprise a 2' O-methyl modification. In embodiments, each of the first 1, 2, 3, or more of the 3' residues comprise a 2' O-methyl modification. In embodiments, the $4^{th}$-to-terminal, $3^{rd}$-to-terminal, and $2^{nd}$-to-terminal 3' residues comprise a 2' O-methyl modification. In embodiments, each of the first 1, 2, 3 or more of the 5' residues comprise a 2' O-methyl modification, and each of the first 1, 2, 3 or more of the 3' residues comprise a 2' O-methyl modification. In an embodiment, each of the first 3 of the 5' residues comprise a 2' O-methyl modification, and each of the first 3 of the 3' residues comprise a 2' O-methyl modification. In embodiments, each of the first 3 of the 5' residues comprise a 2' O-methyl modification, and the $4^{th}$-to-terminal, 3rd-to-terminal, and $2^{nd}$-to-terminal 3' residues comprise a 2' O-methyl modification. In embodiments, any of the 2' O-methyl modifications, e.g., as described above, may be combined with one or more phosphorothioate modifications, e.g., as described above, and/or one or more inverted abasic modifications, e.g., as described above. In an embodiment, the gRNA (e.g., the sgRNA or the tracr and/or crRNA of a dgRNA), e.g., any of the gRNA or gRNA components described above, comprises, e.g., consists of, a phosphorothioate bond between each of the first four 5' residues (e.g., comprises, e.g., consists of three phosphorothioate bonds at the 5' end of the polynucleotide(s)), a phosphorothioate bond between each of the first four 3' residues (e.g., comprises, e.g., consists of three phosphorothioate bonds at the 5' end of the polynucleotide(s)), a 2' O-methyl modification at each of the first three 5' residues, and a 2' O-methyl modification at each of the first three 3' residues. In an embodiment, the gRNA (e.g., the sgRNA or the tracr and/or crRNA of a dgRNA), e.g., any of the gRNA or gRNA components described above, comprises, e.g., consists of, a phosphorothioate bond between each of the first four 5' residues (e.g., comprises, e.g., consists of three phosphorothioate bonds at the 5' end of the polynucleotide(s)), a phosphorothioate bond between each of the first four 3' residues (e.g., comprises, e.g., consists of three phosphorothioate bonds at the 5' end of the polynucleotide(s)), a 2' O-methyl modification at each of the first three 5' residues, and a 2' O-methyl modification at each of the $4^{th}$-to-terminal, $3^{rd}$-to-terminal, and $2^{nd}$-to-terminal 3' residues.

In an embodiment, the gRNA (e.g., the sgRNA or the tracr and/or crRNA of a dgRNA), e.g., any of the gRNA or gRNA components described above, comprises, e.g., consists of, a phosphorothioate bond between each of the first four 5' residues (e.g., comprises, e.g., consists of three phosphorothioate bonds at the 5' end of the polynucleotide(s)), a phosphorothioate bond between each of the first four 3' residues (e.g., comprises, e.g., consists of three phosphorothioate bonds at the 5' end of the polynucleotide(s)), a 2' modification at each of the first three 5' residues, a 2' O-methyl modification at each of the first three 3' residues, and an additional inverted abasic residue at each of the 5' and 3' ends.

In an embodiment, the gRNA (e.g., the sgRNA or the tracr and/or crRNA of a dgRNA), e.g., any of the gRNA or gRNA components described above, comprises, e.g., consists of, a phosphorothioate bond between each of the first four 5' residues (e.g., comprises, e.g., consists of three phosphorothioate bonds at the 5' end of the polynucleotide(s)), a phosphorothioate bond between each of the first four 3' residues (e.g., comprises, e.g., consists of three phosphorothioate bonds at the 5' end of the polynucleotide(s)), a 2' modification at each of the first three 5' residues, and a 2' O-methyl modification at each of the $4^{th}$-to-terminal, $3^{rd}$-to-terminal, and $2^{nd}$-to-terminal 3' residues, and an additional inverted abasic residue at each of the 5' and 3' ends In embodiments, the gRNA is a dgRNA and comprises, e.g., consists of:
crRNA:
mN*mN*mN*NNNNNNNNNNNNNNNNNGUUUU-AGAGCUAU*mG*mC*mU (SEQ ID NO: 10797), where m indicates a base with 2'O-Methyl modification, * indicates a phosphorothioate bond, and N's indicate the residues of the targeting domain, e.g., as described herein, (optionally with an inverted abasic residue at the 5' and/or 3' terminus); and
tracr:
AACAGCAUAGCAAGUUAAAAUAAGGCUAGU-CCGUUAUCAACUUGAAAAAGUGGCACCGA GUCG-GUGCUUUUUUU (SEQ ID NO: 6660) (optionally with an inverted abasic residue at the 5' and/or 3' terminus).

In embodiments, the gRNA is a dgRNA and comprises, e.g., consists of:
crRNA:
mN*mN*mN*NNNNNGUUUUAGAGCUAU*mG*mC*mU (SEQ ID NO: 10797), where m indicates a base with 2'O-Methyl modification, * indicates a phosphorothioate bond, and N's indicate the residues of the targeting domain, e.g., as described herein, (optionally with an inverted abasic residue at the 5' and/or 3' terminus); and
tracr:
mA*mA*mC*AGCAUAGCAAGUUAAAAUAAGGC-UAGUCCGUUAUCAACUUGAAAAAGUGGC ACCGAGUCGGUGCUUUU*mU*mU*mU (SEQ ID NO: 10798), where m indicates a base with 2'O-Methyl modification, * indicates a phosphorothioate bond, and N's indicate the residues of the targeting domain (optionally with an inverted abasic residue at the 5' and/or 3' terminus).

In embodiments, the gRNA is a dgRNA and comprises, e.g., consists of:
crRNA:
mN*mN*mN*NNNNNNNNNNGUUUUAGAGCUA-UGCUGUU*mU*mU*mG (SEQ ID NO), where m indicates a base with 2'O-Methyl modification, * indicates a phosphorothioate bond, and N's indicate the residues of the targeting domain, e.g., as described herein, (optionally with an inverted abasic residue at the 5' and/or 3' terminus); and
tracr:
AACAGCAUAGCAAGUUAAAAUAAGGCUAGU-CCGUUAUCAACUUGAAAAAGUGGCACCGA GUCG-GUGCUUUUUUU (SEQ ID NO: 6660) (optionally with an inverted abasic residue at the 5' and/or 3' terminus).

In embodiments, the gRNA is a dgRNA and comprises, e.g., consists of:
crRNA:
mN*mN*mN*NNNNNNNNNNNNNNNNGUUUU-AGAGCUAUGCUGUU*mU*mU*mG (SEQ ID NO), where m indicates a base with 2'O-Methyl modification, * indicates a phosphorothioate bond, and N's indicate the residues of the targeting domain, e.g., as described herein, (optionally with an inverted abasic residue at the 5' and/or 3' terminus); and
tracr:
mA*mA*mC*AGCAUAGCAAGUUAAAAUAAGG-CUAGUCCGUUAUCAACUUGAAAAAGUGGC ACCGAGUCGGUGCUUUU*mU*mU*mU (SEQ ID NO: 10798), where m indicates a base with 2'O-Methyl modification, and * indicates a phosphorothioate bond (optionally with an inverted abasic residue at the 5' and/or 3' terminus).

In embodiments, the gRNA is a sgRNA and comprises, e.g., consists of:
mN*mN*mN*NNNNNNNNNNNNNNNNGUUUU-AGAGCUAGAAAUAGCAAGUUAAAAUAAG GCUA-GUCCGUUAUCAACUUGAAAAAGUGGCAC-CGAGUCGGUGCU*mU*mU*mU (SEQ ID NO: 10799), where m indicates a base with 2'O-Methyl modification, * indicates a phosphorothioate bond, and N's indicate the residues of the targeting domain, e.g., as described herein, (optionally with an inverted abasic residue at the 5' and/or 3' terminus).

In embodiments, the gRNA is a sgRNA and comprises, e.g., consists of:
mN*mN*mN GUUUUAGAGCUA-GAAAUAGCAAGUUAAAAUAAG GCUAGU-CCGUUAUCAACUUGAAAAAGUGGCACC-GAGUCGGUGCmU*mU*mU*U, where m indicates a base with 2'O-Methyl modification, * indicates a phosphorothioate bond, and N's indicate the residues of the targeting domain, e.g., as described herein, (optionally with an inverted abasic residue at the 5' and/or 3' terminus).

6) First Tracr Extension

Where the gRNA comprises a first flagpole extension, the tracr may comprise a first tracr extension. The first tracr extension may comprise nucleotides that are complementary, e.g., 80%, 85%, 90%, 95% or 99%, e.g., fully complementary, with nucleotides of the first flagpole extension. In some aspects, the first tracr extension nucleotides that hybridize with complementary nucleotides of the first flagpole extension are contiguous. In some aspects, the first tracr extension nucleotides that hybridize with complementary nucleotides of the first flagpole extension are discontinuous, e.g., comprises two or more regions of hybridization separated by nucleotides that do not base pair with nucleotides of the first flagpole extension. In some aspects, the first tracr extension comprises at least 2, 3, 4, 5, 6, 7, 8, 9, 10, 11, 12, 13, 14, 15, 16, 17, 18, 19, 20 or more nucleotides. In some aspects, the first tracr extension comprises SEQ ID NO: 6591. In some aspects the first tracr extension comprises nucleic acid that is at least 80%, 85%, 90%, 95% or 99% homology to SEQ ID NO: 6591.

Some or all of the nucleotides of the first tracr extension can have a modification, e.g., modification found in Section XIII herein.

In some embodiments, the sgRNA may comprise, from 5' to 3', disposed 3' to the targeting domain:

a)

(SEQ ID NO: 6601)
GUUUUAGAGCUAGAAAUAGCAAGUUAAAAUAAGGCUAGUCCGUUAUC

AACUUGAAAAAGUGGCACCGAGUCGGUGC;

b)

(SEQ ID NO: 6602)
GUUUAAGAGCUAGAAAUAGCAAGUUUAAAUAAGGCUAGUCCGUUAUC

AACUUGAAAAAGUGGCACCGAGUCGGUGC;

c)

(SEQ ID NO: 6603)
GUUUUAGAGCUAUGCUGGAAACAGCAUAGCAAGUUAAAAUAAGGCUA

GUCCGUUAUCAACUUGAAAAAGUGGCACCGAGUCGGUGC;

d)

(SEQ ID NO: 6604)
GUUUAAGAGCUAUGCUGGAAACAGCAUAGCAAGUUUAAAUAAGGCUA

GUCCGUUAUCAACUUGAAAAAGUGGCACCGAGUCGGUGC;

e) any of a) to d), above, further comprising, at the 3' end, at least 1, 2, 3, 4, 5, 6 or 7 uracil (U) nucleotides, e.g., 1, 2, 3, 4, 5, 6, or 7 uracil (U) nucleotides;
f) any of a) to d), above, further comprising, at the 3' end, at least 1, 2, 3, 4, 5, 6 or 7 adenine (A) nucleotides, e.g., 1, 2, 3, 4, 5, 6, or 7 adenine (A) nucleotides; or
g) any of a) to f), above, further comprising, at the 5' end (e.g., at the 5' terminus, e.g., 5' to the targeting domain), at least 1, 2, 3, 4, 5, 6 or 7 adenine (A) nucleotides, e.g., 1, 2, 3, 4, 5, 6, or 7 adenine (A) nucleotides.

In an embodiment, a sgRNA of the invention comprises, e.g., consists of, from 5' to 3': [targeting domain]—

(SEQ ID NO: 7811)
GUUUUAGAGCUAGAAAUAGCAAGUUAAAAUAAGGCUAGUCCGUUAUC

AACUUGAAAAAGUGGCACCGAGUCGGUGCUUUU.

In an embodiment, a sgRNA of the invention comprises, e.g., consists of, from 5' to 3': [targeting domain]—

(SEQ ID NO: 7807)
GUUUAAGAGCUAUGCUGGAAACAGCAUAGCAAGUUUAAAUAAGGCUA

GUCCGUUAUCAACUUGAAAAAGUGGCACCGAGUCGGUGCUUUU.

In embodiments, any of a) to g) above is disposed directly 3' to the targeting domain.

In some embodiments, the dgRNA may comprise:

A crRNA comprising, from 5' to 3', preferably disposed directly 3' to the targeting domain:

a) GUUUUAGAGCUA (SEQ ID NO: 6584);
b) GUUUAAGAGCUA (SEQ ID NO: 6585);
c) GUUUUAGAGCUAUGCUG (SEQ ID NO: 6605);
d) GUUUAAGAGCUAUGCUG (SEQ ID NO: 6606);
e) GUUUUAGAGCUAUGCUGUUUUG (SEQ ID NO: 6607);
f) GUUUAAGAGCUAUGCUGUUUUG (SEQ ID NO: 6608); or
g) GUUUUAGAGCUAUGCU (SEQ ID NO: 7806):

and a tracr comprising, from 5' to 3':

a)

(SEQ ID NO: 6589)
UAGCAAGUUAAAAUAAGGCUAGUCCGUUAUCAACUUGAAAAAGUGGCACC

GAGUCGGUGC;

b)

(SEQ ID NO: 6590)
UAGCAAGUUUAAAUAAGGCUAGUCCGUUAUCAACUUGAAAAAGUGGCACC

GAGUCGGUGC;

c)

(SEQ ID NO: 6609)
CAGCAUAGCAAGUUAAAAUAAGGCUAGUCCGUUAUCAACUUGAAAAAGUG

GCACCGAGUCGGUGC;

d)

(SEQ ID NO: 6610)
CAGCAUAGCAAGUUUAAAUAAGGCUAGUCCGUUAUCAACUUGAAAAAGUG

GCACCGAGUCGGUGC;

e)

(SEQ ID NO: 6660)
AACAGCAUAGCAAGUUAAAAUAAGGCUAGUCCGUUAUCAACUUGAAAAAG

UGGCACCGAGUCGGUGCUUUUUUU;

f)

(SEQ ID NO: 6661)
AACAGCAUAGCAAGUUUAAAUAAGGCUAGUCCGUUAUCAACUUGAAAAAG

UGGCACCGAGUCGGUGCUUUUUUU;

g)

(SEQ ID NO: 7807)
GUUUAAGAGCUAUGCUGGAAACAGCAUAGCAAGUUUAAAUAAGGCUAGUC

CGUUAUCAACUUGAAAAAGUGGCACCGAGUCGGUGCUUUU;

h)

(SEQ ID NO: 7808)
AGCAUAGCAAGUUAAAAUAAGGCUAGUCCGUUAUCAACUUGAAAAAGUGG

CACCGAGUCGGUGCUUU;

i)

(SEQ ID NO: 7809)
GUUGGAACCAUUCAAAACAGCAUAGCAAGUUAAAAUAAGGCUAGUCCGUU

AUCAACUUGAAAAAGUGGCACCGAGUCGGUGCUUU;

j)

(SEQ ID NO: 7820)
AACAGCAUAGCAAGUUAAAAUAAGGCUAGUCCGUUAUCAACUUGAAAAAG

UGGCACCGAGUCGGUGC;

k) any of a) to j), above, further comprising, at the 3' end, at least 1, 2, 3, 4, 5, 6 or 7 uracil (U) nucleotides, e.g., 1, 2, 3, 4, 5, 6, or 7 uracil (U) nucleotides;

l) any of a) to j), above, further comprising, at the 3' end, at least 1, 2, 3, 4, 5, 6 or 7 adenine (A) nucleotides, e.g., 1, 2, 3, 4, 5, 6, or 7 adenine (A) nucleotides; or m) any of a) to l), above, further comprising, at the 5' end (e.g., at the 5' terminus), at least 1, 2, 3, 4, 5, 6 or 7 adenine (A) nucleotides, e.g., 1, 2, 3, 4, 5, 6, or 7 adenine (A) nucleotides.

In an embodiment, the sequence of k), above comprises the 3' sequence UUUUUU, e.g., if a U6 promoter is used for transcription. In an embodiment, the sequence of k), above, comprises the 3' sequence UUUU, e.g., if an HI promoter is used for transcription. In an embodiment, sequence of k), above, comprises variable numbers of 3' U's depending, e.g., on the termination signal of the pol-III promoter used. In an embodiment, the sequence of k), above, comprises variable 3' sequence derived from the DNA template if a T7 promoter is used. In an embodiment, the sequence of k), above, comprises variable 3' sequence derived from the DNA template, e.g., if in vitro transcription is used to generate the RNA molecule. In an embodiment, the sequence of k), above, comprises variable 3' sequence derived from the DNA template, e.g, if a pol-II promoter is used to drive transcription.

In an embodiment, the crRNA comprises SEQ ID NO: 6607 and the tracr comprises, e.g., consists of (SEQ ID NO: 6660)
AACAGCAUAGCAAGUUAAAAUAAGGCUAGUCCGUUAUCAACUUGAAAAAG

UGGCACCGAGUCGGUGCUUUUUUU.

In an embodiment, the crRNA comprises SEQ ID NO: 6608 and the tracr comprises, e.g., consists of, (SEQ ID NO: 6661)
AACAGCAUAGCAAGUUUAAAUAAGGCUAGUCCGUUAUCAACUUGAAAAAG

UGGCACCGAGUCGGUGCUUUUUUU.

In an embodiment, the crRNA comprises, e.g., consists of, a targeting domain and, disposed 3' to the targeting domain (e.g., disposed directly 3' to the targeting domain), a sequence comprising, e.g., consisting of, GUUUUAGAGC-UAUGCU (SEQ ID NO: 7806), and the tracr comprises, e.g., consists of, (SEQ ID NO: 7807)
GUUUAAGAGCUAUGCUGGAAACAGCAUAGCAAGUUUAAAUAAGGCUAGUC

CGUUAUCAACUUGAAAAAGUGGCACCGAGUCGGUGCUUUU.

In an embodiment, the crRNA comprises, e.g., consists of, a targeting domain and, disposed 3' to the targeting domain (e.g., disposed directly 3' to the targeting domain), a sequence comprising, e.g., consisting of, GUUUUAGAGC-UAUGCU (SEQ ID NO: 7806), and the tracr comprises, e.g., consists of, (SEQ ID NO: 7808)
AGCAUAGCAAGUUAAAAUAAGGCUAGUCCGUUAUCAACUUGAAAAAGUGG

CACCGAGUCGGUGCUUU.

In an embodiment, the crRNA comprises, e.g., consists of, a targeting domain and, disposed 3' to the targeting domain (e.g., disposed directly 3' to the targeting domain), a sequence comprising, e.g., consisting of, GUUUUAGAGC-UAUGCUGUUUUG (SEQ ID NO: 6607), and the tracr comprises, e.g., consists of, (SEQ ID NO: 7809)
GUUGGAACCAUUCAAAACAGCAUAGCAAGUUAAAAUAAGGCUAGUCCGUU

AUCAACUUGAAAAAGUGGCACCGAGUCGGUGCUUU.

7) Targeting Domains Useful for Altering Expression of Allogeneic T Cell Targets, Inhibitory Molecules and/or Downstream Effectors of an Inhibitory Molecule Provided in the tables below are targeting domains for gRNA molecules for use in the compositions and methods of the present invention, for example, in altering expression of or altering a Allogeneic T Cell Target gene, Inhibitory Molecule gene and/or a Downstream Effectors of An Inhibitory Molecule gene.

Lengthy table referenced here

US12037583-20240716-T00001

Please refer to the end of the specification for access instructions.

Lengthy table referenced here

US12037583-20240716-T00002

Please refer to the end of the specification for access instructions.

Exemplary preferred gRNA targeting domains useful in the compositions and methods of the invention are described in the tables below.

TABLE 3

| gRNA Targeting Domains for human B2M | | | | | |
|---|---|---|---|---|---|
| Id. | Locations | Target | Strand | gRNA Targeting Domain Sequence | SEQ ID NO: |
| CR00438 | Chr15: 44711472-44711494 | B2M | + | CACGCGUUUAAUAUAAGUGG | 5492 |
| CR00439 | Chr15: 44711483-44711505 | B2M | + | UAUAAGUGGAGGCGUCGCGC | 5493 |
| CR00440 | Chr15: 44711486-44711508 | B2M | + | AAGUGGAGGCGUCGCGCUGG | 5494 |
| CR00441 | Chr15: 44711534-44711556 | B2M | + | GGCCGAGAUGUCUCGCUCCG | 5495 |
| CR00442 | Chr15: 44711536-44711558 | B2M | - | GGCCACGGAGCGAGACAUCU | 5496 |
| CR00443 | Chr15: 44711551-44711573 | B2M | - | CGCGAGCACAGCUAAGGCCA | 5497 |
| CR00444 | Chr15: 44711557-44711579 | B2M | - | GAGUAGCGCGAGCACAGCUA | 5498 |
| CR00445 | Chr15: 44711591-44711613 | B2M | - | ACUCACGCUGGAUAGCCUCC | 5499 |
| CR00446 | Chr15: 44711603-44711625 | B2M | - | AGGGUAGGAGAGACUCACGC | 5500 |
| CR00447 | Chr15: 44715412-44715434 | B2M | + | CUCAGGUACUCCAAAGAUUC | 5501 |
| CR00448 | Chr15: 44715422-44715444 | B2M | - | CGUGAGUAAACCUGAAUCUU | 5502 |
| CR00449 | Chr15: 44715507-44715529 | B2M | - | CAGUAAGUCAACUUCAAUGU | 5503 |
| CR00450 | Chr15: 44715567-44715589 | B2M | + | ACUUGUCUUUCAGCAAGGAC | 5504 |
| CR00451 | Chr15: 44715645-44715667 | B2M | - | AGUCACAUGGUUCACACGGC | 5505 |
| CR00452 | Chr15: 44715649-44715671 | B2M | - | ACAAAGUCACAUGGUUCACA | 5506 |
| CR00453 | Chr15: 44715672-44715694 | B2M | + | CACAGCCCAAGAUAGUUAAG | 5507 |
| CR00454 | Chr15: 44715673-44715695 | B2M | + | ACAGCCCAAGAUAGUUAAGU | 5508 |
| CR00455 | Chr15: 44715677-44715699 | B2M | - | UUACCCCACUUAACUAUCUU | 5509 |
| CR00456 | Chr15: 44715678-44715700 | B2M | - | CUUACCCCACUUAACUAUCU | 5510 |
| CR00457 | Chr15: 44717599-44717621 | B2M | + | AGGUUUGAAGAUGCCGCAUU | 5511 |
| CR00458 | Chr15: 44717604-44717626 | B2M | + | UGAAGAUGCCGCAUUUGGAU | 5512 |
| CR00459 | Chr15: 44717612-44717634 | B2M | - | GAAUUCAUCCAAUCCAAAUG | 5513 |
| CR00460 | Chr15: 44717681-44717703 | B2M | + | ACACUUUAUGCACAAAAUGU | 5514 |

TABLE 3-continued gRNA Targeting Domains for human B2M

| Id. | Locations | Target | Strand | gRNA Targeting Domain Sequence | SEQ ID NO: |
|---|---|---|---|---|---|
| CR00461 | Chr15: 44717763-44717785 | B2M | − | CUGCUCAGAUACAUCAAACA | 5515 |
| CR00462 | Chr15: 44717764-44717786 | B2M | + | CAUGUUUGAUGUAUCUGAGC | 5516 |
| CR00463 | Chr15: 44717776-44717798 | B2M | + | AUCUGAGCAGGUUGCUCCAC | 5517 |
| CR00464 | Chr15: 44717789-44717811 | B2M | + | GCUCCACAGGUAGCUCUAGG | 5518 |
| CR00465 | Chr15: 44717805-44717827 | B2M | + | UAGGAGGGCUGGCAACUUAG | 5519 |
| CR00466 | Chr15: 44717808-44717830 | B2M | + | GAGGGCUGGCAACUUAGAGG | 5520 |
| CR00467 | Chr15: 44717809-44717831 | B2M | + | AGGGCUGGCAACUUAGAGGU | 5521 |
| CR00468 | Chr15: 44717810-44717832 | B2M | + | GGGCUGGCAACUUAGAGGUG | 5522 |
| CR00469 | Chr15: 44717851-44717873 | B2M | − | UCUGACCAAGAUGUUGAUGU | 5523 |
| CR00470 | Chr15: 44717939-44717961 | B2M | − | UCUAAGCAGAGUAUGUAAAU | 5524 |
| CR00471 | Chr15: 44717981-44718003 | B2M | + | AAUAUAAUUGACAGGAUUAU | 5525 |
| CR00472 | Chr15: 44718056-44718078 | B2M | + | CUUAUACAUUUGAUAAAGUA | 5526 |
| CR00473 | Chr15: 44718076-44718098 | B2M | + | AGGCAUGGUUGUGGUUAAUC | 5527 |

In the various aspects of the invention, the gRNA molecule may include a targeting domain listed above. In an embodiment, the targeting domain of the gRNA of the invention comprises, e.g. consists of, the targeting domain of CR00465. In an embodiment, the targeting domain of the gRNA of the invention comprises, e.g. consists of, the targeting domain of CR00443. In an embodiment, the targeting domain of the gRNA of the invention comprises, e.g. consists of, the targeting domain of CR00445. In an embodiment, the targeting domain of the gRNA of the invention comprises, e.g. consists of, the targeting domain of CR00444. In an embodiment, the targeting domain of the gRNA of the invention comprises, e.g. consists of, the targeting domain of CR00449. In an embodiment, the targeting domain of the gRNA of the invention comprises, e.g. consists of, the targeting domain of CR00442. In an embodiment, the targeting domain of the gRNA of the invention comprises, e.g. consists of, the targeting domain of CR00453. In an embodiment, the targeting domain of the gRNA of the invention comprises, e.g. consists of, the targeting domain of CR00461. In an embodiment, the targeting domain of the gRNA of the invention comprises, e.g. consists of, the targeting domain of CR00439. In an embodiment, the targeting domain of the gRNA of the invention comprises, e.g. consists of, the targeting domain of CR00452. In an embodiment, the targeting domain of the gRNA of the invention comprises, e.g. consists of, the targeting domain of CR00455. In an embodiment, the targeting domain of the gRNA of the invention comprises, e.g. consists of, the targeting domain of CR00463. In an embodiment, the targeting domain of the gRNA of the invention comprises, e.g. consists of, the targeting domain of CR00467. In an embodiment, the targeting domain of the gRNA of the invention comprises, e.g. consists of, the targeting domain of CR00466. In an embodiment, the targeting domain of the gRNA of the invention comprises, e.g. consists of, the targeting domain of CR00446. In an embodiment, the targeting domain of the gRNA of the invention comprises, e.g. consists of, the targeting domain of CR00440. In an embodiment, the targeting domain of the gRNA of the invention comprises, e.g. consists of, the targeting domain of CR00454. In an embodiment, the targeting domain of the gRNA of the invention comprises, e.g. consists of, the targeting domain of CR00460. In an embodiment, the targeting domain of the gRNA of the invention comprises, e.g. consists of, the targeting domain of CR00438. In an embodiment, the targeting domain of the gRNA of the invention comprises, e.g. consists of, the targeting domain of CR00439. Such gRNA molecules, and combinations thereof, are suitable for use in, for example, the CRISPR systems, methods and cells and other aspects of the invention described herein.

TABLE 4 gRNA targeting domain sequences for human T-Cell Receptor Alpha (TRAC)

| Id. | Target Name | Strand | Genomic Information | gRNA Targeting Domain Sequence | SEQ ID NO: |
|---|---|---|---|---|---|
| CR000920 | TRAC | + | Chr14: 22281089-22281111 | CUCAAGGUUCAGAUCAGAAG | 5528 |
| CR000921 | TRAC | + | Chr14: 22281092-22281114 | AAGGUUCAGAUCAGAAGAGG | 5529 |
| CR000922 | TRAC | + | Chr14: 22281111-22281133 | GAGGCUUCUCACCCUGCAGC | 5530 |
| CR000923 | TRAC | + | Chr14: 22281112-22281134 | AGGCUUCUCACCCUGCAGCA | 5531 |
| CR000924 | TRAC | - | Chr14: 22281122-22281144 | GCUCACAGGUCCCUGCUGCA | 5532 |
| CR000925 | TRAC | - | Chr14: 22281123-22281145 | UGCUCACAGGUCCCUGCUGC | 5533 |
| CR000926 | TRAC | + | Chr14: 22281126-22281148 | GCAGCAGGGACCUGUGAGCA | 5534 |
| CR000927 | TRAC | + | Chr14: 22281136-22281158 | CCUGUGAGCAUGGCAUGCCC | 5535 |
| CR000928 | TRAC | - | Chr14: 22281136-22281158 | CCAGGGCAUGCCAUGCUCAC | 5536 |
| CR000929 | TRAC | - | Chr14: 22281153-22281175 | CAAGUGCCCACAGGAAGCCA | 5537 |
| CR000930 | TRAC | - | Chr14: 22281154-22281176 | ACAAGUGCCCACAGGAAGCC | 5538 |
| CR000931 | TRAC | - | Chr14:22281162-22281184 | UGGAGAUCACAAGUGCCCAC | 5539 |
| CR000932 | TRAC | - | Chr14: 22281182-22281204 | GCCUUCCUUACCAAGACAGG | 5540 |
| CR000933 | TRAC | - | Chr14: 22281185-22281207 | UGCGCCUUCCUUACCAAGAC | 5541 |
| CR000934 | TRAC | + | Chr14:22281432-22281454 | CUUUCCCACAGAAUUUAGCA | 5542 |
| CR000935 | TRAC | + | Chr14: 22281477-22281499 | ACCAGAGAUGUCUGUGCAGG | 5543 |
| CR000936 | TRAC | - | Chr14: 22281478-22281500 | GCCUCCUGCACAGACAUCUC | 5544 |
| CR000937 | TRAC | - | Chr14: 22281506-22281528 | AUAUGUGCAGCUCAGGGUCA | 5545 |
| CR000938 | TRAC | - | Chr14: 22281512-22281534 | GGUGUCAUAUGUGCAGCUCA | 5546 |
| CR000939 | TRAC | - | Chr14: 22281513-22281535 | UGGUGUCAUAUGUGCAGCUC | 5547 |
| CR000940 | TRAC | - | Chr14:22281533-22281555 | UAAAUAAUAAUCACUCUCAC | 5548 |
| CR000941 | TRAC | + | Chr14: 22281539-22281561 | AGAGUGAUUAUUAUUUAUUC | 5549 |
| CR000942 | TRAC | + | Chr14: 22281560-22281582 | GGUACAAGCAGCCUCCCAGC | 5550 |
| CR000943 | TRAC | - | Chr14: 22281571-22281593 | AGAAUCAUCUGCCUGCUGGG | 5551 |
| CR000944 | TRAC | - | Chr14: 22281574-22281596 | ACGAGAAUCAUCUGCCUGCU | 5552 |

TABLE 4-continued gRNA targeting domain sequences for human T-Cell Receptor Alpha (TRAC)

| Id. | Target Name | Strand | Genomic Information | gRNA Targeting Domain Sequence | SEQ ID NO: |
|---|---|---|---|---|---|
| CR000945 | TRAC | - | Chr14: 22281575-22281597 | AACGAGAAUCAUCUGCCUGC | 5553 |
| CR000946 | TRAC | - | Chr14: 22281603-22281625 | UCUGUUGCUUAUAAGCUUCU | 5554 |
| CR000947 | TRAC | - | Chr14: 22338946-22338968 | GUUGGUGAGGUUGAUAAAUU | 5555 |
| CR000948 | TRAC | - | Chr14: 22338959-22338981 | GCUGUAUGUGUGAGUUGGUG | 5556 |
| CR000949 | TRAC | + | Chr14: 22338963-22338985 | ACCAACUCACACAUACAGCC | 5557 |
| CR000950 | TRAC | + | Chr14: 22338964-22338986 | CCAACUCACACAUACAGCCA | 5558 |
| CR000951 | TRAC | - | Chr14: 22338981-22339003 | AGCACAAGAAUAUAGAUCCC | 5559 |
| CR000952 | TRAC | + | Chr14: 22338992-22339014 | UAUUCUUGUGCUCUCAGAGA | 5560 |
| CR000953 | TRAC | + | Chr14: 22513941-22513963 | GGAAACACACCUCUUGUCUU | 5561 |
| CR000954 | TRAC | + | Chr14: 22513946-22513968 | CACACCUCUUGUCUUUGGAA | 5562 |
| CR000955 | TRAC | + | Chr14: 22513947-22513969 | ACACCUCUUGUCUUUGGAAA | 5563 |
| CR000956 | TRAC | - | Chr14: 22513950-22513972 | GUGCCCUUUCCAAAGACAAG | 5564 |
| CR000957 | TRAC | - | Chr14: 22547504-22547526 | ACACGGCAGGGUCAGGGUUC | 5565 |
| CR000958 | TRAC | - | Chr14: 22547511-22547533 | AGCUGGUACACGGCAGGGUC | 5566 |
| CR000959 | TRAC | - | Chr14: 22547516-22547538 | CUCUCAGCUGGUACACGGCA | 5567 |
| CR000960 | TRAC | - | Chr14: 22547517-22547539 | UCUCUCAGCUGGUACACGGC | 5568 |
| CR000961 | TRAC | - | Chr14: 22547521-22547543 | AGAGUCUCUCAGCUGGUACA | 5569 |
| CR000962 | TRAC | - | Chr14: 22547528-22547550 | UGGAUUUAGAGUCUCUCAGC | 5570 |
| CR000963 | TRAC | - | Chr14: 22547548-22547570 | UAGGCAGACAGACUUGUCAC | 5571 |
| CR000964 | TRAC | - | Chr14: 22547567-22547589 | GAGAAUCAAAAUCGGUGAAU | 5572 |
| CR000965 | TRAC | - | Chr14: 22547575-22547597 | AUUUGUUUGAGAAUCAAAAU | 5573 |
| CR000966 | TRAC | + | Chr14: 22547591-22547613 | AACAAAUGUGUCACAAAGUA | 5574 |
| CR000967 | TRAC | + | Chr14: 22547635-22547657 | ACAAAACUGUGCUAGACAUG | 5575 |
| CR000968 | TRAC | + | Chr14: 22547642-22547664 | UGUGCUAGACAUGAGGUCUA | 5576 |
| CR000969 | TRAC | + | Chr14: 22547666-22547688 | CUUCAAGAGCAACAGUGCUG | 5577 |

TABLE 4-continued gRNA targeting domain sequences for human T-Cell Receptor Alpha (TRAC)

| Id. | Target Name | Strand | Genomic Information | gRNA Targeting Domain Sequence | SEQ ID NO: |
|---|---|---|---|---|---|
| CR000970 | TRAC | + | Chr14: 22547671-22547693 | AGAGCAACAGUGCUGUGGCC | 5578 |
| CR000971 | TRAC | - | Chr14: 22547689-22547711 | AAAGUCAGAUUUGUUGCUCC | 5579 |
| CR000972 | TRAC | - | Chr14: 22547725-22547747 | UGGAAUAAUGCUGUUGUUGA | 5580 |
| CR000973 | TRAC | - | Chr14: 22547745-22547767 | CUGGGGAAGAAGGUGUCUUC | 5581 |
| CR000974 | TRAC | - | Chr14: 22547762-22547784 | AGCUGCCCUUACCUGGGCUG | 5582 |
| CR000975 | TRAC | - | Chr14: 22547763-22547785 | AAGCUGCCCUUACCUGGGCU | 5583 |
| CR000976 | TRAC | - | Chr14: 22547764-22547786 | AAAGCUGCCCUUACCUGGGC | 5584 |
| CR000977 | TRAC | - | Chr14: 22547768-22547790 | CACCAAAGCUGCCCUUACCU | 5585 |
| CR000978 | TRAC | - | Chr14: 22547769-22547791 | GCACCAAAGCUGCCCUUACC | 5586 |
| CR000979 | TRAC | + | Chr14: 22549633-22549655 | AAGUUCCUGUGAUGUCAAGC | 5587 |
| CR000980 | TRAC | - | Chr14: 22549638-22549660 | CUCGACCAGCUUGACAUCAC | 5588 |
| CR000981 | TRAC | - | Chr14: 22550558-22550580 | CUGACAGGUUUUGAAAGUUU | 5589 |
| CR000982 | TRAC | + | Chr14: 22550565-22550587 | UUUCAAAACCUGUCAGUGAU | 5590 |
| CR000983 | TRAC | + | Chr14: 22550566-22550588 | UUCAAAACCUGUCAGUGAUU | 5591 |
| CR000984 | TRAC | - | Chr14: 22550573-22550595 | UUCGGAACCCAAUCACUGAC | 5592 |
| CR000985 | TRAC | + | Chr14: 22550591-22550613 | CCGAAUCCUCCUCCUGAAAG | 5593 |
| CR000986 | TRAC | - | Chr14: 22550591-22550613 | CCACUUUCAGGAGGAGGAUU | 5594 |
| CR000987 | TRAC | + | Chr14: 22550595-22550617 | AUCCUCCUCCUGAAAGUGGC | 5595 |
| CR000988 | TRAC | + | Chr14: 22550596-22550618 | UCCUCCUCCUGAAAGUGGCC | 5596 |
| CR000989 | TRAC | - | Chr14: 22550597-22550619 | ACCCGGCCACUUUCAGGAGG | 5597 |
| CR000990 | TRAC | - | Chr14: 22550600-22550622 | UAAACCCGGCCACUUUCAGG | 5598 |
| CR000991 | TRAC | - | Chr14: 22550603-22550625 | GAUUAAACCCGGCCACUUUC | 5599 |
| CR000992 | TRAC | - | Chr14: 22550614-22550636 | CGUCAUGAGCAGAUUAAACC | 5600 |
| CR000993 | TRAC | + | Chr14: 22550620-22550642 | UUAAUCUGCUCAUGACGCUG | 5601 |
| CR000994 | TRAC | + | Chr14: 22550626-22550648 | UGCUCAUGACGCUGCGGCUG | 5602 |

TABLE 4-continued gRNA targeting domain sequences for human T-Cell Receptor Alpha (TRAC)

| Id. | Target Name | Strand | Genomic Information | gRNA Targeting Domain Sequence | SEQ ID NO: |
|---|---|---|---|---|---|
| CR000995 | TRAC | - | Chr14: 22550650-22550672 | UCAAGGCCCCUCACCUCAGC | 5603 |
| CR000996 | TRAC | - | Chr14: 22551620-22551642 | AGGAAGGAGCGAGGGAGCAC | 5604 |
| CR000997 | TRAC | - | Chr14: 22551628-22551650 | CAAUGCAGAGGAAGGAGCGA | 5605 |
| CR000998 | TRAC | - | Chr14: 22551629-22551651 | GCAAUGCAGAGGAAGGAGCG | 5606 |
| CR000999 | TRAC | - | Chr14: 22551636-22551658 | AAGAGGGGCAAUGCAGAGGA | 5607 |
| CR001000 | TRAC | - | Chr14: 22551640-22551662 | GGAGAAGAGGGGCAAUGCAG | 5608 |
| CR001001 | TRAC | - | Chr14: 22551653-22551675 | UCUGUUUGGAGAGGGAGAAG | 5609 |
| CR001002 | TRAC | + | Chr14: 22551655-22551677 | UCUUCUCCCUCUCCAAACAG | 5610 |
| CR001003 | TRAC | + | Chr14: 22551656-22551678 | CUUCUCCCUCUCCAAACAGA | 5611 |
| CR001004 | TRAC | - | Chr14: 22551661-22551683 | GAGUUCCCUCUGUUGGAGA | 5612 |
| CR001005 | TRAC | - | Chr14: 22551662-22551684 | AGAGUUCCCUCUGUUUGGAG | 5613 |
| CR001006 | TRAC | - | Chr14: 22551667-22551689 | GUAGGAGAGUUCCCUCUGUU | 5614 |
| CR001007 | TRAC | + | Chr14: 22551678-22551700 | GAACUCUCCUACCCCAAGG | 5615 |
| CR001008 | TRAC | - | Chr14: 22551685-22551707 | GCUUUCACCUCCUUGGGGU | 5616 |
| CR001009 | TRAC | - | Chr14: 22551689-22551711 | AGCAGCUUUCACCUCCUUGG | 5617 |
| CR001010 | TRAC | - | Chr14: 22551690-22551712 | UAGCAGCUUUCACCUCCUUG | 5618 |
| CR001011 | TRAC | - | Chr14: 22551691-22551713 | GUAGCAGCUUUCACCUCCUU | 5619 |
| CR001012 | TRAC | + | Chr14: 22551710-22551732 | CUACCACCUCUGUGCCCCC | 5620 |
| CR001013 | TRAC | - | Chr14: 22551713-22551735 | UUGCCGGGGGGCACAGAGG | 5621 |
| CR001014 | TRAC | - | Chr14: 22551716-22551738 | GCAUUGCCGGGGGGCACAG | 5622 |
| CR001015 | TRAC | - | Chr14: 22551724-22551746 | AGUUGGUGGCAUUGCCGGGG | 5623 |

In the various aspects of the invention, the gRNA molecule may include a targeting domain listed above. In an embodiment, the targeting domain of the gRNA of the invention comprises, e.g. consists of, the targeting domain of CR000961. In an embodiment, the targeting domain of the gRNA of the invention comprises, e.g. consists of, the targeting domain of CR000977. In an embodiment, the targeting domain of the gRNA of the invention comprises, e.g. consists of, the targeting domain of CR000984. In an embodiment, the targeting domain of the gRNA of the invention comprises, e.g. consists of, the targeting domain of CR000993. In an embodiment, the targeting domain of the gRNA of the invention comprises, e.g. consists of, the targeting domain of CR000981. In an embodiment, the targeting domain of the gRNA of the invention comprises, e.g. consists of, the targeting domain of CR000992. In an embodiment, the targeting domain of the gRNA of the invention comprises, e.g. consists of, the targeting domain of CR000986. In an embodiment, the targeting domain of the gRNA of the invention comprises, e.g. consists of, the targeting domain of CR000963. In an embodiment, the targeting domain of the gRNA of the invention comprises, e.g. consists of, the targeting domain of CR000985. In an embodiment, the targeting domain of the gRNA of the invention comprises, e.g. consists of, the targeting domain of CR000966. In an embodiment, the targeting domain of the gRNA of the invention comprises, e.g. consists of, the targeting domain of CR000990. In an embodiment, the targeting domain of the gRNA of the invention comprises, e.g. consists of, the targeting domain of CR000978. In an embodiment, the targeting domain of the gRNA of the invention comprises, e.g. consists of, the targeting domain of CR000991. In an embodiment, the targeting domain of the gRNA of the invention comprises, e.g. consists of, the targeting domain of CR000983. In an embodiment, the targeting domain of the gRNA of the invention comprises, e.g. consists of, the targeting domain of CR000960. In an embodiment, the targeting domain of the gRNA of the invention comprises, e.g. consists of, the targeting domain of CR001002. In an embodiment, the targeting domain of the gRNA of the invention comprises, e.g. consists of, the targeting domain of CR001000. In an embodiment, the targeting domain of the gRNA of the invention comprises, e.g. consists of, the targeting domain of CR001009. In an embodiment, the targeting domain of the gRNA of the invention comprises, e.g. consists of, the targeting domain of CR001011. In an embodiment, the targeting domain of the gRNA of the invention comprises, e.g. consists of, the targeting domain of CR001012. Such gRNA molecules, and combinations thereof, are suitable for use in, for example, the CRISPR systems, methods and cells and other aspects of the invention described herein.

TABLE 5 gRNA targeting domains for human T-Cell Receptor Beta (Constant Domain 1 and Constant Domain 2)

| Id. | Target Name | gRNA Targeting Domain Sequence | Genomic Information | SEQ ID NO: |
|---|---|---|---|---|
| CR000728 | TRBC1 | CAGGGAAGAAGCCUGUGGCC | Chr7: 142791779-142791801 | 5624 |
| CR000729 | TRBC1 | GUGGUCAGGGAAGAAGCCUG | Chr7: 142791784-142791806 | 5625 |
| CR000730 | TRBC1 | CUGACCACGUGGAGCUGAGC | Chr7: 142791799-142791821 | 5626 |
| CR000731 | TRBC1 | CACGGACCCGCAGCCCCUCA | Chr7: 142791857-142791879 | 5627 |
| CR000732 | TRBC1 | GGUGCACAGUGGGGUCAGCA | Chr7: 142791839-142791861 | 5628 |
| CR000733 | TRBC1 | GACGGGUUUGGCCCUAUCCU | Chr7: 142792015-142792037 | 5629 |
| CR000734 | TRBC1 | UGGCUCAAACACAGCGACCU | Chr7: 142791712-142791734 | 5630 |
| CR000735 | TRBC1 | AGGCUUCUUCCCUGACCACG | Chr7: 142791788-142791810 | 5631 |
| CR000736 | TRBC1 | CAGCUCAGCUCCACGUGGUC | Chr7: 142791798-142791820 | 5632 |
| CR000737 | TRBC1 | GCGCUGACGAUCUGGGUGAC | Chr7: 142792032-142792054 | 5633 |
| CR000738 | TRBC1 | CUUUCCAGAGGACCUGAACA | Chr7: 142791680-142791702 | 5634 |
| CR000739 | TRBC1 | UCAAACACAGCGACCUCGGG | Chr7: 142791708-142791730 | 5635 |
| CR000740 | TRBC1 | UGACGGGUUUGGCCCUAUCC | Chr7: 142792016-142792038 | 5636 |
| CR000741 | TRBC1 | GGCGCUGACGAUCUGGGUGA | Chr7: 142792033-142792055 | 5637 |
| CR000742 | TRBC1 | CGGGUGGGAACACCUUGUUC | Chr7: 142791692-142791714 | 5638 |
| CR000743 | TRBC1 | GAACAAGGUGUUCCCACCCG | Chr7: 142791695-142791717 | 5639 |
| CR000744 | TRBC1 | CAAACACAGCGACCUCGGGU | Chr7: 142791707-142791729 | 5640 |

TABLE 5-continued gRNA targeting domains for human T-Cell Receptor Beta (Constant Domain 1 and Constant Domain 2)

| Id. | Target Name | gRNA Targeting Domain Sequence | Genomic Information | SEQ ID NO: |
|---|---|---|---|---|
| CR000745 | TRBC1 | GGCUCAAACACAGCGACCUC | Chr7: 142791711-142791733 | 5641 |
| CR000746 | TRBC1 | AGCUCAGCUCCACGUGGUCA | Chr7: 142791797-142791819 | 5642 |
| CR000747 | TRBC1 | GACGAUCUGGGUGACGGGUU | Chr7: 142792027-142792049 | 5643 |
| CR000748 | TRBC2 | UAUCAGGCUCCUCUGCUACG | Chr7: 142670776-142670798 | 5644 |
| CR000749 | TRBC2 | AUCAGGCUCCUCUGCUACGU | Chr7: 142670777-142670799 | 5645 |
| CR000750 | TRBC2 | CUACGUGGGCUUUUAUUUUC | Chr7: 142670791-142670813 | 5646 |
| CR000751 | TRBC2 | ACGUGGGCUUUUAUUUUCUG | Chr7: 142670793-142670815 | 5647 |
| CR000752 | TRBC2 | CGUGGGCUUUUAUUUUCUGG | Chr7: 142670794-142670816 | 5648 |
| CR000753 | TRBC2 | AAUAAAAGCCCACGUAGCAG | Chr7: 142670785-142670807 | 5649 |
| CR000754 | TRBC2 | ACCCCAAGAUACCUUGUUAU | Chr7: 142670970-142670992 | 5650 |
| CR000755 | TRBC2 | AGAUACCUUGUUAUAGGGAC | Chr7: 142670976-142670998 | 5651 |
| CR000756 | TRBC2 | GACAGGAAAGAAGAUCACUC | Chr7: 142670993-142671015 | 5652 |
| CR000757 | TRBC2 | UCUGGAAUGUUCUCAAACCA | Chr7: 142671011-142671033 | 5653 |
| CR000758 | TRBC2 | CUGGAAUGUUCUCAAACCAU | Chr7: 142671012-142671034 | 5654 |
| CR000759 | TRBC2 | UACUGGUAUCAACAAGAUCC | Chr7: 142671048-142671070 | 5655 |
| CR000760 | TRBC2 | GUAUCAACAAGAUCCAGGAA | Chr7: 142671053-142671075 | 5656 |
| CR000761 | TRBC2 | CACCUCAUCCACUAUUCCUA | Chr7: 142671081-142671103 | 5657 |
| CR000762 | TRBC2 | GGAGUUAAUUCCACAGAGAA | Chr7: 142671102-142671124 | 5658 |
| CR000763 | TRBC2 | AGUCAACAGUCUCCAGAAUA | Chr7: 142671139-142671161 | 5659 |
| CR000764 | TRBC2 | AACAGUCUCCAGAAUAAGGA | Chr7: 142671143-142671165 | 5660 |
| CR000765 | TRBC2 | CCCUGACCCUGGAGUCUGCC | Chr7: 142671175-142671197 | 5661 |
| CR000766 | TRBC2 | UAACAAGGUAUCUUGGGGUC | Chr7: 142670966-142670988 | 5662 |
| CR000767 | TRBC2 | CCCUAUAACAAGGUAUCUUG | Chr7: 142670971-142670993 | 5663 |
| CR000768 | TRBC2 | UCCCUAUAACAAGGUAUCUU | Chr7: 142670972-142670994 | 5664 |
| CR000769 | TRBC2 | GUCCCUAUAACAAGGUAUCU | Chr7: 142670973-142670995 | 5665 |

TABLE 5-continued gRNA targeting domains for human T-Cell Receptor Beta (Constant Domain 1 and Constant Domain 2)

| Id. | Target Name | gRNA Targeting Domain Sequence | Genomic Information | SEQ ID NO: |
|---|---|---|---|---|
| CR000770 | TRBC2 | UCUUUCCUGUCCCUAUAACA | Chr7: 142670981-142671003 | 5666 |
| CR000771 | TRBC2 | GAUACCAGUACAUUUUGUCA | Chr7: 142671035-142671057 | 5667 |
| CR000772 | TRBC2 | AUGAGGUGUAGUUCCAUUCC | Chr7: 142671066-142671088 | 5668 |
| CR000773 | TRBC2 | CUCCAUAGGAAUAGUGGAUG | Chr7: 142671083-142671105 | 5669 |
| CR000774 | TRBC2 | AAUUAACUCCAUAGGAAUAG | Chr7: 142671089-142671111 | 5670 |
| CR000775 | TRBC2 | CUCUGUGGAAUUAACUCCAU | Chr7: 142671097-142671119 | 5671 |
| CR000776 | TRBC2 | UCUGGAGACUGUUGACUCAG | Chr7: 142671133-142671155 | 5672 |
| CR000777 | TRBC2 | AAAAUGCUCCGUCCUUAUUC | Chr7: 142671151-142671173 | 5673 |
| CR000778 | TRBC2 | CCUGGCAGACUCCAGGGUCA | Chr7: 142671175-142671197 | 5674 |
| CR000779 | TRBC2 | GCCUGGCAGACUCCAGGGUC | Chr7: 142671176-142671198 | 5675 |
| CR000780 | TRBC2 | UGAGGGCCUGGCAGACUCCA | Chr7: 142671181-142671203 | 5676 |
| CR000781 | TRBC2 | GUGAGGGCCUGGCAGACUCC | Chr7: 142671182-142671204 | 5677 |
| CR000782 | TRBC2 | GAGGUACUGAGAGGUAUGUG | Chr7: 142671199-142671221 | 5678 |
| CR000783 | TRBC2 | GCUGGCACAGAGGUACUGAG | Chr7: 142671208-142671230 | 5679 |
| CR000784 | TRBC2 | UGUAUUCACUGCUGGCACAG | Chr7: 142671218-142671240 | 5680 |
| CR000785 | TRBC2 | GAGCUGUCUGGUUCUGGUAG | Chr7: 142791626-142791648 | 5681 |
| CR000786 | TRBC2 | AGAGCUGUCUGGUUCUGGUA | Chr7: 142791627-142791649 | 5682 |
| CR000787 | TRBC2 | GAGAGCUGUCUGGUUCUGGU | Chr7: 142791628-142791650 | 5683 |
| CR000788 | TRBC2 | CUCUGAGAGCUGUCUGGUUC | Chr7: 142791632-142791654 | 5684 |
| CR000789 | TRBC2 | GGGUUGCUCUGAGAGCUGUC | Chr7: 142791638-142791660 | 5685 |
| CR000790 | TRBC2 | GAAAAACGUGUUCCCACCCA | Chr7: 142801042-142801064 | 5686 |
| CR000791 | TRBC2 | AGGCUUCUACCCCGACCACG | Chr7: 142801135-142801157 | 5687 |
| CR000792 | TRBC2 | CCGACCACGUGGAGCUGAGC | Chr7: 142801146-142801168 | 5688 |
| CR000793 | TRBC2 | CACAGACCCGCAGCCCCUCA | Chr7: 142801204-142801226 | 5689 |

TABLE 5-continued gRNA targeting domains for human T-Cell Receptor Beta (Constant Domain 1 and Constant Domain 2)

| Id. | Target Name | gRNA Targeting Domain Sequence | Genomic Information | SEQ ID NO: |
|---|---|---|---|---|
| CR000794 | TRBC2 | UGGGUGGGAACACGUUUUUC | Chr7: 142801039-142801061 | 5690 |
| CR000795 | TRBC2 | CAAACACAGCGACCUUGGGU | Chr7: 142801054-142801076 | 5691 |
| CR000796 | TRBC2 | UCAAACACAGCGACCUUGGG | Chr7: 142801055-142801077 | 5692 |
| CR000797 | TRBC2 | GGCUCAAACACAGCGACCUU | Chr7: 142801058-142801080 | 5693 |
| CR000798 | TRBC2 | UGGCUCAAACACAGCGACCU | Chr7: 142801059-142801081 | 5694 |
| CR000799 | TRBC2 | CGGGGUAGAAGCCUGUGGCC | Chr7: 142801126-142801148 | 5695 |
| CR000800 | TRBC2 | GUGGUCGGGUAGAAGCCUG | Chr7: 142801131-142801153 | 5696 |
| CR000801 | TRBC2 | AGCUCAGCUCCACGUGGUCG | Chr7: 142801144-142801166 | 5697 |
| CR000802 | TRBC2 | CAGCUCAGCUCCACGUGGUC | Chr7: 142801145-142801167 | 5698 |
| CR000803 | TRBC2 | CCAGCUCAGCUCCACGUGGU | Chr7: 142801146-142801168 | 5699 |
| CR000804 | TRBC2 | GACAGGUUUGGCCCUAUCCU | Chr7: 142801362-142801384 | 5700 |
| CR000805 | TRBC2 | UGACAGGUUUGGCCCUAUCC | Chr7: 142801363-142801385 | 5701 |
| CR000806 | TRBC2 | GACGAUCUGGGUGACAGGUU | Chr7: 142801374-142801396 | 5702 |
| CR000807 | TRBC2 | GCGCUGACGAUCUGGGUGAC | Chr7: 142801379-142801401 | 5703 |
| CR000808 | TRBC2 | CCCUGUUUUCUUUCAGACUG | Chr7: 142801922-142801944 | 5704 |
| CR000809 | TRBC2 | AGGAGAGACUCACUUACCGG | Chr7: 142801950-142801972 | 5705 |
| CR000810 | TRBC2 | AAAAGGAGAGACUCACUUAC | Chr7: 142801953-142801975 | 5706 |
| CR000811 | TRBC2 | UCAACAGAGUCUUACCAGCA | Chr7: 142802092-142802114 | 5707 |
| CR000812 | TRBC2 | CAACAGAGUCUUACCAGCAA | Chr7: 142802093-142802115 | 5708 |
| CR000813 | TRBC2 | AACAGAGUCUUACCAGCAAG | Chr7: 142802094-142802116 | 5709 |
| CR000814 | TRBC2 | AUCCUCUAUGAGAUCUUGCU | Chr7: 142802131-142802153 | 5710 |
| CR000815 | TRBC2 | UCCUCUAUGAGAUCUUGCUA | Chr7: 142802132-142802154 | 5711 |
| CR000816 | TRBC2 | CUAUGAGAUCUUGCUAGGGA | Chr7: 142802136-142802158 | 5712 |
| CR000817 | TRBC2 | GGCCACCUUGUAUGCCGUGC | Chr7: 142802157-142802179 | 5713 |
| CR000818 | TRBC2 | GGUCAGUGCCCUCGUGCUGA | Chr7: 142802178-142802200 | 5714 |

TABLE 5-continued gRNA targeting domains for human T-Cell Receptor Beta (Constant Domain 1 and Constant Domain 2)

| Id. | Target Name | gRNA Targeting Domain Sequence | Genomic Information | SEQ ID NO: |
|---|---|---|---|---|
| CR000819 | TRBC2 | UGGCAGACAGGACCCCUUGC | Chr7: 142802106-142802128 | 5715 |
| CR000820 | TRBC2 | CAUAGAGGAUGGUGGCAGAC | Chr7: 142802118-142802140 | 5716 |
| CR000821 | TRBC2 | CAAGAUCUCAUAGAGGAUGG | Chr7: 142802126-142802148 | 5717 |
| CR000822 | TRBC2 | UAGCAAGAUCUCAUAGAGGA | Chr7: 142802129-142802151 | 5718 |
| CR000823 | TRBC2 | UCCCUAGCAAGAUCUCAUAG | Chr7: 142802133-142802155 | 5719 |

In the various aspects of the invention, the gRNA molecule may include a targeting domain listed above. In an embodiment, the targeting domain of the gRNA of the invention comprises, e.g. consists of, the targeting domain of CR000823. In an embodiment, the targeting domain of the gRNA of the invention comprises, e.g. consists of, the targeting domain of CR000798. In an embodiment, the targeting domain of the gRNA of the invention comprises, e.g. consists of, the targeting domain of CR000810. In an embodiment, the targeting domain of the gRNA of the invention comprises, e.g. consists of, the targeting domain of CR000800. In an embodiment, the targeting domain of the gRNA of the invention comprises, e.g. consists of, the targeting domain of CR000815. In an embodiment, the targeting domain of the gRNA of the invention comprises, e.g. consists of, the targeting domain of CR000812. In an embodiment, the targeting domain of the gRNA of the invention comprises, e.g. consists of, the targeting domain of CR000813. In an embodiment, the targeting domain of the gRNA of the invention comprises, e.g. consists of, the targeting domain of CR000816. In an embodiment, the targeting domain of the gRNA of the invention comprises, e.g. consists of, the targeting domain of CR000807. In an embodiment, the targeting domain of the gRNA of the invention comprises, e.g. consists of, the targeting domain of CR000811. In an embodiment, the targeting domain of the gRNA of the invention comprises, e.g. consists of, the targeting domain of CR000791. In an embodiment, the targeting domain of the gRNA of the invention comprises, e.g. consists of, the targeting domain of CR000809. In an embodiment, the targeting domain of the gRNA of the invention comprises, e.g. consists of, the targeting domain of CR000817. In an embodiment, the targeting domain of the gRNA of the invention comprises, e.g. consists of, the targeting domain of CR000819. In an embodiment, the targeting domain of the gRNA of the invention comprises, e.g. consists of, the targeting domain of CR000814. Such gRNA molecules, and combinations thereof, are suitable for use in, for example, the CRISPR systems, methods and cells and other aspects of the invention described herein.

TABLE 6 gRNA Targeting Domains for human PDCD1

| Id. | Target Name | gRNA Targeting Domain Sequence | Genomic Information | SEQ ID NO: |
|---|---|---|---|---|
| CR000824 | PDCD1 | UCAGGCGGAGGUGAGCGGAA | Chr2: 241858873-241858895 | 5720 |
| CR000825 | PDCD1 | CUCAGGCGGAGGUGAGCGGA | Chr2: 241858872-241858894 | 5721 |
| CR000826 | PDCD1 | ACUGCUCAGGCGGAGGUGAG | Chr2: 241858868-241858890 | 5722 |
| CR000827 | PDCD1 | GCUCACCUCCGCCUGAGCAG | Chr2: 241858866-241858888 | 5723 |
| CR000828 | PDCD1 | CUUCUCCACUGCUCAGGCGG | Chr2: 241858861-241858883 | 5724 |
| CR000829 | PDCD1 | CAGUGGAGAAGGCGGCACUC | Chr2: 241858849-241858871 | 5725 |
| CR000830 | PDCD1 | UGGAGAAGGCGGCACUCUGG | Chr2: 241858846-241858868 | 5726 |
| CR000831 | PDCD1 | GGAGAAGGCGGCACUCUGGU | Chr2: 241858845-241858867 | 5727 |

TABLE 6-continued gRNA Targeting Domains for human PDCD1

| Id. | Target Name | gRNA Targeting Domain Sequence | Genomic Information | SEQ ID NO: |
|---|---|---|---|---|
| CR000832 | PDCD1 | GAGAAGGCGGCACUCUGGUG | Chr2: 241858844-241858866 | 5728 |
| CR000833 | PDCD1 | AGGCGCCCUGGCCAGUCGUC | Chr2: 241858797-241858819 | 5729 |
| CR000834 | PDCD1 | GGCGCCCUGGCCAGUCGUCU | Chr2: 241858796-241858818 | 5730 |
| CR000835 | PDCD1 | GCCCUGGCCAGUCGUCUGGG | Chr2: 241858793-241858815 | 5731 |
| CR000836 | PDCD1 | CACCGCCCAGACGACUGGCC | Chr2: 241858791-241858813 | 5732 |
| CR000837 | PDCD1 | UGUAGCACCGCCCAGACGAC | Chr2: 241858786-241858808 | 5733 |
| CR000838 | PDCD1 | CGUCUGGGCGGUGCUACAAC | Chr2: 241858781-241858803 | 5734 |
| CR000839 | PDCD1 | GUCUGGGCGGUGCUACAACU | Chr2: 241858780-241858802 | 5735 |
| CR000840 | PDCD1 | GGGCGGUGCUACAACUGGGC | Chr2: 241858776-241858798 | 5736 |
| CR000841 | PDCD1 | CGGUGCUACAACUGGGCUGG | Chr2: 241858773-241858795 | 5737 |
| CR000842 | PDCD1 | CACCUACCUAAGAACCAUCC | Chr2: 241858750-241858772 | 5738 |
| CR000843 | PDCD1 | GAGAAGGUGGGGGGGUUCCA | Chr2: 241852938-241852960 | 5739 |
| CR000844 | PDCD1 | CGGUCACCACGAGCAGGGCU | Chr2: 241852915-241852937 | 5740 |
| CR000845 | PDCD1 | UCGGUCACCACGAGCAGGGC | Chr2: 241852914-241852936 | 5741 |
| CR000846 | PDCD1 | GCCCUGCUCGUGGUGACCGA | Chr2: 241852911-241852933 | 5742 |
| CR000847 | PDCD1 | CCCUUCGGUCACCACGAGCA | Chr2: 241852910-241852932 | 5743 |
| CR000848 | PDCD1 | CCCUGCUCGUGGUGACCGAA | Chr2: 241852910-241852932 | 5744 |
| CR000849 | PDCD1 | CCCCUUCGGUCACCACGAGC | Chr2: 241852909-241852931 | 5745 |
| CR000850 | PDCD1 | CCUGCUCGUGGUGACCGAAG | Chr2: 241852909-241852931 | 5746 |
| CR000851 | PDCD1 | GAAGGUGGCGUUGUCCCCUU | Chr2: 241852895-241852917 | 5747 |
| CR000852 | PDCD1 | GUUGGAGAAGCUGCAGGUGA | Chr2: 241852877-241852899 | 5748 |
| CR000853 | PDCD1 | CACGAAGCUCUCCGAUGUGU | Chr2: 241852859-241852881 | 5749 |
| CR000854 | PDCD1 | CGGAGAGCUUCGUGCUAAAC | Chr2: 241852850-241852872 | 5750 |

TABLE 6-continued gRNA Targeting Domains for human PDCD1

| Id. | Target Name | gRNA Targeting Domain Sequence | Genomic Information | SEQ ID NO: |
|---|---|---|---|---|
| CR000855 | PDCD1 | UCUGGUUGCUGGGGCUCAUG | Chr2: 241852825-241852847 | 5751 |
| CR000856 | PDCD1 | GCUUGUCCGUCUGGUUGCUG | Chr2: 241852816-241852838 | 5752 |
| CR000857 | PDCD1 | AGCUUGUCCGUCUGGUUGCU | Chr2: 241852815-241852837 | 5753 |
| CR000858 | PDCD1 | CAGCUUGUCCGUCUGGUUGC | Chr2: 241852814-241852836 | 5754 |
| CR000859 | PDCD1 | CAGCAACCAGACGGACAAGC | Chr2: 241852813-241852835 | 5755 |
| CR000860 | PDCD1 | AGGCGGCCAGCUUGUCCGUC | Chr2: 241852807-241852829 | 5756 |
| CR000861 | PDCD1 | CUGGCUGCGGUCCUCGGGGA | Chr2: 241852787-241852809 | 5757 |
| CR000862 | PDCD1 | CGGGCUGGCUGCGGUCCUCG | Chr2: 241852783-241852805 | 5758 |
| CR000863 | PDCD1 | CCGGGCUGGCUGCGGUCCUC | Chr2: 241852782-241852804 | 5759 |
| CR000864 | PDCD1 | CCCGAGGACCGCAGCCAGCC | Chr2: 241852782-241852804 | 5760 |
| CR000865 | PDCD1 | GCCGGGCUGGCUGCGGUCCU | Chr2: 241852781-241852803 | 5761 |
| CR000866 | PDCD1 | CGGAAGCGGCAGUCCUGGCC | Chr2: 241852764-241852786 | 5762 |
| CR000867 | PDCD1 | ACGGAAGCGGCAGUCCUGGC | Chr2: 241852763-241852785 | 5763 |
| CR000868 | PDCD1 | UGACACGGAAGCGGCAGUCC | Chr2: 241852759-241852781 | 5764 |
| CR000869 | PDCD1 | GCAGUUGUGUGACACGGAAG | Chr2: 241852750-241852772 | 5765 |
| CR000870 | PDCD1 | CGUGUCACACAACUGCCCAA | Chr2: 241852743-241852765 | 5766 |
| CR000871 | PDCD1 | GUGUCACACAACUGCCCAAC | Chr2: 241852742-241852764 | 5767 |
| CR000872 | PDCD1 | AUGUGGAAGUCACGCCCGUU | Chr2: 241852728-241852750 | 5768 |
| CR000873 | PDCD1 | CAUGUGGAAGUCACGCCCGU | Chr2: 241852727-241852749 | 5769 |
| CR000874 | PDCD1 | GCGUGACUUCCACAUGAGCG | Chr2: 241852720-241852742 | 5770 |
| CR000875 | PDCD1 | ACUUCCACAUGAGCGUGGUC | Chr2: 241852715-241852737 | 5771 |
| CR000876 | PDCD1 | CUUCCACAUGAGCGUGGUCA | Chr2: 241852714-241852736 | 5772 |

TABLE 6-continued gRNA Targeting Domains for human PDCD1

| Id. | Target Name | gRNA Targeting Domain Sequence | Genomic Information | SEQ ID NO: |
|---|---|---|---|---|
| CR000877 | PDCD1 | GGGCCCUGACCACGCUCAUG | Chr2: 241852711-241852733 | 5773 |
| CR000878 | PDCD1 | ACAUGAGCGUGGUCAGGGCC | Chr2: 241852709-241852731 | 5774 |
| CR000879 | PDCD1 | AGGGCCCGGCGCAAUGACAG | Chr2: 241852695-241852717 | 5775 |
| CR000880 | PDCD1 | GGUGCCGCUGUCAUUGCGCC | Chr2: 241852691-241852713 | 5776 |
| CR000881 | PDCD1 | AGGUGCCGCUGUCAUUGCGC | Chr2: 241852690-241852712 | 5777 |
| CR000882 | PDCD1 | GACAGCGGCACCUACCUCUG | Chr2: 241852680-241852702 | 5778 |
| CR000883 | PDCD1 | ACAGCGGCACCUACCUCUGU | Chr2: 241852679-241852701 | 5779 |
| CR000884 | PDCD1 | CCAGGGAGAUGGCCCCACAG | Chr2: 241852666-241852688 | 5780 |
| CR000885 | PDCD1 | GAUCUGCGCCUUGGGGCCA | Chr2: 241852649-241852671 | 5781 |
| CR000886 | PDCD1 | UGAUCUGCGCCUUGGGGCC | Chr2: 241852648-241852670 | 5782 |
| CR000887 | PDCD1 | CUCUUUGAUCUGCGCCUUGG | Chr2: 241852643-241852665 | 5783 |
| CR000888 | PDCD1 | UCUCUUUGAUCUGCGCCUUG | Chr2: 241852642-241852664 | 5784 |
| CR000889 | PDCD1 | CUCUCUUUGAUCUGCGCCUU | Chr2: 241852641-241852663 | 5785 |
| CR000890 | PDCD1 | GCUCUCUUUGAUCUGCGCCU | Chr2: 241852640-241852662 | 5786 |
| CR000891 | PDCD1 | CGCAGAUCAAAGAGAGCCUG | Chr2: 241852634-241852656 | 5787 |
| CR000892 | PDCD1 | GCAGAUCAAAGAGAGCCUGC | Chr2: 241852633-241852655 | 5788 |
| CR000893 | PDCD1 | AGAGCCUGCGGGCAGAGCUC | Chr2: 241852622-241852644 | 5789 |
| CR000894 | PDCD1 | AGGGUUUGGAACUGGCCGGC | Chr2: 241852278-241852300 | 5790 |
| CR000895 | PDCD1 | CACCAGGGUUUGGAACUGGC | Chr2: 241852274-241852296 | 5791 |
| CR000896 | PDCD1 | CGGCCAGUUCCAAACCCUGG | Chr2: 241852273-241852295 | 5792 |
| CR000897 | PDCD1 | CAACCACCAGGGUUUGGAAC | Chr2: 241852270-241852292 | 5793 |
| CR000898 | PDCD1 | CAGUUCCAAACCCUGGUGGU | Chr2: 241852269-241852291 | 5794 |
| CR000899 | PDCD1 | CGACACCAACCACCAGGGUU | Chr2: 241852264-241852286 | 5795 |
| CR000900 | PDCD1 | AACCCUGGUGGUUGGUGUCG | Chr2: 241852261-241852283 | 5796 |
| CR000901 | PDCD1 | ACCCUGGUGGUUGGUGUCGU | Chr2: 241852260-241852282 | 5797 |

TABLE 6-continued gRNA Targeting Domains for human PDCD1

| Id. | Target Name | gRNA Targeting Domain Sequence | Genomic Information | SEQ ID NO: |
|---|---|---|---|---|
| CR000902 | PDCD1 | GCCCACGACACCAACCACCA | Chr2: 241852259-241852281 | 5798 |
| CR000903 | PDCD1 | CGCCCACGACACCAACCACC | Chr2: 241852258-241852280 | 5799 |
| CR000904 | PDCD1 | CUGGUGGUUGGUGUCGUGGG | Chr2: 241852257-241852279 | 5800 |
| CR000905 | PDCD1 | UGGUGUCGUGGGCGGCCUGC | Chr2: 241852249-241852271 | 5801 |
| CR000906 | PDCD1 | GGUGUCGUGGGCGGCCUGCU | Chr2: 241852248-241852270 | 5802 |
| CR000907 | PDCD1 | GGUGCUGCUAGUCUGGGUCC | Chr2: 241852219-241852241 | 5803 |
| CR000908 | PDCD1 | UCCUGGCCGUCAUCUGCUCC | Chr2: 241852202-241852224 | 5804 |
| CR000909 | PDCD1 | CCCGGGAGCAGAUGACGGCC | Chr2: 241852201-241852223 | 5805 |
| CR000910 | PDCD1 | CCUGGCCGUCAUCUGCUCCC | Chr2: 241852201-241852223 | 5806 |
| CR000911 | PDCD1 | GACGUUACCUCGUGCGGCCC | Chr2: 241852184-241852206 | 5807 |
| CR000912 | PDCD1 | UGACGUUACCUCGUGCGGCC | Chr2: 241852183-241852205 | 5808 |
| CR000913 | PDCD1 | UGGGAUGACGUUACCUCGUG | Chr2: 241852178-241852200 | 5809 |
| CR000914 | PDCD1 | CUGCAGGGACAAUAGGAGCC | Chr2: 241851961-241851983 | 5810 |
| CR000915 | PDCD1 | ACAAUAGGAGCCAGGCGCAC | Chr2: 241851953-241851975 | 5811 |
| CR000916 | PDCD1 | CAGGGGCUGGCCGGUGCGCC | Chr2: 241851943-241851965 | 5812 |
| CR000917 | PDCD1 | AAAAGAGUGAGACUCACCAG | Chr2: 241851926-241851948 | 5813 |
| CR000918 | PDCD1 | GAAAAGAGUGAGACUCACCA | Chr2: 241851925-241851947 | 5814 |
| CR000919 | PDCD1 | GGAAAAGAGUGAGACUCACC | Chr2: 241851924-241851946 | 5815 |

In the various aspects of the invention, the gRNA molecule may include a targeting domain listed above. In an embodiment, the targeting domain of the gRNA of the invention comprises, e.g. consists of, the targeting domain of CR000847. In an embodiment, the targeting domain of the gRNA of the invention comprises, e.g. consists of, the targeting domain of CR000902. In an embodiment, the targeting domain of the gRNA of the invention comprises, e.g. consists of, the targeting domain of CR000852. In an embodiment, the targeting domain of the gRNA of the invention comprises, e.g. consists of, the targeting domain of CR000826. In an embodiment, the targeting domain of the gRNA of the invention comprises, e.g. consists of, the targeting domain of CR000904. In an embodiment, the targeting domain of the gRNA of the invention comprises, e.g. consists of, the targeting domain of CR000839. In an embodiment, the targeting domain of the gRNA of the invention comprises, e.g. consists of, the targeting domain of CR000828. In an embodiment, the targeting domain of the gRNA of the invention comprises, e.g. consists of, the targeting domain of CR000835. In an embodiment, the targeting domain of the gRNA of the invention comprises, e.g. consists of, the targeting domain of CR000829. In an embodiment, the targeting domain of the gRNA of the invention comprises, e.g. consists of, the targeting domain of CR000879. In an embodiment, the targeting domain of the gRNA of the invention comprises, e.g. consists of, the targeting domain of CR000870. In an embodiment, the targeting domain of the gRNA of the invention comprises, e.g. consists of, the targeting domain of CR000831. In an embodiment, the targeting domain of the gRNA of the invention comprises, e.g. consists of, the targeting domain of CR000848. In an embodiment, the targeting domain of the gRNA of the invention comprises, e.g. consists of, the targeting domain of CR000855. In an embodiment, the targeting domain of the gRNA of the invention comprises, e.g. consists of, the targeting domain of CR000838. Such gRNA molecules, and combinations thereof, are suitable for use in, for example, the CRISPR systems, methods and cells, and other aspects of the invention described herein.

TABLE 6b gRNA Targeting Domains for human FKBP1A

| ID | Target | Strand | Target Sequence Location | gRNA Targeting Domain Sequence | SEQ ID NO: |
|---|---|---|---|---|---|
| CR002054 | FKBP1A | - | Chr20: 1393120-1393142 | CGCACGCAGGGCUGGGCGUG | 6662 |
| CR002055 | FKBP1A | - | Chr20: 1393119-1393141 | GCACGCAGGGCUGGGCGUGA | 6663 |
| CR002056 | FKBP1A | - | Chr20: 1393118-1393140 | CACGCAGGGCUGGGCGUGAG | 6664 |
| CR002057 | FKBP1A | - | Chr20: 1393117-1393139 | ACGCAGGGCUGGGCGUGAGG | 6665 |
| CR002058 | FKBP1A | - | Chr20: 1393101-1393123 | GAGGGGGCGUGCGCGUGCGC | 6666 |
| CR002059 | FKBP1A | - | Chr20: 1393088-1393110 | CGUGCGCAGGCGACGCGCCG | 6667 |
| CR002060 | FKBP1A | - | Chr20: 1393081-1393103 | AGGCGACGCGCCGAGGUACU | 6668 |
| CR002061 | FKBP1A | + | Chr20: 1393071-1393093 | CACGGCUCUGCCUAGUACCU | 6669 |
| CR002062 | FKBP1A | - | Chr20: 1393070-1393092 | CGAGGUACUAGGCAGAGCCG | 6670 |
| CR002063 | FKBP1A | - | Chr20: 1393057-1393079 | AGAGCCGUGGAACCGCCGCC | 6671 |
| CR002064 | FKBP1A | + | Chr20: 1393053-1393075 | GCGACCUGGCGGCGGUUCCA | 6672 |
| CR002065 | FKBP1A | - | Chr20: 1393047-1393069 | AACCGCCGCCAGGUCGCUGU | 6673 |
| CR002066 | FKBP1A | + | Chr20: 1393045-1393067 | GACCAACAGCGACCUGGCGG | 6674 |
| CR002067 | FKBP1A | + | Chr20: 1393042-1393064 | GUGGACCAACAGCGACCUGG | 6675 |
| CR002068 | FKBP1A | + | Chr20: 1393039-1393061 | GGCGUGGACCAACAGCGACC | 6676 |
| CR002069 | FKBP1A | + | Chr20: 1393023-1393045 | GGGCGGCGCGACGGGCGCG | 6677 |
| CR002070 | FKBP1A | + | Chr20: 1393018-1393040 | CGGGCGGCGGCGCGACGGG | 6678 |
| CR002071 | FKBP1A | + | Chr20: 1393015-1393037 | GAGCGGGCGGGCGGCGCGAC | 6679 |
| CR002072 | FKBP1A | + | Chr20: 1393014-1393036 | UGAGCGGGCGGGCGGCGCGA | 6680 |
| CR002073 | FKBP1A | + | Chr20: 1393006-1393028 | GCGGACGCUGAGCGGGCGGG | 6681 |
| CR002074 | FKBP1A | + | Chr20: 1393003-1393025 | GCGGCGGACGCUGAGCGGGC | 6682 |
| CR002075 | FKBP1A | + | Chr20: 1393002-1393024 | GGCGGCGGACGCUGAGCGGG | 6683 |
| CR002076 | FKBP1A | + | Chr20: 1392999-1393021 | GGCGGCGGCGGACGCUGAGC | 6684 |

TABLE 6b-continued gRNA Targeting Domains for human FKBP1A

| ID | Target | Strand | Target Sequence Location | gRNA Targeting Domain Sequence | SEQ ID NO: |
|---|---|---|---|---|---|
| CR002077 | FKBP1A | + | Chr20: 1392998-1393020 | UGGCGGCGGCGGACGCUGAG | 6685 |
| CR002078 | FKBP1A | - | Chr20: 1392995-1393017 | CUCAGCGUCCGCCGCCGCCA | 6686 |
| CR002079 | FKBP1A | - | Chr20: 1392994-1393016 | UCAGCGUCCGCCGCCGCCAU | 6687 |
| CR002080 | FKBP1A | + | Chr20: 1392987-1393009 | CUGCACUCCCAUGGCGGCGG | 6688 |
| CR002081 | FKBP1A | - | Chr20: 1392986-1393008 | CGCCGCCGCCAUGGGAGUGC | 6689 |
| CR002082 | FKBP1A | + | Chr20: 1392984-1393006 | CACCUGCACUCCCAUGGCGG | 6690 |
| CR002083 | FKBP1A | - | Chr20: 1392983-1393005 | CGCCGCCAUGGGAGUGCAGG | 6691 |
| CR002084 | FKBP1A | + | Chr20: 1392981-1393003 | UUCCACCUGCACUCCCAUGG | 6692 |
| CR002085 | FKBP1A | + | Chr20: 1392978-1393000 | GGUUUCCACCUGCACUCCCA | 6693 |
| CR002086 | FKBP1A | - | Chr20: 1392967-1392989 | CAGGUGGAAACCAUCUCCCC | 6694 |
| CR002087 | FKBP1A | + | Chr20: 1392957-1392979 | CUCACCGUCUCCUGGGGAGA | 6695 |
| CR002088 | FKBP1A | + | Chr20: 1392951-1392973 | CCACUACUCACCGUCUCUG | 6696 |
| CR002089 | FKBP1A | + | Chr20: 1392950-1392972 | GCCACUACUCACCGUCUCCU | 6697 |
| CR002090 | FKBP1A | + | Chr20: 1392949-1392971 | CGCCACUACUCACCGUCUCC | 6698 |
| CR002091 | FKBP1A | - | Chr20: 1392880-1392902 | UGCCCGUCUCUGUCUCCUCA | 6699 |
| CR002092 | FKBP1A | - | Chr20: 1392860-1392882 | GGGCGCACCUUCCCAAGCG | 6700 |
| CR002093 | FKBP1A | + | Chr20: 1392853-1392875 | GGUCUGGCCGCGCUUGGGGA | 6701 |
| CR002094 | FKBP1A | + | Chr20: 1392849-1392871 | CGCAGGUCUGGCCGCGCUUG | 6702 |
| CR002095 | FKBP1A | + | Chr20: 1392848-1392870 | ACGCAGGUCUGGCCGCGCUU | 6703 |
| CR002096 | FKBP1A | + | Chr20: 1392847-1392869 | CACGCAGGUCUGGCCGCGCU | 6704 |
| CR002097 | FKBP1A | - | Chr20: 1392846-1392868 | CAAGCGCGGCCAGACCUGCG | 6705 |
| CR002098 | FKBP1A | + | Chr20: 1392837-1392859 | UGUAGUGCACCACGCAGGUC | 6706 |
| CR002099 | FKBP1A | + | Chr20: 1392832-1392854 | ACCGGUGUAGUGCACCACGC | 6707 |
| CR002100 | FKBP1A | + | Chr20: 1392814-1392836 | CCGCUGGGCCCCCGACUCAC | 6708 |
| CR002101 | FKBP1A | - | Chr20: 1375602-1375624 | UUACAGUCGUCUUUUUCACA | 6709 |

TABLE 6b-continued gRNA Targeting Domains for human FKBP1A

| ID | Target | Strand | Target Sequence Location | gRNA Targeting Domain Sequence | SEQ ID NO: |
|---|---|---|---|---|---|
| CR002102 | FKBP1A | - | Chr20: 1375588-1375610 | UUCACAGGGAUGCUUGAAGA | 6710 |
| CR002103 | FKBP1A | - | Chr20: 1375566-1375588 | GAAAGAAAUUUGAUUCCUCC | 6711 |
| CR002104 | FKBP1A | - | Chr20: 1375565-1375587 | AAAGAAAUUUGAUUCCUCCC | 6712 |
| CR002105 | FKBP1A | + | Chr20: 1375551-1375573 | GGGCUUGUUUCUGUCCCGGG | 6713 |
| CR002106 | FKBP1A | + | Chr20: 1375548-1375570 | AAAGGGCUUGUUUCUGUCCC | 6714 |
| CR002107 | FKBP1A | + | Chr20: 1375547-1375569 | UAAAGGGCUUGUUUCUGUCC | 6715 |
| CR002108 | FKBP1A | - | Chr20: 1375534-1375556 | AAGCCCUUUAAGUUUAUGCU | 6716 |
| CR002109 | FKBP1A | + | Chr20: 1375531-1375553 | UUGCCUAGCAUAAACUUAAA | 6717 |
| CR002110 | FKBP1A | + | Chr20: 1375530-1375552 | CUUGCCUAGCAUAAACUUAA | 6718 |
| CR002111 | FKBP1A | - | Chr20: 1375526-1375548 | UAAGUUUAUGCUAGGCAAGC | 6719 |
| CR002112 | FKBP1A | - | Chr20: 1375523-1375545 | GUUUAUGCUAGGCAAGCAGG | 6720 |
| CR002113 | FKBP1A | - | Chr20: 1375513-1375535 | GGCAAGCAGGAGGUGAUCCG | 6721 |
| CR002114 | FKBP1A | - | Chr20: 1375509-1375531 | AGCAGGAGGUGAUCCGAGGC | 6722 |
| CR002115 | FKBP1A | - | Chr20: 1375508-1375530 | GCAGGAGGUGAUCCGAGGCU | 6723 |
| CR002116 | FKBP1A | - | Chr20: 1375501-1375523 | GUGAUCCGAGGCUGGGAAGA | 6724 |
| CR002117 | FKBP1A | - | Chr20: 1375500-1375522 | UGAUCCGAGGCUGGGAAGAA | 6725 |
| CR002118 | FKBP1A | - | Chr20: 1375499-1375521 | GAUCCGAGGCUGGGAAGAAG | 6726 |
| CR002119 | FKBP1A | + | Chr20: 1375496-1375518 | CAACCCCUUCUUCCCAGCCU | 6727 |
| CR002120 | FKBP1A | + | Chr20: 1375473-1375495 | ACAAAUGAGAGAGCAUACCU | 6728 |
| CR002121 | FKBP1A | + | Chr20: 1375472-1375494 | AACAAAUGAGAGAGCAUACC | 6729 |
| CR002122 | FKBP1A | - | Chr20: 1372231-1372253 | GUUCUUUUCACAGAUGAGUG | 6730 |
| CR002123 | FKBP1A | - | Chr20: 1372230-1372252 | UUCUUUUCACAGAUGAGUGU | 6731 |
| CR002124 | FKBP1A | + | Chr20: 1372199-1372221 | AUCUGGAGAUAUAGUCAGUU | 6732 |
| CR002125 | FKBP1A | - | Chr20: 1372188-1372210 | AUAUCUCCAGAUUAUGCCUA | 6733 |
| CR002126 | FKBP1A | + | Chr20: 1372182-1372204 | GUGGCACCAUAGGCAUAAUC | 6734 |

TABLE 6b-continued gRNA Targeting Domains for human FKBP1A

| ID | Target | Strand | Target Sequence Location | gRNA Targeting Domain Sequence | SEQ ID NO: |
|---|---|---|---|---|---|
| CR002127 | FKBP1A | - | Chr20: 1372179-1372201 | GAUUAUGCCUAUGGUGCCAC | 6735 |
| CR002128 | FKBP1A | - | Chr20: 1372178-1372200 | AUUAUGCCUAUGGUGCCACU | 6736 |
| CR002129 | FKBP1A | + | Chr20: 1372172-1372194 | UGGGUGCCCAGUGGCACCAU | 6737 |
| CR002130 | FKBP1A | - | Chr20: 1372170-1372192 | UAUGGUGCCACUGGGCACCC | 6738 |
| CR002131 | FKBP1A | + | Chr20: 1372163-1372185 | GAUGAUGCCUGGGUGCCCAG | 6739 |
| CR002132 | FKBP1A | + | Chr20: 1372153-1372175 | CAUGUGGUGGGAUGAUGCCU | 6740 |
| CR002133 | FKBP1A | + | Chr20: 1372152-1372174 | GCAUGUGGUGGGAUGAUGCC | 6741 |
| CR002134 | FKBP1A | + | Chr20: 1372141-1372163 | AGACGAGAGUGGCAUGUGGU | 6742 |
| CR002135 | FKBP1A | + | Chr20: 1372140-1372162 | AAGACGAGAGUGGCAUGUGG | 6743 |
| CR002136 | FKBP1A | + | Chr20: 1372137-1372159 | UCGAAGACGAGAGUGGCAUG | 6744 |
| CR002137 | FKBP1A | - | Chr20: 1372132-1372154 | UGCCACUCUCGUCUUCGAUG | 6745 |
| CR002138 | FKBP1A | + | Chr20: 1372130-1372152 | CUCCACAUCGAAGACGAGAG | 6746 |
| CR002139 | FKBP1A | - | Chr20: 1372117-1372139 | CGAUGUGGAGCUUCUAAAAC | 6747 |
| CR002140 | FKBP1A | - | Chr20: 1372108-1372130 | GCUUCUAAAACUGGAAUGAC | 6748 |
| CR002141 | FKBP1A | - | Chr20: 1372103-1372125 | UAAAACUGGAAUGACAGGAA | 6749 |

In the various aspects of the invention, the gRNA molecule may include a targeting domain listed above. In an embodiment, the targeting domain of the gRNA of the invention comprises, e.g. consists of, the targeting domain of CR002100. In an embodiment, the targeting domain of the gRNA of the invention comprises, e.g. consists of, the targeting domain of CR002097. In an embodiment, the targeting domain of the gRNA of the invention comprises, e.g. consists of, the targeting domain of CR002091. In an embodiment, the targeting domain of the gRNA of the invention comprises, e.g. consists of, the targeting domain of CR002085. In an embodiment, the targeting domain of the gRNA of the invention comprises, e.g. consists of, the targeting domain of CR002086. In an embodiment, the targeting domain of the gRNA of the invention comprises, e.g. consists of, the targeting domain of CR002089. In an embodiment, the targeting domain of the gRNA of the invention comprises, e.g. consists of, the targeting domain of CR002088. In an embodiment, the targeting domain of the gRNA of the invention comprises, e.g. consists of, the targeting domain of CR002095. In an embodiment, the targeting domain of the gRNA of the invention comprises, e.g. consists of, the targeting domain of CR002096. In an embodiment, the targeting domain of the gRNA of the invention comprises, e.g. consists of, the targeting domain of CR002080. In an embodiment, the targeting domain of the gRNA of the invention comprises, e.g. consists of, the targeting domain of CR002109. In an embodiment, the targeting domain of the gRNA of the invention comprises, e.g. consists of, the targeting domain of CR002112. In an embodiment, the targeting domain of the gRNA of the invention comprises, e.g. consists of, the targeting domain of CR002110. In an embodiment, the targeting domain of the gRNA of the invention comprises, e.g. consists of, the targeting domain of CR002108. In an embodiment, the targeting domain of the gRNA of the invention comprises, e.g. consists of, the targeting domain of CR002104. In an embodiment, the targeting domain of the gRNA of the invention comprises, e.g. consists of, the targeting domain of CR002115. In an embodiment, the targeting domain of the gRNA of the invention comprises, e.g. consists of, the targeting domain of CR002116. In an embodiment, the targeting domain of the gRNA of the invention comprises, e.g. consists of, the targeting domain of CR002087. In an embodiment, the targeting domain of the gRNA of the invention comprises, e.g. consists of, the targeting domain of CR002107. In an embodiment, the targeting domain of the gRNA of the invention comprises, e.g. consists of, the targeting domain of CR002113. Such gRNA molecules, including combinations thereof, are suitable for use in, for example, the CRISPR systems, methods and cells and other aspects of the invention described herein.

TABLE 6c gRNA Targeting Domains for human CIITA

| Id | Target | Strand | Chromosomal location | gRNA targeting domain sequence | SEQ ID NO: |
|---|---|---|---|---|---|
| CR002939 | CIITA | + | Chr16: 10877252-10877274 | GGCAUCCUUGGGGAAGCUGA | 7717 |
| CR002940 | CIITA | - | Chr16: 10877257-10877279 | UCGUGCCCUCAGCUUCCCCA | 7718 |
| CR002941 | CIITA | + | Chr16: 10877259-10877281 | UUGGGGAAGCUGAGGGCACG | 7719 |
| CR002942 | CIITA | + | Chr16: 10877262-10877284 | GGGAAGCUGAGGGCACGAGG | 7720 |
| CR002943 | CIITA | + | Chr16: 10877263-10877285 | GGAAGCUGAGGGCACGAGGA | 7721 |
| CR002944 | CIITA | + | Chr16: 10877264-10877286 | GAAGCUGAGGGCACGAGGAG | 7722 |
| CR002945 | CIITA | + | Chr16: 10877278-10877300 | GAGGAGGGGCUGCCAGACUC | 7723 |
| CR002946 | CIITA | + | Chr16: 10877279-10877301 | AGGAGGGGCUGCCAGACUCC | 7724 |
| CR002947 | CIITA | - | Chr16: 10877290-10877312 | AGGCAGCAGCUCCCGGAGUC | 7725 |
| CR002948 | CIITA | + | Chr16: 10877292-10877314 | AGACUCCGGGAGCUGCUGCC | 7726 |
| CR002949 | CIITA | + | Chr16: 10877296-10877318 | UCCGGGAGCUGCUGCCUGGC | 7727 |
| CR002950 | CIITA | + | Chr16: 10877297-10877319 | CCGGGAGCUGCUGCCUGGCU | 7728 |
| CR002951 | CIITA | - | Chr16: 10877297-10877319 | CCCAGCCAGGCAGCAGCUCC | 7729 |
| CR002952 | CIITA | - | Chr16: 10877310-10877332 | AUUGUGUAGGAAUCCCAGCC | 7730 |
| CR002953 | CIITA | + | Chr16: 10877321-10877343 | UUCCUACACAAUGCGUUGCC | 7731 |
| CR002954 | CIITA | - | Chr16: 10877323-10877345 | AGCCAGGCAACGCAUUGUGU | 7732 |
| CR002955 | CIITA | + | Chr16: 10877337-10877359 | UGCCUGGCUCCACGCCCUGC | 7733 |
| CR002956 | CIITA | + | Chr16: 10877338-10877360 | GCCUGGCUCCACGCCCUGCU | 7734 |
| CR002957 | CIITA | - | Chr16: 10877339-10877361 | ACCCAGCAGGGCGUGGAGCC | 7735 |
| CR002958 | CIITA | - | Chr16: 10877346-10877368 | AGGUAGGACCCAGCAGGGCG | 7736 |
| CR002959 | CIITA | - | Chr16: 10877351-10877373 | CUGACAGGUAGGACCCAGCA | 7737 |
| CR002960 | CIITA | - | Chr16: 10877352-10877374 | UCUGACAGGUAGGACCCAGC | 7738 |
| CR002961 | CIITA | + | Chr16: 10895283-10895305 | CAGCUCACAGUGUGCCACCA | 7739 |

TABLE 6c-continued gRNA Targeting Domains for human CIITA

| Id | Target | Strand | Chromosomal location | gRNA targeting domain sequence | SEQ ID NO: |
|---|---|---|---|---|---|
| CR002962 | CIITA | + | Chr16: 10895289-10895311 | ACAGUGUGCCACCAUGGAGU | 7740 |
| CR002963 | CIITA | + | Chr16: 10895290-10895312 | CAGUGUGCCACCAUGGAGUU | 7741 |
| CR002964 | CIITA | + | Chr16: 10895291-10895313 | AGUGUGCCACCAUGGAGUUG | 7742 |
| CR002965 | CIITA | - | Chr16: 10895297-10895319 | UAGGGGCCCCAACUCCAUGG | 7743 |
| CR002966 | CIITA | - | Chr16: 10895300-10895322 | UUCUAGGGGCCCCAACUCCA | 7744 |
| CR002967 | CIITA | + | Chr16: 10895302-10895324 | AUGGAGUUGGGGCCCCUAGA | 7745 |
| CR002968 | CIITA | + | Chr16: 10895305-10895327 | GAGUUGGGGCCCCUAGAAGG | 7746 |
| CR002969 | CIITA | + | Chr16: 10895313-10895335 | GCCCCUAGAAGGUGGCUACC | 7747 |
| CR002970 | CIITA | - | Chr16: 10895314-10895336 | UCCAGGUAGCCACCUUCUAG | 7748 |
| CR002971 | CIITA | - | Chr16: 10895315-10895337 | CUCCAGGUAGCCACCUUCUA | 7749 |
| CR002972 | CIITA | - | Chr16: 10895316-10895338 | GCUCCAGGUAGCCACCUUCU | 7750 |
| CR002973 | CIITA | - | Chr16: 10895331-10895353 | CAUCGCUGUUAAGAAGCUCC | 7751 |
| CR002974 | CIITA | - | Chr16: 10895358-10895380 | AGAAGUGGUAGAGGCACAGG | 7752 |
| CR002975 | CIITA | - | Chr16: 10895359-10895381 | UAGAAGUGGUAGAGGCACAG | 7753 |
| CR002976 | CIITA | - | Chr16: 10895360-10895382 | AUAGAAGUGGUAGAGGCACA | 7754 |
| CR002977 | CIITA | - | Chr16: 10895361-10895383 | CAUAGAAGUGGUAGAGGCAC | 7755 |
| CR002978 | CIITA | - | Chr16: 10895367-10895389 | UCUGGUCAUAGAAGUGGUAG | 7756 |
| CR002979 | CIITA | + | Chr16: 10895370-10895392 | CUACCACUUCUAUGACCAGA | 7757 |
| CR002980 | CIITA | - | Chr16: 10895373-10895395 | GGUCCAUCUGGUCAUAGAAG | 7758 |
| CR002981 | CIITA | + | Chr16: 10895376-10895398 | CUUCUAUGACCAGAUGGACC | 7759 |
| CR002982 | CIITA | + | Chr16: 10895380-10895402 | UAUGACCAGAUGGACCUGGC | 7760 |
| CR002983 | CIITA | - | Chr16: 10895385-10895407 | CUUCUCCAGCCAGGUCCAUC | 7761 |
| CR002984 | CIITA | - | Chr16: 10895394-10895416 | CAAUCUCUUCUUCUCCAGCC | 7762 |
| CR002985 | CIITA | - | Chr16: 10895671-10895693 | CAGUUGAUGGUGUCUGUGUC | 7763 |
| CR002986 | CIITA | - | Chr16: 10895672-10895694 | GCAGUUGAUGGUGUCUGUGU | 7764 |

TABLE 6c-continued gRNA Targeting Domains for human CIITA

| Id | Target | Strand | Chromosomal location | gRNA targeting domain sequence | SEQ ID NO: |
|---|---|---|---|---|---|
| CR002987 | CIITA | - | Chr16: 10895684-10895706 | GCUGAACUGGUCGCAGUUGA | 7765 |
| CR002988 | CIITA | + | Chr16: 10895687-10895709 | UCAACUGCGACCAGUUCAGC | 7766 |
| CR002989 | CIITA | - | Chr16: 10895697-10895719 | CACACAACAGCCUGCUGAAC | 7767 |
| CR002990 | CIITA | + | Chr16: 10895703-10895725 | CAGCAGGCUGUUGUGUGACA | 7768 |
| CR002991 | CIITA | + | Chr16: 10895707-10895729 | AGGCUGUUGUGUGACAUGGA | 7769 |
| CR002992 | CIITA | + | Chr16: 10895723-10895745 | UGGAAGGUGAUGAAGAGACC | 7770 |
| CR002993 | CIITA | + | Chr16: 10895724-10895746 | GGAAGGUGAUGAAGAGACCA | 7771 |
| CR002994 | CIITA | + | Chr16: 10895727-10895749 | AGGUGAUGAAGAGACCAGGG | 7772 |
| CR002995 | CIITA | - | Chr16: 10895741-10895763 | GAUAUUGGCAUAAGCCUCCC | 7773 |
| CR002996 | CIITA | - | Chr16: 10895756-10895778 | AGGUGCUUCCUCACCGAUAU | 7774 |
| CR002997 | CIITA | + | Chr16: 10898674-10898696 | ACUGGACCAGUAUGUCUUCC | 7775 |
| CR002998 | CIITA | - | Chr16: 10898680-10898702 | GGGAGUCCUGGAAGACAUAC | 7776 |
| CR002999 | CIITA | + | Chr16: 10898686-10898708 | UGUCUUCCAGGACUCCCAGC | 7777 |
| CR003000 | CIITA | + | Chr16: 10898689-10898711 | CUUCCAGGACUCCCAGCUGG | 7778 |
| CR003001 | CIITA | + | Chr16: 10898690-10898712 | UUCCAGGACUCCCAGCUGGA | 7779 |
| CR003002 | CIITA | - | Chr16: 10898692-10898714 | GGCCUCCAGCUGGGAGUCC | 7780 |
| CR003003 | CIITA | - | Chr16: 10898700-10898722 | CUUGCUCAGGCCCUCCAGCU | 7781 |
| CR003004 | CIITA | - | Chr16: 10898701-10898723 | CCUUGCUCAGGCCCUCCAGC | 7782 |
| CR003005 | CIITA | + | Chr16: 10898701-10898723 | CCAGCUGGAGGGCCUGAGCA | 7783 |
| CR003006 | CIITA | - | Chr16: 10898713-10898735 | UACUGAAAAUGUCCUUGCUC | 7784 |
| CR003007 | CIITA | + | Chr16: 10898930-10898952 | AUAGGACCAGAUGAAGUGAU | 7785 |
| CR003008 | CIITA | - | Chr16: 10898936-10898958 | CUCUCACCGAUCACUUCAUC | 7786 |
| CR003009 | CIITA | + | Chr16: 10898941-10898963 | UGAAGUGAUCGGUGAGAGUA | 7787 |
| CR003010 | CIITA | + | Chr16: 10898960-10898982 | AUGGAGAUGCCAGCAGAAGU | 7788 |
| CR003011 | CIITA | + | Chr16: 10898961-10898983 | UGGAGAUGCCAGCAGAAGUU | 7789 |

TABLE 6c-continued gRNA Targeting Domains for human CIITA

| Id | Target | Strand | Chromosomal location | gRNA targeting domain sequence | SEQ ID NO: |
|---|---|---|---|---|---|
| CR003012 | CIITA | − | Chr16: 10898969-10898991 | CUUUUCUGCCCAACUUCUGC | 7790 |
| CR003013 | CIITA | − | Chr16: 10901514-10901536 | UGCCGGAAGCUCCUCUGGGA | 7791 |
| CR003014 | CIITA | − | Chr16: 10901518-10901540 | GGUCUGCCGGAAGCUCCUCU | 7792 |
| CR003015 | CIITA | − | Chr16: 10901519-10901541 | AGGUCUGCCGGAAGCUCCUC | 7793 |
| CR003016 | CIITA | + | Chr16: 10901529-10901551 | UUCCGGCAGACCUGAAGCAC | 7794 |
| CR003017 | CIITA | − | Chr16: 10901531-10901553 | UUCCAGUGCUUCAGGUCUGC | 7795 |
| CR003018 | CIITA | + | Chr16: 10902040-10902062 | GAGCCCCCACUGUGGUGAC | 7796 |
| CR003019 | CIITA | − | Chr16: 10902043-10902065 | CUGCCAGUCACCACAGUGGG | 7797 |
| CR003020 | CIITA | − | Chr16: 10902044-10902066 | ACUGCCAGUCACCACAGUGG | 7798 |
| CR003021 | CIITA | − | Chr16: 10902045-10902067 | GACUGCCAGUCACCACAGUG | 7799 |
| CR003022 | CIITA | − | Chr16: 10902046-10902068 | AGACUGCCAGUCACCACAGU | 7800 |
| CR003023 | CIITA | − | Chr16: 10902047-10902069 | GAGACUGCCAGUCACCACAG | 7801 |
| CR003024 | CIITA | + | Chr16: 10902054-10902076 | GGUGACUGGCAGUCUCCUAG | 7802 |
| CR003025 | CIITA | + | Chr16: 10902055-10902077 | GUGACUGGCAGUCUCCUAGU | 7803 |
| CR003026 | CIITA | − | Chr16: 10902069-10902091 | AGUCGCUCACUGGUCCCACU | 7804 |

In the various aspects of the invention, the gRNA molecule may include a targeting domain listed above. In an embodiment, the targeting domain of the gRNA of the invention comprises, e.g. consists of, the targeting domain of CR002939. In an embodiment, the targeting domain of the gRNA of the invention comprises, e.g. consists of, the targeting domain of CR002940. In an embodiment, the targeting domain of the gRNA of the invention comprises, e.g. consists of, the targeting domain of CR002941. In an embodiment, the targeting domain of the gRNA of the invention comprises, e.g. consists of, the targeting domain of CR002942. In an embodiment, the targeting domain of the gRNA of the invention comprises, e.g. consists of, the targeting domain of CR002943. In an embodiment, the targeting domain of the gRNA of the invention comprises, e.g. consists of, the targeting domain of CR002944. In an embodiment, the targeting domain of the gRNA of the invention comprises, e.g. consists of, the targeting domain of CR002945. In an embodiment, the targeting domain of the gRNA of the invention comprises, e.g. consists of, the targeting domain of CR002946. In an embodiment, the targeting domain of the gRNA of the invention comprises, e.g. consists of, the targeting domain of CR002947. In an embodiment, the targeting domain of the gRNA of the invention comprises, e.g. consists of, the targeting domain of CR002948. In an embodiment, the targeting domain of the gRNA of the invention comprises, e.g. consists of, the targeting domain of CR002949. In an embodiment, the targeting domain of the gRNA of the invention comprises, e.g. consists of, the targeting domain of CR002950. In an embodiment, the targeting domain of the gRNA of the invention comprises, e.g. consists of, the targeting domain of CR002951. In an embodiment, the targeting domain of the gRNA of the invention comprises, e.g. consists of, the targeting domain of CR002952. In an embodiment, the targeting domain of the gRNA of the invention comprises, e.g. consists of, the targeting domain of CR002953. In an embodiment, the targeting domain of the gRNA of the invention comprises, e.g. consists of, the targeting domain of CR002954. In an embodiment, the targeting domain of the gRNA of the invention comprises, e.g. consists of, the targeting domain of CR002955. In an embodiment, the targeting domain of the gRNA of the invention comprises, e.g. consists of, the targeting domain of CR002956. In an embodiment, the targeting domain of the gRNA of the invention comprises, e.g. consists of, the targeting domain of CR002957. In an embodiment, the targeting domain of the gRNA of the invention comprises, e.g. consists of, the targeting domain of CR002958. In an embodiment, the targeting domain of the gRNA of the invention comprises, e.g. consists of, the targeting domain of CR002959. In an embodiment, the targeting domain of the gRNA of the invention comprises, e.g. consists of, the targeting domain of CR002960. In an embodiment, the targeting domain of the gRNA of the invention comprises, e.g. consists of, the targeting domain of CR002961. In an embodiment, the targeting domain of the gRNA of the invention comprises, e.g. consists of, the targeting domain of CR002962. In an embodiment, the targeting domain of the gRNA of the invention comprises, e.g. consists of, the targeting domain of CR002963. In an embodiment, the targeting domain of the gRNA of the invention comprises, e.g. consists of, the targeting domain of CR002964. In an embodiment, the targeting domain of the gRNA of the invention comprises, e.g. consists of, the targeting domain of CR002965. In an embodiment, the targeting domain of the gRNA of the invention comprises, e.g. consists of, the targeting domain of CR002966. In an embodiment, the targeting domain of the gRNA of the invention comprises, e.g. consists of, the targeting domain of CR002967. In an embodiment, the targeting domain of the gRNA of the invention comprises, e.g. consists of, the targeting domain of CR002968. In an embodiment, the targeting domain of the gRNA of the invention comprises, e.g. consists of, the targeting domain of CR002969. In an embodiment, the targeting domain of the gRNA of the invention comprises, e.g. consists of, the targeting domain of CR002970. In an embodiment, the targeting domain of the gRNA of the invention comprises, e.g. consists of, the targeting domain of CR002971. In an embodiment, the targeting domain of the gRNA of the invention comprises, e.g. consists of, the targeting domain of CR002972. In an embodiment, the targeting domain of the gRNA of the invention comprises, e.g. consists of, the targeting domain of CR002973. In an embodiment, the targeting domain of the gRNA of the invention comprises, e.g. consists of, the targeting domain of CR002974. In an embodiment, the targeting domain of the gRNA of the invention comprises, e.g. consists of, the targeting domain of CR002975. In an embodiment, the targeting domain of the gRNA of the invention comprises, e.g. consists of, the targeting domain of CR002976. In an embodiment, the targeting domain of the gRNA of the invention comprises, e.g. consists of, the targeting domain of CR002977. In an embodiment, the targeting domain of the gRNA of the invention comprises, e.g. consists of, the targeting domain of CR002978. In an embodiment, the targeting domain of the gRNA of the invention comprises, e.g. consists of, the targeting domain of CR002979. In an embodiment, the targeting domain of the gRNA of the invention comprises, e.g. consists of, the targeting domain of CR002980. In an embodiment, the targeting domain of the gRNA of the invention comprises, e.g. consists of, the targeting domain of CR002981. In an embodiment, the targeting domain of the gRNA of the invention comprises, e.g. consists of, the targeting domain of CR002982. In an embodiment, the targeting domain of the gRNA of the invention comprises, e.g. consists of, the targeting domain of CR002983. In an embodiment, the targeting domain of the gRNA of the invention comprises, e.g. consists of, the targeting domain of CR002984. In an embodiment, the targeting domain of the gRNA of the invention comprises, e.g. consists of, the targeting domain of CR002985. In an embodiment, the targeting domain of the gRNA of the invention comprises, e.g. consists of, the targeting domain of CR002986. In an embodiment, the targeting domain of the gRNA of the invention comprises, e.g. consists of, the targeting domain of CR002987. In an embodiment, the targeting domain of the gRNA of the invention comprises, e.g. consists of, the targeting domain of CR002988. In an embodiment, the targeting domain of the gRNA of the invention comprises, e.g. consists of, the targeting domain of CR002989. In an embodiment, the targeting domain of the gRNA of the invention comprises, e.g. consists of, the targeting domain of CR002990. In an embodiment, the targeting domain of the gRNA of the invention comprises, e.g. consists of, the targeting domain of CR002991. In an embodiment, the targeting domain of the gRNA of the invention comprises, e.g. consists of, the targeting domain of CR002992. In an embodiment, the targeting domain of the gRNA of the invention comprises, e.g. consists of, the targeting domain of CR002993. In an embodiment, the targeting domain of the gRNA of the invention comprises, e.g. consists of, the targeting domain of CR002994. In an embodiment, the targeting domain of the gRNA of the invention comprises, e.g. consists of, the targeting domain of CR002995. In an embodiment, the targeting domain of the gRNA of the invention comprises, e.g. consists of, the targeting domain of CR002996. In an embodiment, the targeting domain of the gRNA of the invention comprises, e.g. consists of, the targeting domain of CR002997. In an embodiment, the targeting domain of the gRNA of the invention comprises, e.g. consists of, the targeting domain of CR002998. In an embodiment, the targeting domain of the gRNA of the invention comprises, e.g. consists of, the targeting domain of CR002999. In an embodiment, the targeting domain of the gRNA of the invention comprises, e.g. consists of, the targeting domain of CR003000. In an embodiment, the targeting domain of the gRNA of the invention comprises, e.g. consists of, the targeting domain of CR003001. In an embodiment, the targeting domain of the gRNA of the invention comprises, e.g. consists of, the targeting domain of CR003002. In an embodiment, the targeting domain of the gRNA of the invention comprises, e.g. consists of, the targeting domain of CR003003. In an embodiment, the targeting domain of the gRNA of the invention comprises, e.g. consists of, the targeting domain of CR003004. In an embodiment, the targeting domain of the gRNA of the invention comprises, e.g. consists of, the targeting domain of CR003005. In an embodiment, the targeting domain of the gRNA of the invention comprises, e.g. consists of, the targeting domain of CR003006. In an embodiment, the targeting domain of the gRNA of the invention comprises, e.g. consists of, the targeting domain of CR003007. In an embodiment, the targeting domain of the gRNA of the invention comprises, e.g. consists of, the targeting domain of CR003008. In an embodiment, the targeting domain of the gRNA of the invention comprises, e.g. consists of, the targeting domain of CR003009. In an embodiment, the targeting domain of the gRNA of the invention comprises, e.g. consists of, the targeting domain of CR003010. In an embodiment, the targeting domain of the gRNA of the invention comprises, e.g. consists of, the targeting domain of CR003011. In an embodiment, the targeting domain of the gRNA of the invention comprises, e.g. consists of, the targeting domain of CR003012. In an embodiment, the targeting domain of the gRNA of the invention comprises, e.g. consists of, the targeting domain of CR003013. In an embodiment, the targeting domain of the gRNA of the invention comprises, e.g. consists of, the targeting domain of CR003014. In an embodiment, the targeting domain of the gRNA of the invention comprises, e.g. consists of, the targeting domain of CR003015. In an embodiment, the targeting domain of the gRNA of the invention comprises, e.g. consists of, the targeting domain of CR003016. In an embodiment, the targeting domain of the gRNA of the invention comprises, e.g. consists of, the targeting domain of CR003017. In an embodiment, the targeting domain of the gRNA of the invention comprises, e.g. consists of, the targeting domain of CR003018. In an embodiment, the targeting domain of the gRNA of the invention comprises, e.g. consists of, the targeting domain of CR003019. In an embodiment, the targeting domain of the gRNA of the invention comprises, e.g. consists of, the targeting domain of CR003020. In an embodiment, the targeting domain of the gRNA of the invention comprises, e.g. consists of, the targeting domain of CR003021. In an embodiment, the targeting domain of the gRNA of the invention comprises, e.g. consists of, the targeting domain of CR003022. In an embodiment, the targeting domain of the gRNA of the invention comprises, e.g. consists of, the targeting domain of CR003023. In an embodiment, the targeting domain of the gRNA of the invention comprises, e.g. consists of, the targeting domain of CR003024. In an embodiment, the targeting domain of the gRNA of the invention comprises, e.g. consists of, the targeting domain of CR003025. In an embodiment, the targeting domain of the gRNA of the invention comprises, e.g. consists of, the targeting domain of CR003026. Such gRNA molecules, and combinations thereof, are suitable for use in, for example, the CRISPR systems, methods and cells and other aspects of the invention described herein.

TABLE 6d

Targeting Domains for human LILRB1, an exemplary target of an NK inhibitory molecule.

| Id | Target | Region | Strand | Chromosomal location | gRNA targeting domain sequence | SEQ ID NO: |
|---|---|---|---|---|---|---|
| 10859_2_1 | LILRB1 | EXON | + | chr19: 54630390-54630410 | UAAAAGGGGAAGUUAAGAG | 10090 |
| 10859_2_2 | LILRB1 | EXON | + | chr19: 54630399-54630419 | GAAGUUAAGAGGGGACUAUU | 10091 |
| 10859_2_23 | LILRB1 | EXON | + | chr19: 54630503-54630523 | CUGCCACACGCAGCUCAGCC | 10092 |
| 10859_2_24 | LILRB1 | EXON | + | chr19: 54630504-54630524 | UGCCACACGCAGCUCAGCCU | 10093 |
| 10859_2_25 | LILRB1 | EXON | + | chr19: 54630507-54630527 | CACACGCAGCUCAGCCUGGG | 10094 |
| 10859_2_29 | LILRB1 | EXON | + | chr19: 54630560-54630580 | AUCUGAGUCUGCCUGCAGCA | 10095 |
| 10859_2_31 | LILRB1 | EXON | + | chr19: 54630566-54630586 | GUCUGCCUGCAGCAUGGACC | 10096 |
| 10859_2_32 | LILRB1 | EXON | + | chr19: 54630567-54630587 | UCUGCCUGCAGCAUGGACCU | 10097 |
| 10859_2_35 | LILRB1 | EXON | + | chr19: 54630589-54630609 | GUCUUCCCUGAAGCAUCUCC | 10098 |
| 10859_2_36 | LILRB1 | EXON | + | chr19: 54630590-54630610 | UCUUCCCUGAAGCAUCUCCA | 10099 |
| 10859_2_39 | LILRB1 | EXON | + | chr19: 54630594-54630614 | CCCUGAAGCAUCUCCAGGGC | 10100 |
| 10859_2_42 | LILRB1 | EXON | + | chr19: 54630597-54630617 | UGAAGCAUCUCCAGGGCUGG | 10101 |
| 10859_2_44 | LILRB1 | EXON | + | chr19: 54630598-54630618 | GAAGCAUCUCCAGGGCUGGA | 10102 |
| 10859_2_45 | LILRB1 | EXON | + | chr19: 54630611-54630631 | GGCUGGAGGGACGACUGCCA | 10103 |
| 10859_2_47 | LILRB1 | EXON | + | chr19: 54630616-54630636 | GAGGGACGACUGCCAUGGUA | 10104 |
| 10859_2_58 | LILRB1 | EXON | - | chr19: 54630436-54630456 | CUUUCUUGACACUGGAUUGU | 10105 |
| 10859_2_60 | LILRB1 | EXON | - | chr19: 54630437-54630457 | UCUUUCUUGACACUGGAUUG | 10106 |
| 10859_2_62 | LILRB1 | EXON | - | chr19: 54630444-54630464 | GUUGACUUCUUUCUUGACAC | 10107 |

TABLE 6d-continued

Targeting Domains for human LILRB1, an exemplary target of an NK inhibitory molecule.

| Id | Target | Region | Strand | Chromosomal location | gRNA targeting domain sequence | SEQ ID NO: |
|---|---|---|---|---|---|---|
| 10859_2_65 | LILRB1 | EXON | - | chr19: 54630474-54630494 | AAGAGAAAUGCAGGGAAAUA | 10108 |
| 10859_2_67 | LILRB1 | EXON | - | chr19: 54630475-54630495 | GAAGAGAAAUGCAGGGAAAU | 10109 |
| 10859_2_70 | LILRB1 | EXON | - | chr19: 54630482-54630502 | GAGCACAGAAGAGAAAUGCA | 10110 |
| 10859_2_72 | LILRB1 | EXON | - | chr19: 54630483-54630503 | UGAGCACAGAAGAGAAAUGC | 10111 |
| 10859_2_80 | LILRB1 | EXON | - | chr19: 54630509-54630529 | CGCCCAGGCUGAGCUGCGUG | 10112 |
| 10859_2_82 | LILRB1 | EXON | - | chr19: 54630524-54630544 | CGCAUCUGGCUGUGCCGCCC | 10113 |
| 10859_2_83 | LILRB1 | EXON | - | chr19: 54630538-54630558 | GCAGAGACGCAUCUCGCAUC | 10114 |
| 10859_2_85 | LILRB1 | EXON | - | chr19: 54630574-54630594 | AAGACCCAGGUCCAUGCUGC | 10115 |
| 10859_2_87 | LILRB1 | EXON | - | chr19: 54630587-54630607 | AGAUGCUUCAGGGAAGACCC | 10116 |
| 10859_2_88 | LILRB1 | EXON | - | chr19: 54630597-54630617 | CCAGCCCUGGAGAUGCUUCA | 10117 |
| 10859_2_90 | LILRB1 | EXON | - | chr19: 54630598-54630618 | UCCAGCCCUGGAGAUGCUUC | 10118 |
| 10859_2_94 | LILRB1 | EXON | - | chr19: 54630610-54630630 | GGCAGUCGUCCCUCCAGCCC | 10119 |
| 10859_2_98 | LILRB1 | EXON | - | chr19: 54630631-54630651 | GUGUUGUGGGGUCCUUACCA | 10120 |
| 10859_3_3 | LILRB1 | EXON | + | chr19: 54631010-54631030 | UCUCUAUCCUGCCAGCACCG | 10121 |
| 10859_3_4 | LILRB1 | EXON | + | chr19: 54631011-54631031 | CUCUAUCCUGCCAGCACCGA | 10122 |
| 10859_3_7 | LILRB1 | EXON | + | chr19: 54631032-54631052 | GGCUCAUCCAUCCACAGAGC | 10123 |
| 10859_3_8 | LILRB1 | EXON | + | chr19: 54631033-54631053 | GCUCAUCCAUCCACAGAGCA | 10124 |
| 10859_3_10 | LILRB1 | EXON | + | chr19: 54631039-54631059 | CCAUCCACAGAGCAGGGCAG | 10125 |
| 10859_3_12 | LILRB1 | EXON | + | chr19: 54631040-54631060 | CAUCCACAGAGCAGGGCAGU | 10126 |
| 10859_3_15 | LILRB1 | EXON | + | chr19: 54631043-54631063 | CCACAGAGCAGGGCAGUGGG | 10127 |
| 10859_3_17 | LILRB1 | EXON | + | chr19: 54631069-54631089 | CGCCAUGACCCCCAUCCUCA | 10128 |
| 10859_3_18 | LILRB1 | EXON | + | chr19: 54631085-54631105 | CUCACGGUCCUGAUCUGUCU | 10129 |
| 10859_3_24 | LILRB1 | EXON | + | chr19: 54631101-54631121 | GUCUCGGUGAGAUUUGAAGA | 10130 |
| 10859_3_25 | LILRB1 | EXON | + | chr19: 54631104-54631124 | UCGGUGAGAUUUGAAGAAGG | 10131 |

TABLE 6d-continued

Targeting Domains for human LILRB1, an exemplary target of an NK inhibitory molecule.

| Id | Target | Region | Strand | Chromosomal location | gRNA targeting domain sequence | SEQ ID NO: |
|---|---|---|---|---|---|---|
| 10859_3_28 | LILRB1 | EXON | - | chr19: 54631020-54631040 | GAUGAGCCCUCGGUGCUGGC | 10132 |
| 10859_3_30 | LILRB1 | EXON | - | chr19: 54631024-54631044 | GAUGGAUGAGCCCUCGGUGC | 10133 |
| 10859_3_31 | LILRB1 | EXON | - | chr19: 54631030-54631050 | UCUGUGGAUGGAUGAGCCCU | 10134 |
| 10859_3_33 | LILRB1 | EXON | - | chr19: 54631042-54631062 | CCACUGCCCUGCUCUGUGGA | 10135 |
| 10859_3_35 | LILRB1 | EXON | - | chr19: 54631046-54631066 | CCUCCCACUGCCCUGCUCUG | 10136 |
| 10859_3_37 | LILRB1 | EXON | - | chr19: 54631074-54631094 | GACCGUGAGGAUGGGGGUCA | 10137 |
| 10859_3_38 | LILRB1 | EXON | - | chr19: 54631080-54631100 | GAUCAGGACCGUGAGGAUGG | 10138 |
| 10859_3_39 | LILRB1 | EXON | - | chr19: 54631081-54631101 | AGAUCAGGACCGUGAGGAUG | 10139 |
| 10859_3_40 | LILRB1 | EXON | - | chr19: 54631082-54631102 | CAGAUCAGGACCGUGAGGAU | 10140 |
| 10859_3_42 | LILRB1 | EXON | - | chr19: 54631083-54631103 | ACAGAUCAGGACCGUGAGGA | 10141 |
| 10859_3_45 | LILRB1 | EXON | - | chr19: 54631087-54631107 | CGAGACAGAUCAGGACCGUG | 10142 |
| 10859_3_50 | LILRB1 | EXON | - | chr19: 54631096-54631116 | AAAUCUCACCGAGACAGAUC | 10143 |
| 10859_4_3 | LILRB1 | EXON | + | chr19: 54631259-54631279 | CUCUCUUCCAGGGCUGAGUC | 10144 |
| 10859_4_4 | LILRB1 | EXON | + | chr19: 54631260-54631280 | UCUCUUCCAGGGCUGAGUCU | 10145 |
| 10859_4_7 | LILRB1 | EXON | + | chr19: 54631267-54631287 | CAGGGCUGAGUCUGGGCCCC | 10146 |
| 10859_4_8 | LILRB1 | EXON | + | chr19: 54631280-54631300 | GGGCCCCCGGACCCACGUGC | 10147 |
| 10859_4_9 | LILRB1 | EXON | + | chr19: 54631284-54631304 | CCCCGGACCCACGUGCAGGC | 10148 |
| 10859_4_11 | LILRB1 | EXON | - | chr19: 54631255-54631275 | CAGCCCUGGAAGAGAGUUCC | 10149 |
| 10859_4_15 | LILRB1 | EXON | - | chr19: 54631269-54631289 | CGGGGGCCCAGACUCAGCCC | 10150 |
| 10859_4_17 | LILRB1 | EXON | - | chr19: 54631286-54631306 | CUGCCUGCACGUGGGUCGG | 10151 |
| 10859_4_18 | LILRB1 | EXON | - | chr19: 54631287-54631307 | CCUGCCUGCACGUGGGUCCG | 10152 |
| 10859_4_20 | LILRB1 | EXON | - | chr19: 54631288-54631308 | ACCUGCCUGCACGUGGGUCC | 10153 |
| 10859_4_21 | LILRB1 | EXON | - | chr19: 54631289-54631309 | CACCUGCCUGCACGUGGGUC | 10154 |
| 10859_4_24 | LILRB1 | EXON | - | chr19: 54631294-54631314 | AGACUCACCUGCCUGCACGU | 10155 |

TABLE 6d-continued

Targeting Domains for human LILRB1, an exemplary target of an NK inhibitory molecule.

| Id | Target | Region | Strand | Chromosomal location | gRNA targeting domain sequence | SEQ ID NO: |
|---|---|---|---|---|---|---|
| 10859_4_25 | LILRB1 | EXON | - | chr19: 54631295-54631315 | CAGACUCACCUGCCUGCACG | 10156 |
| 10859_5_5 | LILRB1 | EXON | + | chr19: 54631502-54631522 | ACCUCCCAAGCCCACCCUC | 10157 |
| 10859_5_6 | LILRB1 | EXON | + | chr19: 54631503-54631523 | CCUCCCAAGCCCACCCUCU | 10158 |
| 10859_5_8 | LILRB1 | EXON | + | chr19: 54631513-54631533 | CCCACCCUCUGGGCUGAACC | 10159 |
| 10859_5_10 | LILRB1 | EXON | + | chr19: 54631530-54631550 | ACCAGGCUCUGUGAUCACCC | 10160 |
| 10859_5_12 | LILRB1 | EXON | + | chr19: 54631531-54631551 | CCAGGCUCUGUGAUCACCCA | 10161 |
| 10859_5_15 | LILRB1 | EXON | + | chr19: 54631532-54631552 | CAGGCUCUGUGAUCACCCAG | 10162 |
| 10859_5_16 | LILRB1 | EXON | + | chr19: 54631550-54631570 | AGGGGAGUCCUGUGACCCUC | 10163 |
| 10859_5_19 | LILRB1 | EXON | + | chr19: 54631557-54631577 | UCCUGUGACCCUCAGGUGUC | 10164 |
| 10859_5_20 | LILRB1 | EXON | + | chr19: 54631558-54631578 | CCUGUGACCCUCAGGUGUCA | 10165 |
| 10859_5_22 | LILRB1 | EXON | + | chr19: 54631559-54631579 | CUGUGACCCUCAGGUGUCAG | 10166 |
| 10859_5_24 | LILRB1 | EXON | + | chr19: 54631560-54631580 | UGUGACCCUCAGGUGUCAGG | 10167 |
| 10859_5_25 | LILRB1 | EXON | + | chr19: 54631561-54631581 | GUGACCCUCAGGUGUCAGGG | 10168 |
| 10859_5_28 | LILRB1 | EXON | + | chr19: 54631566-54631586 | CCUCAGGUGUCAGGGGGCC | 10169 |
| 10859_5_30 | LILRB1 | EXON | + | chr19: 54631575-54631595 | UCAGGGGGCCAGGAGACCC | 10170 |
| 10859_5_38 | LILRB1 | EXON | + | chr19: 54631613-54631633 | GAGAAAAGAAAACAGCACCC | 10171 |
| 10859_5_40 | LILRB1 | EXON | + | chr19: 54631622-54631642 | AAACAGCACCCUGGAUUACA | 10172 |
| 10859_5_42 | LILRB1 | EXON | + | chr19: 54631632-54631652 | CUGGAUUACACGGAUCCCAC | 10173 |
| 10859_5_48 | LILRB1 | EXON | + | chr19: 54631647-54631667 | CCCACAGGAGCUUGUGAAGA | 10174 |
| 10859_5_49 | LILRB1 | EXON | + | chr19: 54631648-54631668 | CCACAGGAGCUUGUGAAGAA | 10175 |
| 10859_5_53 | LILRB1 | EXON | + | chr19: 54631676-54631696 | UCCCAUCCCAUCCAUCACC | 10176 |
| 10859_5_54 | LILRB1 | EXON | + | chr19: 54631677-54631697 | CCCAUCCCAUCCAUCACCU | 10177 |
| 10859_5_58 | LILRB1 | EXON | + | chr19: 54631687-54631707 | UCCAUCACCUGGGAACACAC | 10178 |
| 10859_5_59 | LILRB1 | EXON | + | chr19: 54631688-54631708 | CCAUCACCUGGGAACACACA | 10179 |
| 10859_5_60 | LILRB1 | EXON | + | chr19: 54631691-54631711 | UCACCUGGGAACACACAGGG | 10180 |

TABLE 6d-continued

Targeting Domains for human LILRB1, an exemplary target of an NK inhibitory molecule.

| Id | Target | Region | Strand | Chromosomal location | gRNA targeting domain sequence | SEQ ID NO: |
|---|---|---|---|---|---|---|
| 10859_5_61 | LILRB1 | EXON | + | chr19: 54631708-54631728 | GGGCGGUAUCGCUGUUACUA | 10181 |
| 10859_5_62 | LILRB1 | EXON | + | chr19: 54631723-54631743 | UACUAUGGUAGCGACACUGC | 10182 |
| 10859_5_68 | LILRB1 | EXON | + | chr19: 54631749-54631769 | CUCAGAGAGCAGUGACCCCC | 10183 |
| 10859_5_69 | LILRB1 | EXON | + | chr19: 54631755-54631775 | GAGCAGUGACCCCUGGAGC | 10184 |
| 10859_5_70 | LILRB1 | EXON | + | chr19: 54631758-54631778 | CAGUGACCCCUGGAGCUGG | 10185 |
| 10859_5_71 | LILRB1 | EXON | + | chr19: 54631765-54631785 | CCCCUGGAGCUGGUGGUGAC | 10186 |
| 10859_5_75 | LILRB1 | EXON | + | chr19: 54631781-54631801 | UGACAGGUGAGCUGACACUC | 10187 |
| 10859_5_76 | LILRB1 | EXON | + | chr19: 54631782-54631802 | GACAGGUGAGCUGACACUCA | 10188 |
| 10859_5_77 | LILRB1 | EXON | + | chr19: 54631783-54631803 | ACAGGUGAGCUGACACUCAG | 10189 |
| 10859_5_79 | LILRB1 | EXON | - | chr19: 54631486-54631506 | AGGUGCCCUGGAAGGAAAUC | 10190 |
| 10859_5_82 | LILRB1 | EXON | - | chr19: 54631494-54631514 | GCUUGGGGAGGUGCCCUGGA | 10191 |
| 10859_5_85 | LILRB1 | EXON | - | chr19: 54631498-54631518 | GUGGGCUUGGGGAGGUGCCC | 10192 |
| 10859_5_89 | LILRB1 | EXON | - | chr19: 54631506-54631526 | CCCAGAGGGUGGGCUUGGGG | 10193 |
| 10859_5_90 | LILRB1 | EXON | - | chr19: 54631509-54631529 | CAGCCCAGAGGGUGGGCUUG | 10194 |
| 10859_5_92 | LILRB1 | EXON | - | chr19: 54631510-54631530 | UCAGCCCAGAGGGUGGGCUU | 10195 |
| 10859_5_95 | LILRB1 | EXON | - | chr19: 54631511-54631531 | UUCAGCCCAGAGGGUGGGCU | 10196 |
| 10859_5_97 | LILRB1 | EXON | - | chr19: 54631516-54631536 | CCUGGUUCAGCCCAGAGGGU | 10197 |
| 10859_5_98 | LILRB1 | EXON | - | chr19: 54631517-54631537 | GCCUGGUUCAGCCCAGAGGG | 10198 |
| 10859_5_100 | LILRB1 | EXON | - | chr19: 54631520-54631540 | AGAGCCUGGUUCAGCCCAGA | 10199 |
| 10859_5_101 | LILRB1 | EXON | - | chr19: 54631521-54631541 | CAGAGCCUGGUUCAGCCCAG | 10200 |
| 10859_5_104 | LILRB1 | EXON | - | chr19: 54631534-54631554 | CCCUGGGUGAUCACAGAGCC | 10201 |
| 10859_5_106 | LILRB1 | EXON | - | chr19: 54631550-54631570 | GAGGGUCACAGGACUCCCCU | 10202 |
| 10859_5_107 | LILRB1 | EXON | - | chr19: 54631551-54631571 | UGAGGGUCACAGGACUCCCC | 10203 |
| 10859_5_109 | LILRB1 | EXON | - | chr19: 54631561-54631581 | CCCUGACACCUGAGGGUCAC | 10204 |

TABLE 6d-continued

Targeting Domains for human LILRB1, an exemplary target of an NK inhibitory molecule.

| Id | Target | Region | Strand | Chromosomal location | gRNA targeting domain sequence | SEQ ID NO: |
|---|---|---|---|---|---|---|
| 10859_5_111 | LILRB1 | EXON | - | chr19: 54631568-54631588 | CUGGCCCCCUGACACCUGA | 10205 |
| 10859_5_112 | LILRB1 | EXON | - | chr19: 54631569-54631589 | CCUGGCCCCCUGACACCUG | 10206 |
| 10859_5_115 | LILRB1 | EXON | - | chr19: 54631587-54631607 | GACGGUACUCCUGGGUCUCC | 10207 |
| 10859_5_119 | LILRB1 | EXON | - | chr19: 54631595-54631615 | UCUAUAUAGACGGUACUCCU | 10208 |
| 10859_5_120 | LILRB1 | EXON | - | chr19: 54631596-54631616 | CUCUAUAUAGACGGUACUCC | 10209 |
| 10859_5_125 | LILRB1 | EXON | - | chr19: 54631605-54631625 | UUUUCUUUUCUCUAUAUAGA | 10210 |
| 10859_5_126 | LILRB1 | EXON | - | chr19: 54631633-54631653 | UGUGGGAUCCGUGUAAUCCA | 10211 |
| 10859_5_127 | LILRB1 | EXON | - | chr19: 54631634-54631654 | CUGUGGGAUCCGUGUAAUCC | 10212 |
| 10859_5_131 | LILRB1 | EXON | - | chr19: 54631650-54631670 | CCUUCUUCACAAGCUCCUGU | 10213 |
| 10859_5_132 | LILRB1 | EXON | - | chr19: 54631651-54631671 | CCCUUCUUCACAAGCUCCUG | 10214 |
| 10859_5_135 | LILRB1 | EXON | - | chr19: 54631674-54631694 | UGAUGGAUGGGAUGGGGAAC | 10215 |
| 10859_5_137 | LILRB1 | EXON | - | chr19: 54631680-54631700 | CCCAGGUGAUGGAUGGGAUG | 10216 |
| 10859_5_140 | LILRB1 | EXON | - | chr19: 54631681-54631701 | UCCCAGGUGAUGGAUGGGAU | 10217 |
| 10859_5_141 | LILRB1 | EXON | - | chr19: 54631682-54631702 | UUCCCAGGUGAUGGAUGGGA | 10218 |
| 10859_5_144 | LILRB1 | EXON | - | chr19: 54631686-54631706 | UGUGUUCCCAGGUGAUGGAU | 10219 |
| 10859_5_146 | LILRB1 | EXON | - | chr19: 54631687-54631707 | GUGUGUUCCCAGGUGAUGGA | 10220 |
| 10859_5_148 | LILRB1 | EXON | - | chr19: 54631691-54631711 | CCCUGUGUGUUCCCAGGUGA | 10221 |
| 10859_5_150 | LILRB1 | EXON | - | chr19: 54631697-54631717 | AUACCGCCCUGUGUGUUCCC | 10222 |
| 10859_5_151 | LILRB1 | EXON | - | chr19: 54631749-54631769 | GGGGGUCACUGCUCUCUGAG | 10223 |
| 10859_5_153 | LILRB1 | EXON | - | chr19: 54631767-54631787 | CUGUCACCACCAGCUCCAGG | 10224 |
| 10859_5_154 | LILRB1 | EXON | - | chr19: 54631768-54631788 | CCUGUCACCACCAGCUCCAG | 10225 |
| 10859_5_155 | LILRB1 | EXON | - | chr19: 54631769-54631789 | ACCUGUCACCACCAGCUCCA | 10226 |
| 10859_5_157 | LILRB1 | EXON | - | chr19: 54631770-54631790 | CACCUGUCACCACCAGCUCC | 10227 |
| 10859_6_2 | LILRB1 | EXON | + | chr19: 54631956-54631976 | CUCAGCCCAGCCCAGCCCCG | 10228 |
| 10859_6_6 | LILRB1 | EXON | + | chr19: 54631966-54631986 | CCCAGCCCCGUGGUGAACUC | 10229 |

TABLE 6d-continued

Targeting Domains for human LILRB1, an exemplary target of an NK inhibitory molecule.

| Id | Target | Region | Strand | Chromosomal location | gRNA targeting domain sequence | SEQ ID NO: |
|---|---|---|---|---|---|---|
| 10859_6_8 | LILRB1 | EXON | + | chr19: 54631969-54631989 | AGCCCCGUGGUGAACUCAGG | 10230 |
| 10859_6_10 | LILRB1 | EXON | + | chr19: 54631970-54631990 | GCCCCGUGGUGAACUCAGGA | 10231 |
| 10859_6_12 | LILRB1 | EXON | + | chr19: 54631998-54632018 | AACCCUCCAGUGUGACUCAC | 10232 |
| 10859_6_13 | LILRB1 | EXON | + | chr19: 54632001-54632021 | CCUCCAGUGUGACUCACAGG | 10233 |
| 10859_6_14 | LILRB1 | EXON | + | chr19: 54632011-54632031 | GACUCACAGGUGGCAUUUGA | 10234 |
| 10859_6_17 | LILRB1 | EXON | + | chr19: 54632028-54632048 | UGAUGGCUUCAUUCUGUGUA | 10235 |
| 10859_6_21 | LILRB1 | EXON | + | chr19: 54632032-54632052 | GGCUUCAUUCUGUGUAAGGA | 10236 |
| 10859_6_29 | LILRB1 | EXON | + | chr19: 54632080-54632100 | AACUCCCAGCCCCAUGCCCG | 10237 |
| 10859_6_30 | LILRB1 | EXON | + | chr19: 54632081-54632101 | ACUCCCAGCCCCAUGCCCGU | 10238 |
| 10859_6_32 | LILRB1 | EXON | + | chr19: 54632106-54632126 | GUCCCGCGCCAUCUUCUCCG | 10239 |
| 10859_6_33 | LILRB1 | EXON | + | chr19: 54632107-54632127 | UCCCGCGCCAUCUUCUCCGU | 10240 |
| 10859_6_37 | LILRB1 | EXON | + | chr19: 54632129-54632149 | GCCCCGUGAGCCCGAGUCGC | 10241 |
| 10859_6_38 | LILRB1 | EXON | + | chr19: 54632132-54632152 | CCGUGAGCCCGAGUCGCAGG | 10242 |
| 10859_6_39 | LILRB1 | EXON | + | chr19: 54632135-54632155 | UGAGCCCGAGUCGCAGGUGG | 10243 |
| 10859_6_40 | LILRB1 | EXON | + | chr19: 54632141-54632161 | CGAGUCGCAGGUGGUGGUAC | 10244 |
| 10859_6_44 | LILRB1 | EXON | + | chr19: 54632177-54632197 | ACUCGAACUCUCCCUAUGAG | 10245 |
| 10859_6_46 | LILRB1 | EXON | + | chr19: 54632199-54632219 | GUCUCUACCCAGUGAUCUCC | 10246 |
| 10859_6_48 | LILRB1 | EXON | + | chr19: 54632208-54632228 | CAGUGAUCUCCUGGAGCUCC | 10247 |
| 10859_6_49 | LILRB1 | EXON | + | chr19: 54632215-54632235 | CUCCUGGAGCUCCUGGUCCU | 10248 |
| 10859_6_53 | LILRB1 | EXON | - | chr19: 54631921-54631941 | UAGGCUCCUAGGAGAGAAGG | 10249 |
| 10859_6_57 | LILRB1 | EXON | - | chr19: 54631924-54631944 | AUGUAGGCUCCUAGGAGAGA | 10250 |
| 10859_6_62 | LILRB1 | EXON | - | chr19: 54631932-54631952 | UGGGUUUGAUGUAGGCUCCU | 10251 |
| 10859_6_65 | LILRB1 | EXON | - | chr19: 54631940-54631960 | UGAGAGGGUGGGUUUGAUGU | 10252 |
| 10859_6_66 | LILRB1 | EXON | - | chr19: 54631951-54631971 | CUGGGCUGGGCUGAGAGGGU | 10253 |

TABLE 6d-continued

Targeting Domains for human LILRB1, an exemplary target of an NK inhibitory molecule.

| Id | Target | Region | Strand | Chromosomal location | gRNA targeting domain sequence | SEQ ID NO: |
|---|---|---|---|---|---|---|
| 10859_6_67 | LILRB1 | EXON | - | chr19: 54631952-54631972 | GCUGGGCUGGGCUGAGAGGG | 10254 |
| 10859_6_69 | LILRB1 | EXON | - | chr19: 54631955-54631975 | GGGGCUGGGCUGGGCUGAGA | 10255 |
| 10859_6_70 | LILRB1 | EXON | - | chr19: 54631956-54631976 | CGGGGCUGGGCUGGGCUGAG | 10256 |
| 10859_6_75 | LILRB1 | EXON | - | chr19: 54631964-54631984 | GUUCACCACGGGGCUGGCU | 10257 |
| 10859_6_76 | LILRB1 | EXON | - | chr19: 54631965-54631985 | AGUUCACCACGGGGCUGGGC | 10258 |
| 10859_6_79 | LILRB1 | EXON | - | chr19: 54631969-54631989 | CCUGAGUUCACCACGGGGCU | 10259 |
| 10859_6_80 | LILRB1 | EXON | - | chr19: 54631970-54631990 | UCCUGAGUUCACCACGGGGC | 10260 |
| 10859_6_83 | LILRB1 | EXON | - | chr19: 54631974-54631994 | UCCCUCCUGAGUUCACCACG | 10261 |
| 10859_6_84 | LILRB1 | EXON | - | chr19: 54631975-54631995 | UUCCCUCCUGAGUUCACCAC | 10262 |
| 10859_6_85 | LILRB1 | EXON | - | chr19: 54631976-54631996 | AUUCCCUCCUGAGUUCACCA | 10263 |
| 10859_6_89 | LILRB1 | EXON | - | chr19: 54632003-54632023 | CACCUGUGAGUCACACUGGA | 10264 |
| 10859_6_90 | LILRB1 | EXON | - | chr19: 54632004-54632024 | CCACCUGUGAGUCACACUGG | 10265 |
| 10859_6_92 | LILRB1 | EXON | - | chr19: 54632007-54632027 | AUGCCACCUGUGAGUCACAC | 10266 |
| 10859_6_104 | LILRB1 | EXON | - | chr19: 54632070-54632090 | GCUGGGAGUUCAGGCAUUGU | 10267 |
| 10859_6_105 | LILRB1 | EXON | - | chr19: 54632071-54632091 | GGCUGGGAGUUCAGGCAUUG | 10268 |
| 10859_6_107 | LILRB1 | EXON | - | chr19: 54632079-54632099 | GGGCAUGGGGCUGGGAGUUC | 10269 |
| 10859_6_108 | LILRB1 | EXON | - | chr19: 54632087-54632107 | CGACCCACGGGCAUGGGGCU | 10270 |
| 10859_6_110 | LILRB1 | EXON | - | chr19: 54632088-54632108 | ACGACCCACGGGCAUGGGGC | 10271 |
| 10859_6_113 | LILRB1 | EXON | - | chr19: 54632092-54632112 | CGGGACGACCCACGGGCAUG | 10272 |
| 10859_6_114 | LILRB1 | EXON | - | chr19: 54632093-54632113 | GCGGGACGACCCACGGGCAU | 10273 |
| 10859_6_116 | LILRB1 | EXON | - | chr19: 54632094-54632114 | CGCGGGACGACCCACGGGCA | 10274 |
| 10859_6_118 | LILRB1 | EXON | - | chr19: 54632099-54632119 | GAUGGCGCGGGACGACCCAC | 10275 |
| 10859_6_119 | LILRB1 | EXON | - | chr19: 54632100-54632120 | AGAUGGCGCGGGACGACCCA | 10276 |
| 10859_6_121 | LILRB1 | EXON | - | chr19: 54632111-54632131 | GCCCACGGAGAAGAUGGCGC | 10277 |
| 10859_6_123 | LILRB1 | EXON | - | chr19: 54632112-54632132 | GGCCCACGGAGAAGAUGGCG | 10278 |

TABLE 6d-continued

Targeting Domains for human LILRB1, an exemplary target of an NK inhibitory molecule.

| Id | Target | Region | Strand | Chromosomal location | gRNA targeting domain sequence | SEQ ID NO: |
|---|---|---|---|---|---|---|
| 10859_6_125 | LILRB1 | EXON | - | chr19: 54632117-54632137 | CACGGGGCCCACGGAGAAGA | 10279 |
| 10859_6_129 | LILRB1 | EXON | - | chr19: 54632126-54632146 | ACUCGGGCUCACGGGGCCCA | 10280 |
| 10859_6_131 | LILRB1 | EXON | - | chr19: 54632133-54632153 | ACCUGCGACUCGGGCUCACG | 10281 |
| 10859_6_132 | LILRB1 | EXON | - | chr19: 54632134-54632154 | CACCUGCGACUCGGGCUCAC | 10282 |
| 10859_6_133 | LILRB1 | EXON | - | chr19: 54632135-54632155 | CCACCUGCGACUCGGGCUCA | 10283 |
| 10859_6_136 | LILRB1 | EXON | - | chr19: 54632142-54632162 | UGUACCACCACCUGCGACUC | 10284 |
| 10859_6_137 | LILRB1 | EXON | - | chr19: 54632143-54632163 | CUGUACCACCACCUGCGACU | 10285 |
| 10859_6_143 | LILRB1 | EXON | - | chr19: 54632191-54632211 | CUGGGUAGAGACCACUCAUA | 10286 |
| 10859_6_144 | LILRB1 | EXON | - | chr19: 54632192-54632212 | ACUGGGUAGAGACCACUCAU | 10287 |
| 10859_6_148 | LILRB1 | EXON | - | chr19: 54632209-54632229 | AGGAGCUCCAGGAGAUCACU | 10288 |
| 10859_6_149 | LILRB1 | EXON | - | chr19: 54632210-54632230 | CAGGAGCUCCAGGAGAUCAC | 10289 |
| 10859_6_154 | LILRB1 | EXON | - | chr19: 54632220-54632240 | CACCUAGGACCAGGAGCUCC | 10290 |
| 10859_6_156 | LILRB1 | EXON | - | chr19: 54632229-54632249 | UGAAUUCUCACCUAGGACC | 10291 |
| 10859_6_159 | LILRB1 | EXON | - | chr19: 54632235-54632255 | AUGCUGUGAAUUCUCACCU | 10292 |
| 10859_77 | LILRB1 | EXON | + | chr19: 54632477-54632497 | CCAUCACUCUCAGUGCAGCC | 10293 |
| 10859_7_8 | LILRB1 | EXON | + | chr19: 54632488-54632508 | AGUGCAGCCAGGUCCUAUCG | 10294 |
| 10859_7_12 | LILRB1 | EXON | + | chr19: 54632497-54632517 | AGGUCCUAUCGUGGCCCCUG | 10295 |
| 10859_7_13 | LILRB1 | EXON | + | chr19: 54632519-54632539 | GAGACCCUGACUCUGCAGUG | 10296 |
| 10859_7_14 | LILRB1 | EXON | + | chr19: 54632531-54632551 | CUGCAGUGUGGCUCUGAUGC | 10297 |
| 10859_7_16 | LILRB1 | EXON | + | chr19: 54632557-54632577 | CAACAGAUUUGUUCUGUAUA | 10298 |
| 10859_7_18 | LILRB1 | EXON | + | chr19: 54632561-54632581 | AGAUUUGUUCUGUAUAAGGA | 10299 |
| 10859_7_21 | LILRB1 | EXON | + | chr19: 54632562-54632582 | GAUUUGUUCUGUAUAAGGAC | 10300 |
| 10859_7_23 | LILRB1 | EXON | + | chr19: 54632563-54632583 | AUUUGUUCUGUAUAAGGACG | 10301 |
| 10859_7_27 | LILRB1 | EXON | + | chr19: 54632588-54632608 | CGUGACUUCCUUCAGCUCGC | 10302 |

TABLE 6d-continued

Targeting Domains for human LILRB1, an exemplary target of an NK inhibitory molecule.

| Id | Target | Region | Strand | Chromosomal location | gRNA targeting domain sequence | SEQ ID NO: |
|---|---|---|---|---|---|---|
| 10859_7_30 | LILRB1 | EXON | + | chr19: 54632602-54632622 | GCUCGCUGGCGCACAGCCCC | 10303 |
| 10859_7_32 | LILRB1 | EXON | + | chr19: 54632606-54632626 | GCUGGCGCACAGCCCCAGGC | 10304 |
| 10859_7_33 | LILRB1 | EXON | + | chr19: 54632607-54632627 | CUGGCGCACAGCCCCAGGCU | 10305 |
| 10859_7_34 | LILRB1 | EXON | + | chr19: 54632617-54632637 | GCCCCAGGCUGGGCUCUCCC | 10306 |
| 10859_7_36 | LILRB1 | EXON | + | chr19: 54632632-54632652 | CUCCCAGGCCAACUUCACCC | 10307 |
| 10859_7_37 | LILRB1 | EXON | + | chr19: 54632633-54632653 | UCCCAGGCCAACUUCACCCU | 10308 |
| 10859_7_42 | LILRB1 | EXON | + | chr19: 54632654-54632674 | GGCCCUGUGAGCCGCUCCUA | 10309 |
| 10859_7_43 | LILRB1 | EXON | + | chr19: 54632655-54632675 | GCCCUGUGAGCCGCUCCUAC | 10310 |
| 10859_7_45 | LILRB1 | EXON | + | chr19: 54632656-54632676 | CCCUGUGAGCCGCUCCUACG | 10311 |
| 10859_7_46 | LILRB1 | EXON | + | chr19: 54632657-54632677 | CCUGUGAGCCGCUCCUACGG | 10312 |
| 10859_7_47 | LILRB1 | EXON | + | chr19: 54632675-54632695 | GGGGGCCAGUACAGAUGCUA | 10313 |
| 10859_7_49 | LILRB1 | EXON | + | chr19: 54632700-54632720 | CACACAACCUCUCCUCCGAG | 10314 |
| 10859_7_50 | LILRB1 | EXON | + | chr19: 54632704-54632724 | CAACCUCUCCUCCGAGUGGU | 10315 |
| 10859_7_52 | LILRB1 | EXON | + | chr19: 54632722-54632742 | GUCGGCCCCCAGCGACCCCC | 10316 |
| 10859_7_53 | LILRB1 | EXON | + | chr19: 54632738-54632758 | CCCCUGGACAUCCUGAUCGC | 10317 |
| 10859_7_56 | LILRB1 | EXON | + | chr19: 54632743-54632763 | GGACAUCCUGAUCGCAGGUG | 10318 |
| 10859_7_59 | LILRB1 | EXON | + | chr19: 54632753-54632773 | AUCGCAGGUGAGGAGCCCAG | 10319 |
| 10859_7_60 | LILRB1 | EXON | + | chr19: 54632754-54632774 | UCGCAGGUGAGGAGCCCAGC | 10320 |
| 10859_7_61 | LILRB1 | EXON | - | chr19: 54632446-54632466 | CACCUGGGAAAAGGUGGUCA | 10321 |
| 10859_7_64 | LILRB1 | EXON | - | chr19: 54632452-54632472 | UAGAAACACCUGGGAAAAGG | 10322 |
| 10859_7_65 | LILRB1 | EXON | - | chr19: 54632455-54632475 | UCUUAGAAACACCUGGGAAA | 10323 |
| 10859_7_66 | LILRB1 | EXON | - | chr19: 54632461-54632481 | AUGGCUUCUUAGAAACACCU | 10324 |
| 10859_7_68 | LILRB1 | EXON | - | chr19: 54632462-54632482 | GAUGGCUUCUUAGAAACACC | 10325 |
| 10859_7_72 | LILRB1 | EXON | - | chr19: 54632480-54632500 | CCUGGCUGCACUGAGAGUGA | 10326 |
| 10859_7_75 | LILRB1 | EXON | - | chr19: 54632498-54632518 | UCAGGGGCCACGAUAGGACC | 10327 |

TABLE 6d-continued

Targeting Domains for human LILRB1, an exemplary target of an NK inhibitory molecule.

| Id | Target | Region | Strand | Chromosomal location | gRNA targeting domain sequence | SEQ ID NO: |
|---|---|---|---|---|---|---|
| 10859_7_76 | LILRB1 | EXON | - | chr19: 54632504-54632524 | GUCUCCUCAGGGGCCACGAU | 10328 |
| 10859_7_78 | LILRB1 | EXON | - | chr19: 54632514-54632534 | CAGAGUCAGGGUCUCCUCAG | 10329 |
| 10859_7_79 | LILRB1 | EXON | - | chr19: 54632515-54632535 | GCAGAGUCAGGGUCUCCUCA | 10330 |
| 10859_7_80 | LILRB1 | EXON | - | chr19: 54632516-54632536 | UGCAGAGUCAGGGUCUCCUC | 10331 |
| 10859_7_83 | LILRB1 | EXON | - | chr19: 54632526-54632546 | AGAGCCACACUGCAGAGUCA | 10332 |
| 10859_7_84 | LILRB1 | EXON | - | chr19: 54632527-54632547 | CAGAGCCACACUGCAGAGUC | 10333 |
| 10859_7_93 | LILRB1 | EXON | - | chr19: 54632599-54632619 | GCUGUGCGCCAGCGAGCUGA | 10334 |
| 10859_7_99 | LILRB1 | EXON | - | chr19: 54632621-54632641 | GCCUGGGAGAGCCCAGCCUG | 10335 |
| 10859_7_100 | LILRB1 | EXON | - | chr19: 54632622-54632642 | GGCCUGGGAGAGCCCAGCCU | 10336 |
| 10859_7_102 | LILRB1 | EXON | - | chr19: 54632623-54632643 | UGGCCUGGGAGAGCCCAGCC | 10337 |
| 10859_7_106 | LILRB1 | EXON | - | chr19: 54632637-54632657 | GCCCAGGGUGAAGUUGGCCU | 10338 |
| 10859_7_107 | LILRB1 | EXON | - | chr19: 54632638-54632658 | GGCCCAGGGUGAAGUUGGCC | 10339 |
| 10859_7_110 | LILRB1 | EXON | - | chr19: 54632643-54632663 | CACAGGGCCCAGGGUGAAGU | 10340 |
| 10859_7_112 | LILRB1 | EXON | - | chr19: 54632652-54632672 | GGAGCGGCUCACAGGGCCCA | 10341 |
| 10859_7_113 | LILRB1 | EXON | - | chr19: 54632653-54632673 | AGGAGCGGCUCACAGGGCCC | 10342 |
| 10859_7_115 | LILRB1 | EXON | - | chr19: 54632659-54632679 | CCCCGUAGGAGCGGCUCACA | 10343 |
| 10859_7_116 | LILRB1 | EXON | - | chr19: 54632660-54632680 | CCCCCGUAGGAGCGGCUCAC | 10344 |
| 10859_7_118 | LILRB1 | EXON | - | chr19: 54632668-54632688 | UGUACUGGCCCCGUAGGAG | 10345 |
| 10859_7_119 | LILRB1 | EXON | - | chr19: 54632673-54632693 | GCAUCUGUACUGGCCCCCGU | 10346 |
| 10859_7_123 | LILRB1 | EXON | - | chr19: 54632683-54632703 | GUGCACCGUAGCAUCUGUAC | 10347 |
| 10859_7_124 | LILRB1 | EXON | - | chr19: 54632710-54632730 | GGGCCGACCACUCGGAGGAG | 10348 |
| 10859_7_126 | LILRB1 | EXON | - | chr19: 54632715-54632735 | GCUGGGGCCGACCACUCGG | 10349 |
| 10859_7_129 | LILRB1 | EXON | - | chr19: 54632718-54632738 | GUCGCUGGGGCCGACCACU | 10350 |
| 10859_7_132 | LILRB1 | EXON | - | chr19: 54632730-54632750 | GAUGUCCAGGGGUCGCUGG | 10351 |

TABLE 6d-continued

Targeting Domains for human LILRB1, an exemplary target of an NK inhibitory molecule.

| Id | Target | Region | Strand | Chromosomal location | gRNA targeting domain sequence | SEQ ID NO: |
|---|---|---|---|---|---|---|
| 10859_7_133 | LILRB1 | EXON | - | chr19: 54632731-54632751 | GGAUGUCCAGGGGUCGCUG | 10352 |
| 10859_7_135 | LILRB1 | EXON | - | chr19: 54632732-54632752 | AGGAUGUCCAGGGGUCGCU | 10353 |
| 10859_7_137 | LILRB1 | EXON | - | chr19: 54632733-54632753 | CAGGAUGUCCAGGGGUCGC | 10354 |
| 10859_7_139 | LILRB1 | EXON | - | chr19: 54632740-54632760 | CUGCGAUCAGGAUGUCCAGG | 10355 |
| 10859_7_140 | LILRB1 | EXON | - | chr19: 54632741-54632761 | CCUGCGAUCAGGAUGUCCAG | 10356 |
| 10859_7_141 | LILRB1 | EXON | - | chr19: 54632742-54632762 | ACCUGCGAUCAGGAUGUCCA | 10357 |
| 10859_7_144 | LILRB1 | EXON | - | chr19: 54632743-54632763 | CACCUGCGAUCAGGAUGUCC | 10358 |
| 10859_7_146 | LILRB1 | EXON | - | chr19: 54632752-54632772 | UGGGCUCCUCACCUGCGAUC | 10359 |
| 10859_8_4 | LILRB1 | EXON | + | chr19: 54633022-54633042 | CUAUGACAGAGUCUCCCUCU | 10360 |
| 10859_8_7 | LILRB1 | EXON | + | chr19: 54633031-54633051 | AGUCUCCCUCUCGGUGCAGC | 10361 |
| 10859_8_8 | LILRB1 | EXON | + | chr19: 54633032-54633052 | GUCUCCCUCUCGGUGCAGCC | 10362 |
| 10859_8_9 | LILRB1 | EXON | + | chr19: 54633040-54633060 | CUCGGUGCAGCCGGGCCCCA | 10363 |
| 10859_8_10 | LILRB1 | EXON | + | chr19: 54633043-54633063 | GGUGCAGCCGGGCCCCACGG | 10364 |
| 10859_8_13 | LILRB1 | EXON | + | chr19: 54633050-54633070 | CCGGGCCCCACGGUGGCCUC | 10365 |
| 10859_8_17 | LILRB1 | EXON | + | chr19: 54633082-54633102 | GACCCUGCUGUGUCAGUCAC | 10366 |
| 10859_8_19 | LILRB1 | EXON | + | chr19: 54633083-54633103 | ACCCUGCUGUGUCAGUCACA | 10367 |
| 10859_8_21 | LILRB1 | EXON | + | chr19: 54633087-54633107 | UGCUGUGUCAGUCACAGGGA | 10368 |
| 10859_8_23 | LILRB1 | EXON | + | chr19: 54633112-54633132 | GCAAACUUCCUUCUGACCA | 10369 |
| 10859_8_26 | LILRB1 | EXON | + | chr19: 54633115-54633135 | AACUUCCUUCUGACCAAGG | 10370 |
| 10859_8_28 | LILRB1 | EXON | + | chr19: 54633116-54633136 | ACUUCCUUCUGACCAAGGA | 10371 |
| 10859_8_30 | LILRB1 | EXON | + | chr19: 54633117-54633137 | CUUUCCUUCUGACCAAGGAG | 10372 |
| 10859_8_31 | LILRB1 | EXON | + | chr19: 54633118-54633138 | UUUCCUUCUGACCAAGGAGG | 10373 |
| 10859_8_35 | LILRB1 | EXON | + | chr19: 54633135-54633155 | AGGGGGCAGCUGAUGACCCA | 10374 |
| 10859_8_36 | LILRB1 | EXON | + | chr19: 54633172-54633192 | GUACCAAUCUCAAAAAUACC | 10375 |
| 10859_8_39 | LILRB1 | EXON | + | chr19: 54633187-54633207 | AUACCAGGCUGAAUUCCCCA | 10376 |

TABLE 6d-continued

Targeting Domains for human LILRB1, an exemplary target of an NK inhibitory molecule.

| Id | Target | Region | Strand | Chromosomal location | gRNA targeting domain sequence | SEQ ID NO: |
|---|---|---|---|---|---|---|
| 10859_8_40 | LILRB1 | EXON | + | chr19: 54633188-54633208 | UACCAGGCUGAAUUCCCCAU | 10377 |
| 10859_8_44 | LILRB1 | EXON | + | chr19: 54633211-54633231 | UCCUGUGACCUCAGCCCAUG | 10378 |
| 10859_8_46 | LILRB1 | EXON | + | chr19: 54633212-54633232 | CCUGUGACCUCAGCCCAUGC | 10379 |
| 10859_8_47 | LILRB1 | EXON | + | chr19: 54633213-54633233 | CUGUGACCUCAGCCCAUGCG | 10380 |
| 10859_8_48 | LILRB1 | EXON | + | chr19: 54633222-54633242 | CAGCCCAUGCGGGACCUAC | 10381 |
| 10859_8_49 | LILRB1 | EXON | + | chr19: 54633230-54633250 | GCGGGGACCUACAGGUGCUA | 10382 |
| 10859_8_52 | LILRB1 | EXON | + | chr19: 54633280-54633300 | GACUCACCCAGUGACCCCC | 10383 |
| 10859_8_54 | LILRB1 | EXON | + | chr19: 54633289-54633309 | CAGUGACCCCUGGAGCUCG | 10384 |
| 10859_8_55 | LILRB1 | EXON | + | chr19: 54633296-54633316 | CCCCUGGAGCUCGUGGUCUC | 10385 |
| 10859_8_58 | LILRB1 | EXON | + | chr19: 54633299-54633319 | CUGGAGCUCGUGGUCUCAGG | 10386 |
| 10859_8_59 | LILRB1 | EXON | + | chr19: 54633300-54633320 | UGGAGCUCGUGGUCUCAGGU | 10387 |
| 10859_8_61 | LILRB1 | EXON | + | chr19: 54633301-54633321 | GGAGCUCGUGGUCUCAGGUG | 10388 |
| 10859_8_62 | LILRB1 | EXON | + | chr19: 54633302-54633322 | GAGCUCGUGGUCUCAGGUGG | 10389 |
| 10859_8_63 | LILRB1 | EXON | - | chr19: 54632998-54633018 | GUCCUGGAGAGAAGAAGGAU | 10390 |
| 10859_8_64 | LILRB1 | EXON | - | chr19: 54632999-54633019 | UGUCCUGGAGAGAAGAAGGA | 10391 |
| 10859_8_66 | LILRB1 | EXON | - | chr19: 54633003-54633023 | GAACUGUCCUGGAGAGAAGA | 10392 |
| 10859_8_74 | LILRB1 | EXON | - | chr19: 54633014-54633034 | ACUCUGUCAUAGAACUGUCC | 10393 |
| 10859_8_79 | LILRB1 | EXON | - | chr19: 54633039-54633059 | GGGGCCCGGCUGCACCGAGA | 10394 |
| 10859_8_81 | LILRB1 | EXON | - | chr19: 54633040-54633060 | UGGGGCCCGGCUGCACCGAG | 10395 |
| 10859_8_86 | LILRB1 | EXON | - | chr19: 54633053-54633073 | CCUGAGGCCACCGUGGGGCC | 10396 |
| 10859_8_87 | LILRB1 | EXON | - | chr19: 54633058-54633078 | UCUCUCCUGAGGCCACCGUG | 10397 |
| 10859_8_88 | LILRB1 | EXON | - | chr19: 54633059-54633079 | UUCUCUCCUGAGGCCACCGU | 10398 |
| 10859_8_90 | LILRB1 | EXON | - | chr19: 54633060-54633080 | GUUCUCUCCUGAGGCCACCG | 10399 |
| 10859_8_92 | LILRB1 | EXON | - | chr19: 54633069-54633089 | CAGGGUCACGUUCUCUCCUG | 10400 |

TABLE 6d-continued

Targeting Domains for human LILRB1, an exemplary target of an NK inhibitory molecule.

| Id | Target | Region | Strand | Chromosomal location | gRNA targeting domain sequence | SEQ ID NO: |
|---|---|---|---|---|---|---|
| 10859_8_94 | LILRB1 | EXON | - | chr19: 54633087-54633107 | UCCCUGUGACUGACACAGCA | 10401 |
| 10859_8_95 | LILRB1 | EXON | - | chr19: 54633088-54633108 | AUCCCUGUGACUGACACAGC | 10402 |
| 10859_8_100 | LILRB1 | EXON | - | chr19: 54633124-54633144 | CUGCCCCUCCUUGGUCAGA | 10403 |
| 10859_8_105 | LILRB1 | EXON | - | chr19: 54633132-54633152 | GUCAUCAGCUGCCCCUCCU | 10404 |
| 10859_8_109 | LILRB1 | EXON | - | chr19: 54633154-54633174 | ACGUUGAUCUUAGACGCCAU | 10405 |
| 10859_8_110 | LILRB1 | EXON | - | chr19: 54633155-54633175 | UACGUUGAUCUUAGACGCCA | 10406 |
| 10859_8_117 | LILRB1 | EXON | - | chr19: 54633178-54633198 | CAGCCUGGUAUUUUGAGAU | 10407 |
| 10859_8_119 | LILRB1 | EXON | - | chr19: 54633193-54633213 | GACCCAUGGGGAAUUCAGCC | 10408 |
| 10859_8_120 | LILRB1 | EXON | - | chr19: 54633205-54633225 | CUGAGGUCACAGGACCCAUG | 10409 |
| 10859_8_123 | LILRB1 | EXON | - | chr19: 54633206-54633226 | GCUGAGGUCACAGGACCAU | 10410 |
| 10859_8_125 | LILRB1 | EXON | - | chr19: 54633207-54633227 | GGCUGAGGUCACAGGACCA | 10411 |
| 10859_8_127 | LILRB1 | EXON | - | chr19: 54633215-54633235 | CCCGCAUGGGCUGAGGUCAC | 10412 |
| 10859_8_129 | LILRB1 | EXON | - | chr19: 54633222-54633242 | GUAGGUCCCGCAUGGGCUG | 10413 |
| 10859_8_131 | LILRB1 | EXON | - | chr19: 54633228-54633248 | GCACCUGUAGGUCCCCGCAU | 10414 |
| 10859_8_132 | LILRB1 | EXON | - | chr19: 54633229-54633249 | AGCACCUGUAGGUCCCCGCA | 10415 |
| 10859_8_134 | LILRB1 | EXON | - | chr19: 54633240-54633260 | CUGUGAGCCGUAGCACCUGU | 10416 |
| 10859_8_139 | LILRB1 | EXON | - | chr19: 54633267-54633287 | GUGAGUCAGCAGGUAGGGUU | 10417 |
| 10859_8_141 | LILRB1 | EXON | - | chr19: 54633272-54633292 | CUGGGGUGAGUCAGCAGGUA | 10418 |
| 10859_8_142 | LILRB1 | EXON | - | chr19: 54633273-54633293 | ACUGGGGUGAGUCAGCAGGU | 10419 |
| 10859_8_144 | LILRB1 | EXON | - | chr19: 54633277-54633297 | GGUCACUGGGGUGAGUCAGC | 10420 |
| 10859_8_146 | LILRB1 | EXON | - | chr19: 54633289-54633309 | CGAGCUCCAGGGGUCACUG | 10421 |
| 10859_8_147 | LILRB1 | EXON | - | chr19: 54633290-54633310 | ACGAGCUCCAGGGGUCACU | 10422 |
| 10859_8_149 | LILRB1 | EXON | - | chr19: 54633291-54633311 | CACGAGCUCCAGGGGGUCAC | 10423 |
| 10859_8_151 | LILRB1 | EXON | - | chr19: 54633298-54633318 | CUGAGACCACGAGCUCCAGG | 10424 |
| 10859_8_152 | LILRB1 | EXON | - | chr19: 54633299-54633319 | CCUGAGACCACGAGCUCCAG | 10425 |

TABLE 6d-continued

Targeting Domains for human LILRB1, an exemplary target of an NK inhibitory molecule.

| Id | Target | Region | Strand | Chromosomal location | gRNA targeting domain sequence | SEQ ID NO: |
|---|---|---|---|---|---|---|
| 10859_8_153 | LILRB1 | EXON | - | chr19: 54633300-54633320 | ACCUGAGACCACGAGCUCCA | 10426 |
| 10859_8_156 | LILRB1 | EXON | - | chr19: 54633301-54633321 | CACCUGAGACCACGAGCUCC | 10427 |
| 10859_9_2 | LILRB1 | EXON | + | chr19: 54633624-54633644 | UUCUUUUACCCAGGACCGUC | 10428 |
| 10859_9_5 | LILRB1 | EXON | + | chr19: 54633625-54633645 | UCUUUUACCCAGGACCGUCU | 10429 |
| 10859_9_6 | LILRB1 | EXON | + | chr19: 54633626-54633646 | CUUUUACCCAGGACCGUCUG | 10430 |
| 10859_9_7 | LILRB1 | EXON | + | chr19: 54633627-54633647 | UUUUACCCAGGACCGUCUGG | 10431 |
| 10859_9_12 | LILRB1 | EXON | + | chr19: 54633648-54633668 | GGCCCAGCUCCCCGACAAC | 10432 |
| 10859_9_13 | LILRB1 | EXON | + | chr19: 54633666-54633686 | ACAGGCCCCACCUCCACAUC | 10433 |
| 10859_9_16 | LILRB1 | EXON | + | chr19: 54633679-54633699 | CCACAUCUGGUGAGUCCCUG | 10434 |
| 10859_9_17 | LILRB1 | EXON | - | chr19: 54633620-54633640 | GUCCUGGGUAAAAGAAUGAG | 10435 |
| 10859_9_21 | LILRB1 | EXON | - | chr19: 54633635-54633655 | UGGGGCCCCAGACGGUCCU | 10436 |
| 10859_9_22 | LILRB1 | EXON | - | chr19: 54633636-54633656 | CUGGGGCCCCAGACGGUCC | 10437 |
| 10859_9_25 | LILRB1 | EXON | - | chr19: 54633642-54633662 | GGGGAGCUGGGGCCCCAGA | 10438 |
| 10859_9_26 | LILRB1 | EXON | - | chr19: 54633653-54633673 | GGCCUGUUGUCGGGAGCUG | 10439 |
| 10859_9_27 | LILRB1 | EXON | - | chr19: 54633654-54633674 | GGGCCUGUUGUCGGGAGCU | 10440 |
| 10859_9_28 | LILRB1 | EXON | - | chr19: 54633655-54633675 | GGGGCCUGUUGUCGGGAGC | 10441 |
| 10859_9_31 | LILRB1 | EXON | - | chr19: 54633661-54633681 | GGAGGUGGGGCCUGUUGUCG | 10442 |
| 10859_9_34 | LILRB1 | EXON | - | chr19: 54633662-54633682 | UGGAGGUGGGGCCUGUUGUC | 10443 |
| 10859_9_36 | LILRB1 | EXON | - | chr19: 54633663-54633683 | GUGGAGGUGGGGCCUGUUGU | 10444 |
| 10859_9_38 | LILRB1 | EXON | - | chr19: 54633674-54633694 | ACUCACCAGAUGUGGAGGUG | 10445 |
| 10859_9_39 | LILRB1 | EXON | - | chr19: 54633675-54633695 | GACUCACCAGAUGUGGAGGU | 10446 |
| 10859_9_41 | LILRB1 | EXON | - | chr19: 54633676-54633696 | GGACUCACCAGAUGUGGAGG | 10447 |
| 10859_9_43 | LILRB1 | EXON | - | chr19: 54633679-54633699 | CAGGGACUCACCAGAUGUGG | 10448 |
| 10859_9_44 | LILRB1 | EXON | - | chr19: 54633682-54633702 | CCUCAGGGACUCACCAGAUG | 10449 |

TABLE 6d-continued

Targeting Domains for human LILRB1, an exemplary target of an NK inhibitory molecule.

| Id | Target | Region | Strand | Chromosomal location | gRNA targeting domain sequence | SEQ ID NO: |
|---|---|---|---|---|---|---|
| 10859_10_1 | LILRB1 | EXON | + | chr19: 54633951-54633971 | CCUCCCCGUCCUGACCCAGC | 10450 |
| 10859_10_4 | LILRB1 | EXON | + | chr19: 54633959-54633979 | UCCUGACCCAGCAGGCCCUG | 10451 |
| 10859_10_6 | LILRB1 | EXON | + | chr19: 54633981-54634001 | GACCAGCCCCUCACCCCCAC | 10452 |
| 10859_10_7 | LILRB1 | EXON | + | chr19: 54633982-54634002 | ACCAGCCCCUCACCCCCACC | 10453 |
| 10859_10_9 | LILRB1 | EXON | + | chr19: 54633986-54634006 | GCCCCUCACCCCCACCGGGU | 10454 |
| 10859_10_11 | LILRB1 | EXON | + | chr19: 54633999-54634019 | ACCGGGUCGGAUCCCCAGAG | 10455 |
| 10859_10_14 | LILRB1 | EXON | + | chr19: 54634009-54634029 | AUCCCCAGAGUGGUGAGUGA | 10456 |
| 10859_10_15 | LILRB1 | EXON | + | chr19: 54634010-54634030 | UCCCCAGAGUGGUGAGUGAC | 10457 |
| 10859_10_18 | LILRB1 | EXON | + | chr19: 54634020-54634040 | GGUGAGUGACGGGCUCUGAG | 10458 |
| 10859_10_21 | LILRB1 | EXON | + | chr19: 54634021-54634041 | GUGAGUGACGGGCUCUGAGU | 10459 |
| 10859_10_22 | LILRB1 | EXON | + | chr19: 54634024-54634044 | AGUGACGGGCUCUGAGUGGG | 10460 |
| 10859_10_24 | LILRB1 | EXON | + | chr19: 54634027-54634047 | GACGGGCUCUGAGUGGGAGG | 10461 |
| 10859_10_25 | LILRB1 | EXON | + | chr19: 54634028-54634048 | ACGGGCUCUGAGUGGGAGGU | 10462 |
| 10859_10_27 | LILRB1 | EXON | + | chr19: 54634032-54634052 | GCUCUGAGUGGGAGGUGGGC | 10463 |
| 10859_10_28 | LILRB1 | EXON | + | chr19: 54634033-54634053 | CUCUGAGUGGGAGGUGGGCA | 10464 |
| 10859_10_29 | LILRB1 | EXON | - | chr19: 54633954-54633974 | CCUGCUGGGUCAGGACGGGG | 10465 |
| 10859_10_30 | LILRB1 | EXON | - | chr19: 54633957-54633977 | GGGCCUGCUGGGUCAGGACG | 10466 |
| 10859_10_32 | LILRB1 | EXON | - | chr19: 54633958-54633978 | AGGGCCUGCUGGGUCAGGAC | 10467 |
| 10859_10_34 | LILRB1 | EXON | - | chr19: 54633959-54633979 | CAGGGCCUGCUGGGUCAGGA | 10468 |
| 10859_10_37 | LILRB1 | EXON | - | chr19: 54633963-54633983 | UCCUCAGGGCCUGCUGGGUC | 10469 |
| 10859_10_39 | LILRB1 | EXON | - | chr19: 54633968-54633988 | GCUGGUCCUCAGGGCCUGCU | 10470 |
| 10859_10_40 | LILRB1 | EXON | - | chr19: 54633969-54633989 | GGCUGGUCCUCAGGGCCUGC | 10471 |
| 10859_10_42 | LILRB1 | EXON | - | chr19: 54633977-54633997 | GGGUGAGGGGCUGGUCCUCA | 10472 |
| 10859_10_43 | LILRB1 | EXON | - | chr19: 54633978-54633998 | GGGGUGAGGGGCUGGUCCUC | 10473 |
| 10859_10_45 | LILRB1 | EXON | - | chr19: 54633986-54634006 | ACCCGGUGGGGGUGAGGGGC | 10474 |

TABLE 6d-continued

Targeting Domains for human LILRB1, an exemplary target of an NK inhibitory molecule.

| Id | Target | Region | Strand | Chromosomal location | gRNA targeting domain sequence | SEQ ID NO: |
|---|---|---|---|---|---|---|
| 10859_10_46 | LILRB1 | EXON | - | chr19: 54633990-54634010 | UCCGACCCGGUGGGGGUGAG | 10475 |
| 10859_10_47 | LILRB1 | EXON | - | chr19: 54633991-54634011 | AUCCGACCCGGUGGGGGUGA | 10476 |
| 10859_10_48 | LILRB1 | EXON | - | chr19: 54633992-54634012 | GAUCCGACCCGGUGGGGGUG | 10477 |
| 10859_10_52 | LILRB1 | EXON | - | chr19: 54633997-54634017 | CUGGGGAUCCGACCCGGUGG | 10478 |
| 10859_10_53 | LILRB1 | EXON | - | chr: 54633998-54634018 | UCUGGGGAUCCGACCCGGUG | 10479 |
| 10859_10_55 | LILRB1 | EXON | - | chr19: 54633999-54634019 | CUCUGGGGAUCCGACCCGGU | 10480 |
| 10859_10_57 | LILRB1 | EXON | - | chr: 54634000-54634020 | ACUCUGGGGAUCCGACCCGG | 10481 |
| 10859_10_59 | LILRB1 | EXON | - | chr: 54634003-54634023 | ACCACUCUGGGGAUCCGACC | 10482 |
| 10859_10_60 | LILRB1 | EXON | - | chr: 54634014-54634034 | GCCCGUCACUCACCACUCUG | 10483 |
| 10859_10_62 | LILRB1 | EXON | - | chr: 54634015-54634035 | AGCCCGUCACUCACCACUCU | 10484 |
| 10859_10_64 | LILRB1 | EXON | - | chr: 54634016-54634036 | GAGCCCGUCACUCACCACUC | 10485 |
| 10859_10_67 | LILRB1 | EXON | - | chr: 54634060-54634080 | CUUGGGUGGGACGGAGGGC | 10486 |
| 10859_11_2 | LILRB1 | EXON | + | chr: 54634623-54634643 | ACAUCAUCGUGCUCAAGGUC | 10487 |
| 10859_11_4 | LILRB1 | EXON | + | chr: 54634624-54634644 | CAUCAUCGUGCUCAAGGUCU | 10488 |
| 10859_11_6 | LILRB1 | EXON | + | chr: 54634628-54634648 | AUCGUGCUCAAGGUCUGGGA | 10489 |
| 10859_11_9 | LILRB1 | EXON | + | chr: 54634635-54634655 | UCAAGGUCUGGGAAGGCACC | 10490 |
| 10859_11_11 | LILRB1 | EXON | + | chr: 54634636-54634656 | CAAGGUCUGGGAAGGCACCU | 10491 |
| 10859_11_12 | LILRB1 | EXON | + | chr: 54634637-54634657 | AAGGUCUGGGAAGGCACCUG | 10492 |
| 10859_11_13 | LILRB1 | EXON | + | chr: 54634638-54634658 | AGGUCUGGGAAGGCACCUGG | 10493 |
| 10859_11_14 | LILRB1 | EXON | + | chr: 54634648-54634668 | AGGCACCUGGGGUUGUGAU | 10494 |
| 10859_11_15 | LILRB1 | EXON | + | chr: 54634656-54634676 | GGGGGUUGUGAUCGGCAUCU | 10495 |
| 10859_11_16 | LILRB1 | EXON | + | chr: 54634659-54634679 | GGUUGUGAUCGGCAUCUUGG | 10496 |
| 10859_11_20 | LILRB1 | EXON | + | chr: 54634722-54634742 | CAUCCUCCGACAUCGACGUC | 10497 |
| 10859_11_21 | LILRB1 | EXON | + | chr: 54634723-54634743 | AUCCUCCGACAUCGACGUCA | 10498 |

TABLE 6d-continued

Targeting Domains for human LILRB1, an exemplary target of an NK inhibitory molecule.

| Id | Target | Region | Strand | Chromosomal location | gRNA targeting domain sequence | SEQ ID NO: |
|---|---|---|---|---|---|---|
| 10859_11_23 | LILRB1 | EXON | + | chr19: 54634733-54634753 | AUCGACGUCAGGGCAAACAC | 10499 |
| 10859_11_28 | LILRB1 | EXON | + | chr19: 54634749-54634769 | ACACUGGACAUCGAGUGAGU | 10500 |
| 10859_11_29 | LILRB1 | EXON | + | chr19: 54634750-54634770 | CACUGGACAUCGAGUGAGUA | 10501 |
| 10859_11_32 | LILRB1 | EXON | + | chr19: 54634755-54634775 | GACAUCGAGUGAGUAGGGAA | 10502 |
| 10859_11_35 | LILRB1 | EXON | + | chr19: 54634756-54634776 | ACAUCGAGUGAGUAGGGAAU | 10503 |
| 10859_11_36 | LILRB1 | EXON | + | chr19: 54634757-54634777 | CAUCGAGUGAGUAGGGAAUG | 10504 |
| 10859_11_38 | LILRB1 | EXON | + | chr19: 54634758-54634778 | AUCGAGUGAGUAGGGAAUGG | 10505 |
| 10859_11_40 | LILRB1 | EXON | + | chr19: 54634759-54634779 | UCGAGUGAGUAGGGAAUGGG | 10506 |
| 10859_11_43 | LILRB1 | EXON | - | chr19: 54634656-54634676 | AGAUGCCGAUCACAACCCCC | 10507 |
| 10859_11_44 | LILRB1 | EXON | - | chr19: 54634685-54634705 | CUCCUCCUCCAGUAGGAUGA | 10508 |
| 10859_11_45 | LILRB1 | EXON | - | chr19: 54634692-54634712 | CCUCCUCCUCCUCCUCCAGU | 10509 |
| 10859_12_4 | LILRB1 | EXON | + | chr19: 54635092-54635112 | UCUUCCCCAGCCCAGAGAA | 10510 |
| 10859_12_8 | LILRB1 | EXON | + | chr19: 54635114-54635134 | GCUGAUUUCCAACAUCCUGC | 10511 |
| 10859_12_10 | LILRB1 | EXON | + | chr19: 54635115-54635135 | CUGAUUUCCAACAUCCUGCA | 10512 |
| 10859_12_11 | LILRB1 | EXON | + | chr19: 54635116-54635136 | UGAUUUCCAACAUCCUGCAG | 10513 |
| 10859_12_15 | LILRB1 | EXON | + | chr19: 54635122-54635142 | CCAACAUCCUGCAGGGGCUG | 10514 |
| 10859_12_16 | LILRB1 | EXON | + | chr19: 54635123-54635143 | CAACAUCCUGCAGGGGCUGU | 10515 |
| 10859_12_18 | LILRB1 | EXON | + | chr19: 54635124-54635144 | AACAUCCUGCAGGGGCUGUG | 10516 |
| 10859_12_21 | LILRB1 | EXON | + | chr19: 54635144-54635164 | GGGCCAGAGCCCACAGACAG | 10517 |
| 10859_12_24 | LILRB1 | EXON | + | chr19: 54635154-54635174 | CCACAGACAGAGGCCUGCAG | 10518 |
| 10859_12_25 | LILRB1 | EXON | + | chr19: 54635157-54635177 | CAGACAGAGGCCUGCAGUGG | 10519 |
| 10859_12_30 | LILRB1 | EXON | - | chr19: 54635092-54635112 | UUCUCUGGGCUGGGGGAAGA | 10520 |
| 10859_12_35 | LILRB1 | EXON | - | chr19: 54635099-54635119 | UCAGCCUUUCUCUGGGCUGG | 10521 |
| 10859_12_37 | LILRB1 | EXON | - | chr19: 54635100-54635120 | AUCAGCCUUUCUCUGGGCUG | 10522 |
| 10859_12_40 | LILRB1 | EXON | - | chr19: 54635101-54635121 | AAUCAGCCUUUCUCUGGGCU | 10523 |

TABLE 6d-continued

Targeting Domains for human LILRB1, an exemplary target of an NK inhibitory molecule.

| Id | Target | Region | Strand | Chromosomal location | gRNA targeting domain sequence | SEQ ID NO: |
|---|---|---|---|---|---|---|
| 10859_12_42 | LILRB1 | EXON | - | chr19: 54635102-54635122 | AAAUCAGCCUUUCUCUGGGC | 10524 |
| 10859_12_44 | LILRB1 | EXON | - | chr19: 54635106-54635126 | UUGGAAAUCAGCCUUUCUCU | 10525 |
| 10859_12_45 | LILRB1 | EXON | - | chr19: 54635107-54635127 | GUUGGAAAUCAGCCUUUCUC | 10526 |
| 10859_12_48 | LILRB1 | EXON | - | chr19: 54635125-54635145 | CCACAGCCCCUGCAGGAUGU | 10527 |
| 10859_12_50 | LILRB1 | EXON | - | chr19: 54635132-54635152 | UCUGGCCCCACAGCCCCUGC | 10528 |
| 10859_12_52 | LILRB1 | EXON | - | chr19: 54635150-54635170 | AGGCCUCUGUCUGUGGGCUC | 10529 |
| 10859_12_53 | LILRB1 | EXON | - | chr19: 54635156-54635176 | CACUGCAGGCCUCUGUCUGU | 10530 |
| 10859_12_55 | LILRB1 | EXON | - | chr19: 54635157-54635177 | CCACUGCAGGCCUCUGUCUG | 10531 |
| 10859_12_58 | LILRB1 | EXON | - | chr19: 54635170-54635190 | GGCAGAAUUACCUCCACUGC | 10532 |
| 10859_13_5 | LILRB1 | EXON | + | chr19: 54635261-54635281 | CAGCCCAGCUGCCGAUGCCC | 10533 |
| 10859_13_13 | LILRB1 | EXON | + | chr19: 54635285-54635305 | AGAAAACCUCUGUGAGUGAG | 10534 |
| 10859_13_15 | LILRB1 | EXON | + | chr19: 54635291-54635311 | CCUCUGUGAGUGAGAGGAAG | 10535 |
| 10859_13_16 | LILRB1 | EXON | - | chr19: 54635245-54635265 | GCUGGACCUGGGGAAGAAU | 10536 |
| 10859_13_19 | LILRB1 | EXON | - | chr19: 54635246-54635266 | GGCUGGACCUGGGGAAGAA | 10537 |
| 10859_13_23 | LILRB1 | EXON | - | chr19: 54635254-54635274 | GGCAGCUGGGCUGGACCUGG | 10538 |
| 10859_13_25 | LILRB1 | EXON | - | chr19: 54635255-54635275 | CGGCAGCUGGGCUGGACCUG | 10539 |
| 10859_13_27 | LILRB1 | EXON | - | chr19: 54635256-54635276 | UCGGCAGCUGGGCUGGACCU | 10540 |
| 10859_13_28 | LILRB1 | EXON | - | chr19: 54635257-54635277 | AUCGGCAGCUGGGCUGGACC | 10541 |
| 10859_13_33 | LILRB1 | EXON | - | chr19: 54635263-54635283 | CUGGGCAUCGGCAGCUGGGC | 10542 |
| 10859_13_37 | LILRB1 | EXON | - | chr19: 54635267-54635287 | CUUCCUGGGCAUCGGCAGCU | 10543 |
| 10859_13_38 | LILRB1 | EXON | - | chr19: 54635268-54635288 | UCUUCCUGGGCAUCGGCAGC | 10544 |
| 10859_13_40 | LILRB1 | EXON | - | chr19: 54635275-54635295 | GAGGUUUUCUUCCUGGGCAU | 10545 |
| 10859_13_41 | LILRB1 | EXON | - | chr19: 54635281-54635301 | CUCACAGAGGUUUUCUUCCU | 10546 |
| 10859_13_42 | LILRB1 | EXON | - | chr19: 54635282-54635302 | ACUCACAGAGGUUUUCUUCC | 10547 |

TABLE 6d-continued

Targeting Domains for human LILRB1, an exemplary target of an NK inhibitory molecule.

| Id | Target | Region | Strand | Chromosomal location | gRNA targeting domain sequence | SEQ ID NO: |
|---|---|---|---|---|---|---|
| 10859_13_45 | LILRB1 | EXON | - | chr19: 54635294-54635314 | CCUCUUCCUCUCACUCACAG | 10548 |
| 10859_14_5 | LILRB1 | EXON | + | chr19: 54635563-54635583 | CGUGAAGCACACACAGCCUG | 10549 |
| 10859_14_7 | LILRB1 | EXON | + | chr19: 54635567-54635587 | AAGCACACACAGCCUGAGGA | 10550 |
| 10859_14_9 | LILRB1 | EXON | + | chr19: 54635568-54635588 | AGCACACACAGCCUGAGGAU | 10551 |
| 10859_14_10 | LILRB1 | EXON | + | chr19: 54635569-54635589 | GCACACACAGCCUGAGGAUG | 10552 |
| 10859_14_12 | LILRB1 | EXON | + | chr19: 54635572-54635592 | CACACAGCCUGAGGAUGGGG | 10553 |
| 10859_14_15 | LILRB1 | EXON | + | chr19: 54635578-54635598 | GCCUGAGGAUGGGGUGGAGA | 10554 |
| 10859_14_17 | LILRB1 | EXON | + | chr19: 54635586-54635606 | AUGGGGUGGAGAUGGACACU | 10555 |
| 10859_14_18 | LILRB1 | EXON | + | chr19: 54635587-54635607 | UGGGGUGGAGAUGGACACUC | 10556 |
| 10859_14_20 | LILRB1 | EXON | - | chr19: 54635539-54635559 | CAUCUGCUGGGGCAGAGCAA | 10557 |
| 10859_14_21 | LILRB1 | EXON | - | chr19: 54635540-54635560 | GCAUCUGCUGGGGCAGAGCA | 10558 |
| 10859_14_25 | LILRB1 | EXON | - | chr19: 54635550-54635570 | CUUCACGGCAGCAUCUGCUG | 10559 |
| 10859_14_26 | LILRB1 | EXON | - | chr19: 54635551-54635571 | GCUUCACGGCAGCAUCUGCU | 10560 |
| 10859_14_28 | LILRB1 | EXON | - | chr19: 54635552-54635572 | UGCUUCACGGCAGCAUCUGC | 10561 |
| 10859_14_30 | LILRB1 | EXON | - | chr19: 54635565-54635585 | CUCAGGCUGUGUGUGCUUCA | 10562 |
| 10859_14_31 | LILRB1 | EXON | - | chr19: 54635582-54635602 | UCCAUCUCCACCCCAUCCUC | 10563 |
| 10859_15_3 | LILRB1 | EXON | + | chr19: 54636498-54636518 | CCCACACGAUGAAGACCCCC | 10564 |
| 10859_15_5 | LILRB1 | EXON | + | chr19: 54636516-54636536 | CCAGGCAGUGACGUAUGCCG | 10565 |
| 10859_15_8 | LILRB1 | EXON | + | chr19: 54636536-54636556 | AGGUGAAACACUCCAGACCU | 10566 |
| 10859_15_13 | LILRB1 | EXON | + | chr19: 54636546-54636566 | CUCCAGACCUAGGAGAGAAA | 10567 |
| 10859_15_15 | LILRB1 | EXON | + | chr19: 54636571-54636591 | UCUCCUCCUUCCCCACUGUC | 10568 |
| 10859_15_17 | LILRB1 | EXON | + | chr19: 54636572-54636592 | CUCCUCCUUCCCCACUGUCU | 10569 |
| 10859_15_20 | LILRB1 | EXON | + | chr19: 54636573-54636593 | UCCUCCUUCCCCACUGUCUG | 10570 |
| 10859_15_23 | LILRB1 | EXON | + | chr19: 54636582-54636602 | CCCACUGUCUGGGGAAUUCC | 10571 |
| 10859_15_25 | LILRB1 | EXON | + | chr19: 54636591-54636611 | UGGGGAAUUCCUGGACACAA | 10572 |

TABLE 6d-continued

Targeting Domains for human LILRB1, an exemplary target of an NK inhibitory molecule.

| Id | Target | Region | Strand | Chromosomal location | gRNA targeting domain sequence | SEQ ID NO: |
|---|---|---|---|---|---|---|
| 10859_15_26 | LILRB1 | EXON | + | chr19: 54636600-54636620 | CCUGGACACAAAGGACAGAC | 10573 |
| 10859_15_29 | LILRB1 | EXON | + | chr19: 54636603-54636623 | GGACACAAAGGACAGACAGG | 10574 |
| 10859_15_33 | LILRB1 | EXON | + | chr19: 54636609-54636629 | AAAGGACAGACAGGCGGAAG | 10575 |
| 10859_15_34 | LILRB1 | EXON | + | chr19: 54636614-54636634 | ACAGACAGGCGGAAGAGGAC | 10576 |
| 10859_15_36 | LILRB1 | EXON | + | chr19: 54636621-54636641 | GGCGGAAGAGGACAGGCAGA | 10577 |
| 10859_15_38 | LILRB1 | EXON | + | chr19: 54636630-54636650 | GGACAGGCAGAUGGACACUG | 10578 |
| 10859_15_40 | LILRB1 | EXON | - | chr19: 54636476-54636496 | CUGCUGGAGAGACAGUGG | 10579 |
| 10859_15_41 | LILRB1 | EXON | - | chr19: 54636479-54636499 | GCUCUGCUGGAGAGAGACAG | 10580 |
| 10859_15_46 | LILRB1 | EXON | - | chr19: 54636492-54636512 | CUUCAUCGUGUGGGCUCUGC | 10581 |
| 10859_15_48 | LILRB1 | EXON | - | chr19: 54636501-54636521 | CCUGGGGUCUUCAUCGUGU | 10582 |
| 10859_15_49 | LILRB1 | EXON | - | chr19: 54636502-54636522 | GCCUGGGGGUCUUCAUCGUG | 10583 |
| 10859_15_51 | LILRB1 | EXON | - | chr19: 54636516-54636536 | CGGCAUACGUCACUGCCUGG | 10584 |
| 10859_15_52 | LILRB1 | EXON | - | chr19: 54636517-54636537 | UCGGCAUACGUCACUGCCUG | 10585 |
| 10859_15_55 | LILRB1 | EXON | - | chr19: 54636518-54636538 | CUCGGCAUACGUCACUGCCU | 10586 |
| 10859_15_58 | LILRB1 | EXON | - | chr19: 54636519-54636539 | CCUCGGCAUACGUCACUGCC | 10587 |
| 10859_15_60 | LILRB1 | EXON | - | chr19: 54636536-54636556 | AGGUCUGGAGUGUUUCACCU | 10588 |
| 10859_15_63 | LILRB1 | EXON | - | chr19: 54636551-54636571 | GGCCAUUUCUCUCCUAGGUC | 10589 |
| 10859_15_66 | LILRB1 | EXON | - | chr19: 54636556-54636576 | GGAGAGGCCAUUUCUCUCCU | 10590 |
| 10859_15_68 | LILRB1 | EXON | - | chr19: 54636572-54636592 | AGACAGUGGGGAAGGAGGAG | 10591 |
| 10859_15_70 | LILRB1 | EXON | - | chr19: 54636577-54636597 | UCCCCAGACAGUGGGGAAGG | 10592 |
| 10859_15_74 | LILRB1 | EXON | - | chr19: 54636580-54636600 | AAUUCCCCAGACAGUGGGGA | 10593 |
| 10859_15_76 | LILRB1 | EXON | - | chr19: 54636584-54636604 | CAGGAAUUCCCCAGACAGUG | 10594 |
| 10859_15_80 | LILRB1 | EXON | - | chr19: 54636585-54636605 | CCAGGAAUUCCCCAGACAGU | 10595 |
| 10859_15_82 | LILRB1 | EXON | - | chr19: 54636586-54636606 | UCCAGGAAUUCCCCAGACAG | 10596 |

TABLE 6d-continued

Targeting Domains for human LILRB1, an exemplary target of an NK inhibitory molecule.

| Id | Target | Region | Strand | Chromosomal location | gRNA targeting domain sequence | SEQ ID NO: |
|---|---|---|---|---|---|---|
| 10859_15_87 | LILRB1 | EXON | - | chr19: 54636603-54636623 | CCUGUCUGUCCUUUGUGUCC | 10597 |
| 10859_16_3 | LILRB1 | EXON | + | chr19: 54636733-54636753 | UGCUGCAUCUGAAGCCCCCC | 10598 |
| 10859_16_6 | LILRB1 | EXON | + | chr19: 54636774-54636794 | UGCACAGCUUGACCCUCAGA | 10599 |
| 10859_16_7 | LILRB1 | EXON | + | chr19: 54636775-54636795 | GCACAGCUUGACCCUCAGAC | 10600 |
| 10859_16_9 | LILRB1 | EXON | + | chr19: 54636778-54636798 | CAGCUUGACCCUCAGACGGG | 10601 |
| 10859_16_14 | LILRB1 | EXON | + | chr19: 54636802-54636822 | AACUGAGCCUCCUCCAUCCC | 10602 |
| 10859_16_16 | LILRB1 | EXON | + | chr19: 54636806-54636826 | GAGCCUCCUCCAUCCCAGGA | 10603 |
| 10859_16_17 | LILRB1 | EXON | + | chr19: 54636807-54636827 | AGCCUCCUCCAUCCCAGGAA | 10604 |
| 10859_16_18 | LILRB1 | EXON | + | chr19: 54636844-54636864 | GCCCAGCAUCUACGCCACUC | 10605 |
| 10859_16_21 | LILRB1 | EXON | + | chr19: 54636861-54636881 | CUCUGGCCAUCCACUAGCCC | 10606 |
| 10859_16_22 | LILRB1 | EXON | + | chr19: 54636862-54636882 | UCUGGCCAUCCACUAGCCCA | 10607 |
| 10859_16_25 | LILRB1 | EXON | + | chr19: 54636863-54636883 | CUGGCCAUCCACUAGCCCAG | 10608 |
| 10859_16_27 | LILRB1 | EXON | + | chr19: 54636864-54636884 | UGGCCAUCCACUAGCCCAGG | 10609 |
| 10859_16_28 | LILRB1 | EXON | + | chr19: 54636865-54636885 | GGCCAUCCACUAGCCCAGGG | 10610 |
| 10859_16_30 | LILRB1 | EXON | + | chr19: 54636866-54636886 | GCCAUCCACUAGCCCAGGGG | 10611 |
| 10859_16_32 | LILRB1 | EXON | + | chr19: 54636888-54636908 | GACGCAGACCCCACACUCCA | 10612 |
| 10859_16_35 | LILRB1 | EXON | + | chr19: 54636895-54636915 | ACCCCACACUCCAUGGAGUC | 10613 |
| 10859_16_38 | LILRB1 | EXON | + | chr19: 54636904-54636924 | UCCAUGGAGUCUGGAAUGCA | 10614 |
| 10859_16_40 | LILRB1 | EXON | + | chr19: 54636905-54636925 | CCAUGGAGUCUGGAAUGCAU | 10615 |
| 10859_16_43 | LILRB1 | EXON | + | chr19: 54636922-54636942 | CAUGGGAGCUGCCCCCCCAG | 10616 |
| 10859_16_45 | LILRB1 | EXON | + | chr19: 54636932-54636952 | GCCCCCCAGUGGACACCAU | 10617 |
| 10859_16_47 | LILRB1 | EXON | + | chr19: 54636948-54636968 | CCAUUGGACCCCACCCAGCC | 10618 |
| 10859_16_50 | LILRB1 | EXON | + | chr19: 54636960-54636980 | ACCCAGCCUGGAUCUACCCC | 10619 |
| 10859_16_54 | LILRB1 | EXON | + | chr19: 54636969-54636989 | GGAUCUACCCCAGGAGACUC | 10620 |
| 10859_16_55 | LILRB1 | EXON | + | chr19: 54636970-54636990 | GAUCUACCCCAGGAGACUCU | 10621 |

TABLE 6d-continued

Targeting Domains for human LILRB1, an exemplary target of an NK inhibitory molecule.

| Id | Target | Region | Strand | Chromosomal location | gRNA targeting domain sequence | SEQ ID NO: |
|---|---|---|---|---|---|---|
| 10859_16_58 | LILRB1 | EXON | + | chr19: 54636980-54637000 | AGGAGACUCUGGGAACUUUU | 10622 |
| 10859_16_60 | LILRB1 | EXON | + | chr19: 54636981-54637001 | GGAGACUCUGGGAACUUUUA | 10623 |
| 10859_16_61 | LILRB1 | EXON | + | chr19: 54636982-54637002 | GAGACUCUGGGAACUUUUAG | 10624 |
| 10859_16_70 | LILRB1 | EXON | - | chr19: 54636722-54636742 | GAUGCAGCAGCCUGCAGCGG | 10625 |
| 10859_16_72 | LILRB1 | EXON | - | chr19: 54636723-54636743 | AGAUGCAGCAGCCUGCAGCG | 10626 |
| 10859_16_74 | LILRB1 | EXON | - | chr19: 54636724-54636744 | CAGAUGCAGCAGCCUGCAGC | 10627 |
| 10859_16_75 | LILRB1 | EXON | - | chr19: 54636725-54636745 | UCAGAUGCAGCAGCCUGCAG | 10628 |
| 10859_16_78 | LILRB1 | EXON | - | chr19: 54636750-54636770 | GGCGUAGGUCACAUCCUGGG | 10629 |
| 10859_16_79 | LILRB1 | EXON | - | chr19: 54636751-54636771 | GGGCGUAGGUCACAUCCUGG | 10630 |
| 10859_16_81 | LILRB1 | EXON | - | chr19: 54636752-54636772 | UGGGCGUAGGUCACAUCCUG | 10631 |
| 10859_16_83 | LILRB1 | EXON | - | chr19: 54636753-54636773 | CUGGGCGUAGGUCACAUCCU | 10632 |
| 10859_16_84 | LILRB1 | EXON | - | chr19: 54636754-54636774 | GCUGGGCGUAGGUCACAUCC | 10633 |
| 10859_16_87 | LILRB1 | EXON | - | chr19: 54636765-54636785 | CAAGCUGUGCAGCUGGGCGU | 10634 |
| 10859_16_88 | LILRB1 | EXON | - | chr19: 54636771-54636791 | GAGGGUCAAGCUGUGCAGCU | 10635 |
| 10859_16_89 | LILRB1 | EXON | - | chr19: 54636772-54636792 | UGAGGGUCAAGCUGUGCAGC | 10636 |
| 10859_16_92 | LILRB1 | EXON | - | chr19: 54636789-54636809 | CUCAGUUGCCUCCCGUCUGA | 10637 |
| 10859_16_93 | LILRB1 | EXON | - | chr19: 54636790-54636810 | GCUCAGUUGCCUCCCGUCUG | 10638 |
| 10859_16_97 | LILRB1 | EXON | - | chr19: 54636812-54636832 | GGCCCUUCCUGGGAUGGAGG | 10639 |
| 10859_16_98 | LILRB1 | EXON | - | chr19: 54636815-54636835 | GAGGGCCCUUCCUGGGAUGG | 10640 |
| 10859_16_101 | LILRB1 | EXON | - | chr19: 54636818-54636838 | GGAGAGGGCCCUUCCUGGGA | 10641 |
| 10859_16_104 | LILRB1 | EXON | - | chr19: 54636822-54636842 | AGCUGGAGAGGGCCCUUCCU | 10642 |
| 10859_16_105 | LILRB1 | EXON | - | chr19: 54636823-54636843 | CAGCUGGAGAGGGCCCUUCC | 10643 |
| 10859_16_108 | LILRB1 | EXON | - | chr19: 54636833-54636853 | AUGCUGGGCACAGCUGGAGA | 10644 |
| 10859_16_109 | LILRB1 | EXON | - | chr19: 54636834-54636854 | GAUGCUGGGCACAGCUGGAG | 10645 |

TABLE 6d-continued

Targeting Domains for human LILRB1, an exemplary target of an NK inhibitory molecule.

| Id | Target | Region | Strand | Chromosomal location | gRNA targeting domain sequence | SEQ ID NO: |
|---|---|---|---|---|---|---|
| 10859_16_112 | LILRB1 | EXON | - | chr19: 54636839-54636859 | GCGUAGAUGCUGGGCACAGC | 10646 |
| 10859_16_115 | LILRB1 | EXON | - | chr19: 54636848-54636868 | GCCAGAGUGGCGUAGAUGCU | 10647 |
| 10859_16_116 | LILRB1 | EXON | - | chr19: 54636849-54636869 | GGCCAGAGUGGCGUAGAUGC | 10648 |
| 10859_16_118 | LILRB1 | EXON | - | chr19: 54636861-54636881 | GGGCUAGUGGAUGGCCAGAG | 10649 |
| 10859_16_120 | LILRB1 | EXON | - | chr19: 54636870-54636890 | UCCCCCCUGGGCUAGUGGA | 10650 |
| 10859_16_121 | LILRB1 | EXON | - | chr19: 54636874-54636894 | UGCGUCCCCCCUGGGCUAG | 10651 |
| 10859_16_123 | LILRB1 | EXON | - | chr19: 54636881-54636901 | UGGGGUCUGCGUCCCCCCU | 10652 |
| 10859_16_124 | LILRB1 | EXON | - | chr19: 54636882-54636902 | GUGGGGUCUGCGUCCCCCCC | 10653 |
| 10859_16_127 | LILRB1 | EXON | - | chr19: 54636899-54636919 | UCCAGACUCCAUGGAGUGUG | 10654 |
| 10859_16_128 | LILRB1 | EXON | - | chr19: 54636900-54636920 | UUCCAGACUCCAUGGAGUGU | 10655 |
| 10859_16_129 | LILRB1 | EXON | - | chr19: 54636901-54636921 | AUUCCAGACUCCAUGGAGUG | 10656 |
| 10859_16_132 | LILRB1 | EXON | - | chr19: 54636908-54636928 | CCCAUGCAUUCCAGACUCCA | 10657 |
| 10859_16_135 | LILRB1 | EXON | - | chr19: 54636936-54636956 | UCCAAUGGUGUCCACUGGGG | 10658 |
| 10859_16_136 | LILRB1 | EXON | - | chr19: 54636937-54636957 | GUCCAAUGGUGUCCACUGGG | 10659 |
| 10859_16_137 | LILRB1 | EXON | - | chr19: 54636938-54636958 | GGUCCAAUGGUGUCCACUGG | 10660 |
| 10859_16_139 | LILRB1 | EXON | - | chr19: 54636939-54636959 | GGGUCCAAUGGUGUCCACUG | 10661 |
| 10859_16_141 | LILRB1 | EXON | - | chr19: 54636940-54636960 | GGGGUCCAAUGGUGUCCACU | 10662 |
| 10859_16_143 | LILRB1 | EXON | - | chr19: 54636941-54636961 | UGGGGUCCAAUGGUGUCCAC | 10663 |
| 10859_16_146 | LILRB1 | EXON | - | chr19: 54636951-54636971 | CCAGGCUGGGUGGGGUCCAA | 10664 |
| 10859_16_147 | LILRB1 | EXON | - | chr19: 54636959-54636979 | GGGUAGAUCCAGGCUGGGUG | 10665 |
| 10859_16_148 | LILRB1 | EXON | - | chr19: 54636960-54636980 | GGGGUAGAUCCAGGCUGGGU | 10666 |
| 10859_16_150 | LILRB1 | EXON | - | chr19: 54636961-54636981 | UGGGGUAGAUCCAGGCUGGG | 10667 |
| 10859_16_152 | LILRB1 | EXON | - | chr19: 54636964-54636984 | UCCUGGGGUAGAUCCAGGCU | 10668 |
| 10859_16_153 | LILRB1 | EXON | - | chr19: 54636965-54636985 | CUCCUGGGGUAGAUCCAGGC | 10669 |
| 10859_16_156 | LILRB1 | EXON | - | chr19: 54636969-54636989 | GAGUCCUCCUGGGGUAGAUCC | 10670 |

TABLE 6d-continued

Targeting Domains for human LILRB1, an exemplary target of an NK inhibitory molecule.

| Id | Target | Region | Strand | Chromosomal location | gRNA targeting domain sequence | SEQ ID NO: |
|---|---|---|---|---|---|---|
| 10859_16_157 | LILRB1 | EXON | - | chr19: 54636979-54636999 | AAAGUUCCCAGAGUCUCCUG | 10671 |
| 10859_16_158 | LILRB1 | EXON | - | chr19: 54636980-54637000 | AAAAGUUCCCAGAGUCUCCU | 10672 |
| 10859_16_159 | LILRB1 | EXON | - | chr19: 54636981-54637001 | UAAAAGUUCCCAGAGUCUCC | 10673 |

TABLE 6e

Exemplary preferred targeting domains for gRNA molecules targeting CD3E

| Targeting Domain ID | Strand | Target Sequence Location (hg38) | Targeting domain sequence | SEQ ID NO: |
|---|---|---|---|---|
| CR002230 | + | Chr11: 118304702-118304724 | AGGCCUCUCUACUUCCUGUG | 10677 |
| CR002231 | + | Chr11: 118304703-118304725 | GGCCUCUCUACUUCCUGUGU | 10678 |
| CR002232 | + | Chr11: 118304704-118304726 | GCCUCUCUACUUCCUGUGUG | 10679 |
| CR002233 | - | Chr11: 118304570-118304592 | GACUCUGACAAUACCUGGAG | 10680 |
| CR002234 | - | Chr11: 118304571-118304593 | GGACUCUGACAAUACCUGGA | 10681 |
| CR002235 | - | Chr11: 118304575-118304597 | AAGAGGACUCUGACAAUACC | 10682 |
| CR002236 | - | Chr11: 118304592-118304614 | UUCCUAGAAGGCCAAACAAG | 10683 |
| CR002237 | - | Chr11: 118304604-118304626 | GGUCCCACAGCCUUCCUAGA | 10684 |
| CR002238 | - | Chr11: 118304625-118304647 | UGGACUGGUUGAAGAAAGCU | 10685 |
| CR002239 | - | Chr11: 118304640-118304662 | GCAGAGGCCUCCACCUGGAC | 10686 |
| CR002240 | - | Chr11: 118304656-118304678 | CUUGGAAACGUUCAAGGCAG | 10687 |
| CR002241 | - | Chr11: 118304662-118304684 | ACCUCACUUGGAAACGUUCA | 10688 |
| CR002242 | - | Chr11: 118304674-118304696 | CCUGCGGGUUUUACCUCACU | 10689 |
| CR002243 | - | Chr11: 118304689-118304711 | AGAGAGGCCUCUGGGCCUGC | 10690 |
| CR002244 | - | Chr11: 118304697-118304719 | CAGGAAGUAGAGAGGCCUCU | 10691 |
| CR002245 | - | Chr11: 118304705-118304727 | ACCCCACACAGGAAGUAGAG | 10692 |
| CR002246 | - | Chr11: 118304716-118304738 | AGGGUUUCUGAACCCCACAC | 10693 |
| CR002247 | - | Chr11: 118304736-118304758 | CCUGAGGCUGGGAGGGGAGG | 10694 |
| CR002248 | - | Chr11: 118304747-118304769 | UGAAGCAGGCACCUGAGGCU | 10695 |
| CR002249 | - | Chr11: 118304748-118304770 | CUGAAGCAGGCACCUGAGGC | 10696 |
| CR002250 | - | Chr11: 118304752-118304774 | UUUUCUGAAGCAGGCACCUG | 10697 |
| CR002251 | + | Chr11: 118304889-118304911 | UCCAGAAGUAGUAAGUCUGC | 10698 |
| CR002252 | + | Chr11: 118304940-118304962 | CCAUGAAACAAAGAUGCAGU | 10699 |
| CR002253 | + | Chr11: 118304941-118304963 | CAUGAAACAAAGAUGCAGUC | 10700 |
| CR002254 | + | Chr11: 118304951-118304973 | AGAUGCAGUCGGGCACUCAC | 10701 |

TABLE 6e-continued

Exemplary preferred targeting domains for gRNA molecules targeting CD3E

| Targeting Domain ID | Strand | Target Sequence Location (hg38) | Targeting domain sequence | SEQ ID NO: |
|---|---|---|---|---|
| CR002255 | + | Chr11: 118304961-118304983 | GGGCACUCACUGGAGAGUUC | 10702 |
| CR002256 | + | Chr11: 118304962-118304984 | GGCACUCACUGGAGAGUUCU | 10703 |
| CR002257 | − | Chr11: 118304912-118304934 | UUACUUUACUAAGAUGGCGG | 10704 |
| CR002258 | − | Chr11: 118304915-118304937 | CUGUUACUUUACUAAGAUGG | 10705 |
| CR002259 | − | Chr11: 118304918-118304940 | GGACUGUUACUUUACUAAGA | 10706 |
| CR002260 | − | Chr11: 118304939-118304961 | CGACUGCAUCUUUGUUUCAU | 10707 |
| CR002261 | − | Chr11: 118304940-118304962 | CCGACUGCAUCUUUGUUUCA | 10708 |
| CR002262 | − | Chr11: 118304985-118305007 | ACUCACCUGAUAAGAGGCAG | 10709 |
| CR002263 | − | Chr11: 118304991-118305013 | CAUCCUACUCACCUGAUAAG | 10710 |
| CR002264 | + | Chr11: 118307269-118307291 | UUUCUUAUUUAUUUCUAGU | 10711 |
| CR002265 | + | Chr11: 118307276-118307298 | UUUAUUUUCUAGUUGGCGUU | 10712 |
| CR002266 | + | Chr11: 118307277-118307299 | UUAUUUUCUAGUUGGCGUUU | 10713 |
| CR002267 | + | Chr11: 118307278-118307300 | UAUUUUCUAGUUGGCGUUUG | 10714 |
| CR002268 | + | Chr11: 118307279-118307301 | AUUUUCUAGUUGGCGUUUGG | 10715 |
| CR002269 | + | Chr11: 118308419-118308441 | CUUUUCAGGUAAUGAAGAAA | 10716 |
| CR002270 | + | Chr11: 118312617-118312639 | GCAUAUAAAGUCUCCAUCUC | 10717 |
| CR002271 | + | Chr11: 118312653-118312675 | UUGACAUGCCCUCAGUAUCC | 10718 |
| CR002272 | + | Chr11: 118312669-118312691 | AUCCUGGAUCUGAAAUACUA | 10719 |
| CR002273 | + | Chr11: 118312695-118312717 | CACAAUGAUAAAAACAUAGG | 10720 |
| CR002274 | + | Chr11: 118312703-118312725 | UAAAAACAUAGGCGGUGAUG | 10721 |
| CR002275 | + | Chr11: 118312719-118312741 | GAUGAGGAUGAUAAAAACAU | 10722 |
| CR002276 | + | Chr11: 118312730-118312752 | UAAAAACAUAGGCAGUGAUG | 10723 |
| CR002277 | + | Chr11: 118312748-118312770 | UGAGGAUCACCUGUCACUGA | 10724 |
| CR002278 | + | Chr11: 118312763-118312785 | ACUGAAGGAAUUUCAGAAU | 10725 |
| CR002279 | + | Chr11: 118312773-118312795 | UUUUCAGAAUUGGAGCAAAG | 10726 |
| CR002280 | + | Chr11: 118312838-118312860 | GAACUUUUAUCUCUACCUGA | 10727 |
| CR002281 | − | Chr11: 118312630-118312652 | UAUUACUGUGGUUCCAGAGA | 10728 |
| CR002282 | − | Chr11: 118312642-118312664 | AGGGCAUGUCAAUAUUACUG | 10729 |
| CR002283 | − | Chr11: 118312661-118312683 | UUUCAGAUCCAGGAUACUGA | 10730 |
| CR002284 | − | Chr11: 118312662-118312684 | AUUUCAGAUCCAGGAUACUG | 10731 |
| CR002285 | − | Chr11: 118312671-118312693 | UGCCAUAGUAUUUCAGAUCC | 10732 |
| CR002286 | − | Chr11: 118312757-118312779 | CUGAAAAUUCCUUCAGUGAC | 10733 |
| CR002287 | − | Chr11: 118312811-118312833 | CUUCUGGUUUGCUUCCUCUG | 10734 |
| CR002288 | − | Chr11: 118312812-118312834 | UCUUCUGGUUUGCUUCCUCU | 10735 |
| CR002289 | − | Chr11: 118312813-118312835 | AUCUUCUGGUUUGCUUCCUC | 10736 |
| CR002290 | − | Chr11: 118312827-118312849 | AGAUAAAAGUUCGCAUCUUC | 10737 |

TABLE 6e-continued

Exemplary preferred targeting domains for gRNA molecules targeting CD3E

| Targeting Domain ID | Strand | Target Sequence Location (hg38) | Targeting domain sequence | SEQ ID NO: |
|---|---|---|---|---|
| CR002291 | − | Chr11: 118312853-118312875 | CUGGAUUACCUCUUGCCCUC | 10738 |
| CR002292 | + | Chr11: 118313720-118313742 | CAUGGAGAUGGAUGUGAUGU | 10739 |
| CR002293 | + | Chr11: 118313758-118313780 | UAGUGGACAUCUGCAUCACU | 10740 |
| CR002294 | + | Chr11: 118313760-118313782 | GUGGACAUCUGCAUCACUGG | 10741 |
| CR002295 | + | Chr11: 118313774-118313796 | CACUGGGGCUUGCUGCUGC | 10742 |
| CR002296 | + | Chr11: 118313801-118313823 | CUACUGGAGCAAGAAUAGAA | 10743 |
| CR002297 | + | Chr11: 118313807-118313829 | GAGCAAGAAUAGAAAGGCCA | 10744 |
| CR002298 | + | Chr11: 118313826-118313848 | AAGGCCAAGCCUGUGACACG | 10745 |
| CR002299 | + | Chr11: 118313831-118313853 | CAAGCCUGUGACACGAGGAG | 10746 |
| CR002300 | − | Chr11: 118313746-118313768 | GAUGUCCACUAUGACAAUUG | 10747 |
| CR002301 | − | Chr11: 118313824-118313846 | UCGUGUCACAGGCUUGGCCU | 10748 |
| CR002302 | − | Chr11: 118313830-118313852 | CGCUCCUCGUGUCACAGGCU | 10749 |
| CR002303 | − | Chr11: 118313835-118313857 | GCACCCGCUCCUCGUGUCAC | 10750 |
| CR002304 | + | Chr11: 118314442-118314464 | CCGCAGGACAAAACAAGGAG | 10751 |
| CR002305 | − | Chr11: 118314465-118314487 | UCUGGGUUGGGAACAGGUGG | 10752 |
| CR002306 | − | Chr11: 118314468-118314490 | UAGUCUGGGUUGGGAACAGG | 10753 |
| CR002307 | − | Chr11: 118314471-118314493 | UCAUAGUCUGGGUUGGGAAC | 10754 |
| CR002308 | − | Chr11: 118314477-118314499 | GUUACCUCAUAGUCUGGGUU | 10755 |
| CR002309 | − | Chr11: 118314478-118314500 | CGUUACCUCAUAGUCUGGGU | 10756 |
| CR002310 | − | Chr11: 118314482-118314504 | CCCACGUUACCUCAUAGUCU | 10757 |
| CR002311 | − | Chr11: 118314483-118314505 | UCCCACGUUACCUCAUAGUC | 10758 |
| CR002312 | + | Chr11: 118315472-118315494 | UAUUUCACCCCCAGCCCAUC | 10759 |
| CR002313 | + | Chr11: 118315477-118315499 | CACCCCCAGCCCAUCCGGAA | 10760 |
| CR002314 | + | Chr11: 118315484-118315506 | AGCCCAUCCGGAAAGGCCAG | 10761 |
| CR002315 | + | Chr11: 118315485-118315507 | GCCCAUCCGGAAAGGCCAGC | 10762 |
| CR002316 | + | Chr11: 118315498-118315520 | GGCCAGCGGGACCUGUAUUC | 10763 |
| CR002317 | + | Chr11: 118315528-118315550 | CAGAGACGCAUCUGACCCUC | 10764 |

TABLE 6f

Exemplary preferred targeting domains for gRNA molecules targeting CD3G

| Targeting Domain Id | Exon | Strand | Target Sequence Location (hg38) | Targeting Domain Sequence | SEQ ID NO: |
|---|---|---|---|---|---|
| CR005349 | 3 | − | chr11: 118349904-118349926 | UUACACUGAUACAUCCCUCG | 10765 |
| CR005350 | 4 | − | chr11: 118350673-118350695 | GCAUUCUUUUACCUCUCGAC | 10766 |
| CR005351 | 3 | − | chr11: 118349903-118349925 | UACACUGAUACAUCCCUCGA | 10767 |
| CR005352 | 3 | − | chr11: 118349896-118349918 | AUACAUCCCUCGAGGGUCCU | 10768 |
| CR005353 | 5 | − | chr11: 118351652-118351674 | UACCUGGUAGAGCUGGUCAU | 10769 |

TABLE 6f-continued

Exemplary preferred targeting domains for gRNA molecules targeting CD3G

| Targeting Domain Id | Exon | Strand | Target Sequence Location (hg38) | Targeting Domain Sequence | SEQ ID NO: |
|---|---|---|---|---|---|
| CR005354 | 3 | + | chr11: 118349907-118349929 | CGAGGGAUGUA-UCAGUGUAA | 10770 |
| CR005355 | 4 | + | chr11: 118350640-118350662 | GGUCUACUUCA-UUGCUGGAC | 10771 |
| CR005356 | 3 | + | chr11: 118349890-118349912 | GUAAUGCCAAG-GACCCUCGA | 10772 |
| CR005357 | 5 | − | chr11: 118351651-118351673 | ACCUGGUAGAG-CUGGUCAUU | 10773 |
| CR005358 | 4 | + | chr11: 118350618-118350640 | GCAUUUCGUC-CUUGCUGUU | 10774 |
| CR005359 | 4 | + | chr11: 118350635-118350657 | GUUGGGGUCUA-CUUCAUUGC | 10775 |
| CR005360 | 6 | − | chr11: 118352405-118352427 | GUCAUCUUCUC-GAUCCUUGA | 10776 |
| CR005361 | 6 | − | chr11: 118352404-118352426 | UCAUCUUCUCG-AUCCUUGAG | 10777 |
| CR005362 | 3 | + | chr11: 118349760-118349782 | GUGUAUGACUA-UCAAGAAGA | 10778 |
| CR005363 | 3 | + | chr11: 118349738-118349760 | UUCAGGAAACC-ACUUGGUUA | 10779 |

TABLE 6g

Exemplary preferred targeting domains for gRNA molecules targeting CD3D

| Targeting Domain ID | Exon | Strand | Target Sequence Location (hg38) | Targeting Domain Sequence | SEQ ID NO: |
|---|---|---|---|---|---|
| CR005334 | 2 | + | chr11: 118340373-118340395 | ACUUCGAUAAU-GAACUUGCA | 10780 |
| CR005335 | 5 | + | chr11: 118339204-118339226 | AGCAUCAUCUC-GAUCUCGGA | 10781 |
| CR005336 | 5 | + | chr11: 118339203-118339225 | GAGCAUCAUCU-CGAUCUCGG | 10782 |
| CR005337 | 2 | − | chr11: 118340453-118340475 | GGACCUGGGAA-AACGCAUCC | 10783 |
| CR005338 | 2 | − | chr11: 118340467-118340489 | GACAUUACAAG-ACUGGACCU | 10784 |
| CR005339 | 2 | − | chr11: 118340443-118340465 | AAACGCAUCCU-GGACCCACG | 10785 |
| CR005340 | 5 | + | chr11: 118339004-118339026 | GGCGAGAUCCC-AAGCAAGUC | 10786 |
| CR005341 | 5 | + | chr11: 118339200-118339222 | ACUGAGCAUCA-UCUCGAUCU | 10787 |
| CR005342 | 5 | + | chr11: 118339205-118339227 | GCAUCAUCUCG-AUCUCGGAG | 10788 |
| CR005343 | 4 | − | chr11: 118339469-118339491 | CCGACACACAA-GCUCUGUUG | 10789 |
| CR005344 | 2 | + | chr11: 118340429-118340451 | UACACCUAUAU-AUUCCUCGU | 10790 |
| CR005345 | 2 | − | chr11: 118340558-118340580 | GAUACCUAUAG-AGGAACUUG | 10791 |
| CR005346 | 5 | + | chr11: 118339027-118339049 | ACAACUCCCAC-GCCUUGCCC | 10792 |
| CR005347 | 2 | + | chr11: 118340428-118340450 | UUACACCUAUA-UAUUCCUCG | 10793 |
| CR005348 | 5 | − | chr11: 118339150-118339172 | GGAACAAGUGA-ACCUGAGAC | 10794 |

In aspects of the invention, a gRNA to TRAC which includes the targeting domain of CR00961 (SEQ ID NO: 5569, underlined below, or modified version thereof (also as underlined below)), e.g., one of the gRNA molecules described below, is used in the CRISPR systems, methods, cells and other aspects and embodiments of the invention (and combinations thereof), including in aspects involving more than one gRNA molecule, e.g., described herein:

sgRNA CR00961 #1:
(SEQ ID NO: 7833)
AGAGUCUCUCAGCUGGUACAGUUUUAGAGCUAGAAAUAGCAAGUUAAAAU

AAGGCUAGUCCGUUAUCAACUUGAAAAAGUGGCACCGAGUCGGUGCUUUU sgRNA CR00961 #2:
(SEQ ID NO: 7834)
mA*mG*mA*GUCUCUCAGCUGGUACAGUUUUAGAGCUAGAAAUAGCAAGU

UAAAAUAAGGCUAGUCCGUUAUCAACUUGAAAAAGUGGCACCGAGUCGGU

GCU*mU*mU*mU sgRNA CR00961 #3:
(SEQ ID NO: 7835)
mA*mG*mA*GUCUCUCAGCUGGUACAGUUUUAGAGCUAGAAAUAGCAAGU

UAAAAUAAGGCUAGUCCGUUAUCAACUUGAAAAAGUGGCACCGAGUCGGU

GCmU*mU*mU*U dgRNA CR00961 #1:
crRNA:
(SEQ ID NO: 7836)
AGAGUCUCUCAGCUGGUACAGUUUUAGAGCUAUGCUGUUUUG tracr:
(SEQ ID NO: 6660)
AACAGCAUAGCAAGUUAAAAUAAGGCUAGUCCGUUAUCAACUUGAAAAAG

UGGCACCGAGUCGGUGCUUUUUUU dgRNA CR00961 #2:
crRNA:
(SEQ ID NO: 7837)
mA*mG*mA*GUCUCUCAGCUGGUACAGUUUUAGAGCUAUGCUGUU*mU* mU*mG tracr:
(SEQ ID NO: 10798)
mA*mA*mC*AGCAUAGCAAGUUAAAAUAAGGCUAGUCCGUUAUCAACUUG AAAAAGUGGCACCGAGUCGGUGCUUUU*mU*mU*mU dgRNA CR00961 #3:
crRNA:
(SEQ ID NO: 7837)
mA*mG*mA*GUCUCUCAGCUGGUACAGUUUUAGAGCUAUGCUGUU*mU* mU*mG tracr:
(SEQ ID NO: 6660)
AACAGCAUAGCAAGUUAAAAUAAGGCUAGUCCGUUAUCAACUUGAAAAAG

UGGCACCGAGUCGGUGCUUUUUUU.

In aspects of the invention, a gRNA to TRAC which includes the targeting domain of CR00984 (SEQ ID NO: 5592, underlined below, or modified version thereof (also as underlined below)), e.g., one of the gRNA molecules described below, is used in the CRISPR systems, methods, cells and other aspects and embodiments of the invention (and combinations thereof), including in aspects involving more than one gRNA molecule, e.g., described herein:

sgRNA CR00984 #1:
(SEQ ID NO: 7838)
UUCGGAACCCAAUCACUGACGUUUUAGAGCUAGAAAUAGCAAGUUAAAAU

AAGGCUAGUCCGUUAUCAACUUGAAAAAGUGGCACCGAGUCGGUGCUUUU sgRNA CR00984 #2:
(SEQ ID NO: 7839)
mU*mU*mC*GGAACCCAAUCACUGACGUUUUAGAGCUAGAAAUAGCAAGU

UAAAAUAAGGCUAGUCCGUUAUCAACUUGAAAAAGUGGCACCGAGUCGGU

GCU*mU*mU*mU sgRNA CR00984 #3:
(SEQ ID NO: 7840)
mU*mU*mC*GGAACCCAAUCACUGACGUUUUAGAGCUAGAAAUAGCAAGU

UAAAAUAAGGCUAGUCCGUUAUCAACUUGAAAAAGUGGCACCGAGUCGGU

GCmU*mU*mU*U dgRNA CR00984 #1:
crRNA:
(SEQ ID NO: 7841)
UUCGGAACCCAAUCACUGACGUUUUAGAGCUAUGCUGUUUUG tracr:
(SEQ ID NO: 6660)
AACAGCAUAGCAAGUUAAAAUAAGGCUAGUCCGUUAUCAACUUGAAAAAG

UGGCACCGAGUCGGUGCUUUUUUU dgRNA CR00984 #2:
crRNA:
(SEQ ID NO: 7842)
mU*mU*mC*GGAACCCAAUCACUGACGUUUUAGAGCUAUGCUGUU*mU* mU*mG tracr:
(SEQ ID NO: 10798)
mA*mA*mC*AGCAUAGCAAGUUAAAAUAAGGCUAGUCCGUUAUCAACUUG AAAAAGUGGCACCGAGUCGGUGCUUUU*mU*mU*mU dgRNA CR00984 #3:
crRNA:
(SEQ ID NO: 7842)
mU*mU*mC*GGAACCCAAUCACUGACGUUUUAGAGCUAUGCUGUU*mU* mU*mG tracr:
(SEQ ID NO: 6660)
AACAGCAUAGCAAGUUAAAAUAAGGCUAGUCCGUUAUCAACUUGAAAAAG

UGGCACCGAGUCGGUGCUUUUUUU.

In aspects of the invention, a gRNA to TRBC which includes the targeting domain of CR00798 (SEQ ID NO: 5694, underlined below, or modified version thereof (also as underlined below)), e.g., one of the gRNA molecules described below, is used in the CRISPR systems, methods, cells and other aspects and embodiments of the invention (and combinations thereof), including in aspects involving more than one gRNA molecule, e.g., described herein:

sgRNA CR00798 #1:
(SEQ ID NO: 7843)
UGGCUCAAACACAGCGACCUGUUUUAGAGCUAGAAAUAGCAAGUUAAAAU

AAGGCUAGUCCGUUAUCAACUUGAAAAAGUGGCACCGAGUCGGUGCUUUU sgRNA CR00798 #2:
(SEQ ID NO: 7844)
mU*mG*mG*CUCAAACACAGCGACCUGUUUUAGAGCUAGAAAUAGCAAGU

UAAAAUAAGGCUAGUCCGUUAUCAACUUGAAAAAGUGGCACCGAGUCGGU

GCU*mU*mU*mU sgRNA CR00798 #3:
(SEQ ID NO: 7845)
mU*mG*mG*CUCAAACACAGCGACCUGUUUUAGAGCUAGAAAUAGCAAGU

UAAAAUAAGGCUAGUCCGUUAUCAACUUGAAAAAGUGGCACCGAGUCGGU

GCmU*mU*mU*U dgRNA CR00798 #1:
crRNA:
(SEQ ID NO: 7846)
UGGCUCAAACACAGCGACCUGUUUUAGAGCUAUGCUGUUUUG tracr:
(SEQ ID NO: 6660)
AACAGCAUAGCAAGUUAAAAUAAGGCUAGUCCGUUAUCAACUUGAAAAAG

UGGCACCGAGUCGGUGCUUUUUUU dgRNA CR00798 #2:
crRNA:
(SEQ ID NO: 7847)
mU*mG*mG*CUCAAACACAGCGACCUGUUUUAGAGCUAUGCUGUU*mU* mU*mG tracr:
(SEQ ID NO: 10798)
mA*mA*mC*AGCAUAGCAAGUUAAAAUAAGGCUAGUCCGUUAUCAACUUG AAAAAGUGGCACCGAGUCGGUGCUUUU*mU*mU*mU dgRNA CR00798 #3:
crRNA:
(SEQ ID NO: 7847)
mU*mG*mG*CUCAAACACAGCGACCUGUUUUAGAGCUAUGCUGUU*mU* mU*mG tracr:
(SEQ ID NO: 6660)
AACAGCAUAGCAAGUUAAAAUAAGGCUAGUCCGUUAUCAACUUGAAAAAG

UGGCACCGAGUCGGUGCUUUUUUU.

In aspects of the invention, a gRNA to TRBC which includes the targeting domain of CR00823 (SEQ ID NO: 5719, underlined below, or modified version thereof (also as underlined below)), e.g., one of the gRNA molecules described below, is used in the CRISPR systems, methods, cells and other aspects and embodiments of the invention (and combinations thereof), including in aspects involving more than one gRNA molecule, e.g., described herein:

sgRNA CR00823 #1:
(SEQ ID NO: 7848)
UCCCUAGCAAGAUCUCAUAGGUUUUAGAGCUAGAAAUAGCAAGUUAAAAU

AAGGCUAGUCCGUUAUCAACUUGAAAAAGUGGCACCGAGUCGGUGCUUUU sgRNA CR00823 #2:
(SEQ ID NO: 7849)
mU*mC*mC*CUAGCAAGAUCUCAUAGGUUUUAGAGCUAGAAAUAGCAAGU

UAAAAUAAGGCUAGUCCGUUAUCAACUUGAAAAAGUGGCACCGAGUCGGU

GCU*mU*mU*mU sgRNA CR00823 #3:
(SEQ ID NO: 7850)
mU*mC*mC*CUAGCAAGAUCUCAUAGGUUUUAGAGCUAGAAAUAGCAAGU

UAAAAUAAGGCUAGUCCGUUAUCAACUUGAAAAAGUGGCACCGAGUCGGU

GCmU*mU*mU*U dgRNA CR00823 #1:
crRNA:
(SEQ ID NO: 7851)
UCCCUAGCAAGAUCUCAUAGGUUUUAGAGCUAUGCUGUUUG tracr:
(SEQ ID NO: 6660)
AACAGCAUAGCAAGUUAAAAUAAGGCUAGUCCGUUAUCAACUUGAAAAAG

UGGCACCGAGUCGGUGCUUUUUUU dgRNA CR00823 #2:
crRNA:
(SEQ ID NO: 7852)
mU*mC*mC*CUAGCAAGAUCUCAUAGGUUUUAGAGCUAUGCUGUU*mU* mU*mG tracr:
(SEQ ID NO: 10798)
mA*mA*mC*AGCAUAGCAAGUUAAAAUAAGGCUAGUCCGUUAUCAACUUG AAAAAGUGGCACCGAGUCGGUGCUUUU*mU*mU*mU dgRNA CR00823 #3:
crRNA:
(SEQ ID NO: 7852)
mU*mC*mC*CUAGCAAGAUCUCAUAGGUUUUAGAGCUAUGCUGUU*mU* mU*mG tracr:
(SEQ ID NO: 6660)
AACAGCAUAGCAAGUUAAAAUAAGGCUAGUCCGUUAUCAACUUGAAAAAG

UGGCACCGAGUCGGUGCUUUUUUU.

In aspects of the invention, a gRNA to B2M which includes the targeting domain of CR00442 (SEQ ID NO: 5496, underlined below, or modified version thereof (also as underlined below)), e.g., one of the gRNA molecules described below, is used in the CRISPR systems, methods, cells and other aspects and embodiments of the invention (and combinations thereof), including in aspects involving more than one gRNA molecule, e.g., described herein:

sgRNA CR00442 #1:
(SEQ ID NO: 7853)
GGCCACGGAGCGAGACAUCUGUUUUAGAGCUAGAAAUAGCAAGUUAAAAU

AAGGCUAGUCCGUUAUCAACUUGAAAAAGUGGCACCGAGUCGGUGCUUUU sgRNA CR00442 #2:
(SEQ ID NO: 7854)
mG*mG*mC*CACGGAGCGAGACAUCUGUUUUAGAGCUAGAAAUAGCAAGU

UAAAAUAAGGCUAGUCCGUUAUCAACUUGAAAAAGUGGCACCGAGUCGGU

GCU*mU*mU*mU sgRNA CR00442 #3:
(SEQ ID NO: 7855)
mG*mG*mC*CACGGAGCGAGACAUCUGUUUUAGAGCUAGAAAUAGCAAGU

UAAAAUAAGGCUAGUCCGUUAUCAACUUGAAAAAGUGGCACCGAGUCGGU

GCmU*mU*mU*U dgRNA CR00442 #1:
crRNA:
(SEQ ID NO: 7856)
GGCCACGGAGCGAGACAUCUGUUUUAGAGCUAUGCUGUUUG tracr:
(SEQ ID NO: 6660)
AACAGCAUAGCAAGUUAAAAUAAGGCUAGUCCGUUAUCAACUUGAAAAAG

UGGCACCGAGUCGGUGCUUUUUUU dgRNA CR00442 #2:
crRNA:
(SEQ ID NO: 7857)
mG*mG*mC*CACGGAGCGAGACAUCUGUUUUAGAGCUAUGCUGUU*mU* mU*mG

```
tracr:
                                      (SEQ ID NO: 10798)
mA*mA*mC*AGCAUAGCAAGUUAAAAUAAGGCUAGUCCGUUAUCAACUUG AAAAAGUGGCACCGAGUCGGUGCUUUU*mU*mU*mU dgRNA CR00442 #3:
crRNA:
                                      (SEQ ID NO: 7857)
mG*mG*mC*CACGGAGCGAGACAUCUGUUUUAGAGCUAUGCUGUU*mU* mU*mG tracr:
                                      (SEQ ID NO: 6660)
AACAGCAUAGCAAGUUAAAAUAAGGCUAGUCCGUUAUCAACUUGAAAAAG

UGGCACCGAGUCGGUGCUUUUUUU.
```

In aspects of the invention, a gRNA to B2M which includes the targeting domain of CR00444 (SEQ ID NO: 5498, underlined below, or modified version thereof (also as underlined below)), e.g., one of the gRNA molecules described below, is used in the CRISPR systems, methods, cells and other aspects and embodiments of the invention (and combinations thereof), including in aspects involving more than one gRNA molecule, e.g., described herein:

```
sgRNA CR00444 #1:
                                      (SEQ ID NO: 7858)
GAGUAGCGCGAGCACAGCUAGUUUUAGAGCUAGAAAUAGCAAGUUAAAAU

AAGGCUAGUCCGUUAUCAACUUGAAAAAGUGGCACCGAGUCGGUGCUUUU sgRNA CR00444 #2:
                                      (SEQ ID NO: 7859)
mG*mA*mU*AGCGCGAGCACAGCUAGUUUUAGAGCUAGAAAUAGCAAGUU

AAAAUAAGGCUAGUCCGUUAUCAACUUGAAAAAGUGGCACCGAGUCGGUG

CU*mU*mU*mU sgRNA CR00444 #3:
                                      (SEQ ID NO: 7860)
mG*mA*mU*AGCGCGAGCACAGCUAGUUUUAGAGCUAGAAAUAGCAAGUU

AAAAUAAGGCUAGUCCGUUAUCAACUUGAAAAAGUGGCACCGAGUCGGUG

CmU*mU*mU*U dgRNA CR00444 #1:
crRNA:
                                      (SEQ ID NO: 7861)
GAGUAGCGCGAGCACAGCUAGUUUUAGAGCUAUGCUGUUUUG tracr:
                                      (SEQ ID NO: 6660)
AACAGCAUAGCAAGUUAAAAUAAGGCUAGUCCGUUAUCAACUUGAAAAAG

UGGCACCGAGUCGGUGCUUUUUUU dgRNA CR00444 #2:
crRNA:
                                      (SEQ ID NO: 7862)
mG*mA*mU*AGCGCGAGCACAGCUAGUUUUAGAGCUAUGCUGUU*mU* mU*mG tracr:
                                      (SEQ ID NO: 10798)
mA*mA*mC*AGCAUAGCAAGUUAAAAUAAGGCUAGUCCGUUAUCAACUUG AAAAAGUGGCACCGAGUCGGUGCUUUU*mU*mU*mU dgRNA CR00444 #3:
crRNA:
                                      (SEQ ID NO: 7862)
mG*mA*mU*AGCGCGAGCACAGCUAGUUUUAGAGCUAUGCUGUU*mU* mU*mG tracr:
                                      (SEQ ID NO: 6660)
AACAGCAUAGCAAGUUAAAAUAAGGCUAGUCCGUUAUCAACUUGAAAAAG

UGGCACCGAGUCGGUGCUUUUUUU.
```

In aspects of the invention, a gRNA to FKBP1A which includes the targeting domain of CR002097 (SEQ ID NO: 6705, underlined below, or modified version thereof (also as underlined below)), e.g., one of the gRNA molecules described below, is used in the CRISPR systems, methods, cells and other aspects and embodiments of the invention (and combinations thereof), including in aspects involving more than one gRNA molecule, e.g., described herein:

```
sgRNA CR002097 #1:
                                      (SEQ ID NO: 7863)
CAAGCGCGGCCAGACCUGCGGUUUUAGAGCUAGAAAUAGCAAGUUAAAAU

AAGGCUAGUCCGUUAUCAACUUGAAAAAGUGGCACCGAGUCGGUGCUUUU sgRNA CR002097 #2:
                                      (SEQ ID NO: 7864)
mC*mA*mA*GCGCGGCCAGACCUGCGGUUUUAGAGCUAGAAAUAGCAAGU

UAAAAUAAGGCUAGUCCGUUAUCAACUUGAAAAAGUGGCACCGAGUCGGU

GCU*mU*mU*mU sgRNA CR002097 #3:
                                      (SEQ ID NO: 7865)
mC*mA*mA*GCGCGGCCAGACCUGCGGUUUUAGAGCUAGAAAUAGCAAGU

UAAAAUAAGGCUAGUCCGUUAUCAACUUGAAAAAGUGGCACCGAGUCGGU

GCmU*mU*mU*U dgRNA CR002097 #1:
crRNA:
                                      (SEQ ID NO: 7866)
CAAGCGCGGCCAGACCUGCGGUUUUAGAGCUAUGCUGUUUUG tracr:
                                      (SEQ ID NO: 6660)
AACAGCAUAGCAAGUUAAAAUAAGGCUAGUCCGUUAUCAACUUGAAAAAG

UGGCACCGAGUCGGUGCUUUUUUU dgRNA CR002097 #2:
crRNA:
                                      (SEQ ID NO: 7867)
mC*mA*mA*GCGCGGCCAGACCUGCGGUUUUAGAGCUAUGCUGUU*mU* mU*mG tracr:
                                      (SEQ ID NO: 10798)
mA*mA*mC*AGCAUAGCAAGUUAAAAUAAGGCUAGUCCGUUAUCAACUUG AAAAAGUGGCACCGAGUCGGUGCUUUU*mU*mU*mU dgRNA CR002097 #3:
crRNA:
                                      (SEQ ID NO: 7867)
mC*mA*mA*GCGCGGCCAGACCUGCGGUUUUAGAGCUAUGCUGUU*mU* mU*mG
```

-continued

```
tracr:
                                    (SEQ ID NO: 6660)
AACAGCAUAGCAAGUUAAAAUAAGGCUAGUCCGUUAUCAACUUGAAAAAG

UGGCACCGAGUCGGUGCUUUUUUU.
```

In aspects of the invention, a gRNA to FKBP1A which includes the targeting domain of CR002100 (SEQ ID NO: 6708, underlined below, or modified version thereof (also as underlined below)), e.g., one of the gRNA molecules described below, is used in the CRISPR systems, methods, cells and other aspects and embodiments of the invention (and combinations thereof), including in aspects involving more than one gRNA molecule, e.g., described herein:

```
sgRNA CR002100 #1:
                                    (SEQ ID NO: 7868)
CCGCUGGGCCCCCGACUCACGUUUUAGAGCUAGAAAUAGCAAGUUAAAAU

AAGGCUAGUCCGUUAUCAACUUGAAAAAGUGGCACCGAGUCGGUGCUUUU sgRNA CR002100 #2:
                                    (SEQ ID NO: 7869)
mC*mC*mG*CUGGGCCCCCGACUCACGUUUUAGAGCUAGAAAUAGCAAGU

UAAAAUAAGGCUAGUCCGUUAUCAACUUGAAAAAGUGGCACCGAGUCGGU

GCU*mU*mU*mU sgRNA CR002100 #3:
                                    (SEQ ID NO: 7870)
mC*mC*mG*CUGGGCCCCCGACUCACGUUUUAGAGCUAGAAAUAGCAAGU

UAAAAUAAGGCUAGUCCGUUAUCAACUUGAAAAAGUGGCACCGAGUCGGU

GCmU*mU*mU*U dgRNA CR002100 #1:
crRNA:
                                    (SEQ ID NO: 7871)
CCGCUGGGCCCCCGACUCACGUUUUAGAGCUAUGCUGUUUUG tracr:
                                    (SEQ ID NO: 6660)
AACAGCAUAGCAAGUUAAAAUAAGGCUAGUCCGUUAUCAACUUGAAAAAG

UGGCACCGAGUCGGUGCUUUUUUU dgRNA CR002100 #2:
crRNA:
                                    (SEQ ID NO: 7872)
mC*mC*mG*CUGGGCCCCCGACUCACGUUUUAGAGCUAUGCUGUU*mU* mU*mG tracr:
                                    (SEQ ID NO: 10798)
mA*mA*mC*AGCAUAGCAAGUUAAAAUAAGGCUAGUCCGUUAUCAACUUG AAAAAGUGGCACCGAGUCGGUGCUUUU*mU*mU*mU dgRNA CR002100 #3:
crRNA:
                                    (SEQ ID NO: 7872)
mC*mC*mG*CUGGGCCCCCGACUCACGUUUUAGAGCUAUGCUGUU*mU* mU*mG tracr:
                                    (SEQ ID NO: 6660)
AACAGCAUAGCAAGUUAAAAUAAGGCUAGUCCGUUAUCAACUUGAAAAAG

UGGCACCGAGUCGGUGCUUUUUUU.
```

In each of the gRNA molecules described above, a "*" denotes a phosphorothioate bond between the adjacent nucleotides, and "mN" (where N=A, G, C or U) denotes a 2'-OMe modified nucleotide. In embodiments, any of the gRNA molecules described herein, e.g., described above, is complexed with a Cas9 molecule, e.g., as described herein, to form a ribonuclear protein complex (RNP). Such RNPs are particularly useful in the methods, cells, and other aspects and embodiments of the invention, e.g., described herein.

III. Methods for Designing gRNAs

Methods for designing gRNAs are described herein, including methods for selecting, designing and validating target sequences. Exemplary targeting domains are also provided herein. Targeting Domains discussed herein can be incorporated into the gRNAs described herein.

Methods for selection and validation of target sequences as well as off-target analyses are described, e.g., in. Mali el al., 2013 SCIENCE 339(6121): 823-826; Hsu et al, 2013 NAT BIOTECHNOL, 31 (9): 827-32; Fu et al, 2014 NAT BIOTECHNOL, doi: 10.1038/nbt.2808. PubMed PM ID: 24463574; Heigwer et al, 2014 NAT METHODS 11(2): 122-3. doi: 10.1038/nmeth.2812. PubMed PMID: 24481216; Bae el al, 2014 BIOINFORMATICS PubMed PMID: 24463181; Xiao A el al, 2014 BIOINFORMATICS PubMed PMID: 24389662.

For example, a software tool can be used to optimize the choice of gRNA within a user's target sequence, e.g., to minimize total off-target activity across the genome. Off target activity may be other than cleavage. For each possible gRNA choice e.g., using S. pyogenes Cas9, the tool can identify all off-target sequences (e.g., preceding either NAG or NGG PAMs) across the genome that contain up to certain number (e.g., 1, 2, 3, 4, 5, 6, 7, 8, 9, or 10) of mismatched base-pairs. The cleavage efficiency at each off-target sequence can be predicted, e.g., using an experimentally-derived weighting scheme. Each possible gRNA is then ranked according to its total predicted off-target cleavage; the top-ranked gRNAs represent those that are likely to have the greatest on-target and the least off-target cleavage. Other functions, e.g., automated reagent design for CRISPR construction, primer design for the on-target Surveyor assay, and primer design for high-throughput detection and quantification of off-target cleavage via next-gen sequencing, can also be included in the tool. Candidate gRNA molecules can be evaluated by art-known methods or as described herein.

Although software algorithms may be used to generate an initial list of potential gRNA molecules, cutting efficiency and specificity will not necessarily reflect the predicted values, and gRNA molecules typically require screening in specific cell lines, e.g., primary human cell lines, e.g., primary human immune effector cells, e.g., primary human T cells, to determine, for example, cutting efficiency, indel formation, cutting specificity and change in desired phenotype. These properties may be assayed by the methods described herein.

IV. Cas Molecules

Cas9 Molecules

In preferred embodiments, the Cas molecule is a Cas9 molecule. Cas9 molecules of a variety of species can be used in the methods and compositions described herein. While the S. pyogenes Cas9 molecule are the subject of much of the disclosure herein, Cas9 molecules of, derived from, or based on the Cas9 proteins of other species listed herein can be used as well. In other words, other Cas9 molecules, e.g., S. thermophilus, Staphylococcus aureus and/or Neisseyor men-

*ingitidis* Cas9 molecules, may be used in the systems, methods and compositions described herein. Additional Cas9 species include: *Acidovorax avenae, Actinobacillus pleuropneumoniae, Actinobacillus succinogenes, Actinobacillus suis, Actinomyces* sp., cyclphilus denitrificans, *Aminomonas paucivorans, Bacillus cereus, Bacillus smithii, Bacillus thuringiensis, Bacteroides* sp., *Blastopirellula marina,* Bradyrhiz obium sp., *Brevibacillus laterosporus, Campylobacter coli, Campylobacter jejuni, Campylobacter lad,* Candidatus Puniceispirillum, *Clostridium cellulolyticum, Clostridium perfringens, Corynebacterium accolens, Corynebacterium diphtheria, Corynebacterium matruchotii, Dinoroseobacter sliibae, Eubacterium dolichum, Gamma* proteobacterium, *Gluconacetobacter diazotrophicus, Haemophilus parainfluenzae, Haemophilus sputorum, Helicobacter canadensis, Helicobacter cinaedi, Helicobacter mustelae, Ilyobacter polytropus, Kingella kingae, Lactobacillus crispatus, Listeria ivanovii, Listeria monocytogenes, Listeriaceae bacterium, Methylocystis* sp., *Methylosinus trichosporium, Mobiluncus mulieris, Neisseria bacilliformis, Neisseria cinerea, Neisseria flavescens, Neisseria lactamica. Neisseria* sp., *Neisseria wadsworthii, Nitrosomonas* sp., *Parvibaculum lavamentivorans, Pasteurella multocida, Phascolarctobacterium succinatutens, Ralstonia syzygii, Rhodopseudomonas palustris, Rhodovulum* sp., *Simonsiella muelleri, Sphingomonas* sp., *Sporolactobacillus vineae, Staphylococcus lugdunensis, Streptococcus* sp., *Subdoligranulum* sp., *Tislrella mobilis, Treponema* sp., or *Verminephrobacter eiseniae.*

A Cas9 molecule, as that term is used herein, refers to a molecule that can interact with a gRNA molecule (e.g., sequence of a domain of a tracr) and, in concert with the gRNA molecule, localize (e.g., target or home) to a site which comprises a target sequence and PAM sequence.

In an embodiment, the Cas9 molecule is capable of cleaving a target nucleic acid molecule, which may be referred to herein as an active Cas9 molecule. In an embodiment, an active Cas9 molecule, comprises one or more of the following activities: a nickase activity, i.e., the ability to cleave a single strand, e.g., the non-complementary strand or the complementary strand, of a nucleic acid molecule; a double stranded nuclease activity, i.e., the ability to cleave both strands of a double stranded nucleic acid and create a double stranded break, which in an embodiment is the presence of two nickase activities; an endonuclease activity; an exonuclease activity; and a helicase activity, i.e., the ability to unwind the helical structure of a double stranded nucleic acid.

In an embodiment, an enzymatically active Cas9 molecule cleaves both DNA strands and results in a double stranded break. In an embodiment, a Cas9 molecule cleaves only one strand, e.g., the strand to which the gRNA hybridizes to, or the strand complementary to the strand the gRNA hybridizes with. In an embodiment, an active Cas9 molecule comprises cleavage activity associated with an HNH-like domain. In an embodiment, an active Cas9 molecule comprises cleavage activity associated with an N-terminal RuvC-like domain. In an embodiment, an active Cas9 molecule comprises cleavage activity associated with an HNH-like domain and cleavage activity associated with an N-terminal RuvC-like domain. In an embodiment, an active Cas9 molecule comprises an active, or cleavage competent, HNH-like domain and an inactive, or cleavage incompetent, N-terminal RuvC-like domain. In an embodiment, an active Cas9 molecule comprises an inactive, or cleavage incompetent, HNH-like domain and an active, or cleavage competent, N-terminal RuvC-like domain.

In an embodiment, the ability of an active Cas9 molecule to interact with and cleave a target nucleic acid is PAM sequence dependent. A PAM sequence is a sequence in the target nucleic acid. In an embodiment, cleavage of the target nucleic acid occurs upstream from the PAM sequence. Active Cas9 molecules from different bacterial species can recognize different sequence motifs (e.g., PAM sequences). In an embodiment, an active Cas9 molecule of *S. pyogenes* recognizes the sequence motif NGG and directs cleavage of a target nucleic acid sequence 1 to 10, e.g., 3 to 5, base pairs upstream from that sequence. See, e.g., Mali el al, SCIENCE 2013; 339(6121): 823-826. In an embodiment, an active Cas9 molecule of *S. thermophilus* recognizes the sequence motif NGGNG and NNAG AAW (W=A or T) and directs cleavage of a core target nucleic acid sequence 1 to 10, e.g., 3 to 5, base pairs upstream from these sequences. See, e.g., Horvath et al., SCIENCE 2010; 327(5962): 167-170, and Deveau et al, J BACTERIOL 2008; 190(4): 1390-1400. In an embodiment, an active Cas9 molecule of S. mulans recognizes the sequence motif NGG or NAAR (R-A or G) and directs cleavage of a core target nucleic acid sequence 1 to 10, e.g., 3 to 5 base pairs, upstream from this sequence. See, e.g., Deveau et al., J BACTERIOL 2008; 190(4): 1390-1400.

In an embodiment, an active Cas9 molecule of *S. aureus* recognizes the sequence motif NNGRR (R=A or G) and directs cleavage of a target nucleic acid sequence 1 to 10, e.g., 3 to 5, base pairs upstream from that sequence. See, e.g., Ran F. et al., NATURE, vol. 520, 2015, pp. 186-191. In an embodiment, an active Cas9 molecule of *N. meningitidis* recognizes the sequence motif NNNNGATT and directs cleavage of a target nucleic acid sequence 1 to 10, e.g., 3 to 5, base pairs upstream from that sequence. See, e.g., Hou et al., PNAS EARLY EDITION 2013, 1-6. The ability of a Cas9 molecule to recognize a PAM sequence can be determined, e.g., using a transformation assay described in Jinek et al, SCIENCE 2012, 337:816.

Some Cas9 molecules have the ability to interact with a gRNA molecule, and in conjunction with the gRNA molecule home (e.g., targeted or localized) to a core target domain, but are incapable of cleaving the target nucleic acid, or incapable of cleaving at efficient rates. Cas9 molecules having no, or no substantial, cleavage activity may be referred to herein as an inactive Cas9 (an enzymatically inactive Cas9), a dead Cas9, or a dCas9 molecule. For example, an inactive Cas9 molecule can lack cleavage activity or have substantially less, e.g., less than 20, 10, 5, 1 or 0.1% of the cleavage activity of a reference Cas9 molecule, as measured by an assay described herein.

Exemplary naturally occurring Cas9 molecules are described in Chylinski et al, RNA Biology 2013; 10:5, 727-737. Such Cas9 molecules include Cas9 molecules of a cluster 1 bacterial family, cluster 2 bacterial family, cluster 3 bacterial family, cluster 4 bacterial family, cluster 5 bacterial family, cluster 6 bacterial family, a cluster 7 bacterial family, a cluster 8 bacterial family, a cluster 9 bacterial family, a cluster 10 bacterial family, a cluster 11 bacterial family, a cluster 12 bacterial family, a cluster 13 bacterial family, a cluster 14 bacterial family, a cluster 1 bacterial family, a cluster 16 bacterial family, a cluster 17 bacterial family, a cluster 18 bacterial family, a cluster 19 bacterial family, a cluster 20 bacterial family, a cluster 21 bacterial family, a cluster 22 bacterial family, a cluster 23 bacterial family, a cluster 24 bacterial family, a cluster 25 bacterial family, a cluster 26 bacterial family, a cluster 27 bacterial family, a cluster 28 bacterial family, a cluster 29 bacterial family, a cluster 30 bacterial family, a cluster 31 bacterial family, a cluster 32 bacterial family, a cluster 33 bacterial family, a cluster 34 bacterial family, a cluster 35 bacterial family, a cluster 36 bacterial family, a cluster 37 bacterial family, a cluster 38 bacterial family, a cluster 39 bacterial family, a cluster 40 bacterial family, a cluster 41 bacterial family, a cluster 42 bacterial family, a cluster 43 bacterial family, a cluster 44 bacterial family, a cluster 45 bacterial family, a cluster 46 bacterial family, a cluster 47 bacterial family, a cluster 48 bacterial family, a cluster 49 bacterial family, a cluster 50 bacterial family, a cluster 51 bacterial family, a cluster 52 bacterial family, a cluster 53 bacterial family, a cluster 54 bacterial family, a cluster 55 bacterial family, a cluster 56 bacterial family, a cluster 57 bacterial family, a cluster 58 bacterial family, a cluster 59 bacterial family, a cluster 60 bacterial family, a cluster 61 bacterial family, a cluster 62 bacterial family, a cluster 63 bacterial family, a cluster 64 bacterial family, a cluster 65 bacterial family, a cluster 66 bacterial family, a cluster 67 bacterial family, a cluster 68 bacterial family, a cluster 69 bacterial family, a cluster 70 bacterial family, a cluster 71 bacterial family, a cluster 72 bacterial family, a cluster 73 bacterial family, a cluster 74 bacterial family, a cluster 75 bacterial family, a cluster 76 bacterial family, a cluster 77 bacterial family, or a cluster 78 bacterial family.

Exemplary naturally occurring Cas9 molecules include a Cas9 molecule of a cluster 1 bacterial family. Examples include a Cas9 molecule of: S. pyogenes (e.g., strain SF370, MGAS 10270, MGAS 10750, MGAS2096, MGAS315, MGAS5005, MGAS6180, MGAS9429, NZ131 and SSI-1), S. thermophilus (e.g., strain LMD-9), S. pseudoporcinus (e.g., strain SPIN 20026), S. mutans (e.g., strain UA 159, NN2025), S. macacae (e.g., strain NCTC1 1558), S. gallolyticus (e.g., strain UCN34, ATCC BAA-2069), S. equines (e.g., strain ATCC 9812, MGCS 124), S. dysgalactiae (e.g., strain GGS 124), S. bovis (e.g., strain ATCC 700338), S. cmginosus (e.g.; strain F021 1), S. agalactiae* (e.g., strain NEM316, A909), Listeria monocytogenes (e.g., strain F6854), Listeria innocua (L. innocua, e.g., strain Clip 1 1262), Enterococcus italicus (e.g., strain DSM 15952), or Enterococcus faecium (e.g., strain 1,231,408). Additional exemplary Cas9 molecules are a Cas9 molecule of Neisseria meningitidis (Hou et' al. PNAS Early Edition 2013, 1-6) and a S. aureus Cas9 molecule.

In an embodiment, a Cas9 molecule, e.g., an active Cas9 molecule or inactive Cas9 molecule, comprises an amino acid sequence: having 60%, 65%, 70%, 75%, 80%, 85%, 90%, 95%, 96%, 97%, 98%, or 99% homology with; differs at no more than 1%, 2%, 5%, 10%, 15%, 20%, 30%, or 40% of the amino acid residues when compared with; differs by at least 1, 2, 5, 10 or 20 amino acids but by no more than 100, 80, 70, 60, 50, 40 or 30 amino acids from; or is identical to; any Cas9 molecule sequence described herein or a naturally occurring Cas9 molecule sequence, e.g., a Cas9 molecule from a species listed herein or described in Chylinski et al., RNA Biology 2013, 10:5, T2T-T,1 Hou et al. PNAS Early Edition 2013, 1-6.

In an embodiment, a Cas9 molecule comprises an amino acid sequence having 60%, 65%, 70%, 75%, 80%, 85%, 90%, 95%, 96%, 97%, 98%, or 99% homology with; differs at no more than 1%, 2%, 5%, 10%, 15%, 20%, 30%, or 40% of the amino acid residues when compared with; differs by at least 1, 2, 5, or 20 amino acids but by no more than 100, 80, 70, 60, 50, 40 or 30 amino acids from; or is identical to; S. pyogenes Cas9:

(SEQ ID NO: 6611)

Met Asp Lys Lys Tyr Ser Ile Gly Leu Asp Ile Gly
1               5                   10
Thr Asn Ser Val Gly Trp Ala Val Ile Thr Asp Glu
            15                  20
Tyr Lys Val Pro Ser Lys Lys Phe Lys Val Leu Gly
25                  30                      35
Asn Thr Asp Arg His Ser Ile Lys Lys Asn Leu Ile
            40                  45
Gly Ala Leu Leu Phe Asp Ser Gly Glu Thr Ala Glu
    50                  55                      60
Ala Thr Arg Leu Lys Arg Thr Ala Arg Arg Arg Tyr
            65                  70
Thr Arg Arg Lys Asn Arg Ile Cys Tyr Leu Gln Glu
        75                      80
Ile Phe Ser Asn Glu Met Ala Lys Val Asp Asp Ser
85                  90                      95
Phe Phe His Arg Leu Glu Glu Ser Phe Leu Val Glu
            100                 105
Glu Asp Lys Lys His Glu Arg His Pro Ile Phe Gly
    110                 115                     120
Asn Ile Val Asp Glu Val Ala Tyr His Glu Lys Tyr
                125                 130
Pro Thr Ile Tyr His Leu Arg Lys Lys Leu Val Asp
        135                 140
Ser Thr Asp Lys Ala Asp Leu Arg Leu Ile Tyr Leu
145                 150                     155
Ala Leu Ala His Met Ile Lys Phe Arg Gly His Phe
            160                 165
Leu Ile Glu Gly Asp Leu Asn Pro Asp Asn Ser Asp
    170                 175                     180
Val Asp Lys Leu Phe Ile Gln Leu Val Gln Thr Tyr
                185                 190
Asn Gln Leu Phe Glu Glu Asn Pro Ile Asn Ala Ser
        195                 200
Gly Val Asp Ala Lys Ala Ile Leu Ser Ala Arg Leu
205                 210                     215
Ser Lys Ser Arg Arg Leu Glu Asn Leu Ile Ala Gln
            220                 225
Leu Pro Gly Glu Lys Lys Asn Gly Leu Phe Gly Asn
    230                 235                     240
Leu Ile Ala Leu Ser Leu Gly Leu Thr Pro Asn Phe
                245                 250
Lys Ser Asn Phe Asp Leu Ala Glu Asp Ala Lys Leu
        255                 260
Gln Leu Ser Lys Asp Thr Tyr Asp Asp Asp Leu Asp
265                 270                     275
Asn Leu Leu Ala Gln Ile Gly Asp Gln Tyr Ala Asp
            280                 285
Leu Phe Leu Ala Ala Lys Asn Leu Ser Asp Ala Ile
    290                 295                     300
Leu Leu Ser Asp Ile Leu Arg Val Asn Thr Glu Ile
                305                 310
Thr Lys Ala Pro Leu Ser Ala Ser Met Ile Lys Arg
        315                 320

Tyr Asp Glu His His Gln Asp Leu Thr Leu Leu Lys
325                 330                 335

Ala Leu Val Arg Gln Gln Leu Pro Glu Lys Tyr Lys
        340                 345

Glu Ile Phe Phe Asp Gln Ser Lys Asn Gly Tyr Ala
350                 355                 360

Gly Tyr Ile Asp Gly Gly Ala Ser Gln Glu Glu Phe
            365                 370

Tyr Lys Phe Ile Lys Pro Ile Leu Glu Lys Met Asp
        375                 380

Gly Thr Glu Glu Leu Leu Val Lys Leu Asn Arg Glu
385                 390                 395

Asp Leu Leu Arg Lys Gln Arg Thr Phe Asp Asn Gly
            400                 405

Ser Ile Pro His Gln Ile His Leu Gly Glu Leu His
410                 415                 420

Ala Ile Leu Arg Arg Gln Glu Asp Phe Tyr Pro Phe
            425                 430

Leu Lys Asp Asn Arg Glu Lys Ile Glu Lys Ile Leu
        435                 440

Thr Phe Arg Ile Pro Tyr Tyr Val Gly Pro Leu Ala
445                 450                 455

Arg Gly Asn Ser Arg Phe Ala Trp Met Thr Arg Lys
            460                 465

Ser Glu Glu Thr Ile Thr Pro Trp Asn Phe Glu Glu
        470                 475                 480

Val Val Asp Lys Gly Ala Ser Ala Gln Ser Phe Ile
            485                 490

Glu Arg Met Thr Asn Phe Asp Lys Asn Leu Pro Asn
            495                 500

Glu Lys Val Leu Pro Lys His Ser Leu Leu Tyr Glu
505                 510                 515

Tyr Phe Thr Val Tyr Asn Glu Leu Thr Lys Val Lys
        520                 525

Tyr Val Thr Glu Gly Met Arg Lys Pro Ala Phe Leu
        530                 535                 540

Ser Gly Glu Gln Lys Lys Ala Ile Val Asp Leu Leu
            545                 550

Phe Lys Thr Asn Arg Lys Val Thr Val Lys Gln Leu
        555                 560

Lys Glu Asp Tyr Phe Lys Lys Ile Glu Cys Phe Asp
565                 570                 575

Ser Val Glu Ile Ser Gly Val Glu Asp Arg Phe Asn
            580                 585

Ala Ser Leu Gly Thr Tyr His Asp Leu Leu Lys Ile
            590                 595                 600

Ile Lys Asp Lys Asp Phe Leu Asp Asn Glu Glu Asn
            605                 610

Glu Asp Ile Leu Glu Asp Ile Val Leu Thr Leu Thr
            615                 620

Leu Phe Glu Asp Arg Glu Met Ile Glu Glu Arg Leu
625                 630                 635

Lys Thr Tyr Ala His Leu Phe Asp Asp Lys Val Met
            640                 645

Lys Gln Leu Lys Arg Arg Arg Tyr Thr Gly Trp Gly
                650                 655                 660

Arg Leu Ser Arg Lys Leu Ile Asn Gly Ile Arg Asp
                    665                 670

Lys Gln Ser Gly Lys Thr Ile Leu Asp Phe Leu Lys
                675                 680

Ser Asp Gly Phe Ala Asn Arg Asn Phe Met Gln Leu
685                 690                 695

Ile His Asp Asp Ser Leu Thr Phe Lys Glu Asp Ile
                700                 705

Gln Lys Ala Gln Val Ser Gly Gln Gly Asp Ser Leu
                710                 715                 720

His Glu His Ile Ala Asn Leu Ala Gly Ser Pro Ala
                    725                 730

Ile Lys Lys Gly Ile Leu Gln Thr Val Lys Val Val
                735                 740

Asp Glu Leu Val Lys Val Met Gly Arg His Lys Pro
745                 750                 755

Glu Asn Ile Val Ile Glu Met Ala Arg Glu Asn Gln
                760                 765

Thr Thr Gln Lys Gly Gln Lys Asn Ser Arg Glu Arg
                770                 775                 780

Met Lys Arg Ile Glu Glu Gly Ile Lys Glu Leu Gly
                    785                 790

Ser Gln Ile Leu Lys Glu His Pro Val Glu Asn Thr
                795                 800

Gln Leu Gln Asn Glu Lys Leu Tyr Leu Tyr Tyr Leu
805                 810                 815

Gln Asn Gly Arg Asp Met Tyr Val Asp Gln Glu Leu
                820                 825

Asp Ile Asn Arg Leu Ser Asp Tyr Asp Val Asp His
                830                 835                 840

Ile Val Pro Gln Ser Phe Leu Lys Asp Ser Ile
                    845                 850

Asp Asn Lys Val Leu Thr Arg Ser Asp Lys Asn Arg
                855                 860

Gly Lys Ser Asp Asn Val Pro Ser Glu Glu Val Val
865                 870                 875

Lys Lys Met Lys Asn Tyr Trp Arg Gln Leu Leu Asn
                880                 885

Ala Lys Leu Ile Thr Gln Arg Lys Phe Asp Asn Leu
                890                 895                 900

Thr Lys Ala Glu Arg Gly Gly Leu Ser Glu Leu Asp
                    905                 910

Lys Ala Gly Phe Ile Lys Arg Gln Leu Val Glu Thr
                915                 920

Arg Gln Ile Thr Lys His Val Ala Gln Ile Leu Asp
925                 930                 935

Ser Arg Met Asn Thr Lys Tyr Asp Glu Asn Asp Lys
                940                 945

Leu Ile Arg Glu Val Lys Val Ile Thr Leu Lys Ser
                950                 955                 960

Lys Leu Val Ser Asp Phe Arg Lys Asp Phe Gln Phe
                965                 970

```
Tyr Lys Val Arg Glu Ile Asn Asn Tyr His His Ala
        975                 980

His Asp Ala Tyr Leu Asn Ala Val Val Gly Thr Ala
985                 990                 995

Leu Ile Lys Lys Tyr Pro Lys Leu Glu Ser Glu Phe
            1000                1005

Val Tyr Gly Asp Tyr Lys Val Tyr Asp Val Arg Lys
        1010            1015            1020

Met Ile Ala Lys Ser Glu Gln Glu Ile Gly Lys Ala
            1025                1030

Thr Ala Lys Tyr Phe Phe Tyr Ser Asn Ile Met Asn
        1035                1040

Phe Phe Lys Thr Glu Ile Thr Leu Ala Asn Gly Glu
1045                1050                1055

Ile Arg Lys Arg Pro Leu Ile Glu Thr Asn Gly Glu
            1060                1065

Thr Gly Glu Ile Val Trp Asp Lys Gly Arg Asp Phe
        1070            1075            1080

Ala Thr Val Arg Lys Val Leu Ser Met Pro Gln Val
            1085                1090

Asn Ile Val Lys Lys Thr Glu Val Gln Thr Gly Gly
            1095                1100

Phe Ser Lys Glu Ser Ile Leu Pro Lys Arg Asn Ser
1105                1110                1115

Asp Lys Leu Ile Ala Arg Lys Lys Asp Trp Asp Pro
            1120                1125

Lys Lys Tyr Gly Gly Phe Asp Ser Pro Thr Val Ala
        1130            1135            1140

Tyr Ser Val Leu Val Val Ala Lys Val Glu Lys Gly
                1145                1150

Lys Ser Lys Lys Leu Lys Ser Val Lys Glu Leu Leu
        1155                1160

Gly Ile Thr Ile Met Glu Arg Ser Ser Phe Glu Lys
1165                1170                1175

Asn Pro Ile Asp Phe Leu Glu Ala Lys Gly Tyr Lys
            1180                1185

Glu Val Lys Lys Asp Leu Ile Ile Lys Leu Pro Lys
        1190            1195            1200

Tyr Ser Leu Phe Glu Leu Glu Asn Gly Arg Lys Arg
                1205                1210

Met Leu Ala Ser Ala Gly Glu Leu Gln Lys Gly Asn
            1215                1220

Glu Leu Ala Leu Pro Ser Lys Tyr Val Asn Phe Leu
1225                1230                1235

Tyr Leu Ala Ser His Tyr Glu Lys Leu Lys Gly Ser
                1240                1245

Pro Glu Asp Asn Glu Gln Lys Gln Leu Phe Val Glu
        1250                1255            1260

Gln His Lys His Tyr Leu Asp Glu Ile Ile Glu Gln
                1265                1270

Ile Ser Glu Phe Ser Lys Arg Val Ile Leu Ala Asp
        1275                1280

Ala Asn Leu Asp Lys Val Leu Ser Ala Tyr Asn Lys
1285                1290                1295

His Arg Asp Lys Pro Ile Arg Glu Gln Ala Glu Asn
                1300                1305

Ile Ile His Leu Phe Thr Leu Thr Asn Leu Gly Ala
        1310                1315            1320

Pro Ala Ala Phe Lys Tyr Phe Asp Thr Thr Ile Asp
                1325                1330

Arg Lys Arg Tyr Thr Ser Thr Lys Glu Val Leu Asp
        1335                1340

Ala Thr Leu Ile His Gln Ser Ile Thr Gly Leu Tyr
1345                1350                1355

Glu Thr Arg Ile Asp Leu Ser Gln Leu Gly Gly Asp
            1360                1365
```

In embodiments, the Cas9 molecule is a *S. pyogenes* Cas9 variant of SEQ ID NO: 6611 that includes one or more mutations to positively charged amino acids (e.g., lysine, arginine or histidine) that introduce an uncharged or nonpolar amino acid, e.g., alanine, at said position. In embodiments, the mutation is to one or more positively charged amino acids in the nt-groove of Cas9. In embodiments, the Cas9 molecule is a *S. pyogenes* Cas9 variant of SEQ ID NO: 6611 that includes a mutation at position 855 of SEQ ID NO: 6611, for example a mutation to an uncharged amino acid, e.g., alanine, at position 855 of SEQ ID NO: 6611. In embodiments, the Cas9 molecule has a mutation only at position 855 of SEQ ID NO: 6611, relative to SEQ ID NO: 6611, e.g., to an uncharged amino acid, e.g., alanine. In embodiments, the Cas9 molecule is a *S. pyogenes* Cas9 variant of SEQ ID NO: 6611 that includes a mutation at position 810, a mutation at position 1003, and/or a mutation at position 1060 of SEQ ID NO: 6611, for example a mutation to alanine at position 810, position 1003, and/or position 1060 of SEQ ID NO: 6611. In embodiments, the Cas9 molecule has a mutation only at position 810, position 1003, and position 1060 of SEQ ID NO: 6611, relative to SEQ ID NO: 6611, e.g., where each mutation is to an uncharged amino acid, for example, alanine. In embodiments, the Cas9 molecule is a *S. pyogenes* Cas9 variant of SEQ ID NO: 6611 that includes a mutation at position 848, a mutation at position 1003, and/or a mutation at position 1060 of SEQ ID NO: 6611, for example a mutation to alanine at position 848, position 1003, and/or position 1060 of SEQ ID NO: 6611. In embodiments, the Cas9 molecule has a mutation only at position 848, position 1003, and position 1060 of SEQ ID NO: 6611, relative to SEQ ID NO: 6611, e.g., where each mutation is to an uncharged amino acid, for example, alanine. In embodiments, the Cas9 molecule is a Cas9 molecule as described in Slaymaker et al., Science Express, available online Dec. 1, 2015 at Science DOI: 10.1126/science.aad5227.

In embodiments, the Cas9 molecule is a *S. pyogenes* Cas9 variant of SEQ ID NO: 6611 that includes one or more mutations. In embodiments, the Cas9 variant comprises a mutation at position 80 of SEQ ID NO: 6611, e.g., includes a leucine at position 80 of SEQ ID NO: 6611 (i.e., comprises, e.g., consists of, SEQ ID NO: 6611 with a C80L mutation). In embodiments, the Cas9 variant comprises a mutation at position 574 of SEQ ID NO: 6611, e.g., includes a glutamic acid at position 574 of SEQ ID NO: 6611 (i.e., comprises, e.g., consists of, SEQ ID NO: 6611 with a C574E mutation). In embodiments, the Cas9 variant comprises a mutation at position 80 and a mutation at position 574 of SEQ ID NO: 6611, e.g., includes a leucine at position 80 of SEQ ID NO: 6611, and a glutamic acid at position 574 of SEQ ID NO: 6611 (i.e., comprises, e.g., consists of, SEQ ID NO: 6611 with a C80L mutation and a C574E mutation). Without being bound by theory, it is believed that such mutations improve the solution properties of the Cas9 molecule.

In embodiments, the Cas9 molecule is a *S. pyogenes* Cas9 variant of SEQ ID NO: 6611 that includes one or more mutations. In embodiments, the Cas9 variant comprises a mutation at position 147 of SEQ ID NO: 6611, e.g., includes a tyrosine at position 147 of SEQ ID NO: 6611 (i.e., comprises, e.g., consists of, SEQ ID NO: 6611 with a D147Y mutation). In embodiments, the Cas9 variant comprises a mutation at position 411 of SEQ ID NO: 6611, e.g., includes a threonine at position 411 of SEQ ID NO: 6611 (i.e., comprises, e.g., consists of, SEQ ID NO: 6611 with a P411T mutation). In embodiments, the Cas9 variant comprises a mutation at position 147 and a mutation at position 411 of SEQ ID NO: 6611, e.g., includes a tyrosine at position 147 of SEQ ID NO: 6611, and a threonine at position 411 of SEQ ID NO: 6611 (i.e., comprises, e.g., consists of, SEQ ID NO: 6611 with a D147Y mutation and a P411T mutation). Without being bound by theory, it is believed that such mutations improve the targeting efficiency of the Cas9 molecule, e.g., in yeast.

In embodiments, the Cas9 molecule is a *S. pyogenes* Cas9 variant of SEQ ID NO: 6611 that includes one or more mutations. In embodiments, the Cas9 variant comprises a mutation at position 1135 of SEQ ID NO: 6611, e.g., includes a glutamic acid at position 1135 of SEQ ID NO: 6611 (i.e., comprises, e.g., consists of, SEQ ID NO: 6611 with a D1135E mutation). Without being bound by theory, it is believed that such mutations improve the selectivity of the Cas9 molecule for the NGG PAM sequence versus the NAG PAM sequence.

In embodiments, the Cas9 molecule is a *S. pyogenes* Cas9 variant of SEQ ID NO: 6611 that includes one or more mutations that introduce an uncharged or nonpolar amino acid, e.g., alanine, at certain positions. In embodiments, the Cas9 molecule is a *S. pyogenes* Cas9 variant of SEQ ID NO: 6611 that includes a mutation at position 497, a mutation at position 661, a mutation at position 695 and/or a mutation at position 926 of SEQ ID NO: 6611, for example a mutation to alanine at position 497, position 661, position 695 and/or position 926 of SEQ ID NO: 6611. In embodiments, the Cas9 molecule has a mutation only at position 497, position 661, position 695, and position 926 of SEQ ID NO: 6611, relative to SEQ ID NO: 6611, e.g., where each mutation is to an uncharged amino acid, for example, alanine. Without being bound by theory, it is believed that such mutations reduce the cutting by the Cas9 molecule at off-target sites It will be understood that the mutations described herein to the Cas9 molecule may be combined, and may be combined with any of the fusions or other modifications described herein, and the Cas9 molecule tested in the assays described herein.

Various types of Cas molecules can be used to practice the inventions disclosed herein. In some embodiments, Cas molecules of Type II Cas systems are used. In other embodiments, Cas molecules of other Cas systems are used. For example, Type I or Type III Cas molecules may be used. Exemplary Cas molecules (and Cas systems) are described, e.g., in Haft et al, PLoS COMPUTATIONAL BIOLOGY 2005, 1(6): e60 and Makarova et al, NATURE REVIEW MICROBIOLOGY 2011, 9:467-477, the contents of both references are incorporated herein by reference in their entirety.

In an embodiment, the Cas9 molecule comprises one or more of the following activities: a nickase activity; a double stranded cleavage activity (e.g., an endonuclease and/or exonuclease activity); a helicase activity; or the ability, together with a gRNA molecule, to localize to a target nucleic acid.

Altered Cas9 Molecules

Naturally occurring Cas9 molecules possess a number of properties, including: nickase activity, nuclease activity (e.g., endonuclease and/or exonuclease activity); helicase activity; the ability to associate functionally with a gRNA molecule; and the ability to target (or localize to) a site on a nucleic acid (e.g., PAM recognition and specificity). In an embodiment, a Cas9 molecules can include all or a subset of these properties. In typical embodiments, Cas9 molecules have the ability to interact with a gRNA molecule and, in concert with the gRNA molecule, localize to a site in a nucleic acid. Other activities, e.g., PAM specificity, cleavage activity, or helicase activity can vary more widely in Cas9 molecules.

Cas9 molecules with desired properties can be made in a number of ways, e.g., by alteration of a parental, e.g., naturally occurring Cas9 molecules to provide an altered Cas9 molecule having a desired property. For example, one or more mutations or differences relative to a parental Cas9 molecule can be introduced. Such mutations and differences comprise: substitutions (e.g., conservative substitutions or substitutions of non-essential amino acids); insertions; or deletions. In an embodiment, a Cas9 molecule can comprises one or more mutations or differences, e.g., at least 1, 2, 3, 4, 5, 10, 15, 20, 30, 40 or 50 mutations but less than 200, 100, or 80 mutations relative to a reference Cas9 molecule.

In an embodiment, a mutation or mutations do not have a substantial effect on a Cas9 activity, e.g. a Cas9 activity described herein. In an embodiment, a mutation or mutations have a substantial effect on a Cas9 activity, e.g. a Cas9 activity described herein. In an embodiment, exemplary activities comprise one or more of PAM specificity, cleavage activity, and helicase activity. A mutation(s) can be present, e.g., in: one or more RuvC-like domain, e.g., an N-terminal RuvC-like domain; an HNH-like domain; a region outside the RuvC-like domains and the HNH-like domain. In some embodiments, a mutation(s) is present in an N-terminal RuvC-like domain. In some embodiments, a mutation(s) is present in an HNH-like domain. In some embodiments, mutations are present in both an N-terminal RuvC-like domain and an HNH-like domain.

Whether or not a particular sequence, e.g., a substitution, may affect one or more activity, such as targeting activity, cleavage activity, etc, can be evaluated or predicted, e.g., by evaluating whether the mutation is conservative or by the method described in Section III. In an embodiment, a "non-essential" amino acid residue, as used in the context of a Cas9 molecule, is a residue that can be altered from the wild-type sequence of a Cas9 molecule, e.g., a naturally occurring Cas9 molecule, e.g., an active Cas9 molecule, without abolishing or more preferably, without substantially altering a Cas9 activity (e.g., cleavage activity), whereas changing an "essential" amino acid residue results in a substantial loss of activity (e.g., cleavage activity).

Cas9 Molecules with Altered PAM Recognition or No PAM Recognition

Naturally occurring Cas9 molecules can recognize specific PAM sequences, for example the PAM recognition sequences described above for *S. pyogenes, S. thermophilus, S. mutans, S. aureus* and *N. meningitidis*.

In an embodiment, a Cas9 molecule has the same PAM specificities as a naturally occurring Cas9 molecule. In other embodiments, a Cas9 molecule has a PAM specificity not associated with a naturally occurring Cas9 molecule, or a PAM specificity not associated with the naturally occurring Cas9 molecule to which it has the closest sequence homology. For example, a naturally occurring Cas9 molecule can be altered, e.g., to alter PAM recognition, e.g., to alter the PAM sequence that the Cas9 molecule recognizes to decrease off target sites and/or improve specificity; or eliminate a PAM recognition requirement. In an embodiment, a Cas9 molecule can be altered, e.g., to increase length of PAM recognition sequence and/or improve Cas9 specificity to high level of identity to decrease off target sites and increase specificity. In an embodiment, the length of the PAM recognition sequence is at least 4, 5, 6, 7, 8, 9, 10 or 15 amino acids in length. Cas9 molecules that recognize different PAM sequences and/or have reduced off-target activity can be generated using directed evolution. Exemplary methods and systems that can be used for directed evolution of Cas9 molecules are described, e.g., in Esvelt el al, Nature 2011, 472(7344): 499-503. Candidate Cas9 molecules can be evaluated, e.g., by methods described herein.

Non-Cleaving and Modified-Cleavage Cas9 Molecules

In an embodiment, a Cas9 molecule comprises a cleavage property that differs from naturally occurring Cas9 molecules, e.g., that differs from the naturally occurring Cas9 molecule having the closest homology. For example, a Cas9 molecule can differ from naturally occurring Cas9 molecules, e.g., a Cas9 molecule of S. pyogenes, as follows: its ability to modulate, e.g., decreased or increased, cleavage of a double stranded break (endonuclease and/or exonuclease activity), e.g., as compared to a naturally occurring Cas9 molecule (e.g., a Cas9 molecule of S. pyogenes); its ability to modulate, e.g., decreased or increased, cleavage of a single strand of a nucleic acid, e.g., a non-complimentary strand of a nucleic acid molecule or a complementary strand of a nucleic acid molecule (nickase activity), e.g., as compared to a naturally occurring Cas9 molecule (e.g., a Cas9 molecule of S. pyogenes); or the ability to cleave a nucleic acid molecule, e.g., a double stranded or single stranded nucleic acid molecule, can be eliminated.

Modified Cleavage Active Cas9 Molecules

In an embodiment, an active Cas9 molecule comprises one or more of the following activities: cleavage activity associated with an N-terminal RuvC-like domain; cleavage activity associated with an HNH-like domain; cleavage activity associated with an HNH domain and cleavage activity associated with an N-terminal RuvC-like domain.

In an embodiment, the Cas9 molecule is a Cas9 nickase, e.g., cleaves only a single strand of DNA. In an embodiment, the Cas9 nickase includes a mutation at position 10 and/or a mutation at position 840 of SEQ ID NO: 6611, e.g., comprises a D10A and/or H840A mutation to SEQ ID NO: 6611.

Non-Cleaving Inactive Cas9 Molecules

In an embodiment, the altered Cas9 molecule is an inactive Cas9 molecule which does not cleave a nucleic acid molecule (either double stranded or single stranded nucleic acid molecules) or cleaves a nucleic acid molecule with significantly less efficiency, e.g., less than 20, 10, 5, 1 or 0.1% of the cleavage activity of a reference Cas9 molecule, e.g., as measured by an assay described herein. The reference Cas9 molecule can by a naturally occurring unmodified Cas9 molecule, e.g., a naturally occurring Cas9 molecule such as a Cas9 molecule of S. pyogenes, S. thermophilus, S. aureus or N. meningitidis. In an embodiment, the reference Cas9 molecule is the naturally occurring Cas9 molecule having the closest sequence identity or homology. In an embodiment, the inactive Cas9 molecule lacks substantial cleavage activity associated with an N-terminal RuvC-like domain and cleavage activity associated with an HNH-like domain.

In an embodiment, the Cas9 molecule is dCas9. Tsai et al. (2014), Nat. Biotech. 32:569-577.

A catalytically inactive Cas9 molecule may be fused with a transcription repressor. An inactive Cas9 fusion protein complexes with a gRNA and localizes to a DNA sequence specified by gRNA's targeting domain, but, unlike an active Cas9, it will not cleave the target DNA. Fusion of an effector domain, such as a transcriptional repression domain, to an inactive Cas9 enables recruitment of the effector to any DNA site specified by the gRNA. Site specific targeting of a Cas9 fusion protein to a promoter region of a gene can block or affect polymerase binding to the promoter region, for example, a Cas9 fusion with a transcription factor (e.g., a transcription activator) and/or a transcriptional enhancer binding to the nucleic acid to increase or inhibit transcription activation. Alternatively, site specific targeting of a Cas9– fusion to a transcription repressor to a promoter region of a gene can be used to decrease transcription activation.

Transcription repressors or transcription repressor domains that may be fused to an inactive Cas9 molecule can include ruppel associated box (KRAB or SKD), the Mad mSIN3 interaction domain (SID) or the ERF repressor domain (ERD).

In another embodiment, an inactive Cas9 molecule may be fused with a protein that modifies chromatin. For example, an inactive Cas9 molecule may be fused to heterochromatin protein 1 (HP1), a histone lysine methyltransferase (e.g., SUV39H1, SUV39H2, G9A, ESET/SETDB1, Pr-SET7/8, SUV4-20H 1,RIZ1), a histone lysine demethylates (e.g., LSD1/BHC1 10, SpLsdl/Sw,l/Safl 10, Su(var)3-3, JMJD2A/JHDM3A, JMJD2B, JMJD2C/GASC1, JMJD2D, Rph1, JARID 1 A/RBP2, JARI DIB/PLU-I, JAR1D 1C/SMCX, JARID1 D/SMCY, Lid, Jhn2, Jmj2), a histone lysine deacetylases (e.g., HDAC1, HDAC2, HDAC3, HDAC8, Rpd3, Hos 1, Cir6, HDAC4, HDAC5, HDAC7, HDAC9, Hdal, Cir3, SIRT1, SIRT2, Sir2, Hst1, Hst2, Hst3, Hst4, HDAC11) and a DNA methylases (DNMT1, DNMT2a/DMNT3b, MET1). An inactive Cas9-chromatin modifying molecule fusion protein can be used to alter chromatin status to reduce expression a target gene.

The heterologous sequence (e.g., the transcription repressor domain) may be fused to the N- or C-terminus of the inactive Cas9 protein. In an alternative embodiment, the heterologous sequence (e.g., the transcription repressor domain) may be fused to an internal portion (i.e., a portion other than the N-terminus or C-terminus) of the inactive Cas9 protein.

The ability of a Cas9 molecule/gRNA molecule complex to bind to and cleave a target nucleic acid can be evaluated, e.g., by the methods described herein in Section III. The activity of a Cas9 molecule, e.g., either an active Cas9 or a inactive Cas9, alone or in a complex with a gRNA molecule may also be evaluated by methods well-known in the art, including, gene expression assays and chromatin-based assays, e.g., chromatin immunoprecipitation (ChiP) and chromatin in vivo assay (CiA).

Other Cas9 Molecule Fusions

In embodiments, the Cas9 molecule, e.g, a Cas9 of S. pyogenes, may additionally comprise one or more amino acid sequences that confer additional activity.

In some aspects, the Cas9 molecule may comprise one or more nuclear localization sequences (NLSs), such as at least 1, 2, 3, 4, 5, 6, 7, 8, 9, 10, or more NLSs. In some embodiments, the Cas9 molecule comprises at least 1, 2, 3, 4, 5, 6, 7, 8, 9, 10, or more NLSs at or near the amino-terminus, at least 1, 2, 3, 4, 5, 6, 7, 8, 9, 10, or more NLSs at or near the carboxy-terminus, or a combination of these (e.g. one or more NLS at the amino-terminus and one or more NLS at the carboxy terminus). When more than one NLS is present, each may be selected independently of the others, such that a single NLS may be present in more than one copy and/or in combination with one or more other NLSs present in one or more copies. In some embodiments, an NLS is considered near the N- or C-terminus when the nearest amino acid of the NLS is within about 1, 2, 3, 4, 5, 10, 15, 20, 25, 30, 40, 50, or more amino acids along the polypeptide chain from the N- or C-terminus. Typically, an NLS consists of one or more short sequences of positively charged lysines or arginines exposed on the protein surface, but other types of NLS are known. Non-limiting examples of NLSs include an NLS sequence comprising or derived from: the NLS of the SV40 virus large T-antigen, having the amino acid sequence PKKKRKV (SEQ ID NO: 6612); the NLS from nucleoplasmin (e.g. the nucleoplasmin bipartite NLS with the sequence ICRPAATKKAGQAKICICK. (SEQ ID NO: 6613); the c-myc NLS having the amino acid sequence PAAKRVKLD (SEQ ID NO: 6614) or RQRRNELKRSP (SEQ ID NO: 6615); the hRNPA1 M9 NLS having the sequence NQSSNFGPMKGGNFGGRSSGPYGGGGQYFAKPRNQGGY (SEQ ID NO: 6616); the sequence RMRIZFKNKGKDTAELRRRRVEVSVELRKAKKDEQILKRRNV (SEQ ID NO: 6617) of the IBB domain from importin-alpha; the sequences VSRKRPRP (SEQ ID NO: 6618) and PPKKARED (SEQ ID NO: 6619) of the myoma T protein; the sequence PQPKKKPL (SEQ ID NO: 6620) of human p53; the sequence SALIKKKKKMAP (SEQ ID NO: 6621) of mouse c-abl IV; the sequences DRLRR (SEQ ID NO: 6622) and PKQKKRK (SEQ ID NO: 6623) of the influenza virus NS1; the sequence RKLKKKIKKL (SEQ ID NO: 6624) of the Hepatitis virus delta antigen; the sequence REKKKFLKRR (SEQ ID NO: 6625) of the mouse Mx1 protein; the sequence KRKGDEVDGVDEVAKKKSKK (SEQ ID NO: 6626) of the human poly(ADP-ribose) polymerase; and the sequence RKCLQAGMNLEARKTKK (SEQ ID NO: 6627) of the steroid hormone receptors (human) glucocorticoid. Other suitable NLS sequences are known in the art (e.g., Sorokin, Biochemistry (Moscow) (2007) 72:13, 1439-1457; Lange J Biol Chem. (2007) 282:8, 5101-5).

In some aspects, the Cas9 molecule may comprise one or more amino acid sequences that allow the Cas9 molecule to be specifically recognized, for example a tag. In one embodiment, the tag is a Histidine tag, e.g., a histidine tag comprising at least 3, 4, 5, 6, 7, 8, 9, 10 or more histidine amino acids (SEQ ID NO: 10800). In embodiments, the histidine tag is a His6 tag (six histidines) (SEQ ID NO: 10795). In other embodiments, the histidine tag is a His8 tag (eight histidines). In embodiments, the histidine tag may be separated from one or more other portions of the Cas9 molecule by a linker. In embodiments, the linker is GGS. An example of such a fusion is the Cas9 molecule iProt106520.

In some aspects, the Cas9 molecule may comprise one or more amino acid sequences that are recognized by a protease (e.g., comprise a protease cleavage site). In embodiments, the cleavage site is the tobacco etch virus (TEV) cleavage site, e.g., comprises the sequence ENLYFQG (SEQ ID NO: 7810). In some aspects the protease cleavage site, e.g., the TEV cleavage site is disposed between a tag, e.g., a His tag, e.g., a His6 (SEQ ID NO: 10795) or His8 tag (SEQ ID NO: 10796), and the remainder of the Cas9 molecule. Without being bound by theory it is believed that such introduction will allow for the use of the tag for, e.g., purification of the Cas9 molecule, and then subsequent cleavage so the tag does not interfere with the Cas9 molecule function.

In embodiments, the Cas9 molecule (e.g., a Cas9 molecule as described herein) comprises an N-terminal NLS, and a C-terminal NLS (e.g., comprises, from N- to C-terminal NLS-Cas9-NLS), e.g., wherein each NLS is an SV40 NLS (PKKKRKV (SEQ ID NO: 6612)). In embodiments, the Cas9 molecule (e.g., a Cas9 molecule as described herein) comprises an N-terminal NLS, a C-terminal NLS, and a C-terminal His6 tag (SEQ ID NO: 10795) (e.g., comprises, from N- to C-terminal NLS-Cas9-NLS-His tag), e.g., wherein each NLS is an SV40 NLS (PKKKRKV (SEQ ID NO: 6612)). In embodiments, the Cas9 molecule (e.g., a Cas9 molecule as described herein) comprises an N-terminal His tag (e.g., His6 tag (SEQ ID NO: 10795)), an N-terminal NLS, and a C-terminal NLS (e.g., comprises, from N- to C-terminal His tag-NLS-Cas9-NLS), e.g., wherein each NLS is an SV40 NLS (PKKKRKV (SEQ ID NO: 6612)). In embodiments, the Cas9 molecule (e.g., a Cas9 molecule as described herein) comprises an N-terminal NLS and a C-terminal His tag (e.g., His6 tag (SEQ ID NO: 10795)) (e.g., comprises from N- to C-terminal His tag-Cas9-NLS), e.g., wherein the NLS is an SV40 NLS (PKKKRKV (SEQ ID NO: 6612)). In embodiments, the Cas9 molecule (e.g., a Cas9 molecule as described herein) comprises an N-terminal His tag (e.g., His6 tag (SEQ ID NO: 10795)) and a C-terminal NLS (e.g., comprises from N- to C-terminal NLS-Cas9-His tag), e.g., wherein the NLS is an SV40 NLS (PKKKRKV (SEQ ID NO: 6612)). In embodiments, the Cas9 molecule (e.g., a Cas9 molecule as described herein) comprises an N-terminal His tag (e.g., His8 tag (SEQ ID NO: 10796)), an N-terminal cleavage domain (e.g., a tobacco etch virus (TEV) cleavage domain (e.g., comprises the sequence ENLYFQG (SEQ ID NO: 7810))), an N-terminal NLS (e.g., an SV40 NLS; SEQ ID NO: 6612), and a C-terminal NLS (e.g., an SV40 NLS; SEQ ID NO: 6612) (e.g., comprises from N- to C-terminal His tag-TEV-NLS-Cas9-NLS). In any of the aforementioned embodiments the Cas9 has the sequence of SEQ ID NO: 6611. Alternatively, in any of the aforementioned embodiments, the Cas9 has a sequence of a Cas9 variant of SEQ ID NO: 6611, e.g., as described herein. In any of the aforementioned embodiments, the Cas9 molecule comprises a linker between the His tag and another portion of the molecule, e.g., a GGS linker. Amino acid sequences of exemplary Cas9 molecules described above are provided below. "iProt" identifiers match those in FIG. 60.

```
iProt105026 (also referred to as iProt106154, iProt106331, iProt106545,
and PID426303, depending on the preparation of the protein) (SEQ ID NO: 7821):
MAPKKKRKVD KKYSIGLDIG TNSVGWAVIT DEYKVPSKKF KVLGNTDRHS IKKNLIGALL

FDSGETAEAT RLKRTARRRY TRRKNRICYL QEIFSNEMAK VDDSFFHRLE ESFLVEEDKK
```

```
HERHPIFGNI VDEVAYHEKY PTIYHLRKKL VDSTDKADLR LIYLALAHMI KFRGHFLIEG
DLNPDNSDVD KLFIQLVQTY NQLFEENPIN ASGVDAKAIL SARLSKSRRL ENLIAQLPGE
KKNGLFGNLI ALSLGLTPNF KSNFDLAEDA KLQLSKDTYD DDLDNLLAQI GDQYADLFLA
AKNLSDAILL SDILRVNTEI TKAPLSASMI KRYDEHHQDL TLLKALVRQQ LPEKYKEIFF
DQSKNGYAGY IDGGASQEEF YKFIKPILEK MDGTEELLVK LNREDLLRKQ RTFDNGSIPH
QIHLGELHAI LRRQEDFYPF LKDNREKIEK ILTFRIPYYV GPLARGNSRF AWMTRKSEET
ITPWNFEEVV DKGASAQSFI ERMTNFDKNL PNEKVLPKHS LLYEYFTVYN ELTKVKYVTE
GMRKPAFLSG EQKKAIVDLL FKTNRKVTVK QLKEDYFKKI ECFDSVEISG VEDRFNASLG
TYHDLLKIIK DKDFLDNEEN EDILEDIVLT LTLFEDREMI EERLKTYAHL FDDKVMKQLK
RRRYTGWGRL SRKLINGIRD KQSGKTILDF LKSDGFANRN FMQLIHDDSL TFKEDIQKAQ
VSGQGDSLHE HIANLAGSPA IKKGILQTVK VVDELVKVMG RHKPENIVIE MARENQTTQK
GQKNSRERMK RIEEGIKELG SQILKEHPVE NTQLQNEKLY LYYLQNGRDM YVDQELDINR
LSDYDVDHIV PQSFLKDDSI DNKVLTRSDK NRGKSDNVPS EEVVKKMKNY WRQLLNAKLI
TQRKFDNLTK AERGGLSELD KAGFIKRQLV ETRQITKHVA QILDSRMNTK YDENDKLIRE
VKVITLKSKL VSDFRKDFQF YKVREINNYH HAHDAYLNAV VGTALIKKYP KLESEFVYGD
YKVYDVRKMI AKSEQEIGKA TAKYFFYSNI MNFFKTEITL ANGEIRKRPL IETNGETGEI
VWDKGRDFAT VRKVLSMPQV NIVKKTEVQT GGFSKESILP KRNSDKLIAR KKDWDPKKYG
GFDSPTVAYS VLVVAKVEKG KSKKLKSVKE LLGITIMERS SFEKNPIDFL EAKGYKEVKK
DLIIKLPKYS LFELENGRKR MLASAGELQK GNELALPSKY VNFLYLASHY EKLKGSPEDN
EQKQLFVEQH KHYLDEIIEQ ISEFSKRVIL ADANLDKVLS AYNKHRDKPI REQAENIIHL
FTLTNLGAPA AFKYFDTTID RKRYTSTKEV LDATLIHQSI TGLYETRIDL SQLGGDSRAD
PKKKRKVHHH HHH iProt106518 (SEQ ID NO: 7822):
MAPKKKRKVD KKYSIGLDIG TNSVGWAVIT DEYKVPSKKF KVLGNTDRHS IKKNLIGALL
FDSGETAEAT RLKRTARRRY TRRKNRILYL QEIFSNEMAK VDDSFFHRLE ESFLVEEDKK
HERHPIFGNI VDEVAYHEKY PTIYHLRKKL VDSTDKADLR LIYLALAHMI KFRGHFLIEG
DLNPDNSDVD KLFIQLVQTY NQLFEENPIN ASGVDAKAIL SARLSKSRRL ENLIAQLPGE
KKNGLFGNLI ALSLGLTPNF KSNFDLAEDA KLQLSKDTYD DDLDNLLAQI GDQYADLFLA
AKNLSDAILL SDILRVNTEI TKAPLSASMI KRYDEHHQDL TLLKALVRQQ LPEKYKEIFF
DQSKNGYAGY IDGGASQEEF YKFIKPILEK MDGTEELLVK LNREDLLRKQ RTFDNGSIPH
QIHLGELHAI LRRQEDFYPF LKDNREKIEK ILTFRIPYYV GPLARGNSRF AWMTRKSEET
ITPWNFEEVV DKGASAQSFI ERMTNFDKNL PNEKVLPKHS LLYEYFTVYN ELTKVKYVTE
GMRKPAFLSG EQKKAIVDLL FKTNRKVTVK QLKEDYFKKI EEFDSVEISG VEDRFNASLG
TYHDLLKIIK DKDFLDNEEN EDILEDIVLT LTLFEDREMI EERLKTYAHL FDDKVMKQLK
RRRYTGWGRL SRKLINGIRD KQSGKTILDF LKSDGFANRN FMQLIHDDSL TFKEDIQKAQ
VSGQGDSLHE HIANLAGSPA IKKGILQTVK VVDELVKVMG RHKPENIVIE MARENQTTQK
GQKNSRERMK RIEEGIKELG SQILKEHPVE NTQLQNEKLY LYYLQNGRDM YVDQELDINR
LSDYDVDHIV PQSFLKDDSI DNKVLTRSDK NRGKSDNVPS EEVVKKMKNY WRQLLNAKLI
TQRKFDNLTK AERGGLSELD KAGFIKRQLV ETRQITKHVA QILDSRMNTK YDENDKLIRE
VKVITLKSKL VSDFRKDFQF YKVREINNYH HAHDAYLNAV VGTALIKKYP KLESEFVYGD
YKVYDVRKMI AKSEQEIGKA TAKYFFYSNI MNFFKTEITL ANGEIRKRPL IETNGETGEI
```

-continued

```
VWDKGRDFAT VRKVLSMPQV NIVKKTEVQT GGFSKESILP KRNSDKLIAR KKDWDPKKYG

GFDSPTVAYS VLVVAKVEKG KSKKLKSVKE LLGITIMERS SFEKNPIDFL EAKGYKEVKK

DLIIKLPKYS LFELENGRKR MLASAGELQK GNELALPSKY VNFLYLASHY EKLKGSPEDN

EQKQLFVEQH KHYLDEIIEQ ISEFSKRVIL ADANLDKVLS AYNKHRDKPI REQAENIIHL

FTLTNLGAPA AFKYFDTTID RKRYTSTKEV LDATLIHQSI TGLYETRIDL SQLGGDSRAD

PKKKRKVHHH HHH iProt106519 (SEQ ID NO: 7823):
MGSSHHHHHH HHENLYFQGS MDKKYSIGLD IGTNSVGWAV ITDEYKVPSK KFKVLGNTDR

HSIKKNLIGA LLFDSGETAE ATRLKRTARR RYTRRKNRIC YLQEIFSNEM AKVDDSFFHR

LEESFLVEED KKHERHPIFG NIVDEVAYHE KYPTIYHLRK KLVDSTDKAD LRLIYLALAH

MIKFRGHFLI EGDLNPDNSD VDKLFIQLVQ TYNQLFEENP INASGVDAKA ILSARLSKSR

RLENLIAQLP GEKKNGLFGN LIALSLGLTP NFKSNFDLAE DAKLQLSKDT YDDDLDNLLA

QIGDQYADLF LAAKNLSDAI LLSDILRVNT EITKAPLSAS MIKRYDEHHQ DLTLLKALVR

QQLPEKYKEI FFDQSKNGYA GYIDGGASQE EFYKFIKPIL EKMDGTEELL VKLNREDLLR

KQRTFDNGSI PHQIHLGELH AILRRQEDFY PFLKDNREKI EKILTFRIPY YVGPLARGNS

RFAWMTRKSE ETITPWNFEE VVDKGASAQS FIERMTNFDK NLPNEKVLPK HSLLYEYFTV

YNELTKVKYV TEGMRKPAFL SGEQKKAIVD LLFKTNRKVT VKQLKEDYFK KIECFDSVEI

SGVEDRFNAS LGTYHDLLKI IKDKDFLDNE ENEDILEDIV LTLTLFEDRE MIEERLKTYA

HLFDDKVMKQ LKRRRYTGWG RLSRKLINGI RDKQSGKTIL DFLKSDGFAN RNFMQLIHDD

SLTFKEDIQK AQVSGQGDSL HEHIANLAGS PAIKKGILQT VKVVDELVKV MGRHKPENIV

IEMARENQTT QKGQKNSRER MKRIEEGIKE LGSQILKEHP VENTQLQNEK LYLYYLQNGR

DMYVDQELDI NRLSDYDVDH IVPQSFLKDD SIDNKVLTRS DKNRGKSDNV PSEEVVKKMK

NYWRQLLNAK LITQRKFDNL TKAERGGLSE LDKAGFIKRQ LVETRQITKH VAQILDSRMN

TKYDENDKLI REVKVITLKS KLVSDFRKDF QFYKVREINN YHHAHDAYLN AVVGTALIKK

YPKLESEFVY GDYKVYDVRK MIAKSEQEIG KATAKYFFYS NIMNFFKTEI TLANGEIRKR

PLIETNGETG EIVWDKGRDF ATVRKVLSMP QVNIVKKTEV QTGGFSKESI LPKRNSDKLI

ARKKDWDPKK YGGFDSPTVA YSVLVVAKVE KGKSKKLKSV KELLGITIME RSSFEKNPID

FLEAKGYKEV KKDLIIKLPK YSLFELENGR KRMLASAGEL QKGNELALPS KYVNFLYLAS

HYEKLKGSPE DNEQKQLFVE QHKHYLDEII EQISEFSKRV ILADANLDKV LSAYNKHRDK

PIREQAENII HLFTLTNLGA PAAFKYFDTT IDRKRYTSTK EVLDATLIHQ SITGLYETRI

DLSQLGGDGG GSPKKKRKV iProt106520 (SEQ ID NO: 7824):
MAHHHHHHGG SPKKKRKVDK KYSIGLDIGT NSVGWAVITD EYKVPSKKFK VLGNTDRHSI

KKNLIGALLF DSGETAEATR LKRTARRRYT RRKNRICYLQ EIFSNEMAKV DDSFFHRLEE

SFLVEEDKKH ERHPIFGNIV DEVAYHEKYP TIYHLRKKLV DSTDKADLRL IYLALAHMIK

FRGHFLIEGD LNPDNSDVDK LFIQLVQTYN QLFEENPINA SGVDAKAILS ARLSKSRRLE

NLIAQLPGEK KNGLFGNLIA LSLGLTPNFK SNFDLAEDAK LQLSKDTYDD DLDNLLAQIG

DQYADLFLAA KNLSDAILLS DILRVNTEIT KAPLSASMIK RYDEHHQDLT LLKALVRQQL

PEKYKEIFFD QSKNGYAGYI DGGASQEEFY KFIKPILEKM DGTEELVKL NREDLLRKQR

TFDNGSIPHQ IHLGELHAIL RRQEDFYPFL KDNREKIEKI LTFRIPYYVG PLARGNSRFA

WMTRKSEETI TPWNFEEVVD KGASAQSFIE RMTNFDKNLP NEKVLPKHSL LYEYFTVYNE

LTKVKYVTEG MRKPAFLSGE QKKAIVDLLF KTNRKVTVKQ LKEDYFKKIE CFDSVEISGV
```

```
EDRFNASLGT YHDLLKIIKD KDFLDNEENE DILEDIVLTL TLFEDREMIE ERLKTYAHLF

DDKVMKQLKR RRYTGWGRLS RKLINGIRDK QSGKTILDFL KSDGFANRNF MQLIHDDSLT

FKEDIQKAQV SGQGDSLHEH IANLAGSPAI KKGILQTVKV VDELVKVMGR HKPENIVIEM

ARENQTTQKG QKNSRERMKR IEEGIKELGS QILKEHPVEN TQLQNEKLYL YYLQNGRDMY

VDQELDINRL SDYDVDHIVP QSFLKDDSID NKVLTRSDKN RGKSDNVPSE EVVKKMKNYW

RQLLNAKLIT QRKFDNLTKA ERGGLSELDK AGFIKRQLVE TRQITKHVAQ ILDSRMNTKY

DENDKLIREV KVITLKSKLV SDFRKDFQFY KVREINNYHH AHDAYLNAVV GTALIKKYPK

LESEFVYGDY KVYDVRKMIA KSEQEIGKAT AKYFFYSNIM NFFKTEITLA NGEIRKRPLI

ETNGETGEIV WDKGRDFATV RKVLSMPQVN IVKKTEVQTG GFSKESILPK RNSDKLIARK

KDWDPKKYGG FDSPTVAYSV LVVAKVEKGK SKKLKSVKEL LGITIMERSS FEKNPIDFLE

AKGYKEVKKD LIIKLPKYSL FELENGRKRM LASAGELQKG NELALPSKYV NFLYLASHYE

KLKGSPEDNE QKQLFVEQHK HYLDEIIEQI SEFSKRVILA DANLDKVLSA YNKHRDKPIR

EQAENIIHLF TLTNLGAPAA FKYFDTTIDR KRYTSTKEVL DATLIHQSIT GLYETRIDLS

QLGGDSRADP KKKRKV iProt106521 (SEQ ID NO: 7825):
MAPKKKRKVD KKYSIGLDIG TNSVGWAVIT DEYKVPSKKF KVLGNTDRHS IKKNLIGALL

FDSGETAEAT RLKRTARRRY TRRKNRICYL QEIFSNEMAK VDDSFFHRLE ESFLVEEDKK

HERHPIFGNI VDEVAYHEKY PTIYHLRKKL VDSTDKADLR LIYLALAHMI KFRGHFLIEG

DLNPDNSDVD KLFIQLVQTY NQLFEENPIN ASGVDAKAIL SARLSKSRRL ENLIAQLPGE

KKNGLFGNLI ALSLGLTPNF KSNFDLAEDA KLQLSKDTYD DDLDNLLAQI GDQYADLFLA

AKNLSDAILL SDILRVNTEI TKAPLSASMI KRYDEHHQDL TLLKALVRQQ LPEKYKEIFF

DQSKNGYAGY IDGGASQEEF YKFIKPILEK MDGTEELLVK LNREDLLRKQ RTFDNGSIPH

QIHLGELHAI LRRQEDFYPF LKDNREKIEK ILTFRIPYYV GPLARGNSRF AWMTRKSEET

ITPWNFEEVV DKGASAQSFI ERMTNFDKNL PNEKVLPKHS LLYEYFTVYN ELTKVKYVTE

GMRKPAFLSG EQKKAIVDLL FKTNRKVTVK QLKEDYFKKI ECFDSVEISG VEDRFNASLG

TYHDLLKIIK DKDFLDNEEN EDILEDIVLT LTLFEDREMI EERLKTYAHL FDDKVMKQLK

RRRYTGWGRL SRKLINGIRD KQSGKTILDF LKSDGFANRN FMQLIHDDSL TFKEDIQKAQ

VSGQGDSLHE HIANLAGSPA IKKGILQTVK VVDELVKVMG RHKPENIVIE MARENQTTQK

GQKNSRERMK RIEEGIKELG SQILKEHPVE NTQLQNEKLY LYYLQNGRDM YVDQELDINR

LSDYDVDHIV PQSFLKDDSI DNKVLTRSDK NRGKSDNVPS EEVVKKMKNY WRQLLNAKLI

TQRKFDNLTK AERGGLSELD KAGFIKRQLV ETRQITKHVA QILDSRMNTK YDENDKLIRE

VKVITLKSKL VSDFRKDFQF YKVREINNYH AHDAYLNAV VGTALIKKYP KLESEFVYGD

YKVYDVRKMI AKSEQEIGKA TAKYFFYSNI MNFFKTEITL ANGEIRKRPL IETNGETGEI

VWDKGRDFAT VRKVLSMPQV NIVKKTEVQT GGFSKESILP KRNSDKLIAR KKDWDPKKYG

GFDSPTVAYS VLVVAKVEKG KSKKLKSVKE LLGITIMERS SFEKNPIDFL EAKGYKEVKK

DLIIKLPKYS LFELENGRKR MLASAGELQK GNELALPSKY VNFLYLASHY EKLKGSPEDN

EQKQLFVEQH KHYLDEIIEQ ISEFSKRVIL ADANLDKVLS AYNKHRDKPI REQAENIIHL

FTLTNLGAPA AFKYFDTTID RKRYTSTKEV LDATLIHQSI TGLYETRIDL SQLGGDSRAD

HHHHHH
``` iProt106522 (SEQ ID NO: 7826):
MAHHHHHGG SDKKYSIGLD IGTNSVGWAV ITDEYKVPSK KFKVLGNTDR HSIKKNLIGA

LLFDSGETAE ATRLKRTARR RYTRRKNRIC YLQEIFSNEM AKVDDSFFHR LEESFLVEED

KKHERHPIFG NIVDEVAYHE KYPTIYHLRK KLVDSTDKAD LRLIYLALAH MIKFRGHFLI

EGDLNPDNSD VDKLFIQLVQ TYNQLFEENP INASGVDAKA ILSARLSKSR RLENLIAQLP

GEKKNGLFGN LIALSLGLTP NFKSNFDLAE DAKLQLSKDT YDDDLDNLLA QIGDQYADLF

LAAKNLSDAI LLSDILRVNT EITKAPLSAS MIKRYDEHHQ DLTLLKALVR QQLPEKYKEI

FFDQSKNGYA GYIDGGASQE EFYKFIKPIL EKMDGTEELL VKLNREDLLR KQRTFDNGSI

PHQIHLGELH AILRRQEDFY PFLKDNREKI EKILTFRIPY YVGPLARGNS RFAWMTRKSE

ETITPWNFEE VVDKGASAQS FIERMTNFDK NLPNEKVLPK HSLLYEYFTV YNELTKVKYV

TEGMRKPAFL SGEQKKAIVD LLFKTNRKVT VKQLKEDYFK KIECFDSVEI SGVEDRFNAS

LGTYHDLLKI IKDKDFLDNE ENEDILEDIV LTLTLFEDRE MIEERLKTYA HLFDDKVMKQ

LKRRRYTGWG RLSRKLINGI RDKQSGKTIL DFLKSDGFAN RNFMQLIHDD SLTFKEDIQK

AQVSGQGDSL HEHIANLAGS PAIKKGILQT VKVVDELVKV MGRHKPENIV IEMARENQTT

QKGQKNSRER MKRIEEGIKE LGSQILKEHP VENTQLQNEK LYLYYLQNGR DMYVDQELDI

NRLSDYDVDH IVPQSFLKDD SIDNKVLTRS DKNRGKSDNV PSEEVVKKMK NYWRQLLNAK

LITQRKFDNL TKAERGGLSE LDKAGFIKRQ LVETRQITKH VAQILDSRMN TKYDENDKLI

REVKVITLKS KLVSDFRKDF QFYKVREINN YHHAHDAYLN AVVGTALIKK YPKLESEFVY

GDYKVYDVRK MIAKSEQEIG KATAKYFFYS NIMNFFKTEI TLANGEIRKR PLIETNGETG

EIVWDKGRDF ATVRKVLSMP QVNIVKKTEV QTGGFSKESI LPKRNSDKLI ARKKDWDPKK

YGGFDSPTVA YSVLVVAKVE KGKSKKLKSV KELLGITIME RSSFEKNPID FLEAKGYKEV

KKDLIIKLPK YSLFELENGR KRMLASAGEL QKGNELALPS KYVNFLYLAS HYEKLKGSPE

DNEQKQLFVE QHKHYLDEII EQISEFSKRV ILADANLDKV LSAYNKHRDK PIREQAENII

HLFTLTNLGA PAAFKYFDTT IDRKRYTSTK EVLDATLIHQ SITGLYETRI DLSQLGGDSR

ADPKKKRKV iProt106658 (SEQ ID NO: 7827):
MGSSHHHHHH HHENLYFQGS MDKKYSIGLD IGTNSVGWAV ITDEYKVPSK KFKVLGNTDR

HSIKKNLIGA LLFDSGETAE ATRLKRTARR RYTRRKNRIC YLQEIFSNEM AKVDDSFFHR

LEESFLVEED KKHERHPIFG NIVDEVAYHE KYPTIYHLRK KLVDSTDKAD LRLIYLALAH

MIKFRGHFLI EGDLNPDNSD VDKLFIQLVQ TYNQLFEENP INASGVDAKA ILSARLSKSR

RLENLIAQLP GEKKNGLFGN LIALSLGLTP NFKSNFDLAE DAKLQLSKDT YDDDLDNLLA

QIGDQYADLF LAAKNLSDAI LLSDILRVNT EITKAPLSAS MIKRYDEHHQ DLTLLKALVR

QQLPEKYKEI FFDQSKNGYA GYIDGGASQE EFYKFIKPIL EKMDGTEELL VKLNREDLLR

KQRTFDNGSI PHQIHLGELH AILRRQEDFY PFLKDNREKI EKILTFRIPY YVGPLARGNS

RFAWMTRKSE ETITPWNFEE VVDKGASAQS FIERMTNFDK NLPNEKVLPK HSLLYEYFTV

YNELTKVKYV TEGMRKPAFL SGEQKKAIVD LLFKTNRKVT VKQLKEDYFK KIECFDSVEI

SGVEDRFNAS LGTYHDLLKI IKDKDFLDNE ENEDILEDIV LTLTLFEDRE MIEERLKTYA

HLFDDKVMKQ LKRRRYTGWG RLSRKLINGI RDKQSGKTIL DFLKSDGFAN RNFMQLIHDD

SLTFKEDIQK AQVSGQGDSL HEHIANLAGS PAIKKGILQT VKVVDELVKV MGRHKPENIV

IEMARENQTT QKGQKNSRER MKRIEEGIKE LGSQILKEHP VENTQLQNEK LYLYYLQNGR

DMYVDQELDI NRLSDYDVDH IVPQSFLKDD SIDNKVLTRS DKNRGKSDNV PSEEVVKKMK

-continued

NYWRQLLNAK LITQRKFDNL TKAERGGLSE LDKAGFIKRQ LVETRQITKH VAQILDSRMN

TKYDENDKLI REVKVITLKS KLVSDFRKDF QFYKVREINN YHHAHDAYLN AVVGTALIKK

YPKLESEFVY GDYKVYDVRK MIAKSEQEIG KATAKYFFYS NIMNFFKTEI TLANGEIRKR

PLIETNGETG EIVWDKGRDF ATVRKVLSMP QVNIVKKTEV QTGGFSKESI LPKRNSDKLI

ARKKDWDPKK YGGFDSPTVA YSVLVVAKVE KGKSKKLKSV KELLGITIME RSSFEKNPID

FLEAKGYKEV KKDLIIKLPK YSLFELENGR KRMLASAGEL QKGNELALPS KYVNFLYLAS

HYEKLKGSPE DNEQKQLFVE QHKHYLDEII EQISEFSKRV ILADANLDKV LSAYNKHRDK

PIREQAENII HLFTLTNLGA PAAFKYFDTT IDRKRYTSTK EVLDATLIHQ SITGLYETRI

DLSQLGGDGG GSPKKKRKV iProt106745 (SEQ ID NO: 7828):
MAPKKKRKVD KKYSIGLDIG TNSVGWAVIT DEYKVPSKKF KVLGNTDRHS IKKNLIGALL

FDSGETAEAT RLKRTARRRY TRRKNRICYL QEIFSNEMAK VDDSFFHRLE ESFLVEEDKK

HERHPIFGNI VDEVAYHEKY PTIYHLRKKL VDSTDKADLR LIYLALAHMI KFRGHFLIEG

DLNPDNSDVD KLFIQLVQTY NQLFEENPIN ASGVDAKAIL SARLSKSRRL ENLIAQLPGE

KKNGLFGNLI ALSLGLTPNF KSNFDLAEDA KLQLSKDTYD DDLDNLLAQI GDQYADLFLA

AKNLSDAILL SDILRVNTEI TKAPLSASMI KRYDEHHQDL TLLKALVRQQ LPEKYKEIFF

DQSKNGYAGY IDGGASQEEF YKFIKPILEK MDGTEELLVK LNREDLLRKQ RTFDNGSIPH

QIHLGELHAI LRRQEDFYPF LKDNREKIEK ILTFRIPYYV GPLARGNSRF AWMTRKSEET

ITPWNFEEVV DKGASAQSFI ERMTNFDKNL PNEKVLPKHS LLYEYFTVYN ELTKVKYVTE

GMRKPAFLSG EQKKAIVDLL FKTNRKVTVK QLKEDYFKKI ECFDSVEISG VEDRFNASLG

TYHDLLKIIK DKDFLDNEEN EDILEDIVLT LTLFEDREMI EERLKTYAHL FDDKVMKQLK

RRRYTGWGRL SRKLINGIRD KQSGKTILDF LKSDGFANRN FMQLIHDDSL TFKEDIQKAQ

VSGQGDSLHE HIANLAGSPA IKKGILQTVK VVDELVKVMG RHKPENIVIE MARENQTTQK

GQKNSRERMK RIEEGIKELG SQILKEHPVE NTQLQNEKLY LYYLQNGRDM YVDQELDINR

LSDYDVDHIV PQSFLKDDSI DNAVLTRSDK NRGKSDNVPS EEVVKKMKNY WRQLLNAKLI

TQRKFDNLTK AERGGLSELD KAGFIKRQLV ETRQITKHVA QILDSRMNTK YDENDKLIRE

VKVITLKSKL VSDFRKDFQF YKVREINNYH HAHDAYLNAV VGTALIKKYP KLESEFVYGD

YKVYDVRKMI AKSEQEIGKA TAKYFFYSNI MNFFKTEITL ANGEIRKRPL IETNGETGEI

VWDKGRDFAT VRKVLSMPQV NIVKKTEVQT GGFSKESILP KRNSDKLIAR KKDWDPKKYG

GFDSPTVAYS VLVVAKVEKG KSKKLKSVKE LLGITIMERS SFEKNPIDFL EAKGYKEVKK

DLIIKLPKYS LFELENGRKR MLASAGELQK GNELALPSKY VNFLYLASHY EKLKGSPEDN

EQKQLFVEQH KHYLDEIIEQ ISEFSKRVIL ADANLDKVLS AYNKHRDKPI REQAENIIHL

FTLTNLGAPA AFKYFDTTID RKRYTSTKEV LDATLIHQSI TGLYETRIDL SQLGGDSRAD

PKKKRKVHHH HHH iProt106746 (SEQ ID NO: 7829):
MAPKKKRKVD KKYSIGLDIG TNSVGWAVIT DEYKVPSKKF KVLGNTDRHS IKKNLIGALL

FDSGETAEAT RLKRTARRRY TRRKNRICYL QEIFSNEMAK VDDSFFHRLE ESFLVEEDKK

HERHPIFGNI VDEVAYHEKY PTIYHLRKKL VDSTDKADLR LIYLALAHMI KFRGHFLIEG

DLNPDNSDVD KLFIQLVQTY NQLFEENPIN ASGVDAKAIL SARLSKSRRL ENLIAQLPGE

KKNGLFGNLI ALSLGLTPNF KSNFDLAEDA KLQLSKDTYD DDLDNLLAQI GDQYADLFLA

AKNLSDAILL SDILRVNTEI TKAPLSASMI KRYDEHHQDL TLLKALVRQQ LPEKYKEIFF

DQSKNGYAGY IDGGASQEEF YKFIKPILEK MDGTEELLVK LNREDLLRKQ RTFDNGSIPH

```
QIHLGELHAI LRRQEDFYPF LKDNREKIEK ILTFRIPYYV GPLARGNSRF AWMTRKSEET

ITPWNFEEVV DKGASAQSFI ERMTNFDKNL PNEKVLPKHS LLYEYFTVYN ELTKVKYVTE

GMRKPAFLSG EQKKAIVDLL FKTNRKVTVK QLKEDYFKKI ECFDSVEISG VEDRFNASLG

TYHDLLKIIK DKDFLDNEEN EDILEDIVLT LTLFEDREMI EERLKTYAHL FDDKVMKQLK

RRRYTGWGRL SRKLINGIRD KQSGKTILDF LKSDGFANRN FMQLIHDDSL TFKEDIQKAQ

VSGQGDSLHE HIANLAGSPA IKKGILQTVK VVDELVKVMG RHKPENIVIE MARENQTTQK

GQKNSRERMK RIEEGIKELG SQILKEHPVE NTQLQNEALY LYYLQNGRDM YVDQELDINR

LSDYDVDHIV PQSFLKDDSI DNKVLTRSDK NRGKSDNVPS EEVVKKMKNY WRQLLNAKLI

TQRKFDNLTK AERGGLSELD KAGFIKRQLV ETRQITKHVA QILDSRMNTK YDENDKLIRE

VKVITLKSKL VSDFRKDFQF YKVREINNYH HAHDAYLNAV VGTALIKKYP ALESEFVYGD

YKVYDVRKMI AKSEQEIGKA TAKYFFYSNI MNFFKTEITL ANGEIRKAPL IETNGETGEI

VWDKGRDFAT VRKVLSMPQV NIVKKTEVQT GGFSKESILP KRNSDKLIAR KKDWDPKKYG

GFDSPTVAYS VLVVAKVEKG KSKKLKSVKE LLGITIMERS SFEKNPIDFL EAKGYKEVKK

DLIIKLPKYS LFELENGRKR MLASAGELQK GNELALPSKY VNFLYLASHY EKLKGSPEDN

EQKQLFVEQH KHYLDEIIEQ ISEFSKRVIL ADANLDKVLS AYNKHRDKPI REQAENIIHL

FTLTNLGAPA AFKYFDTTID RKRYTSTKEV LDATLIHQSI TGLYETRIDL SQLGGDSRAD

PKKKRKVHHH HHH iProt106747 (SEQ ID NO: 7830):
MAPKKKRKVD KKYSIGLDIG TNSVGWAVIT DEYKVPSKKF KVLGNTDRHS IKKNLIGALL

FDSGETAEAT RLKRTARRRY TRRKNRICYL QEIFSNEMAK VDDSFFHRLE ESFLVEEDKK

HERHPIFGNI VDEVAYHEKY PTIYHLRKKL VDSTDKADLR LIYLALAHMI KFRGHFLIEG

DLNPDNSDVD KLFIQLVQTY NQLFEENPIN ASGVDAKAIL SARLSKSRRL ENLIAQLPGE

KKNGLFGNLI ALSLGLTPNF KSNFDLAEDA KLQLSKDTYD DDLDNLLAQI GDQYADLFLA

AKNLSDAILL SDILRVNTEI TKAPLSASMI KRYDEHHQDL TLLKALVRQQ LPEKYKEIFF

DQSKNGYAGY IDGGASQEEF YKFIKPILEK MDGTEELLVK LNREDLLRKQ RTFDNGSIPH

QIHLGELHAI LRRQEDFYPF LKDNREKIEK ILTFRIPYYV GPLARGNSRF AWMTRKSEET

ITPWNFEEVV DKGASAQSFI ERMTNFDKNL PNEKVLPKHS LLYEYFTVYN ELTKVKYVTE

GMRKPAFLSG EQKKAIVDLL FKTNRKVTVK QLKEDYFKKI ECFDSVEISG VEDRFNASLG

TYHDLLKIIK DKDFLDNEEN EDILEDIVLT LTLFEDREMI EERLKTYAHL FDDKVMKQLK

RRRYTGWGRL SRKLINGIRD KQSGKTILDF LKSDGFANRN FMQLIHDDSL TFKEDIQKAQ

VSGQGDSLHE HIANLAGSPA IKKGILQTVK VVDELVKVMG RHKPENIVIE MARENQTTQK

GQKNSRERMK RIEEGIKELG SQILKEHPVE NTQLQNEKLY LYYLQNGRDM YVDQELDINR

LSDYDVDHIV PQSFLADDSI DNKVLTRSDK NRGKSDNVPS EEVVKKMKNY WRQLLNAKLI

TQRKFDNLTK AERGGLSELD KAGFIKRQLV ETRQITKHVA QILDSRMNTK YDENDKLIRE

VKVITLKSKL VSDFRKDFQF YKVREINNYH HAHDAYLNAV VGTALIKKYP ALESEFVYGD

YKVYDVRKMI AKSEQEIGKA TAKYFFYSNI MNFFKTEITL ANGEIRKAPL IETNGETGEI

VWDKGRDFAT VRKVLSMPQV NIVKKTEVQT GGFSKESILP KRNSDKLIAR KKDWDPKKYG

GFDSPTVAYS VLVVAKVEKG KSKKLKSVKE LLGITIMERS SFEKNPIDFL EAKGYKEVKK

DLIIKLPKYS LFELENGRKR MLASAGELQK GNELALPSKY VNFLYLASHY EKLKGSPEDN

EQKQLFVEQH KHYLDEIIEQ ISEFSKRVIL ADANLDKVLS AYNKHRDKPI REQAENIIHL
```

```
FTLTNLGAPA AFKYFDTTID RKRYTSTKEV LDATLIHQSI TGLYETRIDL SQLGGDSRAD

PKKKRKVHHH HHH iProt106884 (SEQ ID NO: 7831):
MAPKKKRKVD KKYSIGLDIG TNSVGWAVIT DEYKVPSKKF KVLGNTDRHS IKKNLIGALL

FDSGETAEAT RLKRTARRRY TRRKNRICYL QEIFSNEMAK VDDSFFHRLE ESFLVEEDKK

HERHPIFGNI VDEVAYHEKY PTIYHLRKKL VDSTDKADLR LIYLALAHMI KFRGHFLIEG

DLNPDNSDVD KLFIQLVQTY NQLFEENPIN ASGVDAKAIL SARLSKSRRL ENLIAQLPGE

KKNGLFGNLI ALSLGLTPNF KSNFDLAEDA KLQLSKDTYD DDLDNLLAQI GDQYADLFLA

AKNLSDAILL SDILRVNTEI TKAPLSASMI KRYDEHHQDL TLLKALVRQQ LPEKYKEIFF

DQSKNGYAGY IDGGASQEEF YKFIKPILEK MDGTEELLVK LNREDLLRKQ RTFDNGSIPH

QIHLGELHAI LRRQEDFYPF LKDNREKIEK ILTFRIPYYV GPLARGNSRF AWMTRKSEET

ITPWNFEEVV DKGASAQSFI ERMTAFDKNL PNEKVLPKHS LLYEYFTVYN ELTKVKYVTE

GMRKPAFLSG EQKKAIVDLL FKTNRKVTVK QLKEDYFKKI ECFDSVEISG VEDRFNASLG

TYHDLLKIIK DKDFLDNEEN EDILEDIVLT LTLFEDREMI EERLKTYAHL FDDKVMKQLK

RRRYTGWGAL SRKLINGIRD KQSGKTILDF LKSDGFANRN FMALIHDDSL TFKEDIQKAQ

VSGQGDSLHE HIANLAGSPA IKKGILQTVK VVDELVKVMG RHKPENIVIE MARENQTTQK

GQKNSRERMK RIEEGIKELG SQILKEHPVE NTQLQNEKLY LYYLQNGRDM YVDQELDINR

LSDYDVDHIV PQSFLKDDSI DNKVLTRSDK NRGKSDNVPS EEVVKKMKNY WRQLLNAKLI

TQRKFDNLTK AERGGLSELD KAGFIKRQLV ETRAITKHVA QILDSRMNTK YDENDKLIRE

VKVITLKSKL VSDFRKDFQF YKVREINNYH HAHDAYLNAV VGTALIKKYP KLESEFVYGD

YKVYDVRKMI AKSEQEIGKA TAKYFFYSNI MNFFKTEITL ANGEIRKRPL IETNGETGEI

VWDKGRDFAT VRKVLSMPQV NIVKKTEVQT GGFSKESILP KRNSDKLIAR KKDWDPKKYG

GFDSPTVAYS VLVVAKVEKG KSKKLKSVKE LLGITIMERS SFEKNPIDFL EAKGYKEVKK

DLIIKLPKYS LFELENGRKR MLASAGELQK GNELALPSKY VNFLYLASHY EKLKGSPEDN

EQKQLFVEQH KHYLDEIIEQ ISEFSKRVIL ADANLDKVLS AYNKHRDKPI REQAENIIHL

FTLTNLGAPA AFKYFDTTID RKRYTSTKEV LDATLIHQSI TGLYETRIDL SQLGGDSRAD

PKKKRKVHHH HHH
```

Nucleic Acids Encoding Cas9 Molecules

Nucleic acids encoding the Cas9 molecules, e.g., an active Cas9 molecule or an inactive Cas9 molecule are provided herein.

Exemplary nucleic acids encoding Cas9 molecules are described in Cong et al, SCIENCE 2013, 399(6121):819-823; Wang et al, CELL 2013, 153(4):910-918; Mali et al., SCIENCE 2013, 399(6121):823-826; Jinek et al, SCIENCE 2012, 337(6096):816-821.

In an embodiment, a nucleic acid encoding a Cas9 molecule can be a synthetic nucleic acid sequence. For example, the synthetic nucleic acid molecule can be chemically modified, e.g., as described in Section XIII. In an embodiment, the Cas9 mRNA has one or more of, e.g., all of the following properties: it is capped, polyadenylated, substituted with 5-methylcytidine and/or pseudouridine.

In addition or alternatively, the synthetic nucleic acid sequence can be codon optimized, e.g., at least one non-common codon or less-common codon has been replaced by a common codon. For example, the synthetic nucleic acid can direct the synthesis of an optimized messenger mRNA, e.g., optimized for expression in a mammalian expression system, e.g., described herein.

Provided below is an exemplary codon optimized nucleic acid sequence encoding a Cas9 molecule of *S. pyogenes*.

```
                                                    (SEQ ID NO: 6628)
atggataaaa agtacagcat cgggctggac atcggtacaa actcagtggg gtgggccgtg     60
attacggacg agtacaaggt accctccaaa aaatttaaag tgctgggtaa cacggacaga    120
cactctataa agaaaaatct tattggagcc ttgctgttcg actcaggcga gacagccgaa    180
gccacaaggt tgaagcggac cgccaggagg cggtatacca ggagaaagaa ccgcatatgc    240
```

-continued

```
tacctgcaag aaatcttcag taacgagatg gcaaaggttg acgatagctt tttccatcgc    300
ctggaagaat cctttcttgt tgaggaagac aagaagcacg aacggcaccc catctttggc    360
aatattgtcg acgaagtggc atatcacgaa aagtacccga ctatctacca cctcaggaag    420
aagctggtgg actctaccga taaggcggac ctcagactta tttatttggc actcgcccac    480
atgattaaat ttagaggaca tttcttgatc gagggcgacc tgaacccgga caacagtgac    540
gtcgataagc tgttcatcca acttgtgcag acctacaatc aactgttcga agaaaaccct    600
ataaatgctt caggagtcga cgctaaagca atcctgtccg cgcgcctctc aaaatctaga    660
agacttgaga atctgattgc tcagttgccc ggggaaaaga aaatggatt gtttggcaac     720
ctgatcgccc tcagtctcgg actgaccca aatttcaaaa gtaacttcga cctggccgaa     780
gacgctaagc tccagctgtc caaggacaca tacgatgacg acctcgacaa tctgctggcc    840
cagattgggg atcagtacgc cgatctcttt ttggcagcaa agaacctgtc cgacgccatc    900
ctgttgagcg atatcttgag agtgaacacc gaaattacta aagcaccct tagcgcatct     960
atgatcaagc ggtacgacga gcatcatcag gatctgaccc tgctgaaggc tcttgtgagg   1020
caacagctcc ccgaaaaata caaggaaatc ttctttgacc agagcaaaaa cggctacgct   1080
ggctatatag atggtggggc cagtcaggag gaattctata aattcatcaa gcccattctc   1140
gagaaaatgg acggcacaga ggagttgctg gtcaaactta acaggaggga cctgctgcgg   1200
aagcagcgga cctttgacaa cgggtctatc ccccaccaga ttcatctggg cgaactgcac   1260
gcaatcctga ggaggcagga ggatttttat cctttctta aagataaccg cgagaaaata   1320
gaaaagattc ttacattcag gatcccgtac tacgtgggac ctctcgcccg gggcaattca   1380
cggtttgcct ggatgacaag gaagtcgag gagactatta caccttggaa cttcgaagaa    1440
gtggtggaca agggtgcatc tgcccagtct ttcatcgagc ggatgacaaa ttttgacaag   1500
aacctcccta tgagaaggt gctgcccaaa cattctctgc tctacgagta ctttaccgtc    1560
tacaatgaac tgactaaagt caagtacgtc accgagggaa tgaggaagcc ggcattcctt   1620
agtggagaac agaagaaggc gattgtagac ctgttgttca agaccaacag gaaggtgact   1680
gtgaagcaac ttaaagaaga ctactttaag aagatcgaat gttttgacag tgtggaaatt   1740
tcaggggttg aagaccgctt caatgcgtca ttggggactt accatgatct tctcaagatc   1800
ataaaggaca aagacttcct ggacaacgaa gaaaatgagg atattctcga agacatcgtc   1860
ctcaccctga ccctgttcga agacagggaa atgatagaag agcgcttgaa aacctatgcc   1920
cacctcttcg acgataaagt tatgaagcag ctgaagcgca ggagatacac aggatgggga   1980
agattgtcaa ggaagctgat caatggaatt agggataaac agagtggcaa gaccatactg   2040
gatttcctca aatctgatgg cttcgccaat aggaacttca tgcaactgat tcacgatgac   2100
tctcttacct tcaaggagga cattcaaaag gctcaggtga gcgggcaggg agactccctt   2160
catgaacaca tcgcgaattt ggcaggttcc cccgctatta aaaagggcat ccttcaaact   2220
gtcaaggtgg tggatgaatt ggtcaaggta atgggcagac ataagccaga aaatattgtg   2280
atcgagatgg cccgcgaaaa ccagaccaca cagaagggcc agaaaaatag tagagagcgg   2340
atgaagagga tcgaggaggg catcaaagag ctgggatctc agattctcaa agaacacccc   2400
gtagaaaaca cacagctgca gaacgaaaaa ttgtacttgt actatctgca gaacggcaga   2460
gacatgtacg tcgaccaaga acttgatatt aatagactgt ccgactatga cgtagaccat   2520
atcgtgcccc agtccttcct gaaggacgac tccattgata caaagtctt gacaagaagc   2580
gacaagaaca ggggtaaaag tgataatgtg cctagcgagg aggtggtgaa aaaaatgaag   2640
```

```
                                   -continued
aactactggc gacagctgct taatgcaaag ctcattacac aacggaagtt cgataatctg  2700
acgaaagcag agagaggtgg cttgtctgag ttggacaagg cagggtttat taagcggcag  2760
ctggtggaaa ctaggcagat cacaaagcac gtggcgcaga ttttggacag ccggatgaac  2820
acaaaatacg acgaaaatga taaactgata cgagaggtca aagttatcac gctgaaaagc  2880
aagctggtgt ccgattttcg gaaagacttc cagttctaca aagttcgcga gattaataac  2940
taccatcatg ctcacgatgc gtacctgaac gctgttgtcg ggaccgcctt gataaagaag  3000
tacccaaagc tggaatccga gttcgtatac ggggattaca aagtgtacga tgtgaggaaa  3060
atgatagcca agtccgagca ggagattgga aaggccacag ctaagtactt cttttattct  3120
aacatcatga attttttttaa gacggaaatt accctggcca acggagagat cagaaagcgg  3180 cccttatag agacaaatgg tgaaacaggt gaaatcgtct gggataaggg cagggatttc   3240
gctactgtga ggaaggtgct gagtatgcca caggtaaata tcgtgaaaaa aaccgaagta  3300
cagaccggag gattttccaa ggaaagcatt ttgcctaaaa gaaactcaga caagctcatc  3360
gcccgcaaga aagattggga ccctaagaaa tacggggat ttgactcacc caccgtagcc   3420
tattctgtgc tggtggtagc taaggtggaa aaaggaaagt ctaagaagct gaagtccgtg  3480
aaggaactct tgggaatcac tatcatgaaa agatcatcct ttgaaaagaa ccctatcgat  3540
ttcctggagg ctaagggtta caaggaggtc aagaaagacc tcatcattaa actgccaaaa  3600
tactctctct tcgagctgga aaatggcagg aagagaatgt tggccagcgc cggagagctg  3660
caaaagggaa acgagcttgc tctgccctcc aaatatgtta attttctcta tctcgcttcc  3720
cactatgaaa agctgaaagg gtctcccgaa gataacgagc agaagcagct gttcgtcgaa  3780
cagcacaagc actatctgga tgaaataatc gaacaaataa gcgagttcag caaaagggtt  3840
atcctggcgg atgctaattt ggacaaagta ctgtctgctt ataacaagca ccgggataag  3900
cctattaggg aacaagccga gaatataatt caccctcttta cactcacgaa tctcggagcc  3960
cccgccgcct tcaaatactt tgatacgact atcgaccgga aacggtatac cagtaccaaa  4020
gaggtcctcg atgccaccct catccaccag tcaattactg gcctgtacga aacacggatc  4080
gacctctctc aactgggcgg cgactag                                       4107
```

If the above Cas9 sequences are fused with a peptide or polypeptide at the C-terminus (e.g., an inactive Cas9 fused with a transcription repressor at the C-terminus), it is understood that the stop codon will be removed.

V. Chimeric Antigen Receptors

The invention provides for gRNA molecules and CRISPR systems for use in connection with adoptive immunotherapy methods and reagents such as chimeric antigen receptor (CAR) immune effector cells, e.g., T cells, or chimeric TCR-transduced immune effector cells, e.g., T cells. The gRNA molecules and CRISPR systems of the invention can be used to create adoptive immunotherapy cells and compositions with improved properties, such as efficacy and safety. This section describes CAR technology generally that is useful in conjunction with the gRNA molecules and CRISPR systems of the invention, and describes improved CAR reagents, e.g., cells and compositions, and methods.

In general, aspects of the invention pertain to or include an isolated nucleic acid molecule encoding a chimeric antigen receptor (CAR), wherein the CAR comprises an antigen binding domain (e.g., antibody or antibody fragment, TCR or TCR fragment) that binds to a tumor antigen as described herein, a transmembrane domain (e.g., a transmembrane domain described herein), and an intracellular signaling domain (e.g., an intracellular signaling domain described herein) (e.g., an intracellular signaling domain comprising a costimulatory domain (e.g., a costimulatory domain described herein) and/or a primary signaling domain (e.g., a primary signaling domain described herein). In other aspects, the invention includes: host cells containing the above nucleic acids and isolated proteins encoded by such nucleic acid molecules. CAR nucleic acid constructs, encoded proteins, containing vectors, host cells, pharmaceutical compositions, and methods of administration and treatment related to the present invention are disclosed in detail in International Patent Application Publication No. WO2015142675, which is incorporated by reference in its entirety.

In one aspect, the invention pertains to an isolated nucleic acid molecule encoding a chimeric antigen receptor (CAR), wherein the CAR comprises an antigen binding domain (e.g., antibody or antibody fragment, TCR or TCR fragment) that binds to a tumor-supporting antigen (e.g., a tumor-supporting antigen as described herein), a transmembrane domain (e.g., a transmembrane domain described herein), and an intracellular signaling domain (e.g., an intracellular signaling domain described herein) (e.g., an intracellular signaling domain comprising a costimulatory domain (e.g., a costimulatory domain described herein) and/or a primary signaling domain (e.g., a primary signaling domain described herein). In some embodiments, the tumor-supporting antigen is an antigen present on a stromal cell or a myeloid-derived suppressor cell (MDSC). In other aspects, the invention features polypeptides encoded by such nucleic acids and host cells containing such nucleic acids and/or polypeptides.

Alternatively, aspects of the invention pertain to isolated nucleic acid encoding a chimeric T cell receptor (TCR) comprising a TCR alpha and/or TCR beta variable domain with specificity for a cancer antigen described herein. See for example, Dembic et al., Nature, 320, 232-238 (1986), Schumacher, Nat. Rev. Immunol., 2, 512-519 (2002), Kershaw et al., Nat. Rev. Immunol., 5, 928-940 (2005), Xue et al., Clin. Exp. Immunol., 139, 167-172 (2005), Rossig et al., Mol. Ther., 10, 5-18 (2004), and Murphy et al., Immunity, 22, 403-414 (2005); (Morgan et al. J. Immunol., 171, 3287-3295 (2003), Hughes et al., Hum. Gene Ther., 16, 1-16 (2005), Zhao et al., J. Immunol., 174, 4415-4423 (2005), Roszkowski et al., Cancer Res., 65, 1570-1576 (2005), and Engels et al., Hum. Gene Ther., 16, 799-810 (2005); US2009/03046557, the contents of which are hereby incorporated by reference in their entirety. Such chimeric TCRs may recognize, for example, cancer antigens such as MART-1, gp-100, p53, and NY-ESO-1, MAGE A3/A6, MAGEA3, SSX2, HPV-16 E6 or HPV-16 E7. In other aspects, the invention features polypeptides encoded by such nucleic acids and host cells containing such nucleic acids and/or polypeptides.

Targets

The present invention provides cells, e.g., immune effector cells (e.g., T cells, NK cells), that comprise or at any time comprised a gRNA molecule or CRISPR system as described herein, that are further engineered to contain one or more CARs that direct the immune effector cells to undesired cells (e.g., cancer cells). This is achieved through an antigen binding domain on the CAR that is specific for a cancer associated antigen. There are two classes of cancer associated antigens (tumor antigens) that can be targeted by the CARs of the instant invention: (1) cancer associated antigens that are expressed on the surface of cancer cells; and (2) cancer associated antigens that itself is intracelluar, however, a fragment of such antigen (peptide) is presented on the surface of the cancer cells by MHC (major histocompatibility complex).

In some embodiments, the tumor antigen is chosen from one or more of: CD19; CD123; CD22; CD30; CD171; CS-1 (also referred to as CD2 subset 1, CRACC, SLAMF7, CD319, and 19A24); C-type lectin-like molecule-1 (CLL-1 or CLECL1); CD33; epidermal growth factor receptor variant III (EGFRvIII); ganglioside G2 (GD2); ganglioside GD3 (aNeu5Ac(2-8)aNeu5Ac(2-3)bDGalp(1-4)bDGlcp(1-1) Cer); TNF receptor family member B cell maturation (BCMA); Tn antigen ((Tn Ag) or (GalNAcα-Ser/Thr)); prostate-specific membrane antigen (PSMA); Receptor tyrosine kinase-like orphan receptor 1 (ROR1); Fms-Like Tyrosine Kinase 3 (FLT3); Tumor-associated glycoprotein 72 (TAG72); CD38; CD44v6; Carcinoembryonic antigen (CEA); Epithelial cell adhesion molecule (EPCAM); B7H3 (CD276); KIT (CD117); Interleukin-13 receptor subunit alpha-2 (IL-13Ra2 or CD213A2); Mesothelin; Interleukin 11 receptor alpha (IL-11Ra); prostate stem cell antigen (PSCA); Protease Serine 21 (Testisin or PRSS21); vascular endothelial growth factor receptor 2 (VEGFR2); Lewis(Y) antigen; CD24; Platelet-derived growth factor receptor beta (PDGFR-beta); Stage-specific embryonic antigen-4 (SSEA-4); CD20; Folate receptor alpha; Receptor tyrosine-protein kinase ERBB2 (Her2/neu); Mucin 1, cell surface associated (MUC1); epidermal growth factor receptor (EGFR); neural cell adhesion molecule (NCAM); Prostase; prostatic acid phosphatase (PAP); elongation factor 2 mutated (ELF2M); Ephrin B2; fibroblast activation protein alpha (FAP); insulin-like growth factor 1 receptor (IGF-I receptor), carbonic anhydrase IX (CAIX); Proteasome (Prosome, Macropain) Subunit, Beta Type, 9 (LMP2); glycoprotein 100 (gp100); oncogene fusion protein consisting of breakpoint cluster region (BCR) and Abelson murine leukemia viral oncogene homolog 1 (Abl) (bcr-abl); tyrosinase; ephrin type-A receptor 2 (EphA2); Fucosyl GM1; sialyl Lewis adhesion molecule (sLe); ganglioside GM3 (aNeu5Ac(2-3)bDGalp(1-4) bDGlcp(1-1)Cer); transglutaminase 5 (TGS5); high molecular weight-melanoma-associated antigen (HMW-MAA); o-acetyl-GD2 ganglioside (OAcGD2); Folate receptor beta; tumor endothelial marker 1 (TEM1/CD248); tumor endothelial marker 7-related (TEM7R); claudin 6 (CLDN6); thyroid stimulating hormone receptor (TSHR); G protein-coupled receptor class C group 5, member D (GPRC5D); chromosome X open reading frame 61 (CXORF61); CD97; CD179a; anaplastic lymphoma kinase (ALK); Polysialic acid; placenta-specific 1 (PLAC1); hexasaccharide portion of globoH glycoceramide (GloboH); mammary gland differentiation antigen (NY-BR-1); uroplakin 2 (UPK2); Hepatitis A virus cellular receptor 1 (HAVCR1); adrenoceptor beta 3 (ADRB3); pannexin 3 (PANX3); G protein-coupled receptor 20 (GPR20); lymphocyte antigen 6 complex, locus K9 (LY6K); Olfactory receptor 51E2 (OR51E2); TCR Gamma Alternate Reading Frame Protein (TARP); Wilms tumor protein (WT1); Cancer/testis antigen 1 (NY-ESO-1); Cancer/testis antigen 2 (LAGE-1a); Melanoma-associated antigen 1 (MAGE-A1); ETS translocation-variant gene 6, located on chromosome 12p (ETV6-AML); sperm protein 17 (SPA17); X Antigen Family, Member 1A (XAGE1); angiopoietin-binding cell surface receptor 2 (Tie 2); melanoma cancer testis antigen-1 (MAD-CT-1); melanoma cancer testis antigen-2 (MAD-CT-2); Fos-related antigen 1; tumor protein p53 (p53); p53 mutant; prostein; surviving; telomerase; prostate carcinoma tumor antigen-1 (PCTA-1 or Galectin 8), melanoma antigen recognized by T cells 1 (MelanA or MART1); Rat sarcoma (Ras) mutant; human Telomerase reverse transcriptase (hTERT); sarcoma translocation breakpoints; melanoma inhibitor of apoptosis (ML-IAP); ERG (transmembrane protease, serine 2 (TMPRSS2) ETS fusion gene); N-Acetyl glucosaminyl-transferase V (NA17); paired box protein Pax-3 (PAX3); Androgen receptor; Cyclin B1; v-myc avian myelocytomatosis viral oncogene neuroblastoma derived homolog (MYCN); Ras Homolog Family Member C (RhoC); Tyrosinase-related protein 2 (TRP-2); Cytochrome P450 1B1 (CYP1B1); CCCTC-Binding Factor (Zinc Finger Protein)-Like (BORIS or Brother of the Regulator of Imprinted Sites), Squamous Cell Carcinoma Antigen Recognized By T Cells 3 (SART3); Paired box protein Pax-5 (PAX5); proacrosin binding protein sp32 (OY-TES1); lymphocyte-specific protein tyrosine kinase (LCK); A kinase anchor protein 4 (AKAP-4); synovial sarcoma, X breakpoint 2 (SSX2); Receptor for Advanced Glycation Endproducts (RAGE-1); renal ubiquitous 1 (RU1); renal ubiquitous 2 (RU2); legumain; human papilloma virus E6 (HPV E6); human papilloma virus E7 (HPV E7); intestinal carboxyl esterase; heat shock protein 70-2 mutated (mut hsp70-2); CD79a; CD79b; CD72; Leukocyte-associated immunoglobulin-like receptor 1 (LAIR1);

Fc fragment of IgA receptor (FCAR or CD89); Leukocyte immunoglobulin-like receptor subfamily A member 2 (LILRA2); CD300 molecule-like family member f (CD300LF); C-type lectin domain family 12 member A (CLEC12A); bone marrow stromal cell antigen 2 (BST2); EGF-like module-containing mucin-like hormone receptor-like 2 (EMR2); lymphocyte antigen 75 (LY75); Glypican-3 (GPC3); Fc receptor-like 5 (FCRL5); and immunoglobulin lambda-like polypeptide 1 (IGLL1).

A CAR described herein can comprise an antigen binding domain (e.g., antibody or antibody fragment, TCR or TCR fragment) that binds to a tumor-supporting antigen (e.g., a tumor-supporting antigen as described herein). In some embodiments, the tumor-supporting antigen is an antigen present on a stromal cell or a myeloid-derived suppressor cell (MDSC). Stromal cells can secrete growth factors to promote cell division in the microenvironment. MDSC cells can inhibit T cell proliferation and activation. Without wishing to be bound by theory, in some embodiments, the CAR-expressing cells destroy the tumor-supporting cells, thereby indirectly inhibiting tumor growth or survival.

In embodiments, the stromal cell antigen is chosen from one or more of: bone marrow stromal cell antigen 2 (BST2), fibroblast activation protein (FAP) and tenascin. In an embodiment, the FAP-specific antibody is, competes for binding with, or has the same CDRs as, sibrotuzumab. In embodiments, the MDSC antigen is chosen from one or more of: CD33, CD11b, C14, CD15, and CD66b. Accordingly, in some embodiments, the tumor-supporting antigen is chosen from one or more of: bone marrow stromal cell antigen 2 (BST2), fibroblast activation protein (FAP) or tenascin, CD33, CD11b, C14, CD15, and CD66b.

Antigen Binding Domain Structures

In some embodiments, the antigen binding domain of the encoded CAR molecule comprises an antibody, an antibody fragment, an scFv, a Fv, a Fab, a (Fab')2, a single domain antibody (SDAB), a VH or VL domain, a camelid VHH domain or a bi-functional (e.g. bi-specific) hybrid antibody (e.g., Lanzavecchia et al., Eur. J. Immunol. 17, 105 (1987)).

In some instances, scFvs can be prepared according to method known in the art (see, for example, Bird et al., (1988) Science 242:423-426 and Huston et al., (1988) Proc. Natl. Acad. Sci. USA 85:5879-5883). ScFv molecules can be produced by linking VH and VL regions together using flexible polypeptide linkers. The scFv molecules comprise a linker (e.g., a Ser-Gly linker) with an optimized length and/or amino acid composition. The linker length can greatly affect how the variable regions of a scFv fold and interact. In fact, if a short polypeptide linker is employed (e.g., between 5-10 amino acids) intrachain folding is prevented. Interchain folding is also required to bring the two variable regions together to form a functional epitope binding site. For examples of linker orientation and size see, e.g., Hollinger et al. 1993 Proc Natl Acad. Sci. U.S.A. 90:6444-6448, U.S. Patent Application Publication Nos. 2005/0100543, 2005/0175606, 2007/0014794, and PCT publication Nos. WO2006/020258 and WO2007/024715, is incorporated herein by reference.

An scFv can comprise a linker of at least 1, 2, 3, 4, 5, 6, 7, 8, 9, 10, 11, 12, 13, 14, 15, 16, 17, 18, 19, 20, 25, 30, 35, 40, 45, 50, or more amino acid residues between its VL and VH regions. The linker sequence may comprise any naturally occurring amino acid. In some embodiments, the linker sequence comprises amino acids glycine and serine. In another embodiment, the linker sequence comprises sets of glycine and serine repeats such as (Gly$_4$Ser)n, where n is a positive integer equal to or greater than 1 (SEQ ID NO:6629). In one embodiment, the linker can be (Gly4Ser)$_4$ (SEQ ID NO:6593) or (Gly$_4$Ser) 3 (SEQ ID NO:6594). Variation in the linker length may retain or enhance activity, giving rise to superior efficacy in activity studies.

In another aspect, the antigen binding domain is a T cell receptor ("TCR"), or a fragment thereof, for example, a single chain TCR (scTCR). Methods to make such TCRs are known in the art. See, e.g., Willemsen R A et al, Gene Therapy 7: 1369-1377 (2000); Zhang T et al, Cancer Gene Ther 11: 487-496 (2004); Aggen et al, Gene Ther. 19(4): 365-74 (2012) (references are incorporated herein by its entirety). For example, scTCR can be engineered that contains the Vα and Vβ genes from a T cell clone linked by a linker (e.g., a flexible peptide). This approach is very useful to cancer associated target that itself is intracelluar, however, a fragment of such antigen (peptide) is presented on the surface of the cancer cells by MHC.

In certain embodiments, the encoded antigen binding domain has a binding affinity KD of $10^{-4}$ M to $10^{-8}$ M.

In one embodiment, the encoded CAR molecule comprises an antigen binding domain that has a binding affinity KD of $10^{-4}$ M to $10^{-8}$ M, e.g., $10^{-5}$ M to $10^{-7}$ M, e.g., $10^{-6}$ M or $10^{-7}$ M, for the target antigen. In one embodiment, the antigen binding domain has a binding affinity that is at least five-fold, 10-fold, 20-fold, 30-fold, 50-fold, 100-fold or 1,000-fold less than a reference antibody, e.g., an antibody described herein. In one embodiment, the encoded antigen binding domain has a binding affinity at least 5-fold less than a reference antibody (e.g., an antibody from which the antigen binding domain is derived). In one aspect such antibody fragments are functional in that they provide a biological response that can include, but is not limited to, activation of an immune response, inhibition of signal-transduction origination from its target antigen, inhibition of kinase activity, and the like, as will be understood by a skilled artisan.

In one aspect, the antigen binding domain of the CAR is a scFv antibody fragment that is humanized compared to the murine sequence of the scFv from which it is derived.

In one aspect, the antigen binding domain of a CAR of the invention (e.g., a scFv) is encoded by a nucleic acid molecule whose sequence has been codon optimized for expression in a mammalian cell. In one aspect, entire CAR construct of the invention is encoded by a nucleic acid molecule whose entire sequence has been codon optimized for expression in a mammalian cell. Codon optimization refers to the discovery that the frequency of occurrence of synonymous codons (i.e., codons that code for the same amino acid) in coding DNA is biased in different species. Such codon degeneracy allows an identical polypeptide to be encoded by a variety of nucleotide sequences. A variety of codon optimization methods is known in the art, and include, e.g., methods disclosed in at least U.S. Pat. Nos. 5,786,464 and 6,114,148.

Antigen Binding Domains (and the Targeted Antigens)

In one embodiment, an antigen binding domain against CD19 is an antigen binding portion, e.g., CDRs, of a CAR, antibody or antigen-binding fragment thereof described in, e.g., PCT publication WO2012/079000; PCT publication WO2014/153270; Kochenderfer, J. N. et al., J. Immunother. 32 (7), 689-702 (2009); Kochenderfer, J. N., et al., Blood, 116 (20), 4099-4102 (2010); PCT publication WO2014/031687; Bejcek, Cancer Research, 55, 2346-2351, 1995; or U.S. Pat. No. 7,446,190.

In one embodiment, an antigen binding domain against mesothelin is an antigen binding portion, e.g., CDRs, of an antibody, antigen-binding fragment or CAR described in, e.g., PCT publication WO2015/090230. In one embodiment, an antigen binding domain against mesothelin is an antigen binding portion, e.g., CDRs, of an antibody, antigen-binding fragment, or CAR described in, e.g., PCT publication WO1997/025068, WO1999/028471, WO2005/014652, WO2006/099141, WO2009/045957, WO2009/068204, WO2013/142034, WO2013/040557, or WO2013/063419. In one embodiment, an antigen binding domain against mesothelin is an antigen binding portion, e.g., CDRs, of an antibody, antigen-binding fragment, or CAR described in WO/2015/090230.

In one embodiment, an antigen binding domain against CD123 is an antigen binding portion, e.g., CDRs, of an antibody, antigen-binding fragment or CAR described in, e.g., PCT publication WO2014/130635. In one embodiment, an antigen binding domain against CD123 is an antigen binding portion, e.g., CDRs, of an antibody, antigen-binding fragment, or CAR described in, e.g., PCT publication WO2014/138805, WO2014/138819, WO2013/173820, WO2014/144622, WO2001/66139, WO2010/126066, WO2014/144622, or US2009/0252742. In one embodiment, an antigen binding domain against CD123 is an antigen binding portion, e.g., CDRs, of an antibody, antigen-binding fragment, or CAR described in WO/2016/028896.

Examples include CAR molecules which include an antigen binding domain, or a VL and VH (in the sequences below, separated by a (G4S)3 linker (SEQ ID NO: 6594)) of:

CD123-1:
(SEQ ID NO: 7812)
QVQLVQSGAEVKKPGASVKVSCKASGYTFTGYYMHWVRQAPGQGLEWMG

WINPNSGGTNYAQKFQGRVTMTRDTSISTAYMELSRLRSDDTAVYYCAR

DMNILATVPFDIWGQGTMVTVSSGGGGSGGGGSGGGGSDIQMTQSPSSL

SASVGDRVTITCRASQSISTYLNWYQQKPGKAPNLLIYAAFSLQSGVPS

RFSGSGSGTDFTLTINSLQPEDFATYYCQQGDSVPLTFGGGTKLEIK;

CD123-2:
(SEQ ID NO: 7813)
QVQLVQSGAEVKKPGASVKVSCKASGYTFTGYYMHWVRQAPGQGLEWMG

WINPNSGGTNYAQKFQGRVTLTRDTSISTVYMELSRLRSDDTAVYYCAR

DMNILATVPFDIWGQGTMVTVSSGGGGSGGGGSGGGGSDIQMTQSPSSL

SASVGDRVTITCRASQSISSYLNWYQQKPGKAPKLLIYAASSLQSGVPS

RFSGSGSGTDFTLTVNSLQPEDFATYYCQQGDSVPLTFGGGTRLEIK;

CD123-3:
(SEQ ID NO: 7814)
QVQLVQSGAEVKKPGASVKVSCKASGYIFTGYYIHWVRQAPGQGLEWMG

WINPNSGGTNYAQKFQGRVTMTRDTSISTAYMELSGLRSDDPAVYYCAR

DMNILATVPFDIWGQGTLVTVSSGGGGSGGGGSGGGGSDIQLTQSPSSL

SASVGDRVTITCRASQSISSYLNWYQQKPGKAPKLLIYAASSLQSGVPS

RFSGSGSGTDFTLTVNSLQPEDFATYYCQQGDSVPLTFGGGTKVEIK;
OR

CD123-4:
(SEQ ID NO: 7815)
QVQLQQSGAEVKKSGASVKVSCKASGYTFTDYYMHWLRQAPGQGLEWMG

WINPNSGDTNYAQKFQGRVTLTRDTSISTVYMELSRLRSDDTAVYYCAR

DMNILATVPFDIWGQGTMVTVSSASGGGGSGGRASGGGGSDIQMTQSPS

SLSASVGDRVTITCRASQSISSYLNWYQQKPGKAPKLLIYAASSLQSGV

PSRFSGSGSGTDFTLTISSLQPEDFATYYCQQGDSVPLTFGGGTKVEIK,
from WO2016/0028896.

The CAR comprising said anti-CD123 binding domain may comprise, for example, the amino acid sequence of:

CAR123-2:
(SEQ ID NO: 7816)
MALPVTALLLPLALLLHAARPQVQLVQSGAEVKKPGASVKVSCKASGYTF

TGYYMHWVRQAPGQGLEWMGWINPNSGGTNYAQKFQGRVTLTRDTSISTV

YMELSRLRSDDTAVYYCARDMNILATVPFDIWGQGTMVTVSSGGGGSGGG

GSGGGGSDIQMTQSPSSLSASVGDRVTITCRASQSISSYLNWYQQKPGKA

PKLLIYAASSLQSGVPSRFSGSGSGTDFTLTVNSLQPEDFATYYCQQGDS

VPLTFGGGTRLEIKTTTPAPRPPTPAPTIASQPLSLRPEACRPAAGGAVH

TRGLDFACDIYIWAPLAGTCGVLLLSLVITLYCKRGRKKLLYIFKQPFMR

PVQTTQEEDGCSCRFPEEEEGGCELRVKFSRSADAPAYKQGQNQLYNELN

LGRREEYDVLDKRRGRDPEMGGKPRRKNPQEGLYNELQKDKMAEAYSEIG

MKGERRRGKGHDGLYQGLSTATKDTYDALHMQALPPR;

CAR123-3:
(SEQ ID NO: 7817)
MALPVTALLLPLALLLHAARPQVQLVQSGAEVKKPGASVKVSCKASGYIF

TGYYIHWVRQAPGQGLEWMGWINPNSGGTNYAQKFQGRVTMTRDTSISTA

YMELSGLRSDDPAVYYCARDMNILATVPFDIWGQGTLVTVSSGGGGSGGG

GSGGGGSDIQLTQSPSSLSASVGDRVTITCRASQSISSYLNWYQQKPGKA

PKLLIYAASSLQSGVPSRFSGSGSGTDFTLTVNSLQPEDFATYYCQQGDS

VPLTFGGGTKVEIKTTTPAPRPPTPAPTIASQPLSLRPEACRPAAGGAVH

TRGLDFACDIYIWAPLAGTCGVLLLSLVITLYCKRGRKKLLYIFKQPFMR

PVQTTQEEDGCSCRFPEEEEGGCELRVKFSRSADAPAYKQGQNQLYNELN

LGRREEYDVLDKRRGRDPEMGGKPRRKNPQEGLYNELQKDKMAEAYSEIG

MKGERRRGKGHDGLYQGLSTATKDTYDALHMQALPPR;

CAR123-4:
(SEQ ID NO: 7818)
MALPVTALLLPLALLLHAARPQVQLQQSGAEVKKSGASVKVSCKASGYTF

TDYYMHWLRQAPGQGLEWMGWINPNSGDTNYAQKFQGRVTLTRDTSISTV

YMELSRLRSDDTAVYYCARDMNILATVPFDIWGQGTMVTVSSASGGGGSG

GRASGGGGSDIQMTQSPSSLSASVGDRVTITCRASQSISSYLNWYQQKPG

KAPKLLIYAASSLQSGVPSRFSGSGSGTDFTLTISSLQPEDFATYYCQQG

DSVPLTFGGGTKVEIKTTTPAPRPPTPAPTIASQPLSLRPEACRPAAGGA

VHTRGLDFACDIYIWAPLAGTCGVLLLSLVITLYCK;
OR

CAR123-1:
(SEQ ID NO: 7819)
malpvtalllplalllhaarpqvqlvqsgaevkkpgasvkvsckasgytf tgyymhwvrqapgqglewmgwinpnsggtnyaqkfqgrvtmtrdtsista ymelsrlrsddtavyycardmnilatvpfdiwgqgtmvtvssggggsggg -continued

```
gsggggsdiqmtqspsslsasvgdrvtitcrasqsistylnwyqqkpgka pnlliyaafslqsgvpsrfsgsgsgtdftltinslqpedfatyycqqgds vpltfgggtkleiktttpaprpptpaptiasqplslrpeacrpaaggavh trgldfacdiyiwaplagtcgvlllslvitlyckrgrkkllyifkqpfmr pvqttqeedgcscrfpeeeeggcelrvkfsrsadapaykqgqnqlyneln lgrreeydvldkrrgrdpemggkprrknpqeglynelqkdkmaeayseig mkgerrrgkghdglyqglstatkdtydalhmqalppr.
In each case, the CAR may optionally comprise or
not comprise the leader sequence included in each
of the above sequences (MALPVTALLLPLALLLHAARP;
SEQ ID NO: 6640).
```

In one embodiment, an antigen binding domain against EGFRvIII is an antigen binding portion, e.g., CDRs, of an antibody, antigen-binding fragment or CAR described in, e.g., WO/2014/130657.

In one embodiment, an antigen binding domain against CD22 is an antigen binding portion, e.g., CDRs, of an antibody described in, e.g., Haso et al., Blood, 121(7): 1165-1174 (2013); Wayne et al., Clin Cancer Res 16(6): 1894-1903 (2010); Kato et al., Leuk Res 37(1):83-88 (2013); Creative BioMart (creativebiomart.net): MOM-18047-S(P).

In one embodiment, an antigen binding domain against CS-1 is an antigen binding portion, e.g., CDRs, of Elotuzumab (BMS), see e.g., Tai et al., 2008, Blood 112(4): 1329-37; Tai et al., 2007, Blood. 110(5):1656-63.

In one embodiment, an antigen binding domain against CLL-1 is an antigen binding portion, e.g., CDRs, of an antibody available from R&D, ebiosciences, Abcam, for example, PE-CLL1-hu Cat #353604 (BioLegend); and PE-CLL1 (CLEC12A) Cat #562566 (BD). In one embodiment, an antigen binding domain against CLL-1 is an antigen binding portion, e.g., CDRs, of an antibody, antigen-binding fragment, or CAR described in WO/2016/014535.

In one embodiment, an antigen binding domain against CD33 is an antigen binding portion, e.g., CDRs, of an antibody described in, e.g., Bross et al., Clin Cancer Res 7(6):1490-1496 (2001) (Gemtuzumab Ozogamicin, hP67.6), Caron et al., Cancer Res 52(24):6761-6767 (1992) (Lintuzumab, HuM195), Lapusan et al., Invest New Drugs 30(3):1121-1131 (2012) (AVE9633), Aigner et al., Leukemia 27(5): 1107-1115 (2013) (AMG330, CD33 BiTE), Dutour et al., Adv hematol 2012:683065 (2012), and Pizzitola et al., Leukemia doi:10.1038/Lue.2014.62 (2014). In one embodiment, an antigen binding domain against CD33 is an antigen binding portion, e.g., CDRs, of an antibody, antigen-binding fragment, or CAR described in WO/2016/014576.

In one embodiment, an antigen binding domain against GD2 is an antigen binding portion, e.g., CDRs, of an antibody described in, e.g., Mujoo et al., Cancer Res. 47(4):1098-1104 (1987); Cheung et al., Cancer Res 45(6): 2642-2649 (1985), Cheung et al., J Clin Oncol 5(9):1430-1440 (1987), Cheung et al., J Clin Oncol 16(9):3053-3060 (1998), Handgretinger et al., Cancer Immunol Immunother 35(3):199-204 (1992). In some embodiments, an antigen binding domain against GD2 is an antigen binding portion of an antibody selected from mAb 14.18, 14G2a, ch14.18, hu14.18, 3F8, hu3F8, 3G6, 8B6, 60C3, 10B8, ME36.1, and 8H9, see e.g., WO2012033885, WO2013040371, WO2013192294, WO2013061273, WO2013123061, WO2013074916, and WO201385552. In some embodiments, an antigen binding domain against GD2 is an antigen binding portion of an antibody described in US Publication No.: 20100150910 or PCT Publication No.: WO 2011160119.

In one embodiment, an antigen binding domain against BCMA is an antigen binding portion, e.g., CDRs, of an antibody described in, e.g., WO2012163805, WO200112812, and WO2003062401. In one embodiment, an antigen binding domain against BCMA is an antigen binding portion, e.g., CDRs, of an antibody, antigen-binding fragment, or CAR described in WO/2016/014565.

In one embodiment, an antigen binding domain against Tn antigen is an antigen binding portion, e.g., CDRs, of an antibody described in, e.g., U.S. Pat. No. 8,440,798, Brooks et al., PNAS 107(22):10056-10061 (2010), and Stone et al., OncoImmunology 1(6):863-873(2012).

In one embodiment, an antigen binding domain against PSMA is an antigen binding portion, e.g., CDRs, of an antibody described in, e.g., Parker et al., Protein Expr Purif 89(2):136-145 (2013), US 20110268656 (J591 ScFv); Frigerio et al, European J Cancer 49(9):2223-2232 (2013) (scFvD2B); WO 2006125481 (mAbs 3/A12, 3/E7 and 3/F11) and single chain antibody fragments (scFv A5 and D7).

In one embodiment, an antigen binding domain against ROR1 is an antigen binding portion, e.g., CDRs, of an antibody described in, e.g., Hudecek et al., Clin Cancer Res 19(12):3153-3164 (2013); WO 2011159847; and US20130101607.

In one embodiment, an antigen binding domain against FLT3 is an antigen binding portion, e.g., CDRs, of an antibody described in, e.g., WO2011076922, U.S. Pat. No. 5,777,084, EP0754230, US20090297529, and several commercial catalog antibodies (R&D, ebiosciences, Abcam).

In one embodiment, an antigen binding domain against TAG72 is an antigen binding portion, e.g., CDRs, of an antibody described in, e.g., Hombach et al., Gastroenterology 113(4):1163-1170 (1997); and Abcam ab691.

In one embodiment, an antigen binding domain against FAP is an antigen binding portion, e.g., CDRs, of an antibody described in, e.g., Ostermann et al., Clinical Cancer Research 14:4584-4592 (2008) (FAP5), US Pat. Publication No. 2009/0304718; sibrotuzumab (see e.g., Hofheinz et al., Oncology Research and Treatment 26(1), 2003); and Tran et al., J Exp Med 210(6):1125-1135 (2013).

In one embodiment, an antigen binding domain against CD38 is an antigen binding portion, e.g., CDRs, of daratumumab (see, e.g., Groen et al., Blood 116(21):1261-1262 (2010); MOR202 (see, e.g., U.S. Pat. No. 8,263,746); or antibodies described in U.S. Pat. No. 8,362,211.

In one embodiment, an antigen binding domain against CD44v6 is an antigen binding portion, e.g., CDRs, of an antibody described in, e.g., Casucci et al., Blood 122(20): 3461-3472 (2013).

In one embodiment, an antigen binding domain against CEA is an antigen binding portion, e.g., CDRs, of an antibody described in, e.g., Chmielewski et al., Gastoenterology 143(4):1095-1107 (2012).

In one embodiment, an antigen binding domain against EPCAM is an antigen binding portion, e.g., CDRS, of an antibody selected from MT110, EpCAM-CD3 bispecific Ab (see, e.g., clinicaltrials.gov/ct2/show/NCT00635596); Edrecolomab; 3622W94; ING-1; and adecatumumab (MT201).

In one embodiment, an antigen binding domain against PRSS21 is an antigen binding portion, e.g., CDRs, of an antibody described in U.S. Pat. No. 8,080,650.

In one embodiment, an antigen binding domain against B7H3 is an antigen binding portion, e.g., CDRs, of an antibody MGA271 (Macrogenics).

In one embodiment, an antigen binding domain against KIT is an antigen binding portion, e.g., CDRs, of an antibody described in, e.g., U.S. Pat. No. 7,915,391, US20120288506, and several commercial catalog antibodies.

In one embodiment, an antigen binding domain against IL-13Ra2 is an antigen binding portion, e.g., CDRs, of an antibody described in, e.g., WO2008/146911, WO2004087758, several commercial catalog antibodies, and WO2004087758.

In one embodiment, an antigen binding domain against CD30 is an antigen binding portion, e.g., CDRs, of an antibody described in, e.g., U.S. Pat. No. 7,090,843 B1, and EP0805871.

In one embodiment, an antigen binding domain against GD3 is an antigen binding portion, e.g., CDRs, of an antibody described in, e.g., U.S. Pat. Nos. 7,253,263; 8,207,308; US 20120276046; EP1013761; WO2005035577; and U.S. Pat. No. 6,437,098.

In one embodiment, an antigen binding domain against CD171 is an antigen binding portion, e.g., CDRs, of an antibody described in, e.g., Hong et al., J Immunother 37(2):93-104 (2014).

In one embodiment, an antigen binding domain against IL-11Ra is an antigen binding portion, e.g., CDRs, of an antibody available from Abcam (cat #ab55262) or Novus Biologicals (cat #EPR5446). In another embodiment, an antigen binding domain again IL-11Ra is a peptide, see, e.g., Huang et al., *Cancer Res* 72(1):271-281 (2012).

In one embodiment, an antigen binding domain against PSCA is an antigen binding portion, e.g., CDRs, of an antibody described in, e.g., Morgenroth et al., Prostate 67(10):1121-1131 (2007) (scFv 7F5); Nejatollahi et al., J of Oncology 2013(2013), article ID 839831 (scFv C5-II); and US Pat Publication No. 20090311181.

In one embodiment, an antigen binding domain against VEGFR2 is an antigen binding portion, e.g., CDRs, of an antibody described in, e.g., Chinnasamy et al., J Clin Invest 120(11):3953-3968 (2010).

In one embodiment, an antigen binding domain against LewisY is an antigen binding portion, e.g., CDRs, of an antibody described in, e.g., Kelly et al., Cancer Biother Radiopharm 23(4):411-423 (2008) (hu3S193 Ab (scFvs)); Dolezal et al., Protein Engineering 16(1):47-56 (2003) (NC 10 scFv).

In one embodiment, an antigen binding domain against CD24 is an antigen binding portion, e.g., CDRs, of an antibody described in, e.g., Maliar et al., Gastroenterology 143(5):1375-1384 (2012).

In one embodiment, an antigen binding domain against PDGFR-beta is an antigen binding portion, e.g., CDRs, of an antibody Abcam ab32570.

In one embodiment, an antigen binding domain against SSEA-4 is an antigen binding portion, e.g., CDRs, of antibody MC813 (Cell Signaling), or other commercially available antibodies.

In one embodiment, an antigen binding domain against CD20 is an antigen binding portion, e.g., CDRs, of the antibody Rituximab, Ofatumumab, Ocrelizumab, Veltuzumab, or GA101.

In one embodiment, an antigen binding domain against Folate receptor alpha is an antigen binding portion, e.g., CDRs, of the antibody IMGN853, or an antibody described in US20120009181; U.S. Pat. No. 4,851,332, LK26: U.S. Pat. No. 5,952,484.

In one embodiment, an antigen binding domain against ERBB2 (Her2/neu) is an antigen binding portion, e.g., CDRs, of the antibody trastuzumab, or pertuzumab.

In one embodiment, an antigen binding domain against MUC1 is an antigen binding portion, e.g., CDRs, of the antibody SAR566658.

In one embodiment, the antigen binding domain against EGFR is antigen binding portion, e.g., CDRs, of the antibody cetuximab, panitumumab, zalutumumab, nimotuzumab, or matuzumab.

In one embodiment, an antigen binding domain against NCAM is an antigen binding portion, e.g., CDRs, of the antibody clone 2-2B: MAB5324 (EMD Millipore).

In one embodiment, an antigen binding domain against Ephrin B2 is an antigen binding portion, e.g., CDRs, of an antibody described in, e.g., Abengozar et al., Blood 119(19): 4565-4576 (2012).

In one embodiment, an antigen binding domain against IGF-I receptor is an antigen binding portion, e.g., CDRs, of an antibody described in, e.g., U.S. Pat. No. 8,344,112 B2; EP2322550 A1; WO 2006/138315, or PCT/US2006/022995.

In one embodiment, an antigen binding domain against CAIX is an antigen binding portion, e.g., CDRs, of the antibody clone 303123 (R&D Systems).

In one embodiment, an antigen binding domain against LMP2 is an antigen binding portion, e.g., CDRs, of an antibody described in, e.g., U.S. Pat. No. 7,410,640, or US20050129701.

In one embodiment, an antigen binding domain against gp100 is an antigen binding portion, e.g., CDRs, of the antibody HMB45, NKIbetaB, or an antibody described in WO2013165940, or US20130295007

In one embodiment, an antigen binding domain against tyrosinase is an antigen binding portion, e.g., CDRs, of an antibody described in, e.g., U.S. Pat. No. 5,843,674; or U.S.19950504048.

In one embodiment, an antigen binding domain against EphA2 is an antigen binding portion, e.g., CDRs, of an antibody described in, e.g., Yu et al., Mol Ther 22(1):102-111 (2014).

In one embodiment, an antigen binding domain against GD3 is an antigen binding portion, e.g., CDRs, of an antibody described in, e.g., U.S. Pat. Nos. 7,253,263; 8,207,308; US 20120276046; EP1013761 A3; 20120276046; WO2005035577; or U.S. Pat. No. 6,437,098.

In one embodiment, an antigen binding domain against fucosyl GM1 is an antigen binding portion, e.g., CDRs, of an antibody described in, e.g., US20100297138; or WO2007/067992.

In one embodiment, an antigen binding domain against sLe is an antigen binding portion, e.g., CDRs, of the antibody G193 (for lewis Y), see Scott A M et al, Cancer Res 60: 3254-61 (2000), also as described in Neeson et al, J Immunol May 2013 190 (Meeting Abstract Supplement) 177.10.

In one embodiment, an antigen binding domain against GM3 is an antigen binding portion, e.g., CDRs, of the antibody CA 2523449 (mAb 14F7).

In one embodiment, an antigen binding domain against HMWMAA is an antigen binding portion, e.g., CDRs, of an antibody described in, e.g., Kmiecik et al., Oncoimmunology 3(1):e27185 (2014) (PMID: 24575382) (mAb9.2.27); U.S. Pat. No. 6,528,481; WO2010033866; or US 20140004124.

In one embodiment, an antigen binding domain against o-acetyl-GD2 is an antigen binding portion, e.g., CDRs, of the antibody 8B6.

In one embodiment, an antigen binding domain against TEM1/CD248 is an antigen binding portion, e.g., CDRs, of an antibody described in, e.g., Marty et al., Cancer Lett 235(2):298-308 (2006); Zhao et al., J Immunol Methods 363(2):221-232 (2011).

In one embodiment, an antigen binding domain against CLDN6 is an antigen binding portion, e.g., CDRs, of the antibody IMAB027 (Ganymed Pharmaceuticals), see e.g., clinicaltrial.gov/show/NCT02054351.

In one embodiment, an antigen binding domain against TSHR is an antigen binding portion, e.g., CDRs, of an antibody described in, e.g., U.S. Pat. Nos. 8,603,466; 8,501, 415; or U.S. Pat. No. 8,309,693.

In one embodiment, an antigen binding domain against GPRC5D is an antigen binding portion, e.g., CDRs, of the antibody FAB6300A (R&D Systems); or LS-A4180 (Lifespan Biosciences).

In one embodiment, an antigen binding domain against CD97 is an antigen binding portion, e.g., CDRs, of an antibody described in, e.g., U.S. Pat. No. 6,846,911; de Groot et al., J Immunol 183(6):4127-4134 (2009); or an antibody from R&D:MAB3734.

In one embodiment, an antigen binding domain against ALK is an antigen binding portion, e.g., CDRs, of an antibody described in, e.g., Mino-Kenudson et al., Clin Cancer Res 16(5):1561-1571 (2010).

In one embodiment, an antigen binding domain against polysialic acid is an antigen binding portion, e.g., CDRs, of an antibody described in, e.g., Nagae et al., J Biol Chem 288(47):33784-33796 (2013).

In one embodiment, an antigen binding domain against PLAC1 is an antigen binding portion, e.g., CDRs, of an antibody described in, e.g., Ghods et al., Biotechnol Appl Biochem 2013 doi:10.1002/bab.1177.

In one embodiment, an antigen binding domain against GloboH is an antigen binding portion of the antibody VK9; or an antibody described in, e.g., Kudryashov V et al, Glycoconj J. 15(3):243-9 (1998), Lou et al., Proc Natl Acad Sci USA 111(7):2482-2487 (2014); MBr1: Bremer E-G et al. J Biol Chem 259:14773-14777 (1984).

In one embodiment, an antigen binding domain against NY-BR-1 is an antigen binding portion, e.g., CDRs of an antibody described in, e.g., Jager et al., Appl Immunohistochem Mol Morphol 15(1):77-83 (2007).

In one embodiment, an antigen binding domain against WT-1 is an antigen binding portion, e.g., CDRs, of an antibody described in, e.g., Dao et al., Sci Transl Med 5(176):176ra33 (2013); or WO2012/135854.

In one embodiment, an antigen binding domain against MAGE-A1 is an antigen binding portion, e.g., CDRs, of an antibody described in, e.g., Willemsen et al., J Immunol 174(12):7853-7858 (2005) (TCR– like scFv).

In one embodiment, an antigen binding domain against sperm protein 17 is an antigen binding portion, e.g., CDRs, of an antibody described in, e.g., Song et al., Target Oncol 2013 Aug. 14 (PMID: 23943313); Song et al., Med Oncol 29(4):2923-2931 (2012).

In one embodiment, an antigen binding domain against Tie 2 is an antigen binding portion, e.g., CDRs, of the antibody AB33 (Cell Signaling Technology).

In one embodiment, an antigen binding domain against MAD-CT-2 is an antigen binding portion, e.g., CDRs, of an antibody described in, e.g., PMID: 2450952; U.S. Pat. No. 7,635,753.

In one embodiment, an antigen binding domain against Fos-related antigen 1 is an antigen binding portion, e.g., CDRs, of the antibody 12F9 (Novus Biologicals).

In one embodiment, an antigen binding domain against MelanA/MART1 is an antigen binding portion, e.g., CDRs, of an antibody described in, EP2514766 A2; or U.S. Pat. No. 7,749,719.

In one embodiment, an antigen binding domain against sarcoma translocation breakpoints is an antigen binding portion, e.g., CDRs, of an antibody described in, e.g., Luo et al, EMBO Mol. Med. 4(6):453-461 (2012).

In one embodiment, an antigen binding domain against TRP-2 is an antigen binding portion, e.g., CDRs, of an antibody described in, e.g., Wang et al, J Exp Med. 184(6): 2207-16 (1996).

In one embodiment, an antigen binding domain against CYP1B1 is an antigen binding portion, e.g., CDRs, of an antibody described in, e.g., Maecker et al, Blood 102 (9): 3287-3294 (2003).

In one embodiment, an antigen binding domain against RAGE-1 is an antigen binding portion, e.g., CDRs, of the antibody MAB5328 (EMD Millipore).

In one embodiment, an antigen binding domain against human telomerase reverse transcriptase is an antigen binding portion, e.g., CDRs, of the antibody cat no: LS-B95-100 (Lifespan Biosciences)

In one embodiment, an antigen binding domain against intestinal carboxyl esterase is an antigen binding portion, e.g., CDRs, of the antibody 4F12: cat no: LS-B6190-50 (Lifespan Biosciences).

In one embodiment, an antigen binding domain against mut hsp70-2 is an antigen binding portion, e.g., CDRs, of the antibody Lifespan Biosciences: monoclonal: cat no: LS-C133261-100 (Lifespan Biosciences).

In one embodiment, an antigen binding domain against CD79a is an antigen binding portion, e.g., CDRs, of the antibody Anti-CD79a antibody [HM47/A9] (ab3121), available from Abcam; antibody CD79A Antibody #3351 available from Cell Signalling Technology; or antibody HPA017748-Anti-CD79A antibody produced in rabbit, available from Sigma Aldrich.

In one embodiment, an antigen binding domain against CD79b is an antigen binding portion, e.g., CDRs, of the antibody polatuzumab vedotin, anti-CD79b described in Dornan et al., "Therapeutic potential of an anti-CD79b antibody-drug conjugate, anti-CD79b-vc-MMAE, for the treatment of non-Hodgkin lymphoma" Blood. 2009 Sep. 24; 114(13):2721-9. doi: 10.1182/blood-2009-02-205500. Epub 2009 Jul. 24, or the bispecific antibody Anti-CD79b/CD3 described in "4507 Pre-Clinical Characterization of T Cell-Dependent Bispecific Antibody Anti-CD79b/CD3 As a Potential Therapy for B Cell Malignancies" Abstracts of 56$^{th}$ ASH Annual Meeting and Exposition, San Francisco, CA Dec. 6-9, 2014.

In one embodiment, an antigen binding domain against CD72 is an antigen binding portion, e.g., CDRs, of the antibody J3-109 described in Myers, and Uckun, "An anti-CD72 immunotoxin against therapy-refractory B-lineage acute lymphoblastic leukemia." Leuk Lymphoma. 1995 June; 18(1-2):119-22, or anti-CD72 (10D6.8.1, mIgG1) described in Polson et al., "Antibody-Drug Conjugates for the Treatment of Non-Hodgkin's Lymphoma: Target and Linker-Drug Selection" Cancer Res Mar. 15, 2009 69; 2358.

In one embodiment, an antigen binding domain against LAIR1 is an antigen binding portion, e.g., CDRs, of the antibody ANT-301 LAIR1 antibody, available from ProSpec; or anti-human CD305 (LAIR1) Antibody, available from BioLegend.

In one embodiment, an antigen binding domain against FCAR is an antigen binding portion, e.g., CDRs, of the antibody CD89/FCARAntibody (Catalog #10414-H08H), available from Sino Biological Inc.

In one embodiment, an antigen binding domain against LILRA2 is an antigen binding portion, e.g., CDRs, of the antibody LILRA2 monoclonal antibody (M17), clone 3C7, available from Abnova, or Mouse Anti-LILRA2 antibody, Monoclonal (2D7), available from Lifespan Biosciences.

In one embodiment, an antigen binding domain against CD300LF is an antigen binding portion, e.g., CDRs, of the antibody Mouse Anti-CMRF35-like molecule 1 antibody, Monoclonal[UP-D2, available from BioLegend, or Rat Anti-CMRF35-like molecule 1 antibody, Monoclonal[234903], available from R&D Systems.

In one embodiment, an antigen binding domain against CLEC12A is an antigen binding portion, e.g., CDRs, of the antibody Bispecific T cell Engager (BiTE) scFv-antibody and ADC described in Noordhuis et al., "Targeting of CLEC12A In Acute Myeloid Leukemia by Antibody-Drug-Conjugates and Bispecific CLL-1xCD3 BiTE Antibody" 53$^{rd}$ ASH Annual Meeting and Exposition, Dec. 10-13, 2011, and MCLA-117 (Merus).

In one embodiment, an antigen binding domain against BST2 (also called CD317) is an antigen binding portion, e.g., CDRs, of the antibody Mouse Anti-CD317 antibody, Monoclonal[3H4], available from Antibodies-Online or Mouse Anti-CD317 antibody, Monoclonal [696739], available from R&D Systems.

In one embodiment, an antigen binding domain against EMR2 (also called CD312) is an antigen binding portion, e.g., CDRs, of the antibody Mouse Anti-CD312 antibody, Monoclonal[LS-B8033] available from Lifespan Biosciences, or Mouse Anti-CD312 antibody, Monoclonal available from R&D Systems.

In one embodiment, an antigen binding domain against LY75 is an antigen binding portion, e.g., CDRs, of the antibody Mouse Anti-Lymphocyte antigen 75 antibody, Monoclonal[HD30] available from EMD Millipore or Mouse Anti-Lymphocyte antigen 75 antibody, Monoclonal [A15797] available from Life Technologies.

In one embodiment, an antigen binding domain against GPC3 is an antigen binding portion, e.g., CDRs, of the antibody hGC33 described in Nakano K, Ishiguro T, Konishi H, et al. Generation of a humanized anti-glypican 3 antibody by CDR grafting and stability optimization. Anticancer Drugs. 2010 November; 21(10):907-916, or MDX-1414, HN3, or YP7, all three of which are described in Feng et al., "Glypican-3 antibodies: a new therapeutic target for liver cancer." FEBS Lett. 2014 Jan. 21; 588(2):377-82.

In one embodiment, an antigen binding domain against FCRL5 is an antigen binding portion, e.g., CDRs, of the anti-FcRL5 antibody described in Elkins et al., "FcRL5 as a target of antibody-drug conjugates for the treatment of multiple myeloma" Mol Cancer Ther. 2012 October; 11(10): 2222-32. In one embodiment, an antigen binding domain against FCRL5 is an antigen binding portion, e.g., CDRs, of the anti-FcRL5 antibody described in, for example, WO2001/038490, WO/2005/117986, WO2006/039238, WO2006/076691, WO2010/114940, WO2010/120561, or WO2014/210064.

In one embodiment, an antigen binding domain against IGLL1 is an antigen binding portion, e.g., CDRs, of the antibody Mouse Anti-Immunoglobulin lambda-like polypeptide 1 antibody, Monoclonal[AT1G4] available from Lifespan Biosciences, Mouse Anti-Immunoglobulin lambda-like polypeptide 1 antibody, Monoclonal[HSL11] available from BioLegend.

In one embodiment, the antigen binding domain comprises one, two three (e.g., all three) heavy chain CDRs, HC CDR1, HC CDR2 and HC CDR3, from an antibody listed above, and/or one, two, three (e.g., all three) light chain CDRs, LC CDR1, LC CDR2 and LC CDR3, from an antibody listed above. In one embodiment, the antigen binding domain comprises a heavy chain variable region and/or a variable light chain region of an antibody listed above.

In another aspect, the antigen binding domain comprises a humanized antibody or an antibody fragment. In some aspects, a non-human antibody is humanized, where specific sequences or regions of the antibody are modified to increase similarity to an antibody naturally produced in a human or fragment thereof. In one aspect, the antigen binding domain is humanized.

In an embodiment, the antigen-binding domain of a CAR, e.g., a CAR expressed by a cell of the invention, binds to CD19. CD19 is found on B cells throughout differentiation of the lineage from the pro/pre-B cell stage through the terminally differentiated plasma cell stage. In an embodiment, the antigen binding domain is a murine scFv domain that binds to human CD19, e.g., the antigen binding domain of CTL019 (e.g., SEQ ID NO: 7895). In an embodiment, the antigen binding domain is a humanized antibody or antibody fragment, e.g., scFv domain, derived from the murine CTL019 scFv. In an embodiment, the antigen binding domain is a human antibody or antibody fragment that binds to human CD19. Exemplary scFv domains (and their sequences, e.g., CDRs, VL and VH sequences) that bind to CD19 are provided in Table 14. The scFv domain sequences provided in Table 14 include a light chain variable region (VL) and a heavy chain variable region (VH). The VL and VH are attached by a linker comprising the sequence GGGGSGGGGSGGGGS (SEQ ID NO: 6594), e.g., in the following orientation: VL-linker-VH.

TABLE 14

| Antigen Binding domains that bind CD19 | | | |
|---|---|---|---|
| Antigen | Name | Amino Acid Sequence | SEQ ID NO: |
| CD19 | muCTL019 | DIQMTQTTSSLSASLGDRVTISCRASQDISKYLNWYQQKPDGTVKLLI YHTSRLHSGVPSRFSGSGSGTDYSLTISNLEQEDIATYFCQQGNTLPY TFGGGTKLEITGGGGSGGGGSGGGGSEVKLQESGPGLVAPSQSLSVTC | 7895 |

TABLE 14-continued

Antigen Binding domains that bind CD19

| Antigen | Name | Amino Acid Sequence | SEQ ID NO: |
|---|---|---|---|
| | | TVSGVSLPDYGVSWIRQPPRKGLEWLGVIWGSETTYYNSALKSRLTII KDNSKSQVFLKMNSLQTDDTAIYYCAKHYYYGGSYAMDYWGQGTSVTV SS | |
| CD19 | huscFv1 | EIVMTQSPATLSLSPGERATLSCRASQDISKYLNWYQQKPGQAPRLLI YHTSRLHSGIPARFSGSGSGTDYTLTISSLQPEDFAVYFCQQGNTLPY TFGQGTKLEIKGGGGSGGGGSGGGGSQVQLQESGPGLVKPSETLSLTC TVSGVSLPDYGVSWIRQPPGKGLEWIGVIWGSETTYYSSSLKSRVTIS KDNSKNQVSLKLSSVTAADTAVYYCAKHYYYGGSYAMDYWGQGTLVTV SS | 7883 |
| CD19 | huscFv2 | EIVMTQSPATLSLSPGERATLSCRASQDISKYLNWYQQKPGQAPRLLI YHTSRLHSGIPARFSGSGSGTDYTLTISSLQPEDFAVYFCQQGNTLPY TFGQGTKLEIKGGGGSGGGGSGGGGSQVQLQESGPGLVKPSETLSLTC TVSGVSLPDYGVSWIRQPPGKGLEWIGVIWGSETTYYQSSLKSRVTIS KDNSKNQVSLKLSSVTAADTAVYYCAKHYYYGGSYAMDYWGQGTLVTV SS | 7884 |
| CD19 | huscFv3 | QVQLQESGPGLVKPSETLSLTCTVSGVSLPDYGVSWIRQPPGKGLEWI GVIWGSETTYYSSSLKSRVTISKDNSKNQVSLKLSSVTAADTAVYYCA KHYYYGGSYAMDYWGQGTLVTVSSGGGGSGGGGSGGGGSEIVMTQSPA TLSLSPGERATLSCRASQDISKYLNWYQQKPGQAPRLLIYHTSRLHSG IPARFSGSGSGTDYTLTISSLQPEDFAVYFCQQGNTLPYTFGQGTKLE IK | 7885 |
| CD19 | huscFv4 | QVQLQESGPGLVKPSETLSLTCTVSGVSLPDYGVSWIRQPPGKGLEWI GVIWGSETTYYQSSLKSRVTISKDNSKNQVSLKLSSVTAADTAVYYCA KHYYYGGSYAMDYWGQGTLVTVSSGGGGSGGGGSGGGGSEIVMTQSPA TLSLSPGERATLSCRASQDISKYLNWYQQKPGQAPRLLIYHTSRLHSG IPARFSGSGSGTDYTLTISSLQPEDFAVYFCQQGNTLPYTFGQGTKLE IK | 7886 |
| CD19 | huscFv5 | EIVMTQSPATLSLSPGERATLSCRASQDISKYLNWYQQKPGQAPRLLI YHTSRLHSGIPARFSGSGSGTDYTLTISSLQPEDFAVYFCQQGNTLPY TFGQGTKLEIKGGGGSGGGGSGGGGSGGGGSQVQLQESGPGLVKPSET LSLTCTVSGVSLPDYGVSWIRQPPGKGLEWIGVIWGSETTYYSSSLKS RVTISKDNSKNQVSLKLSSVTAADTAVYYCAKHYYYGGSYAMDYWGQG TLVTVSS | 7887 |
| CD19 | huscFv6 | EIVMTQSPATLSLSPGERATLSCRASQDISKYLNWYQQKPGQAPRLLI YHTSRLHSGIPARFSGSGSGTDYTLTISSLQPEDFAVYFCQQGNTLPY TFGQGTKLEIKGGGGSGGGGSGGGGSGGGGSQVQLQESGPGLVKPSET LSLTCTVSGVSLPDYGVSWIRQPPGKGLEWIGVIWGSETTYYQSSLKS RVTISKDNSKNQVSLKLSSVTAADTAVYYCAKHYYYGGSYAMDYWGQG TLVTVSS | 7888 |
| CD19 | huscFv7 | QVQLQESGPGLVKPSETLSLTCTVSGVSLPDYGVSWIRQPPGKGLEWI GVIWGSETTYYSSSLKSRVTISKDNSKNQVSLKLSSVTAADTAVYYCA KHYYYGGSYAMDYWGQGTLVTVSSGGGGSGGGGSGGGGSGGGGSEIVM TQSPATLSLSPGERATLSCRASQDISKYLNWYQQKPGQAPRLLIYHTS RLHSGIPARFSGSGSGTDYTLTISSLQPEDFAVYFCQQGNTLPYTFGQ GTKLEIK | 7889 |
| CD19 | huscFv8 | QVQLQESGPGLVKPSETLSLTCTVSGVSLPDYGVSWIRQPPGKGLEWI GVIWGSETTYYQSSLKSRVTISKDNSKNQVSLKLSSVTAADTAVYYCA KHYYYGGSYAMDYWGQGTLVTVSSGGGGSGGGGSGGGGSGGGGSEIVM TQSPATLSLSPGERATLSCRASQDISKYLNWYQQKPGQAPRLLIYHTS RLHSGIPARFSGSGSGTDYTLTISSLQPEDFAVYFCQQGNTLPYTFGQ GTKLEIK | 7890 |
| CD19 | huscFv9 | EIVMTQSPATLSLSPGERATLSCRASQDISKYLNWYQQKPGQAPRLLI YHTSRLHSGIPARFSGSGSGTDYTLTISSLQPEDFAVYFCQQGNTLPY TFGQGTKLEIKGGGGSGGGGSGGGGSGGGGSQVQLQESGPGLVKPSET LSLTCTVSGVSLPDYGVSWIRQPPGKGLEWIGVIWGSETTYYNSSLKS RVTISKDNSKNQVSLKLSSVTAADTAVYYCAKHYYYGGSYAMDYWGQG TLVTVSS | 7891 |
| CD19 | HuscFv10 | QVQLQESGPGLVKPSETLSLTCTVSGVSLPDYGVSWIRQPPGKGLEWI GVIWGSETTYYNSSLKSRVTISKDNSKNQVSLKLSSVTAADTAVYYCA KHYYYGGSYAMDYWGQGTLVTVSSGGGGSGGGGSGGGGSGGGGSEIVM TQSPATLSLSPGERATLSCRASQDISKYLNWYQQKPGQAPRLLIYHTS RLHSGIPARFSGSGSGTDYTLTISSLQPEDFAVYFCQQGNTLPYTFGQ GTKLEIK | 7892 |

TABLE 14-continued

Antigen Binding domains that bind CD19

| Antigen | Name | Amino Acid Sequence | SEQ ID NO: |
|---|---|---|---|
| CD19 | HuscFv11 | EIVMTQSPATLSLSPGERATLSCRASQDISKYLNWYQQKPGQAPRLLI YHTSRLHSGIPARFSGSGSGTDYTLTISSLQPEDFAVYFCQQGNTLPY TFGQGTKLEIKGGGGSGGGGSGGGGSQVQLQESGPGLVKPSETLSLTC TVSGVSLPDYGVSWIRQPPGKGLEWIGVIWGSETTYYNSSLKSRVTIS KDNSKNQVSLKLSSVTAADTAVYYCAKHYYYGGSYAMDYWGQGTLVTV SS | 7893 |
| CD19 | HuscFv12 | QVQLQESGPGLVKPSETLSLTCTVSGVSLPDYGVSWIRQPPGKGLEWI GVIWGSETTYYNSSLKSRVTISKDNSKNQVSLKLSSVTAADTAVYYCA KHYYYGGSYAMDYWGQGTLVTVSSGGGGSGGGGSGGGGSEIVMTQSPA TLSLSPGERATLSCRASQDISKYLNWYQQKPGQAPRLLIYHTSRLHSG IPARFSGSGSGTDYTLTISSLQPEDFAVYFCQQGNTLPYTFGQGTKLE IK | 7894 |

The sequences of the CDR sequences of the scFv domains of the CD19 antigen binding domains provided in Table 14 are shown in Table 15 for the heavy chain variable domains and in Table 16 for the light chain variable domains. "ID" stands for the respective SEQ ID NO for each CDR.

TABLE 15

Heavy Chain Variable Domain CDRs

| Description | FW | HCDR1 | ID | HCDR2 | ID | HCDR3 | ID |
|---|---|---|---|---|---|---|---|
| murine_CART19 | | GVSLPDYGVS | 7899 | VIWGSETTYYNSALKS | 7900 | HYYYGGSYAMDY | 7904 |
| humanized_CART19 a | VH4 | GVSLPDYGVS | 7899 | VIWGSETTYY*SS*LKS | 7901 | HYYYGGSYAMDY | 7904 |
| humanized_CART19 b | VH4 | GVSLPDYGVS | 7899 | VIWGSETTYY*QS*LKS | 7902 | HYYYGGSYAMDY | 7904 |
| humanized_CART19 c | VH4 | GVSLPDYGVS | 7899 | VIWGSETTYYNS*S*LKS | 7903 | HYYYGGSYAMDY | 7904 |

TABLE 16

Light Chain Variable Domain CDRs

| Description | FW | LCDR1 | ID | LCDR2 | ID | LCDR3 | ID |
|---|---|---|---|---|---|---|---|
| murine_CART19 | | RASQDISKYLN | 7905 | HTSRLHS | 7906 | QQGNTLPYT | 7907 |
| humanized_CART19 a | VK3 | RASQDISKYLN | 7905 | HTSRLHS | 7906 | QQGNTLPYT | 7907 |
| humanized_CART19 b | VK3 | RASQDISKYLN | 7905 | HTSRLHS | 7906 | QQGNTLPYT | 7907 |
| humanized_CART19 c | VK3 | RASQDISKYLN | 7905 | HTSRLHS | 7906 | QQGNTLPYT | 7907 |

In an embodiment, the antigen binding domain comprises an anti-CD19 antibody, or fragment thereof, e.g., an scFv. For example, the antigen binding domain comprises a variable heavy chain and a variable light chain listed in Table 17. The linker sequence joining the variable heavy and variable light chains can be any of the linker sequences described herein, or alternatively, can be GSTSGSGKPGSGEGSTKG (SEQ ID NO: 8167). The light chain variable region and heavy chain variable region of a scFv can be, e.g., in any of the following orientations: light chain variable region-linker-heavy chain variable region or heavy chain variable region-linker-light chain variable region.

TABLE 17

Additional Anti-CD19 antibody binding domains

| Ab Name | VH Sequence | VL Sequence |
|---|---|---|
| SJ25-C1 | QVQLLESGAELVRPGSSVKISCKASG YAFSSYWMNWVKQRPGQGLEWIGQIY PGDGDTNYNGKFKGQATLTADKSSST AYMQLSGLTSEDSAVYSCARKTISSV VDFYFDYWGQGTTVT (SEQ ID | ELVLTQSPKFMSTVGDRVSVTCKASQNV GTNVAWYQQKPGQSPKPLIYSATYRNSGV PDRFTGSGSGTDFTLTITNVQSKDLADYF YFCQYNRYPYTSGGGTKLEIKRRS (SEQ ID NO: 7897) |

TABLE 17-continued

Additional Anti-CD19 antibody binding domains

NO: 7896)

ScFv Sequence

SJ25-C1 scFv
QVQLLESGAELVRPGSSVKISCKASGYAFSSYWMNWVKQRPGQGLEWIGQIYPGDGD
TNYNGKFKGQATLTADKSSSTAYMQLSGLTSEDSAVYSCARKTISSVVDFYFDYWGQ
GTTVTGSTSGSGKPGSGEGSTKGELVLTQSPKFMSTSVGDRVSVTCKASQNVGTNVA
WYQQKPGQSPKPLIYSATYRNSGVPDRFTGSGSGTDFTLTITNVQSKDLADYFYFCQ
YNRYPYTSGGGTKLEIKRRS (SEQ ID NO: 7898)

In one embodiment, the CD19 binding domain comprises one or more (e.g., all three) light chain complementary determining region 1 (LC CDR1), light chain complementary determining region 2 (LC CDR2), and light chain complementary determining region 3 (LC CDR3) of a CD19 binding domain described herein, e.g., provided in Table 14 or 15, and/or one or more (e.g., all three) heavy chain complementary determining region 1 (HC CDR1), heavy chain complementary determining region 2 (HC CDR2), and heavy chain complementary determining region 3 (HC CDR3) of a CD19 binding domain described herein, e.g., provided in Table 14 or 16. In one embodiment, the CD19 binding domain comprises one, two, or all of LC CDR1, LC CDR2, and LC CDR3 of any amino acid sequences as provided in Table 16, incorporated herein by reference; and one, two or all of HC CDR1, HC CDR2, and HC CDR3 of any amino acid sequences as provided in Table 15.

In one embodiment, the CD19 antigen binding domain comprises:
  (i) (a) a LC CDR1 amino acid sequence of SEQ ID NO: 7905, a LC CDR2 amino acid sequence of SEQ ID NO: 7906, and a LC CDR3 amino acid sequence of SEQ ID NO: 7907; and (b) a HC CDR1 amino acid sequence of SEQ ID NO: 7899, a HC CDR2 amino acid sequence of SEQ ID NO: 7900, and a HC CDR3 amino acid sequence of SEQ ID NO: 7904
  (ii) (a) a LC CDR1 amino acid sequence of SEQ ID NO: 7905, a LC CDR2 amino acid sequence of SEQ ID NO: 7906, and a LC CDR3 amino acid sequence of SEQ ID NO: 7907; and (b) a HC CDR1 amino acid sequence of SEQ ID NO: 7899, a HC CDR2 amino acid sequence of SEQ ID NO: 7901, and a HC CDR3 amino acid sequence of SEQ ID NO: 7904;
  (iii) (a) a LC CDR1 amino acid sequence of SEQ ID NO: 7905, a LC CDR2 amino acid sequence of SEQ ID NO: 7906, and a LC CDR3 amino acid sequence of SEQ ID NO: 7907; and (b) a HC CDR1 amino acid sequence of SEQ ID NO: 7899, a HC CDR2 amino acid sequence of SEQ ID NO: 7902, and a HC CDR3 amino acid sequence of SEQ ID NO: 7904; or
  (iv) (a) a LC CDR1 amino acid sequence of SEQ ID NO: 7905, a LC CDR2 amino acid sequence of SEQ ID NO: 7906, and a LC CDR3 amino acid sequence of SEQ ID NO: 7907; and (b) a HC CDR1 amino acid sequence of SEQ ID NO: 7899, a HC CDR2 amino acid sequence of SEQ ID NO: 7903, and a HC CDR3 amino acid sequence of SEQ ID NO: 7904.

In one embodiment, the CD19 binding domain comprises a light chain variable region described herein (e.g., in Table 14 or 17) and/or a heavy chain variable region described herein (e.g., in Table 14 or 17). In one embodiment, the CD19 binding domain is a scFv comprising a light chain and a heavy chain of an amino acid sequence listed in Table 14 or 17. In one embodiment, the CD19 binding domain (e.g., an scFv) comprises: a light chain variable region comprising an amino acid sequence having at least one, two or three modifications (e.g., substitutions, e.g., conservative substitutions) but not more than 30, 20 or 10 modifications (e.g., substitutions, e.g., conservative substitutions) of an amino acid sequence of a light chain variable region provided in Table 14 or 17, or a sequence with 95-99% identity with an amino acid sequence provided in Table 14 or 17; and/or a heavy chain variable region comprising an amino acid sequence having at least one, two or three modifications (e.g., substitutions, e.g., conservative substitutions) but not more than 30, 20 or 10 modifications (e.g., substitutions, e.g., conservative substitutions) of an amino acid sequence of a heavy chain variable region provided in Table 14 or 17, or a sequence with 95-99% identity to an amino acid sequence provided in Table 14 or 17.

In one embodiment, the CD19 binding domain comprises an amino acid sequence selected from a group consisting of SEQ ID NO: 7883; SEQ ID NO: 7884, SEQ ID NO: 7885; SEQ ID NO: 7886; SEQ ID NO: 7887; SEQ ID NO: 7888; SEQ ID NO: 7889, SEQ ID NO: 7890, SEQ ID NO: 7891, SEQ ID NO: 7892, SEQ ID NO: 7893, SEQ ID NO: 7894, SEQ ID NO: 7895, and SEQ ID NO: 7898; or an amino acid sequence having at least one, two or three modifications (e.g., substitutions, e.g., conservative substitutions) but not more than 30, 20 or 10 modifications (e.g., substitutions, e.g., conservative substitutions) to any of the aforesaid sequences; or a sequence with 95-99% identity to any of the aforesaid sequences. In one embodiment, the CD19 binding domain is a scFv, and a light chain variable region comprising an amino acid sequence described herein, e.g., in Table 14 or 17, is attached to a heavy chain variable region comprising an amino acid sequence described herein, e.g., in Table 14 or 17, via a linker, e.g., a linker described herein. In one embodiment, the CD19 binding domain includes a (Gly4-Ser)n linker, wherein n is 1, 2, 3, 4, 5, or 6, preferably 3 (SEQ ID NO: 10801). The light chain variable region and heavy chain variable region of a scFv can be, e.g., in any of the following orientations: light chain variable region-linker-heavy chain variable region or heavy chain variable region-linker-light chain variable region.

Any known CD19 CAR, e.g., the CD19 antigen binding domain of any known CD19 CAR, in the art can be used in accordance with the instant invention to construct a CAR. For example, LG-740; CD19 CAR described in the U.S. Pat. Nos. 8,399,645; 7,446,190; Xu et al., Leuk Lymphoma. 2013 54(2):255-260(2012); Cruz et al., Blood 122(17): 2965-2973 (2013); Brentjens et al., Blood, 118(18):4817-4828 (2011); Kochenderfer et al., Blood 116(20):4099-102 (2010); Kochenderfer et al., Blood 122 (25):4129-39(2013); and 16th Annu Meet Am Soc Gen Cell Ther (ASGCT) (May 15-18, Salt Lake City) 2013, Abst 10. In one embodiment, an antigen binding domain against CD19 is an antigen binding portion, e.g., CDRs, of a CAR, antibody or antigen-binding fragment thereof described in, e.g., PCT publication WO2012/079000; PCT publication WO2014/153270; Kochenderfer, J. N. et al., J. Immunother. 32 (7), 689-702 (2009); Kochenderfer, J. N., et al., Blood, 116 (20), 4099-4102 (2010); PCT publication WO2014/031687; Bejcek Cancer Research, 55, 2346-2351, 1995; or U.S. Pat. No. 7,446,190.

In an embodiment, the antigen-binding domain of CAR, e.g., a CAR expressed by a cell of the invention, binds to BCMA. BCMA is found preferentially expressed in mature B lymphocytes. In an embodiment, the antigen binding domain is a murine scFv domain that binds to human BCMA. In an embodiment, the antigen binding domain is a humanized antibody or antibody fragment, e.g., scFv domain, that binds human BCMA. In an embodiment, the antigen binding domain is a human antibody or antibody fragment that binds to human BCMA. Exemplary scFv domains (and their sequences, e.g., CDRs, VL and VH sequences) that bind to BCMA are provided in Table 18, Table 19, Table 20 and Table 21. The scFv domain sequences provided in Table 18 and Table 19 include a light chain variable region (VL) and a heavy chain variable region (VH). The VL and VH are attached by a linker, e.g., in the following orientation: VH-linker-VL.

TABLE 18

Antigen Binding domains that bind BCMA
The amino acid sequences variable heavy chain and variable light chain sequences for each scFv is also provided.

| Name/ Description | SEQ ID NO: | Sequence |
|---|---|---|
| 139109 | | |
| 139109-aa ScFv domain | 7949 | EVQLVESGGGLVQPGGSLRLSCAVSGFALSNHGMSWVRRAPGKGLEWVSG IVYSGSTYYAASVKGRFTISRDNSRNTLYLQMNSLRPEDTAIYYCSAHGG ESDVWGQGTTVTVSSASGGGGSGGRASGGGGSDIQLTQSPSSLSASVGDR VTITCRASQSISSYLNWYQQKPGKAPKLLIYAASSLQSGVPSRFSGSGSG TDFTLTISSLQPEDFATYYCQQSYSTPYTEGQGTKVEIK |
| 139109-nt ScFv domain | 7964 | GAAGTGCAATTGGTGGAATCAGGGGGAGGACTTGTGCAGCCTGGAGGATC GCTGAGACTGTCATGTGCCGTGTCCGGCTTTGCCCTGTCCAACCACGGGA TGTCCTGGGTCCGCCGCGCGCCTGGAAAGGGCCTCGAATGGGTGTCGGGT ATTGTGTACAGCGGTAGCACCTACTATGCCGCATCCGTGAAGGGAGATT CACCATCAGCCGGGACAACTCCAGGAACACTCTGTACCTCCAAATGAATT CGCTGAGGCCAGAGGACACTGCCATCTACTACTGCTCCGCGCATGGCGGA GAGTCCGACGTCTGGGGACAGGGGACCACCGTGACCGTGTCTAGCGCGTC CGGCGGAGGCGGCAGCGGGGGTCGGGCATCAGGGGGCGGCGGATCGGACA TCCAGCTCACCCAGTCCCCGAGCTCGCTGTCCGCCTCCGTGGGAGATCGG GTCACCATCACGTGCCGCGCCAGCCAGTCGATTTCCTCCTACCTGAACTG GTACCAACAGAAGCCCGGAAAAGCCCCGAAGCTTCTCATCTACGCCGCCT CGAGCCTGCAGTCAGGAGTGCCCTCACGGTTCTCCGGCTCCGGTTCCGGT ACTGATTTCACCCTGACCATTTCCTCCCTGCAACCGGAGGACTTCGCTAC TTACTACTGCCAGCAGTCGTACTCCACCCCCTACACTTTCGGACAAGGCA CCAAGGTCGAAATCAAG |
| 139109-aa VH | 7979 | EVQLVESGGGLVQPGGSLRLSCAVSGFALSNHGMSWVRRAPGKGLEWVSG IVYSGSTYYAASVKGRFTISRDNSRNTLYLQMNSLRPEDTAIYYCSAHGG ESDVWGQGTTVTVSS |
| 139109-aa VL | 7994 | DIQLTQSPSSLSASVGDRVTITCRASQSISSYLNWYQQKPGKAPKLLIYA ASSLQSGVPSRFSGSGSGTDFTLTISSLQPEDFATYYCQQSYSTPYTFGQ GTKVEIK |
| 139103 | | |
| 139103-aa ScFv domain | 7939 | QVQLVESGGGLVQPGRSLRLSCAASGFTFSNYAMSWVRQAPGKGLGWVSG ISRSGENTYYADSVKGRFTISRDNSKNTLYLQMNSLRDEDTAVYYCARSP AHYYGGMDVWGQGTTVTVSSASGGGGSGGRASGGGGSDIVLTQSPGTLSL SPGERATLSCRASQSISSSFLAWYQQKPGQAPRLLIYGASRRATGIPDRF SGSGSGTDFTLTISRLEPEDSAVYYCQQYHSSPSWTFGQGTKLEIK |
| 139103-nt ScFv domain | 7954 | CAAGTGCAACTCGTGGAATCTGGTGGAGGACTCGTGCAACCCGGAAGATC GCTTAGACTGTCGTGTGCCGCCAGCGGGTTCACTTTCTCGAACTACGCGA TGTCCTGGGTCCGCCAGGCACCCGGAAAGGGACTCGGTTGGGTGTCCGGC ATTTCCCGGTCCGGCGAAAATACCTACTACGCCGACTCCGTGAAGGGCCG CTTCACCATCTCAAGGGACAACAGCAAAAACACCCTGTACTTGCAAATGA ACTCCCTGCGGGATGAAGATACAGCCGTGTACTATTGCGCCCGGTCGCCT GCCCATTACTACGGCGGAATGGACGTCTGGGGACAGGGAACCACTGTGAC TGTCAGCAGCGCGTCGGGTGGCGGCGGCTCAGGGGGTCGGGCCTCCGGGG GGGAGGGGTCCGACATCGTGCTGACCCAGTCCCCGGGAACCCTGAGCCTG AGCCCGGGAGAGCGCGCGACCCTGTCATGCCGGGCATCCCAGAGCATTAG CTCCTCCTTTCTCGCCTGGTATCAGCAGAAGCCCGGACAGGCCCCGAGGC TGCTGATCTACGGCGCTAGCAGAAGGGCTACCGGAATCCCAGACCGGTTC TCCGGCTCCGGTTCCGGGACCGATTTCACCCTTACTATCTCGCGCCTGGA ACCTGAGGACTCCGCCGTCTACTACTGCCAGCAGTACCACTCATCCCCGT CGTGGACGTTCGGACAGGGCACCAAGCTGGAGATTAAG |

TABLE 18-continued

Antigen Binding domains that bind BCMA
The amino acid sequences variable heavy chain and variable light chain
sequences for each scFv is also provided.

| Name/<br>Description | SEQ ID<br>NO: | Sequence |
| --- | --- | --- |
| 139103-aa<br>VH | 7969 | QVQLVESGGGLVQPGRSLRLSCAASGFTFSNYAMSWVRQAPGKGLGWVSG<br>ISRSGENTYYADSVKGRFTISRDNSKNTLYLQMNSLRDEDTAVYYCARSP<br>AHYYGGMDVWGQGTTVTVSS |
| 139103-aa<br>VL | 7984 | DIVLTQSPGTLSLSPGERATLSCRASQSISSSFLAWYQQKPGQAPRLLIY<br>GASRRATGIPDRFSGSGSGTDFTLTISRLEPEDSAVYYCQQYHSSPSWTF<br>GQGTKLEIK |

139105

| 139105-aa<br>ScFv domain | 7940 | QVQLVESGGGLVQPGRSLRLSCAASGFTFDDYAMHWVRQAPGKGLEWVSG<br>ISWNSGSIGYADSVKGRFTISRDNAKNSLYLQMNSLRAEDTALYYCSVHS<br>FLAYWGQGTLVTVSSASGGGGSGGRASGGGGSDIVMTQTPLSLPVTPGEP<br>ASISCRSSQSLLHSNGYNYLDWYLQKPGQSPQLLIYLGSNRASGVPDRFS<br>GSGSGTDFTLKISRVEAEDVGVYYCMQALQTPYTFGQGTKVEIK |
| --- | --- | --- |
| 139105-nt<br>ScFv domain | 7955 | CAAGTGCAACTCGTCGAATCCGGTGGAGGTCTGGTCCAACCTGGTAGAAG<br>CCTGAGACTGTCGTGTGCGGCCAGCGGATTCACCTTTGATGACTATGCTA<br>TGCACTGGGTGCGGCAGGCCCCAGGAAAGGGCCTGGAATGGGTGTCGGGA<br>ATTAGCTGGAACTCCGGGTCCATTGGCTACGCCGACTCCGTGAAGGGCCG<br>CTTCACCATCTCCCGCGACAACGCAAAGAACTCCCTGTACTTGCAAATGA<br>ACTCGCTCAGGGCTGAGGATACCGCGCTGTACTACTGCTCCGTGCATTCC<br>TTCCTGGCCTACTGGGGACAGGGAACTCTGGTCACCGTGTCGAGCGCCTC<br>CGGCGGCGGGGGCTCGGGTGGACGGGCCTCGGGCGGAGGGGGTCCGACA<br>TCGTGATGACCCAGACCCCGCTGAGCTTGCCCGTGACTCCCGGAGAGCCT<br>GCATCCATCTCCTGCCGGTCATCCCAGTCCCTTCTCCACTCCAACGGATA<br>CAACTACCTCGACTGGTACCTCCAGAAGCCGGGACAGAGCCCTCAGCTTC<br>TGATCTACCTGGGGTCAAATAGAGCCTCAGGAGTGCCGGATCGGTTCAGC<br>GGATCTGGTTCGGGAACTGATTTCACTCTGAAGATTTCCCGCGTGGAAGC<br>CGAGGACGTGGGCGTCTACTACTGTATGCAGGCGCTGCAGACCCCCTATA<br>CCTTCGGCCAAGGGACGAAAGTGGAGATCAAG |
| 139105-aa<br>VH | 7970 | QVQLVESGGGLVQPGRSLRLSCAASGFTFDDYAMHWVRQAPGKGLEWVSG<br>ISWNSGSIGYADSVKGRFTISRDNAKNSLYLQMNSLRAEDTALYYCSVHS<br>FLAYWGQGTLVTVSS |
| 139105-aa<br>VL | 7985 | DIVMTQTPLSLPVTPGEPASISCRSSQSLLHSNGYNYLDWYLQKPGQSPQ<br>LLIYLGSNRASGVPDRFSGSGSGTDFTLKISRVEAEDVGVYYCMQALQTP<br>YTFGQGTKVEIK |

139111

| 139111-aa<br>ScFv domain | 7941 | EVQLLESGGGLVQPGGSLRLSCAVSGFALSNHGMSWVRRAPGKGLEWVSG<br>IVYSGSTYYAASVKGRFTISRDNSRNTLYLQMNSLRPEDTAIYYCSAHGG<br>ESDVWGQGTTVTVSSASGGGGSGGRASGGGGSDIVMTQTPLSLSVTPGQP<br>ASISCKSSQSLLRNDGKTPLYWYLQKAGQPPQLLIYEVSNRFSGVPDRFS<br>GSGSGTDFTLKISRVEAEDVGAYYCMQNIQFPSFGGGTKLEIK |
| --- | --- | --- |
| 139111-nt<br>ScFv domain | 7956 | GAAGTGCAATTGTTGGAATCTGGAGGAGGACTTGTGCAGCCTGGAGGATC<br>ACTGAGACTTTCGTGTGCGGTGTCAGGCTTCGCCCTGAGCAACCACGGCA<br>TGAGCTGGGTGCGGAGAGCCCCGGGGAAGGGTCTGGAATGGGTGTCCGGG<br>ATCGTCTACTCCGGTTCAACTTACTACGCCGCAAGCGTGAAGGGTCGCTT<br>CACCATTTCCCGCGATAACTCCCGGAACACCCTGTACCTCCAAATGAACT<br>CCCTGCGGCCCGAGGACACCGCCATCTACTACTGTTCCGCGCATGGAGGA<br>GAGTCCGATGTCTGGGGACAGGGCACTACCGTGACCGTGTCGAGCGCCTC<br>GGGGGGAGGAGGCTCCGGCGGTCGCGCCTCCGGGGGGGTGGCAGCGACA<br>TTGTGATGACGCAGACTCCACTCTCGCTGTCCGTGACCCCGGGACAGCCC<br>GCGTCCATCTCGTGCAAGAGCTCCCAGAGCCTGCTGAGGAACGACGGAAA<br>GACTCCTCTGTATTGGTACCTCCAGAAGGCTGGACAGCCCCCGCAACTGC<br>TCATCTACGAAGTGTCAAATCGCTTCTCCGGGGTGCCGGATCGGTTTTCC<br>GGCTCGGATCGGGCACCGACTTCACCCTGAAAATCTCCAGGGTCGAGGC<br>CGAGGACGTGGGAGCCTACTACTGCATGCAAAACATCCAGTTCCCTTCCT<br>TCGGCGGCGGCACAAAGCTGGAGATTAAG |
| 139111-aa<br>VH | 7971 | EVQLLESGGGLVQPGGSLRLSCAVSGFALSNHGMSWVRRAPGKGLEWVSG<br>IVYSGSTYYAASVKGRFTISRDNSRNTLYLQMNSLRPEDTAIYYCSAHGG<br>ESDVWGQGTTVTVSS |
| 139111-aa<br>VL | 7986 | DIVMTQTPLSLSVTPGQPASISCKSSQSLLRNDGKTPLYWYLQKAGQPPQ<br>LLIYEVSNRFSGVPDRFSGSGSGTDFTLKISRVEAEDVGAYYCMQNIQFP<br>SFGGGTKLEIK |

TABLE 18-continued

Antigen Binding domains that bind BCMA
The amino acid sequences variable heavy chain and variable light chain sequences for each scFv is also provided.

| Name/ Description | SEQ ID NO: | Sequence |
|---|---|---|
| 139100 | | |
| 139100-aa ScFv domain | 7942 | QVQLVQSGAEVRKTGASVKVSCKASGYIFDNEGINWVRQAPGQGLEWMGW INPKNNNTNYAQKFQGRVTITADESTNTAYMEVSSLRSEDTAVYYCARGP YYYQSYMDVWGQGTMVTVSSASGGGGSGGRASGGGGSDIVMTQTPLSLPV TPGEPASISCRSSQSLLHSNGYNYLNWYLQKPGQSPQLLIYLGSKRASGV PDRFSGSGSGTDFTLHITRVGAEDVGVYYCMQALQTPYTFGQGTKLEIK |
| 139100-nt ScFv domain | 7957 | CAAGTCCAACTCGTCCAGTCCGGCGCAGAAGTCAGAAAAACCGGTGCTAG CGTGAAAGTGTCCTGCAAGGCCTCCGGCTACATTTTCGATAACTTCGGAA TCAACTGGGTCAGACAGGCCCCGGGCCAGGGGCTGGAATGGATGGGATGG ATCAACCCCAAGAACAACAACACCAACTACGCACAGAAGTTCCAGGGCCG CGTGACTATCACCGCCGATGAATCGACCAATACCGCCTACATGGAGGTGT CCTCCCTGCGGTCGGAGGACACTGCCGTGTATTACTGCGCGAGGGGCCCA TACTACTACCAAAGCTACATGGACGTCTGGGGACAGGGAACCATGGTGAC CGTGTCATCCGCCTCCGGTGGTGGAGGCTCCGGGGGGCGGGCTTCAGGAG GCGGAGGAAGCGATATTGTGATGACCCAGACTCCGCTTAGCCTGCCCGTG ACTCCTGGAGAACCGGCCTCCATTTCCTGCCGGTCCTCGCAATCACTCCT GCATTCAACGGTTACAACTACCTGAATTGGTACCTCCAGAAGCCTGGCC AGTCGCCCCAGTTGCTGATCTATCTGGGCTCGAAGCGCGCCTCCGGGGTG CCTGACCGGTTTAGCGGATCTGGGAGCGGCACGGACTTCACTCTCCACAT CACCCGCGTGGGAGCGGAGGACGTGGGAGTGTACTACTGTATGCAGGCGC TGCAGACTCCGTACACATTCGGACAGGGCACCAAGCTGGAGATCAAG |
| 139100-aa VH | 7972 | QVQLVQSGAEVRKTGASVKVSCKASGYIFDNFGINWVRQAPGQGLEWMGW INPKNNNTNYAQKFQGRVTITADESTNTAYMEVSSLRSEDTAVYYCARGP YYYQSYMDVWGQGTMVTVSS |
| 139100-aa VL | 7987 | DIVMTQTPLSLPVTPGEPASISCRSSQSLLHSNGYNYLNWYLQKPGQSPQ LLIYLGSKRASGVPDRFSGSGSGTDFTLHITRVGAEDVGVYYCMQALQTP YTFGQGTKLEIK |
| 139101 | | |
| 139101-aa ScFv domain | 7943 | QVQLQESGGGLVQPGGSLRLSCAASGFTFSSDAMTWVRQAPGKGLEWVSV ISGSGGTTYYADSVKGRFTISRDNSKNTLYLQMNSLRAEDTAVYYCAKLD SSGYYYARGPRYWGQGTLVTVSSASGGGGSGGRASGGGGSDIQLTQSPSS LSASVGDRVTITCRASQSISSYLNWYQQKPGKAPKLLIYGASTLASGVPA RFSGSGSGTHFTLTINSLQSEDSATYYCQQSYKRASFGQGTKVEIK |
| 139101-nt ScFv domain | 7958 | CAAGTGCAACTTCAAGAATCAGGCGGAGGACTCGTGCAGCCCGGAGGATC ATTGCGGCTCTCGTGCGCCGCCTCGGGCTTCACCTTCTCGAGCGACGCCA TGACCTGGGTCCGCCAGGCCCCGGGGAAGGGGCTGGAATGGGTGTCTGTG ATTTCCGGCTCCGGGGGAACTACGTACTACGCCGATTCCGTGAAAGGTCG CTTCACTATCTCCCGGGACAACAGCAAGAACACCCTTTATCTGCAAATGA ATTCCCTCCGCGCCGAGGACACCGCCGTGTACTACTGCGCCAAGCTGGAC TCCTCGGGCTACTACTATGCCCGGGGTCCGAGATACTGGGGACAGGGAAC CCTCGTGACCGTGTCCTCCGCGTCCGGCGGAGGAGGGTCGGGAGGGCGGG CCTCCGGCGGCGGCGGTTCGGACATCCAGCTGACCCAGTCCCCATCCTCA CTGAGCGCAAGCGTGGGCGACAGAGTCACCATTACATGCAGGGCGTCCCA GAGCATCAGCTCCTACCTGAACTGGTACCAACAGAAGCCTGGAAAGGCTC CTAAGCTGTTGATCTACGGGGCTTCGACCCTGGCATCCGGGGTGCCCGCG AGGTTTAGCGGAAGCGGTAGCGGCACTCACTTCACTCTGACCATTAACAG CCTCCAGTCCGAGGATTCAGCCACTTACTACTGTCAGCAGTCCTACAAGC GGGCCAGCTTCGGACAGGGCACTAAGGTCGAGATCAAG |
| 139101-aa VH | 7973 | QVQLQESGGGLVQPGGSLRLSCAASGFTFSSDAMTWVRQAPGKGLEWVSV ISGSGGTTYYADSVKGRFTISRDNSKNTLYLQMNSLRAEDTAVYYCAKLD SSGYYYARGPRYWGQGTLVTVSS |
| 139101-aa VL | 7988 | DIQLTQSPSSLSASVGDRVTITCRASQSISSYLNWYQQKPGKAPKLLIYG ASTLASGVPARFSGSGSGTHFTLTINSLQSEDSATYYCQQSYKRASFGQG TKVEIK |
| 139102 | | |
| 139102-aa ScFv domain | 7944 | QVQLVQSGAEVKKPGASVKVSCKASGYTFSNYGITWVRQAPGQGLEWMGW ISAYNGNTNYAQKFQGRVTMTRNTSISTAYMELSSLRSEDTAVYYCARGP YYYYMDVWGKGTMVTVSSASGGGGSGGRASGGGGSEIVMTQSPLSLVTP GEPASISCRSSQSLLYSNGYNYVDWYLQKPGQSPQLLIYLGSNRASGVPD RFSGSGSGTDFKLQISRVEAEDVGIYYCMQGRQFPYSFGQGTKVEIK |

TABLE 18-continued

Antigen Binding domains that bind BCMA
The amino acid sequences variable heavy chain and variable light chain
sequences for each scFv is also provided.

| Name/<br>Description | SEQ ID<br>NO: | Sequence |
|---|---|---|
| 139102-nt<br>ScFv domain | 7959 | CAAGTCCAACTGGTCCAGAGCGGTGCAGAAGTGAAGAAGCCCGGAGCGAG<br>CGTGAAAGTGTCCTGCAAGGCTTCCGGGTACACCTTCTCCAACTACGGCA<br>TCACTTGGGTGCGCCAGGCCCCGGGACAGGGCCTGGAATGGATGGGGTGG<br>ATTTCCGCGTACAACGGCAATACGAACTACGCTCAGAAGTTCCAGGGTAG<br>AGTGACCATGACTAGGAACACCTCCATTTCCACCGCCTACATGGAACTGT<br>CCTCCCTGCGGAGCGAGGACACCGCCGTGTACTATTGCGCCCGGGGACCA<br>TACTACTACTACATGGATGTCTGGGGGAAGGGGACTATGGTCACCGTGTC<br>ATCCGCCTCGGGAGGCGGCGGATCAGGAGGACGCGCCTCTGGTGGTGGAG<br>GATCGGAGATCGTGATGACCCAGAGCCCTCTCTCCTTGCCCGTGACTCCT<br>GGGGAGCCCGCATCCATTTCATGCCGGAGCTCCCAGTCACTTCTCTACTC<br>CAACGGCTATAACTACGTGGATTGGTACCTCCAAAAGCCGGGCCAGAGCC<br>CGCAGCTGCTGATCTACCTGGGCTCGAACAGGGCCAGCGGAGTGCCTGAC<br>CGGTTCTCCGGGTCGGGAAGCGGGACCGACTTCAAGCTGCAAATCTCGAG<br>AGTGGAGGCCGAGGACGTGGGAATCTACTACTGTATGCAGGGCCGCCAGT<br>TTCCGTACTCGTTCGGACAGGGCACCAAAGTGGAAATCAAG |
| 139102-aa<br>VH | 7974 | QVQLVQSGAEVKKPGASVKVSCKASGYTFSNYGITWVRQAPGQGLEWMGW<br>ISAYNGNTNYAQKFQGRVTMTRNTSISTAYMELSSLRSEDTAVYYCARGP<br>YYYYMDVWGKGTMVTVSS |
| 139102-aa<br>VL | 7989 | EIVMTQSPLSLPVTPGEPASISCRSSQSLLYSNGYNYVDWYLQKPGQSPQ<br>LLIYLGSNRASGVPDRFSGSGSGTDFKLQISRVEAEDVGIYYCMQGRQFP<br>YSFGQGTKVEIK |
| 139104 | | |
| 139104-aa<br>ScFv domain | 7945 | EVQLLETGGGLVQPGGSLRLSCAVSGFALSNHGMSWVRRAPGKGLEWVSG<br>IVYSGSTYYAASVKGRFTISRDNSRNTLYLQMNSLRPEDTAIYYCSAHGG<br>ESDVWGQGTTVTVSSASGGGGSGGRASGGGGSEIVLTQSPATLSVSPGES<br>ATLSCRASQSVSSNLAWYQQKPGQAPRLLIYGASTRASGIPDRFSGSGSG<br>TDFTLTISSLQAEDVAVYYCQQYGSSLTFGGGTKVEIK |
| 139104-nt<br>ScFv domain | 7960 | GAAGTGCAATTGCTCGAAACTGGAGGAGGTCTGGTGCAACCTGGAGGATC<br>ACTTCGCCTGTCCTGCGCCGTGTCGGGCTTTGCCCTGTCCAACCATGGAA<br>TGAGCTGGGTCCGCCGCGCGCCGGGGAAGGGCCTCGAATGGGTGTCCGGC<br>ATCGTCTACTCCGGCTCCACCTACTACGCCGCGTCCGTGAAGGGCCGGTT<br>CACGATTTCACGGGACAACTCGCGGAACACCCTGTACCTCCAAATGAATT<br>CCCTTCGGCCGGAGGATACTGCCATCTACTACTGCTCCGCCCACGGTGGC<br>GAATCCGACGTCTGGGGCCAGGGAACCACCGTGACCGTGTCCAGCGCGTC<br>CGGGGGAGGAGGAAGCGGGGGTAGAGCATCGGGTGGAGGCGGATCAGAGA<br>TCGTGCTGACCCAGTCCCCCGCCACCTTGAGCGTGTCACCAGGAGAGTCC<br>GCCACCCTGTCATGCCGCGCCAGCCAGTCCGTGTCCTCCAACCTGGCTTG<br>GTACCAGCAGAAGCCGGGGCAGGCCCCTAGACTCCTGATCTATGGGGCGT<br>CGACCCGGGCATCTGGAATTCCCGATAGGTTCAGCGGATCGGGCTCGGGC<br>ACTGACTTCACTCTGACCATCTCCTCGCTGCAAGCCGAGGACGTGGCTGT<br>GTACTACTGTCAGCAGTACGGAAGCTCCCTGACTTTCGGTGGCGGGACCA<br>AAGTCGAGATTAAG |
| 139104-aa<br>VH | 7975 | EVQLLETGGGLVQPGGSLRLSCAVSGFALSNHGMSWVRRAPGKGLEWVSG<br>IVYSGSTYYAASVKGRFTISRDNSRNTLYLQMNSLRPEDTAIYYCSAHGG<br>ESDVWGQGTTVTVSS |
| 139104-aa<br>VL | 7990 | EIVLTQSPATLSVSPGESAILSCHASQSYSSNLAWYQQKPGQAPRLLIYG<br>ASTRASGIPDRFSGSGSGTDFTLTISSLQAEDVAVYYCQQYGSSLTFGGG<br>TKVEIK |
| 139106 | | |
| 139106-aa<br>ScFv domain | 7946 | EVQLVETGGGLVQPGGSLRLSCAVSGFALSNHGMSWVRRAPGKGLEWVSG<br>IVYSGSTYYAASVKGRFTISRDNSRNTLYLQMNSLRPEDTAIYYCSAHGG<br>ESDVWGQGTTVTVSSASGGGGSGGRASGGGGSEIVMTQSPATLSVSPGER<br>ATLSCRASQSVSSKLAWYQQKPGQAPRLLMYGASIRATGIPDRFSGSGSG<br>TEFTLTISSLEPEDFAVYYCQQYGSSSWTFGQGTKVEIK |
| 139106-nt<br>ScFv domain | 7961 | GAAGTGCAATTGGTGGAAACTGGAGGAGGACTTGTGCAACCTGGAGGATC<br>ATTGAGACTGAGCTGCGCAGTGTCGGATTCGCCCTGAGCAACCATGGAA<br>TGTCCTGGGTCAGAAGGGCCCCTGGAAAAGGCCTCGAATGGGTGTCAGGG<br>ATCGTGTACTCCGGTTCCACTTACTACGCCGCTCCGTGAAGGGGCGCTT<br>CACTATCTCACGGGATAACTCCCGCAATACCCTGTACCTCCAAATGAACA<br>GCCTGCGGCCGAGGATACCGCCATCTACTACTGTTCCGCCCACGGTGGA<br>GAGTCTGACGTCTGGGGCCAGGGAACTACCGTGACCGTGTCCTCCGCGTC<br>CGGCGGTGGAGGGAGCGGCGGCCGCGCCAGCGGCGGCGGAGGCTCCGAGA<br>TCGTGATGACCCAGAGCCCCGCTACTCTGTCGGTGTCGCCCGGAGAAAGG |

TABLE 18-continued

Antigen Binding domains that bind BCMA
The amino acid sequences variable heavy chain and variable light chain sequences for each scFv is also provided.

| Name/<br>Description | SEQ ID<br>NO: | Sequence |
|---|---|---|
| | | GCGACCCTGTCCTGCCGGGCGTCGCAGTCCGTGAGCAGCAAGCTGGCTTG<br>GTACCAGCAGAAGCCGGGCCAGGCACCACGCCTGCTTATGTACGGTGCCT<br>CCATTCGGGCCACCGGAATCCCGGACCGGTTCTCGGGGTCGGGGTCCGGT<br>ACCGAGTTCACACTGACCATTTCCTCGCTCGAGCCCGAGGACTTTGCCGT<br>CTATTACTGCCAGCAGTACGGCTCCTCCTCATGGACGTTCGGCCAGGGGA<br>CCAAGGTCGAAATCAAG |
| 139106-aa<br>VH | 7976 | EVQLVETGGGLVQPGGSLRLSCAVSGFALSNHGMSWVRRAPGKGLEWVSG<br>IVYSGSTYYAASVKGRFTISRDNSRNTLYLQMNSLRPEDTAIYYCSAHGG<br>ESDVWGQGTTVTVSS |
| 139106-aa<br>VL | 7991 | EIVMTQSPATLSVSPGERATLSCRASQSVSSKLAWYQQKPGQAPRLLMYG<br>ASIRATGIPDRFSGSGSGTEFTLTISSLEPEDFAVYYCQQYGSSSWTFGQ<br>GTKVEIK |
| | | 139107 |
| 139107-aa<br>ScFv domain | 7947 | EVQLVETGGGVVQPGGSLRLSCAVSGFALSNHGMSWVRRAPGKGLEWVSG<br>IVYSGSTYYAASVKGRFTISRDNSRNTLYLQMNSLRPEDTAIYYCSAHGG<br>ESDVWGQGTTVTVSSASGGGGSGGRASGGGGSEIVLTQSPGTLSLSPGER<br>ATLSCRASQSVGSTNLAWYQQKPGQAPRLLIYDASNRATGIPDRFSGGGS<br>GTDFTLTISRLEPEDFAVYYCQQYGSSPPWTFGQGTKVEIK |
| 139107-nt<br>ScFv domain | 7962 | GAAGTGCAATTGGTGGAGACTGGAGGAGGAGTGGTGCAACCTGGAGGAAG<br>CCTGAGACTGTCATGCGCGGTGTCGGGCTTCGCCCTCTCCAACCACGGAA<br>TGTCCTGGGTCCGCCGGGCCCCTGGGAAAGGACTTGAATGGGTGTCCGGC<br>ATCGTGTACTCGGGTTCCACCTACTACGCGGCCTCAGTGAAGGGCCGGTT<br>TACTATTAGCCGCGACAACTCCAGAAACACACTGTACCTCCAAATGAACT<br>CGCTGCGGCCGGAAGATACCGCTATCTACTACTGCTCCGCCCATGGGGGA<br>GAGTCGGACGTCTGGGGACAGGGCACCACTGTCACTGTGTCCAGCGCTTC<br>CGGCGGTGGTGGAAGCGGGGGACGGGCCTCAGGAGGCGGTGGCAGCGAGA<br>TTGTGCTGACCCAGTCCCCGGGACCCTGAGCCTGTCCCGGGAGAAAGG<br>GCCACCCTCTCCTGTCGGGCATCCCAGTCCGTGGGGTCTACTAACCTTGC<br>ATGGTACCAGCAGAAGCCCGGCCAGGCCCCTCGCCTGCTGATCTACGACG<br>CGTCCAATAGAGCCACCGGCATCCCGGATCGCTTCAGCGGAGGCGGATCG<br>GGCACCGACTTCACCCTCACCATTTCAAGGCTGGAACCGGAGGACTTCGC<br>CGTGTACTACTGCCAGCAGTATGGTTCGTCCCCACCCTGGACGTTCGGCC<br>AGGGGACTAAGGTCGAGATCAAG |
| 139107-aa<br>VH | 7977 | EVQLVETGGGVVQPGGSLRLSCAVSGFALSNHGMSWVRRAPGKGLEWVSG<br>IVYSGSTYYAASVKGRFTISRDNSRNTLYLQMNSLRPEDTAIYYCSAHGG<br>ESDVWGQGTTVTVSS |
| 139107-aa<br>VL | 7992 | EIVLTQSPGTLSLSPGERATLSCRASQSVGSTNLAWYQQKPGQAPRLLIY<br>DASNRATGIPDRFSGGGSGTDFTLTISRLEPEDFAVYYCQQYGSSPPWTF<br>GQGTKVEIK |
| | | 139108 |
| 139108-aa<br>ScFv domain | 7948 | QVQLVESGGGLVKPGGSLRLSCAASGFTFSDYYMSWIRQAPGKGLEWVSY<br>ISSSGSTIYYADSVKGRFTISRDNAKNSLYLQMNSLRAEDTAVYYCARES<br>GDGMDVWGQGTTVTVSSASGGGGSGGRASGGGGSDIQMTQSPSSLSASVG<br>DRVTITCRASQSISSYLNWYQQKPGKAPKLLIYAASSLQSGVPSRFSGSG<br>SGTDFTLTISSLQPEDFATYYCQQSYTLAFGQGTKVDIK |
| 139108-nt<br>ScFv domain | 7963 | CAAGTGCAACTCGTGGAATCTGGTGGAGGACTCGTGAAACCTGGAGGATC<br>ATTGAGACTGTCATGCGCGGCCTCGGGATTCACGTTCTCCGATTACTACA<br>TGAGCTGGATTCGCCAGGCTCCGGGGAAGGGACTGGAATGGGTGTCCTAC<br>ATTTCCTCATCCGGCTCCACCATCTACTACGCGGACTCCGTGAAGGGGAG<br>ATTCACCATTAGCCGCGATAACGCCAAGAACAGCCTGTACCTTCAGATGA<br>ACTCCCTGCGGGCTGAAGATACTGCCGTCTACTACTGCGCAAGGGAGAGC<br>GGAGATGGGATGGACGTCTGGGACAGGGTACCACTGTGACCGTGTCGTC<br>GGCCTCCGGCGGAGGGGGTTCGGGTGGAAGGGCCAGCGGCGGCGGAGGCA<br>GCGACATCCAGATGACCCAGTCCCCCTCATCGCTGTCCGCCTCCGTGGGC<br>GACCGCGTCACCATCACATGCCGGGCCTCACAGTCGATCTCCTCCTACCT<br>CAATTGGTATCAGCAGAAGCCCGGAAAGGCCCCTAAGCTTCTGATCTACG<br>CAGCGTCCTCCCTGCAATCCGGGGTCCCATCTCGGTTCTCCGGCTCGGGC<br>AGCGGTACCGACTTCACTCTGACCATCTCCGAGCCTGCAGCCGGAGGACTT<br>CGCCACTTACTACTGTCAGCAAAGCTACACCCTCGCGTTTGGCCAGGGCA<br>CCAAAGTGGACATCAAG |

TABLE 18-continued

Antigen Binding domains that bind BCMA
The amino acid sequences variable heavy chain and variable light chain
sequences for each scFv is also provided.

| Name/ Description | SEQ ID NO: | Sequence |
|---|---|---|
| 139108-aa VH | 7978 | QVQLVESGGGLVKPGGSLRLSCAASGFTFSDYYMSWIRQAPGKGLEWVSY ISSSGSTIYYADSVKGRFTISRDNAKNSLYLQMNSLRAEDTAVYYCARES GDGMDVWGQGTTVTVSS |
| 139108-aa VL | 7993 | DIQMTQSPSSLSASVGDRVTITCRASQSISSYLNWYQQKPGKAPKLLIYA ASSLQSGVPSRFSGSGSGTDFTLTISSLQPEDFATYYCQQSYTLAFGQGT KVDIK |

139110

| Name/ Description | SEQ ID NO: | Sequence |
|---|---|---|
| 139110-aa ScFv domain | 7950 | QVQLVQSGGGLVKPGGSLRLSCAASGFTFSDYYMSWIRQAPGKGLEWVSY ISSSGNTIYYADSVKGRFTISRDNAKNSLYLQMNSLRAEDTAVYYCARST MVREDYWGQGTLVTVSSASGGGGSGGRASGGGGSDIVLTQSPLSLPVTLG QPASISCKSSESLVHNSGKTYLNWFHQRPGQSPRRLIYEVSNRDSGVPDR FTGSGSGTDFTLKISRVEAEDVGVYYCMQGTHWPGTFGQGTKLEIK |
| 139110-nt ScFv domain | 7965 | CAAGTGCAACTGGTGCAAAGCGGAGGAGGATTGGTCAAACCCGGAGGAAG CCTGAGACTGTCATGCGCGGCCTCTGGATTCACCTTCTCCGATTACTACA TGTCATGGATCAGACAGGCCCCGGGGAAGGGCCTCGAATGGGTGTCCTAC ATCTCGTCCTCGGGAACACCATCTACTACGCCGACAGCGTGAAGGGCCG CTTTACCATTTCCCGCGACAACGCAAAGAACTCGCTGTACCTTCAGATGA ATTCCCTGCGGGCTGAAGATACCGCGGTGTACTATTGCGCCCGGTCCACT ATGGTCCGGGAGGACTACTGGGGACAGGGCACACTCGTGACCGTGTCCAG CGCGAGCGGGGTGGAGGCAGCGGTGGACGCGCCTCCGGCGGCGGCGGTT CAGACATCGTGCTGACTCAGTCGCCCCTGTCGCTGCCGGTCACCCTGGGC CAACCGGCCTCAATTAGCTGCAAGTCCTCGGAGAGCCTGGTGCACAACTC AGGAAAGACTTACCTGAACTGGTTCCATCAGCGGCCTGGACAGTCCCCAC GGAGGCTCATCTATGAAGTGTCCAACAGGGATTCGGGGGTGCCCGACCGC TTCACTGGCTCCGGGTCCGGCACCGACTTCACCTTGAAAATCTCCAGAGT GGAAGCCGAGGACGTGGGCGTGTACTACTGTATGCAGGGTACCCACTGGC CTGGAACCTTTGGACAAGGAACTAAGCTCGAGATTAAG |
| 139110-aa VH | 7980 | QVQLVQSGGGLVKPGGSLRLSCAASGFTFSDYYMSWIRQAPGKGLEWVSY ISSSGNTIYYADSVKGRFTISRDNAKNSLYLQMNSLRAEDTAVYYCARST MVREDYWGQGTLVTVSS |
| 139110-aa VL | 7995 | DIVLTQSPLSLPVTLGQPASISCKSSESLVHNSGKTYLNWFHQRPGQSPR RLIYEVSNRDSGVPDRFTGSGSGTDFTLKISRVEAEDVGVYYCMQGTHWP GTFGQGTKLEIK |

139112

| Name/ Description | SEQ ID NO: | Sequence |
|---|---|---|
| 139112-aa ScFv domain | 7951 | QVQLVESGGGLVQPGGSLRLSCAVSGFALSNHGMSWVRRAPGKGLEWVSG IVYSGSTYYAASVKGRFTISRDNSRNTLYLQMNSLRPEDTAIYYCSAHGG ESDVWGQGTTVTVSSASGGGGSGGRASGGGGSDIRLTQSPSPLSASVGDR VTITCQASEDINKFLNWYHQTPGKAPKLLIYDASTLQTGVPSRFSGSGSG TDFTLTINSLQPEDIGTYYCQQYESLPLTFGGGTKVEIK |
| 139112-nt ScFv domain | 7966 | CAAGTGCAACTCGTGGAATCTGGTGGAGGACTCGTGCAACCCGGTGGAAG CCTTAGGCTGTCGTGCGCCGTCAGCGGGTTTGCTCTGAGCAACCATGGAA TGTCCTGGGTCCGCCGGGCACCGGGAAAAGGGCTGGAATGGGTGTCCGGC ATCGTGTACAGCGGGTCAACCTATTACGCCGCGTCCGTGAAGGGCAGATT CACTATCTCAAGAGACAACAGCCGGAACACCCTGTACTTGCAAATGAATT CCCTGCGCCCCGAGGACACCGCCATCTACTACTGCTCCGCCCACGGAGGA GAGTCGGACGTGTGGGGCCAGGGAACGACTGTGACTGTGTCCAGCGCATC AGGAGGGGGTGGTTCGGGCGGCCGGGCCTCGGGGGGAGGAGGTTCCGACA TTCGGCTGACCCAGTCCCCGTCCCCACTGTCGGCCTCCGTCGGCGACCGC GTGACCATCACTTGTCAGGCGTCCGAGGACATTAACAAGTTCCTGAACTG GTACCACCAGACCCCTGGAAAGGCCCCCAAGCTGCTGATCTACGATGCCT CGACCCTTCAAACTGGAGTGCCTAGCCGGTTCTCCGGGTCCGGCTCCGGC ACTGATTTCACTCTGACCATCAACTCATTGCAGCCGGAAGATATCGGGAC CTACTATTGCCAGCAGTACGAATCCCTCCCGCTCACATTCGGCGGGGAA CCAAGGTCGAGATTAAG |
| 139112-aa VH | 7981 | QVQLVESGGGLVQPGGSLRLSCAVSGFALSNHGMSWVRRAPGKGLEWVSG IVYSGSTYYAASVKGRFTISRDNSRNTLYLQMNSLRPEDTAIYYCSAHGG ESDVWGQGTTVTVSS |
| 139112-aa VL | 7996 | DIRLTQSPSPLSASVGDRVTITCQASEDINKFLNWYHQTPGKAPKLLIYD ASTLQTGVPSRFSGSGSGTDFTLTINSLQPEDIGTYYCQQYESLPLTFGG GTKVEIK |

TABLE 18-continued

Antigen Binding domains that bind BCMA
The amino acid sequences variable heavy chain and variable light chain
sequences for each scFv is also provided.

| Name/<br>Description | SEQ ID<br>NO: | Sequence |
|---|---|---|
| | | 139113 |
| 139113-aa<br>ScFv domain | 7952 | EVQLVETGGGLVQPGGSLRLSCAVSGFALSNHGMSWVRRAPGKGLEWVSG<br>IVYSGSTYYAASVKGRFTISRDNSRNTLYLQMNSLRPEDTAIYYCSAHGG<br>ESDVWGQGTTVTVSSASGGGGSGGRASGGGGSETTLTQSPATLSVSPGER<br>ATLSCRASQSVGSNLAWYQQKPGQGPRLLIYGASTRATGIPARESGSGSG<br>TEFTLTISSLQPEDFAVYYCQQYNDWLPVTFGQGTKVEIK |
| 139113-nt<br>ScFv domain | 7967 | GAAGTGCAATTGGTGGAAACTGGAGGAGGACTTGTGCAACCTGGAGGATC<br>ATTGCGGCTCTCATGCGCTGTCTCCGGCTTCGCCCTGTCAAATCACGGGA<br>TGTCGTGGGTCAGACGGGCCCCGGGAAAGGGTCTGGAATGGGTGTCGGGG<br>ATTGTGTACAGCGGCTCCACCTACTACGCCGCTTCGGTCAAGGGCCGCTT<br>CACTATTTCACGGGACAACAGCCGCAACACCCTCTATCTGCAAATGAACT<br>CTCTCCGCCCGGAGGATACCGCCATCTACTACTGCTCCGCACACGGCGGC<br>GAATCCGACGTGTGGGGACAGGGAACCACTGTCACCGTGTCGTCCGCATC<br>CGGTGGCGGAGGATCGGGTGGCCGGGCCTCCGGGGGCGGCGGCAGCGAGA<br>CTACCCTGACCCAGTCCCCTGCCACTCTGTCCGTGAGCCCGGAGAGAGA<br>GCCACCCTTAGCTGCCGGGCCAGCCAGAGCGTGGGCTCCAACCTGGCCTG<br>GTACCAGCAGAAGCCAGGACAGGGTCCCAGGCTGCTGATCTACGGAGCCT<br>CCACTCGCGCGACCGGCATCCCCGCGAGGTTCTCCGGGTCGGGTTCCGGG<br>ACCGAGTTCACCCTGACCATCTCCTCCCTCCAACCGGAGGACTTCGCGGT<br>GTACTACTGTCAGCAGTACAACGATTGGCTGCCCGTGACATTTGGACAGG<br>GGACGAAGGTGGAAATCAAA |
| 139113-aa<br>VH | 7982 | EVQLVETGGGLVQPGGSLRLSCAVSGFALSNHGMSWVRRAPGKGLEWVSG<br>IVYSGSTYYAASVKGRFTISRDNSRNTLYLQMNSLRPEDTAIYYCSAHGG<br>ESDVWGQGTTVTVSS |
| 139113-aa<br>VL | 7997 | ETTLTQSPATLSVSPGERATLSCRASQSVGSNLAWYQQKPGQGPRLLIYG<br>ASTRATGIPARESGSGSGTEFTLTISSLQPEDFAVYYCQQYNDWLPVTFG<br>QGTKVEIK |
| | | 139114 |
| 139114-aa<br>ScFv domain | 7953 | EVQLVESGGGLVQPGGSLRLSCAVSGFALSNHGMSWVRRAPGKGLEWVSG<br>IVYSGSTYYAASVKGRFTISRDNSRNTLYLQMNSLRPEDTAIYYCSAHGG<br>ESDVWGQGTTVTVSSASGGGGSGGRASGGGGSEIVLTQSPGTLSLSPGER<br>ATLSCRASQSIGSSSLAWYQQKPGQAPRLLMYGASSRASGIPDRFSGSGS<br>GTDFTLTISRLEPEDFAVYYCQQYAGSPPFTFGQGTKVEIK |
| 139114-nt<br>ScFv domain | 7968 | GAAGTGCAATTGGTGGAATCTGGTGGAGGACTTGTGCAACCTGGAGGATC<br>ACTGAGACTGTCATGCGCGGTGTCCGGTTTTGCCCTGAGCAATCATGGGA<br>TGTCGTGGGTCCGGCGCGCCCCCGGAAAGGGTCTGGAATGGGTGTCGGGT<br>ATCGTCTACTCCGGGAGCACTTACTACGCCGCGAGCGTGAAGGGCCGCTT<br>CACCATTTCCCGCGATAACTCCCGCAACACCCTGTACTTGCAAATGAACT<br>CGCTCCGGCCTGAGGACACTGCCATCTACTACTGCTCCGCACACGGAGGA<br>GAATCCGACGTGTGGGGCCAGGGAACTACCGTGACCGTCAGCAGCGCCTC<br>CGGCGGCGGGGGCTCAGGCGGACGGGCTAGCGGCGGCGGTGGCTCCGAGA<br>TCGTGCTGACCCAGTCGCCTGGCACTCTCTCGCTGAGCCCCGGGGAAAGG<br>GCAACCCTGTCCTGTCGGGCCAGCCAGTCCATTGGATCATCCTCCCTCGC<br>CTGGTATCAGCAGAAACCGGGACAGGCTCCGCGGCTGCTTATGTATGGGG<br>CCAGCTCAAGAGCCTCCGGCATTCCCGACCGGTTCTCCGGGTCCGGTTCC<br>GGCACCGATTTCACCCTGACTATCTCGAGGCTGGAGCCAGAGGACTTCGC<br>CGTGTACTACTGCCAGCAGTACGCGGGGTCCCCGCCGTTCACGTTCGGAC<br>AGGGAACCAAGGTCGAGATCAAG |
| 139114-aa<br>VH | 7983 | EVQLVESGGGLVQPGGSLRLSCAVSGFALSNHGMSWVRRAPGKGLEWVSG<br>IVYSGSTYYAASVKGRFTISRDNSRNTLYLQMNSLRPEDTAIYYCSAHGG<br>ESDVWGQGTTVTVSS |
| 139114-aa<br>VL | 7998 | EIVLTQSPGTLSLSPGERATLSCRASQSIGSSSLAWYQQKPGQAPRLLMY<br>GASSRASGIPDRFSGSGSGTDFTLTISRLEPEDFAVYYCQQYAGSPPFTF<br>GQGTKVEIK |
| | | 149362 |
| 149362-aa<br>ScFv domain | 8029 | QVQLQESGPGLVKPSETLSLTCTVSGGSISSSYYYWGWIRQPPGKGLEWI<br>GSIYYSGSAYYNPSLKSRVTISVDTSKNQFSLRLSSVTAADTAVYYCARH<br>WQEWPDAFDIWGQGTMVTVSSGGGGSGGGGSGGGGSETTLTQSPAFMSAT<br>PGDKVIISCKASQDIDDAMNWYQQKPGEAPLFIIQSATSPVPGIPPRFSG<br>SGFGTDFSLTINNIESEDAAYYFCLQHDNFPLTFGQGTKLEIK |

TABLE 18-continued

Antigen Binding domains that bind BCMA
The amino acid sequences variable heavy chain and variable light chain
sequences for each scFv is also provided.

| Name/ Description | SEQ ID NO: | Sequence |
|---|---|---|
| 149362-nt ScFv domain | 8050 | CAAGTGCAGCTTCAGGAAAGCGGACCGGGCCTGGTCAAGCCATCCGAAAC TCTCTCCCTGACTTGCACTGTGTCTGGCGGTTCCATCTCATCGTCGTACT ACTACTGGGGCTGGATTAGGCAGCCGCCCGGAAAGGGACTGGAGTGGATC GGAAGCATCTACTATTCCGGCTCGGCTACTACAACCCTAGCCTCAAGTC GAGAGTGACCATCTCCGTGGATACCTCCAAGAACCAGTTTTCCCTGCGCC TGAGCTCCGTGACCGCCGCTGACACCGCCGTGTACTACTGTGCTCGGCAT TGGCAGGAATGGCCCGATGCCTTCGACATTTGGGGCCAGGGCACTATGGT CACTGTGTCATCCGGGGGTGGAGGCAGCGGGGGAGGAGGGTCCGGGGGGG GAGGTTCAGAGACAACCTTGACCCAGTCACCCGCATTCATGTCCGCCACT CCGGGAGACAAGGTCATCATCTCGTGCAAAGCGTCCCAGGATATCGACGA TGCCATGAATTGGTACCAGCAGAAGCCTGGCGAAGCGCCGCTGTTCATTA TCCAATCCGCAACCTCGCCCGTGCCTGGAATCCCACCGCGGTTCAGCGGC AGCGGTTTCGGAACCGACTTTTCCCTGACCATTAACAACATTGAGTCCGA GGACGCCGCCTACTACTTCTGCCTGCAACACGACAACTTCCCTCTCACGT TCGGCCAGGGAACCAAGCTGGAAATCAAG |
| 149362-aa VH | 8071 | QVQLQESGPGLVKPSETLSLTCTVSGGSISSSYYYWGWIRQPPGKGLEWI GSIYYSGSAYYNPSLKSRVTISVDTSKNQFSLRLSSVTAADTAVYYCARH WQEWPDAFDIWGQGTMVTVSS |
| 149362-aa VL | 8092 | ETTLTQSPAFMSATPGDKVIISCKASQDIDDAMNWYQQKPGEAPLFIIQS ATSPVPGIPPRFSGSGFGTDFSLTINNIESEDAAYYFCLQHDNFPLTFGQ GTKLEIK |

149363

| 149363-aa ScFv domain | 8030 | QVNLRESGPALVKPTQTLTLTCTFSGFSLRTSGMCVSWIRQPPGKALEWL ARIDWDEDKFYSTSLKTRLTISKDTSDNQVVLRMTNMDPADTATYYCARS GAGGTSATAFDIWGPGTMVTVSSGGGGSGGGGSGGGGSDIQMTQSPSSLS ASVGDRVTITCRASQDIYNNLAWFQLKPGSAPRSLMYAANKSQSGVPSRF SGSASGTDFTLTISSLQPEDFATYYCQHYYRFPYSFGQGTKLEIK |
| 149363-nt ScFv domain | 8051 | CAAGTCAATCTGCGCGAATCCGGCCCCGCCTTGGTCAAGCCTACCCAGAC CCTCACTCTGACCTGTACTTTCTCCGGCTTCTCCCTGCGGACTTCCGGGA TGTGCGTGTCCTGGATCAGACAGCCTCCGGGAAAGGCCCTGGAGTGGCTC GCTCGCATTGACTGGGATGAGGACAAGTTCTACTCCACCTCACTCAAGAC CAGGCTGACCATCAGCAAAGATACCTCTGACAACCAAGTGGTGCTCCGCA TGACCAACATGGACCCAGCCGACACTGCCACTTACTACTGCGCGAGGAGC GGAGCGGGCGGAACCTCCGCCACCGCCTTCGATATTTGGGGCCCGGGTAC CATGGTCACCGTGTCAAGCGGAGGAGGGGGGTCCGGGGGCGGCGGTTCCG GGGGAGGCGGATCGGACATTCAGATGACTCAGTCACCATCGTCCCTGAGC GCTAGCGTGGGCGACAGAGTGACAATCACTTGCCGGGCATCCCAGGACAT CTATAACAACCTTGCGTGGTTCCAGCTGAAGCCTGGTTCCGCACCGCGGT CACTTATGTACGCCGCCAACAAGAGCCAGTCGGGAGTGCCGTCCCGGTTT TCCGGTTCGGCCTCGGGAACTGACTTCACCCTGACGATCTCCAGCCTGCA ACCCGAGGATTTCGCCACCTACTACTGCCAGCACTACTACCGCTTTCCCT ACTCGTTCGGACAGGGAACCAAGCTGGAAATCAAG |
| 149363-aa VH | 8072 | QVNLRESGPALVKPTQTLTLTCTFSGFSLRTSGMCVSWIRQPPGKALEWL ARIDWDEDKFYSTSLKTRLTISKDTSDNQVVLRMTNMDPADTATYYCARS GAGGTSATAFDIWGPGTMVTVSS |
| 149363-aa VL | 8093 | DIQMTQSPSSLSASVGDRVTITCRASQDIYNNLAWFQLKPGSAPRSLMYA ANKSQSGVPSRFSGSASGTDFTLTISSLQPEDFATYYCQHYYRFPYSFGQ GTKLEIK |

149364

| 149364-aa ScFv domain | 8031 | EVQLVESGGGLVKPGGSLRLSCAASGFTFSSYSMNWVRQAPGKGLEWVSS ISSSSSYIYYADSVKGRFTISRDNAKNSLYLQMNSLRAEDTAVYYAKTI AAVYAFDIWGQGTTVTVSSGGGGSGGGGSGGGGSEIVLTQSPLSLPVTPE EPASISCRSSQSLLHSNGYNYLDWYLQKPGQSPQLLIYLGSNRASGVPDR FSGSGSGTDFTLKISRVEAEDVGVYYCMQALQTPYTFGQGTKLEIK |
| 149364-nt ScFv domain | 8052 | GAAGTGCAGCTTGTCGAATCCGGGGGGGACTGGTCAAGCCGGGCGGATC ACTGAGACTGTCCTGCGCCGCGAGCGGCTTCACGTTCTCCTCCTACTCCA TGAACTGGGTCCGCCAAGCCCCGGGAAGGGACTGGAATGGGTGTCCTCT ATCTCCTCGTCGTCGTCCTACATCTACTACGCCGACTCCGTGAAGGGAAG ATTCACCATTTCCCGCGACAACGCAAAGAACTCACTGTACTTGCAAATGA ACTCACTCCGGGCCGAAGATACTGCTGTGTACTATTGCGCCAAGACTATT GCCGCCGTCTACGCTTTCGACATCTGGGGCCAGGGAACCACCGTGACTGT GTCGTCCGGTGGTGGTGGCTCGGGCGGAGGAGGAAGCGGCGGCGGGGGT CCGAGATTGTGCTGACCCAGTCGCCACTGAGCCTTCCCTGTGACCCCCGAG |

TABLE 18-continued

Antigen Binding domains that bind BCMA
The amino acid sequences variable heavy chain and variable light chain
sequences for each scFv is also provided.

| Name/ Description | SEQ ID NO: | Sequence |
|---|---|---|
| | | GAACCCGCCAGCATCAGCTGCCGGTCCAGCCAGTCCCTGCTCCACTCCAA CGGATACAATTACCTCGATTGGTACCTTCAGAAGCCTGGACAAAGCCCGC AGCTGCTCATCTACTTGGGATCAAACCGCGCGTCAGGAGTGCCTGACCGG TTCTCCGGCTCGGGCAGCGGTACCGATTTCACCCTGAAAATCTCCAGGGT GGAGGCAGAGGACGTGGGAGTGTATTACTGTATGCAGGCGCTGCAGACTC CGTACACATTTGGGCAGGGCACCAAGCTGGAGATCAAG |
| 149364-aa VH | 8073 | EVQLVESGGGLVKPGGSLRLSCAASGFTFSSYSMNWVRQAPGKGLEWVSS ISSSSSYIYYADSVKGRFTISRDNAKNSLYLQMNSLRAEDTAVYYCAKTI AAVYAFDIWGQGTTVTVSS |
| 149364-aa VL | 8094 | EIVLTQSPLSLPVTPEEPASISCRSSQSLLHSNGYNYLDWYLQKPGQSPQ LLIYLGSNRASGVPDRFSGSGSGTDFTLKISRVEAEDVGVYYCMQALQTP YTFGQGTKLEIK |
| | 149365 | |
| 149365-aa ScFv domain | 8032 | EVQLVESGGGLVKPGGSLRLSCAASGFTFSDYYMSWIRQAPGKGLEWVSY ISSSGSTIYYADSVKGRFTISRDNAKNSLYLQMNSLRAEDTAVYYCARDL RGAFDIWGQGTMVTVSSGGGGSGGGGSGGGGSSYVLTQSPSVSAAPGYTA TISCGGNNIGTKSVHWYQQKPGQAPLLVIRDDSVRPSKIPGRFSGSNSGN MATLTISGVQAGDEADFYCQVWDSDSEHVVFGGGTKLTVL |
| 149365-nt ScFv domain | 8053 | GAAGTCCAGCTCGTGGAGTCCGGCGGAGGCCTTGTGAAGCCTGGAGGTTC GCTGAGACTGTCCTGCGCCGCCTCCGGCTTCACCTTCTCCGACTACTACA TGTCCTGGATCAGACAGGCCCCGGGAAAGGGCCTGGAATGGGTGTCCTAC ATCTCGTCATCGGGCAGCACTATCTACTACGCGGACTCAGTGAAGGGGCG GTTCACCATTTCCCGGGATAACGCGAAGAACTCGCTGTATCTGCAAATGA ACTCACTGAGGGCCGAGGACACCGCCGTGTACTACTGCGCCCGCGATCTC CGCGGGGCATTTGACATCTGGGGACAGGGAACCATGGTCACAGTGTCCAG CGGAGGGGGAGGATCGGGTGGCGGAGGTTCCGGGGGTGGAGGCTCCTCCT ACGTGCTGACTCAGAGCCCAAGCGTCAGCGCTGCGCCCGGTTACACGGCA ACCATCTCCTGTGGCGGAAACAACATTGGGACCAAGTCTGTGCACTGGTA TCAGCAGAAGCCGGGCCAAGCTCCCCTGTTGGTGATCCGCGATGACTCCG TGCGGCCTAGCAAAATTCCGGGACGGTTCTCCGGCTCCAACAGCGGCAAT ATGGCCACTCTCACCATCTCGGGAGTGCAGGCCGGAGATGAAGCCGACTT CTACTGCCAAGTCTGGGACTCAGACTCCGAGCATGTGGTGTTCGGGGGCG GAACCAAGCTGACTGTGCTC |
| 149365-aa VH | 8074 | EVQLVESGGGLVKPGGSLRLSCAASGFTFSDYYMSWIRQAPGKGLEWVSY ISSSGSTIYYADSVKGRFTISRDNAKNSLYLQMNSLRAEDTAVYYCARDL RGAFDIWGQGTMVTVSS |
| 149365-aa VL | 8095 | SYVLTQSPSVSAAPGYTATISCGGNNTGTKSVHWYQQKPGQAPLLVIRDD SVRPSKIPGRFSGSNSGNMATLTISGVQAGDEADFYCQVWDSDSEHVVFG GGTKLTVL |
| | 149366 | |
| 149366-aa ScFv domain | 8033 | QVQLVQSGAEVKKPGASVKVSCKPSGYTVTSHYIHWVRRAPGQGLEWMGM INPSGGVTAYSQTLQGRVTMTSDTSSSTVYMELSSLRSEDTAMYYCAREG SGSGWYFDFWGRGTLVTVSSGGGGSGGGGSGGGGSSYVLTQPPSVSVSPG QTASITCSGDGLSKKYVSWYQQKAGQSPVVLISRDKERPSGIPDRFSGSN SADTATLTISGTQAMDEADYYCQAWDDTTVVFGGGTKLTVL |
| 149366-nt ScFv domain | 8054 | CAAGTGCAGCTGGTGCAGAGCGGGGCCGAAGTCAAGAAGCCGGGAGCCTC CGTGAAAGTGTCCTGCAAGCCTTCGGGATACACCGTGACCTCCCACTACA TTCATTGGGTCCGCCGCGCCCCCGGCCAAGGACTCGAGTGGATGGGCATG ATCAACCCTAGCGGCGGAGTGACCGCGTACAGCCAGACGCTGCAGGGACG CGTGACTATGACCTCGGATACCTCCTCCTCCACCGTCTATATGGAACTGT CCAGCCTGCGGTCCGAGGATACCGCCATGTACTACTGCGCCCGGGAAGGA TCAGGCTCCGGGTGGTATTTCGACTTCTGGGGAAGAGGCACCCTCGTGAC TGTGTCATCTGGGGAGGGGGTTCCGGTGGTGGCGGATCGGGAGGAGGCG GTTCATCCTACGTGCTGACCCAGCCACCCTCCGTGTCCGTGAGCCCCGGC CAGACTGCATCGATTACATGTAGCGGCGACGGCCTCTCCAAGAAATACGT GTCGTGGTACCAGCAGAAGGCCGGACAGAGCCCGGTGGTGCTGATCTCAA GAGATAAGGAGCGGCCTAGCGGAATCCCGGACAGGTTCTCGGGTTCCAAC TCCGCGGACACTGCTACTCTGACCATCTCGGGGACCCAGGCTATGGACGA AGCCGATTACTACTGCCAAGCCTGGGACGACACTACTGTCGTGTTTGGAG GGGGCACCAAGTTGACCGTCCTT |

TABLE 18-continued

Antigen Binding domains that bind BCMA
The amino acid sequences variable heavy chain and variable light chain
sequences for each scFv is also provided.

| Name/<br>Description | SEQ ID<br>NO: | Sequence |
|---|---|---|
| 149366-aa VH | 8075 | QVQLVQSGAEVKKPGASVKVSCKPSGYTVTSHYIHWVRRAPGQGLEWMGM<br>INPSGGVTAYSQTLQGRVTMTSDTSSSTVYMELSSLRSEDTAMYYCAREG<br>SGSGWYFDFWGRGTLVTVSS |
| 149366-aa VL | 8096 | SYVLTQPPSVSVSPGQTASITCSGDGLSKKYVSWYQQKAGQSPVVLISRD<br>KERPSGIPDRFSGSNSADTATLTISGTQAMDEADYYCQAWDDTTVVFGGG<br>TKLTVL |

149367

| 149367-aa<br>ScFv domain | 8034 | QVQLQESGPGLVKPSQTLSLTCTVSGGSISSGGYYWSWIRQHPGKGLEWI<br>GYIYYSGSTYYNPSLKSRVTISVDTSKNQFSLKLSSVTAADTAVYYCARA<br>GIAARLRGAFDIWGQGTMVTVSSGGGGSGGGGSGGGGSDIVMTQSPSSVS<br>ASVGDRVIITCRASQGIRNWLAWYQQKPGKAPNLLIYAASNLQSGVPSRF<br>SGSGSGADFTLTISSLQPEDVATYYCQKYNSAPFTFGPGTKVDIK |
| 149367-nt<br>ScFv domain | 8055 | CAAGTGCAGCTTCAGGAGAGCGGCCCGGGACTCGTGAAGCCGTCCCAGAC<br>CCTGTCCCTGACTTGCACCGTGTCGGAGGAAGCATCTCGAGCGGAGGCT<br>ACTATTGGTCGTGGATTCGGCAGCACCCTGGAAAGGGCCTGGAATGGATC<br>GGCTACATCTACTACTCCGGCTCGACCTACTACAACCCATCGCTGAAGTC<br>CAGAGTGACAATCTCAGTGGACACGTCCAAGAATCAGTTCAGCCTGAAGC<br>TCTCTTCCGTGACTGCGGCCGACACCGCCGTGTACTACTGCGCACGCGCT<br>GGAATTGCCGCCCGGCTGAGGGGTGCCTTCGACATTTGGGGACAGGGCAC<br>CATGGTCACCGTGTCCTCCGGCGGCGGAGGTTCCGGGGGTGGAGGCTCAG<br>GAGGAGGGGGGTCCGACATCGTCATGACTCAGTCGCCCTCAAGCGTCAGC<br>GCGTCCGTCGGGGACAGAGTGATCATCACCTGTCGGGCGTCCCAGGGAAT<br>TCGCAACTGGCTGGCCTGGTATCAGCAGAAGCCCGGAAAGGCCCCCAACC<br>TGTTGATCTACGCCGCCTCAAACCTCCAATCCGGGGTGCCGAGCCGCTTC<br>AGCGGCTCCGGTTCGGGTGCCGATTTCACTCTGACCATCTCCTCCCTGCA<br>ACCTGAAGATGTGGCTACCTACTACTGCCAAAAGTACAACTCCGCACCTT<br>TTACTTTCGGACCGGGGACCAAAGTGGACATTAAG |
| 149367-aa VH | 8076 | QVQLQESGPGLVKPSQTLSLTCTVSGGSISSGGYYWSWIRQHPGKGLEWI<br>GYIYYSGSTYYNPSLKSRVTISVDTSKNQFSLKLSSVTAADTAVYYCARA<br>GIAARLRGAFDIWGQGTMVTVSS |
| 149367-aa VL | 8097 | DIVMTQSPSSVSASVGDRVIITCHASQGTHNWLAWYQQKPGKAPNLLIYA<br>ASNLQSGVPSRFSGSGSGADFTLTISSLQPEDVATYYCQKYNSAPFTFGP<br>GTKVDIK |

149368

| 149368-aa<br>ScFv domain | 8035 | QVQLVQSGAEVKKPGSSVKVSCKASGGTFSSYAISWVRQAPGQGLEWMGG<br>IIPIFGTANYAQKFQGRVTITADESTSTAYMELSSLRSEDTAVYYCARRG<br>GYQLLRWDVGLLRSAFDIWGQGTMVTVSSGGGGSGGGGSGGGGSSYVLTQ<br>PPSVSVAPGQTARITCGGNNIGSKSVHWYQQKPGQAPVLVLYGKNNRPSG<br>VPDRFSGSRSGTTASLTITGAQAEDEADYYCSSRDSSGDHLRVFGTGTKV<br>TVL |
| 149368-nt<br>ScFv domain | 8056 | CAAGTGCAGCTGGTCCAGTCGGGCGCCGAGGTCAAGAAGCCCGGGAGCTC<br>TGTGAAAGTGTCCTGCAAGGCCTCCGGGGGCACCTTTAGCTCCTACGCCA<br>TCTCCTGGGTCCGCCAAGCACCGGGTCAAGGCCTGGAGTGGATGGGGGGA<br>ATTATCCCTATCTTCGGCACTGCCAACTACGCCCAGAAGTTCCAGGGACG<br>CGTGACCATTACCGCGGACGAATCCACCTCCACCGCTTATATGGAGCTGT<br>CCAGCTTGCGCTCGGAAGATACCGCCGTGTACTACTGCGCCCGGAGGGGT<br>GGATACCAGCTGCTGAGATGGGACGTGGGCCTCCTGCGGTCGGCGTTCGA<br>CATCTGGGGCCAGGGCACTATGGTCACTGTGTCCAGCGGAGGAGGCGGAT<br>CGGGAGGCGGCGGATCAGGGGGAGGCGGTTCCAGCTACGTGCTTACTCAA<br>CCCCCTTCGGTGTCCGTGGCCCCGGGACAGACCGCCAGAATCACTTGCGG<br>AGGAAACAACATTGGGTCCAAGAGCGTGCATTGGTACCAGCAGAAGCCAG<br>GACAGGCCCCTGTGCTGGTGCTCTACGGGAAGAACAATCGGCCCAGCGGA<br>GTGCCGGACAGGTTCTCGGGTTCACGCTCCGGTACAACCGCTTCACTGAC<br>TATCACCGGGGCCCAGGCAGAGGATGAAGCGGACTACTACTGTTCCTCCC<br>GGGATTCATCCGGCGACCACCTCCGGGTGTTCGGAACCGGAACGAAGGTC<br>ACCGTGCTG |
| 149368-aa VH | 8077 | QVQLVQSGAEVKKPGSSVKVSCKASGGTFSSYAISWVRQAPGQGLEWMGG<br>IIPIFGTANYAQKFQGRVTITADESTSTAYMELSSLRSEDTAVYYCARRG<br>GYQLLRWDVGLLRSAFDIWGQGTMVTVSS |

TABLE 18-continued

Antigen Binding domains that bind BCMA
The amino acid sequences variable heavy chain and variable light chain
sequences for each scFv is also provided.

| Name/ Description | SEQ ID NO: | Sequence |
|---|---|---|
| 149368-aa VL | 8098 | SYVLTQPPSVSVAPGQTARITCGGNNIGSKSVHWYQQKPGQAPVLVLYGK NNRPSGVPDRFSGSRSGTTASLTITGAQAEDEADYYCSSRDSSGDHLRVF GTGTKVTVL |
| 149369 | | |
| 149369-aa ScFv domain | 8036 | EVQLQQSGPGLVKPSQTLSLTCAISGDSVSSNSAAWNWIRQSPSRGLEWL GRTYYRSKWYSFYAISLKSRIIINPDTSKNQFSLQLKSVTPEDTAVYYCA RSSPEGLFLYWFDPWGQGTLVTVSSGGDGSGGGGSGGGGSSSELTQDPAV SVALGQTIRITCQGDSLGNYYATWYQQKPGQAPVLVIYGTNNRPSGIPDR FSASSSGNTASLTITGAQAEDEADYYCNSRDSSGHHLLFGTGTKVTVL |
| 149369-nt ScFv domain | 8057 | GAAGTGCAGCTCCAACAGTCAGGACCGGGGCTCGTGAAGCCATCCCAGAC CCTGTCCCTGACTTGTGCCATCTCGGGAGATAGCGTGTCATCGAACTCCG CCGCCTGGAACTGGATTCGGCAGAGCCCGTCCCGCGGACTGGAGTGGCTT GGAAGGACCTACTACCGGTCCAAGTGGTACTCTTTCTACGCGATCTCGCT GAAGTCCCGCATTATCATTAACCCTGATACCTCCAAGAATCAGTTCTCCC TCCAACTGAAATCCGTCACCCCCGAGGACACAGCAGTGTATTACTGCGCA CGGAGCAGCCCCGAAGGACTGTTCCTGTATTGGTTTGACCCCTGGGGCCA GGGGACTCTTGTGACCGTGTCGAGCGGCGGAGATGGGTCCGGTGGCGGTG GTTCGGGGGGCGGCGGATCATCATCCGAACTGACCCAGGACCCGGCTGTG TCCGTGGCGCTGGGACAAACCATCCGCATTACGTGCCAGGGAGACTCCCT GGGCAACTACTACGCCACTTGGTACCAGCAGAAGCCGGGCCAAGCCCCTG TGTTGGTCATCTACGGGACCAACAACAGACCTTCCGGCATCCCCGACCGG TTCAGCGCTTCGTCCTCCGGCAACACTGCCAGCCTGACCATCACTGGAGC GCAGGCCGAAGATGAGGCCGACTACTACTGCAACAGCAGAGACTCCTCGG GTCATCACCTCTTGTTCGGAACTGGAACCAAGGTCACCGTGCTG |
| 149369-aa VH | 8078 | EVQLQQSGPGLVKPSQTLSLTCAISGDSVSSNSAAWNWIRQSPSRGLEWL GRTYYRSKWYSFYAISLKSRIIINPDTSKNQFSLQLKSVTPEDTAVYYCA RSSPEGLFLYWFDPWGQGTLVTVSS |
| 149369-aa VL | 8099 | SSELTQDPAVSVALGQTIRITCQGDSLGNYYATWYQQKPGQAPVLVIYGT NNRPSGIPDRFSASSSGNTASLTITGAQAEDEADYYCNSRDSSGHHLLFG TGTKVTVL |
| BCMA_EBB-C1978-A4 | | |
| BCMA_EBB-C1978-A4-aa ScFv domain | 8037 | EVQLVESGGGLVQPGGSLRLSCAASGFTFSSYAMSWVRQAPGKGLEWVSA ISGSGGSTYYADSVKGRFTISRDNSKNTLYLQMNSLRAEDTAVYYCAKVE GSGSLDYWGQGTLVTVSSGGGGSGGGGSGGGGSEIVMTQSPGTLSLSPGE RATLSCRASQSVSSAYLAWYQQKPGQPPRLLISGASTRATGIPDRFGGSG SGTDFTLTISRLEPEDFAVYYCQHYGSSENGSSLFTEGQGTRLEIK |
| BCMA_EBB-C1978-A4-nt ScFv domain | 8058 | GAAGTGCAGCTCGTGGAGTCAGGAGGCGGCCTGGTCCAGCCGGGAGGGTC CCTTAGACTGTCATGCGCCGCAAGCGGATTCACTTTCTCCTCCTATGCCA TGAGCTGGGTCCGCCAAGCCCCCGGAAAGGGACTGGAATGGGTGTCCGCC ATCTCGGGGTCTGGAGGCTCAACTTACTACGCTGACTCCGTGAAGGGACG GTTCACCATTAGCCGCGACAACTCCAAGAACACCCTCTACCTCCAAATGA ACTCCCTGCGGGCCGAGGATACCGCCGTCTACTACTGCGCCAAAGTGGAA GGTTCAGGATCGCTGGACTACTGGGGACAGGGTACTCTCGTGACCGTGTC ATCGGGCGGAGGAGGTTCCGGCGGTGGCGGCTCCGGCGGCGGAGGGTCGG AGATCGTGATGACCCAGAGCCCTGGTACTCTGAGCCTTTCGCCGGGAGAA AGGGCCACCCTGTCCTGCCGCGCTTCCCAATCCGTGTCCTCCGCGTACTT GGCGTGGTACCAGCAGAAGCCGGGACAGCCCCTCGGCTGCTGATCAGCGG GGGCCAGCACCCGGGCAACCGGAATCCCAGACAGATTCGGGGGTTCCGGC AGCGGCACAGATTTCACCCTGACTATTTCGAGGTTGGAGCCCGAGGACTT TGCGGTGTATTACTGTCAGCACTACGGGTCGTCCTTTAATGGCTCCAGCC TGTTCACGTTCGGACAGGGGACCCGCCTGGAAATCAAG |
| BCMA_EBB-C1978-A4-aa VH | 8079 | EVQLVESGGGLVQPGGSLRLSCAASGFTFSSYAMSWVRQAPGKGLEWVSA ISGSGGSTYYADSVKGRFTISRDNSKNTLYLQMNSLRAEDTAVYYCAKVE GSGSLDYWGQGTLVTVSS |
| BCMA_EBB-C1978-A4-aa VL | 8100 | EIVMTQSPGTLSLSPGERATLSCRASQSYSSAYLAWYQQKPGQPPRLLIS GASTRATGIPDRFGGSGSGTDFTLTISRLEPEDFAVYYCQHYGSSFNGSS LFTFGQGTRLEIK |
| BCMA_EBB-C1978-G1 | | |
| BCMA_EBB-C1978-G1-aa | 8038 | EVQLVETGGGLVQPGGSLRLSCAASGITFSRYPMSWVRQAPGKGLEWVSG ISDSGVSTYYADSAKGRFTISRDNSKNTLFLQMSSLRDEDTAVYYCVTRA |

TABLE 18-continued

Antigen Binding domains that bind BCMA
The amino acid sequences variable heavy chain and variable light chain sequences for each scFv is also provided.

| Name/ Description | SEQ ID NO: | Sequence |
| --- | --- | --- |
| ScFv domain | | GSEASDIWGQGTMVTVSSGGGGSGGGGSGGGGSEIVLTQSPATLSLSPGE RATLSCRASQSVSNSLAWYQQKPGQAPRLLIYDASSRATGIPDRFSGSGS GTDFTLTISRLEPEDFAIYYCQQFGTSSGLTFGGGTKLEIK |
| BCMA_EBB-C1978-G1-nt ScFv domain | 8059 | GAAGTGCAACTGGTGGAAACCGGTGGCGGCCTGGTGCAGCCTGGAGGATC ATTGAGGCTGTCATGCGCGGCCAGCGGTATTACCTTCTCCCGGTACCCCA TGTCCTGGGTCAGACAGGCCCCGGGGAAAGGGCTTGAATGGGTGTCCGGG ATCTCGGACTCCGGTGTCAGCACTTACTACGCCGACTCCGCCAAGGGACG CTTCACCATTTCCCGGGACAACTCGAAGAACACCCTGTTCCTCCAAATGA GCTCCCTCCGGGACGAGGATACTGCAGTGTACTACTGCGTGACCCGCGCC GGGTCCGAGGCGTCTGACATTTGGGGACAGGGCACTATGGTCACCGTGTC GTCCGGCGGAGGGGGCTCGGGAGGCGGTGGCAGCGGAGGAGGAGGGTCCG AGATCGTGCTGACCCAATCCCCGGCCACCCTCTCGCTGAGCCCTGGAGAA AGGGCAACCTTGTCCTGTCGCGCGAGCCAGTCCGTGAGCAACTCCCTGGC CTGGTACCAGCAGAAGCCCGGACAGGCTCCGAGACTTCTGATCTACGACG CTTCGAGCCGGGCCACTGGAATCCCCGACCGCTTTTCGGGGTCCGGCTCA GGAACCGATTTCACCCTGACAATCTCACGGCTGGAGCCAGAGGATTTCGC CATCTATTACTGCCAGCAGTTCGGTACTTCCTCCGGCCTGACTTTCGGAG GCGGCACGAAGCTCGAAATCAAG |
| BCMA_EBB-C1978-G1-aa VH | 8080 | EVQLVETGGGLVQPGGSLRLSCAASGITFSRYPMSWVRQAPGKGLEWVSG ISDSGVSTYYADSAKGRFTISRDNSKNTLFLQMSSLRDEDTAVYYCVTRA GSEASDIWGQGTMVTVSS |
| BCMA_EBB-C1978-G1-aa VL | 8101 | EIVLTQSPATLSLSPGERATLSCRASQSYSNSLAWYQQKPGQAPRLLIYD ASSRATGIPDRFSGSGSGTDFTLTISRLEPEDFAIYYCQQFGTSSGLTFG GGTKLEIK |
| BCMA_EBB-C1979-C1 | | |
| BCMA_EBB-C1979-C1-aa ScFv domain | 8039 | QVQLVESGGGLVQPGGSLRLSCAASGFTFSSYAMSWVRQAPGKGLEWVSA ISGSGGSTYYADSVKGRFTISRDNAKNSLYLQMNSLRAEDTAIYYCARAT YKRELRYYYGMDVWGQGTMVTVSSGGGGSGGGGSGGGGSEIVMTQSPGTV SLSPGERATLSCRASQSVSSSFLAWYQQKPGQAPRLLIYGASSRATGIPD RFSGSGSGTDFTLTISRLEPEDSAVYYCQQYHSSPSWTFGQGTRLEIK |
| BCMA_EBB-C1979-C1-nt ScFv domain | 8060 | CAAGTGCAGCTCGTGGAATCGGTGGCGGACTGGTGCAGCCGGGGGGCTC ACTTAGACTGTCCTGCGCGGCCAGCGGATTCACTTTCTCCTCCTACGCCA TGTCCTGGGTCAGACAGGCCCCTGGAAAGGGCCTGGAATGGGTCCGCA ATCAGCGGCAGCGGCGGCTCGACCTATTACGCGGATTCAGTGAAGGGCAG ATTCACCATTTCCCGGGACAACGCCAAGAACTCCTTGTACCTTCAAATGA ACTCCCTCCGCGCGGAAGATACCGCAATCTACTACTGCGCTCGGGCCACT TACAAGAGGGAACTGCGCTACTACTACGGGATGGACGTCTGGGGCCAGGG AACCATGGTCACCGTGTCCAGCGGAGGAGGAGGATCGGGAGGAGGCGGTA GCGGGGGTGGAGGGTCGGAGATCGTGATGACCCAGTCCCCCGGCACTGTG TCGCTGTCCCCGGCGAACGGGCCACCCTGTCATGTCGGGCCAGCCAGTC AGTGTCGTCAAGCTTCCTCGCCTGGTACCAGCAGAAACCGGGACAAGCTC CCCGCCTGCTGATCTACGGAGCCAGCAGCCGGGCCACCGGTATTCCTGAC CGGTTCTCCGGTTCGGGTCCGGGACCGACTTTACTCTGACTATCTCTCG CCTCGAGCCAGAGGACTCCGCCGTGTATTACTGCCAGCAGTACCACTCCT CCCCGTCCTGGACGTTCGGACAGGGCACAAGGCTGGAGATTAAG |
| BCMA_EBB-C1979-C1-aa VH | 8081 | QVQLVESGGGLVQPGGSLRLSCAASGFTFSSYAMSWVRQAPGKGLEWVSA ISGSGGSTYYADSVKGRFTISRDNAKNSLYLQMNSLRAEDTAIYYCARAT YKRELRYYYGMDVWGQGTMVTVSS |
| BCMA_EBB-C1979-C1-aa VL | 8102 | EIVMTQSPGTVSLSPGERATLSCRASQSYSSSFLAWYQQKPGQAPRLLIY GASSRATGIPDRFSGSGSGTDFTLTISRLEPEDSAVYYCQQYHSSPSWTF GQGTRLEIK |
| BCMA_EBB-C1978-C7 | | |
| BCMA_EBB-C1978-C7-aa ScFv domain | 8040 | EVQLVETGGGLVQPGGSLRLSCAASGFTFSSYAMSWVRQAPGKGLEWVSA ISGSGGSTYYADSVKGRFTISRDNSKNTLYLQMNTLKAEDTAVYYCARAT YKRELRYYYGMDVWGQGTTVTVSSGGGGSGGGGSGGGGSEIVLTQSPSTL SLSPGESATLSCRASQSVSTTFLAWYQQKPGQAPRLLIYGSSNRATGIPD RFSGSGSGTDFTLTIRRLEPEDFAVYYCQQYHSSPSWTFGQGTKVEIK |
| BCMA_EBB-C1978-C7-nt ScFv domain | 8061 | GAGGTGCAGCTTGTGGAAACCGGTGGCGGACTGGTGCAGCCCGGAGGAAG CCTCAGGCTGTCCTGCGCCGCGTCCGGCTTCACCTTCTCCTCGTACGCCA TGTCCTGGGTCCGCCAGGCCCCCGAAAGGGCCTGGAATGGGTGTCCGCC ATCTCTGGAAGCGGAGGTTCCACGTACTACGCGGACAGCGTCAAGGGAAG GTTCACAATCTCCCGCGATAATTCGAAGAACACTCTGTACCTTCAAATGA |

TABLE 18-continued

Antigen Binding domains that bind BCMA
The amino acid sequences variable heavy chain and variable light chain
sequences for each scFv is also provided.

| Name/<br>Description | SEQ ID<br>NO: | Sequence |
|---|---|---|
| | | ACACCCTGAAGGCCGAGGACACTGCTGTGTACTACTGCGCACGGGCCACC<br>TACAAGAGAGAGCTCCGGTACTACTACGGAATGGACGTCTGGGGCCAGGG<br>AACTACTGTGACCGTGTCCTCGGGAGGGGTGGCTCCGGGGGGGCGGCT<br>CCGGCGGAGGCGGTTCCGAGATTGTGCTGACCCAGTCACCTTCAACTCTG<br>TCGCTGTCCCCGGGAGAGAGCGCTACTCTGAGCTGCCGGGCCAGCCAGTC<br>CGTGTCCACCACCTTCCTCGCCTGGTATCAGCAGAAGCCGGGCAGGCAC<br>CACGGCTCTTGATCTACGGGTCAAGCAACAGAGCGACCGGAATTCCTGAC<br>CGCTTCTCGGGGAGCGGTTCAGGCACCGACTTCACCCTGACTATCCGGCG<br>CCTGGAACCCGAAGATTTCGCCGTGTATTACTGTCAACAGTACCACTCCT<br>CGCCGTCCTGGACCTTTGGCCAAGGAACCAAAGTGGAAATCAAG |
| BCMA_EBB-<br>C1978-C7-aa<br>VH | 8082 | EVQLVETGGGLVQPGGSLRLSCAASGFTFSSYAMSWVRQAPGKGLEWVSA<br>ISGSGGSTYYADSVKGRFTISRDNSKNTLYLQMNTLKAEDTAVYYCARAT<br>YKRELRYYYGMDVWGQGTTVTVSS |
| BCMA_EBB-<br>C1978-C7-aa<br>VL | 8103 | EIVLTQSPSTLSLSPGESATLSCRASQSYSTTFLAWYQQKPGQAPRLLIY<br>GSSNRATGIPDRFSGSGSGTDFTLTIRRLEPEDFAVYYCQQYHSSPSWTF<br>GQGTKVEIK |
| BCMA_EBB-C1978-D10 | | |
| BCMA_EBB-<br>C1978-D10-<br>aa<br>ScFv domain | 8041 | EVQLVETGGGLVQPGRSLRLSCAASGFTFDDYAMHWVRQAPGKGLEWVSG<br>ISWNSGSIGYADSVKGRFTISRDNAKNSLYLQMNSLRDEDTAVYYCARVG<br>KAVPDVWGQGTTVTVSSGGGGSGGGGSGGGGSDIVMTQTPSSLSASVGDR<br>VTITCRASQSISSYLNWYQQKPGKAPKLLIYAASSLQSGVPSRFSGSGSG<br>TDFTLTISSLQPEDFATYYCQQSYSTPYSFGQGTRLEIK |
| BCMA_EBB-<br>C1978-D10-nt<br>ScFv domain | 8062 | GAAGTGCAGCTCGTGGAAACTGGAGGTGGACTCGTGCAGCCTGGACGGTC<br>GCTGCGGCTGAGCTGCGCTGCATCCGGCTTCACCTTCGACGATTATGCCA<br>TGCACTGGGTCAGACAGGCGCCAGGGAAGGGACTTGAGTGGGTGTCCGGT<br>ATCAGCTGGAATAGCGGCTCAATCGGATACGCGGACTCCGTGAAGGGAAG<br>GTTCACCATTTCCCGCGACAACGCCAAGAACTCCCTGTACTTGCAAATGA<br>ACAGCCTCCGGGATGAGGACACTGCCGTGTACTACTGCGCCCGCGTCGGA<br>AAAGCTGTGCCCGACGTCTGGGGCCAGGGAACCACTGTGACCGTGTCCAG<br>CGGCGGGGTGGATCGGCGGTGGAGGGTCCGGTGGAGGGGGCTCAGATA<br>TTGTGATGACCCAGACCCCCTCGTCCCTGTCCGCCTCGGTCGGCGACCGC<br>GTGACTATCACATGTAGAGCCTCGCAGAGCATCTCCAGCTACCTGAACTG<br>GTATCAGCAGAAGCCGGGAAGGCCCCGAAGCTCCTGATCTACGCGGCAT<br>CATCACTGCAATCGGGAGTGCCGAGCCGGTTTTCCGGGTCCGGCTCCGGC<br>ACCGACTTCACGCTGACCATTTCTTCCCTGCAACCCGAGGACTTCGCCAC<br>TTACTACTGCCAGCAGTCCTACTCCACCCCTTACTCCTTCGGCCAAGGAA<br>CCAGGCTGGAAATCAAG |
| BCMA_EBB-<br>C1978-D10-<br>aa<br>VH | 8083 | EVQLVETGGGLVQPGRSLRLSCAASGFTFDDYAMHWVRQAPGKGLEWVSG<br>ISWNSGSIGYADSVKGRFTISRDNAKNSLYLQMNSLRDEDTAVYYCARVG<br>KAVPDVWGQGTTVTVSS |
| BCMA_EBB-<br>C1978-D10-aa<br>VL | 8104 | DIVMTQTPSSLSASVGDRVTITCRASQSISSYLNWYQQKPGKAPKLLIYA<br>ASSLQSGVPSRFSGSGSGTDFTLTISSLQPEDFATYYCQQSYSTPYSFGQ<br>GTRLEIK |
| BCMA_EBB-C1979-C12 | | |
| BCMA_EBB-<br>C1979-C12-aa<br>ScFv domain | 8042 | EVQLVESGGGLVQPGRSLRLSCTASGFTFDDYAMHWVRQRPGKGLEWVAS<br>INWKGNSLAYGDSVKGRFAISRDNAKNTVFLQMNSLRTEDTAVYYCASHQ<br>GVAYYNYAMDVWGRGTLVTVSSGGGGSGGGGSGGGGSEIVLTQSPGTLSL<br>SPGERATLSCRATQSIGSSFLAWYQQRPGQAPRLLIYGASQRATGIPDRF<br>SGRGSGTDFTLTISRVEPEDSAVYYCQHYESSPSWTFGQGTKVEIK |
| BCMA_EBB-<br>C1979-C12-nt<br>ScFv domain | 8063 | GAAGTGCAGCTCGTGGAGAGCGGGGAGGATTGGTGCAGCCCGGAAGGTC<br>CCTGCGGCTCTCCTGCACTGCGTCGGCTTCACCTTCGACGACTACGCGA<br>TGCACTGGGTCAGACAGCGCCCGGGAAAGGGCCTGGAATGGGTCGCCTCA<br>ATCAACTGGAAGGGAAATCCCTGGCCTATGGCGACAGCGTGAAGGGCCG<br>CTTCGCCATTTCGCGCGACAACGCCAAGAACACCGTGTTTCTGCAAATGA<br>ATTCCCTGCGGACCGAGGATACCGCTGTGTACTACTGCGCCAGCCACCAG<br>GGCGTGGCATACTATAACTACGCCATGGACGTGTGGGGAAGAGGGACGCT<br>CGTCACCGTGTCCTCCGGGGGCGGTGGATCGGGTGGTGAGGGGGAAGCGGTG<br>GCGGGGGCAGCGAAATCGTGCTGACTCAGAGCCCGGGAACTCTTTCACTG<br>TCCCGGGAGAACGGGCCACTCTCTCGTGCCGGGCCACCCAGTCCATCGG<br>CTCCTCCTTCCTTGCCTGGTACCAGCAGAGGCCAGGACAGGCGCCCCGCC<br>TGCTGATCTACGGTGCTTCCCAACGCGCCACTGGCATTCCTGACCGGTTC<br>AGCGGCAGAGGGTCGGGAACCGATTTCACACTGACCATTTCCCGGGTGGA |

TABLE 18-continued

Antigen Binding domains that bind BCMA
The amino acid sequences variable heavy chain and variable light chain
sequences for each scFv is also provided.

| Name/Description | SEQ ID NO: | Sequence |
|---|---|---|
| | | GCCCGAAGATTCGGCAGTCTACTACTGTCAGCATTACGAGTCCTCCCCTT<br>CATGGACCTTCGGTCAAGGGACCAAAGTGGAGATCAAG |
| BCMA_EBB-C1979-C12-aa VH | 8084 | EVQLVESGGGLVQPGRSLRLSCTASGFTFDDYAMHWVRQRPGKGLEWVAS<br>INWKGNSLAYGDSVKGRFAISRDNAKNTVFLQMNSLRTEDTAVYYCASHQ<br>GVAYYNYAMDVWGRGTLVTVSS |
| BCMA_EBB-C1979-C12-aa VL | 8105 | EIVLTQSPGTLSLSPGERATLSCRATQSIGSSFLAWYQQRPGQAPRLLIY<br>GASQRATGIPDRFSGRGSGTDFTLTISRVEPEDSAVYYCQHYESSPSWTF<br>GQGTKVEIK |
| BCMA_EBB-C1980-G4 | | |
| BCMA_EBB-C1980-G4-aa ScFv domain | 8043 | EVQLVESGGGLVQPGGSLRLSCAASGFTFSSYAMSWVRQAPGKGLEWVSA<br>ISGSGGSTYYADSVKGRFTISRDNSKNTLYLQMNSLRAEDTAVYYCAKVV<br>RDGMDVWGQGTTVTVSSGGGGSGGGGSGGGGSEIVLTQSPATLSLSPGER<br>ATLSCRASQSVSSSYLAWYQQKPGQAPRLLIYGASSRATGIPDRFSGNGS<br>GTDFTLTISRLEPEDFAVYYCQQYGSPPRETFGPGTKVDIK |
| BCMA_EBB-C1980-G4-nt ScFv domain | 8064 | GAGGTGCAGTTGGTCGAAAGCGGGGGCGGGCTTGTGCAGCCTGGCGGATC<br>ACTGCGGCTGTCCTGCGCGGCATCAGGCTTCACGTTTTCTTCCTACGCCA<br>TGTCCTGGGTGCGCCAGGCCCCTGGAAAGGGACTGGAATGGGTGTCCGCG<br>ATTTCGGGGTCCGGCGGGAGCACCTACTACGCCGATTCCGTGAAGGGCCG<br>CTTCACTATCTCGCGGGACAACTCCAAGAACACCCTCTACCTCCAAATGA<br>ATAGCCTGCGGGCCGAGGATACCGCCGTCTACTATTGCGCTAAGGTCGTG<br>CGCGACGGAATGGACGTGTGGGGACAGGGTACCACCGTGACAGTGTCCTC<br>GGGGGGAGGCGGTAGCGGCGGAGGAGGAAGCGGTGGTGGAGGTTCCGAGA<br>TTGTGCTGACTCAATCACCCGCGACCCTGAGCCTGTCCCCCGGCGAAAGG<br>GCCACTCTGTCCTGTCGGGCCAGCCAATCAGTCTCCTCCTCGTACCTGGC<br>CTGGTACCAGCAGAAGCCAGGACAGGCTCCGAGACTCCTTATCTATGGCG<br>CATCCTCCCGCGCCACCGGAATCCCGGATAGGTTCTCGGGAAACGGATCG<br>GGGACCGACTTCACTCTCACCATCTCCCGGCTGGAACCGGAGGACTTCGC<br>CGTGTACTACTGCCAGCAGTACGGCAGCCCGCCTAGATTCACTTTCGGCC<br>CCGGCACCAAAGTGGACATCAAG |
| BCMA_EBB-C1980-G4-aa VH | 8085 | EVQLVESGGGLVQPGGSLRLSCAASGFTFSSYAMSWVRQAPGKGLEWVSA<br>ISGSGGSTYYADSVKGRFTISRDNSKNTLYLQMNSLRAEDTAVYYCAKVV<br>RDGMDVWGQGTTVTVSS |
| BCMA_EBB-C1980-G4-aa VL | 8106 | EIVLTQSPATLSLSPGERATLSCRAsQsysSSYLAWYQQKPGQAPRLLIY<br>GASSRATGIPDRFSGNGSGTDFTLTISRLEPEDFAVYYCQQYGSPPRFTF<br>GPGTKVDIK |
| BCMA_EBB-C1980-D2 | | |
| BCMA_EBB-C1980-D2-aa ScFv domain | 8044 | EVQLLESGGGLVQPGGSLRLSCAASGFTFSSYAMSWVRQAPGKGLEWVSA<br>ISGSGGSTYYADSVKGRFTISRDNSKNTLYLQMNSLRAEDTAVYYCAKIP<br>QTGTFDYWGQGTLVTVSSGGGGSGGGGSGGGGSEIVLTQSPGTLSLSPGE<br>RATLSCRASQSVSSSYLAWYQQRPGQAPRLLIYGASSRATGIPDRFSGSG<br>SGTDFTLTISRLEPEDFAVYYCQHYGSSPSWTFGQGTRLEIK |
| BCMA_EBB-C1980-D2-nt ScFv domain | 8065 | GAAGTGCAGCTGCTGGAGTCCGGCGGTGGATTGGTGCAACCGGGGGGATC<br>GCTCAGACTGTCCTGTGCGGCGTCAGGCTTCACCTTCTCGAGCTACGCCA<br>TGTCATGGGTCAGACAGGCCCCTGGAAAGGGTCTGGAATGGGTGTCCGCC<br>ATTTCCGGGAGCGGGGATCTACATACTACGCCGATAGCGTGAAGGGCCG<br>CTTCACCATTTCCCGGGACAACTCCAAGAACACTCTCTATCTGCAAATGA<br>ACTCCCTCCGCGCTGAGGACACTGCCGTGTACTACTGCGCCAAAATCCCT<br>CAGACCGGCACCTTCGACTACTGGGGACAGGGGACTCTGGTCACCGTCAG<br>CAGCGGTGGCGAGGTTCGGGGGAGGAGGAAGCGGCGGCGGAGGGTCCG<br>AGATTGTGCTGACCCAGTCACCCGGCACTTTGTCCCTGTCGCCTGGAGAA<br>AGGGCCACCCTTTCCTGCCGGGCATCCCAATCCGTGTCCTCCTCGTACCT<br>GGCCTGGTACCAGCAGAGGCCCGGACAGGCCCCACGGCTTCTGATCTACG<br>GAGCAAGCAGCCGCGCGACCGGTATCCCGGACCGGTTTTCGGGCTCGGGC<br>TCAGGAACTGACTTCACCCTCACCATCTCCCGCCTGGAACCCGAAGATTT<br>CGCTGTGTATTACTGCCAGCACTACGGCAGCTCCCCGTCCTGGACGTTCG<br>GCCAGGGAACTCGGCTGGAGATCAAG |
| BCMA_EBB-C1980-D2-aa VH | 8086 | EVQLLESGGGLVQPGGSLRLSCAASGFTFSSYAMSWVRQAPGKGLEWVSA<br>ISGSGGSTYYADSVKGRFTISRDNSKNTLYLQMNSLRAEDTAVYYCAKIP<br>QTGTFDYWGQGTLVTVSS |

TABLE 18-continued

Antigen Binding domains that bind BCMA
The amino acid sequences variable heavy chain and variable light chain
sequences for each scFv is also provided.

| Name/ Description | SEQ ID NO: | Sequence |
|---|---|---|
| BCMA_EBB-C1980-D2-aa VL | 8107 | EIVLTQSPGTLSLSPGERATLSCRASQSVSSSYLAWYQQRPGQAPRLLIY GASSRATGIPDRFSGSGSGTDFTLTISRLEPEDFAVYYCQHYGSSPSWTF GQGTRLEIK |

BCMA_EBB-C1978-A10

| Name/ Description | SEQ ID NO: | Sequence |
|---|---|---|
| BCMA_EBB-C1978-A10-aa ScFv domain | 8045 | EVQLVETGGGLVQPGGSLRLSCAASGFTFSSYAMSWVRQAPGKGLEWVSA ISGSGGSTYYADSVKGRFTMSRENDKNSVFLQMNSLRVEDTGVYYCARAN YKRELRYYYGMDVWGQGTMVTVSSGGGGSGGGGSGGGGSEIVMTQSPGTL SLSPGESATLSCRASQRVASNYLAWYQHKPGQAPSLLISGASSRATGVPD RFSGSGSGTDFTLAISRLEPEDSAVYYCQHYDSSPSWTFGQGTKVEIK |
| BCMA_EBB-C1978-A10-nt ScFv domain | 8066 | GAAGTGCAACTGGTGGAAACCGGTGGAGGACTCGTGCAGCCTGGCGGCAG CCTCCGGCTGAGCTGCGCCGCTTCGGGATTCACCTTTTCCTCCTACGCGA TGTCTTGGGTCAGACAGGCCCCCGGAAAGGGGCTGGAATGGGTGTCAGCC ATCTCCGGCTCCGGCGGATCAACGTACTACGCCGACTCCGTGAAAGGCCG GTTCACCATGTCGCGCGAGAATGACAAGAACTCCGTGTTCCTGCAAATGA ACTCCCTGAGGGTGGAGGACACCGGAGTGTACTATTGTGCGCGCGCCAAC TACAAGAGAGAGCTGCGGTACTACTACGGAATGGACGTCTGGGGACAGGG AACTATGGTGACCGTGTCATCCGGTGGAGGGGGAAGCGGCGGTGGAGGCA GCGGGGGCGGGGGTTCAGAAATTGTCATGACCCAGTCCCCGGGAACTCTT TCCCTCTCCCCCGGGGAATCCGCGACTTTGTCCTGCCGGGCCAGCCAGCG CGTGGCCTCGAACTACCTCGCATGGTACCAGCATAAGCCAGGCCAAGCCC CTTCCCTGCTGATTTCCGGGGCTAGCAGCCGCGCCACTGGCGTGCCGGAT AGGTTCTCGGGAAGCGGCTCGGGTACCGATTTCACCCTGGCAATCTCGCG GCTGGAACCGGAGGATTCGGCCGTGTACTACTGCCAGCACTATGACTCAT CCCCCTCCTGGACATTCGGACAGGGCACCAAGGTCGAGATCAAG |
| BCMA_EBB-C1978-A10-aa VH | 8087 | EVQLVETGGGLVQPGGSLRLSCAASGFTFSSYAMSWVRQAPGKGLEWVSA ISGSGGSTYYADSVKGRFTMSRENDKNSVFLQMNSLRVEDTGVYYCARAN YKRELRYYYGMDVWGQGTMVTVSS |
| BCMA_EBB-C1978-A10-aa VL | 8108 | EIVMTQSPGTLSLSPGESATLSCRASQRVASNYLAWYQHKPGQAPSLLIS GASSRATGVPDRFSGSGSGTDFTLAISRLEPEDSAVYYCQHYDSSPSWTF GQGTKVEIK |

BCMA_EBB-C1978-D4

| Name/ Description | SEQ ID NO: | Sequence |
|---|---|---|
| BCMA_EBB-C1978-D4-aa ScFv domain | 8046 | EVQLLETGGGLVQPGGSLRLSCAASGFSFSSYAMSWVRQAPGKGLEWVSA ISGSGGSTYYADSVKGRFTISRDNSKNTLYLQMNSLRAEDTAVYYCAKAL VGATGAFDIWGQGTLVTVSSGGGGSGGGGSGGGGSEIVLTQSPGTLSLSP GERATLSCRASQSLSSNFLAWYQQKPGQAPGLLIYGASNWATGTPDRFSG SGSGTDFTLTITRLEPEDFAVYYCQYYGTSPMYTFGQGTKVEIK |
| BCMA_EBB-C1978-D4-nt ScFv domain | 8067 | GAAGTGCAGCTGCTCGAAACCGGTGGAGGGCTGGTGCAGCCAGGGGCTC CCTGAGGCTTTCATGCGCCGCTAGCGGATTCTCCTTCTCCTCTTACGCCA TGTCGTGGGTCCGCCAAGCCCCTGGAAAAGGCCTGGAATGGGTGTCCGCG ATTTCCGGGAGCGGAGGTTCGACCTATTACGCCGACTCCGTGAAGGGCCG CTTTACCATCTCCCGGGATAACTCCAAGAACACTCTGTACCTCCAAATGA ACTCGCTGAGAGCCGAGGACACCGCCGTGTATTACTGCGCGAAGGCGCTG GTCGGCGCGACTGGGGCATTCGACATCTGGGGACAGGGAACTCTTGTGAC CGTGTCGAGCGGAGGCGGCGGCTCCGGCGGAGGAGGGAGCGGGGGCGGTG GTTCCGAAATCGTGTTGACTCAGTCCCCGGGAACCCTGAGCTTGTCACCC GGGGAGCGGGCCACTCTCTCCTGTCGCGCCTCCCAATCGCTCTCATCCAA TTTCCTGGCCTGGTACCAGCAGAAGCCCGACAGGCCCCGGGCCTGCTCA TCTACGGCGCTTCAAACTGGGCAACGGGAACCCCTGATCGGTTCAGCGGA AGCGGATCGGGTACTGACTTTACCCTGACCATCACCAGACTGGAACCGGA GGACTTCGCCGTGTACTACTGCCAGTACTACGGCACCTCCCCCATGTACA CATTCGGACAGGGTACCAAGGTCGAGATTAAG |
| BCMA_EBB-C1978-D4-aa VH | 8088 | EVQLLETGGGLVQPGGSLRLSCAASGFSFSSYAMSWVRQAPGKGLEWVSA ISGSGGSTYYADSVKGRFTISRDNSKNTLYLQMNSLRAEDTAVYYCAKAL VGATGAFDIWGQGTLVTVSS |
| BCMA_EBB-C1978-D4-aa VL | 8109 | EIVLTQSPGTLSLSPGERATLSCRASQSLSSNFLAWYQQKPGQAPGLLIY GASNWATGTPDRFSGSGSGTDFTLTITRLEPEDFAVYYCQYYGTSPMYTF GQGTKVEIK |

BCMA_EBB-C1980-A2

| Name/ Description | SEQ ID NO: | Sequence |
|---|---|---|
| BCMA_EBB-C1980-A2-aa ScFv domain | 8047 | EVQLLESGGGLVQPGGSLRLSCAASGFTFSSYAMSWVRQAPGKGLEWVSA ISGSGGSTYYADSVKGRFTISRDNSKNTLYLQMNSLRAEDTAVYYCVLWF GEGFDPWGQGTLVTVSSGGGGSGGGGSGGGGSDIVLTQSPLSLPVTPGEP |

TABLE 18-continued

Antigen Binding domains that bind BCMA
The amino acid sequences variable heavy chain and variable light chain
sequences for each scFv is also provided.

| Name/Description | SEQ ID NO: | Sequence |
|---|---|---|
|  |  | ASISCRSSQSLLHSNGYNYLDWYLQKPGQSPQLLIYLGSNRASGVPDRFS<br>GSGSGTDFTLKISRVEAEDVGVYYCMQALQTPLTFGGGTKVDIK |
| BCMA_EBB-C1980-A2-nt<br>ScFv domain | 8068 | GAAGTGCAGCTGCTTGAGAGCGGTGGAGGTCTGGTGCAGCCCGGGGATC<br>ACTCGCCTGTCCTGTGCCGCGTCCGGTTTCACTTTCTCCTCGTACGCCA<br>TGTCGTGGGTCAGACAGGCACCGGGAAAGGGACTGGAATGGGTGTCAGCC<br>ATTTCGGGTTCGGGGGGCAGCACCTACTACGCTGACTCCGTGAAGGGCCG<br>GTTCACCATTTCCCGCGACAACTCCAAGAACACCTTGTACCTCCAAATGA<br>ACTCCCTGCGGGCCGAAGATACCGCCGTGTATTACTGCGTGCTGTGGTTC<br>GGAGAGGGATTCGACCCGTGGGGACAAGGAACACTCGTGACTGTGTCATC<br>CGGCGGAGGCGGCAGCGGTGGCGGCGGTTCCGGCGGCGGCGGATCTGACA<br>TCGTGTTGACCCAGTCCCCTCTGAGCCTGCCGGTCACTCCTGGCGAACCA<br>GCCAGCATCTCCTGCCGGTCGAGCCAGTCCCTCCTGCACTCCAATGGGTA<br>CAACTACCTCGATTGGTATCTGCAAAAGCCGGGCCAGAGCCCCCAGCTGC<br>TGATCTACCTTGGGTCAAACCGCGCTTCCGGGGTGCCTGATAGATTCTCC<br>GGGTCCGGGAGCGGAACCGACTTTACCCTGAAAATCTCGAGGGTGGAGGC<br>CGAGGACGTCGGAGTGTACTACTGCATGCAGGCGCTCCAGACTCCCCTGA<br>CCTTCGGAGGAGGAACGAAGGTCGACATCAAGA |
| BCMA_EBB-C1980-A2-aa<br>VH | 8089 | EVQLLESGGGLVQPGGSLRLSCAASGFTFSSYAMSWVRQAPGKGLEWVSA<br>ISGSGGSTYYADSVKGRFTISRDNSKNTLYLQMNSLRAEDTAVYYCVLWF<br>GEGFDPWGQGTLVTVSS |
| BCMA_EBB-C1980-A2-aa<br>VL | 8110 | DIVLTQSPLSLPVTPGEPASISCRSSQSLLHSNGYNYLDWYLQKPGQSPQ<br>LLIYLGSNRASGVPDRFSGSGSGTDFTLKISRVEAEDVGVYYCMQALQTP<br>LTFGGGTKVDIK |
| BCMA_EBB-C1981-C3 |  |  |
| BCMA_EBB-C1981-C3-aa<br>ScFv domain | 8048 | QVQLVESGGGLVQPGGSLRLSCAASGFTFSSYAMSWVRQAPGKGLEWVSA<br>ISGSGGSTYYADSVKGRFTISRDNSKNTLYLQMNSLRAEDTAVYYCAKVG<br>YDSSGYYRDYYGMDVWGQGTTVTVSSGGGGSGGGGSGGGGSEIVLTQSPG<br>TLSLSPGERATLSCRASQSVSSSYLAWYQQKPGQAPRLLIYGTSSRATGI<br>SDRFSGSGSGTDFTLTISRLEPEDFAVYYCQHYGNSPPKFTFGPGTKLEIK |
| BCMA_EBB-C1981-C3-nt<br>ScFv domain | 8069 | CAAGTGCAGCTCGTGGAGTCAGGCGGAGGACTGGTGCAGCCCGGGGGCTC<br>CCTGAGACTTTCCTGCGCGGCATCGGGTTTTACCTTCTCCTCCTATGCTA<br>TGTCCTGGGTGCGCCAGGCCCCGGGAAAGGGACTGGAATGGGTGTCCGCA<br>ATCAGCGGTAGCGGGGGCTCAACATACTACGCCGACTCCGTCAAGGGTCG<br>CTTCACTATTTCCCGGGACAACTCCAAGAATACCCTGTACCTCCAAATGA<br>ACAGCCTCAGGGCCGAGGATACTGCCGTGTACTACTGCGCCAAAGTCGGA<br>TACGATAGCTCCGGTTACTACCGGGACTACTACGGAATGGACGTGTGGGG<br>ACAGGGCACCACCGTGACCGTGTCAAGCGGCGGAGGCGGTTCAGGAGGGG<br>GAGGCTCCGGCGGTGGAGGGTCCGAAATCGTCCTGACTCAGTCGCCTGGC<br>ACTCTGTCGTTGTCCCCGGGGGAGCGCGCTACCCTGTCGTGTCGGGCGTC<br>GCAGTCCGTGTCGAGCTCCTACCTCGCGTGGTACCAGCAGAAGCCCGGAC<br>AGGCCCCTAGACTTCTGATCTACGGACACTTCTTCACGCGCCACCGGGATC<br>AGCGACAGGTTCAGCGGCTCCGGCTCCGGGACCGACTTCACCCTGACCAT<br>TAGCCGGCTGGAGCCTGAAGATTTCGCCGTGTATTACTGCCAACACTACG<br>GAAACTCGCCGCCAAAGTTCACGTTCGGACCCGGAACCAAGCTGGAAATC<br>AAG |
| BCMA_EBB-C1981-C3-aa<br>VH | 8090 | QVQLVESGGGLVQPGGSLRLSCAASGFTFSSYAMSWVRQAPGKGLEWVSA<br>ISGSGGSTYYADSVKGRFTISRDNSKNTLYLQMNSLRAEDTAVYYCAKVG<br>YDSSGYYRDYYGMDVWGQGTTVTVSS |
| BCMA_EBB-C1981-C3-aa<br>VL | 8111 | EIVLTQSPGTLSLSPGERATLSCRASQSYSSSYLAWYQQKPGQAPRLLIY<br>GTSSRATGISDRFSGSGSGTDFTLTISRLEPEDFAVYYCQHYGNSPPKFT<br>FGPGTKLEIK |
| BCMA_EBB-C1978-G4 |  |  |
| BCMA_EBB-C1978-G4-aa<br>ScFv domain | 8049 | EVQLVESGGGLVQPGGSLRLSCAASGFTFSSYAMSWVRQAPGKGLEWVSA<br>ISGSGGSTYYADSVKGRFTISRDNSKNTLYLQMNSLRAEDTAVYYCAKMG<br>WSSGYLGAFDIWGQGTTVTVSSGGGGSGGGGSGGGGSEIVLTQSPGTLSL<br>SPGERATLSCRASQSVASSFLAWYQQKPGQAPRLLIYGASGRATGIPDRF<br>SGSGSGTDFTLTISRLEPEDFAVYYCQHYGGSPRLTFGGGTKVDIK |
| BCMA_EBB-C1978-G4-nt<br>ScFv domain | 8070 | GAAGTCCAACTGGTGGAGTCCGGGGGAGGGCTCGTGCAGCCCGGAGGCAG<br>CCTTCGGCTGTCGTGCGCCGCCTCCGGGTTCACGTTCTCATCCTACGCGA<br>TGTCGTGGGTCAGACAGGCACCAGGAAAGGGACTGGAATGGGTGTCCGCC<br>ATTAGCGGCTCCGGCGGTAGCACCTACTATGCCGACTCAGTGAAGGGAAG<br>GTTCACTATCTCCCGCGACAACAGCAAGAACACCCTGTACCTCCAAATGA |

TABLE 18-continued

Antigen Binding domains that bind BCMA
The amino acid sequences variable heavy chain and variable light chain
sequences for each scFv is also provided.

| Name/<br>Description | SEQ ID<br>NO: | Sequence |
|---|---|---|
| | | ACTCTCTGCGGGCCGAGGATACCGCGGTGTACTATTGCGCCAAGATGGGT<br>TGGTCCAGCGGATACTTGGGAGCCTTCGACATTTGGGGACAGGGCACTAC<br>TGTGACCGTGTCCTCCGGGGGTGGCGGATCGGGAGGCGGCGGCTCGGGTG<br>GAGGGGGTTCCGAAATCGTGTTGACCCAGTCACCGGGAACCCTCTCGCTG<br>TCCCCGGGAGAACGGGCTACACTGTCATGTAGAGCGTCCCAGTCCGTGGC<br>TTCCTCGTTCCTGGCCTGGTACCAGCAGAAGCCGGGACAGGCACCCCGCC<br>TGCTCATCTACGGAGCCAGCGGCCGGGCGACCGGCATCCCTGACCGCTTC<br>TCCGGTTCCGGCTCGGGCACCGACTTTACTCTGACCATTAGCAGGCTTGA<br>GCCCGAGGATTTTGCCGTGTACTACTGCCAACACTACGGGGGGAGCCCTC<br>GCCTGACCTTCGGAGGCGGAACTAAGGTCGATATCAAAA |
| BCMA_EBB-<br>C1978-G4-aa<br>VH | 8091 | EVQLVESGGGLVQPGGSLRLSCAASGFTFSSYAMSWVRQAPGKGLEWVSA<br>ISGSGGSTYYADSVKGRFTISRDNSKNTLYLQMNSLRAEDTAVYYCAKMG<br>WSSGYLGAFDIWGQGTTVTVSS |
| BCMA_EBB-<br>C1978-G4-aa<br>VL | 8112 | EIVLTQSPGTLSLSPGERATLSCRASQSVASSFLAWYQQKPGQAPRLLIY<br>GASGRATGIPDRFSGSGSGTDFTLTISRLEPEDFAVYYCQHYGGSPRLTF<br>GGGTKVDIK |

In embodiments, additional exemplary BCMA CAR constructs are generated using the VH and VL sequences from PCT Publication WO2012/0163805 (the contents of which are hereby incorporated by reference in its entirety). In embodiments, additional exemplary BCMA CAR constructs are generated using the VH and VL sequences from PCT Publication WO2016/014565 (the contents of which are hereby incorporated by reference in its entirety). In embodiments, additional exemplary BCMA CAR constructs are generated using the VH and VL sequences from PCT Publication WO2014/122144 (the contents of which are hereby incorporated by reference in its entirety). In embodiments, additional exemplary BCMA CAR constructs are generated using the CAR molecules, and/or the VH and VL sequences from PCT Publication WO2016/014789 (the contents of which are hereby incorporated by reference in its entirety). In embodiments, additional exemplary BCMA CAR constructs are generated using the CAR molecules, and/or the VH and VL sequences from PCT Publication WO2014/089335 (the contents of which are hereby incorporated by reference in its entirety). In embodiments, additional exemplary BCMA CAR constructs are generated using the CAR molecules, and/or the VH and VL sequences from PCT Publication WO2014/140248 (the contents of which are hereby incorporated by reference in its entirety).

In embodiments, additional exemplary BCMA CAR constructs can also be generated using the VH and VL sequences found in Table 19. The amino acid sequences of exemplary scFv domains comprising the VH and VL domains and a linker sequence, and full-length CARs are also found in Table 19.

TABLE 19

Additional exemplary BCMA binding domain sequences

| Name | Sequence | SEQ ID<br>NO: |
|---|---|---|
| A7D12.2<br>VH | QIQLVQSGPDLKKPGETVKLSCKASGYTFTNFGMNWVKQAPGKGFKWMAWINTY<br>TGESYFADDFKGRFAFSVETSATTAYLQINNLKTEDTATYFCARGEIYYGYDGG<br>FAYWGQGTLVTVSA | 8155 |
| A7D12.2<br>VL | DVVMTQSHRFMSTSVGDRVSITCRASQDVNTAVSWYQQKPGQSPKLLIFSASYR<br>YTGVPDRFTGSGSGADFTLTISSVQAEDLAVYYCQQHYSTPWTFGGGTKLDIK | 8159 |
| A7D12.2<br>scFv<br>domain | QIQLVQSGPDLKKPGETVKLSCKASGYTFTNFGMNWVKQAPGKGFKWMAWINTY<br>TGESYFADDFKGRFAFSVETSATTAYLQINNLKTEDTATYFCARGEIYYGYDGG<br>FAYWGQGTLVTVSAGGGGSGGGGSGGGGSDVVMTQSHRFMSTSVGDRVSITCRA<br>SQDVNTAVSWYQQKPGQSPKLLIFSASYRYTGVPDRFTGSGSGADFTLTISSVQ<br>AEDLAVYYCQQHYSTPWTFGGGTKLDIK | 8163 |
| C11D5.3<br>VH | QIQLVQSGPELKKPGETVKISCKASGYTFTDYSINWVKRAPGKGLKWMGWINTE<br>TREPAYAYDFRGRFAFSLETSASTAYLQINNLKYEDTATYFCALDYSYAMDYWG<br>QGTSVTVSS | 8156 |
| C11D5.3<br>VL | DIVLTQSPASLAMSLGKRATISCRASESVSVIGAHLIHWYQQKPGQPPKLLIYL<br>ASNLETGVPARFSGSGSGTDFTLTIDPVEEDDVAIYSCLQSRIFPRTFGGGTKL<br>EIK | 8160 |
| C11D53<br>scFv<br>domain | QIQLVQSGPELKKPGETVKISCKASGYTFTDYSINWVKRAPGKGLKWMGWINTE<br>TREPAYAYDFRGRFAFSLETSASTAYLQINNLKYEDTATYFCALDYSYAMDYWG<br>QGTSVTVSSGGGGSGGGGSGGGGSQIQLVQSGPELKKPGETVKISCKASGYTFT | 8164 |

TABLE 19-continued

Additional exemplary BCMA binding domain sequences

| Name | Sequence | SEQ ID NO: |
|---|---|---|
|  | DYSINWVKRAPGKGLKWMGWINTETREPAYAYDFRGRFAFSLETSASTAYLQIN NLKYEDTATYFCALDYSYAMDYWGQGTSVTVSS |  |
| C12A3.2 VH | QIQLVQSGPELKKPGETVKISCKASGYTFRHYSMNWVKQAPGKGLKWMGRINTE SGVPIYADDFKGRFAFSVETSASTAYLVINNLKDEDTASYFCSNDYLYSLDFWG QGTALTVSS | 8157 |
| C12A3.2 VL | DIVLTQSPPSLAMSLGKRATISCRASESVTILGSHLIYWYQQKPGQPPTLLIQL ASNVQTGVPARFSGSGSRTDFTLTIDPVEEDDVAVYYCLQSRTIPRTFGGGTKL EIK | 8161 |
| C12A3.2 scFv domain | QIQLVQSGPELKKPGETVKISCKASGYTFRHYSMNWVKQAPGKGLKWMGRINTE SGVPIYADDFKGRFAFSVETSASTAYLVINNLKDEDTASYFCSNDYLYSLDFWG QGTALTVSSGGGGSGGGGSGGGGSDIVLTQSPPSLAMSLGKRATISCRASESVT ILGSHLIYWYQQKPGQPPTLLIQLASNVQTGVPARFSGSGSRTDFTLTIDPVEE DDVAVYYCLQSRTIPRTFGGGTKLEIK | 8165 |
| C13F12.1 VH | QIQLVQSGPELKKPGETVKISCKASGYTFTHYSMNWVKQAPGKGLKWMGRINTE TGEPLYADDFKGRFAFSLETSASTAYLVINNLKNEDTATFFCSNDYLYSCDYWG QGTTLTVSS | 8158 |
| C13F12.1 VL | DIVLTQSPPSLAMSLGKRATISCRASESVTILGSHLIYWYQQKPGQPPTLLIQL ASNVQTGVPARFSGSGSRTDFTLTIDPVEEDDVAVYYCLQSRTIPRTFGGGTKL EIK | 8162 |
| C13FE2.1 scFv domain | QIQLVQSGPELKKPGETVKISCKASGYTFTHYSMNWVKQAPGKGLKWMGRINTE TGEPLYADDFKGRFAFSLETSASTAYLVINNLKNEDTATFFCSNDYLYSCDYWG QGTTLTVSSGGGGSGGGGSGGGGSDIVLTQSPPSLAMSLGKRATISCRASESVT ILGSHLIYWYQQKPGQPPTLLIQLASNVQTGVPARFSGSGSRTDFTLTIDPVEE DDVAVYYCLQSRTIPRTFGGGTKLEIK | 8166 |

The sequences of human CDR sequences of the scFv domains are shown in Table 20 for the heavy chain variable domains and in Table 21 for the light chain variable domains. "ID" stands for the respective SEQ ID NO for each CDR. The CDRs are shown according to the Kabat definition, however, the CDRs under other convention, for example, Chothia or the combined Kabat/Chothia definitions may be readily deduced based on the VH and VL sequences above.

TABLE 20

Heavy Chain Variable Domain CDRs according to the Kabat numbering scheme (Kabat et al. (1991), "Sequences of Proteins of Immunological Interest," 5th Ed. Public Health Service, National Institutes of Health, Bethesda, MD)

| Candidate | HCDR1 | ID | HCDR2 | ID | HCDR3 | ID |
|---|---|---|---|---|---|---|
| 139109 | NHGMS | 8294 | GIVYSGSTYYAASVKG | 8334 | HGGESDV | 8374 |
| 139103 | NYAMS | 8284 | GISRSGENTYYADSVKG | 8324 | SPAHYYGGMDV | 8364 |
| 139105 | DYAMH | 8285 | GISWNSGSIGYADSVKG | 8325 | HSFLAY | 8365 |
| 139111 | NHGMS | 8286 | GIVYSGSTYYAASVKG | 8326 | HGGESDV | 8366 |
| 139100 | NFGIN | 8287 | WINPKNNNTNYAQKFQG | 8327 | GPYYYQSYMDV | 8367 |
| 139101 | SDAMT | 8288 | VISGSGGTTYYADSVKG | 8328 | LDSSGYYYARGPRY | 8368 |
| 139102 | NYGIT | 8289 | WISAYNGNTNYAQKFQG | 8329 | GPYYYYMDV | 8369 |
| 139104 | NHGMS | 8290 | GIVYSGSTYYAASVKG | 8330 | HGGESDV | 8370 |
| 139106 | NHGMS | 8291 | GIVYSGSTYYAASVKG | 8331 | HGGESDV | 8371 |

TABLE 20-continued

Heavy Chain Variable Domain CDRs according to the Kabat numbering scheme (Kabat et al. (1991), "Sequences of Proteins of Immunological Interest," 5th Ed. Public Health Service, National Institutes of Health, Bethesda, MD)

| Candidate | HCDR1 | ID | HCDR2 | ID | HCDR3 | ID |
|---|---|---|---|---|---|---|
| 139107 | NHGMS | 8292 | GIVYSGSTYYAASVKG | 8332 | HGGESDV | 8372 |
| 139108 | DYYMS | 8293 | YISSSGSTIYYADSVKG | 8333 | ESGDGMDV | 8373 |
| 139110 | DYYMS | 8295 | YISSSGNTIYYADSVKG | 8335 | STMVREDY | 8375 |
| 139112 | NHGMS | 8296 | GIVYSGSTYYAASVKG | 8336 | HGGESDV | 8376 |
| 139113 | NHGMS | 8297 | GIVYSGSTYYAASVKG | 8337 | HGGESDV | 8377 |
| 139114 | NHGMS | 8298 | GIVYSGSTYYAASVKG | 8338 | HGGESDV | 8378 |
| 149362 | SSYYWG | 8299 | SIYYSGSAYYNPSLKS | 8339 | HWQEWPDAFDI | 8379 |
| 149363 | TSGMCVS | 8300 | RIDWDEDKFYSTSLKT | 8340 | SGAGGTSATAFDI | 8380 |
| 149364 | SYSMN | 8301 | SISSSSSYIYYADSVKG | 8341 | TIAAVYAFDI | 8381 |
| 149365 | DYYMS | 8302 | YISSSGSTIYYADSVKG | 8342 | DLRGAFDI | 8382 |
| 149366 | SHYIH | 8303 | MINPSGGVTAYSQTLQG | 8343 | EGSGSGWYFDF | 8383 |
| 149367 | SGGYYWS | 8304 | YIYYSGSTYYNPSLKS | 8344 | AGIAARLRGAFDI | 8384 |
| 149368 | SYAIS | 8305 | GIIPIFGTANYAQKFQG | 8345 | RGGYQLLRWDVGLLRSAFDI | 8385 |
| 149369 | SNSAAWN | 8306 | RTYYRSKWYSFYAISLKS | 8346 | SSPEGLFLYWFDP | 8386 |
| BCMA_EBB-C1978-A4 | SYAMS | 8307 | AISGSGGSTYYADSVKG | 8347 | VEGSGSLDY | 8387 |
| BCMA_EBB-C1978-G1 | RYPMS | 8308 | GISDSGVSTYYADSAKG | 8348 | RAGSEASDI | 8388 |
| BCMA_EBB-C1979-C1 | SYAMS | 8309 | AISGSGGSTYYADSVKG | 8349 | ATYKRELRYYYGMDV | 8389 |
| BCMA_EBB-C1978-C7 | SYAMS | 8310 | AISGSGGSTYYADSVKG | 8350 | ATYKRELRYYYGMDV | 8390 |
| BCMA_EBB-C1978-D10 | DYAMH | 8311 | GISWNSGSIGYADSVKG | 8351 | VGKAVPDV | 8391 |
| BCMA_EBB-C1979-C12 | DYAMH | 8312 | SINWKGNSLAYGDSVKG | 8352 | HQGVAYYNYAMDV | 8392 |
| BCMA_EBB-C1980-G4 | SYAMS | 8313 | AISGSGGSTYYADSVKG | 8353 | VVRDGMDV | 8393 |
| BCMA_EBB-C1980-D2 | SYAMS | 8314 | AISGSGGSTYYADSVKG | 8354 | IPQTGTFDY | 8394 |

TABLE 20-continued

Heavy Chain Variable Domain CDRs according to the Kabat numbering scheme
(Kabat et al. (1991), "Sequences of Proteins of Immunological Interest,"
5th Ed. Public Health Service, National Institutes of Health, Bethesda, MD)

| Candidate | HCDR1 | ID | HCDR2 | ID | HCDR3 | ID |
| --- | --- | --- | --- | --- | --- | --- |
| BCMA_EBB-C1978-A10 | SYAMS | 8315 | AISGSGGSTYYADSVKG | 8355 | ANYKRELRYYYGMDV | 8395 |
| BCMA_EBB-C1978-D4 | SYAMS | 8316 | AISGSGGSTYYADSVKG | 8356 | ALVGATGAFDI | 8396 |
| BCMA_EBB-C1980-A2 | SYAMS | 8317 | AISGSGGSTYYADSVKG | 8357 | WFGEGFDP | 8397 |
| BCMA_EBB-C1981-C3 | SYAMS | 8318 | AISGSGGSTYYADSVKG | 8358 | VGYDSSGYYRDYYGMDV | 8398 |
| BCMA_EBB-C1978-G4 | SYAMS | 8319 | AISGSGGSTYYADSVKG | 8359 | MGWSSGYLGAFDI | 8399 |
| A7D12.2 | NFGMN | 8320 | WINTYTGESYFADDFKG | 8360 | GEIYYGYDGGFAY | 8400 |
| C11D5.3 | DYSIN | 8321 | WINTETREPAYAYDFRG | 8361 | DYSYAMDY | 8401 |
| C12A3.2 | HYSMN | 8322 | RINTESGVPIYADDFKG | 8362 | DYLYSLDF | 8402 |
| C13F12.1 | HYSMN | 8323 | RINTETGEPLYADDFKG | 8363 | DYLYSCDY | 8403 |

TABLE 21

Light Chain Variable Domain CDRs according to the Kabat numbering scheme
(Kabat et al. (1991), "Sequences of Proteins of Immunological Interest,"
5th Ed. Public Health Service, National Institutes of Health, Bethesda, MD)

| Candidate | LCDR1 | ID | LCDR2 | ID | LCDR3 | ID |
| --- | --- | --- | --- | --- | --- | --- |
| 139109 | RASQSISSYLN | 8414 | AASSLQS | 8454 | QQSYSTPYT | 8494 |
| 139103 | RASQSISSSFLA | 8404 | GASRRAT | 8444 | QQYHSSPSWT | 8484 |
| 139105 | RSSQSLLHSNGYNYLD | 8405 | LGSNRAS | 8445 | MQALQTPYT | 8485 |
| 139111 | KSSQSLLRNDGKTPLY | 8406 | EVSNRFS | 8446 | MQNIQFPS | 8486 |
| 139100 | RSSQSLLHSNGYNYLN | 8407 | LGSKRAS | 8447 | MQALQTPYT | 8487 |
| 139101 | RASQSISSYLN | 8408 | GASTLAS | 8448 | QQSYKRAS | 8488 |
| 139102 | RSSQSLLYSNGYNYVD | 8409 | LGSNRAS | 8449 | MQGRQFPYS | 8489 |
| 139104 | RASQSVSSNLA | 8410 | GASTRAS | 8450 | QQYGSSLT | 8490 |
| 139106 | RASQSVSSKLA | 8411 | GASIRAT | 8451 | QQYGSSSWT | 8491 |
| 139107 | RASQSVGSTNLA | 8412 | DASNRAT | 8452 | QQYGSSPPWT | 8492 |
| 139108 | RASQSISSYLN | 8413 | AASSLQS | 8453 | QQSYTLA | 8493 |
| 139110 | KSSESLVHNSGKTYLN | 8415 | EVSNRDS | 8455 | MQGTHWPGT | 8495 |
| 139112 | QASEDINKFLN | 8416 | DASTLQT | 8456 | QQYESLPLT | 8496 |

TABLE 21-continued

Light Chain Variable Domain CDRs according to the Kabat numbering scheme
(Kabat et al. (1991), "Sequences of Proteins of Immunological Interest,"
5th Ed. Public Health Service, National Institutes of Health, Bethesda, MD)

| Candidate | LCDR1 | ID | LCDR2 | ID | LCDR3 | ID |
|---|---|---|---|---|---|---|
| 139113 | RASQSVGSNLA | 8417 | GASTRAT | 8457 | QQYNDWLPVT | 8497 |
| 139114 | RASQSIGSSSLA | 8418 | GASSRAS | 8458 | QQYAGSPPFT | 8498 |
| 149362 | KASQDIDDAMN | 8419 | SATSPVP | 8459 | LQHDNFPLT | 8499 |
| 149363 | RASQDIYNNLA | 8420 | AANKSQS | 8460 | QHYYRFPYS | 8500 |
| 149364 | RSSQSLLHSNGYNYLD | 8421 | LGSNRAS | 8461 | MQALQTPYT | 8501 |
| 149365 | GGNNIGTKSVH | 8422 | DDSVRPS | 8462 | QVWDSDSEHVV | 8502 |
| 149366 | SGDGLSKKYVS | 8423 | RDKERPS | 8463 | QAWDDTTVV | 8503 |
| 149367 | RASQGIRNWLA | 8424 | AASNLQS | 8464 | QKYNSAPFT | 8504 |
| 149368 | GGNNIGSKSVH | 8425 | GKNNRPS | 8465 | SSRDSSGDHLRV | 8505 |
| 149369 | QGDSLGNYYAT | 8426 | GTNNRPS | 8466 | NSRDSSGHHLL | 8506 |
| BCMA_EBB-C1978-A4 | RASQSVSSAYLA | 8427 | GASTRAT | 8467 | QHYGSSFNGSSLFT | 8507 |
| BCMA_EBB-C1978-G1 | RASQSVSNSLA | 8428 | DASSRAT | 8468 | QQFGTSSGLT | 8508 |
| BCMA_EBB-C1979-C1 | RASQSVSSSFLA | 8429 | GASSRAT | 8469 | QQYHSSPSWT | 8509 |
| BCMA_EBB-C1978-C7 | RASQSVSTTFLA | 8430 | GSSNRAT | 8470 | QQYHSSPSWT | 8510 |
| BCMA_EBB-C1978-D10 | RASQSISSYLN | 8431 | AASSLQS | 8471 | QQSYSTPYS | 8511 |
| BCMA_EBB-C1979-C12 | RATQSIGSSFLA | 8432 | GASQRAT | 8472 | QHYESSPSWT | 8512 |
| BCMA_EBB-C1980-G4 | RASQSVSSSYLA | 8433 | GASSRAT | 8473 | QQYGSPPRFT | 8513 |
| BCMA_EBB-C1980-D2 | RASQSVSSSYLA | 8434 | GASSRAT | 8474 | QHYGSSPSWT | 8514 |
| BCMA_EBB-C1978-A10 | RASQRVASNYLA | 8435 | GASSRAT | 8475 | QHYDSSPSWT | 8515 |
| BCMA_EBB-C1978-D4 | RASQSLSSNFLA | 8436 | GASNWAT | 8476 | QYYGTSPMYT | 8516 |
| BCMA_EBB-C1980-A2 | RSSQSLLHSNGYNYLD | 8437 | LGSNRAS | 8477 | MQALQTPLT | 8517 |
| BCMA_EBB-C1981-C3 | RASQSVSSSYLA | 8438 | GTSSRAT | 8478 | QHYGNSPPKFT | 8518 |
| BCMA_EBB-C1978-G4 | RASQSVASSFLA | 8439 | GASGRAT | 8479 | QHYGGSPRLT | 8519 |
| A7D12.2 | RASQDVNTAVS | 8440 | SASYRYT | 8480 | QQHYSTPWT | 8520 |
| C11D5.3 | RASESVSVIGAHLIH | 8441 | LASNLET | 8481 | LQSRIFPRT | 8521 |
| C12A3.2 | RASESVTILGSHLIY | 8442 | LASNVQT | 8482 | LQSRTIPRT | 8522 |
| C13F12.1 | RASESVTILGSHLIY | 8443 | LASNVQT | 8483 | LQSRTIPRT | 8523 |

In one embodiment, the BCMA binding domain comprises one or more (e.g., all three) light chain complementary determining region 1 (LC CDR1), light chain complementary determining region 2 (LC CDR2), and light chain complementary determining region 3 (LC CDR3) of a BCMA binding domain described herein, e.g., provided in Table 18, 19 or 21, and/or one or more (e.g., all three) heavy chain complementary determining region 1 (HC CDR1), heavy chain complementary determining region 2 (HC CDR2), and heavy chain complementary determining region 3 (HC CDR3) of a BCMA binding domain described herein, e.g., provided in Table 18, 19 or 20. In one embodiment, the BCMA binding domain comprises one, two, or all of LC CDR1, LC CDR2, and LC CDR3 of any amino acid sequences as provided in Table 18, incorporated herein by reference; and one, two or all of HC CDR1, HC CDR2, and HC CDR3 of any amino acid sequences as provided in Table 18.

In one embodiment, the BCMA antigen binding domain comprises:

(i) (a) a LC CDR1 amino acid sequence of SEQ ID NO: 8414, a LC CDR2 amino acid sequence of SEQ ID NO: 8454, and a LC CDR3 amino acid sequence of SEQ ID NO: 8494; and
  (b) a HC CDR1 amino acid sequence of SEQ ID NO: 8294, a HC CDR2 amino acid sequence of SEQ ID NO: 8334, and a HC CDR3 amino acid sequence of SEQ ID NO: 8374

(ii) (a) a LC CDR1 amino acid sequence of SEQ ID NO: 8404, a LC CDR2 amino acid sequence of SEQ ID NO: 8444, and a LC CDR3 amino acid sequence of SEQ ID NO: 8484; and
  (b) a HC CDR1 amino acid sequence of SEQ ID NO: 8284, a HC CDR2 amino acid sequence of SEQ ID NO: 8324, and a HC CDR3 amino acid sequence of SEQ ID NO: 8364

(iii) (a) a LC CDR1 amino acid sequence of SEQ ID NO: 8405, a LC CDR2 amino acid sequence of SEQ ID NO: 8445, and a LC CDR3 amino acid sequence of SEQ ID NO: 8485; and
  (b) a HC CDR1 amino acid sequence of SEQ ID NO: 8285, a HC CDR2 amino acid sequence of SEQ ID NO: 8325, and a HC CDR3 amino acid sequence of SEQ ID NO: 8365

(iv) (a) a LC CDR1 amino acid sequence of SEQ ID NO: 8406, a LC CDR2 amino acid sequence of SEQ ID NO: 8446, and a LC CDR3 amino acid sequence of SEQ ID NO: 8486; and
  (b) a HC CDR1 amino acid sequence of SEQ ID NO: 8286, a HC CDR2 amino acid sequence of SEQ ID NO: 8326, and a HC CDR3 amino acid sequence of SEQ ID NO: 8366

(v) (a) a LC CDR1 amino acid sequence of SEQ ID NO: 8407, a LC CDR2 amino acid sequence of SEQ ID NO: 8447, and a LC CDR3 amino acid sequence of SEQ ID NO: 8487; and
  (b) a HC CDR1 amino acid sequence of SEQ ID NO: 8287, a HC CDR2 amino acid sequence of SEQ ID NO: 8327, and a HC CDR3 amino acid sequence of SEQ ID NO: 8367

(vi) (a) a LC CDR1 amino acid sequence of SEQ ID NO: 8408, a LC CDR2 amino acid sequence of SEQ ID NO: 8448, and a LC CDR3 amino acid sequence of SEQ ID NO: 8488; and
  (b) a HC CDR1 amino acid sequence of SEQ ID NO: 8288, a HC CDR2 amino acid sequence of SEQ ID NO: 8328, and a HC CDR3 amino acid sequence of SEQ ID NO: 8368

(vii) (a) a LC CDR1 amino acid sequence of SEQ ID NO: 8409, a LC CDR2 amino acid sequence of SEQ ID NO: 8449, and a LC CDR3 amino acid sequence of SEQ ID NO: 8489; and
  (b) a HC CDR1 amino acid sequence of SEQ ID NO: 8289, a HC CDR2 amino acid sequence of SEQ ID NO: 8329, and a HC CDR3 amino acid sequence of SEQ ID NO: 8369

(viii) (a) a LC CDR1 amino acid sequence of SEQ ID NO: 8410, a LC CDR2 amino acid sequence of SEQ ID NO: 8450, and a LC CDR3 amino acid sequence of SEQ ID NO: 8490; and
  (b) a HC CDR1 amino acid sequence of SEQ ID NO: 8290, a HC CDR2 amino acid sequence of SEQ ID NO: 8330, and a HC CDR3 amino acid sequence of SEQ ID NO: 8370

(ix) (a) a LC CDR1 amino acid sequence of SEQ ID NO: 8411, a LC CDR2 amino acid sequence of SEQ ID NO: 8451, and a LC CDR3 amino acid sequence of SEQ ID NO: 8491; and
  (b) a HC CDR1 amino acid sequence of SEQ ID NO: 8291, a HC CDR2 amino acid sequence of SEQ ID NO: 8331, and a HC CDR3 amino acid sequence of SEQ ID NO: 8371

(x) (a) a LC CDR1 amino acid sequence of SEQ ID NO: 8412, a LC CDR2 amino acid sequence of SEQ ID NO: 8452, and a LC CDR3 amino acid sequence of SEQ ID NO: 8492; and
  (b) a HC CDR1 amino acid sequence of SEQ ID NO: 8292, a HC CDR2 amino acid sequence of SEQ ID NO: 8332, and a HC CDR3 amino acid sequence of SEQ ID NO: 8372

(xi) (a) a LC CDR1 amino acid sequence of SEQ ID NO: 8413, a LC CDR2 amino acid sequence of SEQ ID NO: 8453, and a LC CDR3 amino acid sequence of SEQ ID NO: 8493; and
  (b) a HC CDR1 amino acid sequence of SEQ ID NO: 8293, a HC CDR2 amino acid sequence of SEQ ID NO: 8333, and a HC CDR3 amino acid sequence of SEQ ID NO: 8373

(xii) (a) a LC CDR1 amino acid sequence of SEQ ID NO: 8415, a LC CDR2 amino acid sequence of SEQ ID NO: 8455, and a LC CDR3 amino acid sequence of SEQ ID NO: 8495; and
  (b) a HC CDR1 amino acid sequence of SEQ ID NO: 8295, a HC CDR2 amino acid sequence of SEQ ID NO: 8335, and a HC CDR3 amino acid sequence of SEQ ID NO: 8375

(xiii) (a) a LC CDR1 amino acid sequence of SEQ ID NO: 8416, a LC CDR2 amino acid sequence of SEQ ID NO: 8456, and a LC CDR3 amino acid sequence of SEQ ID NO: 8496; and
  (b) a HC CDR1 amino acid sequence of SEQ ID NO: 8296, a HC CDR2 amino acid sequence of SEQ ID NO: 8336, and a HC CDR3 amino acid sequence of SEQ ID NO: 8376

(xiv) (a) a LC CDR1 amino acid sequence of SEQ ID NO: 8417, a LC CDR2 amino acid sequence of SEQ ID NO: 8457, and a LC CDR3 amino acid sequence of SEQ ID NO: 8497; and (b) a HC CDR1 amino acid sequence of SEQ ID NO: 8297, a HC CDR2 amino acid sequence of SEQ ID NO: 8337, and a HC CDR3 amino acid sequence of SEQ ID NO: 8377

(xv) (a) a LC CDR1 amino acid sequence of SEQ ID NO: 8418, a LC CDR2 amino acid sequence of SEQ ID NO: 8458, and a LC CDR3 amino acid sequence of SEQ ID NO: 8498; and (b) a HC CDR1 amino acid sequence of SEQ ID NO: 8298, a HC CDR2 amino acid sequence of SEQ ID NO: 8338, and a HC CDR3 amino acid sequence of SEQ ID NO: 8378

(xvi) (a) a LC CDR1 amino acid sequence of SEQ ID NO: 8419, a LC CDR2 amino acid sequence of SEQ ID NO: 8459, and a LC CDR3 amino acid sequence of SEQ ID NO: 8499; and (b) a HC CDR1 amino acid sequence of SEQ ID NO: 8299, a HC CDR2 amino acid sequence of SEQ ID NO: 8339, and a HC CDR3 amino acid sequence of SEQ ID NO: 8379

(xvii) (a) a LC CDR1 amino acid sequence of SEQ ID NO: 8420, a LC CDR2 amino acid sequence of SEQ ID NO: 8460, and a LC CDR3 amino acid sequence of SEQ ID NO: 8500; and (b) a HC CDR1 amino acid sequence of SEQ ID NO: 8300, a HC CDR2 amino acid sequence of SEQ ID NO: 8340, and a HC CDR3 amino acid sequence of SEQ ID NO: 8380

(xviii) (a) a LC CDR1 amino acid sequence of SEQ ID NO: 8421, a LC CDR2 amino acid sequence of SEQ ID NO: 8461, and a LC CDR3 amino acid sequence of SEQ ID NO: 8501; and (b) a HC CDR1 amino acid sequence of SEQ ID NO: 8301, a HC CDR2 amino acid sequence of SEQ ID NO: 8341, and a HC CDR3 amino acid sequence of SEQ ID NO: 8381

(xix) (a) a LC CDR1 amino acid sequence of SEQ ID NO: 8422, a LC CDR2 amino acid sequence of SEQ ID NO: 8462, and a LC CDR3 amino acid sequence of SEQ ID NO: 8502; and (b) a HC CDR1 amino acid sequence of SEQ ID NO: 8302, a HC CDR2 amino acid sequence of SEQ ID NO: 8342, and a HC CDR3 amino acid sequence of SEQ ID NO: 8382

(xx) (a) a LC CDR1 amino acid sequence of SEQ ID NO: 8423, a LC CDR2 amino acid sequence of SEQ ID NO: 8463, and a LC CDR3 amino acid sequence of SEQ ID NO: 8503; and (b) a HC CDR1 amino acid sequence of SEQ ID NO: 8303, a HC CDR2 amino acid sequence of SEQ ID NO: 8343, and a HC CDR3 amino acid sequence of SEQ ID NO: 8383

(xxi) (a) a LC CDR1 amino acid sequence of SEQ ID NO: 8424, a LC CDR2 amino acid sequence of SEQ ID NO: 8464, and a LC CDR3 amino acid sequence of SEQ ID NO: 8504; and (b) a HC CDR1 amino acid sequence of SEQ ID NO: 8304, a HC CDR2 amino acid sequence of SEQ ID NO: 8344, and a HC CDR3 amino acid sequence of SEQ ID NO: 8384

(xxii) (a) a LC CDR1 amino acid sequence of SEQ ID NO: 8425, a LC CDR2 amino acid sequence of SEQ ID NO: 8465, and a LC CDR3 amino acid sequence of SEQ ID NO: 8505; and (b) a HC CDR1 amino acid sequence of SEQ ID NO: 8305, a HC CDR2 amino acid sequence of SEQ ID NO: 8345, and a HC CDR3 amino acid sequence of SEQ ID NO: 8385 or (xxiii) (a) a LC CDR1 amino acid sequence of SEQ ID NO: 8426, a LC CDR2 amino acid sequence of SEQ ID NO: 8466, and a LC CDR3 amino acid sequence of SEQ ID NO: 8506; and (b) a HC CDR1 amino acid sequence of SEQ ID NO: 8306, a HC CDR2 amino acid sequence of SEQ ID NO: 8346, and a HC CDR3 amino acid sequence of SEQ ID NO: 8386.

In one embodiment, the BCMA binding domain comprises a light chain variable region described herein (e.g., in Table 18 or 19) and/or a heavy chain variable region described herein (e.g., in Table 18 or 19). In one embodiment, the BCMA binding domain is a scFv comprising a light chain and a heavy chain of an amino acid sequence listed in Table 18 or 19. In an embodiment, the BCMA binding domain (e.g., an scFv) comprises: a light chain variable region comprising an amino acid sequence having at least one, two or three modifications (e.g., substitutions, e.g., conservative substitutions) but not more than 30, 20 or 10 modifications (e.g., substitutions, e.g., conservative substitutions) of an amino acid sequence of a light chain variable region provided in Table 18 or 19, or a sequence with 95-99% identity with an amino acid sequence provided in Table 18 or 19; and/or a heavy chain variable region comprising an amino acid sequence having at least one, two or three modifications (e.g., substitutions, e.g., conservative substitutions) but not more than 30, 20 or 10 modifications (e.g., substitutions, e.g., conservative substitutions) of an amino acid sequence of a heavy chain variable region provided in Table 18 or 19, or a sequence with 95-99% identity to an amino acid sequence provided in Table 18 or 19.

In one embodiment, the BCMA binding domain comprises an amino acid sequence selected from a group consisting of SEQ ID NO: 7949; SEQ ID NO: 7939, SEQ ID NO: 7940; SEQ ID NO: 7941; SEQ ID NO: 7942; SEQ ID NO: 7943; SEQ ID NO: 7944, SEQ ID NO: 7945, SEQ ID NO: 7946, SEQ ID NO: 7947, SEQ ID NO: 7948, SEQ ID NO: 7950, SEQ ID NO: 7951, SEQ ID NO: 7952, SEQ ID NO: 7953, SEQ ID NO: 8029, SEQ ID NO: 8030, SEQ ID NO: 8031, SEQ ID NO: 8032, SEQ ID NO: 8033, SEQ ID NO: 8034, SEQ ID NO: 8035, SEQ ID NO: 8036, SEQ ID NO: 8037, SEQ ID NO: 8038, SEQ ID NO: 8039, SEQ ID NO: 8040, SEQ ID NO: 8041, SEQ ID NO: 8042, SEQ ID NO: 8043, SEQ ID NO: 8044, SEQ ID NO: 8045, SEQ ID NO: 8046, SEQ ID NO: 8047, SEQ ID NO: 8048, SEQ ID NO: 8049, SEQ ID NO: 8163, SEQ ID NO: 8164, SEQ ID NO: 8165 and SEQ ID NO: 8166; or an amino acid sequence having at least one, two or three modifications (e.g., substitutions, e.g., conservative substitutions) but not more than 30, 20 or 10 modifications (e.g., substitutions, e.g., conservative substitutions) to any of the aforesaid sequences; or a sequence with 95-99% identity to any of the aforesaid sequences. In one embodiment, the BCMA binding domain is a scFv, and a light chain variable region comprising an amino acid sequence described herein, e.g., in Table 18 or 19, is attached to a heavy chain variable region comprising an amino acid sequence described herein, e.g., in Table 18 or 19, via a linker, e.g., a linker described herein. In one embodiment, the BCMA binding domain includes a (Gly4-Ser)n linker, wherein n is 1, 2, 3, 4, 5, or 6, preferably 3 (SEQ ID NO: 10801). The light chain variable region and heavy chain variable region of a scFv can be, e.g., in any of the following orientations: light chain variable region-linker-heavy chain variable region or heavy chain variable region-linker-light chain variable region.

Any known BCMA CAR, e.g., the BMCA antigen binding domain of any known BCMA CAR, in the art can be used in accordance with the instant invention. For example, those described herein.

Exemplary CAR Molecules

In one aspect, a CAR, e.g., a CAR expressed by the cell of the invention, comprises a CAR molecule comprising an antigen binding domain that binds to a B cell antigen, e.g., as described herein, such as CD19 or BCMA.

In one embodiment, the CAR comprises a CAR molecule comprising a CD19 antigen binding domain (e.g., a murine, human or humanized antibody or antibody fragment that specifically binds to CD19), a transmembrane domain, and an intracellular signaling domain (e.g., an intracellular signaling domain comprising a costimulatory domain and/or a primary signaling domain).

Exemplary CAR molecules described herein are provided in Table 22. The CAR molecules in Table 22 comprise a CD19 antigen binding domain, e.g., an amino acid sequence of any CD19 antigen binding domain provided in Table 14.

TABLE 22

Exemplary CD19 CAR molecules

| Antigen | Name | Amino Acid Sequence | SEQ ID NO: |
|---------|------|---------------------|------------|
| CD19 | CTL019 | MALPVTALLLPLALLLHAARPDIQMTQTTSSLSASLGDRVTISCRASQ DISKYLNWYQQKPDGTVKLLIYHTSRLHSGVPSRFSGSGSGTDYSLTI SNLEQEDIATYFCQQGNTLPYTFGGGTKLEITGGGSGGGGSGGGGSE VKLQESGPGLVAPSQSLSVTCTVSGVSLPDYGVSWIRQPPRKGLEWLG VIWGSETTYYNSALKSRLTIIKDNSKSQVFLKMNSLQTDDTAIYYCAK HYYYGGSYAMDYWGQGTSVTVSSTTTPAPRPPTPAPTIASQPLSLRPE ACRPAAGGAVHTRGLDFACDIYIWAPLAGTCGVLLLSLVITLYCKRGR KKLLYIFKQPFMRPVQTTQEEDGCSCRFPEEEEGGCELRVKFSRSADA PAYKQGQNQLYNELNLGRREEYDVLDKRRGRDPEMGGKPRRKNPQEGL YNELQKDKMAEAYSEIGMKGERRRGKGHDGLYQGLSTATKDTYDALHM QALPPR | 7920 |
| CD19 | CAR 1 | MALPVTALLLPLALLLHAARPEIVMTQSPATLSLSPGERATLSCRASQ DISKYLNWYQQKPGQAPRLLIYHTSRLHSGIPARFSGSGSGTDYTLTI SSLQPEDFAVYFCQQGNTLPYTFGQGTKLEIKGGGSGGGGSGGGGSQ VQLQESGPGLVKPSETLSLTCTVSGVSLPDYGVSWIRQPPGKGLEWIG VIWGSETTYYSSSLKSRVTISKDNSKNQVSLKLSSVTAADTAVYYCAK HYYYGGSYAMDYWGQGTLVTVSSTTTPAPRPPTPAPTIASQPLSLRPE ACRPAAGGAVHTRGLDFACDIYIWAPLAGTCGVLLLSLVITLYCKRGR KKLLYIFKQPFMRPVQTTQEEDGCSCRFPEEEEGGCELRVKFSRSADA PAYKQGQNQLYNELNLGRREEYDVLDKRRGRDPEMGGKPRRKNPQEGL YNELQKDKMAEAYSEIGMKGERRRGKGHDGLYQGLSTATKDTYDALHM QALPPR | 7908 |
| CD19 | CAR 2 | MALPVTALLLPLALLLHAARPEIVMTQSPATLSLSPGERATLSCRASQ DISKYLNWYQQKPGQAPRLLIYHTSRLHSGIPARFSGSGSGTDYTLTI SSLQPEDFAVYFCQQGNTLPYTFGQGTKLEIKGGGSGGGGSGGGGSQ VQLQESGPGLVKPSETLSLTCTVSGVSLPDYGVSWIRQPPGKGLEWIG VIWGSETTYYQSSLKSRVTISKDNSKNQVSLKLSSVTAADTAVYYCAK HYYYGGSYAMDYWGQGTLVTVSSTTTPAPRPPTPAPTIASQPLSLRPE ACRPAAGGAVHTRGLDFACDIYIWAPLAGTCGVLLLSLVITLYCKRGR KKLLYIFKQPFMRPVQTTQEEDGCSCRFPEEEEGGCELRVKFSRSADA PAYKQGQNQLYNELNLGRREEYDVLDKRRGRDPEMGGKPRRKNPQEGL YNELQKDKMAEAYSEIGMKGERRRGKGHDGLYQGLSTATKDTYDALHM QALPPR | 7909 |
| CD19 | CAR 3 | MALPVTALLLPLALLLHAARPQVQLQESGPGLVKPSETLSLTCTVSGV SLPDYGVSWIRQPPGKGLEWIGVIWGSETTYYSSSLKSRVTISKDNSK NQVSLKLSSVTAADTAVYYCAKHYYYGGSYAMDYWGQGTLVTVSSGGG GSGGGGSGGGGSEIVMTQSPATLSLSPGERATLSCRASQDISKYLNWY QQKPGQAPRLLIYHTSRLHSGIPARFSGSGSGTDYTLTISSLQPEDFA VYFCQQGNTLPYTFGQGTKLEIKTTTPAPRPPTPAPTIASQPLSLRPE ACRPAAGGAVHTRGLDFACDIYIWAPLAGTCGVLLLSLVITLYCKRGR KKLLYIFKQPFMRPVQTTQEEDGCSCRFPEEEEGGCELRVKFSRSADA PAYKQGQNQLYNELNLGRREEYDVLDKRRGRDPEMGGKPRRKNPQEGL YNELQKDKMAEAYSEIGMKGERRRGKGHDGLYQGLSTATKDTYDALHM QALPPR | 7910 |
| CD19 | CAR 4 | MALPVTALLLPLALLLHAARPQVQLQESGPGLVKPSETLSLTCTVSGV SLPDYGVSWIRQPPGKGLEWIGVIWGSETTYYQSSLKSRVTISKDNSK NQVSLKLSSVTAADTAVYYCAKHYYYGGSYAMDYWGQGTLVTVSSGGG GSGGGGSGGGGSEIVMTQSPATLSLSPGERATLSCRASQDISKYLNWY QQKPGQAPRLLIYHTSRLHSGIPARFSGSGSGTDYTLTISSLQPEDFA VYFCQQGNTLPYTFGQGTKLEIKTTTPAPRPPTPAPTIASQPLSLRPE ACRPAAGGAVHTRGLDFACDIYIWAPLAGTCGVLLLSLVITLYCKRGR KKLLYIFKQPFMRPVQTTQEEDGCSCRFPEEEEGGCELRVKFSRSADA PAYKQGQNQLYNELNLGRREEYDVLDKRRGRDPEMGGKPRRKNPQEGL YNELQKDKMAEAYSEIGMKGERRRGKGHDGLYQGLSTATKDTYDALHM QALPPR | 7911 |

TABLE 22-continued

Exemplary CD19 CAR molecules

| Antigen | Name | Amino Acid Sequence | SEQ ID NO: |
|---|---|---|---|
| CD19 | CAR 5 | MALPVTALLLPLALLLHAARPEIVMTQSPATLSLSPGERATLSCRASQ DISKYLNWYQQKPGQAPRLLIYHTSRLHSGIPARFSGSGSGTDYTLTI SSLQPEDFAVYFCQQGNTLPYTFGQGTKLEIKGGGGSGGGGSGGGGS GGGSQVQLQESGPGLVKPSETLSLTCTVSGVSLPDYGVSWIRQPPGKG LEWIGVIWGSETTYYSSSLKSRVTISKDNSKNQVSLKLSSVTAADTAV YYCAKHYYYGGSYAMDYWGQGTLVTVSSTTTPAPRPPTPAPTIASQPL SLRPEACRPAAGGAVHTRGLDFACDIYIWAPLAGTCGVLLLSLVITLY CKRGRKKLLYIFKQPFMRPVQTTQEEDGCSCRFPEEEEGGCELRVKFS RSADAPAYKQGQNQLYNELNLGRREEYDVLDKRRGRDPEMGGKPRRKN PQEGLYNELQKDKMAEAYSEIGMKGERRRGKGHDGLYQGLSTATKDTY DALHMQALPPR | 7912 |
| CD19 | CAR 6 | MALPVTALLLPLALLLHAARPEIVMTQSPATLSLSPGERATLSCRASQ DISKYLNWYQQKPGQAPRLLIYHTSRLHSGIPARFSGSGSGTDYTLTI SSLQPEDFAVYFCQQGNTLPYTFGQGTKLEIKGGGGSGGGGSGGGGS GGGSQVQLQESGPGLVKPSETLSLTCTVSGVSLPDYGVSWIRQPPGKG LEWIGVIWGSETTYYQSSLKSRVTISKDNSKNQVSLKLSSVTAADTAV YYCAKHYYYGGSYAMDYWGQGTLVTVSSTTTPAPRPPTPAPTIASQPL SLRPEACRPAAGGAVHTRGLDFACDIYIWAPLAGTCGVLLLSLVITLY CKRGRKKLLYIFKQPFMRPVQTTQEEDGCSCRFPEEEEGGCELRVKFS RSADAPAYKQGQNQLYNELNLGRREEYDVLDKRRGRDPEMGGKPRRKN PQEGLYNELQKDKMAEAYSEIGMKGERRRGKGHDGLYQGLSTATKDTY DALHMQALPPR | 7913 |
| CD19 | CAR 7 | MALPVTALLLPLALLLHAARPQVQLQESGPGLVKPSETLSLTCTVSGV SLPDYGVSWIRQPPGKGLEWIGVIWGSETTYYSSSLKSRVTISKDNSK NQVSLKLSSVTAADTAVYYCAKHYYYGGSYAMDYWGQGTLVTVSSGGG GSGGGGSGGGGSGGGGSEIVMTQSPATLSLSPGERATLSCRASQDISK YLNWYQQKPGQAPRLLIYHTSRLHSGIPARFSGSGSGTDYTLTISSLQ PEDFAVYFCQQGNTLPYTFGQGTKLEIKTTTPAPRPPTPAPTIASQPL SLRPEACRPAAGGAVHTRGLDFACDIYIWAPLAGTCGVLLLSLVITLY CKRGRKKLLYIFKQPFMRPVQTTQEEDGCSCRFPEEEEGGCELRVKFS RSADAPAYKQGQNQLYNELNLGRREEYDVLDKRRGRDPEMGGKPRRKN PQEGLYNELQKDKMAEAYSEIGMKGERRRGKGHDGLYQGLSTATKDTY DALHMQALPPR | 7914 |
| CD19 | CAR 8 | MALPVTALLLPLALLLHAARPQVQLQESGPGLVKPSETLSLTCTVSGV SLPDYGVSWIRQPPGKGLEWIGVIWGSETTYYQSSLKSRVTISKDNSK NQVSLKLSSVTAADTAVYYCAKHYYYGGSYAMDYWGQGTLVTVSSGGG GSGGGGSGGGGSGGGGSEIVMTQSPATLSLSPGERATLSCRASQDISK YLNWYQQKPGQAPRLLIYHTSRLHSGIPARFSGSGSGTDYTLTISSLQ PEDFAVYFCQQGNTLPYTFGQGTKLEIKTTTPAPRPPTPAPTIASQPL SLRPEACRPAAGGAVHTRGLDFACDIYIWAPLAGTCGVLLLSLVITLY CKRGRKKLLYIFKQPFMRPVQTTQEEDGCSCRFPEEEEGGCELRVKFS RSADAPAYKQGQNQLYNELNLGRREEYDVLDKRRGRDPEMGGKPRRKN PQEGLYNELQKDKMAEAYSEIGMKGERRRGKGHDGLYQGLSTATKDTY DALHMQALPPR | 7915 |
| CD19 | CAR 9 | MALPVTALLLPLALLLHAARPEIVMTQSPATLSLSPGERATLSCRASQ DISKYLNWYQQKPGQAPRLLIYHTSRLHSGIPARFSGSGSGTDYTLTI SSLQPEDFAVYFCQQGNTLPYTFGQGTKLEIKGGGGSGGGGSGGGGS GGGSQVQLQESGPGLVKPSETLSLTCTVSGVSLPDYGVSWIRQPPGKG LEWIGVIWGSETTYYNSLKSRVTISKDNSKNQVSLKLSSVTAADTAV YYCAKHYYYGGSYAMDYWGQGTLVTVSSTTTPAPRPPTPAPTIASQPL SLRPEACRPAAGGAVHTRGLDFACDIYIWAPLAGTCGVLLLSLVITLY CKRGRKKLLYIFKQPFMRPVQTTQEEDGCSCRFPEEEEGGCELRVKFS RSADAPAYKQGQNQLYNELNLGRREEYDVLDKRRGRDPEMGGKPRRKN PQEGLYNELQKDKMAEAYSEIGMKGERRRGKGHDGLYQGLSTATKDTY DALHMQALPPR | 7916 |
| CD19 | CAR 10 | MALPVTALLLPLALLLHAARPEIVMTQSPATLSLSPGERATLSCRASQ DISKYLNWYQQKPGQAPRLLIYHTSRLHSGIPARFSGSGSGTDYTLTI SSLQPEDFAVYFCQQGNTLPYTFGQGTKLEIKGGGGSGGGGSGGGGS GGGSQVQLQESGPGLVKPSETLSLTCTVSGVSLPDYGVSWIRQPPGKG LEWIGVIWGSETTYYNSSLKSRVTISKDNSKNQVSLKLSSVTAADTAV YYCAKHYYYGGSYAMDYWGQGTLVTVSSTTTPAPRPPTPAPTIASQPL SLRPEACRPAAGGAVHTRGLDFACDIYIWAPLAGTCGVLLLSLVITLY CKRGRKKLLYIFKQPFMRPVQTTQEEDGCSCRFPEEEEGGCELRVKFS RSADAPAYKQGQNQLYNELNLGRREEYDVLDKRRGRDPEMGGKPRRKN PQEGLYNELQKDKMAEAYSEIGMKGERRRGKGHDGLYQGLSTATKDTY DALHMQALPPR | 7917 |
| CD19 | CAR 11 | MALPVTALLLPLALLLHAARPQVQLQESGPGLVKPSETLSLTCTVSGV SLPDYGVSWIRQPPGKGLEWIGVIWGSETTYYNSSLKSRVTISKDNSK | 7918 |

TABLE 22-continued

Exemplary CD19 CAR molecules

| Antigen | Name | Amino Acid Sequence | SEQ ID NO: |
|---|---|---|---|
| | | NQVSLKLSSVTAADTAVYYCAKHYYYGGSYAMDYWGQGTLVTVSSGGG GSGGGGSGGGGSGGGGSEIVMTQSPATLSLSPGERATLSCRASQDISK YLNWYQQKPGQAPRLLIYHTSRLHSGIPARFSGSGSGTDYTLTISSLQ PEDFAVYFCQQGNTLPYTFGQGTKLEIKTTTPAPRPPTPAPTIASQPL SLRPEACRPAAGGAVHTRGLDFACDIYIWAPLAGTCGVLLLSLVITLY CKRGRKKLLYIFKQPFMRPVQTTQEEDGCSCRFPEEEEGGCELRVKFS RSADAPAYKQGQNQLYNELNLGRREEYDVLDKRRGRDPEMGGKPRRKN PQEGLYNELQKDKMAEAYSEIGMKGERRRGKGHDGLYQGLSTATKDTY DALHMQALPPR | |
| CD19 | CAR 12 | MALPVTALLLPLALLLHAARPEIVMTQSPATLSLSPGERATLSCRASQ DISKYLNWYQQKPGQAPRLLIYHTSRLHSGIPARFSGSGSGTDYTLTI SSLQPEDFAVYFCQQGNTLPYTFGQGTKLEIKGGGGSGGGGSGGGGSQ VQLQESGPGLVKPSETLSLTCTVSGVSLPDYGVSWIRQPPGKGLEWIG VIWGSETTYYNSSLKSRVTISKDNSKNQVSLKLSSVTAADTAVYYCAK HYYYGGSYAMDYWGQGTLVTVSSTTTPAPRPPTPAPTIASQPLSLRPE ACRPAAGGAVHTRGLDFACDIYIWAPLAGTCGVLLLSLVITLYCKRGR KKLLYIFKQPFMRPVQTTQEEDGCSCRFPEEEEGGCELRVKFSRSADA PAYKQGQNQLYNELNLGRREEYDVLDKRRGRDPEMGGKPRRKNPQEGL YNELQKDKMAEAYSEIGMKGERRRGKGHDGLYQGLSTATKDTYDALHM QALPPR | 7919 |

In one embodiment, the CAR molecule comprises (e.g., consists of) an amino acid sequence as provided in Table 22, or in Table 3 of International Publication No. WO2014/153270, filed Mar. 15, 2014; incorporated herein by reference. In one embodiment, the CAR molecule comprises (e.g., consists of) an amino acid sequence of SEQ ID NO: 7908, SEQ ID NO: 7909, SEQ ID NO: 7910, SEQ ID NO: 7911, SEQ ID NO: 7912, SEQ ID NO: 7913, SEQ ID NO: 7914, SEQ ID NO: 7915, SEQ ID NO: 7916, SEQ ID NO: 7917, SEQ ID NO: 7918, SEQ ID NO: 7919, or SEQ ID NO: 7920; or an amino acid sequence having at least one, two, three, four, five, 10, 15, 20 or 30 modifications (e.g., substitutions, e.g., conservative substitutions) but not more than 60, 50, or 40 modifications (e.g., substitutions, e.g., conservative substitutions) of an amino acid sequence of SEQ ID NO: 7908, SEQ ID NO: 7909, SEQ ID NO: 7910, SEQ ID NO: 7911, SEQ ID NO: 7912, SEQ ID NO: 7913, SEQ ID NO: 7914, SEQ ID NO: 7915, SEQ ID NO: 7916, SEQ ID NO: 7917, SEQ ID NO: 7918, SEQ ID NO: 7919, or SEQ ID NO: 7920; or an amino acid sequence having 85%, 90%, 95%, 96%, 97%, 98%, 99% identity to an amino acid sequence of SEQ ID NO: 7908, SEQ ID NO: 7909, SEQ ID NO: 7910, SEQ ID NO: 7911, SEQ ID NO: 7912, SEQ ID NO: 7913, SEQ ID NO: 7914, SEQ ID NO: 7915, SEQ ID NO: 7916, SEQ ID NO: 7917, SEQ ID NO: 7918, SEQ ID NO: 7919, or SEQ ID NO: 7920.

In one aspect, a CAR, e.g., a CAR expressed by the cell of the invention, comprises a CAR molecule comprising an antigen binding domain that binds to BCMA, e.g., comprises a BCMA antigen binding domain (e.g., a murine, human or humanized antibody or antibody fragment that specifically binds to BCMA, e.g., human BCMA), a transmembrane domain, and an intracellular signaling domain (e.g., an intracellular signaling domain comprising a costimulatory domain and/or a primary signaling domain).

Exemplary CAR molecules of a CAR described herein are provided in Table 23, or Table 1 of WO2016/014565, or as otherwise described herein. The CAR molecules in Table 23 comprise a BCMA antigen binding domain, e.g., an amino acid sequence of any BCMA antigen binding domain provided in Table 18 or 19.

TABLE 23

Exemplary BCMA CAR molecules. Sequences are provided with a leader sequence.

| Name/ Description | SEQ ID NO: | Sequence |
|---|---|---|
| 139109 | | |
| 139109-aa Full CAR | 8559 | MALPVTALLLPLALLLHAARPEVQLVESGGGLVQPGGSLRLSCAVSGFALS NHGMSWVRRAPGKGLEWVSGIVYSGSTYYAASVKGRFTISRDNSRNTLYLQ MNSLRPEDTAIYYCSAHGGESDVWGQGTTVTVSSASGGGGSGGRASGGGGS DIQLTQSPSSLSASVGDRVTITCRASQSISSYLNWYQQKPGKAPKLLIYAA SSLQSGVPSRFSGSGSGTDFTLTISSLQPEDFATYYCQQSYSTPYTFGQGT KVEIKTTTPAPRPPTPAPTIASQPLSLRPEACRPAAGGAVHTRGLDFACDI YIWAPLAGTCGVLLLSLVITLYCKRGRKKLLYIFKQPFMRPVQTTQEEDGC SCRFPEEEEGGCELRVKFSRSADAPAYKQGQNQLYNELNLGRREEYDVLDK RRGRDPEMGGKPRRKNPQEGLYNELQKDKMAEAYSEIGMKGERRRGKGHDG LYQGLSTATKDTYDALHMQALPPR |
| 139109-nt Full CAR | 8574 | ATGGCCCTCCCTGTCACCGCCCTGCTGCTTCCGCTGGCTCTTCTGCTCCAC GCCGCTCGGCCCGAAGTGCAATTGGTGGAATCAGGGGGAGGACTTGTGCAG CCTGGAGGATCGCTGAGACTGTCATGTGCCGTGTCCGGCTTTGCCCTGTCC AACCACGGGATGTCCTGGGTCCGCCGCGCGCCTGGAAAGGGCCTCGAATGG GTGTCGGGTATTGTGTACAGCGGTAGCACCTACTATGCCGCATCCGTGAAG |

TABLE 23-continued

Exemplary BCMA CAR molecules. Sequences are provided with a leader sequence.

| Name/<br>Description | SEQ ID<br>NO: | Sequence |
|---|---|---|
| | | GGGAGATTCACCATCAGCCGGGACAACTCCAGGAACACTCTGTACCTCCAA<br>ATGAATTCGCTGAGGCCAGAGGACACTGCCATCTACTACTGCTCCGCGCAT<br>GGCGGAGAGTCCGACGTCTGGGGACAGGGGACCACCGTGACCGTGTCTAGC<br>GCGTCCGGCGGAGGCGGCAGCGGGGGTCGGGCATCAGGGGCGGCGGATCG<br>GACATCCAGCTCACCCAGTCCCCGAGCTCGCTGTCCGCCTCCGTGGGAGAT<br>CGGGTCACCATCACGTGCCGCGCCAGCCAGTCGATTTCCTCCTACCTGAAC<br>TGGTACCAACAGAAGCCCGGAAAAGCCCCGAAGCTTCTCATCTACGCCGCC<br>TCGAGCCTGCAGTCAGGAGTGCCCTCACGGTTCTCCGGCTCCGGTTCCGGT<br>ACTGATTTCACCCTGACCATTTCCTCCCTGCAACCGGAGGACTTCGCTACT<br>TACTACTGCCAGCAGTCGTACTCCACCCCCTACACTTTCGGACAAGGCACC<br>AAGGTCGAAATCAAGACCACTACCCCAGCACCGAGGCCACCCACCCCGGCT<br>CCTACCATCGCCTCCCAGCCTCTGTCCCTGCGTCCGGAGGCATGTAGACCC<br>GCAGCTGGTGGGGCCGTGCATACCCGGGGTCTTGACTTCGCCTGCGATATC<br>TACATTTGGGCCCCTCTGGCTGGTACTTGCGGGGTCCTGCTGCTTTCACTC<br>GTGATCACTCTTTACTGTAAGCGCGGTCGGAAGAAGCTGCTGTACATCTTT<br>AAGCAACCCTTCATGAGGCCTGTGCAGACTACTCAAGAGGAGGACGGCTGT<br>TCATGCCGGTTCCCAGAGGAGGAGGAAGGCGGCTGCGAACTGCGCGTGAAA<br>TTCAGCCGCAGCGCAGATGCTCCAGCCTACAAGCAGGGGCAGAACCAGCTC<br>TACAACGAACTCAATCTTGGTCGGAGAGAGGAGTACGACGTGCTGGACAAG<br>CGGAGAGGACGGGACCCAGAAATGGGCGGGAAGCCGCGCAGAAAGAATCCC<br>CAAGAGGGCCTGTACAACGAGCTCCAAAAGGATAAGATGGCAGAAGCCTAT<br>AGCGAGATTGGTATGAAAGGGGAACGCAGAAGAGGCAAAGGCCACGACGGA<br>CTGTACCAGGGACTCAGCACCGCCACCAAGGACACCTATGACGCTCTTCAC<br>ATGCAGGCCCTGCCGCCTCGG |
| 139103 | | |
| 139103-aa<br>Full CAR | 8549 | MALPVTALLLPLALLLHAARPQVQLVESGGGLVQPGRSLRLSCAASGFTFS<br>NYAMSWVRQAPGKGLGWVSGISRSGENTYYADSVKGRFTISRDNSKNTLYL<br>QMNSLRDEDTAVYYCARSPAHYYGGMDVWGQGTTVTVSSASGGGGSGGRAS<br>GGGGSDIVLTQSPGTLSLSPGERATLSCRASQSISSSFLAWYQQKPGQAPR<br>LLIYGASRRATGIPDRFSGSGSGTDFTLTISRLEPEDSAVYYCQQYHSSPS<br>WTFGQGTKLEIKTTTPAPRPPTPAPTIASQPLSLRPEACRPAAGGAVHTRG<br>LDFACDIYIWAPLAGTCGVLLLSLVITLYCKRGRKKLLYIFKQPFMRPVQT<br>TQEEDGCSCRFPEEEEGGCELRVKFSRSADAPAYKQGQNQLYNELNLGRRE<br>EYDVLDKRRGRDPEMGGKPRRKNPQEGLYNELQKDKMAEAYSEIGMKGERR<br>RGKGHDGLYQGLSTATKDTYDALHMQALPPR |
| 139103-nt<br>Full CAR | 8564 | ATGGCCCTCCCTGTCACCGCCCTGCTGCTTCCGCTGGCTCTTCTGCTCCAC<br>GCCGCTCGGCCCCAAGTGCAACTCGTGGAATCTGGTGGAGGACTCGTGCAA<br>CCCGGAAGATCGCTTAGACTGTCGTGTGCCGCCAGCGGGTTCACTTTCTCG<br>AACTACGCGATGTCCTGGGTCCGCCAGGCACCCGGAAAGGGACTCGGTTGG<br>GTGTCCGGCATTTCCCGGTCCGGCGAAAATACCTACTACGCCGACTCCGTG<br>AAGGGCCGCTTCACCATCTCAAGGGACAACAGCAAAAACACCCTGTACTTG<br>CAAATGAACTCCCTGCGGGATGAAGATACAGCCGTGTACTATTGCGCCCGG<br>TCGCCTGCCCATTACTACGGCGGAATGGACGTCTGGGGACAGGGAACCACT<br>GTGACTGTCAGCAGCGCGTCGGGTGGCGGCGGCTCAGGGGGTCGGGCCTCC<br>GGGGGGGGAGGGTCCGACATCGTGCTGACCCAGTCCCCGGGAACCCTGAGC<br>CTGAGCCCGGGAGAGCGCGCGACCCTGTCATGCCGGGCATCCCAGAGCATT<br>AGCTCCTCCTTTCTCGCCTGGTATCAGCAGAAGCCCGGACAGGCCCCGAGG<br>CTGCTGATCTACGGCGCTAGCAGAAGGGCTACCGGAATCCCAGACCGGTTC<br>TCCGGCTCCGGTTCCGGGACCGATTTCACCCTTACTATCTCGCGCCTGGAA<br>CCTGAGGACTCCGCCGTCTACTACTGCCAGCAGTACCACTCATCCCCGTCG<br>TGGACGTTCGGACAGGGCACCAAGCTGGAGATTAAGACCACTACCCCAGCA<br>CCGAGGCCACCCACCCCGGCTCCTACCATCGCCTCCCAGCCTCTGTCCCTG<br>CGTCCGGAGGCATGTAGACCCGCAGCTGGTGGGGCCGTGCATACCCGGGGT<br>CTTGACTTCGCCTGCGATATCTACATTTGGGCCCCTCTGGCTGGTACTTGC<br>GGGGTCCTGCTGCTTTCACTCGTGATCACTCTTTACTGTAAGCGCGGTCGG<br>AAGAAGCTGCTGTACATCTTTAAGCAACCCTTCATGAGGCCTGTGCAGACT<br>ACTCAAGAGGAGGACGGCTGTTCATGCCGGTTCCCAGAGGAGGAGGAAGGC<br>GGCTGCGAACTGCGCGTGAAATTCAGCCGCAGCGCAGATGCTCCAGCCTAC<br>AAGCAGGGGCAGAACCAGCTCTACAACGAACTCAATCTTGGTCGGAGAGAG<br>GAGTACGACGTGCTGGACAAGCGGAGAGGACGGGACCCAGAAATGGGCGGG<br>AAGCCGCGCAGAAAGAATCCCCAAGAGGGCCTGTACAACGAGCTCCAAAAG<br>GATAAGATGGCAGAAGCCTATAGCGAGATTGGTATGAAAGGGGAACGCAGA<br>AGAGGCAAAGGCCACGACGGACTGTACCAGGGACTCAGCACCGCCACCAAG<br>GACACCTATGACGCTCTTCACATGCAGGCCCTGCCGCCTCGG |
| 139105 | | |
| 139105-aa<br>Full CAR | 8550 | MALPVTALLLPLALLLHAARPQVQLVESGGGLVQPGRSLRLSCAASGFTFD<br>DYAMHWVRQAPGKGLEWVSGISWNSGSIGYADSVKGRFTISRDNAKNSLYL<br>QMNSLRAEDTALYYCSVHSFPLAYWGQGTLVTVSSASGGGGSGGRASGGGGS<br>DIVMTQTPLSLPVTPGEPASISCRSSQSLLHSNGYNYLDWYLQKPGQSPQL<br>LIYLGSNRASGVPDRFSGSGSGTDFTLKISRVEAEDVGVYYCMQALQTPYT<br>FGQGTKVEIKTTTPAPRPPTPAPTIASQPLSLRPEACRPAAGGAVHTRGLD |

TABLE 23-continued

Exemplary BCMA CAR molecules. Sequences are provided with a leader sequence.

| Name/<br>Description | SEQ ID<br>NO: | Sequence |
|---|---|---|
| | | FACDIYIWAPLAGTCGVLLLSLVITLYCKRGRKKLLYIFKQPFMRPVQTTQ<br>EEDGCSCRFPEEEEGGCELRVKFSRSADAPAYKQGQNQLYNELNLGRREEY<br>DVLDKRRGRDPEMGGKPRRKNPQEGLYNELQKDKMAEAYSEIGMKGERRRG<br>KGHDGLYQGLSTATKDTYDALHMQALPPR |
| 139105-nt<br>Full CAR | 8565 | ATGGCCCTCCCTGTCACCGCCCTGCTGCTTCCGCTGGCTCTTCTGCTCCAC<br>GCCGCTCGGCCCAAGTGCAACTCGTCGAATCCGGTGGAGGTCTGGTCCAA<br>CCTGGTAGAAGCCTGAGACTGTCGTGTGCGGCCAGCGGATTCACCTTTGAT<br>GACTATGCTATGCACTGGGTGCGGCAGGCCCCAGGAAAGGGCCTGGAATGG<br>GTGTCGGGAATTAGCTGGAACTCCGGGTCCATTGGCTACGCCGACTCCGTG<br>AAGGGCCGCTTCACCATCTCCCGCGACAACGCAAAGAACTCCCTGTACTTG<br>CAAATGAACTCGCTCAGGGCTGAGGATACCGCGCTGTACTACTGCTCCGTG<br>CATTCCTTCCTGGCCTACTGGGGACAGGGAACTCTGGTCACCGTGTCGAGC<br>GCCTCCGGCGGCGGGGGCTCGGGTGGACGGGCCTCGGGCGGAGGGGGGTCC<br>GACATCGTGATGACCCAGACCCCGCTGAGCTTGCCCGTGACTCCCGGAGAG<br>CCTGCATCCATCTCCTGCCGGTCATCCCAGTCCCTTCTCCACTCCAACGGA<br>TACAACTACCTCGACTGGTACCTCCAGAAGCCGGGACAGAGCCCTCAGCTT<br>CTGATCTACCTGGGGTCAAATAGAGCCTCAGGAGTGCCGGATCGGTTCAGC<br>GGATCTGGTTCGGGAACTGATTTCACTCTGAAGATTTCCCGCGTGGAAGCC<br>GAGGACGTGGGCGTCTACTACTGTATGCAGGCGCTGCAGACCCCTATACC<br>TTCGGCCAAGGGACGAAAGTGGAGATCAAGACCACTACCCCAGCACCGAGG<br>CCACCCACCCCGGCTCCTACCATCGCCTCCCAGCCTCTGTCCCTGCGTCCG<br>GAGGCATGTAGACCCGCAGCTGGTGGGCCGTGCATACCCGGGGTCTTGAC<br>TTCGCCTGCGATATCTACATTTGGGCCCCTCTGGCTGGTACTTGCGGGGTC<br>CTGCTGCTTTCACTCGTGATCACTCTTTACTGTAAGCGCGGTCGGAAGAAG<br>CTGCTGTACATCTTTAAGCAACCCTTCATGAGGCCTGTGCAGACTACTCAA<br>GAGGAGGACGGCTGTTCATGCCGGTTCCCAGAGGAGGAGGAAGGCGGCTGC<br>GAACTGCGCGTGAAATTCAGCCGCAGCGCAGATGCTCCAGCCTACAAGCAG<br>GGGCAGAACCAGCTCTACAACGAACTCAATCTTGGTCGGAGAGAGGAGTAC<br>GACGTGCTGGACAAGCGGAGAGGACGGGACCCAGAAATGGGCGGGAAGCCG<br>CGCAGAAAGAATCCCCAAGAGGGCCTGTACAACGAGCTCCAAAAGGATAAG<br>ATGGCAGAAGCCTATAGCGAGATTGGTATGAAAGGGGAACGCAGAAGAGGC<br>AAAGGCCACGACGGACTGTACCAGGGACTCAGCACCGCCACCAAGGACACC<br>TATGACGCTCTTCACATGCAGGCCCTGCCGCCTCGG |

139111

| 139111-aa<br>Full CAR | 8551 | MALPVTALLLPLALLLHAARPEVQLLESGGGLVQPGGSLRLSCAVSGFALS<br>NHGMSWVRRAPGKGLEWVSGIVYSGSTYYAASVKGRFTISRDNSRNTLYLQ<br>MNSLRPEDTAIYYCSAHGGESDVWGQGTTVTVSSASGGGGSGGRASGGGGS<br>DIVMTQTPLSLSVTPGQPASISCKSSQSLLRNDGKTPLYWYLQKAGQPPQL<br>LIYEVSNRFSGVPDRFSGSGSGTDFTLKISRVEAEDVGAYYCMQNIQFPSF<br>GGGTKLEIKTTTPAPRPPTPAPTIASQPLSLRPEACRPAAGGAVHTRGLDF<br>ACDIYIWAPLAGTCGVLLLSLVITLYCKRGRKKLLYIFKQPFMRPVQTTQE<br>EDGCSCRFPEEEEGGCELRVKFSRSADAPAYKQGQNQLYNELNLGRREEYD<br>VLDKRRGRDPEMGGKPRRKNPQEGLYNELQKDKMAEAYSEIGMKGERRRGK<br>GHDGLYQGLSTATKDTYDALHMQALPPR |
| 139111-nt<br>Full CAR | 8566 | ATGGCCCTCCCTGTCACCGCCCTGCTGCTTCCGCTGGCTCTTCTGCTCCAC<br>GCCGCTCGGCCCGAAGTGCAATTGTTGGAATCTGGAGGAGGACTTGTGCAG<br>CCTGGAGGATCACTGAGACTTTCGTGTGCGGTGTCAGGCTTCGCCGTGAGC<br>AACCACGGCATGAGCTGGGTGCGGAGAGCCCCGGGGAAGGGTCTGGAATGG<br>GTGTCCGGGATCGTCTACTCCGGTTCAACTTACTACGCCGCAAGCGTGAAG<br>GGTCGCTTCACCATTTCCCGCGATAACTCCCGGAACACCCTGTACCTCCAA<br>ATGAACTCCCTGCGGCCCGAGGACACCGCCATCTACTACTGTTCCGCGCAT<br>GGAGGAGAGTCCGATGTCTGGGGACAGGGCACTACCGTGACCGTGTCGAGC<br>GCCTCGGGGGGAGGAGGCTCCGGCGGTCGCGCCTCCGGGGGGGTGGCAGC<br>GACATTGTGATGACGCAGACTCCACTCTCGCTGTCCGTGACCCCGGGACAG<br>CCCGCGTCCATCTCGTGCAAGAGCTCCCAGAGCCTGCTGAGGAACGACGGA<br>AAGACTCCTCTGTATTGGTACCTCCAGAAGGCTGGACAGCCCCCGCAACTG<br>CTCATCTACGAAGTGTCAAATCGCTTCTCCGGGGTGCCGGATCGGTTTTCC<br>GGCTCGGGATCGGCACCGACTTCACCCTGAAAATCTCCAGGGTCGAGGCC<br>GAGGACGTGGGAGCCTACTACTGCATGCAAAACATCCAGTTCCCTTCCTTC<br>GGCGGCGGCACAAAGCTGGAGATTAAGACCACTACCCCAGCACCGAGGCCA<br>CCCACCCCGGCTCCTACCATCGCCTCCCAGCCTCTGTCCCTGCGTCCGGAG<br>GCATGTAGACCCGCAGCTGGTGGGCCGTGCATACCCGGGGTCTTGACTTC<br>GCCTGCGATATCTACATTTGGGCCCCTCTGGCTGGTACTTGCGGGGTCCTG<br>CTGCTTTCACTCGTGATCACTCTTTACTGTAAGCGCGGTCGGAAGAAGCTG<br>CTGTACATCTTTAAGCAACCCTTCATGAGGCCTGTGCAGACTACTCAAGAG<br>GAGGACGGCTGTTCATGCCGGTTCCCAGAGGAGGAGGAAGGCGGCTGCGAA<br>CTGCGCGTGAAATTCAGCCGCAGCGCAGATGCTCCAGCCTACAAGCAGGGG<br>CAGAACCAGCTCTACAACGAACTCAATCTTGGTCGGAGAGAGGAGTACGAC<br>GTGCTGGACAAGCGGAGAGGACGGGACCCAGAAATGGGCGGGAAGCCGCGC<br>AGAAAGAATCCCCAAGAGGGCCTGTACAACGAGCTCCAAAAGGATAAGATG<br>GCAGAAGCCTATAGCGAGATTGGTATGAAAGGGGAACGCAGAAGAGGCAAA<br>GGCCACGACGGACTGTACCAGGGACTCAGCACCGCCACCAAGGACACCTAT<br>GACGCTCTTCACATGCAGGCCCTGCCGCCTCGG |

TABLE 23-continued

Exemplary BCMA CAR molecules. Sequences are provided with a leader sequence.

| Name/Description | SEQ ID NO: | Sequence |
|---|---|---|
| 139100 | | |
| 139100-aa Full CAR | 8552 | MALPVTALLLPLALLLHAARPQVQLVQSGAEVRKTGASVKVSCKASGYIFD NEGINWVRQAPGQGLEWMGWINPKNNNTNYAQKFQGRVTITADESTNTAYM EVSSLRSEDTAVYYCARGPYYYQSYMDVWGQGTMVTVSSASGGGGSGGRAS GGGGSDIVMTQTPLSLPVTPGEPASISCRSSQSLLHSNGYNYLNWYLQKPG QSPQLLIYLGSKRASGVPDRFSGSGSGTDFTLHITRVGAEDVGVYYCMQAL QTPYTFGQGTKLEIKTTTPAPRPPTPAPTIASQPLSLRPEACRPAAGGAVH TRGLDFACDIYIWAPLAGTCGVLLLSLVITLYCKRGRKKLLYIFKQPFMRP VQTTQEEDGCSCRFPEEEEGGCELRVKFSRSADAPAYKQGQNQLYNELNLG RREEYDVLDKRRGRDPEMGGKPRRKNPQEGLYNELQKDKMAEAYSEIGMKG ERRRGKGHDGLYQGLSTATKDTYDALHMQALPPR |
| 139100-nt Full CAR | 8567 | ATGGCCCTCCCTGTCACCGCCCTGCTGCTTCCGCTGGCTCTTCTGCTCCAC GCCGCTCGGCCCCAAGTCCAACTCGTCCAGTCCGGCGCAGAAGTCAGAAAA ACCGGTGCTAGCGTGAAAGTGTCCTGCAAGGCCTCCGGCTACATTTTCGAT AACTTCGGAATCAACTGGGTCAGACAGGCCCCGGGCCAGGGGCTGGAATGG ATGGGATGGATCAACCCCAAGAACAACAACACCAACTACGCACAGAAGTTC CAGGGCCGCGTGACTATCACCGCCGATGAATCGACCAATACCGCCTACATG GAGGTGTCCTCCCTGCGGTCGGAGGACACTGCCGTGTATTACTGCGCGAGG GGCCCATACTACTACCAAAGCTACATGGACGTCTGGGGACAGGGAACCATG GTGACCGTGTCATCCGCCTCCGGTGGTGGAGGCTCCGGGGGCGGGCTTCA GGAGGCGGAGGAAGCGATATTGTGATGACCCAGACTCCGCTTAGCCTGCCC GTGACTCCTGGAGAACCGGCCTCCATTTCCTGCCGGTCCTCGCAATCACTC CTGCATTCCAACGGTTACAACTACCTGAATTGGTACCTCCAGAAGCCTGGC CAGTCGCCCCAGTTGCTGATCTATCTGGGCTCGAAGCGCGCCTCCGGGGTG CCTGACCGGTTTAGCGGATCTGGGAGCGGCACGGACTTCACTCTCCACATC ACCCGCGTGGGAGCGGAGGACGTGGGAGTGTACTACTGTATGCAGGCGCTG CAGACTCCGTACACATTCGGACAGGGCACCAAGCTGGAGATCAAGACCACT ACCCCAGCACCGAGGCCACCCACCCCGGCTCCTACCATCGCCTCCCAGCCT CTGTCCCTGCGTCGGAGGCATGTAGACCCGCAGCTGGTGGGGCCGTGCAT ACCCGGGGTCTTGACTTCGCCTGCGATATCTACATTTGGGCCCCTCTGGCT GGTACTTGCGGGGTCCTGCTGCTTTCACTCGTGATCACTCTTTACTGTAAG CGCGGTCGGAAGAAGCTGCTGTACATCTTTAAGCAACCCTTCATGAGGCCT GTGCAGACTACTCAAGAGGAGGACGGCTGTTCATGCCGGTTCCCAGAGGAG GAGGAAGGCGGCTGCGAACTGCGCGTGAAATTCAGCCGCAGCGCAGATGCT CCAGCCTACAAGCAGGGGCAGAACCAGCTCTACAACGAACTCAATCTTGGT CGGAGAGAGGAGTACGACGTGCTGGACAAGCGGAGAGGACGGGACCCAGAA ATGGGCGGGAAGCCGCGCAGAAAGAATCCCCAAGAGGGCCTGTACAACGAG CTCCAAAAGGATAAGATGGCAGAAGCCTATAGCGAGATTGGTATGAAAGGG GAACGCAGAAGAGGCAAAGGCCACGACGGACTGTACCAGGGACTCAGCACC GCCACCAAGGACACCTATGACGCTCTTCACATGCAGGCCCTGCCGCCTCGG |
| 139101 | | |
| 139101-aa Full CAR | 8553 | MALPVTALLLPLALLLHAARPQVQLQESGGGLVQPGGSLRLSCAASGFTFS SDAMTWVRQAPGKGLEWVSVISGSGGTTYYADSVKGRFTISRDNSKNTLYL QMNSLRAEDTAVYYCAKLDSSGYYYARGPRYWGQGTLVTVSSASGGGGSGG RASGGGGSDIQLTQSPSSLSASVGDRVTITCRASQSISSYLNWYQQKPGKA PKLLIYGASTLASGVPARFSGSGSGTHFTLTINSLQSEDSATYYCQQSYKR ASFGQGTKVEIKTTTPAPRPPTPAPTIASQPLSLRPEACRPAAGGAVHTRG LDFACDIYIWAPLAGTCGVLLLSLVITLYCKRGRKKLLYIFKQPFMRPVQT TQEEDGCSCRFPEEEEGGCELRVKFSRSADAPAYKQGQNQLYNELNLGRRE EYDVLDKRRGRDPEMGGKPRRKNPQEGLYNELQKDKMAEAYSEIGMKGERR RGKGHDGLYQGLSTATKDTYDALHMQALPPR |
| 139101-nt Full CAR | 8568 | ATGGCCCTCCCTGTCACCGCCCTGCTGCTTCCGCTGGCTCTTCTGCTCCAC GCCGCTCGGCCCCAAGTGCAACTTCAAGAATCAGGCGGAGGACTCGTGCAG CCCGGAGGATCATTGCGGCTCTCGTGCGCCGCCTCGGGCTTCACCTTCTCG AGCGACGCCATGACCTGGGTCCGCCAGGCCCGGGGAAGGGGCTGGAATGG GTGTCTGTGATTTCCGGCTCCGGGGGAACTACTACTACGCCGATTCCGTG AAAGGTCGCTTCACTATCTCCCGGGACAACAGCAAGAACACCCTTTATCTG CAAATGAATTCCCTGCGCGCCGAGGACACCGCCGTGTACTACTGCGCCAAG CTGGACTCCTCGGGCTACTACTATGCCCGGGGTCCGAGATACTGGGGACAG GGAACCCTCGTGACCGTGTCCTCCGCGTCCGGCGGAGGAGGGTCGGAGGG CGGGCCTCCGGCGGCGGCGGTTCGGACATCCAGCTGACCCAGTCCCCATCC TCACTGAGCGCAAGCGTGGGCGACAGAGTCACCATTACATGCAGGGCGTCC CAGAGCATCAGCTCCTACCTGAACTGGTACCAACAGAAGCCTGGAAAGGCT CCTAAGCTGTTGATCTACGGGGCTTGACCCTGGCATCCGGGGTGCCCGCG AGGTTTAGCGGAAGCGGTAGCGGCACTCACTTCACTCTGACCATTAACAGC CTCCAGTCCGAGGATTCAGCCACTTACTACTGTCAGCAGTCCTACAAGCGG GCCAGCTTCGGACAGGGCACTAAGGTCGAGATCAAGACCACTACCCCAGCA CCGAGGCCACCCACCCCGGCTCCTACCATCGCCTCCCAGCCTCTGTCCCTG CGTCCGGAGGCATGTAGACCCGCAGCTGGTGGGGCCGTGCATACCCGGGGT CTTGACTTCGCCTGCGATATCTACATTTGGGCCCCTCTGGCTGGTACTTGC GGGGTCCTGCTGCTTTCACTCGTGATCACTCTTTACTGTAAGCGCGGTCGG |

TABLE 23-continued

Exemplary BCMA CAR molecules. Sequences are provided with a leader sequence.

| Name/<br>Description | SEQ ID<br>NO: | Sequence |
|---|---|---|
| | | AAGAAGCTGCTGTACATCTTTAAGCAACCCTTCATGAGGCCTGTGCAGACT<br>ACTCAAGAGGAGGACGGCTGTTCATGCCGGTTCCCAGAGGAGGAGGAAGGC<br>GGCTGCGAACTGCGCGTGAAATTCAGCCGCAGCGCAGATGCTCCAGCCTAC<br>AAGCAGGGGCAGAACCAGCTCTACAACGAACTCAATCTTGGTCGGAGAGAG<br>GAGTACGACGTGCTGGACAAGCGGAGAGGACGGGACCCAGAAATGGGCGGG<br>AAGCCGCGCAGAAAGAATCCCCAAGAGGGCCTGTACAACGAGCTCCAAAAG<br>GATAAGATGGCAGAAGCCTATAGCGAGATTGGTATGAAAGGGGAACGCAGA<br>AGAGGCAAAGGCCACGACGGACTGTACCAGGGACTCAGCACCGCCACCAAG<br>GACACCTATGACGCTCTTCACATGCAGGCCCTGCCGCCTCGG |
| 139102 | | |
| 139102-aa<br>Full CAR | 8554 | MALPVTALLLPLALLLHAARPQVQLVQSGAEVKKPGASVKVSCKASGYTFS<br>NYGITWVRQAPGQGLEWMGWISAYNGNTNYAQKFQGRVTMTRNTSISTAYM<br>ELSSLRSEDTAVYYCARGPYYYYMDVWGKGTMVTVSSASGGGGSGGRASGG<br>GGSEIVMTQSPLSLPVTPGEPASISCRSSQSLLYSNGYNYVDWYLQKPGQS<br>PQLLIYLGSNRASGVPDRFSGSGSGTDFKLQISRVEAEDVGIYYCMQGRQF<br>PYSFGQGTKVEIKTTTPAPRPPTPAPTIASQPLSLRPEACRPAAGGAVHTR<br>GLDFACDIYIWAPLAGTCGVLLLSLVITLYCKRGRKKLLYIFKQPFMRPVQ<br>TTQEEDGCSCRFPEEEEGGCELRVKFSRSADAPAYKQGQNQLYNELNLGRR<br>EEYDVLDKRRGRDPEMGGKPRRKNPQEGLYNELQKDKMAEAYSEIGMKGER<br>RRGKGHDGLYQGLSTATKDTYDALHMQALPPR |
| 139102-nt<br>Full CAR | 8569 | ATGGCCCTCCCTGTCACCGCCCTGCTGCTTCCGCTGGCTCTTCTGCTCCAC<br>GCCGCTCGGCCCCAAGTCCAACTGGTCCAGAGCGGTGCAGAAGTGAAGAAG<br>CCCGGAGCGAGCGTGAAAGTGTCCTGCAAGGCTTCCGGGTACACCTTCTCC<br>AACTACGGCATCACTTGGGTGCGCCAGGCCCCGGGACAGGGCCTGGAATGG<br>ATGGGGTGGATTTCCGCGTACAACGGCAATACGAACTACGCTCAGAAGTTC<br>CAGGGTAGAGTGACCATGACTAGGAACACCTCCATTTCCACCGCCTACATG<br>GAACTGTCCTCCCTGCGGAGCGAGGACACCGCCGTGTACTATTGCGCCCGG<br>GGACCATACTACTACTACATGGATGTCTGGGGGAAGGGGACTATGGTCACC<br>GTGTCATCCGCCTCGGGAGGCGGCGGATCAGGAGGACGCGCCTCTGGTGGT<br>GGAGGATCGGAGATCGTGATGACCCAGAGCCCTCTCTCCTTGCCCGTGACT<br>CCTGGGGAGCCCGCATCCATTTCATGCCGGAGCTCCAGTCACTTCTCTAC<br>TCCAACGGCTATAACTACGTGGATTGGTACCTCCAAAAGCCGGGCCAGAGC<br>CCGCAGCTGCTGATCTACCTGGGCTCGAACAGGGCCAGCGGAGTGCCTGAC<br>CGGTTCTCCGGGTCGGGAAGCGGGACCGACTTCAAGCTGCAAATCTCGAGA<br>GTGGAGGCCGAGGACGTGGGAATCTACTACTGTATGCAGGGCCGCCAGTTT<br>CCGTACTCGTTCGGACAGGGCACCAAAGTGGAAATCAAGACCACTACCCCA<br>GCACCGAGGCCACCCACCCCGGCTCCTACCATCGCCTCCCAGCCTCTGTCC<br>CTGCGTCCGGAGGCATGTAGACCCGCAGCTGGTGGGGCCGTGCATACCCGG<br>GGTCTTGACTTCGCCTGCGATATCTACATTTGGGCCCCTCTGGCTGGTACT<br>TGCGGGGTCCTGCTGCTTTCACTCGTGATCACTCTTTACTGTAAGCGCGGT<br>CGGAAGAAGCTGCTGTACATCTTTAAGCAACCCTTCATGAGGCCTGTGCAG<br>ACTACTCAAGAGGAGGACGGCTGTTCATGCCGGTTCCCAGAGGAGGAGGAA<br>GGCGGCTGCGAACTGCGCGTGAAATTCAGCCGCAGCGCAGATGCTCCAGCC<br>TACAAGCAGGGGCAGAACCAGCTCTACAACGAACTCAATCTTGGTCGGAGA<br>GAGGAGTACGACGTGCTGGACAAGCGGAGAGGACGGGACCCAGAAATGGGC<br>GGGAAGCCGCGCAGAAAGAATCCCCAAGAGGGCCTGTACAACGAGCTCCAA<br>AAGGATAAGATGGCAGAAGCCTATAGCGAGATTGGTATGAAAGGGGAACGC<br>AGAAGAGGCAAAGGCCACGACGGACTGTACCAGGGACTCAGCACCGCCACC<br>AAGGACACCTATGACGCTCTTCACATGCAGGCCCTGCCGCCTCGG |
| 139104 | | |
| 139104-aa<br>Full CAR | 8555 | MALPVTALLLPLALLLHAARPEVQLLETGGGLVQPGGSLRLSCAVSGFALS<br>NHGMSWVRRAPGKGLEWVSGIVYSGSTYYAASVKGRFTISRDNSRNTLYLQ<br>MNSLRPEDTAIYYCSAHGGESDVWGQGTTVTVSSASGGGGSGGRASGGGGS<br>EIVLTQSPATLSVSPGESATLSCRASQSVSSNLAWYQQKPGQAPRLLIYGA<br>STRASGIPDRFSGSGSGTDFTLTISSLQAEDVAVYYCQQYGSSLTFGGGTK<br>VEIKTTTPAPRPPTPAPTIASQPLSLRPEACRPAAGGAVHTRGLDFACDIY<br>IWAPLAGTCGVLLLSLVITLYCKRGRKKLLYIFKQPFMRPVQTTQEEDGCS<br>CRFPEEEEGGCELRVKFSRSADAPAYKQGQNQLYNELNLGRREEYDVLDKR<br>RGRDPEMGGKPRRKNPQEGLYNELQKDKMAEAYSEIGMKGERRRGKGHDGL<br>YQGLSTATKDTYDALHMQALPPR |
| 139104-nt<br>Full CAR | 8570 | ATGGCCCTCCCTGTCACCGCCCTGCTGCTTCCGCTGGCTCTTCTGCTCCAC<br>GCCGCTCGGCCCGAAGTGCAATTGCTCGAAACTGGAGGAGGTCTGGTGCAA<br>CCTGGAGGATCACTTCGCCTGTCCTGCGCCGTGTCGGGCTTTGCCCTGTCC<br>AACCATGGAATGAGCTGGGTCCGCCGCGCGCCGGGGAAGGGCCTCGAATGG<br>GTGTCCGGCATCGTCTACTCCGGCTCCACCTACTACGCCGCGTCCGTGAAG<br>GGCCGGTTCACGATTTCACGGGACAACTCGCGGAACACCCTGTACCTCCAA<br>ATGAATTCCCTTCGGCCGGAGGATACTGCCATCTACTACTGCTCCGCCCAC<br>GGTGGCGAATCCGACGTCTGGGGCCAGGGAACCACCGTGACCGTGTCCAGC<br>GCGTCCGGGGAGGAGGAAGCGGGGGTAGAGCATCGGGTGGAGGCGGATCA<br>GAGATCGTGCTGACCCAGTCCCCCGCCACCCTTGAGCGTGTCACCAGGAGAG<br>TCCGCCACCCTGTCATGCCGCGCCAGCCAGTCCGTGTCCTCCAACCTGGCT

TABLE 23-continued

Exemplary BCMA CAR molecules. Sequences are provided with a leader sequence.

| Name/<br>Description | SEQ ID<br>NO: | Sequence |
|---|---|---|
| | | TGGTACCAGCAGAAGCCGGGGCAGGCCCCTAGACTCCTGATCTATGGGCG<br>TCGACCCGGGCATCTGGAATTCCCGATAGGTTCAGCGGATCGGGCTCGGGC<br>ACTGACTTCACTCTGACCATCTCCTCGCTGCAAGCCGAGGACGTGGCTGTG<br>TACTACTGTCAGCAGTACGGAAGCTCCCTGACTTTCGGTGGCGGGACCAAA<br>GTCGAGATTAAGACCACTACCCCAGCACCGAGGCCACCCACCCCGGCTCCT<br>ACCATCGCCTCCCAGCCTCTGTCCCTGCGTCCGGAGGCATGTAGACCCGCA<br>GCTGGTGGGGCCGTGCATACCCGGGGTCTTGACTTCGCCTGCGATATCTAC<br>ATTTGGGCCCCTCTGGCTGGTACTTGCGGGGTCCTGCTGCTTTCACTCGTG<br>ATCACTCTTTACTGTAAGCGCGGTCGGAAGAAGCTGCTGTACATCTTTAAG<br>CAACCCTTCATGAGGCCTGTGCAGACTACTCAAGAGGAGGACGGCTGTTCA<br>TGCCGGTTCCCAGAGGAGGAGGAAGGCGGCTGCGAACTGCGCGTGAAATTC<br>AGCCGCAGCGCAGATGCTCCAGCCTACAAGCAGGGGCAGAACCAGCTCTAC<br>AACGAACTCAATCTTGGTCGGAGAGAGGAGTACGACGTGCTGGACAAGCGG<br>AGAGGACGGGACCCAGAAATGGGCGGGAAGCCGCGCAGAAAGAATCCCCAA<br>GAGGGCCTGTACAACGAGCTCCAAAAGGATAAGATGGCAGAAGCCTATAGC<br>GAGATTGGTATGAAAGGGGAACGCAGAAGAGGCAAAGGCCACGACGGACTG<br>TACCAGGGACTCAGCACCGCCACCAAGGACACCTATGACGCTCTTCACATG<br>CAGGGCCCTGCCGCCTCGG |
| 139106 | | |
| 139106-aa<br>Full CAR | 8556 | MALPVTALLLPLALLLHAARPEVQLVETGGGLVQPGGSLRLSCAVSGFALS<br>NHGMSWVRRAPGKGLEWVSGIVYSGSTYYAASVKGRFTISRDNSRNTLYLQ<br>MNSLRPEDTAIYYCSAHGGESDVWQGTTVTVSSASGGGGSGGRASGGGGS<br>EIVMTQSPATLSVSPGERATLSCRASQSVSSKLAWYQQKPGQAPRLLMYGA<br>SIRATGIPDRFSGSGSGTEFTLTISSLEPEDFAVYYCQQYGSSSWTFGQGT<br>KVEIKTTTPAPRPPTPAPTIASQPLSLRPEACRPAAGGAVHTRGLDFACDI<br>YIWAPLAGTCGVLLLSLVITLYCKRGRKKLLYIFKQPFMRPVQTTQEEDGC<br>SCRFPEEEEGGCELRVKFSRSADAPAYKQGQNQLYNELNLGRREEYDVLDK<br>RRGRDPEMGGKPRRKNPQEGLYNELQKDKMAEAYSEIGMKGERRRGKGHDG<br>LYQGLSTATKDTYDALHMQALPPR |
| 139106-nt<br>Full CAR | 8571 | ATGGCCCTCCCTGTCACCGCCCTGCTGCTTCCGCTGGCTCTTCTGCTCCAC<br>GCCGCTCGGCCCGAAGTGCAATTGGTGGAAACTGGAGGAGGACTTGTGCAA<br>CCTGGAGGATCATTGAGACTGAGCTGCGCAGTGTCGGGATTCGCCCTGAGC<br>AACCATGGAATGTCCTGGGTCAGAAGGGCCCCTGGAAAAGGCCTCGAATGG<br>GTGTCAGGGATCGTGTACTCCGGTTCCACTTACTACGCCGCCTCCGTGAAG<br>GGGCGCTTCACTATCTCACGGGATAACTCCCGCAATACCCTGTACCTCCAA<br>ATGAACAGCCTGCGGCCGGAGGATACCGCCATCTACTACTGTTCCGCCCAC<br>GGTGGAGAGTCTGACGTCTGGGGCCAGGGAACTACCGTGACCGTGTCCTCC<br>GCGTCCGGCGGTGGAGGGAGCGGCGGCCGCGCCAGCGGCGGCGGAGGCTCC<br>GAGATCGTGATGACCCAGAGCCCCGCTACTCTGTCGGTGTCGCCCGGAGAA<br>AGGGCGACCCTGTCCTGCCGGGCGTCGCAGTCCGTGAGCAGCAAGCTGGCT<br>TGGTACCAGCAGAAGCCGGGCCAGGCACCACGCCTGCTTATGTACGGTGCC<br>TCCATTCGGGCCACCGGAATCCCGGACCGGTTCTCGGGGTCGGGGTCCGGT<br>ACCGAGTTCACACTGACCATTTCCTCGCTCGAGCCCGAGGACTTTGCCGTC<br>TATTACTGCCAGCAGTACGGCTCCTCCTCATGGACGTTCGGCCAGGGGACC<br>AAGGTCGAAATCAAGACCACTACCCCAGCACCGAGGCCACCCACCCCGGCT<br>CCTACCATCGCCTCCCAGCCTCTGTCCCTGCGTCCGGAGGCATGTAGACCC<br>GCAGCTGGTGGGGCCGTGCATACCCGGGGTCTTGACTTCGCCTGCGATATC<br>TACATTTGGGCCCCTCTGGCTGGTACTTGCGGGGTCCTGCTGCTTTCACTC<br>GTGATCACTCTTTACTGTAAGCGCGGTCGGAAGAAGCTGCTGTACATCTTT<br>AAGCAACCCTTCATGAGGCCTGTGCAGACTACTCAAGAGGAGGACGGCTGT<br>TCATGCCGGTTCCCAGAGGAGGAGGAAGGCGGCTGCGAACTGCGCGTGAAA<br>TTCAGCCGCAGCGCAGATGCTCCAGCCTACAAGCAGGGGCAGAACCAGCTC<br>TACAACGAACTCAATCTTGGTCGGAGAGAGGAGTACGACGTGCTGGACAAG<br>CGGAGAGGACGGGACCCAGAAATGGGCGGGAAGCCGCGCAGAAAGAATCCC<br>CAAGAGGGCCTGTACAACGAGCTCCAAAAGGATAAGATGGCAGAAGCCTAT<br>AGCGAGATTGGTATGAAAGGGGAACGCAGAAGAGGCAAAGGCCACGACGGA<br>CTGTACCAGGGACTCAGCACCGCCACCAAGGACACCTATGACGCTCTTCAC<br>ATGCAGGGCCCTGCCGCCTCGG |
| 139107 | | |
| 139107-aa<br>Full CAR | 8557 | MALPVTALLLPLALLLHAARPEVQLVETGGGVVQPGGSLRLSCAVSGFALS<br>NHGMSWVRRAPGKGLEWVSGIVYSGSTYYAASVKGRFTISRDNSRNTLYLQ<br>MNSLRPEDTAIYYCSAHGGESDVWQGTTVTVSSASGGGGSGGRASGGGGS<br>EIVLTQSPGTLSLSPGERATLSCRASQSVGSTNLAWYQQKPGQAPRLLIYD<br>ASNRATGIPDRFSGGGSGTDFTLTISRLEPEDFAVYYCQQYGSSPPWTFGQ<br>GTKVEIKTTTPAPRPPTPAPTIASQPLSLRPEACRPAAGGAVHTRGLDFAC<br>DIYIWAPLAGTCGVLLLSLVITLYCKRGRKKLLYIFKQPFMRPVQTTQEED<br>GCSCRFPEEEEGGCELRVKFSRSADAPAYKQGQNQLYNELNLGRREEYDVL<br>DKRRGRDPEMGGKPRRKNPQEGLYNELQKDKMAEAYSEIGMKGERRRGKGH<br>DGLYQGLSTATKDTYDALHMQALPPR |
| 139107-nt<br>Full CAR | 8572 | ATGGCCCTCCCTGTCACCGCCCTGCTGCTTCCGCTGGCTCTTCTGCTCCAC<br>GCCGCTCGGCCCGAAGTGCAATTGGTGGAGACTGGAGGAGGAGTGGTGCAA |

TABLE 23-continued

Exemplary BCMA CAR molecules. Sequences are provided with a leader sequence.

| Name/Description | SEQ ID NO: | Sequence |
|---|---|---|
| | | CCTGGAGGAAGCCTGAGACTGTCATGCGCGGTGTCGGGCTTCGCCCTCTCC<br>AACCACGGAATGTCCTGGGTCCGCCGGGCCCTGGGAAAGGACTTGAATGG<br>GTGTCCGGCATCGTGTACTCGGGTTCCACCTACTACGCGGCCTCAGTGAAG<br>GGCCGGTTTACTATTAGCCGCGACAACTCCAGAAACACACTGTACCTCCAA<br>ATGAACTCGCTGCGGCCGGAAGATACCGCTATCTACTACTGCTCCGCCCAT<br>GGGGGAGAGTCGGACGTCTGGGGACAGGGCACCACTGTCACTGTGTCCAGC<br>GCTTCCGGCGGTGGTGGAAGCGGGGGACGGGCCTCAGGAGGCGGTGGCAGC<br>GAGATTGTGCTGACCCAGTCCCCCGGGACCCTGAGCCTGTCCCCGGGAGAA<br>AGGGCCACCCTCTCCTGTCGGGCATCCCAGTCCGTGGGGTCTACTAACCTT<br>GCATGGTACCAGCAGAAGCCCGGCCAGGCCCCTCGCCTGCTGATCTACGAC<br>GCGTCCAATAGAGCCACCGGCATCCCGGATCGCTTCAGCGGAGGCGGATCG<br>GGCACCGACTTCACCCTCACCATTTCAAGGCTGGAACCGGAGGACTTCGCC<br>GTGTACTACTGCCAGCAGTATGGTTCGTCCCCACCCTGGACGTTCGGCCAG<br>GGGACTAAGGTCGAGATCAAGACCACTACCCCAGCACCGAGGCCACCCACC<br>CCGGCTCCTACCATCGCCTCCCAGCCTCTGTCCCTGCGTCCGGAGGCATGT<br>AGACCCGCAGCTGGTGGGGCCGTGCATACCCGGGGTCTTGACTTCGCCTGC<br>GATATCTACATTTGGGCCCCTCTGGCTGGTACTTGCGGGGTCCTGCTGCTT<br>TCACTCGTGATCACTCTTTACTGTAAGCGCGGTCGGAAGAAGCTGCTGTAC<br>ATCTTTAAGCAACCCTTCATGAGGCCTGTGCAGACTACTCAAGAGGAGGAC<br>GGCTGTTCATGCCGGTTCCCAGAGGAGGAGGAAGGCGGCTGCGAACTGCGC<br>GTGAAATTCAGCCGCAGCGCAGATGCTCCAGCCTACAAGCAGGGGCAGAAC<br>CAGCTCTACAACGAACTCAATCTTGGTCGGAGAGAGGAGTACGACGTGCTG<br>GACAAGCGGAGAGGACGGGACCCAGAAATGGGCGGGAAGCCGCGCAGAAAG<br>AATCCCCAAGAGGGCCTGTACAACGAGCTCCAAAAGGATAAGATGGCAGAA<br>GCCTATAGCGAGATTGGTATGAAAGGGGAACGCAGAAGAGGCAAAGGCCAC<br>GACGGACTGTACCAGGGACTCAGCACCGCCACCAAGGACACCTATGACGCT<br>CTTCACATGCAGGCCCTGCCGCCTCGG |
| 139108 | | |
| 139108-aa Full CAR | 8558 | MALPVTALLLPLALLLHAARPQVQLVESGGGLVKPGGSLRLSCAASGFTFS<br>DYYMSWIRQAPGKGLEWVSYISSSGSTIYYADSVKGRFTISRDNAKNSLYL<br>QMNSLRAEDTAVYYCARESGDGMDVWGQGTTVTVSSASGGGSGGGGRASGG<br>GSDIQMTQSPSSLSASVGDRVTITCRASQSISSYLNWYQQKPGKAPKLLIY<br>AASSLQSGVPSRFSGSGSGTDFTLTISSLQPEDFATYYCQQSYTLAFGQGT<br>KVDIKTTTPAPRPPTPAPTIASQPLSLRPEACRPAAGGAVHTRGLDFACDI<br>YIWAPLAGTCGVLLLSLVITLYCKRGRKKLLYIFKQPFMRPVQTTQEEDGC<br>SCRFPEEEEGGCELRVKFSRSADAPAYKQGQNQLYNELNLGRREEYDVLDK<br>RRGRDPEMGGKPRRKNPQEGLYNELQKDKMAEAYSEIGMKGERRRGKGHDG<br>LYQGLSTATKDTYDALHMQALPPR |
| 139108-nt Full CAR | 8573 | ATGGCCCTCCCTGTCACCGCCCTGCTGCTTCCGCTGGCTCTTCTGCTCCAC<br>GCCGCTCGGCCCCAAGTGCAACTCGTGGAATCTGGTGGAGGACTCGTGAAA<br>CCTGGAGGATCATTGAGACTGTCATGCGCGGCCTCGGGATTCACGTTCTCC<br>GATTACTACATGAGCTGGATTCGCCAGGCTCCGGGGAAGGGACTGGAATGG<br>GTGTCCTACATTTCCTCATCCGGCTCCACCATCTACTACGCGGACTCCGTG<br>AAGGGGAGATTCACCATTAGCCGCGATAACGCCAAGAACAGCCTGTACCTT<br>CAGATGAACTCCCTGCGGGCTGAAGATACTGCCGTCTACTACTGCGCAAGG<br>GAGAGCGGAGATGGGATGGACGTCTGGGGACAGGGTACCACTGTGACCGTG<br>TCGTCGGCCTCCGGCGGAGGGGGTTCGGGTGGAAGGGCCAGCGGCGGCGGA<br>GGCAGCGACATCCAGATGACCCAGTCCCCCCTCATCGCTGTCCGCCTCCGTG<br>GGCGACCGCGTCACCATCACATGCCGGGCCTCACAGTCGATCTCCTCCTAC<br>CTCAATTGGTATCAGCAGAAGCCCGGAAAGGCCCCTAAGCTTCTGATCTAC<br>GCAGCGTCCTCCCTGCAATCCGGGGTCCCATCTCGGTTCTCCGGCTCGGGC<br>AGCGGTACCGACTTCACTCTGACCATCTCGAGCCTGCAGCCGGAGGACTTC<br>GCCACTTACTACTGTCAGCAAAGCTACACCCTCGCGTTTGGCCAGGGCACC<br>AAAGTGGACATCAAGACCACTACCCCAGCACCGAGGCCACCCACCCCGGCT<br>CCTACCATCGCCTCCCAGCCTCTGTCCCTGCGTCCGGAGGCATGTAGACCC<br>GCAGCTGGTGGGGCCGTGCATACCCGGGGTCTTGACTTCGCCTGCGATATC<br>TACATTTGGGCCCCTCTGGCTGGTACTTGCGGGGTCCTGCTGCTTTCACTC<br>GTGATCACTCTTTACTGTAAGCGCGGTCGGAAGAAGCTGCTGTACATCTTT<br>AAGCAACCCTTCATGAGGCCTGTGCAGACTACTCAAGAGGAGGACGGCTGT<br>TCATGCCGGTTCCCAGAGGAGGAGGAAGGCGGCTGCGAACTGCGCGTGAAA<br>TTCAGCCGCAGCGCAGATGCTCCAGCCTACAAGCAGGGGCAGAACCAGCTC<br>TACAACGAACTCAATCTTGGTCGGAGAGAGGAGTACGACGTGCTGGACAAG<br>CGGAGAGGACGGGACCCAGAAATGGGCGGGAAGCCGCGCAGAAAGAATCCC<br>CAAGAGGGCCTGTACAACGAGCTCCAAAAGGATAAGATGGCAGAAGCCTAT<br>AGCGAGATTGGTATGAAAGGGGAACGCAGAAGAGGCAAAGGCCACGACGGA<br>CTGTACCAGGGACTCAGCACCGCCACCAAGGACACCTATGACGCTCTTCAC<br>ATGCAGGCCCTGCCGCCTCGG |
| 139110 | | |
| 139110-aa Full CAR | 8560 | MALPVTALLLPLALLLHAARPQVQLVQSGGGLVKPGGSLRLSCAASGFTFS<br>DYYMSWIRQAPGKGLEWVSYISSSGNTIYYADSVKGRFTISRDNAKNSLYL<br>QMNSLRAEDTAVYYCARSTMVREDYWGQGTLVTVSSASGGGGSGGRASGGG |

TABLE 23-continued

Exemplary BCMA CAR molecules. Sequences are provided with a leader sequence.

| Name/<br>Description | SEQ ID<br>NO: | Sequence |
|---|---|---|
| | | GSDIVLTQSPLSLPVTLGQPASISCKSSESLVHNSGKTYLNWFHQRPGQSP<br>RRLIYEVSNRDSGVPDRFTGSGSGTDFTLKISRVEAEDVGVYYCMQGTHWP<br>GTFGQGTKLEIKTTTPAPRPPTPAPTIASQPLSLRPEACRPAAGGAVHTRG<br>LDFACDIYIWAPLAGTCGVLLLSLVITLYCKRGRKKLLYIFKQPFMRPVQT<br>TQEEDGCSCRFPEEEEGGCELRVKFSRSADAPAYKQGQNQLYNELNLGRRE<br>EYDVLDKRRGRDPEMGGKPRRKNPQEGLYNELQKDKMAEAYSEIGMKGERR<br>RGKGHDGLYQGLSTATKDTYDALHMQALPPR |
| 139110-nt<br>Full CAR | 8575 | ATGGCCCTCCCTGTCACCGCCCTGCTGCTTCCGCTGGCTCTTCTGCTCCAC<br>GCCGCTCGGCCCCAAGTGCAACTGGTGCAAAGCGGAGGAGGATTGGTCAAA<br>CCCGGAGGAAGCCTGAGACTGTCATGCGCGGCCTCTGGATTCACCTTCTCC<br>GATTACTACATGTCATGGATCAGACAGGCCCCGGGGAAGGGCCTCGAATGG<br>GTGTCCTACATCTCGTCCTCCGGGAACACCATCTACTACGCCGACAGCGTG<br>AAGGGCCGCTTTACCATTTCCCGCGACAACGCAAAGAACTCGCTGTACCTT<br>CAGATGAATTCCTGCGGGCTGAAGATACCGCGGTGTACTATTGCGCCCGG<br>TCCACTATGGTCCGGGAGGACTACTGGGGACAGGGCACACTCGTGACCGTG<br>TCCAGCGCGAGCGGGGGTGGAGGCAGCGGTGGACGCGCCTCCGGCGGCGGC<br>GGTTCAGACATCGTGCTGACTCAGTCGCCCCTGTCGCTGCCGGTCACCCTG<br>GGCCAACCGGCCTCAATTAGCTGCAAGTCCTCGGAGAGCCTGGTGCACAAC<br>TCAGGAAAGACTTACCTGAACTGGTTCCATCAGCGGCCTGGACAGTCCCCA<br>CGGAGGCTCATCTATGAAGTGTCCAACAGGGATTCGGGGGTGCCCGACCGC<br>TTCACTGGCTCCGGGTCCGGCACCGACTTCACCTTGAAAATCTCCAGAGTG<br>GAAGCCGAGGACGTGGGCGTGTACTACTGTATGCAGGGTACCCACTGGCCT<br>GGAACCTTTGGACAAGGAACTAAGCTCGAGATTAAGACCACTACCCCAGCA<br>CCGAGGCCACCCACCCCGGCTCCTACCATCGCCTCCCAGCCTCTGTCCCTG<br>CGTCCGGAGGCATGTAGACCCGCAGCTGGTGGGGCCGTGCATACCCGGGGT<br>CTTGACTTCGCCTGCGATATCTACATTTGGGCCCCTCTGGCTGGTACTTGC<br>GGGGTCCTGCTGCTTTCACTCGTGATCACTCTTTACTGTAAGCGCGGTCGG<br>AAGAAGCTGCTGTACATCTTTAAGCAACCCTTCATGAGGCCTGTGCAGACT<br>ACTCAAGAGGAGGACGGCTGTTCATGCCGGTTCCCAGAGGAGGAGGAAGGC<br>GGCTGCGAACTGCGCGTGAAATTCAGCCGCAGCGCAGATGCTCCAGCCTAC<br>AAGCAGGGGCAGAACCAGCTCTACAACGAACTCAATCTTGGTCGGAGAGAG<br>GAGTACGACGTGCTGGACAAGCGGAGAGGACGGGACCCAGAAATGGGCGGG<br>AAGCCGCGCAGAAAGAATCCCCAAGAGGGCCTGTACAACGAGCTCCAAAAG<br>GATAAGATGGCAGAAGCCTATAGCGAGATTGGTATGAAAGGGGAACGCAGA<br>AGAGGCAAAGGCCACGACGGACTGTACCAGGGACTCAGCACCGCCACCAAG<br>GACACCTATGACGCTCTTCACATGCAGGCCCTGCCGCCTCGG |
| 139112 | | |
| 139112-aa<br>Full CAR | 8561 | MALPVTALLLPLALLLHAARPQVQLVESGGGLVQPGGSLRLSCAVSGFALS<br>NHGMSWVRRAPGKGLEWVSGIVYSGSTYYAASVKGRFTISRDNSRNTLYLQ<br>MNSLRPEDTAIYYCSAHGGESDVWGQGTTVTVSSASGGGGSGGRASGGGGS<br>DIRLTQSPSPLSASVGDRVTITCQASEDINKFLNWYHQTPGKAPKLLIYDA<br>STLQTGVPSRFSGSGSGTDFTLTINSLQPEDIGTYYCQQYESLPLTFGGGT<br>KVEIKTTTPAPRPPTPAPTIASQPLSLRPEACRPAAGGAVHTRGLDFACDI<br>YIWAPLAGTCGVLLLSLVITLYCKRGRKKLLYIFKQPFMRPVQTTQEEDGC<br>SCRFPEEEEGGCELRVKFSRSADAPAYKQGQNQLYNELNLGRREEYDVLDK<br>RRGRDPEMGGKPRRKNPQEGLYNELQKDKMAEAYSEIGMKGERRRGKHDG<br>LYQGLSTATKDTYDALHMQALPPR |
| 139112-nt<br>Full CAR | 8576 | ATGGCCCTCCCTGTCACCGCCCTGCTGCTTCCGCTGGCTCTTCTGCTCCAC<br>GCCGCTCGGCCCCAAGTGCAACTCGTGGAATCTGGTGGAGGACTCGTGCAA<br>CCCGGTGGAAGCCTTAGGCTGTCGTGCGCCGTCAGCGGGTTTGCTCTGAGC<br>AACCATGGAATGTCCTGGGTCCGCCGGGCACCGGGAAAAGGGCTGGAATGG<br>GTGTCCGGCATCGTGTACAGCGGGTCAACCTATTACGCGCGTCCGTGAAG<br>GGCAGATTCACTATCTCAAGAGACAACAGCCGGAACACCCTGTACTTGCAA<br>ATGAATTCCCTGCGCCCCGAGGACACCGCCATCTACTACTGCTCCGCCCAC<br>GGAGGAGAGTCGGACGTGTGGGGCCAGGGAACGACTGTGACTGTGTCCAGC<br>GCATCAGGAGGGGTGGTTCGGGCGGCCGGGCCTCGGGGGGAGGAGGTTCC<br>GACATTCGGCTGACCCAGTCCCCGTCCCCACTGTCGGCCTCCGTCGGCGAC<br>CGCGTGACCATCACTTGTCAGGCGTCCGAGGACATTAACAAGTTCCTGAAC<br>TGGTACCACCAGACCCCTGGAAAGGCCCCCAAGCTGCTGATCTACGATGCC<br>TCGACCCTTCAAACTGGAGTGCCTAGCCGGTTCTCCGGGTCCGGCTCCGGC<br>ACTGATTTCACTCTGACCATCAACTCATTGCAGCCGGAAGATATCGGGACC<br>TACTATTGCCAGCAGTACGAATCCCTCCCGCTCACATTCGGCGGGGGAACC<br>AAGGTCGAGATTAAGACCACTACCCCAGCACCGAGGCCACCCACCCCGGCT<br>CCTACCATCGCCTCCCAGCCTCTGTCCCTGCGTCCGGAGGCATGTAGACCC<br>GCAGCTGGTGGGGCCGTGCATACCCGGGGTCTTGACTTCGCCTGCGATATC<br>TACATTTGGGCCCCTCTGGCTGGTACTTGCGGGGTCCTGCTGCTTTCACTC<br>GTGATCACTCTTTACTGTAAGCGCGGTCGGAAGAAGCTGCTGTACATCTTT<br>AAGCAACCCTTCATGAGGCCTGTGCAGACTACTCAAGAGGAGGACGGCTGT<br>TCATGCCGGTTCCCAGAGGAGGAGGAAGGCGGCTGCGAACTGCGCGTGAAA<br>TTCAGCCGCAGCGCAGATGCTCCAGCCTACAAGCAGGGGCAGAACCAGCTC<br>TACAACGAACTCAATCTTGGTCGGAGAGAGGAGTACGACGTGCTGGACAAG<br>CGGAGAGGACGGGACCCAGAAATGGGCGGGAAGCCGCGCAGAAAGAATCCC<br>CAAGAGGGCCTGTACAACGAGCTCCAAAAGGATAAGATGGCAGAAGCCTAT<br>AGCGAGATTGGTATGAAAGGGGAACGCAGAAGAGGCAAAGGCCACGACGGA |

TABLE 23-continued

Exemplary BCMA CAR molecules. Sequences are provided with a leader sequence.

| Name/<br>Description | SEQ ID<br>NO: | Sequence |
|---|---|---|
| | | CTGTACCAGGGACTCAGCACCGCCACCAAGGACACCTATGACGCTCTTCAC<br>ATGCAGGCCCTGCCGCCTCGG |
| 139113 | | |
| 139113-aa<br>Full CAR | 8562 | MALPVTALLLPLALLLHAARPEVQLVETGGGLVQPGGSLRLSCAVSGFALS<br>NHGMSWVRRAPGKGLEWVSGIVYSGSTYYAASVKGRFTISRDNSRNTLYLQ<br>MNSLRPEDTAIYYCSAHGGESDVWGQGTTVTVSSASGGGGSGGRASGGGGS<br>ETTLTQSPATLSVSPGERATLSCRASQSVGSNLAWYQQKPGQGPRLLIYGA<br>STRATGIPARFSGSGSGTEFTLTISSLQPEDFAVYYCQQYNDWLPVTFGQG<br>TKVEIKTTTPAPRPPTPAPTIASQPLSLRPEACRPAAGGAVHTRGLDFACD<br>IYIWAPLAGTCGVLLLSLVITLYCKRGRKKLLYIFKQPFMRPVQTTQEEDG<br>CSCRFPEEEEGGCELRVKFSRSADAPAYKQGQNQLYNELNLGRREEYDVLD<br>KRRGRDPEMGGKPRRKNPQEGLYNELQKDKMAEAYSEIGMKGERRRGKGHD<br>GLYQGLSTATKDTYDALHMQALPPR |
| 139113-nt<br>Full CAR | 8577 | ATGGCCCTCCCTGTCACCGCCCTGCTGCTTCCGCTGGCTCTTCTGCTCCAC<br>GCCGCTCGGCCCGAAGTGCAATTGGTGGAAACTGGAGGAGGACTTGTGCAA<br>CCTGGAGGATCATTGCGGCTCTCATGCGCTGTCTCCGGCTTCGCCCTGTCA<br>AATCACGGGATGTCGTGGGTCAGACGGGCCCCGGGAAAGGGTCTGGAATGG<br>GTGTCGGGGATTGTGTACAGCGGCTCCACCTACTACGCCGCTTCGGTCAAG<br>GGCCGCTTCACTATTTCACGGGACAACAGCCGCAACACCCTCTATCTGCAA<br>ATGAACTCTCTCCGCCCGGAGGATACCGCCATCTACTACTGCTCCGCACAC<br>GGCGGCGAATCCGACGTGTGGGGACAGGGAACCACTGTCACCGTGTCGTCC<br>GCATCCGGTGGCGGAGGATCGGGTGGCCGGGCCTCCGGGGGCGGCGGCAGC<br>GAGACTACCCTGACCCAGTCCCCTGCCACTCTGTCCGTGAGCCCGGGAGAG<br>AGAGCCACCCTTAGCTGCCGGGCCAGCCAGAGCGTGGGCTCCAACCTGGCC<br>TGGTACCAGCAGAAGCCAGGACAGGGTCCCAGGCTGCTGATCTACGGAGCC<br>TCCACTCGCGCGACCGGCATCCCCGCGAGGTTCTCCGGGTCGGGTTCCGGG<br>ACCGAGTTCACCCTGACCATCTCCTCCCTCCAACCGGAGGACTTCGCGGTG<br>TACTACTGTCAGCAGTACAACGATTGGCTGCCCGTGACATTTGGACAGGGG<br>ACGAAGGTGGAAATCAAAACCACTACCCCAGCACCGAGGCCACCCACCCCG<br>GCTCCTACCATCGCCTCCCAGCCTCTGTCCCTGCGTCCGGAGGCATGTAGA<br>CCCGCAGCTGGTGGGGCCGTGCATACCCGGGGTCTTGACTTCGCCTGCGAT<br>ATCTACATTTGGGCCCCTCTGGCTGGTACTTGCGGGGTCCTGCTGCTTTCA<br>CTCGTGATCACTCTTTACTGTAAGCGCGGTCGGAAGAAGCTGCTGTACATC<br>TTTAAGCAACCCTTCATGAGGCCTGTGCAGACTACTCAAGAGGAGGACGGC<br>TGTTCATGCCGGTTCCCAGAGGAGGAGGAAGGCGGCTGCGAACTGCGCGTG<br>AAATTCAGCCGCAGCGCAGATGCTCCAGCCTACAAGCAGGGGCAGAACCAG<br>CTCTACAACGAACTCAATCTTGGTCGGAGAGAGGAGTACGACGTGCTGGAC<br>AAGCGGAGAGGACGGGACCCAGAAATGGGCGGGAAGCCGCGCAGAAAGAAT<br>CCCCAAGAGGGCCTGTACAACGAGCTCCAAAAGGATAAGATGGCAGAAGCC<br>TATAGCGAGATTGGTATGAAAGGGGAACGCAGAAGAGGCAAAGGCCACGAC<br>GGACTGTACCAGGGACTCAGCACCGCCACCAAGGACACCTATGACGCTCTT<br>CACATGCAGGCCCTGCCGCCTCGG |
| 139114 | | |
| 139114-aa<br>Full CAR | 8563 | MALPVTALLLPLALLLHAARPEVQLVESGGGLVQPGGSLRLSCAVSGFALS<br>NHGMSWVRRAPGKGLEWVSGIVYSGSTYYAASVKGRFTISRDNSRNTLYLQ<br>MNSLRPEDTAIYYCSAHGGESDVWGQGTTVTVSSASGGGGSGGRASGGGGS<br>EIVLTQSPGTLSLSPGERATLSCRASQSIGSSSLAWYQQKPGQAPRLLMYG<br>ASSRASGIPDRFSGSGSGTDFTLTISRLEPEDFAVYYCQQYAGSPPFTFGQ<br>GTKVEIKTTTPAPRPPTPAPTIASQPLSLRPEACRPAAGGAVHTRGLDFAC<br>DIYIWAPLAGTCGVLLLSLVITLYCKRGRKKLLYIFKQPFMRPVQTTQEED<br>GCSCRFPEEEEGGCELRVKFSRSADAPAYKQGQNQLYNELNLGRREEYDVL<br>DKRRGRDPEMGGKPRRKNPQEGLYNELQKDKMAEAYSEIGMKGERRRGKGH<br>DGLYQGLSTATKDTYDALHMQALPPR |
| 139114-nt<br>Full CAR | 8578 | ATGGCCCTCCCTGTCACCGCCCTGCTGCTTCCGCTGGCTCTTCTGCTCCAC<br>GCCGCTCGGCCCGAAGTGCAATTGGTGGAATCTGGTGGAGGACTTGTGCAA<br>CCTGGAGGATCACTGAGACTGTCATGCGCGGTGTCCGGTTTTGCCCTGAGC<br>AATCATGGGATGTCGTGGGTCCGGCGCGCCCCCGGAAAGGGTCTGGAATGG<br>GTGTCGGGTATCGTCTACTCCGGGAGCACTTACTACGCCGCGAGCGTGAAG<br>GGCCGCTTCACCATTTCCCGCGATAACTCCCGCAACACCCTGTACTTGCAA<br>ATGAACTCGCTCCGGCCTGAGGACACTGCCATCTACTACTGCTCCGCACAC<br>GGAGGAGAATCCGACGTGTGGGGCCAGGGAACTACCGTGACCGTCAGCAGC<br>GCCTCCGGCGGCGGGGGCTCAGGCGGACGGGCTAGCGGCGGCGGTGGCTCC<br>GAGATCGTGCTGACCCAGTCGCCTGGCACTCTCTCGCTGAGCCCCGGGGAA<br>AGGGCAACCCTGTCCTGTCGGGCCAGCCAGTCCATTGGATCATCCTCCCTC<br>GCCTGGTATCAGCAGAAACCGGGACAGGCTCCGCGGCTGCTTATGTATGGG<br>GCCAGCTCAAGAGCCTCCGGCATTCCCGACCGGTTCTCCGGGTCCGGTTCC<br>GGCACCGATTTCACCCTGACTATCTCGAGGCTGGAGCCAGAGGACTTCGCC<br>GTGTACTACTGCCAGCAGTACGCGGGTCCCGCCGTTCACGTTCGGACAG<br>GGAACCAAGGTCGAGATCAAGACCACTACCCCAGCACCGAGGCCACCCACC<br>CCGGCTCCTACCATCGCCTCCCAGCCTCTGTCCCTGCGTCCGGAGGCATGT<br>AGACCCGCAGCTGGTGGGGCCGTGCATACCCGGGGTCTTGACTTCGCCTGC |

TABLE 23-continued

Exemplary BCMA CAR molecules. Sequences are provided with a leader sequence.

| Name/ Description | SEQ ID NO: | Sequence |
| --- | --- | --- |
| | | GATATCTACATTTGGGCCCCTCTGGCTGGTACTTGCGGGGTCCTGCTGCTT TCACTCGTGATCACTCTTTACTGTAAGCGCGGTCGGAAGAAGCTGCTGTAC ATCTTTAAGCAACCCTTCATGAGGCCTGTGCAGACTACTCAAGAGGAGGAC GGCTGTTCATGCCGGTTCCCAGAGGAGGAGGAAGGCGGCTGCGAACTGCGC GTGAAATTCAGCCGCAGCGCAGATGCTCCAGCCTACAAGCAGGGGCAGAAC CAGCTCTACAACGAACTCAATCTTGGTCGGAGAGAGGAGTACGACGTGCTG GACAAGCGGAGAGGACGGGACCCAGAAATGGGCGGGAAGCCGCGCAGAAAG AATCCCCAAGAGGGCCTGTACAACGAGCTCCAAAAGGATAAGATGGCAGAA GCCTATAGCGAGATTGGTATGAAAGGGGAACGCAGAAGAGGCAAAGGCCAC GACGGACTGTACCAGGGACTCAGCACCGCCACCAAGGACACCTATGACGCT CTTCACATGCAGGCCCTGCCGCCTCGG |
| 149362 | | |
| 149362-aa Full CAR | 8579 | MALPVTALLLPLALLLHAARPQVQLQESGPGLVKPSETLSLTCTVSGGSIS SSYYYWGWIRQPPGKGLEWIGSIYYSGSAYYNPSLKSRVTISVDTSKNQFS LRLSSVTAADTAVYYCARHWQEWPDAFDIWGQGTMVTVSSGGGGSGGGGSG GGGSETTLTQSPAFMSATPGDKVIISCKASQDIDDAMNWYQQKPGEAPLFI IQSATSPVPGIPPRFSGSGFGTDFSLTINNIESEDAAYYFCLQHDNFPLTF GQGTKLEIKTTTPAPRPPTPAPTIASQPLSLRPEACRPAAGGAVHTRGLDF ACDIYIWAPLAGTCGVLLLSLVITLYCKRGRKKLLYIFKQPFMRPVQTTQE EDGCSCRFPEEEEGGCELRVKFSRSADAPAYKQGQNQLYNELNLGRREEYD VLDKRRGRDPEMGGKPRRKNPQEGLYNELQKDKMAEAYSEIGMKGERRRGK GHDGLYQGLSTATKDTYDALHMQALPPR |
| 149362-nt Full CAR | 8601 | ATGGCCCTCCCTGTCACCGCCCTGCTGCTTCCGCTGGCTCTTCTGCTCCAC GCCGCTCGGCCCAAGTGCAGCTTCAGGAAAGCGGACCGGGCCTGGTCAAG CCATCCGAAACTCTCTCCCTGACTTGCACTGTGTCTGGCGGTTCCATCTCA TCGTCGTACTACTACTGGGGCTGGATTAGGCAGCCGCCCGGAAAGGGACTG GAGTGGATCGGAAGCATCTACTATTCCGGCTCGGCGTACTACAACCCTAGC CTCAAGTCGAGAGTGACCATCTCCGTGGATACCTCCAAGAACCAGTTTTCC CTGCGCCTGAGCTCCGTGACCGCCGCTGACACCGCCGTGTACTACTGTGCT CGGCATTGGCAGGAATGGCCCGATGCCTTCGACATTTGGGGCCAGGGCACT ATGGTCACTGTGTCATCCGGGGGTGGAGGCAGCGGGGGAGGAGGGTCCGGG GGGGGAGGTTCAGAGACAACCTTGACCCAGTCACCCGCATTCATGTCCGCC ACTCCGGGAGACAAGGTCATCATCTCGTGCAAAGCGTCCCAGGATATCGAC GATGCCATGAATTGGTACCAGCAGAAGCCTGGCGAAGCGCCGCTGTTCATT ATCCAATCCGCAACCTCGCCCGTGCCTGGAATCCCACCGCGGTTCAGCGGC AGCGGTTTCGGAACCGACTTTTCCCTGACCATTAACAACATTGAGTCCGAG GACGCCGCCTACTACTTCTGCCTGCAACACGACAACTTCCCTCTCACGTTC GGCCAGGGAACCAAGCTGGAAATCAAGACCACTACCCCAGCACCGAGGCCA CCCACCCCGGCTCCTACCATCGCCTCCCAGCCTCTGTCCCTGCGTCCGGAG GCATGTAGACCCGCAGCTGGTGGGGCCGTGCATACCCGGGGTCTTGACTTC GCCTGCGATATCTACATTTGGGCCCCTCTGGCTGGTACTTGCGGGGTCCTG CTGCTTTCACTCGTGATCACTCTTTACTGTAAGCGCGGTCGGAAGAAGCTG CTGTACATCTTTAAGCAACCCTTCATGAGGCCTGTGCAGACTACTCAAGAG GAGGACGGCTGTTCATGCCGGTTCCCAGAGGAGGAGGAAGGCGGCTGCGAA CTGCGCGTGAAATTCAGCCGCAGCGCAGATGCTCCAGCCTACAAGCAGGGG CAGAACCAGCTCTACAACGAACTCAATCTTGGTCGGAGAGAGGAGTACGAC GTGCTGGACAAGCGGAGAGGACGGGACCCAGAAATGGGCGGGAAGCCGCGC AGAAAGAATCCCCAAGAGGGCCTGTACAACGAGCTCCAAAAGGATAAGATG GCAGAAGCCTATAGCGAGATTGGTATGAAAGGGGAACGCAGAAGAGGCAAA GGCCACGACGGACTGTACCAGGGACTCAGCACCGCCACCAAGGACACCTAT GACGCTCTTCACATGCAGGCCCTGCCGCCTCGG |
| 149363 | | |
| 149363-aa Full CAR | 8580 | MALPVTALLLPLALLLHAARPQVNLRESGPALVKPTQTLTLTCTFSGFSLR TSGMCVSWIRQPPGKALEWLARIDWDEDKFYSTSLKTRLTISKDTSDNQVV LRMTNMDPADTATYYCARSGAGGTSATAFDIWGPGTMVTVSSGGGGSGGGG SGGGGSDIQMTQSPSSLSASVGDRVTITCRASQDIYNNLAWFQLKPGSAPR SLMYAANKSQSGVPSRFSGSASGTDFTLTISSLQPEDFATYYCQHYYRFPY SFGQGTKLEIKTTTPAPRPPTPAPTIASQPLSLRPEACRPAAGGAVHTRGL DFACDIYIWAPLAGTCGVLLLSLVITLYCKRGRKKLLYIFKQPFMRPVQTT QEEDGCSCRFPEEEEGGCELRVKFSRSADAPAYKQGQNQLYNELNLGRREE YDVLDKRRGRDPEMGGKPRRKNPQEGLYNELQKDKMAEAYSEIGMKGERRR GKGHDGLYQGLSTATKDTYDALHMQALPPR |
| 149363-nt Full CAR | 8602 | ATGGCCCTCCCTGTCACCGCCCTGCTGCTTCCGCTGGCTCTTCTGCTCCAC GCCGCTCGGCCCAAGTCAATCTGCGCGAATCCGGCCCGCCTTGGTCAAG CCTACCCAGACCCTCACTCTGACCTGTACTTTCTCCGGCTTCTCCCTGCGG ACTTCCGGGATGTGCGTGTCCTGGATCAGACAGCCTCCGGGAAAGGCCCTG GAGTGGCTCGCTCGCATTGACTGGGATGAGGACAAGTTCTACTCCACCTCA CTCAAGACCAGGCTGACCATCAGCAAGATACCTCTGACAACCAAGTGGTG CTCCGCATGACCAACATGGACCCAGCCGACACTGCCACTTACTACTGCGCG AGGAGCGGAGCGGGCGGAACCTCCGCCACCGCCTTCGATATTTGGGGCCCG GGTACCATGGTCACCGTGTCAAGCGGAGGAGGGGGGTCCGGGGGCGGCGGT |

TABLE 23-continued

Exemplary BCMA CAR molecules. Sequences are provided with a leader sequence.

| Name/ Description | SEQ ID NO: | Sequence |
|---|---|---|
| | | TCCGGGGGAGGCGGATCGGACATTCAGATGACTCAGTCACCATCGTCCCTG<br>AGCGCTAGCGTGGGCGACAGAGTGACAATCACTTGCCGGGCATCCCAGGAC<br>ATCTATAACAACCTTGCGGTTCCAGCTGAAGCCTGGTTCCGCACCGCGG<br>TCACTTATGTACGCCGCCAACAAGAGCCAGTCGGGAGTGCCGTCCCGGTTT<br>TCCGGTTCGGCCTCGGGAACTGACTTCACCCTGACGATCTCCAGCCTGCAA<br>CCCGAGGATTTCGCCACCTACTACTGCCAGCACTACTACCGCTTTCCCTAC<br>TCGTTCGGACAGGGAACCAAGCTGGAAATCAAGACCACTACCCCAGCACCG<br>AGGCCACCCACCCCGGCTCCTACCATCGCCTCCCAGCCTCTGTCCCTGCGT<br>CCGGAGGCATGTAGACCCGCAGCTGGTGGGGCCGTGCATACCCGGGGTCTT<br>GACTTCGCCTGCGATATCTACATTTGGGCCCCTCTGGCTGGTACTTGCGGG<br>GTCCTGCTGCTTTCACTCGTGATCACTCTTTACTGTAAGCGCGGTCGGAAG<br>AAGCTGCTGTACATCTTTAAGCAACCCTTCATGAGGCCTGTGCAGACTACT<br>CAAGAGGAGGACGGCTGTTCATGCCGGTTCCCAGAGGAGGAGGAAGGCGGC<br>TGCGAACTGCGCGTGAAATTCAGCCGCAGCGCAGATGCTCCAGCCTACAAG<br>CAGGGGCAGAACCAGCTCTACAACGAACTCAATCTTGGTCGGAGAGAGGAG<br>TACGACGTGCTGGACAAGCGGAGAGGACGGGACCCAGAAATGGGCGGGAAG<br>CCGCGCAGAAAGAATCCCCAAGAGGGCCTGTACAACGAGCTCCAAAAGGAT<br>AAGATGGCAGAAGCCTATAGCGAGATTGGTATGAAAGGGGAACGCAGAAGA<br>GGCAAAGGCCACGACGGACTGTACCAGGGACTCAGCACCGCCACCAAGGAC<br>ACCTATGACGCTCTTCACATGCAGGCCCTGCCGCCTCGG |
| 149364 | | |
| 149364-aa Full CAR | 8581 | MALPVTALLLPLALLLHAARPEVQLVESGGGLVKPGGSLRLSCAASGFTFS<br>SYSMNWVRQAPGKGLEWVSSISSSSSYIYYADSVKGRFTISRDNAKNSLYL<br>QMNSLRAEDTAVYYCAKTIAAVYAFDIWGQGTTVTVSSGGGGSGGGGSGGG<br>GSEIVLTQSPLSLPVTPEEPASISCRSSQSLLHSNGYNYLDWYLQKPGQSP<br>QLLIYLGSNRASGVPDRFSGSGSGTDFTLKISRVEAEDVGVYYCMQALQTP<br>YTFGQGTKLEIKTTTPAPRPPTPAPTIASQPLSLRPEACRPAAGGAVHTRG<br>LDFACDIYIWAPLAGTCGVLLLSLVITLYCKRGRKKLLYIFKQPFMRPVQT<br>TQEEDGCSCRFPEEEEGGCELRVKFSRSADAPAYKQGQNQLYNELNLGRRE<br>EYDVLDKRRGRDPEMGGKPRRKNPQEGLYNELQKDKMAEAYSEIGMKGERR<br>RGKGHDGLYQGLSTATKDTYDALHMQALPPR |
| 149364-nt Full CAR | 8603 | ATGGCCCTCCCTGTCACCGCCCTGCTGCTTCCGCTGGCTCTTCTGCTCCAC<br>GCCGCTCGGCCCGAAGTGCAGCTTGTCGAATCCGGGGGGGACTGGTCAAG<br>CCGGGCGGATCACTGAGACTGTCCTGCGCCGCGAGCGGCTTCACGTTCTCC<br>TCCTACTCCATGAACTGGGTCCGCCAAGCCCCCGGGAAGGGACTGGAATGG<br>GTGTCCTCTATCTCCTCGTCGTCGTCCTACATCTACTACGCCGACTCCGTG<br>AAGGGAAGATTCACCATTTCCCGCGACAACGCAAAGAACTCACTGTACTTG<br>CAAATGAACTCACTCCGGGCCGAAGATACTGCTGTGTACTATTGCGCCAAG<br>ACTATTGCCGCCGTCTACGCTTTCGACATCTGGGGCCAGGGAACCACCGTG<br>ACTGTGTCGTCCGGTGGTGGTGGCTCGGCGGAGGAGGAAGCGGCGGCGGG<br>GGGTCCGAGATTGTGCTGACCCAGTCGCCACTGAGCCTCCCTGTGACCCCC<br>GAGGAACCCGCCAGCATCAGCTGCCGGTCCAGCCAGTCCCTGCTCCACTCC<br>AACGGATACAATTACCTCGATTGGTACCTTCAGAAGCCTGGACAAAGCCCG<br>CAGCTGCTCATCTACTTGGGATCAAACCGCGCGTCAGGAGTGCCTGACCGG<br>TTCTCCGGCTCGGGCAGCGGTACCGATTTCACCCTGAAAATCTCCAGGGTG<br>GAGGCAGAGGACGTGGGAGTGTATTACTGTATGCAGGCGCTGCAGACTCCG<br>TACACATTTGGGCAGGGCACCAAGCTGGAGATCAAGACCACTACCCCAGCA<br>CCGAGGCCACCCACCCCGGCTCCTACCATCGCCTCCCAGCCTCTGTCCCTG<br>CGTCCGGAGGCATGTAGACCCGCAGCTGGTGGGGCCGTGCATACCCGGGGT<br>CTTGACTTCGCCTGCGATATCTACATTTGGGCCCCTCTGGCTGGTACTTGC<br>GGGGTCCTGCTGCTTTCACTCGTGATCACTCTTTACTGTAAGCGCGGTCGG<br>AAGAAGCTGCTGTACATCTTTAAGCAACCCTTCATGAGGCCTGTGCAGACT<br>ACTCAAGAGGAGGACGGCTGTTCATGCCGGTTCCCAGAGGAGGAGGAAGGC<br>GGCTGCGAACTGCGCGTGAAATTCAGCCGCAGCGCAGATGCTCCAGCCTAC<br>AAGCAGGGGCAGAACCAGCTCTACAACGAACTCAATCTTGGTCGGAGAGAG<br>GAGTACGACGTGCTGGACAAGCGGAGAGGACGGGACCCAGAAATGGGCGGG<br>AAGCCGCGCAGAAAGAATCCCCAAGAGGGCCTGTACAACGAGCTCCAAAAG<br>GATAAGATGGCAGAAGCCTATAGCGAGATTGGTATGAAAGGGGAACGCAGA<br>AGAGGCAAAGGCCACGACGGACTGTACCAGGGACTCAGCACCGCCACCAAG<br>GACACCTATGACGCTCTTCACATGCAGGCCCTGCCGCCTCGG |
| 149365 | | |
| 149365-aa Full CAR | 8582 | MALPVTALLLPLALLLHAARPEVQLVESGGGLVKPGGSLRLSCAASGFTFS<br>DYYMSWIRQAPGKGLEWVSYISSSGSTIYYADSVKGRFTISRDNAKNSLYL<br>QMNSLRAEDTAVYYCARDLRGAFDIWGQGTMVTVSSGGGGSGGGGSGGGGS<br>SYVLTQSPSVSAAPGYTATISCGGNNIGTKSVHWYQQKPGQAPLLVIRDDS<br>VRPSKIPGRFSGSNSGNMATLTISGVQAGDEADFYCQVWDSDSEHVVEGGG<br>TKLTVLTTTPAPRPPTPAPTIASQPLSLRPEACRPAAGGAVHTRGLDFACD<br>IYIWAPLAGTCGVLLLSLVITLYCKRGRKKLLYIFKQPFMRPVQTTQEEDG<br>CSCRFPEEEEGGCELRVKFSRSADAPAYKQGQNQLYNELNLGRREEYDVLD<br>KRRGRDPEMGGKPRRKNPQEGLYNELQKDKMAEAYSEIGMKGERRRGKGHD<br>GLYQGLSTATKDTYDALHMQALPPR |

TABLE 23-continued

Exemplary BCMA CAR molecules. Sequences are provided with a leader sequence.

| Name/ Description | SEQ ID NO: | Sequence |
|---|---|---|
| 149365-nt Full CAR | 8604 | ATGGCCCTCCCTGTCACCGCCCTGCTGCTTCCGCTGGCTCTTCTGCTCCAC GCCGCTCGGCCCGAAGTCCAGCTCGTGGAGTCCGGCGGAGGCCTTGTGAAG CCTGGAGGTTCGCTGAGACTGTCCTGCGCCGCCTCCGGCTTCACCTTCTCC GACTACTACATGTCCTGGATCAGACAGGCCCCGGGAAAGGGCCTGGAATGG GTGTCCTACATCTCGTCATCGGGCAGCACTATCTACTACGCGGACTCAGTG AAGGGGCGGTTCACCATTTCCCGGGATAACGCGAAGAACTCGCTGTATCTG CAAATGAACTCACTGAGGGCCGAGGACACCGCCGTGTACTACTGCGCCCGC GATCTCCGCGGGGCATTTGACATCTGGGGACAGGGAACCATGGTCACAGTG TCCAGCGGAGGGGGAGGATCGGGTGGCGGAGGTTCCGGGGGTGGAGGCTCC TCCTACGTGCTGACTCAGAGCCCAAGCGTCAGCGCTGCGCCCGGTTACACG GCAACCATCTCCTGTGGCGGAAACAACATTGGGACCAAGTCTGTGCACTGG TATCAGCAGAAGCGGGCCAAGCTCCCTGTTGGTGATCCGCGATGACTCC GTGCGGCCTAGCAAAATTCCGGGACGGTTCTCCGGCTCCAACAGCGGCAAT ATGGCCACTCTCACCATCTCGGGAGTGCAGGCCGGAGATGAAGCCGACTTC TACTGCCAAGTCTGGGACTCAGACTCCGAGCATGTGGTGTTCGGGGGCGGA ACCAAGCTGACTGTGCTCACCACTACCCCAGCACCGAGGCCACCCACCCCG GCTCCTACCATCGCCTCCCAGCCTCTGTCCCTGCGTCCGGAGGCATGTAGA CCCGCAGCTGGTGGGGCCGTGCATACCCGGGGTCTTGACTTCGCCTGCGAT ATCTACATTTGGGCCCCTCTGGCTGGTACTTGCGGGGTCCTGCTGCTTTCA CTCGTGATCACTCTTTACTGTAAGCGCGGTCGGAAGAAGCTGCTGTACATC TTTAAGCAACCCTTCATGAGGCCTGTGCAGACTACTCAAGAGGAGGACGGC TGTTCATGCCGGTTCCCAGAGGAGGAGGAAGGCGGCTGCGAACTGCGCGTG AAATTCAGCCGCAGCGCAGATGCTCCAGCCTACAAGCAGGGGCAGAACCAG CTCTACAACGAACTCAATCTTGGTCGGAGAGAGGAGTACGACGTGCTGGAC AAGCGGAGAGGACGGGACCCAGAAATGGGCGGGAAGCCGCGCAGAAAGAAT CCCCAAGAGGGCCTGTACAACGAGCTCCAAAAGGATAAGATGGCAGAAGCC TATAGCGAGATTGGTATGAAAGGGGAACGCAGAAGAGGCAAAGGCCACGAC GGACTGTACCAGGGACTCAGCACCGCCACCAAGGACACCTATGACGCTCTT CACATGCAGGCCCTGCCGCCTCGG |
| 149366 | | |
| 149366-aa Full CAR | 8583 | MALPVTALLLPLALLLHAARPQVQLVQSGAEVKKPGASVKVSCKPSGYTVT SHYIHWVRRAPGQGLEWMGMINPSGGVTAYSQTLQGRVTMTSDTSSSTVYM ELSSLRSEDTAMYYCAREGSGSGWYFDFWGRGTLVTVSSGGGGSGGGGSGG GGSSYVLTQPPSVSVSPGQTASITCSGDGLSKKYVSWYQQKAGQSPVVLIS RDKERPSGIPDRFSGSNSADTATLTISGTQAMDEADYYCQAWDDTTVVEGG GTKLTVLTTTPAPRPPTPAPTIASQPLSLRPEACRPAAGGAVHTRGLDFAC DIYIWAPLAGTCGVLLLSLVITLYCKRGRKKLLYIFKQPFMRPVQTTQEED GCSCRFPEEEEGGCELRVKFSRSADAPAYKQGQNQLYNELNLGRREEYDVL DKRRGRDPEMGGKPRRKNPQEGLYNELQKDKMAEAYSEIGMKGERRRGKGH DGLYQGLSTATKDTYDALHMQALPPR |
| 149366-nt Full CAR | 8605 | ATGGCCCTCCCTGTCACCGCCCTGCTGCTTCCGCTGGCTCTTCTGCTCCAC GCCGCTCGGCCCAAGTGCAGCTGGTGCAGAGCGGGCCGAAGTCAAGAAG CCGGGGAGCCTCCGTGAAAGTGTCCTGCAAGCCTTCGGGATACACCGTGACC TCCCACTACATTCATTGGGTCCGCCGCGCCCCCGGCCAAGGACTCGAGTGG ATGGGCATGATCAACCCTAGCGGCGGAGTGACCGCGTACAGCCAGACGCTG CAGGGACGCGTGACTATGACCTCGGATACCTCCTCCTCCACCGTCTATATG GAACTGTCCAGCCTGCGGTCCGAGGATACCGCCATGTACTACTGCGCCCGG GAAGGATCAGGCTCCGGGTGGTATTTCGACTTCTGGGGAAGAGGCACCCTC GTGACTGTGTCATCTGGGGAGGGGGTTCCGGTGGTGGCGGATCGGGAGGA GGCGGTTCATCCTACGTGCTGACCCAGCCACCCTCCGTGTCCGTGAGCCCC GGCCAGACTGCATCGATTACATGTAGCGGCGACGGCCTCTCCAAGAAATAC GTGTCGTGGTACCAGCAGAAGGCCGGACAGAGCCCGGTGGTGCTGATCTCA AGAGATAAGGAGCGGCCTAGCGGAATCCCGGACAGGTTCTCGGGTTCCAAC TCCGCGGACACTGCTACTCTGACCATCTCGGGGACCCAGGCTATGGACGAA GCCGATTACTACTGCCAAGCTGGGACGACACTACTGTCGTGTTTGGAGGG GGCACCAAGTTGACCGTCCTTACCACTACCCCAGCACCGAGGCCACCCACC CCGGCTCCTACCATCGCCTCCCAGCCTCTGTCCCTGCGTCCGGAGGCATGT AGACCCGCAGCTGGTGGGGCCGTGCATACCCGGGGTCTTGACTTCGCCTGC GATATCTACATTTGGGCCCCTCTGGCTGGTACTTGCGGGGTCCTGCTGCTT TCACTCGTGATCACTCTTTACTGTAAGCGCGGTCGGAAGAAGCTGCTGTAC ATCTTTAAGCAACCCTTCATGAGGCCTGTGCAGACTACTCAAGAGGAGGAC GGCTGTTCATGCCGGTTCCCAGAGGAGGAGGAAGGCGGCTGCGAACTGCGC GTGAAATTCAGCCGCAGCGCAGATGCTCCAGCCTACAAGCAGGGGCAGAAC CAGCTCTACAACGAACTCAATCTTGGTCGGAGAGAGGAGTACGACGTGCTG GACAAGCGGAGAGGACGGGACCCAGAAATGGGCGGGAAGCCGCGCAGAAAG AATCCCCAAGAGGGCCTGTACAACGAGCTCCAAAAGGATAAGATGGCAGAA GCCTATAGCGAGATTGGTATGAAAGGGGAACGCAGAAGAGGCAAAGGCCAC GACGGACTGTACCAGGGACTCAGCACCGCCACCAAGGACACCTATGACGCT CTTCACATGCAGGCCCTGCCGCCTCGG |

TABLE 23-continued

Exemplary BCMA CAR molecules. Sequences are provided with a leader sequence.

| Name/ Description | SEQ ID NO: | Sequence |
|---|---|---|
| 149367 | | |
| 149367-aa Full CAR | 8584 | MALPVTALLLPLALLLHAARPQVQLQESGPGLVKPSQTLSLTCTVSGGSIS SGGYYWSWIRQHPGKGLEWIGYIYYSGSTYYNPSLKSRVTISVDTSKNQFS LKLSSVTAADTAVYYCARAGIAARLRGAFDIWGQGTMVTVSSGGGGSGGGG SGGGGSDIVMTQSPSSVSASVGDRVIITCRASQGIRNWLAWYQQKPGKAPN LLIYAASNLQSGVPSRFSGSGSGADFTLTISSLQPEDVATYYCQKYNSAPF TFGPGTKVDIKTTTPAPRPPTPAPTIASQPLSLRPEACRPAAGGAVHTRGL DFACDIYIWAPLAGTCGVLLLSLVITLYCKRGRKKLLYIFKQPFMRPVQTT QEEDGCSCRFPEEEEGGCELRVKFSRSADAPAYKQGQNQLYNELNLGRREE YDVLDKRRGRDPEMGGKPRRKNPQEGLYNELQKDKMAEAYSEIGMKGERRR GKGHDGLYQGLSTATKDTYDALHMQALPPR |
| 149367-nt Full CAR | 8606 | ATGGCCCTCCCTGTCACCGCCCTGCTGCTTCCGCTGGCTCTTCTGCTCCAC GCCGCTCGGCCCCAAGTGCAGCTTCAGGAGAGCGGCCCGGGACTCGTGAAG CCGTCCCAGACCCTGTCCCTGACTTGCACCGTGTCGGGAGGAAGCATCTCG AGCGGAGGCTACTATTGGTCGTGGATTCGGCAGCACCCTGGAAAGGGCCTG GAATGGATCGGCTACATCTACTACTCCGGCTCGACCTACTACAACCCATCG CTGAAGTCCAGAGTGACAATCTCAGTGGACACGTCCAAGAATCAGTTCAGC CTGAAGCTCTCTTCCGTGACTGCGGCCGACACCGCCGTGTACTACTGCGCA CGCGCTGGAATTGCCGCCCGGCTGAGGGGTGCCTTCGACATTTGGGGACAG GGCACCATGGTCACCGTGTCCTCCGGCGGCGGAGGTTCCGGGGGTGGAGGC TCAGGAGGAGGGGGTCCGACATCGTCATGACTCAGTCGCCCTCAAGCGTC AGCGCGTCCGTCGGGGACAGAGTGATCATCACCTGTCGGGCGTCCCAGGGA ATTCGCAACTGGCTGGCCTGGTATCAGCAGAAGCCCGGAAAGGCCCCCAAC CTGTTGATCTACGCCGCCTCAAACCTCCAATCCGGGGTGCCGAGCCGCTTC AGCGGCTCCGGTTCGGGTGCCGATTTCACTCTGACCATCTCCTCCCTGCAA CCTGAAGATGTGGCTACCTACTACTGCCAAAAGTACAACTCCGCACCTTTT ACTTTCGGACCGGGGACCAAAGTGGACATTAAGACCACTACCCCAGCACCG AGGCCACCCACCCCGGCTCCTACCATCGCCTCCCAGCCTCTGTCCCTGCGT CCGGAGGCATGTAGACCCGCAGCTGGTGGGGCCGTGCATACCCGGGGTCTT GACTTCGCCTGCGATATCTACATTTGGGCCCCTCTGGCTGGTACTTGCGGG GTCCTGCTGCTTTCACTCGTGATCACTCTTTACTGTAAGCGCGGTCGGAAG AAGCTGCTGTACATCTTTAAGCAACCCTTCATGAGGCCTGTGCAGACTACT CAAGAGGAGGACGGCTGTTCATGCCGGTTCCCAGAGGAGGAGGAAGGCGGC TGCGAACTGCGCGTGAAATTCAGCCGCAGCGCAGATGCTCCAGCCTACAAG CAGGGGCAGAACCAGCTCTACAACGAACTCAATCTTGGTCGGAGAGAGGAG TACGACGTGCTGGACAAGCGGAGAGGACGGGACCCAGAAATGGGCGGGAAG CCGCGCAGAAAGAATCCCCAAGAGGGCCTGTACAACGAGCTCCAAAAGGAT AAGATGGCAGAAGCCTATAGCGAGATTGGTATGAAAGGGGAACGCAGAAGA GGCAAAGGCCACGACGGACTGTACCAGGGACTCAGCACCGCCACCAAGGAC ACCTATGACGCTCTTCACATGCAGGCCCTGCCGCCTCGG |
| 149368 | | |
| 149368-aa Full CAR | 8585 | MALPVTALLLPLALLLHAARPQVQLVQSGAEVKKPGSSVKVSCKASGGTFS SYAISWVRQAPGQGLEWMGGIIPIFGTANYAQKFQGRVTITADESTSTAYM ELSSLRSEDTAVYYCARRGGYQLLRWDVGLLRSAFDIWGQGTMVTVSSGGG GSGGGGSGGGGSSYVLTQPPSVSVAPGQTARITCGGNNIGSKSVHWYQQKP GQAPVLVLYGKNNRPSGVPDRFSGSRSGTTASLTITGAQAEDEADYYCSSR DSSGDHLRVFGTGTKVTVLTTTPAPRPPTPAPTIASQPLSLRPEACRPAAG GAVHTRGLDFACDIYIWAPLAGTCGVLLLSLVITLYCKRGRKKLLYIFKQP FMRPVQTTQEEDGCSCRFPEEEEGGCELRVKFSRSADAPAYKQGQNQLYNE LNLGRREEYDVLDKRRGRDPEMGGKPRRKNPQEGLYNELQKDKMAEAYSEI GMKGERRRGKGHDGLYQGLSTATKDTYDALHMQALPPR |
| 149368-nt Full CAR | 8607 | ATGGCCCTCCCTGTCACCGCCCTGCTGCTTCCGCTGGCTCTTCTGCTCCAC GCCGCTCGGCCCCAAGTGCAGCTGGTCCAGTCGGGCGCCGAGGTCAAGAAG CCCGGGAGCTCTGTGAAAGTGTCCTGCAAGGCCTCCGGGGGCACCTTTAGC TCCTACGCCATCTCCTGGGTCCGCCAAGCACCGGGTCAAGGCCTGGAGTGG ATGGGGGGAATTATCCCTATCTTCGGCACTGCCAACTACGCCCAGAAGTTC CAGGGACGCGTGACCATTACCGCGGACGAATCCACCTCCACCGCTTATATG GAGCTGTCCAGCTTGCGCTCGGAAGATACCGCCGTGTACTACTGCGCCCGG AGGGGTGGATACCAGCTGCTGAGATGGGACGTGGGCCTCCTGCGGTCGGCG TTCGACATCTGGGGCCAGGGCACTATGGTCACTGTGTCCAGCGGAGGAGGC GGATCGGGAGGCGGCGGATCAGGGGGAGGCGGTTCCAGCTACGTGCTTACT CAACCCCCTTCGGTGTCCGTGGCCCCGGGACAGACCGCCAGAATCACTTGC GGAGGGAAACAACATTGGGTCCAAGAGCGTGCATTGGTACCAGCAGAAGCCA GGACAGGCCCCTGTGCTGGTGCTCTACGGGAAGAACAATCGGCCCAGCGGA GTGCCGGACAGGTTCTCGGGTTCACGCTCCGGTACAACCGCTTCACTGACT ATCACCGGGGCCCAGGCAGAGGATGAAGCGGACTACTACTGTTCCTCCCGG GATTCATCCGGCGACCACCTCCGGGTGTTCGGAACCGGAACGAAGGTCACC GTGCTGACCACTACCCCAGCACCGAGGCCACCCACCCCGGCTCCTACCATC GCCTCCCAGCCTCTGTCCCTGCGTCCGGAGGCATGTAGACCCGCAGCTGGT GGGGCCGTGCATACCCGGGGTCTTGACTTCGCCTGCGATATCTACATTTGG GCCCCTCTGGCTGGTACTTGCGGGGTCCTGCTGCTTTCACTCGTGATCACT |

TABLE 23-continued

Exemplary BCMA CAR molecules. Sequences are provided with a leader sequence.

| Name/<br>Description | SEQ ID<br>NO: | Sequence |
|---|---|---|
| | | CTTTACTGTAAGCGCGGTCGGAAGAAGCTGCTGTACATCTTTAAGCAACCC<br>TTCATGAGGCCTGTGCAGACTACTCAAGAGGAGGACGGCTGTTCATGCCGG<br>TTCCCAGAGGAGGAGGAAGGCGGCTGCGAACTGCGCGTGAAATTCAGCCGC<br>AGCGCAGATGCTCCAGCCTACAAGCAGGGGCAGAACCAGCTCTACAACGAA<br>CTCAATCTTGGTCGGAGAGAGGAGTACGACGTGCTGGACAAGCGGAGAGGA<br>CGGGACCCAGAAATGGGCGGGAAGCCGCGCAGAAAGAATCCCCAAGAGGGC<br>CTGTACAACGAGCTCCAAAAGGATAAGATGGCAGAAGCCTATAGCGAGATT<br>GGTATGAAAGGGGAACGCAGAAGAGGCAAAGGCCACGACGGACTGTACCAG<br>GGACTCAGCACCGCCACCAAGGACACCTATGACGCTCTTCACATGCAGGCC<br>CTGCCGCCTCGG |
| 149369 | | |
| 149369-aa<br>Full CAR | 8586 | MALPVTALLLPLALLLHAARPEVQLQQSGPGLVKPSQTLSLTCAISGDSVS<br>SNSAAWNWIRQSPSRGLEWLGRTYYRSKWYSFYAISLKSRIIINPDTSKNQ<br>FSLQLKSVTPEDTAVYYCARSSPEGLFLYWFDPWGQGTLVTVSSGGDGSGG<br>GGSGGGGSSSELTQDPAVSVALGQTIRITCQGDSLGNYYATWYQQKPGQAP<br>VLVIYGTNNRPSGIPDRFSASSSGNTASLTITGAQAEDEADYYCNSRDSSG<br>HHLLFGTGTKVTVLTTTPAPRPPTPAPTIASQPLSLRPEACRPAAGGAVHT<br>RGLDFACDIYIWAPLAGTCGVLLLSLVITLYCKRGRKKLLYIFKQPFMRPV<br>QTTQEEDGCSCRFPEEEEGGCELRVKFSRSADAPAYKQGQNQLYNELNLGR<br>REEYDVLDKRRGRDPEMGGKPRRKNPQEGLYNELQKDKMAEAYSEIGMKGE<br>RRRGKGHDGLYQGLSTATKDTYDALHMQALPPR |
| 149369-nt<br>Full CAR | 8608 | ATGGCCCTCCCTGTCACCGCCCTGCTGCTTCCGCTGGCTCTTCTGCTCCAC<br>GCCGCTCGGCCCGAAGTGCAGCTCCAACAGTCAGGACCGGGGCTCGTGAAG<br>CCATCCCAGACCCTGTCCCTGACTTGTGCCATCTCGGGAGATAGCGTGTCA<br>TCGAACTCCGCCGCCTGGAACTGGATTCGGCAGAGCCCGTCCCGCGGACTG<br>GAGTGGCTTGGAAGGACCTACTACCGGTCCAAGTGGTACTCTTTCTACGCG<br>ATCTCGCTGAAGTCCCGCATTATCATTAACCCTGATACCTCCAAGAATCAG<br>TTCTCCCTCCAACTGAAATCCGTCACCCCCGAGGACACAGCAGTGTATTAC<br>TGCGCACGGAGCAGCCCCGAAGGACTGTTCCTGTATTGGTTTGACCCCTGG<br>GGCCAGGGGACTCTTGTGACCGTGTCGAGCGGCGGAGATGGGTCCGGTGGC<br>GGTGGTTCGGGGGGCGGCGGATCATCATCCGAACTGACCCAGGACCCGGCT<br>GTGTCCGTGGCGCTGGGACAAACCATCCGCATTACGTGCCAGGGAGACTCC<br>CTGGGCAACTACTACGCCACTTGGTACCAGCAGAAGCCGGGCCAAGCCCCT<br>GTGTTGGTCATCTACGGGACCAACAACAGACCTTCCGGCATCCCCGACCGG<br>TTCAGCGCTTCGTCCTCCGGCAACACTGCCAGCCTGACCATCACTGGAGCG<br>CAGGCCGAAGATGAGGCCGACTACTACTGCAACAGCAGAGACTCCTCGGGT<br>CATCACCTCTTGTTCGGAACTGGAACCAAGGTCACCGTGCTGACCACTACC<br>CCAGCACCGAGGCCACCCACCCCGGCTCCTACCATCGCCTCCCAGCCTCTG<br>TCCCTGCGTCCGGAGGCATGTAGACCCGCAGCTGGTGGGGCCGTGCATACC<br>CGGGGTCTTGACTTCGCCTGCGATATCTACATTTGGGCCCCTCTGGCTGGT<br>ACTTGCGGGGTCCTGCTGCTTTCACTCGTGATCACTCTTTACTGTAAGCGC<br>GGTCGGAAGAAGCTGCTGTACATCTTTAAGCAACCCTTCATGAGGCCTGTG<br>CAGACTACTCAAGAGGAGGACGGCTGTTCATGCCGGTTCCCAGAGGAGGAG<br>GAAGGCGGCTGCGAACTGCGCGTGAAATTCAGCCGCAGCGCAGATGCTCCA<br>GCCTACAAGCAGGGGCAGAACCAGCTCTACAACGAACTCAATCTTGGTCGG<br>AGAGAGGAGTACGACGTGCTGGACAAGCGGAGAGGACGGGACCCAGAAATG<br>GGCGGGAAGCCGCGCAGAAAGAATCCCCAAGAGGGCCTGTACAACGAGCTC<br>CAAAAGGATAAGATGGCAGAAGCCTATAGCGAGATTGGTATGAAAGGGGAA<br>CGCAGAAGAGGCAAAGGCCACGACGGACTGTACCAGGGACTCAGCACCGCC<br>ACCAAGGACACCTATGACGCTCTTCACATGCAGGCCCTGCCGCCTCGG |
| BCMA_EBB-<br>C1978-A4 | | |
| BCMA_EBB-<br>C1978-A4-<br>aa<br>Full CAR | 8587 | MALPVTALLLPLALLLHAARPEVQLVESGGGLVQPGGSLRLSCAASGFTFS<br>SYAMSWVRQAPGKGLEWVSAISGSGGSTYYADSVKGRFTISRDNSKNTLYL<br>QMNSLRAEDTAVYYCAKVEGSGSLDYWGQGTLVTVSSGGGGSGGGGSGGGG<br>SEIVMTQSPGTLSLSPGERATLSCRASQSVSSAYLAWYQQKPGQPPRLLIS<br>GASTRATGIPDRFGGSGSGTDFTLTISRLEPEDFAVYYCQHYGSSFNGSSL<br>FTFGQGTRLEIKTTTPAPRPPTPAPTIASQPLSLRPEACRPAAGGAVHTRG<br>LDFACDIYIWAPLAGTCGVLLLSLVITLYCKRGRKKLLYIFKQPFMRPVQT<br>TQEEDGCSCRFPEEEEGGCELRVKFSRSADAPAYKQGQNQLYNELNLGRRE<br>EYDVLDKRRGRDPEMGGKPRRKNPQEGLYNELQKDKMAEAYSEIGMKGERR<br>RGKGHDGLYQGLSTATKDTYDALHMQALPPR |
| BCMA_EBB-<br>C1978-A4-<br>nt<br>Full CAR | 8609 | ATGGCCCTCCCTGTCACCGCCCTGCTGCTTCCGCTGGCTCTTCTGCTCCAC<br>GCCGCTCGGCCCGAAGTGCAGCTCGTGGAGTCAGGAGGCGGCCTGGTCCAG<br>CCGGGAGGGTCCCTTAGACTGTCATGCGCCGCAAGCGGATTCACTTTCTCC<br>TCCTATGCCATGAGCTGGGTCCGCCAAGCCCCCGGAAAGGGACTGGAATGG<br>GTGTCCGCCATCTCGGGGTCTGGAGGCTCAACTTACTACGCTGACTCCGTG<br>AAGGGACGGTTCACCATTAGCCGCGACAACTCCAAGAACACCCTCTACCTC<br>CAAATGAACTCCCTGCGGGCCGAGGATACCGCCGTCTACTACTGCGCCAAA<br>GTGGAAGGTTCAGGATCGCTGGACTACTGGGGACAGGGTACTCTCGTGACC<br>GTGTCATCGGGCGGAGGAGGTTCCGGCGGTGGCGGCTCCGGCGGCGGAGGG |

TABLE 23-continued

Exemplary BCMA CAR molecules. Sequences are provided with a leader sequence.

| Name/ Description | SEQ ID NO: | Sequence |
|---|---|---|
| | | TCGGAGATCGTGATGACCCAGAGCCCTGGTACTCTGAGCCTTTCGCCGGGA GAAAGGGCCACCCTGTCCTGCCGCGCTTCCCAATCCGTGTCCTCCGCGTAC TTGGCGTGGTACCAGCAGAAGCCGGGACAGCCCCTCGGCTGCTGATCAGC GGGGCCAGCACCCGGGCAACCGGAATCCCAGACAGATTCGGGGGTTCCGGC AGCGGCACAGATTTCACCCTGACTATTTCGAGGTTGGAGCCCGAGGACTTT GCGGTGTATTACTGTCAGCACTACGGGTCGTCCTTTAATGGCTCCAGCCTG TTCACGTTCGGACAGGGGACCCGCCTGGAAATCAAGACCACTACCCCAGCA CCGAGGCCACCCACCCCGGCTCCTACCATCGCCTCCCAGCCTCTGTCCCTG CGTCCGGAGGCATGTAGACCCGCAGCTGGTGGGGCCGTGCATACCCGGGGT CTTGACTTCGCCTGCGATATCTACATTTGGGCCCCTCTGGCTGGTACTTGC GGGGTCCTGCTGCTTTCACTCGTGATCACTCTTTACTGTAAGCGCGGTCGG AAGAAGCTGCTGTACATCTTTAAGCAACCCTTCATGAGGCCTGTGCAGACT ACTCAAGAGGAGGACGGCTGTTCATGCCGGTTCCCAGAGGAGGAGGAAGGC GGCTGCGAACTGCGCGTGAAATTCAGCCGCAGCGCAGATGCTCCAGCCTAC AAGCAGGGGCAGAACCAGCTCTACAACGAACTCAATCTTGGTCGGAGAGAG GAGTACGACGTGCTGGACAAGCGGAGAGGACGGGACCCAGAAATGGGCGGG AAGCCGCGCAGAAAGAATCCCCAAGAGGGCCTGTACAACGAGCTCCAAAAG GATAAGATGGCAGAAGCCTATAGCGAGATTGGTATGAAAGGGGAACGCAGA AGAGGCAAAGGCCACGACGGACTGTACCAGGGACTCAGCACCGCCACCAAG GACACCTATGACGCTCTTCACATGCAGGCCCTGCCGCCTCGG |
| BCMA_EBB-C1978-G1 | | |
| BCMA_EBB-C1978-G1-aa Full CAR | 8588 | MALPVTALLLPLALLLHAARPEVQLVETGGGLVQPGGSLRLSCAASGITFS RYPMSWVRQAPGKGLEWVSGISDSGVSTYYADSAKGRFTISRDNSKNTLFL QMSSLRDEDTAVYYCVTRAGSEASDIWGQGTMVTVSSGGGGSGGGGSGGGG SEIVLTQSPATLSLSPGERATLSCRASQSVSNSLAWYQQKPGQAPRLLIYD ASSRATGIPDRFSGSGSGTDFTLTISRLEPEDFAIYYCQQFGTSSGLTFGG GTKLEIKTTTPAPRPPTPAPTIASQPLSLRPEACRPAAGGAVHTRGLDFAC DIYIWAPLAGTCGVLLLSLVITLYCKRGRKKLLYIFKQPFMRPVQTTQEED GCSCRFPEEEEGGCELRVKFSRSADAPAYKQGQNQLYNELNLGRREEYDVL DKRRGRDPEMGGKPRRKNPQEGLYNELQKDKMAEAYSEIGMKGERRRGKGH DGLYQGLSTATKDTYDALHMQALPPR |
| BCMA_EBB-C1978-G1-nt Full CAR | 8610 | ATGGCCCTCCCTGTCACCGCCCTGCTGCTTCCGCTGGCTCTTCTGCTCCAC GCCGCTCGGCCCGAAGTGCAACTGGTGGAAACCGGTGGCGGCCTGGTGCAG CCTGGAGGATCATTGAGGCTGTCATGCGCGGCCAGCGGTATTACCTTCTCC CGGTACCCCATGTCCTGGGTCAGACAGGCCCCGGGGAAAGGGCTTGAATGG GTGTCCGGGATCTCGGACTCCGGTGTCAGCACTTACTACGCCGACTCCGCC AAGGGACGCTTCACCATTTCCCGGGACAACTCGAAGAACACCCTGTTCCTC CAAATGAGCTCCCTCCGGGACGAGGATACTGCAGTGTACTACTGCGTGACC CGCGCCGGGTCCGAGGCGTCTGACATTTGGGGACAGGGCACTATGGTCACC GTGTCGTCCGGCGGAGGGGGCTCGGGAGGCGGTGGCAGCGGAGGAGGAGGG TCCGAGATCGTGCTGACCCAATCCCCGGCCACCCTCTCGCTGAGCCCTGGA GAAAGGGCAACCTTGTCCTGTCGCGCGAGCCAGTCCGTGAGCAACTCCCTG GCCTGGTACCAGCAGAAGCCCGGACAGGCTCCGAGACTTCTGATCTACGAC GCTTCGAGCCGGGCCACTGGAATCCCCGACCGCTTTTCGGGGTCCGGCTCA GGAACCGATTTCACCCTGACAATCTCACGGCTGGAGCCAGAGGATTTCGCC ATCTATTACTGCCAGCAGTTCGGTACTTCCTCCGGCCTGACTTTCGGAGGC GGCACGAAGCTGAAATCAAGACCACTACCCCAGCACCGAGGCCACCCACC CCGGCTCCTACCATCGCCTCCCAGCCTCTGTCCCTGCTCCGGAGGCATGT AGACCCGCAGCTGGTGGGGCCGTGCATACCCGGGGTCTTGACTTCGCCTGC GATATCTACATTTGGGCCCCTCTGGCTGGTACTTGCGGGGTCCTGCTGCTT TCACTCGTGATCACTCTTTACTGTAAGCGCGGTCGGAAGAAGCTGCTGTAC ATCTTTAAGCAACCCTTCATGAGGCCTGTGCAGACTACTCAAGAGGAGGAC GGCTGTTCATGCCGGTTCCCAGAGGAGGAGGAAGGCGGCTGCGAACTGCGC GTGAAATTCAGCCGCAGCGCAGATGCTCCAGCCTACAAGCAGGGGCAGAAC CAGCTCTACAACGAACTCAATCTTGGTCGGAGAGAGGAGTACGACGTGCTG GACAAGCGGAGAGGACGGGACCCAGAAATGGGCGGGAAGCCGCGCAGAAAG AATCCCCAAGAGGGCCTGTACAACGAGCTCCAAAAGGATAAGATGGCAGAA GCCTATAGCGAGATTGGTATGAAAGGGGAACGCAGAAGAGGCAAAGGCCAC GACGGACTGTACCAGGGACTCAGCACCGCCACCAAGGACACCTATGACGCT CTTCACATGCAGGCCCTGCCGCCTCGG |
| BCMA_EBB-C1979-C1 | | |
| BCMA_EBB-C1979-C1-aa Full CAR | 8589 | MALPVTALLLPLALLLHAARPQVQLVESGGGLVQPGGSLRLSCAASGFTFS SYAMSWVRQAPGKGLEWVSAISGSGGSTYYADSVKGRFTISRDNAKNSLYL QMNSLRAEDTAIYYCARATYKRELRYYYGMDVWGQGTMVTVSSGGGGSGGG GSGGGGSEIVMTQSPGTVSLSPGERATLSCRASQSVSSSFLAWYQQKPGQA PRLLIYGASSRATGIPDRFSGSGSGTDFTLTISRLEPEDSAVYYCQQYHSS PSWTFGQGTRLEIKTTTPAPRPPTPAPTIASQPLSLRPEACRPAAGGAVHT RGLDFACDIYIWAPLAGTCGVLLLSLVITLYCKRGRKKLLYIFKQPFMRPV QTTQEEDGCSCRFPEEEEGGCELRVKFSRSADAPAYKQGQNQLYNELNLGR |

TABLE 23-continued

Exemplary BCMA CAR molecules. Sequences are provided with a leader sequence.

| Name/<br>Description | SEQ ID<br>NO: | Sequence |
|---|---|---|
| | | REEYDVLDKRRGRDPEMGGKPRRKNPQEGLYNELQKDKMAEAYSEIGMKGE<br>RRRGKGHDGLYQGLSTATKDTYDALHMQALPPR |
| BCMA_EBB-<br>C1979-C1-<br>nt<br>Full CAR | 8611 | ATGGCCCTCCCTGTCACCGCCCTGCTGCTTCCGCTGGCTCTTCTGCTCCAC<br>GCCGCTCGGCCCCAAGTGCAGCTCGTGGAATCGGGTGGCGGACTGGTGCAG<br>CCGGGGGGCTCACTTAGACTGTCCTGCGCGGCCAGCGGATTCACTTTCTCC<br>TCCTACGCCATGTCCTGGGTCAGACAGGCCCCTGGAAAGGGCCTGGAATGG<br>GTGTCCGCAATCAGCGGCAGCGGCGGCTCGACCTATTACGCGGATTCAGTG<br>AAGGGCAGATTCACCATTTCCCGGGACAACGCCAAGAACTCCTTGTACCTT<br>CAAATGAACTCCCTCCGCGCGGAAGATACCGCAATCTACTACTGCGCTCGG<br>GCCACTTACAAGAGGGAACTGCGCTACTACTACGGGATGGACGTCTGGGGC<br>CAGGGAACCATGGTCACCGTGTCCAGCGGAGGAGGAGGATCGGGAGGAGGC<br>GGTAGCGGGGGTGGAGGGTCGGAGATCGTGATGACCCAGTCCCCCGGCACT<br>GTGTCGCTGTCCCCCGGCGAACGGGCCACCCTGTCATGTCGGGCCAGCCAG<br>TCAGTGTCGTCAAGCTTCCTCGCCTGGTACCAGCAGAAACCGGGACAAGCT<br>CCCCGCCTGCTGATCTACGGAGCCAGCAGCCGGGCCACCGGTATTCCTGAC<br>CGGTTCTCCGGTTCGGGGTCCGGGACCGACTTTACTCTGACTATCTCTCGC<br>CTCGAGCCAGAGGACTCCGCCGTGTATTACTGCCAGCAGTACCACTCCTCC<br>CCGTCCTGGACGTTCGGACAGGGCACAAGGCTGGAGATTAAGACCACTACC<br>CCAGCACCGAGGCCACCCACCCCGGCTCCTACCATCGCCTCCCAGCCTCTG<br>TCCCTGCGTCCGGAGGCATGTAGACCCGCAGCTGGTGGGGCCGTGCATACC<br>CGGGGTCTTGACTTCGCCTGCGATATCTACATTTGGGCCCCTCTGGCTGGT<br>ACTTGCGGGGTCCTGCTGCTTTCACTCGTGATCACTCTTTACTGTAAGCGC<br>GGTCGGAAGAAGCTGCTGTACATCTTTAAGCAACCCTTCATGAGGCCTGTG<br>CAGACTACTCAAGAGGAGGACGGCTGTTCATGCCGGTTCCCAGAGGAGGAG<br>GAAGGCGGCTGCGAACTGCGCGTGAAATTCAGCCGCAGCGCAGATGCTCCA<br>GCCTACAAGCAGGGGCAGAACCAGCTCTACAACGAACTCAATCTTGGTCGG<br>AGAGAGGAGTACGACGTGCTGGACAAGCGGAGAGGACGGGACCCAGAAATG<br>GGCGGGAAGCCGCGCAGAAAGAATCCCCAAGAGGGCCTGTACAACGAGCTC<br>CAAAAGGATAAGATGGCAGAAGCCTATAGCGAGATTGGTATGAAAGGGGAA<br>CGCAGAAGAGGCAAAGGCCACGACGGACTGTACCAGGGACTCAGCACCGCC<br>ACCAAGGACACCTATGACGCTCTTCACATGCAGGCCCTGCCGCCTCGG |
| BCMA_EBB-<br>C1978-C7 | | |
| BCMA_EBB-<br>C1978-C7-<br>aa<br>Full CAR | 8590 | MALPVTALLLPLALLLHAARPEVQLVETGGGLVQPGGSLRLSCAASGFTFS<br>SYAMSWVRQAPGKGLEWVSAISGSGGSTYYADSVKGRFTISRDNSKNTLYL<br>QMNTLKAEDTAVYYCARATYKRELRYYYGMDVWGQGTTVTVSSGGGGSGGG<br>GSGGGGSEIVLTQSPSTLSLSPGESATLSCRASQSVSTTFLAWYQQKPGQA<br>PRLLIYGSSNRATGIPDRFSGSGSGTDFTLTIRRLEPEDFAVYYCQQYHSS<br>PSWTFGQGTKVEIKTTTPAPRPPTPAPTIASQPLSLRPEACRPAAGGAVHT<br>RGLDFACDIYIWAPLAGTCGVLLLSLVITLYCKRGRKKLLYIFKQPFMRPV<br>QTTQEEDGCSCRFPEEEEGGCELRVKFSRSADAPAYKQGQNQLYNELNLGR<br>REEYDVLDKRRGRDPEMGGKPRRKNPQEGLYNELQKDKMAEAYSEIGMKGE<br>RRRGKGHDGLYQGLSTATKDTYDALHMQALPPR |
| BCMA_EBB-<br>C1978-C7-<br>nt<br>Full CAR | 8612 | ATGGCCCTCCCTGTCACCGCCCTGCTGCTTCCGCTGGCTCTTCTGCTCCAC<br>GCCGCTCGGCCCGAGGTGCAGCTTGTGGAAACCGGTGGCGGACTGGTGCAG<br>CCCGGAGGAAGCCTCAGGCTGTCCTGCGCCGCGTCCGGCTTCACCTTCTCC<br>TCGTACGCCATGTCCTGGGTCCGCCAGGCCCCCGGAAAGGGCCTGGAATGG<br>GTGTCCGCCATCTCTGGAAGCGGAGGTTCCACGTACTACGCGGACAGCGTC<br>AAGGGAAGGTTCACAATCTCCCGCGATAATTCGAAGAACACTCTGTACCTT<br>CAAATGAACACCCTGAAGGCCGAGGACACTGCTGTGTACTACTGCGCACGG<br>GCCACCTACAAGAGAGAGCTCCGGTACTACTACGGGAATGGACGTCTGGGGC<br>CAGGGAACTACTGTGACCGTGTCCTCGGGAGGGGGTGGCTCCGGGGGGGGC<br>GGCTCCGGCGGAGGCGGTTCCGAGATTGTGCTGACCCAGTCACCTTCAACT<br>CTGTCGCTGTCCCGGGAGAGAGCGCTACTCTGAGCTGCCGGGCCAGCCAG<br>TCCGTGTCCACCACCTTCCTCGCCTGGTATCAGCAGAAGCCGGGCAGGCA<br>CCACGGCTCTTGATCTACGGGTCAAGCAACAGAGCGACCGGAATTCCTGAC<br>CGCTTCTCGGGGAGCGGTTCAGGCACCGACTTCACCCTGACTATCCGGCGC<br>CTGGAACCCGAAGATTTCGCCGTGTATTACTGTCAACAGTACCACTCCTCG<br>CCGTCCTGGACCTTTGGCCAAGGAACCAAAGTGGAAATCAAGACCACTACC<br>CCAGCACCGAGGCCACCCACCCCGGCTCCTACCATCGCCTCCCAGCCTCTG<br>TCCCTGCGTCCGGAGGCATGTAGACCCGCAGCTGGTGGGGCCGTGCATACC<br>CGGGGTCTTGACTTCGCCTGCGATATCTACATTTGGGCCCCTCTGGCTGGT<br>ACTTGCGGGGTCCTGCTGCTTTCACTCGTGATCACTCTTTACTGTAAGCGC<br>GGTCGGAAGAAGCTGCTGTACATCTTTAAGCAACCCTTCATGAGGCCTGTG<br>CAGACTACTCAAGAGGAGGACGGCTGTTCATGCCGGTTCCCAGAGGAGGAG<br>GAAGGCGGCTGCGAACTGCGCGTGAAATTCAGCCGCAGCGCAGATGCTCCA<br>GCCTACAAGCAGGGGCAGAACCAGCTCTACAACGAACTCAATCTTGGTCGG<br>AGAGAGGAGTACGACGTGCTGGACAAGCGGAGAGGACGGGACCCAGAAATG<br>GGCGGGAAGCCGCGCAGAAAGAATCCCCAAGAGGGCCTGTACAACGAGCTC<br>CAAAAGGATAAGATGGCAGAAGCCTATAGCGAGATTGGTATGAAAGGGGAA<br>CGCAGAAGAGGCAAAGGCCACGACGGACTGTACCAGGGACTCAGCACCGCC<br>ACCAAGGACACCTATGACGCTCTTCACATGCAGGCCCTGCCGCCTCGG |

TABLE 23-continued

Exemplary BCMA CAR molecules. Sequences are provided with a leader sequence.

| Name/ Description | SEQ ID NO: | Sequence |
|---|---|---|
| BCMA_EBB-C1978-D10 | | |
| BCMA_EBB-C1978-D10-aa Full CAR | 8591 | MALPVTALLLPLALLLHAARPEVQLVETGGGLVQPGRSLRLSCAASGFTFD DYAMHWVRQAPGKGLEWVSGISWNSGSIGYADSVKGRFTISRDNAKNSLYL QMNSLRDEDTAVYYCARVGKAVPDVWGQGTTVTVSSGGGGSGGGGSGGGGS DIVMTQTPSSLSASVGDRVTITCRASQSISSYLNWYQQKPGKAPKLLIYAA SSLQSGVPSRFSGSGSGTDFTLTISSLQPEDFATYYCQQSYSTPYSFGQGT RLEIKTTTPAPRPPTPAPTIASQPLSLRPEACRPAAGGAVHTRGLDFACDI YIWAPLAGTCGVLLLSLVITLYCKRGRKKLLYIFKQPFMRPVQTTQEEDGC SCRFPEEEEGGCELRVKFSRSADAPAYKQGQNQLYNELNLGRREEYDVLDK RRGRDPEMGGKPRRKNPQEGLYNELQKDKMAEAYSEIGMKGERRRGKGHDG LYQGLSTATKDTYDALHMQALPPR |
| BCMA_EBB-C1978-D10-nt Full CAR | 8613 | ATGGCCCTCCCTGTCACCGCCCTGCTGCTTCCGCTGGCTCTTCTGCTCCAC GCCGCTCGGCCCGAAGTGCAGCTCGTGGAAACTGGAGGTGGACTCGTGCAG CCTGGACGGTCGCTGCGGCTGAGCTGCGCTGCATCCGGCTTCACCTTCGAC GATTATGCCATGCACTGGGTCAGACAGGCGCCAGGGAAGGGACTTGAGTGG GTGTCCGGTATCAGCTGGAATAGCGGCTCAATCGGATACGCGGACTCCGTG AAGGGAAGGTTCACCATTTCCCGCGACAACGCCAAGAACTCCCTGTACTTG CAAATGAACAGCCTCCGGGATGAGGACACTGCCGTGTACTACTGCGCCCGC GTCGGAAAAGCTGTGCCCGACGTCTGGGGCCAGGGAACCACTGTGACCGTG TCCAGCGGCGGGGGTGGATCGGGCGGTGGAGGGTCCGGTGGAGGGGGCTCA GATATTGTGATGACCCAGACCCCCTCGTCCCTGTCCGCCTCGGTCGGCGAC CGCGTGACTATCACATGTAGAGCCTCGCAGAGCATCTCCAGCTACCTGAAC TGGTATCAGCAGAAGCCGGGGAAGGCCCCGAAGCTCCTGATCTACGCGGCA TCATCACTGCAATCGGGAGTGCCGAGCCGGTTTTCCGGGTCCGGCTCCGGC ACCGACTTCACGCTGACCATTTCTTCCCTGCAACCCGAGGACTTCGCCACT TACTACTGCCAGCAGTCCTACTCCACCCCTTACTCCTTCGGCCAAGGAACC AGGCTGGAAATCAAGACCACTACCCCAGCACCGAGGCCACCCACCCCGGCT CCTACCATCGCCTCCCAGCCTCTGTCCCTGCGTCCGGAGGCATGTAGACCC GCAGCTGGTGGGGCCGTGCATACCCGGGGTCTTGACTTCGCCTGCGATATC TACATTTGGGCCCCTCTGGCTGGTACTTGCGGGGTCCTGCTGCTTTCACTC GTGATCACTCTTTACTGTAAGCGCGGTCGGAAGAAGCTGCTGTACATCTTT AAGCAACCCTTCATGAGGCCTGTGCAGACTACTCAAGAGGAGGACGGCTGT TCATGCCGGTTCCCAGAGGAGGAGGAAGGCGGCTGCGAACTGCGCGTGAAA TTCAGCCGCAGCGCAGATGCTCCAGCCTACAAGCAGGGGCAGAACCAGCTC TACAACGAACTCAATCTTGGTCGGAGAGAGGAGTACGACGTGCTGGACAAG CGGAGAGGACGGGACCCAGAAATGGGCGGGAAGCCGCGCAGAAAGAATCCC CAAGAGGGCCTGTACAACGAGCTCCAAAAGGATAAGATGGCAGAAGCCTAT AGCGAGATTGGTATGAAAGGGGAACGCAGAAGAGGCAAAGGCCACGACGGA CTGTACCAGGGACTCAGCACCGCCACCAAGGACACCTATGACGCTCTTCAC ATGCAGGCCCTGCCGCCTCGG |
| BCMA_EBB-C1979-C12 | | |
| BCMA_EBB-C1979-C12-aa Full CAR | 8592 | MALPVTALLLPLALLLHAARPEVQLVESGGGLVQPGRSLRLSCTASGFTFD DYAMHWVRQRPGKGLEWVASINWKGNSLAYGDSVKGRFAISRDNAKNTVFL QMNSLRTEDTAVYYCASHQGVAYYNYAMDVWGRGTLVTVSSGGGGSGGGGS GGGGSEIVLTQSPGTLSLSPGERATLSCRATQSIGSSFLAWYQQRPGQAPR LLIYGASQRATGIPDRFSGRGSGTDFTLTISRVEPEDSAVYYCQHYESSPS WTFGQGTKVEIKTTTPAPRPPTPAPTIASQPLSLRPEACRPAAGGAVHTRG LDFACDIYIWAPLAGTCGVLLLSLVITLYCKRGRKKLLYIFKQPFMRPVQT TQEEDGCSCRFPEEEEGGCELRVKFSRSADAPAYKQGQNQLYNELNLGRRE EYDVLDKRRGRDPEMGGKPRRKNPQEGLYNELQKDKMAEAYSEIGMKGERR RGKGHDGLYQGLSTATKDTYDALHMQALPPR |
| BCMA_EBB-C1979-C12-nt Full CAR | 8614 | ATGGCCCTCCCTGTCACCGCCCTGCTGCTTCCGCTGGCTCTTCTGCTCCAC GCCGCTCGGCCCGAAGTGCAGCTCGTGGAGAGCGGGGGAGGATTGGTGCAG CCCGGAAGGTCCCTGCGGCTCTCCTGCACTGCGTCTGGCTTCACCTTCGAC GACTACGCGATGCACTGGGTCAGACAGCGCCCGGGAAAGGGCCTGGAATGG GTCGCCTCAATCAACTGGAAGGGAAACTCCCTGGCCTATGGCGACAGCGTG AAGGGCCGCTTCGCCATTTCGCGCGACAACGCCAAGAACACCGTGTTTCTG CAAATGAATTCCCTGCGGACCGAGGATACCGCTGTGTACTACTGCGCCAGC CACCAGGGCGTGGCATACTATAACTACGCCATGGACGTGTGGGGAAGAGGG ACGCTCGTCACCGTGTCCTCCGGGGGCGGTGGATCGGGTGGAGGAGGAAGC GGTGGCGGGGGCAGCGAAATCGTGCTGACTCAGAGCCCGGGAACTCTTTCA CTGTCCCCGGGAGAACGGGCCACTCTCTCGTGCCGGGCCACCCAGTCCATC GGCTCCTCCTTCCTTGCCTGGTACCAGCAGAGGCCAGGACAGGCGCCCCGC CTGCTGATCTACGGTGCTTCCCAACGCGCCACTGGCATTCCTGACCGGTTC AGCGGCAGAGGGTCGGGAACCGATTTCACACTGACCATTTCCCGGGTGGAG CCCGAAGATTCGGCAGTCTACTACTGTCAGCATTACGAGTCCTCCCCTTCA TGGACCTTCGGTCAAGGGACCAAAGTGGAGATCAAGACCACTACCCCAGCA CCGAGGCCACCCACCCCGGCTCCTACCATCGCCTCCCAGCCTCTGTCCCTG CGTCCGGAGGCATGTAGACCCGCAGCTGGTGGGGCCGTGCATACCCGGGGT CTTGACTTCGCCTGCGATATCTACATTTGGGCCCCTCTGGCTGGTACTTGC |

TABLE 23-continued

Exemplary BCMA CAR molecules. Sequences are provided with a leader sequence.

| Name/<br>Description | SEQ ID<br>NO: | Sequence |
|---|---|---|
| | | GGGGTCCTGCTGCTTTCACTCGTGATCACTCTTTACTGTAAGCGCGGTCGG<br>AAGAAGCTGCTGTACATCTTTAAGCAACCCTTCATGAGGCCTGTGCAGACT<br>ACTCAAGAGGAGGACGGCTGTTCATGCCGGTTCCCAGAGGAGGAGGAAGGC<br>GGCTGCGAACTGCGCGTGAAATTCAGCCGCAGCGCAGATGCTCCAGCCTAC<br>AAGCAGGGGCAGAACCAGCTCTACAACGAACTCAATCTTGGTCGGAGAGAG<br>GAGTACGACGTGCTGGACAAGCGGAGAGGACGGGACCCAGAAATGGGCGGG<br>AAGCCGCGCAGAAAGAATCCCCAAGAGGGCCTGTACAACGAGCTCCAAAAG<br>GATAAGATGGCAGAAGCCTATAGCGAGATTGGTATGAAAGGGGAACGCAGA<br>AGAGGCAAAGGCCACGACGGACTGTACCAGGGACTCAGCACCGCCACCAAG<br>GACACCTATGACGCTCTTCACATGCAGGCCCTGCCGCCTCGG |
| BCMA_EBB-<br>C1980-G4 | | |
| BCMA_EBB-<br>C1980-G4-<br>aa<br>Full CAR | 8593 | MALPVTALLLPLALLLHAARPEVQLVESGGGLVQPGGSLRLSCAASGFTFS<br>SYAMSWVRQAPGKGLEWVSAISGSGGSTYYADSVKGRFTISRDNSKNTLYL<br>QMNSLRAEDTAVYYCAKVVRDGMDVWGQGTTVTVSSGGGGSGGGGSGGGGS<br>EIVLTQSPATLSLSPGERATLSCRASQSVSSSYLAWYQQKPGQAPRLLIYG<br>ASSRATGIPDRFSGNGSGTDFTLTISRLEPEDFAVYYCQQYGSPPRFTFGP<br>GTKVDIKTTTPAPRPPTPAPTIASQPLSLRPEACRPAAGGAVHTRGLDFAC<br>DIYIWAPLAGTCGVLLLSLVITLYCKRGRKKLLYIFKQPFMRPVQTTQEED<br>GCSCRFPEEEEGGCELRVKFSRSADAPAYKQGQNQLYNELNLGRREEYDVL<br>DKRRGRDPEMGGKPRRKNPQEGLYNELQKDKMAEAYSEIGMKGERRRGKGH<br>DGLYQGLSTATKDTYDALHMQALPPR |
| BCMA_EBB-<br>C1980-G4-<br>nt<br>Full CAR | 8615 | ATGGCCCTCCCTGTCACCGCCCTGCTGCTTCCGCTGGCTCTTCTGCTCCAC<br>GCCGCTCGGCCCGAGGTGCAGTTGGTCGAAAGCGGGGGCGGGCTTGTGCAG<br>CCTGGCGGATCACTGCGGCTGTCCTGCGCGGCATCAGGCTTCACGTTTCT<br>TCCTACGCCATGTCCTGGGTGCGCCAGGCCCCTGGAAAGGGACTGGAATGG<br>GTGTCCGCGATTTCGGGGTCCGGCGGGAGCACCTACTACGCCGATTCCGTG<br>AAGGGCCGCTTCACTATCTCGCGGGACAACTCCAAGAACACCCTCTACCTC<br>CAAATGAATAGCCTGCGGGCCGAGGATACCGCCGTCTACTATTGCGCTAAG<br>GTCGTGCGCGACGGAATGGACGTGTGGGGACAGGGTACCACCGTGACAGTG<br>TCCTCGGGGGGAGGCGGTAGCGGCGGAGGAGGAAGCGGTGGTGGAGGTTCC<br>GAGATTGTGCTGACTCAATCACCCGCGACCCTGAGCCTGTCCCCCGGCGAA<br>AGGGCCACTCTGTCCTGTCGGGCCAGCCAATCAGTCTCCTCCTCGTACCTG<br>GCCTGGTACCAGCAGAAGCCAGGACAGGCTCCGAGACTCCTTATCTATGGC<br>GCATCCTCCCGCGCCACCGGAATCCCGGATAGGTTCTCGGGAAACGGATCG<br>GGGACCGACTTCACTCTCACCATCTCCCGGCTGGAACCGGAGGACTTCGCC<br>GTGTACTACTGCCAGCAGTACGGCAGCCCGCCTAGATTCACTTTCGGCCCC<br>GGCACCAAAGTGGACATCAAGACCACTACCCCAGCACCGAGGCCACCCACC<br>CCGGCTCCTACCATCGCCTCCCAGCCTCTGTCCCTGCGTCCGGAGGCATGT<br>AGACCCGCAGCTGGTGGGGCCGTGCATACCCGGGGTCTTGACTTCGCCTGC<br>GATATCTACATTTGGGCCCCTCTGGCTGGTACTTGCGGGGTCCTGCTGCTT<br>TCACTCGTGATCACTCTTTACTGTAAGCGCGGTCGGAAGAAGCTGCTGTAC<br>ATCTTTAAGCAACCCTTCATGAGGCCTGTGCAGACTACTCAAGAGGAGGAC<br>GGCTGTTCATGCCGGTTCCCAGAGGAGGAGGAAGGCGGCTGCGAACTGCGC<br>GTGAAATTCAGCCGCAGCGCAGATGCTCCAGCCTACAAGCAGGGGCAGAAC<br>CAGCTCTACAACGAACTCAATCTTGGTCGGAGAGAGGAGTACGACGTGCTG<br>GACAAGCGGAGAGGACGGGACCCAGAAATGGGCGGGAAGCCGCGCAGAAAG<br>AATCCCCAAGAGGGCCTGTACAACGAGCTCCAAAAGGATAAGATGGCAGAA<br>GCCTATAGCGAGATTGGTATGAAAGGGGAACGCAGAAGAGGCAAAGGCCAC<br>GACGGACTGTACCAGGGACTCAGCACCGCCACCAAGGACACCTATGACGCT<br>CTTCACATGCAGGCCCTGCCGCCTCGG |
| BCMA_EBB-<br>C1980-D2 | | |
| BCMA_EBB-<br>C1980-D2-<br>aa<br>Full CAR | 8594 | MALPVTALLLPLALLLHAARPEVQLLESGGGLVQPGGSLRLSCAASGFTFS<br>SYAMSWVRQAPGKGLEWVSAISGSGGSTYYADSVKGRFTISRDNSKNTLYL<br>QMNSLRAEDTAVYYCAKIPQTGTFDYWGQGTLVTVSSGGGGSGGGGSGGGG<br>SEIVLTQSPGTLSLSPGERATLSCRASQSVSSSYLAWYQQRPGQAPRLLIY<br>GASSRATGIPDRFSGSGSGTDFTLTISRLEPEDFAVYYCQHYGSSPSWTFG<br>QGTRLEIKTTTPAPRPPTPAPTIASQPLSLRPEACRPAAGGAVHTRGLDFA<br>CDIYIWAPLAGTCGVLLLSLVITLYCKRGRKKLLYIFKQPFMRPVQTTQEE<br>DGCSCRFPEEEEGGCELRVKFSRSADAPAYKQGQNQLYNELNLGRREEYDV<br>LDKRRGRDPEMGGKPRRKNPQEGLYNELQKDKMAEAYSEIGMKGERRRGKG<br>HDGLYQGLSTATKDTYDALHMQALPPR |
| BCMA_EBB-<br>C1980-D2-<br>nt<br>Full CAR | 8616 | ATGGCCCTCCCTGTCACCGCCCTGCTGCTTCCGCTGGCTCTTCTGCTCCAC<br>GCCGCTCGGCCCGAAGTGCAGCTGCTGGAGTCCGGCGGTGGATTGGTGCAA<br>CCGGGGGGATCGCTCAGACTGTCCTGTGCGGCGTCAGGCTTCACCTTCTCG<br>AGCTACGCCATGTCATGGGTCAGACAGGCCCCTGGAAAGGGTCTGGAATGG<br>GTGTCCGCCATTTCCGGGAGCGGGGATCTACATACTACGCCGATAGCGTG<br>AAGGGCCGCTTCACCATTTCCCGGGACAACTCCAAGAACACTCTCTATCTG<br>CAAATGAACTCCCTCCGCGCTGAGGACACTGCCGTGTACTACTGCGCCAAA<br>ATCCCTCAGACCGGCACCTTCGACTACTGGGGACAGGGGACTCTGGTCACC |

TABLE 23-continued

Exemplary BCMA CAR molecules. Sequences are provided with a leader sequence.

| Name/<br>Description | SEQ ID<br>NO: | Sequence |
|---|---|---|
| | | GTCAGCAGCGGTGGCGGAGGTTCGGGGGGAGGAGGAAGCGGCGGCGGAGGG<br>TCCGAGATTGTGCTGACCCAGTCACCCGGCACTTTGTCCCTGTCGCCTGGA<br>GAAAGGGCCACCCTTTCCTGCCGGGCATCCCAATCCGTGTCCTCCTCGTAC<br>CTGGCCTGGTACCAGCAGAGGCCCGGACAGGCCCCACGGCTTCTGATCTAC<br>GGAGCAAGCAGCCGCGCGACCGGTATCCCGGACCGGTTTTCGGGCTCGGGC<br>TCAGGAACTGACTTCACCCTCACCATCTCCCGCCTGGAACCCGAAGATTTC<br>GCTGTGTATTACTGCCAGCACTACGGCAGCTCCCCGTCCTGGACGTTCGGC<br>CAGGGAACTCGGCTGGAGATCAAGACCACTACCCCAGCACCGAGGCCACCC<br>ACCCCGGCTCCTACCATCGCCTCCCAGCCTCTGTCCCTGCGTCCGGAGGCA<br>TGTAGACCCGCAGCTGGTGGGGCCGTGCATACCCGGGGTCTTGACTTCGCC<br>TGCGATATCTACATTTGGGCCCCTCTGGCTGGTACTTGCGGGGTCCTGCTG<br>CTTTCACTCGTGATCACTCTTTACTGTAAGCGCGGTCGGAAGAAGCTGCTG<br>TACATCTTTAAGCAACCCTTCATGAGGCCTGTGCAGACTACTAAGAGGAG<br>GACGGCTGTTCATGCCGGTTCCCAGAGGAGGAGGAAGGCGGCTGCGAACTG<br>CGCGTGAAATTCAGCCGCAGCGCAGATGCTCCAGCCTACAAGCAGGGGCAG<br>AACCAGCTCTACAACGAACTCAATCTTGGTCGGAGAGAGGATACGACGTG<br>CTGGACAAGCGGAGAGGACGGGACCCAGAAATGGGCGGGAAGCCGCGCAGA<br>AAGAATCCCCAAGAGGGCCTGTACAACGAGCTCCAAAAGGATAAGATGGCA<br>GAAGCCTATAGCGAGATTGGTATGAAAGGGGAACGCAGAAGAGGCAAAGGC<br>CACGACGGACTGTACCAGGGACTCAGCACCGCCACCAAGGACACCTATGAC<br>GCTCTTCACATGCAGGCCCTGCCGCCTCGG |
| BCMA_EBB-<br>C1978-A10 | | |
| BCMA_EBB-<br>C1978-A10-<br>aa<br>Full CAR | 8595 | MALPVTALLLPLALLLHAARPEVQLVETGGGLVQPGGSLRLSCAASGFTFS<br>SYAMSWVRQAPGKGLEWVSAISGSGGSTYYADSVKGRFTMSRENDKNSVFL<br>QMNSLRVEDTGVYYCARANYKRELRYYYGMDVWGQGTMVTVSSGGGGSGGG<br>GSGGGGSEIVMTQSPGTLSLSPGESATLSCRASQRVASNYLAWYQHKPGQA<br>PSLLISGASSRATGVPDRFSGSGSGTDFTLAISRLEPEDSAVYYCQHYDSS<br>PSWTFGQGTKVEIKTTTPAPRPPTPAPTIASQPLSLRPEACRPAAGGAVHT<br>RGLDFACDIYIWAPLAGTCGVLLLSLVITLYCKRGRKKLLYIFKQPFMRPV<br>QTTQEEDGCSCRFPEEEEGGCELRVKFSRSADAPAYKQGQNQLYNELNLGR<br>REEYDVLDKRRGRDPEMGGKPRRKNPQEGLYNELQKDKMAEAYSEIGMKGE<br>RRRGKGHDGLYQGLSTATKDTYDALHMQALPPR |
| BCMA_EBB-<br>C1978-A10-<br>nt<br>Full CAR | 8617 | ATGGCCCTCCCTGTCACCGCCCTGCTGCTTCCGCTGGCTCTTCTGCTCCAC<br>GCCGCTCGGCCCGAAGTGCAACTGGTGGAAACCGGTGGAGGACTCGTGCAG<br>CCTGGCGGCAGCCTCCGGCTGAGCTGCGCCGCTTCGGGATTCACCTTTTCC<br>TCCTACGCGATGTCTTGGGTCAGACAGGCCCCCGGAAAGGGGCTGGAATGG<br>GTGTCAGCCATCTCCGGCTCCGGCGGATCAACGTACTACGCCGACTCCGTG<br>AAAGGCCGGTTCACCATGTCGCGCGAGAATGACAAGAACTCCGTGTTCCTG<br>CAAATGAACTCCCTGAGGGTGGAGGACACCGGAGTGTACTATTGTGCGCGC<br>GCCAACTACAAGAGAGAGCTGCGGTACTACTACGGAATGGACGTCTGGGGA<br>CAGGGAACTATGGTGACCGTGTCATCCGGTGGAGGGGGAAGCGGCGGTGGA<br>GGCAGCGGGGGCGGGGTTCAGAAATTGTCATGACCCAGTCCCCGGGAACT<br>CTTTCCCTCTCCCCGGGGAATCCGCGACTTTGTCCTGCCGGGCCAGCCAG<br>CGCGTGGCCTCGAACTACCTCGCATGGTACCAGCATAAGCCAGGCCAAGCC<br>CCTTCCCTGCTGATTTCCGGGGCTAGCAGCCGCGCCACTGGCGTGCCGGAT<br>AGGTTCTCGGGAAGCGGCTCGGGTACCGATTTCACCCTGGCAATCTCGCGG<br>CTGGAACCGGAGGATTCGGCCGTGTACTACTGCCAGCACTATGACTCATCC<br>CCCTCCTGGACATTCGGACAGGGCACCAAGGTCGAGATCAAGACCACTACC<br>CCAGCACCGAGGCCACCCACCCCGGCTCCTACCATCGCCTCCCAGCCTCTG<br>TCCCTGCGTCCGGAGGCATGTAGACCCGCAGCTGGTGGGGCCGTGCATACC<br>CGGGGTCTTGACTTCGCCTGCGATATCTACATTTGGGCCCCTCTGGCTGGT<br>ACTTGCGGGGTCCTGCTGCTTTCACTCGTGATCACTCTTTACTGTAAGCGC<br>GGTCGGAAGAAGCTGCTGTACATCTTTAAGCAACCCTTCATGAGGCCTGTG<br>CAGACTACTAAGAGGAGGACGGCTGTTCATGCCGGTTCCCAGAGGAGGAG<br>GAAGGCGGCTGCGAACTGCGCGTGAAATTCAGCCGCAGCGCAGATGCTCCA<br>GCCTACAAGCAGGGGCAGAACCAGCTCTACAACGAACTCAATCTTGGTCGG<br>AGAGAGGAGTACGACGTGCTGGACAAGCGGAGAGGACGGGACCCAGAAATG<br>GGCGGGAAGCCGCGCAGAAAGAATCCCCAAGAGGGCCTGTACAACGAGCTC<br>CAAAAGGATAAGATGGCAGAAGCCTATAGCGAGATTGGTATGAAAGGGGAA<br>CGCAGAAGAGGCAAAGGCCACGACGGACTGTACCAGGGACTCAGCACCGCC<br>ACCAAGGACACCTATGACGCTCTTCACATGCAGGCCCTGCCGCCTCGG |
| BCMA_EBB-<br>C1978-D4 | | |
| BCMA_EBB-<br>C1978-D4-<br>aa<br>Full CAR | 8596 | MALPVTALLLPLALLLHAARPEVQLLETGGGLVQPGGSLRLSCAASGFSFS<br>SYAMSWVRQAPGKGLEWVSAISGSGGSTYYADSVKGRFTISRDNSKNTLYL<br>QMNSLRAEDTAVYYCAKALVGATGAFDIWGQGTLVTVSSGGGGSGGGGSGG<br>GGSEIVLTQSPGTLSLSPGERATLSCRASQSLSSNFLAWYQQKPGQAPGLL<br>IYGASNWATGTPDRFSGSGSGTDFTLTITRLEPEDFAVYYCQYYGTSPMYT<br>FGQGTKVEIKTTTPAPRPPTPAPTIASQPLSLRPEACRPAAGGAVHTRGLD<br>FACDIYIWAPLAGTCGVLLLSLVITLYCKRGRKKLLYIFKQPFMRPVQTTQ |

TABLE 23-continued

Exemplary BCMA CAR molecules. Sequences are provided with a leader sequence.

| Name/<br>Description | SEQ ID<br>NO: | Sequence |
|---|---|---|
| | | EEDGCSCRFPEEEEGGCELRVKFSRSADAPAYKQGQNQLYNELNLGRREEY<br>DVLDKRRGRDPEMGGKPRRKNPQEGLYNELQKDKMAEAYSEIGMKGERRRG<br>KGHDGLYQGLSTATKDTYDALHMQALPPR |
| BCMA_EBB-<br>C1978-D4-<br>nt<br>Full CAR | 8618 | ATGGCCCTCCCTGTCACCGCCCTGCTGCTTCCGCTGGCTCTTCTGCTCCAC<br>GCCGCTCGGCCCGAAGTGCAGCTGCTCGAAACCGGTGGAGGGCTGGTGCAG<br>CCAGGGGGCTCCCTGAGGCTTTCATGCGCCGCTAGCGGATTCTCCTTCTCC<br>TCTTACGCCATGTCGTGGGTCCGCCAAGCCCCTGGAAAAGGCCTGGAATGG<br>GTGTCCGCGATTTCCGGGAGCGGAGGTTCGACCTATTACGCCGACTCCGTG<br>AAGGGCCGCTTTACCATCTCCCGGGATAACTCCAAGAACACTCTGTACCTC<br>CAAATGAACTCGCTGAGAGCCGAGGACACCGCCGTGTATTACTGCGCGAAG<br>GCGCTGGTCGGCGCGACTGGGGCATTCGACATCTGGGGACAGGGAACTCTT<br>GTGACCGTGTCGAGCGGAGGCGGCGGCTCCGGCGGAGGAGGGAGCGGGGGC<br>GGTGGTTCCGAAATCGTGTTGACTCAGTCCCCGGGAACCCTGAGCTTGTCA<br>CCCGGGGAGCGGGCCACTCTCTCCTGTCGCGCCTCCCAATGCTCTCATCC<br>AATTTCCTGGCCTGGTACCAGCAGAAGCCCGGACAGGCCCCGGGCCTGCTC<br>ATCTACGGCGCTTCAAACTGGGCAACGGGAACCCCTGATCGGTTCAGCGGA<br>AGCGGATCGGGTACTGACTTTACCCTGACCATCACCAGACTGGAACCGGAG<br>GACTTCGCCGTGTACTACTGCCAGTACTACGGCACCTCCCCCATGTACACA<br>TTCGGACAGGGTACCAAGGTCGAGATTAAGACCACTACCCCAGCACCGAGG<br>CCACCCACCCCGGCTCCTACCATCGCCTCCCAGCCTCTGTCCCTGCGTCCG<br>GAGGCATGTAGACCCGCAGCTGGTGGGGCCGTGCATACCCGGGGTCTTGAC<br>TTCGCCTGCGATATCTACATTTGGGCCCCTCTGGCTGGTACTTGCGGGGTC<br>CTGCTGCTTTCACTCGTGATCACTCTTTACTGTAAGCGCGGTCGGAAGAAG<br>CTGCTGTACATCTTTAAGCAACCCTTCATGAGGCCTGTGCAGACTACTCAA<br>GAGGAGGACGGCTGTTCATGCCGGTTCCCAGAGGAGGAGGAAGGCGGCTGC<br>GAACTGCGCGTGAAATTCAGCCGCAGCGCAGATGCTCCAGCCTACAAGCAG<br>GGGCAGAACCAGCTCTACAACGAACTCAATCTTGGTCGGAGAGAGGAGTAC<br>GACGTGCTGGACAAGCGGAGAGGACGGGACCCAGAAATGGGCGGGAAGCCG<br>CGCAGAAAGAATCCCCAAGAGGGCCTGTACAACGAGCTCCAAAAGGATAAG<br>ATGGCAGAAGCCTATAGCGAGATTGGTATGAAAGGGGAACGCAGAAGAGGC<br>AAAGGCCACGACGGACTGTACCAGGGACTCAGCACCGCCACCAAGGACACC<br>TATGACGCTCTTCACATGCAGGCCCTGCCGCCTCGG |
| BCMA_EBB-<br>C1980-A2 | | |
| BCMA_EBB-<br>C1980-A2-<br>aa<br>Full CAR | 8597 | MALPVTALLLPLALLLHAARPEVQLLESGGGLVQPGGSLRLSCAASGFTFS<br>SYAMSWVRQAPGKGLEWVSAISGSGGSTYYADSVKGRFTISRDNSKNTLYL<br>QMNSLRAEDTAVYYCVLWFGEGFDPWGQGTLVTVSSGGGGSGGGGSGGGGS<br>DIVLTQSPLSLPVTPGEPASISCRSSQSLLHSNGYNYLDWYLQKPGQSPQL<br>LIYLGSNRASGVPDRFSGSGSGTDFTLKISRVEAEDVGVYYCMQALQTPLT<br>FGGGTKVDIKTTTPAPRPPTPAPTIASQPLSLRPEACRPAAGGAVHTRGLD<br>FACDIYIWAPLAGTCGVLLLSLVITLYCKRGRKKLLYIFKQPFMRPVQTTQ<br>EEDGCSCRFPEEEEGGCELRVKFSRSADAPAYKQGQNQLYNELNLGRREEY<br>DVLDKRRGRDPEMGGKPRRKNPQEGLYNELQKDKMAEAYSEIGMKGERRRG<br>KGHDGLYQGLSTATKDTYDALHMQALPPR |
| BCMA_EBB-<br>C1980-A2-<br>nt<br>Full CAR | 8619 | ATGGCCCTCCCTGTCACCGCCCTGCTGCTTCCGCTGGCTCTTCTGCTCCAC<br>GCCGCTCGGCCCGAAGTGCAGCTGCTTGAGAGCGGTGGAGGTCTGGTGCAG<br>CCCGGGGGATCACTGCGCCTGTCCTGTGCCGCGTCCGGTTTCACTTTCTCC<br>TCGTACGCCATGTCGTGGGTCAGACAGGCACCGGGAAAGGGACTGGAATGG<br>GTGTCAGCCATTTCGGGTTCGGGGGGCAGCACCTACTACGCTGACTCCGTG<br>AAGGGCCGGTTCACCATTTCCCGCGACAACTCCAAGAACACCTTGTACCTC<br>CAAATGAACTCCCTGCGGGCCGAAGATACCGCCGTGTATTACTGCGTGCTG<br>TGGTTCGGAGAGGGATTCGACCCGTGGGACAAGGAACACTCGTGACTGTG<br>TCATCCGGCGGAGGCGGCAGCGGTGGCGGCGGTTCCGGCGGCGGCGGATCT<br>GACATCGTGTTGACCCAGTCCCCTCTGAGCCTGCCGGTCACTCCTGGCGAA<br>CCAGCCAGCATCTCCTGCCGGTCGAGCCAGTCCCTCCTGCACTCCAATGGG<br>TACAACTACCTCGATTGGTATCTGCAAAAGCCGGGCCAGACCCCCAGCTG<br>CTGATCTACCTTGGGTCAAACCGCGCTTCCGGGGTGCCTGATAGATTCTCC<br>GGGTCCGGGAGCGGAACCGACTTTACCCTGAAAATCTCGAGGGTGGAGGCC<br>GAGGACGTCGGAGTGTACTACTGCATGCAGGCGCTCCAGACTCCCCTGACC<br>TTCGGAGGAGGAACGAAGGTCGACATCAAGACCACTACCCCAGCACCGAGG<br>CCACCCACCCCGGCTCCTACCATCGCCTCCCAGCCTCTGTCCCTGCGTCCG<br>GAGGCATGTAGACCCGCAGCTGGTGGGGCCGTGCATACCCGGGGTCTTGAC<br>TTCGCCTGCGATATCTACATTTGGGCCCCTCTGGCTGGTACTTGCGGGGTC<br>CTGCTGCTTTCACTCGTGATCACTCTTTACTGTAAGCGCGGTCGGAAGAAG<br>CTGCTGTACATCTTTAAGCAACCCTTCATGAGGCCTGTGCAGACTACTCAA<br>GAGGAGGACGGCTGTTCATGCCGGTTCCCAGAGGAGGAGGAAGGCGGCTGC<br>GAACTGCGCGTGAAATTCAGCCGCAGCGCAGATGCTCCAGCCTACAAGCAG<br>GGGCAGAACCAGCTCTACAACGAACTCAATCTTGGTCGGAGAGAGGAGTAC<br>GACGTGCTGGACAAGCGGAGAGGACGGGACCCAGAAATGGGCGGGAAGCCG<br>CGCAGAAAGAATCCCCAAGAGGGCCTGTACAACGAGCTCCAAAAGGATAAG<br>ATGGCAGAAGCCTATAGCGAGATTGGTATGAAAGGGGAACGCAGAAGAGGC<br>AAAGGCCACGACGGACTGTACCAGGGACTCAGCACCGCCACCAAGGACACC<br>TATGACGCTCTTCACATGCAGGCCCTGCCGCCTCGG |

TABLE 23-continued

Exemplary BCMA CAR molecules. Sequences are provided with a leader sequence.

| Name/<br>Description | SEQ ID<br>NO: | Sequence |
|---|---|---|
| BCMA_EBB-<br>C1981-C3 | | |
| BCMA_EBB-<br>C1981-C3-<br>aa<br>Full CAR | 8598 | MALPVTALLLPLALLLHAARPQVQLVESGGGLVQPGGSLRLSCAASGFTFS<br>SYAMSWVRQAPGKGLEWVSAISGSGGSTYYADSVKGRFTISRDNSKNTLYL<br>QMNSLRAEDTAVYYCAKVGYDSSGYYRDYYGMDVWGQGTTVTVSSGGGGSG<br>GGGSGGGGSEIVLTQSPGTLSLSPGERATLSCRASQSVSSSYLAWYQQKPG<br>QAPRLLIYGTSSRATGISDRFSGSGSGTDFTLTISRLEPEDFAVYYCQHYG<br>NSPPKFTFGPGTKLEIKTTTPAPRPPTPAPTIASQPLSLRPEACRPAAGGA<br>VHTRGLDFACDIYIWAPLAGTCGVLLLSLVITLYCKRGRKKLLYIFKQPFM<br>RPVQTTQEEDGCSCRFPEEEEGGCELRVKFSRSADAPAYKQGQNQLYNELN<br>LGRREEYDVLDKRRGRDPEMGGKPRRKNPQEGLYNELQKDKMAEAYSEIGM<br>KGERRRGKGHDGLYQGLSTATKDTYDALHMQALPPR |
| BCMA_EBB-<br>C1981-C3-<br>nt<br>Full CAR | 8620 | ATGGCCCTCCCTGTCACCGCCCTGCTGCTTCCGCTGGCTCTTCTGCTCCAC<br>GCCGCTCGGCCCCAAGTGCAGCTCGTGGAGTCAGGCGGAGGACTGGTGCAG<br>CCCGGGGGCTCCCTGAGACTTTCCTGCGCGGCATCGGGTTTTACCTTCTCC<br>TCCTATGCTATGTCCTGGGTGCGCCAGGCCCCGGGAAAGGGACTGGAATGG<br>GTGTCCGCAATCAGCGGTAGCGGGGGCTCAACATACTACGCCGACTCCGTC<br>AAGGGTCGCTTCACTATTTCCCGGGACAACTCCAAGAATACCCTGTACCTC<br>CAAATGAACAGCCTCAGGGCCGAGGATACTGCCGTGTACTACTGCGCCAAA<br>GTCGGATACGATAGCTCCGGTTACTACCGGGACTACTACGGAATGGACGTG<br>TGGGGACAGGGCACCACCGTGACCGTGTCAAGCGGCGGAGGCGGTTCAGGA<br>GGGGGAGGCTCCGGCGGTGGAGGGTCCGAAATCGTCCTGACTCAGTCGCCT<br>GGCACTCTGTCGTTGTCCCCGGGGGAGCGCGCTACCCTGTCGTGTCGGGCG<br>TCGCAGTCCGTGTCGAGCTCCTACCTCGCGTGGTACCAGCAGAAGCCCGGA<br>CAGGCCCCTAGACTTCTGATCTACGGCACTTCTTCACGCGCCACCGGGATC<br>AGCGACAGGTTCAGCGGCTCCGGCTCCGGGACCGACTTCACCCTGACCATT<br>AGCCGGCTGGAGCCTGAAGATTTCGCCGTGTATTACTGCCAACACTACGGA<br>AACTCGCCGCCAAAGTTCACGTTCGGACCCGGAACCAAGCTGGAAATCAAG<br>ACCACTACCCCAGCACCGAGGCCACCCACCCCGGCTCCTACCATCGCCTCC<br>CAGCCTCTGTCCCTGCGTCCGGAGGCATGTAGACCCGCAGCTGGTGGGGCC<br>GTGCATACCCGGGGTCTTGACTTCGCCTGCGATATCTACATTTGGGCCCCT<br>CTGGCTGGTACTTGCGGGGTCCTGCTGCTTTCACTCGTGATCACTCTTTAC<br>TGTAAGCGCGGTCGGAAGAAGCTGCTGTACATCTTTAAGCAACCCTTCATG<br>AGGCCTGTGCAGACTACTCAAGAGGAGGACGGCTGTTCATGCCGGTTCCCA<br>GAGGAGGAGGAAGGCGGCTGCGAACTGCGCGTGAAATTCAGCCGCAGCGCA<br>GATGCTCCAGCCTACAAGCAGGGCAGAACCAGCTCTACAACGAACTCAAT<br>CTTGGTCGGAGAGAGGAGTACGACGTGCTGGACAAGCGGAGAGGACGGGAC<br>CCAGAAATGGGCGGGAAGCCGCGCAGAAAGAATCCCCAAGAGGGCCTGTAC<br>AACGAGCTCCAAAAGGATAAGATGGCAGAAGCCTATAGCGAGATTGGTATG<br>AAAGGGGAACGCAGAAGAGGCAAAGGCCACGACGGACTGTACCAGGGACTC<br>AGCACCGCCACCAAGGACACCTATGACGCTCTTCACATGCAGGCCCTGCCG<br>CCTCGG |
| BCMA_EBB-<br>C1978-G4 | | |
| BCMA_EBB-<br>C1978-G4-<br>aa<br>Full CAR | 8599 | MALPVTALLLPLALLLHAARPEVQLVESGGGLVQPGGSLRLSCAASGFTFS<br>SYAMSWVRQAPGKGLEWVSAISGSGGSTYYADSVKGRFTISRDNSKNTLYL<br>QMNSLRAEDTAVYYCAKMGWSSGYLGAFDIWGQGTTVTVSSGGGGSGGGGS<br>GGGGSEIVLTQSPGTLSLSPGERATLSCRASQSVASSFLAWYQQKPGQAPR<br>LLIYGASGRATGIPDRFSGSGSGTDFTLTISRLEPEDFAVYYCQHYGGSPR<br>LTFGGGTKVDIKTTTPAPRPPTPAPTIASQPLSLRPEACRPAAGGAVHTRG<br>LDFACDIYIWAPLAGTCGVLLLSLVITLYCKRGRKKLLYIFKQPFMRPVQT<br>TQEEDGCSCRFPEEEEGGCELRVKFSRSADAPAYKQGQNQLYNELNLGRRE<br>EYDVLDKRRGRDPEMGGKPRRKNPQEGLYNELQKDKMAEAYSEIGMKGERR<br>RGKGHDGLYQGLSTATKDTYDALHMQALPPR |
| BCMA_EBB-<br>C1978-G4-<br>nt<br>Full CAR | 8621 | ATGGCCCTCCCTGTCACCGCCCTGCTGCTTCCGCTGGCTCTTCTGCTCCAC<br>GCCGCTCGGCCCGAAGTCCAACTGGTGGAGTCCGGGGGAGGGCTCGTGCAG<br>CCCGGAGGCAGCCTTCGGCTGTCGTGCGCCGCCTCCGGGTTCACGTTCTCA<br>TCCTACGCGATGTCGTGGGTCAGACAGGCACCAGGAAAGGGACTGGAATGG<br>GTGTCCGCCATTAGCGGCTCCGGCGGTAGCACCTACTATGCCGACTCAGTG<br>AAGGGAAGGTTCACTATCTCCCGCGACAACAGCAAGAACACCCTGTACCTC<br>CAAATGAACTCTCTGCGGGCCGAGGATACCGCGGTGTACTATTGCGCCAAG<br>ATGGGTTGGTCAGCGGATACTTGGGAGCCTTCGACATTTGGGGACAGGGC<br>ACTACTGTGACCGTGTCCTCCGGGGGTGGCGGATCGGGAGGCGGCGGCTCG<br>GGTGGAGGGGGTTCCGAAATCGTGTTGACCCAGTCACCGGGAACCCTCTCG<br>CTGTCCCCGGGAGAACGGGCTACACTGTCATGTAGAGCGTCCCAGTCCGTG<br>GCTTCCTCGTTCCTGGCCTGGTACCAGCAGAAGCCGGGACAGGCACCCCGC<br>CTGCTCATCTACGGAGCCAGCGGCCGGGCGACCGGCATCCCTGACCGCTTC<br>TCCGGTTCCGGCTCGGGCACCGACTTTACTCTGACCATTAGCAGGCTTGAG<br>CCCGAGGATTTTGCCGTGTACTACTGCCAACACTACGGGGGAGCCCTCGC<br>CTGACCTTCGGAGGCGGAACTAAGGTCGATATCAAAACCACTACCCCAGCA<br>CCGAGGCCACCCACCCCGGCTCCTACCATCGCCTCCCAGCCTCTGTCCCTG |

TABLE 23-continued

Exemplary BCMA CAR molecules. Sequences are provided with a leader sequence.

| Name/<br>Description | SEQ ID<br>NO: | Sequence |
|---|---|---|
| | | CGTCCGGAGGCATGTAGACCCGCAGCTGGTGGGGCCGTGCATACCCGGGGT<br>CTTGACTTCGCCTGCGATATCTACATTTGGGCCCCTCTGGCTGGTACTTGC<br>GGGGTCCTGCTGCTTTCACTCGTGATCACTCTTTACTGTAAGCGCGGTCGG<br>AAGAAGCTGCTGTACATCTTTAAGCAACCCTTCATGAGGCCTGTGCAGACT<br>ACTCAAGAGGAGGACGGCTGTTCATGCCGGTTCCCAGAGGAGGAGGAAGGC<br>GGCTGCGAACTGCGCGTGAAATTCAGCCGCAGCGCAGATGCTCCAGCCTAC<br>AAGCAGGGGCAGAACCAGCTCTACAACGAACTCAATCTTGGTCGGAGAGAG<br>GAGTACGACGTGCTGGACAAGCGGAGAGGACGGGACCCAGAAATGGGCGGG<br>AAGCCGCGCAGAAAGAATCCCCAAGAGGGCCTGTACAACGAGCTCCAAAAG<br>GATAAGATGGCAGAAGCCTATAGCGAGATTGGTATGAAAGGGGAACGCAGA<br>AGAGGCAAAGGCCACGACGGACTGTACCAGGGACTCAGCACCGCCACCAAG<br>GACACCTATGACGCTCTTCACATGCAGGCCCTGCCGCCTCGG |

In one embodiment, the CAR molecule comprises (e.g., consists of) an amino acid sequence provided in Table 23, or Table 1 of WO2016/014565, or as otherwise described herein. In one embodiment, the CAR molecule comprises (e.g., consists of) an amino acid sequence of SEQ ID NO: 8549, SEQ ID NO: 8550, SEQ ID NO: 8551, SEQ ID NO: 8552, SEQ ID NO: 8553, SEQ ID NO: 8554, SEQ ID NO: 8555, SEQ ID NO: 8556, SEQ ID NO: 8557, SEQ ID NO: 8558, SEQ ID NO: 8559, SEQ ID NO: 8560, SEQ ID NO: 8561, SEQ ID NO: 8562, SEQ ID NO: 8563, SEQ ID NO: 8579, SEQ ID NO: 8580, SEQ ID NO: 8581, SEQ ID NO: 8582, SEQ ID NO: 8583, SEQ ID NO: 8584, SEQ ID NO: 8585, SEQ ID NO: 8586, SEQ ID NO: 8587, SEQ ID NO: 8588, SEQ ID NO: 8589, SEQ ID NO: 8590, SEQ ID NO: 8591, SEQ ID NO: 8592, SEQ ID NO: 8593, SEQ ID NO: 8594, SEQ ID NO: 8595, SEQ ID NO: 8596, SEQ ID NO: 8597, SEQ ID NO: 8598, or SEQ ID NO: 8599; or an amino acid sequence having at least one, two, three, four, five, 10, 15, 20 or 30 modifications (e.g., substitutions, e.g., conservative substitutions) but not more than 60, 50, or 40 modifications (e.g., substitutions, e.g., conservative substitutions) of an amino acid sequence of SEQ ID NO: 8549, SEQ ID NO: 8550, SEQ ID NO: 8551, SEQ ID NO: 8552, SEQ ID NO: 8553, SEQ ID NO: 8554, SEQ ID NO: 8555, SEQ ID NO: 8556, SEQ ID NO: 8557, SEQ ID NO: 8558, SEQ ID NO: 8559, SEQ ID NO: 8560, SEQ ID NO: 8561, SEQ ID NO: 8562, SEQ ID NO: 8563, SEQ ID NO: 8579, SEQ ID NO: 8580, SEQ ID NO: 8581, SEQ ID NO: 8582, SEQ ID NO: 8583, SEQ ID NO: 8584, SEQ ID NO: 8585, SEQ ID NO: 8586, SEQ ID NO: 8587, SEQ ID NO: 8588, SEQ ID NO: 8589, SEQ ID NO: 8590, SEQ ID NO: 8591, SEQ ID NO: 8592, SEQ ID NO: 8593, SEQ ID NO: 8594, SEQ ID NO: 8595, SEQ ID NO: 8596, SEQ ID NO: 8597, SEQ ID NO: 8598, or SEQ ID NO: 8599; or an amino acid sequence having 85%, 90%, 95%, 96%, 97%, 98%, 99% identity to an amino acid sequence of SEQ ID NO: 8549, SEQ ID NO: 8550, SEQ ID NO: 8551, SEQ ID NO: 8552, SEQ ID NO: 8553, SEQ ID NO: 8554, SEQ ID NO: 8555, SEQ ID NO: 8556, SEQ ID NO: 8557, SEQ ID NO: 8558, SEQ ID NO: 8559, SEQ ID NO: 8560, SEQ ID NO: 8561, SEQ ID NO: 8562, SEQ ID NO: 8563, SEQ ID NO: 8579, SEQ ID NO: 8580, SEQ ID NO: 8581, SEQ ID NO: 8582, SEQ ID NO: 8583, SEQ ID NO: 8584, SEQ ID NO: 8585, SEQ ID NO: 8586, SEQ ID NO: 8587, SEQ ID NO: 8588, SEQ ID NO: 8589, SEQ ID NO: 8590, SEQ ID NO: 8591, SEQ ID NO: 8592, SEQ ID NO: 8593, SEQ ID NO: 8594, SEQ ID NO: 8595, SEQ ID NO: 8596, SEQ ID NO: 8597, SEQ ID NO: 8598, or SEQ ID NO: 8599.

Transmembrane Domains

With respect to the transmembrane domain, in various embodiments, a CAR can be designed to comprise a transmembrane domain that is attached to the extracellular domain of the CAR. A transmembrane domain can include one or more additional amino acids adjacent to the transmembrane region, e.g., one or more amino acid associated with the extracellular region of the protein from which the transmembrane was derived (e.g., 1, 2, 3, 4, 5, 6, 7, 8, 9, 10 up to 15 amino acids of the extracellular region) and/or one or more additional amino acids associated with the intracellular region of the protein from which the transmembrane protein is derived (e.g., 1, 2, 3, 4, 5, 6, 7, 8, 9, 10 up to 15 amino acids of the intracellular region). In one aspect, the transmembrane domain is one that is associated with one of the other domains of the CAR e.g., in one embodiment, the transmembrane domain may be from the same protein that the signaling domain, costimulatory domain or the hinge domain is derived from. In another aspect, the transmembrane domain is not derived from the same protein that any other domain of the CAR is derived from. In some instances, the transmembrane domain can be selected or modified by amino acid substitution to avoid binding of such domains to the transmembrane domains of the same or different surface membrane proteins, e.g., to minimize interactions with other members of the receptor complex. In one aspect, the transmembrane domain is capable of homodimerization with another CAR on the cell surface of a CAR-expressing cell. In a different aspect, the amino acid sequence of the transmembrane domain may be modified or substituted so as to minimize interactions with the binding domains of the native binding partner present in the same CAR-expressing cell.

The transmembrane domain may be derived either from a natural or from a recombinant source. Where the source is natural, the domain may be derived from any membrane-bound or transmembrane protein. In one aspect the transmembrane domain is capable of signaling to the intracellular domain(s) whenever the CAR has bound to a target. A transmembrane domain of particular use in this invention may include at least the transmembrane region(s) of e.g., the alpha, beta or zeta chain of the T-cell receptor, CD28, CD27, CD3 epsilon, CD45, CD4, CD5, CD8, CD9, CD16, CD22, CD33, CD37, CD64, CD80, CD86, CD134, CD137, CD154. In some embodiments, a transmembrane domain may include at least the transmembrane region(s) of, e.g., KIRDS2, OX40, CD2, CD27, LFA-1 (CD11a, CD18), ICOS (CD278), 4-1BB (CD137), GITR, CD40, BAFFR, HVEM (LIGHTR), SLAMF7, NKp80 (KLRF1), NKp44, NKp30, NKp46, CD160, CD19, IL2R beta, IL2R gamma, IL7Rα, ITGA1, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, TNFR2, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), SLAMF6 (NTB-A, Ly108), SLAM (SLAMF1, CD150, IPO-3), BLAME (SLAMF8), SELPLG (CD162), LTBR, PAG/Cbp, NKG2D, NKG2C.

In some instances, the transmembrane domain can be attached to the extracellular region of the CAR, e.g., the antigen binding domain of the CAR, via a hinge, e.g., a hinge from a human protein. For example, in one embodiment, the hinge can be a human Ig (immunoglobulin) hinge (e.g., an IgG4 hinge, an IgD hinge), a GS linker (e.g., a GS linker described herein), a KIR2DS2 hinge or a CD8a hinge. In one embodiment, the hinge or spacer comprises (e.g., consists of) the amino acid sequence of SEQ ID NO:6642. In one aspect, the transmembrane domain comprises (e.g., consists of) a transmembrane domain of SEQ ID NO: 6644.

In certain embodiments, the encoded transmembrane domain comprises an amino acid sequence of a CD8 transmembrane domain having at least one, two or three modifications but not more than 20, 10 or 5 modifications of an amino acid sequence of SEQ ID NO: 6644, or a sequence with 95-99% identity to an amino acid sequence of SEQ ID NO: 6644. In one embodiment, the encoded transmembrane domain comprises the sequence of SEQ ID NO: 6644.

In other embodiments, the nucleic acid molecule encoding the CAR comprises a nucleotide sequence of a CD8 transmembrane domain, e.g., comprising the sequence of SEQ ID NO: 6645, or a sequence with 95-99% identity thereof.

In certain embodiments, the encoded antigen binding domain is connected to the transmembrane domain by a hinge region. In one embodiment, the encoded hinge region comprises the amino acid sequence of a CD8 hinge, e.g., SEQ ID NO: 6642; or the amino acid sequence of an IgG4 hinge, e.g., SEQ ID NO: 6630, or a sequence with 95-99% identity to SEQ ID NO: 6642 or 6630. In other embodiments, the nucleic acid sequence encoding the hinge region comprises a sequence of SEQ ID NO: 6643 or SEQ ID NO: 6631, corresponding to a CD8 hinge or an IgG4 hinge, respectively, or a sequence with 95-99% identity to SEQ ID NO:6643 or 6631.

In one aspect, the hinge or spacer comprises an IgG4 hinge. For example, in one embodiment, the hinge or spacer comprises a hinge of the amino acid sequence ESKYGPPCPPCPAPEFLGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQ VYTLPPSQEEMTKNQVSLTCLVKGFYP SDIAVEWESNGQPENNYKTTPPVLDSDGSFFLYSRLTVDKSRWQEGNVFSCSVMHEALHNHYTQKSLSLSLGKM (SEQ ID NO:6630). In some embodiments, the hinge or spacer comprises a hinge encoded by a nucleotide sequence of

```
                                         (SEQ ID NO: 6631)
GAGAGCAAGTACGGCCCTCCCTGCCCCCCTTGCCCTGCCCCCGAGTTCCT

GGGCGGACCCAGCGTGTTCCTGTTCCCCCCCAAGCCCAAGGACACCCTGA

TGATCAGCCGGACCCCCGAGGTGACCTGTGTGGTGGTGGACGTGTCCCAG
```

```
-continued
GAGGACCCCGAGGTCCAGTTCAACTGGTACGTGGACGGCGTGGAGGTGCA

CAACGCCAAGACCAAGCCCCGGGAGGAGCAGTTCAATAGCACCTACCGGG

TGGTGTCCGTGCTGACCGTGCTGCACCAGGACTGGCTGAACGGCAAGGAA

TACAAGTGTAAGGTGTCCAACAAGGGCCTGCCCAGCAGCATCGAGAAAAC

CATCAGCAAGGCCAAGGGCCAGCCTCGGGAGCCCCAGGTGTACACCCTGC

CCCCTAGCCAAGAGGAGATGACCAAGAACCAGGTGTCCCTGACCTGCCTG

GTGAAGGGCTTCTACCCCAGCGACATCGCCGTGGAGTGGGAGAGCAACGG

CCAGCCCGAGAACAACTACAAGACCACCCCCCCTGTGCTGGACAGCGACG

GCAGCTTCTTCCTGTACAGCCGGCTGACCGTGGACAAGAGCCGGTGGCAG

GAGGGCAACGTCTTTAGCTGCTCCGTGATGCACGAGGCCCTGCACAACCA

CTACACCCAGAAGAGCCTGAGCCTGTCCCTGGGCAAGATG.
```

In one aspect, the hinge or spacer comprises an IgD hinge. For example, in one embodiment, the hinge or spacer comprises a hinge of the amino acid sequence RWPESPKAQASSVPTAQPQAEGSLAKATTAPATTRNTGRGGEEKKKEKEKEEQEERETKTPECP SHTQPLGVYLLTPAVQDLWLRDKATFTCFVVGSDLKDAHLTWEVAGKVPTGGVEEGLLERHSN GSQSQHSRLTLPRSLWNAGTSVTCTLNHPSLPPQRLMALREPAAQAPVKLSLNLLASSDPPEAAS WLLCEVSGFSPPNILLMWLEDQREVNTSGFAPARPPPQPGSTTFWAWSVLRVPAPPSPQPATYTC VVSHEDSRTLLNASRSLEVSYVTDH (SEQ ID NO:6632). In some embodiments, the hinge or spacer comprises a hinge encoded by a nucleotide sequence of

```
                                         (SEQ ID NO: 6633)
AGGTGGCCCGAAAGTCCCAAGGCCCAGGCATCTAGTGTTCCTACTGCACA

GCCCCAGGCAGAAGGCAGCCTAGCCAAAGCTACTACTGCACCTGCCACTA

CGCGCAATACTGGCCGTGGCGGGGAGGAGAAGAAAAAGGAGAAAGAGAAA

GAAGAACAGGAAGAGAGGGGAGACCAAGACCCCTGAATGTCCATCCCATAC

CCAGCCGCTGGGCGTCTATCTCTTGACTCCCGCAGTACAGGACTTGTGGC

TTAGAGATAAGGCCACCTTTACATGTTTCGTCGTGGGCTCTGACCTGAAG

GATGCCCATTTGACTTGGGAGGTTGCCGGAAAGGTACCCACAGGGGGGT

TGAGGAAGGGTTGCTGGAGCGCCATTCCAATGGCTCTCAGAGCCAGCACT

CAAGACTCACCCTTCCGAGATCCCTGTGGAACGCCGGGACCTCTGTCACA

TGTACTCTAAATCATCCTAGCCTGCCCCCACAGCGTCTGATGGCCCTTAG

AGAGCCAGCCGCCCAGGCACCAGTTAAGCTTAGCCTGAATCTGCTCGCCA

GTAGTGATCCCCCAGAGGCCGCCAGCTGGCTCTTATGCGAAGTGTCCGGC

TTTAGCCCGCCCAACATCTTGCTCATGTGGCTGGAGGACCAGCGAGAAGT

GAACACCAGCGGCTTCGCTCCAGCCCGGCCCCCACCCCAGCCGGGTTCTA

CCACATTCTGGGCCTGGAGTGTCTTAAGGGTCCCAGCACCACCTAGCCCC

CAGCCAGCCACATACACCTGTGTTGTGTCCCATGAAGATAGCAGGACCCT

GCTAAATGCTTCTAGGAGTCTGGAGGTTTCCTACGTGACTGACCATT.
```

In one aspect, the transmembrane domain may be recombinant, in which case it will comprise predominantly hydrophobic residues such as leucine and valine. In one aspect a triplet of phenylalanine, tryptophan and valine can be found at each end of a recombinant transmembrane domain.

Optionally, a short oligo- or polypeptide linker, between 2 and 10 amino acids in length may form the linkage between the transmembrane domain and the cytoplasmic region of the CAR. A glycine-serine doublet provides a particularly suitable linker. For example, in one aspect, the linker comprises the amino acid sequence of GGGGSGGGGS (SEQ ID NO:6634). In some embodiments, the linker is encoded by a nucleotide sequence of GGTGGCGGAGGTTCTGGAGGTGGAGGTTCC (SEQ ID NO:6635).

In one aspect, the hinge or spacer comprises a KIR2DS2 hinge.

Signaling Domains

In embodiments of the invention having an intracellular signaling domain, such a domain can contain, e.g., one or more of a primary signaling domain and/or a costimulatory signaling domain. In some embodiments, the intracellular signaling domain comprises a sequence encoding a primary signaling domain. In some embodiments, the intracellular signaling domain comprises a costimulatory signaling domain. In some embodiments, the intracellular signaling domain comprises a primary signaling domain and a costimulatory signaling domain.

The intracellular signaling sequences within the cytoplasmic portion of the CAR of the invention may be linked to each other in a random or specified order. Optionally, a short oligo- or polypeptide linker, for example, between 2 and 10 amino acids (e.g., 2, 3, 4, 5, 6, 7, 8, 9, or 10 amino acids) in length may form the linkage between intracellular signaling sequences. In one embodiment, a glycine-serine doublet can be used as a suitable linker. In one embodiment, a single amino acid, e.g., an alanine, a glycine, can be used as a suitable linker.

In one aspect, the intracellular signaling domain is designed to comprise two or more, e.g., 2, 3, 4, 5, or more, costimulatory signaling domains. In an embodiment, the two or more, e.g., 2, 3, 4, 5, or more, costimulatory signaling domains, are separated by a linker molecule, e.g., a linker molecule described herein. In one embodiment, the intracellular signaling domain comprises two costimulatory signaling domains. In some embodiments, the linker molecule is a glycine residue. In some embodiments, the linker is an alanine residue.

Primary Signaling Domains

A primary signaling domain regulates primary activation of the TCR complex either in a stimulatory way, or in an inhibitory way. Primary intracellular signaling domains that act in a stimulatory manner may contain signaling motifs which are known as immunoreceptor tyrosine-based activation motifs or ITAMs.

Examples of ITAM containing primary intracellular signaling domains that are of particular use in the invention include those of CD3 zeta, common FcR gamma (FCER1G), Fc gamma RIIa, FcR beta (Fc Epsilon R1b), CD3 gamma, CD3 delta, CD3 epsilon, CD79a, CD79b, DAP10, and DAP12. In one embodiment, a CAR of the invention comprises an intracellular signaling domain, e.g., a primary signaling domain of CD3-zeta.

In one embodiment, the encoded primary signaling domain comprises a functional signaling domain of CD3 zeta. The encoded CD3 zeta primary signaling domain can comprise an amino acid sequence having at least one, two or three modifications but not more than 20, 10 or 5 modifications of an amino acid sequence of SEQ ID NO: 6648 or SEQ ID NO: 6650, or a sequence with 95-99% identity to an amino acid sequence of SEQ ID NO: 6648 or SEQ ID NO: 6650. In some embodiments, the encoded primary signaling domain comprises a sequence of SEQ ID NO: 6648 or SEQ ID NO: 6650. In other embodiments, the nucleic acid sequence encoding the primary signaling domain comprises a sequence of SEQ ID NO: 6649 or SEQ ID NO: 6651, or a sequence with 95-99% identity thereof.

Costimulatory Signaling Domains

In some embodiments, the encoded intracellular signaling domain comprises a costimulatory signaling domain. For example, the intracellular signaling domain can comprise a primary signaling domain and a costimulatory signaling domain. In some embodiments, the encoded costimulatory signaling domain comprises a functional signaling domain of a protein chosen from one or more of CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, a ligand that specifically binds with CD83, CDS, ICAM-1, GITR, BAFFR, HVEM (LIGHTR), SLAMF7, NKp80 (KLRF1), CD160, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, NKp44, NKp30, NKp46, or NKG2D.

In certain embodiments, the encoded costimulatory signaling domain comprises an amino acid sequence having at least one, two or three modifications but not more than 20, 10 or 5 modifications of an amino acid sequence of SEQ ID NO: 6646 or SEQ ID NO: 6636, or a sequence with 95-99% identity to an amino acid sequence of SEQ ID NO: 6646 or SEQ ID NO: 6636. In one embodiment, the encoded costimulatory signaling domain comprises a sequence of SEQ ID NO: 6646 or SEQ ID NO: 6636. In other embodiments, the nucleic acid sequence encoding the costimulatory signaling domain comprises a sequence of SEQ ID NO: 6647 or SEQ ID NO: 6637, or a sequence with 95-99% identity thereof.

In other embodiments, the encoded intracellular domain comprises the sequence of SEQ ID NO: 6646 or SEQ ID NO: 6636, and the sequence of SEQ ID NO: 6648 or SEQ ID NO: 6650, wherein the sequences comprising the intracellular signaling domain are expressed in the same frame and as a single polypeptide chain.

In certain embodiments, the nucleic acid sequence encoding the intracellular signaling domain comprises a sequence of SEQ ID NO: 6647 or SEQ ID NO: 6637, or a sequence with 95-99% identity thereof, and a sequence of SEQ ID NO: 6649 or SEQ ID NO: 6651, or a sequence with 95-99% identity thereof.

In some embodiments, the nucleic acid molecule further encodes a leader sequence. In one embodiment, the leader sequence comprises the sequence of SEQ ID NO: 6640.

In one aspect, the intracellular signaling domain is designed to comprise the signaling domain of CD3-zeta and the signaling domain of CD28. In one aspect, the intracellular signaling domain is designed to comprise the signaling domain of CD3-zeta and the signaling domain of 4-1BB. In one aspect, the signaling domain of 4-1BB is a signaling domain of SEQ ID NO: 6646. In one aspect, the signaling domain of CD3-zeta is a signaling domain of SEQ ID NO: 6648.

In one aspect, the intracellular signaling domain is designed to comprise the signaling domain of CD3-zeta and the signaling domain of CD27. In one aspect, the signaling domain of CD27 comprises an amino acid sequence of QRRKYRSNKGESPVEPAEPCRYSCPREEEGSTIP-IQEDYRKPEPACSP (SEQ ID NO: 6636). In one aspect, the signalling domain of CD27 is encoded by a nucleic acid sequence of (SEQ ID NO: 6637)
AGGAGTAAGAGGAGCAGGCTCCTGCACAGTGACTACATGAACATGACTCC

CCGCCGCCCCGGGCCCACCCGCAAGCATTACCAGCCCTATGCCCCACCAC

GCGACTTCGCAGCCTATCGCTCC.

Vectors

In another aspect, the invention pertains to a vector comprising a nucleic acid sequence encoding a CAR described herein. In one embodiment, the vector is chosen from a DNA vector, an RNA vector, a plasmid, a lentivirus vector, adenoviral vector, or a retrovirus vector. In one embodiment, the vector is a lentivirus vector. These vectors or portions thereof may, among other things, be used to create template nucleic acids, as described herein for use with the CRISPR systems as described herein. Alternatively, the vectors may be used to deliver nucleic acid directly to the cell, e.g., the immune effector cell, e.g., the T cell, e.g., the allogeneic T cell, independent of the CRISPR system.

The present invention also provides vectors in which a DNA of the present invention is inserted. Vectors derived from retroviruses such as the lentivirus are suitable tools to achieve long-term gene transfer since they allow long-term, stable integration of a transgene and its propagation in daughter cells. Lentiviral vectors have the added advantage over vectors derived from onco-retroviruses such as murine leukemia viruses in that they can transduce non-proliferating cells, such as hepatocytes. They also have the added advantage of low immunogenicity. A retroviral vector may also be, e.g., a gammaretroviral vector. A gammaretroviral vector may include, e.g., a promoter, a packaging signal (ψ), a primer binding site (PBS), one or more (e.g., two) long terminal repeats (LTR), and a transgene of interest, e.g., a gene encoding a CAR. A gammaretroviral vector may lack viral structural gens such as gag, pol, and env. Exemplary gammaretroviral vectors include Murine Leukemia Virus (MLV), Spleen-Focus Forming Virus (SFFV), and Myeloproliferative Sarcoma Virus (MPSV), and vectors derived therefrom. Other gammaretroviral vectors are described, e.g., in Tobias Maetzig et al., "Gammaretroviral Vectors: Biology, Technology and Application" Viruses. 2011 June; 3(6): 677-713.

In another embodiment, the vector comprising the nucleic acid encoding the desired CAR of the invention is an adenoviral vector (A5/35). In another embodiment, the expression of nucleic acids encoding CARs can be accomplished using of transposons such as sleeping beauty, crisper, CAS9, and zinc finger nucleases. See below June et al. 2009 *Nature Reviews Immunology* 9.10: 704-716, is incorporated herein by reference.

The nucleic acid can be cloned into a number of types of vectors. For example, the nucleic acid can be cloned into a vector including, but not limited to a plasmid, a phagemid, a phage derivative, an animal virus, and a cosmid. Vectors of particular interest include expression vectors, replication vectors, probe generation vectors, and sequencing vectors.

Disclosed herein are methods for producing an in vitro transcribed RNA CAR. The present invention also includes a CAR encoding RNA construct that can be directly transfected into a cell. A method for generating mRNA for use in transfection can involve in vitro transcription (IVT) of a template with specially designed primers, followed by polyA addition, to produce a construct containing 3' and 5' untranslated sequence ("UTR"), a 5' cap and/or Internal Ribosome Entry Site (IRES), the nucleic acid to be expressed, and a polyA tail, typically 50-2000 bases in length (SEQ ID NO: 6638). RNA so produced can efficiently transfect different kinds of cells. In one aspect, the template includes sequences for the CAR.

Non-Viral Delivery Methods

In some aspects, non-viral methods can be used to deliver a nucleic acid encoding a CAR described herein into a cell or tissue or a subject.

In some embodiments, the non-viral method includes the use of a transposon (also called a transposable element). In some embodiments, a transposon is a piece of DNA that can insert itself at a location in a genome, for example, a piece of DNA that is capable of self-replicating and inserting its copy into a genome, or a piece of DNA that can be spliced out of a longer nucleic acid and inserted into another place in a genome. For example, a transposon comprises a DNA sequence made up of inverted repeats flanking genes for transposition.

In some embodiments, cells, e.g., T or NK cells, are generated that express a CAR described herein by using a combination of gene insertion using the SBTS and genetic editing using a nuclease (e.g., Zinc finger nucleases (ZFNs), Transcription Activator-Like Effector Nucleases (TALENs), the CRISPR/Cas system, or engineered meganuclease re-engineered homing endonucleases).

In some embodiments, cells of the invention, e.g., T or NK cells, e.g., allogeneic T cells, e.g., described herein, (e.g., that express a CAR described herein) are generated by contacting the cells with (a) a composition comprising one or more gRNA molecules, e.g., as described herein, and one or more Cas molecules, e.g., a Cas9 molecule, e.g., as described herein, and (b) nucleic acid comprising sequence encoding a CAR, e.g., described herein (such as a template nucleic acid molecule as described herein).

Without being bound by theory, said composition of (a), above, will induce a break at or near the genomic DNA targeted by the targeting domain of the gRNA molecule(s), and the nucleic acid of (b) will incorporate, e.g., partially or wholly, into the genome at or near said break, such that upon integration, the encoded CAR molecule is expressed. In embodiments, expression of the CAR will be controlled by promoters or other regulatory elements endogenous to the genome (e.g., the promoter controlling expression from the gene in which the nucleic acid of (b) was inserted). In other embodiments, the nucleic acid of (b) further comprises a promoter and/or other regulatory elements, e.g., as described herein, e.g., an EF1-alpha promoter, operably linked to the sequence encoding the CAR, such that upon integration, expression of the CAR is controlled by that promoter and/or other regulatory elements. Additional features of the invention relating to use of CRISPR/Cas9 systems, e.g., as described herein, to direct incorporation of nucleic acid sequence encoding a CAR, e.g., as described herein, are described elsewhere in this application, e.g., in the section relating to gene insertion and homologous recombination. In embodiments, the composition of a) above is a composition comprising RNPs comprising the one or more gRNA molecules. In embodiments, RNPs comprising gRNAs targeting unique target sequences are introduced into the cell simultaneously, e.g., as a mixture of RNPs comprising the one or more gRNAs. In embodiments, RNPs comprising gRNAs targeting unique target sequences are introduced into the cell sequentially.

In some embodiments, use of a non-viral method of delivery permits reprogramming of cells, e.g., T or NK cells, and direct infusion of the cells into a subject. Advantages of non-viral vectors include but are not limited to the ease and relatively low cost of producing sufficient amounts required to meet a patient population, stability during storage, and lack of immunogenicity.

Inhibitory Domains

In an embodiment, the vector comprises a nucleic acid sequence that encodes a CAR, e.g., a CAR described herein, and a nucleic acid sequence that encodes an inhibitory molecule comprising: an inhKIR cytoplasmic domain; a transmembrane domain, e.g., a KIR transmembrane domain; and an inhibitor cytoplasmic domain, e.g., an ITIM domain, e.g., an inhKIR ITIM domain. In an embodiment the inhibitory molecule is a naturally occurring inhKIR, or a sequence sharing at least 50, 60, 70, 80, 85, 90, or 99% homology with, or that differs by no more than 1, 2, 3, 4, 5, 6, 7, 8, 9, 10, 15, or 20 residues from, a naturally occurring inhKIR.

In an embodiment, the nucleic acid sequence that encodes an inhibitory molecule comprises: a SLAM family cytoplasmic domain; a transmembrane domain, e.g., a SLAM family transmembrane domain; and an inhibitor cytoplasmic domain, e.g., a SLAM family domain, e.g., an SLAM family ITIM domain. In an embodiment the inhibitory molecule is a naturally occurring SLAM family member, or a sequence sharing at least 50, 60, 70, 80, 85, 90, 95, or 99% homology with, or that differs by no more than 1, 2, 3, 4, 5, 6, 7, 8, 9, 10, 15, or 20 residues from, a naturally occurring SLAM family member.

In one embodiment, the vector is an in vitro transcribed vector, e.g., a vector that transcribes RNA of a nucleic acid molecule described herein. In one embodiment, the nucleic acid sequence in the vector further comprises a poly(A) tail, e.g., a poly A tail. In one embodiment, the nucleic acid sequence in the vector further comprises a 3'UTR, e.g., a 3' UTR described herein, e.g., comprising at least one repeat of a 3'UTR derived from human beta-globulin. In one embodiment, the nucleic acid sequence in the vector further comprises promoter, e.g., a T2A promoter.

Promoters

In one embodiment, the vector further comprises a promoter. In some embodiments, the promoter is chosen from an EF-1 promoter, a CMV IE gene promoter, an EF-1α promoter, an ubiquitin C promoter, or a phosphoglycerate kinase (PGK) promoter. In one embodiment, the promoter is an EF-1 promoter. In one embodiment, the EF-1 promoter comprises a sequence of SEQ ID NO: 6639.

Host Cells for CAR Expression

As noted above, in some aspects the invention pertains to a cell, e.g., an immune effector cell, (e.g., a population of cells, e.g., a population of immune effector cells) comprising a nucleic acid molecule, a CAR polypeptide molecule, or a vector as described herein.

In certain aspects of the present disclosure, immune effector cells, e.g., T cells, can be obtained from a unit of blood collected from a subject using any number of techniques known to the skilled artisan, such as Ficoll™ separation. In one preferred aspect, cells from the circulating blood of an individual are obtained by apheresis. The apheresis product typically contains lymphocytes, including T cells, monocytes, granulocytes, B cells, other nucleated white blood cells, red blood cells, and platelets. In one aspect, the cells collected by apheresis may be washed to remove the plasma fraction and, optionally, to place the cells in an appropriate buffer or media for subsequent processing steps. In one embodiment, the cells are washed with phosphate buffered saline (PBS). In an alternative embodiment, the wash solution lacks calcium and may lack magnesium or may lack many if not all divalent cations.

Initial activation steps in the absence of calcium can lead to magnified activation. As those of ordinary skill in the art would readily appreciate a washing step may be accomplished by methods known to those in the art, such as by using a semi-automated "flow-through" centrifuge (for example, the Cobe 2991 cell processor, the Baxter CytoMate, or the Haemonetics Cell Saver 5) according to the manufacturer's instructions. After washing, the cells may be resuspended in a variety of biocompatible buffers, such as, for example, Ca-free, Mg-free PBS, PlasmaLyte A, or other saline solution with or without buffer.

Alternatively, the undesirable components of the apheresis sample may be removed and the cells directly resuspended in culture media.

It is recognized that the methods of the application can utilize culture media conditions comprising 5% or less, for example 2%, human AB serum, and employ known culture media conditions and compositions, for example those described in Smith et al., "Ex vivo expansion of human T cells for adoptive immunotherapy using the novel Xeno-free CTS Immune Cell Serum Replacement" *Clinical & Translational Immunology* (2015) 4, e31; doi:10.1038/cti.2014.31.

In one aspect, T cells are isolated from peripheral blood lymphocytes by lysing the red blood cells and depleting the monocytes, for example, by centrifugation through a PERCOLL™ gradient or by counterflow centrifugal elutriation.

The methods described herein can include, e.g., selection of a specific subpopulation of immune effector cells, e.g., T cells, that are a T regulatory cell-depleted population, CD25+ depleted cells, using, e.g., a negative selection technique, e.g., described herein. Preferably, the population of T regulatory depleted cells contains less than 30%, 25%, 20%, 15%, 10%, 5%, 4%, 3%, 2%, 1% of CD25+ cells.

In one embodiment, T regulatory cells, e.g., CD25+ T cells, are removed from the population using an anti-CD25 antibody, or fragment thereof, or a CD25-binding ligand, IL-2. In one embodiment, the anti-CD25 antibody, or fragment thereof, or CD25-binding ligand is conjugated to a substrate, e.g., a bead, or is otherwise coated on a substrate, e.g., a bead. In one embodiment, the anti-CD25 antibody, or fragment thereof, is conjugated to a substrate as described herein.

In one embodiment, the T regulatory cells, e.g., CD25+ T cells, are removed from the population using CD25 depletion reagent from Miltenyi™. In one embodiment, the ratio of cells to CD25 depletion reagent is 1e7 cells to 20 uL, or 1e7 cells to 15 uL, or 1e7 cells to 10 uL, or 1e7 cells to 5 uL, or 1e7 cells to 2.5 uL, or 1e7 cells to 1.25 uL. In one embodiment, e.g., for T regulatory cells, e.g., CD25+ depletion, greater than 500 million cells/ml is used. In a further aspect, a concentration of cells of 600, 700, 800, or 900 million cells/ml is used.

In one embodiment, the population of immune effector cells to be depleted includes about $6 \times 10^9$ CD25+ T cells. In other aspects, the population of immune effector cells to be depleted include about $1 \times 10^9$ to $1 \times 10^{10}$ CD25+ T cell, and any integer value in between. In one embodiment, the resulting population T regulatory depleted cells has $2 \times 10^9$ T regulatory cells, e.g., CD25+ cells, or less (e.g., $1 \times 10^9$, $5 \times 10^8$, $1 \times 10^8$, $5 \times 10^7$, $1 \times 10^7$, or less CD25+ cells).

In one embodiment, the T regulatory cells, e.g., CD25+ cells, are removed from the population using the CliniMAC system with a depletion tubing set, such as, e.g., tubing 162-01. In one embodiment, the CliniMAC system is run on a depletion setting such as, e.g., DEPLETION2.1.

Without wishing to be bound by a particular theory, decreasing the level of negative regulators of immune cells (e.g., decreasing the number of unwanted immune cells, e.g., $T_{REG}$ cells), in a subject prior to apheresis or during manufacturing of a CAR-expressing cell product can reduce the risk of subject relapse. For example, methods of depleting $T_{REG}$ cells are known in the art. Methods of decreasing $T_{REG}$ cells include, but are not limited to, cyclophosphamide, anti-GITR antibody (an anti-GITR antibody described herein), CD25-depletion, and combinations thereof.

In some embodiments, the manufacturing methods comprise reducing the number of (e.g., depleting) $T_{REG}$ cells prior to manufacturing of the CAR-expressing cell. For example, manufacturing methods comprise contacting the sample, e.g., the apheresis sample, with an anti-GITR antibody and/or an anti-CD25 antibody (or fragment thereof, or a CD25-binding ligand), e.g., to deplete $T_{REG}$ cells prior to manufacturing of the CAR-expressing cell (e.g., T cell, NK cell) product.

In an embodiment, a subject is pre-treated with one or more therapies that reduce $T_{REG}$ cells prior to collection of cells for CAR-expressing cell product manufacturing, thereby reducing the risk of subject relapse to CAR-expressing cell treatment. In an embodiment, methods of decreasing $T_{REG}$ cells include, but are not limited to, administration to the subject of one or more of cyclophosphamide, anti-GITR antibody, CD25-depletion, or a combination thereof. Administration of one or more of cyclophosphamide, anti-GITR antibody, CD25-depletion, or a combination thereof, can occur before, during or after an infusion of the CAR-expressing cell product.

In an embodiment, a subject is pre-treated with cyclophosphamide prior to collection of cells for CAR-expressing cell product manufacturing, thereby reducing the risk of subject relapse to CAR-expressing cell treatment. In an embodiment, a subject is pre-treated with an anti-GITR antibody prior to collection of cells for CAR-expressing cell product manufacturing, thereby reducing the risk of subject relapse to CAR-expressing cell treatment.

In one embodiment, the population of cells to be removed are neither the regulatory T cells or tumor cells, but cells that otherwise negatively affect the expansion and/or function of CART cells, e.g. cells expressing CD14, CD11b, CD33, CD15, or other markers expressed by potentially immune suppressive cells. In one embodiment, such cells are envisioned to be removed concurrently with regulatory T cells and/or tumor cells, or following said depletion, or in another order.

The methods described herein can include more than one selection step, e.g., more than one depletion step. Enrichment of a T cell population by negative selection can be accomplished, e.g., with a combination of antibodies directed to surface markers unique to the negatively selected cells. One method is cell sorting and/or selection via negative magnetic immunoadherence or flow cytometry that uses a cocktail of monoclonal antibodies directed to cell surface markers present on the cells negatively selected. For example, to enrich for CD4+ cells by negative selection, a monoclonal antibody cocktail can include antibodies to CD14, CD20, CD11b, CD16, HLA-DR, and CD8.

The methods described herein can further include removing cells from the population which express a tumor antigen, e.g., a tumor antigen that does not comprise CD25, e.g., CD19, CD30, CD38, CD123, CD20, CD14 or CD11b, to thereby provide a population of T regulatory depleted, e.g., CD25+ depleted, and tumor antigen depleted cells that are suitable for expression of a CAR, e.g., a CAR described herein. In one embodiment, tumor antigen expressing cells are removed simultaneously with the T regulatory, e.g., CD25+ cells. For example, an anti-CD25 antibody, or fragment thereof, and an anti-tumor antigen antibody, or fragment thereof, can be attached to the same substrate, e.g., bead, which can be used to remove the cells or an anti-CD25 antibody, or fragment thereof, or the anti-tumor antigen antibody, or fragment thereof, can be attached to separate beads, a mixture of which can be used to remove the cells. In other embodiments, the removal of T regulatory cells, e.g., CD25+ cells, and the removal of the tumor antigen expressing cells is sequential, and can occur, e.g., in either order.

Also provided are methods that include removing cells from the population which express a check point inhibitor, e.g., a check point inhibitor described herein, e.g., one or more of PD1+ cells, LAG3+ cells, and TIM3+ cells, to thereby provide a population of T regulatory depleted, e.g., CD25+ depleted cells, and check point inhibitor depleted cells, e.g., PD1+, LAG3+ and/or TIM3+ depleted cells. Exemplary check point inhibitors include B7-H1, B7-1, CD160, P1H, 2B4, PD1, TIM3, CEACAM (e.g., CEACAM-1, CEACAM-3 and/or CEACAM-5), LAG3, TIGIT, CTLA-4, BTLA and LAIR1. In one embodiment, check point inhibitor expressing cells are removed simultaneously with the T regulatory, e.g., CD25+ cells. For example, an anti-CD25 antibody, or fragment thereof, and an anti-check point inhibitor antibody, or fragment thereof, can be attached to the same bead which can be used to remove the cells, or an anti-CD25 antibody, or fragment thereof, and the anti-check point inhibitor antibody, or fragment there, can be attached to separate beads, a mixture of which can be used to remove the cells. In other embodiments, the removal of T regulatory cells, e.g., CD25+ cells, and the removal of the check point inhibitor expressing cells is sequential, and can occur, e.g., in either order.

Methods described herein can include a positive selection step. For example, T cells can isolated by incubation with anti-CD3/anti-CD28 (e.g., 3×28)-conjugated beads, such as DYNABEADS® M-450 CD3/CD28 T, for a time period sufficient for positive selection of the desired T cells. In one embodiment, the time period is about 30 minutes. In a further embodiment, the time period ranges from 30 minutes to 36 hours or longer and all integer values there between. In a further embodiment, the time period is at least 1, 2, 3, 4, 5, or 6 hours. In yet another embodiment, the time period is 10 to 24 hours, e.g., 24 hours. Longer incubation times may be used to isolate T cells in any situation where there are few T cells as compared to other cell types, such in isolating tumor infiltrating lymphocytes (TIL) from tumor tissue or from immunocompromised individuals. Further, use of longer incubation times can increase the efficiency of capture of CD8+ T cells. Thus, by simply shortening or lengthening the time T cells are allowed to bind to the CD3/CD28 beads and/or by increasing or decreasing the ratio of beads to T cells (as described further herein), subpopulations of T cells can be preferentially selected for or against at culture initiation or at other time points during the process. Additionally, by increasing or decreasing the ratio of anti-CD3 and/or anti-CD28 antibodies on the beads or other surface, subpopulations of T cells can be preferentially selected for or against at culture initiation or at other desired time points.

In one embodiment, a T cell population can be selected that expresses one or more of IFN-γ, TNFα, IL-17A, IL-2, IL-3, IL-4, GM-CSF, IL-10, IL-13, granzyme B, and perforin, or other appropriate molecules, e.g., other cytokines. Methods for screening for cell expression can be determined, e.g., by the methods described in PCT Publication No.: WO 2013/126712.

For isolation of a desired population of cells by positive or negative selection, the concentration of cells and surface (e.g., particles such as beads) can be varied. In certain aspects, it may be desirable to significantly decrease the volume in which beads and cells are mixed together (e.g., increase the concentration of cells), to ensure maximum contact of cells and beads. For example, in one aspect, a concentration of 10 billion cells/ml, 9 billion/ml, 8 billion/ml, 7 billion/ml, 6 billion/ml, or 5 billion/ml is used. In one aspect, a concentration of 1 billion cells/ml is used. In yet one aspect, a concentration of cells from 75, 80, 85, 90, 95, or 100 million cells/ml is used. In further aspects, concentrations of 125 or 150 million cells/ml can be used.

Using high concentrations can result in increased cell yield, cell activation, and cell expansion. Further, use of high cell concentrations allows more efficient capture of cells that may weakly express target antigens of interest, such as CD28-negative T cells, or from samples where there are many tumor cells present (e.g., leukemic blood, tumor tissue, etc.). Such populations of cells may have therapeutic value and would be desirable to obtain. For example, using high concentration of cells allows more efficient selection of CD8+ T cells that normally have weaker CD28 expression.

In a related aspect, it may be desirable to use lower concentrations of cells. By significantly diluting the mixture of T cells and surface (e.g., particles such as beads), interactions between the particles and cells is minimized. This selects for cells that express high amounts of desired antigens to be bound to the particles. For example, CD4+ T cells express higher levels of CD28 and are more efficiently captured than CD8+ T cells in dilute concentrations. In one aspect, the concentration of cells used is $5\times10^6$/ml. In other aspects, the concentration used can be from about $1\times10^5$/ml to $1\times10^6$/ml, and any integer value in between.

In other aspects, the cells may be incubated on a rotator for varying lengths of time at varying speeds at either 2-10° C. or at room temperature.

T cells for stimulation can also be frozen after a washing step. Wishing not to be bound by theory, the freeze and subsequent thaw step provides a more uniform product by removing granulocytes and to some extent monocytes in the cell population. After the washing step that removes plasma and platelets, the cells may be suspended in a freezing solution. While many freezing solutions and parameters are known in the art and will be useful in this context, one method involves using PBS containing 20% DMSO and 8% human serum albumin, or culture media containing 10% Dextran 40 and 5% Dextrose, 20% Human Serum Albumin and 7.5% DMSO, or 31.25% Plasmalyte-A, 31.25% Dextrose 5%, 0.45% NaCl, 10% Dextran 40 and 5% Dextrose, 20% Human Serum Albumin, and 7.5% DMSO or other suitable cell freezing media containing for example, Hespan and PlasmaLyte A, the cells then are frozen to −80° C. at a rate of 1° per minute and stored in the vapor phase of a liquid nitrogen storage tank. Other methods of controlled freezing may be used as well as uncontrolled freezing immediately at −20° C. or in liquid nitrogen.

In certain aspects, cryopreserved cells are thawed and washed as described herein and allowed to rest for one hour at room temperature prior to activation using the methods of the present invention.

Also contemplated in the context of the invention is the collection of blood samples or apheresis product from a subject at a time period prior to when the expanded cells as described herein might be needed. As such, the source of the cells to be expanded can be collected at any time point necessary, and desired cells, such as T cells, isolated and frozen for later use in immune effector cell therapy for any number of diseases or conditions that would benefit from immune effector cell therapy, such as those described herein. In one aspect a blood sample or an apheresis is taken from a generally healthy subject. In certain aspects, a blood sample or an apheresis is taken from a generally healthy subject who is at risk of developing a disease, but who has not yet developed a disease, and the cells of interest are isolated and frozen for later use. In certain aspects, the T cells may be expanded, frozen, and used at a later time. In certain aspects, samples are collected from a patient shortly after diagnosis of a particular disease as described herein but prior to any treatments. In a further aspect, the cells are isolated from a blood sample or an apheresis from a subject prior to any number of relevant treatment modalities, including but not limited to treatment with agents such as natalizumab, efalizumab, antiviral agents, chemotherapy, radiation, immunosuppressive agents, such as cyclosporin, azathioprine, methotrexate, mycophenolate, and FK506, antibodies, or other immunoablative agents such as CAMPATH, anti-CD3 antibodies, cytoxan, fludarabine, cyclosporin, FK506, rapamycin, mycophenolic acid, steroids, FR901228, and irradiation.

In a further aspect of the present invention, T cells are obtained from a patient directly following treatment that leaves the subject with functional T cells. In this regard, it has been observed that following certain cancer treatments, in particular treatments with drugs that damage the immune system, shortly after treatment during the period when patients would normally be recovering from the treatment, the quality of T cells obtained may be optimal or improved for their ability to expand ex vivo. Likewise, following ex vivo manipulation using the methods described herein, these cells may be in a preferred state for enhanced engraftment and in vivo expansion. Thus, it is contemplated within the context of the present invention to collect blood cells, including T cells, dendritic cells, or other cells of the hematopoietic lineage, during this recovery phase. Further, in certain aspects, mobilization (for example, mobilization with GM-CSF) and conditioning regimens can be used to create a condition in a subject wherein repopulation, recirculation, regeneration, and/or expansion of particular cell types is favored, especially during a defined window of time following therapy. Illustrative cell types include T cells, B cells, dendritic cells, and other cells of the immune system.

In one embodiment, the immune effector cells expressing a CAR molecule, e.g., a CAR molecule described herein, are obtained from a subject that has received a low, immune enhancing dose of an mTOR inhibitor. In an embodiment, the population of immune effector cells, e.g., T cells, to be engineered to express a CAR, are harvested after a sufficient time, or after sufficient dosing of the low, immune enhancing, dose of an mTOR inhibitor, such that the level of PD1 negative immune effector cells, e.g., T cells, or the ratio of PD1 negative immune effector cells, e.g., T cells/PD1 positive immune effector cells, e.g., T cells, in the subject or harvested from the subject has been, at least transiently, increased.

In other embodiments, population of immune effector cells, e.g., T cells, which have, or will be engineered to express a CAR, can be treated ex vivo by contact with an amount of an mTOR inhibitor that increases the number of PD1 negative immune effector cells, e.g., T cells or increases the ratio of PD1 negative immune effector cells, e.g., T cells/PD1 positive immune effector cells, e.g., T cells.

In one embodiment, a T cell population is diaglycerol kinase (DGK)-deficient. DGK-deficient cells include cells that do not express DGK RNA or protein, or have reduced or inhibited DGK activity. DGK-deficient cells can be generated by genetic approaches, e.g., administering RNA-interfering agents, e.g., siRNA, shRNA, miRNA, to reduce or prevent DGK expression. Alternatively, DGK-deficient cells can be generated by treatment with DGK inhibitors described herein.

In one embodiment, a T cell population is Ikaros-deficient. Ikaros-deficient cells include cells that do not express Ikaros RNA or protein, or have reduced or inhibited Ikaros activity, Ikaros-deficient cells can be generated by genetic approaches, e.g., administering RNA-interfering agents, e.g., siRNA, shRNA, miRNA, to reduce or prevent Ikaros expression. Alternatively, Ikaros-deficient cells can be generated by treatment with Ikaros inhibitors, e.g., lenalidomide.

In embodiments, a T cell population is DGK-deficient and Ikaros-deficient, e.g., does not express DGK and Ikaros, or has reduced or inhibited DGK and Ikaros activity. Such DGK and Ikaros-deficient cells can be generated by any of the methods described herein.

In an embodiment, the NK cells are obtained from the subject. In another embodiment, the NK cells are an NK cell line, e.g., NK-92 cell line (Conkwest).

In some aspects, the cells of the invention (e.g., the immune effector cells of the invention, e.g., the CAR-expressing cells of the invention) are induced pluripotent stem cells ("iPSCs") or embryonic stem cells (ESCs), or are T cells generated from (e.g., differentiated from) said iPSC and/or ESC. iPSCs can be generated, for example, by methods known in the art, from peripheral blood T lymphocytes, e.g., peripheral blood T lymphocytes isolated from a healthy volunteer. As well, such cells may be differentiated into T cells by methods known in the art. See e.g., Themeli M. et al., *Nat. Biotechnol.,* 31, pp. 928-933 (2013); doi: 10.1038/nbt.2678; WO2014/165707, the contents of each of which are incorporated herein by reference in their entirety.

Additional Expressed Agents

In another embodiment, a CAR-expressing immune effector cell described herein can further express another agent, e.g., an agent which enhances the activity of a CAR-expressing cell. For example, in one embodiment, the agent can be an agent which inhibits an inhibitory molecule. Examples of inhibitory molecules include PD-1, PD-L1, CTLA-4, TIM-3, CEACAM (e.g., CEACAM-1, CEACAM-3 and/or CEACAM-5), LAG-3, VISTA, BTLA, TIGIT, LAIR1, CD160, 2B4 and TGF beta, e.g., as described herein. In one embodiment, the agent that inhibits an inhibitory molecule comprises a first polypeptide, e.g., an inhibitory molecule, associated with a second polypeptide that provides a positive signal to the cell, e.g., an intracellular signaling domain described herein. In one embodiment, the agent comprises a first polypeptide, e.g., of an inhibitory molecule such as PD-1, PD-L1, CTLA-4, TIM-3, CEACAM (e.g., CEACAM-1, CEACAM-3 and/or CEACAM-5), LAG-3, VISTA, BTLA, TIGIT, LAIR1, CD160, 2B4 or TGF beta, or a fragment of any of these, and a second polypeptide which is an intracellular signaling domain described herein (e.g., comprising a costimulatory domain (e.g., 41BB, CD27 or CD28, e.g., as described herein) and/or a primary signaling domain (e.g., a CD3 zeta signaling domain described herein). In one embodiment, the agent comprises a first polypeptide of PD-1 or a fragment thereof, and a second polypeptide of an intracellular signaling domain described herein (e.g., a CD28, CD27, OX40 or 4-1BB signaling domain described herein and/or a CD3 zeta signaling domain described herein). In embodiments, the agent comprises a first polypeptide of an extracellular domain of an inhibitory molecule and a second polypeptide of an intracellular signaling domain of a costimulatory molecule described herein or primary signaling molecule described herein. Such molecules in which an inhibitory molecule (e.g., a domain of an inhibitory molecule) is associated with a molecule that provides a positive signal (e.g., a domain of a costimulatory molecule or primary signaling molecule) are further described in, for example, WO2013/019615.

In one embodiment, the CAR-expressing immune effector cell described herein can further comprise a second CAR, e.g., a second CAR that includes a different antigen binding domain, e.g., to the same target (e.g., a target described above) or a different target. In one embodiment, the second CAR includes an antigen binding domain to a target expressed on the same cancer cell type as the target of the first CAR. In one embodiment, the CAR-expressing immune effector cell comprises a first CAR that targets a first antigen and includes an intracellular signaling domain having a costimulatory signaling domain but not a primary signaling domain, and a second CAR that targets a second, different, antigen and includes an intracellular signaling domain having a primary signaling domain but not a costimulatory signaling domain.

While not wishing to be bound by theory, placement of a costimulatory signaling domain, e.g., 4-1BB, CD28, CD27 or OX-40, onto the first CAR, and the primary signaling domain, e.g., CD3 zeta, on the second CAR can limit the CAR activity to cells where both targets are expressed. In one embodiment, the CAR expressing immune effector cell comprises a first CAR that includes an antigen binding domain that targets, e.g., a target described above, a transmembrane domain and a costimulatory domain and a second CAR that targets an antigen other than antigen targeted by the first CAR (e.g., an antigen expressed on the same cancer cell type as the first target) and includes an antigen binding domain, a transmembrane domain and a primary signaling domain. In another embodiment, the CAR expressing immune effector cell comprises a first CAR that includes an antigen binding domain that targets, e.g., a target described above, a transmembrane domain and a primary signaling domain and a second CAR that targets an antigen other than antigen targeted by the first CAR (e.g., an antigen expressed on the same cancer cell type as the first target) and includes an antigen binding domain to the antigen, a transmembrane domain and a costimulatory signaling domain.

In one embodiment, the CAR-expressing immune effector cell comprises a CAR described herein, e.g., a CAR to a target described above, and an inhibitory CAR. In one embodiment, the inhibitory CAR comprises an antigen binding domain that binds an antigen found on normal cells but not cancer cells, e.g., normal cells that also express the target. In one embodiment, the inhibitory CAR comprises the antigen binding domain, a transmembrane domain and an intracellular domain of an inhibitory molecule. For example, the intracellular domain of the inhibitory CAR can be an intracellular domain of PD1, PD-L1, CTLA-4, TIM-3, CEACAM (e.g., CEACAM-1, CEACAM-3 and/or CEACAM-5), LAG-3, VISTA, BTLA, TIGIT, LAIR1, CD160, 2B4 or TGF beta.

In one embodiment, an immune effector cell (e.g., T cell, NK cell) comprises a first CAR comprising an antigen binding domain that binds to a tumor antigen as described herein, and a second CAR comprising a PD1 extracellular domain or a fragment thereof.

In one embodiment, the cell further comprises an inhibitory molecule as described above.

In one embodiment, the second CAR in the cell is an inhibitory CAR, wherein the inhibitory CAR comprises an antigen binding domain, a transmembrane domain, and an intracellular domain of an inhibitory molecule. The inhibitory molecule can be chosen from one or more of: PD1, PD-L1, CTLA-4, TIM-3, LAG-3, VISTA, BTLA, TIGIT, LAIR1, CD160, 2B4, TGF beta, CEACAM-1, CEACAM-3, and CEACAM-5. In one embodiment, the second CAR molecule comprises the extracellular domain of PD1 or a fragment thereof.

In embodiments, the second CAR molecule in the cell further comprises an intracellular signaling domain comprising a primary signaling domain and/or an intracellular signaling domain.

In other embodiments, the intracellular signaling domain in the cell comprises a primary signaling domain comprising the functional domain of CD3 zeta and a costimulatory signaling domain comprising the functional domain of 4-1BB.

In one embodiment, the second CAR molecule in the cell comprises the amino acid sequence of SEQ ID NO: 6654.

In certain embodiments, the antigen binding domain of the first CAR molecule comprises a scFv and the antigen binding domain of the second CAR molecule does not comprise a scFv. For example, the antigen binding domain of the first CAR molecule comprises a scFv and the antigen binding domain of the second CAR molecule comprises a camelid VHH domain.

In other aspects and embodiments, a cell of the invention, e.g., a cell engineered to express a CAR, is also engineered to express a safety molecule, such as a molecule (or set of molecules) which mediates the depleting of the cells, e.g., CAR T cells, when appropriate (e.g., after the T cells have accomplished the anti-tumor function, or if the T cells are causing life-threatening side effects). In one exemplary aspect, the safety molecule a molecule that does not affect the function of the cell, but which can be targeted by another agent, e.g., an antibody or ADC molecule targeting said molecule. One exemplary embodiment of such a molecule is a truncated receptor, e.g., a receptor comprising the extracellular domain and transmembrane domain of a receptor, but lacking all or a substantial portion of the intracellular domain of the receptor. An example is a truncated EGFR receptor, e.g., as described in WO2011/056894. Without being bound by theory, targeting said truncated EGFR receptor with an anti-EGFR antibody, e.g., cetuximab, will deplete cells expressing the truncated EGFR receptor. A second example is a iCasp9 switch polypeptide, e.g., a polypeptide having a dimerization domain, an optional linker, and a caspase domain oriented such that, when expressed in the presence of a dimerization compound in a mammalian host cell, the iCasp9 switch polypeptide homodimerizes, resulting in apoptosis of the host cell. In embodiments, the dimerization domain is a FKBP-based dimerization domain, e.g., the sequence harbors a mutation (F37V) which provides a complementary fitting cavity for AP1903 and AP1903-structurally related ligands (such as AP20187), which molecules may act as a dimerization compound. Such iCasp9 switch polypeptides (and associated dimerization compounds) are described in, for example, WO1997/031899, US2011/286980, WO2014/164348, WO2013/040371, US2013/071414, WO2014/255360, and N Engl J Med. 2011 Nov. 3; 365(18):1673-83. A third example of such a molecule is a molecule targeted by an anti-CD20 antibody, wherein, for example, administering an anti-CD20 antibody (e.g., rituximab) allows said cells to be depleted. Examples of molecules targeted by an anti-CD20 antibody include CD20, and truncated versions thereof (e.g., molecules comprising an extracellular domain recognizable by an anti-CD20 antibody, a transmembrane domain, and lacking at least a portion of an intracellular domain).

In other aspects and embodiments, the cell of the invention, e.g., a cell engineered to express a CAR, is also engineered to express an NK inhibitory molecule. As used herein, the term "NK inhibitory molecule" refers to a molecule which inhibits a function, e.g., a cytolytic function, of NK cells. Without being bound by theory, it is believed that a cell, e.g., a cell of the invention, which has reduced or eliminated expression of one or more MHC class I molecules (e.g., which have reduced or eliminated expression of B2M, NLRC5 and/or CIITA, e.g., by introduction of a CRISPR system targeting B2M, NLRC5 and/or CIITA as described herein into said cell) may be recognized by NK cells as non-self, and targeted for cytolysis. Thus, expression of one or more NK inhibitory molecules on said cell protects it from NK cell destruction. In one aspect, the NK inhibitory molecule is a ligand for an NK inhibitory receptor. Non-limiting examples of NK inhibitory receptors include NK cell surface receptors which have or which associate with an immunoreceptor tyrosine-based inhibitory motif (ITIM). Non-limiting examples of such receptors include 2B4 (also known as CD244); a member of the NK-cell-receptor protein 1 (NKR-P1) family (e.g., NKR-P1A, NKR-P1B, NKR-P1C, NKR-P1D, NKR-P1E and NKR-P1F, e.g., NKR-P1B and NKR-P1D); a member of the carcinoembryonic-antigen-related cell-adhesion molecule (CEACAM) family (e.g., CEACAM1); Sialic acid-binding immunoglobulin-like lectin (SIGLEC) family members (e.g., SIGLEC7 and SIGLEC9); Leukocyte-associated immunoglobulin-like receptor 1 (LAIR1); Glycoprotein 49 B1 (gp49B1) or human homolog thereof; CD81; and a member of the signal-regulatory protein (SIRP) family. In embodiments, the NK inhibitory molecule is a non-MHC class I molecule. Non-limiting examples of NK inhibitory molecules include ligands for the aforementioned receptors, e.g., CD48, a member of the C-type lectin-related family (e.g., CLR-B (also known as OCIL), CLR-F and CLR-G (also known as OCILrP2)), CEACAM1, a polypeptide displaying sialic acid, and alpha V beta 3 integrin. In embodiments, the NK inhibitory molecule is a fragment of a naturally occurring molecule, e.g., comprises the extracellular domain and transmembrane domain of the NK inhibitory molecule, but lacks the all or a portion of the intracellular domain (e.g., lacks an intracellular ITIM or inhibitory domain). In other embodiments, the NK inhibitory molecule is an HLA-G molecule. HLA-G has been shown to arrest or reduce the function of the immune system, e.g., NK cells. Carosella et al., *Advances in Immunol.*, vol. 127, pp. 33-144, 2015; Torikai H. et al., *Blood.*, vol. 122(8), pp. 1341-1349, 2013. Without being bound by theory, the presence of HLA-G on the surface of a CAR-expressing cell, e.g., an allogeneic CAR-expressing cell, e.g., as described herein, e.g., a CAR-expressing cell that has reduced or eliminated expression of TCR, (B2M or NLRC5) and/or CIITA, e.g., as described herein, may protect the cell from NK cell attack. In embodiments, the NK inhibitory molecule is an isoform of HLA-G that does not require B2M, e.g., HLA-G2, HLA-G3, HLA-G4. Such embodiments are preferred with the cell of the invention, e.g., as described herein comprises an agent or system (e.g., a CRISPR/Cas system, e.g., as described herein) which inhibits the function and/or expression of B2M. Alternatively, in other embodiments in which the cell of the invention, e.g., as described herein, comprises (or at any time comprised) an agent or system (e.g., a CRISPR/Cas system, e.g., as described herein) which inhibits the function and/or expression of B2M (i.e., a cell in which the function and/or expression of B2M has been reduced or eliminated, e.g., as described herein), the NK inhibitory molecule may be an HLA-G molecule which under natural conditions forms a complex with B2M, provided that the NK inhibitory molecule comprises a fusion with a B2M molecule. Such fusions, and methods for their creation, are known in the art. See, e.g., Favier B, HoWangYin K Y, Wu J, Caumartin J, Daouya M, et al. (2011) Tolerogenic Function of Dimeric Forms of HLA-G Recombinant Proteins: A Comparative Study In Vivo. PLoS ONE 6(7): e21011. doi:10.1371/journal.pone.0021011. In such embodiments, to the extent the gene encoding the HLA-G:B2M fusion molecule comprises a B2M-encoding sequence which comprises a target sequence of a B2M targeting gRNA molecule, the sequence of said nucleic acid may be altered to reduce or eliminate binding of the gRNA to the HLA-G:B2M fusion-encoding nucleic acid so that expression and/or function of the HLA-G:B2M fusion is not reduced or eliminated. In embodiments, the HLA-G:B2M fusion may further comprise a transmembrane domain or sequence suitable for attachment of a membrane anchor molecule (such as a GPI anchor). An exemplary HLA-G:B2M fusion molecule (e.g., an HLA-G1:B2M fusion molecule) is provided below ((G4S)3 linker (SEQ ID NO: 6594) is indicated in bold text). The linker may be present or absent, and may alternatively comprise any peptidic linker, e.g., as described herein). This particular construct has the format B2M-linker ((G4S)3)-HLA-G:

SEQ ID NO: 10674
MSRSVALAVLALLSLSGLEAIQRTPKIQVYSRHPAENGKSNFLNCYVSG

FHPSDIEVDLLKNGERIEKVEHSDLSFSKDWSFYLLYYTEFTPTEKDEY

ACRVNHVTLSQPKIVKWDRDMGGGGSGGGGSGGGGSGSHSMRYFSAAVS

RPGRGEPRFIAMGYVDDTQFVRFDSDSACPRMEPRAPWVEQEGPEYWEE

ETRNTKAHAQTDRMNLQTLRGYYNQSEASSHTLQWMIGCDLGSDGRLLR

GYEQYAYDGKDYLALNEDLRSWTAADTAAQISKRKCEAANVAEQRRAYL

EGTCVEWLHRYLENGKEMLQRADPPKTHVTHHPVFDYEATLRCWALGFY

PAEIILTWQRDGEDQTQDVELVETRPAGDGTFQKWAAVVVPSGEEQRYT

CHVQHEGLPEPLMLRWKQSSLPTIPIMGIVAGLVVLAAVVTGAAVAAVL

WRKKSSD

An exemplary codon-optimized nucleic acid sequence encoding the above HLA-G:B2M fusion is provided below:

SEQ ID NO: 10675
GCC ACC ATG AGC AGA TCT GTG GCC CTG GCT GTG CTG

GCC CTG CTG TCT CTG TCT GGC CTG GAA GCC ATC CAG

CGG ACC CCC AAG ATC CAG GTG TAC AGC AGA CAC CCC

GCC GAA AAC GGC AAG AGC AAC TTC CTG AAC TGC TAC

GTG TCC GGC TTC CAC CCC AGC GAC ATC GAG GTG GAC

CTG CTG AAG AAC GGC GAG CGG ATC GAA AAG GTG GAA

CAT AGC GAC CTG AGC TTC AGC AAG GAC TGG TCC TTC

TAC CTG CTG TAC TAC ACC GAG TTC ACC CCC ACC GAA

AAG GAC GAG TAC GCC TGC AGA GTG AAC CAC GTG ACC

CTG AGC CAG CCC AAG ATC GTG AAG TGG GAC CGG GAT

ATG GGC GGA GGC GGA TCC GGC GGC GGA GGA TCA GGG

GGG GGA GGG TCC GGA TCC CAC AGC ATG CGG TAC TTC

TCT GCC GCC GTG TCC AGA CCT GGA AGA GGC GAG CCC

CGG TTT ATC GCC ATG GGC TAC GTG GAC GAC ACC CAG

TTC GTC AGA TTC GAC AGC GAC AGC GCC TGC CCC CGG

ATG GAA CCT AGA GCA CCT TGG GTG GAA CAG GAA GGC

CCC GAG TAC TGG GAG GAA GAG ACA CGG AAC ACC AAG

GCC CAC GCC CAG ACC GAC AGA ATG AAC CTG CAG ACC

CTG CGG GGC TAC TAC AAC CAG AGC GAG GCC AGC AGC

CAC ACC CTG CAG TGG ATG ATC GGC TGC GAT CTG GGC

AGC GAC GGC AGA CTG CTG AGA GGT TAC GAA CAG TAC

GCC TAC GAC GGC AAG GAC TAC CTG GCC CTG AAC GAG

GAC CTG CGG TCT TGG ACA GCC GCC GAT ACA GCC GCC

CAG ATC AGC AAG AGA AAG TGC GAG GCC GCC AAC GTG

GCC GAG CAG AGA AGG GCT TAC CTG GAA GGC ACC TGT

GTG GAA TGG CTG CAT AGA TAC CTG GAA AAC GGC AAA

GAG ATG CTG CAG CGG GCC GAC CCC CCT AAG ACA CAC

GTG ACA CAC CAC CCC GTG TTC GAC TAC GAG GCC ACC

CTG AGA TGT TGG GCC CTG GGC TTC TAT CCT GCC GAG

ATC ATC CTG ACC TGG CAG AGG GAT GGC GAG GAC CAG

ACC CAG GAC GTG GAA CTG GTG GAA ACC AGA CCT GCC

```
                            -continued
GGC GAC GGC ACC TTC CAG AAA TGG GCT GCT GTG GTG

GTG CCC AGC GGC GAA GAA CAG AGA TAC ACC TGT CAC

GTG CAG CAC GAG GGC CTG CCC GAA CCC CTG ATG CTG

AGA TGG AAG CAG AGC AGC CTG CCC ACC ATC CCC ATC

ATG GGA ATC GTG GCC GGA CTG GTG GTG CTG GCC GCT

GTC GTG ACA GGC GCT GCA GTG GCC GCC GTG CTG TGG

CGG AAG AAG TCC AGC GAC TAA
```

Another exemplary HLA-G molecule, which may be combined with a B2M sequence, or used without, is provided below (optional leader sequence is indicated in bold text):

SEQ ID NO: 10676

MVVMAPRTLFLLLSGALTLTETWAGSHSMRYFSAAVSRPSRGEPRFIAM

GYVDDTQFVRFDSDSACPRMEPRAPWVEREGPEYWEEETRNTKAHAQTD

RMNLQTLRGYYNQSEASSHTLQWMIGCDLGSDGRLLRGYEQYAYDGKDY

LALNEDLRSWTAADTAAQISKRKCEAANVAEQRRAYLEGTCVEWLHRYL

ENGKEMLQRADPPKTHVTHHPVFDYEATLRCWALGFYPAEIILTWQRDG

EDQTQDVELVETKPAGDGTFQKWAAVVVPSGEEQRYTCHVQHEGLPEPL

MLRWKQSSLPTIPIMGIVAGLVVLAAVVTGAAVAAVLWRKKSSD

In other embodiments where the NK inhibitory molecule requires B2M, and it is desirable to reduce or eliminate expression of one or more HLA Class I molecules, a CRISPR/Cas system (e.g., as described herein) may be used which comprises a gRNA comprising a targeting domain which is complementary to a target sequence of NLRC5 (human NLRC5: Entrez 84166; UniProt Q86WI3) or its regulatory elements, e.g., a gRNA which comprises a targeting domain listed in Table 1 to NLRC5 (or a fragment of such targeting domain, e.g., the 3' 20 nucleotides of such targeting domain, listed in Table 1 to NLRC5; e.g., a gRNA comprising a targeting domain comprising of any one of SEQ ID NO: 8622 to SEQ ID NO: 10089 or fragment (e.g., 3' 20 nucleotide fragment) thereof). Without being bound by theory, it is believed that reduced or eliminated expression and/or function of NLRC5 will reduce or eliminate expression and/or function of one or more MHC Class I molecules, even in the presence of B2M. See e.g., Downs, I., Vijayan, S., Sidiq, T. and Kobayashi, K. S. (2016), CITA/NLRC5: A critical transcriptional regulator of MHC class I gene expression. *BioFactors*, 42: 349-357. doi:10.1002/biof.1285.

In other embodiements, the NK inhibitory molecule is a membrane-bound isoform of HLA-G, e.g., HLA-G1, HLA-G2, HLA-G3 and/or HLA-G4. In other embodiments, the NK inhibitory molecule is a soluble isoform of HLA-G, e.g., sHLA-G1 (shed), HLA-G5, HLA-G6, and/or HLA-G7. In embodiments, the NK inhibitory molecule is selected from one or more of HLA-G2, HLA-G3 and HLA-G4. In an embodiment, the NK inhibitory molecule is HLA-G2.

In other embodiments, the NK inhibitory molecule is an HLA-E molecule. HLA-E has been shown to arrest or reduce the function of NK cells against HLA Class I-negative cells. Torikai H. et al., *Blood*, vol. 122(8), pp. 1341-1349, 2013. Without being bound by theory, the presence of HLA-E on the surface of a CAR-expressing cell, e.g., an allogeneic CAR-expressing cell, e.g., as described herein, e.g., a CAR-expressing cell that has reduced or eliminated expression of TCR, (B2M or NLRC5) and/or CIITA, e.g., as described herein, may protect the cell from NK cell attack. In an embodiment, the NK inhibitory molecule is an HLA-G molecule and an HLA-E molecule.

In embodiments where the cell of the invention, e.g., the CAR expressing cell of the invention, e.g., as described herein, is engineered to express an NK inhibitory molecule, the cell may be further engineered to reduce or eliminate expression and/or function of one or more ligands or binding partners of said NK inhibitory molecule (herein referred to as "target of an NK inhibitory molecule"). Without being bound by theory, it is believed that reduction or elimination of expression and/or function, e.g., surface expression, of a target of an NK inhibitory molecule will reduce or avoid inhibition of the cell of interest, e.g., the CAR expressing cell of the invention, e.g., as described herein, by the expression of the NK inhibitory molecule, thereby improving the function of the cell of the invention, e.g., the CAR expressing cell of the invention, e.g., as described herein. In other embodiments, the inhibitory effects of the NK inhibitory molecule may be reduced or eliminated in the cell of interest, e.g., the CAR expressing cell of the invention, e.g., as described herein, by expressing a dominant negative mutant or fragment of the target of an NK inhibitory molecule, e.g., a target of an NK inhibitory molecule which has a modified or eliminated (partially or wholly) intracellular inhibitory domain (e.g., one or more ITIM domains), such that the inhibitory signal is not propagated upon binding of the NK inhibitory molecule. In embodiments where the NK inhibitory molecule is an HLA-G molecule, e.g., as described herein, the target of an NK inhibitory molecule is LILRB1 (e.g., human LILRB1: Entrez: 10859; UniProt Q8NHL6). In embodiments, the reduction or elimination of expression and/or function of the target of an NK inhibitory molecule, e.g., LILRB1, is accomplished by introducing a nucleic acid inhibitor of the target of an NK inhibitory molecule (e.g., an shRNA or siRNA molecule specific for LILRB1). In other embodiments, the reduction or elimination of expression and/or function of the target of an NK inhibitory molecule, e.g., LILRB1, is accomplished by introducing a gene editing system, e.g. a CRISPR/Cas gene editing system, e.g., as described herein, which recognizes a target sequence in the gene or its regulatory elements of the target of an NK inhibitory molecule (e.g., recognizes a target sequence in the LILRB1 gene or its regulatory elements), such that expression and/or function of the target of an NK inhibitory molecule, e.g., LILRB1, is reduced or eliminated. In embodiments, where the target of an NK inhibitory molecule is LILRB1, the gene editing system is a CRISPR/Cas system, e.g., as described herein, comprising a gRNA molecule comprising a targeting domain listed in Table 6d (or, as described herein, comprising a fragment, e.g., a 20 nucleotide fragment, e.g., the 3' 20 nucleotides, of a targeting domain listed in Table 6d).

In embodiments and aspects, the invention relates to a cell, e.g., an immune effector cell, (or population of said cells) comprising nucleic acid encoding an NK inhibitory molecule, e.g., such that the NK inhibitory molecule is expressed in said cell, e.g., comprises nucleic acid encoding an NK inhibitory molecule operably linked to a promoter operable in the cell. In embodiments, the nucleic acid molecule encoding an NK inhibitory molecule comprises additional sequence encoding a CAR. In embodiments, the nucleic acid sequence encoding an NK inhibitory molecule and the nucleic acid sequence encoding a CAR are operably linked to separate promoters, as described herein. In other embodiments, an NK inhibitory molecule the nucleic acid sequence encoding an NK inhibitory molecule and the nucleic acid sequence encoding a CAR are expressed from a single promoter, optionally with a sequence encoding a cleavable peptide (e.g., a 2A peptide) disposed between the sequences encoding the two molecules.

The cell of the invention, e.g., the cells engineered to express a CAR, may be engineered to express more than one of the additional molecules described above. In embodiments, the cell is engineered to express a CAR, e.g., as described herein, an iCasp9 switch polypeptide and an NK inhibitory molecule.

In embodiments and aspects, a cell of the invention, e.g., an immune effector cell (or population of said cells), e.g., a CAR-expressing cell as described herein, has reduced or eliminated expression of the protein comprising the target antigen of the CAR molecule (e.g., a target antigen described herein). Such reduced or eliminated expression of the protein comprising the target antigen of the CAR molecule may be affected, by for example, introducing a mutation (e.g., an indel) within the gene sequence encoding said protein comprising the target antigen (or its regulatory elements) using a gene editing system, e.g., a CRISPR gene editing system (e.g., comprising a gRNA molecule complementary to a target sequence within said gene), e.g., described herein. Without being bound by theory, reduced or eliminated expression of the protein comprising the target antigen of the CAR molecule may protect said CAR-expressing cells from self-recognition and/or attack. In embodiments, the reduced or eliminated expression of said protein comprising the target antigen of the CAR molecule is relative to the expression of said protein comprising the target antigen of the CAR molecule in a resting cell, e.g., resting T cell. In other embodiments, the reduced or eliminated expression of said protein comprising the target antigen of the CAR molecule is relative to the expression of said protein comprising the target antigen of the CAR molecule in an activated cell, e.g., an activated T cell, e.g., a T cell activated by CD3 and/or CD28 stimulation, or by activation through signaling of the CAR molecule.

Split CAR

In some embodiments, the CAR-expressing cell uses a split CAR. The split CAR approach is described in more detail in publications WO2014/055442 and WO2014/055657. Briefly, a split CAR system comprises a cell expressing a first CAR having a first antigen binding domain and a costimulatory domain (e.g., 41BB), and the cell also expresses a second CAR having a second antigen binding domain and an intracellular signaling domain (e.g., CD3 zeta). When the cell encounters the first antigen, the costimulatory domain is activated, and the cell proliferates. When the cell encounters the second antigen, the intracellular signaling domain is activated and cell-killing activity begins. Thus, the CAR-expressing cell is only fully activated in the presence of both antigens.

Multiple CAR Expression

In one aspect, the CAR-expressing cell described herein can further comprise a second CAR, e.g., a second CAR that includes a different antigen binding domain, e.g., to the same target or a different target (e.g., a target other than a cancer associated antigen described herein or a different cancer associated antigen described herein). In one embodiment, the second CAR includes an antigen binding domain to a target expressed the same cancer cell type as the cancer associated antigen. In one embodiment, the CAR-expressing cell comprises a first CAR that targets a first antigen and includes an intracellular signaling domain having a costimulatory signaling domain but not a primary signaling domain, and a second CAR that targets a second, different, antigen and includes an intracellular signaling domain having a primary signaling domain but not a costimulatory signaling domain. While not wishing to be bound by theory, placement of a costimulatory signaling domain, e.g., 4-1BB, CD28, CD27 or OX-40, onto the first CAR, and the primary signaling domain, e.g., CD3 zeta, on the second CAR can limit the CAR activity to cells where both targets are expressed. In one embodiment, the CAR expressing cell comprises a first cancer associated antigen CAR that includes an antigen binding domain that binds a target antigen described herein, a transmembrane domain and a costimulatory domain and a second CAR that targets a different target antigen (e.g., an antigen expressed on that same cancer cell type as the first target antigen) and includes an antigen binding domain, a transmembrane domain and a primary signaling domain. In another embodiment, the CAR expressing cell comprises a first CAR that includes an antigen binding domain that binds a target antigen described herein, a transmembrane domain and a primary signaling domain and a second CAR that targets an antigen other than the first target antigen (e.g., an antigen expressed on the same cancer cell type as the first target antigen) and includes an antigen binding domain to the antigen, a transmembrane domain and a costimulatory signaling domain.

In some embodiments, the claimed invention comprises a first and second CAR, wherein the antigen binding domain of one of said first CAR said second CAR does not comprise a variable light domain and a variable heavy domain. In some embodiments, the antigen binding domain of one of said first CAR said second CAR is an scFv, and the other is not an scFv. In some embodiments, the antigen binding domain of one of said first CAR said second CAR comprises a single VH domain, e.g., a camelid, shark, or lamprey single VH domain, or a single VH domain derived from a human or mouse sequence. In some embodiments, the antigen binding domain of one of said first CAR said second CAR comprises a nanobody. In some embodiments, the antigen binding domain of one of said first CAR said second CAR comprises a camelid VHH domain.

Telomerase Expression

While not wishing to be bound by any particular theory, in some embodiments, a therapeutic T cell has short term persistence in a patient, due to shortened telomeres in the T cell; accordingly, transfection with a telomerase gene can lengthen the telomeres of the T cell and improve persistence of the T cell in the patient. See Carl June, "Adoptive T cell therapy for cancer in the clinic", Journal of Clinical Investigation, 117:1466-1476 (2007). Thus, in an embodiment, an immune effector cell, e.g., a T cell, ectopically expresses a telomerase subunit, e.g., the catalytic subunit of telomerase, e.g., TERT, e.g., hTERT. In some aspects, this disclosure provides a method of producing a CAR-expressing cell, comprising contacting a cell with a nucleic acid encoding a telomerase subunit, e.g., the catalytic subunit of telomerase, e.g., TERT, e.g., hTERT. The cell may be contacted with the nucleic acid before, simultaneous with, or after being contacted with a construct encoding a CAR.

In embodiments in which a cell is engineered to express more than one molecule, sequence encoding each of said molecules (e.g., sequence encoding a CAR and sequence encoding an NK inhibitory molecule) can be disposed on the same nucleic acid molecule, e.g., the same plasmid or vector, e.g., viral vector, e.g., lentiviral vector. In an embodiment, (i) sequence encoding a CAR, as described herein, and (ii) sequence encoding an NK inhibitory molecule, as described herein, can be present on the same nucleic acid, e.g., vector. Production of the corresponding proteins can be achieved, e.g., by the use of separate promoters, or by the use of a bicistronic transcription product (which can result in the production of two proteins by cleavage of a single translation product or by the translation of two separate protein products). In an embodiment, a sequence encoding a cleavable peptide, e.g., a P2A, T2A or F2A sequence, is disposed between (i) and (ii). In an embodiment, a sequence encoding an IRES, e.g., an EMCV or EV71 IRES, is disposed between (i) and (ii). In these embodiments, (i) and (ii) are transcribed as a single RNA. In other aspects, each molecule may be expressed from a different promoter. In an embodiment, a first promoter is operably linked to (i) and a second promoter is operably linked to (ii), such that (i) and (ii) are transcribed as separate mRNAs.

Alternatively, the sequence encoding the more than one molecules can be disposed on the different nucleic acid molecules, e.g., different plasmids or vectors, e.g., viral vector, e.g., lentiviral vector. E.g., the (i) sequence encoding a CAR as described herein can be present on a first nucleic acid, e.g., a first vector, and the (ii) sequence encoding a NK inhibitory molecule can be present on the second nucleic acid, e.g., the second vector.

TABLE 7

Exemplary sequences of various components of CAR (aa-amino acids, na-nucleic acids that encodes the corresponding protein)

| SEQ ID NO | description | Sequence | Corresp. To huCD19 |
|---|---|---|---|
| 6639 | EF-1 promoter | CGTGAGGCTCCGGTGCCCGTCAGTGGGCAGAGCGCACA TCGCCCACAGTCCCCGAGAAGTTGGGGGGAGGGGTCGG CAATTGAACCGGTGCCTAGAGAAGGTGGCGCGGGGTAA ACTGGGAAAGTGATGTCGTGTACTGGCTCCGCCTTTTC CCGAGGGTGGGGGAGAACCGTATATAAGTGCAGTAGTC GCCGTGAACGTTCTTTTTCGCAACGGGTTTGCCGCCAGA ACACAGGTAAGTGCCGTGTGTGGTTCCCGCGGGCCTGG CCTCTTTACGGGTTATGGCCCTTGCGTGCCTTGAATTAC TTCCACCTGGCTGCAGTACGTGATTCTTGATCCCGAGCT TCGGGTTGGAAGTGGGTGGGAGAGTTCGAGGCCTTGCG CTTAAGGAGCCCCTTCGCCTCGTGCTTGAGTTGAGGCCT GGCCTGGGCGCTGGGGCCGCCGCGTGCGAATCTGGTGG CACCTTCGCGCCTGTCTCGCTGCTTTCGATAAGTCTCTA GCCATTTAAAATTTTTGATGACCTGCTGCGACGCTTTTT TTCTGGCAAGATAGTCTTGTAAATGCGGGCCAAGATCT GCACACTGGTATTTCGGTTTTTGGGGCCGCGGGCGGCG ACGGGGCCCGTGCGTCCCAGCGCACATGTTCGGCGAGG CGGGGCCTGCGAGCGCGGCCACCGAGAATCGGACGGG GGTAGTCTCAAGCTGGCCGGCCTGCTCTGGTGCCTGGC CTCGCGCCGCCGTGTATCGCCCCGCCCTGGGCGGCAAG GCTGGCCCGGTCGGCACCAGTTGCGTGAGCGGAAAGAT GGCCGCTTCCCGGCCCTGCTGCAGGGAGCTCAAAATGG AGGACGCGGCGCTCGGGAGAGCGGGCGGGTGAGTCAC CCACACAAAGGAAAAGGGCCTTTCCGTCCTCAGCCGTC GCTTCATGTGACTCCACGGAGTACCGGGCGCCGTCCAG GCACCTCGATTAGTTCTCGAGCTTTTGGAGTACGTCGTC TTTAGGTTGGGGGAGGGGTTTTATGCGATGGAGTTTC CCCACACTGAGTGGGTGGAGACTGAAGTTAGGCCAGCT TGGCACTTGATGTAATTCTCCTTGGAATTTGCCCTTTTT GAGTTTGGATCTTGGTTCATTCTCAAGCCTCAGACAGTG GTTCAAAGTTTTTTCTTCCATTTCAGGTGTCGTGA | 100 |
| 6640 | Leader (aa) | MALPVTALLLPLALLLHAARP | 13 |
| 6641 | Leader (na) | ATGGCCCTGCCTGTGACAGCCCTGCTGCTGCCTCTGGCT CTGCTGCTGCATGCCGCTAGACCC | 54 |
| 10802 | Leader (na) | ATGGCCCTCCCTGTCACCGCCCTGCTGCTTCCGCTGGCT CTTCTGCTCCACGCCGCTCGGCCC | |
| 6642 | CD 8 hinge (aa) | TTTPAPRPPTPAPTIASQPLSLRPEACRPAAGGAVHTRGLD FACD | 14 |
| 6643 | CD8 hinge (na) | ACCACGACGCCAGCGCCGCGACCACCAACACCGGCGCC CACCATCGCGTCGCAGCCCCTGTCCCTGCGCCCAGAGG CGTGCCGGCCAGCGGCGGGGGGCGCAGTGCACACGAG GGGGCTGGACTTCGCCTGTGAT | 55 |
| 6630 | Ig4 hinge (aa) | ESKYGPPCPPCPAPEFLGGPSVFLFPPKPKDTLMISRTPEVT CVVVDVSQEDPEVQFNWYVDGVEVHNAKTKPREEQFNS TYRVVSVLTVLHQDWLNGKEYKCKVSNKGLPSSIEKTISK AKGQPREPQVYTLPPSQEEMTKNQVSLTCLVKGFYPSDIA VEWESNGQPENNYKTTPPVLDSDGSFFLYSRLTVDKSRW QEGNVFSCSVMHEALHNHYTQKSLSLSLGKM | 102 |

TABLE 7-continued

Exemplary sequences of various components of CAR (aa-amino acids, na-nucleic acids that encodes the corresponding protein)

| SEQ ID NO | description | Sequence | Corresp. To huCD19 |
|---|---|---|---|
| 6631 | Ig4 hinge (na) | GAGAGCAAGTACGGCCCTCCCTGCCCCCCTTGCCCTGC CCCCGAGTTCCTGGGCGGACCCAGCGTGTTCCTGTTCCC CCCCAAGCCCAAGGACACCCTGATGATCAGCCGGACCC CCGAGGTGACCTGTGTGGTGGTGGACGTGTCCCAGGAG GACCCCGAGGTCCAGTTCAACTGGTACGTGGACGGCGT GGAGGTGCACAACGCCAAGACCAAGCCCCGGGAGGAG CAGTTCAATAGCACCTACCGGGTGGTGTCCGTGCTGAC CGTGCTGCACCAGGACTGGCTGAACGGCAAGGAATACA AGTGTAAGGTGTCCAACAAGGGCCTGCCCAGCAGCATC GAGAAAACCATCAGCAAGGCCAAGGGCCAGCCTCGGG AGCCCCAGGTGTACACCCTGCCCCCTAGCCAAGAGGAG ATGACCAAGAACCAGGTGTCCCTGACCTGCCTGGTGAA GGGCTTCTACCCCAGCGACATCGCCGTGGAGTGGGAGA GCAACGGCCAGCCCGAGAACAACTACAAGACCACCCCC CCTGTGCTGGACAGCGACGGCAGCTTCTTCCTGTACAG CCGGCTGACCGTGGACAAGAGCCGGTGGCAGGAGGGC AACGTCTTTAGCTGCTCCGTGATGCACGAGGCCCTGCA CAACCACTACACCCAGAAGAGCCTGAGCCTGTCCCTGG GCAAGATG | 103 |
| 6632 | IgD hinge (aa) | RWPESPKAQASSVPTAQPQAEGSLAKATTAPATTRNTGR GGEEKKKEKEKEEQEERETKTPECPSHTQPLGVYLLTPAV QDLWLRDKATFTCFVVGSDLKDAHLTWEVAGKVPTGGV EEGLLERHSNGSQSQHSRLTLPRSLWNAGTSVTCTLNHPS LPPQRLMALREPAAQAPVKLSLNLLASSDPPEAASWLLCE VSGFSPPNILLMWLEDQREVNTSGFAPARPPPQPGSTTFW AWSVLRVPAPPSPQPATYTCVVSHEDSRTLLNASRSLEVS YVTDH | 47 |
| 6633 | IgD hinge (na) | AGGTGGCCCGAAAGTCCCAAGGCCCAGGCATCTAGTGT TCCTACTGCACAGCCCCAGGCAGAAGGCAGCCTAGCCA AAGCTACTACTGCACCTGCCACTACGCGCAATACTGGC CGTGGCGGGGAGGAGAAGAAAAAGGAGAAAGAGAAA GAAGAACAGGAAGAGAGGGAGACCAAGACCCCTGAAT GTCCATCCCATACCCAGCCGCTGGGCGTCTATCTCTTGA CTCCCGCAGTACAGGACTTGTGGCTTAGAGATAAGGCC ACCTTTACATGTTTCGTCGTGGGCTCTGACCTGAAGGAT GCCCATTTGACTTGGGAGGTTGCCGGAAAGGTACCCAC AGGGGGGGTTGAGGAAGGGTTGCTGGAGCGCCATTCCA ATGGCTCTCAGAGCCAGCACTCAAGACTCACCCTTCCG AGATCCCTGTGGAACGCCGGGACCTCTGTCACATGTAC TCTAAATCATCCTAGCCTGCCCCCACAGCGTCTGATGGC CCTTAGAGAGCCAGCCGCCCAGGCACCAGTTAAGCTTA GCTGAATCTGCTCGCCAGTAGTGATCCCCCAGAGGCC GCCAGCTGGCTCTTATGCGAAGTGTCCGGCTTTAGCCCG CCCAACATCTTGCTCATGTGGCTGGAGGACCAGCGAGA AGTGAACACCAGCGGCTTCGCTCCAGCCCGGCCCCCAC CCCAGCCGGGTTCTACCACATTCTGGGCCTGGAGTGTCT TAAGGGTCCAGCACCACCTAGCCCCCAGCCAGCCACA TACACCTGTGTTGTGTCCCATGAAGATAGCAGGACCCT GCTAAATGCTTCTAGGAGTCTGGAGGTTTCCTACGTGAC TGACCATT | 48 |
| 6634 | GS hinge/linker (aa) | GGGGSGGGGS | 49 |
| 6635 | GS hinge/linker (na) | GGTGGCGGAGGTTCTGGAGGTGGAGGTTCC | 50 |
| 6644 | CD8TM (aa) | IYIWAPLAGTCGVLLLSLVITLYC | 15 |
| 6645 | CD8 TM (na) | ATCTACATCTGGGCGCCCTTGGCCGGGACTTGTGGGGT CCTTCTCCTGTCACTGGTTATCACCCTTTACTGC | 56 |
| 10803 | CD8 TM (na) | ATCTACATTTGGGCCCCTCTGGCTGGTACTTGCGGGGTC CTGCTGCTTTCACTCGTGATCACTCTTTACTGT | |
| 6646 | 4-1BB intracellular domain (aa) | KRGRKKLLYIFKQPFMRPVQTTQEEDGCSCRFPEEEEGGC EL | 16 |

TABLE 7-continued

Exemplary sequences of various components of CAR (aa-amino acids, na-nucleic acids that encodes the corresponding protein)

| SEQ ID NO | description | Sequence | Corresp. To huCD19 |
|---|---|---|---|
| 6647 | 4-1BB intracellular domain (na) | AAACGGGGCAGAAAGAAACTCCTGTATATATTCAAACA ACCATTTATGAGACCAGTACAAACTACTCAAGAGGAAG ATGGCTGTAGCTGCCGATTTCCAGAAGAAGAAGAAGGA GGATGTGAACTG | 60 |
| 10804 | 4-1BB intracellular domain (na) | AAGCGCGGTCGGAAGAAGCTGCTGTACATCTTTAAGCA ACCCTTCATGAGGCCTGTGCAGACTACTCAAGAGGAGG ACGGCTGTTCATGCCGGTTCCCAGAGGAGGAGGAAGGC GGCTGCGAACTG | |
| 6636 | CD27 (aa) | QRRKYRSNKGESPVEPAEPCRYSCPREEEGSTIPIQEDYRK PEPACSP | 51 |
| 6637 | CD27 (na) | AGGAGTAAGAGGAGCAGGCTCCTGCACAGTGACTACAT GAACATGACTCCCCGCCGCCCCGGGCCCACCCGCAAGC ATTACCAGCCCTATGCCCCACCACGCGACTTCGCAGCCT ATCGCTCC | 52 |
| 6648 | CD3-zeta (aa) | RVKFSRSADAPAYKQGQNQLYNELNLGRREEYDVLDKRR GRDPEMGGKPRRKNPQEGLYNELQKDKMAEAYSEIGMK GERRRGKGHDGLYQGLSTATKDTYDALHMQALPPR | 17 |
| 6649 | CD3-zeta (na) | AGAGTGAAGTTCAGCAGGAGCGCAGACGCCCCCGCGTA CAAGCAGGGCCAGAACCAGCTCTATAACGAGCTCAATC TAGGACGAAGAGAGGAGTACGATGTTTTGGACAAGAG ACGTGGCCGGGACCCTGAGATGGGGGGAAAGCCGAGA AGGAAGAACCCTCAGGAAGGCCTGTACAATGAACTGCA GAAAGATAAGATGGCGGAGGCCTACAGTGAGATTGGG ATGAAAGGCGAGCGCCGGAGGGGCAAGGGGCACGATG GCCTTTACCAGGGTCTCAGTACAGCCACCAAGGACACC TACGACGCCCTTCACATGCAGGCCCTGCCCCCTCGC | 101 |
| 10805 | CD3-zeta (na) | CGCGTGAAATTCAGCCGCAGCGCAGATGCTCCAGCCTA CAAGCAGGGGCAGAACCAGCTCTACAACGAACTCAATC TTGGTCGGAGAGAGGAGTACGACGTGCTGGACAAGCG GAGAGGACGGGACCCAGAAATGGGCGGGAAGCCGCGC AGAAAGAATCCCCAAGAGGGCCTGTACAACGAGCTCCA AAAGGATAAGATGGCAGAAGCCTATAGCGAGATTGGT ATGAAAGGGAACGCAGAAGAGGCAAAGGCCACGACG GACTGTACCAGGGACTCAGCACCGCCACCAAGGACACC TATGACGCTCTTCACATGCAGGCCCTGCCGCCTCGG | |
| 6650 | CD3-zeta (aa) | RVKFSRSADAPAYQQGQNQLYNELNLGRREEYDVLDKRR GRDPEMGGKPRRKNPQEGLYNELQKDKMAEAYSEIGMK GERRRGKGHDGLYQGLSTATKDTYDALHMQALPPR | 43 |
| 6651 | CD3-zeta (na) | AGAGTGAAGTTCAGCAGGAGCGCAGACGCCCCCGCGTA CCAGCAGGGCCAG AACCAGCTCTATAACGAGCTCAATCTAGGACGAAGAGA GGAGTACGATGTTT TGGACAAGAGACGTGGCCGGGACCCTGAGATGGGGGG AAAGCCGAGAAGGA AGAACCCTCAGGAAGGCCTGTACAATGAACTGCAGAAA GATAAGATGGCGG AGGCCTACAGTGAGATTGGGATGAAAGGCGAGCGCCG GAGGGGCAAGGGGC ACGATGGCCTTTACCAGGGTCTCAGTACAGCCACCAAG GACACCTACGACGC CCTTCACATGCAGGCCCTGCCCCCTCGC | 44 |
| 6629 | linker | GGGGS | 18 |
| 6635 | linker | GGTGGCGGAGGTTCTGGAGGTGGAGGTTCC | 50 |
| 6652 | PD-1 extracellular domain (aa) | Pgwfldspdrpwnpptfspallvvtegdnatftcsfsntsesfvlnwyrmspsnqtdkla afpedrsqpgqdcrfrvtqlpngrdfhmsvvrarrndsgtylcgaislapkaqikeslrael rvterraevptahpspsprpagqfqtlv | |
| 6653 | PD-1 extracellular domain (na) | Cccggatggtttctggactctccggatcgcccgtggaatcccccaaccttctcaccggcact cttggttgtgactgagggcgataatgcgaccttcacgtgctcgttctccaacacctccgaatca ttcgtgctgaactggtaccgcatgagcccgtcaaaccagaccgacaagctcgccgcgtttcc ggaagatcggtcgcaaccgggacaggattgtcggttccgcgtgactcaactgccgaatgg | |

TABLE 7-continued

Exemplary sequences of various components of CAR (aa-amino acids, na-nucleic acids that encodes the corresponding protein)

| SEQ ID NO | description | Sequence | Corresp. To huCD19 |
|---|---|---|---|
| | | cagagacttccacatgagcgtggtccgcgctaggcgaaacgactccgggacctacctgtg<br>ggagccatctcgctggcgcctaagggcccaaatcaaagagagcttgagggccgaactgaga<br>gtgaccgagcgcagagctgaggtgccaactgcacatccatcccatcgcctcggcctgcg<br>gggcagtttcagaccctggtc | |
| 6654 | PD-1 CAR (aa) with signal | Malpvtalllplalllhaarppgwfldspdrpwnpptfspallvvtegdnatftcsfsntses<br>fvlnwyrmspsnqtdklaafpedrsqpgqdcrfrvtqlpngrdfhmsvvrarrndsgtyl<br>cgaislapkaqikeslraelrvterraevptahpspsprpagqfqtlvttttpaprpptpaptia<br>sqplslrpeacrpaaggavhtrgldfacdiyiwaplagtcgvlllslvitlyckrgrkkllyif<br>kqpfmrpvqttqeedgcscrfpeeeeggcelrvkfsrsadapaykqgqnqlynelnlgrr<br>eeydvldkrrgrdpemggkprrknpqeglynelqkdkmaeayseigmkgerrrgkg<br>hdglyqglstatkdtydalhmqalppr | |
| 6655 | PD-1 CAR (na) | Atggccctccctgtcactgccctgcttctcccctcgcactcctgctccacgccgctagacc<br>acccggatggtttctggactctccggatcgcccgtggaatcccccaaccttctcaccggcact<br>cttggttgtgactgagggcgataatgcgaccttcacgtgctcgttctccaacacctccgaatca<br>ttcgtgctgaactggtaccgcatgagcccgtcaaaccagaccgacaagctcgccgcgtttcc<br>ggaagatcggtcgcaaccgggacaggattgtcggttccgcgtgactcaactgccgaatgg<br>cagagacttccacatgagcgtggtccgcgctaggcgaaacgactccgggacctacctgtgc<br>ggagccatctcgctggcgcctaagggcccaaatcaaagagagcttgagggccgaactgaga<br>gtgaccgagcgcagagctgaggtgccaactgcacatccatcccatcgcctcggcctgcg<br>gggcagtttcagaccctggtcaccgaccactccggcgccgcgccaccgactccggcccca<br>actatcgcgagccagcccctgtcgctgaggccggaagcatgccgccctgccgccggaggt<br>gctgtgcatacccggggattggacttcgcatgcgacatctacatttgggctcctctcgccgga<br>acttgtggcgtgctccttctgtccctggtcatcaccctgtactgcaagcggggtcggaaaaag<br>cttctgtacattttcaagcagcccttcatgaggcccgtgcaaaccacccaggaggaggacgg<br>ttgctcctgccggttccccgaagaggaagaaggaggttgcgagctgcgcgtgaagttctcc<br>cggagcgccgacgccccgcctataagcagggccagaaccagctgtacaacgaactgaa<br>cctgggacggcgggaagagtacgatgtgctggacaagcggcgcggccgggaccccgaa<br>atgggcgggaagcctagaagaaagaaccctcaggaaggcctgtataacgagctgcagaa<br>ggacaagatggccgaggcctactccgaaattgggatgaagggagagcggcggagggga<br>aaggggcacgacggcctgtaccaaggactgtccaccgccaccaaggacacatacgatgc<br>cctgcacatgcaggcccttccccctcgc | |
| 6592 | linker | (Gly-Gly-Gly-Ser)n, where n = 1-10 | 105 |
| 6593 | linker | (Gly4 Ser)4 | 106 |
| 6594 | linker | (Gly4 Ser)3 | 107 |
| 6595 | linker | (Gly3 Ser) | 108 |
| 6656 | PD1 CAR (aa) | Pgwfldspdrpwnpptfspallvvtegdnatftcsfsntsesfvlnwyrmspsnqtdkla<br>afpedrsqpgqdcrfrvtqlpngrdfhmsvvrarrndsgtylcgaislapkaqikeslrael<br>rvterraevptahpspsprpagqfqtlvttttpaprpptpaptiasqplslrpeacrpaaggav<br>htrgldfacdiyiwaplagtcgvlllslvitlyckrgrkkllyifkqpfmrpvqttqeedgcs<br>crfpeeeeggcelrvkfsrsadapaykqgqnqlynelnlgrreeydvldkrrgrdpemg<br>gkprrknpqeglynelqkdkmaeayseigmkgerrrgkghdglyqglstatkdtydal<br>hmqalppr | |

VI. Cells

In another aspect, the invention provides cells which comprise, or which at any time comprised, a gRNA molecule, e.g., one or more gRNA molecules, as described herein, or a CRISPR system as described herein. In an embodiment, the cell has been altered, e.g., the target sequence targeted by the gRNA molecule has been altered, e.g., to create an indel, by introduction of a gRNA molecule as described herein (or nucleic acid encoding said gRNA molecule), or a CRISPR system (or nucleic acid encoding one or more components of said CRISPR system) as described herein, e.g., altered by a method described herein. In an embodiment, the alteration results in reduced or no expression of the functional (e.g., wild type) gene product of the gene comprising the target site.

In one aspect, the cell is an animal cell. In embodiments, the cell is a mammalian, primate, or human cell. In embodiments, the cell is a human cell. In embodiments, the cell is an immune effector cell (e.g., a population of immune effector cells), for example a T cell or NK cell. In embodiments, the T cell (e.g., population of T cells) is or comprises a CD4+ T cell, a CD8+ T cell, or a combination thereof. In embodiments, the cell is autologous. In embodiments, the cell is allogeneic.

In a preferred embodiment the cell (e.g., the population of cells) has been, or will be, engineered to express a chimeric antigen receptor (CAR), e.g., a CAR as described in Section V. In embodiments, the cell is engineered to express a BCMA CAR, e.g., as described herein. In embodiments, the CAR-engineered cell is allogeneic. In embodiments, the CAR-engineered cell is autologous.

In another aspect, the invention provides cells, such as those described above, which include, has at any time included, or will include a second gRNA molecule as described herein, e.g., a second gRNA molecule with a targeting domain different from that of the first gRNA molecule. In embodiments, the two gRNA molecules are complementary to target sites within the same gene, for example, are complementary to two target sites within the gene for the same allogeneic T cell target, e.g., comprise two target sites within the TRAC gene. Such cells may comprise a large, e.g., 20-60, 20-70, 20-80, 20-90, 20-100, or greater than 1000, greater than 2000, greater than 3000, greater than 4000, greater than 5000, greater than 6000 base pair excision of DNA located between the target sites of the two gRNA molecules, as described herein in Section VIII. Alternatively, the two gRNAs targeting target sequences of the same gene may not lead to an excision, but may instead, for example, create an indel at or near each of the targeted sites. In other embodiments, the two or more gRNA molecules are complementary to target sites within two different genes whose gene products associate to form a molecular complex. An example of such an embodiment is a first gRNA molecule targeting TRAC, and a second gRNA molecule targeting TRBC1 (wherein both the TCR alpha constant chain and the TCR beta constant chain 1 are components of the TCR on the cell surface). Without being bound by theory, introducing CRISPR systems which target two or more target sequences of the same gene, or which target two or more genes of the same molecular complex (e.g., in the case of targeting TRAC and TRBC1) may lead to further reduced or eliminated expression of the target gene product, relative to introducing a CRISPR system which targets only a single target sequence of the target gene.

It will be understood that in any of the aspects and embodiments of the invention in which two or more target sites of different genes (or different molecular complexes, e.g., when targeting TCR, and B2M) are targeted, that for any or all of the different gene (or molecular complex) targets, two or more gRNAs may be employed with respect to one or more of said different genes or different molecular complexes. For example, in embodiments and aspects in which expression of TCR and expression of B2M is reduced or eliminated, the reduced or eliminated expression of TCR may be accomplished by, for example, one gRNA targeting TRAC, by more than one gRNA molecule targeting TRAC, or by one gRNA molecule targeting TRAC and a second gRNA targeting a different component of the TCR, e.g., TRBC1; while at the same time, or alternatively, targeting of B2M may be accomplished by, for example, one gRNA molecule targeting B2M or by two or more gRNA molecules targeting B2M.

In other embodiments, the two or more, e.g. two, gRNA molecules are complementary to target sites within different genes. Such cells may comprise alterations, e.g., indels, at or near each target site such that expression of the functional gene product of more than one gene is reduced or eliminated. As discussed above, in such embodiments, more than one gRNA molecule targeted to each of the different genes may be employed.

In embodiments, the cell comprises, has comprised or will comprise a first gRNA molecule comprising a targeting domain complementary with a target sequence of an allogeneic T-cell target (e.g., a targeting domain described in Tables 1, 3, 4 or 5), and a second gRNA molecule comprising a targeting domain complementary with a target sequence of an inhibitory molecule or downstream effector of signaling through an inhibitory molecule (e.g., comprises a targeting domain described in Table 2 or Table 6). In embodiments, the inhibitory molecule or downstream effector of signaling through an inhibitory molecule is CD274, HAVCR2, LAGS, PDCD1, PD-L2, CTLA4, CEACAM (e.g., CEACAM-1, CEACAM-3 and/or CEACAM-5), VISTA, BTLA, TIGIT, LAIR1, CD160, 2B4, CD80, CD86, B7-H3 (CD113), B7-H4 (VTCN1), HVEM (TNERSF14 or CD107), KIR, A2aR, MHC class I, MHC class II, GAL9, adenosine, and TGF beta, or PTPN11.

In embodiments, the cell comprises, has comprised or will comprise a first gRNA molecule comprising a targeting domain complementary with a target sequence of TRAC, TRBC1, TRBC2, CD247, CD3D, CD3E, or CD3G, and a second gRNA molecule comprising a targeting domain complementary with a target sequence of B2M, NLRC5, HLA-A, HLA-B or HLA-C.

In embodiments, a cell of the invention comprises, has comprised or will comprise a first gRNA molecule comprising a targeting domain complementary with a target sequence of TRAC, TRBC1, TRBC2, CD247, CD3D, CD3E, or CD3G; a second gRNA molecule comprising a targeting domain complementary with a target sequence of B2M, NLRC5, HLA-A, HLA-B or HLA-C; and a third gRNA molecule comprising a targeting domain complementary with a target sequence of CIITA. Without being bound by theory, it is believed that reducing or eliminating expression of a MHC class I molecule, e.g., by a method described herein employing a gRNA to B2M or a gRNA to NLRC5, may cause the modified cell to upregulate expression of one or more MHC class II molecules. In such circumstances, in order to create, for example, an allogeneic cell (e.g., an allogeneic T cell, e.g., a CAR-expressing allogeneic T cell described herein) able to avoid a host versus graft disease response, it may be beneficial to reduce or eliminate expression of one or more MHC class II molecules (in addition to the one or more MHC class I molecules), for example, by a method described herein employing a gRNA to CIITA. In one embodiment, the cell, e.g., a CAR-expressing cell, e.g., as described herein, comprises, has comprised or will comprise, a first gRNA to TRAC, e.g., as described herein, a second gRNA to B2M, e.g., as described herein, and a third gRNA to CIITA, e.g., as described herein. In one embodiment, the cell, e.g., a CAR-expressing cell, e.g., as described herein, comprises, has comprised or will comprise, a first gRNA to TRAC, e.g., as described herein, a second gRNA to NLRC5, e.g., as described herein, and a third gRNA to CIITA, e.g., as described herein.

In embodiments, the invention provides a cell, e.g., a CAR-expressing cell, e.g., as described herein, that comprises one or more modifications (e.g., nucleotide insertions or deletions) to an endogenous gene encoding a component of the TCR, e.g., TRAC or TRBC (e.g., TRBC1 or TRBC2); one or more modifications (e.g., nucleotide insertions or deletions) to an endogenous B2M gene; and/or one or more modifications (e.g., nucleotide insertions or deletions) to an endogenous CIITA gene. In embodiments, said modifications reduce or eliminate expression of said gene. In embodiments, the invention provides a cell, e.g., a CAR-expressing cell, e.g., as described herein, that is TCR– (e.g., has a level of expression of TCR greater than 50%, 60%, 70%, 80%, 90%, 95%, 96%, 97%, 98%, or 99% lower than that of an unmodified cell of the same type, as detected by FACS, e.g., FACS using an anti-CD3 antibody), B2M– (e.g., has a level of expression of B2M and/or one or more MHC class I proteins greater than 50%, 60%, 70%, 80%, 90%, 95%, 96%, 97%, 98%, or 99% lower than that of an unmodified cell of the same type, as detected by FACS, e.g., FACS using an anti-B2M antibody) and/or CIITA– (e.g., has a level of expression of CIITA and/or a MHC class II protein greater than 50%, 60%, 70%, 80%, 90%, 95%, 96%, 97%, 98%, or 99% lower than that of an unmodified cell of the same type, as detected by FACS, e.g., FACS using an anti-CIITA antibody). In an embodiment, the cell is engineered to express a CAR molecule, e.g., as described herein. In embodiments, the CAR is a CD19 CAR, e.g., as described herein. In other embodiments, the CAR is a BCMA CAR, e.g., as described herein. In other embodiments, the CAR is a CD123 CAR, e.g., as described herein.

In embodiments, the invention provides a cell, e.g., a CAR-expressing cell, e.g., as described herein, that comprises one or more modifications (e.g., nucleotide insertions or deletions) to an endogenous gene encoding a component of the TCR, e.g., TRAC or TRBC (e.g., TRBC1 or TRBC2); one or more modifications (e.g., nucleotide insertions or deletions) to an endogenous NLRC5 gene; and/or one or more modifications (e.g., nucleotide insertions or deletions) to an endogenous CIITA gene. In embodiments, said modifications reduce or eliminate expression of said gene. In embodiments, the invention provides a cell, e.g., a CAR-expressing cell, e.g., as described herein, that is TCR− (e.g., has a level of expression of TCR greater than 50%, 60%, 70%, 80%, 90%, 95%, 96%, 97%, 98%, or 99% lower than that of an unmodified cell of the same type, as detected by FACS, e.g., FACS using an anti-CD3 antibody), NLRC5− (e.g., has a level of expression of NLRC5 and/or one or more MHC class I proteins greater than 50%, 60%, 70%, 80%, 90%, 95%, 96%, 97%, 98%, or 99% lower than that of an unmodified cell of the same type, as detected by FACS, e.g., FACS using an anti-NLRC5 antibody) and/or CIITA− (e.g., has a level of expression of CIITA and/or a MHC class II protein greater than 50%, 60%, 70%, 80%, 90%, 95%, 96%, 97%, 98%, or 99% lower than that of an unmodified cell of the same type, as detected by FACS, e.g., FACS using an anti-CIITA antibody). In an embodiment, the cell is engineered to express a CAR molecule, e.g., as described herein. In embodiments, the CAR is a CD19 CAR, e.g., as described herein. In other embodiments, the CAR is a BCMA CAR, e.g., as described herein. In other embodiments, the CAR is a CD123 CAR, e.g., as described herein.

In embodiments, the cell comprises, has comprised or will comprise a first gRNA molecule comprising a targeting domain complementary with a target sequence of TRAC, TRBC1, TRBC2, CD247, CD3D, CD3E, or CD3G, and a second gRNA molecule comprises a targeting domain complementary with a target sequence of NR3C1, DCK, CD52 or FKBP1A.

In embodiments, the cell comprises, has comprised or will comprise a first gRNA molecule and a second gRNA molecule, wherein: (1) the first gRNA molecule comprises a targeting domain selected from the group consisting of SEQ ID NO: 5528 to SEQ ID NO: 5623 or SEQ ID NO: 5816 to SEQ ID NO: 5965, and the second guide RNA molecule comprises a targeting domain selected from the group consisting of SEQ ID NO: 1 to SEQ ID NO: 83 and SEQ ID NO: 5492 to SEQ ID NO: 5527; (2) the first gRNA molecule comprises a targeting domain selected from the group consisting of SEQ ID NO: 5528 to SEQ ID NO: 5623 or SEQ ID NO: 5816 to SEQ ID NO: 5965, and the second guide RNA molecule comprises a targeting domain selected from the group consisting of SEQ ID NO: 969 to SEQ ID NO: 1345; (3) the first gRNA molecule comprises a targeting domain selected from the group consisting of SEQ ID NO: 5528 to SEQ ID NO: 5623 or SEQ ID NO: 5816 to SEQ ID NO: 5965, and the second guide RNA molecule comprises a targeting domain selected from the group consisting of SEQ ID NO: 1346 to SEQ ID NO: 1698; (4) the first gRNA molecule comprises a targeting domain selected from the group consisting of SEQ ID NO: 5528 to SEQ ID NO: 5623 or SEQ ID NO: 5816 to SEQ ID NO: 5965, and the second guide RNA molecule comprises a targeting domain selected from the group consisting of SEQ ID NO: 1699 to SEQ ID NO: 2068; (5) the first gRNA molecule comprises a targeting domain selected from the group consisting of SEQ ID NO: 5528 to SEQ ID NO: 5623 or SEQ ID NO: 5816 to SEQ ID NO: 5965, and the second guide RNA molecule comprises a targeting domain selected from the group consisting of SEQ ID NO: 2069 to SEQ ID NO: 2941; (6) the first gRNA molecule comprises a targeting domain selected from the group consisting of SEQ ID NO: 5528 to SEQ ID NO: 5623 or SEQ ID NO: 5816 to SEQ ID NO: 5965, and the second guide RNA molecule comprises a targeting domain selected from the group consisting of SEQ ID NO: 5278 to SEQ ID NO: 5491; (7) the first gRNA molecule comprises a targeting domain selected from the group consisting of SEQ ID NO: 5528 to SEQ ID NO: 5623 or SEQ ID NO: 5816 to SEQ ID NO: 5965, and the second guide RNA molecule comprises a targeting domain selected from the group consisting of SEQ ID NO: 6227 to SEQ ID NO: 6324; (8) the first gRNA molecule comprises a targeting domain selected from the group consisting of SEQ ID NO: 5528 to SEQ ID NO: 5623 or SEQ ID NO: 5816 to SEQ ID NO: 5965, and the second guide RNA molecule comprises a targeting domain selected from the group consisting of SEQ ID NO: 6325 to SEQ ID NO: 6583; (9) the first gRNA molecule comprises a targeting domain selected from the group consisting of SEQ ID NO: 5624 to SEQ ID NO: 5643 or SEQ ID NO: 5966 to SEQ ID NO: 6097, and the second guide RNA molecule comprises a targeting domain selected from the group consisting of SEQ ID NO: 1 to SEQ ID NO: 83 and SEQ ID NO: 5492 to SEQ ID NO: 5527; (10) the first gRNA molecule comprises a targeting domain selected from the group consisting of SEQ ID NO: 5624 to SEQ ID NO: 5643 or SEQ ID NO: 5966 to SEQ ID NO: 6097, and the second guide RNA molecule comprises a targeting domain selected from the group consisting of SEQ ID NO: 969 to SEQ ID NO: 1345; (11) the first gRNA molecule comprises a targeting domain selected from the group consisting of SEQ ID NO: 5624 to SEQ ID NO: 5643 or SEQ ID NO: 5966 to SEQ ID NO: 6097, and the second guide RNA molecule comprises a targeting domain selected from the group consisting of SEQ ID NO: 1346 to SEQ ID NO: 1698; (12) the first gRNA molecule comprises a targeting domain selected from the group consisting of SEQ ID NO: 5624 to SEQ ID NO: 5643 or SEQ ID NO: 5966 to SEQ ID NO: 6097, and the second guide RNA molecule comprises a targeting domain selected from the group consisting of SEQ ID NO: 1699 to SEQ ID NO: 2068; (13) the first gRNA molecule comprises a targeting domain selected from the group consisting of SEQ ID NO: 5624 to SEQ ID NO: 5643 or SEQ ID NO: 5966 to SEQ ID NO: 6097, and the second guide RNA molecule comprises a targeting domain selected from the group consisting of SEQ ID NO: 2069 to SEQ ID NO: 2941; (14) the first gRNA molecule comprises a targeting domain selected from the group consisting of SEQ ID NO: 5624 to SEQ ID NO: 5643 or SEQ ID NO: 5966 to SEQ ID NO: 6097, and the second guide RNA molecule comprises a targeting domain selected from the group consisting of SEQ ID NO: 5278 to SEQ ID NO: 5491; (15) the first gRNA molecule comprises a targeting domain selected from the group consisting of SEQ ID NO: 5624 to SEQ ID NO: 5643 or SEQ ID NO: 5966 to SEQ ID NO: 6097, and the second guide RNA molecule comprises a targeting domain selected from the group consisting of SEQ ID NO: 6227 to SEQ ID NO: 6324; (16) the first gRNA molecule comprises a targeting domain selected from the group consisting of SEQ ID NO: 5624 to SEQ ID NO: 5643 or SEQ ID NO: 5966 to SEQ ID NO: 6097, and the second guide RNA molecule comprises a targeting domain selected from the group consisting of SEQ ID NO: 6325 to SEQ ID NO: 6583; (17) the first gRNA molecule comprises a targeting domain selected from the group consisting of SEQ ID NO: 5644 to SEQ ID NO: 5719 or SEQ ID NO: 6098 to SEQ ID NO: 6226, and the second guide RNA molecule comprises a targeting domain selected from the group consisting of SEQ ID NO: 1 to SEQ ID NO: 83 and SEQ ID NO: 5492 to SEQ ID NO: 5527; (18) the first gRNA molecule comprises a targeting domain selected from the group consisting of SEQ ID NO: 5644 to SEQ ID NO: 5719 or SEQ ID NO: 6098 to SEQ ID NO: 6226, and the second guide RNA molecule comprises a targeting domain selected from the group consisting of SEQ ID NO: 969 to SEQ ID NO: 1345; (19) the first gRNA molecule comprises a targeting domain selected from the group consisting of SEQ ID NO: 5644 to SEQ ID NO: 5719 or SEQ ID NO: 6098 to SEQ ID NO: 6226, and the second guide RNA molecule comprises a targeting domain selected from the group consisting of SEQ ID NO: 1346 to SEQ ID NO: 1698; (20) the first gRNA molecule comprises a targeting domain selected from the group consisting of SEQ ID NO: NO: 5644 to SEQ ID NO: NO: 5719 or SEQ ID NO: 6098 to SEQ ID NO: 6226, and the second guide RNA molecule comprises a targeting domain selected from the group consisting of SEQ ID NO: 1699 to SEQ ID NO: 2068; (21) the first gRNA molecule comprises a targeting domain selected from the group consisting of SEQ ID NO: 5644 to SEQ ID NO: 5719 or SEQ ID NO: 6098 to SEQ ID NO: 6226, and the second guide RNA molecule comprises a targeting domain selected from the group consisting of SEQ ID NO: 2069 to SEQ ID NO: 2941; (22) the first gRNA molecule comprises a targeting domain selected from the group consisting of SEQ ID NO: 5644 to SEQ ID NO: 5719 or SEQ ID NO: 6098 to SEQ ID NO: 6226, and the second guide RNA molecule comprises a targeting domain selected from the group consisting of SEQ ID NO: 5278 to SEQ ID NO: 5491; (23) the first gRNA molecule comprises a targeting domain selected from the group consisting of SEQ ID NO: 5644 to SEQ ID NO: 5719 or SEQ ID NO: 6098 to SEQ ID NO: 6226, and the second guide RNA molecule comprises a targeting domain selected from the group consisting of SEQ ID NO: 6227 to SEQ ID NO: 6324; (24) the first gRNA molecule comprises a targeting domain selected from the group consisting of SEQ ID NO: 5644 to SEQ ID NO: 5719 or SEQ ID NO: 6098 to SEQ ID NO: 6226, and the second guide RNA molecule comprises a targeting domain selected from the group consisting of SEQ ID NO: 6325 to SEQ ID NO: 6583; (25) the first gRNA molecule comprises a targeting domain selected from the group consisting of SEQ ID NO: 84 to SEQ ID NO: 392, and the second guide RNA molecule comprises a targeting domain selected from the group consisting of SEQ ID NO: 1 to SEQ ID NO: 83 and SEQ ID NO: 5492 to SEQ ID NO: 5527; (26) the first gRNA molecule comprises a targeting domain selected from the group consisting of SEQ ID NO: 84 to SEQ ID NO: 392, and the second guide RNA molecule comprises a targeting domain selected from the group consisting of SEQ ID NO: 969 to SEQ ID NO: 1345; (27) the first gRNA molecule comprises a targeting domain selected from the group consisting of SEQ ID NO: 84 to SEQ ID NO: 392, and the second guide RNA molecule comprises a targeting domain selected from the group consisting of SEQ ID NO: 1346 to SEQ ID NO: 1698; (28) the first gRNA molecule comprises a targeting domain selected from the group consisting of SEQ ID NO: 84 to SEQ ID NO: 392, and the second guide RNA molecule comprises a targeting domain selected from the group consisting of SEQ ID NO: 1699 to SEQ ID NO: 2068; (29) the first gRNA molecule comprises a targeting domain selected from the group consisting of SEQ ID NO: 84 to SEQ ID NO: 392, and the second guide RNA molecule comprises a targeting domain selected from the group consisting of SEQ ID NO: 2069 to SEQ ID NO: 2941; (30) the first gRNA molecule comprises a targeting domain selected from the group consisting of SEQ ID NO: 84 to SEQ ID NO: 392, and the second guide RNA molecule comprises a targeting domain selected from the group consisting of SEQ ID NO: 5278 to SEQ ID NO: 5491; (31) the first gRNA molecule comprises a targeting domain selected from the group consisting of SEQ ID NO: 84 to SEQ ID NO: 392, and the second guide RNA molecule comprises a targeting domain selected from the group consisting of SEQ ID NO: 6227 to SEQ ID NO: 6324; (32) the first gRNA molecule comprises a targeting domain selected from the group consisting of SEQ ID NO: 84 to SEQ ID NO: 392, and the second guide RNA molecule comprises a targeting domain selected from the group consisting of SEQ ID NO: 6325 to SEQ ID NO: 6583; (33) the first gRNA molecule comprises a targeting domain selected from the group consisting of SEQ ID NO: 393 to SEQ ID NO: 532, and the second guide RNA molecule comprises a targeting domain selected from the group consisting of SEQ ID NO: 1 to SEQ ID NO: 83 and SEQ ID NO: 5492 to SEQ ID NO: 5527; (34) the first gRNA molecule comprises a targeting domain selected from the group consisting of SEQ ID NO: 393 to SEQ ID NO: 532, and the second guide RNA molecule comprises a targeting domain selected from the group consisting of SEQ ID NO: 969 to SEQ ID NO: 1345; (35) the first gRNA molecule comprises a targeting domain selected from the group consisting of SEQ ID NO: 393 to SEQ ID NO: 532, and the second guide RNA molecule comprises a targeting domain selected from the group consisting of SEQ ID NO: 1346 to SEQ ID NO: 1698; (36) the first gRNA molecule comprises a targeting domain selected from the group consisting of SEQ ID NO: 393 to SEQ ID NO: 532, and the second guide RNA molecule comprises a targeting domain selected from the group consisting of SEQ ID NO: 1699 to SEQ ID NO: 2068; (37) the first gRNA molecule comprises a targeting domain selected from the group consisting of SEQ ID NO: 393 to SEQ ID NO: 532, and the second guide RNA molecule comprises a targeting domain selected from the group consisting of SEQ ID NO: 2069 to SEQ ID NO: 2941; (38) the first gRNA molecule comprises a targeting domain selected from the group consisting of SEQ ID NO: 393 to SEQ ID NO: 532, and the second guide RNA molecule comprises a targeting domain selected from the group consisting of SEQ ID NO: 5278 to SEQ ID NO: 5491; (39) the first gRNA molecule comprises a targeting domain selected from the group consisting of SEQ ID NO: 393 to SEQ ID NO: 532, and the second guide RNA molecule comprises a targeting domain selected from the group consisting of SEQ ID NO: 6227 to SEQ ID NO: 6324; (40) the first gRNA molecule comprises a targeting domain selected from the group consisting of SEQ ID NO: 393 to SEQ ID NO: 532, and the second guide RNA molecule comprises a targeting domain selected from the group consisting of SEQ ID NO: 6325 to SEQ ID NO: 6583; (41) the first gRNA molecule comprises a targeting domain selected from the group consisting of SEQ ID NO: 533 to SEQ ID NO: 839, and the second guide RNA molecule comprises a targeting domain selected from the group consisting of SEQ ID NO: 1 to SEQ ID NO: 83 and SEQ ID NO: 5492 to SEQ ID NO: 5527; (42) the first gRNA molecule comprises a targeting domain selected from the group consisting of SEQ ID NO: 533 to SEQ ID NO: 839, and the second guide RNA molecule comprises a targeting domain selected from the group consisting of SEQ ID NO: 969 to SEQ ID NO: 1345; (43) the first gRNA molecule comprises a targeting domain selected from the group consisting of SEQ ID NO: 533 to SEQ ID NO: 839, and the second guide RNA molecule comprises a targeting domain selected from the group consisting of SEQ ID NO: 1346 to SEQ ID NO: 1698; (44) the first gRNA molecule comprises a targeting domain selected from the group consisting of SEQ ID NO: 533 to SEQ ID NO: 839, and the second guide RNA molecule comprises a targeting domain selected from the group consisting of SEQ ID NO: 1699 to SEQ ID NO: 2068; (45) the first gRNA molecule comprises a targeting domain selected from the group consisting of SEQ ID NO: 533 to SEQ ID NO: 839, and the second guide RNA molecule comprises a targeting domain selected from the group consisting of SEQ ID NO: 2069 to SEQ ID NO: 2941; (46) the first gRNA molecule comprises a targeting domain selected from the group consisting of SEQ ID NO: 533 to SEQ ID NO: 839, and the second guide RNA molecule comprises a targeting domain selected from the group consisting of SEQ ID NO: 5278 to SEQ ID NO: 5491; (47) the first gRNA molecule comprises a targeting domain selected from the group consisting of SEQ ID NO: 533 to SEQ ID NO: 839, and the second guide RNA molecule comprises a targeting domain selected from the group consisting of SEQ ID NO: 6227 to SEQ ID NO: 6324; (48) the first gRNA molecule comprises a targeting domain selected from the group consisting of SEQ ID NO: 533 to SEQ ID NO: 839, and the second guide RNA molecule comprises a targeting domain selected from the group consisting of SEQ ID NO: 6325 to SEQ ID NO: 6583; (49) the first gRNA molecule comprises a targeting domain selected from the group consisting of SEQ ID NO: 840 to SEQ ID NO: 968, and the second guide RNA molecule comprises a targeting domain selected from the group consisting of SEQ ID NO: 1 to SEQ ID NO: 83 and SEQ ID NO: 5492 to SEQ ID NO: 5527; (50) the first gRNA molecule comprises a targeting domain selected from the group consisting of SEQ ID NO: 840 to SEQ ID NO: 968, and the second guide RNA molecule comprises a targeting domain selected from the group consisting of SEQ ID NO: 969 to SEQ ID NO: 1345; (51) the first gRNA molecule comprises a targeting domain selected from the group consisting of SEQ ID NO: 840 to SEQ ID NO: 968, and the second guide RNA molecule comprises a targeting domain selected from the group consisting of SEQ ID NO: 1346 to SEQ ID NO: 1698; (52) the first gRNA molecule comprises a targeting domain selected from the group consisting of SEQ ID NO: 840 to SEQ ID NO: 968, and the second guide RNA molecule comprises a targeting domain selected from the group consisting of SEQ ID NO: 1699 to SEQ ID NO: 2068; (53) the first gRNA molecule comprises a targeting domain selected from the group consisting of SEQ ID NO: 840 to SEQ ID NO: 968, and the second guide RNA molecule comprises a targeting domain selected from the group consisting of SEQ ID NO: 2069 to SEQ ID NO: 2941; (54) the first gRNA molecule comprises a targeting domain selected from the group consisting of SEQ ID NO: 840 to SEQ ID NO: 968, and the second guide RNA molecule comprises a targeting domain selected from the group consisting of SEQ ID NO: 5278 to SEQ ID NO: 5491; (55) the first gRNA molecule comprises a targeting domain selected from the group consisting of SEQ ID NO: 840 to SEQ ID NO: 968, and the second guide RNA molecule comprises a targeting domain selected from the group consisting of SEQ ID NO: 6227 to SEQ ID NO: 6324; (55) the first gRNA molecule comprises a targeting domain selected from the group consisting of SEQ ID NO: 840 to SEQ ID NO: 968, and the second guide RNA molecule comprises a targeting domain selected from the group consisting of SEQ ID NO: 6325 to SEQ ID NO: 6583; (56) the first gRNA molecule comprises a targeting domain selected from the group consisting of SEQ ID NO: 5528 to SEQ ID NO: 5623 or SEQ ID NO: 5816 to SEQ ID NO: 5965, and the second guide RNA molecule comprises a targeting domain selected from the group consisting of SEQ ID NO: 2942 to SEQ ID NO: 3270; (57) the first gRNA molecule comprises a targeting domain selected from the group consisting of SEQ ID NO: 5528 to SEQ ID NO: 5623 or SEQ ID NO: 5816 to SEQ ID NO: 5965, and the second guide RNA molecule comprises a targeting domain selected from the group consisting of SEQ ID NO: 3271 to SEQ ID NO: 3541; (58) the first gRNA molecule comprises a targeting domain selected from the group consisting of SEQ ID NO: 5528 to SEQ ID NO: 5623 or SEQ ID NO: 5816 to SEQ ID NO: 5965, and the second guide RNA molecule comprises a targeting domain selected from the group consisting of SEQ ID NO: 3542 to SEQ ID NO: 4032; (59) the first gRNA molecule comprises a targeting domain selected from the group consisting of SEQ ID NO: 5528 to SEQ ID NO: 5623 or SEQ ID NO: 5816 to SEQ ID NO: 5965, and the second guide RNA molecule comprises a targeting domain selected from the group consisting of SEQ ID NO: 4033 to SEQ ID NO: 4589 and SEQ ID NO: 5720 to SEQ ID NO: 5815; (60) the first gRNA molecule comprises a targeting domain selected from the group consisting of SEQ ID NO: 5528 to SEQ ID NO: 5623 or SEQ ID NO: 5816 to SEQ ID NO: 5965, and the second guide RNA molecule comprises a targeting domain selected from the group consisting of SEQ ID NO: 4590 to SEQ ID NO: 5277; (61) the first gRNA molecule comprises a targeting domain selected from the group consisting of SEQ ID NO: 5624 to SEQ ID NO: 5643 or SEQ ID NO: 5966 to SEQ ID NO: 6097, and the second guide RNA molecule comprises a targeting domain selected from the group consisting of SEQ ID NO: 2942 to SEQ ID NO: 3270; (62) the first gRNA molecule comprises a targeting domain selected from the group consisting of SEQ ID NO: 5624 to SEQ ID NO: 5643 or SEQ ID NO: 5966 to SEQ ID NO: 6097, and the second guide RNA molecule comprises a targeting domain selected from the group consisting of SEQ ID NO: 3271 to SEQ ID NO: 3541; (63) the first gRNA molecule comprises a targeting domain selected from the group consisting of SEQ ID NO: 5624 to SEQ ID NO: 5643 or SEQ ID NO: 5966 to SEQ ID NO: 6097, and the second guide RNA molecule comprises a targeting domain selected from the group consisting of SEQ ID NO: 3542 to SEQ ID NO: 4032; (64) the first gRNA molecule comprises a targeting domain selected from the group consisting of SEQ ID NO: 5624 to SEQ ID NO: 5643 or SEQ ID NO: 5966 to SEQ ID NO: 6097, and the second guide RNA molecule comprises a targeting domain selected from the group consisting of SEQ ID NO: 4033 to SEQ ID NO: 4589 and SEQ ID NO: 5720 to SEQ ID NO: 5815; (65) the first gRNA molecule comprises a targeting domain selected from the group consisting of SEQ ID NO: 5624 to SEQ ID NO: 5643 or SEQ ID NO: 5966 to SEQ ID NO: 6097, and the second guide RNA molecule comprises a targeting domain selected from the group consisting of SEQ ID NO: 4590 to SEQ ID NO: 5277; (66) the first gRNA molecule comprises a targeting domain selected from the group consisting of SEQ ID NO: 5644 to SEQ ID NO: 5719 or SEQ ID NO: 6098 to SEQ ID NO: 6226, and the second guide RNA molecule comprises a targeting domain selected from the group consisting of SEQ ID NO: 2942 to SEQ ID NO: 3270; (67) the first gRNA molecule comprises a targeting domain selected from the group consisting of SEQ ID NO: 5644 to SEQ ID NO: 5719 or SEQ ID NO: 6098 to SEQ ID NO: 6226, and the second guide RNA molecule comprises a targeting domain selected from the group consisting of SEQ ID NO: 3271 to SEQ ID NO: 3541; (68) the first gRNA molecule comprises a targeting domain selected from the group consisting of SEQ ID NO: 5644 to SEQ ID NO: 5719 or SEQ ID NO: 6098 to SEQ ID NO: 6226, and the second guide RNA molecule comprises a targeting domain selected from the group consisting of SEQ ID NO: 3542 to SEQ ID NO: 4032; (69) the first gRNA molecule comprises a targeting domain selected from the group consisting of SEQ ID NO: 5644 to SEQ ID NO: 5719 or SEQ ID NO: 6098 to SEQ ID NO: 6226, and the second guide RNA molecule comprises a targeting domain selected from the group consisting of SEQ ID NO: 4033 to SEQ ID NO: 4589 and SEQ ID NO: 5720 to SEQ ID NO: 5815; (70) the first gRNA molecule comprises a targeting domain selected from the group consisting of SEQ ID NO: 5644 to SEQ ID NO: 5719 or SEQ ID NO: 6098 to SEQ ID NO: 6226, and the second guide RNA molecule comprises a targeting domain selected from the group consisting of SEQ ID NO: 4590 to SEQ ID NO: 5277; (71) the first gRNA molecule comprises a targeting domain selected from the group consisting of SEQ ID NO: 84 to SEQ ID NO: 392, and the second guide RNA molecule comprises a targeting domain selected from the group consisting of SEQ ID NO: 2942 to SEQ ID NO: 3270; (72) the first gRNA molecule comprises a targeting domain selected from the group consisting of SEQ ID NO: 84 to SEQ ID NO: 392, and the second guide RNA molecule comprises a targeting domain selected from the group consisting of SEQ ID NO: 3271 to SEQ ID NO: 3541; (73) the first gRNA molecule comprises a targeting domain selected from the group consisting of SEQ ID NO: 84 to SEQ ID NO: 392, and the second guide RNA molecule comprises a targeting domain selected from the group consisting of SEQ ID NO: 3542 to SEQ ID NO: 4032; (74) the first gRNA molecule comprises a targeting domain selected from the group consisting of SEQ ID NO: 84 to SEQ ID NO: 392, and the second guide RNA molecule comprises a targeting domain selected from the group consisting of SEQ ID NO: 4033 to SEQ ID NO: 4589 and SEQ ID NO: 5720 to SEQ ID NO: 5815; (75) the first gRNA molecule comprises a targeting domain selected from the group consisting of SEQ ID NO: 84 to SEQ ID NO: 392, and the second guide RNA molecule comprises a targeting domain selected from the group consisting of SEQ ID NO: 4590 to SEQ ID NO: 5277; (76) the first gRNA molecule comprises a targeting domain selected from the group consisting of SEQ ID NO: 393 to SEQ ID NO: 532, and the second guide RNA molecule comprises a targeting domain selected from the group consisting of SEQ ID NO: 2942 to SEQ ID NO: 3270; (77) the first gRNA molecule comprises a targeting domain selected from the group consisting of SEQ ID NO: 393 to SEQ ID NO: 532, and the second guide RNA molecule comprises a targeting domain selected from the group consisting of SEQ ID NO: 3271 to SEQ ID NO: 3541; (78) the first gRNA molecule comprises a targeting domain selected from the group consisting of SEQ ID NO: 393 to SEQ ID NO: 532, and the second guide RNA molecule comprises a targeting domain selected from the group consisting of SEQ ID NO: 3542 to SEQ ID NO: 4032; (79) the first gRNA molecule comprises a targeting domain selected from the group consisting of SEQ ID NO: 393 to SEQ ID NO: 532, and the second guide RNA molecule comprises a targeting domain selected from the group consisting of SEQ ID NO: 4033 to SEQ ID NO: 4589 and SEQ ID NO: 5720 to SEQ ID NO: 5815; (80) the first gRNA molecule comprises a targeting domain selected from the group consisting of SEQ ID NO: 393 to SEQ ID NO: 532, and the second guide RNA molecule comprises a targeting domain selected from the group consisting of SEQ ID NO: 4590 to SEQ ID NO: 5277; (81) the first gRNA molecule comprises a targeting domain selected from the group consisting of SEQ ID NO: 533 to SEQ ID NO: 839, and the second guide RNA molecule comprises a targeting domain selected from the group consisting of SEQ ID NO: 2942 to SEQ ID NO: 3270; (82) the first gRNA molecule comprises a targeting domain selected from the group consisting of SEQ ID NO: 533 to SEQ ID NO: 839, and the second guide RNA molecule comprises a targeting domain selected from the group consisting of SEQ ID NO: 3271 to SEQ ID NO: 3541; (83) the first gRNA molecule comprises a targeting domain selected from the group consisting of SEQ ID NO: 533 to SEQ ID NO: 839, and the second guide RNA molecule comprises a targeting domain selected from the group consisting of SEQ ID NO: 3542 to SEQ ID NO: 4032; (85) the first gRNA molecule comprises a targeting domain selected from the group consisting of SEQ ID NO: 533 to SEQ ID NO: 839, and the second guide RNA molecule comprises a targeting domain selected from the group consisting of SEQ ID NO: 4033 to SEQ ID NO: 4589 and SEQ ID NO: 5720 to SEQ ID NO: 5815; (86) the first gRNA molecule comprises a targeting domain selected from the group consisting of SEQ ID NO: 533 to SEQ ID NO: 839, and the second guide RNA molecule comprises a targeting domain selected from the group consisting of SEQ ID NO: 4590 to SEQ ID NO: 5277; (87) the first gRNA molecule comprises a targeting domain selected from the group consisting of SEQ ID NO: 840 to SEQ ID NO: 968, and the second guide RNA molecule comprises a targeting domain selected from the group consisting of SEQ ID NO: 2942 to SEQ ID NO: 3270; (88) the first gRNA molecule comprises a targeting domain selected from the group consisting of SEQ ID NO: 840 to SEQ ID NO: 968, and the second guide RNA molecule comprises a targeting domain selected from the group consisting of SEQ ID NO: 3271 to SEQ ID NO: 3541; (89) the first gRNA molecule comprises a targeting domain selected from the group consisting of SEQ ID NO: 840 to SEQ ID NO: 968, and the second guide RNA molecule comprises a targeting domain selected from the group consisting of SEQ ID NO: 3542 to SEQ ID NO: 4032; (90) the first gRNA molecule comprises a targeting domain selected from the group consisting of SEQ ID NO: 840 to SEQ ID NO: 968, and the second guide RNA molecule comprises a targeting domain selected from the group consisting of SEQ ID NO: 4033 to SEQ ID NO: 4589 and SEQ ID NO: 5720 to SEQ ID NO: 5815; or (91) the first gRNA molecule comprises a targeting domain selected from the group consisting of SEQ ID NO: 840 to SEQ ID NO: 968, and the second guide RNA molecule comprises a targeting domain selected from the group consisting of SEQ ID NO: 4590 to SEQ ID NO: 5277.

In an embodiment, the cell comprises, has comprised or will comprise a first gRNA molecule comprising a targeting domain comprising, e.g., consisting of, SEQ ID NO: 5569 or 5586, and a second gRNA molecule comprising a targeting domain comprising, e.g., consisting of, SEQ ID NO: 5775. Said cell preferably comprises an alteration to both TRAC and PDCD1, such that expression of functional TCR and expression of functional PD-1 is reduced or eliminated. In an embodiment, the cell is an immune effector cell, e.g., a T cell or NK cell. In an embodiment, the cell is allogeneic. In an embodiment, the cell is autologous. In an embodiment, the cell is or will be further engineered to express a CAR as described herein.

In embodiments of the invention, a cell of the invention comprises, has comprised or will comprise a first gRNA molecule comprising a targeting domain complementary to a target sequence of a component of the T cell receptor (e.g., TRAC); a second gRNA molecule comprising a targeting domain complementary to a target sequence of B2M; and a third gRNA molecule comprising a targeting domain complementary to a target sequence of CIITA. Said cell preferably comprises a modification at or near the target sequence of said first gRNA, said second gRNA, and said third gRNA molecules, such that expression of functional TCR, expression of functional B2M and expression of functional CIITA is reduced or eliminated. In an embodiment, the cell is an immune effector cell, e.g., a T cell or NK cell. In an embodiment, the cell is allogeneic. In an embodiment, the cell is autologous. In an embodiment, the cell is or will be further engineered to express a CAR as described herein.

In an aspect, a cell of the invention comprises (e.g., a population of cells of the invention comprises one or more cells which comprise):
 (a) Nucleic acid sequence encoding a CAR, e.g., as described herein;
 (b) Nucleic acid sequence encoding an NK inhibitory molecule, e.g., as described herein, e.g., nucleic acid encoding an HLA-G or HLA-G:B2M fusion as described herein;
 (c) An indel at or near a sequence of a gene encoding a component of a TCR (e.g., TRAC, TRBC1 or TRBC2, e.g. TRAC) or its regulatory elements, e.g., an indel at or near a target sequence of a gRNA comprising a targeting domain to a component of a TCR (e.g., TRAC, TRBC1 or TRBC2, e.g. TRAC), e.g., comprising a targeting domain listed in Table 1, Table 4 or Table 5;
 (d) An indel at or near a sequence of the gene encoding B2M or its regulatory elements, e.g., an indel at or near a target sequence of a gRNA comprising a targeting domain to B2M, e.g., comprising a targeting domain listed in Table 1 or Table 3;
 (e) Optionally, an indel at or near a sequence of the gene encoding CIITA or its regulatory elements, e.g., an indel at or near a target sequence of a gRNA comprising a targeting domain to CIITA, e.g., comprising a targeting domain listed in Table 1 or Table 6c; and
 (f) Optionally, an indel at or near a sequence of the gene encoding LILRB1 or its regulatory elements, e.g., an indel at or near a target sequence of a gRNA comprising a targeting domain to LILRB1, e.g., comprising a targeting domain listed in Table 6d;

Wherein the cell (or population of cells comprises one or more cells which) expresses the CAR and the NK inhibitory molecule, and exhibits reduced or eliminated expression and/or function of one or more of: i) a component of a TCR (e.g., TRAC, TRBC1 or TRBC2, e.g. TRAC), ii) B2M, iii) CIITA, and/or iv) LILRB1. In embodiments the indels are In an aspect, a cell of the invention comprises (e.g., a population of cells of the invention comprises one or more cells which comprise):
 (a) Nucleic acid sequence encoding a CAR, e.g., as described herein;
 (b) Nucleic acid sequence encoding an NK inhibitory molecule, e.g., as described herein, e.g., nucleic acid encoding an HLA-G as described herein;
 (c) An indel at or near a sequence of a gene encoding a component of a TCR (e.g., TRAC, TRBC1 or TRBC2, e.g. TRAC) or its regulatory elements, e.g., an indel at or near a target sequence of a gRNA comprising a targeting domain to a component of a TCR (e.g., TRAC, TRBC1 or TRBC2, e.g. TRAC), e.g., comprising a targeting domain listed in Table 1, Table 4 or Table 5;
 (d) An indel at or near a sequence of the gene encoding NLRC5 or its regulatory elements, e.g., an indel at or near a target sequence of a gRNA comprising a targeting domain to NLRC5, e.g., comprising a targeting domain listed in Table 1;
 (e) Optionally, an indel at or near a sequence of the gene encoding CIITA or its regulatory elements, e.g., an indel at or near a target sequence of a gRNA comprising a targeting domain to CIITA, e.g., comprising a targeting domain listed in Table 1 or Table 6c; and
 (f) Optionally, an indel at or near a sequence of the gene encoding LILRB1 or its regulatory elements, e.g., an indel at or near a target sequence of a gRNA comprising a targeting domain to LILRB1, e.g., comprising a targeting domain listed in Table 6d;

Wherein the cell (or population of cells comprises one or more cells which) expresses the CAR and the NK inhibitory molecule, and exhibits reduced or eliminated expression and/or function of one or more of: i) a component of a TCR (e.g., TRAC, TRBC1 or TRBC2, e.g. TRAC), ii) B2M, iii) NLRC5, and/or iv) LILRB1.

In an aspect, a cell of the invention comprises (e.g., a population of cells of the invention comprises one or more cells which comprise):
 (a) Nucleic acid sequence encoding a CAR, e.g., as described herein;
 (b) An indel at or near a sequence of a gene encoding a component of a TCR (e.g., TRAC, TRBC1 or TRBC2, e.g. TRAC) or its regulatory elements, e.g., an indel at or near a target sequence of a gRNA comprising a targeting domain to a component of a TCR (e.g., TRAC, TRBC1 or TRBC2, e.g. TRAC), e.g., comprising a targeting domain listed in Table 1, Table 4 or Table 5; and
 (c) An indel at or near a sequence of the gene encoding FKBP1A or its regulatory elements, e.g., an indel at or near a target sequence of a gRNA comprising a targeting domain to FKBP1A, e.g., comprising a targeting domain listed in Table 1 or Table 6b;

Wherein the cell (or population of cells comprises one or more cells which) expresses the CAR, and exhibits reduced or eliminated expression and/or function of one or more of: i) a component of a TCR (e.g., TRAC, TRBC1 or TRBC2, e.g. TRAC), and/or ii) FKBP12. Such cells (or population of cells comprising said cells) are particularly useful, for example, in methods of treatment which comprise administering an immunosuppressant (e.g., cyclosporine, rapamycin or rapalog, or mTor inhibitor, e.g., RAD001).

In an aspect, a cell of the invention comprises (e.g., a population of cells of the invention comprises one or more cells which comprise):
 (a) Nucleic acid sequence encoding a CAR, e.g., as described herein;
 (b) Nucleic acid sequence encoding a rapamycin-resistant mTor, e.g., as described herein, e.g., nucleic acid sequence encoding an mTor comprising a S2035 mutation, e.g., an S2035I mutation; and;
 (c) An indel at or near a sequence of a gene encoding a component of a TCR (e.g., TRAC, TRBC1 or TRBC2, e.g. TRAC) or its regulatory elements, e.g., an indel at or near a target sequence of a gRNA comprising a targeting domain to a component of a TCR (e.g., TRAC, TRBC1 or TRBC2, e.g. TRAC), e.g., comprising a targeting domain listed in Table 1, Table 4 or Table 5;

Wherein the cell (or population of cells comprises one or more cells which) expresses the CAR and the rapamycin-resistant mTor, and exhibits reduced or eliminated expression and/or function of a component of a TCR (e.g., TRAC, TRBC1 or TRBC2, e.g. TRAC). Such cells (or population of cells comprising said cells) are particularly useful, for example, in methods of treatment which comprise administering an immunosuppressant (e.g., cyclosporine, rapamycin or rapalog, or mTor inhibitor, e.g., RAD001).

In any of the aforementioned embodiments and aspects the cell comprises one or more CRISPR systems, e.g., as described herein, comprising the gRNA molecule(s) indicated. In embodiments, the cell comprises one or more ribonuclear protein (RNP) complexes each comprising a Cas9 molecule, e.g., as described herein, and a gRNA molecule comprising the indicated targeting domain, e.g., as described herein. In embodiments, including in any of the methods described herein, where gRNAs to more than one target sequence are employed, the gRNAs (and CRISPR systems comprising said gRNAs) may be introduced into the cell simultaneously. In other embodiments, including in any of the methods described herein, where gRNAs to more than one target sequence are employed, the gRNAs (and CRISPR systems comprising said gRNAs) may be introduced into the cell sequentially.

In an aspect involving any of the aforementioned embodiments or aspects, the population of cells comprises at least 20%, e.g., at least 30%, at least 40%, at least 50%, at least 60%, at least 70%, at least 80%, at least 90%, at least 95%, or at least 99%, of cells which include an indel at or near each of the target sequences targeted by each of the gRNA molecules. Said population may be obtained, for example, by utilizing high efficiency gRNA molecules (e.g., gRNA molecules which cause an indel in >85% of said cells which are exposed to said gRNA molecule), or by enriching the population for the desired cell, e.g., by selecting for the desired cell population, e.g., by affinity chromatography or cell sorting.

VII. Template Nucleic Acids (for Introduction of Nucleic Acids)

The term "template nucleic acid" or "donor template" as used herein refers to a nucleic acid to be inserted at or near a target sequence that has been modified, e.g., cleaved, by a CRISPR system of the present invention. In an embodiment, nucleic acid sequence at or near the target sequence is modified to have some or all of the sequence of the template nucleic acid, typically at or near cleavage site(s). In an embodiment, the template nucleic acid is single stranded. In an alternate embodiment, the template nucleic acid is double stranded. In an embodiment, the template nucleic acid is DNA, e.g., double stranded DNA. In an alternate embodiment, the template nucleic acid is single stranded DNA.

In embodiments, the template nucleic acid comprises sequence encoding a chimeric antigen receptor (CAR), e.g., a CAR as described above in section V.

In an embodiment, the template nucleic acid alters the structure of the target position by participating in a homology directed repair event. In an embodiment, the template nucleic acid alters the sequence of the target position. In an embodiment, the template nucleic acid results in the incorporation of a modified, or non-naturally occurring base into the target nucleic acid.

Mutations in a gene or pathway described herein may be corrected using one of the approaches discussed herein. In an embodiment, a mutation in a gene or pathway described herein is corrected by homology directed repair (HDR) using a template nucleic acid. In an embodiment, a mutation in a gene or pathway described herein is corrected by homologous recombination (HR) using a template nucleic acid. In an embodiment, a mutation in a gene or pathway described herein is corrected by Non-Homologous End Joining (NHEJ) repair using a template nucleic acid. In other embodiments, nucleic acid encoding molecules of interest may be inserted at or near a site modified by a CRISPR system of the present invention. In an embodiment, the nucleic acid inserted encodes a chimeric antigen receptor as described herein. In embodiments, the template nucleic acid comprises regulatory elements, e.g., one or more promotors and/or enhancers, operably linked to the nucleic acid sequence encoding a molecule of interest, e.g., a chimeric antigen receptor, e.g., as described herein.

HDR Repair and Template Nucleic Acids

As described herein, nuclease-induced homology directed repair (HDR) can be used to alter a target sequence and correct (e.g., repair or edit) a mutation in the genome. While not wishing to be bound by theory, it is believed that alteration of the target sequence occurs by homology-directed repair (HDR) with a donor template or template nucleic acid. For example, the donor template or the template nucleic acid provides for alteration of the target sequence. It is contemplated that a plasmid donor can be used as a template for homologous recombination. It is further contemplated that a single stranded donor template can be used as a template for alteration of the target sequence by alternate methods of homology directed repair (e.g., single strand annealing) between the target sequence and the donor template. Donor template-effected alteration of a target sequence depends on cleavage by a Cas9 molecule. Cleavage by Cas9 can comprise a double strand break or two single strand breaks.

In an embodiment, a mutation can be corrected by either a single double-strand break or two single strand breaks. In an embodiment, a mutation can be corrected by (1) a single double-strand break, (2) two single strand breaks, (3) two double stranded breaks with a break occurring on each side of the target sequence, (4) one double stranded breaks and two single strand breaks with the double strand break and two single strand breaks occurring on each side of the target sequence or (5) four single stranded breaks with a pair of single stranded breaks occurring on each side of the target sequence.

Double Strand Break Mediated Correction

In an embodiment, double strand cleavage is effected by a Cas9 molecule having cleavage activity associated with an HNH-like domain and cleavage activity associated with a RuvC-like domain, e.g., an N-terminal RuvC-like domain, e.g., a wild type Cas9. Such embodiments require only a single gRNA.

Single Strand Break Mediated Correction

In other embodiments, two single strand breaks, or nicks, are effected by a Cas9 molecule having nickase activity, e.g., cleavage activity associated with an HNH-like domain or cleavage activity associated with an N-terminal RuvC-like domain. Such embodiments require two gRNAs, one for placement of each single strand break. In an embodiment, the Cas9 molecule having nickase activity cleaves the strand to which the gRNA hybridizes, but not the strand that is complementary to the strand to which the gRNA hybridizes. In an embodiment, the Cas9 molecule having nickase activity does not cleave the strand to which the gRNA hybridizes, but rather cleaves the strand that is complementary to the strand to which the gRNA hybridizes.

In an embodiment, the nickase has HNH activity, e.g., a Cas9 molecule having the RuvC activity inactivated, e.g., a Cas9 molecule having a mutation at D10, e.g., the D10A mutation. D10A inactivates RuvC; therefore, the Cas9 nickase has (only) HN H activity and will cut on the strand to which the gRNA hybridizes (e.g., the complementary strand, which does not have the NGG PAM on it). In other embodiments, a Cas9 molecule having an H840, e.g., an H840A, mutation can be used as a nickase. H840A inactivates HNH; therefore, the Cas9 nickase has (only) RuvC activity and cuts on the non-complementary strand (e.g., the strand that has the NGG PAM and whose sequence is identical to the gRNA).

In an embodiment, in which a nickase and two gRNAs are used to position two single strand nicks, one nick is on the + strand and one nick is on the − strand of the target nucleic acid. The PAMs are outwardly facing. The gRNAs can be selected such that the gRNAs are separated by, from about 0-50, 0-100, or 0-200 nucleotides. In an embodiment, there is no overlap between the target sequence that is complementary to the targeting domains of the two gRNAs. In an embodiment, the gRNAs do not overlap and are separated by as much as 50, 100, or 200 nucleotides. In an embodiment, the use of two gRNAs can increase specificity, e.g., by decreasing off-target binding (Ran el cil., CELL 2013).

In an embodiment, a single nick can be used to induce HDR. It is contemplated herein that a single nick can be used to increase the ratio of HDR, HR or NHEJ at a given cleavage site.

Placement of the Double Strand Break or a Single Strand Break Relative to Target Position The double strand break or single strand break in one of the strands should be sufficiently close to target position such that correction occurs. In an embodiment, the distance is not more than 50, 100, 200, 300, 350 or 400 nucleotides. While not wishing to be bound by theory, it is believed that the break should be sufficiently close to target position such that the break is within the region that is subject to exonuclease-mediated removal during end resection. If the distance between the target position and a break is too great, the mutation may not be included in the end resection and, therefore, may not be corrected, as donor sequence may only be used to correct sequence within the end resection region.

In an embodiment, in which a gRNA (unimolecular (or chimeric) or modular gRNA) and Cas9 nuclease induce a double strand break for the purpose of inducing HDR- or HR-mediated correction, the cleavage site is between 0-200 bp (e.g., 0 to 175, 0 to 150, 0 to 125, 0 to 100, 0 to 75, 0 to 50, 0 to 25, 25 to 200, 25 to 175, 25 to 150, 25 to 125, 25 to 100, 25 to 75, 25 to 50, 50 to 200, 50 to 175, 50 to 150, 50 to 125, 50 to 100, 50 to 75, 75 to 200, 75 to 175, 75 to 150, 75 to 125, 75 to 100 bp) away from the target position. In an embodiment, the cleavage site is between 0-100 bp (e.g., 0 to 75, 0 to 50, 0 to 25, 25 to 100, 25 to 25 to 50, 50 to 100, 50 to 75 or 75 to 100 bp) away from the target position.

In an embodiment, in which two gRNAs (independently, unimolecular (or chimeric) or modular gRNA) complexing with Cas9 nickases induce two single strand breaks for the purpose of inducing HDR-mediated correction, the closer nick is between 0-200 bp (e.g., 0 to 175, 0 to 150, 0 to 125, 0 to 100, 0 to 0 to 50, 0 to 25, 25 to 200, 25 to 175, 25 to 150, 25 to 125, 25 to 100, 25 to 75, 25 to 50, 50 to 200, 50 to 175, 50 to 150, 50 to 125, 50 to 100, 50 to 75, 75 to 200, 75 to 175, 75 to 150, 75 to 125, 75 to 100 bp) away from the target position and the two nicks will ideally be within 25-55 bp of each other (e.g., 25 to 25 to 45, 25 to 40, 25 to 35, 25 to 30, 30 to 55, 30 to 50, 30 to 45, 30 to 40, 30 to 35, 35 to 55, 35 to 35 to 45, 35 to 40, 40 to 55, 40 to 50, 40 to 45 bp) and no more than 100 bp away from each other (e.g., no more than 90, 80, 70, 60, 50, 40, 30, 20, 10 or 5 bp away from each other). In an embodiment, the cleavage site is between 0-100 bp (e.g., 0 to 75, 0 to 50, 0 to 25, 25 to 100, 25 to 75, 25 to 50, 50 to 100, 50 to 75 or 75 to 100 bp) away from the target position.

In one embodiment, two gRNAs, e.g., independently, unimolecular (or chimeric) or modular gRNA, are configured to position a double-strand break on both sides of a target position. In an alternate embodiment, three gRNAs, e.g., independently, unimolecular (or chimeric) or modular gRNA, are configured to position a double strand break (i.e., one gRNA complexes with a Cas9 nuclease) and two single strand breaks or paired single stranded breaks (i.e., two gRNAs complex with Cas9 nickases) on either side of the target position (e.g., the first gRNA is used to target upstream (i.e., 5') of the target position and the second gRNA is used to target downstream (i.e., 3') of the target position). In another embodiment, four gRNAs, e.g., independently, unimolecular (or chimeric) or modular gRNA, are configured to generate two pairs of single stranded breaks (i.e., two pairs of two gRNAs complex with Cas9 nickases) on either side of the target position (e.g., the first gRNA is used to target upstream (i.e., 5') of the target position and the second gRNA is used to target downstream (i.e., 3') of the target position). The double strand break(s) or the closer of the two single strand nicks in a pair will ideally be within 0-500 bp of the target position (e.g., no more than 450, 400, 350, 300, 250, 200, 150,100, 50 or 25 bp from the target position). When nickases are used, the two nicks in a pair are within 25-55 bp of each other (e.g., between 25 to 50, 25 to 45, 25 to 40, 25 to 35, 25 to 30, 50 to 55, 45 to 55, 40 to 55, 35 to 55, 30 to 30 to 50, 35. to 50, 40 to 50, 45 to 50, 35 to 45, or 40 to 45 bp) and no more than 100 bp away from each other (e.g., no more than 90, 80, 70, 60, 50, 40, 30, 20 or 10 bp).

In one embodiment, two gRNAs, e.g., independently, unimolecular (or chimeric) or modular gRNA, are configured to position a double-strand break on both sides of a target position. In an alternate embodiment, three gRNAs, e.g., independently, unimolecular (or chimeric) or modular gRNA, are configured to position a double strand break (i.e., one gRNA complexes with a Cas9 nuclease) and two single strand breaks or paired single stranded breaks (i.e., two gRNAs complex with Cas9 nickases) on two target sequences (e.g., the first gRNA is used to target an upstream (i.e., 5') target sequence and the second gRNA is used to target a downstream (i.e., 3') target sequence of an insertion site. In another embodiment, four gRNAs, e.g., independently, unimolecular (or chimeric) or modular gRNA, are configured to generate two pairs of single stranded breaks (i.e., two pairs of two gRNAs complex with Cas9 nickases) on either side of an insertion site (e.g., the first gRNA is used to target an upstream (i.e., target sequence described herein, and the second gRNA is used to target a downstream (i.e., 3') target sequence described herein). The double strand break(s) or the closer of the two single strand nicks in a pair will ideally be within 0-500 bp of the target position (e.g., no more than 450, 400, 350, 300, 250, 200, 150, 100, 50 or 25 bp from the target position). When nickases are used, the two nicks in a pair are within 25-55 bp of each other (e.g., between 25 to 50, 25 to 45, 25 to 40, 25 to 35, 25 to 30, 50 to 55, 45 to 55, 40 to 55, 35 to 55, 30 to 55, 30 to 50, 35 to 50, 40 to 50, 45 to 50, 35 to 45, or 40 to 45 bp) and no more than 100 bp away from each other (e.g., no more than 90, 80, 70, 60, 50, 40, 30, 20 or 10 bp).

Length of the Homology Arms

The homology arm should extend at least as far as the region in which end resection may occur, e.g., in order to allow the resected single stranded overhang to find a complementary region within the donor template. The overall length could be limited by parameters such as plasmid size or viral packaging limits. In an embodiment, a homology arm does not extend into repeated elements, e.g., ALU repeats, LINE repeats. A template may have two homology arms of the same or different lengths.

Exemplary homology arm lengths include at least 25, 50, 100, 250, 500, 750 or 1000 nucleotides.

Target position, as used herein, refers to a site on a target nucleic acid (e.g., the chromosome) that is modified by a Cas9 molecule-dependent process. For example, the target position can be a modified Cas9 molecule cleavage of the target nucleic acid and template nucleic acid directed modification, e.g., correction, of the target position. In an embodiment, a target position can be a site between two nucleotides, e.g., adjacent nucleotides, on the target nucleic acid into which one or more nucleotides is added. The target position may comprise one or more nucleotides that are altered, e.g., corrected, by a template nucleic acid. In an embodiment, the target position is within a target sequence (e.g., the sequence to which the gRNA binds). In an embodiment, a target position is upstream or downstream of a target sequence (e.g., the sequence to which the gRNA binds).

Typically, the template sequence undergoes a breakage mediated or catalyzed recombination with the target sequence. In an embodiment, the template nucleic acid includes sequence that corresponds to a site on the target sequence that is cleaved by a Cas9 mediated cleavage event. In an embodiment, the template nucleic acid includes sequence that corresponds to both, a first site on the target sequence that is cleaved in a first Cas9 mediated event, and a second site on the target sequence that is cleaved in a second Cas9 mediated event.

In an embodiment, the template nucleic acid can include sequence which results in an alteration in the coding sequence of a translated sequence, e.g., one which results in the substitution of one amino acid for another in a protein product, e.g., transforming a mutant allele into a wild type allele, transforming a wild type allele into a mutant allele, and/or introducing a stop codon, insertion of an amino acid residue, deletion of an amino acid residue, or a nonsense mutation.

In other embodiments, the template nucleic acid can include sequence which results in an alteration in a non-coding sequence, e.g., an alteration in an exon or in a 5' or 3' non-translated or non-transcribed region. Such alterations include an alteration in a control element, e.g., a promoter, enhancer, and an alteration in a cis-acting or trans-acting control element.

The template nucleic acid can include sequence which, when integrated, results in:
  decreasing the activity of a positive control element;
  increasing the activity of a positive control element;
  decreasing the activity of a negative control element;
  increasing the activity of a negative control element;
  decreasing the expression of a gene;
  increasing the expression of a gene;
  increasing resistance to a disorder or disease;
  increasing resistance to viral entry;
  correcting a mutation or altering an unwanted amino acid residue
  conferring, increasing, abolishing or decreasing a biological property of a gene product, e.g., increasing the enzymatic activity of an enzyme, or increasing the ability of a gene product to interact with another molecule.

The template nucleic acid can include sequence which results in:
  a change in sequence of 1, 2, 3, 4, 5, 6, 7, 8, 9, 10, 11, 12 or more nucleotides of the target sequence.

In an embodiment, the template nucleic acid is 20+/−10, 30+/−10, 40+/−10, 50+/−10, 60+/−10, 70+/−10, 10, 90+/−10, 100+/−10, 110+/−10, 120+/−10, 130+/−10, 140+/−10, 150+/−10, 160+/−10, 170+/−80+/−10, 190+/−10, 200+/−10, 210+/−10, 220+/−10, 200-300, 300-400, 400-500, 500-600, 600-700, 700-800, 800-900, 900-1000, 1000-2000, 2000-3000 or more than 3000 nucleotides in length.

A template nucleic acid comprises the following components:
  [5' homology arm]-[insertion sequence]-[3' homology arm].

The homology arms provide for recombination into the chromosome, which can replace the undesired element, e.g., a mutation or signature, with the replacement sequence. In an embodiment, the homology arms flank the most distal cleavage sites.

In an embodiment, the 3' end of the 5' homology arm is the position next to the 5' end of the replacement sequence. In an embodiment, the 5' homology arm can extend at least 10, 20, 30, 40, 50, 60, 70, 80, 90, 100, 120, 150, 180, 200, 300, 400, 500, 600, 700, 800, 900, 1000, 1500, or 2000 nucleotides 5' from the 5' end of the replacement sequence.

In an embodiment, the 5' end of the 3' homology arm is the position next to the 3' end of the replacement sequence. In an embodiment, the 3' homology arm can extend at least 10, 20, 30, 40, 50, 60, 70, 80, 90, 100, 120, 150, 180, 200, 300, 400, 500, 600, 700, 800, 900, 1000, 1500, or 2000 nucleotides 3' from the 3' end of the replacement sequence.

It is contemplated herein that one or both homology arms may be shortened to avoid including certain sequence repeat elements, e.g., Alu repeats, LINE elements. For example, a 5' homology arm may be shortened to avoid a sequence repeat element. In other embodiments, a 3' homology arm may be shortened to avoid a sequence repeat element. In some embodiments, both the 5' and the 3' homology arms may be shortened to avoid including certain sequence repeat elements.

It is contemplated herein that template nucleic acids for correcting a mutation may designed for use as a single-stranded oligonucleotide (ssODN). When using a ssODN, 5' and 3' homology arms may range up to about 200 base pairs (bp) in length, e.g., at least 25, 50, 75, 100, 125, 150, 175, or 200 bp in length. Longer homology arms are also contemplated for ssODNs as improvements in oligonucleotide synthesis continue to be made.

In one aspect, the insertion sequence comprises nucleic acid sequence that encodes a chimeric antigen receptor, e.g., as described herein. In one embodiment the insertion sequence further comprises a promotor operably linked to the nucleic acid sequence encoding a chimeric antigen receptor, e.g., an EF-1 alpha promoter. In one aspect, the insertion sequence comprises a vector encoding a chimeric antigen receptor, e.g., as described herein, or a portion thereof.

NHEJ Approaches for Gene Targeting

As described herein, nuclease-induced non-homologous end-joining (NHEJ) can be used to target gene-specific knockouts. Nuclease-induced NHEJ can also be used to remove (e.g., delete) sequence in a gene of interest.

While not wishing to be bound by theory, it is believed that, in an embodiment, the genomic alterations associated with the methods described herein rely on nuclease-induced NHEJ and the error-prone nature of the NHEJ repair pathway. NHEJ repairs a double-strand break in the DNA by joining together the two ends; however, generally, the original sequence is restored only if two compatible ends, exactly as they were formed by the double-strand break, are perfectly ligated. The DNA ends of the double-strand break are frequently the subject of enzymatic processing, resulting in the addition or removal of nucleotides, at one or both strands, prior to rejoining of the ends. This results in the presence of insertion and/or deletion (indel) mutations in the DNA sequence at the site of the NHEJ repair. Two-thirds of these mutations may alter the reading frame and, therefore, produce a non-functional protein. Additionally, mutations that maintain the reading frame, but which insert or delete a significant amount of sequence, can destroy functionality of the protein. This is locus dependent as mutations in critical functional domains are likely less tolerable than mutations in non-critical regions of the protein.

The indel mutations generated by NHEJ are unpredictable in nature; however, at a given break site certain indel sequences are favored and are over represented in the population. The lengths of deletions can vary widely; most commonly in the 1-50 bp range, but they can easily reach greater than 100-200 bp. Insertions tend to be shorter and often include short duplications of the sequence immediately surrounding the break site. However, it is possible to obtain large insertions, and in these cases, the inserted sequence has often been traced to other regions of the genome or to plasmid DNA present in the cells.

Because NHEJ is a mutagenic process, it can also be used to delete small sequence motifs as long as the generation of a specific final sequence is not required. If a double-strand break is targeted near to a short target sequence, the deletion mutations caused by the NHEJ repair often span, and therefore remove, the unwanted nucleotides. For the deletion of larger DNA segments, introducing two double-strand breaks, one on each side of the sequence, can result in NHEJ between the ends with removal of the entire intervening sequence. Both of these approaches can be used to delete specific DNA sequences; however, the error-prone nature of NHEJ may still produce indel mutations at the site of repair.

Both double strand cleaving Cas9 molecules and single strand, or nickase, Cas9 molecules can be used in the methods and compositions described herein to generate NHEJ-mediated indels. NHEJ-mediated indels targeted to the gene, e.g., a coding region, e.g., an early coding region of a gene of interest can be used to knockout (i.e., eliminate expression of) a gene of interest. For example, early coding region of a gene of interest includes sequence immediately following a transcription start site, within a first exon of the coding sequence, or within 500 bp of the transcription start site (e.g., less than 500, 450, 400, 350, 300, 250, 200, 150, 100 or 50 bp).

Placement of Double Strand or Single Strand Breaks Relative to the Target Position In an embodiment, in which a gRNA and Cas9 nuclease generate a double strand break for the purpose of inducing NHEJ-mediated indels, a gRNA, e.g., a unimolecular (or chimeric) or modular gRNA molecule, is configured to position one double-strand break in close proximity to a nucleotide of the target position. In an embodiment, the cleavage site is between 0-500 bp away from the target position (e.g., less than 500, 400, 300, 200, 100, 50, 40, 30, 25, 20, 15, 10, 9, 8, 7, 6, 5, 4, 3, 2 or 1 bp from the target position).

In an embodiment, in which two gRNAs complexing with Cas9 nickases induce two single strand breaks for the purpose of inducing NHEJ-mediated indels, two gRNAs, e.g., independently, unimolecular (or chimeric) or modular gRNA, are configured to position two single-strand breaks to provide for NHEJ repair a nucleotide of the target position. In an embodiment, the gRNAs are configured to position cuts at the same position, or within a few nucleotides of one another, on different strands, essentially mimicking a double strand break. In an embodiment, the closer nick is between 0-30 bp away from the target position (e.g., less than 30, 25, 20, 1, 10, 9, 8, 7, 6, 5, 4, 3, 2 or 1 bp from the target position), and the two nicks are within 25-55 bp of each other (e.g., between 25 to 50, 25 to 45, 25 to 40, 25 to 35, 25 to 30, 50 to 55, 45 to 55, 40 to 55, 35 to 55, 30 to 55, 30 to 50, 35 to 50, 40 to 50, 45 to 50, 35 to 45, or 40 to 45 bp) and no more than 100 bp away from each other (e.g., no more than 90, 80, 70, 60, 50, 40, 30, 20 or 10 bp). In an embodiment, the gRNAs are configured to place a single strand break on either side of a nucleotide of the target position.

Both double strand cleaving Cas9 molecules and single strand, or nickase, Cas9 molecules can be used in the methods and compositions described herein to generate breaks both sides of a target position. Double strand or paired single strand breaks may be generated on both sides of a target position to remove the nucleic acid sequence between the two cuts (e.g., the region between the two breaks is deleted). In one embodiment, two gRNAs, e.g., independently, unimolecular (or chimeric) or modular gRNA, are configured to position a double-strand break on both sides of a target position (e.g., the first gRNA is used to target upstream (i.e., 5') of the mutation in a gene or pathway described herein, and the second gRNA is used to target downstream (i.e., 3') of the mutation in a gene or pathway described herein). In an alternate embodiment, three gRNAs, e.g., independently, unimolecular (or chimeric) or modular gRNA, are configured to position a double strand break (i.e., one gRNA complexes with a Cas9 nuclease) and two single strand breaks or paired single stranded breaks (i.e., two gRNAs complex with Cas9 nickases) on either side of a target position (e.g., the first gRNA is used to target upstream (i.e., 5') of the mutation in a gene or pathway described herein, and the second gRNA is used to target downstream (i.e., 3') of the mutation in a gene or pathway described herein). In another embodiment, four gRNAs, e.g., independently, unimolecular (or chimeric) or modular gRNA, are configured to generate two pairs of single stranded breaks (i.e., two pairs of two gRNAs complex with Cas9 nickases) on either side of the target position (e.g., the first gRNA is used to target upstream (i.e., 5') of the mutation in a gene or pathway described herein, and the second gRNA is used to target downstream (i.e., 3') of the mutation in a gene or pathway described herein). The double strand break(s) or the closer of the two single strand nicks in a pair will ideally be within 0-500 bp of the target position (e.g., no more than 450, 400, 350, 300, 250, 200, 150, 100, 50 or 25 bp from the target position). When nickases are used, the two nicks in a pair are within 25-55 bp of each other (e.g., between 25 to 50, 25 to 45, 25 to 40, 25 to 35, 25 to 30, 50 to 45 to 55, 40 to 55, 35 to 55, 30 to 55, 30 to 50, 35 to 50, 40 to 50, 45 to 50, 35 to 45, or 40 to 45 bp) and no more than 100 bp away from each other (e.g., no more than 90, 80, 70, 60, 50, 40, 30, 20 or 10 bp).

VIII. Systems Comprising More than One gRNA Molecule

While not intending to be bound by theory, it has been surprisingly shown herein that the targeting of two target sequences (e.g., by two gRNA molecule/Cas9 molecule complexes which each induce a single- or double-strand break at or near their respective target sequences) located in close proximity on a continuous nucleic acid induces excision (e.g., deletion) of the nucleic acid sequence (or at least 80%, 85%, 90%, 95%, 96%, 97%, 98%, 99% of the nucleic acid sequence) located between the two target sequences. In some aspects, the present disclosure provides for the use of two or more gRNA molecules that comprise targeting domains targeting target sequences in close proximity on a continuous nucleic acid, e.g., a chromosome, e.g., a gene or gene locus, including its introns, exons and regulatory elements. The use may be, for example, by introduction of the two or more gRNA molecules, together with one or more Cas9 molecules (or nucleic acid encoding the two or more gRNA molecules and/or the one or more Cas9 molecules) into a cell.

In some aspects, the target sequences of the two or more gRNA molecules are located at least 5, 6, 7, 8, 9, 20, 30, 40, 50, 60, 70, 80, 90, 100, 200, 300, 400, 500, 600, 700, 800, 900, 1000, 2000, 3000, 4000, 5000, 6000, or 70000 nucleotides apart on a continuous nucleic acid, but not more than 10000 nucleotides apart on a continuous nucleic acid. In an embodiment, the target sequences are located about 4000 nucleotides apart. In an embodiment, the target sequences are located about 6000 nucleotides apart.

In some aspects, the plurality of gRNA molecules each target sequences within the same gene or gene locus. In another aspect, the plurality of gRNA molecules each target sequences within 2 or more different genes.

In some aspects, the invention provides compositions and cells comprising a plurality, for example, 2 or more, for example, 2, gRNA molecules of the invention, wherein the plurality of gRNA molecules target sequences less than 10,000, less than 9,000, less than 8,000, less than 7,000, less than 6,000, less than less than 4,000, less than 3,000, less than 2,000, less than 1,000, less than 900, less than 800, less than 700, less than 600, less than 500, less than 400, less than 300, less than 200, less than 100, less than less than 80, less than 70, less than 60, less than 50, less than 40, or less than 30 nucleotides apart. In an embodiment, the target sequences are on the same strand of duplex nucleic acid. In an embodiment, the target sequences are on different strands of duplex nucleic acid.

In one embodiment, the invention provides a method for excising (e.g., deleting) nucleic acid disposed between two gRNA binding sites disposed less than 10,000, less than 9,000, less than 8,000, less than 7,000, less than 6,000, less than 5,000, less than 4,000, less than 3,000, less than 2,000, less than 1,000, less than 900, less than 800, less than 700, less than 600, less than 500, less than 400, less than 300, less than 200, less than 100, less than 90, less than 80, less than 70, less than 60, less than 50, less than 40, or less than 30 nucleotides apart on the same or different strands of duplex nucleic acid. In an embodiment, the method provides for deletion of more than 50%, more than 60%, more than 70%, more than 80%, more than 85%, more than 86%, more than 87%, more than 88%, more than 89%, more than 90%, more than 91%, more than 92%, more than 93%, more than 94%, more than 95%, more than 96%, more than 97%, more than 98%, more than 99%, or 100% of the nucleotides disposed between the PAM sites associated with each gRNA binding site. In embodiments, the deletion further comprises of one or more nucleotides within one or more of the PAM sites associated with each gRNA binding site. In embodiments, the deletion also comprises one or more nucleotides outside of the region between the PAM sites associated with each gRNA binding site.

In one aspect, the two or more gRNA molecules comprise targeting domains targeting target sequences flanking a gene regulatory element, e.g., a promotor binding site, an enhancer region, or a repressor region, such that excision of the intervening sequence (or a portion of the intervening sequence) causes up- or down-regulation of a gene of interest.

In an embodiment, the two or more gRNA molecules are selected from the gRNA molecules of Table 1. In aspects, the two or more gRNA molecules comprise targeting domains that are complementary with sequences in the same gene. In aspects, the two or more gRNA molecules comprise targeting domains that are complementary with sequences of different genes. In an embodiment, the two or more gRNA molecules are selected from the gRNA molecules of Table 2. In aspects, the two or more gRNA molecules comprise targeting domains that are complementary with sequences in the same gene. In aspects, the two or more gRNA molecules comprise targeting domains that are complementary with sequences of different genes. In an embodiment, the two or more gRNA molecules are selected from the gRNA molecules of Table 3. In an embodiment, the two or more gRNA molecules are selected from the gRNA molecules of Table 4. In an embodiment, the two or more gRNA molecules are selected from the gRNA molecules of Table 5. In an embodiment, the two or more gRNA molecules are selected from the gRNA molecules of Table 6. In an embodiment, the first and second gRNA molecules are selected from Tables 1-6, and are selected from different tables, e.g., and comprise targeting domains that are complementary with sequences of different genes. In embodiments, such two or more gRNA molecules may additionally be combined with one or more additional gRNA molecules which are complementary to a target domain of a different gene, as described herein.

In aspects of the invention that utilize two or more, e.g., two, gRNA molecules, it may be particularly useful for a first gRNA molecule (or more than one gRNA molecules) to comprise a targeting domain specific for a sequence of TRAC and a second gRNA molecule (or more than one gRNA molecules) to comprise a targeting domain specific for a sequence of B2M. In such aspects, it is particularly preferred that the first gRNA molecule to TRAC comprises a targeting domain of any gRNA molecule of FIG. 12, and the second gRNA molecule to B2M comprises a targeting domain of any gRNA molecule of FIG. 14. In an aspect, the first gRNA molecule to TRAC includes a targeting domain comprising, e.g., consisting of, SEQ ID NO: 5569, SEQ ID NO: 5587, SEQ ID NO: 5592 or SEQ ID NO: 5586, and the second gRNA molecule to B2M includes a targeting domain comprising, e.g., consisting of, SEQ ID NO: 5496, SEQ ID NO: 5498, or SEQ ID NO: 5509. In an aspect, the first gRNA molecule and the second gRNA molecule include targeting domains comprising, e.g., consisting of, SEQ ID NO: 5569 and SEQ ID NO: 5519, respectively. In an aspect, the first gRNA molecule and the second gRNA molecule include targeting domains comprising, e.g., consisting of, SEQ ID NO: 5569 and SEQ ID NO: 5497, respectively. In an aspect, the first gRNA molecule and the second gRNA molecule include targeting domains comprising, e.g., consisting of, SEQ ID NO: 5569 and SEQ ID NO: 5499, respectively. In an aspect, the first gRNA molecule and the second gRNA molecule include targeting domains comprising, e.g., consisting of, SEQ ID NO: 5569 and SEQ ID NO: 5498, respectively. In an aspect, the first gRNA molecule and the second gRNA molecule include targeting domains comprising, e.g., consisting of, SEQ ID NO: 5569 and SEQ ID NO: 5503, respectively. In an aspect, the first gRNA molecule and the second gRNA molecule include targeting domains comprising, e.g., consisting of, SEQ ID NO: 5569 and SEQ ID NO: 5496, respectively. In an aspect, the first gRNA molecule and the second gRNA molecule include targeting domains comprising, e.g., consisting of, SEQ ID NO: 5569 and SEQ ID NO: 5507, respectively. In an aspect, the first gRNA molecule and the second gRNA molecule include targeting domains comprising, e.g., consisting of, SEQ ID NO: 5569 and SEQ ID NO: 5515, respectively. In an aspect, the first gRNA molecule and the second gRNA molecule include targeting domains comprising, e.g., consisting of, SEQ ID NO: 5569 and SEQ ID NO: 5493, respectively. In an aspect, the first gRNA molecule and the second gRNA molecule include targeting domains comprising, e.g., consisting of, SEQ ID NO: 5569 and SEQ ID NO: 5506, respectively. In an aspect, the first gRNA molecule and the second gRNA molecule include targeting domains comprising, e.g., consisting of, SEQ ID NO: 5569 and SEQ ID NO: 5509, respectively. In an aspect, the first gRNA molecule and the second gRNA molecule include targeting domains comprising, e.g., consisting of, SEQ ID NO: 5569 and SEQ ID NO: 5517, respectively. In an aspect, the first gRNA molecule and the second gRNA molecule include targeting domains comprising, e.g., consisting of, SEQ ID NO: 5569 and SEQ ID NO: 5521, respectively. In an aspect, the first gRNA molecule and the second gRNA molecule include targeting domains comprising, e.g., consisting of, SEQ ID NO: 5569 and SEQ ID NO: 5520, respectively. In an aspect, the first gRNA molecule and the second gRNA molecule include targeting domains comprising, e.g., consisting of, SEQ ID NO: 5569 and SEQ ID NO: 5500, respectively. In an aspect, the first gRNA molecule and the second gRNA molecule include targeting domains comprising, e.g., consisting of, SEQ ID NO: 5569 and SEQ ID NO: 5494, respectively. In an aspect, the first gRNA molecule and the second gRNA molecule include targeting domains comprising, e.g., consisting of, SEQ ID NO: 5569 and SEQ ID NO: 5508, respectively. In an aspect, the first gRNA molecule and the second gRNA molecule include targeting domains comprising, e.g., consisting of, SEQ ID NO: 5569 and SEQ ID NO: 5514, respectively. In an aspect, the first gRNA molecule and the second gRNA molecule include targeting domains comprising, e.g., consisting of, SEQ ID NO: 5569 and SEQ ID NO: 5492, respectively. In an aspect, the first gRNA molecule and the second gRNA molecule include targeting domains comprising, e.g., consisting of, SEQ ID NO: 5585 and SEQ ID NO: 5519, respectively. In an aspect, the first gRNA molecule and the second gRNA molecule include targeting domains comprising, e.g., consisting of, SEQ ID NO: 5585 and SEQ ID NO: 5497, respectively. In an aspect, the first gRNA molecule and the second gRNA molecule include targeting domains comprising, e.g., consisting of, SEQ ID NO: 5585 and SEQ ID NO: 5499, respectively. In an aspect, the first gRNA molecule and the second gRNA molecule include targeting domains comprising, e.g., consisting of, SEQ ID NO: 5585 and SEQ ID NO: 5498, respectively. In an aspect, the first gRNA molecule and the second gRNA molecule include targeting domains comprising, e.g., consisting of, SEQ ID NO: 5585 and SEQ ID NO: 5503, respectively. In an aspect, the first gRNA molecule and the second gRNA molecule include targeting domains comprising, e.g., consisting of, SEQ ID NO: 5585 and SEQ ID NO: 5496, respectively. In an aspect, the first gRNA molecule and the second gRNA molecule include targeting domains comprising, e.g., consisting of, SEQ ID NO: 5585 and SEQ ID NO: 5507, respectively. In an aspect, the first gRNA molecule and the second gRNA molecule include targeting domains comprising, e.g., consisting of, SEQ ID NO: 5585 and SEQ ID NO: 5515, respectively. In an aspect, the first gRNA molecule and the second gRNA molecule include targeting domains comprising, e.g., consisting of, SEQ ID NO: 5585 and SEQ ID NO: 5493, respectively. In an aspect, the first gRNA molecule and the second gRNA molecule include targeting domains comprising, e.g., consisting of, SEQ ID NO: 5585 and SEQ ID NO: 5506, respectively. In an aspect, the first gRNA molecule and the second gRNA molecule include targeting domains comprising, e.g., consisting of, SEQ ID NO: 5585 and SEQ ID NO: 5509, respectively. In an aspect, the first gRNA molecule and the second gRNA molecule include targeting domains comprising, e.g., consisting of, SEQ ID NO: 5585 and SEQ ID NO: 5517, respectively. In an aspect, the first gRNA molecule and the second gRNA molecule include targeting domains comprising, e.g., consisting of, SEQ ID NO: 5585 and SEQ ID NO: 5521, respectively. In an aspect, the first gRNA molecule and the second gRNA molecule include targeting domains comprising, e.g., consisting of, SEQ ID NO: 5585 and SEQ ID NO: 5520, respectively. In an aspect, the first gRNA molecule and the second gRNA molecule include targeting domains comprising, e.g., consisting of, SEQ ID NO: 5585 and SEQ ID NO: 5500, respectively. In an aspect, the first gRNA molecule and the second gRNA molecule include targeting domains comprising, e.g., consisting of, SEQ ID NO: 5585 and SEQ ID NO: 5494, respectively. In an aspect, the first gRNA molecule and the second gRNA molecule include targeting domains comprising, e.g., consisting of, SEQ ID NO: 5585 and SEQ ID NO: 5508, respectively. In an aspect, the first gRNA molecule and the second gRNA molecule include targeting domains comprising, e.g., consisting of, SEQ ID NO: 5585 and SEQ ID NO: 5514, respectively. In an aspect, the first gRNA molecule and the second gRNA molecule include targeting domains comprising, e.g., consisting of, SEQ ID NO: 5585 and SEQ ID NO: 5492, respectively. In an aspect, the first gRNA molecule and the second gRNA molecule include targeting domains comprising, e.g., consisting of, SEQ ID NO: 5592 and SEQ ID NO: 5519, respectively. In an aspect, the first gRNA molecule and the second gRNA molecule include targeting domains comprising, e.g., consisting of, SEQ ID NO: 5592 and SEQ ID NO: 5497, respectively. In an aspect, the first gRNA molecule and the second gRNA molecule include targeting domains comprising, e.g., consisting of, SEQ ID NO: 5592 and SEQ ID NO: 5499, respectively. In an aspect, the first gRNA molecule and the second gRNA molecule include targeting domains comprising, e.g., consisting of, SEQ ID NO: 5592 and SEQ ID NO: 5498, respectively. In an aspect, the first gRNA molecule and the second gRNA molecule include targeting domains comprising, e.g., consisting of, SEQ ID NO: 5592 and SEQ ID NO: 5503, respectively. In an aspect, the first gRNA molecule and the second gRNA molecule include targeting domains comprising, e.g., consisting of, SEQ ID NO: 5592 and SEQ ID NO: 5496, respectively. In an aspect, the first gRNA molecule and the second gRNA molecule include targeting domains comprising, e.g., consisting of, SEQ ID NO: 5592 and SEQ ID NO: 5507, respectively. In an aspect, the first gRNA molecule and the second gRNA molecule include targeting domains comprising, e.g., consisting of, SEQ ID NO: 5592 and SEQ ID NO: 5515, respectively. In an aspect, the first gRNA molecule and the second gRNA molecule include targeting domains comprising, e.g., consisting of, SEQ ID NO: 5592 and SEQ ID NO: 5493, respectively. In an aspect, the first gRNA molecule and the second gRNA molecule include targeting domains comprising, e.g., consisting of, SEQ ID NO: 5592 and SEQ ID NO: 5506, respectively. In an aspect, the first gRNA molecule and the second gRNA molecule include targeting domains comprising, e.g., consisting of, SEQ ID NO: 5592 and SEQ ID NO: 5509, respectively. In an aspect, the first gRNA molecule and the second gRNA molecule include targeting domains comprising, e.g., consisting of, SEQ ID NO: 5592 and SEQ ID NO: 5517, respectively. In an aspect, the first gRNA molecule and the second gRNA molecule include targeting domains comprising, e.g., consisting of, SEQ ID NO: 5592 and SEQ ID NO: 5521, respectively. In an aspect, the first gRNA molecule and the second gRNA molecule include targeting domains comprising, e.g., consisting of, SEQ ID NO: 5592 and SEQ ID NO: 5520, respectively. In an aspect, the first gRNA molecule and the second gRNA molecule include targeting domains comprising, e.g., consisting of, SEQ ID NO: 5592 and SEQ ID NO: 5500, respectively. In an aspect, the first gRNA molecule and the second gRNA molecule include targeting domains comprising, e.g., consisting of, SEQ ID NO: 5592 and SEQ ID NO: 5494, respectively. In an aspect, the first gRNA molecule and the second gRNA molecule include targeting domains comprising, e.g., consisting of, SEQ ID NO: 5592 and SEQ ID NO: 5508, respectively. In an aspect, the first gRNA molecule and the second gRNA molecule include targeting domains comprising, e.g., consisting of, SEQ ID NO: 5592 and SEQ ID NO: 5514, respectively. In an aspect, the first gRNA molecule and the second gRNA molecule include targeting domains comprising, e.g., consisting of, SEQ ID NO: 5592 and SEQ ID NO: 5492, respectively. In an aspect, the first gRNA molecule and the second gRNA molecule include targeting domains comprising, e.g., consisting of, SEQ ID NO: 5601 and SEQ ID NO: 5519, respectively. In an aspect, the first gRNA molecule and the second gRNA molecule include targeting domains comprising, e.g., consisting of, SEQ ID NO: 5601 and SEQ ID NO: 5497, respectively. In an aspect, the first gRNA molecule and the second gRNA molecule include targeting domains comprising, e.g., consisting of, SEQ ID NO: 5601 and SEQ ID NO: 5499, respectively. In an aspect, the first gRNA molecule and the second gRNA molecule include targeting domains comprising, e.g., consisting of, SEQ ID NO: 5601 and SEQ ID NO: 5498, respectively. In an aspect, the first gRNA molecule and the second gRNA molecule include targeting domains comprising, e.g., consisting of, SEQ ID NO: 5601 and SEQ ID NO: 5503, respectively. In an aspect, the first gRNA molecule and the second gRNA molecule include targeting domains comprising, e.g., consisting of, SEQ ID NO: 5601 and SEQ ID NO: 5496, respectively. In an aspect, the first gRNA molecule and the second gRNA molecule include targeting domains comprising, e.g., consisting of, SEQ ID NO: 5601 and SEQ ID NO: 5507, respectively. In an aspect, the first gRNA molecule and the second gRNA molecule include targeting domains comprising, e.g., consisting of, SEQ ID NO: 5601 and SEQ ID NO: 5515, respectively. In an aspect, the first gRNA molecule and the second gRNA molecule include targeting domains comprising, e.g., consisting of, SEQ ID NO: 5601 and SEQ ID NO: 5493, respectively. In an aspect, the first gRNA molecule and the second gRNA molecule include targeting domains comprising, e.g., consisting of, SEQ ID NO: 5601 and SEQ ID NO: 5506, respectively. In an aspect, the first gRNA molecule and the second gRNA molecule include targeting domains comprising, e.g., consisting of, SEQ ID NO: 5601 and SEQ ID NO: 5509, respectively. In an aspect, the first gRNA molecule and the second gRNA molecule include targeting domains comprising, e.g., consisting of, SEQ ID NO: 5601 and SEQ ID NO: 5517, respectively. In an aspect, the first gRNA molecule and the second gRNA molecule include targeting domains comprising, e.g., consisting of, SEQ ID NO: 5601 and SEQ ID NO: 5521, respectively. In an aspect, the first gRNA molecule and the second gRNA molecule include targeting domains comprising, e.g., consisting of, SEQ ID NO: 5601 and SEQ ID NO: 5520, respectively. In an aspect, the first gRNA molecule and the second gRNA molecule include targeting domains comprising, e.g., consisting of, SEQ ID NO: 5601 and SEQ ID NO: 5500, respectively. In an aspect, the first gRNA molecule and the second gRNA molecule include targeting domains comprising, e.g., consisting of, SEQ ID NO: 5601 and SEQ ID NO: 5494, respectively. In an aspect, the first gRNA molecule and the second gRNA molecule include targeting domains comprising, e.g., consisting of, SEQ ID NO: 5601 and SEQ ID NO: 5508, respectively. In an aspect, the first gRNA molecule and the second gRNA molecule include targeting domains comprising, e.g., consisting of, SEQ ID NO: 5601 and SEQ ID NO: 5514, respectively. In an aspect, the first gRNA molecule and the second gRNA molecule include targeting domains comprising, e.g., consisting of, SEQ ID NO: 5601 and SEQ ID NO: 5492, respectively. In an aspect, the first gRNA molecule and the second gRNA molecule include targeting domains comprising, e.g., consisting of, SEQ ID NO: 5589 and SEQ ID NO: 5519, respectively. In an aspect, the first gRNA molecule and the second gRNA molecule include targeting domains comprising, e.g., consisting of, SEQ ID NO: 5589 and SEQ ID NO: 5497, respectively. In an aspect, the first gRNA molecule and the second gRNA molecule include targeting domains comprising, e.g., consisting of, SEQ ID NO: 5589 and SEQ ID NO: 5499, respectively. In an aspect, the first gRNA molecule and the second gRNA molecule include targeting domains comprising, e.g., consisting of, SEQ ID NO: 5589 and SEQ ID NO: 5498, respectively. In an aspect, the first gRNA molecule and the second gRNA molecule include targeting domains comprising, e.g., consisting of, SEQ ID NO: 5589 and SEQ ID NO: 5503, respectively. In an aspect, the first gRNA molecule and the second gRNA molecule include targeting domains comprising, e.g., consisting of, SEQ ID NO: 5589 and SEQ ID NO: 5496, respectively. In an aspect, the first gRNA molecule and the second gRNA molecule include targeting domains comprising, e.g., consisting of, SEQ ID NO: 5589 and SEQ ID NO: 5507, respectively. In an aspect, the first gRNA molecule and the second gRNA molecule include targeting domains comprising, e.g., consisting of, SEQ ID NO: 5589 and SEQ ID NO: 5515, respectively. In an aspect, the first gRNA molecule and the second gRNA molecule include targeting domains comprising, e.g., consisting of, SEQ ID NO: 5589 and SEQ ID NO: 5493, respectively. In an aspect, the first gRNA molecule and the second gRNA molecule include targeting domains comprising, e.g., consisting of, SEQ ID NO: 5589 and SEQ ID NO: 5506, respectively. In an aspect, the first gRNA molecule and the second gRNA molecule include targeting domains comprising, e.g., consisting of, SEQ ID NO: 5589 and SEQ ID NO: 5509, respectively. In an aspect, the first gRNA molecule and the second gRNA molecule include targeting domains comprising, e.g., consisting of, SEQ ID NO: 5589 and SEQ ID NO: 5517, respectively. In an aspect, the first gRNA molecule and the second gRNA molecule include targeting domains comprising, e.g., consisting of, SEQ ID NO: 5589 and SEQ ID NO: 5521, respectively. In an aspect, the first gRNA molecule and the second gRNA molecule include targeting domains comprising, e.g., consisting of, SEQ ID NO: 5589 and SEQ ID NO: 5520, respectively. In an aspect, the first gRNA molecule and the second gRNA molecule include targeting domains comprising, e.g., consisting of, SEQ ID NO: 5589 and SEQ ID NO: 5500, respectively. In an aspect, the first gRNA molecule and the second gRNA molecule include targeting domains comprising, e.g., consisting of, SEQ ID NO: 5589 and SEQ ID NO: 5494, respectively. In an aspect, the first gRNA molecule and the second gRNA molecule include targeting domains comprising, e.g., consisting of, SEQ ID NO: 5589 and SEQ ID NO: 5508, respectively. In an aspect, the first gRNA molecule and the second gRNA molecule include targeting domains comprising, e.g., consisting of, SEQ ID NO: 5589 and SEQ ID NO: 5514, respectively. In an aspect, the first gRNA molecule and the second gRNA molecule include targeting domains comprising, e.g., consisting of, SEQ ID NO: 5589 and SEQ ID NO: 5492, respectively. In an aspect, the first gRNA molecule and the second gRNA molecule include targeting domains comprising, e.g., consisting of, SEQ ID NO: 5600 and SEQ ID NO: 5519, respectively. In an aspect, the first gRNA molecule and the second gRNA molecule include targeting domains comprising, e.g., consisting of, SEQ ID NO: 5600 and SEQ ID NO: 5497, respectively. In an aspect, the first gRNA molecule and the second gRNA molecule include targeting domains comprising, e.g., consisting of, SEQ ID NO: 5600 and SEQ ID NO: 5499, respectively. In an aspect, the first gRNA molecule and the second gRNA molecule include targeting domains comprising, e.g., consisting of, SEQ ID NO: 5600 and SEQ ID NO: 5498, respectively. In an aspect, the first gRNA molecule and the second gRNA molecule include targeting domains comprising, e.g., consisting of, SEQ ID NO: 5600 and SEQ ID NO: 5503, respectively. In an aspect, the first gRNA molecule and the second gRNA molecule include targeting domains comprising, e.g., consisting of, SEQ ID NO: 5600 and SEQ ID NO: 5496, respectively. In an aspect, the first gRNA molecule and the second gRNA molecule include targeting domains comprising, e.g., consisting of, SEQ ID NO: 5600 and SEQ ID NO: 5507, respectively. In an aspect, the first gRNA molecule and the second gRNA molecule include targeting domains comprising, e.g., consisting of, SEQ ID NO: 5600 and SEQ ID NO: 5515, respectively. In an aspect, the first gRNA molecule and the second gRNA molecule include targeting domains comprising, e.g., consisting of, SEQ ID NO: 5600 and SEQ ID NO: 5493, respectively. In an aspect, the first gRNA molecule and the second gRNA molecule include targeting domains comprising, e.g., consisting of, SEQ ID NO: 5600 and SEQ ID NO: 5506, respectively. In an aspect, the first gRNA molecule and the second gRNA molecule include targeting domains comprising, e.g., consisting of, SEQ ID NO: 5600 and SEQ ID NO: 5509, respectively. In an aspect, the first gRNA molecule and the second gRNA molecule include targeting domains comprising, e.g., consisting of, SEQ ID NO: 5600 and SEQ ID NO: 5517, respectively. In an aspect, the first gRNA molecule and the second gRNA molecule include targeting domains comprising, e.g., consisting of, SEQ ID NO: 5600 and SEQ ID NO: 5521, respectively. In an aspect, the first gRNA molecule and the second gRNA molecule include targeting domains comprising, e.g., consisting of, SEQ ID NO: 5600 and SEQ ID NO: 5520, respectively. In an aspect, the first gRNA molecule and the second gRNA molecule include targeting domains comprising, e.g., consisting of, SEQ ID NO: 5600 and SEQ ID NO: 5500, respectively. In an aspect, the first gRNA molecule and the second gRNA molecule include targeting domains comprising, e.g., consisting of, SEQ ID NO: 5600 and SEQ ID NO: 5494, respectively. In an aspect, the first gRNA molecule and the second gRNA molecule include targeting domains comprising, e.g., consisting of, SEQ ID NO: 5600 and SEQ ID NO: 5508, respectively. In an aspect, the first gRNA molecule and the second gRNA molecule include targeting domains comprising, e.g., consisting of, SEQ ID NO: 5600 and SEQ ID NO: 5514, respectively. In an aspect, the first gRNA molecule and the second gRNA molecule include targeting domains comprising, e.g., consisting of, SEQ ID NO: 5600 and SEQ ID NO: 5492, respectively. In an aspect, the first gRNA molecule and the second gRNA molecule include targeting domains comprising, e.g., consisting of, SEQ ID NO: 5594 and SEQ ID NO: 5519, respectively. In an aspect, the first gRNA molecule and the second gRNA molecule include targeting domains comprising, e.g., consisting of, SEQ ID NO: 5594 and SEQ ID NO: 5497, respectively. In an aspect, the first gRNA molecule and the second gRNA molecule include targeting domains comprising, e.g., consisting of, SEQ ID NO: 5594 and SEQ ID NO: 5499, respectively. In an aspect, the first gRNA molecule and the second gRNA molecule include targeting domains comprising, e.g., consisting of, SEQ ID NO: 5594 and SEQ ID NO: 5498, respectively. In an aspect, the first gRNA molecule and the second gRNA molecule include targeting domains comprising, e.g., consisting of, SEQ ID NO: 5594 and SEQ ID NO: 5503, respectively. In an aspect, the first gRNA molecule and the second gRNA molecule include targeting domains comprising, e.g., consisting of, SEQ ID NO: 5594 and SEQ ID NO: 5496, respectively. In an aspect, the first gRNA molecule and the second gRNA molecule include targeting domains comprising, e.g., consisting of, SEQ ID NO: 5594 and SEQ ID NO: 5507, respectively. In an aspect, the first gRNA molecule and the second gRNA molecule include targeting domains comprising, e.g., consisting of, SEQ ID NO: 5594 and SEQ ID NO: 5515, respectively. In an aspect, the first gRNA molecule and the second gRNA molecule include targeting domains comprising, e.g., consisting of, SEQ ID NO: 5594 and SEQ ID NO: 5493, respectively. In an aspect, the first gRNA molecule and the second gRNA molecule include targeting domains comprising, e.g., consisting of, SEQ ID NO: 5594 and SEQ ID NO: 5506, respectively. In an aspect, the first gRNA molecule and the second gRNA molecule include targeting domains comprising, e.g., consisting of, SEQ ID NO: 5594 and SEQ ID NO: 5509, respectively. In an aspect, the first gRNA molecule and the second gRNA molecule include targeting domains comprising, e.g., consisting of, SEQ ID NO: 5594 and SEQ ID NO: 5517, respectively. In an aspect, the first gRNA molecule and the second gRNA molecule include targeting domains comprising, e.g., consisting of, SEQ ID NO: 5594 and SEQ ID NO: 5521, respectively. In an aspect, the first gRNA molecule and the second gRNA molecule include targeting domains comprising, e.g., consisting of, SEQ ID NO: 5594 and SEQ ID NO: 5520, respectively. In an aspect, the first gRNA molecule and the second gRNA molecule include targeting domains comprising, e.g., consisting of, SEQ ID NO: 5594 and SEQ ID NO: 5500, respectively. In an aspect, the first gRNA molecule and the second gRNA molecule include targeting domains comprising, e.g., consisting of, SEQ ID NO: 5594 and SEQ ID NO: 5494, respectively. In an aspect, the first gRNA molecule and the second gRNA molecule include targeting domains comprising, e.g., consisting of, SEQ ID NO: 5594 and SEQ ID NO: 5508, respectively. In an aspect, the first gRNA molecule and the second gRNA molecule include targeting domains comprising, e.g., consisting of, SEQ ID NO: 5594 and SEQ ID NO: 5514, respectively. In an aspect, the first gRNA molecule and the second gRNA molecule include targeting domains comprising, e.g., consisting of, SEQ ID NO: 5594 and SEQ ID NO: 5492, respectively. In an aspect, the first gRNA molecule and the second gRNA molecule include targeting domains comprising, e.g., consisting of, SEQ ID NO: 5571 and SEQ ID NO: 5519, respectively. In an aspect, the first gRNA molecule and the second gRNA molecule include targeting domains comprising, e.g., consisting of, SEQ ID NO: 5571 and SEQ ID NO: 5497, respectively. In an aspect, the first gRNA molecule and the second gRNA molecule include targeting domains comprising, e.g., consisting of, SEQ ID NO: 5571 and SEQ ID NO: 5499, respectively. In an aspect, the first gRNA molecule and the second gRNA molecule include targeting domains comprising, e.g., consisting of, SEQ ID NO: 5571 and SEQ ID NO: 5498, respectively. In an aspect, the first gRNA molecule and the second gRNA molecule include targeting domains comprising, e.g., consisting of, SEQ ID NO: 5571 and SEQ ID NO: 5503, respectively. In an aspect, the first gRNA molecule and the second gRNA molecule include targeting domains comprising, e.g., consisting of, SEQ ID NO: 5571 and SEQ ID NO: 5496, respectively. In an aspect, the first gRNA molecule and the second gRNA molecule include targeting domains comprising, e.g., consisting of, SEQ ID NO: 5571 and SEQ ID NO: 5507, respectively. In an aspect, the first gRNA molecule and the second gRNA molecule include targeting domains comprising, e.g., consisting of, SEQ ID NO: 5571 and SEQ ID NO: 5515, respectively. In an aspect, the first gRNA molecule and the second gRNA molecule include targeting domains comprising, e.g., consisting of, SEQ ID NO: 5571 and SEQ ID NO: 5493, respectively. In an aspect, the first gRNA molecule and the second gRNA molecule include targeting domains comprising, e.g., consisting of, SEQ ID NO: 5571 and SEQ ID NO: 5506, respectively. In an aspect, the first gRNA molecule and the second gRNA molecule include targeting domains comprising, e.g., consisting of, SEQ ID NO: 5571 and SEQ ID NO: 5509, respectively. In an aspect, the first gRNA molecule and the second gRNA molecule include targeting domains comprising, e.g., consisting of, SEQ ID NO: 5571 and SEQ ID NO: 5517, respectively. In an aspect, the first gRNA molecule and the second gRNA molecule include targeting domains comprising, e.g., consisting of, SEQ ID NO: 5571 and SEQ ID NO: 5521, respectively. In an aspect, the first gRNA molecule and the second gRNA molecule include targeting domains comprising, e.g., consisting of, SEQ ID NO: 5571 and SEQ ID NO: 5520, respectively. In an aspect, the first gRNA molecule and the second gRNA molecule include targeting domains comprising, e.g., consisting of, SEQ ID NO: 5571 and SEQ ID NO: 5500, respectively. In an aspect, the first gRNA molecule and the second gRNA molecule include targeting domains comprising, e.g., consisting of, SEQ ID NO: 5571 and SEQ ID NO: 5494, respectively. In an aspect, the first gRNA molecule and the second gRNA molecule include targeting domains comprising, e.g., consisting of, SEQ ID NO: 5571 and SEQ ID NO: 5508, respectively. In an aspect, the first gRNA molecule and the second gRNA molecule include targeting domains comprising, e.g., consisting of, SEQ ID NO: 5571 and SEQ ID NO: 5514, respectively. In an aspect, the first gRNA molecule and the second gRNA molecule include targeting domains comprising, e.g., consisting of, SEQ ID NO: 5571 and SEQ ID NO: 5492, respectively. In an aspect, the first gRNA molecule and the second gRNA molecule include targeting domains comprising, e.g., consisting of, SEQ ID NO: 5593 and SEQ ID NO: 5519, respectively. In an aspect, the first gRNA molecule and the second gRNA molecule include targeting domains comprising, e.g., consisting of, SEQ ID NO: 5593 and SEQ ID NO: 5497, respectively. In an aspect, the first gRNA molecule and the second gRNA molecule include targeting domains comprising, e.g., consisting of, SEQ ID NO: 5593 and SEQ ID NO: 5499, respectively. In an aspect, the first gRNA molecule and the second gRNA molecule include targeting domains comprising, e.g., consisting of, SEQ ID NO: 5593 and SEQ ID NO: 5498, respectively. In an aspect, the first gRNA molecule and the second gRNA molecule include targeting domains comprising, e.g., consisting of, SEQ ID NO: 5593 and SEQ ID NO: 5503, respectively. In an aspect, the first gRNA molecule and the second gRNA molecule include targeting domains comprising, e.g., consisting of, SEQ ID NO: 5593 and SEQ ID NO: 5496, respectively. In an aspect, the first gRNA molecule and the second gRNA molecule include targeting domains comprising, e.g., consisting of, SEQ ID NO: 5593 and SEQ ID NO: 5507, respectively. In an aspect, the first gRNA molecule and the second gRNA molecule include targeting domains comprising, e.g., consisting of, SEQ ID NO: 5593 and SEQ ID NO: 5515, respectively. In an aspect, the first gRNA molecule and the second gRNA molecule include targeting domains comprising, e.g., consisting of, SEQ ID NO: 5593 and SEQ ID NO: 5493, respectively. In an aspect, the first gRNA molecule and the second gRNA molecule include targeting domains comprising, e.g., consisting of, SEQ ID NO: 5593 and SEQ ID NO: 5506, respectively. In an aspect, the first gRNA molecule and the second gRNA molecule include targeting domains comprising, e.g., consisting of, SEQ ID NO: 5593 and SEQ ID NO: 5509, respectively. In an aspect, the first gRNA molecule and the second gRNA molecule include targeting domains comprising, e.g., consisting of, SEQ ID NO: 5593 and SEQ ID NO: 5517, respectively. In an aspect, the first gRNA molecule and the second gRNA molecule include targeting domains comprising, e.g., consisting of, SEQ ID NO: 5593 and SEQ ID NO: 5521, respectively. In an aspect, the first gRNA molecule and the second gRNA molecule include targeting domains comprising, e.g., consisting of, SEQ ID NO: 5593 and SEQ ID NO: 5520, respectively. In an aspect, the first gRNA molecule and the second gRNA molecule include targeting domains comprising, e.g., consisting of, SEQ ID NO: 5593 and SEQ ID NO: 5500, respectively. In an aspect, the first gRNA molecule and the second gRNA molecule include targeting domains comprising, e.g., consisting of, SEQ ID NO: 5593 and SEQ ID NO: 5494, respectively. In an aspect, the first gRNA molecule and the second gRNA molecule include targeting domains comprising, e.g., consisting of, SEQ ID NO: 5593 and SEQ ID NO: 5508, respectively. In an aspect, the first gRNA molecule and the second gRNA molecule include targeting domains comprising, e.g., consisting of, SEQ ID NO: 5593 and SEQ ID NO: 5514, respectively. In an aspect, the first gRNA molecule and the second gRNA molecule include targeting domains comprising, e.g., consisting of, SEQ ID NO: 5593 and SEQ ID NO: 5492, respectively. In an aspect, the first gRNA molecule and the second gRNA molecule include targeting domains comprising, e.g., consisting of, SEQ ID NO: 5574 and SEQ ID NO: 5519, respectively. In an aspect, the first gRNA molecule and the second gRNA molecule include targeting domains comprising, e.g., consisting of, SEQ ID NO: 5574 and SEQ ID NO: 5497, respectively. In an aspect, the first gRNA molecule and the second gRNA molecule include targeting domains comprising, e.g., consisting of, SEQ ID NO: 5574 and SEQ ID NO: 5499, respectively. In an aspect, the first gRNA molecule and the second gRNA molecule include targeting domains comprising, e.g., consisting of, SEQ ID NO: 5574 and SEQ ID NO: 5498, respectively. In an aspect, the first gRNA molecule and the second gRNA molecule include targeting domains comprising, e.g., consisting of, SEQ ID NO: 5574 and SEQ ID NO: 5503, respectively. In an aspect, the first gRNA molecule and the second gRNA molecule include targeting domains comprising, e.g., consisting of, SEQ ID NO: 5574 and SEQ ID NO: 5496, respectively. In an aspect, the first gRNA molecule and the second gRNA molecule include targeting domains comprising, e.g., consisting of, SEQ ID NO: 5574 and SEQ ID NO: 5507, respectively. In an aspect, the first gRNA molecule and the second gRNA molecule include targeting domains comprising, e.g., consisting of, SEQ ID NO: 5574 and SEQ ID NO: 5515, respectively. In an aspect, the first gRNA molecule and the second gRNA molecule include targeting domains comprising, e.g., consisting of, SEQ ID NO: 5574 and SEQ ID NO: 5493, respectively. In an aspect, the first gRNA molecule and the second gRNA molecule include targeting domains comprising, e.g., consisting of, SEQ ID NO: 5574 and SEQ ID NO: 5506, respectively. In an aspect, the first gRNA molecule and the second gRNA molecule include targeting domains comprising, e.g., consisting of, SEQ ID NO: 5574 and SEQ ID NO: 5509, respectively. In an aspect, the first gRNA molecule and the second gRNA molecule include targeting domains comprising, e.g., consisting of, SEQ ID NO: 5574 and SEQ ID NO: 5517, respectively. In an aspect, the first gRNA molecule and the second gRNA molecule include targeting domains comprising, e.g., consisting of, SEQ ID NO: 5574 and SEQ ID NO: 5521, respectively. In an aspect, the first gRNA molecule and the second gRNA molecule include targeting domains comprising, e.g., consisting of, SEQ ID NO: 5574 and SEQ ID NO: 5520, respectively. In an aspect, the first gRNA molecule and the second gRNA molecule include targeting domains comprising, e.g., consisting of, SEQ ID NO: 5574 and SEQ ID NO: 5500, respectively. In an aspect, the first gRNA molecule and the second gRNA molecule include targeting domains comprising, e.g., consisting of, SEQ ID NO: 5574 and SEQ ID NO: 5494, respectively. In an aspect, the first gRNA molecule and the second gRNA molecule include targeting domains comprising, e.g., consisting of, SEQ ID NO: 5574 and SEQ ID NO: 5508, respectively. In an aspect, the first gRNA molecule and the second gRNA molecule include targeting domains comprising, e.g., consisting of, SEQ ID NO: 5574 and SEQ ID NO: 5514, respectively. In an aspect, the first gRNA molecule and the second gRNA molecule include targeting domains comprising, e.g., consisting of, SEQ ID NO: 5574 and SEQ ID NO: 5492, respectively. In an aspect, the first gRNA molecule and the second gRNA molecule include targeting domains comprising, e.g., consisting of, SEQ ID NO: 5598 and SEQ ID NO: 5519, respectively. In an aspect, the first gRNA molecule and the second gRNA molecule include targeting domains comprising, e.g., consisting of, SEQ ID NO: 5598 and SEQ ID NO: 5497, respectively. In an aspect, the first gRNA molecule and the second gRNA molecule include targeting domains comprising, e.g., consisting of, SEQ ID NO: 5598 and SEQ ID NO: 5499, respectively. In an aspect, the first gRNA molecule and the second gRNA molecule include targeting domains comprising, e.g., consisting of, SEQ ID NO: 5598 and SEQ ID NO: 5498, respectively. In an aspect, the first gRNA molecule and the second gRNA molecule include targeting domains comprising, e.g., consisting of, SEQ ID NO: 5598 and SEQ ID NO: 5503, respectively. In an aspect, the first gRNA molecule and the second gRNA molecule include targeting domains comprising, e.g., consisting of, SEQ ID NO: 5598 and SEQ ID NO: 5496, respectively. In an aspect, the first gRNA molecule and the second gRNA molecule include targeting domains comprising, e.g., consisting of, SEQ ID NO: 5598 and SEQ ID NO: 5507, respectively. In an aspect, the first gRNA molecule and the second gRNA molecule include targeting domains comprising, e.g., consisting of, SEQ ID NO: 5598 and SEQ ID NO: 5515, respectively. In an aspect, the first gRNA molecule and the second gRNA molecule include targeting domains comprising, e.g., consisting of, SEQ ID NO: 5598 and SEQ ID NO: 5493, respectively. In an aspect, the first gRNA molecule and the second gRNA molecule include targeting domains comprising, e.g., consisting of, SEQ ID NO: 5598 and SEQ ID NO: 5506, respectively. In an aspect, the first gRNA molecule and the second gRNA molecule include targeting domains comprising, e.g., consisting of, SEQ ID NO: 5598 and SEQ ID NO: 5509, respectively. In an aspect, the first gRNA molecule and the second gRNA molecule include targeting domains comprising, e.g., consisting of, SEQ ID NO: 5598 and SEQ ID NO: 5517, respectively. In an aspect, the first gRNA molecule and the second gRNA molecule include targeting domains comprising, e.g., consisting of, SEQ ID NO: 5598 and SEQ ID NO: 5521, respectively. In an aspect, the first gRNA molecule and the second gRNA molecule include targeting domains comprising, e.g., consisting of, SEQ ID NO: 5598 and SEQ ID NO: 5520, respectively. In an aspect, the first gRNA molecule and the second gRNA molecule include targeting domains comprising, e.g., consisting of, SEQ ID NO: 5598 and SEQ ID NO: 5500, respectively. In an aspect, the first gRNA molecule and the second gRNA molecule include targeting domains comprising, e.g., consisting of, SEQ ID NO: 5598 and SEQ ID NO: 5494, respectively. In an aspect, the first gRNA molecule and the second gRNA molecule include targeting domains comprising, e.g., consisting of, SEQ ID NO: 5598 and SEQ ID NO: 5508, respectively. In an aspect, the first gRNA molecule and the second gRNA molecule include targeting domains comprising, e.g., consisting of, SEQ ID NO: 5598 and SEQ ID NO: 5514, respectively. In an aspect, the first gRNA molecule and the second gRNA molecule include targeting domains comprising, e.g., consisting of, SEQ ID NO: 5598 and SEQ ID NO: 5492, respectively. In an aspect, the first gRNA molecule and the second gRNA molecule include targeting domains comprising, e.g., consisting of, SEQ ID NO: 5586 and SEQ ID NO: 5519, respectively. In an aspect, the first gRNA molecule and the second gRNA molecule include targeting domains comprising, e.g., consisting of, SEQ ID NO: 5586 and SEQ ID NO: 5497, respectively. In an aspect, the first gRNA molecule and the second gRNA molecule include targeting domains comprising, e.g., consisting of, SEQ ID NO: 5586 and SEQ ID NO: 5499, respectively. In an aspect, the first gRNA molecule and the second gRNA molecule include targeting domains comprising, e.g., consisting of, SEQ ID NO: 5586 and SEQ ID NO: 5498, respectively. In an aspect, the first gRNA molecule and the second gRNA molecule include targeting domains comprising, e.g., consisting of, SEQ ID NO: 5586 and SEQ ID NO: 5503, respectively. In an aspect, the first gRNA molecule and the second gRNA molecule include targeting domains comprising, e.g., consisting of, SEQ ID NO: 5586 and SEQ ID NO: 5496, respectively. In an aspect, the first gRNA molecule and the second gRNA molecule include targeting domains comprising, e.g., consisting of, SEQ ID NO: 5586 and SEQ ID NO: 5507, respectively. In an aspect, the first gRNA molecule and the second gRNA molecule include targeting domains comprising, e.g., consisting of, SEQ ID NO: 5586 and SEQ ID NO: 5515, respectively. In an aspect, the first gRNA molecule and the second gRNA molecule include targeting domains comprising, e.g., consisting of, SEQ ID NO: 5586 and SEQ ID NO: 5493, respectively. In an aspect, the first gRNA molecule and the second gRNA molecule include targeting domains comprising, e.g., consisting of, SEQ ID NO: 5586 and SEQ ID NO: 5506, respectively. In an aspect, the first gRNA molecule and the second gRNA molecule include targeting domains comprising, e.g., consisting of, SEQ ID NO: 5586 and SEQ ID NO: 5509, respectively. In an aspect, the first gRNA molecule and the second gRNA molecule include targeting domains comprising, e.g., consisting of, SEQ ID NO: 5586 and SEQ ID NO: 5517, respectively. In an aspect, the first gRNA molecule and the second gRNA molecule include targeting domains comprising, e.g., consisting of, SEQ ID NO: 5586 and SEQ ID NO: 5521, respectively. In an aspect, the first gRNA molecule and the second gRNA molecule include targeting domains comprising, e.g., consisting of, SEQ ID NO: 5586 and SEQ ID NO: 5520, respectively. In an aspect, the first gRNA molecule and the second gRNA molecule include targeting domains comprising, e.g., consisting of, SEQ ID NO: 5586 and SEQ ID NO: 5500, respectively. In an aspect, the first gRNA molecule and the second gRNA molecule include targeting domains comprising, e.g., consisting of, SEQ ID NO: 5586 and SEQ ID NO: 5494, respectively. In an aspect, the first gRNA molecule and the second gRNA molecule include targeting domains comprising, e.g., consisting of, SEQ ID NO: 5586 and SEQ ID NO: 5508, respectively. In an aspect, the first gRNA molecule and the second gRNA molecule include targeting domains comprising, e.g., consisting of, SEQ ID NO: 5586 and SEQ ID NO: 5514, respectively. In an aspect, the first gRNA molecule and the second gRNA molecule include targeting domains comprising, e.g., consisting of, SEQ ID NO: 5586 and SEQ ID NO: 5492, respectively. In an aspect, the first gRNA molecule and the second gRNA molecule include targeting domains comprising, e.g., consisting of, SEQ ID NO: 5599 and SEQ ID NO: 5519, respectively. In an aspect, the first gRNA molecule and the second gRNA molecule include targeting domains comprising, e.g., consisting of, SEQ ID NO: 5599 and SEQ ID NO: 5497, respectively. In an aspect, the first gRNA molecule and the second gRNA molecule include targeting domains comprising, e.g., consisting of, SEQ ID NO: 5599 and SEQ ID NO: 5499, respectively. In an aspect, the first gRNA molecule and the second gRNA molecule include targeting domains comprising, e.g., consisting of, SEQ ID NO: 5599 and SEQ ID NO: 5498, respectively. In an aspect, the first gRNA molecule and the second gRNA molecule include targeting domains comprising, e.g., consisting of, SEQ ID NO: 5599 and SEQ ID NO: 5503, respectively. In an aspect, the first gRNA molecule and the second gRNA molecule include targeting domains comprising, e.g., consisting of, SEQ ID NO: 5599 and SEQ ID NO: 5496, respectively. In an aspect, the first gRNA molecule and the second gRNA molecule include targeting domains comprising, e.g., consisting of, SEQ ID NO: 5599 and SEQ ID NO: 5507, respectively. In an aspect, the first gRNA molecule and the second gRNA molecule include targeting domains comprising, e.g., consisting of, SEQ ID NO: 5599 and SEQ ID NO: 5515, respectively. In an aspect, the first gRNA molecule and the second gRNA molecule include targeting domains comprising, e.g., consisting of, SEQ ID NO: 5599 and SEQ ID NO: 5493, respectively. In an aspect, the first gRNA molecule and the second gRNA molecule include targeting domains comprising, e.g., consisting of, SEQ ID NO: 5599 and SEQ ID NO: 5506, respectively. In an aspect, the first gRNA molecule and the second gRNA molecule include targeting domains comprising, e.g., consisting of, SEQ ID NO: 5599 and SEQ ID NO: 5509, respectively. In an aspect, the first gRNA molecule and the second gRNA molecule include targeting domains comprising, e.g., consisting of, SEQ ID NO: 5599 and SEQ ID NO: 5517, respectively. In an aspect, the first gRNA molecule and the second gRNA molecule include targeting domains comprising, e.g., consisting of, SEQ ID NO: 5599 and SEQ ID NO: 5521, respectively. In an aspect, the first gRNA molecule and the second gRNA molecule include targeting domains comprising, e.g., consisting of, SEQ ID NO: 5599 and SEQ ID NO: 5520, respectively. In an aspect, the first gRNA molecule and the second gRNA molecule include targeting domains comprising, e.g., consisting of, SEQ ID NO: 5599 and SEQ ID NO: 5500, respectively. In an aspect, the first gRNA molecule and the second gRNA molecule include targeting domains comprising, e.g., consisting of, SEQ ID NO: 5599 and SEQ ID NO: 5494, respectively. In an aspect, the first gRNA molecule and the second gRNA molecule include targeting domains comprising, e.g., consisting of, SEQ ID NO: 5599 and SEQ ID NO: 5508, respectively. In an aspect, the first gRNA molecule and the second gRNA molecule include targeting domains comprising, e.g., consisting of, SEQ ID NO: 5599 and SEQ ID NO: 5514, respectively. In an aspect, the first gRNA molecule and the second gRNA molecule include targeting domains comprising, e.g., consisting of, SEQ ID NO: 5599 and SEQ ID NO: 5492, respectively. In an aspect, the first gRNA molecule and the second gRNA molecule include targeting domains comprising, e.g., consisting of, SEQ ID NO: 5591 and SEQ ID NO: 5519, respectively. In an aspect, the first gRNA molecule and the second gRNA molecule include targeting domains comprising, e.g., consisting of, SEQ ID NO: 5591 and SEQ ID NO: 5497, respectively. In an aspect, the first gRNA molecule and the second gRNA molecule include targeting domains comprising, e.g., consisting of, SEQ ID NO: 5591 and SEQ ID NO: 5499, respectively. In an aspect, the first gRNA molecule and the second gRNA molecule include targeting domains comprising, e.g., consisting of, SEQ ID NO: 5591 and SEQ ID NO: 5498, respectively. In an aspect, the first gRNA molecule and the second gRNA molecule include targeting domains comprising, e.g., consisting of, SEQ ID NO: 5591 and SEQ ID NO: 5503, respectively. In an aspect, the first gRNA molecule and the second gRNA molecule include targeting domains comprising, e.g., consisting of, SEQ ID NO: 5591 and SEQ ID NO: 5496, respectively. In an aspect, the first gRNA molecule and the second gRNA molecule include targeting domains comprising, e.g., consisting of, SEQ ID NO: 5591 and SEQ ID NO: 5507, respectively. In an aspect, the first gRNA molecule and the second gRNA molecule include targeting domains comprising, e.g., consisting of, SEQ ID NO: 5591 and SEQ ID NO: 5515, respectively. In an aspect, the first gRNA molecule and the second gRNA molecule include targeting domains comprising, e.g., consisting of, SEQ ID NO: 5591 and SEQ ID NO: 5493, respectively. In an aspect, the first gRNA molecule and the second gRNA molecule include targeting domains comprising, e.g., consisting of, SEQ ID NO: 5591 and SEQ ID NO: 5506, respectively. In an aspect, the first gRNA molecule and the second gRNA molecule include targeting domains comprising, e.g., consisting of, SEQ ID NO: 5591 and SEQ ID NO: 5509, respectively. In an aspect, the first gRNA molecule and the second gRNA molecule include targeting domains comprising, e.g., consisting of, SEQ ID NO: 5591 and SEQ ID NO: 5517, respectively. In an aspect, the first gRNA molecule and the second gRNA molecule include targeting domains comprising, e.g., consisting of, SEQ ID NO: 5591 and SEQ ID NO: 5521, respectively. In an aspect, the first gRNA molecule and the second gRNA molecule include targeting domains comprising, e.g., consisting of, SEQ ID NO: 5591 and SEQ ID NO: 5520, respectively. In an aspect, the first gRNA molecule and the second gRNA molecule include targeting domains comprising, e.g., consisting of, SEQ ID NO: 5591 and SEQ ID NO: 5500, respectively. In an aspect, the first gRNA molecule and the second gRNA molecule include targeting domains comprising, e.g., consisting of, SEQ ID NO: 5591 and SEQ ID NO: 5494, respectively. In an aspect, the first gRNA molecule and the second gRNA molecule include targeting domains comprising, e.g., consisting of, SEQ ID NO: 5591 and SEQ ID NO: 5508, respectively. In an aspect, the first gRNA molecule and the second gRNA molecule include targeting domains comprising, e.g., consisting of, SEQ ID NO: 5591 and SEQ ID NO: 5514, respectively. In an aspect, the first gRNA molecule and the second gRNA molecule include targeting domains comprising, e.g., consisting of, SEQ ID NO: 5591 and SEQ ID NO: 5492, respectively. In an aspect, the first gRNA molecule and the second gRNA molecule include targeting domains comprising, e.g., consisting of, SEQ ID NO: 5568 and SEQ ID NO: 5519, respectively. In an aspect, the first gRNA molecule and the second gRNA molecule include targeting domains comprising, e.g., consisting of, SEQ ID NO: 5568 and SEQ ID NO: 5497, respectively. In an aspect, the first gRNA molecule and the second gRNA molecule include targeting domains comprising, e.g., consisting of, SEQ ID NO: 5568 and SEQ ID NO: 5499, respectively. In an aspect, the first gRNA molecule and the second gRNA molecule include targeting domains comprising, e.g., consisting of, SEQ ID NO: 5568 and SEQ ID NO: 5498, respectively. In an aspect, the first gRNA molecule and the second gRNA molecule include targeting domains comprising, e.g., consisting of, SEQ ID NO: 5568 and SEQ ID NO: 5503, respectively. In an aspect, the first gRNA molecule and the second gRNA molecule include targeting domains comprising, e.g., consisting of, SEQ ID NO: 5568 and SEQ ID NO: 5496, respectively. In an aspect, the first gRNA molecule and the second gRNA molecule include targeting domains comprising, e.g., consisting of, SEQ ID NO: 5568 and SEQ ID NO: 5507, respectively. In an aspect, the first gRNA molecule and the second gRNA molecule include targeting domains comprising, e.g., consisting of, SEQ ID NO: 5568 and SEQ ID NO: 5515, respectively. In an aspect, the first gRNA molecule and the second gRNA molecule include targeting domains comprising, e.g., consisting of, SEQ ID NO: 5568 and SEQ ID NO: 5493, respectively. In an aspect, the first gRNA molecule and the second gRNA molecule include targeting domains comprising, e.g., consisting of, SEQ ID NO: 5568 and SEQ ID NO: 5506, respectively. In an aspect, the first gRNA molecule and the second gRNA molecule include targeting domains comprising, e.g., consisting of, SEQ ID NO: 5568 and SEQ ID NO: 5509, respectively. In an aspect, the first gRNA molecule and the second gRNA molecule include targeting domains comprising, e.g., consisting of, SEQ ID NO: 5568 and SEQ ID NO: 5517, respectively. In an aspect, the first gRNA molecule and the second gRNA molecule include targeting domains comprising, e.g., consisting of, SEQ ID NO: 5568 and SEQ ID NO: 5521, respectively. In an aspect, the first gRNA molecule and the second gRNA molecule include targeting domains comprising, e.g., consisting of, SEQ ID NO: 5568 and SEQ ID NO: 5520, respectively. In an aspect, the first gRNA molecule and the second gRNA molecule include targeting domains comprising, e.g., consisting of, SEQ ID NO: 5568 and SEQ ID NO: 5500, respectively. In an aspect, the first gRNA molecule and the second gRNA molecule include targeting domains comprising, e.g., consisting of, SEQ ID NO: 5568 and SEQ ID NO: 5494, respectively. In an aspect, the first gRNA molecule and the second gRNA molecule include targeting domains comprising, e.g., consisting of, SEQ ID NO: 5568 and SEQ ID NO: 5508, respectively. In an aspect, the first gRNA molecule and the second gRNA molecule include targeting domains comprising, e.g., consisting of, SEQ ID NO: 5568 and SEQ ID NO: 5514, respectively. In an aspect, the first gRNA molecule and the second gRNA molecule include targeting domains comprising, e.g., consisting of, SEQ ID NO: 5568 and SEQ ID NO: 5492, respectively. In an aspect, the first gRNA molecule and the second gRNA molecule include targeting domains comprising, e.g., consisting of, SEQ ID NO: 5610 and SEQ ID NO: 5519, respectively. In an aspect, the first gRNA molecule and the second gRNA molecule include targeting domains comprising, e.g., consisting of, SEQ ID NO: 5610 and SEQ ID NO: 5497, respectively. In an aspect, the first gRNA molecule and the second gRNA molecule include targeting domains comprising, e.g., consisting of, SEQ ID NO: 5610 and SEQ ID NO: 5499, respectively. In an aspect, the first gRNA molecule and the second gRNA molecule include targeting domains comprising, e.g., consisting of, SEQ ID NO: 5610 and SEQ ID NO: 5498, respectively. In an aspect, the first gRNA molecule and the second gRNA molecule include targeting domains comprising, e.g., consisting of, SEQ ID NO: 5610 and SEQ ID NO: 5503, respectively. In an aspect, the first gRNA molecule and the second gRNA molecule include targeting domains comprising, e.g., consisting of, SEQ ID NO: 5610 and SEQ ID NO: 5496, respectively. In an aspect, the first gRNA molecule and the second gRNA molecule include targeting domains comprising, e.g., consisting of, SEQ ID NO: 5610 and SEQ ID NO: 5507, respectively. In an aspect, the first gRNA molecule and the second gRNA molecule include targeting domains comprising, e.g., consisting of, SEQ ID NO: 5610 and SEQ ID NO: 5515, respectively. In an aspect, the first gRNA molecule and the second gRNA molecule include targeting domains comprising, e.g., consisting of, SEQ ID NO: 5610 and SEQ ID NO: 5493, respectively. In an aspect, the first gRNA molecule and the second gRNA molecule include targeting domains comprising, e.g., consisting of, SEQ ID NO: 5610 and SEQ ID NO: 5506, respectively. In an aspect, the first gRNA molecule and the second gRNA molecule include targeting domains comprising, e.g., consisting of, SEQ ID NO: 5610 and SEQ ID NO: 5509, respectively. In an aspect, the first gRNA molecule and the second gRNA molecule include targeting domains comprising, e.g., consisting of, SEQ ID NO: 5610 and SEQ ID NO: 5517, respectively. In an aspect, the first gRNA molecule and the second gRNA molecule include targeting domains comprising, e.g., consisting of, SEQ ID NO: 5610 and SEQ ID NO: 5521, respectively. In an aspect, the first gRNA molecule and the second gRNA molecule include targeting domains comprising, e.g., consisting of, SEQ ID NO: 5610 and SEQ ID NO: 5520, respectively. In an aspect, the first gRNA molecule and the second gRNA molecule include targeting domains comprising, e.g., consisting of, SEQ ID NO: 5610 and SEQ ID NO: 5500, respectively. In an aspect, the first gRNA molecule and the second gRNA molecule include targeting domains comprising, e.g., consisting of, SEQ ID NO: 5610 and SEQ ID NO: 5494, respectively. In an aspect, the first gRNA molecule and the second gRNA molecule include targeting domains comprising, e.g., consisting of, SEQ ID NO: 5610 and SEQ ID NO: 5508, respectively. In an aspect, the first gRNA molecule and the second gRNA molecule include targeting domains comprising, e.g., consisting of, SEQ ID NO: 5610 and SEQ ID NO: 5514, respectively. In an aspect, the first gRNA molecule and the second gRNA molecule include targeting domains comprising, e.g., consisting of, SEQ ID NO: 5610 and SEQ ID NO: 5492, respectively. In an aspect, the first gRNA molecule and the second gRNA molecule include targeting domains comprising, e.g., consisting of, SEQ ID NO: 5608 and SEQ ID NO: 5519, respectively. In an aspect, the first gRNA molecule and the second gRNA molecule include targeting domains comprising, e.g., consisting of, SEQ ID NO: 5608 and SEQ ID NO: 5497, respectively. In an aspect, the first gRNA molecule and the second gRNA molecule include targeting domains comprising, e.g., consisting of, SEQ ID NO: 5608 and SEQ ID NO: 5499, respectively. In an aspect, the first gRNA molecule and the second gRNA molecule include targeting domains comprising, e.g., consisting of, SEQ ID NO: 5608 and SEQ ID NO: 5498, respectively. In an aspect, the first gRNA molecule and the second gRNA molecule include targeting domains comprising, e.g., consisting of, SEQ ID NO: 5608 and SEQ ID NO: 5503, respectively. In an aspect, the first gRNA molecule and the second gRNA molecule include targeting domains comprising, e.g., consisting of, SEQ ID NO: 5608 and SEQ ID NO: 5496, respectively. In an aspect, the first gRNA molecule and the second gRNA molecule include targeting domains comprising, e.g., consisting of, SEQ ID NO: 5608 and SEQ ID NO: 5507, respectively. In an aspect, the first gRNA molecule and the second gRNA molecule include targeting domains comprising, e.g., consisting of, SEQ ID NO: 5608 and SEQ ID NO: 5515, respectively. In an aspect, the first gRNA molecule and the second gRNA molecule include targeting domains comprising, e.g., consisting of, SEQ ID NO: 5608 and SEQ ID NO: 5493, respectively. In an aspect, the first gRNA molecule and the second gRNA molecule include targeting domains comprising, e.g., consisting of, SEQ ID NO: 5608 and SEQ ID NO: 5506, respectively. In an aspect, the first gRNA molecule and the second gRNA molecule include targeting domains comprising, e.g., consisting of, SEQ ID NO: 5608 and SEQ ID NO: 5509, respectively. In an aspect, the first gRNA molecule and the second gRNA molecule include targeting domains comprising, e.g., consisting of, SEQ ID NO: 5608 and SEQ ID NO: 5517, respectively. In an aspect, the first gRNA molecule and the second gRNA molecule include targeting domains comprising, e.g., consisting of, SEQ ID NO: 5608 and SEQ ID NO: 5521, respectively. In an aspect, the first gRNA molecule and the second gRNA molecule include targeting domains comprising, e.g., consisting of, SEQ ID NO: 5608 and SEQ ID NO: 5520, respectively. In an aspect, the first gRNA molecule and the second gRNA molecule include targeting domains comprising, e.g., consisting of, SEQ ID NO: 5608 and SEQ ID NO: 5500, respectively. In an aspect, the first gRNA molecule and the second gRNA molecule include targeting domains comprising, e.g., consisting of, SEQ ID NO: 5608 and SEQ ID NO: 5494, respectively. In an aspect, the first gRNA molecule and the second gRNA molecule include targeting domains comprising, e.g., consisting of, SEQ ID NO: 5608 and SEQ ID NO: 5508, respectively. In an aspect, the first gRNA molecule and the second gRNA molecule include targeting domains comprising, e.g., consisting of, SEQ ID NO: 5608 and SEQ ID NO: 5514, respectively. In an aspect, the first gRNA molecule and the second gRNA molecule include targeting domains comprising, e.g., consisting of, SEQ ID NO: 5608 and SEQ ID NO: 5492, respectively. In an aspect, the first gRNA molecule and the second gRNA molecule include targeting domains comprising, e.g., consisting of, SEQ ID NO: 5617 and SEQ ID NO: 5519, respectively. In an aspect, the first gRNA molecule and the second gRNA molecule include targeting domains comprising, e.g., consisting of, SEQ ID NO: 5617 and SEQ ID NO: 5497, respectively. In an aspect, the first gRNA molecule and the second gRNA molecule include targeting domains comprising, e.g., consisting of, SEQ ID NO: 5617 and SEQ ID NO: 5499, respectively. In an aspect, the first gRNA molecule and the second gRNA molecule include targeting domains comprising, e.g., consisting of, SEQ ID NO: 5617 and SEQ ID NO: 5498, respectively. In an aspect, the first gRNA molecule and the second gRNA molecule include targeting domains comprising, e.g., consisting of, SEQ ID NO: 5617 and SEQ ID NO: 5503, respectively. In an aspect, the first gRNA molecule and the second gRNA molecule include targeting domains comprising, e.g., consisting of, SEQ ID NO: 5617 and SEQ ID NO: 5496, respectively. In an aspect, the first gRNA molecule and the second gRNA molecule include targeting domains comprising, e.g., consisting of, SEQ ID NO: 5617 and SEQ ID NO: 5507, respectively. In an aspect, the first gRNA molecule and the second gRNA molecule include targeting domains comprising, e.g., consisting of, SEQ ID NO: 5617 and SEQ ID NO: 5515, respectively. In an aspect, the first gRNA molecule and the second gRNA molecule include targeting domains comprising, e.g., consisting of, SEQ ID NO: 5617 and SEQ ID NO: 5493, respectively. In an aspect, the first gRNA molecule and the second gRNA molecule include targeting domains comprising, e.g., consisting of, SEQ ID NO: 5617 and SEQ ID NO: 5506, respectively. In an aspect, the first gRNA molecule and the second gRNA molecule include targeting domains comprising, e.g., consisting of, SEQ ID NO: 5617 and SEQ ID NO: 5509, respectively. In an aspect, the first gRNA molecule and the second gRNA molecule include targeting domains comprising, e.g., consisting of, SEQ ID NO: 5617 and SEQ ID NO: 5517, respectively. In an aspect, the first gRNA molecule and the second gRNA molecule include targeting domains comprising, e.g., consisting of, SEQ ID NO: 5617 and SEQ ID NO: 5521, respectively. In an aspect, the first gRNA molecule and the second gRNA molecule include targeting domains comprising, e.g., consisting of, SEQ ID NO: 5617 and SEQ ID NO: 5520, respectively. In an aspect, the first gRNA molecule and the second gRNA molecule include targeting domains comprising, e.g., consisting of, SEQ ID NO: 5617 and SEQ ID NO: 5500, respectively. In an aspect, the first gRNA molecule and the second gRNA molecule include targeting domains comprising, e.g., consisting of, SEQ ID NO: 5617 and SEQ ID NO: 5494, respectively. In an aspect, the first gRNA molecule and the second gRNA molecule include targeting domains comprising, e.g., consisting of, SEQ ID NO: 5617 and SEQ ID NO: 5508, respectively. In an aspect, the first gRNA molecule and the second gRNA molecule include targeting domains comprising, e.g., consisting of, SEQ ID NO: 5617 and SEQ ID NO: 5514, respectively. In an aspect, the first gRNA molecule and the second gRNA molecule include targeting domains comprising, e.g., consisting of, SEQ ID NO: 5617 and SEQ ID NO: 5492, respectively. In an aspect, the first gRNA molecule and the second gRNA molecule include targeting domains comprising, e.g., consisting of, SEQ ID NO: 5619 and SEQ ID NO: 5519, respectively. In an aspect, the first gRNA molecule and the second gRNA molecule include targeting domains comprising, e.g., consisting of, SEQ ID NO: 5619 and SEQ ID NO: 5497, respectively. In an aspect, the first gRNA molecule and the second gRNA molecule include targeting domains comprising, e.g., consisting of, SEQ ID NO: 5619 and SEQ ID NO: 5499, respectively. In an aspect, the first gRNA molecule and the second gRNA molecule include targeting domains comprising, e.g., consisting of, SEQ ID NO: 5619 and SEQ ID NO: 5498, respectively. In an aspect, the first gRNA molecule and the second gRNA molecule include targeting domains comprising, e.g., consisting of, SEQ ID NO: 5619 and SEQ ID NO: 5503, respectively. In an aspect, the first gRNA molecule and the second gRNA molecule include targeting domains comprising, e.g., consisting of, SEQ ID NO: 5619 and SEQ ID NO: 5496, respectively. In an aspect, the first gRNA molecule and the second gRNA molecule include targeting domains comprising, e.g., consisting of, SEQ ID NO: 5619 and SEQ ID NO: 5507, respectively. In an aspect, the first gRNA molecule and the second gRNA molecule include targeting domains comprising, e.g., consisting of, SEQ ID NO: 5619 and SEQ ID NO: 5515, respectively. In an aspect, the first gRNA molecule and the second gRNA molecule include targeting domains comprising, e.g., consisting of, SEQ ID NO: 5619 and SEQ ID NO: 5493, respectively. In an aspect, the first gRNA molecule and the second gRNA molecule include targeting domains comprising, e.g., consisting of, SEQ ID NO: 5619 and SEQ ID NO: 5506, respectively. In an aspect, the first gRNA molecule and the second gRNA molecule include targeting domains comprising, e.g., consisting of, SEQ ID NO: 5619 and SEQ ID NO: 5509, respectively. In an aspect, the first gRNA molecule and the second gRNA molecule include targeting domains comprising, e.g., consisting of, SEQ ID NO: 5619 and SEQ ID NO: 5517, respectively. In an aspect, the first gRNA molecule and the second gRNA molecule include targeting domains comprising, e.g., consisting of, SEQ ID NO: 5619 and SEQ ID NO: 5521, respectively. In an aspect, the first gRNA molecule and the second gRNA molecule include targeting domains comprising, e.g., consisting of, SEQ ID NO: 5619 and SEQ ID NO: 5520, respectively. In an aspect, the first gRNA molecule and the second gRNA molecule include targeting domains comprising, e.g., consisting of, SEQ ID NO: 5619 and SEQ ID NO: 5500, respectively. In an aspect, the first gRNA molecule and the second gRNA molecule include targeting domains comprising, e.g., consisting of, SEQ ID NO: 5619 and SEQ ID NO: 5494, respectively. In an aspect, the first gRNA molecule and the second gRNA molecule include targeting domains comprising, e.g., consisting of, SEQ ID NO: 5619 and SEQ ID NO: 5508, respectively. In an aspect, the first gRNA molecule and the second gRNA molecule include targeting domains comprising, e.g., consisting of, SEQ ID NO: 5619 and SEQ ID NO: 5514, respectively. In an aspect, the first gRNA molecule and the second gRNA molecule include targeting domains comprising, e.g., consisting of, SEQ ID NO: 5619 and SEQ ID NO: 5492, respectively. In an aspect, the first gRNA molecule and the second gRNA molecule include targeting domains comprising, e.g., consisting of, SEQ ID NO: 5620 and SEQ ID NO: 5519, respectively. In an aspect, the first gRNA molecule and the second gRNA molecule include targeting domains comprising, e.g., consisting of, SEQ ID NO: 5620 and SEQ ID NO: 5497, respectively. In an aspect, the first gRNA molecule and the second gRNA molecule include targeting domains comprising, e.g., consisting of, SEQ ID NO: 5620 and SEQ ID NO: 5499, respectively. In an aspect, the first gRNA molecule and the second gRNA molecule include targeting domains comprising, e.g., consisting of, SEQ ID NO: 5620 and SEQ ID NO: 5498, respectively. In an aspect, the first gRNA molecule and the second gRNA molecule include targeting domains comprising, e.g., consisting of, SEQ ID NO: 5620 and SEQ ID NO: 5503, respectively. In an aspect, the first gRNA molecule and the second gRNA molecule include targeting domains comprising, e.g., consisting of, SEQ ID NO: 5620 and SEQ ID NO: 5496, respectively. In an aspect, the first gRNA molecule and the second gRNA molecule include targeting domains comprising, e.g., consisting of, SEQ ID NO: 5620 and SEQ ID NO: 5507, respectively. In an aspect, the first gRNA molecule and the second gRNA molecule include targeting domains comprising, e.g., consisting of, SEQ ID NO: 5620 and SEQ ID NO: 5515, respectively. In an aspect, the first gRNA molecule and the second gRNA molecule include targeting domains comprising, e.g., consisting of, SEQ ID NO: 5620 and SEQ ID NO: 5493, respectively. In an aspect, the first gRNA molecule and the second gRNA molecule include targeting domains comprising, e.g., consisting of, SEQ ID NO: 5620 and SEQ ID NO: 5506, respectively. In an aspect, the first gRNA molecule and the second gRNA molecule include targeting domains comprising, e.g., consisting of, SEQ ID NO: 5620 and SEQ ID NO: 5509, respectively. In an aspect, the first gRNA molecule and the second gRNA molecule include targeting domains comprising, e.g., consisting of, SEQ ID NO: 5620 and SEQ ID NO: 5517, respectively. In an aspect, the first gRNA molecule and the second gRNA molecule include targeting domains comprising, e.g., consisting of, SEQ ID NO: 5620 and SEQ ID NO: 5521, respectively. In an aspect, the first gRNA molecule and the second gRNA molecule include targeting domains comprising, e.g., consisting of, SEQ ID NO: 5620 and SEQ ID NO: 5520, respectively. In an aspect, the first gRNA molecule and the second gRNA molecule include targeting domains comprising, e.g., consisting of, SEQ ID NO: 5620 and SEQ ID NO: 5500, respectively. In an aspect, the first gRNA molecule and the second gRNA molecule include targeting domains comprising, e.g., consisting of, SEQ ID NO: 5620 and SEQ ID NO: 5494, respectively. In an aspect, the first gRNA molecule and the second gRNA molecule include targeting domains comprising, e.g., consisting of, SEQ ID NO: 5620 and SEQ ID NO: 5508, respectively. In an aspect, the first gRNA molecule and the second gRNA molecule include targeting domains comprising, e.g., consisting of, SEQ ID NO: 5620 and SEQ ID NO: 5514, respectively. In an aspect, the first gRNA molecule and the second gRNA molecule include targeting domains comprising, e.g., consisting of, SEQ ID NO: 5620 and SEQ ID NO: 5492, respectively. In any of the aforementioned combinations, the aspect or the embodiment of the invention may additionally include a third gRNA molecule (or more than one gRNA molecules)

comprising a targeting domain specific for a sequence of CIITA, e.g. as described herein, e.g., as described herein in Table 6c.

In aspects of the invention that utilize two or more, e.g., two, gRNA molecules, it may be particularly useful for a first gRNA molecule to comprise a targeting domain specific for a sequence of TRBC (e.g., TRBC1 or TRBC2) and a second gRNA molecule to comprise a targeting domain specific for a sequence of B2M. In such aspects, it is particularly preferred that the first gRNA molecule to TRBC comprises a targeting domain of any gRNA molecule of FIG. 13, and the second gRNA molecule to B2M comprises a targeting domain of any gRNA molecule of FIG. 14. In an aspect, the first gRNA molecule and the second gRNA molecule include targeting domains comprising, e.g., consisting of, SEQ ID NO: 5719 and SEQ ID NO: 5519, respectively. In an aspect, the first gRNA molecule and the second gRNA molecule include targeting domains comprising, e.g., consisting of, SEQ ID NO: 5719 and SEQ ID NO: 5497, respectively. In an aspect, the first gRNA molecule and the second gRNA molecule include targeting domains comprising, e.g., consisting of, SEQ ID NO: 5719 and SEQ ID NO: 5499, respectively. In an aspect, the first gRNA molecule and the second gRNA molecule include targeting domains comprising, e.g., consisting of, SEQ ID NO: 5719 and SEQ ID NO: 5498, respectively. In an aspect, the first gRNA molecule and the second gRNA molecule include targeting domains comprising, e.g., consisting of, SEQ ID NO: 5719 and SEQ ID NO: 5503, respectively. In an aspect, the first gRNA molecule and the second gRNA molecule include targeting domains comprising, e.g., consisting of, SEQ ID NO: 5719 and SEQ ID NO: 5496, respectively. In an aspect, the first gRNA molecule and the second gRNA molecule include targeting domains comprising, e.g., consisting of, SEQ ID NO: 5719 and SEQ ID NO: 5507, respectively. In an aspect, the first gRNA molecule and the second gRNA molecule include targeting domains comprising, e.g., consisting of, SEQ ID NO: 5719 and SEQ ID NO: 5515, respectively. In an aspect, the first gRNA molecule and the second gRNA molecule include targeting domains comprising, e.g., consisting of, SEQ ID NO: 5719 and SEQ ID NO: 5493, respectively. In an aspect, the first gRNA molecule and the second gRNA molecule include targeting domains comprising, e.g., consisting of, SEQ ID NO: 5719 and SEQ ID NO: 5506, respectively. In an aspect, the first gRNA molecule and the second gRNA molecule include targeting domains comprising, e.g., consisting of, SEQ ID NO: 5719 and SEQ ID NO: 5509, respectively. In an aspect, the first gRNA molecule and the second gRNA molecule include targeting domains comprising, e.g., consisting of, SEQ ID NO: 5719 and SEQ ID NO: 5517, respectively. In an aspect, the first gRNA molecule and the second gRNA molecule include targeting domains comprising, e.g., consisting of, SEQ ID NO: 5719 and SEQ ID NO: 5521, respectively. In an aspect, the first gRNA molecule and the second gRNA molecule include targeting domains comprising, e.g., consisting of, SEQ ID NO: 5719 and SEQ ID NO: 5520, respectively. In an aspect, the first gRNA molecule and the second gRNA molecule include targeting domains comprising, e.g., consisting of, SEQ ID NO: 5719 and SEQ ID NO: 5500, respectively. In an aspect, the first gRNA molecule and the second gRNA molecule include targeting domains comprising, e.g., consisting of, SEQ ID NO: 5719 and SEQ ID NO: 5494, respectively. In an aspect, the first gRNA molecule and the second gRNA molecule include targeting domains comprising, e.g., consisting of, SEQ ID NO: 5719 and SEQ ID NO: 5508, respectively. In an aspect, the first gRNA molecule and the second gRNA molecule include targeting domains comprising, e.g., consisting of, SEQ ID NO: 5719 and SEQ ID NO: 5514, respectively. In an aspect, the first gRNA molecule and the second gRNA molecule include targeting domains comprising, e.g., consisting of, SEQ ID NO: 5719 and SEQ ID NO: 5492, respectively. In an aspect, the first gRNA molecule and the second gRNA molecule include targeting domains comprising, e.g., consisting of, SEQ ID NO: 5694 and SEQ ID NO: 5519, respectively. In an aspect, the first gRNA molecule and the second gRNA molecule include targeting domains comprising, e.g., consisting of, SEQ ID NO: 5694 and SEQ ID NO: 5497, respectively. In an aspect, the first gRNA molecule and the second gRNA molecule include targeting domains comprising, e.g., consisting of, SEQ ID NO: 5694 and SEQ ID NO: 5499, respectively. In an aspect, the first gRNA molecule and the second gRNA molecule include targeting domains comprising, e.g., consisting of, SEQ ID NO: 5694 and SEQ ID NO: 5498, respectively. In an aspect, the first gRNA molecule and the second gRNA molecule include targeting domains comprising, e.g., consisting of, SEQ ID NO: 5694 and SEQ ID NO: 5503, respectively. In an aspect, the first gRNA molecule and the second gRNA molecule include targeting domains comprising, e.g., consisting of, SEQ ID NO: 5694 and SEQ ID NO: 5496, respectively. In an aspect, the first gRNA molecule and the second gRNA molecule include targeting domains comprising, e.g., consisting of, SEQ ID NO: 5694 and SEQ ID NO: 5507, respectively. In an aspect, the first gRNA molecule and the second gRNA molecule include targeting domains comprising, e.g., consisting of, SEQ ID NO: 5694 and SEQ ID NO: 5515, respectively. In an aspect, the first gRNA molecule and the second gRNA molecule include targeting domains comprising, e.g., consisting of, SEQ ID NO: 5694 and SEQ ID NO: 5493, respectively. In an aspect, the first gRNA molecule and the second gRNA molecule include targeting domains comprising, e.g., consisting of, SEQ ID NO: 5694 and SEQ ID NO: 5506, respectively. In an aspect, the first gRNA molecule and the second gRNA molecule include targeting domains comprising, e.g., consisting of, SEQ ID NO: 5694 and SEQ ID NO: 5509, respectively. In an aspect, the first gRNA molecule and the second gRNA molecule include targeting domains comprising, e.g., consisting of, SEQ ID NO: 5694 and SEQ ID NO: 5517, respectively. In an aspect, the first gRNA molecule and the second gRNA molecule include targeting domains comprising, e.g., consisting of, SEQ ID NO: 5694 and SEQ ID NO: 5521, respectively. In an aspect, the first gRNA molecule and the second gRNA molecule include targeting domains comprising, e.g., consisting of, SEQ ID NO: 5694 and SEQ ID NO: 5520, respectively. In an aspect, the first gRNA molecule and the second gRNA molecule include targeting domains comprising, e.g., consisting of, SEQ ID NO: 5694 and SEQ ID NO: 5500, respectively. In an aspect, the first gRNA molecule and the second gRNA molecule include targeting domains comprising, e.g., consisting of, SEQ ID NO: 5694 and SEQ ID NO: 5494, respectively. In an aspect, the first gRNA molecule and the second gRNA molecule include targeting domains comprising, e.g., consisting of, SEQ ID NO: 5694 and SEQ ID NO: 5508, respectively. In an aspect, the first gRNA molecule and the second gRNA molecule include targeting domains comprising, e.g., consisting of, SEQ ID NO: 5694 and SEQ ID NO: 5514, respectively. In an aspect, the first gRNA molecule and the second gRNA molecule include targeting domains comprising, e.g., consisting of, SEQ ID NO: 5694 and SEQ ID NO: 5492, respectively. In an aspect, the first gRNA molecule and the second gRNA molecule include targeting domains comprising, e.g., consisting of, SEQ ID NO: 5706 and SEQ ID NO: 5519, respectively. In an aspect, the first gRNA molecule and the second gRNA molecule include targeting domains comprising, e.g., consisting of, SEQ ID NO: 5706 and SEQ ID NO: 5497, respectively. In an aspect, the first gRNA molecule and the second gRNA molecule include targeting domains comprising, e.g., consisting of, SEQ ID NO: 5706 and SEQ ID NO: 5499, respectively. In an aspect, the first gRNA molecule and the second gRNA molecule include targeting domains comprising, e.g., consisting of, SEQ ID NO: 5706 and SEQ ID NO: 5498, respectively. In an aspect, the first gRNA molecule and the second gRNA molecule include targeting domains comprising, e.g., consisting of, SEQ ID NO: 5706 and SEQ ID NO: 5503, respectively. In an aspect, the first gRNA molecule and the second gRNA molecule include targeting domains comprising, e.g., consisting of, SEQ ID NO: 5706 and SEQ ID NO: 5496, respectively. In an aspect, the first gRNA molecule and the second gRNA molecule include targeting domains comprising, e.g., consisting of, SEQ ID NO: 5706 and SEQ ID NO: 5507, respectively. In an aspect, the first gRNA molecule and the second gRNA molecule include targeting domains comprising, e.g., consisting of, SEQ ID NO: 5706 and SEQ ID NO: 5515, respectively. In an aspect, the first gRNA molecule and the second gRNA molecule include targeting domains comprising, e.g., consisting of, SEQ ID NO: 5706 and SEQ ID NO: 5493, respectively. In an aspect, the first gRNA molecule and the second gRNA molecule include targeting domains comprising, e.g., consisting of, SEQ ID NO: 5706 and SEQ ID NO: 5506, respectively. In an aspect, the first gRNA molecule and the second gRNA molecule include targeting domains comprising, e.g., consisting of, SEQ ID NO: 5706 and SEQ ID NO: 5509, respectively. In an aspect, the first gRNA molecule and the second gRNA molecule include targeting domains comprising, e.g., consisting of, SEQ ID NO: 5706 and SEQ ID NO: 5517, respectively. In an aspect, the first gRNA molecule and the second gRNA molecule include targeting domains comprising, e.g., consisting of, SEQ ID NO: 5706 and SEQ ID NO: 5521, respectively. In an aspect, the first gRNA molecule and the second gRNA molecule include targeting domains comprising, e.g., consisting of, SEQ ID NO: 5706 and SEQ ID NO: 5520, respectively. In an aspect, the first gRNA molecule and the second gRNA molecule include targeting domains comprising, e.g., consisting of, SEQ ID NO: 5706 and SEQ ID NO: 5500, respectively. In an aspect, the first gRNA molecule and the second gRNA molecule include targeting domains comprising, e.g., consisting of, SEQ ID NO: 5706 and SEQ ID NO: 5494, respectively. In an aspect, the first gRNA molecule and the second gRNA molecule include targeting domains comprising, e.g., consisting of, SEQ ID NO: 5706 and SEQ ID NO: 5508, respectively. In an aspect, the first gRNA molecule and the second gRNA molecule include targeting domains comprising, e.g., consisting of, SEQ ID NO: 5706 and SEQ ID NO: 5514, respectively. In an aspect, the first gRNA molecule and the second gRNA molecule include targeting domains comprising, e.g., consisting of, SEQ ID NO: 5706 and SEQ ID NO: 5492, respectively. In an aspect, the first gRNA molecule and the second gRNA molecule include targeting domains comprising, e.g., consisting of, SEQ ID NO: 5696 and SEQ ID NO: 5519, respectively. In an aspect, the first gRNA molecule and the second gRNA molecule include targeting domains comprising, e.g., consisting of, SEQ ID NO: 5696 and SEQ ID NO: 5497, respectively. In an aspect, the first gRNA molecule and the second gRNA molecule include targeting domains comprising, e.g., consisting of, SEQ ID NO: 5696 and SEQ ID NO: 5499, respectively. In an aspect, the first gRNA molecule and the second gRNA molecule include targeting domains comprising, e.g., consisting of, SEQ ID NO: 5696 and SEQ ID NO: 5498, respectively. In an aspect, the first gRNA molecule and the second gRNA molecule include targeting domains comprising, e.g., consisting of, SEQ ID NO: 5696 and SEQ ID NO: 5503, respectively. In an aspect, the first gRNA molecule and the second gRNA molecule include targeting domains comprising, e.g., consisting of, SEQ ID NO: 5696 and SEQ ID NO: 5496, respectively. In an aspect, the first gRNA molecule and the second gRNA molecule include targeting domains comprising, e.g., consisting of, SEQ ID NO: 5696 and SEQ ID NO: 5507, respectively. In an aspect, the first gRNA molecule and the second gRNA molecule include targeting domains comprising, e.g., consisting of, SEQ ID NO: 5696 and SEQ ID NO: 5515, respectively. In an aspect, the first gRNA molecule and the second gRNA molecule include targeting domains comprising, e.g., consisting of, SEQ ID NO: 5696 and SEQ ID NO: 5493, respectively. In an aspect, the first gRNA molecule and the second gRNA molecule include targeting domains comprising, e.g., consisting of, SEQ ID NO: 5696 and SEQ ID NO: 5506, respectively. In an aspect, the first gRNA molecule and the second gRNA molecule include targeting domains comprising, e.g., consisting of, SEQ ID NO: 5696 and SEQ ID NO: 5509, respectively. In an aspect, the first gRNA molecule and the second gRNA molecule include targeting domains comprising, e.g., consisting of, SEQ ID NO: 5696 and SEQ ID NO: 5517, respectively. In an aspect, the first gRNA molecule and the second gRNA molecule include targeting domains comprising, e.g., consisting of, SEQ ID NO: 5696 and SEQ ID NO: 5521, respectively. In an aspect, the first gRNA molecule and the second gRNA molecule include targeting domains comprising, e.g., consisting of, SEQ ID NO: 5696 and SEQ ID NO: 5520, respectively. In an aspect, the first gRNA molecule and the second gRNA molecule include targeting domains comprising, e.g., consisting of, SEQ ID NO: 5696 and SEQ ID NO: 5500, respectively. In an aspect, the first gRNA molecule and the second gRNA molecule include targeting domains comprising, e.g., consisting of, SEQ ID NO: 5696 and SEQ ID NO: 5494, respectively. In an aspect, the first gRNA molecule and the second gRNA molecule include targeting domains comprising, e.g., consisting of, SEQ ID NO: 5696 and SEQ ID NO: 5508, respectively. In an aspect, the first gRNA molecule and the second gRNA molecule include targeting domains comprising, e.g., consisting of, SEQ ID NO: 5696 and SEQ ID NO: 5514, respectively. In an aspect, the first gRNA molecule and the second gRNA molecule include targeting domains comprising, e.g., consisting of, SEQ ID NO: 5696 and SEQ ID NO: 5492, respectively. In an aspect, the first gRNA molecule and the second gRNA molecule include targeting domains comprising, e.g., consisting of, SEQ ID NO: 5711 and SEQ ID NO: 5519, respectively. In an aspect, the first gRNA molecule and the second gRNA molecule include targeting domains comprising, e.g., consisting of, SEQ ID NO: 5711 and SEQ ID NO: 5497, respectively. In an aspect, the first gRNA molecule and the second gRNA molecule include targeting domains comprising, e.g., consisting of, SEQ ID NO: 5711 and SEQ ID NO: 5499, respectively. In an aspect, the first gRNA molecule and the second gRNA molecule include targeting domains comprising, e.g., consisting of, SEQ ID NO: 5711 and SEQ ID NO: 5498, respectively. In an aspect, the first gRNA molecule and the second gRNA molecule include targeting domains comprising, e.g., consisting of, SEQ ID NO: 5711 and SEQ ID NO: 5503, respectively. In an aspect, the first gRNA molecule and the second gRNA molecule include targeting domains comprising, e.g., consisting of, SEQ ID NO: 5711 and SEQ ID NO: 5496, respectively. In an aspect, the first gRNA molecule and the second gRNA molecule include targeting domains comprising, e.g., consisting of, SEQ ID NO: 5711 and SEQ ID NO: 5507, respectively. In an aspect, the first gRNA molecule and the second gRNA molecule include targeting domains comprising, e.g., consisting of, SEQ ID NO: 5711 and SEQ ID NO: 5515, respectively. In an aspect, the first gRNA molecule and the second gRNA molecule include targeting domains comprising, e.g., consisting of, SEQ ID NO: 5711 and SEQ ID NO: 5493, respectively. In an aspect, the first gRNA molecule and the second gRNA molecule include targeting domains comprising, e.g., consisting of, SEQ ID NO: 5711 and SEQ ID NO: 5506, respectively. In an aspect, the first gRNA molecule and the second gRNA molecule include targeting domains comprising, e.g., consisting of, SEQ ID NO: 5711 and SEQ ID NO: 5509, respectively. In an aspect, the first gRNA molecule and the second gRNA molecule include targeting domains comprising, e.g., consisting of, SEQ ID NO: 5711 and SEQ ID NO: 5517, respectively. In an aspect, the first gRNA molecule and the second gRNA molecule include targeting domains comprising, e.g., consisting of, SEQ ID NO: 5711 and SEQ ID NO: 5521, respectively. In an aspect, the first gRNA molecule and the second gRNA molecule include targeting domains comprising, e.g., consisting of, SEQ ID NO: 5711 and SEQ ID NO: 5520, respectively. In an aspect, the first gRNA molecule and the second gRNA molecule include targeting domains comprising, e.g., consisting of, SEQ ID NO: 5711 and SEQ ID NO: 5500, respectively. In an aspect, the first gRNA molecule and the second gRNA molecule include targeting domains comprising, e.g., consisting of, SEQ ID NO: 5711 and SEQ ID NO: 5494, respectively. In an aspect, the first gRNA molecule and the second gRNA molecule include targeting domains comprising, e.g., consisting of, SEQ ID NO: 5711 and SEQ ID NO: 5508, respectively. In an aspect, the first gRNA molecule and the second gRNA molecule include targeting domains comprising, e.g., consisting of, SEQ ID NO: 5711 and SEQ ID NO: 5514, respectively. In an aspect, the first gRNA molecule and the second gRNA molecule include targeting domains comprising, e.g., consisting of, SEQ ID NO: 5711 and SEQ ID NO: 5492, respectively. In an aspect, the first gRNA molecule and the second gRNA molecule include targeting domains comprising, e.g., consisting of, SEQ ID NO: 5708 and SEQ ID NO: 5519, respectively. In an aspect, the first gRNA molecule and the second gRNA molecule include targeting domains comprising, e.g., consisting of, SEQ ID NO: 5708 and SEQ ID NO: 5497, respectively. In an aspect, the first gRNA molecule and the second gRNA molecule include targeting domains comprising, e.g., consisting of, SEQ ID NO: 5708 and SEQ ID NO: 5499, respectively. In an aspect, the first gRNA molecule and the second gRNA molecule include targeting domains comprising, e.g., consisting of, SEQ ID NO: 5708 and SEQ ID NO: 5498, respectively. In an aspect, the first gRNA molecule and the second gRNA molecule include targeting domains comprising, e.g., consisting of, SEQ ID NO: 5708 and SEQ ID NO: 5503, respectively. In an aspect, the first gRNA molecule and the second gRNA molecule include targeting domains comprising, e.g., consisting of, SEQ ID NO: 5708 and SEQ ID NO: 5496, respectively. In an aspect, the first gRNA molecule and the second gRNA molecule include targeting domains comprising, e.g., consisting of, SEQ ID NO: 5708 and SEQ ID NO: 5507, respectively. In an aspect, the first gRNA molecule and the second gRNA molecule include targeting domains comprising, e.g., consisting of, SEQ ID NO: 5708 and SEQ ID NO: 5515, respectively. In an aspect, the first gRNA molecule and the second gRNA molecule include targeting domains comprising, e.g., consisting of, SEQ ID NO: 5708 and SEQ ID NO: 5493, respectively. In an aspect, the first gRNA molecule and the second gRNA molecule include targeting domains comprising, e.g., consisting of, SEQ ID NO: 5708 and SEQ ID NO: 5506, respectively. In an aspect, the first gRNA molecule and the second gRNA molecule include targeting domains comprising, e.g., consisting of, SEQ ID NO: 5708 and SEQ ID NO: 5509, respectively. In an aspect, the first gRNA molecule and the second gRNA molecule include targeting domains comprising, e.g., consisting of, SEQ ID NO: 5708 and SEQ ID NO: 5517, respectively. In an aspect, the first gRNA molecule and the second gRNA molecule include targeting domains comprising, e.g., consisting of, SEQ ID NO: 5708 and SEQ ID NO: 5521, respectively. In an aspect, the first gRNA molecule and the second gRNA molecule include targeting domains comprising, e.g., consisting of, SEQ ID NO: 5708 and SEQ ID NO: 5520, respectively. In an aspect, the first gRNA molecule and the second gRNA molecule include targeting domains comprising, e.g., consisting of, SEQ ID NO: 5708 and SEQ ID NO: 5500, respectively. In an aspect, the first gRNA molecule and the second gRNA molecule include targeting domains comprising, e.g., consisting of, SEQ ID NO: 5708 and SEQ ID NO: 5494, respectively. In an aspect, the first gRNA molecule and the second gRNA molecule include targeting domains comprising, e.g., consisting of, SEQ ID NO: 5708 and SEQ ID NO: 5508, respectively. In an aspect, the first gRNA molecule and the second gRNA molecule include targeting domains comprising, e.g., consisting of, SEQ ID NO: 5708 and SEQ ID NO: 5514, respectively. In an aspect, the first gRNA molecule and the second gRNA molecule include targeting domains comprising, e.g., consisting of, SEQ ID NO: 5708 and SEQ ID NO: 5492, respectively. In an aspect, the first gRNA molecule and the second gRNA molecule include targeting domains comprising, e.g., consisting of, SEQ ID NO: 5709 and SEQ ID NO: 5519, respectively. In an aspect, the first gRNA molecule and the second gRNA molecule include targeting domains comprising, e.g., consisting of, SEQ ID NO: 5709 and SEQ ID NO: 5497, respectively. In an aspect, the first gRNA molecule and the second gRNA molecule include targeting domains comprising, e.g., consisting of, SEQ ID NO: 5709 and SEQ ID NO: 5499, respectively. In an aspect, the first gRNA molecule and the second gRNA molecule include targeting domains comprising, e.g., consisting of, SEQ ID NO: 5709 and SEQ ID NO: 5498, respectively. In an aspect, the first gRNA molecule and the second gRNA molecule include targeting domains comprising, e.g., consisting of, SEQ ID NO: 5709 and SEQ ID NO: 5503, respectively. In an aspect, the first gRNA molecule and the second gRNA molecule include targeting domains comprising, e.g., consisting of, SEQ ID NO: 5709 and SEQ ID NO: 5496, respectively. In an aspect, the first gRNA molecule and the second gRNA molecule include targeting domains comprising, e.g., consisting of, SEQ ID NO: 5709 and SEQ ID NO: 5507, respectively. In an aspect, the first gRNA molecule and the second gRNA molecule include targeting domains comprising, e.g., consisting of, SEQ ID NO: 5709 and SEQ ID NO: 5515, respectively. In an aspect, the first gRNA molecule and the second gRNA molecule include targeting domains comprising, e.g., consisting of, SEQ ID NO: 5709 and SEQ ID NO: 5493, respectively. In an aspect, the first gRNA molecule and the second gRNA molecule include targeting domains comprising, e.g., consisting of, SEQ ID NO: 5709 and SEQ ID NO: 5506, respectively. In an aspect, the first gRNA molecule and the second gRNA molecule include targeting domains comprising, e.g., consisting of, SEQ ID NO: 5709 and SEQ ID NO: 5509, respectively. In an aspect, the first gRNA molecule and the second gRNA molecule include targeting domains comprising, e.g., consisting of, SEQ ID NO: 5709 and SEQ ID NO: 5517, respectively. In an aspect, the first gRNA molecule and the second gRNA molecule include targeting domains comprising, e.g., consisting of, SEQ ID NO: 5709 and SEQ ID NO: 5521, respectively. In an aspect, the first gRNA molecule and the second gRNA molecule include targeting domains comprising, e.g., consisting of, SEQ ID NO: 5709 and SEQ ID NO: 5520, respectively. In an aspect, the first gRNA molecule and the second gRNA molecule include targeting domains comprising, e.g., consisting of, SEQ ID NO: 5709 and SEQ ID NO: 5500, respectively. In an aspect, the first gRNA molecule and the second gRNA molecule include targeting domains comprising, e.g., consisting of, SEQ ID NO: 5709 and SEQ ID NO: 5494, respectively. In an aspect, the first gRNA molecule and the second gRNA molecule include targeting domains comprising, e.g., consisting of, SEQ ID NO: 5709 and SEQ ID NO: 5508, respectively. In an aspect, the first gRNA molecule and the second gRNA molecule include targeting domains comprising, e.g., consisting of, SEQ ID NO: 5709 and SEQ ID NO: 5514, respectively. In an aspect, the first gRNA molecule and the second gRNA molecule include targeting domains comprising, e.g., consisting of, SEQ ID NO: 5709 and SEQ ID NO: 5492, respectively. In an aspect, the first gRNA molecule and the second gRNA molecule include targeting domains comprising, e.g., consisting of, SEQ ID NO: 5712 and SEQ ID NO: 5519, respectively. In an aspect, the first gRNA molecule and the second gRNA molecule include targeting domains comprising, e.g., consisting of, SEQ ID NO: 5712 and SEQ ID NO: 5497, respectively. In an aspect, the first gRNA molecule and the second gRNA molecule include targeting domains comprising, e.g., consisting of, SEQ ID NO: 5712 and SEQ ID NO: 5499, respectively. In an aspect, the first gRNA molecule and the second gRNA molecule include targeting domains comprising, e.g., consisting of, SEQ ID NO: 5712 and SEQ ID NO: 5498, respectively. In an aspect, the first gRNA molecule and the second gRNA molecule include targeting domains comprising, e.g., consisting of, SEQ ID NO: 5712 and SEQ ID NO: 5503, respectively. In an aspect, the first gRNA molecule and the second gRNA molecule include targeting domains comprising, e.g., consisting of, SEQ ID NO: 5712 and SEQ ID NO: 5496, respectively. In an aspect, the first gRNA molecule and the second gRNA molecule include targeting domains comprising, e.g., consisting of, SEQ ID NO: 5712 and SEQ ID NO: 5507, respectively. In an aspect, the first gRNA molecule and the second gRNA molecule include targeting domains comprising, e.g., consisting of, SEQ ID NO: 5712 and SEQ ID NO: 5515, respectively. In an aspect, the first gRNA molecule and the second gRNA molecule include targeting domains comprising, e.g., consisting of, SEQ ID NO: 5712 and SEQ ID NO: 5493, respectively. In an aspect, the first gRNA molecule and the second gRNA molecule include targeting domains comprising, e.g., consisting of, SEQ ID NO: 5712 and SEQ ID NO: 5506, respectively. In an aspect, the first gRNA molecule and the second gRNA molecule include targeting domains comprising, e.g., consisting of, SEQ ID NO: 5712 and SEQ ID NO: 5509, respectively. In an aspect, the first gRNA molecule and the second gRNA molecule include targeting domains comprising, e.g., consisting of, SEQ ID NO: 5712 and SEQ ID NO: 5517, respectively. In an aspect, the first gRNA molecule and the second gRNA molecule include targeting domains comprising, e.g., consisting of, SEQ ID NO: 5712 and SEQ ID NO: 5521, respectively. In an aspect, the first gRNA molecule and the second gRNA molecule include targeting domains comprising, e.g., consisting of, SEQ ID NO: 5712 and SEQ ID NO: 5520, respectively. In an aspect, the first gRNA molecule and the second gRNA molecule include targeting domains comprising, e.g., consisting of, SEQ ID NO: 5712 and SEQ ID NO: 5500, respectively. In an aspect, the first gRNA molecule and the second gRNA molecule include targeting domains comprising, e.g., consisting of, SEQ ID NO: 5712 and SEQ ID NO: 5494, respectively. In an aspect, the first gRNA molecule and the second gRNA molecule include targeting domains comprising, e.g., consisting of, SEQ ID NO: 5712 and SEQ ID NO: 5508, respectively. In an aspect, the first gRNA molecule and the second gRNA molecule include targeting domains comprising, e.g., consisting of, SEQ ID NO: 5712 and SEQ ID NO: 5514, respectively. In an aspect, the first gRNA molecule and the second gRNA molecule include targeting domains comprising, e.g., consisting of, SEQ ID NO: 5712 and SEQ ID NO: 5492, respectively. In an aspect, the first gRNA molecule and the second gRNA molecule include targeting domains comprising, e.g., consisting of, SEQ ID NO: 5703 and SEQ ID NO: 5519, respectively. In an aspect, the first gRNA molecule and the second gRNA molecule include targeting domains comprising, e.g., consisting of, SEQ ID NO: 5703 and SEQ ID NO: 5497, respectively. In an aspect, the first gRNA molecule and the second gRNA molecule include targeting domains comprising, e.g., consisting of, SEQ ID NO: 5703 and SEQ ID NO: 5499, respectively. In an aspect, the first gRNA molecule and the second gRNA molecule include targeting domains comprising, e.g., consisting of, SEQ ID NO: 5703 and SEQ ID NO: 5498, respectively. In an aspect, the first gRNA molecule and the second gRNA molecule include targeting domains comprising, e.g., consisting of, SEQ ID NO: 5703 and SEQ ID NO: 5503, respectively. In an aspect, the first gRNA molecule and the second gRNA molecule include targeting domains comprising, e.g., consisting of, SEQ ID NO: 5703 and SEQ ID NO: 5496, respectively. In an aspect, the first gRNA molecule and the second gRNA molecule include targeting domains comprising, e.g., consisting of, SEQ ID NO: 5703 and SEQ ID NO: 5507, respectively. In an aspect, the first gRNA molecule and the second gRNA molecule include targeting domains comprising, e.g., consisting of, SEQ ID NO: 5703 and SEQ ID NO: 5515, respectively. In an aspect, the first gRNA molecule and the second gRNA molecule include targeting domains comprising, e.g., consisting of, SEQ ID NO: 5703 and SEQ ID NO: 5493, respectively. In an aspect, the first gRNA molecule and the second gRNA molecule include targeting domains comprising, e.g., consisting of, SEQ ID NO: 5703 and SEQ ID NO: 5506, respectively. In an aspect, the first gRNA molecule and the second gRNA molecule include targeting domains comprising, e.g., consisting of, SEQ ID NO: 5703 and SEQ ID NO: 5509, respectively. In an aspect, the first gRNA molecule and the second gRNA molecule include targeting domains comprising, e.g., consisting of, SEQ ID NO: 5703 and SEQ ID NO: 5517, respectively. In an aspect, the first gRNA molecule and the second gRNA molecule include targeting domains comprising, e.g., consisting of, SEQ ID NO: 5703 and SEQ ID NO: 5521, respectively. In an aspect, the first gRNA molecule and the second gRNA molecule include targeting domains comprising, e.g., consisting of, SEQ ID NO: 5703 and SEQ ID NO: 5520, respectively. In an aspect, the first gRNA molecule and the second gRNA molecule include targeting domains comprising, e.g., consisting of, SEQ ID NO: 5703 and SEQ ID NO: 5500, respectively. In an aspect, the first gRNA molecule and the second gRNA molecule include targeting domains comprising, e.g., consisting of, SEQ ID NO: 5703 and SEQ ID NO: 5494, respectively. In an aspect, the first gRNA molecule and the second gRNA molecule include targeting domains comprising, e.g., consisting of, SEQ ID NO: 5703 and SEQ ID NO: 5508, respectively. In an aspect, the first gRNA molecule and the second gRNA molecule include targeting domains comprising, e.g., consisting of, SEQ ID NO: 5703 and SEQ ID NO: 5514, respectively. In an aspect, the first gRNA molecule and the second gRNA molecule include targeting domains comprising, e.g., consisting of, SEQ ID NO: 5703 and SEQ ID NO: 5492, respectively. In an aspect, the first gRNA molecule and the second gRNA molecule include targeting domains comprising, e.g., consisting of, SEQ ID NO: 5707 and SEQ ID NO: 5519, respectively. In an aspect, the first gRNA molecule and the second gRNA molecule include targeting domains comprising, e.g., consisting of, SEQ ID NO: 5707 and SEQ ID NO: 5497, respectively. In an aspect, the first gRNA molecule and the second gRNA molecule include targeting domains comprising, e.g., consisting of, SEQ ID NO: 5707 and SEQ ID NO: 5499, respectively. In an aspect, the first gRNA molecule and the second gRNA molecule include targeting domains comprising, e.g., consisting of, SEQ ID NO: 5707 and SEQ ID NO: 5498, respectively. In an aspect, the first gRNA molecule and the second gRNA molecule include targeting domains comprising, e.g., consisting of, SEQ ID NO: 5707 and SEQ ID NO: 5503, respectively. In an aspect, the first gRNA molecule and the second gRNA molecule include targeting domains comprising, e.g., consisting of, SEQ ID NO: 5707 and SEQ ID NO: 5496, respectively. In an aspect, the first gRNA molecule and the second gRNA molecule include targeting domains comprising, e.g., consisting of, SEQ ID NO: 5707 and SEQ ID NO: 5507, respectively. In an aspect, the first gRNA molecule and the second gRNA molecule include targeting domains comprising, e.g., consisting of, SEQ ID NO: 5707 and SEQ ID NO: 5515, respectively. In an aspect, the first gRNA molecule and the second gRNA molecule include targeting domains comprising, e.g., consisting of, SEQ ID NO: 5707 and SEQ ID NO: 5493, respectively. In an aspect, the first gRNA molecule and the second gRNA molecule include targeting domains comprising, e.g., consisting of, SEQ ID NO: 5707 and SEQ ID NO: 5506, respectively. In an aspect, the first gRNA molecule and the second gRNA molecule include targeting domains comprising, e.g., consisting of, SEQ ID NO: 5707 and SEQ ID NO: 5509, respectively. In an aspect, the first gRNA molecule and the second gRNA molecule include targeting domains comprising, e.g., consisting of, SEQ ID NO: 5707 and SEQ ID NO: 5517, respectively. In an aspect, the first gRNA molecule and the second gRNA molecule include targeting domains comprising, e.g., consisting of, SEQ ID NO: 5707 and SEQ ID NO: 5521, respectively. In an aspect, the first gRNA molecule and the second gRNA molecule include targeting domains comprising, e.g., consisting of, SEQ ID NO: 5707 and SEQ ID NO: 5520, respectively. In an aspect, the first gRNA molecule and the second gRNA molecule include targeting domains comprising, e.g., consisting of, SEQ ID NO: 5707 and SEQ ID NO: 5500, respectively. In an aspect, the first gRNA molecule and the second gRNA molecule include targeting domains comprising, e.g., consisting of, SEQ ID NO: 5707 and SEQ ID NO: 5494, respectively. In an aspect, the first gRNA molecule and the second gRNA molecule include targeting domains comprising, e.g., consisting of, SEQ ID NO: 5707 and SEQ ID NO: 5508, respectively. In an aspect, the first gRNA molecule and the second gRNA molecule include targeting domains comprising, e.g., consisting of, SEQ ID NO: 5707 and SEQ ID NO: 5514, respectively. In an aspect, the first gRNA molecule and the second gRNA molecule include targeting domains comprising, e.g., consisting of, SEQ ID NO: 5707 and SEQ ID NO: 5492, respectively. In an aspect, the first gRNA molecule and the second gRNA molecule include targeting domains comprising, e.g., consisting of, SEQ ID NO: 5687 and SEQ ID NO: 5519, respectively. In an aspect, the first gRNA molecule and the second gRNA molecule include targeting domains comprising, e.g., consisting of, SEQ ID NO: 5687 and SEQ ID NO: 5497, respectively. In an aspect, the first gRNA molecule and the second gRNA molecule include targeting domains comprising, e.g., consisting of, SEQ ID NO: 5687 and SEQ ID NO: 5499, respectively. In an aspect, the first gRNA molecule and the second gRNA molecule include targeting domains comprising, e.g., consisting of, SEQ ID NO: 5687 and SEQ ID NO: 5498, respectively. In an aspect, the first gRNA molecule and the second gRNA molecule include targeting domains comprising, e.g., consisting of, SEQ ID NO: 5687 and SEQ ID NO: 5503, respectively. In an aspect, the first gRNA molecule and the second gRNA molecule include targeting domains comprising, e.g., consisting of, SEQ ID NO: 5687 and SEQ ID NO: 5496, respectively. In an aspect, the first gRNA molecule and the second gRNA molecule include targeting domains comprising, e.g., consisting of, SEQ ID NO: 5687 and SEQ ID NO: 5507, respectively. In an aspect, the first gRNA molecule and the second gRNA molecule include targeting domains comprising, e.g., consisting of, SEQ ID NO: 5687 and SEQ ID NO: 5515, respectively. In an aspect, the first gRNA molecule and the second gRNA molecule include targeting domains comprising, e.g., consisting of, SEQ ID NO: 5687 and SEQ ID NO: 5493, respectively. In an aspect, the first gRNA molecule and the second gRNA molecule include targeting domains comprising, e.g., consisting of, SEQ ID NO: 5687 and SEQ ID NO: 5506, respectively. In an aspect, the first gRNA molecule and the second gRNA molecule include targeting domains comprising, e.g., consisting of, SEQ ID NO: 5687 and SEQ ID NO: 5509, respectively. In an aspect, the first gRNA molecule and the second gRNA molecule include targeting domains comprising, e.g., consisting of, SEQ ID NO: 5687 and SEQ ID NO: 5517, respectively. In an aspect, the first gRNA molecule and the second gRNA molecule include targeting domains comprising, e.g., consisting of, SEQ ID NO: 5687 and SEQ ID NO: 5521, respectively. In an aspect, the first gRNA molecule and the second gRNA molecule include targeting domains comprising, e.g., consisting of, SEQ ID NO: 5687 and SEQ ID NO: 5520, respectively. In an aspect, the first gRNA molecule and the second gRNA molecule include targeting domains comprising, e.g., consisting of, SEQ ID NO: 5687 and SEQ ID NO: 5500, respectively. In an aspect, the first gRNA molecule and the second gRNA molecule include targeting domains comprising, e.g., consisting of, SEQ ID NO: 5687 and SEQ ID NO: 5494, respectively. In an aspect, the first gRNA molecule and the second gRNA molecule include targeting domains comprising, e.g., consisting of, SEQ ID NO: 5687 and SEQ ID NO: 5508, respectively. In an aspect, the first gRNA molecule and the second gRNA molecule include targeting domains comprising, e.g., consisting of, SEQ ID NO: 5687 and SEQ ID NO: 5514, respectively. In an aspect, the first gRNA molecule and the second gRNA molecule include targeting domains comprising, e.g., consisting of, SEQ ID NO: 5687 and SEQ ID NO: 5492, respectively. In an aspect, the first gRNA molecule and the second gRNA molecule include targeting domains comprising, e.g., consisting of, SEQ ID NO: 5705 and SEQ ID NO: 5519, respectively. In an aspect, the first gRNA molecule and the second gRNA molecule include targeting domains comprising, e.g., consisting of, SEQ ID NO: 5705 and SEQ ID NO: 5497, respectively. In an aspect, the first gRNA molecule and the second gRNA molecule include targeting domains comprising, e.g., consisting of, SEQ ID NO: 5705 and SEQ ID NO: 5499, respectively. In an aspect, the first gRNA molecule and the second gRNA molecule include targeting domains comprising, e.g., consisting of, SEQ ID NO: 5705 and SEQ ID NO: 5498, respectively. In an aspect, the first gRNA molecule and the second gRNA molecule include targeting domains comprising, e.g., consisting of, SEQ ID NO: 5705 and SEQ ID NO: 5503, respectively. In an aspect, the first gRNA molecule and the second gRNA molecule include targeting domains comprising, e.g., consisting of, SEQ ID NO: 5705 and SEQ ID NO: 5496, respectively. In an aspect, the first gRNA molecule and the second gRNA molecule include targeting domains comprising, e.g., consisting of, SEQ ID NO: 5705 and SEQ ID NO: 5507, respectively. In an aspect, the first gRNA molecule and the second gRNA molecule include targeting domains comprising, e.g., consisting of, SEQ ID NO: 5705 and SEQ ID NO: 5515, respectively. In an aspect, the first gRNA molecule and the second gRNA molecule include targeting domains comprising, e.g., consisting of, SEQ ID NO: 5705 and SEQ ID NO: 5493, respectively. In an aspect, the first gRNA molecule and the second gRNA molecule include targeting domains comprising, e.g., consisting of, SEQ ID NO: 5705 and SEQ ID NO: 5506, respectively. In an aspect, the first gRNA molecule and the second gRNA molecule include targeting domains comprising, e.g., consisting of, SEQ ID NO: 5705 and SEQ ID NO: 5509, respectively. In an aspect, the first gRNA molecule and the second gRNA molecule include targeting domains comprising, e.g., consisting of, SEQ ID NO: 5705 and SEQ ID NO: 5517, respectively. In an aspect, the first gRNA molecule and the second gRNA molecule include targeting domains comprising, e.g., consisting of, SEQ ID NO: 5705 and SEQ ID NO: 5521, respectively. In an aspect, the first gRNA molecule and the second gRNA molecule include targeting domains comprising, e.g., consisting of, SEQ ID NO: 5705 and SEQ ID NO: 5520, respectively. In an aspect, the first gRNA molecule and the second gRNA molecule include targeting domains comprising, e.g., consisting of, SEQ ID NO: 5705 and SEQ ID NO: 5500, respectively. In an aspect, the first gRNA molecule and the second gRNA molecule include targeting domains comprising, e.g., consisting of, SEQ ID NO: 5705 and SEQ ID NO: 5494, respectively. In an aspect, the first gRNA molecule and the second gRNA molecule include targeting domains comprising, e.g., consisting of, SEQ ID NO: 5705 and SEQ ID NO: 5508, respectively. In an aspect, the first gRNA molecule and the second gRNA molecule include targeting domains comprising, e.g., consisting of, SEQ ID NO: 5705 and SEQ ID NO: 5514, respectively. In an aspect, the first gRNA molecule and the second gRNA molecule include targeting domains comprising, e.g., consisting of, SEQ ID NO: 5705 and SEQ ID NO: 5492, respectively. In an aspect, the first gRNA molecule and the second gRNA molecule include targeting domains comprising, e.g., consisting of, SEQ ID NO: 5713 and SEQ ID NO: 5519, respectively. In an aspect, the first gRNA molecule and the second gRNA molecule include targeting domains comprising, e.g., consisting of, SEQ ID NO: 5713 and SEQ ID NO: 5497, respectively. In an aspect, the first gRNA molecule and the second gRNA molecule include targeting domains comprising, e.g., consisting of, SEQ ID NO: 5713 and SEQ ID NO: 5499, respectively. In an aspect, the first gRNA molecule and the second gRNA molecule include targeting domains comprising, e.g., consisting of, SEQ ID NO: 5713 and SEQ ID NO: 5498, respectively. In an aspect, the first gRNA molecule and the second gRNA molecule include targeting domains comprising, e.g., consisting of, SEQ ID NO: 5713 and SEQ ID NO: 5503, respectively. In an aspect, the first gRNA molecule and the second gRNA molecule include targeting domains comprising, e.g., consisting of, SEQ ID NO: 5713 and SEQ ID NO: 5496, respectively. In an aspect, the first gRNA molecule and the second gRNA molecule include targeting domains comprising, e.g., consisting of, SEQ ID NO: 5713 and SEQ ID NO: 5507, respectively. In an aspect, the first gRNA molecule and the second gRNA molecule include targeting domains comprising, e.g., consisting of, SEQ ID NO: 5713 and SEQ ID NO: 5515, respectively. In an aspect, the first gRNA molecule and the second gRNA molecule include targeting domains comprising, e.g., consisting of, SEQ ID NO: 5713 and SEQ ID NO: 5493, respectively. In an aspect, the first gRNA molecule and the second gRNA molecule include targeting domains comprising, e.g., consisting of, SEQ ID NO: 5713 and SEQ ID NO: 5506, respectively. In an aspect, the first gRNA molecule and the second gRNA molecule include targeting domains comprising, e.g., consisting of, SEQ ID NO: 5713 and SEQ ID NO: 5509, respectively. In an aspect, the first gRNA molecule and the second gRNA molecule include targeting domains comprising, e.g., consisting of, SEQ ID NO: 5713 and SEQ ID NO: 5517, respectively. In an aspect, the first gRNA molecule and the second gRNA molecule include targeting domains comprising, e.g., consisting of, SEQ ID NO: 5713 and SEQ ID NO: 5521, respectively. In an aspect, the first gRNA molecule and the second gRNA molecule include targeting domains comprising, e.g., consisting of, SEQ ID NO: 5713 and SEQ ID NO: 5520, respectively. In an aspect, the first gRNA molecule and the second gRNA molecule include targeting domains comprising, e.g., consisting of, SEQ ID NO: 5713 and SEQ ID NO: 5500, respectively. In an aspect, the first gRNA molecule and the second gRNA molecule include targeting domains comprising, e.g., consisting of, SEQ ID NO: 5713 and SEQ ID NO: 5494, respectively. In an aspect, the first gRNA molecule and the second gRNA molecule include targeting domains comprising, e.g., consisting of, SEQ ID NO: 5713 and SEQ ID NO: 5508, respectively. In an aspect, the first gRNA molecule and the second gRNA molecule include targeting domains comprising, e.g., consisting of, SEQ ID NO: 5713 and SEQ ID NO: 5514, respectively. In an aspect, the first gRNA molecule and the second gRNA molecule include targeting domains comprising, e.g., consisting of, SEQ ID NO: 5713 and SEQ ID NO: 5492, respectively. In an aspect, the first gRNA molecule and the second gRNA molecule include targeting domains comprising, e.g., consisting of, SEQ ID NO: 5715 and SEQ ID NO: 5519, respectively. In an aspect, the first gRNA molecule and the second gRNA molecule include targeting domains comprising, e.g., consisting of, SEQ ID NO: 5715 and SEQ ID NO: 5497, respectively. In an aspect, the first gRNA molecule and the second gRNA molecule include targeting domains comprising, e.g., consisting of, SEQ ID NO: 5715 and SEQ ID NO: 5499, respectively. In an aspect, the first gRNA molecule and the second gRNA molecule include targeting domains comprising, e.g., consisting of, SEQ ID NO: 5715 and SEQ ID NO: 5498, respectively. In an aspect, the first gRNA molecule and the second gRNA molecule include targeting domains comprising, e.g., consisting of, SEQ ID NO: 5715 and SEQ ID NO: 5503, respectively. In an aspect, the first gRNA molecule and the second gRNA molecule include targeting domains comprising, e.g., consisting of, SEQ ID NO: 5715 and SEQ ID NO: 5496, respectively. In an aspect, the first gRNA molecule and the second gRNA molecule include targeting domains comprising, e.g., consisting of, SEQ ID NO: 5715 and SEQ ID NO: 5507, respectively. In an aspect, the first gRNA molecule and the second gRNA molecule include targeting domains comprising, e.g., consisting of, SEQ ID NO: 5715 and SEQ ID NO: 5515, respectively. In an aspect, the first gRNA molecule and the second gRNA molecule include targeting domains comprising, e.g., consisting of, SEQ ID NO: 5715 and SEQ ID NO: 5493, respectively. In an aspect, the first gRNA molecule and the second gRNA molecule include targeting domains comprising, e.g., consisting of, SEQ ID NO: 5715 and SEQ ID NO: 5506, respectively. In an aspect, the first gRNA molecule and the second gRNA molecule include targeting domains comprising, e.g., consisting of, SEQ ID NO: 5715 and SEQ ID NO: 5509, respectively. In an aspect, the first gRNA molecule and the second gRNA molecule include targeting domains comprising, e.g., consisting of, SEQ ID NO: 5715 and SEQ ID NO: 5517, respectively. In an aspect, the first gRNA molecule and the second gRNA molecule include targeting domains comprising, e.g., consisting of, SEQ ID NO: 5715 and SEQ ID NO: 5521, respectively. In an aspect, the first gRNA molecule and the second gRNA molecule include targeting domains comprising, e.g., consisting of, SEQ ID NO: 5715 and SEQ ID NO: 5520, respectively. In an aspect, the first gRNA molecule and the second gRNA molecule include targeting domains comprising, e.g., consisting of, SEQ ID NO: 5715 and SEQ ID NO: 5500, respectively. In an aspect, the first gRNA molecule and the second gRNA molecule include targeting domains comprising, e.g., consisting of, SEQ ID NO: 5715 and SEQ ID NO: 5494, respectively. In an aspect, the first gRNA molecule and the second gRNA molecule include targeting domains comprising, e.g., consisting of, SEQ ID NO: 5715 and SEQ ID NO: 5508, respectively. In an aspect, the first gRNA molecule and the second gRNA molecule include targeting domains comprising, e.g., consisting of, SEQ ID NO: 5715 and SEQ ID NO: 5514, respectively. In an aspect, the first gRNA molecule and the second gRNA molecule include targeting domains comprising, e.g., consisting of, SEQ ID NO: 5715 and SEQ ID NO: 5492, respectively. In an aspect, the first gRNA molecule and the second gRNA molecule include targeting domains comprising, e.g., consisting of, SEQ ID NO: 5710 and SEQ ID NO: 5519, respectively. In an aspect, the first gRNA molecule and the second gRNA molecule include targeting domains comprising, e.g., consisting of, SEQ ID NO: 5710 and SEQ ID NO: 5497, respectively. In an aspect, the first gRNA molecule and the second gRNA molecule include targeting domains comprising, e.g., consisting of, SEQ ID NO: 5710 and SEQ ID NO: 5499, respectively. In an aspect, the first gRNA molecule and the second gRNA molecule include targeting domains comprising, e.g., consisting of, SEQ ID NO: 5710 and SEQ ID NO: 5498, respectively. In an aspect, the first gRNA molecule and the second gRNA molecule include targeting domains comprising, e.g., consisting of, SEQ ID NO: 5710 and SEQ ID NO: 5503, respectively. In an aspect, the first gRNA molecule and the second gRNA molecule include targeting domains comprising, e.g., consisting of, SEQ ID NO: 5710 and SEQ ID NO: 5496, respectively. In an aspect, the first gRNA molecule and the second gRNA molecule include targeting domains comprising, e.g., consisting of, SEQ ID NO: 5710 and SEQ ID NO: 5507, respectively. In an aspect, the first gRNA molecule and the second gRNA molecule include targeting domains comprising, e.g., consisting of, SEQ ID NO: 5710 and SEQ ID NO: 5515, respectively. In an aspect, the first gRNA molecule and the second gRNA molecule include targeting domains comprising, e.g., consisting of, SEQ ID NO: 5710 and SEQ ID NO: 5493, respectively. In an aspect, the first gRNA molecule and the second gRNA molecule include targeting domains comprising, e.g., consisting of, SEQ ID NO: 5710 and SEQ ID NO: 5506, respectively. In an aspect, the first gRNA molecule and the second gRNA molecule include targeting domains comprising, e.g., consisting of, SEQ ID NO: 5710 and SEQ ID NO: 5509, respectively. In an aspect, the first gRNA molecule and the second gRNA molecule include targeting domains comprising, e.g., consisting of, SEQ ID NO: 5710 and SEQ ID NO: 5517, respectively. In an aspect, the first gRNA molecule and the second gRNA molecule include targeting domains comprising, e.g., consisting of, SEQ ID NO: 5710 and SEQ ID NO: 5521, respectively. In an aspect, the first gRNA molecule and the second gRNA molecule include targeting domains comprising, e.g., consisting of, SEQ ID NO: 5710 and SEQ ID NO: 5520, respectively. In an aspect, the first gRNA molecule and the second gRNA molecule include targeting domains comprising, e.g., consisting of, SEQ ID NO: 5710 and SEQ ID NO: 5500, respectively. In an aspect, the first gRNA molecule and the second gRNA molecule include targeting domains comprising, e.g., consisting of, SEQ ID NO: 5710 and SEQ ID NO: 5494, respectively. In an aspect, the first gRNA molecule and the second gRNA molecule include targeting domains comprising, e.g., consisting of, SEQ ID NO: 5710 and SEQ ID NO: 5508, respectively. In an aspect, the first gRNA molecule and the second gRNA molecule include targeting domains comprising, e.g., consisting of, SEQ ID NO: 5710 and SEQ ID NO: 5514, respectively. In an aspect, the first gRNA molecule and the second gRNA molecule include targeting domains comprising, e.g., consisting of, SEQ ID NO: 5710 and SEQ ID NO: 5492, respectively. In any of the aforementioned combinations, the aspect or the embodiment of the invention may additionally include a third gRNA molecule (or more than one gRNA molecules) comprising a targeting domain specific for a sequence of CIITA, e.g. as described herein, e.g., as described herein in Table 6c.

In aspects of the invention that utilize two or more, e.g., two, gRNA molecules, it may be particularly useful for a first gRNA molecule to comprise a targeting domain specific for a sequence of TRAC and a second gRNA molecule to comprise a targeting domain specific for a sequence of PDCD1. In such aspects, it is particularly preferred that the first gRNA molecule to TRAC comprises a targeting domain of any gRNA molecule of FIG. 12, and the second gRNA molecule to PDCD1 comprises a targeting domain of any gRNA molecule of FIG. 16. In an aspect, the first gRNA molecule and the second gRNA molecule include targeting domains comprising, e.g., consisting of, SEQ ID NO: 5569 and SEQ ID NO: 5743, respectively. In an aspect, the first gRNA molecule and the second gRNA molecule include targeting domains comprising, e.g., consisting of, SEQ ID NO: 5569 and SEQ ID NO: 5497, respectively. In an aspect, the first gRNA molecule and the second gRNA molecule include targeting domains comprising, e.g., consisting of, SEQ ID NO: 5569 and SEQ ID NO: 5499, respectively. In an aspect, the first gRNA molecule and the second gRNA molecule include targeting domains comprising, e.g., consisting of, SEQ ID NO: 5569 and SEQ ID NO: 5498, respectively. In an aspect, the first gRNA molecule and the second gRNA molecule include targeting domains comprising, e.g., consisting of, SEQ ID NO: 5569 and SEQ ID NO: 5503, respectively. In an aspect, the first gRNA molecule and the second gRNA molecule include targeting domains comprising, e.g., consisting of, SEQ ID NO: 5569 and SEQ ID NO: 5496, respectively. In an aspect, the first gRNA molecule and the second gRNA molecule include targeting domains comprising, e.g., consisting of, SEQ ID NO: 5569 and SEQ ID NO: 5507, respectively. In an aspect, the first gRNA molecule and the second gRNA molecule include targeting domains comprising, e.g., consisting of, SEQ ID NO: 5569 and SEQ ID NO: 5515, respectively. In an aspect, the first gRNA molecule and the second gRNA molecule include targeting domains comprising, e.g., consisting of, SEQ ID NO: 5569 and SEQ ID NO: 5493, respectively. In an aspect, the first gRNA molecule and the second gRNA molecule include targeting domains comprising, e.g., consisting of, SEQ ID NO: 5569 and SEQ ID NO: 5506, respectively. In an aspect, the first gRNA molecule and the second gRNA molecule include targeting domains comprising, e.g., consisting of, SEQ ID NO: 5569 and SEQ ID NO: 5509, respectively. In an aspect, the first gRNA molecule and the second gRNA molecule include targeting domains comprising, e.g., consisting of, SEQ ID NO: 5569 and SEQ ID NO: 5517, respectively. In an aspect, the first gRNA molecule and the second gRNA molecule include targeting domains comprising, e.g., consisting of, SEQ ID NO: 5569 and SEQ ID NO: 5521, respectively. In an aspect, the first gRNA molecule and the second gRNA molecule include targeting domains comprising, e.g., consisting of, SEQ ID NO: 5569 and SEQ ID NO: 5520, respectively. In an aspect, the first gRNA molecule and the second gRNA molecule include targeting domains comprising, e.g., consisting of, SEQ ID NO: 5569 and SEQ ID NO: 5500, respectively. In an aspect, the first gRNA molecule and the second gRNA molecule include targeting domains comprising, e.g., consisting of, SEQ ID NO: 5585 and SEQ ID NO: 5743, respectively. In an aspect, the first gRNA molecule and the second gRNA molecule include targeting domains comprising, e.g., consisting of, SEQ ID NO: 5585 and SEQ ID NO: 5798, respectively. In an aspect, the first gRNA molecule and the second gRNA molecule include targeting domains comprising, e.g., consisting of, SEQ ID NO: 5585 and SEQ ID NO: 5748, respectively. In an aspect, the first gRNA molecule and the second gRNA molecule include targeting domains comprising, e.g., consisting of, SEQ ID NO: 5585 and SEQ ID NO: 5722, respectively. In an aspect, the first gRNA molecule and the second gRNA molecule include targeting domains comprising, e.g., consisting of, SEQ ID NO: 5585 and SEQ ID NO: 5800, respectively. In an aspect, the first gRNA molecule and the second gRNA molecule include targeting domains comprising, e.g., consisting of, SEQ ID NO: 5585 and SEQ ID NO: 5735, respectively. In an aspect, the first gRNA molecule and the second gRNA molecule include targeting domains comprising, e.g., consisting of, SEQ ID NO: 5585 and SEQ ID NO: 5724, respectively. In an aspect, the first gRNA molecule and the second gRNA molecule include targeting domains comprising, e.g., consisting of, SEQ ID NO: 5585 and SEQ ID NO: 5731, respectively. In an aspect, the first gRNA molecule and the second gRNA molecule include targeting domains comprising, e.g., consisting of, SEQ ID NO: 5585 and SEQ ID NO: 5725, respectively. In an aspect, the first gRNA molecule and the second gRNA molecule include targeting domains comprising, e.g., consisting of, SEQ ID NO: 5585 and SEQ ID NO: 5775, respectively. In an aspect, the first gRNA molecule and the second gRNA molecule include targeting domains comprising, e.g., consisting of, SEQ ID NO: 5585 and SEQ ID NO: 5766, respectively. In an aspect, the first gRNA molecule and the second gRNA molecule include targeting domains comprising, e.g., consisting of, SEQ ID NO: 5585 and SEQ ID NO: 5727, respectively. In an aspect, the first gRNA molecule and the second gRNA molecule include targeting domains comprising, e.g., consisting of, SEQ ID NO: 5585 and SEQ ID NO: 5744, respectively. In an aspect, the first gRNA molecule and the second gRNA molecule include targeting domains comprising, e.g., consisting of, SEQ ID NO: 5585 and SEQ ID NO: 5751, respectively. In an aspect, the first gRNA molecule and the second gRNA molecule include targeting domains comprising, e.g., consisting of, SEQ ID NO: 5585 and SEQ ID NO: 5734, respectively. In an aspect, the first gRNA molecule and the second gRNA molecule include targeting domains comprising, e.g., consisting of, SEQ ID NO: 5592 and SEQ ID NO: 5743, respectively. In an aspect, the first gRNA molecule and the second gRNA molecule include targeting domains comprising, e.g., consisting of, SEQ ID NO: 5592 and SEQ ID NO: 5798, respectively. In an aspect, the first gRNA molecule and the second gRNA molecule include targeting domains comprising, e.g., consisting of, SEQ ID NO: 5592 and SEQ ID NO: 5748, respectively. In an aspect, the first gRNA molecule and the second gRNA molecule include targeting domains comprising, e.g., consisting of, SEQ ID NO: 5592 and SEQ ID NO: 5722, respectively. In an aspect, the first gRNA molecule and the second gRNA molecule include targeting domains comprising, e.g., consisting of, SEQ ID NO: 5592 and SEQ ID NO: 5800, respectively. In an aspect, the first gRNA molecule and the second gRNA molecule include targeting domains comprising, e.g., consisting of, SEQ ID NO: 5592 and SEQ ID NO: 5735, respectively. In an aspect, the first gRNA molecule and the second gRNA molecule include targeting domains comprising, e.g., consisting of, SEQ ID NO: 5592 and SEQ ID NO: 5724, respectively. In an aspect, the first gRNA molecule and the second gRNA molecule include targeting domains comprising, e.g., consisting of, SEQ ID NO: 5592 and SEQ ID NO: 5731, respectively. In an aspect, the first gRNA molecule and the second gRNA molecule include targeting domains comprising, e.g., consisting of, SEQ ID NO: 5592 and SEQ ID NO: 5725, respectively. In an aspect, the first gRNA molecule and the second gRNA molecule include targeting domains comprising, e.g., consisting of, SEQ ID NO: 5592 and SEQ ID NO: 5775, respectively. In an aspect, the first gRNA molecule and the second gRNA molecule include targeting domains comprising, e.g., consisting of, SEQ ID NO: 5592 and SEQ ID NO: 5766, respectively. In an aspect, the first gRNA molecule and the second gRNA molecule include targeting domains comprising, e.g., consisting of, SEQ ID NO: 5592 and SEQ ID NO: 5727, respectively. In an aspect, the first gRNA molecule and the second gRNA molecule include targeting domains comprising, e.g., consisting of, SEQ ID NO: 5592 and SEQ ID NO: 5744, respectively. In an aspect, the first gRNA molecule and the second gRNA molecule include targeting domains comprising, e.g., consisting of, SEQ ID NO: 5592 and SEQ ID NO: 5751, respectively. In an aspect, the first gRNA molecule and the second gRNA molecule include targeting domains comprising, e.g., consisting of, SEQ ID NO: 5592 and SEQ ID NO: 5734, respectively. In an aspect, the first gRNA molecule and the second gRNA molecule include targeting domains comprising, e.g., consisting of, SEQ ID NO: 5601 and SEQ ID NO: 5743, respectively. In an aspect, the first gRNA molecule and the second gRNA molecule include targeting domains comprising, e.g., consisting of, SEQ ID NO: 5601 and SEQ ID NO: 5798, respectively. In an aspect, the first gRNA molecule and the second gRNA molecule include targeting domains comprising, e.g., consisting of, SEQ ID NO: 5601 and SEQ ID NO: 5748, respectively. In an aspect, the first gRNA molecule and the second gRNA molecule include targeting domains comprising, e.g., consisting of, SEQ ID NO: 5601 and SEQ ID NO: 5722, respectively. In an aspect, the first gRNA molecule and the second gRNA molecule include targeting domains comprising, e.g., consisting of, SEQ ID NO: 5601 and SEQ ID NO: 5800, respectively. In an aspect, the first gRNA molecule and the second gRNA molecule include targeting domains comprising, e.g., consisting of, SEQ ID NO: 5601 and SEQ ID NO: 5735, respectively. In an aspect, the first gRNA molecule and the second gRNA molecule include targeting domains comprising, e.g., consisting of, SEQ ID NO: 5601 and SEQ ID NO: 5724, respectively. In an aspect, the first gRNA molecule and the second gRNA molecule include targeting domains comprising, e.g., consisting of, SEQ ID NO: 5601 and SEQ ID NO: 5731, respectively. In an aspect, the first gRNA molecule and the second gRNA molecule include targeting domains comprising, e.g., consisting of, SEQ ID NO: 5601 and SEQ ID NO: 5725, respectively. In an aspect, the first gRNA molecule and the second gRNA molecule include targeting domains comprising, e.g., consisting of, SEQ ID NO: 5601 and SEQ ID NO: 5775, respectively. In an aspect, the first gRNA molecule and the second gRNA molecule include targeting domains comprising, e.g., consisting of, SEQ ID NO: 5601 and SEQ ID NO: 5766, respectively. In an aspect, the first gRNA molecule and the second gRNA molecule include targeting domains comprising, e.g., consisting of, SEQ ID NO: 5601 and SEQ ID NO: 5727, respectively. In an aspect, the first gRNA molecule and the second gRNA molecule include targeting domains comprising, e.g., consisting of, SEQ ID NO: 5601 and SEQ ID NO: 5744, respectively. In an aspect, the first gRNA molecule and the second gRNA molecule include targeting domains comprising, e.g., consisting of, SEQ ID NO: 5601 and SEQ ID NO: 5751, respectively. In an aspect, the first gRNA molecule and the second gRNA molecule include targeting domains comprising, e.g., consisting of, SEQ ID NO: 5601 and SEQ ID NO: 5734, respectively. In an aspect, the first gRNA molecule and the second gRNA molecule include targeting domains comprising, e.g., consisting of, SEQ ID NO: 5589 and SEQ ID NO: 5743, respectively. In an aspect, the first gRNA molecule and the second gRNA molecule include targeting domains comprising, e.g., consisting of, SEQ ID NO: 5589 and SEQ ID NO: 5798, respectively. In an aspect, the first gRNA molecule and the second gRNA molecule include targeting domains comprising, e.g., consisting of, SEQ ID NO: 5589 and SEQ ID NO: 5748, respectively. In an aspect, the first gRNA molecule and the second gRNA molecule include targeting domains comprising, e.g., consisting of, SEQ ID NO: 5589 and SEQ ID NO: 5722, respectively. In an aspect, the first gRNA molecule and the second gRNA molecule include targeting domains comprising, e.g., consisting of, SEQ ID NO: 5589 and SEQ ID NO: 5800, respectively. In an aspect, the first gRNA molecule and the second gRNA molecule include targeting domains comprising, e.g., consisting of, SEQ ID NO: 5589 and SEQ ID NO: 5735, respectively. In an aspect, the first gRNA molecule and the second gRNA molecule include targeting domains comprising, e.g., consisting of, SEQ ID NO: 5589 and SEQ ID NO: 5724, respectively. In an aspect, the first gRNA molecule and the second gRNA molecule include targeting domains comprising, e.g., consisting of, SEQ ID NO: 5589 and SEQ ID NO: 5731, respectively. In an aspect, the first gRNA molecule and the second gRNA molecule include targeting domains comprising, e.g., consisting of, SEQ ID NO: 5589 and SEQ ID NO: 5725, respectively. In an aspect, the first gRNA molecule and the second gRNA molecule include targeting domains comprising, e.g., consisting of, SEQ ID NO: 5589 and SEQ ID NO: 5775, respectively. In an aspect, the first gRNA molecule and the second gRNA molecule include targeting domains comprising, e.g., consisting of, SEQ ID NO: 5589 and SEQ ID NO: 5766, respectively. In an aspect, the first gRNA molecule and the second gRNA molecule include targeting domains comprising, e.g., consisting of, SEQ ID NO: 5589 and SEQ ID NO: 5727, respectively. In an aspect, the first gRNA molecule and the second gRNA molecule include targeting domains comprising, e.g., consisting of, SEQ ID NO: 5589 and SEQ ID NO: 5744, respectively. In an aspect, the first gRNA molecule and the second gRNA molecule include targeting domains comprising, e.g., consisting of, SEQ ID NO: 5589 and SEQ ID NO: 5751, respectively. In an aspect, the first gRNA molecule and the second gRNA molecule include targeting domains comprising, e.g., consisting of, SEQ ID NO: 5589 and SEQ ID NO: 5734, respectively. In an aspect, the first gRNA molecule and the second gRNA molecule include targeting domains comprising, e.g., consisting of, SEQ ID NO: 5600 and SEQ ID NO: 5743, respectively. In an aspect, the first gRNA molecule and the second gRNA molecule include targeting domains comprising, e.g., consisting of, SEQ ID NO: 5600 and SEQ ID NO: 5798, respectively. In an aspect, the first gRNA molecule and the second gRNA molecule include targeting domains comprising, e.g., consisting of, SEQ ID NO: 5600 and SEQ ID NO: 5748, respectively. In an aspect, the first gRNA molecule and the second gRNA molecule include targeting domains comprising, e.g., consisting of, SEQ ID NO: 5600 and SEQ ID NO: 5722, respectively. In an aspect, the first gRNA molecule and the second gRNA molecule include targeting domains comprising, e.g., consisting of, SEQ ID NO: 5600 and SEQ ID NO: 5800, respectively. In an aspect, the first gRNA molecule and the second gRNA molecule include targeting domains comprising, e.g., consisting of, SEQ ID NO: 5600 and SEQ ID NO: 5735, respectively. In an aspect, the first gRNA molecule and the second gRNA molecule include targeting domains comprising, e.g., consisting of, SEQ ID NO: 5600 and SEQ ID NO: 5724, respectively. In an aspect, the first gRNA molecule and the second gRNA molecule include targeting domains comprising, e.g., consisting of, SEQ ID NO: 5600 and SEQ ID NO: 5731, respectively. In an aspect, the first gRNA molecule and the second gRNA molecule include targeting domains comprising, e.g., consisting of, SEQ ID NO: 5600 and SEQ ID NO: 5725, respectively. In an aspect, the first gRNA molecule and the second gRNA molecule include targeting domains comprising, e.g., consisting of, SEQ ID NO: 5600 and SEQ ID NO: 5775, respectively. In an aspect, the first gRNA molecule and the second gRNA molecule include targeting domains comprising, e.g., consisting of, SEQ ID NO: 5600 and SEQ ID NO: 5766, respectively. In an aspect, the first gRNA molecule and the second gRNA molecule include targeting domains comprising, e.g., consisting of, SEQ ID NO: 5600 and SEQ ID NO: 5727, respectively. In an aspect, the first gRNA molecule and the second gRNA molecule include targeting domains comprising, e.g., consisting of, SEQ ID NO: 5600 and SEQ ID NO: 5744, respectively. In an aspect, the first gRNA molecule and the second gRNA molecule include targeting domains comprising, e.g., consisting of, SEQ ID NO: 5600 and SEQ ID NO: 5751, respectively. In an aspect, the first gRNA molecule and the second gRNA molecule include targeting domains comprising, e.g., consisting of, SEQ ID NO: 5600 and SEQ ID NO: 5734, respectively. In an aspect, the first gRNA molecule and the second gRNA molecule include targeting domains comprising, e.g., consisting of, SEQ ID NO: 5594 and SEQ ID NO: 5743, respectively. In an aspect, the first gRNA molecule and the second gRNA molecule include targeting domains comprising, e.g., consisting of, SEQ ID NO: 5594 and SEQ ID NO: 5798, respectively. In an aspect, the first gRNA molecule and the second gRNA molecule include targeting domains comprising, e.g., consisting of, SEQ ID NO: 5594 and SEQ ID NO: 5748, respectively. In an aspect, the first gRNA molecule and the second gRNA molecule include targeting domains comprising, e.g., consisting of, SEQ ID NO: 5594 and SEQ ID NO: 5722, respectively. In an aspect, the first gRNA molecule and the second gRNA molecule include targeting domains comprising, e.g., consisting of, SEQ ID NO: 5594 and SEQ ID NO: 5800, respectively. In an aspect, the first gRNA molecule and the second gRNA molecule include targeting domains comprising, e.g., consisting of, SEQ ID NO: 5594 and SEQ ID NO: 5735, respectively. In an aspect, the first gRNA molecule and the second gRNA molecule include targeting domains comprising, e.g., consisting of, SEQ ID NO: 5594 and SEQ ID NO: 5724, respectively. In an aspect, the first gRNA molecule and the second gRNA molecule include targeting domains comprising, e.g., consisting of, SEQ ID NO: 5594 and SEQ ID NO: 5731, respectively. In an aspect, the first gRNA molecule and the second gRNA molecule include targeting domains comprising, e.g., consisting of, SEQ ID NO: 5594 and SEQ ID NO: 5725, respectively. In an aspect, the first gRNA molecule and the second gRNA molecule include targeting domains comprising, e.g., consisting of, SEQ ID NO: 5594 and SEQ ID NO: 5775, respectively. In an aspect, the first gRNA molecule and the second gRNA molecule include targeting domains comprising, e.g., consisting of, SEQ ID NO: 5594 and SEQ ID NO: 5766, respectively. In an aspect, the first gRNA molecule and the second gRNA molecule include targeting domains comprising, e.g., consisting of, SEQ ID NO: 5594 and SEQ ID NO: 5727, respectively. In an aspect, the first gRNA molecule and the second gRNA molecule include targeting domains comprising, e.g., consisting of, SEQ ID NO: 5594 and SEQ ID NO: 5744, respectively. In an aspect, the first gRNA molecule and the second gRNA molecule include targeting domains comprising, e.g., consisting of, SEQ ID NO: 5594 and SEQ ID NO: 5751, respectively. In an aspect, the first gRNA molecule and the second gRNA molecule include targeting domains comprising, e.g., consisting of, SEQ ID NO: 5594 and SEQ ID NO: 5734, respectively. In an aspect, the first gRNA molecule and the second gRNA molecule include targeting domains comprising, e.g., consisting of, SEQ ID NO: 5571 and SEQ ID NO: 5743, respectively. In an aspect, the first gRNA molecule and the second gRNA molecule include targeting domains comprising, e.g., consisting of, SEQ ID NO: 5571 and SEQ ID NO: 5798, respectively. In an aspect, the first gRNA molecule and the second gRNA molecule include targeting domains comprising, e.g., consisting of, SEQ ID NO: 5571 and SEQ ID NO: 5748, respectively. In an aspect, the first gRNA molecule and the second gRNA molecule include targeting domains comprising, e.g., consisting of, SEQ ID NO: 5571 and SEQ ID NO: 5722, respectively. In an aspect, the first gRNA molecule and the second gRNA molecule include targeting domains comprising, e.g., consisting of, SEQ ID NO: 5571 and SEQ ID NO: 5800, respectively. In an aspect, the first gRNA molecule and the second gRNA molecule include targeting domains comprising, e.g., consisting of, SEQ ID NO: 5571 and SEQ ID NO: 5735, respectively. In an aspect, the first gRNA molecule and the second gRNA molecule include targeting domains comprising, e.g., consisting of, SEQ ID NO: 5571 and SEQ ID NO: 5724, respectively. In an aspect, the first gRNA molecule and the second gRNA molecule include targeting domains comprising, e.g., consisting of, SEQ ID NO: 5571 and SEQ ID NO: 5731, respectively. In an aspect, the first gRNA molecule and the second gRNA molecule include targeting domains comprising, e.g., consisting of, SEQ ID NO: 5571 and SEQ ID NO: 5725, respectively. In an aspect, the first gRNA molecule and the second gRNA molecule include targeting domains comprising, e.g., consisting of, SEQ ID NO: 5571 and SEQ ID NO: 5775, respectively. In an aspect, the first gRNA molecule and the second gRNA molecule include targeting domains comprising, e.g., consisting of, SEQ ID NO: 5571 and SEQ ID NO: 5766, respectively. In an aspect, the first gRNA molecule and the second gRNA molecule include targeting domains comprising, e.g., consisting of, SEQ ID NO: 5571 and SEQ ID NO: 5727, respectively. In an aspect, the first gRNA molecule and the second gRNA molecule include targeting domains comprising, e.g., consisting of, SEQ ID NO: 5571 and SEQ ID NO: 5744, respectively. In an aspect, the first gRNA molecule and the second gRNA molecule include targeting domains comprising, e.g., consisting of, SEQ ID NO: 5571 and SEQ ID NO: 5751, respectively. In an aspect, the first gRNA molecule and the second gRNA molecule include targeting domains comprising, e.g., consisting of, SEQ ID NO: 5571 and SEQ ID NO: 5734, respectively. In an aspect, the first gRNA molecule and the second gRNA molecule include targeting domains comprising, e.g., consisting of, SEQ ID NO: 5593 and SEQ ID NO: 5743, respectively. In an aspect, the first gRNA molecule and the second gRNA molecule include targeting domains comprising, e.g., consisting of, SEQ ID NO: 5593 and SEQ ID NO: 5798, respectively. In an aspect, the first gRNA molecule and the second gRNA molecule include targeting domains comprising, e.g., consisting of, SEQ ID NO: 5593 and SEQ ID NO: 5748, respectively. In an aspect, the first gRNA molecule and the second gRNA molecule include targeting domains comprising, e.g., consisting of, SEQ ID NO: 5593 and SEQ ID NO: 5722, respectively. In an aspect, the first gRNA molecule and the second gRNA molecule include targeting domains comprising, e.g., consisting of, SEQ ID NO: 5593 and SEQ ID NO: 5800, respectively. In an aspect, the first gRNA molecule and the second gRNA molecule include targeting domains comprising, e.g., consisting of, SEQ ID NO: 5593 and SEQ ID NO: 5735, respectively. In an aspect, the first gRNA molecule and the second gRNA molecule include targeting domains comprising, e.g., consisting of, SEQ ID NO: 5593 and SEQ ID NO: 5724, respectively. In an aspect, the first gRNA molecule and the second gRNA molecule include targeting domains comprising, e.g., consisting of, SEQ ID NO: 5593 and SEQ ID NO: 5731, respectively. In an aspect, the first gRNA molecule and the second gRNA molecule include targeting domains comprising, e.g., consisting of, SEQ ID NO: 5593 and SEQ ID NO: 5725, respectively. In an aspect, the first gRNA molecule and the second gRNA molecule include targeting domains comprising, e.g., consisting of, SEQ ID NO: 5593 and SEQ ID NO: 5775, respectively. In an aspect, the first gRNA molecule and the second gRNA molecule include targeting domains comprising, e.g., consisting of, SEQ ID NO: 5593 and SEQ ID NO: 5766, respectively. In an aspect, the first gRNA molecule and the second gRNA molecule include targeting domains comprising, e.g., consisting of, SEQ ID NO: 5593 and SEQ ID NO: 5727, respectively. In an aspect, the first gRNA molecule and the second gRNA molecule include targeting domains comprising, e.g., consisting of, SEQ ID NO: 5593 and SEQ ID NO: 5744, respectively. In an aspect, the first gRNA molecule and the second gRNA molecule include targeting domains comprising, e.g., consisting of, SEQ ID NO: 5593 and SEQ ID NO: 5751, respectively. In an aspect, the first gRNA molecule and the second gRNA molecule include targeting domains comprising, e.g., consisting of, SEQ ID NO: 5593 and SEQ ID NO: 5734, respectively. In an aspect, the first gRNA molecule and the second gRNA molecule include targeting domains comprising, e.g., consisting of, SEQ ID NO: 5574 and SEQ ID NO: 5743, respectively. In an aspect, the first gRNA molecule and the second gRNA molecule include targeting domains comprising, e.g., consisting of, SEQ ID NO: 5574 and SEQ ID NO: 5798, respectively. In an aspect, the first gRNA molecule and the second gRNA molecule include targeting domains comprising, e.g., consisting of, SEQ ID NO: 5574 and SEQ ID NO: 5748, respectively. In an aspect, the first gRNA molecule and the second gRNA molecule include targeting domains comprising, e.g., consisting of, SEQ ID NO: 5574 and SEQ ID NO: 5722, respectively. In an aspect, the first gRNA molecule and the second gRNA molecule include targeting domains comprising, e.g., consisting of, SEQ ID NO: 5574 and SEQ ID NO: 5800, respectively. In an aspect, the first gRNA molecule and the second gRNA molecule include targeting domains comprising, e.g., consisting of, SEQ ID NO: 5574 and SEQ ID NO: 5735, respectively. In an aspect, the first gRNA molecule and the second gRNA molecule include targeting domains comprising, e.g., consisting of, SEQ ID NO: 5574 and SEQ ID NO: 5724, respectively. In an aspect, the first gRNA molecule and the second gRNA molecule include targeting domains comprising, e.g., consisting of, SEQ ID NO: 5574 and SEQ ID NO: 5731, respectively. In an aspect, the first gRNA molecule and the second gRNA molecule include targeting domains comprising, e.g., consisting of, SEQ ID NO: 5574 and SEQ ID NO: 5725, respectively. In an aspect, the first gRNA molecule and the second gRNA molecule include targeting domains comprising, e.g., consisting of, SEQ ID NO: 5574 and SEQ ID NO: 5775, respectively. In an aspect, the first gRNA molecule and the second gRNA molecule include targeting domains comprising, e.g., consisting of, SEQ ID NO: 5574 and SEQ ID NO: 5766, respectively. In an aspect, the first gRNA molecule and the second gRNA molecule include targeting domains comprising, e.g., consisting of, SEQ ID NO: 5574 and SEQ ID NO: 5727, respectively. In an aspect, the first gRNA molecule and the second gRNA molecule include targeting domains comprising, e.g., consisting of, SEQ ID NO: 5574 and SEQ ID NO: 5744, respectively. In an aspect, the first gRNA molecule and the second gRNA molecule include targeting domains comprising, e.g., consisting of, SEQ ID NO: 5574 and SEQ ID NO: 5751, respectively. In an aspect, the first gRNA molecule and the second gRNA molecule include targeting domains comprising, e.g., consisting of, SEQ ID NO: 5574 and SEQ ID NO: 5734, respectively. In an aspect, the first gRNA molecule and the second gRNA molecule include targeting domains comprising, e.g., consisting of, SEQ ID NO: 5598 and SEQ ID NO: 5743, respectively. In an aspect, the first gRNA molecule and the second gRNA molecule include targeting domains comprising, e.g., consisting of, SEQ ID NO: 5598 and SEQ ID NO: 5798, respectively. In an aspect, the first gRNA molecule and the second gRNA molecule include targeting domains comprising, e.g., consisting of, SEQ ID NO: 5598 and SEQ ID NO: 5748, respectively. In an aspect, the first gRNA molecule and the second gRNA molecule include targeting domains comprising, e.g., consisting of, SEQ ID NO: 5598 and SEQ ID NO: 5722, respectively. In an aspect, the first gRNA molecule and the second gRNA molecule include targeting domains comprising, e.g., consisting of, SEQ ID NO: 5598 and SEQ ID NO: 5800, respectively. In an aspect, the first gRNA molecule and the second gRNA molecule include targeting domains comprising, e.g., consisting of, SEQ ID NO: 5598 and SEQ ID NO: 5735, respectively. In an aspect, the first gRNA molecule and the second gRNA molecule include targeting domains comprising, e.g., consisting of, SEQ ID NO: 5598 and SEQ ID NO: 5724, respectively. In an aspect, the first gRNA molecule and the second gRNA molecule include targeting domains comprising, e.g., consisting of, SEQ ID NO: 5598 and SEQ ID NO: 5731, respectively. In an aspect, the first gRNA molecule and the second gRNA molecule include targeting domains comprising, e.g., consisting of, SEQ ID NO: 5598 and SEQ ID NO: 5725, respectively. In an aspect, the first gRNA molecule and the second gRNA molecule include targeting domains comprising, e.g., consisting of, SEQ ID NO: 5598 and SEQ ID NO: 5775, respectively. In an aspect, the first gRNA molecule and the second gRNA molecule include targeting domains comprising, e.g., consisting of, SEQ ID NO: 5598 and SEQ ID NO: 5766, respectively. In an aspect, the first gRNA molecule and the second gRNA molecule include targeting domains comprising, e.g., consisting of, SEQ ID NO: 5598 and SEQ ID NO: 5727, respectively. In an aspect, the first gRNA molecule and the second gRNA molecule include targeting domains comprising, e.g., consisting of, SEQ ID NO: 5598 and SEQ ID NO: 5744, respectively. In an aspect, the first gRNA molecule and the second gRNA molecule include targeting domains comprising, e.g., consisting of, SEQ ID NO: 5598 and SEQ ID NO: 5751, respectively. In an aspect, the first gRNA molecule and the second gRNA molecule include targeting domains comprising, e.g., consisting of, SEQ ID NO: 5598 and SEQ ID NO: 5734, respectively. In an aspect, the first gRNA molecule and the second gRNA molecule include targeting domains comprising, e.g., consisting of, SEQ ID NO: 5586 and SEQ ID NO: 5743, respectively. In an aspect, the first gRNA molecule and the second gRNA molecule include targeting domains comprising, e.g., consisting of, SEQ ID NO: 5586 and SEQ ID NO: 5798, respectively. In an aspect, the first gRNA molecule and the second gRNA molecule include targeting domains comprising, e.g., consisting of, SEQ ID NO: 5586 and SEQ ID NO: 5748, respectively. In an aspect, the first gRNA molecule and the second gRNA molecule include targeting domains comprising, e.g., consisting of, SEQ ID NO: 5586 and SEQ ID NO: 5722, respectively. In an aspect, the first gRNA molecule and the second gRNA molecule include targeting domains comprising, e.g., consisting of, SEQ ID NO: 5586 and SEQ ID NO: 5800, respectively. In an aspect, the first gRNA molecule and the second gRNA molecule include targeting domains comprising, e.g., consisting of, SEQ ID NO: 5586 and SEQ ID NO: 5735, respectively. In an aspect, the first gRNA molecule and the second gRNA molecule include targeting domains comprising, e.g., consisting of, SEQ ID NO: 5586 and SEQ ID NO: 5724, respectively. In an aspect, the first gRNA molecule and the second gRNA molecule include targeting domains comprising, e.g., consisting of, SEQ ID NO: 5586 and SEQ ID NO: 5731, respectively. In an aspect, the first gRNA molecule and the second gRNA molecule include targeting domains comprising, e.g., consisting of, SEQ ID NO: 5586 and SEQ ID NO: 5725, respectively. In an aspect, the first gRNA molecule and the second gRNA molecule include targeting domains comprising, e.g., consisting of, SEQ ID NO: 5586 and SEQ ID NO: 5775, respectively. In an aspect, the first gRNA molecule and the second gRNA molecule include targeting domains comprising, e.g., consisting of, SEQ ID NO: 5586 and SEQ ID NO: 5766, respectively. In an aspect, the first gRNA molecule and the second gRNA molecule include targeting domains comprising, e.g., consisting of, SEQ ID NO: 5586 and SEQ ID NO: 5727, respectively. In an aspect, the first gRNA molecule and the second gRNA molecule include targeting domains comprising, e.g., consisting of, SEQ ID NO: 5586 and SEQ ID NO: 5744, respectively. In an aspect, the first gRNA molecule and the second gRNA molecule include targeting domains comprising, e.g., consisting of, SEQ ID NO: 5586 and SEQ ID NO: 5751, respectively. In an aspect, the first gRNA molecule and the second gRNA molecule include targeting domains comprising, e.g., consisting of, SEQ ID NO: 5586 and SEQ ID NO: 5734, respectively. In an aspect, the first gRNA molecule and the second gRNA molecule include targeting domains comprising, e.g., consisting of, SEQ ID NO: 5599 and SEQ ID NO: 5743, respectively. In an aspect, the first gRNA molecule and the second gRNA molecule include targeting domains comprising, e.g., consisting of, SEQ ID NO: 5599 and SEQ ID NO: 5798, respectively. In an aspect, the first gRNA molecule and the second gRNA molecule include targeting domains comprising, e.g., consisting of, SEQ ID NO: 5599 and SEQ ID NO: 5748, respectively. In an aspect, the first gRNA molecule and the second gRNA molecule include targeting domains comprising, e.g., consisting of, SEQ ID NO: 5599 and SEQ ID NO: 5722, respectively. In an aspect, the first gRNA molecule and the second gRNA molecule include targeting domains comprising, e.g., consisting of, SEQ ID NO: 5599 and SEQ ID NO: 5800, respectively. In an aspect, the first gRNA molecule and the second gRNA molecule include targeting domains comprising, e.g., consisting of, SEQ ID NO: 5599 and SEQ ID NO: 5735, respectively. In an aspect, the first gRNA molecule and the second gRNA molecule include targeting domains comprising, e.g., consisting of, SEQ ID NO: 5599 and SEQ ID NO: 5724, respectively. In an aspect, the first gRNA molecule and the second gRNA molecule include targeting domains comprising, e.g., consisting of, SEQ ID NO: 5599 and SEQ ID NO: 5731, respectively. In an aspect, the first gRNA molecule and the second gRNA molecule include targeting domains comprising, e.g., consisting of, SEQ ID NO: 5599 and SEQ ID NO: 5725, respectively. In an aspect, the first gRNA molecule and the second gRNA molecule include targeting domains comprising, e.g., consisting of, SEQ ID NO: 5599 and SEQ ID NO: 5775, respectively. In an aspect, the first gRNA molecule and the second gRNA molecule include targeting domains comprising, e.g., consisting of, SEQ ID NO: 5599 and SEQ ID NO: 5766, respectively. In an aspect, the first gRNA molecule and the second gRNA molecule include targeting domains comprising, e.g., consisting of, SEQ ID NO: 5599 and SEQ ID NO: 5727, respectively. In an aspect, the first gRNA molecule and the second gRNA molecule include targeting domains comprising, e.g., consisting of, SEQ ID NO: 5599 and SEQ ID NO: 5744, respectively. In an aspect, the first gRNA molecule and the second gRNA molecule include targeting domains comprising, e.g., consisting of, SEQ ID NO: 5599 and SEQ ID NO: 5751, respectively. In an aspect, the first gRNA molecule and the second gRNA molecule include targeting domains comprising, e.g., consisting of, SEQ ID NO: 5599 and SEQ ID NO: 5734, respectively. In an aspect, the first gRNA molecule and the second gRNA molecule include targeting domains comprising, e.g., consisting of, SEQ ID NO: 5591 and SEQ ID NO: 5743, respectively. In an aspect, the first gRNA molecule and the second gRNA molecule include targeting domains comprising, e.g., consisting of, SEQ ID NO: 5591 and SEQ ID NO: 5798, respectively. In an aspect, the first gRNA molecule and the second gRNA molecule include targeting domains comprising, e.g., consisting of, SEQ ID NO: 5591 and SEQ ID NO: 5748, respectively. In an aspect, the first gRNA molecule and the second gRNA molecule include targeting domains comprising, e.g., consisting of, SEQ ID NO: 5591 and SEQ ID NO: 5722, respectively. In an aspect, the first gRNA molecule and the second gRNA molecule include targeting domains comprising, e.g., consisting of, SEQ ID NO: 5591 and SEQ ID NO: 5800, respectively. In an aspect, the first gRNA molecule and the second gRNA molecule include targeting domains comprising, e.g., consisting of, SEQ ID NO: 5591 and SEQ ID NO: 5735, respectively. In an aspect, the first gRNA molecule and the second gRNA molecule include targeting domains comprising, e.g., consisting of, SEQ ID NO: 5591 and SEQ ID NO: 5724, respectively. In an aspect, the first gRNA molecule and the second gRNA molecule include targeting domains comprising, e.g., consisting of, SEQ ID NO: 5591 and SEQ ID NO: 5731, respectively. In an aspect, the first gRNA molecule and the second gRNA molecule include targeting domains comprising, e.g., consisting of, SEQ ID NO: 5591 and SEQ ID NO: 5725, respectively. In an aspect, the first gRNA molecule and the second gRNA molecule include targeting domains comprising, e.g., consisting of, SEQ ID NO: 5591 and SEQ ID NO: 5775, respectively. In an aspect, the first gRNA molecule and the second gRNA molecule include targeting domains comprising, e.g., consisting of, SEQ ID NO: 5591 and SEQ ID NO: 5766, respectively. In an aspect, the first gRNA molecule and the second gRNA molecule include targeting domains comprising, e.g., consisting of, SEQ ID NO: 5591 and SEQ ID NO: 5727, respectively. In an aspect, the first gRNA molecule and the second gRNA molecule include targeting domains comprising, e.g., consisting of, SEQ ID NO: 5591 and SEQ ID NO: 5744, respectively. In an aspect, the first gRNA molecule and the second gRNA molecule include targeting domains comprising, e.g., consisting of, SEQ ID NO: 5591 and SEQ ID NO: 5751, respectively. In an aspect, the first gRNA molecule and the second gRNA molecule include targeting domains comprising, e.g., consisting of, SEQ ID NO: 5591 and SEQ ID NO: 5734, respectively. In an aspect, the first gRNA molecule and the second gRNA molecule include targeting domains comprising, e.g., consisting of, SEQ ID NO: 5568 and SEQ ID NO: 5743, respectively. In an aspect, the first gRNA molecule and the second gRNA molecule include targeting domains comprising, e.g., consisting of, SEQ ID NO: 5568 and SEQ ID NO: 5798, respectively. In an aspect, the first gRNA molecule and the second gRNA molecule include targeting domains comprising, e.g., consisting of, SEQ ID NO: 5568 and SEQ ID NO: 5748, respectively. In an aspect, the first gRNA molecule and the second gRNA molecule include targeting domains comprising, e.g., consisting of, SEQ ID NO: 5568 and SEQ ID NO: 5722, respectively. In an aspect, the first gRNA molecule and the second gRNA molecule include targeting domains comprising, e.g., consisting of, SEQ ID NO: 5568 and SEQ ID NO: 5800, respectively. In an aspect, the first gRNA molecule and the second gRNA molecule include targeting domains comprising, e.g., consisting of, SEQ ID NO: 5568 and SEQ ID NO: 5735, respectively. In an aspect, the first gRNA molecule and the second gRNA molecule include targeting domains comprising, e.g., consisting of, SEQ ID NO: 5568 and SEQ ID NO: 5724, respectively. In an aspect, the first gRNA molecule and the second gRNA molecule include targeting domains comprising, e.g., consisting of, SEQ ID NO: 5568 and SEQ ID NO: 5731, respectively. In an aspect, the first gRNA molecule and the second gRNA molecule include targeting domains comprising, e.g., consisting of, SEQ ID NO: 5568 and SEQ ID NO: 5725, respectively. In an aspect, the first gRNA molecule and the second gRNA molecule include targeting domains comprising, e.g., consisting of, SEQ ID NO: 5568 and SEQ ID NO: 5775, respectively. In an aspect, the first gRNA molecule and the second gRNA molecule include targeting domains comprising, e.g., consisting of, SEQ ID NO: 5568 and SEQ ID NO: 5766, respectively. In an aspect, the first gRNA molecule and the second gRNA molecule include targeting domains comprising, e.g., consisting of, SEQ ID NO: 5568 and SEQ ID NO: 5727, respectively. In an aspect, the first gRNA molecule and the second gRNA molecule include targeting domains comprising, e.g., consisting of, SEQ ID NO: 5568 and SEQ ID NO: 5744, respectively. In an aspect, the first gRNA molecule and the second gRNA molecule include targeting domains comprising, e.g., consisting of, SEQ ID NO: 5568 and SEQ ID NO: 5751, respectively. In an aspect, the first gRNA molecule and the second gRNA molecule include targeting domains comprising, e.g., consisting of, SEQ ID NO: 5568 and SEQ ID NO: 5734, respectively. In an aspect, the first gRNA molecule and the second gRNA molecule include targeting domains comprising, e.g., consisting of, SEQ ID NO: 5610 and SEQ ID NO: 5743, respectively. In an aspect, the first gRNA molecule and the second gRNA molecule include targeting domains comprising, e.g., consisting of, SEQ ID NO: 5610 and SEQ ID NO: 5798, respectively. In an aspect, the first gRNA molecule and the second gRNA molecule include targeting domains comprising, e.g., consisting of, SEQ ID NO: 5610 and SEQ ID NO: 5748, respectively. In an aspect, the first gRNA molecule and the second gRNA molecule include targeting domains comprising, e.g., consisting of, SEQ ID NO: 5610 and SEQ ID NO: 5722, respectively. In an aspect, the first gRNA molecule and the second gRNA molecule include targeting domains comprising, e.g., consisting of, SEQ ID NO: 5610 and SEQ ID NO: 5800, respectively. In an aspect, the first gRNA molecule and the second gRNA molecule include targeting domains comprising, e.g., consisting of, SEQ ID NO: 5610 and SEQ ID NO: 5735, respectively. In an aspect, the first gRNA molecule and the second gRNA molecule include targeting domains comprising, e.g., consisting of, SEQ ID NO: 5610 and SEQ ID NO: 5724, respectively. In an aspect, the first gRNA molecule and the second gRNA molecule include targeting domains comprising, e.g., consisting of, SEQ ID NO: 5610 and SEQ ID NO: 5731, respectively. In an aspect, the first gRNA molecule and the second gRNA molecule include targeting domains comprising, e.g., consisting of, SEQ ID NO: 5610 and SEQ ID NO: 5725, respectively. In an aspect, the first gRNA molecule and the second gRNA molecule include targeting domains comprising, e.g., consisting of, SEQ ID NO: 5610 and SEQ ID NO: 5775, respectively. In an aspect, the first gRNA molecule and the second gRNA molecule include targeting domains comprising, e.g., consisting of, SEQ ID NO: 5610 and SEQ ID NO: 5766, respectively. In an aspect, the first gRNA molecule and the second gRNA molecule include targeting domains comprising, e.g., consisting of, SEQ ID NO: 5610 and SEQ ID NO: 5727, respectively. In an aspect, the first gRNA molecule and the second gRNA molecule include targeting domains comprising, e.g., consisting of, SEQ ID NO: 5610 and SEQ ID NO: 5744, respectively. In an aspect, the first gRNA molecule and the second gRNA molecule include targeting domains comprising, e.g., consisting of, SEQ ID NO: 5610 and SEQ ID NO: 5751, respectively. In an aspect, the first gRNA molecule and the second gRNA molecule include targeting domains comprising, e.g., consisting of, SEQ ID NO: 5610 and SEQ ID NO: 5734, respectively. In an aspect, the first gRNA molecule and the second gRNA molecule include targeting domains comprising, e.g., consisting of, SEQ ID NO: 5608 and SEQ ID NO: 5743, respectively. In an aspect, the first gRNA molecule and the second gRNA molecule include targeting domains comprising, e.g., consisting of, SEQ ID NO: 5608 and SEQ ID NO: 5798, respectively. In an aspect, the first gRNA molecule and the second gRNA molecule include targeting domains comprising, e.g., consisting of, SEQ ID NO: 5608 and SEQ ID NO: 5748, respectively. In an aspect, the first gRNA molecule and the second gRNA molecule include targeting domains comprising, e.g., consisting of, SEQ ID NO: 5608 and SEQ ID NO: 5722, respectively. In an aspect, the first gRNA molecule and the second gRNA molecule include targeting domains comprising, e.g., consisting of, SEQ ID NO: 5608 and SEQ ID NO: 5800, respectively. In an aspect, the first gRNA molecule and the second gRNA molecule include targeting domains comprising, e.g., consisting of, SEQ ID NO: 5608 and SEQ ID NO: 5735, respectively. In an aspect, the first gRNA molecule and the second gRNA molecule include targeting domains comprising, e.g., consisting of, SEQ ID NO: 5608 and SEQ ID NO: 5724, respectively. In an aspect, the first gRNA molecule and the second gRNA molecule include targeting domains comprising, e.g., consisting of, SEQ ID NO: 5608 and SEQ ID NO: 5731, respectively. In an aspect, the first gRNA molecule and the second gRNA molecule include targeting domains comprising, e.g., consisting of, SEQ ID NO: 5608 and SEQ ID NO: 5725, respectively. In an aspect, the first gRNA molecule and the second gRNA molecule include targeting domains comprising, e.g., consisting of, SEQ ID NO: 5608 and SEQ ID NO: 5775, respectively. In an aspect, the first gRNA molecule and the second gRNA molecule include targeting domains comprising, e.g., consisting of, SEQ ID NO: 5608 and SEQ ID NO: 5766, respectively. In an aspect, the first gRNA molecule and the second gRNA molecule include targeting domains comprising, e.g., consisting of, SEQ ID NO: 5608 and SEQ ID NO: 5727, respectively. In an aspect, the first gRNA molecule and the second gRNA molecule include targeting domains comprising, e.g., consisting of, SEQ ID NO: 5608 and SEQ ID NO: 5744, respectively. In an aspect, the first gRNA molecule and the second gRNA molecule include targeting domains comprising, e.g., consisting of, SEQ ID NO: 5608 and SEQ ID NO: 5751, respectively. In an aspect, the first gRNA molecule and the second gRNA molecule include targeting domains comprising, e.g., consisting of, SEQ ID NO: 5608 and SEQ ID NO: 5734, respectively. In an aspect, the first gRNA molecule and the second gRNA molecule include targeting domains comprising, e.g., consisting of, SEQ ID NO: 5617 and SEQ ID NO: 5743, respectively. In an aspect, the first gRNA molecule and the second gRNA molecule include targeting domains comprising, e.g., consisting of, SEQ ID NO: 5617 and SEQ ID NO: 5798, respectively. In an aspect, the first gRNA molecule and the second gRNA molecule include targeting domains comprising, e.g., consisting of, SEQ ID NO: 5617 and SEQ ID NO: 5748, respectively. In an aspect, the first gRNA molecule and the second gRNA molecule include targeting domains comprising, e.g., consisting of, SEQ ID NO: 5617 and SEQ ID NO: 5722, respectively. In an aspect, the first gRNA molecule and the second gRNA molecule include targeting domains comprising, e.g., consisting of, SEQ ID NO: 5617 and SEQ ID NO: 5800, respectively. In an aspect, the first gRNA molecule and the second gRNA molecule include targeting domains comprising, e.g., consisting of, SEQ ID NO: 5617 and SEQ ID NO: 5735, respectively. In an aspect, the first gRNA molecule and the second gRNA molecule include targeting domains comprising, e.g., consisting of, SEQ ID NO: 5617 and SEQ ID NO: 5724, respectively. In an aspect, the first gRNA molecule and the second gRNA molecule include targeting domains comprising, e.g., consisting of, SEQ ID NO: 5617 and SEQ ID NO: 5731, respectively. In an aspect, the first gRNA molecule and the second gRNA molecule include targeting domains comprising, e.g., consisting of, SEQ ID NO: 5617 and SEQ ID NO: 5725, respectively. In an aspect, the first gRNA molecule and the second gRNA molecule include targeting domains comprising, e.g., consisting of, SEQ ID NO: 5617 and SEQ ID NO: 5775, respectively. In an aspect, the first gRNA molecule and the second gRNA molecule include targeting domains comprising, e.g., consisting of, SEQ ID NO: 5617 and SEQ ID NO: 5766, respectively. In an aspect, the first gRNA molecule and the second gRNA molecule include targeting domains comprising, e.g., consisting of, SEQ ID NO: 5617 and SEQ ID NO: 5727, respectively. In an aspect, the first gRNA molecule and the second gRNA molecule include targeting domains comprising, e.g., consisting of, SEQ ID NO: 5617 and SEQ ID NO: 5744, respectively. In an aspect, the first gRNA molecule and the second gRNA molecule include targeting domains comprising, e.g., consisting of, SEQ ID NO: 5617 and SEQ ID NO: 5751, respectively. In an aspect, the first gRNA molecule and the second gRNA molecule include targeting domains comprising, e.g., consisting of, SEQ ID NO: 5617 and SEQ ID NO: 5734, respectively. In an aspect, the first gRNA molecule and the second gRNA molecule include targeting domains comprising, e.g., consisting of, SEQ ID NO: 5619 and SEQ ID NO: 5743, respectively. In an aspect, the first gRNA molecule and the second gRNA molecule include targeting domains comprising, e.g., consisting of, SEQ ID NO: 5619 and SEQ ID NO: 5798, respectively. In an aspect, the first gRNA molecule and the second gRNA molecule include targeting domains comprising, e.g., consisting of, SEQ ID NO: 5619 and SEQ ID NO: 5748, respectively. In an aspect, the first gRNA molecule and the second gRNA molecule include targeting domains comprising, e.g., consisting of, SEQ ID NO: 5619 and SEQ ID NO: 5722, respectively. In an aspect, the first gRNA molecule and the second gRNA molecule include targeting domains comprising, e.g., consisting of, SEQ ID NO: 5619 and SEQ ID NO: 5800, respectively. In an aspect, the first gRNA molecule and the second gRNA molecule include targeting domains comprising, e.g., consisting of, SEQ ID NO: 5619 and SEQ ID NO: 5735, respectively. In an aspect, the first gRNA molecule and the second gRNA molecule include targeting domains comprising, e.g., consisting of, SEQ ID NO: 5619 and SEQ ID NO: 5724, respectively. In an aspect, the first gRNA molecule and the second gRNA molecule include targeting domains comprising, e.g., consisting of, SEQ ID NO: 5619 and SEQ ID NO: 5731, respectively. In an aspect, the first gRNA molecule and the second gRNA molecule include targeting domains comprising, e.g., consisting of, SEQ ID NO: 5619 and SEQ ID NO: 5725, respectively. In an aspect, the first gRNA molecule and the second gRNA molecule include targeting domains comprising, e.g., consisting of, SEQ ID NO: 5619 and SEQ ID NO: 5775, respectively. In an aspect, the first gRNA molecule and the second gRNA molecule include targeting domains comprising, e.g., consisting of, SEQ ID NO: 5619 and SEQ ID NO: 5766, respectively. In an aspect, the first gRNA molecule and the second gRNA molecule include targeting domains comprising, e.g., consisting of, SEQ ID NO: 5619 and SEQ ID NO: 5727, respectively. In an aspect, the first gRNA molecule and the second gRNA molecule include targeting domains comprising, e.g., consisting of, SEQ ID NO: 5619 and SEQ ID NO: 5744, respectively. In an aspect, the first gRNA molecule and the second gRNA molecule include targeting domains comprising, e.g., consisting of, SEQ ID NO: 5619 and SEQ ID NO: 5751, respectively. In an aspect, the first gRNA molecule and the second gRNA molecule include targeting domains comprising, e.g., consisting of, SEQ ID NO: 5619 and SEQ ID NO: 5734, respectively. In an aspect, the first gRNA molecule and the second gRNA molecule include targeting domains comprising, e.g., consisting of, SEQ ID NO: 5620 and SEQ ID NO: 5743, respectively. In an aspect, the first gRNA molecule and the second gRNA molecule include targeting domains comprising, e.g., consisting of, SEQ ID NO: 5620 and SEQ ID NO: 5798, respectively. In an aspect, the first gRNA molecule and the second gRNA molecule include targeting domains comprising, e.g., consisting of, SEQ ID NO: 5620 and SEQ ID NO: 5748, respectively. In an aspect, the first gRNA molecule and the second gRNA molecule include targeting domains comprising, e.g., consisting of, SEQ ID NO: 5620 and SEQ ID NO: 5722, respectively. In an aspect, the first gRNA molecule and the second gRNA molecule include targeting domains comprising, e.g., consisting of, SEQ ID NO: 5620 and SEQ ID NO: 5800, respectively. In an aspect, the first gRNA molecule and the second gRNA molecule include targeting domains comprising, e.g., consisting of, SEQ ID NO: 5620 and SEQ ID NO: 5735, respectively. In an aspect, the first gRNA molecule and the second gRNA molecule include targeting domains comprising, e.g., consisting of, SEQ ID NO: 5620 and SEQ ID NO: 5724, respectively. In an aspect, the first gRNA molecule and the second gRNA molecule include targeting domains comprising, e.g., consisting of, SEQ ID NO: 5620 and SEQ ID NO: 5731, respectively. In an aspect, the first gRNA molecule and the second gRNA molecule include targeting domains comprising, e.g., consisting of, SEQ ID NO: 5620 and SEQ ID NO: 5725, respectively. In an aspect, the first gRNA molecule and the second gRNA molecule include targeting domains comprising, e.g., consisting of, SEQ ID NO: 5620 and SEQ ID NO: 5775, respectively. In an aspect, the first gRNA molecule and the second gRNA molecule include targeting domains comprising, e.g., consisting of, SEQ ID NO: 5620 and SEQ ID NO: 5766, respectively. In an aspect, the first gRNA molecule and the second gRNA molecule include targeting domains comprising, e.g., consisting of, SEQ ID NO: 5620 and SEQ ID NO: 5727, respectively. In an aspect, the first gRNA molecule and the second gRNA molecule include targeting domains comprising, e.g., consisting of, SEQ ID NO: 5620 and SEQ ID NO: 5744, respectively. In an aspect, the first gRNA molecule and the second gRNA molecule include targeting domains comprising, e.g., consisting of, SEQ ID NO: 5620 and SEQ ID NO: 5751, respectively. In an aspect, the first gRNA molecule and the second gRNA molecule include targeting domains comprising, e.g., consisting of, SEQ ID NO: 5620 and SEQ ID NO: 5734, respectively.

As described herein, it is contemplated to generate a cell (or population of cells), e.g., an immune effector cell, e.g., a CAR-expressing immune effector cell, e.g., as described herein, which has reduced or eliminated expression of TRAC, B2M and CIITA. While it is contemplated that gRNAs comprising any targeting domain disclosed herein to each of these targets may be used in combination, particularly preferred targeting domain sequences to be used, for example, in combination are provided in the Table 33 below. In embodiments, each of the gRNA molecules are provided in dual guide RNA format and include a crRNA comprising, e.g., consisting of, the sequence [targeting domain]-SEQ ID NO: 6607, and a tracr comprising, e.g., consisting of, the sequence of SEQ ID NO: 6660. In other embodiments, each of the gRNA molecules are provided in single guide RNA format comprising, e.g., consisting of, the sequence: [targeting domain]-SEQ ID NO: 6601. In other embodiments, each of the gRNA molecules are provided in single guide RNA format comprising, e.g., consisting of, the sequence: [targeting domain]-SEQ ID NO: 7811. In embodiments, one or more of the gRNA molecules, e.g., all of the gRNA molecules, additionally comprise one or more modifications described herein, e.g., comprise one or more, e.g., 3, 3' and/or 5' phosphorothioate bonds, and/or one or more, e.g., 3, 3' and/or 5' 2'-OMe modifications. In embodiments, each of the gRNA molecules is complexed with a Cas9 molecule (e.g., described herein) and delivered to the cell (or population of cells, e.g., as described herein) as RNP, e.g., by electroporation. In embodiments, the RNP comprising each gRNA molecule are mixed with the cells and introduced simultaneously, e.g., by a single electroporation step. In other embodiments, the RNP may be introduced sequentially. Where it is contemplated to reduce or eliminate expression of both B2M and CIITA in a cell (such as here), in embodiments the cells may be further engineered to express a NK inhibitory molecule, e.g., as described herein, e.g., an HLA-G:B2M fusion described herein.

TABLE 33

Examples of preferred targeting domains of first, second and third gRNA molecules that can be used in combination to reduce or eliminate expression of TRAC, B2M and CIITA in a cell (as described herein).

| Combination Number | SEQ ID NO: s of targeting domains of first gRNA, second gRNA and third gRNA, respectively |
|---|---|
| A1 | SEQ ID NO: 5569 and SEQ ID NO: 7769 and SEQ ID NO: 5496 |
| A2 | SEQ ID NO: 5569 and SEQ ID NO: 7771 and SEQ ID NO: 5496 |
| A3 | SEQ ID NO: 5569 and SEQ ID NO: 7739 and SEQ ID NO: 5496 |
| A4 | SEQ ID NO: 5569 and SEQ ID NO: 7785 and SEQ ID NO: 5496 |
| A5 | SEQ ID NO: 5569 and SEQ ID NO: 7769 and SEQ ID NO: 5498 |
| A6 | SEQ ID NO: 5569 and SEQ ID NO: 7771 and SEQ ID NO: 5498 |
| A7 | SEQ ID NO: 5569 and SEQ ID NO: 7739 and SEQ ID NO: 5498 |
| A8 | SEQ ID NO: 5569 and SEQ ID NO: 7785 and SEQ ID NO: 5498 |

TABLE 33-continued

Examples of preferred targeting domains of first, second and third gRNA molecules that can be used in combination to reduce or eliminate expression of TRAC, B2M and CIITA in a cell (as described herein).

| Combination Number | SEQ ID NO: s of targeting domains of first gRNA, second gRNA and third gRNA, respectively |
|---|---|
| A9 | SEQ ID NO: 5569 and SEQ ID NO: 7769 and SEQ ID NO: 5509 |
| A10 | SEQ ID NO: 5569 and SEQ ID NO: 7771 and SEQ ID NO: 5509 |
| A11 | SEQ ID NO: 5569 and SEQ ID NO: 7739 and SEQ ID NO: 5509 |
| A12 | SEQ ID NO: 5569 and SEQ ID NO: 7785 and SEQ ID NO: 5509 |
| A13 | SEQ ID NO: 5586 and SEQ ID NO: 7769 and SEQ ID NO: 5496 |
| A14 | SEQ ID NO: 5586 and SEQ ID NO: 7771 and SEQ ID NO: 5496 |
| A15 | SEQ ID NO: 5586 and SEQ ID NO: 7739 and SEQ ID NO: 5496 |
| A16 | SEQ ID NO: 5586 and SEQ ID NO: 7785 and SEQ ID NO: 5496 |
| A17 | SEQ ID NO: 5586 and SEQ ID NO: 7769 and SEQ ID NO: 5498 |
| A18 | SEQ ID NO: 5586 and SEQ ID NO: 7771 and SEQ ID NO: 5498 |
| A19 | SEQ ID NO: 5586 and SEQ ID NO: 7739 and SEQ ID NO: 5498 |
| A20 | SEQ ID NO: 5586 and SEQ ID NO: 7785 and SEQ ID NO: 5498 |
| A21 | SEQ ID NO: 5586 and SEQ ID NO: 7769 and SEQ ID NO: 5509 |
| A22 | SEQ ID NO: 5586 and SEQ ID NO: 7771 and SEQ ID NO: 5509 |
| A23 | SEQ ID NO: 5586 and SEQ ID NO: 7739 and SEQ ID NO: 5509 |
| A24 | SEQ ID NO: 5586 and SEQ ID NO: 7785 and SEQ ID NO: 5509 |
| A25 | SEQ ID NO: 5587 and SEQ ID NO: 7769 and SEQ ID NO: 5496 |
| A26 | SEQ ID NO: 5587 and SEQ ID NO: 7771 and SEQ ID NO: 5496 |
| A27 | SEQ ID NO: 5587 and SEQ ID NO: 7739 and SEQ ID NO: 5496 |
| A28 | SEQ ID NO: 5587 and SEQ ID NO: 7785 and SEQ ID NO: 5496 |
| A29 | SEQ ID NO: 5587 and SEQ ID NO: 7769 and SEQ ID NO: 5498 |
| A30 | SEQ ID NO: 5587 and SEQ ID NO: 7771 and SEQ ID NO: 5498 |
| A31 | SEQ ID NO: 5587 and SEQ ID NO: 7739 and SEQ ID NO: 5498 |
| A32 | SEQ ID NO: 5587 and SEQ ID NO: 7785 and SEQ ID NO: 5498 |
| A33 | SEQ ID NO: 5587 and SEQ ID NO: 7769 and SEQ ID NO: 5509 |
| A34 | SEQ ID NO: 5587 and SEQ ID NO: 7771 and SEQ ID NO: 5509 |
| A35 | SEQ ID NO: 5587 and SEQ ID NO: 7739 and SEQ ID NO: 5509 |
| A36 | SEQ ID NO: 5587 and SEQ ID NO: 7785 and SEQ ID NO: 5509 |
| A37 | SEQ ID NO: 5592 and SEQ ID NO: 7769 and SEQ ID NO: 5496 |
| A38 | SEQ ID NO: 5592 and SEQ ID NO: 7771 and SEQ ID NO: 5496 |
| A39 | SEQ ID NO: 5592 and SEQ ID NO: 7739 and SEQ ID NO: 5496 |
| A40 | SEQ ID NO: 5592 and SEQ ID NO: 7785 and SEQ ID NO: 5496 |
| A41 | SEQ ID NO: 5592 and SEQ ID NO: 7769 and SEQ ID NO: 5498 |
| A42 | SEQ ID NO: 5592 and SEQ ID NO: 7771 and SEQ ID NO: 5498 |
| A43 | SEQ ID NO: 5592 and SEQ ID NO: 7739 and SEQ ID NO: 5498 |

TABLE 33-continued

Examples of preferred targeting domains of first, second and third gRNA molecules that can be used in combination to reduce or eliminate expression of TRAC, B2M and CIITA in a cell (as described herein).

| Combination Number | SEQ ID NO: s of targeting domains of first gRNA, second gRNA and third gRNA, respectively |
|---|---|
| A44 | SEQ ID NO: 5592 and SEQ ID NO: 7785 and SEQ ID NO: 5498 |
| A45 | SEQ ID NO: 5592 and SEQ ID NO: 7769 and SEQ ID NO: 5509 |
| A46 | SEQ ID NO: 5592 and SEQ ID NO: 7771 and SEQ ID NO: 5509 |
| A47 | SEQ ID NO: 5592 and SEQ ID NO: 7739 and SEQ ID NO: 5509 |
| A48 | SEQ ID NO: 5592 and SEQ ID NO: 7785 and SEQ ID NO: 5509 |
| A49 | SEQ ID NO: 5599 and SEQ ID NO: 7769 and SEQ ID NO: 5496 |
| A50 | SEQ ID NO: 5599 and SEQ ID NO: 7771 and SEQ ID NO: 5496 |
| A51 | SEQ ID NO: 5599 and SEQ ID NO: 7739 and SEQ ID NO: 5496 |
| A52 | SEQ ID NO: 5599 and SEQ ID NO: 7785 and SEQ ID NO: 5496 |
| A53 | SEQ ID NO: 5599 and SEQ ID NO: 7769 and SEQ ID NO: 5498 |
| A54 | SEQ ID NO: 5599 and SEQ ID NO: 7771 and SEQ ID NO: 5498 |
| A55 | SEQ ID NO: 5599 and SEQ ID NO: 7739 and SEQ ID NO: 5498 |
| A56 | SEQ ID NO: 5599 and SEQ ID NO: 7785 and SEQ ID NO: 5498 |
| A57 | SEQ ID NO: 5599 and SEQ ID NO: 7769 and SEQ ID NO: 5509 |
| A58 | SEQ ID NO: 5599 and SEQ ID NO: 7771 and SEQ ID NO: 5509 |
| A59 | SEQ ID NO: 5599 and SEQ ID NO: 7739 and SEQ ID NO: 5509 |
| A60 | SEQ ID NO: 5599 and SEQ ID NO: 7785 and SEQ ID NO: 5509 |
| A61 | SEQ ID NO: 5600 and SEQ ID NO: 7769 and SEQ ID NO: 5496 |
| A62 | SEQ ID NO: 5600 and SEQ ID NO: 7771 and SEQ ID NO: 5496 |
| A63 | SEQ ID NO: 5600 and SEQ ID NO: 7739 and SEQ ID NO: 5496 |
| A64 | SEQ ID NO: 5600 and SEQ ID NO: 7785 and SEQ ID NO: 5496 |
| A65 | SEQ ID NO: 5600 and SEQ ID NO: 7769 and SEQ ID NO: 5498 |
| A66 | SEQ ID NO: 5600 and SEQ ID NO: 7771 and SEQ ID NO: 5498 |
| A67 | SEQ ID NO: 5600 and SEQ ID NO: 7739 and SEQ ID NO: 5498 |
| A68 | SEQ ID NO: 5600 and SEQ ID NO: 7785 and SEQ ID NO: 5498 |
| A69 | SEQ ID NO: 5600 and SEQ ID NO: 7769 and SEQ ID NO: 5509 |
| A70 | SEQ ID NO: 5600 and SEQ ID NO: 7771 and SEQ ID NO: 5509 |
| A71 | SEQ ID NO: 5600 and SEQ ID NO: 7739 and SEQ ID NO: 5509 |
| A72 | SEQ ID NO: 5600 and SEQ ID NO: 7785 and SEQ ID NO: 5509 |

Particularly preferred combinations include combination A1 to A4, combination A5 to A8, combination A37 to A40, or combination A41 to A44.

As described herein, it is contemplated to generate a cell (or population of cells), e.g., an immune effector cell, e.g., a CAR-expressing immune effector cell, e.g., as described herein, which has reduced or eliminated expression of CD3E, B2M and CIITA. While it is contemplated that gRNAs comprising any targeting domain disclosed herein to each of these targets may be used in combination, particularly preferred targeting domain sequences to be used, for example, in combination are provided in the Table 34 below. In embodiments, each of the gRNA molecules are provided in dual guide RNA format and include a crRNA comprising, e.g., consisting of, the sequence [targeting domain]-SEQ ID NO: 6607, and a tracr comprising, e.g., consisting of, the sequence of SEQ ID NO: 6660. In other embodiments, each of the gRNA molecules are provided in single guide RNA format comprising, e.g., consisting of, the sequence: [targeting domain]-SEQ ID NO: 6601. In other embodiments, each of the gRNA molecules are provided in single guide RNA format comprising, e.g., consisting of, the sequence: [targeting domain]-SEQ ID NO: 7811. In embodiments, one or more of the gRNA molecules, e.g., all of the gRNA molecules, additionally comprise one or more modifications described herein, e.g., comprise one or more, e.g., 3, 3' and/or 5' phosphorothioate bonds, and/or one or more, e.g., 3, 3' and/or 5' 2'-OMe modifications. In embodiments, each of the gRNA molecules is complexed with a Cas9 molecule (e.g., described herein) and delivered to the cell (or population of cells, e.g., as described herein) as RNP, e.g., by electroporation. In embodiments, the RNP comprising each gRNA molecule are mixed with the cells and introduced simultaneously, e.g., by a single electroporation step. In other embodiments, the RNP may be introduced sequentially. Where it is contemplated to reduce or eliminate expression of both B2M and CIITA in a cell (such as here), in embodiments the cells may be further engineered to express a NK inhibitory molecule, e.g., as described herein, e.g., an HLA-G:B2M fusion described herein.

TABLE 34

Examples of preferred targeting domains of first, second and third gRNA molecules that can be used in combination to reduce or eliminate expression of CD3E, B2M and CIITA in a cell (as described herein).

| Combination Number | SEQ ID NO: s of targeting domains of first gRNA, second gRNA and third gRNA, respectively |
|---|---|
| B1 | SEQ ID NO: 10729 and SEQ ID NO: 7769 and SEQ ID NO: 5496 |
| B2 | SEQ ID NO: 10729 and SEQ ID NO: 7771 and SEQ ID NO: 5496 |
| B3 | SEQ ID NO: 10729 and SEQ ID NO: 7739 and SEQ ID NO: 5496 |
| B4 | SEQ ID NO: 10729 and SEQ ID NO: 7785 and SEQ ID NO: 5496 |
| B5 | SEQ ID NO: 10729 and SEQ ID NO: 7769 and SEQ ID NO: 5498 |
| B6 | SEQ ID NO: 10729 and SEQ ID NO: 7771 and SEQ ID NO: 5498 |
| B7 | SEQ ID NO: 10729 and SEQ ID NO: 7739 and SEQ ID NO: 5498 |
| B8 | SEQ ID NO: 10729 and SEQ ID NO: 7785 and SEQ ID NO: 5498 |
| B9 | SEQ ID NO: 10729 and SEQ ID NO: 7769 and SEQ ID NO: 5509 |
| B10 | SEQ ID NO: 10729 and SEQ ID NO: 7771 and SEQ ID NO: 5509 |
| B11 | SEQ ID NO: 10729 and SEQ ID NO: 7739 and SEQ ID NO: 5509 |
| B12 | SEQ ID NO: 10729 and SEQ ID NO: 7785 and SEQ ID NO: 5509 |
| B13 | SEQ ID NO: 10719 and SEQ ID NO: 7769 and SEQ ID NO: 5496 |
| B14 | SEQ ID NO: 10719 and SEQ ID NO: 7771 and SEQ ID NO: 5496 |
| B15 | SEQ ID NO: 10719 and SEQ ID NO: 7739 and SEQ ID NO: 5496 |

TABLE 34-continued

Examples of preferred targeting domains of first, second and third gRNA molecules that can be used in combination to reduce or eliminate expression of CD3E, B2M and CIITA in a cell (as described herein).

| Combination Number | SEQ ID NO: s of targeting domains of first gRNA, second gRNA and third gRNA, respectively |
|---|---|
| B16 | SEQ ID NO: 10719 and SEQ ID NO: 7785 and SEQ ID NO: 5496 |
| B17 | SEQ ID NO: 10719 and SEQ ID NO: 7769 and SEQ ID NO: 5498 |
| B18 | SEQ ID NO: 10719 and SEQ ID NO: 7771 and SEQ ID NO: 5498 |
| B19 | SEQ ID NO: 10719 and SEQ ID NO: 7739 and SEQ ID NO: 5498 |
| B20 | SEQ ID NO: 10719 and SEQ ID NO: 7785 and SEQ ID NO: 5498 |
| B21 | SEQ ID NO: 10719 and SEQ ID NO: 7769 and SEQ ID NO: 5509 |
| B22 | SEQ ID NO: 10719 and SEQ ID NO: 7771 and SEQ ID NO: 5509 |
| B23 | SEQ ID NO: 10719 and SEQ ID NO: 7739 and SEQ ID NO: 5509 |
| B24 | SEQ ID NO: 10719 and SEQ ID NO: 7785 and SEQ ID NO: 5509 |
| B25 | SEQ ID NO: 10764 and SEQ ID NO: 7769 and SEQ ID NO: 5496 |
| B26 | SEQ ID NO: 10764 and SEQ ID NO: 7771 and SEQ ID NO: 5496 |
| B27 | SEQ ID NO: 10764 and SEQ ID NO: 7739 and SEQ ID NO: 5496 |
| B28 | SEQ ID NO: 10764 and SEQ ID NO: 7785 and SEQ ID NO: 5496 |
| B29 | SEQ ID NO: 10764 and SEQ ID NO: 7769 and SEQ ID NO: 5498 |
| B30 | SEQ ID NO: 10764 and SEQ ID NO: 7771 and SEQ ID NO: 5498 |
| B31 | SEQ ID NO: 10764 and SEQ ID NO: 7739 and SEQ ID NO: 5498 |
| B32 | SEQ ID NO: 10764 and SEQ ID NO: 7785 and SEQ ID NO: 5498 |
| B33 | SEQ ID NO: 10764 and SEQ ID NO: 7769 and SEQ ID NO: 5509 |
| B34 | SEQ ID NO: 10764 and SEQ ID NO: 7771 and SEQ ID NO: 5509 |
| B35 | SEQ ID NO: 10764 and SEQ ID NO: 7739 and SEQ ID NO: 5509 |
| B36 | SEQ ID NO: 10764 and SEQ ID NO: 7785 and SEQ ID NO: 5509 |
| B37 | SEQ ID NO: 10689 and SEQ ID NO: 7769 and SEQ ID NO: 5496 |
| B38 | SEQ ID NO: 10689 and SEQ ID NO: 7771 and SEQ ID NO: 5496 |
| B39 | SEQ ID NO: 10689 and SEQ ID NO: 7739 and SEQ ID NO: 5496 |
| B40 | SEQ ID NO: 10689 and SEQ ID NO: 7785 and SEQ ID NO: 5496 |
| B41 | SEQ ID NO: 10689 and SEQ ID NO: 7769 and SEQ ID NO: 5498 |
| B42 | SEQ ID NO: 10689 and SEQ ID NO: 7771 and SEQ ID NO: 5498 |
| B43 | SEQ ID NO: 10689 and SEQ ID NO: 7739 and SEQ ID NO: 5498 |
| B44 | SEQ ID NO: 10689 and SEQ ID NO: 7785 and SEQ ID NO: 5498 |
| B45 | SEQ ID NO: 10689 and SEQ ID NO: 7769 and SEQ ID NO: 5509 |
| B46 | SEQ ID NO: 10689 and SEQ ID NO: 7771 and SEQ ID NO: 5509 |
| B47 | SEQ ID NO: 10689 and SEQ ID NO: 7739 and SEQ ID NO: 5509 |
| B48 | SEQ ID NO: 10689 and SEQ ID NO: 7785 and SEQ ID NO: 5509 |
| B49 | SEQ ID NO: 10701 and SEQ ID NO: 7769 and SEQ ID NO: 5496 |
| B50 | SEQ ID NO: 10701 and SEQ ID NO: 7771 and SEQ ID NO: 5496 |
| B51 | SEQ ID NO: 10701 and SEQ ID NO: 7739 and SEQ ID NO: 5496 |
| B52 | SEQ ID NO: 10701 and SEQ ID NO: 7785 and SEQ ID NO: 5496 |
| B53 | SEQ ID NO: 10701 and SEQ ID NO: 7769 and SEQ ID NO: 5498 |
| B54 | SEQ ID NO: 10701 and SEQ ID NO: 7771 and SEQ ID NO: 5498 |
| B55 | SEQ ID NO: 10701 and SEQ ID NO: 7739 and SEQ ID NO: 5498 |
| B56 | SEQ ID NO: 10701 and SEQ ID NO: 7785 and SEQ ID NO: 5498 |
| B57 | SEQ ID NO: 10701 and SEQ ID NO: 7769 and SEQ ID NO: 5509 |
| B58 | SEQ ID NO: 10701 and SEQ ID NO: 7771 and SEQ ID NO: 5509 |
| B59 | SEQ ID NO: 10701 and SEQ ID NO: 7739 and SEQ ID NO: 5509 |
| B60 | SEQ ID NO: 10701 and SEQ ID NO: 7785 and SEQ ID NO: 5509 |
| B61 | SEQ ID NO: 10700 and SEQ ID NO: 7769 and SEQ ID NO: 5496 |
| B62 | SEQ ID NO: 10700 and SEQ ID NO: 7771 and SEQ ID NO: 5496 |
| B63 | SEQ ID NO: 10700 and SEQ ID NO: 7739 and SEQ ID NO: 5496 |
| B64 | SEQ ID NO: 10700 and SEQ ID NO: 7785 and SEQ ID NO: 5496 |
| B65 | SEQ ID NO: 10700 and SEQ ID NO: 7769 and SEQ ID NO: 5498 |
| B66 | SEQ ID NO: 10700 and SEQ ID NO: 7771 and SEQ ID NO: 5498 |
| B67 | SEQ ID NO: 10700 and SEQ ID NO: 7739 and SEQ ID NO: 5498 |
| B68 | SEQ ID NO: 10700 and SEQ ID NO: 7785 and SEQ ID NO: 5498 |
| B69 | SEQ ID NO: 10700 and SEQ ID NO: 7769 and SEQ ID NO: 5509 |
| B70 | SEQ ID NO: 10700 and SEQ ID NO: 7771 and SEQ ID NO: 5509 |
| B71 | SEQ ID NO: 10700 and SEQ ID NO: 7739 and SEQ ID NO: 5509 |
| B72 | SEQ ID NO: 10700 and SEQ ID NO: 7785 and SEQ ID NO: 5509 |
| B73 | SEQ ID NO: 10722 and SEQ ID NO: 7769 and SEQ ID NO: 5496 |
| B74 | SEQ ID NO: 10722 and SEQ ID NO: 7771 and SEQ ID NO: 5496 |
| B75 | SEQ ID NO: 10722 and SEQ ID NO: 7739 and SEQ ID NO: 5496 |
| B76 | SEQ ID NO: 10722 and SEQ ID NO: 7785 and SEQ ID NO: 5496 |
| B77 | SEQ ID NO: 10722 and SEQ ID NO: 7769 and SEQ ID NO: 5498 |
| B78 | SEQ ID NO: 10722 and SEQ ID NO: 7771 and SEQ ID NO: 5498 |
| B79 | SEQ ID NO: 10722 and SEQ ID NO: 7739 and SEQ ID NO: 5498 |
| B80 | SEQ ID NO: 10722 and SEQ ID NO: 7785 and SEQ ID NO: 5498 |
| B81 | SEQ ID NO: 10722 and SEQ ID NO: 7769 and SEQ ID NO: 5509 |
| B82 | SEQ ID NO: 10722 and SEQ ID NO: 7771 and SEQ ID NO: 5509 |
| B83 | SEQ ID NO: 10722 and SEQ ID NO: 7739 and SEQ ID NO: 5509 |
| B84 | SEQ ID NO: 10722 and SEQ ID NO: 7785 and SEQ ID NO: 5509 |

As described herein, it is contemplated to generate a cell (or population of cells), e.g., an immune effector cell, e.g., a CAR-expressing immune effector cell, e.g., as described herein, which has reduced or eliminated expression of TRBC, B2M and CIITA. While it is contemplated that gRNAs comprising any targeting domain disclosed herein to each of these targets may be used in combination, particularly preferred targeting domain sequences to be used, for example, in combination are provided in the Table 38 below. In embodiments, each of the gRNA molecules are provided in dual guide RNA format and include a crRNA comprising, e.g., consisting of, the sequence [targeting domain]-SEQ ID NO: 6607, and a tracr comprising, e.g., consisting of, the sequence of SEQ ID NO: 6660. In other embodiments, each of the gRNA molecules are provided in single guide RNA format comprising, e.g., consisting of, the sequence: [targeting domain]-SEQ ID NO: 6601. In other embodiments, each of the gRNA molecules are provided in single guide RNA format comprising, e.g., consisting of, the sequence: [targeting domain]-SEQ ID NO: 7811. In embodiments, one or more of the gRNA molecules, e.g., all of the gRNA molecules, additionally comprise one or more modifications described herein, e.g., comprise one or more, e.g., 3, 3' and/or 5' phosphorothioate bonds, and/or one or more, e.g., 3, 3' and/or 5' 2'-OMe modifications. In embodiments, each of the gRNA molecules is complexed with a Cas9 molecule (e.g., described herein) and delivered to the cell (or population of cells, e.g., as described herein) as RNP, e.g., by electroporation. In embodiments, the RNP comprising each gRNA molecule are mixed with the cells and introduced simultaneously, e.g., by a single electroporation step. In other embodiments, the RNP may be introduced sequentially. Where it is contemplated to reduce or eliminate expression of both B2M and CIITA in a cell (such as here), in embodiments the cells may be further engineered to express a NK inhibitory molecule, e.g., as described herein, e.g., an HLA-G:B2M fusion described herein.

TABLE 38

Examples of preferred targeting domains of first, second and third gRNA molecules that can be used in combination to reduce or eliminate expression of TRBC, B2M and CIITA in a cell (as described herein).

| Combination Number | SEQ ID NO: s of targeting domains of first gRNA, second gRNA and third gRNA, respectively |
|---|---|
| F1 | SEQ ID NO: 5719 and SEQ ID NO: 5496 and SEQ ID NO: 7769 |
| F2 | SEQ ID NO: 5719 and SEQ ID NO: 5496 and SEQ ID NO: 7771 |
| F3 | SEQ ID NO: 5719 and SEQ ID NO: 5496 and SEQ ID NO: 7739 |
| F4 | SEQ ID NO: 5719 and SEQ ID NO: 5496 and SEQ ID NO: 7785 |
| F5 | SEQ ID NO: 5719 and SEQ ID NO: 5498 and SEQ ID NO: 7769 |
| F6 | SEQ ID NO: 5719 and SEQ ID NO: 5498 and SEQ ID NO: 7771 |
| F7 | SEQ ID NO: 5719 and SEQ ID NO: 5498 and SEQ ID NO: 7739 |
| F8 | SEQ ID NO: 5719 and SEQ ID NO: 5498 and SEQ ID NO: 7785 |
| F9 | SEQ ID NO: 5719 and SEQ ID NO: 5499 and SEQ ID NO: 7769 |
| F10 | SEQ ID NO: 5719 and SEQ ID NO: 5499 and SEQ ID NO: 7771 |
| F11 | SEQ ID NO: 5719 and SEQ ID NO: 5499 and SEQ ID NO: 7739 |
| F12 | SEQ ID NO: 5719 and SEQ ID NO: 5499 and SEQ ID NO: 7785 |
| F13 | SEQ ID NO: 5694 and SEQ ID NO: 5496 and SEQ ID NO: 7769 |
| F14 | SEQ ID NO: 5694 and SEQ ID NO: 5496 and SEQ ID NO: 7771 |
| F15 | SEQ ID NO: 5694 and SEQ ID NO: 5496 and SEQ ID NO: 7739 |
| F16 | SEQ ID NO: 5694 and SEQ ID NO: 5496 and SEQ ID NO: 7785 |
| F17 | SEQ ID NO: 5694 and SEQ ID NO: 5498 and SEQ ID NO: 7769 |
| F18 | SEQ ID NO: 5694 and SEQ ID NO: 5498 and SEQ ID NO: 7771 |
| F19 | SEQ ID NO: 5694 and SEQ ID NO: 5498 and SEQ ID NO: 7739 |
| F20 | SEQ ID NO: 5694 and SEQ ID NO: 5498 and SEQ ID NO: 7785 |
| F21 | SEQ ID NO: 5694 and SEQ ID NO: 5499 and SEQ ID NO: 7769 |
| F22 | SEQ ID NO: 5694 and SEQ ID NO: 5499 and SEQ ID NO: 7771 |
| F23 | SEQ ID NO: 5694 and SEQ ID NO: 5499 and SEQ ID NO: 7739 |
| F24 | SEQ ID NO: 5694 and SEQ ID NO: 5499 and SEQ ID NO: 7785 |
| F25 | SEQ ID NO: 5706 and SEQ ID NO: 5496 and SEQ ID NO: 7769 |
| F26 | SEQ ID NO: 5706 and SEQ ID NO: 5496 and SEQ ID NO: 7771 |
| F27 | SEQ ID NO: 5706 and SEQ ID NO: 5496 and SEQ ID NO: 7739 |
| F28 | SEQ ID NO: 5706 and SEQ ID NO: 5496 and SEQ ID NO: 7785 |
| F29 | SEQ ID NO: 5706 and SEQ ID NO: 5498 and SEQ ID NO: 7769 |
| F30 | SEQ ID NO: 5706 and SEQ ID NO: 5498 and SEQ ID NO: 7771 |

TABLE 38-continued

Examples of preferred targeting domains of first, second and third gRNA molecules that can be used in combination to reduce or eliminate expression of TRBC, B2M and CIITA in a cell (as described herein).

| Combination Number | SEQ ID NO: s of targeting domains of first gRNA, second gRNA and third gRNA, respectively |
|---|---|
| F31 | SEQ ID NO: 5706 and SEQ ID NO: 5498 and SEQ ID NO: 7739 |
| F32 | SEQ ID NO: 5706 and SEQ ID NO: 5498 and SEQ ID NO: 7785 |
| F33 | SEQ ID NO: 5706 and SEQ ID NO: 5499 and SEQ ID NO: 7769 |
| F34 | SEQ ID NO: 5706 and SEQ ID NO: 5499 and SEQ ID NO: 7771 |
| F35 | SEQ ID NO: 5706 and SEQ ID NO: 5499 and SEQ ID NO: 7739 |
| F36 | SEQ ID NO: 5706 and SEQ ID NO: 5499 and SEQ ID NO: 7785 |
| F37 | SEQ ID NO: 5696 and SEQ ID NO: 5496 and SEQ ID NO: 7769 |
| F38 | SEQ ID NO: 5696 and SEQ ID NO: 5496 and SEQ ID NO: 7771 |
| F39 | SEQ ID NO: 5696 and SEQ ID NO: 5496 and SEQ ID NO: 7739 |
| F40 | SEQ ID NO: 5696 and SEQ ID NO: 5496 and SEQ ID NO: 7785 |
| F41 | SEQ ID NO: 5696 and SEQ ID NO: 5498 and SEQ ID NO: 7769 |
| F42 | SEQ ID NO: 5696 and SEQ ID NO: 5498 and SEQ ID NO: 7771 |
| F43 | SEQ ID NO: 5696 and SEQ ID NO: 5498 and SEQ ID NO: 7739 |
| F44 | SEQ ID NO: 5696 and SEQ ID NO: 5498 and SEQ ID NO: 7785 |
| F45 | SEQ ID NO: 5696 and SEQ ID NO: 5499 and SEQ ID NO: 7769 |
| F46 | SEQ ID NO: 5696 and SEQ ID NO: 5499 and SEQ ID NO: 7771 |
| F47 | SEQ ID NO: 5696 and SEQ ID NO: 5499 and SEQ ID NO: 7739 |
| F48 | SEQ ID NO: 5696 and SEQ ID NO: 5499 and SEQ ID NO: 7785 |
| F49 | SEQ ID NO: 5711 and SEQ ID NO: 5496 and SEQ ID NO: 7769 |
| F50 | SEQ ID NO: 5711 and SEQ ID NO: 5496 and SEQ ID NO: 7771 |
| F51 | SEQ ID NO: 5711 and SEQ ID NO: 5496 and SEQ ID NO: 7739 |
| F52 | SEQ ID NO: 5711 and SEQ ID NO: 5496 and SEQ ID NO: 7785 |
| F53 | SEQ ID NO: 5711 and SEQ ID NO: 5498 and SEQ ID NO: 7769 |
| F54 | SEQ ID NO: 5711 and SEQ ID NO: 5498 and SEQ ID NO: 7771 |
| F55 | SEQ ID NO: 5711 and SEQ ID NO: 5498 and SEQ ID NO: 7739 |
| F56 | SEQ ID NO: 5711 and SEQ ID NO: 5498 and SEQ ID NO: 7785 |
| F57 | SEQ ID NO: 5711 and SEQ ID NO: 5499 and SEQ ID NO: 7769 |
| F58 | SEQ ID NO: 5711 and SEQ ID NO: 5499 and SEQ ID NO: 7771 |
| F59 | SEQ ID NO: 5711 and SEQ ID NO: 5499 and SEQ ID NO: 7739 |
| F60 | SEQ ID NO: 5711 and SEQ ID NO: 5499 and SEQ ID NO: 7785 |

Particularly preferred combinations include combination F1 to F4, combination F5 to F8, combination F13 to F16, or combination F17 to F20.

As described herein, it is contemplated to generate a cell (or population of cells), e.g., an immune effector cell, e.g., a CAR-expressing immune effector cell, e.g., as described herein, which has reduced or eliminated expression of CD3E and FKBP1A. While it is contemplated that gRNAs comprising any targeting domain disclosed herein to each of these targets may be used in combination, particularly preferred targeting domain sequences to be used, for example, in combination are provided in the Table below. In embodiments, each of the gRNA molecules are provided in dual guide RNA format and include a crRNA comprising, e.g., consisting of, the sequence [targeting domain]-SEQ ID NO: 6607, and a tracr comprising, e.g., consisting of, the sequence of SEQ ID NO: 6660. In other embodiments, each of the gRNA molecules are provided in single guide RNA format comprising, e.g., consisting of, the sequence: [targeting domain]-SEQ ID NO: 6601. In other embodiments, each of the gRNA molecules are provided in single guide RNA format comprising, e.g., consisting of, the sequence: [targeting domain]-SEQ ID NO: 7811. In embodiments, one or more of the gRNA molecules, e.g., all of the gRNA molecules, additionally comprise one or more modifications described herein, e.g., comprise one or more, e.g., 3, 3' and/or 5' phosphorothioate bonds, and/or one or more, e.g., 3, 3' and/or 5' 2'-OMe modifications. In embodiments, each of the gRNA molecules is complexed with a Cas9 molecule (e.g., described herein) and delivered to the cell (or population of cells) as RNP, e.g., by electroporation. In embodiments, the RNP comprising each gRNA molecule are mixed with the cells and introduced simultaneously, e.g., by a single electroporation step. In other embodiments, the RNP may be introduced sequentially.

TABLE 35

Examples of preferred targeting domains of first, second and (optionally) third gRNA molecules that can be used in combination to reduce or eliminate expression of CD3E and FKBP1A in a cell (as described herein).

| Combination Number | SEQ ID NO: s of targeting domains of first gRNA, second, gRNA and, optionally, third gRNA respectively |
|---|---|
| C1 | SEQ ID NO: 10729 and SEQ ID NO: 6693 |
| C2 | SEQ ID NO: 10729 and SEQ ID NO: 6705 |
| C3 | SEQ ID NO: 10729 and SEQ ID NO: 6694 |
| C4 | SEQ ID NO: 10729 and SEQ ID NO: 6708 |
| C5 | SEQ ID NO: 10729 and SEQ ID NO: 6699 |
| C6 | SEQ ID NO: 10729 and SEQ ID NO: 6705 and SEQ ID NO: 6694 |
| C7 | SEQ ID NO: 10719 and SEQ ID NO: 6693 |
| C8 | SEQ ID NO: 10719 and SEQ ID NO: 6705 |
| C9 | SEQ ID NO: 10719 and SEQ ID NO: 6694 |
| C10 | SEQ ID NO: 10719 and SEQ ID NO: 6708 |
| C11 | SEQ ID NO: 10719 and SEQ ID NO: 6699 |
| C12 | SEQ ID NO: 10719 and SEQ ID NO: 6705 and SEQ ID NO: 6694 |
| C13 | SEQ ID NO: 10764 and SEQ ID NO: 6693 |
| C14 | SEQ ID NO: 10764 and SEQ ID NO: 6705 |
| C15 | SEQ ID NO: 10764 and SEQ ID NO: 6694 |
| C16 | SEQ ID NO: 10764 and SEQ ID NO: 6708 |
| C17 | SEQ ID NO: 10764 and SEQ ID NO: 6699 |

TABLE 35-continued

Examples of preferred targeting domains of first, second and (optionally) third gRNA molecules that can be used in combination to reduce or eliminate expression of CD3E and FKBP1A in a cell (as described herein).

| Combination Number | SEQ ID NO: s of targeting domains of first gRNA, second, gRNA and, optionally, third gRNA respectively |
|---|---|
| C18 | SEQ ID NO: 10764 and SEQ ID NO: 6705 and SEQ ID NO: 6694 |
| C19 | SEQ ID NO: 10689 and SEQ ID NO: 6693 |
| C20 | SEQ ID NO: 10689 and SEQ ID NO: 6705 |
| C21 | SEQ ID NO: 10689 and SEQ ID NO: 6694 |
| C22 | SEQ ID NO: 10689 and SEQ ID NO: 6708 |
| C23 | SEQ ID NO: 10689 and SEQ ID NO: 6699 |
| C24 | SEQ ID NO: 10689 and SEQ ID NO: 6705 and SEQ ID NO: 6694 |
| C25 | SEQ ID NO: 10701 and SEQ ID NO: 6693 |
| C26 | SEQ ID NO: 10701 and SEQ ID NO: 6705 |
| C27 | SEQ ID NO: 10701 and SEQ ID NO: 6694 |
| C28 | SEQ ID NO: 10701 and SEQ ID NO: 6708 |
| C29 | SEQ ID NO: 10701 and SEQ ID NO: 6699 |
| C30 | SEQ ID NO: 10701 and SEQ ID NO: 6705 and SEQ ID NO: 6694 |
| C31 | SEQ ID NO: 10700 and SEQ ID NO: 6693 |
| C32 | SEQ ID NO: 10700 and SEQ ID NO: 6705 |
| C33 | SEQ ID NO: 10700 and SEQ ID NO: 6694 |
| C34 | SEQ ID NO: 10700 and SEQ ID NO: 6708 |
| C35 | SEQ ID NO: 10700 and SEQ ID NO: 6699 |
| C36 | SEQ ID NO: 10700 and SEQ ID NO: 6705 and SEQ ID NO: 6694 |
| C37 | SEQ ID NO: 10722 and SEQ ID NO: 6693 |
| C38 | SEQ ID NO: 10722 and SEQ ID NO: 6705 |
| C39 | SEQ ID NO: 10722 and SEQ ID NO: 6694 |
| C40 | SEQ ID NO: 10722 and SEQ ID NO: 6708 |
| C41 | SEQ ID NO: 10722 and SEQ ID NO: 6699 |
| C42 | SEQ ID NO: 10722 and SEQ ID NO: 6705 and SEQ ID NO: 6694 |

As described herein, it is contemplated to generate a cell (or population of cells), e.g., an immune effector cell, e.g., a CAR-expressing immune effector cell, e.g., as described herein, which has reduced or eliminated expression of TRAC and FKBP1A. While it is contemplated that gRNAs comprising any targeting domain disclosed herein to each of these targets may be used in combination, particularly preferred targeting domain sequences to be used, for example, in combination are provided in the Table 36 below. In embodiments, each of the gRNA molecules are provided in dual guide RNA format and include a crRNA comprising, e.g., consisting of, the sequence [targeting domain]-SEQ ID NO: 6607, and a tracr comprising, e.g., consisting of, the sequence of SEQ ID NO: 6660. In other embodiments, each of the gRNA molecules are provided in single guide RNA format comprising, e.g., consisting of, the sequence: [targeting domain]-SEQ ID NO: 6601. In other embodiments, each of the gRNA molecules are provided in single guide RNA format comprising, e.g., consisting of, the sequence: [targeting domain]-SEQ ID NO: 7811. In embodiments, one or more of the gRNA molecules, e.g., all of the gRNA molecules, additionally comprise one or more modifications described herein, e.g., comprise one or more, e.g., 3, 3' and/or 5' phosphorothioate bonds, and/or one or more, e.g., 3, 3' and/or 5' 2'-OMe modifications. In embodiments, each of the gRNA molecules is complexed with a Cas9 molecule (e.g., described herein) and delivered to the cell (or population of cells, e.g., as described herein) as RNP, e.g., by electroporation. In embodiments, the RNP comprising each gRNA molecule are mixed with the cells and introduced simultaneously, e.g., by a single electroporation step. In other embodiments, the RNP may be introduced sequentially.

TABLE 36

Examples of preferred targeting domains of first, second and (optionally) third gRNA molecules that can be used in combination to reduce or eliminate expression of TRAC and FKBP1A in a cell (as described herein).

| Combination Number | SEQ ID NO: s of targeting domains of first gRNA, second gRNA and, optionally, third gRNA, respectively |
|---|---|
| D1 | SEQ ID NO: 5569 and SEQ ID NO: 6693 |
| D2 | SEQ ID NO: 5569 and SEQ ID NO: 6705 |
| D3 | SEQ ID NO: 5569 and SEQ ID NO: 6694 |
| D4 | SEQ ID NO: 5569 and SEQ ID NO: 6708 |
| D5 | SEQ ID NO: 5569 and SEQ ID NO: 6699 |
| D6 | SEQ ID NO: 5569 and SEQ ID NO: 6705 and SEQ ID NO: 6694 |
| D7 | SEQ ID NO: 5586 and SEQ ID NO: 6693 |
| D8 | SEQ ID NO: 5586 and SEQ ID NO: 6705 |
| D9 | SEQ ID NO: 5586 and SEQ ID NO: 6694 |
| D10 | SEQ ID NO: 5586 and SEQ ID NO: 6708 |
| D11 | SEQ ID NO: 5586 and SEQ ID NO: 6699 |
| D12 | SEQ ID NO: 5586 and SEQ ID NO: 6705 and SEQ ID NO: 6694 |
| D13 | SEQ ID NO: 5587 and SEQ ID NO: 6693 |
| D14 | SEQ ID NO: 5587 and SEQ ID NO: 6705 |
| D15 | SEQ ID NO: 5587 and SEQ ID NO: 6694 |
| D16 | SEQ ID NO: 5587 and SEQ ID NO: 6708 |
| D17 | SEQ ID NO: 5587 and SEQ ID NO: 6699 |
| D18 | SEQ ID NO: 5587 and SEQ ID NO: 6705 and SEQ ID NO: 6694 |
| D19 | SEQ ID NO: 5592 and SEQ ID NO: 6693 |
| D20 | SEQ ID NO: 5592 and SEQ ID NO: 6705 |
| D21 | SEQ ID NO: 5592 and SEQ ID NO: 6694 |
| D22 | SEQ ID NO: 5592 and SEQ ID NO: 6708 |
| D23 | SEQ ID NO: 5592 and SEQ ID NO: 6699 |
| D24 | SEQ ID NO: 5592 and SEQ ID NO: 6705 and SEQ ID NO: 6694 |
| D25 | SEQ ID NO: 5599 and SEQ ID NO: 6693 |

TABLE 36-continued

Examples of preferred targeting domains of first, second and (optionally) third gRNA molecules that can be used in combination to reduce or eliminate expression of TRAC and FKBP1A in a cell (as described herein).

| Combination Number | SEQ ID NO: s of targeting domains of first gRNA, second gRNA and, optionally, third gRNA, respectively |
|---|---|
| D26 | SEQ ID NO: 5599 and SEQ ID NO: 6705 |
| D27 | SEQ ID NO: 5599 and SEQ ID NO: 6694 |
| D28 | SEQ ID NO: 5599 and SEQ ID NO: 6708 |
| D29 | SEQ ID NO: 5599 and SEQ ID NO: 6699 |
| D30 | SEQ ID NO: 5599 and SEQ ID NO: 6705 and SEQ ID NO: 6694 |
| D31 | SEQ ID NO: 5600 and SEQ ID NO: 6693 |
| D32 | SEQ ID NO: 5600 and SEQ ID NO: 6705 |
| D33 | SEQ ID NO: 5600 and SEQ ID NO: 6694 |
| D34 | SEQ ID NO: 5600 and SEQ ID NO: 6708 |
| D35 | SEQ ID NO: 5600 and SEQ ID NO: 6699 |
| D36 | SEQ ID NO: 5600 and SEQ ID NO: 6705 and SEQ ID NO: 6694 |

Particularly preferred combinations include combination D2, combination D4, combination D20, or combination D22.

As described herein, it is contemplated to generate a cell (or population of cells), e.g., an immune effector cell, e.g., a CAR-expressing immune effector cell, e.g., as described herein, which has reduced or eliminated expression of TRBC and FKBP1A. While it is contemplated that gRNAs comprising any targeting domain disclosed herein to each of these targets may be used in combination, particularly preferred targeting domain sequences to be used, for example, in combination are provided in the Table 37 below. In embodiments, each of the gRNA molecules are provided in dual guide RNA format and include a crRNA comprising, e.g., consisting of, the sequence [targeting domain]-SEQ ID NO: 6607, and a tracr comprising, e.g., consisting of, the sequence of SEQ ID NO: 6660. In other embodiments, each of the gRNA molecules are provided in single guide RNA format comprising, e.g., consisting of, the sequence: [targeting domain]-SEQ ID NO: 6601. In other embodiments, each of the gRNA molecules are provided in single guide RNA format comprising, e.g., consisting of, the sequence: [targeting domain]-SEQ ID NO: 7811. In embodiments, one or more of the gRNA molecules, e.g., all of the gRNA molecules, additionally comprise one or more modifications described herein, e.g., comprise one or more, e.g., 3, 3' and/or 5' phosphorothioate bonds, and/or one or more, e.g., 3, 3' and/or 5' 2'-OMe modifications. In embodiments, each of the gRNA molecules is complexed with a Cas9 molecule (e.g., described herein) and delivered to the cell (or population of cells) as RNP, e.g., by electroporation. In embodiments, the RNP comprising each gRNA molecule are mixed with the cells and introduced simultaneously, e.g., by a single electroporation step. In other embodiments, the RNP may be introduced sequentially.

TABLE 37

Examples of preferred targeting domains of first, second and (optionally) third gRNA molecules that can be used in combination to reduce or eliminate expression of TRBC and FKBP1A in a cell (as described herein).

| Combination Number | SEQ ID NO: s of targeting domains of first gRNA, second gRNA and, optionally third gRNA, respectively |
|---|---|
| E1 | SEQ ID NO: 5719 and SEQ ID NO: 6693 |
| E2 | SEQ ID NO: 5719 and SEQ ID NO: 6705 |
| E3 | SEQ ID NO: 5719 and SEQ ID NO: 6694 |
| E4 | SEQ ID NO: 5719 and SEQ ID NO: 6708 |
| E5 | SEQ ID NO: 5719 and SEQ ID NO: 6699 |
| E6 | SEQ ID NO: 5719 and SEQ ID NO: 6705 and SEQ ID NO: 6694 |
| E7 | SEQ ID NO: 5694 and SEQ ID NO: 6693 |
| E8 | SEQ ID NO: 5694 and SEQ ID NO: 6705 |
| E9 | SEQ ID NO: 5694 and SEQ ID NO: 6694 |
| E10 | SEQ ID NO: 5694 and SEQ ID NO: 6708 |
| E11 | SEQ ID NO: 5694 and SEQ ID NO: 6699 |
| E12 | SEQ ID NO: 5694 and SEQ ID NO: 6705 and SEQ ID NO: 6694 |
| E13 | SEQ ID NO: 5706 and SEQ ID NO: 6693 |
| E14 | SEQ ID NO: 5706 and SEQ ID NO: 6705 |
| E15 | SEQ ID NO: 5706 and SEQ ID NO: 6694 |
| E16 | SEQ ID NO: 5706 and SEQ ID NO: 6708 |
| E17 | SEQ ID NO: 5706 and SEQ ID NO: 6699 |
| E18 | SEQ ID NO: 5706 and SEQ ID NO: 6705 and SEQ ID NO: 6694 |
| E19 | SEQ ID NO: 5696 and SEQ ID NO: 6693 |
| E20 | SEQ ID NO: 5696 and SEQ ID NO: 6705 |
| E21 | SEQ ID NO: 5696 and SEQ ID NO: 6694 |
| E22 | SEQ ID NO: 5696 and SEQ ID NO: 6708 |
| E23 | SEQ ID NO: 5696 and SEQ ID NO: 6699 |
| E24 | SEQ ID NO: 5696 and SEQ ID NO: 6705 and SEQ ID NO: 6694 |
| E25 | SEQ ID NO: 5711 and SEQ ID NO: 6693 |
| E26 | SEQ ID NO: 5711 and SEQ ID NO: 6705 |
| E27 | SEQ ID NO: 5711 and SEQ ID NO: 6694 |
| E28 | SEQ ID NO: 5711 and SEQ ID NO: 6708 |
| E29 | SEQ ID NO: 5711 and SEQ ID NO: 6699 |
| E30 | SEQ ID NO: 5711 and SEQ ID NO: 6705 and SEQ ID NO: 6694 |

Particularly preferred combinations include combination E2, combination E4, combination E8, or combination E10.

While not intending to be bound by theory, it has also been surprisingly shown herein that the targeting of two or more target sequences located within different genes may induce mutations (e.g., insertions or deletions or one or more nucleic acid residues) at each of the targeted sites, thereby reducing or eliminating expression of two or more proteins within the cell. Combinations of gRNAs targeting two or more different genes of interest are described herein.

As described herein, when utilizing more than one gRNA molecule (or CRISPR system comprising more than one gRNA molecule, e.g., a CRISPR system comprising a first gRNA molecule and a CRISPR system comprising a second gRNA molecule, e.g., wherein each gRNA molecule is complexed with a Cas molecule, e.g., a Cas9 molecule, e.g., as described herein), the more than one gRNA molecules may be introduced into a cell simultaneously, e.g., in a single introduction step, e.g., a single electroporation step. Alternatively, the more than one gRNA molecules (or CRISPR systems comprising said gRNA molecules) can be introduced into a cell in more than one steps, e.g., more than one electroporations. If multiple introduction steps are utilized, the steps may be separated by a period of hours, days, or weeks, e.g., by a period of 1 hour, 2 hours, 5 hours, 10 hours, 15 hours, 20 hours, 24 hours, 2 days, 3, days, 4 days, 5 days, 6 days, 7 days, 8 days, 9 days, 10 days, or more.

IX. Properties of the gRNA

It has further been surprisingly shown herein that gRNA molecules and CRISPR systems comprising said gRNA molecules produce similar or identical indel patterns in different cell types, across different methods of delivery and using different crRNA/tracr components. Without being bound by theory, it is believed that some indel patterns may be more advantageous than others. For example, indels which predominantly include insertions and/or deletions which result in a "frameshift mutation" (e.g., 1- or 2-base pair insertion or deletions, or any insertion or deletion where n/3 is not a whole number (where n=the number of nucleotides in the insertion or deletion)) may be beneficial in reducing or eliminating expression of a functional protein. Likewise, indels which predominantly include "large deletions" (deletions of more than 10, 11, 12, 13, 14, 15, 20, 25, or 30 nucleotides) may also be beneficial in, for example, removing critical regulatory sequences such as promoter binding sites, which may similarly have an improved effect on expression of functional protein. While the indel patterns induced by a given gRNA/CRISPR system have surprisingly been found to be consistently reproduced across cell types, as described herein, not any single indel structure will inevitably be produced in a given cell upon introduction of a gRNA/CRISPR system.

The invention thus provides for gRNA molecules which create a beneficial indel pattern or structure, for example, which have indel patterns or structures predominantly composed of frameshift mutation(s) and/or large deletions. Such gRNA molecules may be selected by assessing the indel pattern or structure created by a candidate gRNA molecule in a test cell (for example, a HEK293 cell or in the cell of interest, e.g., a T cell) by NGS, as described herein. As shown in the Examples, gRNA molecules have been discovered, which, when introduced into the desired cell population, result in a population of cells comprising a significant fraction of the cells having a frameshift mutation in the targeted gene. In some cases, the rate of frameshift mutation is as high as 75%, 80%, 85%, 90% or more. The invention thus provides for populations of cells which comprise at least about 40% of cells (e.g., at least about 45%, at least about 50%, at least about 55%, at least about 60%, at least about 65%, at least about 70%, at least about 75%, at least about 80%, at least about 85%, at least about 90%, at least about 95%, or at least about 99%) having a frameshift mutation, e.g., as described herein, at or near the target site of a gRNA molecule described herein. The invention also provides for populations of cells which comprise at least about 50% of cells (e.g., at least about 55%, at least about 60%, at least about 65%, at least about 70%, at least about 75%, at least about 80%, at least about 85%, at least about 90%, at least about 95%, or at least about 99%) having a frameshift mutation, e.g., as described herein, at or near the target site of a gRNA molecule described herein.

The invention thus provides methods of selecting gRNA molecules for use in the therapeutic methods of the invention comprising: 1) providing a plurality of gRNA molecules to a target of interest, 2) assessing the indel pattern or structure created by use of said gRNA molecules, 3) selecting a gRNA molecule that forms an indel pattern or structure composed predominantly of frameshift mutations, large deletions or a combination thereof, and 4) using said selected gRNA in a methods of the invention.

The invention further provides methods of altering cells, and altered cells, wherein a particular indel pattern is consistently produced with a given gRNA/CRISPR system in that cell type. The indel patterns, including the top 5 most frequently occurring indels observed with the gRNA/CRISPR systems described herein are disclosed, for example, in the Examples. As shown in the examples, populations of cells are generated, wherein a significant fraction of the cells comprises one of the top 5 indels (for example, populations of cells wherein one of the top 5 indels is present in more than 30%, more than 40%, more than 50%, more than 60% or more of the cells of the population. Thus, the invention provides cells, e.g., immune effector cells, e.g., CAR-expressing immune effector cells (as described herein), which comprise an indel of any one of the top 5 indels observed with a given gRNA/CRISPR system. Further, the invention provides populations of cells, e.g., immune effector cells, e.g., CAR-expressing immune effector cells (as described herein), which when assessed by, for example, NGS, comprise a high percentage of cells comprising one of the top 5 indels described herein for a given gRNA/CRISPR system. When used in connection with indel pattern analysis, a "high percentage" refers to at least about 50% (e.g., at least about 55%, at least about 60%, at least about 65%, at least about 70%, at least about 75%, at least about 80%, at least about 85%, at least about 90%, at least about 95%, or at least about 99%) of the cells of the population comprising one of the top 5 indels described herein for a given gRNA/CRISPR system. In other embodiments, the population of cells comprises at least about 25% (e.g., from about 25% to about 60%, e.g., from about 25% to about 50%, e.g., from about 25% to about 40%, e.g., from about 25% to about 35%) of cells which have one of the top 5 indels described herein for a given gRNA/CRISPR system. In embodiments, the top 5 indels for a given gRNA/CRISPR system which targets TRAC are provided in FIG. 34A, FIG. 34B and FIG. 49. In embodiments, the top 5 indels for a given gRNA/CRISPR system which targets B2M are provided in FIG. 36 and FIG. 48. In embodiments, the top 5 indels for a given gRNA/CRISPR system which targets CIITA are provided in FIG. 38, FIG. 41, FIG. 44, and FIG. 50. In embodiments, the top 5 indels for a given gRNA/CRISPR system which targets FKBP1A are provided in FIG. 53.

It has also been discovered that certain gRNA molecules do not create indels at off-target sequences within the genome of the target cell type, or produce indels at off target sites at very low frequencies (e.g., <5% of cells within a population) relative to the frequency of indel creation at the target site. Thus, the invention provides for gRNA molecules and CRISPR systems which do not exhibit off-target indel formation in the target cell type, or which produce a frequency of off-target indel formation of <5%. In embodiments, the invention provides gRNA molecules and CRISPR systems which do not exhibit any off target indel formation in the target cell type. Thus, the invention further provides a cell, e.g., a population of cells, e.g., immune effector cells, e.g., CAR-expressing immune effector cells, e.g., as described herein, which comprise an indel at or near a target site of a gRNA molecule described herein (e.g., a frameshift indel, or any one of the top 5 indels produced by a given gRNA/CRISPR system, e.g., as described herein), but does not comprise an indel at any off-target site of the gRNA molecule. In other embodiments, the invention further provides a population of cells, e.g., immune effector cells, e.g., CAR-expressing immune effector cells, e.g., as described herein, which comprises >50% of cells which have an indel at or near a target site of a gRNA molecule described herein (e.g., a frameshift indel, or any one of the top 5 indels produced by a given gRNA/CRISPR system, e.g., as described herein), but which comprises less than 5%, e.g., less than 4%, less than 3%, less than 2% or less than 1%, of cells comprising an indel at any off-target site of the gRNA molecule.

X. Delivery/Constructs

The components, e.g., a Cas9 molecule or gRNA molecule, or both, can be delivered, formulated, or administered in a variety of forms. As a non-limiting example, the gRNA molecule and Cas9 molecule can be formulated (in one or more compositions), directly delivered or administered to a cell in which a genome editing event is desired. Alternatively, nucleic acid encoding one or more components, e.g., a Cas9 molecule or gRNA molecule, or both, can be formulated (in one or more compositions), delivered or administered. In one aspect, the gRNA molecule is provided as DNA encoding the gRNA molecule and the Cas9 molecule is provided as DNA encoding the Cas9 molecule. In one embodiment, the gRNA molecule and Cas9 molecule are encoded on separate nucleic acid molecules. In one embodiment, the gRNA molecule and Cas9 molecule are encoded on the same nucleic acid molecule. In one aspect, the gRNA molecule is provided as RNA and the Cas9 molecule is provided as DNA encoding the Cas9 molecule. In one embodiment, the gRNA molecule is provided with one or more modifications, e.g., as described herein. In one aspect, the gRNA molecule is provided as RNA and the Cas9 molecule is provided as mRNA encoding the Cas9 molecule. In one aspect, the gRNA molecule is provided as RNA and the Cas9 molecule is provided as a protein. In one embodiment, the gRNA and Cas9 molecule are provided as a ribonuclear protein complex (RNP). In one aspect, the gRNA molecule is provided as DNA encoding the gRNA molecule and the Cas9 molecule is provided as a protein.

Delivery may be accomplished by, for example, electroporation (e.g., as known in the art) or other method that renders the cell membrane permeable to nucleic acid and/or polypeptide molecules. Additional techniques for rendering the membrane permeable are known in the art and include, for example, cell squeezing (e.g., as described in WO2015/023982 and WO2013/059343, the contents of which are hereby incorporated by reference in their entirety), nanoneedles (e.g., as described in Chiappini et al., Nat. Mat., 14; 532-39, or US2014/0295558, the contents of which are hereby incorporated by reference in their entirety) and nanostraws (e.g., as described in Xie, ACS Nano, 7(5); 4351-58, the contents of which are hereby incorporated by reference in their entirety).

When a component is delivered encoded in DNA the DNA will typically include a control region, e.g., comprising a promoter, to effect expression. Useful promoters for Cas9 molecule sequences include CMV, EF-1 alpha, MSCV, PGK, CAG control promoters. Useful promoters for gRNAs include H1, EF-1a and U6 promoters. Promoters with similar or dissimilar strengths can be selected to tune the expression of components. Sequences encoding a Cas9 molecule can comprise a nuclear localization signal (NLS), e.g., an SV40 NLS. In an embodiment, a promoter for a Cas9 molecule or a gRNA molecule can be, independently, inducible, tissue specific, or cell specific.

DNA-Based Delivery of a Cas9 Molecule and or a gRNA Molecule

DNA encoding Cas9 molecules and/or gRNA molecules, can be administered to subjects or delivered into cells by art-known methods or as described herein. For example, Cas9-encoding and/or gRNA-encoding DNA can be delivered, e.g., by vectors (e.g., viral or non-viral vectors), non-vector based methods (e.g., using naked DNA or DNA complexes), or a combination thereof.

In some embodiments, the Cas9- and/or gRNA-encoding DNA is delivered by a vector (e.g., viral vector/virus, plasmid, minicircle or nanoplasmid).

A vector can comprise a sequence that encodes a Cas9 molecule and/or a gRNA molecule. A vector can also comprise a sequence encoding a signal peptide (e.g., for nuclear localization, nucleolar localization, mitochondrial localization), fused, e.g., to a Cas9 molecule sequence. For example, a vector can comprise one or more nuclear localization sequence (e.g., from SV40) fused to the sequence encoding the Cas9 molecule.

One or more regulatory/control elements, e.g., a promoter, an enhancer, an intron, a polyadenylation signal, a Kozak consensus sequence, internal ribosome entry sites (IRES), a 2A sequence, and a splice acceptor or donor can be included in the vectors. In some embodiments, the promoter is recognized by RNA polymerase II (e.g., a CMV promoter). In other embodiments, the promoter is recognized by RNA polymerase III (e.g., a U6 promoter). In some embodiments, the promoter is a regulated promoter (e.g., inducible promoter). In other embodiments, the promoter is a constitutive promoter. In some embodiments, the promoter is a tissue specific promoter. In some embodiments, the promoter is a viral promoter. In other embodiments, the promoter is a non-viral promoter.

In some embodiments, the vector or delivery vehicle is a minicircle. In some embodiments, the vector or delivery vehicle is a nanoplasmid.

In some embodiments, the vector or delivery vehicle is a viral vector (e.g., for generation of recombinant viruses). In some embodiments, the virus is a DNA virus (e.g., dsDNA or ssDNA virus). In other embodiments, the virus is an RNA virus (e.g., an ssRNA virus).

Exemplary viral vectors/viruses include, e.g., retroviruses, lentiviruses, adenovirus, adeno-associated virus (AAV), vaccinia viruses, poxviruses, and herpes simplex viruses. Viral vector technology is well known in the art and is described, for example, in Sambrook et al., 2012, MOLECULAR CLONING: A LABORATORY MANUAL, volumes 1-4, Cold Spring Harbor Press, NY), and in other virology and molecular biology manuals.

In some embodiments, the virus infects dividing cells. In other embodiments, the virus infects non-dividing cells. In some embodiments, the virus infects both dividing and non-dividing cells. In some embodiments, the virus can integrate into the host genome. In some embodiments, the virus is engineered to have reduced immunity, e.g., in human. In some embodiments, the virus is replication-competent. In other embodiments, the virus is replication-defective, e.g., having one or more coding regions for the genes necessary for additional rounds of virion replication and/or packaging replaced with other genes or deleted. In some embodiments, the virus causes transient expression of the Cas9 molecule and/or the gRNA molecule. In other embodiments, the virus causes long-lasting, e.g., at least 1 week, 2 weeks, 1 month, 2 months, 3 months, 6 months, 9 months, 1 year, 2 years, or permanent expression, of the Cas9 molecule and/or the gRNA molecule. The packaging capacity of the viruses may vary, e.g., from at least about 4 kb to at least about 30 kb, e.g., at least about 5 kb, 10 kb, 15 kb, 20 kb, 25 kb, 30 kb, 35 kb, 40 kb, kb, or 50 kb.

In some embodiments, the Cas9- and/or gRNA-encoding DNA is delivered by a recombinant retrovirus. In some embodiments, the retrovirus (e.g., Moloney murine leukemia vims) comprises a reverse transcriptase, e.g., that allows integration into the host genome. In some embodiments, the retrovirus is replication-competent. In other embodiments, the retrovirus is replication-defective, e.g., having one of more coding regions for the genes necessary for additional rounds of virion replication and packaging replaced with other genes, or deleted.

In some embodiments, the Cas9- and/or gRNA-encoding DNA is delivered by a recombinant lentivirus. For example, the lentivirus is replication-defective, e.g., does not comprise one or more genes required for viral replication.

In some embodiments, the Cas9- and/or gRNA-encoding DNA is delivered by a recombinant adenovirus. In some embodiments, the adenovirus is engineered to have reduced immunity in human.

In some embodiments, the Cas9- and/or gRNA-encoding DNA is delivered by a recombinant AAV. In some embodiments, the AAV can incorporate its genome into that of a host cell, e.g., a target cell as described herein. In some embodiments, the AAV is a self-complementary adeno-associated virus (scAAV), e.g., a scAAV that packages both strands which anneal together to form double stranded DNA. AAV serotypes that may be used in the disclosed methods include, e.g., AAV1, AAV2, modified AAV2 (e.g., modifications at Y444F, Y500F, Y730F and/or S662V), AAV3, modified AAV3 (e.g., modifications at Y705F, Y731F and/or. T492V), AAV4, AAV5, AAV6, modified AAV6 (e.g., modifications at S663V and/or T492V), AAV8. AAV 8.2, AAV9, AAV rh 10, and pseudotyped AAV, such as AAV2/8, AAV2/5 and AAV2/6 can also be used in the disclosed methods.

In some embodiments, the Cas9- and/or gRNA-encoding DNA is delivered by a hybrid virus, e.g., a hybrid of one or more of the viruses described herein.

A Packaging cell is used to form a virus particle that is capable of infecting a host or target cell. Such a cell includes a 293 cell, which can package adenovirus, and a ψ2 cell or a PA317 cell, which can package retrovirus. A viral vector used in gene therapy is usually generated by a producer cell line that packages a nucleic acid vector into a viral particle. The vector typically contains the minimal viral sequences required for packaging and subsequent integration into a host or target cell (if applicable), with other viral sequences being replaced by an expression cassette encoding the protein to be expressed. For example, an AAV vector used in gene therapy typically only possesses inverted terminal repeat (ITR) sequences from the AAV genome which are required for packaging and gene expression in the host or target cell. The missing viral functions are supplied in trans by the packaging cell line. Henceforth, the viral DNA is packaged in a cell line, which contains a helper plasmid encoding the other AAV genes, namely rep and cap, but lacking ITR sequences. The cell line is also infected with adenovirus as a helper. The helper virus promotes replication of the AAV vector and expression of AAV genes from the helper plasmid. The helper plasmid is not packaged in significant amounts due to a lack of ITR sequences. Contamination with adenovirus can be reduced by, e.g., heat treatment to which adenovirus is more sensitive than AAV.

In an embodiment, the viral vector has the ability of cell type and/or tissue type recognition. For example, the viral vector can be pseudotyped with a different/alternative viral envelope glycoprotein; engineered with a cell type-specific receptor (e.g., genetic modification of the viral envelope glycoproteins to incorporate targeting ligands such as a peptide ligand, a single chain antibodies, a growth factor); and/or engineered to have a molecular bridge with dual specificities with one end recognizing a viral glycoprotein and the other end recognizing a moiety of the target cell surface (e.g., ligand-receptor, monoclonal antibody, avidin-biotin and chemical conjugation).

In an embodiment, the viral vector achieves cell type specific expression. For example, a tissue-specific promoter can be constructed to restrict expression of the transgene (Cas 9 and gRNA) in only the target cell. The specificity of the vector can also be mediated by microRNA-dependent control of transgene expression. In an embodiment, the viral vector has increased efficiency of fusion of the viral vector and a target cell membrane. For example, a fusion protein such as fusion-competent hemagglutinin (HA) can be incorporated to increase viral uptake into cells. In an embodiment, the viral vector has the ability of nuclear localization. For example, a virus that requires the breakdown of the cell wall (during cell division) and therefore will not infect a non-diving cell can be altered to incorporate a nuclear localization peptide in the matrix protein of the virus thereby enabling the transduction of non-proliferating cells.

In some embodiments, the Cas9- and/or gRNA-encoding DNA is delivered by a non-vector based method (e.g., using naked DNA or DNA complexes). For example, the DNA can be delivered, e.g., by organically modified silica or silicate (Ormosil), electroporation, gene gun, sonoporation, magnetofection, lipid-mediated transfection, dendrimers, inorganic nanoparticles, calcium phosphates, or a combination thereof.

In some embodiments, the Cas9- and/or gRNA-encoding DNA is delivered by a combination of a vector and a non-vector based method. For example, a virosome comprises a liposome combined with an inactivated virus (e.g., HIV or influenza virus), which can result in more efficient gene transfer, e.g., in a respiratory epithelial cell than either a viral or a liposomal method alone.

In an embodiment, the delivery vehicle is a non-viral vector. In an embodiment, the non-viral vector is an inorganic nanoparticle (e.g., attached to the payload to the surface of the nanoparticle). Exemplary inorganic nanoparticles include, e.g., magnetic nanoparticles (e.g., Fe lvln0$_2$), or silica. The outer surface of the nanoparticle can be conjugated with a positively charged polymer (e.g., polyethylenimine, polylysine, polyserine) which allows for attachment (e.g., conjugation or entrapment) of payload. In an embodiment, the non-viral vector is an organic nanoparticle (e.g., entrapment of the payload inside the nanoparticle). Exemplary organic nanoparticles include, e.g., SNALP liposomes that contain cationic lipids together with neutral helper lipids which are coated with polyethylene glycol (PEG) and protamine and nucleic acid complex coated with lipid coating.

Exemplary lipids and/or polymers for transfer of CRISPR systems or nucleic acid, e.g., vectors, encoding CRISPR systems or components thereof include, for example, those described in WO2011/076807, WO2014/136086, WO2005/060697, WO2014/140211, WO2012/031046, WO2013/103467, WO2013/006825, WO2012/006378, WO2015/095340, and WO2015/095346, the contents of each of the foregoing are hereby incorporated by reference in their entirety. In an embodiment, the vehicle has targeting modifications to increase target cell update of nanoparticles and liposomes, e.g., cell specific antigens, monoclonal antibodies, single chain antibodies, aptamers, polymers, sugars, and cell penetrating peptides. In an embodiment, the vehicle uses fusogenic and endosome-destabilizing peptides/polymers. In an embodiment, the vehicle undergoes acid-triggered conformational changes (e.g., to accelerate endosomal escape of the cargo). In an embodiment, a stimuli-cleavable polymer is used, e.g., for release in a cellular compartment. For example, disulfide-based cationic polymers that are cleaved in the reducing cellular environment can be used.

In an embodiment, the delivery vehicle is a biological non-viral delivery vehicle. In an embodiment, the vehicle is an attenuated bacterium (e.g., naturally or artificially engineered to be invasive but attenuated to prevent pathogenesis and expressing the transgene (e.g., *Listeria monocytogenes*, certain *Salmonella* strains, *Bifidobacterium longum*, and modified *Escherichia coli*), bacteria having nutritional and tissue-specific tropism to target specific tissues, bacteria having modified surface proteins to alter target tissue specificity). In an embodiment, the vehicle is a genetically modified bacteriophage (e.g., engineered phages having large packaging capacity, less immunogenic, containing mammalian plasmid maintenance sequences and having incorporated targeting ligands). In an embodiment, the vehicle is a mammalian virus-like particle. For example, modified viral particles can be generated (e.g., by purification of the "empty" particles followed by ex vivo assembly of the virus with the desired cargo). The vehicle can also be engineered to incorporate targeting ligands to alter target tissue specificity. In an embodiment, the vehicle is a biological liposome. For example, the biological liposome is a phospholipid-based particle derived from human cells (e.g., erythrocyte ghosts, which are red blood cells broken down into spherical structures derived from the subject (e.g., tissue targeting can be achieved by attachment of various tissue or cell-specific ligands), or secretory exosomes—subject (i.e., patient) derived membrane-bound nanovesicle (30-100 nm) of endocytic origin (e.g., can be produced from various cell types and can therefore be taken up by cells without the need of for targeting ligands).

In an embodiment, one or more nucleic acid molecules (e.g., DNA molecules) other than the components of a Cas system, e.g., the Cas9 molecule component and/or the gRNA molecule component described herein, are delivered. In an embodiment, the nucleic acid molecule is delivered at the same time as one or more of the components of the Cas system are delivered. In an embodiment, the nucleic acid molecule is delivered before or after (e.g., less than about 30 minutes, 1 hour, 2 hours, 3 hours, 6 hours, 9 hours, 12 hours, 1 day, 2 days, 3 days, 1 week, 2 weeks, or 4 weeks) one or more of the components of the Cas9 system are delivered. In an embodiment, the nucleic acid molecule is delivered by a different means than one or more of the components of the Cas9 system, e.g., the Cas9 molecule component and/or the gRNA molecule component, are delivered. The nucleic acid molecule can be delivered by any of the delivery methods described herein. For example, the nucleic acid molecule can be delivered by a viral vector, e.g., an integration-deficient lentivirus, and the Cas9 molecule component and/or the gRNA molecule component can be delivered by electroporation, e.g., such that the toxicity caused by nucleic acids (e.g., DNAs) can be reduced. In an embodiment, the nucleic acid molecule encodes a therapeutic protein, e.g., a protein described herein. In an embodiment, the nucleic acid molecule encodes an RNA molecule, e.g., an RNA molecule described herein.

Delivery of RNA encoding a Cas9 molecule

RNA encoding Cas9 molecules (e.g., active Cas9 molecules, inactive Cas9 molecules or inactive Cas9 fusion proteins) and/or gRNA molecules, can be delivered into cells, e.g., target cells described herein, by art-known methods or as described herein. For example, Cas9-encoding and/or gRNA-encoding RNA can be delivered, e.g., by microinjection, electroporation, lipid-mediated transfection, peptide-mediated delivery, or a combination thereof.

Delivery of Cas9 Molecule as Protein

Cas9 molecules (e.g., active Cas9 molecules, inactive Cas9 molecules or inactive Cas9 fusion proteins) can be delivered into cells by art-known methods or as described herein. For example, Cas9 protein molecules can be delivered, e.g., by microinjection, electroporation, lipid-mediated transfection, peptide-mediated delivery, cell squeezing or abrasion (e.g., by nanoneedles) or a combination thereof. Delivery can be accompanied by DNA encoding a gRNA or by a gRNA.

In an embodiment the Cas9 molecule, e.g., as described herein, is delivered as a protein and the gRNA molecule is delivered at one or more RNAs (e.g., as a dgRNA or sgRNA, as described herein). In embodiments, the Cas9 protein is complexed with the gRNA molecule prior to delivery to a cell, e.g., as described herein, as a ribonuclear protein complex ("RNP"). In embodiments, the RNP can be delivered into cells, e.g., described herein, by any art-known method, e.g., electroporation. As described herein, and without being bound by theory, it can be preferable to use a gRNA molecule and Cas9 molecule which result in high % editing at the target sequence (e.g., >85%, >90%, >95%, >98%, or >99%) in the target cell, e.g., described herein, even when the concentration of RNP delivered to the cell is reduced. Again, without being bound by theory, delivering a reduced or low concentration of RNP comprising a gRNA molecule that produces a high % editing at the target sequence in the target cell (including at the low RNP concentration), can be beneficial because it may reduce the frequency and number of off-target editing events. In one aspect, where a low or reduced concentration of RNP is to be used, the following procedure can be used to generate the RNP:

1. Provide the Cas9 molecule and the tracr in solution at a high concentration (e.g., a concentration higher than the final RNP concentration to be delivered to the cell), and allow the two components to equilibrate;
2. Provide the crRNA molecule, and allow the components to equilibrate (thereby forming a high-concentration solution of the RNP);
3. Dilute the RNP solution to the desired concentration;
4. Deliver said RNP at said desired concentration to the target cells, e.g., by electroporation.

The above procedure may be modified for use with sgRNA molecules by omitting step 2, above, and in step 1, providing the Cas9 molecule and the sgRNA molecule in solution at high concentration, and allowing the components to equilibrate. In embodiments, the Cas9 molecule and each gRNA component are provided in solution at a 1:2 ratio (Cas9:gRNA), e.g., a 1:2 molar ratio of Cas9:gRNA molecule. Where dgRNA molecules are used, the ratio, e.g., molar ratio, is 1:2:2 (Cas9:tracr:crRNA). In embodiments, the RNP is formed at a concentration of 20 uM or higher, e.g., a concentration from about to about 50 uM. In embodiments, the RNP is formed at a concentration of 10 uM or higher, e.g., a concentration from about 10 uM to about 30 uM. In embodiments, the RNP is diluted to a final concentration of 10 uM or less (e.g., a concentration from about 0.01 uM to about 10 uM) in a solution comprising the target cell (e.g., described herein) for delivery to said target cell. In embodiments, the RNP is diluted to a final concentration of 3 uM or less (e.g., a concentration from about 0.01 uM to about 3 uM) in a solution comprising the target cell (e.g., described herein) for delivery to said target cell. In embodiments, the RNP is diluted to a final concentration of 1 uM or less (e.g., a concentration from about 0.01 uM to about 1 uM) in a solution comprising the target cell (e.g., described herein) for delivery to said target cell. In embodiments, the RNP is diluted to a final concentration of 0.3 uM or less (e.g., a concentration from about 0.01 uM to about 0.3 uM) in a solution comprising the target cell (e.g., described herein) for delivery to said target cell. In embodiments, the RNP is provided at a final concentration of about 3 uM in a solution comprising the target cell (e.g., described herein) for delivery to said target cell. In embodiments, the RNP is provided at a final concentration of about 1 uM in a solution comprising the target cell (e.g., described herein) for delivery to said target cell. In embodiments, the RNP is provided at a final concentration of about 0.3 uM in a solution comprising the target cell (e.g., described herein) for delivery to said target cell. In embodiments, the RNP is provided at a final concentration of about 0.1 uM in a solution comprising the target cell (e.g., described herein) for delivery to said target cell. In embodiments, the RNP is provided at a final concentration of about 0.05 uM in a solution comprising the target cell (e.g., described herein) for delivery to said target cell. In embodiments, the RNP is provided at a final concentration of about 0.03 uM in a solution comprising the target cell (e.g., described herein) for delivery to said target cell. In embodiments, the RNP is provided at a final concentration of about 0.01 uM in a solution comprising the target cell (e.g., described herein) for delivery to said target cell.

Bi-Modal or Differential Delivery of Components

Separate delivery of the components of a Cas system, e.g., the Cas9 molecule component and the gRNA molecule component, and more particularly, delivery of the components by differing modes, can enhance performance, e.g., by improving tissue specificity and safety.

In an embodiment, the Cas9 molecule and the gRNA molecule are delivered by different modes, or as sometimes referred to herein as differential modes. Different or differential modes, as used herein, refer modes of delivery that confer different pharmacodynamic or pharmacokinetic properties on the subject component molecule, e.g., a Cas9 molecule, gRNA molecule, or template nucleic acid. For example, the modes of delivery can result in different tissue distribution, different half-life, or different temporal distribution, e.g., in a selected compartment, tissue, or organ.

Some modes of delivery, e.g., delivery by a nucleic acid vector that persists in a cell, or in progeny of a cell, e.g., by autonomous replication or insertion into cellular nucleic acid, result-in more persistent expression of and presence of a component.

XI. Methods of Treatment

The Cas systems, e.g., one or more gRNA molecules and one or more Cas molecules (e.g., Cas9 molecules), described herein are useful for the treatment of disease in a mammal, e.g., in a human. The terms "treat," "treated," "treating," and "treatment," include the administration of cas systems, e.g., one or more gRNA molecules and one or more Cas9 molecules, to cells to prevent or delay the onset of the symptoms, complications, or biochemical indicia of a disease, alleviating the symptoms or arresting or inhibiting further development of the disease, condition, or disorder. Treatment may be prophylactic (to prevent or delay the onset of the disease, or to prevent the manifestation of clinical or subclinical symptoms thereof) or therapeutic suppression or alleviation of symptoms after the manifestation of the disease. Treatment can be measured by the therapeutic measures described herein. The methods of "treatment" of the present invention also include administration of cells altered by the introduction of a cas system (e.g., one or more gRNA molecules and one or more Cas molecules) into said cells to a subject in order to cure, reduce the severity of, or ameliorate one or more symptoms of a disease or condition, in order to prolong the health or survival of a subject beyond that expected in the absence of such treatment. For example, "treatment" includes the alleviation of a disease symptom in a subject by at least 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95% or more.

Methods of Treatment/Combination Therapies

In another aspect, the present invention provides a method comprising administering a cell of the invention, e.g., a cell which comprises or which at any time comprised a gRNA molecule as described herein, to a subject. In embodiments, the cell has been altered by the introduction of the gRNA molecule such that the gene comprising sequence complementary to the gRNA molecule targeting domain is altered, such that expression of functional product of that gene is reduced or eliminated relative to an unmodified cell. In embodiments, the cell is further engineered to express a CAR, e.g., as described herein. In embodiments, the cell is an immune effector cell, e.g., an NK cell or T cell. In embodiments, the cell is allogeneic. In embodiments, the cell is autologous.

In another aspect, the present invention provides a method comprising administering a gRNA molecule, e.g., a gRNA molecule described herein, or a cell comprising or which at any time comprised a gRNA molecule, e.g., a gRNA molecule described herein, to a subject in need thereof. In one embodiment, the subject has a disorder described herein, e.g., the subject has cancer, e.g., the subject has a cancer which expresses a target antigen described herein. In one embodiment, the subject is a human.

In another aspect, the invention pertains to a method of treating a subject having a disease associated with expression of a cancer associated antigen as described herein comprising administering to the subject an effective amount of a gRNA molecule, e.g., a gRNA molecule described herein, or a cell comprising or which at any time comprised a gRNA molecule, e.g., a gRNA molecule described herein.

In yet another aspect, the invention features a method of treating a subject having a disease associated with expression of a tumor antigen (e.g., an antigen described herein), comprising administering to the subject an effective amount of a cell, e.g., an immune effector cell (e.g., a population of immune effector cells) comprising or which at any time comprised a gRNA molecule, e.g., a gRNA molecule described herein, further comprising a CAR molecule, wherein the CAR molecule comprises an antigen binding domain, a transmembrane domain, and an intracellular domain, said intracellular domain comprises a costimulatory domain and/or a primary signaling domain, wherein said antigen binding domain binds to the tumor antigen associated with the disease, e.g. a tumor antigen as described herein.

In a related aspect, the invention features a method of treating a subject having a disease associated with expression of a tumor antigen. The method comprises administering to the subject an effective amount of a gRNA molecule, e.g., a gRNA molecule described herein, or a cell comprising or which at any time comprised a gRNA molecule, e.g., a gRNA molecule described herein, in combination with an agent that increases the efficacy of the cell, wherein:
the agent that increases the efficacy of the immune cell is chosen from one or more of:
a protein phosphatase inhibitor;
a kinase inhibitor;
a cytokine;
an inhibitor of an immune inhibitory molecule; or
an agent that decreases the level or activity of a TREE cell.

In another aspect, the invention features a composition comprising an immune effector cell (e.g., a population of immune effector cells) comprising or which at any time comprised a gRNA molecule, e.g., a gRNA molecule described herein, for use in the treatment of a subject having a disease associated with expression of a tumor antigen, e.g., a disorder as described herein.

In certain embodiments of any of the aforesaid methods or uses, the cell comprising or which at any time comprised a gRNA described herein, has been altered such that the expression of the functional gene product of the gene comprising the target sequence complementary to the gRNA targeting domain has been reduced or abolished. In an embodiment, expression of the functional gene product of the gene comprising the target sequence complementary to the gRNA targeting domain has been abolished. In embodiments, the cell further expresses a CAR, e.g., as described herein. In embodiments the cell is allogeneic. In embodiments, the cell is autologous.

In certain embodiments of any of the aforesaid methods or uses, the disease associated with a tumor antigen, e.g., a tumor antigen described herein, is selected from a proliferative disease such as a cancer or malignancy or a precancerous condition such as a myelodysplasia, a myelodysplastic syndrome or a preleukemia, or is a non-cancer related indication associated with expression of a tumor antigen described herein. In one embodiment, the disease is a cancer described herein, e.g., a cancer described herein as being associated with a target described herein. In one embodiment, the disease is a hematologic cancer. In one embodiment, the hematologic cancer is leukemia. In one embodiment, the cancer is selected from the group consisting of one or more acute leukemias including but not limited to B-cell acute lymphoid leukemia ("BALL"), T-cell acute lymphoid leukemia ("TALL"), acute lymphoid leukemia (ALL); one or more chronic leukemias including but not limited to chronic myelogenous leukemia (CML), chronic lymphocytic leukemia (CLL); additional hematologic cancers or hematologic conditions including, but not limited to B cell prolymphocytic leukemia, blastic plasmacytoid dendritic cell neoplasm, Burkitt's lymphoma, diffuse large B cell lymphoma, follicular lymphoma, hairy cell leukemia, small cell- or a large cell-follicular lymphoma, malignant lymphoproliferative conditions, MALT lymphoma, mantle cell lymphoma, Marginal zone lymphoma, multiple myeloma, myelodysplasia and myelodysplastic syndrome, non-Hodgkin lymphoma, Hodgkin lymphoma, plasmablastic lymphoma, plasmacytoid dendritic cell neoplasm, Waldenstrom macroglobulinemia, and "preleukemia" which are a diverse collection of hematological conditions united by ineffective production (or dysplasia) of myeloid blood cells, and to disease associated with expression of a tumor antigen described herein include, but not limited to, atypical and/or non-classical cancers, malignancies, precancerous conditions or proliferative diseases expressing a tumor antigen as described herein; and any combination thereof. In another embodiment, the disease associated with a tumor antigen described herein is a solid tumor.

In certain embodiments, the methods or uses are carried out in combination with an agent that increases the efficacy of the immune effector cell, e.g., an agent as described herein.

In any of the aforesaid methods or uses, the disease associated with expression of the tumor antigen is selected from the group consisting of a proliferative disease, a precancerous condition, a cancer, and a non-cancer related indication associated with expression of the tumor antigen.

The cancer can be a hematologic cancer, e.g., a cancer chosen from one or more of chronic lymphocytic leukemia (CLL), acute leukemias, acute lymphoid leukemia (ALL), B-cell acute lymphoid leukemia (B-ALL), T-cell acute lymphoid leukemia (T-ALL), chronic myelogenous leukemia (CML), B cell prolymphocytic leukemia, blastic plasmacytoid dendritic cell neoplasm, Burkitt's lymphoma, diffuse large B cell lymphoma, follicular lymphoma, hairy cell leukemia, small cell- or a large cell-follicular lymphoma, malignant lymphoproliferative conditions, MALT lymphoma, mantle cell lymphoma, marginal zone lymphoma, multiple myeloma, myelodysplasia and myelodysplastic syndrome, non-Hodgkin's lymphoma, Hodgkin's lymphoma, plasmablastic lymphoma, plasmacytoid dendritic cell neoplasm, Waldenstrom macroglobulinemia, or preleukemia.

The cancer can also be chosen from colon cancer, rectal cancer, renal-cell carcinoma, liver cancer, non-small cell carcinoma of the lung, cancer of the small intestine, cancer of the esophagus, melanoma, bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, Hodgkin's Disease, non-Hodgkin's lymphoma, cancer of the endocrine system, cancer of the thyroid gland, cancer of the parathyroid gland, cancer of the adrenal gland, sarcoma of soft tissue, cancer of the urethra, cancer of the penis, solid tumors of childhood, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers, combinations of said cancers, and metastatic lesions of said cancers.

In certain embodiments of the methods or uses described herein, the cell is administered in combination with an agent that increases the efficacy of the immune effector cell, e.g., one or more of a protein phosphatase inhibitor, a kinase inhibitor, a cytokine, an inhibitor of an immune inhibitory molecule; or an agent that decreases the level or activity of a TRE G cell.

In certain embodiments of the methods or uses described herein, the protein phosphatase inhibitor is a SHP-1 inhibitor and/or an SHP-2 inhibitor.

In other embodiments of the methods or uses described herein, kinase inhibitor is chosen from one or more of a CDK4 inhibitor, a CDK4/6 inhibitor (e.g., palbociclib), a BTK inhibitor (e.g., ibrutinib or RN-486), an mTOR inhibitor (e.g., rapamycin or everolimus (RAD001)), an MNK inhibitor, or a dual P13K/mTOR inhibitor. In one embodiment, the BTK inhibitor does not reduce or inhibit the kinase activity of interleukin-2-inducible kinase (ITK).

In other embodiments of the methods or uses described herein, the agent that decreases the level or activity of the $T_{REG}$ cells is chosen from cyclophosphamide, anti-GITR antibody, CD25-depletion, or a combination thereof.

In other embodiments, the agent that inhibits the inhibitory molecule comprises a first polypeptide comprising an inhibitory molecule or a fragment thereof and a second polypeptide that provides a positive signal to the cell, and wherein the first and second polypeptides are expressed on the CAR-containing immune cells, wherein (i) the first polypeptide comprises PD1, PD-L1, CTLA-4, TIM-3, LAG3, VISTA, BTLA, TIGIT, LAIR1, CD160, 2B4, TGF beta, CEACAM-1, CEACAM-3, and CEACAM-5 or a fragment thereof; and/or (ii) the second polypeptide comprises an intracellular signaling domain comprising a primary signaling domain and/or a costimulatory signaling domain. In one embodiment, the primary signaling domain comprises a functional domain of CD3 zeta; and/or the costimulatory signaling domain comprises a functional domain of a protein selected from 41BB, CD27 and CD28.

In other embodiments, cytokine is chosen from IL-7; IL-15; a composition comprising a interleukin-15 (IL-15) polypeptide, a interleukin-15 receptor alpha (IL-15Ra) polypeptide, or a combination of both a IL-15 polypeptide and a IL-15Ra polypeptide e.g., hetIL-15; IL-18; IL-21, or a combination thereof. Exemplary hetIL-15 are heterodimeric non-covalent complexes of IL-15 and IL-15Ra (Admune Therapeutics, LLC). Such hetIL-15 is described in, e.g., U.S. Pat. No. 8,124,084, U.S. 2012/0177598, U.S. 2009/0082299, U.S. 2012/0141413, and U.S. 2011/0081311, incorporated herein by reference. hetIL-15 is described in, e.g., U.S. Pat. No. 8,124,084, U.S. 2012/0177598, U.S. 2009/0082299, U.S. 2012/0141413, and U.S. 2011/0081311, incorporated herein by reference. Other exemplary embodiments of hetIL-15 are covalent complexes between an IL-15 polypeptide and an IL-15R (e.g., IL-15Ra) polypeptide.

In other embodiments, the cell and a second, e.g., any of the combination therapies disclosed herein (e.g., the agent that that increases the efficacy of the cell) are administered substantially simultaneously or sequentially.

In other embodiments, the cell is administered in combination with a molecule that targets GITR and/or modulates GITR function. In certain embodiments, the molecule targeting GITR and/or modulating GITR function is administered prior to the CAR-expressing cell or population of cells, or prior to apheresis.

In one embodiment, lymphocyte infusion, for example allogeneic lymphocyte infusion, is used in the treatment of the cancer, wherein the lymphocyte infusion comprises at least one cell, e.g., CAR-expressing cell, of the present invention. In one embodiment, autologous lymphocyte infusion is used in the treatment of the cancer, wherein the autologous lymphocyte infusion comprises at least one cell, e.g., CAR-expressing cell described herein.

In one embodiment, the cell is a T cell and the T cell is diaglycerol kinase (DGK) deficient. In one embodiment, the cell is a T cell and the T cell is Ikaros deficient. In one embodiment, the cell is a T cell and the T cell is both DGK and Ikaros deficient.

In one embodiment, the method includes administering a cell of the invention, as described herein, in combination with an agent which enhances the activity of the cell, wherein the agent is a cytokine, e.g., IL-7; IL-15; a composition comprising a interleukin-15 (IL-15) polypeptide, a interleukin-15 receptor alpha (IL-15Ra) polypeptide, or a combination of both a IL-15 polypeptide and a IL-15Ra polypeptide e.g., hetIL-15; IL-18; IL-21; or a combination thereof. The cytokine can be delivered in combination with, e.g., simultaneously or shortly after, administration of the cell. Alternatively, the cytokine can be delivered after a prolonged period of time after administration of the cell, e.g., after assessment of the subject's response to the cell. In one embodiment the cytokine is administered to the subject simultaneously (e.g., administered on the same day) with or shortly after administration (e.g., administered 1 day, 2 days, 3 days, 4 days, 5 days, 6 days, or 7 days after administration) of the cell or a population of cells. In other embodiments, the cytokine is administered to the subject after a prolonged period of time (e.g., e.g., at least 2 weeks, 3 weeks, 4 weeks, 6 weeks, 8 weeks, weeks, or more) after administration of the cell or a population of cells, or after assessment of the subject's response to the cell.

In other embodiments, the cells of the invention that are further engineered to express a CAR are administered in combination with an agent that ameliorates one or more side effects associated with administration of a cell expressing a CAR molecule. Side effects associated with the CAR-expressing cell can be chosen from cytokine release syndrome (CRS) or hemophagocytic lymphohistiocytosis (HLH).

In embodiments of any of the aforesaid methods or uses, the cells expressing the CAR molecule are administered in combination with an agent that treats the disease associated with expression of the tumor antigen, e.g., any of the second or third therapies disclosed herein. Additional exemplary combinations include one or more of the following.

In another embodiment, the cell, e.g., as described herein, can be administered in combination with another agent, e.g., a kinase inhibitor and/or checkpoint inhibitor described herein. In an embodiment, a cell of the invention can further express another agent, e.g., an agent which enhances the activity of the cell.

For example, in one embodiment, the agent that enhances the activity of the cell can be an agent which inhibits an inhibitory molecule.

In one embodiment, the agent that inhibits the inhibitory molecule is an inhibitory nucleic acid is a dsRNA, a siRNA, or a shRNA.

In another embodiment, the agent which inhibits an inhibitory molecule, e.g., is a molecule described herein, e.g., an agent that comprises a first polypeptide, e.g., an inhibitory molecule, associated with a second polypeptide that provides a positive signal to the cell, e.g., an intracellular signaling domain described herein. In one embodiment, the agent comprises a first polypeptide, e.g., of an inhibitory molecule, or a fragment thereof (e.g., at least a portion of the extracellular domain of any of these), and a second polypeptide which is an intracellular signaling domain described herein (e.g., comprising a costimulatory domain (e.g., 41BB, CD27 or CD28, e.g., as described herein) and/or a primary signaling domain (e.g., a CD3 zeta signaling domain described herein). In one embodiment, the agent comprises a first polypeptide of PD1 or a fragment thereof (e.g., at least a portion of the extracellular domain of PD1), and a second polypeptide of an intracellular signaling domain described herein (e.g., a CD28 signaling domain described herein and/or a CD3 zeta signaling domain described herein).

In one embodiment, the cell of the present invention, e.g., T cell or NK cell, is administered to a subject that has received a previous stem cell transplantation, e.g., autologous stem cell transplantation.

In one embodiment, the cell of the present invention, e.g., T cell or NK cells, is administered to a subject that has received a previous dose of melphalan.

In one embodiment, the cell of the invention, is administered in combination with an agent that increases the efficacy of the cell, e.g., an agent described herein.

In one embodiment, the cells of the invention, are administered in combination with a low, immune enhancing dose of an mTOR inhibitor. While not wishing to be bound by theory, it is believed that treatment with a low, immune enhancing, dose (e.g., a dose that is insufficient to completely suppress the immune system but sufficient to improve immune function) is accompanied by a decrease in PD-1 positive T cells or an increase in PD-1 negative cells. PD-1 positive T cells, but not PD-1 negative T cells, can be exhausted by engagement with cells which express a PD-1 ligand, e.g., PD-L1 or PD-L2. In an embodiment this approach can be used to optimize the performance of the cells described herein in the subject. While not wishing to be bound by theory, it is believed that, in an embodiment, the performance of endogenous, non-modified immune effector cells, e.g., T cells or NK cells, is improved. While not wishing to be bound by theory, it is believed that, in an embodiment, the performance of a CAR-expressing cell is improved. In other embodiments, cells, e.g., T cells or NK cells, which comprise or will be engineered to comprise a gRNA molecule of the invention, can be treated ex vivo by contact with an amount of an mTOR inhibitor that increases the number of PD1 negative immune effector cells, e.g., T cells or increases the ratio of PD1 negative immune effector cells, e.g., T cells/PD1 positive immune effector cells, e.g., T cells.

In an embodiment, administration of a low, immune enhancing, dose of an mTOR inhibitor, e.g., an allosteric inhibitor, e.g., RAD001, or a catalytic inhibitor, is initiated prior to administration of an CAR expressing cell described herein, e.g., T cells or NK cells. In an embodiment, the cells are administered after a sufficient time, or sufficient dosing, of an mTOR inhibitor, such that the level of PD1 negative immune effector cells, e.g., T cells or NK cells, or the ratio of PD1 negative immune effector cells, e.g., T cells/PD1 positive immune effector cells, e.g., T cells, has been, at least transiently, increased.

In an embodiment, the cell, e.g., T cell or NK cell, to be engineered to comprise a gRNA of the invention, is harvested after a sufficient time, or after sufficient dosing of the low, immune enhancing, dose of an mTOR inhibitor, such that the level of PD1 negative immune effector cells, e.g., T cells, or the ratio of PD1 negative immune effector cells, e.g., T cells/PD1 positive immune effector cells, e.g., T cells, in the subject or harvested from the subject has been, at least transiently, increased.

In one embodiment, the cell of the invention, is administered in combination with an agent that ameliorates one or more side effect associated with administration of a cell, e.g., an agent described herein.

In one embodiment, the cell is administered in combination with an agent that treats the disease associated with a cancer associated antigen as described herein, e.g., an agent described herein.

In one embodiment, the cell is administered at a dose and/or dosing schedule described herein.

In one embodiment, the subject (e.g., human) receives an initial administration of cells of the invention, and one or more subsequent administrations of cells of the invention, wherein the one or more subsequent administrations are administered less than 15 days, e.g., 14, 13, 12, 11, 10, 9, 8, 7, 6, 5, 4, 3, or 2 days after the previous administration. In one embodiment, more than one administration of cells of the invention are administered to the subject (e.g., human) per week, e.g., 2, 3, or 4 administrations of cells comprising a CAR molecule are administered per week. In one embodiment, the subject (e.g., human subject) receives more than one administration of cells of the invention per week (e.g., 2, 3 or 4 administrations per week) (also referred to herein as a cycle), followed by a week of no administration of cells of the invention, and then one or more additional administration of cells of the invention (e.g., more than one administration of the cells of the invention per week) is administered to the subject. In another embodiment, the subject (e.g., human subject) receives more than one cycle of cells of the invention, and the time between each cycle is less than 10, 9, 8, 7, 6, 5, 4, or 3 days. In one embodiment, the cells of the invention are administered every other day for 3 administrations per week. In one embodiment, the cells of the invention are administered for at least two, three, four, five, six, seven, eight or more weeks.

In one embodiment, the cells of the invention, are administered as a first line treatment for the disease, e.g., the cancer, e.g., the cancer described herein. In another embodiment, the cells of the invention, are administered as a second, third, fourth line treatment for the disease, e.g., the cancer, e.g., the cancer described herein.

In one embodiment, a population of cells described herein is administered.

In another aspect, the invention pertains to the isolated nucleic acid molecule encoding a gRNA of the invention, the gRNA molecule of the invention, and the cell comprising or which at any time comprised a gRNA of the invention for use as a medicament. In embodiments, the cell comprising or which at any time comprised a gRNA of the invention is or will be altered such that expression of the functional product of the gene comprising sequence complimentary to the gRNA targeting domain is reduced or abolished.

In another aspect, the invention pertains to the isolated nucleic acid molecule encoding a gRNA of the invention, the gRNA molecule of the invention, and the cell comprising or which at any time comprised a gRNA of the invention for use in the treatment of a disease expressing a cancer associated antigen as described herein. In embodiments, the cell comprising or which at any time comprised a gRNA of the invention is or will be altered such that expression of the functional product of the gene comprising sequence complimentary to the gRNA targeting domain is reduced or abolished.

In another aspect, the invention pertains to the isolated nucleic acid molecule encoding a gRNA of the invention, the gRNA molecule of the invention, and the cell comprising or which at any time comprised a gRNA of the invention for use as a medicament in combination with a cytokine, e.g., IL-7; IL-15; a composition comprising a interleukin-15 (IL-15) polypeptide, a interleukin-15 receptor alpha (IL-15Ra) polypeptide, or a combination of both a IL-15 polypeptide and a IL-15Ra polypeptide e.g., hetIL-15; IL-18; and/or IL-21; and/or combinations thereof as described herein. In another aspect, the invention pertains to a cytokine described herein for use as a medicament in combination with a cell described herein. In embodiments, the cell comprising or which at any time comprised a gRNA of the invention is or will be altered such that expression of the functional product of the gene comprising sequence complimentary to the gRNA targeting domain is reduced or abolished.

In another aspect, the invention pertains to the isolated nucleic acid molecule encoding a gRNA of the invention, the gRNA molecule of the invention, and the cell comprising or which at any time comprised a gRNA of the invention for use as a medicament in combination with a kinase inhibitor and/or a checkpoint inhibitor as described herein. In another aspect, the invention pertains to a kinase inhibitor and/or a checkpoint inhibitor described herein for use as a medicament in combination with a cell comprising or which at any time comprised a gRNA of the invention.

In another aspect, the invention features a composition comprising a cell of the invention for use in the treatment of a subject having a disease associated with expression of a tumor-supporting antigen, e.g., a disorder as described herein.

In any of the aforesaid methods or uses, the disease associated with expression of the tumor-supporting antigen is selected from the group consisting of a proliferative disease, a precancerous condition, a cancer, and a non-cancer related indication associated with expression of the tumor-supporting antigen. In an embodiment, the disease associated with a tumor-supporting antigen described herein is a solid tumor.

In one embodiment of the methods or uses described herein, the cell of the invention is administered in combination with another agent. In one embodiment, the agent can be a kinase inhibitor, e.g., a CDK4/6 inhibitor, a BTK inhibitor, an mTOR inhibitor, a MNK inhibitor, or a dual PI3K/mTOR inhibitor, and combinations thereof. In one embodiment, the kinase inhibitor is a CDK4 inhibitor, e.g., a CDK4 inhibitor described herein, e.g., a CD4/6 inhibitor, such as, e.g., 6-Acetyl-8-cyclopentyl-5-methyl-2-(5-piperazin-1-yl-pyridin-2-ylamino)-8H-pyrido[2,3-d]pyrimidin-7-one, hydrochloride (also referred to as palbociclib or PD0332991). In one embodiment, the kinase inhibitor is a BTK inhibitor, e.g., a BTK inhibitor described herein, such as, e.g., ibrutinib. In one embodiment, the kinase inhibitor is an mTOR inhibitor, e.g., an mTOR inhibitor described herein, such as, e.g., rapamycin, a rapamycin analog, OSI-027. The mTOR inhibitor can be, e.g., an mTORC1 inhibitor and/or an mTORC2 inhibitor, e.g., an mTORC1 inhibitor and/or mTORC2 inhibitor described herein. In one embodiment, the kinase inhibitor is a MNK inhibitor, e.g., a MNK inhibitor described herein, such as, e.g., 4-amino-5-(4-fluoroanilino)-pyrazolo[3,4-d]pyrimidine. The MNK inhibitor can be, e.g., a MNK1a, MNK1b, MNK2a and/or MNK2b inhibitor. The dual PI3K/mTOR inhibitor can be, e.g., PF-04695102.

In one embodiment of the methods or uses described herein, the kinase inhibitor is a CDK4 inhibitor selected from aloisine A; flavopiridol or HMR-1275, 2-(2-chlorophenyl)-5,7-dihydroxy-8-[(3S,4R)-3-hydroxy-1-methyl-4-piperidinyl]-4-chromenone; crizotinib (PF-02341066; 2-(2-Chlorophenyl)-5,7-dihydroxy-8-[(2R,3S)-2-(hydroxymethyl)-1-methyl-3-pyrrolidinyl]-4H-1-benzopyran-4-one, hydrochloride (P276-00); 1-methyl-5-[[2-[5-(trifluoromethyl)-1H-imidazol-2-yl]-4-pyridinyl]oxy]-N-[4-(trifluoromethyl)phenyl]-1H-benzimidazol-2-amine (RAF265); indisulam (E7070); roscovitine (CYC202); palbociclib (PD0332991); dinaciclib (SCH727965); N-[5-[[(5-tert-butyloxazol-2-yl)methyl]thio]thiazol-2-yl]piperidine-4-carboxamide (BMS 387032); 4-[[9-chloro-7-(2,6-difluorophenyl)-5H-pyrimido[5,4-d][2]benzazepin-2-yl]amino]-benzoic acid (MLN8054); 5-[3-(4,6-difluoro-1H-benzimidazol-2-yl)-1H-indazol-5-yl]-N-ethyl-4-methyl-3-pyridinemethanamine (AG-024322); 4-(2,6-dichlorobenzoylamino)-1H-pyrazole-3-carboxylic acid N-(piperidin-4-yl)amide (AT7519); 4-[2-methyl-1-(1-methylethyl)-1H-imidazol-5-yl]-N-[4]-N-[4-(methylsulfonyl)phenyl]-2-pyrimidinamine (AZD5438); and XL281 (BMS908662).

In one embodiment of the methods or uses described herein, the kinase inhibitor is a CDK4 inhibitor, e.g., palbociclib (PD0332991), and the palbociclib is administered at a dose of about 50 mg, 60 mg, 70 mg, 75 mg, 80 mg, 90 mg, 100 mg, 105 mg, 110 mg, 115 mg, 120 mg, 125 mg, 130 mg, 135 mg (e.g., 75 mg, 100 mg or 125 mg) daily for a period of time, e.g., daily for 14-21 days of a 28 day cycle, or daily for 7-12 days of a 21 day cycle. In one embodiment, 1, 2, 3, 4, 5, 6, 7, 8, 9, 10, 11, 12 or more cycles of palbociclib are administered.

In one embodiment of the methods or uses described herein, the kinase inhibitor is a BTK inhibitor selected from ibrutinib (PCI-32765); GDC-0834; RN-486; CGI-560; CGI-1764; HM-71224; CC-292; ONO-4059; CNX-774; and LFM-A13. In one embodiment, the BTK inhibitor does not reduce or inhibit the kinase activity of interleukin-2-inducible kinase (ITK), and is selected from GDC-0834; RN-486; CGI-560; CGI-1764; HM-71224; CC-292; ONO-4059; CNX-774; and LFM-A13.

In one embodiment of the methods or uses described herein, the kinase inhibitor is a BTK inhibitor, e.g., ibrutinib (PCI-32765), and the ibrutinib is administered at a dose of about 250 mg, 300 mg, 350 mg, 400 mg, 420 mg, 440 mg, 460 mg, 480 mg, 500 mg, 520 mg, 540 mg, 560 mg, 580 mg, 600 mg (e.g., 250 mg, 420 mg or 560 mg) daily for a period of time, e.g., daily for 21 day cycle, or daily for 28 day cycle. In one embodiment, 1, 2, 3, 4, 5, 6, 7, 8, 9, 10, 11, 12 or more cycles of ibrutinib are administered.

In one embodiment of the methods or uses described herein, the kinase inhibitor is a BTK inhibitor that does not inhibit the kinase activity of ITK, e.g., RN-486, and RN-486 is administered at a dose of about 100 mg, 110 mg, 120 mg, 130 mg, 140 mg, 150 mg, 160 mg, 170 mg, 180 mg, 190 mg, 200 mg, 210 mg, 220 mg, 230 mg, 240 mg, 250 mg (e.g., 150 mg, 200 mg or 250 mg) daily for a period of time, e.g., daily a 28 day cycle. In one embodiment, 1, 2, 3, 4, 5, 6, 7, or more cycles of RN-486 are administered.

In one embodiment of the methods or uses described herein, the kinase inhibitor is an mTOR inhibitor selected from temsirolimus; ridaforolimus (1R,2R,4S)-4-[(2R)-2 [(1R,9S,12S,15R,16E,18R,19R,21R, 23S,24E,26E,28Z, 30S,32S,35R)-1,18-dihydroxy-19,30-dimethoxy-15,17,21, 23,29,35-hexamethyl-2,3,10,14,20-pentaoxo-11,36-dioxa-4-azatricyclo[30.3.1.0$^{4,9}$]hexatriaconta-16,24,26,28-tetraen-12-yl]propyl]-2-methoxycyclohexyl dimethylphosphinate, also known as AP23573 and MK8669; everolimus (RAD001); rapamycin (AY22989); simapimod; (5-{2,4-bis[(3S)-3-methylmorpholin-4-yl]pyrido[2,3-d]pyrimidin-7-yl}-2-methoxyphenyl)methanol (AZD8055); 2-amino-8-[trans-4-(2-hydroxyethoxy)cyclohexyl]-6-(6-methoxy-3-pyridinyl)-4-methyl-pyrido[2,3-d]pyrimidin-7(8H)-one (PF04691502); and N$^2$-[1,4-dioxo-4-[[4-(4-oxo-8-phenyl-4H-1-benzopyran-2-yl)morpholinium-4-yl]methoxy]butyl]-arginylglycyl-L-α-aspartylL-serine—(SEQ ID NO: 6659), inner salt (SF1126); and XL765.

In one embodiment of the methods or uses described herein, the kinase inhibitor is an mTOR inhibitor, e.g., rapamycin, and the rapamycin is administered at a dose of about 3 mg, 4 mg, 5 mg, 6 mg, 7 mg, 8 mg, 9 mg, 10 mg (e.g., 6 mg) daily for a period of time, e.g., daily for 21 day cycle, or daily for 28 day cycle. In one embodiment, 1, 2, 3, 4, 5, 6, 7, 8, 9, 10, 11, 12 or more cycles of rapamycin are administered. In one embodiment, the kinase inhibitor is an mTOR inhibitor, e.g., everolimus and the everolimus is administered at a dose of about 2 mg, 2.5 mg, 3 mg, 4 mg, 5 mg, 6 mg, 7 mg, 8 mg, 9 mg, mg, 11 mg, 12 mg, 13 mg, 14 mg, 15 mg (e.g., 10 mg) daily for a period of time, e.g., daily for 28 day cycle. In one embodiment, 1, 2, 3, 4, 5, 6, 7, 8, 9, 10, 11, 12 or more cycles of everolimus are administered.

In one embodiment of the methods or uses described herein, the kinase inhibitor is an MNK inhibitor selected from CGP052088; 4-amino-3-(p-fluorophenylamino)-pyrazolo[3,4-d]pyrimidine (CGP57380); cercosporamide; ETC-1780445-2; and 4-amino-5-(4-fluoroanilino)-pyrazolo[3,4-d]pyrimidine.

In one embodiment of the methods or uses described herein, the kinase inhibitor is a dual phosphatidylinositol 3-kinase (PI3K) and mTOR inhibitor selected from 2-Amino-8-[trans-4-(2-hydroxyethoxy)cyclohexyl]-6-(6-methoxy-3-pyridinyl)-4-methyl-pyrido[2,3-d]pyrimidin-7 (8H)-one (PF-04691502); N-[4-[[4-(Dimethylamino)-1-piperidinyl]carbonyl]phenyl]-N'-[4-(4,6-di-4-morpholinyl-1,3,5-triazin-2-yl)phenyl]urea (PF-05212384, PKI-587); 2-Methyl-2-{4-[3-methyl-2-oxo-8-(quinolin-3-yl)-2,3-di-hydro-1H-imidazo[4,5-c]quinolin-1-yl]phenyl}propanenitrile (BEZ-235); apitolisib (GDC-0980, RG7422); 2,4-Difluoro-N-{2-(methyloxy)-5[4-(4-pyridazinyl)-6-quinolinyl]-3-pyridinyl}benzenesulfonamide (GSK2126458); 8-(6-methoxypyridin-3-yl)-3-methyl-1-(4-(piperazin-1-yl)-3-(trifluoromethyl)phenyl)-1H-imidazo[4,5-c]quinolin-2(3H)-one Maleic acid (NVP-BGT226); 3-[4-(4-Morpholinylpyrido[3',2':4,5]furo[3,2-d]pyrimidin-2-yl] phenol (PI-103); 5-(9-isopropyl-8-methyl-2-morpholino-9H-purin-6-yl)pyrimidin-2-amine (VS-5584, SB2343); and N-[2-[(3,5-Dimethoxyphenyl)amino]quinoxalin-3-yl]-4-[(4-methyl-3-methoxyphenyl)carbonyl]aminophenylsulfonamide (XL765).

In one embodiment of the methods or uses described herein, a CAR expressing immune effector cell described herein is administered to a subject in combination with a protein tyrosine phosphatase inhibitor, e.g., a protein tyrosine phosphatase inhibitor described herein. In one embodiment, the protein tyrosine phosphatase inhibitor is an SHP-1 inhibitor, e.g., an SHP-1 inhibitor described herein, such as, e.g., sodium stibogluconate. In one embodiment, the protein tyrosine phosphatase inhibitor is an SHP-2 inhibitor.

In one embodiment of the methods or uses described herein, the cell of the invention is administered in combination with another agent, and the agent is a cytokine. The cytokine can be, e.g., IL-7; IL-15; a composition comprising a interleukin-15 (IL-15) polypeptide, a interleukin-15 receptor alpha (IL-15Ra) polypeptide, or a combination of both a IL-15 polypeptide and a IL-15Ra polypeptide e.g., hetIL-15; IL-18; IL-21; or a combination thereof. In another embodiment, the cell of the invention is administered in combination with a checkpoint inhibitor, e.g., a checkpoint inhibitor described herein. For example, in one embodiment, the check point inhibitor inhibits an inhibitory molecule selected from PD-1, PD-L1, CTLA-4, TIM-3, CEACAM (e.g., CEACAM-1, CEACAM-3 and/or CEACAM-5), LAG-3, VISTA, BTLA, TIGIT, LAIR1, CD160, 2B4 and TGF beta.

In one aspect, the invention provides a method of treating a subject, e.g., a subject having a condition described herein, with an allogeneic cell, for example an allogeneic immune effector cell, for example an allogeneic CAR-expressing T cell, comprising or which at any time comprised a gRNA molecule of the invention. In embodiments, the cell has been altered such that expression of the functional gene product of a gene comprising a target sequence complementary to the gRNA targeting domain has been reduced or eliminated.

In one aspect, the invention provides a method of treatment comprising:
(a) providing a population of cells from an allogeneic donor;
(b) introducing into the cells a CRISPR System (e.g., an *S. pyogenes* Cas9 CRISPR system) comprising a first gRNA molecule of the invention (or nucleic acid encoding said gRNA molecule);
(c) optionally, selecting those cells in which expression of the gene product (e.g., functional gene product) of the gene comprising the target sequence complementary to the targeting domain of the first gRNA has been reduced or eliminated;
(d) transducing the cells with nucleic acid encoding a CAR as described herein; and
(e) administering the cells to a patient in need thereof, e.g., a patient who has a disease associated with expression of an antigen recognized by the CAR.

In embodiments, the first gRNA molecule comprises a targeting domain complementary to an allogeneic T cell target, e.g., a component of the TCR, for example, a first gRNA molecule comprising a targeting domain complementary to a target sequence in a gene selected from CD247, CD3D, CD3E, CD3G, TRAC, TRBC1, and TRBC2. In embodiments, the first gRNA to CD247, CD3D, CD3E, CD3G, TRAC, TRBC1, or TRBC2 is a first gRNA comprising a targeting domain listed in Table 1, Table 4 or Table 5. In embodiments, step (c) comprises selected those cells which are negative for TCR expression. In embodiments, the method further comprises administering to the patient an agent which selectively inhibits or depletes NK cells, for example and antibody or antigen binding fragment to an antigen specific to NK cells, e.g., which is not expressed on T cells.

In embodiments, the method further comprises introducing into the cells a second gRNA molecule of the invention (or nucleic acid encoding said gRNA molecule), e.g., introducing into the cells a CRISPR System (e.g., an *S. pyogenes* Cas9 CRISPR system) comprising a second gRNA molecule of the invention (or nucleic acid encoding said gRNA molecule). In embodiments, the second gRNA molecule comprises a targeting domain complementary to an allogeneic T cell target, e.g., a second gRNA molecule comprising a targeting domain complementary to a target sequence in a gene selected from B2M, HLA-A, HLA-B and HLA-C. In embodiments, the second gRNA to B2M, HLA-A, HLA-B or HLA-C is a second gRNA comprising a targeting domain of Table 1, or Table 3. In embodiments, step (c) optionally includes, selecting those cells in which expression of the gene product (e.g., functional gene product) of the gene comprising the target sequence complementary to the targeting domain of the first gRNA and in which expression of the gene product (e.g., functional gene product) of the gene comprising the target sequence complementary to the targeting domain of the second gRNA has been reduced or eliminated. In embodiments, step (c) comprises selected those cells which are negative for TCR expression and/or negative for B2M or HLA expression. In embodiments, the method further comprises administering to the patient an agent which selectively inhibits or depletes NK cells, for example and antibody or antigen binding fragment to an antigen specific to NK cells, e.g., which is not expressed on T cells.

In embodiments, the method further comprises introducing into the cells a third gRNA molecule of the invention (or nucleic acid encoding said gRNA molecule), e.g., introducing into the cells a CRISPR System (e.g., an S. pyogenes Cas9 CRISPR system) comprising a second gRNA molecule of the invention (or nucleic acid encoding said gRNA molecule). In embodiments, the third gRNA molecule comprises a targeting domain complementary to a target sequence in a gene of an inhibitory molecule or downstream effector of signaling through an inhibitory molecule, e.g., a third gRNA molecule comprising a targeting domain complementary to a target sequence in a gene selected from CD274, HAVCR2, LAG3, PDCD1, PD-L2, CTLA4, CEACAM (e.g., CEACAM-1, CEACAM-3 and/or CEACAM-5), VISTA, BTLA, TIGIT, LAIR1, CD160, 2B4, CD80, CD86, B7-H3 (CD113), B7-H4 (VTCN1), HVEM (TNFRSF14 or CD107), KIR, A2aR, MHC class I, MHC class II, GAL9, adenosine, and TGF beta, and PTPN11. In embodiments, the third gRNA comprises a targeting domain to CD274, HAVCR2, LAG3, PDCD1 or PTPN11 selected from the targeting domains of Table 2, or Table 6. In embodiments, step (c) optionally includes, selecting those cells in which expression of the gene product (e.g., functional gene product) of the gene comprising the target sequence complementary to the targeting domain of the first gRNA, in which expression of the gene product (e.g., functional gene product) of the gene comprising the target sequence complementary to the targeting domain of the second gRNA, and/or in which expression of the gene product (e.g., functional gene product) of the gene comprising the target sequence complementary to the targeting domain of the third gRNA has been reduced or eliminated. In embodiments, step (c) comprises selecting those cells which are negative for TCR expression, negative for B2M or HLA expression, and/or negative for expression of a targeted inhibitory molecule or downstream effector of signaling through an inhibitory molecule. In embodiments, the method further comprises administering to the patient an agent which selectively inhibits or depletes NK cells, for example and antibody or antigen binding fragment to an antigen specific to NK cells, e.g., which is not expressed on T cells. In other embodiments, the third gRNA comprises a targeting domain complementary to a target sequence in a gene selected from CIITA, RFXANK, RFX5, RFXAP, e.g., as described herein. In embodiments, the third gRNA comprises a targeting domain complementary to a target sequence in a CIITA gene, e.g., as described herein, e.g., in Table 6c.

In any of the aforementioned aspects and embodiments the CAR is a CAR as described herein. In any of the aforementioned aspects and embodiments, the CAR is a BCMA CAR, e.g., a BCMA CAR described herein, e.g., comprises or is engineered to express a CAR comprising SEQ ID NO:8559. In aspects, the nucleic acid encoding the CAR is introduced into the cell by viral vector, e.g., lentiviral vector, transduction. In other aspects, the nucleic acid encoding the CAR is introduced as DNA that is incorporated in the host cell genome at or near a site modified by one of the CRISPR systems introduced into said cells.

In one aspect, the invention provides a method of treatment comprising:
(a) providing a population of cells, e.g, immune effector cells, e.g., T cell or NK cells, e.g., as described herein, (e.g., a population of said cells from an allogeneic donor);
(b) introducing into the population of cells a CRISPR System (e.g., an S. pyogenes Cas9 CRISPR system) comprising a first gRNA molecule of the invention (or nucleic acid encoding said gRNA molecule) comprising a targeting domain complementary to a target sequence in CD247, CD3D, CD3E, CD3G, TRAC, TRBC1, TRBC2, e.g., a target sequence in TRAC, TRBC1 or TRBC2, e.g., a target sequence in TRAC, e.g., as described herein;
(c) introducing into the population of cells a CRISPR System (e.g., an S. pyogenes Cas9 CRISPR system) comprising a second gRNA molecule of the invention (or nucleic acid encoding said gRNA molecule) comprising a targeting domain complementary to a target sequence in B2M, e.g., as described herein;
(d) optionally, selecting those cells in which expression of functional TCR has been reduced or eliminated;
(e) transducing the population of cells with nucleic acid encoding a CAR, e.g., as described herein, e.g., a BCMA CAR as described herein; and
(f) administering the population of cells to a patient in need thereof, e.g., a patient who has a disease associated with expression of an antigen recognized by the CAR.

In one embodiment, the method further comprises the step of (g) introducing into said population of cells into the population of cells a CRISPR System (e.g., an S. pyogenes Cas9 CRISPR system) comprising a third gRNA molecule of the invention (or nucleic acid encoding said gRNA molecule) comprising a targeting domain complementary to a target sequence in CIITA, RFXANK, RFX5 or RFXAP, e.g., complementary to a target sequence in CIITA, e.g., as described herein.

In one aspect, the invention provides a method of treatment comprising:
(a) providing a population of cells, e.g, immune effector cells, e.g., T cell or NK cells, e.g., as described herein, (e.g., a population of said cells from an allogeneic donor);
(b) introducing into the population of cells a CRISPR System (e.g., an S. pyogenes Cas9 CRISPR system) comprising a first gRNA molecule of the invention (or nucleic acid encoding said gRNA molecule) comprising a targeting domain complementary to a target sequence in CD247, CD3D, CD3E, CD3G, TRAC, TRBC1, TRBC2, e.g., a target sequence in TRAC, TRBC1 or TRBC2, e.g., a target sequence in TRAC, e.g., as described herein;

(c) introducing into the population of cells a CRISPR System (e.g., an *S. pyogenes* Cas9 CRISPR system) comprising a second gRNA molecule of the invention (or nucleic acid encoding said gRNA molecule) comprising a targeting domain complementary to a target sequence in NLRC5, e.g., as described herein;

(d) optionally, selecting those cells in which expression of functional TCR has been reduced or eliminated;

(e) transducing the population of cells with nucleic acid encoding a CAR, e.g., as described herein, e.g., a BCMA CAR as described herein; and (f) administering the population of cells to a patient in need thereof, e.g., a patient who has a disease associated with expression of an antigen recognized by the CAR.

In one embodiment, the method further comprises the step of (g) introducing into said population of cells into the population of cells a CRISPR System (e.g., an *S. pyogenes* Cas9 CRISPR system) comprising a third gRNA molecule of the invention (or nucleic acid encoding said gRNA molecule) comprising a targeting domain complementary to a target sequence in CIITA, RFXANK, RFX5 or RFXAP, e.g., complementary to a target sequence in CIITA, e.g., as described herein.

In one aspect, the invention provides a method of treatment comprising:

(a) providing a population of cells, for example immune effector cells (e.g., NK or T cells), from an allogeneic or autologous donor;

(b) introducing into the cells a CRISPR System (e.g., an *S. pyogenes* Cas9 CRISPR system) comprising a first gRNA molecule of the invention (or nucleic acid encoding said gRNA molecule);

(c) optionally, selecting those cells in which expression of the gene product (e.g., functional gene product) of the gene comprising the target sequence complementary to the targeting domain of the first gRNA has been reduced or eliminated;

(d) transducing the cells with nucleic acid encoding a CAR as described herein; and (e) administering the cells to a patient in need thereof, e.g., a patient who has a disease associated with expression of an antigen recognized by the CAR.

In embodiments, the first gRNA molecule comprises a targeting domain complementary to a target sequence in a gene of an inhibitory molecule or downstream effector of signaling through an inhibitory molecule, e.g., a first gRNA molecule comprising a targeting domain complementary to a target sequence in a gene selected from CD274, HAVCR2, LAG3, PDCD1, PD-L2, CTLA4, CEACAM (e.g., CEACAM-1, CEACAM-3 and/or CEACAM-5), VISTA, BTLA, TIGIT, LAIR1, CD160, 2B4, CD80, CD86, B7-H3 (CD113), B7-H4 (VTCN1), HVEM (TNFRSF14 or CD107), KIR, A2aR, MHC class I, MHC class II, GAL9, adenosine, and TGF beta, and PTPN11. In embodiments, the first gRNA comprises a targeting domain to CD274, HAVCR2, LAG3, PDCD1 or PTPN11 selected from the targeting domains of Table 2 or Table 6. In embodiments, step (c) optionally includes selecting those cells in which expression of the gene product (e.g., functional gene product) of the gene comprising the target sequence complementary to the targeting domain of the first gRNA has been reduced or eliminated.

In embodiments, the method further comprises introducing into the cells at least a second gRNA molecule (e.g., 2 or more gRNA molecules) of the invention (or nucleic acid encoding said gRNA molecule(s)). In embodiments, each additional gRNA molecule(s), e.g., the second gRNA molecule, comprises a targeting domain complementary to a target sequence in a gene of an inhibitory molecule or downstream effector of signaling through an inhibitory molecule, e.g., to a target sequence in a gene selected from CD274, HAVCR2, LAG3, PDCD1, PD-L2, CTLA4, CEACAM (e.g., CEACAM-1, CEACAM-3 and/or CEACAM-5), VISTA, BTLA, TIGIT, LAIR1, CD160, 2B4, CD80, CD86, B7-H3 (CD113), B7-H4 (VTCN1), HVEM (TNFRSF14 or CD107), KIR, A2aR, MHC class I, MHC class II, GAL9, adenosine, and TGF beta, and PTPN11. In embodiments, the third gRNA comprises a targeting domain to CD274, HAVCR2, LAG3, PDCD1 or PTPN11 selected from the targeting domains of Table 2 or Table 6. In embodiments, each additional gRNA molecule comprises a targeting domain complementary to a sequence in the gene of a different inhibitory molecule or downstream effector of signaling through an inhibitory molecule In embodiments, step (c) optionally includes, selecting those cells in which expression of the gene product (e.g., functional gene product) of the gene comprising the target sequence complementary to the targeting domain of the first gRNA, in which expression of the gene product (e.g., functional gene product) of the gene comprising the target sequence complementary to the targeting domain of the second gRNA, and/or in which expression of the gene product (e.g., functional gene product) of the gene comprising the target sequence complementary to the targeting domain of the third or more gRNA (if present) has been reduced or eliminated.

In one aspect, the invention provides a method of treating a subject, e.g., a subject having a condition described herein, with an allogeneic cell, for example an allogeneic immune effector cell, for example an allogeneic CAR-expressing T cell, comprising or which at any time comprised a gRNA molecule targeting a component of the TCR and a gRNA molecule targeting a target of an immunosuppressant. In embodiments, the cell has been altered such that expression of a functional TCR and expression of a functional target of an immunosuppressant has been reduced or eliminated.

In one aspect, the invention provides a method of treatment comprising:

(a) providing a population of cells from an allogeneic donor;

(b) introducing into the cells a CRISPR System (e.g., an *S. pyogenes* Cas9 CRISPR system) comprising a first gRNA molecule of the invention (or nucleic acid encoding said gRNA molecule) comprising a targeting domain complementary to a target sequence in CD247, CD3D, CD3E, CD3G, TRAC, TRBC1, TRBC2;

(c) introducing into the cells a CRISPR System (e.g., an *S. pyogenes* Cas9 CRISPR system) comprising a second gRNA molecule of the invention (or nucleic acid encoding said gRNA molecule) comprising a targeting domain complementary to a target sequence in DCK, CD52, FKBP1A or NR3C1;

(d) optionally, selecting those cells in which expression of functional TCR, expression of functional target of an immunosuppressant, or expression of functional TCR and functional target of an immunosuppressant has been reduced or eliminated;

(e) transducing the cells with nucleic acid encoding a CAR as described herein; and (f) administering the cells to a patient in need thereof, e.g., a patient who has a disease associated with expression of an antigen recognized by the CAR; and (g) administering to the patient an immunosuppressant that binds to the target of an immunosuppressant targeted by the gRNA of (c).

In embodiments, the first gRNA to CD247, CD3D, CD3E, CD3G, TRAC, TRBC1, or TRBC2 is a first gRNA comprising a targeting domain listed in Table 1, Table 4 or Table 5. In embodiments, the second gRNA to DCK, CD52, FKBP1A or NR3C1 is a second gRNA molecule comprising a targeting domain listed in Table 1. In embodiments, the first gRNA targets TRAC, TRBC1 or TRBC2. In embodiments, the second gRNA targets DCK, and the immunosuppressant of (g) is a nucleoside analog-based drug such as cytarabine (cytosine arabinoside) or gemcitabine. In an embodiment, the second gRNA targets NR3C1 (the gene encoding for glucocorticoid receptor (GR)), and the immunosuppressant is a corticosteroid such as dexamethasone. In an embodiment, the second gRNA targets CD52, and the immunosuppressant is an anti-CD52 antibody or antigen-binding fragment thereof such as alemtuzumab (CAMPATH®). In an embodiment, the second gRNA targets FKBP1A, and the immunosuppressant is FK506 (or FKBP12-binding fragment or analog thereof), cyclosporine, rapamycin or rapalog, or mTor inhibitor such as RAD001.

In any of the embodiments and aspects of the invention, including in any of the aforementioned aspects and embodiments, the population of cells may be enriched, for example, during manufacturing, for a particular subset or subpopulation, e.g., for T-cells, e.g., for stem-cell memory-like T cells.

In another aspect, a method of treating a subject, e.g., reducing or ameliorating, a hyperproliferative condition or disorder (e.g., a cancer), e.g., solid tumor, a soft tissue tumor, or a metastatic lesion, in a subject is provided. As used herein, the term "cancer" is meant to include all types of cancerous growths or oncogenic processes, metastatic tissues or malignantly transformed cells, tissues, or organs, irrespective of histopathologic type or stage of invasiveness. Examples of solid tumors include malignancies, e.g., sarcomas, adenocarcinomas, and carcinomas, of the various organ systems, such as those affecting liver, lung, breast, lymphoid, gastrointestinal (e.g., colon), genitourinary tract (e.g., renal, urothelial cells), prostate and pharynx. Adenocarcinomas include malignancies such as most colon cancers, rectal cancer, renal-cell carcinoma, liver cancer, non-small cell carcinoma of the lung, cancer of the small intestine and cancer of the esophagus. In one embodiment, the cancer is a melanoma, e.g., an advanced stage melanoma. Metastatic lesions of the aforementioned cancers can also be treated or prevented using the methods and compositions of the invention. Examples of other cancers that can be treated include bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, Hodgkin Disease, non-Hodgkin lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemias including acute myeloid leukemia, chronic myeloid leukemia, acute lymphoblastic leukemia, chronic lymphocytic leukemia, solid tumors of childhood, lymphocytic lymphoma, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers including those induced by asbestos, and combinations of said cancers. Treatment of metastatic cancers, e.g., metastatic cancers that express PD-L1 (Iwai et al. (2005) Int. Immunol. 17:133-144) can be effected using the antibody molecules described herein.

Exemplary cancers whose growth can be inhibited include cancers typically responsive to immunotherapy. Non-limiting examples of cancers for treatment include melanoma (e.g., metastatic malignant melanoma), renal cancer (e.g. clear cell carcinoma), prostate cancer (e.g. hormone refractory prostate adenocarcinoma), breast cancer, colon cancer and lung cancer (e.g. non-small cell lung cancer). Additionally, refractory or recurrent malignancies can be treated using the molecules described herein.

In one aspect, the invention pertains to a method of treating cancer in a subject. In one aspect, the cancer associated with expression of a cancer associate antigen as described herein is a hematological cancer. In one aspect, the hematological cancer is a leukemia or a lymphoma. In one aspect, a cancer associated with expression of a cancer associate antigen as described herein includes cancers and malignancies including, but not limited to, e.g., one or more acute leukemias including but not limited to, e.g., B-cell acute Lymphoid Leukemia ("BALL"), T-cell acute Lymphoid Leukemia ("TALL"), acute lymphoid leukemia (ALL); one or more chronic leukemias including but not limited to, e.g., chronic myelogenous leukemia (CML), Chronic Lymphoid Leukemia (CLL). Additional cancers or hematologic conditions associated with expression of a cancer associate antigen as described herein include, but are not limited to, e.g., B cell prolymphocytic leukemia, blastic plasmacytoid dendritic cell neoplasm, Burkitt's lymphoma, diffuse large B cell lymphoma, Follicular lymphoma, Hairy cell leukemia, small cell- or a large cell-follicular lymphoma, malignant lymphoproliferative conditions, MALT lymphoma, mantle cell lymphoma, Marginal zone lymphoma, multiple myeloma, myelodysplasia and myelodysplastic syndrome, non-Hodgkin lymphoma, plasmablastic lymphoma, plasmacytoid dendritic cell neoplasm, Waldenstrom macroglobulinemia, and "preleukemia" which are a diverse collection of hematological conditions united by ineffective production (or dysplasia) of myeloid blood cells, and the like. Further a disease associated with a cancer associate antigen as described herein expression include, but not limited to, e.g., atypical and/or non-classical cancers, malignancies, precancerous conditions or proliferative diseases associated with expression of a cancer associate antigen as described herein.

In some embodiments, a cancer that can be treated is multiple myeloma. Generally, myeloma cells are thought to be negative for a cancer associate antigen as described herein expression by flow cytometry.

Thus, in some embodiments, a cell further engineered to express a CAR as described herein, e.g., a CD19 CAR or BCMA CAR as described herein, may be used to target myeloma cells. In some embodiments, cars of the present invention therapy can be used in combination with one or more additional therapies, e.g., lenalidomide treatment.

In various aspects, the immune effector cells (e.g., T cells, NK cells) of the invention administered to the patient, or their progeny, persist in the patient for at least four months, five months, six months, seven months, eight months, nine months, ten months, eleven months, twelve months, thirteen months, fourteen month, fifteen months, sixteen months, seventeen months, eighteen months, nineteen months, twenty months, twenty-one months, twenty-two months, twenty-three months, two years, three years, four years, or five years after administration of the T cell or NK cell to the patient.

The invention also includes a type of cellular therapy where immune effector cells (e.g., T cells, NK cells) are further modified, e.g., by in vitro transcribed RNA, to transiently express a chimeric antigen receptor (CAR) and the CAR T cell or NK cell is infused to a recipient in need thereof. The infused cell is able to kill tumor cells in the recipient. Thus, in various aspects, the immune effector cells (e.g., T cells, NK cells) administered to the patient, is present for less than one month, e.g., three weeks, two weeks, one week, after administration of the T cell or NK cell to the patient.

Without wishing to be bound by any particular theory, the anti-tumor immunity response elicited by the CAR-modified immune effector cells (e.g., T cells, NK cells) may be an active or a passive immune response, or alternatively may be due to a direct vs indirect immune response. In one aspect, the CAR transduced immune effector cells (e.g., T cells, NK cells) exhibit specific proinflammatory cytokine secretion and potent cytolytic activity in response to human cancer cells expressing the a cancer associate antigen as described herein, resist soluble a cancer associate antigen as described herein inhibition, mediate bystander killing and mediate regression of an established human tumor. For example, antigen-less tumor cells within a heterogeneous field of a cancer associate antigen as described herein-expressing tumor may be susceptible to indirect destruction by a cancer associate antigen as described herein-redirected immune effector cells (e.g., T cells, NK cells) that has previously reacted against adjacent antigen-positive cancer cells.

Ex vivo procedures are well known in the art and are discussed more fully below. Briefly, cells are isolated from a mammal (e.g., a human) and genetically modified (i.e., transduced or transfected in vitro) with a gRNA molecule of the invention, and optionally, a vector expressing a CAR disclosed herein. The modified cell can be administered to a mammalian recipient to provide a therapeutic benefit. The mammalian recipient may be a human and the cell can be autologous with respect to the recipient. Alternatively, the cells can be allogeneic with respect to the recipient.

The procedure for ex vivo expansion of hematopoietic stem and progenitor cells is described in U.S. Pat. No. 5,199,942, incorporated herein by reference, can be applied to the cells of the present invention. Other suitable methods are known in the art, therefore the present invention is not limited to any particular method of ex vivo expansion of the cells. Briefly, ex vivo culture and expansion of immune effector cells (e.g., T cells, NK cells) comprises: (1) collecting CD34+ hematopoietic stem and progenitor cells from a mammal from peripheral blood harvest or bone marrow explants; and (2) expanding such cells ex vivo. In addition to the cellular growth factors described in U.S. Pat. No. 5,199,942, other factors such as flt3-L, IL-1, IL-3 and c-kit ligand, can be used for culturing and expansion of the cells.

Procedures for ex vivo expansion of immune effector cells, e.g., T cells, are described, for example, in WO2015/142675, the contents of which are hereby incorporated by reference in their entirety. Such procedures may be useful when used in conjunction with the methods described herein.

In addition to using a cell-based vaccine in terms of ex vivo immunization, the present invention also provides compositions and methods for in vivo immunization to elicit an immune response directed against an antigen in a patient.

Generally, the cells activated and expanded as described herein may be utilized in the treatment and prevention of diseases that arise in individuals who are immunocompromised. In particular, the CAR-modified immune effector cells (e.g., T cells, NK cells) of the invention are used in the treatment of diseases, disorders and conditions associated with expression of a cancer associate antigen as described herein. In certain aspects, the cells of the invention are used in the treatment of patients at risk for developing diseases, disorders and conditions associated with expression of a cancer associate antigen as described herein. Thus, the present invention provides methods for the treatment or prevention of diseases, disorders and conditions associated with expression of a cancer associate antigen as described herein comprising administering to a subject in need thereof, a therapeutically effective amount of the CAR-modified immune effector cells (e.g., T cells, NK cells) of the invention.

In one aspect the cells of the invention, including the cells further engineered to express a CAR, may be used to treat a proliferative disease such as a cancer or malignancy or is a precancerous condition such as a myelodysplasia, a myelodysplastic syndrome or a preleukemia. Further a disease associated with a cancer associate antigen as described herein expression include, but not limited to, e.g., atypical and/or non-classical cancers, malignancies, precancerous conditions or proliferative diseases expressing a cancer associated antigen as described herein. Non-cancer related indications associated with expression of a cancer associate antigen as described herein include, but are not limited to, e.g., autoimmune disease, (e.g., lupus), inflammatory disorders (allergy and asthma) and transplantation.

The cells (e.g., T cells, NK cells) of the present invention may be administered either alone, or as a pharmaceutical composition in combination with diluents and/or with other components such as IL-2 or other cytokines or cell populations.

Hematologic Cancer

Hematological cancer conditions are the types of cancer such as leukemia, lymphoma, and malignant lymphoproliferative conditions that affect blood, bone marrow and the lymphatic system.

Leukemia can be classified as acute leukemia and chronic leukemia. Acute leukemia can be further classified as acute myelogenous leukemia (AML) and acute lymphoid leukemia (ALL). Chronic leukemia includes chronic myelogenous leukemia (CML) and chronic lymphoid leukemia (CLL). Other related conditions include myelodysplastic syndromes (MDS, formerly known as "preleukemia") which are a diverse collection of hematological conditions united by ineffective production (or dysplasia) of myeloid blood cells and risk of transformation to AML.

Lymphoma is a group of blood cell tumors that develop from lymphocytes. Exemplary lymphomas include non-Hodgkin lymphoma and Hodgkin lymphoma.

The present invention also provides methods for inhibiting the proliferation or reducing a cancer associated antigen as described herein-expressing cell population, the methods comprising contacting a population of cells comprising a cancer associated antigen as described herein-expressing cell with a cell of the invention (e.g., an NK cell or T cell) further engineered to express a CAR that binds to the a cancer associated antigen as described herein-expressing cell. In a specific aspect, the present invention provides methods for inhibiting the proliferation or reducing the population of cancer cells expressing a cancer associated antigen as described herein, the methods comprising contacting a cancer associate antigen as described herein-expressing cancer cell population with a T cell or NK cell of the invention further engineered to express a CAR that binds to a cancer associated antigen as described herein-expressing cell. In one aspect, the present invention provides methods for inhibiting the proliferation or reducing the population of cancer cells expressing a cancer associated antigen as described herein, the methods comprising contacting a cancer associated antigen as described herein-expressing cancer cell population with a T cell or NK cell of the invention further engineered to express a CAR that binds to a cancer associated antigen as described herein-expressing cell. In certain aspects, T cell or NK cell of the invention reduces the quantity, number, amount or percentage of cells and/or cancer cells by at least 25%, at least 30%, at least 40%, at least 50%, at least 65%, at least 75%, at least 85%, at least 95%, or at least 99% in a subject with or animal model for myeloid leukemia or another cancer associated with a cancer associated antigen as described herein-expressing cells relative to a negative control. In one aspect, the subject is a human.

The present invention also provides methods for preventing, treating and/or managing a disease associated with a cancer associated antigen as described herein-expressing cells (e.g., a hematologic cancer or atypical cancer expressing a cancer associated antigen as described herein), the methods comprising administering to a subject in need a T cell or NK cell of the invention, including those further engineered to express a CAR that binds to a cancer associated antigen as described herein-expressing cell. In one aspect, the subject is a human. Non-limiting examples of disorders associated with a cancer associated antigen as described herein-expressing cells include autoimmune disorders (such as lupus), inflammatory disorders (such as allergies and asthma) and cancers (such as hematological cancers or atypical cancers expressing a cancer associated antigen as described herein).

The present invention also provides methods for preventing, treating and/or managing a disease associated with a cancer associated antigen as described herein-expressing cells, the methods comprising administering to a subject in need a T cell or NK cell of the invention, including those further engineered to express a CAR that binds to a cancer associated antigen as described herein-expressing cell. In one aspect, the subject is a human.

The present invention provides methods for preventing relapse of cancer associated with a cancer associated antigen as described herein-expressing cells, the methods comprising administering to a subject in need thereof a T cell or NK cell of the invention, including those further engineered to express a CAR that binds to a cancer associated antigen as described herein-expressing cell. In one aspect, the methods comprise administering cell in combination with an effective amount of another therapy.

Pharmaceutical Compositions and Treatments

Pharmaceutical compositions of the present invention may comprise a cell, e.g., a plurality of cells, as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the present invention are in one aspect formulated for intravenous administration.

Pharmaceutical compositions of the present invention may be administered in a manner appropriate to the disease to be treated (or prevented). The quantity and frequency of administration will be determined by such factors as the condition of the patient, and the type and severity of the patient's disease, although appropriate dosages may be determined by clinical trials.

In one embodiment, the pharmaceutical composition is substantially free of, e.g., there are no detectable levels of a contaminant, e.g., selected from the group consisting of endotoxin, *mycoplasma*, replication competent lentivirus (RCL), p24, VSV-G nucleic acid, HIV gag, residual anti-CD3/anti-CD28 coated beads, mouse antibodies, pooled human serum, bovine serum albumin, bovine serum, culture media components, vector packaging cell or plasmid components, a bacterium and a fungus. In one embodiment, the bacterium is at least one selected from the group consisting of *Alcaligenes faecalis, Candida albicans, Escherichia coli, Haemophilus influenza, Neisseria meningitides, Pseudomonas aeruginosa, Staphylococcus aureus, Streptococcus pneumonia*, and *Streptococcus pyogenes* group A.

When "an immunologically effective amount," "an anti-tumor effective amount," "a tumor-inhibiting effective amount," or "therapeutic amount" is indicated, the precise amount of the compositions of the present invention to be administered can be determined by a physician with consideration of individual differences in age, weight, tumor size, extent of infection or metastasis, and condition of the patient (subject). It can generally be stated that a pharmaceutical composition comprising the immune effector cells (e.g., T cells, NK cells) described herein may be administered at a dosage of $10^4$ to $10^9$ cells/kg body weight, in some instances $10^5$ to $10^6$ cells/kg body weight, including all integer values within those ranges. T cell compositions may also be administered multiple times at these dosages. The cells can be administered by using infusion techniques that are commonly known in immunotherapy (see, e.g., Rosenberg et al., New Eng. J. of Med. 319:1676, 1988).

In certain aspects, it may be desired to administer activated immune effector cells (e.g., T cells, NK cells) to a subject and then subsequently redraw blood (or have an apheresis performed), activate immune effector cells (e.g., T cells, NK cells) therefrom according to the present invention, and reinfuse the patient with these activated and expanded immune effector cells (e.g., T cells, NK cells). This process can be carried out multiple times every few weeks. In certain aspects, immune effector cells (e.g., T cells, NK cells) can be activated from blood draws of from 10 cc to 400 cc. In certain aspects, immune effector cells (e.g., T cells, NK cells) are activated from blood draws of 20 cc, 30 cc, 40 cc, 50 cc, 60 cc, 70 cc, 80 cc, 90 cc, or 100 cc.

The administration of the subject compositions may be carried out in any convenient manner, including by aerosol inhalation, injection, ingestion, transfusion, implantation or transplantation. The compositions described herein may be administered to a patient trans arterially, subcutaneously, intradermally, intratumorally, intranodally, intramedullary, intramuscularly, by intravenous (i.v.) injection, or intraperitoneally. In one aspect, the T cell compositions of the present invention are administered to a patient by intradermal or subcutaneous injection. In one aspect, the T cell compositions of the present invention are administered by i.v. injection. The compositions of immune effector cells (e.g., T cells, NK cells) may be injected directly into a tumor, lymph node, or site of infection.

In a particular exemplary aspect, subjects may undergo leukapheresis, wherein leukocytes are collected, enriched, or depleted ex vivo to select and/or isolate the cells of interest, e.g., T cells. These T cell isolates may be expanded by methods known in the art and treated as described herein thereby creating a T cell of the invention. Subjects in need thereof may subsequently undergo standard treatment with high dose chemotherapy followed by peripheral blood stem cell transplantation. In certain aspects, following or concurrent with the transplant, subjects receive an infusion of the expanded T cells of the present invention. In an additional aspect, expanded cells are administered before or following surgery.

The dosage of the above treatments to be administered to a patient will vary with the precise nature of the condition being treated and the recipient of the treatment. The scaling of dosages for human administration can be performed according to art-accepted practices. The dose for CAMPATH, for example, will generally be in the range 1 to about 100 mg for an adult patient, usually administered daily for a period between 1 and 30 days. The preferred daily dose is 1 to 10 mg per day although in some instances larger doses of up to 40 mg per day may be used (described in U.S. Pat. No. 6,120,766).

In one aspect, CAR-expressing cells of the present inventions are generated using lentiviral viral vectors, such as lentivirus. Cells, e.g., CARTs, generated that way will have stable CAR expression.

In one aspect, CAR-expressing cells, e.g., CARTs, are generated using a viral vector such as a gammaretroviral vector, e.g., a gammaretroviral vector described herein. CARTs generated using these vectors can have stable CAR expression.

In one aspect, CARTs transiently express CAR vectors for 4, 5, 6, 7, 8, 9, 10, 11, 12, 13, 14, 15 days after transduction. Transient expression of CARs can be effected by RNA CAR vector delivery. In one aspect, the CAR RNA is transduced into the T cell by electroporation.

A potential issue that can arise in patients being treated using transiently expressing CAR immune effector cells (e.g., T cells, NK cells) (particularly with murine scFv bearing CARTs) is anaphylaxis after multiple treatments.

Without being bound by this theory, it is believed that such an anaphylactic response might be caused by a patient developing humoral anti-CAR response, i.e., anti-CAR antibodies having an anti-IgE isotype. It is thought that a patient's antibody producing cells undergo a class switch from IgG isotype (that does not cause anaphylaxis) to IgE isotype when there is a ten to fourteen day break in exposure to antigen.

If a patient is at high risk of generating an anti-CAR antibody response during the course of transient CAR therapy (such as those generated by RNA transductions), CART infusion breaks should not last more than ten to fourteen days.

Methods of Making Modified CAR-Expressing Cells

In another aspect, the invention pertains to a method of making a cell (e.g., an immune effector cell or population thereof) comprising introducing into (e.g., transducing) a cell, e.g., a T cell or a NK cell described herein, with a vector of comprising a nucleic acid encoding a CAR, e.g., a CAR described herein; or a nucleic acid encoding a CAR molecule e.g., a CAR described herein.

The cell in the methods is an immune effector cell (e.g., a T cell or a NK cell, or a combination thereof). In some embodiments, the cell in the methods is diaglycerol kinase (DGK) and/or Ikaros deficient.

In some embodiments, the introducing the nucleic acid molecule encoding a CAR comprises transducing a vector comprising the nucleic acid molecule encoding a CAR, or transfecting the nucleic acid molecule encoding a CAR, wherein the nucleic acid molecule is an in vitro transcribed RNA.

In some embodiments, the method further comprises:
providing a population of immune effector cells (e.g., T cells or NK cells); and
removing T regulatory cells from the population, thereby providing a population of T regulatory-depleted cells;
wherein steps a) and b) are performed prior to introducing the nucleic acid encoding the CAR and/or CRISPR system to the population.

In embodiments of the methods, the T regulatory cells comprise CD25+ T cells, and are removed from the cell population using an anti-CD25 antibody, or fragment thereof. The anti-CD25 antibody, or fragment thereof, can be conjugated to a substrate, e.g., a bead.

In other embodiments, the population of T regulatory-depleted cells provided from step (b) contains less than 30%, 25%, 20%, 15%, 10%, 5%, 4%, 3%, 2%, 1% of CD25+ cells.

In yet other embodiments, the method further comprises removing cells from the population which express a tumor antigen that does not comprise CD25 to provide a population of T regulatory-depleted and tumor antigen depleted cells prior to introducing the nucleic acid encoding a CAR to the population. The tumor antigen can be selected from CD19, CD30, CD38, CD123, CD20, CD14 or CD11b, or a combination thereof.

In other embodiments, the method further comprises removing cells from the population which express a checkpoint inhibitor, to provide a population of T regulatory-depleted and inhibitory molecule depleted cells prior to introducing the nucleic acid encoding a CAR or CRISPR system to the population. The checkpoint inhibitor can be chosen from PD-1, LAG-3, TIM3, B7-H1, CD160, P1H, 2B4, CEACAM (e.g., CEACAM-1, CEACAM-3, and/or CEACAM-5), TIGIT, CTLA-4, BTLA, and LAIR1.

Further embodiments disclosed herein encompass providing a population of immune effector cells. The population of immune effector cells provided can be selected based upon the expression of one or more of CD3, CD28, CD4, CD8, CD45RA, and/or CD45RO. In certain embodiments, the population of immune effector cells provided are CD3+ and/or CD28+.

In certain embodiments of the method, the method further comprises expanding the population of cells after the nucleic acid molecule encoding a CAR has been introduced.

In embodiments, the population of cells is expanded for a period of 8 days or less.

In certain embodiments, the population of cells is expanded in culture for 5 days, and the resulting cells are more potent than the same cells expanded in culture for 9 days under the same culture conditions.

In other embodiments, the population of cells is expanded in culture for 5 days show at least a one, two, three or four fold increase in cell doublings upon antigen stimulation as compared to the same cells expanded in culture for 9 days under the same culture conditions.

In yet other embodiments, the population of cells is expanded in culture for 5 days, and the resulting cells exhibit higher proinflammatory IFN-γ and/or GM-CSF levels, as compared to the same cells expanded in culture for 9 days under the same culture conditions.

In other embodiments, the population of cells is expanded by culturing the cells in the presence of an agent that stimulates a CD3/TCR complex associated signal and/or a ligand that stimulates a costimulatory molecule on the surface of the cells. The agent can be a bead conjugated with anti-CD3 antibody, or a fragment thereof, and/or anti-CD28 antibody, or a fragment thereof.

In other embodiments, the population of cells is expanded in an appropriate media that includes one or more interleukin that result in at least a 200-fold, 250-fold, 300-fold, or 350-fold increase in cells over a 14 day expansion period, as measured by flow cytometry.

In other embodiments, the population of cells is expanded in the presence IL-15 and/or IL-7.

In certain embodiments, the method further includes cryopreserving the population of the cells after the appropriate expansion period.

In yet other embodiments, the method of making disclosed herein further comprises contacting the population of immune effector cells with a nucleic acid encoding a telomerase subunit, e.g., hTERT. The the nucleic acid encoding the telomerase subunit can be DNA.

The present invention also provides a method of generating a population of RNA-engineered cells, e.g., cells described herein, e.g., immune effector cells (e.g., T cells, NK cells), transiently expressing exogenous RNA. The method comprises introducing an in vitro transcribed RNA or synthetic RNA into a cell, where the RNA comprises a nucleic acid encoding a CAR molecule described herein.

In another aspect, the invention pertains to a method of providing an anti-tumor immunity in a subject comprising administering to the subject an effective amount of a cell comprising a CAR molecule, e.g., a cell expressing a CAR molecule described herein. In one embodiment, the cell is an autologous T cell or NK cell. In one embodiment, the cell is an allogeneic T cell or NK cell. In one embodiment, the subject is a human.

In one aspect, the invention includes a population of autologous cells that are transfected or transduced with a vector comprising a nucleic acid molecule encoding a CAR molecule, e.g., as described herein. In one embodiment, the vector is a retroviral vector. In one embodiment, the vector is a self-inactivating lentiviral vector as described elsewhere herein. In one embodiment, the vector is delivered (e.g., by transfecting or electroporating) to a cell, e.g., a T cell or a NK cell, wherein the vector comprises a nucleic acid molecule encoding a CAR of the present invention as described herein, which is transcribed as an mRNA molecule, and the CARs of the present invention is translated from the RNA molecule and expressed on the surface of the cell.

In another aspect, the present invention provides a population of CAR-expressing cells, e.g., CAR-expressing immune effector cells (e.g., T cells or NK cells). In some embodiments, the population of CAR-expressing cells comprises a mixture of cells expressing different CARs. For example, in one embodiment, the population of CAR-expressing immune effector cells (e.g., T cells or NK cells) can include a first cell expressing a CAR having an antigen binding domain that binds to a first tumor antigen as described herein, and a second cell expressing a CAR having a different antigen binding domain that binds to a second tumor antigen as described herein. As another example, the population of CAR-expressing cells can include a first cell expressing a CAR that includes an antigen binding domain that binds to a tumor antigen as described herein, and a second cell expressing a CAR that includes an antigen binding domain to a target other than a tumor antigen as described herein. In one embodiment, the population of CAR-expressing cells includes, e.g., a first cell expressing a CAR that includes a primary intracellular signaling domain, and a second cell expressing a CAR that includes a secondary signaling domain, e.g., a costimulatory signaling domain.

In another aspect, the present invention provides a population of cells wherein at least one cell in the population expresses a CAR having an antigen binding domain that binds to a tumor antigen as described herein, and a second cell expressing another agent, e.g., an agent which enhances the activity of a CAR-expressing cell. For example, in one embodiment, the agent can be an agent which inhibits an inhibitory molecule. Examples of inhibitory molecules include PD-1, PD-L1, CTLA-4, TIM-3, CEACAM (e.g., CEACAM-1, CEACAM-3 and/or CEACAM-5), LAG-3, VISTA, BTLA, TIGIT, LAIR1, CD160, 2B4 and TGF beta. In one embodiment, the agent which inhibits an inhibitory molecule, e.g., is a molecule described herein, e.g., an agent that comprises a first polypeptide, e.g., an inhibitory molecule, associated with a second polypeptide that provides a positive signal to the cell, e.g., an intracellular signaling domain described herein. In one embodiment, the agent comprises a first polypeptide, e.g., of an inhibitory molecule such as PD-1, LAG-3, CTLA-4, CD160, BTLA, LAIR1, TIM-3, CEACAM (e.g., CEACAM-1, CEACAM-3 and/or CEACAM-5), 2B4 and TIGIT, or a fragment of any of these, and a second polypeptide which is an intracellular signaling domain described herein (e.g., comprising a costimulatory domain (e.g., 41BB, CD27 or CD28, e.g., as described herein) and/or a primary signaling domain (e.g., a CD3 zeta signaling domain described herein). In one embodiment, the agent comprises a first polypeptide of PD-1 or a fragment thereof, and a second polypeptide of an intracellular signaling domain described herein (e.g., a CD28, CD27, OX40 or 4-1BB signaling domain described herein and/or a CD3 zeta signaling domain described herein).

In one embodiment, the nucleic acid molecule encoding a CAR of the present invention molecule, e.g., as described herein, is expressed as an mRNA molecule. In one embodiment, the genetically modified CAR of the present invention-expressing cells, e.g., immune effector cells (e.g., T cells, NK cells), can be generated by transfecting or electroporating an RNA molecule encoding the desired CARS (e.g., without a vector sequence) into the cell. In one embodiment, a CAR of the present invention molecule is translated from the RNA molecule once it is incorporated and expressed on the surface of the recombinant cell.

A method for generating mRNA for use in transfection involves in vitro transcription (IVT) of a template with specially designed primers, followed by polyA addition, to produce a construct containing 3' and 5' untranslated sequence ("UTR") (e.g., a 3' and/or 5' UTR described herein), a 5' cap (e.g., a 5' cap described herein) and/or Internal Ribosome Entry Site (IRES) (e.g., an IRES described herein), the nucleic acid to be expressed, and a polyA tail, typically 50-2000 bases in length (SEQ ID NO: 6638). RNA so produced can efficiently transfect different kinds of cells. In one embodiment, the template includes sequences for the CAR. In an embodiment, an RNA CAR vector is transduced into a cell, e.g., a T cell or a NK cell, by electroporation.

XII. Methods of Manufacture

The disclosure provides methods of manufacturing cells, e.g., T cells, e.g., allogeneic T cells, e.g., CAR-engineered cells modified, or to be modified, with the gRNA molecules described herein.

Introduction of CRISPR Systems

The invention comprises cells, e.g immune effector cells, e.g., allogeneic or autologous cells, which comprise, or at one time comprised, one or more gRNA molecules as described herein. The CRISPR systems described herein may be introduced into the cells by any of the methods described herein. The cells may further be engineered to express a CAR as described herein.

In one aspect, the disclosure provides a method for making a cell comprising:
 a) introducing a gRNA molecule, or nucleic acid encoding said gRNA molecule, as described herein into said cell;
 b) introducing a Cas9 molecule as described herein, or nucleic acid encoding said Cas9 molecule, into said cell;
 c) introducing nucleic acid encoding a CAR into said cell; and
 d) expanding and activating the cells.

In embodiments, the introduction of a) and b) occur before steps c) and d). In embodiments, the introduction of c) occurs before the introduction of a) and b). In embodiments, the introduction of c) and the expanding and activating of d) occurs before the introduction of a) and b). In embodiments, the method further comprises e) selecting the cells which are CAR-expressing. In embodiments, the method further comprises f) selecting the cells which have no or reduced expression of the gene targeted by the gRNA molecule of step a). For example, if the gRNA molecule comprises a targeting domain complementary to a target sequence in the TRAC gene (e.g., comprises a targeting domain comprising any one of SEQ ID NO: 5816 to SEQ ID NO: 5965 or SEQ ID NO: 5528 to SEQ ID NO: 5623), after the introduction of a) and b), cells which lack TCR expression (e.g., as detectible by, for example, an anti-CD3 antibody) may be sorted for further application in the methods of manufacture as described herein, or for further application in the therapeutic methods described herein. Such sorting may be done by methods known in the art such as cell sorting or mechanical separation (e.g., separation by magnetic bead-bound anti-CD3 antibody to remove those cells still expressing CD3/TCR).

Expansion and Activation of Cells

Immune effector cells such as T cells may be activated and expanded generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Patent Application Publication No. 20060121005, each of which is incorporated by reference in its entirety.

Generally, a population of immune effector cells e.g., T regulatory cell depleted cells, may be expanded by contact with a surface having attached thereto an agent that stimulates a CD3/TCR complex associated signal and a ligand that stimulates a costimulatory molecule on the surface of the T cells. In particular, T cell populations may be stimulated as described herein, such as by contact with an anti-CD3 antibody, or antigen-binding fragment thereof, or an anti-CD2 antibody immobilized on a surface, or by contact with a protein kinase C activator (e.g., bryostatin) in conjunction with a calcium ionophore. For co-stimulation of an accessory molecule on the surface of the T cells, a ligand that binds the accessory molecule is used. For example, a population of T cells can be contacted with an anti-CD3 antibody and an anti-CD28 antibody, under conditions appropriate for stimulating proliferation of the T cells. To stimulate proliferation of either CD4+ T cells or CD8+ T cells, an anti-CD3 antibody and an anti-CD28 antibody can be used. Examples of an anti-CD28 antibody include 9.3, B-T3, XR-CD28 (Diaclone, Besancon, France) can be used as can other methods commonly known in the art (Berg et al., Transplant Proc. 1998; Haanen et al., J. Exp. Med. 190(9):13191328, 1999; Garland et al., J. Immunol Meth. 227(1-2):53-63, 1999).

In embodiments in which the cells have reduced or absent levels of expression or levels of a component of the TCR, activation may be achieved through means other than interaction with CD3. In cells which further express a CAR, activation may be achieved by contacting said cells with the antigen bound by the antigen-binding domain of the CAR, or a fragment thereof capable of binding the CAR. Such antigen or fragment thereof may be present on, for example, an antibody scaffold, a cell (e.g., an antigen presenting cell, e.g., a cell which naturally expresses said antigen or one which has been artificially engineered to express said antigen on its cell surface), or a solid support such as a bead or membrane.

In certain aspects, the primary stimulatory signal and the costimulatory signal for the T cell may be provided by different protocols. For example, the agents providing each signal may be in solution or coupled to a surface. When coupled to a surface, the agents may be coupled to the same surface (i.e., in "cis" formation) or to separate surfaces (i.e., in "trans" formation). Alternatively, one agent may be coupled to a surface and the other agent in solution. In one aspect, the agent providing the costimulatory signal is bound to a cell surface and the agent providing the primary activation signal is in solution or coupled to a surface. In certain aspects, both agents can be in solution. In one aspect, the agents may be in soluble form, and then cross-linked to a surface, such as a cell expressing Fc receptors or an antibody or other binding agent which will bind to the agents. In this regard, see for example, U.S. Patent Application Publication Nos. 20040101519 and 20060034810 for artificial antigen presenting cells (aAPCs) that are contemplated for use in activating and expanding T cells in the present invention.

In one aspect, the two agents are immobilized on beads, either on the same bead, i.e., "cis," or to separate beads, i.e., "trans." By way of example, the agent providing the primary activation signal is an anti-CD3 antibody or an antigen-binding fragment thereof and the agent providing the costimulatory signal is an anti-CD28 antibody or antigen-binding fragment thereof; and both agents are co-immobilized to the same bead in equivalent molecular amounts. In one aspect, a 1:1 ratio of each antibody bound to the beads for CD4+ T cell expansion and T cell growth is used. In certain aspects of the present invention, a ratio of anti CD3:CD28 antibodies bound to the beads is used such that an increase in T cell expansion is observed as compared to the expansion observed using a ratio of 1:1. In one particular aspect an increase of from about 1 to about 3 fold is observed as compared to the expansion observed using a ratio of 1:1. In one aspect, the ratio of CD3:CD28 antibody bound to the beads ranges from 100:1 to 1:100 and all integer values there between. In one aspect, more anti-CD28 antibody is bound to the particles than anti-CD3 antibody, i.e., the ratio of CD3:CD28 is less than one. In certain aspects, the ratio of anti CD28 antibody to anti CD3 antibody bound to the beads is greater than 2:1. In one particular aspect, a 1:100 CD3:CD28 ratio of antibody bound to beads is used. In one aspect, a 1:75 CD3:CD28 ratio of antibody bound to beads is used. In a further aspect, a 1:50 CD3:CD28 ratio of antibody bound to beads is used. In one aspect, a 1:30 CD3:CD28 ratio of antibody bound to beads is used. In one preferred aspect, a 1:10 CD3:CD28 ratio of antibody bound to beads is used. In one aspect, a 1:3 CD3:CD28 ratio of antibody bound to the beads is used. In yet one aspect, a 3:1 CD3:CD28 ratio of antibody bound to the beads is used.

Ratios of particles to cells from 1:500 to 500:1 and any integer values in between may be used to stimulate T cells or other target cells. As those of ordinary skill in the art can readily appreciate, the ratio of particles to cells may depend on particle size relative to the target cell. For example, small sized beads could only bind a few cells, while larger beads could bind many. In certain aspects the ratio of cells to particles ranges from 1:100 to 100:1 and any integer values in-between and in further aspects the ratio comprises 1:9 to 9:1 and any integer values in between, can also be used to stimulate T cells. The ratio of anti-CD3- and anti-CD28-coupled particles to T cells that result in T cell stimulation can vary as noted above, however certain preferred values include 1:100, 1:50, 1:40, 1:30, 1:20, 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, 10:1, and 15:1 with one preferred ratio being at least 1:1 particles per T cell. In one aspect, a ratio of particles to cells of 1:1 or less is used. In one particular aspect, a preferred particle:cell ratio is 1:5. In further aspects, the ratio of particles to cells can be varied depending on the day of stimulation. For example, in one aspect, the ratio of particles to cells is from 1:1 to 10:1 on the first day and additional particles are added to the cells every day or every other day thereafter for up to 10 days, at final ratios of from 1:1 to 1:10 (based on cell counts on the day of addition). In one particular aspect, the ratio of particles to cells is 1:1 on the first day of stimulation and adjusted to 1:5 on the third and fifth days of stimulation. In one aspect, particles are added on a daily or every other day basis to a final ratio of 1:1 on the first day, and 1:5 on the third and fifth days of stimulation. In one aspect, the ratio of particles to cells is 2:1 on the first day of stimulation and adjusted to 1:10 on the third and fifth days of stimulation. In one aspect, particles are added on a daily or every other day basis to a final ratio of 1:1 on the first day, and 1:10 on the third and fifth days of stimulation. One of skill in the art will appreciate that a variety of other ratios may be suitable for use in the present invention. In particular, ratios will vary depending on particle size and on cell size and type. In one aspect, the most typical ratios for use are in the neighborhood of 1:1, 2:1 and 3:1 on the first day.

In further aspects, the cells, such as T cells, are combined with agent-coated beads, the beads and the cells are subsequently separated, and then the cells are cultured. In an alternative aspect, prior to culture, the agent-coated beads and cells are not separated but are cultured together. In a further aspect, the beads and cells are first concentrated by application of a force, such as a magnetic force, resulting in increased ligation of cell surface markers, thereby inducing cell stimulation.

By way of example, cell surface proteins may be ligated by allowing paramagnetic beads to which anti-CD3 and anti-CD28 are attached (3×28 beads) to contact the T cells. In one aspect the cells (for example, $10^4$ to $10^9$ T cells) and beads (for example, DYNABEADS® M-450 CD3/CD28 T paramagnetic beads at a ratio of 1:1) are combined in a buffer, for example PBS (without divalent cations such as, calcium and magnesium). Again, those of ordinary skill in the art can readily appreciate any cell concentration may be used. For example, the target cell may be very rare in the sample and comprise only 0.01% of the sample or the entire sample (i.e., 100%) may comprise the target cell of interest. Accordingly, any cell number is within the context of the present invention. In certain aspects, it may be desirable to significantly decrease the volume in which particles and cells are mixed together (i.e., increase the concentration of cells), to ensure maximum contact of cells and particles. For example, in one aspect, a concentration of about 10 billion cells/ml, 9 billion/ml, 8 billion/ml, 7 billion/ml, 6 billion/ml, 5 billion/ml, or 2 billion cells/ml is used. In one aspect, greater than 100 million cells/ml is used. In a further aspect, a concentration of cells of 10, 15, 20, 25, 30, 35, 40, 45, or 50 million cells/ml is used. In yet one aspect, a concentration of cells from 75, 80, 85, 90, 95, or 100 million cells/ml is used. In further aspects, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T cells. Such populations of cells may have therapeutic value and would be desirable to obtain in certain aspects. For example, using high concentration of cells allows more efficient selection of CD8+ T cells that normally have weaker CD28 expression.

In one embodiment, cells of the invention, e.g., cells comprising or which at any time comprised or will comprise a gRNA molecule as described herein, e.g., said cells transduced with a nucleic acid encoding a CAR, e.g., a CAR described herein, are expanded, e.g., by a method described herein. In one embodiment, the cells are expanded in culture for a period of several hours (e.g., about 2, 3, 4, 5, 6, 7, 8, 9, 10, 15, 18, 21 hours) to about 14 days (e.g., 1, 2, 3, 4, 5, 6, 7, 8, 9, 10, 11, 12, 13 or 14 days). In one embodiment, the cells are expanded for a period of 4 to 9 days. In one embodiment, the cells are expanded for a period of 8 days or less, e.g., 7, 6 or 5 days. In one embodiment, the cells are expanded in culture for 5 days, and the resulting cells are more potent than the same cells expanded in culture for 9 days under the same culture conditions. Potency can be defined, e.g., by various T cell functions, e.g. proliferation, target cell killing, cytokine production, activation, migration, or combinations thereof. In one embodiment, the cells are expanded for 5 days show at least a one, two, three or four fold increase in cells doublings upon antigen stimulation as compared to the same cells expanded in culture for 9 days under the same culture conditions. In one embodiment, the cells are expanded in culture for 5 days, and the resulting cells exhibit higher proinflammatory cytokine production, e.g., IFN-γ and/or GM-CSF levels, as compared to the same cells expanded in culture for 9 days under the same culture conditions. In one embodiment, the cells expanded for 5 days show at least a one, two, three, four, five, ten fold or more increase in pg/ml of proinflammatory cytokine production, e.g., IFN-γ and/or GM-CSF levels, as compared to the same cells expanded in culture for 9 days under the same culture conditions.

Several cycles of stimulation may also be desired such that culture time of T cells can be 60 days or more. Conditions appropriate for T cell culture include an appropriate media (e.g., Minimal Essential Media or RPMI Media 1640 or, X-vivo 15, (Lonza)) that may contain factors necessary for proliferation and viability, including serum (e.g., fetal bovine or human serum), interleukin-2 (IL-2), insulin, IFN-γ, IL-4, IL-7, GM-CSF, IL-10, IL-12, IL-15, TGFβ, and TNF-α or any other additives for the growth of cells known to the skilled artisan. Other additives for the growth of cells include, but are not limited to, surfactant, plasmanate, and reducing agents such as N-acetyl-cysteine and 2-mercaptoethanol. Media can include RPMI 1640, AIM-V, DMEM, MEM, α-MEM, F-12, X-Vivo 15, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells. Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% $CO_2$).

In one embodiment, the cells are expanded in an appropriate media (e.g., media described herein) that includes one or more interleukin that result in at least a 200-fold (e.g., 200-fold, 250-fold, 300-fold, 350-fold) increase in cells over a 14 day expansion period, e.g., as measured by a method described herein such as flow cytometry. In one embodiment, the cells are expanded in the presence of IL-15 and/or IL-7 (e.g., IL-15 and IL-7).

In embodiments, methods described herein, manufacturing methods for cells of the invention, e.g., cells comprising or which at any time comprised or will comprise a gRNA molecule as described herein, e.g., said cells expressing a CAR, comprise removing T regulatory cells, e.g., CD25+ T cells, from a cell population, e.g., using an anti-CD25 antibody, or fragment thereof, or a CD25-binding ligand, IL-2. Methods of removing T regulatory cells, e.g., CD25+ T cells, from a cell population are described herein.

In embodiments, the methods, e.g., manufacturing methods, further comprise contacting a cell population (e.g., a cell population in which T regulatory cells, such as CD25+ T cells, have been depleted; or a cell population that has previously contacted an anti-CD25 antibody, fragment thereof, or CD25-binding ligand) with IL-15 and/or IL-7. For example, the cell population (e.g., that has previously contacted an anti-CD25 antibody, fragment thereof, or CD25-binding ligand) is expanded in the presence of IL-15 and/or IL-7.

In some embodiments the cells of the invention, e.g., cells comprising or which at any time comprised or will comprise a gRNA molecule as described herein, e.g., said cells expressing a CAR as described herein, are contacted with a composition comprising a interleukin-15 (IL-15) polypeptide, a interleukin-15 receptor alpha (IL-15Ra) polypeptide, or a combination of both a IL-15 polypeptide and a IL-15Ra polypeptide e.g., hetIL-15, during the manufacturing of the CAR-expressing cell, e.g., ex vivo. In embodiments, a cell described herein is contacted with a composition comprising a IL-15 polypeptide during the manufacturing of the cell, e.g., ex vivo. In embodiments, a cell described herein is contacted with a composition comprising a combination of both a IL-15 polypeptide and a IL-15 Ra polypeptide during the manufacturing of the CAR-expressing cell, e.g., ex vivo. In embodiments, a cell described herein is contacted with a composition comprising hetIL-15 during the manufacturing of the CAR-expressing cell, e.g., ex vivo.

In one embodiment the cells of the invention, e.g., cells comprising or which at any time comprised or will comprise a gRNA molecule as described herein, e.g., said cells expressing a CAR as described herein, is contacted with a composition comprising hetIL-15 during ex vivo expansion. In an embodiment, the cell described herein is contacted with a composition comprising an IL-15 polypeptide during ex vivo expansion. In an embodiment, the CAR-expressing cell described herein is contacted with a composition comprising both an IL-15 polypeptide and an IL-15Ra polypeptide during ex vivo expansion. In one embodiment the contacting results in the survival and proliferation of a lymphocyte subpopulation, e.g., CD8+ T cells.

T cells that have been exposed to varied stimulation times may exhibit different characteristics. For example, typical blood or apheresed peripheral blood mononuclear cell products have a helper T cell population (TH, CD4+) that is greater than the cytotoxic or suppressor T cell population (TC, CD8+). Ex vivo expansion of T cells by stimulating CD3 and CD28 receptors produces a population of T cells that prior to about days 8-9 consists predominately of TH cells, while after about days 8-9, the population of T cells comprises an increasingly greater population of TC cells. Accordingly, depending on the purpose of treatment, infusing a subject with a T cell population comprising predominately of TH cells may be advantageous. Similarly, if an antigen-specific subset of TC cells has been isolated it may be beneficial to expand this subset to a greater degree.

Further, in addition to CD4 and CD8 markers, other phenotypic markers vary significantly, but in large part, reproducibly during the course of the cell expansion process. Thus, such reproducibility enables the ability to tailor an activated T cell product for specific purposes.

Once a cell of the invention has been engineered to express a CAR described herein is constructed, various assays can be used to evaluate the activity of the molecule, such as but not limited to, the ability to expand T cells following antigen stimulation, sustain T cell expansion in the absence of re-stimulation, and anti-cancer activities in appropriate in vitro and animal models. Assays to evaluate the effects of a cars of the present invention are described in further detail below Western blot analysis of CAR expression in primary T cells can be used to detect the presence of monomers and dimers. See, e.g., Milone et al., Molecular Therapy 17(8): 1453-1464 (2009). Very briefly, T cells (1:1 mixture of $CD4^+$ and $CD8^+$ T cells) expressing the CARs are expanded in vitro for more than 10 days followed by lysis and SDS-PAGE under reducing conditions. CARs containing the full length TCR-ζ cytoplasmic domain and the endogenous TCR-ζ chain are detected by western blotting using an antibody to the TCR-ζ chain. The same T cell subsets are used for SDS-PAGE analysis under non-reducing conditions to permit evaluation of covalent dimer formation.

In vitro expansion of CARP T cells following antigen stimulation can be measured by flow cytometry. For example, a mixture of $CD4^+$ and $CD8^+$ T cells are stimulated with αCD3/αCD28 aAPCs followed by transduction with lentiviral vectors expressing GFP under the control of promoters to be analyzed. Exemplary promoters include the CMV IE gene, EF-1α, ubiquitin C, or phosphoglycerokinase (PGK) promoters. GFP fluorescence is evaluated on day 6 of culture in the CD4+ and/or CD8+ T cell subsets by flow cytometry. See, e.g., Milone et al., Molecular Therapy 17(8): 1453-1464 (2009). Alternatively, a mixture of CD4+ and CD8' T cells are stimulated with αCD3/αCD28 coated magnetic beads on day 0, and transduced with CAR on day 1 using a bicistronic lentiviral vector expressing CAR along with eGFP using a 2A ribosomal skipping sequence. Cultures are re-stimulated with either a cancer associated antigen as described herein+ K562 cells (K562 expressing a cancer associated antigen as described herein), wild-type K562 cells (K562 wild type) or K562 cells expressing hCD32 and 4-1BBL in the presence of antiCD3 and anti-CD28 antibody (K562-BBL-3/28) following washing. Exogenous IL-2 is added to the cultures every other day at 100 IU/ml. GFP+ T cells are enumerated by flow cytometry using bead-based counting. See, e.g., Milone et al., Molecular Therapy 17(8): 1453-1464 (2009).

Sustained CAR+ T cell expansion in the absence of re-stimulation can also be measured. See, e.g., Milone et al., Molecular Therapy 17(8): 1453-1464 (2009). Briefly, mean T cell volume (fl) is measured on day 8 of culture using a Coulter Multisizer III particle counter, a Nexcelom Cellometer Vision or Millipore Scepter, following stimulation with αCD3/αCD28 coated magnetic beads on day 0, and transduction with the indicated CAR on day 1.

Animal models can also be used to measure a CART activity. For example, xenograft model using human a cancer associated antigen described herein-specific CARP T cells to treat a primary human pre-B ALL in immunodeficient mice can be used. See, e.g., Milone et al., Molecular Therapy 17(8): 1453-1464 (2009). Very briefly, after establishment of ALL, mice are randomized as to treatment groups. Different numbers of a cancer associated antigen-specific CAR engineered T cells are coinjected at a 1:1 ratio into NOD-SCID-$\gamma^{-/-}$ mice bearing B-ALL. The number of copies of a cancer associated antigen-specific CAR vector in spleen DNA from mice is evaluated at various times following T cell injection. Animals are assessed for leukemia at weekly intervals. Peripheral blood a cancer associate antigen as described herein+ B-ALL blast cell counts are measured in mice that are injected with a cancer associated antigen described herein-ζ CAR+ T cells or mock-transduced T cells. Survival curves for the groups are compared using the log-rank test. In addition, absolute peripheral blood CD4+ and CD8+ T cell counts 4 weeks following T cell injection in NOD-SCID-$\gamma^{-/-}$ mice can also be analyzed. Mice are injected with leukemic cells and 3 weeks later are injected with T cells engineered to express CAR by a bicistronic lentiviral vector that encodes the CAR linked to eGFP. T cells are normalized to 45-50% input GFP+ T cells by mixing with mock-transduced cells prior to injection, and confirmed by flow cytometry. Animals are assessed for leukemia at 1-week intervals. Survival curves for the CAR+ T cell groups are compared using the log-rank test.

Dose dependent CAR treatment response can be evaluated. See, e.g., Milone et al., Molecular Therapy 17(8): 1453-1464 (2009). For example, peripheral blood is obtained 35-70 days after establishing leukemia in mice injected on day 21 with CAR T cells, an equivalent number of mock-transduced T cells, or no T cells. Mice from each group are randomly bled for determination of peripheral blood a cancer associate antigen as described herein+ ALL blast counts and then killed on days 35 and 49. The remaining animals are evaluated on days 57 and 70.

Assessment of cell proliferation and cytokine production has been previously described, e.g., at Milone et al., Molecular Therapy 17(8): 1453-1464 (2009). Briefly, assessment of CAR-mediated proliferation is performed in microtiter plates by mixing washed T cells with K562 cells expressing a cancer associated antigen described herein (K19) or CD32 and CD137 (KT32-BBL) for a final T-cell:K562 ratio of 2:1. K562 cells are irradiated with gamma-radiation prior to use. Anti-CD3 (clone OKT3) and anti-CD28 (clone 9.3) monoclonal antibodies are added to cultures with KT32-BBL cells to serve as a positive control for stimulating T-cell proliferation since these signals support long-term CD8+ T cell expansion ex vivo. T cells are enumerated in cultures using CountBright™ fluorescent beads (Invitrogen, Carlsbad, CA) and flow cytometry as described by the manufacturer. CAR+ T cells are identified by GFP expression using T cells that are engineered with eGFP-2A linked CAR-expressing lentiviral vectors. For CAR+ T cells not expressing GFP, the CAR+ T cells are detected with biotinylated recombinant a cancer associate antigen as described herein protein and a secondary avidin-PE conjugate. CD4+ and CD8+ expression on T cells are also simultaneously detected with specific monoclonal antibodies (BD Biosciences). Cytokine measurements are performed on supernatants collected 24 hours following re-stimulation using the human TH1/TH2 cytokine cytometric bead array kit (BD Biosciences, San Diego, CA) according the manufacturer's instructions. Fluorescence is assessed using a FACScalibur flow cytometer, and data is analyzed according to the manufacturer's instructions.

Cytotoxicity can be assessed by a standard 51Cr-release assay. See, e.g., Milone et al., Molecular Therapy 17(8): 1453-1464 (2009). Briefly, target cells (K562 lines and primary pro-B-ALL cells) are loaded with 51Cr (as NaCrO4, New England Nuclear, Boston, MA) at 37° C. for 2 hours with frequent agitation, washed twice in complete RPMI and plated into microtiter plates. Effector T cells are mixed with target cells in the wells in complete RPMI at varying ratios of effector cell:target cell (E:T). Additional wells containing media only (spontaneous release, SR) or a 1% solution of triton-X 100 detergent (total release, TR) are also prepared. After 4 hours of incubation at 37° C., supernatant from each well is harvested. Released 51Cr is then measured using a gamma particle counter (Packard Instrument Co., Waltham, MA). Each condition is performed in at least triplicate, and the percentage of lysis is calculated using the formula: % Lysis=(ER−SR)/(TR−SR), where ER represents the average 51Cr released for each experimental condition.

Imaging technologies can be used to evaluate specific trafficking and proliferation of CARs in tumor-bearing animal models. Such assays have been described, for example, in Barrett et al., Human Gene Therapy 22:1575-1586 (2011). Briefly, NOD/SCID/$\gamma c^{-/-}$ (NSG) mice are injected IV with Nalm-6 cells followed 7 days later with T cells 4 hour after electroporation with the CAR constructs. The T cells are stably transfected with a lentiviral construct to express firefly luciferase, and mice are imaged for bioluminescence. Alternatively, therapeutic efficacy and specificity of a single injection of CAR P T cells in Nalm-6 xenograft model can be measured as the following: NSG mice are injected with Nalm-6 transduced to stably express firefly luciferase, followed by a single tail-vein injection of T cells electroporated with cars of the present invention 7 days later. Animals are imaged at various time points post injection. For example, photon-density heat maps of firefly luciferase positive leukemia in representative mice at day 5 (2 days before treatment) and day 8 (24 hr post CAR+ PBLs) can be generated.

Other assays, including those described in the Example section herein as well as those that are known in the art can also be used to evaluate the cells and cells expressing CARs described herein.

Delivery Timing

In an embodiment, one or more nucleic acid molecules (e.g., DNA molecules) other than the components of a Cas system, e.g., the Cas9 molecule component and/or the gRNA molecule component described herein, are delivered. In an embodiment, the nucleic acid molecule is delivered at the same time as one or more of the components of the Cas system are delivered. In an embodiment, the nucleic acid molecule is delivered before or after (e.g., less than about 30 minutes, 1 hour, 2 hours, 3 hours, 6 hours, 9 hours, 12 hours, 1 day, 2 days, 3 days, 1 week, 2 weeks, or 4 weeks) one or more of the components of the Cas system are delivered. In an embodiment, the nucleic acid molecule is delivered by a different means than one or more of the components of the Cas system, e.g., the Cas9 molecule component and/or the gRNA molecule component, are delivered. The nucleic acid molecule can be delivered by any of the delivery methods described herein. For example, the nucleic acid molecule can be delivered by a viral vector, e.g., an integration-deficient lentivirus, and the Cas9 molecule component and/or the gRNA molecule component can be delivered by electroporation, e.g., such that the toxicity caused by nucleic acids (e.g., DNAs) can be reduced. In an embodiment, the nucleic acid molecule encodes a therapeutic protein, e.g., a protein described herein. In an embodiment, the nucleic acid molecule encodes an RNA molecule, e.g, an RNA molecule described herein.

Bi-Modal or Differential Delivery of Components

Separate delivery of the components of a Cas system, e.g., the Cas9 molecule component and the gRNA molecule component, and more particularly, delivery of the components by differing modes, can enhance performance, e.g., by improving tissue specificity and safety. In an embodiment, the Cas9 molecule and the gRNA molecule are delivered by different modes, or as sometimes referred to herein as differential modes. Different or differential modes, as used herein, refer modes of delivery, that confer different pharmacodynamic or pharmacokinetic properties on the subject component molecule, e.g., a Cas9 molecule, gRNA molecule, template nucleic acid, or payload. E.g., the modes of delivery can result in different tissue distribution, different half-life, or different temporal distribution, e.g., in a selected compartment, tissue, or organ.

Some modes of delivery, e.g., delivery by a nucleic acid vector that persists in a cell, or in progeny of a cell, e.g., by autonomous replication or insertion into cellular nucleic acid, result in more persistent expression of and presence of a component. Examples include viral, e.g., adeno associated virus or lentivirus, delivery.

By way of example, the components, e.g., a Cas9 molecule and a gRNA molecule, can be delivered by modes that differ in terms of resulting half life or persistent of the delivered component the body, or in a particular compartment, tissue or organ. In an embodiment, a gRNA molecule can be delivered by such modes. The Cas9 molecule component can be delivered by a mode which results in less persistence or less exposure of its to the body or a particular compartment or tissue or organ.

More generally, in an embodiment, a first mode of delivery is used to deliver a first component and a second mode of delivery is used to deliver a second component. The first mode of delivery confers a first pharmacodynamic or pharmacokinetic property. The first pharmacodynamic property can be, e.g., distribution, persistence, or exposure, of the component, or of a nucleic acid that encodes the component, in the body, a compartment, tissue or organ. The second mode of delivery confers a second pharmacodynamic or pharmacokinetic property. The second pharmacodynamic property can be, e.g., distribution, persistence, or exposure, of the component, or of a nucleic acid that encodes the component, in the body, a compartment, tissue or organ.

In an embodiment, the first pharmacodynamic or pharmacokinetic property, e.g., distribution, persistence or exposure, is more limited than the second pharmacodynamic or pharmacokinetic property.

In an embodiment, the first mode of delivery is selected to optimize, e.g., minimize, a pharmacodynamic or pharmacokinetic property, e.g., distribution, persistence or exposure.

In an embodiment, the second mode of delivery is selected to optimize, e.g., maximize, a pharmacodynamic or pharmcokinetic property, e.g., distribution, persistence or exposure.

In an embodiment, the first mode of delivery comprises the use of a relatively persistent element, e.g., a nucleic acid, e.g., a plasmid or viral vector, e.g., an AAV or lentivirus. As such vectors are relatively persistent product transcribed from them would be relatively persistent.

In an embodiment, the second mode of delivery comprises a relatively transient element, e.g., an RNA or protein.

In an embodiment, the first component comprises gRNA, and the delivery mode is relatively persistent, e.g., the gRNA is transcribed from a plasmid or viral vector, e.g., an AAV or lentivirus. Transcription of these genes would be of little physiological consequence because the genes do not encode for a protein product, and the gR As are incapable of acting in isolation. The second component, a Cas9 molecule, is delivered in a transient manner, for example as mRNA or as protein, ensuring that the full Cas9 molecule/gRNA molecule complex is only present and active for a short period of time.

Furthermore, the components can be delivered in different molecular form or with different delivery vectors that complement one another to enhance safety and tissue specificity.

Use of differential delivery modes can enhance performance, safety and efficacy. For example, the likelihood of an eventual off-target modification can be reduced. Delivery of immunogenic components, e.g., Cas9 molecules, by less persistent modes can reduce immunogenicity, as peptides from the bacterially-derived Cas enzyme are displayed on the surface of the cell by MHC molecules. A two-part delivery system can alleviate these drawbacks.

Differential delivery modes can be used to deliver components to different, but overlapping target regions. The formation active complex is minimized outside the overlap of the target regions. Thus, in an embodiment, a first component, e.g., a gRNA molecule is delivered by a first delivery mode that results in a first spatial, e.g., tissue, distribution. A second component, e.g., a Cas9 molecule is delivered by a second delivery mode that results in a second spatial, e.g., tissue, distribution. In an embodiment, the first mode comprises a first element selected from a liposome, nanoparticle, e.g., polymeric nanoparticle, and a nucleic acid, e.g., viral vector. The second mode comprises a second element selected from the group. In an embodiment, the first mode of delivery comprises a first targeting element, e.g., a cell specific receptor or an antibody, and the second mode of delivery does not include that element. In an embodiment, the second mode of delivery comprises a second targeting element, e.g., a second cell specific receptor or second antibody.

When the Cas9 molecule is delivered in a virus delivery vector, a liposome, or polymeric nanoparticle, there is the potential for delivery to and therapeutic activity in multiple tissues, when it may be desirable to only target a single tissue. A two-part delivery system can resolve this challenge and enhance tissue specificity. If the gRNA molecule and the Cas9 molecule are packaged in separated delivery vehicles with distinct but overlapping tissue tropism, the fully functional complex is only be formed in the tissue that is targeted by both vectors.

In one aspect, the delivery is accomplished ex vivo.

XIII. Modified Nucleosides, Nucleotides, and Nucleic Acids

Modified nucleosides and modified nucleotides can be present in nucleic acids, e.g., particularly gRNA, but also other forms of RNA, e.g., mRNA, RNAi, or siRNA. As described herein "nucleoside" is defined as a compound containing a five-carbon sugar molecule (a pentose or ribose) or derivative thereof, and an organic base, purine or pyrimidine, or a derivative thereof. As described herein, "nucleotide" is defined as a nucleoside further comprising a phosphate group.

Modified nucleosides and nucleotides can include one or more of:
  (i) alteration, e.g., replacement, of one or both of the non-linking phosphate oxygens and/or of one or more of the linking phosphate oxygens in the phosphodiester backbone linkage;
  (ii) alteration, e.g., replacement, of a constituent of the ribose sugar, e.g., of the 2' hydroxyl on the ribose sugar;
  (iii) wholesale replacement of the phosphate moiety with "diphospho" linkers;
  (iv) modification or replacement of a naturally occurring nucleobase, including with a non-canonical nucleobase;
  (v) replacement or modification of the ribose-phosphate backbone;
  (vi) modification of the 3' end or 5' end of the oligonucleotide, e.g., removal, modification or replacement of a terminal phosphate group or conjugation of a moiety, cap or linker; and
  (vii) modification or replacement of the sugar.

The modifications listed above can be combined to provide modified nucleosides and nucleotides that can have two, three, four, or more modifications. For example, a modified nucleoside or nucleotide can have a modified sugar and a modified nucleobase. In an embodiment, every base of a gRNA is modified, e.g., all bases have a modified phosphate group, e.g., all are phosphorothioate groups. In an embodiment, all, or substantially all, of the phosphate groups of a unimolecular or modular gRNA molecule are replaced with phosphorothioate groups.

In an embodiment, modified nucleotides, e.g., nucleotides having modifications as described herein, can be incorporated into a nucleic acid, e.g., a "modified nucleic acid." In some embodiments, the modified nucleic acids comprise one, two, three or more modified nucleotides. In some embodiments, at least 5% (e.g., at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100%) of the positions in a modified nucleic acid are a modified nucleotides.

Unmodified nucleic acids can be prone to degradation by, e.g., cellular nucleases. For example, nucleases can hydrolyze nucleic acid phosphodiester bonds. Accordingly, in one aspect the modified nucleic acids described herein can contain one or more modified nucleosides or nucleotides, e.g., to introduce stability toward nucleases.

In some embodiments, the modified nucleosides, modified nucleotides, and modified nucleic acids described herein can exhibit a reduced innate immune response when introduced into a population of cells, both in vivo and ex vivo. The term "innate immune response" includes a cellular response to exogenous nucleic acids, including single stranded nucleic acids, generally of viral or bacterial origin, which involves the induction of cytokine expression and release, particularly the interferons, and cell death. In some embodiments, the modified nucleosides, modified nucleotides, and modified nucleic acids described herein can disrupt binding of a major groove interacting partner with the nucleic acid. In some embodiments, the modified nucleosides, modified nucleotides, and modified nucleic acids described herein can exhibit a reduced innate immune response when introduced into a population of cells, both in vivo and ex vivo, and also disrupt binding of a major groove interacting partner with the nucleic acid.

Definitions of Chemical Groups

As used herein, "alkyl" is meant to refer to a saturated hydrocarbon group which is straight-chained or branched. Example alkyl groups include methyl (Me), ethyl (Et), propyl (e.g., n-propyl and isopropyl), butyl (e.g., n-butyl, isobutyl, t-butyl), pentyl (e.g., n-pentyl, isopentyl, neopentyl), and the like. An alkyl group can contain from 1 to about 20, from 2 to about 20, from 1 to about 12, from 1 to about 8, from 1 to about 6, from 1 to about 4, or from 1 to about 3 carbon atoms.

As used herein, "aryl" refers to monocyclic or polycyclic (e.g., having 2, 3 or 4 fused rings) aromatic hydrocarbons such as, for example, phenyl, naphthyl, anthracenyl, phenanthrenyl, indanyl, indenyl, and the like. In some embodiments, aryl groups have from 6 to about 20 carbon atoms.

As used herein, "alkenyl" refers to an aliphatic group containing at least one double bond. As used herein, "alkynyl" refers to a straight or branched hydrocarbon chain containing 2-12 carbon atoms and characterized in having one or more triple bonds. Examples of alkynyl groups include, but are not limited to, ethynyl, propargyl, and 3-hexynyl.

As used herein, "arylalkyl" or "aralkyl" refers to an alkyl moiety in which an alkyl hydrogen atom is replaced by an aryl group. Aralkyl includes groups in which more than one hydrogen atom has been replaced by an aryl group. Examples of "arylalkyl" or "aralkyl" include benzyl, 2-phenylethyl, 3-phenylpropyl, 9-fluorenyl, benzhydryl, and trityl groups.

As used herein, "cycloalkyl" refers to a cyclic, bicyclic, tricyclic, or polycyclic non-aromatic hydrocarbon groups having 3 to 12 carbons. Examples of cycloalkyl moieties include, but are not limited to, cyclopropyl, cyclopentyl, and cyclohexyl.

As used herein, "heterocyclyl" refers to a monovalent radical of a heterocyclic ring system. Representative heterocyclyls include, without limitation, tetrahydrofuranyl, tetrahydrothienyl, pyrrolidinyl, pyrrolidonyl, piperidinyl, pyrrolinyl, piperazinyl, dioxanyl, dioxolanyl, diazepinyl, oxazepinyl, thiazepinyl, and morpholinyl.

As used herein, "heteroaryl" refers to a monovalent radical of a heteroaromatic ring system. Examples of heteroaryl moieties include, but are not limited to, imidazolyl, oxazolyl, thiazolyl, triazolyl, pyrrolyl, furanyl, indolyl, thiophenyl pyrazolyl, pyridinyl, pyrazinyl, pyridazinyl, pyrimidinyl, indolizinyl, purinyl, naphthyridinyl, quinolyl, and pteridinyl.

Phosphate Backbone Modifications

The Phosphate Group

In some embodiments, the phosphate group of a modified nucleotide can be modified by replacing one or more of the oxygens with a different substituent. Further, the modified nucleotide, e.g., modified nucleotide present in a modified nucleic acid, can include the wholesale replacement of an unmodified phosphate moiety with a modified phosphate as described herein. In some embodiments, the modification of the phosphate backbone can include alterations that result in either an uncharged linker or a charged linker with unsymmetrical charge distribution.

Examples of modified phosphate groups include, phosphorothioate, phosphoroselenates, borano phosphates, borano phosphate esters, hydrogen phosphonates, phosphoroamidates, alkyl or aryl phosphonates and phosphotriesters. In some embodiments, one of the non-bridging phosphate oxygen atoms in the phosphate backbone moiety can be replaced by any of the following groups: sulfur (S), selenium (Se), BR 3 (wherein R can be, e.g., hydrogen, alkyl, or aryl), C (e.g., an alkyl group, an aryl group, and the like), H, NR2 (wherein R can be, e.g., hydrogen, alkyl, or aryl), or OR (wherein R can be, e.g., alkyl or aryl). The phosphorous atom in an unmodified phosphate group is achiral. However, replacement of one of the non-bridging oxygens with one of the above atoms or groups of atoms can render the phosphorous atom chiral; that is to say that a phosphorous atom in a phosphate group modified in this way is a stereogenic center. The stereogenic phosphorous atom can possess either the "R" configuration (herein Rp) or the "S" configuration (herein Sp).

Phosphorodithioates have both non-bridging oxygens replaced by sulfur. The phosphorus center in the phosphorodithioates is achiral which precludes the formation of oligoribonucleotide diastereomers. In some embodiments, modifications to one or both non-bridging oxygens can also include the replacement of the non-bridging oxygens with a group independently selected from S, Se, B, C, H, N, and OR (R can be, e.g., alkyl or aryl).

The phosphate linker can also be modified by replacement of a bridging oxygen, (i.e., the oxygen that links the phosphate to the nucleoside), with nitrogen (bridged phosphoroamidates), sulfur (bridged phosphorothioates) and carbon (bridged methylenephosphonates). The replacement can occur at either linking oxygen or at both of the linking oxygens.

Replacement of the Phosphate Group

The phosphate group can be replaced by non-phosphorus containing connectors. In some embodiments, the charge phosphate group can be replaced by a neutral moiety.

Examples of moieties which can replace the phosphate group can include, without limitation, e.g., methyl phosphonate, hydroxylamino, siloxane, carbonate, carboxymethyl, carbamate, amide, thioether, ethylene oxide linker, sulfonate, sulfonamide, thioformacetal, formacetyl, oxime, methyleneimino, methylenemethylimino, methylenehydrazono, methylenedimethylhydrazo and methyleneoxymethylimino.

Replacement of the Ribophosphate Backbone

Scaffolds that can mimic nucleic acids can also be constructed wherein the phosphate linker and ribose sugar are replaced by nuclease resistant nucleoside or nucleotide surrogates. In some embodiments, the nucleobases can be tethered by a surrogate backbone. Examples can include, without limitation, the morpholino, cyclobutyl, pyrrolidine and peptide nucleic acid (PNA) nucleoside surrogates.

Sugar Modifications

The modified nucleosides and modified nucleotides can include one or more modifications to the sugar group. For example, the 2' hydroxyl group (OH) can be modified or replaced with a number of different "oxy" or "deoxy" substituents. In some embodiments, modifications to the 2' hydroxyl group can enhance the stability of the nucleic acid since the hydroxyl can no longer be deprotonated to form a 2'-alkoxide ion. The 2'-alkoxide can catalyze degradation by intramolecular nucleophilic attack on the linker phosphorus atom.

Examples of "oxy"-2' hydroxyl group modifications can include alkoxy or aryloxy (OR, wherein "R" can be, e.g., alkyl, cycloalkyl, aryl, aralkyl, heteroaryl or a sugar); polyethyleneglycols (PEG), wherein R can be, e.g., H or optionally substituted alkyl, and n can be an integer from 0 to 20 (e.g., from 0 to 4, from 0 to 8, from 0 to 10, from 0 to 16, from 1 to 4, from 1 to 8, from 1 to 10, from 1 to 16, from 1 to 20, from 2 to 4, from 2 to 8, from 2 to 10, from 2 to 16, from 2 to 20, from 4 to 8, from 4 to 10, from 4 to 16, and from 4 to 20). In some embodiments, the "oxy"-2' hydroxyl group modification can include "locked" nucleic acids (LNA) in which the 2' hydroxyl can be connected, e.g., by a $C_{i-6}$ alkylene or $C_{j-6}$ heteroalkylene bridge, to the 4' carbon of the same ribose sugar, where exemplary bridges can include methylene, propylene, ether, or amino bridges; O-amino (wherein amino can be, e.g., $NH_2$; alkylamino, dialkylamino, heterocyclyl, arylamino, diarylamino, heteroarylamino, or diheteroarylamino, ethylenediamine, or polyamino) and aminoalkoxy, $O(CH_2)_n$-amino, (wherein amino can be, e.g., $NH_2$; alkylamino, dialkylamino, heterocyclyl, arylamino, diarylamino, heteroarylamino, or diheteroarylamino, ethylenediamine, or polyamino). In some embodiments, the "oxy"-2' hydroxyl group modification can include the methoxyethyl group (MOE), ($OCH_2CH_2OCH_3$, e.g., a PEG derivative).

"Deoxy" modifications can include hydrogen (i.e. deoxyribose sugars, e.g., at the overhang portions of partially ds RNA); halo (e.g., bromo, chloro, fluoro, or iodo); amino (wherein amino can be, e.g., $NH_2$; alkylamino, dialkylamino, heterocyclyl, arylamino, diarylamino, heteroarylamino, diheteroarylamino, or amino acid); $NH(CH_2CH_2NH)_nCH_2CH_2$-amino (wherein amino can be, e.g., as described herein), —NHC(O)R (wherein R can be, e.g., alkyl, cycloalkyl, aryl, aralkyl, heteroaryl or sugar), cyano; mercapto; alkyl-thio-alkyl; thioalkoxy; and alkyl, cycloalkyl, aryl, alkenyl and alkynyl, which may be optionally substituted with e.g., an amino as described herein.

The sugar group can also contain one or more carbons that possess the opposite stereochemical configuration than that of the corresponding carbon in ribose. Thus, a modified nucleic acid can include nucleotides containing e.g., arabinose, as the sugar. The nucleotide "monomer" can have an alpha linkage at the F position on the sugar, e.g., alpha-nucleosides. The modified nucleic acids can also include "abasic" sugars, which lack a nucleobase at C–. These abasic sugars can also be further modified at one or more of the constituent sugar atoms. The modified nucleic acids can also include one or more sugars that are in the L form, e.g. L-nucleosides.

Generally, RNA includes the sugar group ribose, which is a 5-membered ring having an oxygen. Exemplary modified nucleosides and modified nucleotides can include, without limitation, replacement of the oxygen in ribose (e.g., with sulfur (S), selenium (Se), or alkylene, such as, e.g., methylene or ethylene); addition of a double bond (e.g., to replace ribose with cyclopentenyl or cyclohexenyl); ring contraction of ribose (e.g., to form a 4-membered ring of cyclobutane or oxetane); ring expansion of ribose (e.g., to form a 6- or 7-membered ring having an additional carbon or heteroatom, such as for example, anhydrohexitol, altritol, mannitol, cyclohexanyl, cyclohexenyl, and morpholino that also has a phosphoramidate backbone). In some embodiments, the modified nucleotides can include multicyclic forms (e.g., tricyclo; and "unlocked" forms, such as glycol nucleic acid (GNA) (e.g., R-GNA or S-GNA, where ribose is replaced by glycol units attached to phosphodiester bonds), threose nucleic acid (TNA, where ribose is replaced with a-L-threofuranosyl-(3'→2')).

Modifications on the Nucleobase

The modified nucleosides and modified nucleotides described herein, which can be incorporated into a modified nucleic acid, can include a modified nucleobase. Examples of nucleobases include, but are not limited to, adenine (A), guanine (G), cytosine (C), and uracil (U). These nucleobases can be modified or wholly replaced to provide modified nucleosides and modified nucleotides that can be incorporated into modified nucleic acids. The nucleobase of the nucleotide can be independently selected from a purine, a pyrimidine, a purine or pyrimidine analog. In some embodiments, the nucleobase can include, for example, naturally-occurring and synthetic derivatives of a base.

Uracil

In some embodiments, the modified nucleobase is a modified uracil. Exemplary nucleobases and nucleosides having a modified uracil include without limitation pseudouridine (ψ), pyridin-4-one ribonucleoside, 5-aza-uridine, 6-aza-uridine, 2-thio-5-aza-uridine, 2-thio-uridine (s2U), 4-thio-uridine (s4U), 4-thio-pseudouridine, 2-thio-pseudouridine, 5-hydroxy-uridine (ho$^5$U), 5-aminoallyl-uridine, 5-halo-uridine (e.g., 5-iodo-uridine or 5-bromo-uridine), 3-methyl-uridine (m$^3$U), 5-methoxy-uridine (mo$^5$U), uridine 5-oxyacetic acid (cmo$^5$U), uridine 5-oxyacetic acid methyl ester (mcmo^U), 5-carboxymethyl-uridine (cm$^5$U), 1-carboxymethyl-pseudouridine, 5-carboxyhydroxymethyl-uridine (chm$^5$U), 5-carboxyhydroxymethyl-uridine methyl ester (mchm$^5$U), 5-methoxycarbonylmethyl-uridine (mcm$^5$U), 5-methoxycarbonylmethyl-2-thio-uridine (mcm$^5$s2U), 5-aminomethyl-2-thio-uridine (nm$^5$s2U), 5-methylaminomethyl-uridine (mnm$^5$U), 5-methylaminomethyl-2-thio-uridine (mnm$^5$s2U), 5-methylaminomethyl-2-seleno-uridine (mnm$^5$se$^2$U), 5-carbamoylmethyl-uridine (ncm$^5$U), 5-carboxymethylaminomethyl-uridine (cmnm$^5$U), 5-carboxymethylaminomethyl-2-thio-uridine (cmnm\s2U), 5-propynyl-uridine, 1-propynyl-pseudouridine, 5-taurinomethyl-uridine (xcm$^5$U), 1-taurinomethyl-pseudouridine, 5-taurinomethyl-2-thio-uridine (Trn$^5$s2U), 1-taurinomethyl-4-thio-pseudouridine, 5-methyl-uridine (m$^5$U, i.e., having the nucleobase deoxythymine), 1-methyl-pseudouridine (ιπι'ψ). 5-methyl-2-thio-uridine (m$^5$s2U), 1-methyl-4-thio-pseudouridine (m's ψ), 4-thio-1-methyl-pseudouridine, 3-methyl-pseudouridine (m'V), 2-thio-1-methyl-pseudouridine, 1-methyl-1-deaza-pseudouridine, 2-thio-1-methyl-1-deaza-pseudouridine, dihydroindene (D), dihydropseudouridine, 5,6-dihydrouridine, 5-methyl-dihydrouridine (m$^5$D), 2-thio-dihydrouridine, 2-thio-dihydropseudouridine, 2-methoxy-uridine, 2-methoxy-4-thio-uridine, 4-methoxy-pseudouridine, 4-methoxy-2-thio-pseudouridine, N1-methyl-pseudouridine, 3-(3-amino-3-carboxypropyl) uridine (acp$^3$U), 1-methyl-3-(3-amino-3-carboxypropy pseudouridine 5-(isopentenylaminomethyl)uridine (inm$^5$U), 5-(isopentenylaminomethy])-2-thio-uridine (inm$^5$s2U), a-thio-uridine, 2'-O-methyl-uridine (Urn), 5,2'-O-dimethyl-uridine (m$^5$Um), 2'-O-methyl-pseudouridine (ψπι), 2-thio-2'-O-methyl-uridine (s2Um), 5-methoxycarbonylmethyl-2'-O-methyl-uridine (mcm$^5$Um), 5-carbamoylmethyl-2'-O-methyl-uridine (ncm$^5$Um), 5-carboxymethylaminomethyl-2'-O-methyl-uridine (cmnm$^5$Um), 3,2'-O-dimethyl-uridine (m$^3$Um), (inm$^5$Um), 1-thio-uridine, deoxythymidine, 2'-F-ara-uridine, 2'-F-uridine, 2'-OH-ara-uridine, 5-(2-carbomethoxyvinyl) uridine, 5-[3-(1-E-propenylamino)uridine, pyrazolo[3,4-d]pyrimidines, xanthine, and hypoxanthine.

Cytosine

In some embodiments, the modified nucleobase is a modified cytosine. Exemplary nucleobases and nucleosides having a modified cytosine include without limitation 5-aza-cytidine, 6-aza-cytidine, pseudoisocytidine, 3-methyl-cytidine (m$^3$C), N4-acetyl-cytidine (act), 5-formyl-cytidine (f$^5$C), N4-methyl-cytidine (m$^4$C), 5-methyl-cytidine (m$^5$C), 5-halo-cytidine (e.g., 5-iodo-cytidine), 5-hydroxymethyl-cytidine (hm$^5$C), 1-methyl-pseudoisocytidine, pyrrolo-cytidine, pyrrolo-pseudoisocytidine, 2-thio-cytidine (s2C), 2-thio-5-methyl-cytidine, 4-thio-pseudoisocytidine, 4-thio-1-methyl-pseudoisocytidine, 4-thio-1-methyl-1-deaza-pseudoisocytidine, 1-methyl-1-deaza-pseudoisocytidine, zebularine, 5-aza-zebularine, 5-methyl-zebularine, 5-aza-2-thio-zebularine, 2-thio-zebularine, 2-methoxy-cytidine, 2-methoxy-5-methyl-cytidine, 4-methoxy-pseudoisocytidine, 4-methoxy-1-methyl-pseudoisocytidine, lysidine (k$^2$C), a-thio-cytidine, 2'-O-methyl-cytidine (Cm), 5,2'-O-dimethyl-cytidine (m$^5$Cm), N4-acetyl-2'-O-methyl-cytidine (ac$^4$Cm), N4,2'-O-dimethyl-cytidine (m$^4$Cm), (f$^5$Cm), N4,N4,2'-O-trimethyl-cytidine (m$^4$₂Cm), 1-thio-cytidine, 2'-F-ara-cytidine, 2'-F-cytidine, and 2'-OH-ara-cytidine.

Adenine

In some embodiments, the modified nucleobase is a modified adenine. Exemplary nucleobases and nucleosides having a modified adenine include without limitation 2-amino-purine, 2,6-diaminopurine, 2-amino-6-halo-purine (e.g., 2-amino-6-chloro-purine), 6-halo-purine (e.g., 6-chloi-purine), 2-amino-6-methyl-purine, 8-azido-adenosine, 7-deaza-adenine, 7-deaza-8-aza-adenine, 7-deaza-2-amino-purine, 7-deaza-8-aza-2-amino-purine, 7-deaza-2,6-diaminopurine, 7-deaza-8-aza-2,6-diaminopurine, 1-methyl-adenosine (m'A), 2-methyl-adenine (m A), N6-methyl-adenosine (m$^6$A), 2-methylthio-N6-methyl-adenosine (ms2m$^6$A), N6-isopentenyl-adenosine (i$^6$A), 2-methylthio-N6-isopentenyl-adenosine (ms$^2$i$^6$A), N6-(cis-hydroxyisopentenyl)adenosine (io$^6$A), 2-methylthio-N6-(cis-hydroxy-isopentenyl)adenosine (ms2io$^6$A), N6-glycinylcarbamoyl-adenosine (g$^6$A), N6-threonylcarbamoyl-adenosine (t$^6$A), N6-methyl-N6-threonylcarbamoyl-adenosine (m$^6$t$^6$A), 2-methylthio-N6-threonylcarbamoyl-adenosine (ms$^2$g$^6$A), N6,N6-dimethyl-adenosine (m$^6$₂A), N6-hydroxynorvalyl-carbamoyl-adenosine (hn$^6$A), 2-methylthio-N6-hydroxynorvalylcarbamoyl-adenosine (ms2hn$^6$A), N6-acetyl-adenosine (ac$^6$A), 7-methyl-adenine, 2-methylthio-adenine, 2-methoxy-adenine, a-thio-adenosine, 2'-O-methyl-adenosine (Am), N$^6$,2'-O-dimethyl-adenosine (m$^5$Am), N6-Methyl-2'-deoxyadenosine, N6,N6,2'-O-trimethyl-adenosine (m$^6$₂Am), 1,2'-O-dimethyl-adenosine (m' Am), 2'-O-ribosyladenosine (phosphate) (Ar(p)), 2-amino-N6-methyl-purine, 1-thio-adenosine, 8-azido-adenosine, 2'-F-ara-adenosine, 2'-F-adenosine, 2'-OH-ara-adenosine, and N6-(19-amino-pentaoxanonadecyl)-adenosine.

Guanine

In some embodiments, the modified nucleobase is a modified guanine. Exemplary nucleobases and nucleosides having a modified guanine include without limitation inosine (I), 1-methyl-inosine (m'1), wyosine (imG), methyl-wyosine (mimG), 4-demethyl-wyosine (imG-14), isowyosine (imG2), wybutosine (yW), peroxywybutosine (o$_2$yW), hydroxywybutosine (OHyW), undermodified hydroxywybutosine (OHyW*), 7-deaza-guanosine, queuosine (Q), epoxyqueuosine (oQ), galactosyl-queuosine (galQ), mannosyl-queuosine (manQ), 7-cyano-7-deaza-guanosine (preQ$_0$), 7-aminomethyl-7-deaza-guanosine (preQi), archaeosine (G$^+$), 7-deaza-8-aza-guanosine, 6-thio-guanosine, 6-thio-7-deaza-guanosine, 6-thio-7-deaza-8-aza-guanosine, 7-methyl-guanosine (m$^7$G), 6-thio-7-methyl-guanosine, 7-methyl-inosine, 6-methoxy-guanosine, 1-methyl-guanosine (m'G), N2-methyl-guanosine (m$^2$G), N2,N2-dimethyl-guanosine (m$^2_2$G), N2,7-dimethyl-guanosine (m$^2$,7G), N2,N2,7-dimethyl-guanosine (m$^2$,2,7G), 8-oxo-guanosine, 7-methyl-8-oxo-guanosine, 1-meth thio-guanosine, N2-methyl-6-thio-guanosine, N2,N2-dimethyl-6-thio-guanosine, a-thio-guanosine, 2'-O-methyl-guanosine (Gm), N2-methyl-2'-O-methyl-guanosine (m$^{3/4}$m), N2,N2-dimethyl-2'-O-methyl-guanosine (m$^2_2$Gm), 1-methyl-2'-O-methyl-guanosine (m'Gm), N2,7-dimethyl-2'-O-methyl-guanosine (m$^2$,7Gm), 2'-O-methyl-inosine (Im), 1,2'-O-dimethyl-inosine (m'lm), O$^6$-phenyl-2'-deoxyinosine, 2'-O-ribosylguanosine (phosphate) (Gr(p)), 1-thio-guanosine, O$^6$-methyl]-guanosine, O$^6$-Methyl-2'-deoxyguanosine, 2'-F-ara-guanosine, and 2'-F-guanosine.

Modified gRNAs

In some embodiments, the modified nucleic acids can be modified gRNAs. In some embodiments, gRNAs can be modified at the 3' end. In this embodiment, the gRNAs can be modified at the 3' terminal U ribose. For example, the two terminal hydroxyl groups of the U ribose can be oxidized to aldehyde groups and a concomitant opening of the ribose ring to afford a modified nucleoside, wherein U can be an unmodified or modified uridine.

In another embodiment, the 3' terminal U can be modified with a 2' 3' cyclic phosphate, wherein U can be an unmodified or modified uridine. In some embodiments, the gRNA molecules may contain 3' nucleotides which can be stabilized against degradation, e.g., by incorporating one or more of the modified nucleotides described herein. In this embodiment, e.g., uridines can be replaced with modified uridines, e.g., 5-(2-amino)propyl uridine, and 5-bromo uridine, or with any of the modified uridines described herein; adenosines and guanosines can be replaced with modified adenosines and guanosines, e.g., with modifications at the 8-position, e.g., 8-bromo guanosine, or with any of the modified adenosines or guanosines described herein. In some embodiments, deaza nucleotides, e.g., 7-deaza-adenosine, can be incorporated into the gRNA. In some embodiments, O- and N-alkylated nucleotides, e.g., N6-methyl adenosine, can be incorporated into the gRNA. In some embodiments, sugar-modified ribonucleotides can be incorporated, e.g., wherein the 2' OH— group is replaced by a group selected from H, —OR, —R (wherein R can be, e.g., methyl, alkyl, cycloalkyl, aryl, aralkyl, heteroaryl or sugar), halo, —SH, —SR (wherein R can be, e.g., alkyl, cycloalkyl, aryl, aralkyl, heteroaryl or sugar), amino (wherein amino can be, e.g., NH$_2$; alkylamino, dialkylamino, heterocyclyl, arylamino, diarylamino, heteroarylamino, diheteroarylamino, or amino acid); or cyano (—CN). In some embodiments, the phosphate backbone can be modified as described herein, e.g., with a phosphothioate group. In some embodiments, the nucleotides in the overhang region of the gRNA can each independently be a modified or unmodified nucleotide including, but not limited to 2'-sugar modified, such as, 2-F2'-O-methyl, thymidine (T), 2'-O-methoxyethyl-5-methyluridine (Teo), 2'-O-methoxyethyladenosine (Aeo), 2'-O-methoxyethyl-5-methylcytidine (m5Ceo), and any combinations thereof.

In an embodiment, a one or more or all of the nucleotides in single stranded overhang of an RNA molecule, e.g., a gRNA molecule, are deoxynucleotides.

Candidate Cas molecules, e.g., Cas9 molecules, candidate gRNA molecules, candidate Cas9 molecule/gRNA molecule complexes, and candidate CRISPR systems, can be evaluated by art-known methods or as described herein. For example, exemplary methods for evaluating the endonuclease activity of Cas9 molecule are described, e.g., in Jinek el al., SCIENCE 2012; 337(6096):816-821.

EXAMPLES

Example 1: Assays

Guide Selection

Initial guide selection was performed in silico using a human reference genome and user defined genomic regions of interest (e.g., a gene, an exon of a gene, non-coding regulatory region, etc), for identifying PAMs in the regions of interest. For each identified PAM, analyses were performed and statistics reported. gRNA molecules were further selected and rank-ordered based on a number of criteria known in the art. gRNA molecules were then tested as described herein for cutting efficiency and indel formation as described herein.

Throughout the Examples, in the experiments below, either sgRNA molecules or dgRNA molecules were used. Unless indicated otherwise, experiments referring to a CRxxxxx identifier for the targeting domain employed a dgRNA format. Unless indicated otherwise, where dgRNA molecules were used, the gRNA includes the following:

crRNA: [targeting domain]-[SEQ ID NO: 6607]
tracr (trRNA): SEQ ID NO: 6660.

Unless indicated otherwise, in experiments employing a sgRNA molecule, the following sequence was used:

[targeting domain]-[SEQ ID NO: 6601]-UUUU

Transfection of HEK-293_Cas9GFP Cells for Primary Guide Screening

Transfection of Cas9GFP-expressing HEK293 cells (HEK-293_Cas9GFP) was used for primary screening of target specific crRNAs. In this example, target specific crRNAs were designed and selected for primary screening using defined criteria including in silico off-target detection, e.g., as described herein. Selected crRNAs were chemically synthesized and delivered in a 96 well format. HEK-293-Cas9GFP cells were transfected with target crRNAs comprising a flagpole region of SEQ ID NO: 6607 in a 1:1 ratio with stock trRNA of SEQ ID NO: 6660. The transfection was mediated using lipofection technology according to manufacturer's protocol (DharmaFECT Duo, GE Life-Sciences; or RNAiMax, LifeTechnologies). Transfected cells were lysed 24 h following lipofection and editing (e.g., cleavage) was detected within lysates with the T7E1 assay and/or next generation sequencing (NGS; below).

T7E1 Assay

The T7E1 assay was used to detect mutation events in genomic DNA such as insertions, deletions and substitutions created through non-homologous end joining (NHEJ) following DNA cleavage by Cas9 (See Cho et al., Targeted genome engineering in human cells with the Cas9 RNA-guided endonuclease. *Nature Biotechnology.* 2013; 31, 230-232).

Genomic DNA regions that have been targeted for cutting by CRISPR/Cas9 were amplified by PCR, denatured at 95° C. for 10 minutes, and then re-annealed by ramping down from 95° C. to 25° C. at 0.5° C. per second. If mutations were present within the amplified region, the DNA combined to form heteroduplexes. The re-annealed heteroduplexes were then digested with T7E1 (New England Biolabs) at 37° C. for 1 hour. T7E1 endonuclease recognizes DNA mismatches, heteroduplexes and nicked double stranded DNA and generates a double stranded break at these sites. The resulting DNA fragments were analyzed using a Fragment Analyzer and quantified to determine cleavage efficiency.

Next-Generation Sequencing (NGS) and Analysis for On-Target Cleavage Efficiency and Indel Formation To determine the efficiency of editing (e.g., cleaving) the target location in the genome, deep sequencing was utilized to identify the presence of insertions and deletions introduced by non-homologous end joining.

PCR primers were first designed around the target site, and the genomic area of interest PCR amplified. Additional PCR was performed according to manufacturer's protocols (Illumina) to add the necessary chemistry for sequencing. The amplicons were then sequenced on an Illumina MiSeq instrument. The reads were then aligned to the human reference genome (e.g., hg38) after eliminating those having low quality scores. From the resulting files containing the reads mapped to the reference genome (BAM files), reads which overlap the target region of interest were selected and the number of wild type reads versus the number of reads which contain an insertion or deletion was calculated. The editing percentage was then defined as the total number of reads with insertions or deletions over the total number of reads, including wild type. To determine the pattern of insertions and/or deletions that resulted from the edit, the aligned reads with indels were selected and the number of a reads with a given indel were summed. This information was then displayed as a list as well as visualized in the form on histograms which represent the frequency of each indel.

RNP Generation

The addition of crRNA and trRNA (for a dgRNA), or chimeric gRNA (for sgRNA) to Cas9 protein results in the formation of the active Cas9 ribonucleoprotein complex (RNP), which mediates binding to the target region specified by the crRNA and specific cleavage of the targeted genomic DNA. This complex was formed by loading trRNA and crRNA into Cas9, which is believed to cause conformational changes to Cas9 allowing it to bind and cleave dsDNA.

The crRNA and trRNA were separately denatured at 95° C. for 2 minutes, and allowed to come to room temperature. Cas9 protein (10 mg/ml) was added to 5×CCE buffer (20 mM HEPES, 100 mM KCl, $MgCl_2$, 1 mM DTT, 5% glycerol), to which trRNA and crRNAs were added (in separate reactions) and incubated at 37° C. for 10 minutes, thereby forming the active RNP complex. The complex was delivered by electroporation and other methods into a wide variety of cells, including HEK-293 and CD3+ T cells.

Delivery of RNPs to T Cells

CD3+ T cells are comprised of multiple T cell populations including CD4+ T helper cells and CD8+ cytotoxic T cells. These cells can be isolated from whole blood or from leukophoresis samples. T cells can be modified to specifically target cancerous cells and to be less immunogenic, by engineering patient T cells using Cas9-mediated editing. This example describes a basic method used to deliver Cas9 RNP, for example, Cas9 RNP targeting B2M, in T cells. Only the targeting crRNA in the RNP would need to be changed to adapt this protocol to a different T cell target (e.g., any of those provided herein).

T cells were first enriched from a leukopak using a commercially available kit (e.g., EasySep™ Human T Cell Isolation Kit, Stem Cell Technology). Enriched T cells were aliquoted and frozen down (at 10×106/vial) for future use. Vials were subsequently thawed as needed, and activated by addition of 3:1 ratio of CD3/CD28 beads (Dynabeads, Life Technologies) or using ImmunoCult Human CD3/CD28 T cell Activator (Stem Cell Technologies) in T cell media (RPMI 1640, FBS, L-glutamine, non-essential amino acids, sodium pyruvate, HEPES buffer, 2-mercaptoethanol and optionally IL2). RNPs were generated as described herein, and were added to ~50,000-100,000 CD3+ T cells resuspended in P3 buffer and nucleofected using the Amaxa nucleofection program EO-115. T cell media was added to cells immediately post-nucleofection and cultured for 24 h or more.

Example 2: Editing of B2M

Results of Editing Using B2M-Targeted gRNAs in HEK-293 Cells Stably Expressing Cas9

Figure 14:
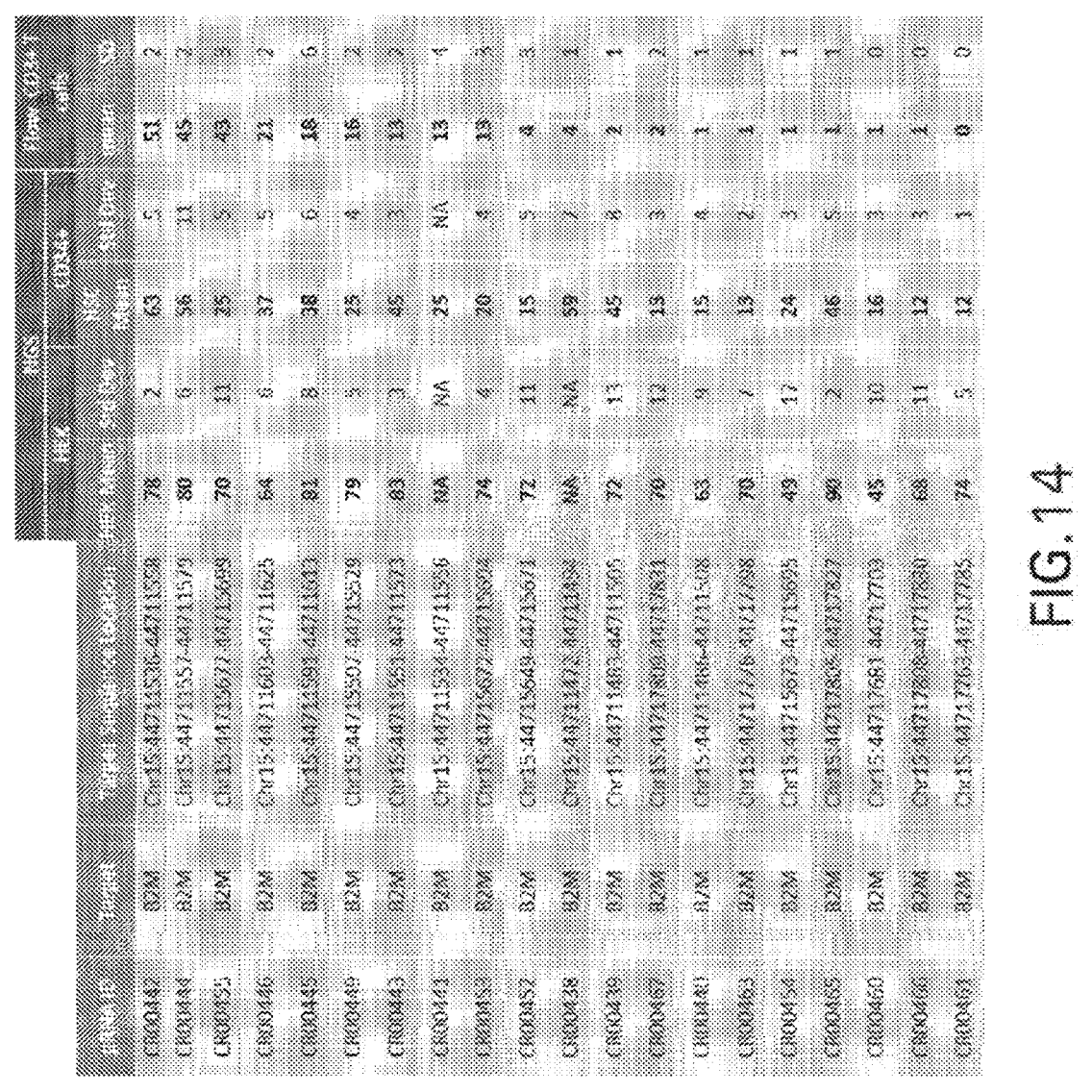

NGS assay results for cutting efficiency of gRNAs targeting B2M are summarized in Table 9, and in FIG. 1. These results demonstrate that multiple guide RNA molecules are able to mediate high efficiency editing of the B2M locus. The top gRNA molecules, as ranked by % editing in HEK cells (followed by % editing in CD34+ cells) are shown in FIG. 14, together with the results of 1) % editing in CD34+ cells as measured by NGS, and 2) % loss of B2M as measured by flow cytometry in CD3+ T cells). As shown in FIG. 14, three dgRNA molecules, e.g., dgRNA molecules that include the targeting domain of CR00442, CR00444 and CR00455 showed greater than 40% editing in CD3+ T cells as measured by flow cytometry.

TABLE 9

Editing of B2M by dgRNA-CRISPR systems in HEK-293 Cas9GFP as determined by NGS. gRNAs are ranked according to % editing in HEK cells.

| gRNA ID | target name | HEK (NGS) % Editing | |
|---|---|---|---|
| | | Mean | Std Dev |
| CR00465 | B2M | 89.7 | 1.7 |
| CR00443 | B2M | 82.9 | 3.2 |
| CR00445 | B2M | 80.9 | 8.4 |
| CR00444 | B2M | 80.4 | 5.8 |
| CR00449 | B2M | 79.3 | 5.1 |
| CR00442 | B2M | 77.7 | 2.1 |
| CR00453 | B2M | 74.3 | 3.6 |
| CR00461 | B2M | 73.6 | 5.2 |
| CR00439 | B2M | 71.8 | 12.5 |
| CR00452 | B2M | 71.7 | 10.6 |
| CR00455 | B2M | 70.4 | 11.1 |
| CR00463 | B2M | 70.2 | 6.7 |
| CR00467 | B2M | 69.6 | 12.5 |
| CR00466 | B2M | 67.6 | 11.4 |

TABLE 9-continued

Editing of B2M by dgRNA-CRISPR systems in HEK-293 Cas9GFP as determined by NGS. gRNAs are ranked according to % editing in HEK cells.

| gRNA ID | target name | HEK (NGS) % Editing | |
|---|---|---|---|
| | | Mean | Std Dev |
| CR00446 | B2M | 64.4 | 6.0 |
| CR00440 | B2M | 62.6 | 9.1 |
| CR00472 | B2M | 57.5 | 4.0 |
| CR00459 | B2M | 55.8 | 19.8 |
| CR00468 | B2M | 54.8 | 11.9 |
| CR00469 | B2M | 52.6 | 13.6 |
| CR00450 | B2M | 51.6 | 4.5 |
| CR00456 | B2M | 50.3 | 9.6 |
| CR00454 | B2M | 49.2 | 16.8 |
| CR00464 | B2M | 47.3 | 8.2 |
| CR00460 | B2M | 45.1 | 9.8 |
| CR00457 | B2M | 43.6 | 11.5 |
| CR00451 | B2M | 39.8 | 8.0 |
| CR00462 | B2M | 34.6 | 9.5 |
| CR00470 | B2M | 31.3 | 7.0 |
| CR00447 | B2M | 31.2 | 7.0 |
| CR00458 | B2M | 20.6 | 9.0 |
| CR00471 | B2M | 17.1 | 4.7 |
| CR00473 | B2M | 15.6 | 2.1 |
| CR000129 | B2M | NA | NA |
| CR000131 | B2M | NA | NA |
| CR00438 | B2M | NA | NA |

Flow Cytometric Analysis of B2M Expression

A flow based assay was developed to monitor editing efficiency following RNP formulation and delivery. Beta-2-microglobin (B2M) is an essential component of the MHC class I (HLA-type 1) complex that is presented on the surface of all nucleated cells. MHC class I presents endogenous (e.g., self and non-self) peptides to the immune system. A series of crRNAs targeting B2M were tested using flow cytometry assay to detect B2M expression. From this initial screen, crRNAs were identified which showed consistent editing ranging between 5-25%.

Cells in suspension were labeled with APC conjugated anti-human B2M (BioLegend, cat #316312), PE conjugated anti-human HLA-A,B,C (BioLegend, cat #311405), and propidium iodide (0.5 mg/ml diluted to 1/1000). Appropriate controls were established (e.g., isotype-APC, isotype-PE, PE-anti-HLA separately, APC-anti-B2M separately). The samples were then run on a flow cytometer. In this example, loss of B2M expression as assessed by surface marker staining was indicative of Cas9-mediated editing (e.g., cleavage). Results are reported in FIG. 14.

Example 3: Editing of TCR and/or PD-1 in T Cells, Including in CAR-T Cells

Table 10 lists gRNA targeting domains for editing of the genes for TCR alpha and for PD-1. gRNA molecules were generated as described below as sgRNAs comprising, from 5' to 3' the indicated targeting domain-SEQ ID NO: 6601-(U)$_7$.

TABLE 10 gRNA targeting domains to TCR alpha and PD-1

| Id. | gRNA Targeting Domain | SEQ ID NO: |
|---|---|---|
| TRAC-1 (CR000960) | UCUCUCAGCUGGUACACGGC | 5568 |
| TRAC-2 (CR000964) | GAGAAUCAAAAUCGGUGAAU | 5572 |
| TRAC-3 (CR000966) | AACAAAUGUGUCACAAAGUA | 5574 |
| TRAC-5 (CR000971) | AAAGUCAGAUUUGUUGCUCC | 5579 |
| TRAC-6 (CR000973) | CUGGGGAAGAAGGUGUCUUC | 5581 |
| TRAC-7 (CR000980) | CUCGACCAGCUUGACAUCAC | 5588 |
| TRAC-8 (CR000979) | AAGUUCCUGUGAUGUCAAGC | 5587 |
| TRAC-9 (CR000984) | UUCGGAACCCAAUCACUGAC | 5592 |
| TRAC-10 (CR000991) | GAUUAAACCCGGCCACUUUC | 5599 |
| PD1-1 (CR000837) | UGUAGCACCGCCCAGACGAC | 5733 |
| PD1-2 (3'-20 nt of 5133_1_37) | UGCAGAUCCCACAGGCGCCC | 6657 |
| PD1-3 (CR000868) | UGACACGGAAGCGGCAGUCC | 5764 |
| PD1-4 (CR000853) | CACGAAGCUCUCCGAUGUGU | 5749 |
| PD1-5 (CR000881) | AGGUGCCGCUGUCAUUGCGC | 5777 |
| PD1-6 | AGGGCCCGGCGCAAUGACAG | 5775 |
| PD1-7 (CR000859) | CAGCAACCAGACGGACAAGC | 5755 |
| PD1-8 (CR000850) | CCUGCUCGUGGUGACCGAAG | 5746 |

Figure 2:
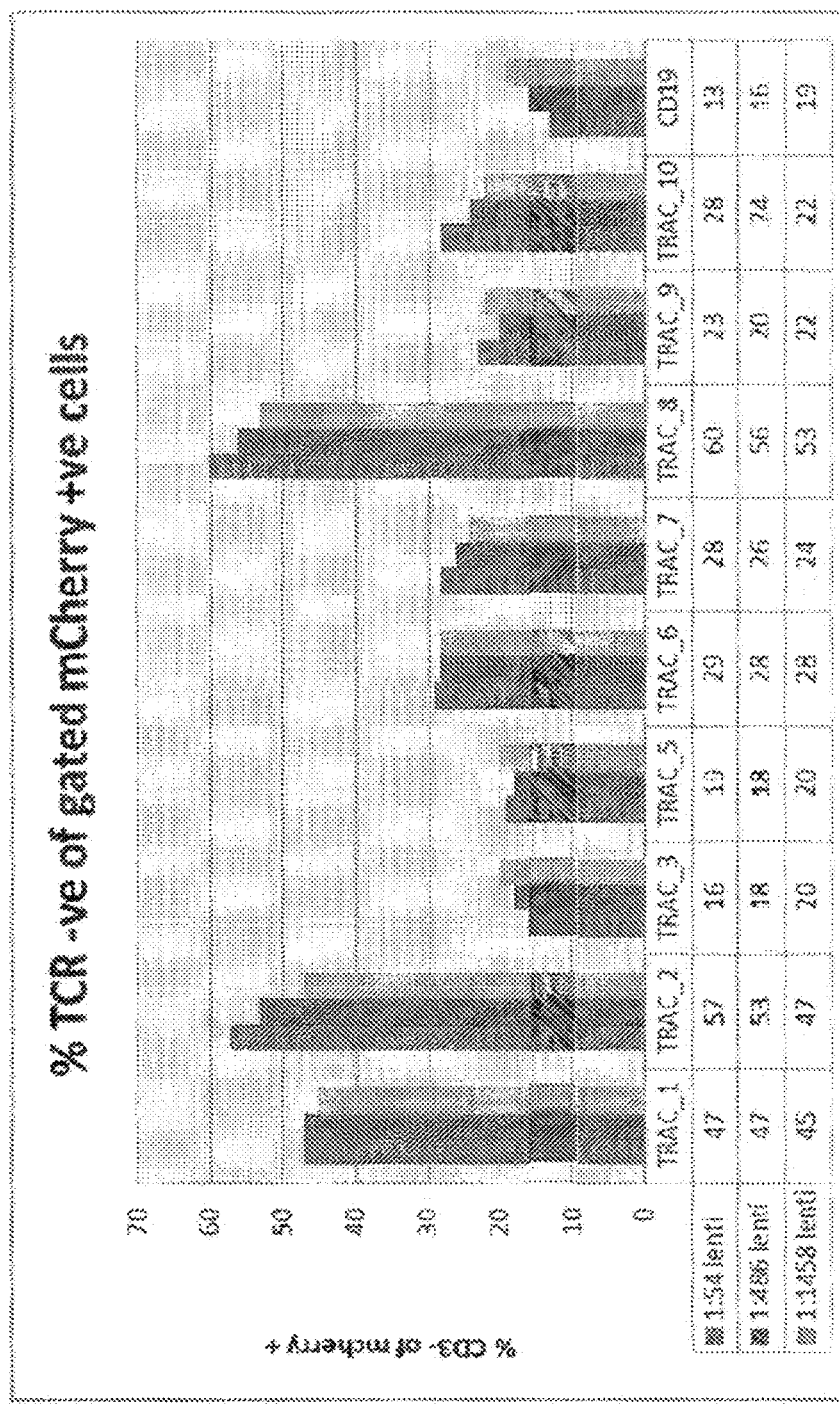
FIG. 2: Histogram for TCR expression after editing with gRNA molecules comprising targeting domains to TCR-alpha, as listed in table 1. Shown is the % mCherry+TCR− cells after 7 days in Jurkat cells, using three different concentrations of lentivirus.

Forward and reverse DNA oligonucleotides encoding gRNA molecules comprising the targeting domains listed above in Table 10 were cloned into a lentiviral vector downstream of a U6 promoter. Using standard procedures, briefly, the vector was digested with BBSI for 1 hour at 37° C. The vector was purified using a PCR-purification kit (Qiagen). The gRNA forward and reverse DNA oligonucleotides were synthesized by IDT (Integrated DNA Technologies) with the addition of BBSI site overhangs (ACCG 5' of the forward oligo and AAAC 5' of the reverse strand). The oligos were annealed using IDT duplex buffer by heating up to 95° C. and letting cool down at room temperature. The annealed oligo was then ligated to the cut and purified vector using NEB quick ligation kit. The vector also contains nucleic acid encoding Cas9 and a mCherry reporter (mCherry is expressed using a T2A sequence downstream of CAS9) downstream of an EF1-alpha promoter. Lentivirus was packaged using a packaging system (Cellecta catalog number CPCP-K2A). The virus was concentrated 200× for all the CRISPR viral productions. In a 96 well flat bottom plate, 1E5 Jurkat cells were plated in 100 ul RPMI 10% FBS media. 50 ul of concentrated virus was added directly to each well. Then 24 hours post viral addition 100 ul of media was added to the cells. Cells were cultured by passaging every 3 days by adding new media to maintain the cells at 0.5e6 cells/mL. Expression of the TCR was measured 7 days post viral transduction. The TCR was detected using anti-CD3 epsilon antibody clone OKT3 conjugated to APC from ebioscience (catalog number 17-0037-42). 1E5 cells were incubated with 2 ul of antibody for 20 minutes, analyzed by flow cytometry (BD Fortessa). Data was analyzed using Flow Jo software. mCherry positive cells were gated first to detect CRISPR/Cas9 positive cells. This population was analyzed for TCR loss. The results are shown in FIG. 2. These results demonstrate that TCR-alpha targeted gRNAs are able to cause loss of surface TCR expression in Jurkat cells.

Generation of TCR-Primary T Cells Using TCR-Alpha Targeting gRNAs

Figure 3:
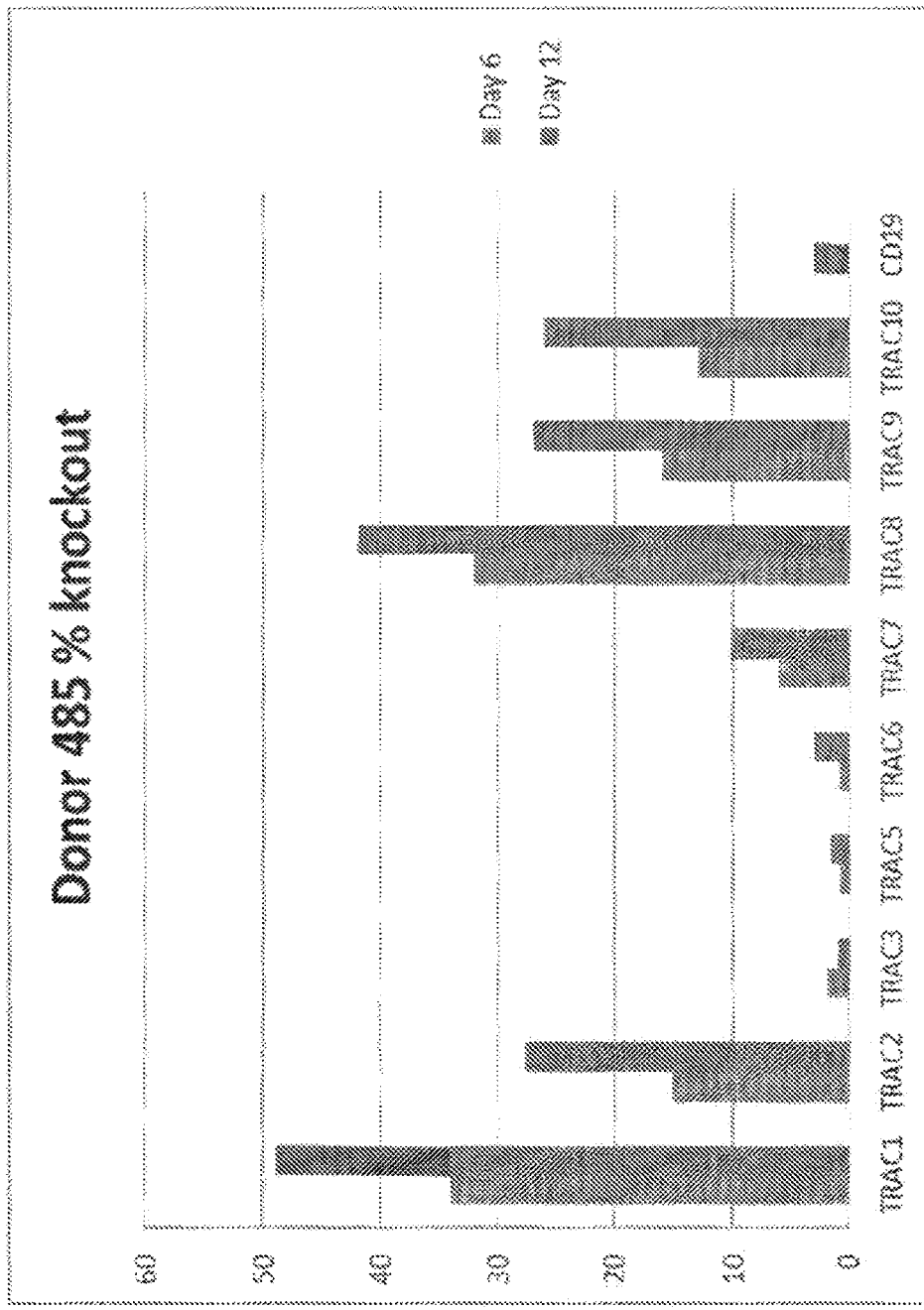
FIG. 3: Shown is the % TCR− primary T cells 6 and 12 days after introduction of lentivirus encoding the gRNA shown and Cas9/mCherry. Data represents % mCherry+ TCR− edited cells.

The procedure noted above was followed for assessing editing and loss of TCR in primary T cells, with the following modifications. 1E5 primary T cells were activated on Day 0 using 3:1 dyna beads anti-CD3/CD28 in 10 ul T cells media in a 96 well flat bottom plate. On Day 1 50 ul of lentivirus encoding gRNA and Cas9/mCherry (as described above) was added. T cells were cultured for 12 days by adding fresh media every 2 days to maintain a concentration of 5E5 cells/ml. Loss of TCR was measured as described above at day 6 and day 12 after lentivirus introduction. The results are shown in FIG. 3. These results demonstrate that TCR-alpha targeted gRNAs are able to cause loss of surface TCR expression in primary T cells.

Generation of PD1-Primary T Cells Using PDCD1 Targeting gRNAs

Figure 4:
FIG. 4: Shown is the % PD1-primary T cells in the mCherry+ gated population 3 days post restimulation (with CD3/CD28 beads) and 8 days post activation, in cells transfected with lentivirus encoding the gRNA indicated and Cas9/mCherry.

Editing of the PD-1 locus and loss of PD-1 expression was assessed as described above using lentiviral vectors encoding gRNA molecules to PD-1 listed in Table 10. Experiments were performed as described above for assessing TCR knockout in primary T cells, except that cells were restimulated with 3:1 dyna beads anti-CD3/CD28 in culture on Day 5 to drive increased expression of PD-1, enabling better detection of the protein. The results are reported in FIG. 4. These results demonstrate that gRNA molecules of the invention targeting PD-1 (PDCD1) lead to high efficiency loss of PD-1 expression in primary T cells.

Editing of PD-1 or TCR in Primary T Cells Using RNP

Figure 5A:
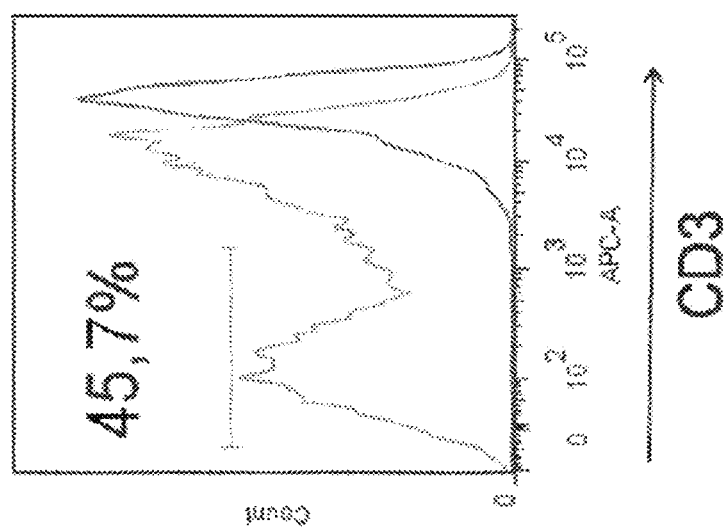
FIGS. 5A and 5B: Shown is expression of TCR on day 7 of culture using TRAC-8 gRNA (FIG. 5A) and PD-1 on day 8 of culture using PD1-6 gRNA (FIG. 5B) histograms.
Figure 5B:
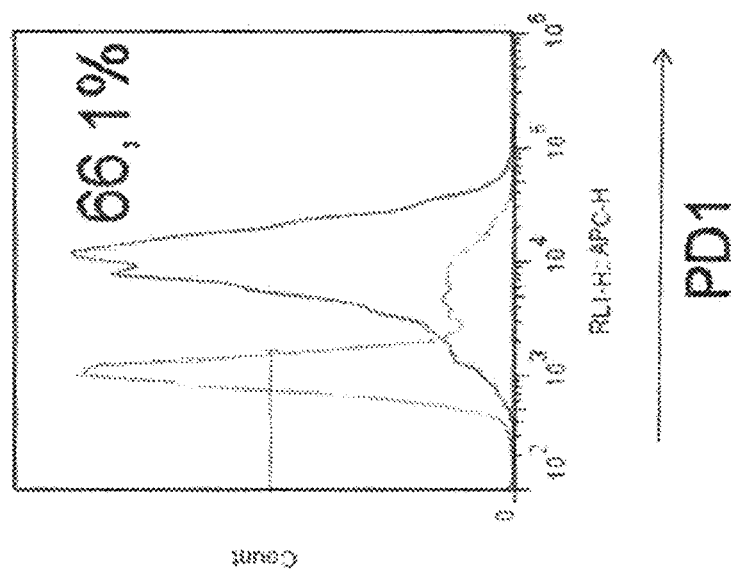

Editing of TCR or PD-1 in primary T cells was tested using Cas9/gRNA Ribonucleoprotein (RNP) complexes. RNPs were generated by mixing 20 ug of CAS9 (PNA bio) and 20 ug of chemically synthesized sgRNA (TriLink biotech) comprising either the targeting domain of TRAC-8 or of PD1-6, and incubating for 15 minutes at room temperature. T cells were isolated from Leukopak PBMCs using Pan T cell Isolation kit (Miltenyi) then activated with 3:1 CD3/CD28 dyna beads (invitrogen). 48 hours post activation, 2E5 T cells (without bead removal) were centrifuged at 300 g for 6 minutes and resuspended in 20 ul of Optimem and the RNP complex was added and mixed. Then the cells were transferred into a 1 mm electroporation cuvette (BTX) and pulsed using the BTX ECM 830 machine at 250V for 500 us and 1 pulse. The cells were returned into their T cell media and cultured for 5 days before analyses. FIG. 5 shows histograms of TCR or PD-1 expression as detected by flow cytometry after 7 days in culture. These results show that gRNAs targeting TCR alpha and PD-1 are effective at generating either TCR negative or PD1 negative T cells when introduced as RNP.

TCR Negative CAR T Cells

The ability of gRNA molecules targeting the TRAC locus to edit and lead to TCR negative phenotype in T cells engineered to express a chimeric antigen receptor (CAR) was determined. On Day 0 primary T cells were activated with 3:1 CD3/CD28 dyna beads at a concentration of 5E5 cells/ml in T cell media. On Day 1, T cells were engineered to express a CD19 CAR using lentiviral particles. T cells were engineered to express a CD19 CAR using lentiviral particles (lentivirus, as described in WO2012/079000) at MOI of 5–. On Day 2, T cells were electroporated with RNP comprising Cas9 protein and a gRNA molecule comprising the targeting domain of either TRAC-1 or TRAC-8. On Day 4 onwards, T cells were replenished with fresh media every 2 days to maintain a concentration of 5E5 cells/ml. On day 11 of T cell culture, the T cells were counted, and CD3 microbeads from Miltenyi biotech were added per manufacturer protocol. An LD magnetic column (Miltenyi) was used to perform the positive selection. As shown in FIG. 6, T cell populations which were ~40-50% TCR negative could be enriched to create isolated populations of TCRnegative CART cells at greater than 98% purity.

Activity of TCR Negative CART Cells

The T cells were cultured under standard culture conditions with the following modifications. On day 2 T cells were electroporated with RNP comprising gRNA targeting TCR alpha (TRAC-1 or TRAC-8) as described in "Editing of PD-1 or TCR in primary T cells using RNP," above, or were transduced with lentivirus encoding said gRNA and Cas9/mCherry, as described in Generation of TCR– primary T cells using TCR-alpha targeting gRNAs," above. On day 11 a purification of TCR– cells was added described in "TCR– CAR T cells," above. Isolated TCR negative cells were co-cultured with luciferase-expressing CD19+NALM6 (B-ALL cell) or CD19–K562 (CML cell) cells and the ability of the TCR-CART cells to specifically kill CD19+ cells was assessed. The results are shown in FIG. 7 (% cell lysis), and demonstrate that TCR negative CD19 CART cells comprising TCR-targeting gRNAs (by either lentiviral or RNP transfection) are capable of specifically killing CD19+ cells.

Example 4: B2M Excision Using Two gRNA Molecules

Figure 8:
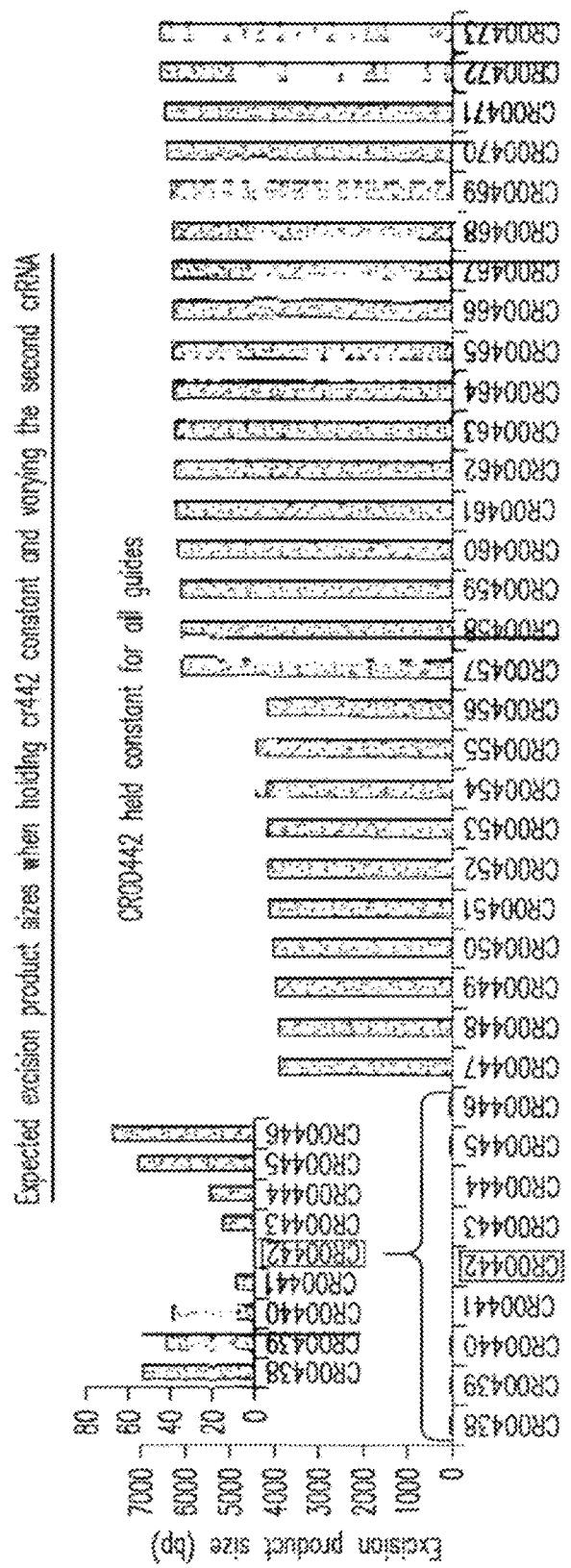
FIG. 8: Excision within the B2M gene employing CRISPR systems comprising two gRNA molecules. In each experiment, cells were exposed to gRNA with the targeting domain of CR00442 and a second gRNA molecule, as indicated. Shown is the predicted excision product size.
Figure 9:
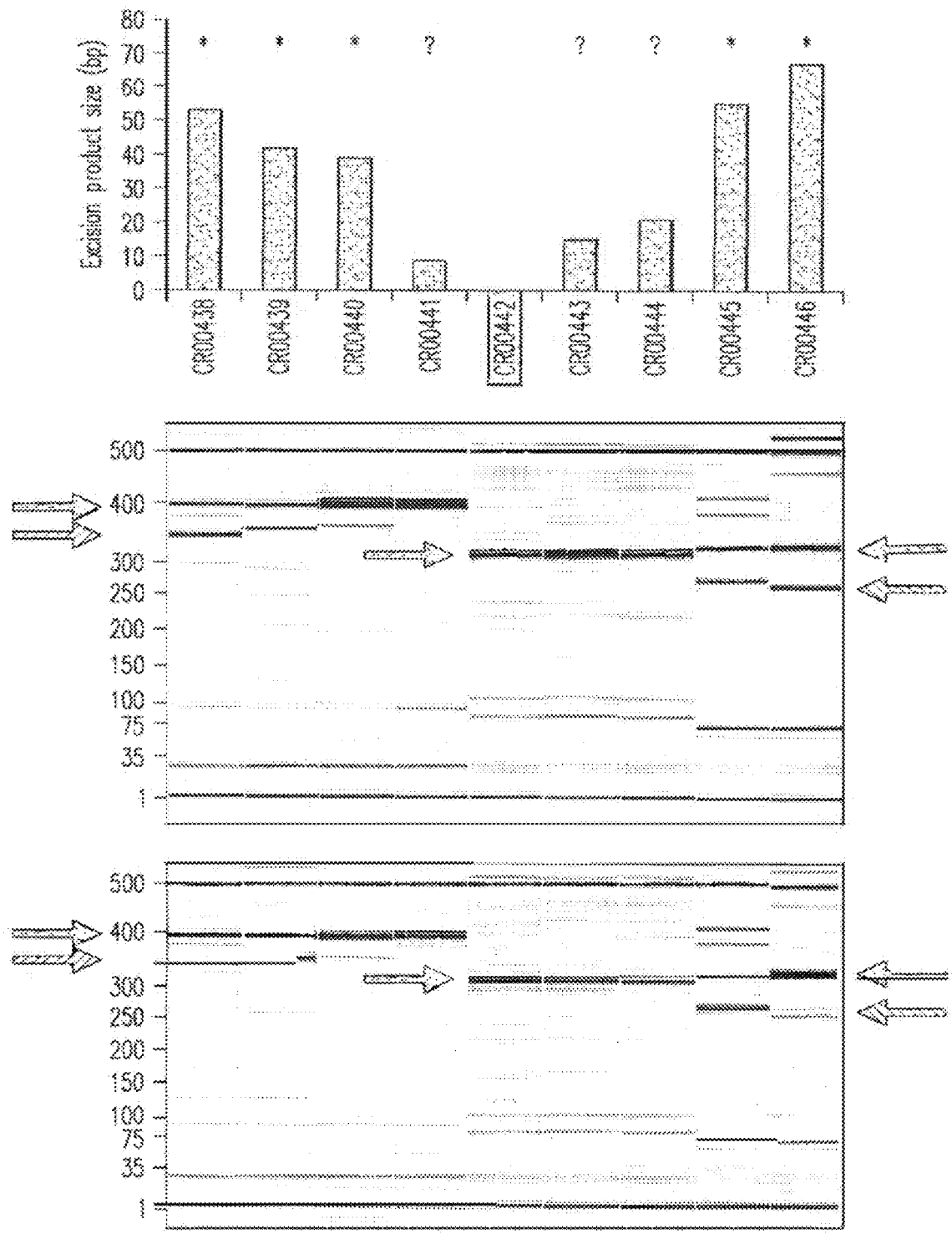
FIG. 9: Results of gRNA pair exposure to B2M gene with expected excision products of less than 100. * indicates expected excision product seen (green arrow); ?=expected excision product could not be resolved from the assay. Yellow arrow indicates wild type fragment.
Figure 10:
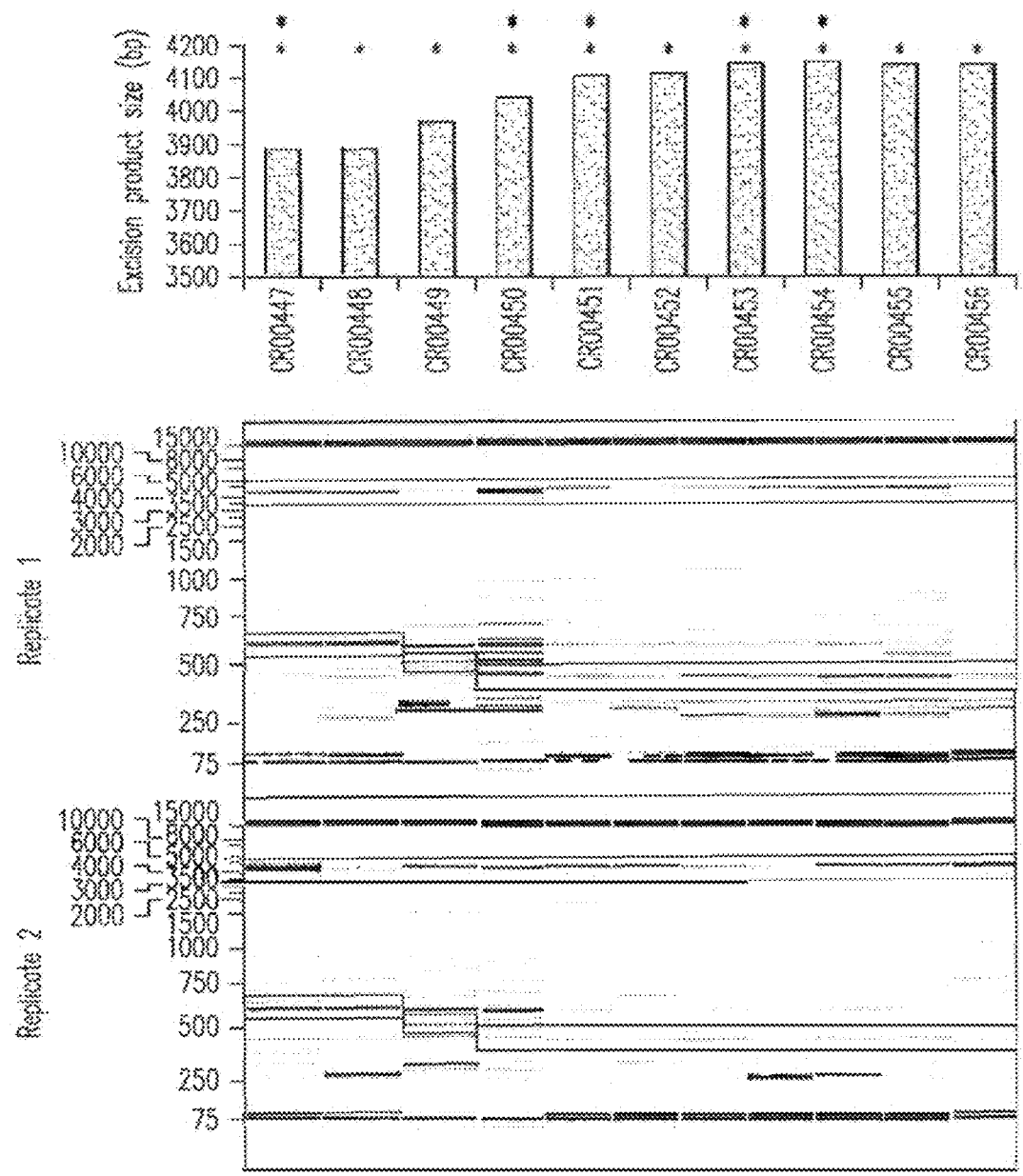
FIG. 10: Results of gRNA pair exposure to B2M gene with expected excision products ~4000 base pairs. Red * indicates expected excision product seen (green box); Purple *=less than 10% editing efficiency. Orange boxes indicate wild type fragment.
Figure 11:
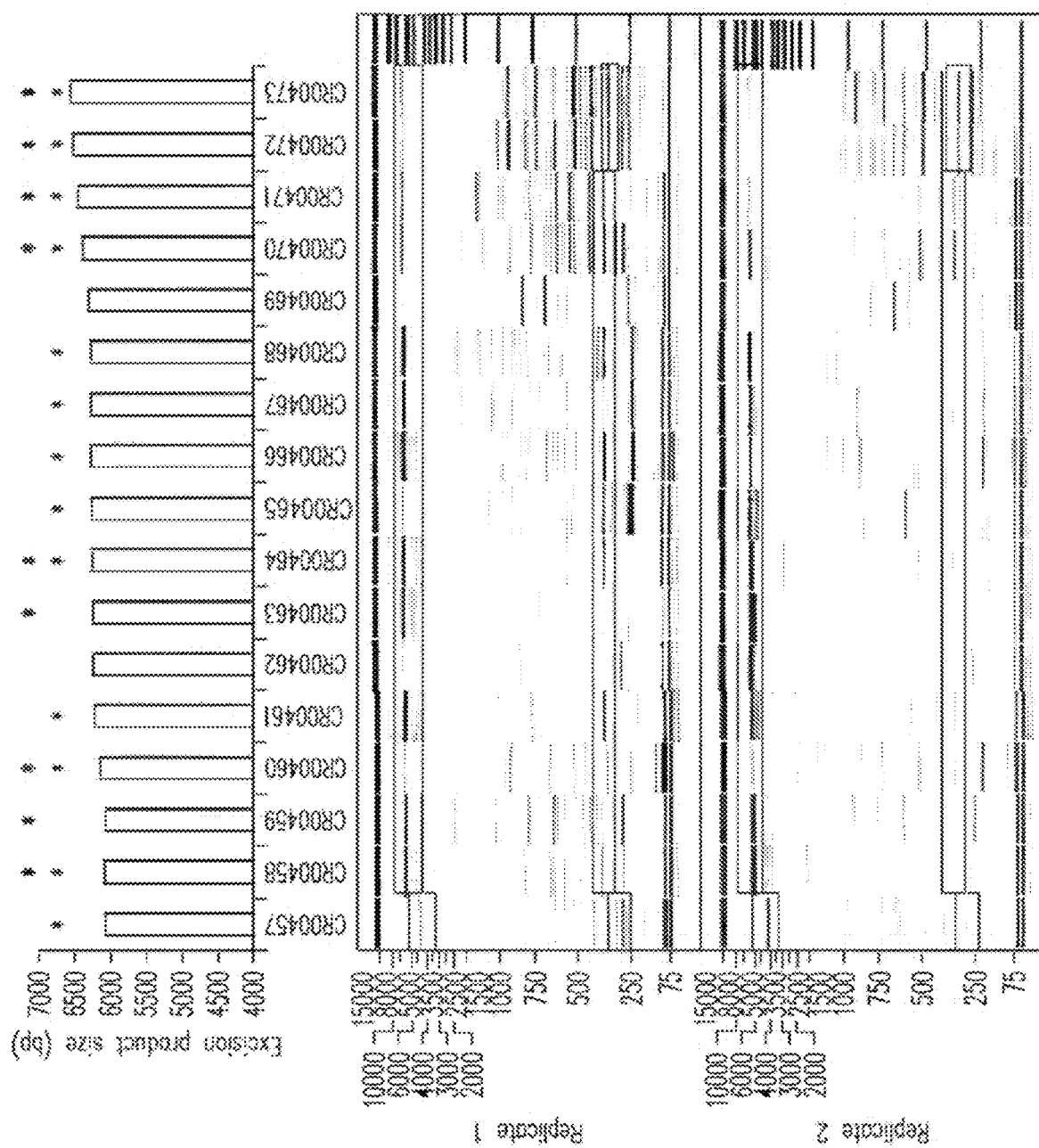
FIG. 11: Results of gRNA pair exposure to B2M gene with expected excision products ~6000 base pairs. Red * indicates expected excision product seen (green box); Purple *=less than 10% editing efficiency. Orange boxes indicate wild type fragment.

To test the ability of two gRNA molecules which bind to the same gene to excise large section of the target gene, we exposed cells to two gRNA molecules. In each experiment, CR00442 was used, in addition to a second gRNA molecule predicted to bind to a target site located from about 10 to about 6000 base pairs away from the binding site of CR00442. FIG. 8 shows the predicted excision product size based on the number of base pairs between the two gRNA molecule target sites. Experiments were performed as above, with crRNA molecules comprising the targeting domains of the indicated gRNA molecule (e.g., CR00442) and trRNA being transfected into HEK293 cells engineered to stably express Cas9. Cell lysates were collected at 24 hours and subjected to PCR. FIGS. 9-11 show the results of these experiments. As shown in FIG. 9, CR00442 paired with CR00438, CR00439, CR00440, CR00445 or CR00446 showed DNA fragments corresponding to the expected excision product, ranging from 40-65 base pairs. Pairs of gRNA molecules expected to yield excision products less than 20 base pairs did not result in a detectable excision product as measured by PCR. As shown in FIGS. 10 and 11, when the expected excision product is about 4000 base pairs (FIG. 10) or about 6000 base pairs (FIG. 11), many of the guide pairs produced the expected excision with >10% editing. These results demonstrate the feasibility of excising large portions of DNA from a host gene or genome through the use of two gRNA molecules, and offer an alternative approach to deactivate a gene or gene product.

Example 5: Editing of TRAC in HEK and Primary Human CD3+ Cells

Editing of CRISPR systems containing dgRNA molecules comprising targeting domains to sequences of TRAC were tested for editing in HEK (gRNA delivered to cells stably expressing Cas9) and in primary CD3+ T cells (gRNA/Cas9 RNP delivered by electroporation) according to the methods described herein.

As well, surface expression of TCR after editing was assayed by flow cytometry. Briefly, edited CD3+ cells were stained with antibodies against CD3 (OKT3, eBioscience) and/or TCR-alpha/beta (IP26 #, Biolegend) at day 3-5 post-electroporation. Expression of CD3 or TCR-alpha/beta in live cells (identified by propidium iodide exclusion) relative to the un-edited controls was used to determine frequency of RNP editing.

Figure 12:
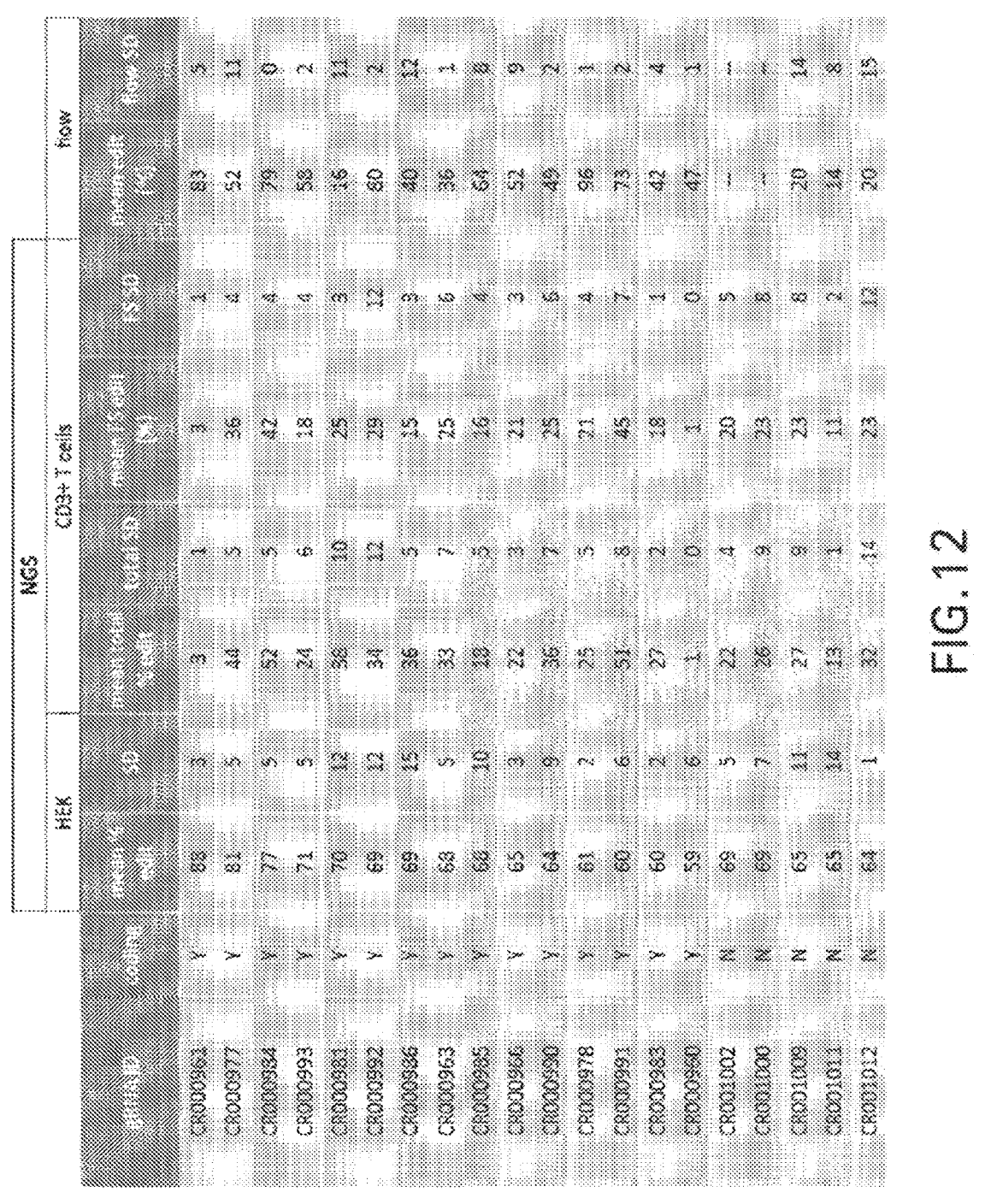

The results are reported in Table 11. All mean editing % are as measured by NGS and are based on at least 3 experiments. gRNA molecules are ranked by the % editing in HEK cells. FIG. 12 shows the top gRNA molecules to TRAC as ranked according to the % editing in HEK cells, together with the flow cytometry data showing the % editing in primary human CD3+ T cells as measured by loss of surface expression of TCR.

The indels formed after editing in CD3+ T cells were also assayed. The % of edited cells containing a frameshift mutation is shown in Table 11 ("mean FS edit %). As the TRAC locus results in an expressed protein, it is possible that 3 bp deletions or insertions may not result in disruption and degradation of TRAC. In contrast, frameshift mutations (1-2 bp in/dels) would cause the sequence subsequent to the edit to be out of frame and likely result in nonsense mediated degradation. Of note, there were often large differences in the editing % between the HEK and CD3+ T cells, namely the % editing in T cells was typically less than that observed in HEK cells. These differences were reproducible across multiple samples, including in Jurkat cells and different donor sources of primary T cells (not shown). Without being bound by theory, one explanation may be that the TCR locus undergoes rearrangement in T cells and Jurkat cells, but not in HEK cells. Indeed, NGS sequencing runs consistently failed or were of poor quality for the T cells or the Jurkat cells, regardless of donor, primers used or days post-editing that the cells were harvested for analysis (not shown). Thus, a more reliable measurement of % editing in primary T cells may be knockout at the protein level (e.g., loss of TCR by flow cytometry).

TABLE 11

| gRNA ID | Target | CD3+ (NGS) | | | | HEK (NGS) | |
|---|---|---|---|---|---|---|---|
| | | mean total % edit | SD | mean FS edit (%) | SD2 | mean % edit | SD |
| CR000961 | TRAC | 3.4 | 0.9 | 3.1 | 0.7 | 87.9 | 2.8 |
| CR000924 | TRAC | 37.4 | 6.1 | 30.9 | 5.5 | 87.3 | 2.9 |
| CR000948 | TRAC | 20.3 | 4.5 | 18.4 | 6.1 | 84.5 | 5.6 |
| CR000931 | TRAC | 37.7 | 11.4 | 34.9 | 9.3 | 83.6 | 7.6 |
| CR000929 | TRAC | 40.3 | 6.3 | 36.1 | 4.8 | 81.6 | 0.7 |
| CR000977 | TRAC | 44.2 | 4.5 | 35.7 | 4.4 | 80.6 | 4.8 |
| CR000944 | TRAC | 4.3 | 4.5 | 4.3 | 4.6 | 77.6 | 8.5 |
| CR000984 | TRAC | 52.1 | 4.6 | 42.1 | 4.2 | 77.0 | 5.3 |
| CR000933 | TRAC | 30.6 | 12.5 | 25.2 | 8.3 | 74.8 | 8.6 |
| CR000926 | TRAC | 22.5 | 9.2 | 19.9 | 6.9 | 73.0 | 4.5 |
| CR000943 | TRAC | 18.1 | 13.9 | 14.5 | 11.3 | 72.4 | 9.2 |
| CR000959 | TRAC | 2.4 | 0.4 | 2.1 | 0.2 | 71.9 | 4.1 |
| CR000993 | TRAC | 24.1 | 5.7 | 17.8 | 3.9 | 71.0 | 5.3 |
| CR000947 | TRAC | 7.2 | 3.3 | 6.5 | 2.8 | 70.7 | 9.5 |
| CR000981 | TRAC | 37.6 | 10.0 | 25.1 | 3.5 | 70.0 | 11.6 |
| CR000992 | TRAC | 33.7 | 12.0 | 29.1 | 12.0 | 69.2 | 12.4 |
| CR001002 | TRAC | 21.8 | 3.7 | 19.7 | 4.8 | 69.1 | 5.2 |
| CR001000 | TRAC | 26.2 | 9.5 | 22.7 | 7.6 | 68.9 | 7.4 |
| CR000927 | TRAC | 23.8 | 4.5 | 22.6 | 4.1 | 68.7 | 7.2 |
| CR000986 | TRAC | 36.4 | 5.1 | 14.8 | 3.0 | 68.6 | 14.9 |
| CR000963 | TRAC | 32.5 | 7.1 | 25.3 | 6.3 | 68.4 | 5.4 |
| CR000985 | TRAC | 17.7 | 5.4 | 16.3 | 4.4 | 68.1 | 10.0 |
| CR000923 | TRAC | 37.3 | 6.5 | 32.7 | 4.6 | 67.4 | 3.3 |
| CR000953 | TRAC | 17.7 | 2.1 | 14.4 | 1.1 | 66.0 | 12.8 |
| CR000946 | TRAC | 9.8 | 2.9 | 9.2 | 2.3 | 65.9 | 10.1 |
| CR000932 | TRAC | 9.9 | 3.3 | 7.9 | 4.1 | 65.7 | 7.8 |
| CR001009 | TRAC | 27.3 | 9.4 | 22.8 | 7.8 | 65.3 | 10.6 |
| CR000966 | TRAC | 22.0 | 2.9 | 21.0 | 2.6 | 65.2 | 2.7 |
| CR001011 | TRAC | 13.2 | 1.2 | 10.8 | 1.8 | 64.8 | 13.5 |
| CR001012 | TRAC | 31.5 | 14.2 | 22.9 | 12.0 | 64.5 | 1.4 |
| CR000990 | TRAC | 36.1 | 7.0 | 25.3 | 5.9 | 63.7 | 8.9 |
| CR000951 | TRAC | 6.7 | 3.0 | 6.0 | 3.5 | 63.5 | 16.5 |
| CR001001 | TRAC | 14.4 | 0.2 | 10.9 | 0.4 | 61.8 | 8.0 |
| CR000978 | TRAC | 24.7 | 5.1 | 20.8 | 4.4 | 60.7 | 2.3 |
| CR000934 | TRAC | 4.4 | 3.0 | 4.1 | 2.6 | 60.6 | 4.6 |
| CR000950 | TRAC | 7.5 | 0.8 | 5.4 | 0.4 | 60.4 | 9.2 |
| CR000920 | TRAC | 12.8 | 1.9 | 10.5 | 0.4 | 60.2 | 12.9 |
| CR000991 | TRAC | 51.2 | 8.1 | 45.4 | 6.9 | 60.1 | 6.4 |
| CR000956 | TRAC | 2.2 | 0.5 | 1.9 | 0.0 | 59.9 | 10.5 |
| CR000983 | TRAC | 26.6 | 2.0 | 18.2 | 0.7 | 59.8 | 1.8 |
| CR000936 | TRAC | NA | NA | NA | NA | 59.7 | 12.9 |
| CR000960 | TRAC | 1.2 | 0.1 | 1.2 | 0.2 | 59.4 | 6.5 |
| CR001007 | TRAC | 22.0 | 4.4 | 19.0 | 3.2 | 58.4 | 13.9 |
| CR000921 | TRAC | 12.7 | 2.0 | 11.3 | 1.1 | 58.3 | 9.1 |
| CR000952 | TRAC | 5.8 | 1.7 | 5.6 | 1.8 | 57.9 | 7.9 |
| CR000925 | TRAC | 19.1 | 4.3 | 12.3 | 5.1 | 56.9 | 6.1 |
| CR001006 | TRAC | 13.6 | 4.3 | 10.4 | 3.2 | 56.8 | 14.3 |
| CR000942 | TRAC | 9.8 | 6.4 | 9.8 | 6.3 | 56.8 | 1.6 |
| CR000938 | TRAC | 13.9 | 0.3 | 12.5 | 2.2 | 55.0 | 7.1 |
| CR000940 | TRAC | 22.1 | 4.7 | 14.4 | 4.1 | 55.0 | 10.4 |
| CR000989 | TRAC | 28.2 | 12.5 | 18.2 | 7.6 | 54.5 | 1.1 |
| CR000928 | TRAC | 18.1 | 1.8 | 14.6 | 0.4 | 54.2 | 22.1 |
| CR000935 | TRAC | NA | NA | NA | NA | 54.2 | 8.2 |
| CR001003 | TRAC | 13.6 | 4.6 | 10.1 | 4.3 | 53.5 | 9.5 |
| CR001014 | TRAC | 27.3 | 6.8 | 24.3 | 5.9 | 52.7 | 4.3 |
| CR000996 | TRAC | 11.1 | 0.7 | 8.6 | 0.2 | 52.3 | 7.3 |
| CR000967 | TRAC | 31.1 | 6.3 | 27.3 | 3.8 | 51.9 | 2.7 |
| CR000968 | TRAC | 26.1 | 4.1 | 24.1 | 4.2 | 51.6 | 10.5 |
| CR000964 | TRAC | 27.0 | 7.9 | 23.5 | 8.9 | 51.2 | 8.9 |
| CR000937 | TRAC | 15.8 | 3.4 | 10.8 | 2.0 | 50.9 | 6.6 |
| CR001005 | TRAC | 13.9 | 2.4 | 13.0 | 2.4 | 50.5 | 12.9 |
| CR001010 | TRAC | 21.2 | 4.4 | 18.6 | 3.2 | 48.3 | 7.0 |
| CR000982 | TRAC | 28.5 | 8.9 | 23.2 | 7.3 | 48.1 | 9.5 |
| CR001004 | TRAC | 6.7 | 2.8 | 6.4 | 2.5 | 47.2 | 15.3 |
| CR000994 | TRAC | 21.5 | 2.7 | 10.8 | 0.6 | 46.9 | 3.4 |
| CR000988 | TRAC | 22.3 | 4.7 | 17.4 | 3.5 | 41.9 | 5.4 |
| CR000973 | TRAC | 16.2 | 1.0 | 12.4 | 1.1 | 39.7 | 16.1 |
| CR000987 | TRAC | 20.6 | 1.8 | 18.2 | 2.2 | 39.6 | 4.0 |
| CR000922 | TRAC | 6.4 | 4.5 | 5.0 | 3.4 | 37.8 | 7.6 |
| CR001015 | TRAC | 21.8 | 0.2 | 20.4 | 0.0 | 35.9 | 17.5 |
| CR000969 | TRAC | 24.8 | 6.0 | 20.9 | 4.4 | 34.0 | 4.9 |
| CR000941 | TRAC | 9.6 | 4.5 | 7.6 | 4.1 | 33.4 | 3.9 |
| CR000945 | TRAC | 2.3 | 1.1 | 2.2 | 1.1 | 32.3 | 7.2 |
| CR000949 | TRAC | 2.5 | 2.0 | 2.5 | 1.9 | 30.2 | 6.2 |
| CR001013 | TRAC | 19.6 | 11.5 | 17.6 | 10.0 | 29.7 | 5.3 |
| CR000939 | TRAC | 13.5 | 3.1 | 12.1 | 2.2 | 27.7 | 5.2 |
| CR000995 | TRAC | 1.9 | 1.8 | 2.5 | 1.2 | 23.2 | 6.3 |
| CR000954 | TRAC | 2.7 | 0.4 | 2.6 | 0.3 | 22.3 | 6.7 |

TABLE 11-continued

| | | CD3 + (NGS) | | | | HEK (NGS) | |
|---|---|---|---|---|---|---|---|
| gRNA ID | Target | mean total % edit | SD | mean FS edit (%) | SD2 | mean % edit | SD |
| CR000962 | TRAC | 10.4 | 1.3 | 8.6 | 1.2 | 21.3 | 5.0 |
| CR000958 | TRAC | 1.0 | 0.3 | 1.0 | 0.3 | 20.4 | 4.4 |
| CR000972 | TRAC | 6.9 | 2.5 | 6.4 | 2.3 | 16.2 | 4.9 |
| CR001008 | TRAC | 5.1 | 1.1 | 4.5 | 0.9 | 13.6 | 1.7 |
| CR000970 | TRAC | 10.9 | 2.3 | 9.3 | 2.8 | 13.4 | 4.7 |
| CR000999 | TRAC | 12.0 | 2.4 | 11.4 | 2.1 | 13.1 | 17.9 |
| CR000930 | TRAC | 9.9 | 0.6 | 7.1 | 3.2 | 12.2 | 1.6 |
| CR000997 | TRAC | 6.7 | 0.8 | 6.4 | 0.8 | 11.6 | 4.7 |
| CR000955 | TRAC | 2.7 | 0.7 | 2.7 | 0.7 | 10.0 | 1.5 |
| CR000975 | TRAC | 3.8 | 2.0 | 3.1 | 1.4 | 8.0 | 0.8 |
| CR000998 | TRAC | 2.4 | 0.6 | 2.2 | 0.8 | 4.3 | 1.3 |
| CR000974 | TRAC | 1.9 | 0.5 | 1.8 | 0.6 | 3.3 | 0.8 |
| CR000971 | TRAC | 3.0 | 1.0 | 2.4 | 0.5 | 3.1 | 0.6 |
| CR000979 | TRAC | 2.2 | 1.0 | 2.2 | 1.0 | 3.0 | 0.4 |
| CR000976 | TRAC | 1.8 | 0.6 | 1.7 | 0.6 | 2.8 | 0.1 |
| CR000957 | TRAC | 1.3 | 0.0 | 1.3 | 0.0 | 1.6 | 0.4 |
| CR000965 | TRAC | 1.0 | 0.1 | 1.0 | 0.1 | 1.4 | 0.1 |
| CR000980 | TRAC | 33.0 | 5.0 | 26.1 | 3.7 | N/A | N/A |

Figure 15:
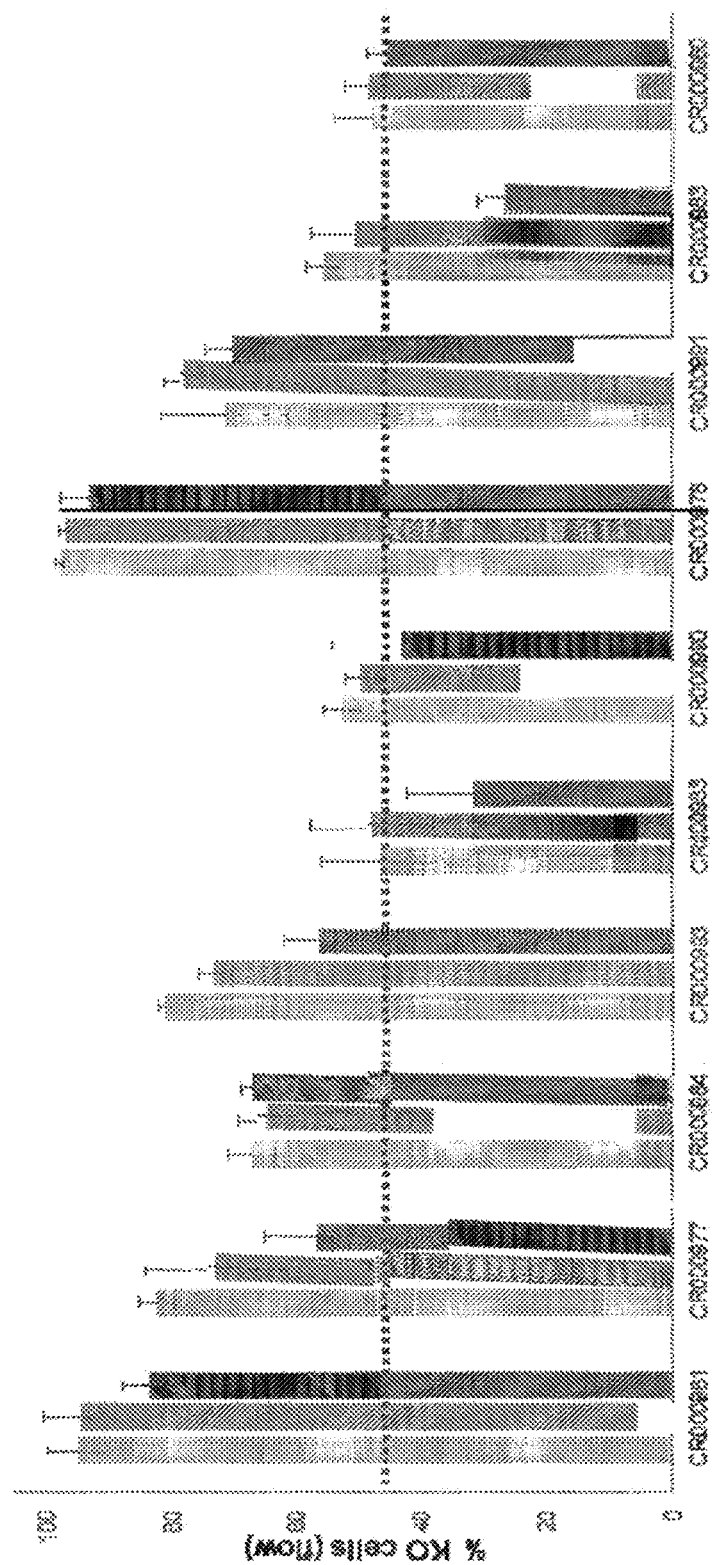
FIG. 15: Editing as measured by loss of TCR (flow cytometry) of CRISPR systems comprising the indicated gRNA molecule in primary human CD3+ T cells from three different donors. For each gRNA, left bar=donor #1; middle bar=donor #2; right bar=donor #3.

Editing in primary human T cells with systems comprising gRNAs targeting TRAC were next tested in primary human CD3+ T cells from 3 different donors. As shown in FIG. 15, % editing (as determined by loss of TCR by flow cytometry) was consistent across all donors. These data demonstrated that certain gRNA molecules, in combination with Cas9, were capable of creating indels within the TCR-alpha sub-unit that result in loss of TCR expression on the surface of T cells. The editing efficiency is donor independent thus showing the broad applicability of this approach.

Example 6: Editing of TRBC1 and TRBC2 in HEK Cells

Figure 13:
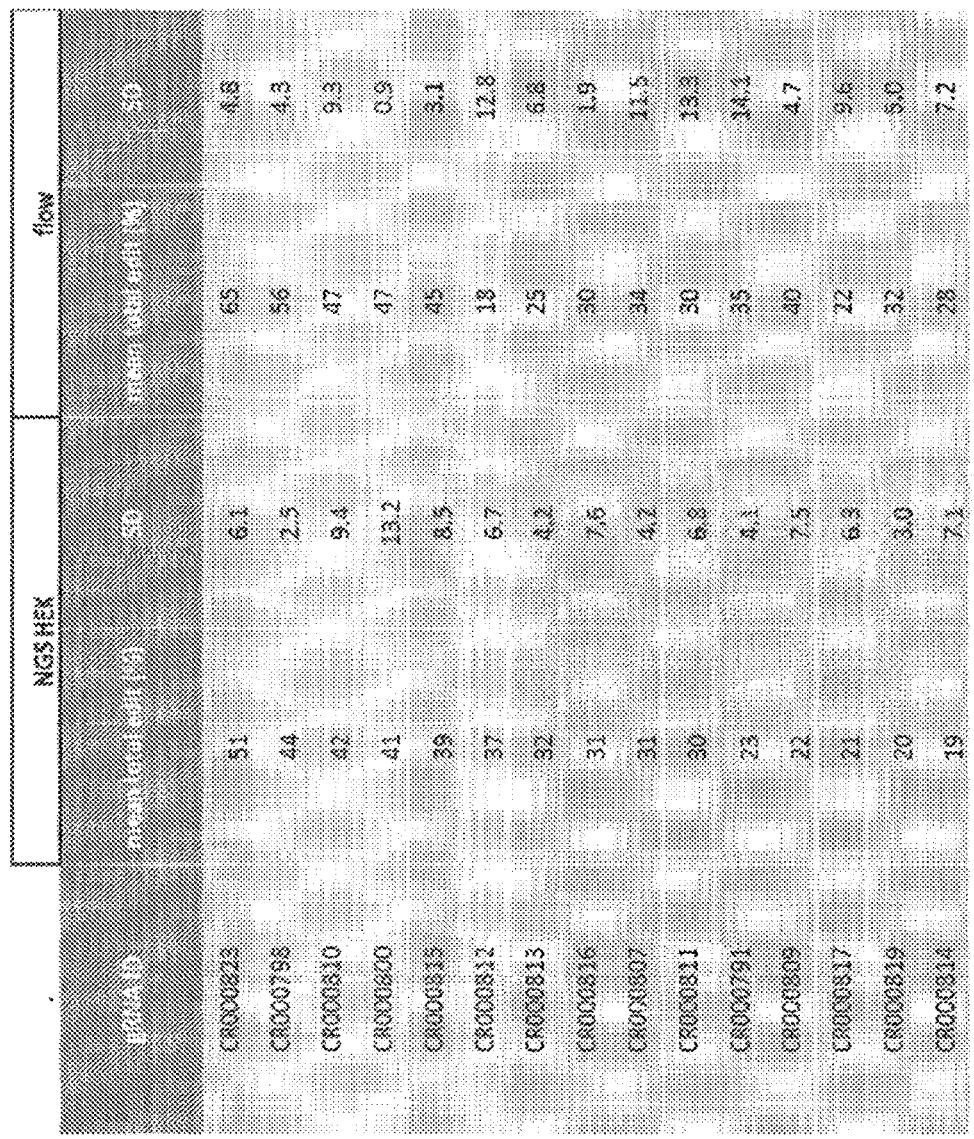
FIG. 13: Mean (n≥3) editing of CRISPR systems with dgRNAs as indicated to coding regions of TRBC1 and TRBC2 in HEK cells (stably expressing Cas9). Also shown is % of T cells exhibiting loss of TCR as determined by flow cytometry using an anti-TCR a/b antibody.

Editing of CRISPR systems containing dgRNA molecules comprising targeting domains to sequences of TRBC1 and TRBC2 were tested for editing in HEK (gRNA delivered to cells stably expressing Cas9) and CD3+ T cells (gRNA and Cas9 delivered as RNP) according to the methods described herein. The results are reported in Table 12. All mean editing % are as measured by NGS and are based on at least 3 experiments. FIG. 13 shows the top gRNA molecules to TRBC1 and TRBC2 as ranked according to the % editing in HEK cells, together with the flow cytometry data showing the % editing in primary human CD3+ T cells as measured by loss of surface expression of TCR.

TABLE 12

| | | | HEK (NGS) | |
|---|---|---|---|---|
| gRNA ID | Target | Coding vs non-coding targeted region | mean total % edit | SD |
| CR000789 | TRBC2 | Non-coding | 62% | 3% |
| CR000780 | TRBC2 | Non-coding | 60% | 9% |
| CR000734 | TRBC1 | Non-coding | 59% | 6% |
| CR000761 | TRBC2 | Non-coding | 57% | 2% |
| CR000776 | TRBC2 | Non-coding | 54% | 9% |
| CR000786 | TRBC2 | Non-coding | 53% | 7% |
| CR000785 | TRBC2 | Non-coding | 52% | 4% |
| CR000737 | TRBC1 | Non-coding | 52% | 5% |
| CR000775 | TRBC2 | Non-coding | 51% | 5% |
| CR000783 | TRBC2 | Non-coding | 51% | 5% |
| CR000823 | TRBC2 | Coding | 51% | 6% |
| CR000756 | TRBC2 | Non-coding | 45% | 2% |
| CR000798 | TRBC2 | Non-coding | 44% | 2% |
| CR000735 | TRBC1 | Non-coding | 44% | 7% |
| CR000731 | TRBC1 | Non-coding | 44% | 5% |
| CR000729 | TRBC1 | Non-coding | 43% | 4% |
| CR000774 | TRBC2 | Non-coding | 43% | 5% |
| CR000810 | TRBC2 | Coding | 42% | 9% |
| CR000800 | TRBC2 | Coding | 41% | 13% |
| CR000784 | TRBC2 | Non-coding | 40% | 3% |
| CR000762 | TRBC2 | Non-coding | 40% | 5% |
| CR000782 | TRBC2 | Non-coding | 40% | 4% |
| CR000815 | TRBC2 | Coding | 39% | 9% |
| CR000748 | TRBC2 | Non-coding | 39% | 3% |
| CR000760 | TRBC2 | Non-coding | 38% | 3% |
| CR000781 | TRBC2 | Non-coding | 37% | 4% |
| CR000812 | TRBC2 | Coding | 37% | 7% |
| CR000732 | TRBC1 | Non-coding | 36% | 5% |
| CR000788 | TRBC2 | Coding | 36% | 7% |
| CR000752 | TRBC2 | Non-coding | 36% | 13% |
| CR000745 | TRBC1 | Non-coding | 34% | 4% |
| CR000759 | TRBC2 | Non-coding | 33% | 7% |
| CR000813 | TRBC2 | Coding | 32% | 4% |
| CR000770 | TRBC2 | Non-coding | 32% | 7% |
| CR000738 | TRBC1 | Coding | 31% | 5% |
| CR000816 | TRBC2 | Coding | 31% | 8% |
| CR000744 | TRBC1 | Non-coding | 31% | 2% |
| CR000807 | TRBC2 | Coding | 31% | 4% |
| CR000811 | TRBC2 | Coding | 30% | 7% |
| CR000766 | TRBC2 | Non-coding | 30% | 2% |
| CR000787 | TRBC2 | Non-coding | 30% | 1% |
| CR000751 | TRBC2 | Non-coding | 30% | 6% |
| CR000730 | TRBC1 | Non-coding | 29% | 3% |
| CR000739 | TRBC1 | Non-coding | 28% | 6% |
| CR000768 | TRBC2 | Non-coding | 28% | 2% |
| CR000771 | TRBC2 | Non-coding | 27% | 4% |
| CR000763 | TRBC2 | Non-coding | 26% | 4% |
| CR000754 | TRBC2 | Non-coding | 26% | 7% |
| CR000755 | TRBC2 | Non-coding | 24% | 4% |
| CR000769 | TRBC2 | Non-coding | 24% | 1% |
| CR000777 | TRBC2 | Non-coding | 23% | 1% |
| CR000764 | TRBC2 | Non-coding | 23% | 6% |
| CR000749 | TRBC2 | Non-coding | 23% | 5% |
| CR000767 | TRBC2 | Non-coding | 23% | 5% |
| CR000791 | TRBC2 | Non-coding | 23% | 4% |
| CR000809 | TRBC2 | Coding | 22% | 8% |
| CR000773 | TRBC2 | Non-coding | 22% | 7% |
| CR000817 | TRBC2 | Coding | 21% | 6% |
| CR000746 | TRBC1 | Non-coding | 21% | 4% |
| CR000753 | TRBC2 | Non-coding | 21% | 1% |
| CR000757 | TRBC2 | Non-coding | 21% | 1% |
| CR000793 | TRBC2 | Non-coding | 21% | 4% |
| CR000743 | TRBC1 | Non-coding | 20% | 4% |
| CR000741 | TRBC1 | Non-coding | 20% | 2% |
| CR000819 | TRBC2 | | 20% | 3% |
| CR000740 | TRBC1 | Non-coding | 19% | 2% |
| CR000814 | TRBC2 | Coding | 19% | 7% |
| CR000728 | TRBC1 | Non-coding | 16% | 6% |
| CR000742 | TRBC1 | Non-coding | 14% | 3% |
| CR000733 | TRBC1 | Non-coding | 10% | 4% |
| CR000747 | TRBC1 | Non-coding | 8% | 1% |
| CR000736 | TRBC1 | Non-coding | 8% | 1% |

These data demonstrated that certain gRNA molecules, in combination with Cas9, were capable of creating indels within the TCR-beta sub-unit that result in loss of TCR expression on the surface of T cells.

Example 7: Editing of PDCD1 in HEK Cells and Primary Human CD3+ T Cells

Editing of CRISPR systems containing dgRNA molecules comprising targeting domains to sequences of PDCD1 were tested for editing in HEK (gRNA delivered to cells stably expressing Cas9) and CD3+ T cells (gRNA and Cas9 delivered as RNP) according to the methods described herein.

Figure 16:
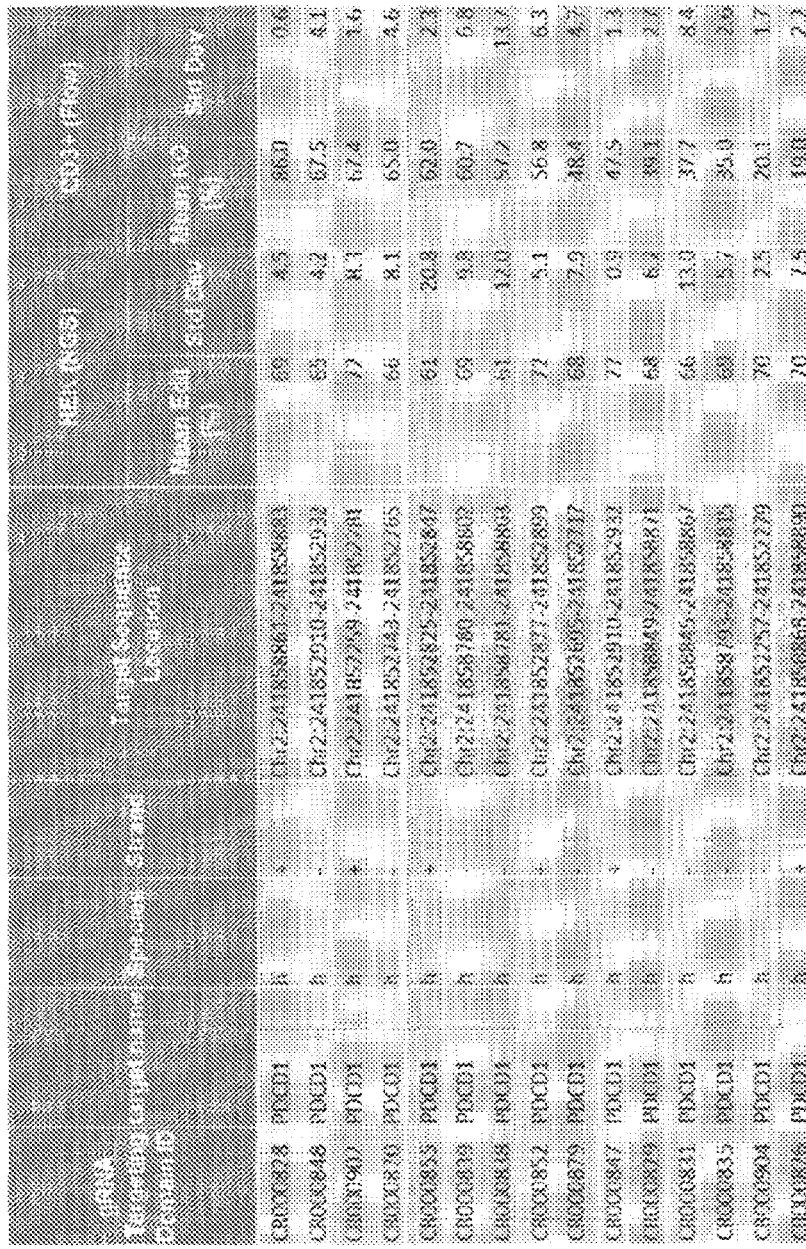
FIG. 16: Mean (n≥3) editing of CRISPR systems with dgRNAs as indicated to PDCD1 in HEK cells (stably expressing Cas9) as measured by NGS, and in primary human CD3+ cells (RNP electroporation) as measured by loss of PD-1 (flow cytometry using anti-PD-1 antibody).
Figure 17A:
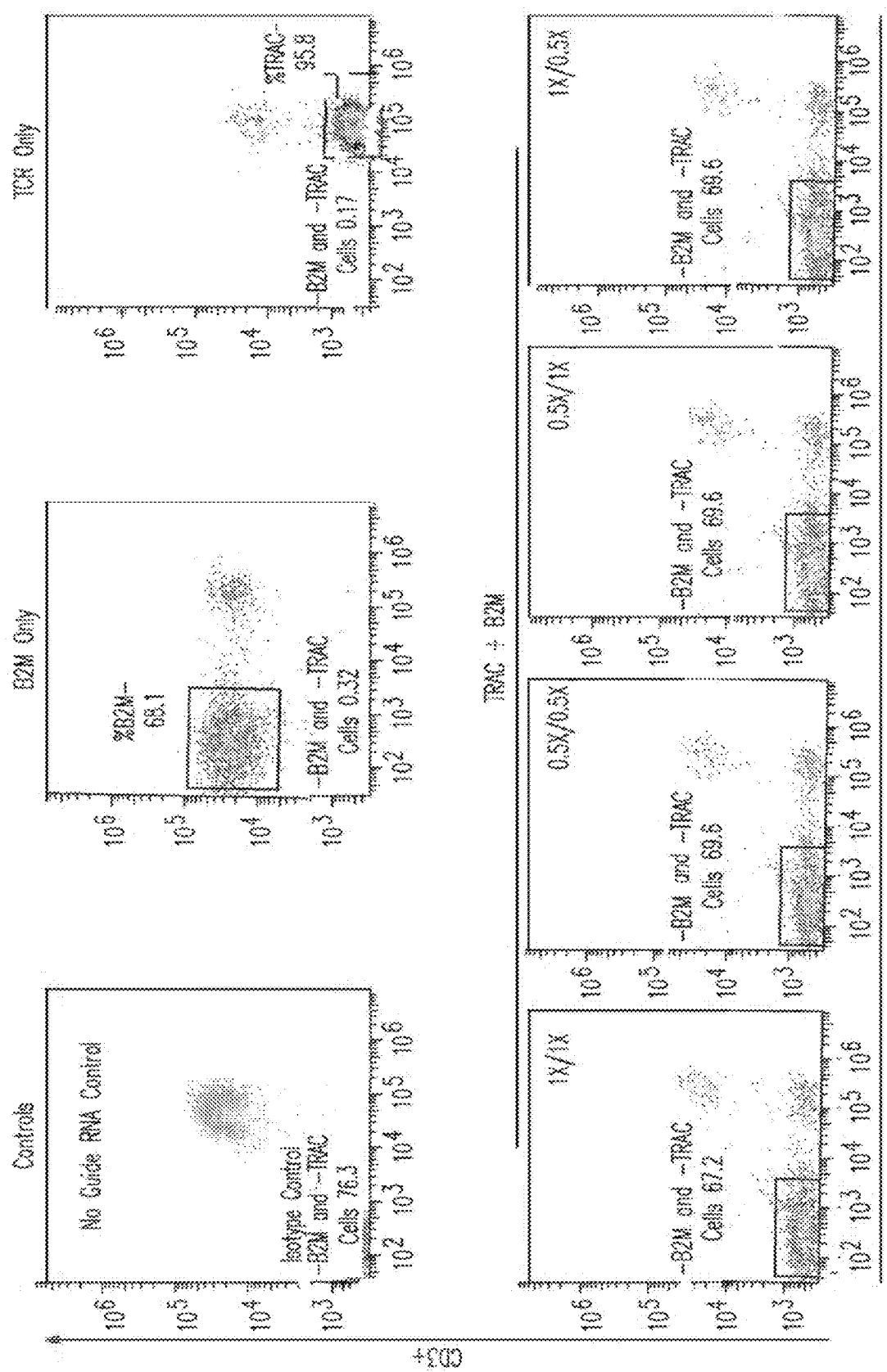
FIG. 17A: Flow Cytometry expression of TCR and/or B2M after electroporation of gRNA to TRAC and/or B2M at the indicated ratios.
Figure 17C:
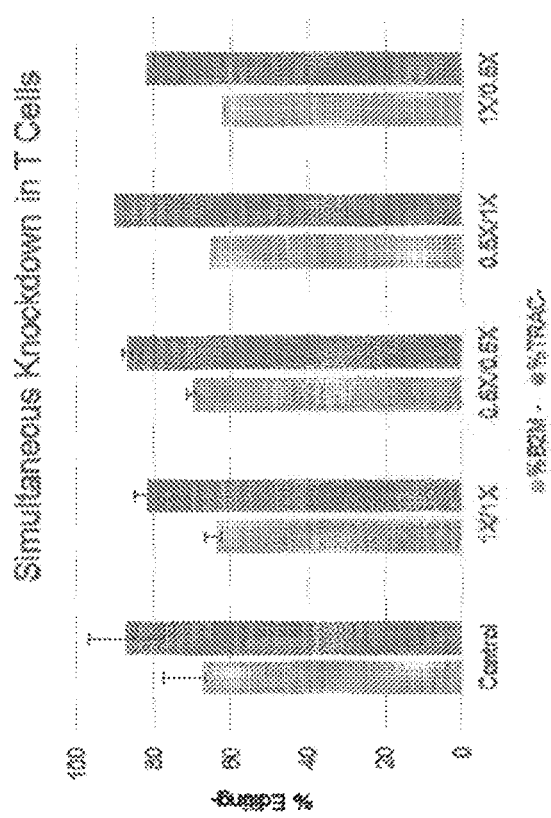
FIG. 17C: editing of either B2M or TCR as measured by flow cytometry.
Figure 17D:
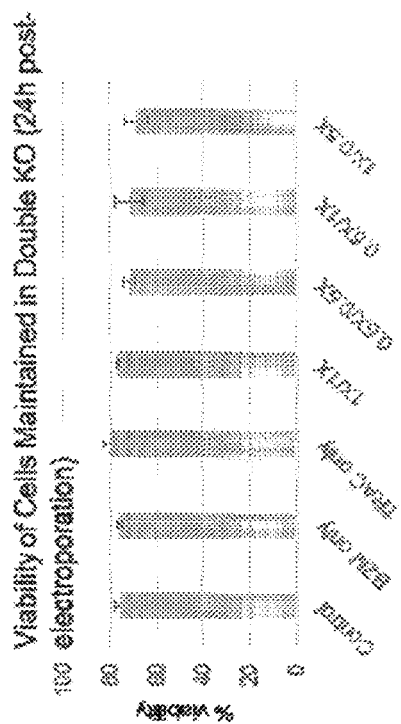
FIG. 17D: Viability of cells 24 hours after electroporation.

The results of editing in HEK cells are reported in Table 13. All mean editing % are as measured by NGS and are based on at least 3 experiments. FIG. 16 shows the top gRNA molecules to PDCD1 as ranked according to the % editing in HEK cells. FIG. 16 also shows % of cells with loss of PD-1 expression as measured by flow cytometry using an anti-PD-1 antibody (ceBioJ105, eBioscience). Briefly, primary human CD3+ T cells were activated with StemCell ImmunoCult beginning on day 0. RNP containing the indicated dgRNA were electroporated into the cells on day 3 (Neon; 1600 V, 10 ms, 3 pulses). 2 days after transfection (day 5), cells were stimulated with antiCD3/CD28 Dynabeads (1:3 cell:bead ratio). PD-1 expression was assessed on day 10.

TABLE 13

| gRNA ID | target name | HEK (NGS) % Editing Mean | Std Dev |
|---|---|---|---|
| CR000847 | PDCD1 | 77% | 1% |
| CR000902 | PDCD1 | 72% | 8% |
| CR000852 | PDCD1 | 72% | 5% |
| CR000826 | PDCD1 | 70% | 7% |
| CR000904 | PDCD1 | 70% | 2% |
| CR000839 | PDCD1 | 69% | 10% |
| CR000828 | PDCD1 | 69% | 4% |
| CR000835 | PDCD1 | 69% | 6% |
| CR000829 | PDCD1 | 68% | 6% |
| CR000879 | PDCD1 | 68% | 8% |
| CR000870 | PDCD1 | 66% | 8% |
| CR000831 | PDCD1 | 66% | 13% |
| CR000848 | PDCD1 | 65% | 4% |
| CR000855 | PDCD1 | 61% | 21% |
| CR000838 | PDCD1 | 61% | 12% |
| CR000840 | PDCD1 | 59% | 5% |
| CR000884 | PDCD1 | 59% | 7% |
| CR000830 | PDCD1 | 57% | 12% |
| CR000871 | PDCD1 | 57% | 8% |
| CR000850 | PDCD1 | 55% | 9% |
| CR000869 | PDCD1 | 55% | 6% |
| CR000903 | PDCD1 | 54% | 8% |
| CR000824 | PDCD1 | 54% | 7% |
| CR000882 | PDCD1 | 50% | 11% |
| CR000918 | PDCD1 | 50% | 9% |
| CR000895 | PDCD1 | 49% | 10% |
| CR000832 | PDCD1 | 49% | 8% |
| CR000874 | PDCD1 | 47% | 5% |
| CR000868 | PDCD1 | 47% | 7% |
| CR000846 | PDCD1 | 46% | 6% |
| CR000887 | PDCD1 | 46% | 6% |
| CR000825 | PDCD1 | 46% | 6% |
| CR000892 | PDCD1 | 45% | 11% |
| CR000917 | PDCD1 | 43% | 9% |
| CR000896 | PDCD1 | 42% | 7% |
| CR000919 | PDCD1 | 42% | 8% |
| CR000863 | PDCD1 | 40% | 9% |
| CR000842 | PDCD1 | 40% | 15% |
| CR000827 | PDCD1 | 39% | 11% |
| CR000837 | PDCD1 | 36% | 8% |
| CR000915 | PDCD1 | 35% | 10% |
| CR000833 | PDCD1 | 34% | 5% |
| CR000853 | PDCD1 | 33% | 4% |
| CR000891 | PDCD1 | 29% | 11% |
| CR000849 | PDCD1 | 29% | 7% |
| CR000897 | PDCD1 | 26% | 2% |
| CR000872 | PDCD1 | 26% | 5% |
| CR000844 | PDCD1 | 25% | 3% |
| CR000854 | PDCD1 | 24% | 6% |
| CR000867 | PDCD1 | 24% | 4% |
| CR000856 | PDCD1 | 23% | 4% |
| CR000845 | PDCD1 | 21% | 6% |
| CR000881 | PDCD1 | 21% | 3% |

TABLE 13-continued

| gRNA ID | target name | HEK (NGS) % Editing Mean | Std Dev |
|---|---|---|---|
| CR000894 | PDCD1 | 19% | 3% |
| CR000834 | PDCD1 | 19% | 7% |
| CR000841 | PDCD1 | 19% | 1% |
| CR000858 | PDCD1 | 16% | 2% |
| CR000859 | PDCD1 | 12% | 3% |
| CR000898 | PDCD1 | 11% | 3% |
| CR000880 | PDCD1 | 10% | 2% |
| CR000893 | PDCD1 | 10% | 1% |
| CR000885 | PDCD1 | 10% | 1% |
| CR000883 | PDCD1 | 9% | 1% |
| CR000843 | PDCD1 | 8% | 2% |
| CR000864 | PDCD1 | 7% | 1% |
| CR000875 | PDCD1 | 6% | 2% |
| CR000899 | PDCD1 | 5% | 3% |
| CR000890 | PDCD1 | 5% | 2% |
| CR000914 | PDCD1 | 5% | 1% |
| CR000836 | PDCD1 | 5% | 1% |
| CR000916 | PDCD1 | 5% | 1% |
| CR000877 | PDCD1 | 5% | 1% |
| CR000888 | PDCD1 | 4% | 1% |
| CR000866 | PDCD1 | 4% | 1% |
| CR000851 | PDCD1 | 4% | 0% |
| CR000865 | PDCD1 | 4% | 1% |
| CR000889 | PDCD1 | 3% | 0% |
| CR000876 | PDCD1 | 3% | 0% |
| CR000886 | PDCD1 | 2% | 0% |
| CR000857 | PDCD1 | 1% | 0% |
| CR000878 | PDCD1 | 1% | 0% |
| CR000860 | PDCD1 | NA | NA |
| CR000861 | PDCD1 | NA | NA |
| CR000862 | PDCD1 | NA | NA |
| CR000873 | PDCD1 | NA | NA |
| CR000900 | PDCD1 | NA | NA |
| CR000901 | PDCD1 | NA | NA |
| CR000905 | PDCD1 | NA | NA |
| CR000906 | PDCD1 | NA | NA |
| CR000907 | PDCD1 | NA | NA |
| CR000908 | PDCD1 | NA | NA |
| CR000909 | PDCD1 | NA | NA |
| CR000910 | PDCD1 | NA | NA |
| CR000911 | PDCD1 | NA | NA |
| CR000912 | PDCD1 | NA | NA |
| CR000913 | PDCD1 | NA | NA |

Figure 18:
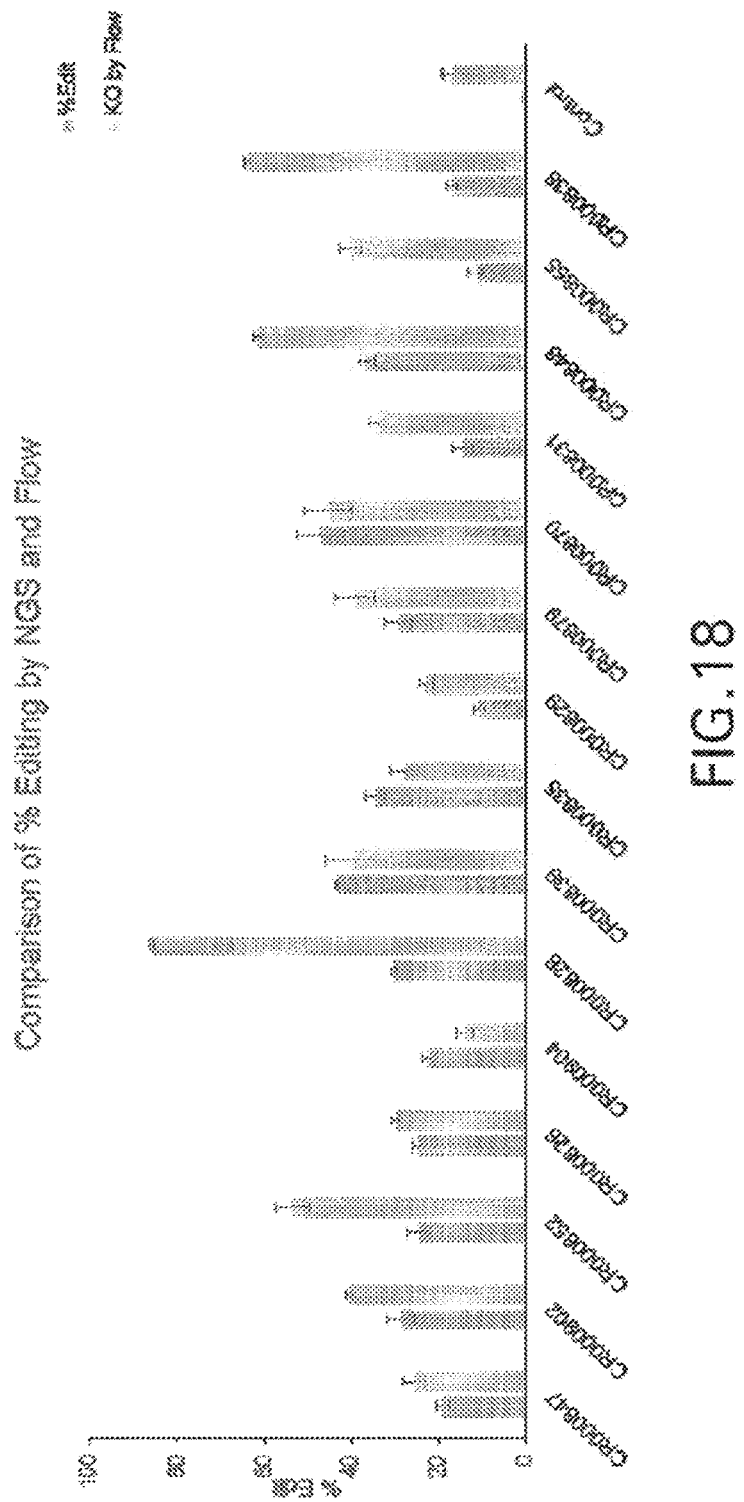
FIG. 18: % Editing using dgRNAs containing targeting domains to PDCD1 (the targeting domain of the CRxxxx sequence indicated) in primary CD3+ T cells as measured by NGS (yellow bars) or loss of PD-1 by flow cytometry (using anti-PD-1 antibody). NGS sequencing was performed 24 hours post-RNP delivery; flow cytometry performed at day 5 post-RNP delivery.
Figure 19:
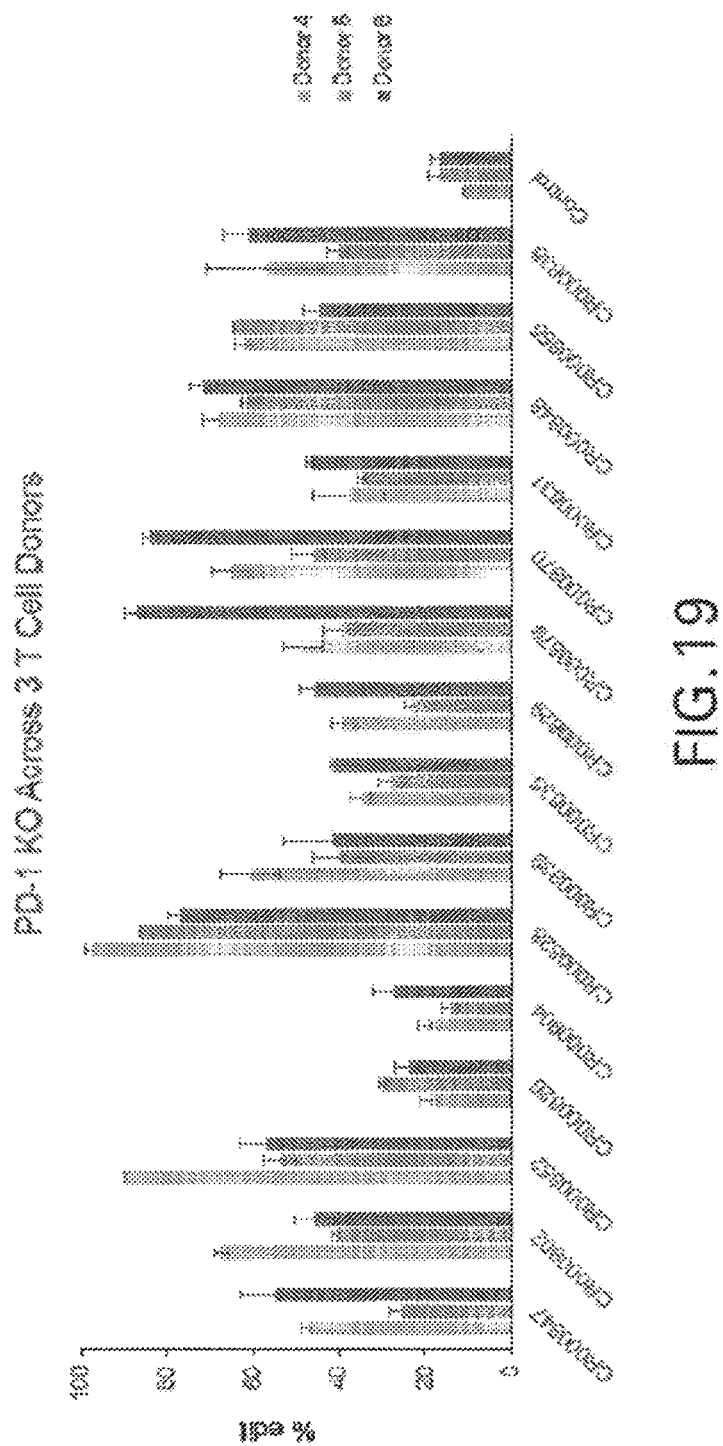
FIG. 19: % Editing (n>=3) using dgRNAs containing targeting domains to PDCD1 (the targeting domain of the CRxxxx sequence indicated) in primary CD3+ T cells as measured by loss of PD-1 by flow cytometry (using anti-PD-1 antibody) across three different donors (donor #4, left-most bar; donor $5, middle bar; donor #6, right-most bar). Systems with targeting domains to some targets show >50% loss of PD-1, with consistent results across multiple donors. gRNAs including the targeting domain of CR00852, CR00828, CR00870, CR00848, CR00855 and CR00838 show greater than 50% editing across at least 2 donors.
Figure 20:
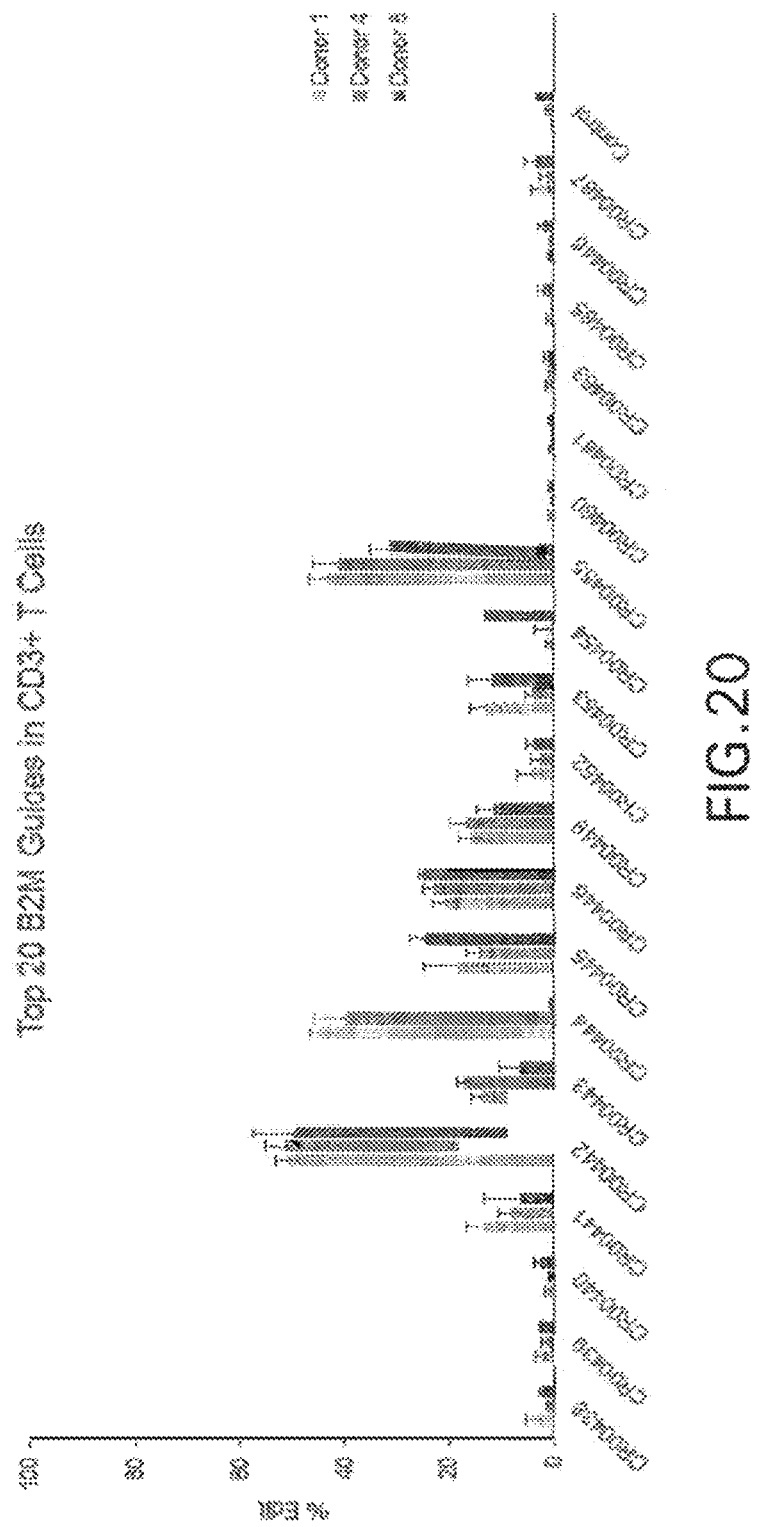
FIG. 20: % Editing (n>=3) using dgRNAs containing targeting domains to B2M (the targeting domain of the CRxxxx sequence indicated) in primary CD3+ T cells as measured by loss of B2M by flow cytometry across three different donors (donor #1, left-most bar; donor #4, middle bar; donor #5, right-most bar). Systems with targeting domains to some target sequences show >40% loss of B2M, with consistent results across multiple donors. gRNAs including the targeting domain of CR00442, CR00444 and CR00455 show greater than 40% editing across at least 2 donors.

Next, editing of PDCD1 by RNPs comprising dgRNA molecules that include the targeting domain of the indicated CRxxxx ID was assayed in primary human CD3+ T cells as measured by NGS, and loss of PD-1 surface expression was assayed by flow cytometry, as described herein. The results are reported at FIG. 18. Several gRNA molecules show good editing and loss of PD-1. These same guides were then tested in CD3+ T cells from three different donors. The data is reported at FIG. 19. As shown, gRNAs including the targeting domain of CR00852, CR00828, CR00870, CR00848, CR00855 and CR00838 show greater than 50% editing across at least 2 donors.

Example 8: Simultaneous and Sequential Knockout of TRAC and B2M in Primary Human CD3+ T Cells Primary human CD3+ T cells were activated and electroporated with RNP containing gRNA to B2M (CR000442) and/or TRAC (CR000984). Briefly, RNPs targeting B2M and/or TRAC were electroporated into CD3+ T cells in the following ratios: B2M RNP only; TRAC RNP only; B2M RNP+TRAC RNP; B2M RNP+0.5×TRAC RNP; 0.5×B2M RNP+1×TRAC RNP; 1×B2M RNP+0.5×TRAC RNP; no RNPs. This allowed us to determine the effect of various amounts of RNP (1 or 2 targets) on cell viability and editing efficiency of the targeted genes. Cells were assessed by flow cytometry for both TCR expression and B2M expression. The results are showing in FIG. 17A-17D. These results showed that RNPs targeting two separate targets could be delivered simultaneously to CD3+ T cells by electroporation without negative impact on viability or compromising the editing efficiency of either guide. Additionally, a high frequency of CD3+ T cells were successfully edited at both targets resulting in a CD3−B2M− population.

Figure 25:
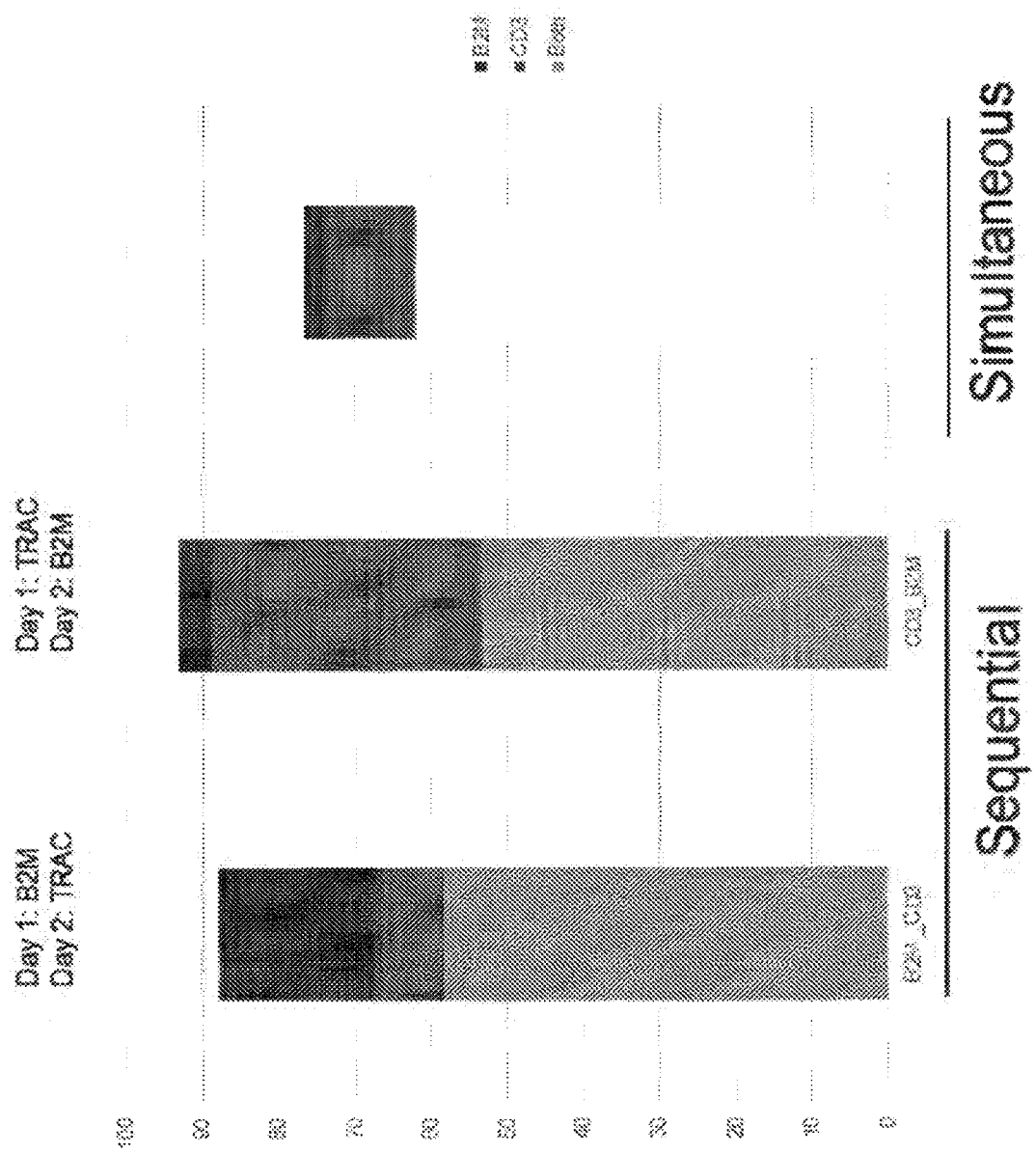
FIG. 25: % of CD3+ T cells that are B2M−, TCR−(as measured by anti-CD3 Ab), or B2M−/TCR− (double negative) as measured by FACS (at day 4 following first electroporation) following either sequential electroporation of RNPs comprising gRNAs to the targets, or simultaneous electroporation of RNPs comprising gRNAs to the targets.
Figure 26:
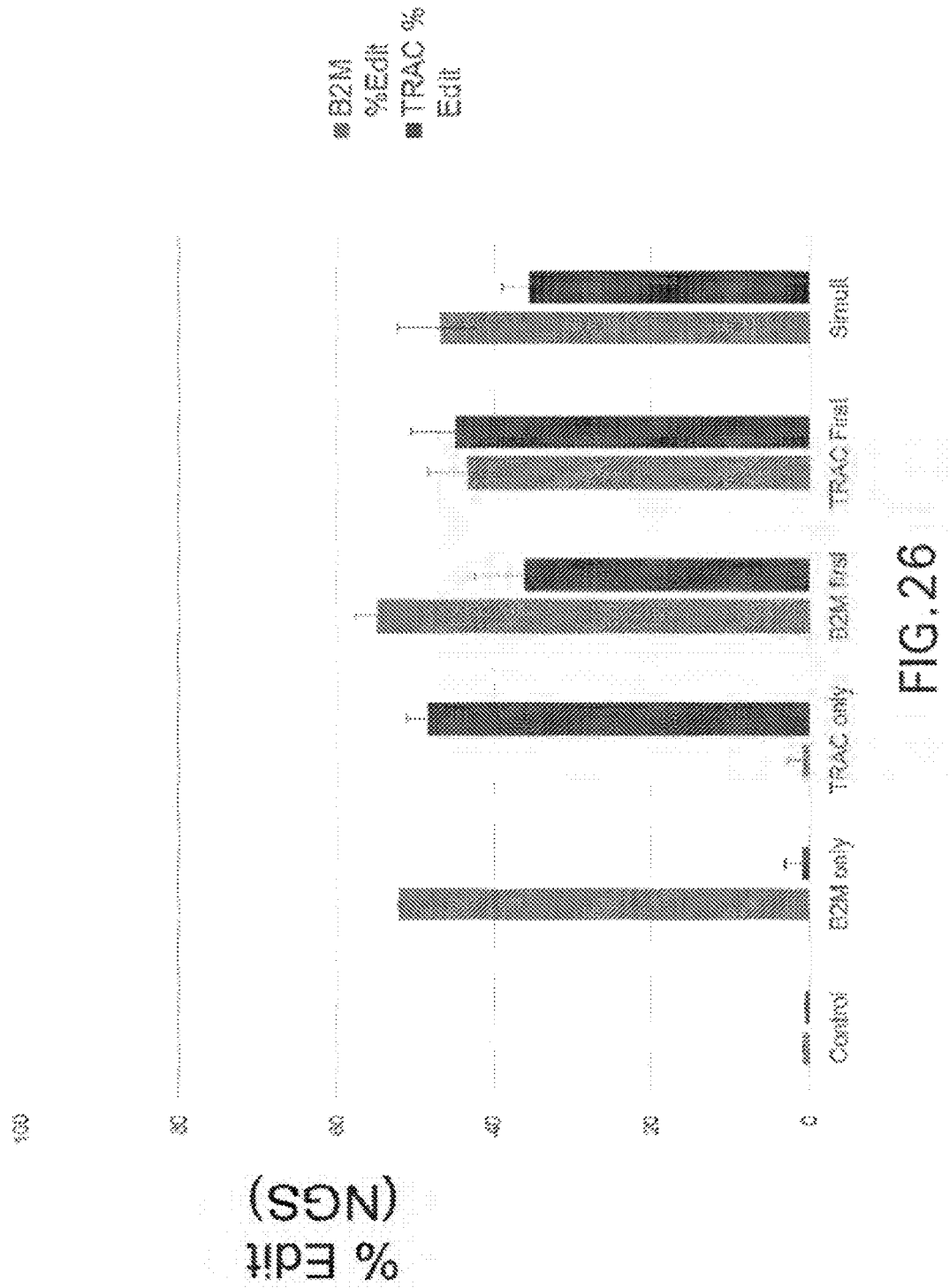
FIG. 26: % of CD3 T cells that are B2M−, TCR−(as measured by anti-CD3 Ab), or B2M−/TCR− (double negative) as measured by NGS (48 hours following first electroporation) following either single electroporation, sequential electroporation of RNPs comprising gRNAs to the targets, or simultaneous ("Simult") electroporation of RNPs comprising gRNAs to the targets (B2M and TRAC).

Next, the effect of editing two targets, B2M and TRAC by either simultaneous or sequential introduction of RNPs containing dgRNAs to B2M and TRAC. For this experiment, RNPs were generated as described above using a dgRNA comprising the targeting domain of CR000442 for targeting of B2M and using a dgRNA comprising the targeting domain of CR000984 for targeting TRAC. Briefly, CD3+ T cells were thawed, activated for 3 days (Immunocult CD3/CD28 T cell activator from StemCell Technologies). On day 3 and day 4 (sequential) or day 3 (Simultaneous), cells were electroporated to introduce RNPs, and maintained until day 5 post-delivery (Day 9), when expression of B2M and/or TCR was assessed by FACS (then by NGS following cell lysis). T cells were maintained in the presence of activating reagent throughout the electroporation and post-electroporation process. Expression of B2M and TCR were assessed by FACS (using anti-B2M clone 2M2 or anti-CD3 clone OKT3 at 1:200 dilution). Cells were subsequently lysed and editing of the targeted loci assessed by NGS. The results are reported at FIGS. 25 and 26. These results indicate that both sequential and simultaneous targeting of B2M and TRAC yield similar double knockout frequencies.

Example 9: Editing of FKBP1A

Figure 21:
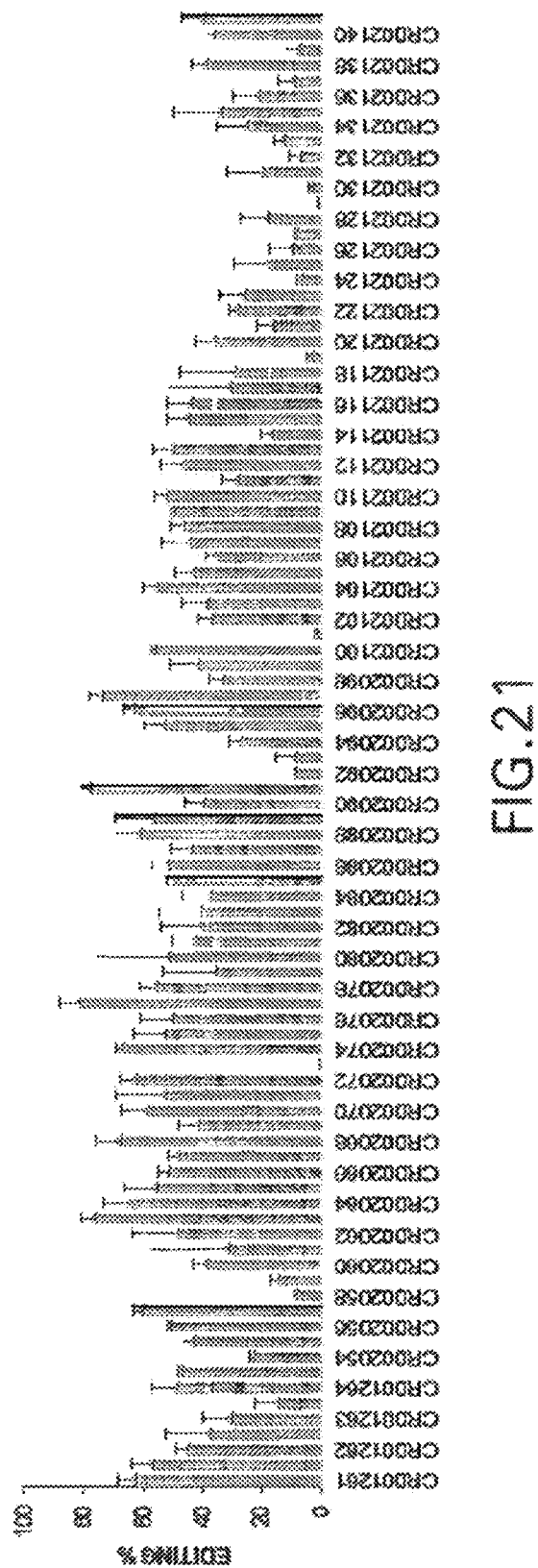
FIG. 21: % editing (N=3) as measured by NGS in HEK293 cells stably expressing Cas9 using dgRNAs that include the targeting domain to FKBP1A as indicated (each unlabeled bar uses the targeting domain of the odd-numbered CRxxxx that falls between the labeled numbers. For example, the data for the dgRNA that includes the targeting domain of CR002073 is reported at the bar falling between that labeled CR002072 and CR002074).
Figure 22:
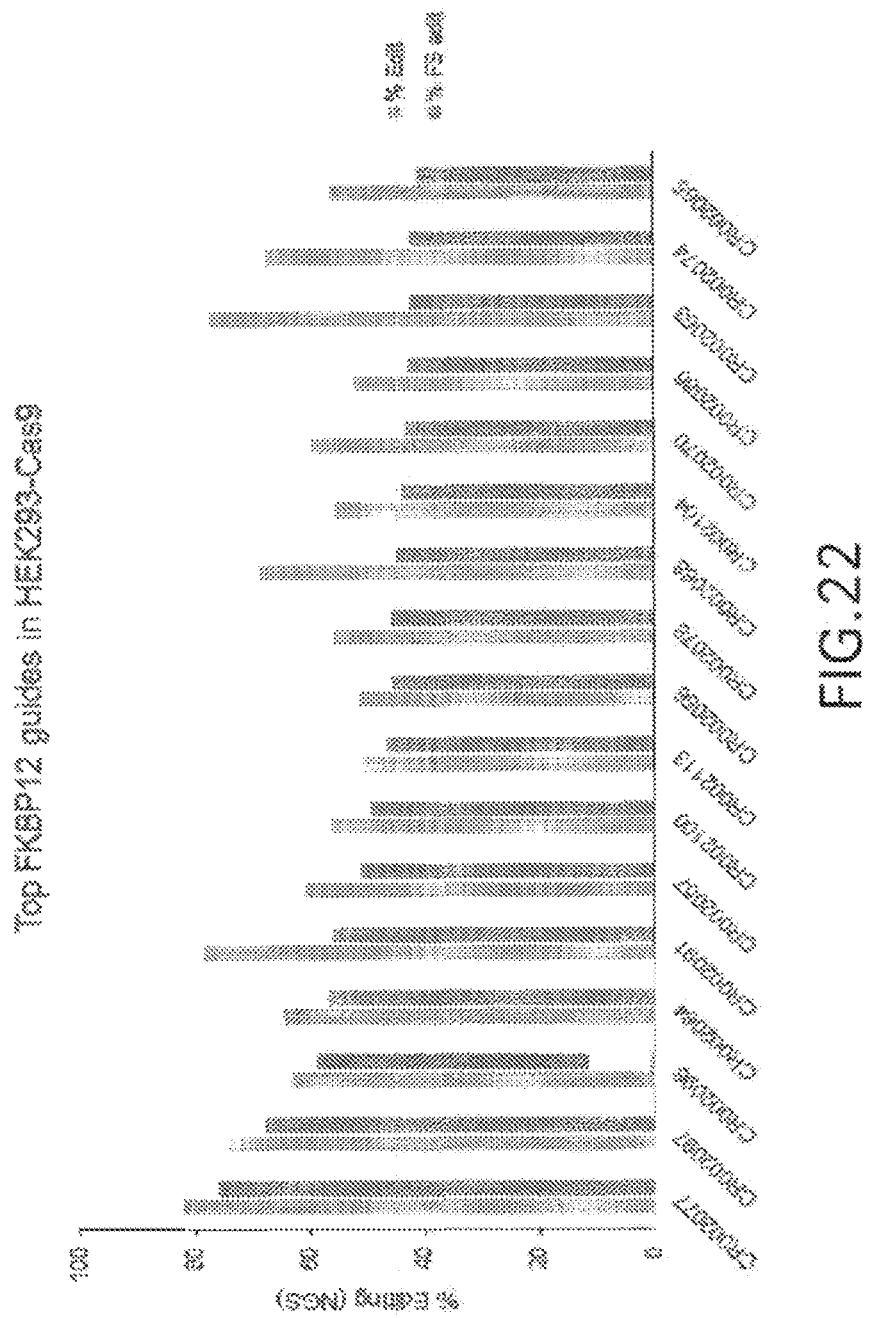
FIG. 22: % editing (N=3) and % Frameshift edit (FS) as measured by NGS in HEK293 cells stably expressing Cas9 using dgRNAs that include the targeting domain to FKBP1A as indicated.

Editing of FKBP1A with dgRNAs targeted to the FKBP1A gene were assayed in HEK293 cells engineered to express Cas9, as described above. The data, including % editing and the % of frameshift (FS) edit, are reported in FIG. 21, FIG. 22, and FIG. 23. Based on these results, the top 15 gRNA molecules were identified by highest percent FS edit. These gRNA molecules, including their targeting domains, are reported in FIG. 23. Next, editing of FKBP1A in CD3+ T cells was assayed using RNPs comprising dual guides comprising the identified targeting domain to FKBP1A. Cells, RNPs and all methods were formed and performed as described above. The results are reported in FIG. 24.

To follow up on the previous experiments, gRNAs comprising the targeting domains of the most efficient editing gRNAs were tested again in primary human T cells. FIG. 52 shows the genomic editing of the FKBP1A locus resulting from human primary T cell electroporation with RNPs containing the indicated gRNAs targeting FKBP1A in dgRNA format (as described above). The frequency of insertions or deletions is indicated (% indels) and the percentage of these edits that result in frameshifting of the coding sequence is shown. The results demonstrate a subset of gRNAs which are able to achieve high editing efficiency (>80%) with a high proportion of frameshift edits (>65%). FIG. 53 shows the top 5 most frequently observed sequence changes (indels) for each FKBP1A targeting gRNA used for primary human T cell editing.

Example 10: Editing of CIITA

Editing of CIITA with dgRNAs targeted to the CIITA gene were assayed in HEK293 cells engineered to express Cas9, as described above in Example 1. The data, including % editing and the % of frameshift (FS) edit, are reported below in Table 24.

TABLE 24

% editing (N = 3) and % Frameshift edit (FS) as measured by NGS in HEK293 cells stably expressing Cas9 using dgRNAs that include the targeting domain to CIITA as indicated. gRNA molecules are ranked in the table by % edit.

| ID | Target | Avg. % Edit | StdDev % Edit | Avg. % FS | StdDev % FS | Rank |
|---|---|---|---|---|---|---|
| CR002993 | CIITA | 60.16 | 6.68 | 48.86 | 4.24 | 1 |
| CR002991 | CIITA | 59.11 | 9.04 | 51.40 | 8.37 | 2 |
| CR002995 | CIITA | 52.74 | 11.49 | 43.64 | 9.45 | 3 |
| CR002948 | CIITA | 52.71 | 7.63 | 48.08 | 6.93 | 4 |
| CR002980 | CIITA | 50.30 | 13.62 | 42.41 | 11.48 | 5 |
| CR002961 | CIITA | 50.29 | 6.60 | 38.41 | 4.64 | 6 |
| CR003001 | CIITA | 47.64 | 11.32 | 43.30 | 10.38 | 7 |
| CR002992 | CIITA | 46.54 | 12.64 | 31.23 | 7.79 | 8 |
| CR002971 | CIITA | 45.94 | 13.74 | 33.61 | 9.92 | 9 |
| CR002976 | CIITA | 45.36 | 14.84 | 37.66 | 12.71 | 10 |
| CR002967 | CIITA | 44.47 | 21.39 | 38.77 | 18.85 | 11 |
| CR003007 | CIITA | 43.64 | 12.08 | 32.22 | 8.81 | 12 |
| CR002953 | CIITA | 43.60 | 11.37 | 34.95 | 9.42 | 13 |
| CR002994 | CIITA | 42.35 | 8.53 | 31.32 | 5.55 | 14 |
| CR002965 | CIITA | 41.85 | 16.72 | 29.63 | 10.99 | 15 |
| CR002972 | CIITA | 41.06 | 12.07 | 28.56 | 9.07 | 16 |
| CR003011 | CIITA | 38.96 | 19.22 | 22.19 | 10.64 | 17 |
| CR002978 | CIITA | 38.34 | 18.04 | 34.11 | 16.14 | 18 |
| CR003013 | CIITA | 37.75 | 11.18 | 29.94 | 8.82 | 19 |
| CR002962 | CIITA | 37.71 | 10.14 | 26.10 | 7.04 | 20 |
| CR002966 | CIITA | 37.12 | 18.00 | 31.49 | 15.77 | 21 |
| CR002981 | CIITA | 36.28 | 15.11 | 29.98 | 12.29 | 22 |

TABLE 24-continued

% editing (N = 3) and % Frameshift edit (FS) as measured by NGS in HEK293 cells stably expressing Cas9 using dgRNAs that include the targeting domain to CIITA as indicated. gRNA molecules are ranked in the table by % edit.

| ID | Target | Avg. % Edit | StdDev % Edit | Avg. % FS | StdDev % FS | Rank |
|---|---|---|---|---|---|---|
| CR002983 | CIITA | 35.90 | 10.82 | 33.83 | 10.53 | 23 |
| CR002970 | CIITA | 35.40 | 15.32 | 25.50 | 10.63 | 24 |
| CR002943 | CIITA | 35.24 | 3.38 | 26.47 | 2.47 | 25 |
| CR002990 | CIITA | 35.19 | 11.07 | 24.08 | 7.77 | 26 |
| CR003003 | CIITA | 35.07 | 16.21 | 27.91 | 12.76 | 27 |
| CR002941 | CIITA | 34.89 | 4.47 | 21.77 | 3.02 | 28 |
| CR002956 | CIITA | 34.30 | 9.28 | 29.66 | 8.14 | 29 |
| CR002944 | CIITA | 34.04 | 2.10 | 22.26 | 1.09 | 30 |
| CR002945 | CIITA | 33.37 | 9.71 | 17.29 | 4.42 | 31 |
| CR002985 | CIITA | 32.99 | 11.62 | 29.52 | 10.46 | 32 |
| CR002940 | CIITA | 32.80 | 8.06 | 22.25 | 6.09 | 33 |
| CR002958 | CIITA | 32.78 | 8.06 | 22.49 | 4.77 | 34 |
| CR003009 | CIITA | 32.69 | 14.75 | 25.62 | 11.60 | 35 |
| CR003014 | CIITA | 32.51 | 14.39 | 26.93 | 11.72 | 36 |
| CR002963 | CIITA | 32.48 | 13.28 | 26.80 | 11.02 | 37 |
| CR002946 | CIITA | 31.12 | 11.15 | 14.20 | 4.24 | 38 |
| CR002959 | CIITA | 30.79 | 8.79 | 29.78 | 8.64 | 39 |
| CR002973 | CIITA | 30.60 | 11.08 | 23.55 | 8.17 | 40 |
| CR003021 | CIITA | 29.94 | 10.67 | 26.88 | 9.37 | 41 |
| CR003026 | CIITA | 29.63 | 6.59 | 20.05 | 4.52 | 42 |
| CR002968 | CIITA | 29.53 | 17.36 | 22.22 | 12.73 | 43 |
| CR003023 | CIITA | 29.38 | 7.13 | 16.83 | 3.71 | 44 |
| CR002979 | CIITA | 28.91 | 13.80 | 23.07 | 10.56 | 45 |
| CR003018 | CIITA | 27.72 | 9.36 | 26.54 | 9.18 | 46 |
| CR002987 | CIITA | 27.56 | 11.04 | 24.06 | 9.81 | 47 |
| CR003015 | CIITA | 27.40 | 7.88 | 24.05 | 6.97 | 48 |
| CR002989 | CIITA | 27.38 | 13.31 | 8.45 | 4.26 | 49 |
| CR002964 | CIITA | 26.56 | 11.21 | 19.56 | 7.74 | 50 |
| CR003010 | CIITA | 25.45 | 10.54 | 14.37 | 5.52 | 51 |
| CR002988 | CIITA | 25.29 | 13.48 | 11.35 | 5.56 | 52 |
| CR002951 | CIITA | 25.09 | 6.28 | 16.13 | 3.91 | 53 |
| CR003025 | CIITA | 24.52 | 6.66 | 19.21 | 4.70 | 54 |
| CR002996 | CIITA | 23.91 | 7.13 | 17.83 | 5.34 | 55 |
| CR003022 | CIITA | 23.73 | 11.35 | 17.96 | 8.69 | 56 |
| CR003020 | CIITA | 23.67 | 9.57 | 16.44 | 6.58 | 57 |
| CR002999 | CIITA | 23.50 | 12.38 | 18.58 | 9.69 | 58 |
| CR002939 | CIITA | 22.02 | 5.58 | 17.27 | 4.64 | 59 |
| CR003017 | CIITA | 21.90 | 4.21 | 15.22 | 2.47 | 60 |
| CR003005 | CIITA | 21.11 | 6.97 | 18.08 | 5.97 | 61 |
| CR002969 | CIITA | 20.82 | 14.36 | 14.85 | 9.88 | 62 |
| CR003024 | CIITA | 20.40 | 6.26 | 16.33 | 4.88 | 63 |
| CR003006 | CIITA | 19.46 | 9.28 | 14.66 | 6.72 | 64 |
| CR002954 | CIITA | 19.43 | 7.05 | 6.28 | 2.27 | 65 |
| CR003004 | CIITA | 19.43 | 7.68 | 15.63 | 6.01 | 66 |
| CR002975 | CIITA | 19.31 | 3.56 | 15.82 | 2.58 | 67 |
| CR002977 | CIITA | 19.11 | 9.48 | 12.99 | 6.31 | 68 |
| CR003016 | CIITA | 17.86 | 4.27 | 13.55 | 3.56 | 69 |
| CR002942 | CIITA | 17.14 | 1.59 | 8.91 | 0.97 | 70 |
| CR002950 | CIITA | 16.64 | 4.84 | 8.65 | 2.46 | 71 |
| CR002947 | CIITA | 15.86 | 4.03 | 8.10 | 2.13 | 72 |
| CR003008 | CIITA | 15.30 | 10.49 | 10.91 | 7.58 | 73 |
| CR003000 | CIITA | 12.83 | 7.31 | 10.53 | 5.76 | 74 |
| CR003002 | CIITA | 11.85 | 4.06 | 9.78 | 3.32 | 75 |
| CR003019 | CIITA | 11.80 | 2.88 | 9.74 | 2.19 | 76 |
| CR003012 | CIITA | 10.67 | 6.52 | 7.51 | 4.18 | 77 |
| CR002960 | CIITA | 10.56 | 3.88 | 6.96 | 2.14 | 78 |
| CR002982 | CIITA | 10.45 | 4.28 | 9.05 | 3.66 | 79 |
| CR002952 | CIITA | 10.37 | 4.96 | 8.22 | 4.17 | 80 |
| CR002974 | CIITA | 8.99 | 2.67 | 6.92 | 1.79 | 81 |
| CR002955 | CIITA | 7.88 | 3.56 | 5.04 | 2.25 | 82 |
| CR002998 | CIITA | 4.95 | 6.44 | 4.84 | 6.27 | 83 |
| CR002957 | CIITA | 3.73 | 0.70 | 3.15 | 0.48 | 84 |
| CR002949 | CIITA | 2.39 | 0.64 | 1.83 | 0.32 | 85 |
| CR002984 | CIITA | 2.33 | 0.18 | 2.19 | 0.17 | 86 |
| CR002986 | CIITA | 1.77 | 0.51 | 1.48 | 0.27 | 87 |
| CR002997 | CIITA | N/A | N/A | N/A | N/A | 88 |

Next, editing of the CIITA gRNA molecules with the highest Editing % was assessed in CD3+ primary human T cells, as described in Example 1. The results are shown in Table 32.

TABLE 32

% Editing and % Frameshift Edit (as measured by NGS) by dgRNA molecules targeting CIITA delivered as RNP to CD3+ T cells

| | CD3+ NGS | | | |
|---|---|---|---|---|
| Targeting Domain ID | Editing % | Edit % Std. Dev. | Frameshift Edit % | Frameshift % Std. Dev. |
| CR002948 | 41.6 | 2.3 | 33.6 | 1.7 |
| CR003001 | 36.3 | 1.8 | 32.0 | 1.3 |
| CR002991 | 33.9 | 3.4 | 29.2 | 3.3 |
| CR002993 | 33.8 | 2.6 | 27.2 | 1.7 |
| CR003007 | 31.6 | 1.6 | 28.8 | 1.7 |
| CR002961 | 30.3 | 2.0 | 24.7 | 1.2 |
| CR002965 | 29.0 | 3.9 | 24.4 | 3.2 |
| CR002967 | 28.0 | 0.7 | 25.6 | 0.5 |
| CR002972 | 26.6 | 1.1 | 20.9 | 1.9 |
| CR002994 | 22.0 | 2.7 | 18.1 | 2.3 |
| CR002992 | 16.0 | 1.6 | 11.6 | 0.8 |
| CR003013 | 11.5 | 0.9 | 9.0 | 0.6 |
| CR002971 | 7.2 | 0.7 | 5.4 | 0.4 |
| CR002980 | 6.1 | 0.5 | 3.6 | 0.6 |
| CR003011 | 5.2 | 0.6 | 4.9 | 0.6 |
| CR002953 | 5.1 | 0.7 | 4.8 | 0.7 |
| CR002978 | 4.7 | 0.7 | 2.7 | 0.2 |
| CR002976 | 4.0 | 0.3 | 3.6 | 0.3 |
| CR002962 | 3.4 | 0.4 | 2.9 | 0.4 |
| CR002995 | 3.1 | 0.2 | 2.5 | 0.4 |

Figure 37:
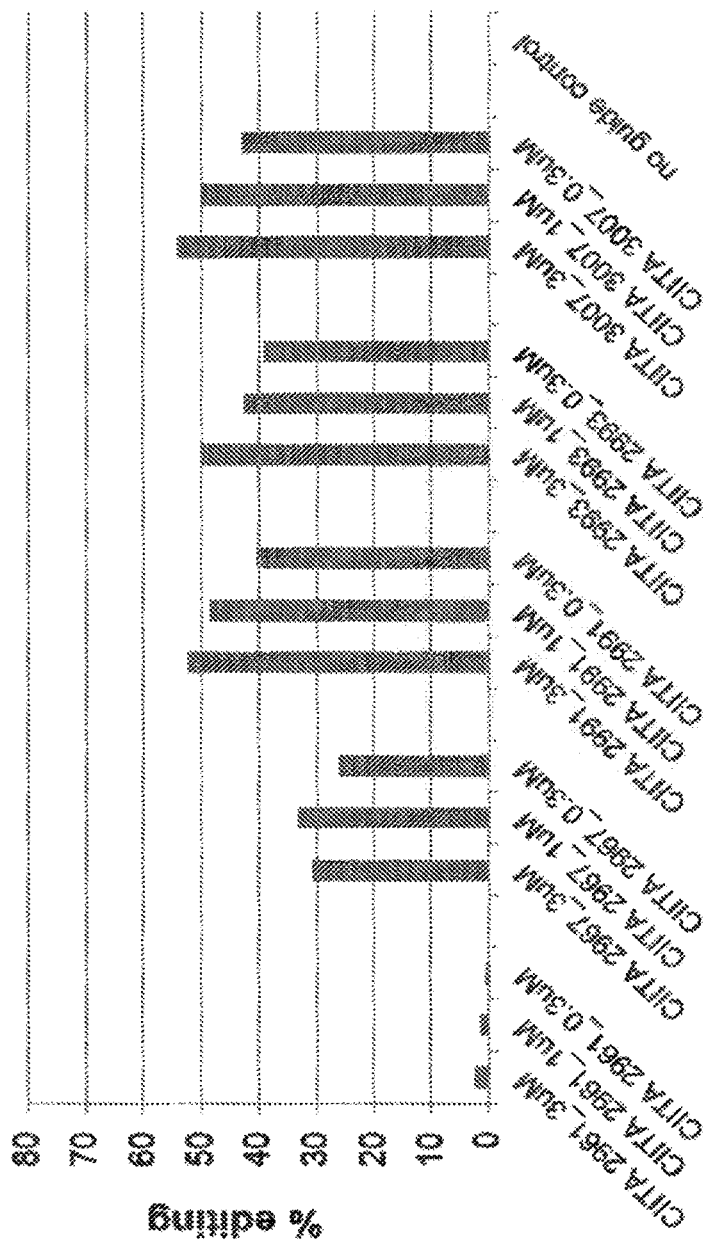
FIG. 37: % editing at Day 3 post electroporation (Day 5 of cell culture) in primary human T cells by RNPs that include the indicated dgRNA to CIITA (number indicates CRxxxxx identifier of targeting domain) at the indicated concentration, as measured by flow cytometry using an anti-HLA-DR reagent.

Next, editing, and loss of MHC class II molecule expression, in response to a subset of gRNA molecules targeting CIITA was assessed in primary human T cells. Briefly, primary human T cells were prepared in culture and activated using CD3/CD28 bead stimulation (DynaBeads Invitrogen Cat #111.41D) at bead to cell ratio of 3:1. At day 2, RNP consisting of *S. pyogenes* Cas9 precomplexed with dgRNA molecules (using the crRNA and tracr sequences described above) comprising the indicated targeting domains were electroporated into the T cells using the Neon electroporator at three different concentrations of RNP (0.3 uM, 1.0 uM and 3.0 uM; diluted after formation of RNP). On Day 5 and Day 7, % editing was assessed by loss of expression of HLA-DR, as assessed by flow cytometry. The results from Day 5 and Day 7 were comparable. % editing in T cells (e.g., % of cells which are CD3+ and HLA-DR-) at day 5 is shown in FIG. 37. As shown, at the highest concentration tested, RNP that included dgRNA molecules CR02991, CR02993 and CR03007 each resulted in >50% editing, as measured by loss of HLA-DR surface staining. As shown below, the lack of editing observed for gRNA CR002961 was due to a mistake in the experimental protocol. When the experiment was repeated (data shown in FIG. 39), RNP comprising gRNA CR002961 resulted in dose-responsive levels of reduction of HLA-DR expression.

Figure 38:
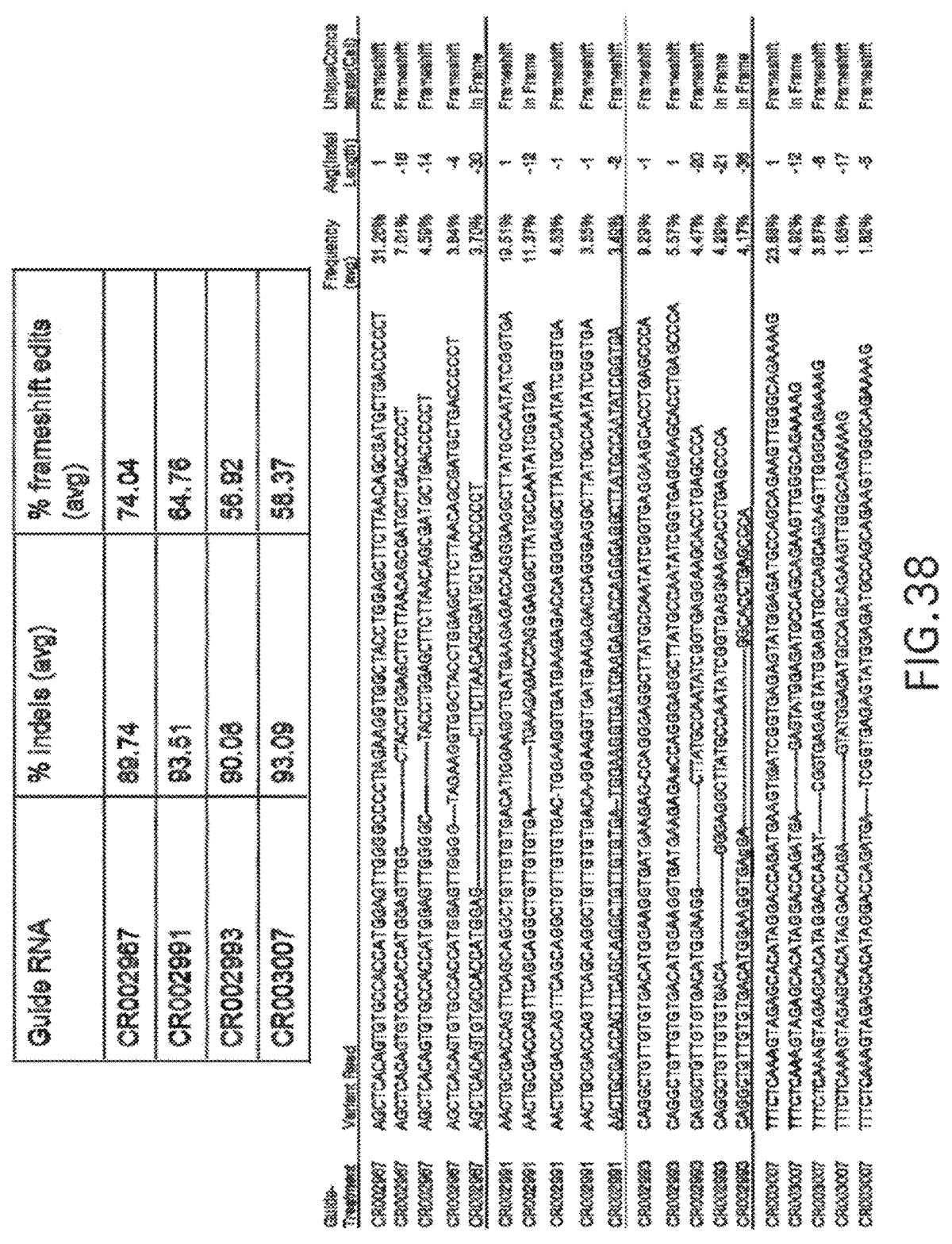

The experiments described above were repeated for another set of gRNA molecules targeting CIITA. FIG. 38 shows the results of this experiment, with genomic editing of the CIITA locus resulting from human primary T cell electroporation with RNP containing the indicated gRNA targeting the CIITA locus. The frequency of insertions or deletions is indicated (% indels) and the percentage of these edits that result in frameshifting of the coding sequence is shown (% frameshift edits). The top 5 most frequently observed sequence changes are shown in detail in the bottom panel. These data indicate that gRNAs targeting CIITA are able to achieve >90% editing with up to 74% frameshift editing in primary human T cells.

Figure 39:
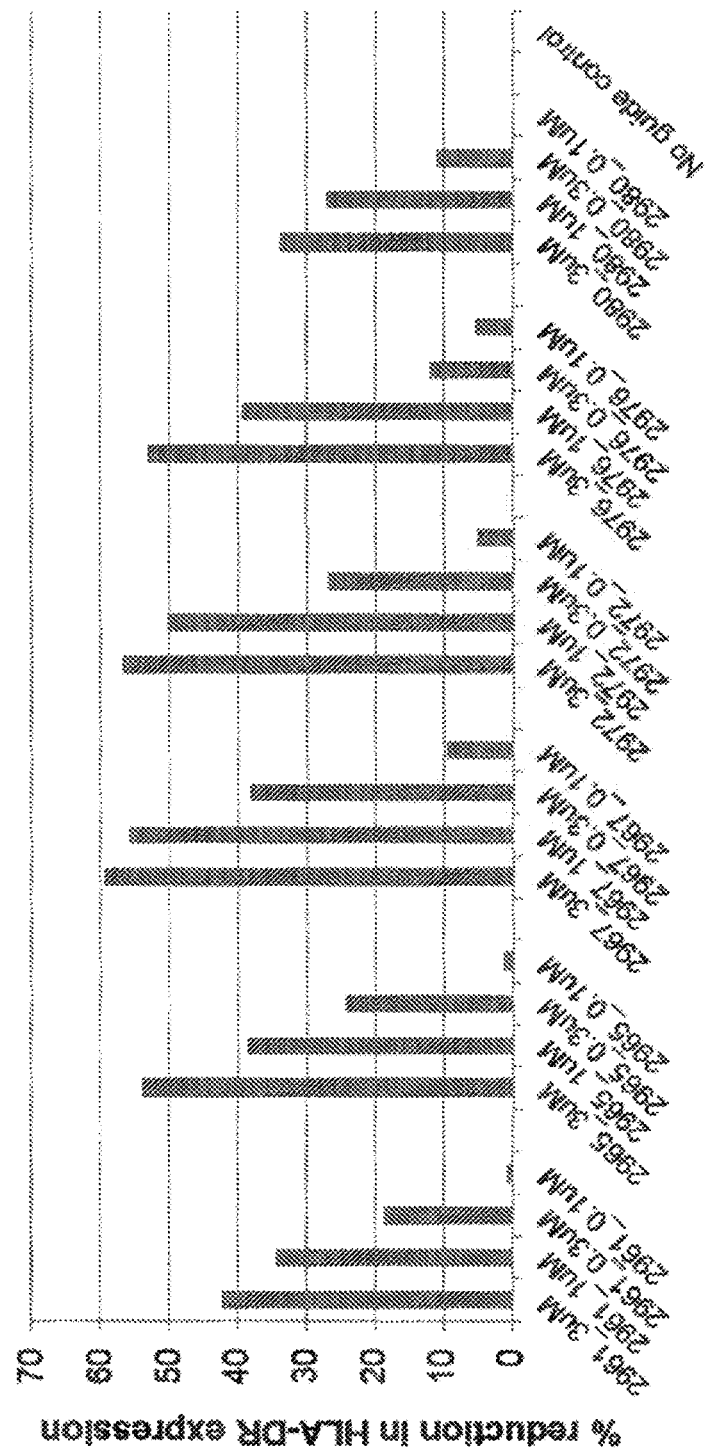
FIG. 39: % editing at Day 3 post electroporation in primary human T cells by RNPs that include the indicated dgRNA to CIITA (number indicates CR00xxxx identifier of targeting domain) at the indicated concentration, as measured by flow cytometry using an anti-HLA-DR reagent. % editing represents the expression of HLA-DR at the cell surface in cells electroporated with CIITA guide relative to the expression in cells electroporated without guide RNA.

The experiment was again performed using a third set of grNAs targeting CIITA at various concentrations of RNP. FIG. 39 shows the % editing at Day 3 post electroporation in primary human T cells by RNPs that include the indicated dgRNA to CIITA (number indicates CR00xxxx identifier of targeting domain) at the indicated concentration, as measured by flow cytometry using an anti-HLA-DR reagent. % editing represents the expression of HLA-DR at the cell surface in cells electroporated with CIITA guide relative to the expression in cells electroporated without guide RNA. As mentioned above, activity of gRNA CR002961 was confirmed in this experiment. FIG. 40 shows the frequency of insertions or deletions is indicated (% indels) and the percentage of these edits that result in frameshifting of the coding sequence is shown (% frameshift edits). These data indicate that another set of gRNAs targeting CIITA is identified which are able to achieve >85% editing with up to 87% frameshift editing (CR002967) in primary human T cells. The top 5 most frequently observed sequence changes for each CIITA targeting gRNA used for primary human T cell editing are shown in FIG. 41.

Figure 42:
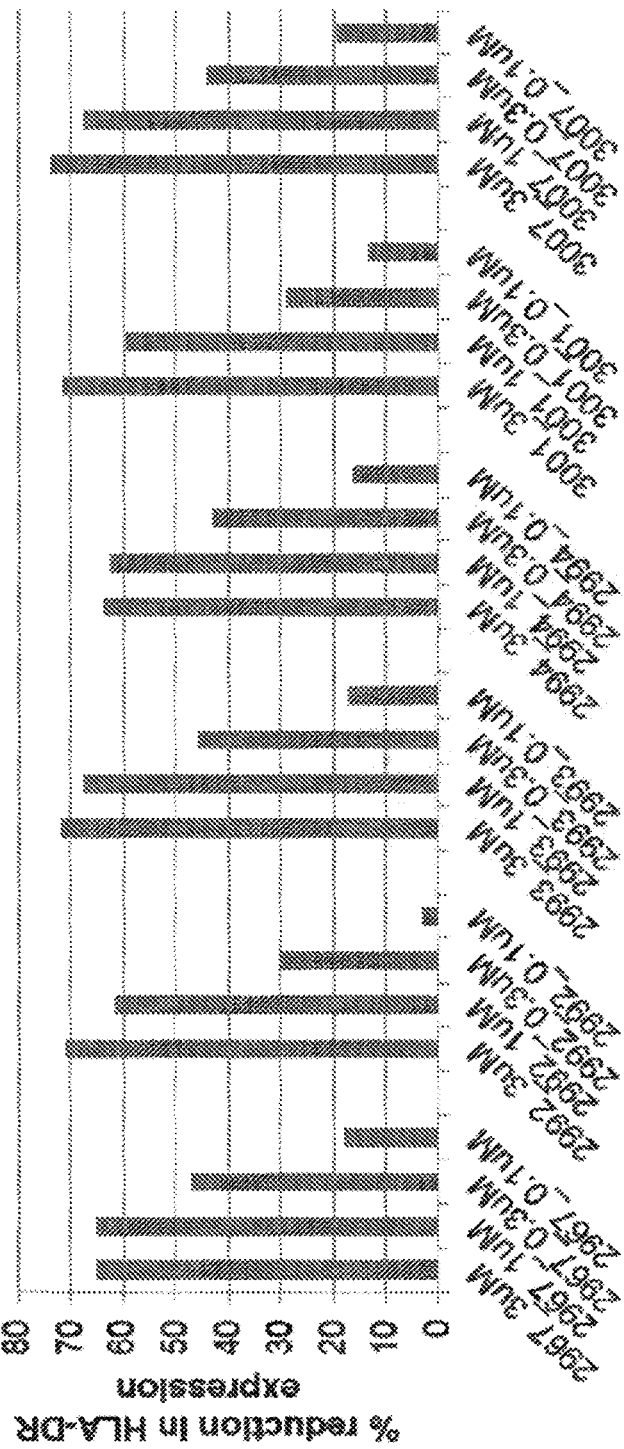
FIG. 42: % editing at Day 3 post electroporation in primary human T cells by RNPs that include the indicated dgRNA to CIITA (number indicates CR00xxxx identifier of targeting domain) at the indicated concentration, as measured by flow cytometry using an anti-HLA-DR reagent. % editing represents the expression of HLA-DR at the cell surface in cells electroporated with CIITA guide relative to the expression in cells electroporated without guide RNA.

The experiment was again performed using a different set of gRNAs targeting CIITA, and compared to the highest performing gRNA (CR0002967) from the previous experiment. FIG. 42 shows the results of % editing at Day 3 post electroporation in primary human T cells by RNPs that include the indicated dgRNA to CIITA (number indicates CR00xxxx identifier of targeting domain) at the indicated concentration, as measured by flow cytometry using an anti-HLA-DR reagent. FIG. 42 shows the frequency of insertions or deletions is indicated (% indels) and the percentage of these edits that result in frameshifting of the coding sequence (% frameshift edits) when these gRNAs are used. FIG. 44 shows the top 5 most frequently observed sequence changes (indels) for each of these CIITA targeting gRNA in primary human T cells. These data confirm the high editing/frameshift/loss of HLA-DR for RNP comprising dgRNA CR002967 and additionally identify other CIITA-targeted gRNAs which result in high editing (>90%) and high frameshift mutations (>80%) in primary human T cells.

Example 11: Editing of TCR (TRAC) and B2M in BCMA CAR T Cells

TABLE 25

| Reagents used for flow cytometry | | | | |
|---|---|---|---|---|
| Name | Catalog Number | Company | Nick name | Clone |
| R-PE Strepetavidin | 016-110-084 | Jackson Immuno Research | SAPE | |
| Streptavidin APC-eFluor780 | 47-43-17-82 | ebiosciences | SA-APC-e780 | |
| APC-Anti Hum B2Microglobulin | 316312 | Biolegend | B2M-APC | |

TABLE 25-continued

Reagents used for flow cytometry

| Name | Catalog Number | Company | Nick name | Clone |
|---|---|---|---|---|
| PerCP-Cyanine5.5 Anti human CD3 | 45-0037-42 | ebiosciences | CD3 PerCPcy5.5 | OKT3 |
| Anti Human CD8a APC | 17-0087-42 | ebiosciences | CD8 APC | SK1 |
| Anti Human CD8a Alexafluor700 | 300920 | Biolegend | CD8 Af700 | |
| Anti Human HLA-DR efluor 450 | 48-9956-42 | ebiosciences | HLA-DR V450 | LN3 |
| Anti Human CD8a eFluor 450 | 48-0086-42 | ebiosciences | CD8 V450 | OKT8 |
| Anti Human CD4 eFluor 450 | 48-0047-42 | ebiosciences | CD4 V450 | SK3 |
| Fixable Viability Dye eFlour780 | 65-0865-14 | ebiosciences | L/D e780 | |

TABLE 26

T cell media components

| Component | Invitrogen Catalog # | Concentration |
|---|---|---|
| RPMI 1640 | 22400-089 | |
| FBS | 16140 | 10% final |
| L-glutamine | 25030-081 | 200 mM (100x stock) |
| Non-essential amino acids | 11140-050 | 10 mM (100x stock) |
| Sodium pyruvate | 11360-070 | 100 mM (100x stock) |
| HEPES buffer | 15630-080 | 1M (100x stock) |
| 2-mercaptoethanol | 21985-023 | 55 mM (1000x stock) |

Figure 27:
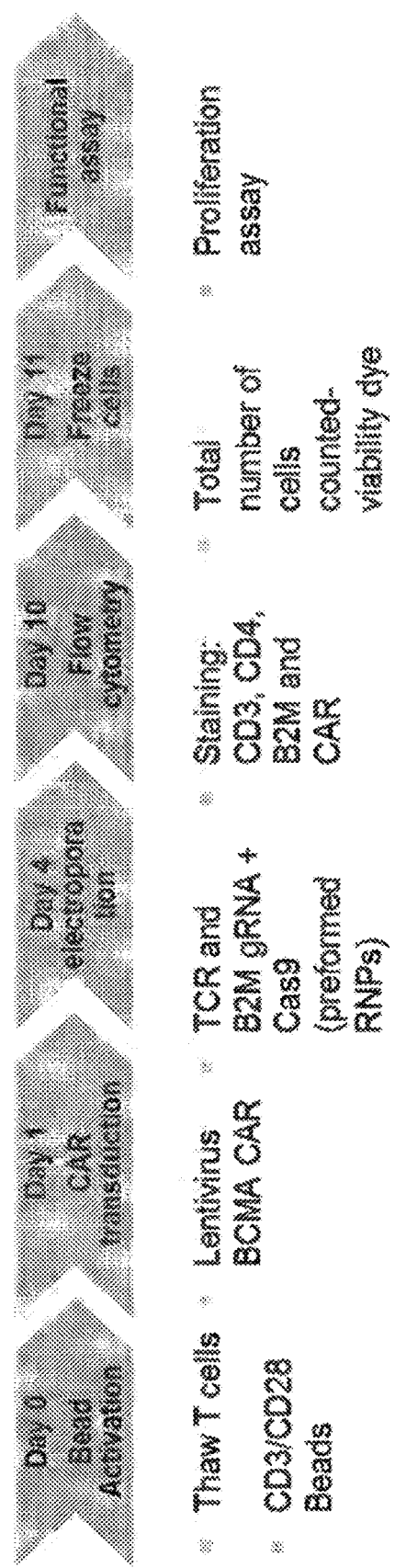
FIG. 27: Schematic for preparation of gene edited TCR−/B2M− BCMA CAR transduced T cells.
Figure 28A:
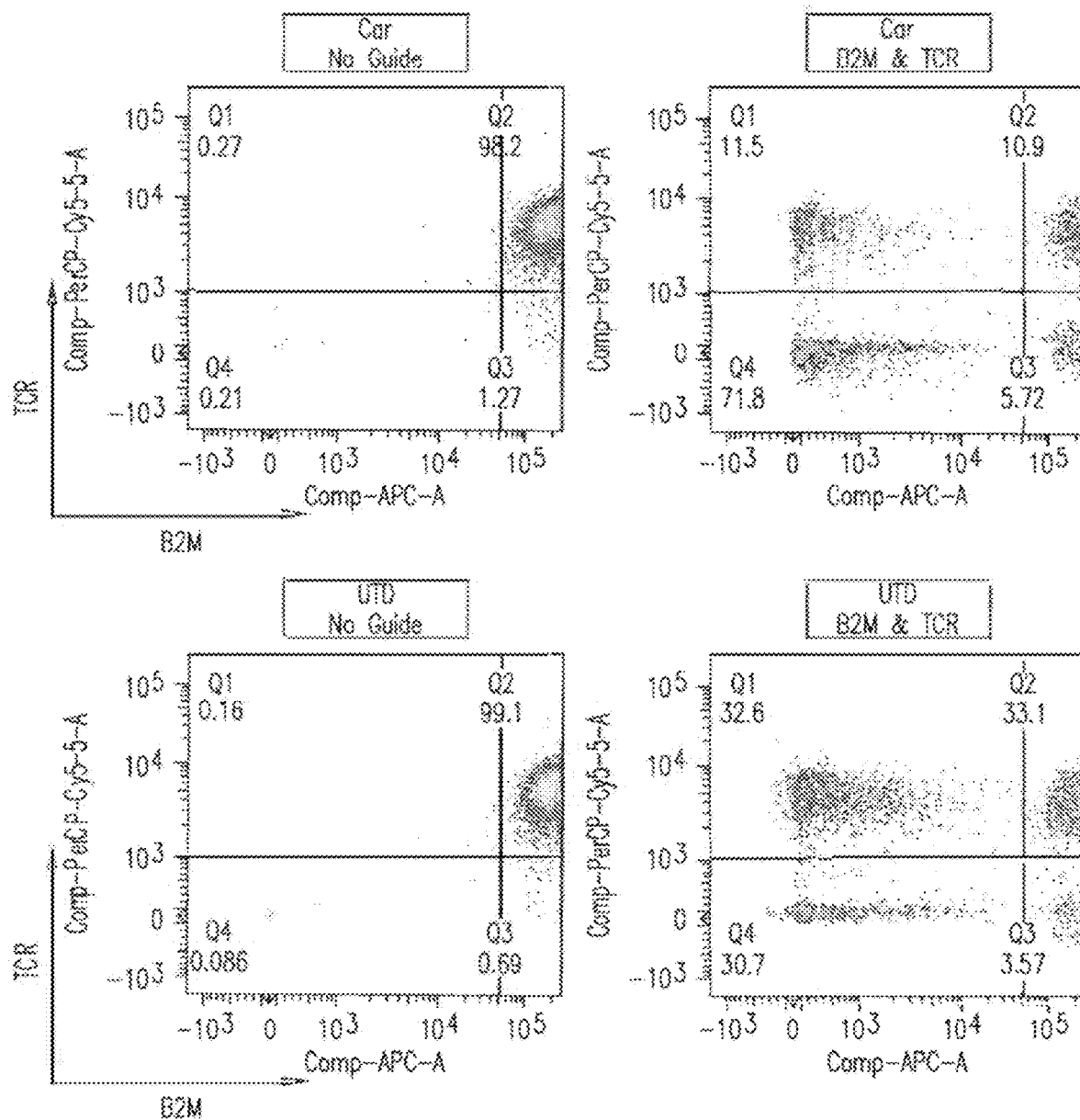
FIG. 28: Surface expression of TCR (using anti-CD3-PercpCy5.5) and B2M (using anti-B2M-APC) five days post (RNP) electroporation. T-cells transduced with RNPs containing gRNA to B2M labeled "B2M"; T-cells transduced with RNPs containing gRNA to TRAC labeled "TCR". T-cells transduced with BCMA CAR are indicated as "CAR". Untransduced cells are indicated as "UTD". Cells electroporated with Cas9 but no guide RNA are indicated as "no guide". CD4 staining using anti-CD4-V450 is shown in the lower panel to verify that the loss of CD3 staining is due to loss of the TCR and not due to loss of T-cells.
Figure 28B:
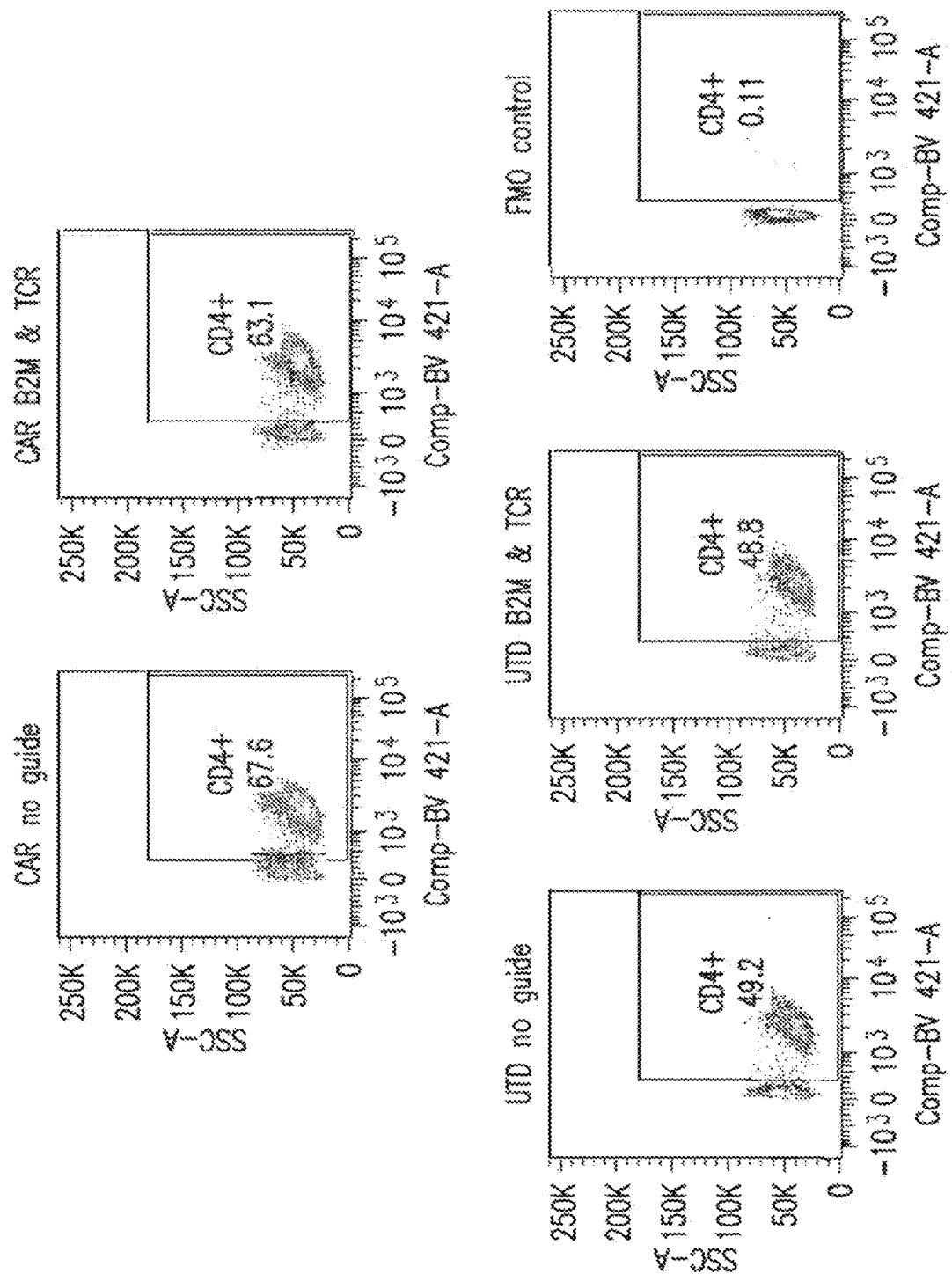
Figure 29:
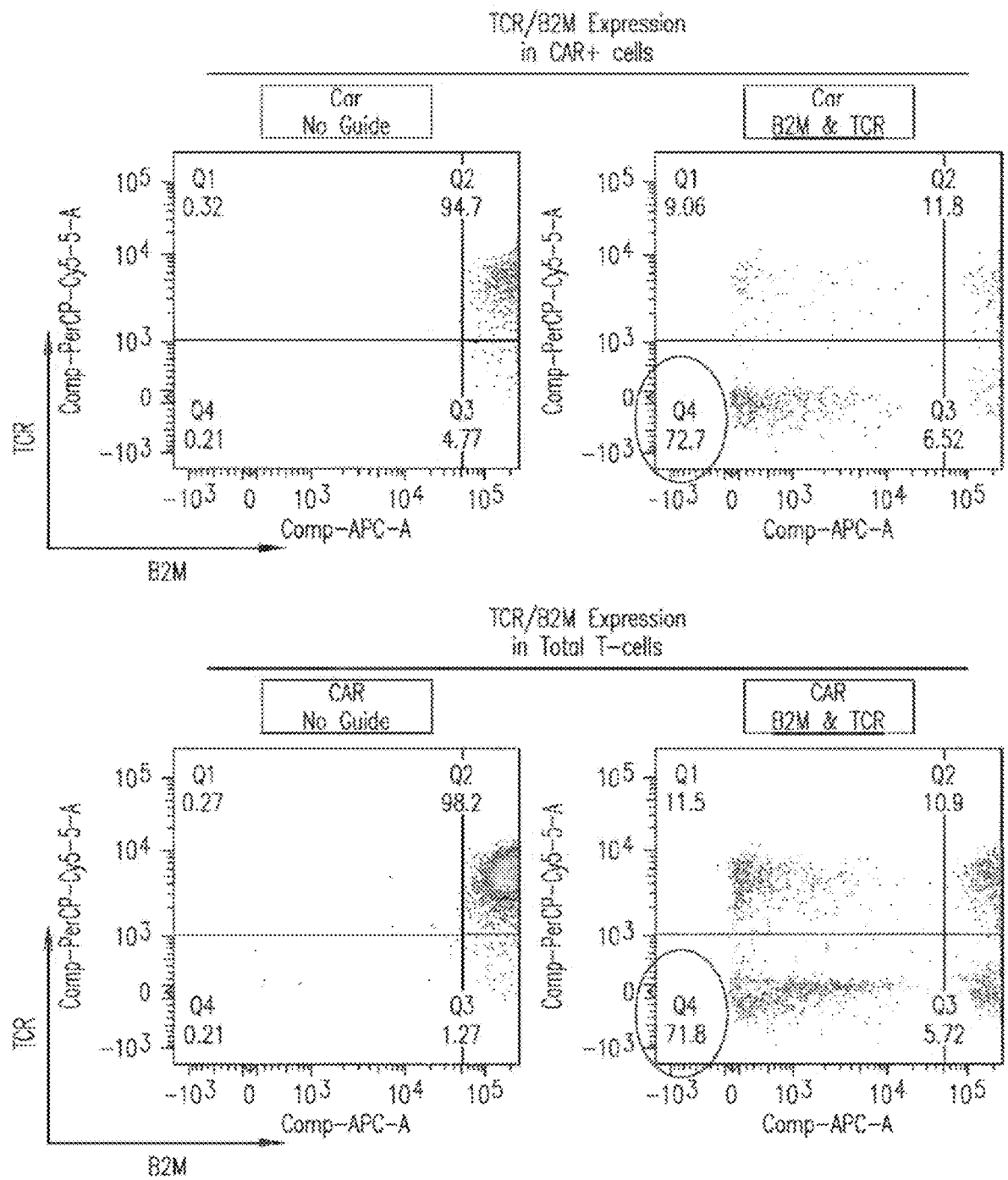
FIG. 29: Surface expression of TCR and B2M compared in total T cells versus CAR+ T cells from each population. "CAR" indicates CAR transduction; "No Guide" indicates Cas9 electroporation with no gRNA; "B2M" indicates electroporation with RNP containing gRNA specific for B2M; "TCR" indicates electroporation with RNP containing gRNA specific for TRAC.

Editing of allogeneic T cell targets in T cells engineered to express a BCMA CART, and the function of edited cells was assessed. T cells, including TCR-B2M-BCMA CAR+ T cells, used in these experiments were prepared as described schematically in FIG. 27. Briefly, PBMC were isolated from human blood by using centrifugation method using Ficoll. Total T cells were isolated from these PBMC's (Hemacare) using human Pan T Cell Isolation Kit (Miltenyi Biotec #130-096-535). These cells were aliquoted and frozen using CRYOSTOR CS10 media (Biolife Solution-210102), and stored in liquid nitrogen. These frozen cell aliquots were then thawed in a 37 degree waterbath for 20 seconds and then transferred to a 50 ml conical tube with 10 ml of prewarmed T cell media and centrifuged at 300 rpm for 5-10 mins at 24 degrees to remove the freezing media and resuspended with prewarmed T cell media. Cells were then transferred to a 24-well dish and activated by adding CD3/CD28 beads (DynaBeads Invitrogen Cat #111.41D) at bead to cell ratio of 3:1. Day 1 post activation, lentivirus comprising sequence encoding CAR BCMA-13 (139112 from Table 23, above) was transduced into these cells at a multiplicity of infection (MOI) of 5. UTD (untransduced cells) were not treated with virus. Day 4 post activation, 250,000 cells per condition either CAR BCMA-13 or Untransduced T cells were then electroporated with RNP using BTX (settings: 1000V/0.6 ms/1 pulse) with or without guide RNA as indicated. For RNP generation, dgRNA molecules comprising tracr RNA and crRNA for TRAC and B2M were heated together at 95° C. for 2 minutes and gradually were cooled to come to room temperature, upon which they were incubated with Cas9 Protein and 5×CCE buffer for 10 mins at 37° C. For TRAC editing the targeting domain of CR000985 (Sequence: CCGAAUCCUCCUC-CUGAAAG (SEQ ID NO: 5593)) was used, and for B2M editing the targeting domain of CR000442 (Sequence: GGC-CACGGAGCGAGACAUCU (SEQ ID NO: 5496)) was used. In each case, dgRNA were used with the crRNA sequence: [targeting domain]-GULTUUAGAGC-UAUGCUGUUUUG (SEQ ID NO: 6607), and the tracr sequence:

AACAGCAUAGCAAGUUAAAAUAAGGCUAGU-CCGUUAUCAACUUGAAAAAGUGGCACCGA GUCG-GUGCUUUUUUU (SEQ ID NO: 6660). After electroporation cells were returned to 0.5 ml of T cell media in a 24 well plate. Two days after electroporation, cells were split every other day to maintain cells at 0.5 million/ml. Five days post electroporation, 100,000 cells were analyzed by flow cytometry (BD Fortessa) using FlowJo software. 100,000 cells were aliquoted to each well of round bottom 96 welled plate. Cells were taken from each sample, pipetted to dissociate them from beads, and beads were removed by using 96 welled plate magnet, and centrifuged with 100 ul of FACS buffer (Miltenyi MACS buffer catalog #130-092-987 with 0.5% BSA (Miltenyi-catalog #130-091-376) to wash the cells. Cells were then incubated with different antibodies diluted in 100 ul FACS buffer for 30 mins on ice. Cells were then washed two times with 200 ul of FACS buffer. Cells were then resuspended in 150 ul of FACS buffer and run on 5 laser Fortessa flow cytometer (Becton Dickenson). Expression of TCR was detected by using anti-CD3-PercpCy5.5 (Ebiosciences 45-0037-42) and expression of B2M was detected by using anti-B2M-APC (316312 Biolegend). Cell surface expression of CAR was evaluated by staining with Biotinylated Protein L followed by Streptavidin-PE (016-110-084 Jackson Immuno Research). T cells were detected by staining CD4 using anti-CD4-V450 (48-0047-42 Ebiosciences) or CD8 using anti-CD8-alexa700 (300920 Biolegend). Expression of TCR (using anti-CD3-PercpCy5.5) and B2M (using anti-B2M-APC) is shown in FIG. 28. T-cells transduced with BCMA CAR BCMA-13 are indicated as "CAR". Untransduced cells are indicated as "UTD". Cells electroporated with Cas9 but no guide RNA are indicated as "no guide". CD4 staining using anti-CD4-V450 is shown in the lower panels of FIG. 28 to verify that the loss of CD3 staining is due to loss of the TCR and not due to loss of T-cells. These results demonstrate that simultaneous introduction of CRISPR systems to B2M and TRAC can be used to generate a population of T cells which lack TCR expression and B2M expression in high yield, with 72% of T cell in the CAR-transduced set staining negative for both TCR and B2M. Next, the ending of TRAC and B2M was evaluated in the CAR+ subset of cells assessed in FIG. 28. The results are shown in FIG. 29. Briefly, the cells from FIG. 28 were analyzed by gating for CAR+ cells (stained using Biotinylated Protein L followed by Streptavidin-PE) for the left-hand panel or without CAR gating (total T-cells; right panel). Editing levels are similar in the CAR+ and total T-cell populations, indicating that CAR expression did not have an effect on editing efficiency.

Figure 30:
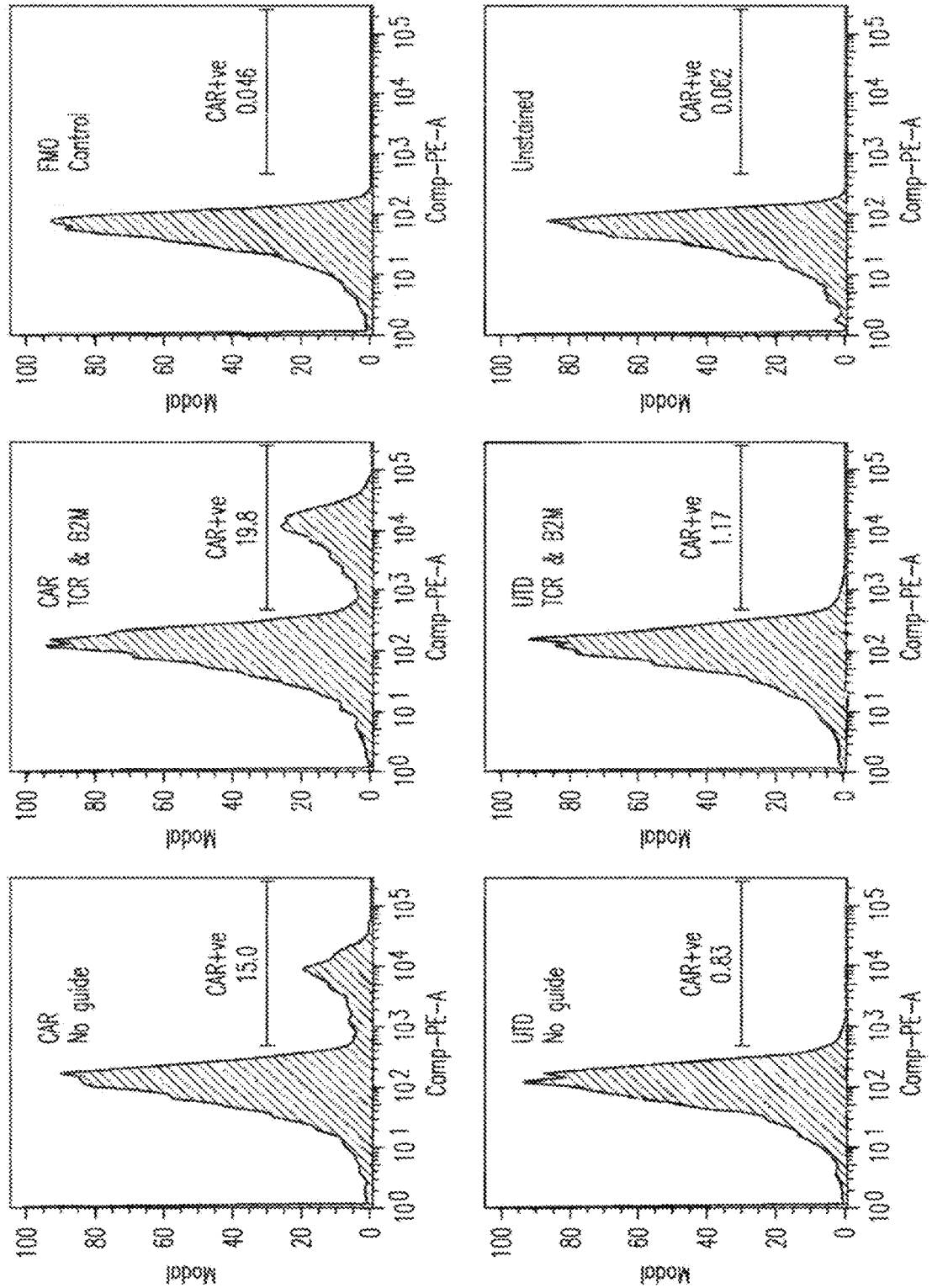
FIG. 30: CAR expression levels in cells electroporated with RNPs containing gRNAs specific for B2M ("B2M") and TRAC ("TCR") or electroporated with Cas9 without grNA ("No guide").

Next, the cells from FIG. 28 were analyzed for CAR expression by analyzing the PE channel. As shown in FIG. 30, the percentage of CAR positive cells was similar in the cells receiving guide RNAs (TRAC and B2M) and those that did not (no guide), indicating that TCR and B2M editing did not have an effect on CAR expression. UTD indicates untransduced cells. CAR indicates cells that were transduced with BCMA CAR.

Figure 31:
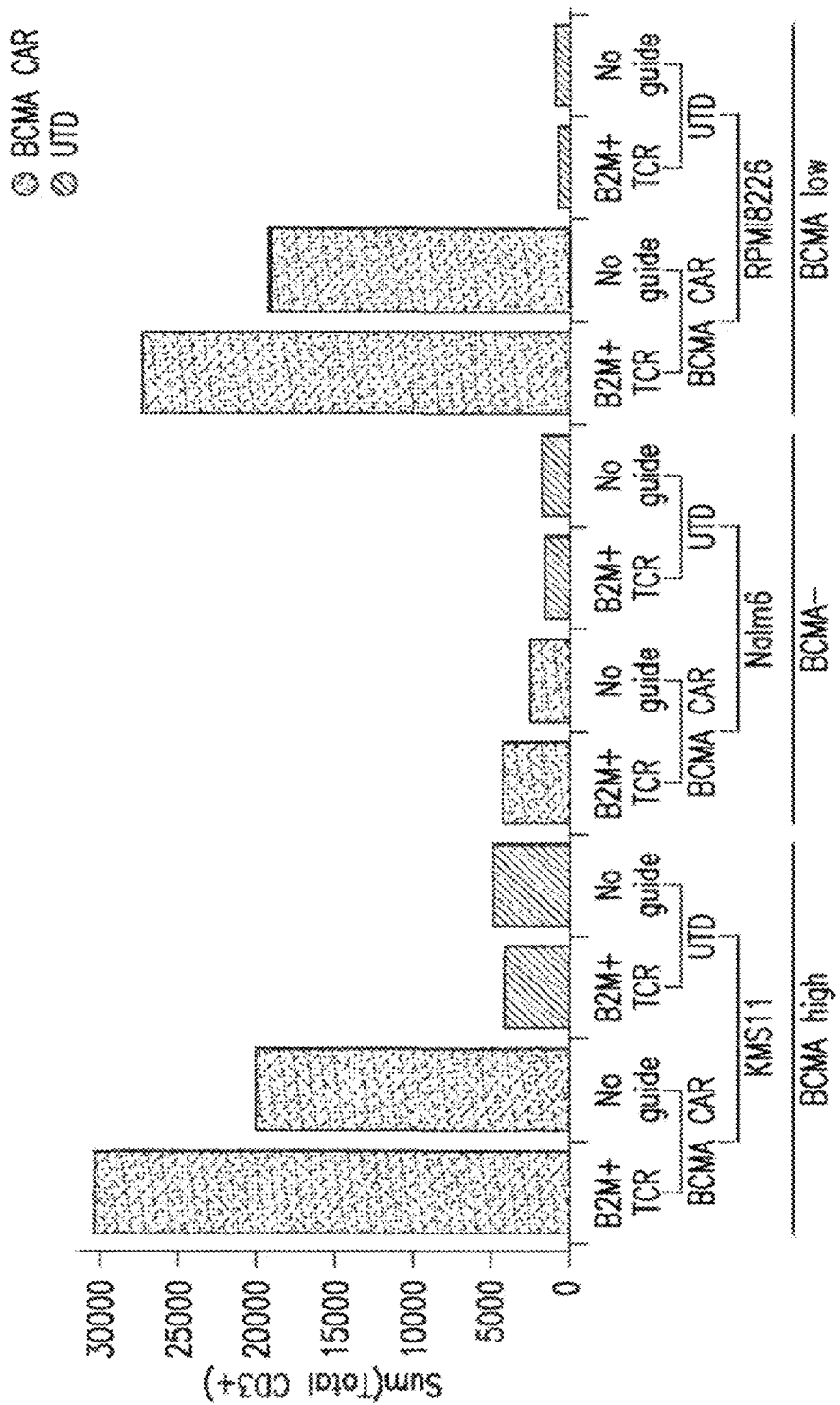
FIG. 31: Evaluation of T-cell proliferation in response to tumor cell lines expressing a high level of BCMA (KMS11), a low level of BCMA (RPMI8226) or which are BCMA- (Nalm6). T cells are either electroporated with cas9 with no gRNA ("No guide") or electroporated with RNP containing gRNAs to B2M and TRAC ("B2M+TCR"); and/or either transduced with lentiviral vector encoding a BCMA CAR ("BCMA CAR") or untransduced ("UTD"), as indicated.
Figure 32:
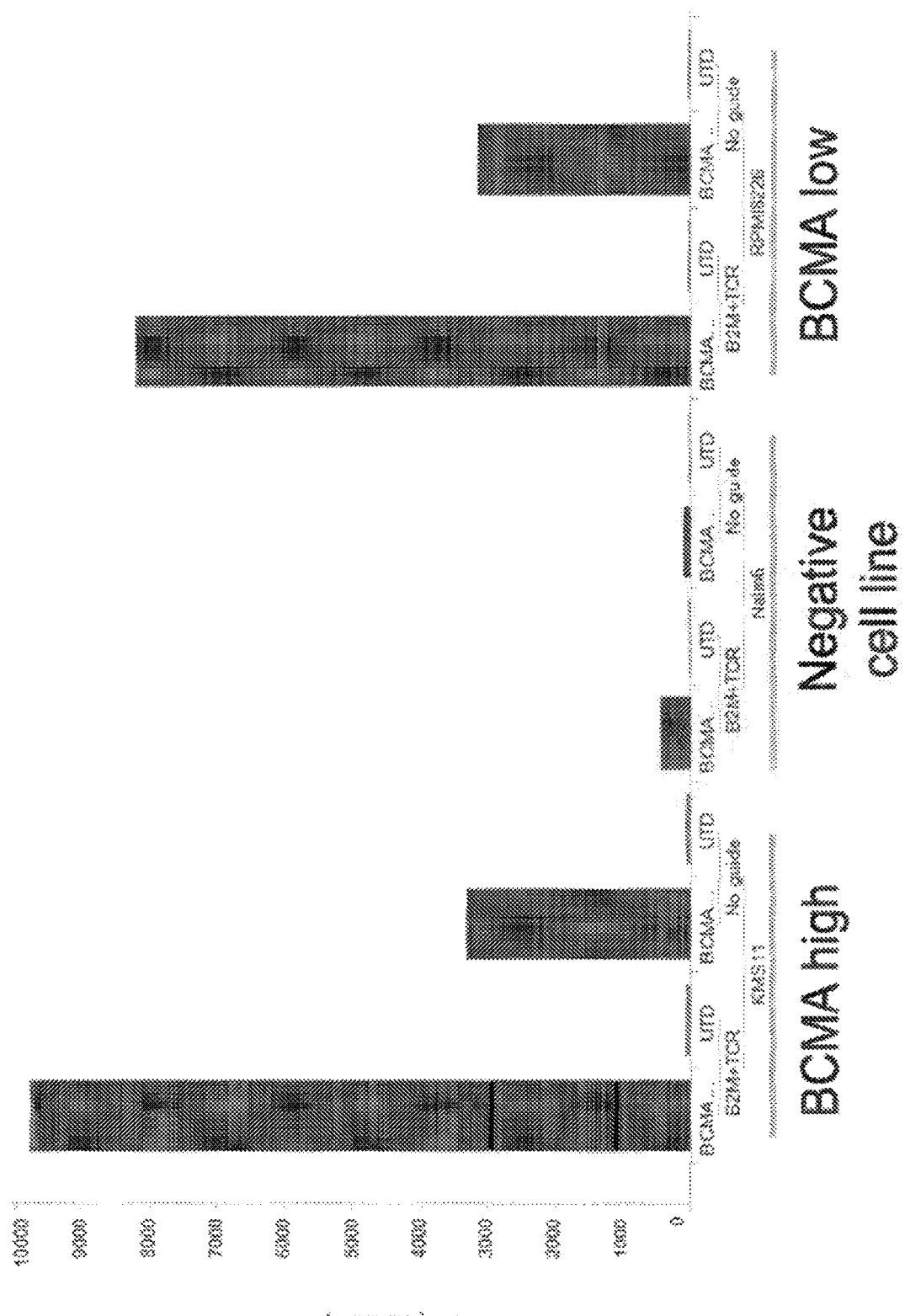
FIG. 32: Proliferation of CAR+CD4+ and/or CD8+ T cells in response to tumor cell lines expressing a high level of BCMA (KMS11), a low level of BCMA (RPM18226) or which are BCMA- (Nalm6). Cells are either electroporated with cas9 with no gRNA ("No guide") or electroporated with RNP containing gRNAs to B2M and TRAC ("B2M+TCR"); and/or either transduced with lentiviral vector encoding a BCMA CAR ("BCMA CAR") or untransduced ("UTD"), as indicated.

Next, the ability of T cells to proliferate in response to BCMA (the target antigen of the CAR molecule) was assessed. Briefly, cells were prepared as described above, were thawed and co-cultured with target cells expressing BCMA (KMS11 (high), RPMI8226 (low)) or not expressing BCMA (Nalm6). T-cells transduced with CAR BCMA-13 are indicated as "BCMA CAR". Untransduced cells are indicated as "UTD". Cells electroporated with Cas9 but no guide RNA are indicated as "no guide". Cells electroporated with RNP containing B2M and TCR guides are indicated as "B2M+TCR". 25,000 irradiated target tumor cells were co-cultured with T cells at 1:1 ratio for 4 days followed by flow cytometry analysis. The number of T-cells (stained with anti-CD4-V450 and anti-CD8-alexa700) was determined by the number of CD4+ plus CD8+ cells relative to 3000 counting beads (Life technology, Catalog #C36950). As shown in FIG. 31, both populations of cells transduced with BCMA CAR lentivirus exhibited proliferation in response to both BCMA-expressing cell types, with the population of cells receiving RNPs containing B2M and TRAC-targeting gRNA molecules exhibiting higher T cell counts after 4 days of co-culture. As shown in FIG. 32, when proliferation of CAR+CD4+ and/or CD8+ T cells was assessed separately, results were similar, with CAR+(gated by staining with biotinylated Protein L followed by Streptavidin-APC-efluor780) T cells proliferating in response to both BCMA-expressing cell types. The foregoing written specification is considered to be sufficient to enable one skilled in the art to practice the invention.

Example 12: Analysis of RNP Concentration Effects and Indel Patterns Using RNPs Targeting TCR or B2M, and Generation of CIITA−/B2M−/TCR− CAR T Cells Methods PBMC were isolated from human blood (Hemacare) by using centrifugation method using Ficoll. Total T cells were isolated from these PBMC's using human Pan T Cell Isolation Kit (Miltenyi Biotec #130-096-535). These cells were aliquoted and frozen. These frozen cell aliquots were then thawed and activated using CD3/CD28 beads (DynaBeads Invitrogen Cat #111.41D) at bead to cell ratio of 3:1. On day 2 or day 3 after bead activation, 200,000 cells were removed from culture for electroporation. RNP complex used for T cell genome editing was formed using a 1:2 molar ratio of Cas9 protein to RNA (crRNA and tracRNA). 100 µM crRNA and 100 µM tracrRNA were denatured separately at 95° C. for 2 min and cooled to room temperature. In a final volume of 5 µL, 1.4 µL of Cas9 protein at a concentration of 5.9 µg/µL (NLS-Cas9-NLS) was mixed with 1.6 µL of Cas9 buffer (20 mM Tris, pH8.0; 200 mM KCL, 10 mM MgCL2) and mixed with 1 µL, of 100 uM tracrRNA at room temperature. Next 1 µL of 100 µM crRNA was added, mixed and incubated for 10 min at 37° C. If more than one RNP was added during the electroporation step, each RNP with a crRNA targeting a different gene was assembled separately using the above method, then combined together with the addition of Cas9 buffer in order to obtain different RNP final concentrations for different conditions. For "triple editing", i.e. simultaneous addition of 3 RNPs targeting different genes, details of RNP quantities are provided in the figures. The assembled RNPs were then mixed with 200,000 cells in 10 ul of T Buffer (neon transfection system 10 ul Kit). Electroporation was performed by Neon electroporator using Neon® Transfection System 10 µL Kit (MPK1096) at 1600V, 10 ms, 3 pulses. For CIITA, editing was quantitated by measuring loss of cell surface expression of HLA-DR by flow cytometry 3 days after electroporation. Cells were stained with anti-CD3 (PerCP-Cy5.5), anti-HLA-DR-V450, and a live/dead cell dye e780 (APC-Cy7) and analyzed by flow cytometry. Editing of TRAC was quantitated by measuring loss of cell surface expression of CD3 epsilon by flow cytometry 3 days after electroporation using anti-CD3 antibody (PerCP-Cy5.5). Editing of B2M was measured by loss of cell surface expression using flow cytometry 4 days after electroporation using anti-B2M antibody-APC (316312 Biolegend). To evaluate the editing frequency and sequence changes resulting from gene editing in the above prepared T cells, genomic DNA was isolated and subjected to sequencing. Briefly, frozen cell pellets were thawed and processed using *DNeasy Blood & Tissue Kit (Qiagen, 69506)* to isolate genomic DNA. Eluted DNA was used to run PCR using *Titanium Taq PCR kit (Clontech Laboratories, 639211)* and primers in Table 27.

TABLE 27 primer design for PCR.

| Target | Forward Primer | SEQ ID NO: | Reverse Primer | SEQ ID NO: |
|---|---|---|---|---|
| B2M | GCACGCGTTTAATA TAAGTGGAGG | 10819 | GACCCTCCCGTCGCC | 10832 |
| FKBP12 | CCTCATCTGTGCAG CGGGCAT | 10820 | CGAGGTACTAGGCAG AGCCGTGG | 10833 |
| TRAC (guides CR000961, CR000978) | CATCACGAGCAGCT GGTTTC | 10821 | GGACTGCCAGAACA AGGCTC | 10834 |
| TRAC (guides CR000979) | GAGCCGAGGTATC GGTCCTG | 10822 | ATTCAGGAGAGACCC CACCC | 10835 |

TABLE 27-continued primer design for PCR.

| Target | Forward Primer | SEQ ID NO: | Reverse Primer | SEQ ID NO: |
|---|---|---|---|---|
| TRAC guides (CR000984, CR000991, CR000992, CR000993) | TGTTTGTAAGGGGA TATGCACAGA | 10823 | GTTTCAGGCCATTAT TATTGCACA | 10836 |
| CIITA (guides CR002961, CR002967) | TGTTGTAGGTGTCA ATTTTCTGCC | 10824 | AATTTCCCCTGATTG CCGTCTCTA | 10837 |
| CIITA (Guide CR002991) | CCCTCTTTCCAGAA ATTTCCTTCTTC | 10825 | GACTGACGTGGCTCA TGATGAAT | 10838 |
| CIITA (Guide CR003007) | AATAGAGACTCAC CTTGGGCTTTC | 10826 | GTACATTTTAAGGCT CCTGTTGGC | 10839 |
| CIITA (Guide CR003001) | GCCTTCAGTTAGAC CTTGTTGATT | 10827 | GAGTCTCTATTGTAC CCACCTTGG | 10840 |
| CIITA (Guide CR002994) | TCCTTCTTCATCCA AGGGACTTTT | 10828 | CCCTTGCAATGATTT CTGTGGG | 10841 |
| CIITA (Guide CR002992, CR002993) | TTCTTCATCCAAGG GACTTTTCCT | 10829 | GACTGACGTGGCTCA TGATGAAT | 10842 |
| CIITA (Guide CR002961, CR002967, CR002965) | TGTTGTAGGTGTCA ATTTTCTGCC | 10830 | AATTTCCCCTGATTG CCGTCTCTA | 10843 |
| CIITA (Guide CR002972, CR002980, CR002976) | TGTAGGTGTCAATT TTCTGCCTCT | 10831 | GAATTTCCCCTGATT GCCGTCT | 10844 |

PCR product was purified using *QIAquick PCR Purification Kit* (*Qiagen,* 28104). Purified PCR product was then used for T7E1 assay to detect base pair mismatches and confirm gene editing. PCR amplicons were subjected to standard Nextera NGS library prep (Illumina) and sequenced with paired-end reads on an Illumina MiSeq sequencer. Sequencing reads were aligned to the reference genome and variants were called.

Results

Figure 33A:
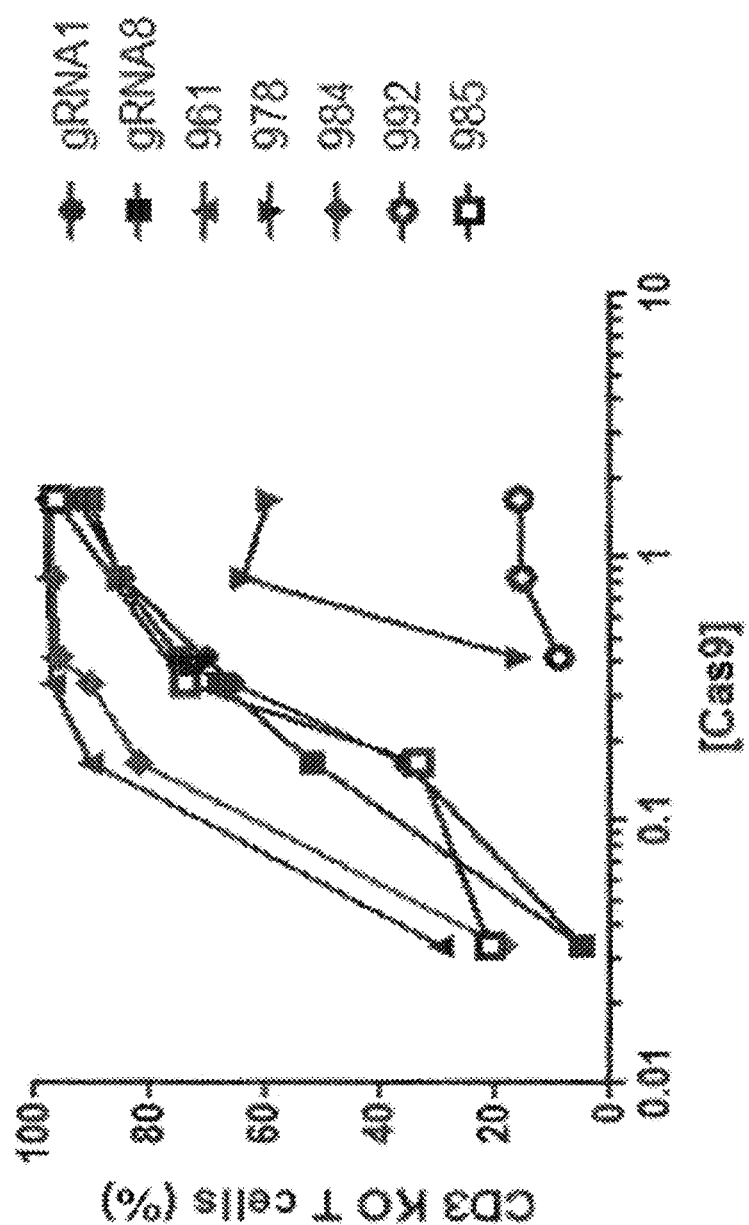
FIGS. 33A and 33B: Evaluation of TRAC targeting gRNAs for effects on cell surface TCR expression. 33A shows loss of CD3 staining is shown for RNPs containing guides CR000961 (961), CR000978 (978), CR000984 (984), CR000992 (992), CR000985 (985), and CR000960 (gRNA1) and CR000979 (gRNA8). 33B shows loss of CD3 staining is shown for RNPs containing guides CR000991 (991), CR000992 (992), CR000993 (993), and CR000978 (978). 991 and 992 are nearly superimposable.
Figure 33B:
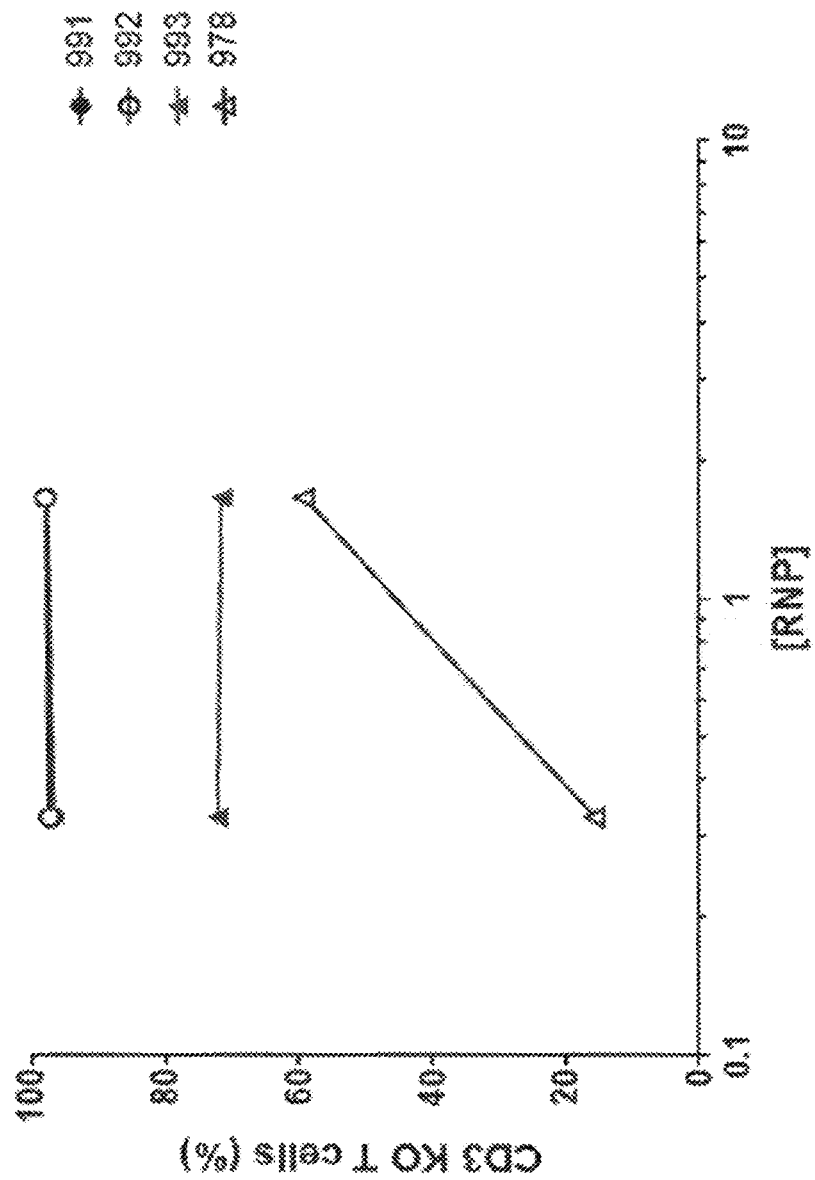

First, gRNAs targeting TRAC were evaluated for effects on cell surface TCR expression at various concentrations of Cas9 (RNP). Human primary T cells were electroporated on day 3 after CD3/CD28 bead activation with RNPs at the indicated concentrations (uM) containing the indicated gRNAs in dual guide format. Additional guide numbers indicate CRxxxxx identifier of targeting domain of the gRNA. Loss of TCR expression was evaluated by staining with anti-CD3 antibody and analysis by flow cytometry 3 days after electroporation (CD3 KO T cells (%). FIG. 33A shows lss of CD3 staining upon electroporation of RNPs containing guides CR000961 (961), CR000978 (978), CR000984 (984), CR000992 (992), CR000985 (985), and CR000960 (gRNA1) and CR000979 (gRNA8). These data show that nearly maximal editing (as shown by loss of CD3 staining) is achieved for RNPs with CR000961 and CR000984-containing gRNAs at RNP concentrations of between 0.2 and 0.3 uM. Other gRNAs achieved maximal editing at concentrations of 1 uM. FIG. 33B shows loss of CD3 staining upon electroporation of RNPs containing guides CR000991 (991), CR000992 (992), CR000993 (993), and CR000978 (978). 991 and 992 are nearly superimposable. Here again, for RNP containing gRNAs 991, 992 and 993, maximum editing was observed at RNP concentrations of 0.3 uM, while gRNA 978% editing continued to increase up to 1.1 uM. As shown in FIG. 33C, electroporate of T cells with gRNA targeting the TRAC locus results in high levels of indel formation at the targeted sites (up to 97% editing) and high levels of frameshift mutations, which are predicted to result in loss of protein expression (up to 78%). Next, the mutations (indels) at each targeted locus were assessed by next generation sequencing. FIG. 34A and FIG. 34B show the top 5 most frequently observed sequence changes for each TRAC targeting dgRNA used for primary human T cell editing. Figures A and B are the outcome from 2 independently performed electroporation experiments. Data are the average from triplicate PCR products. These data show consistent patterns of editing across multiple experiments when the same gRNA format and RNP are used, in with the same delivery technique.

Figure 35:
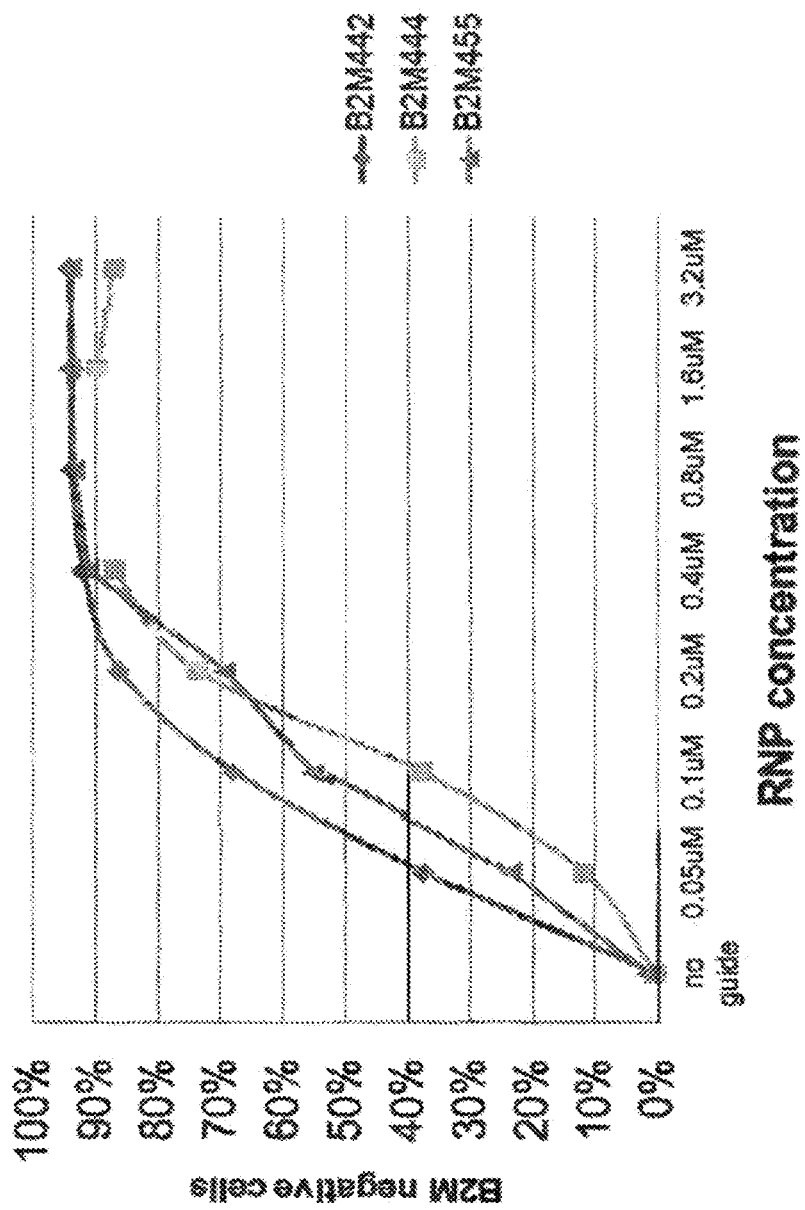
FIG. 35: Evaluation of B2M targeting gRNAs for effects on cell surface B2M expression. Guide numbers indicate CR00xxx identifier of targeting domain.
Figure 36:
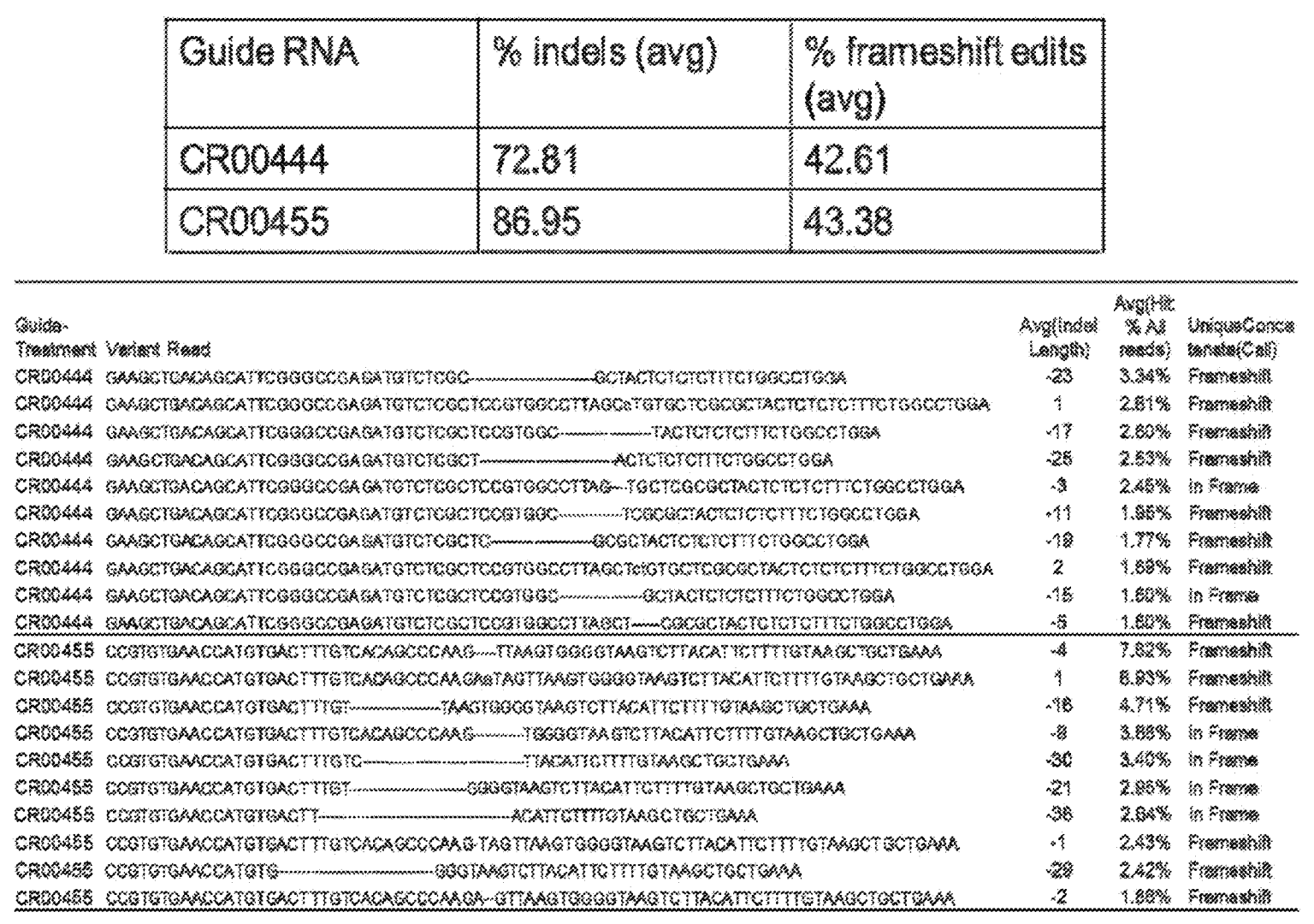

Next, similar experiments were performed with gRNAs (dual guide format) targeting B2M. The effect of RNP concentration was first assessed. Human primary T cells were electroporated on day 2 after CD3/CD28 bead activation with RNPs at the indicated concentrations containing the indicated gRNAs. Guide numbers indicate CR00xxx identifier of targeting domain. Loss of B2M expression was evaluated by staining with anti-B2M antibody and analysis by flow cytometry 4 days after electroporation (B2M negative cells). The results are reported in FIG. 35, and demonstrate that >85% editing (as assayed by loss of B2M surface expression) was achieved by gRNA 442 at 0.2 uM, and at slightly higher RNP concentration (0.4 uM) for gRNA 442 and 455. As shown in FIG. 36, RNPs comprising gRNAs CR000444 and CR000455 result in high levels of editing and high levels of frameshift editing in primary human T cells. Top ten indels produced by each gRNA are shown in the lower panel. Data are the average from triplicate PCR products.

Figure 45:
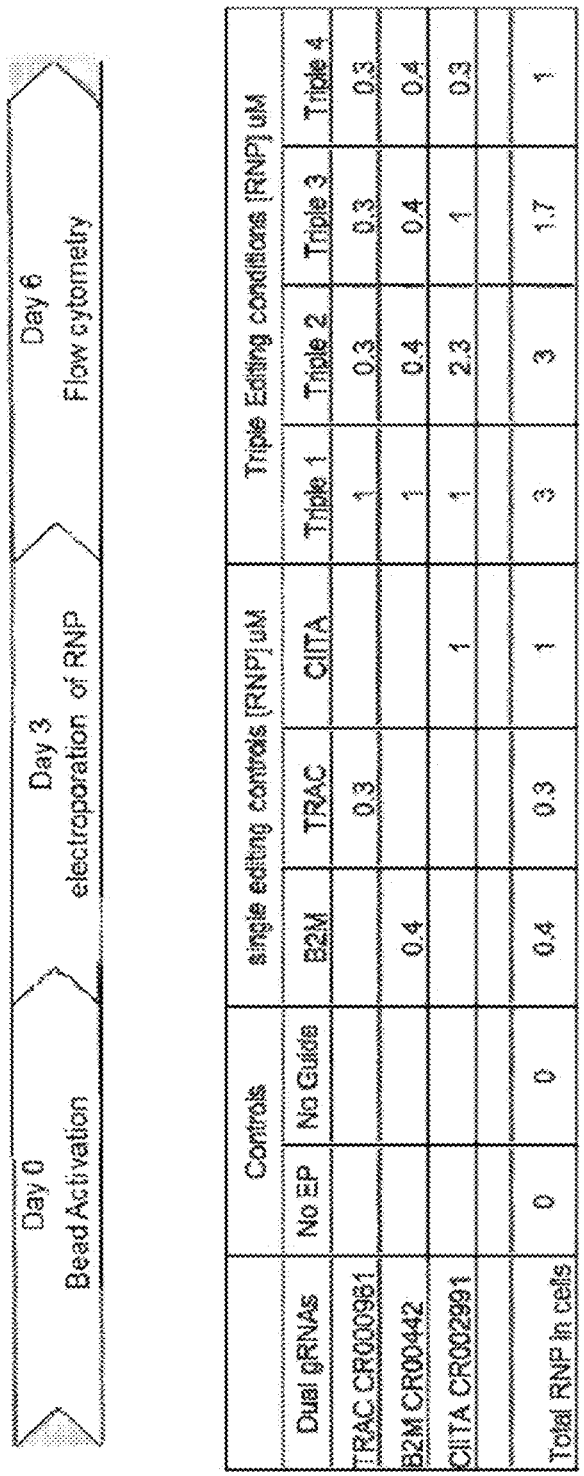
FIG. 45: Schematic protocol for preparation of primary human T cells edited at the B2M, TRAC, and CIITA loci (triple edited cells).
Figure 46:
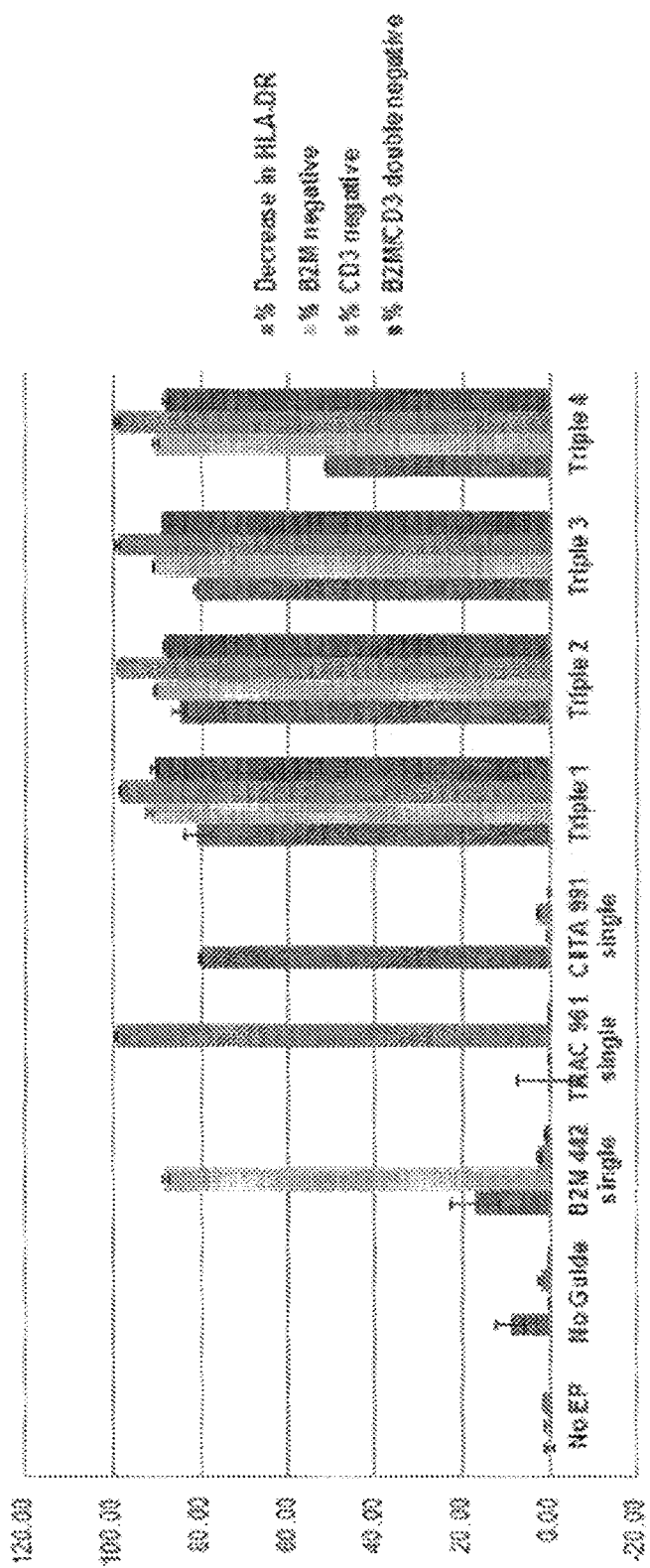
FIG. 46: Evaluation of editing of TRAC, B2M, and CIITA by testing cell surface expression of CD3 epsilon, B2M, and HLA-DR, respectively, by flow cytometry. Cell surface expression was tested in cells that had been electroporated with a single targeting RNP (B2M 442 single, TRAC 961 single, or CIITA 991 single) or with 3 RNPs simultaneously (Triple 1, Triple 2, Triple 3, Triple 4; according to the details in FIG. 45). Cells without electroporation are indicated as "No EP". Cells electroporated with Cas9 but no guide RNA are indicated as "No Guide".
Figure 48:
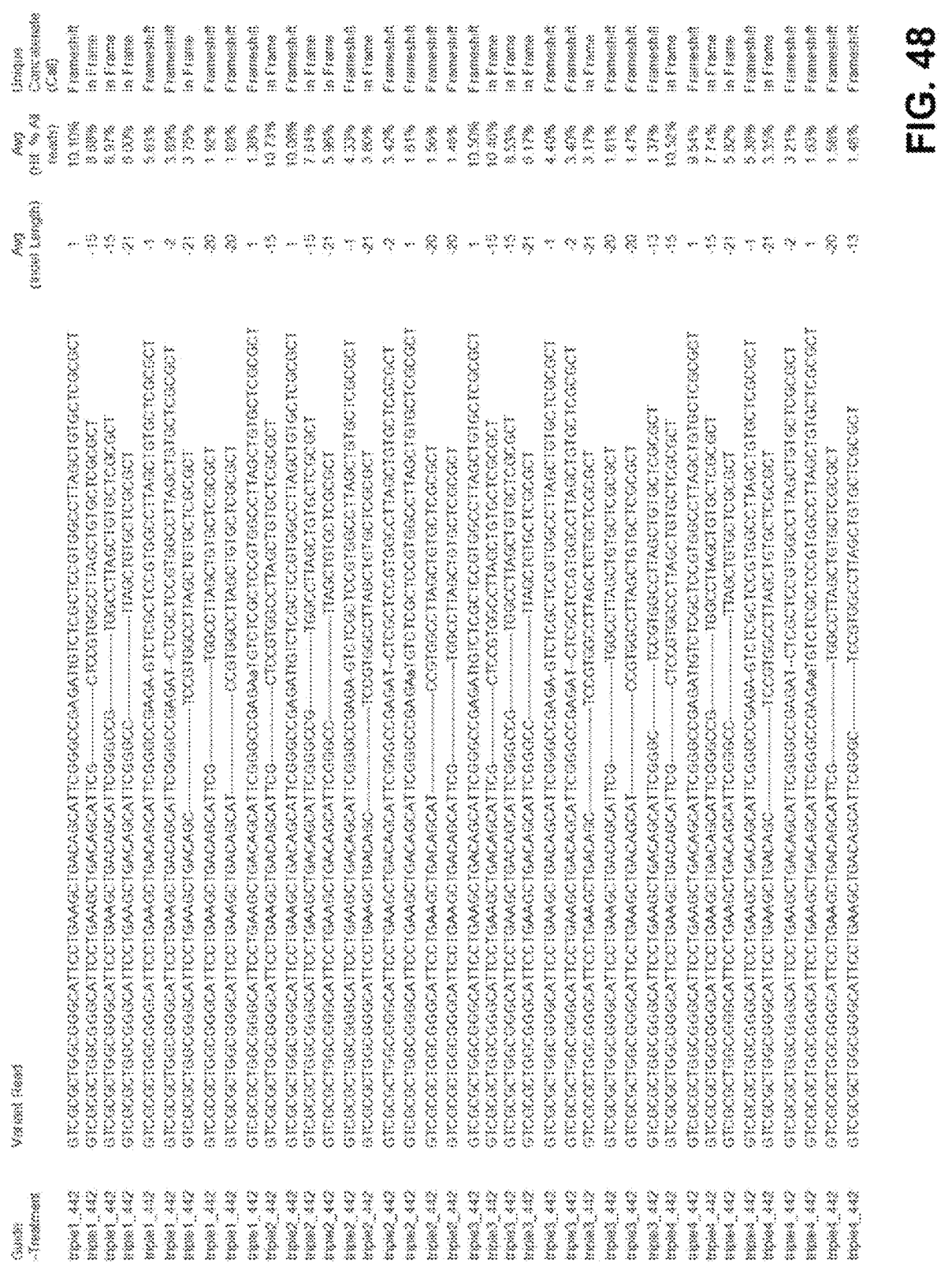
Figure 49:
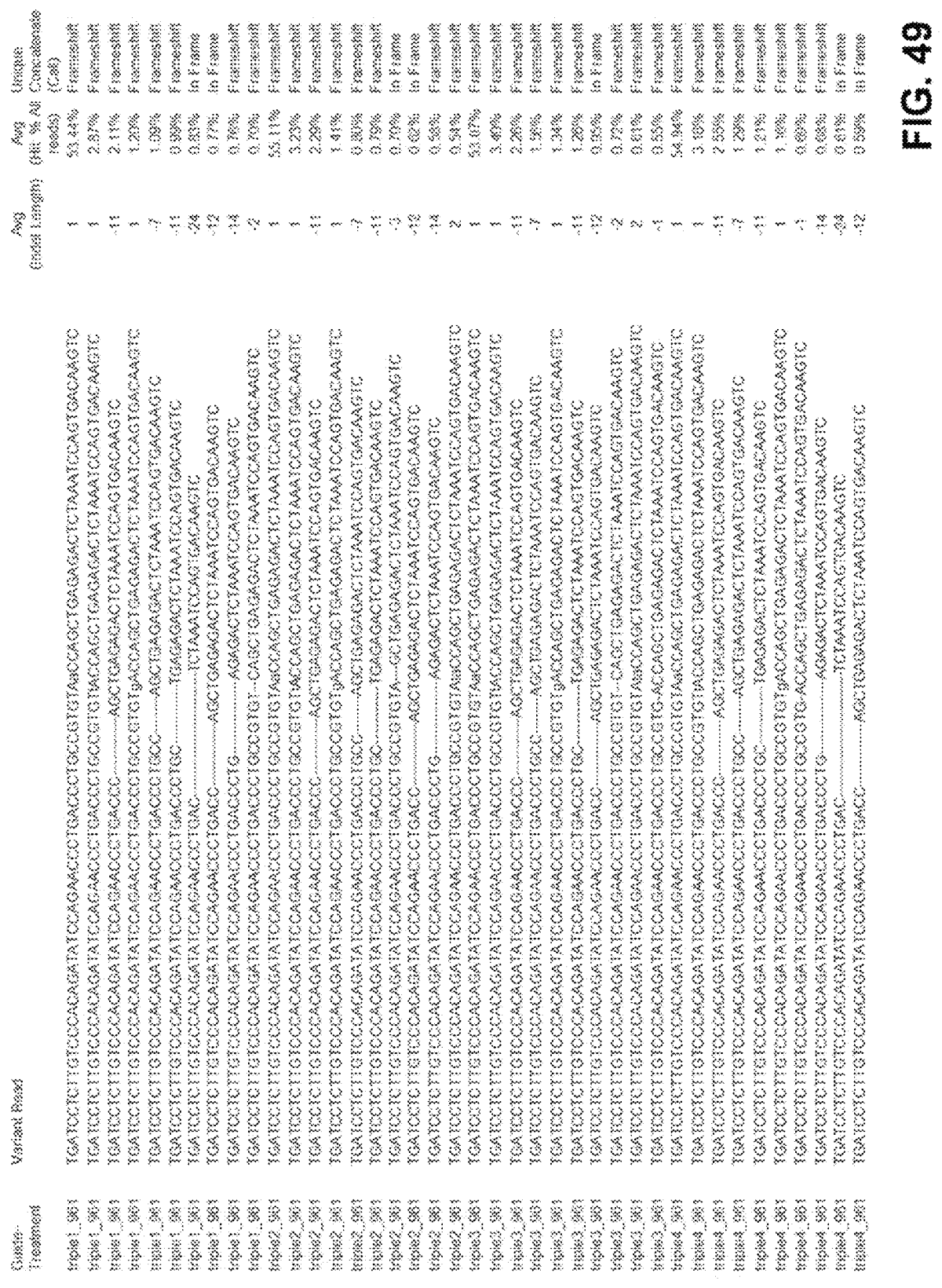
Figure 50:
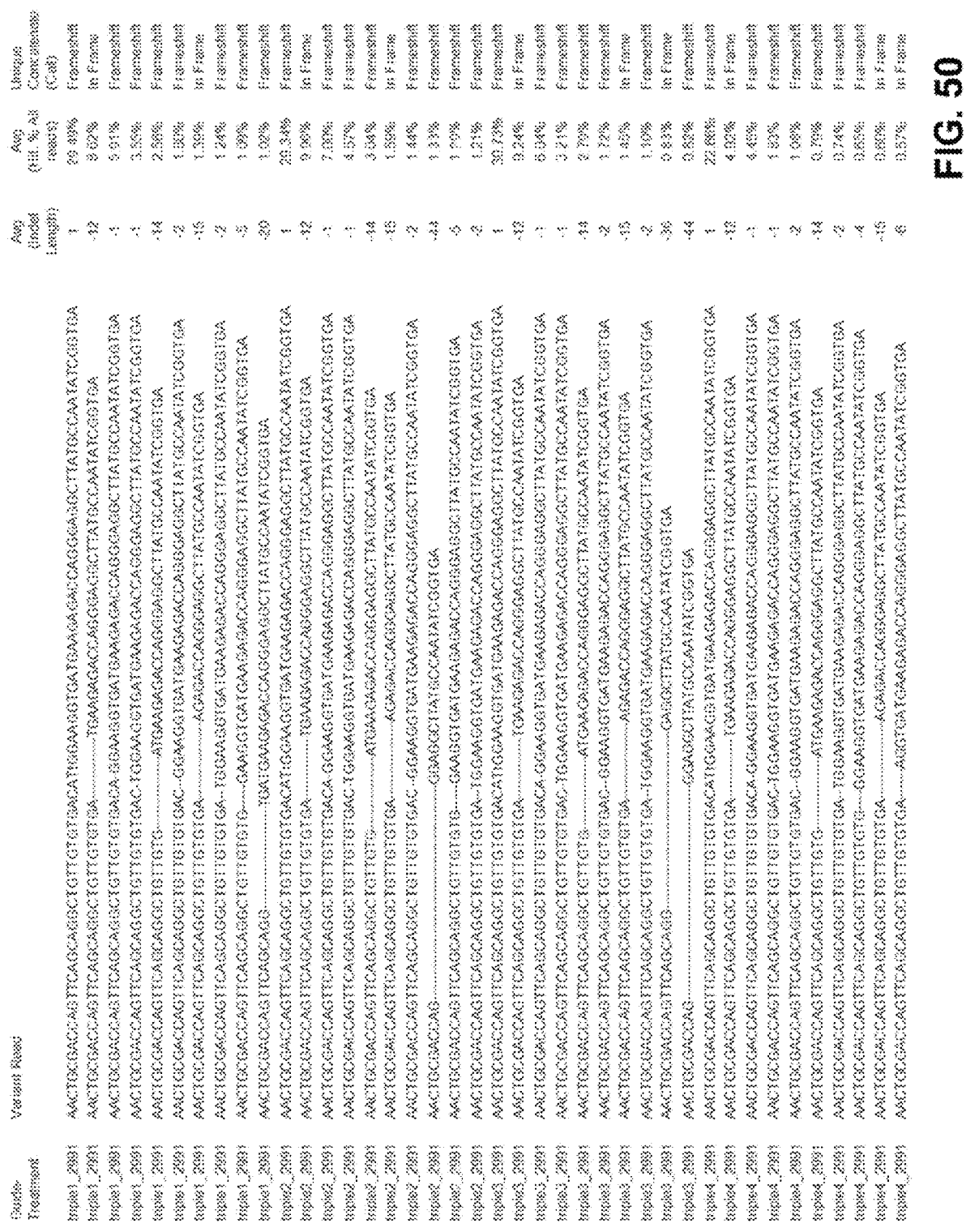

Next, the simultaneous editing of TCR, B2M and CIITA was performed in CART cells, and the function of such CART cells was assessed. FIG. 45 shows the schematic protocol that was followed for these experiments for preparation of primary human T cells edited at the B2M, TRAC, and CIITA loci (triple edited cells). FIG. 46 shows the % loss of cell surface expression of CD3 epsilon, B2M, and HLA-DR, respectively, by flow cytometry (as indicators of editing at TRAC, B2M and CIITA, respectively). As expected, cells electroporated with only single gRNA showed loss of only the expected protein. In cells treated with 3 RNPs, each containing a gRNA to a different target, cells from each population exhibited over 80% loss of each of the target proteins, as well as >80% loss of both B2M and TRAC, with the exception of the lowest concentration of the CIITA-targeting gRNA (triple 4), which resulted in a lower loss of HLA-DR than when higher concentrations of this RNP are delivered to the cells. FIG. 47 shows the genomic editing of the B2M, TRAC, and CIITA loci resulting from human primary T cell simultaneous electroporation with 3 RNPs containing gRNAs targeting the B2M, TRAC, and CIITA loci. The frequency of insertions or deletions is indicated (% indels) and the percentage of these edits that result in frameshifting of the coding sequence is shown in parentheses). FIG. 48, FIG. 49 and FIG. 50 show the top 10 most frequently observed sequence changes at the B2M locus (in response to gRNA comprising CR000442), the TRAC locus (in response to gRNA comprising CR000961) and at the CIITA locus (in response to gRNA comprising CR002991), respectively, in primary human T cells in the context of simultaneous editing of 3 loci (triple editing) with different concentrations of each RNP as shown in the schematic in FIG. 45. These data indicate that the efficient gRNA molecules used here efficiently knock out TRAC, CIITA and B2M in primary human T cells to with high efficiencies, and result in T cells which have reduced graft versus host disease capability (via loss of TCR) and reduced host versus graft disease capability (through loss of both B2M and CIITA), representing an important step toward an allogenic, off-the-shelf T cell product.

Figure 51:
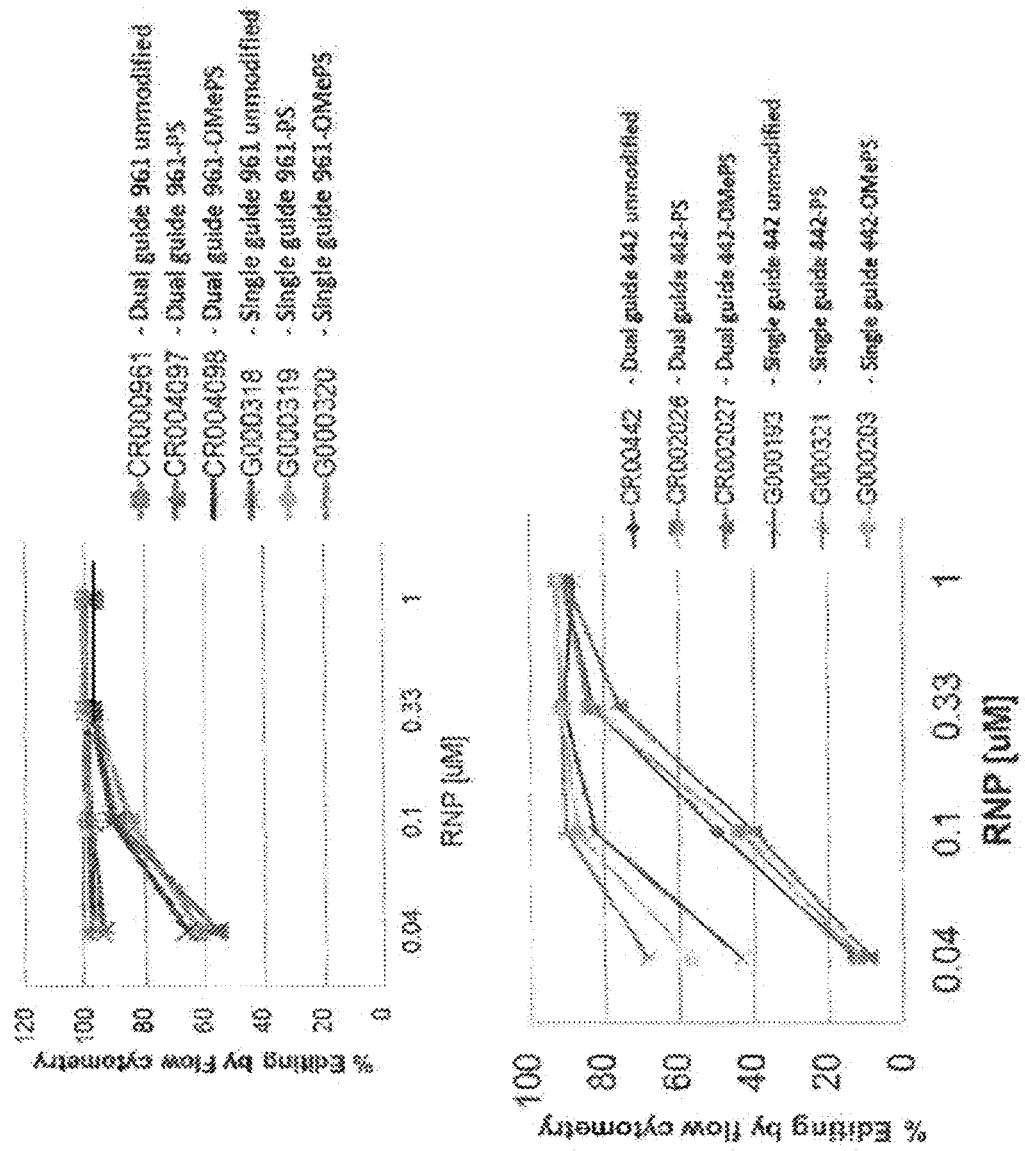
FIG. 51: The format of the guide RNA was evaluated for efficiency of editing. Guide RNAs against TRAC (CR000961; upper panel) or B2M (CR00442; lower panel) were synthesized in the single guide or dual guide format with or without the indicated chemical modifications (PS or OMePS). RNPs were electroporated into human primary T cells at the indicated concentrations. Editing efficiency was evaluated by analysis of cell surface staining of CD3 epsilon for TRAC editing (upper) and B2M protein for B2M editing (lower) by flow cytometry.

Next, the effects of the format of the gRNA molecule was assessed. Guide RNAs against TRAC (comprising the targeting domain of CR000961; upper panel) or B2M (comprising the targeting domain of CR00442; lower panel) were synthesized in the single guide or dual guide format with or without the indicated chemical modifications (PS (3 nt at both 5' and 3' ends are phosphorothioate) or OMePS (3 nt at both 5' and 3' ends are 2'-OMe and phosphorothioate); for dual guide RNA, both the crRNA and the tracr RNA comprised the modifications). RNPs were electroporated into human primary T cells at the indicated concentrations. FIG. 51 shows the results of these experiments: editing efficiency was evaluated by analysis of cell surface staining of CD3 epsilon for TRAC editing (upper) and B2M protein for B2M editing (lower) by flow cytometry. As shown in FIG. 51, all formats were capable of achieving high efficiency editing at RNP concentration of 1 uM, however, sgRNA format was able to maintain high editing efficiencies at lower concentrations than dgRNA formats (down to 0.04 uM for gRNAs comprising the targeting domain of CR000961, and down to 0.1 uM for gRNAs comprising the targeting domain of CR000442). For the TRAC-targeting gRNA, chemical modification had no effect on editing efficiency at the rNP concentrations tested. For the B2M-targeting gRNA, chemical modification of the sgRNAs had an effect on editing efficiency at the lowest concentration tested, with the PS-modified sgRNA having the highest editing efficiency at 0.04 uM RNP concentration.

Example 13: T Cell Resistance to Immunosuppression after Genome Editing of FKBP1A, and Functional Assessment of TCR−/FKBP12− CART Cells Without being bound by theory, as described herein, it is believed that another strategy for generating off-the-shelf ("universal") CART cells is to reduce or eliminate expression of TCR (to, e.g., reduce or suppress graft versus host disease), and also to reduce or eliminate expression of a target of an immunosuppressive agent (e.g., an mTor inhibitor). Subsequent treatment of a patient with such genome edited CART cells in combination with said immunosuppressive agent will inhibit the host immune response (e.g., thereby inhibiting host versus graft responses) without inhibiting the function of the CART cell (e.g., the antitumor function of the CART cell). Towards that end, function of T cells edited to make them TCR− and FKBP12− were assayed, including in the presence of the mTor inhibitor RAD001.

Methods:

After thawing, isolated human T cells were activated with CD3/CD28 beads for 3 days at a bead to cell ratio of 3:1. Cells were then electroporated with RNP containing dual guide RNA molecules (as indicated, as described above in these examples), and Cas9 protein using the Neon instrument with the 100 ul tip kit. RNPs were prepared in the following manner. crRNA and trRNA (10 ul of each at 100 uM) were heated in separate tubes to 95 degrees C. for two minutes and then cooled for 5 minutes at room temperature. Cas9 protein (1.5 mg/ml), 20 uM trRNA, and 20 uM crRNA and 17 ul of buffer (20 mM Tris, PH8.0, 200 nM KCl, 10 mM MgCl2) were combined in a total of 50 ul volume and incubated at 37 degrees for 10 minutes. The RNP was then mixed with 100 ul of cells at a cell count of 2 million cells per ml of T buffer (Invitrogen; Cat #: MPK1096). 100 ul of cells mixed with RNP was transferred to the Neon pipette tip and electroporated at 1600V, 10 ms, 3 pulses. The RNP was at a final concentration of 3.3 uM as a measure of Cas9 protein.

After electroporation, cells were then transferred into a 6-well plate with 2 ml of T cell media with beads at a 3:1 bead to cell ratio. Fresh media was added every other day. On day 4 after electroporation, cells were debeaded and re-plated at a density of 0.5 million per well in a 96-well plate with 100 ul of media and fresh beads were added at a bead to cell ratio of 1:1 for 2 hours. To determine the functional effects of FKBP1A editing, cells were then treated with or without 2.5 nM RAD001 (as indicated) for 3 hours. The phosphorylation of S6 was detected by flow cytometry, and was used as an indication of immunosuppressing by RAD001. For preparation of samples for flow cytometry, cells were spun down and washed with FACS buffer (MACS running buffer+0.5% sBSA), the stained with Dead/live stain (Zombie violet fixable viability kit, Biolegend, Catalog #423114) for 10 minutes. Cells were then washed with FACS buffer and fixed overnight with Cytofix/Cytoperm solution (Becton Dickenson, Catalog #554714). Cells were then washed twice with PBS and permeabilized with Cytofix/Cytoperm solution (Becton Dickenson, Catalog #554714) for 20 minutes. Cells were then washed twice with PBS and incubated with PE conjugated anti-phospho-S6 antibody (phospho-S6 ribosomal protein Ser240/244 (D68F8) Rabbit mAb, Cell Signaling Technologies, Catalog #14236) for 1 hour at 4 degrees. Cells were then washed twice with PBS and analyzed by flow cytometry on the Becton Dickenson LSR Fortessa using FloJo-V10 software.

Figure 54A:
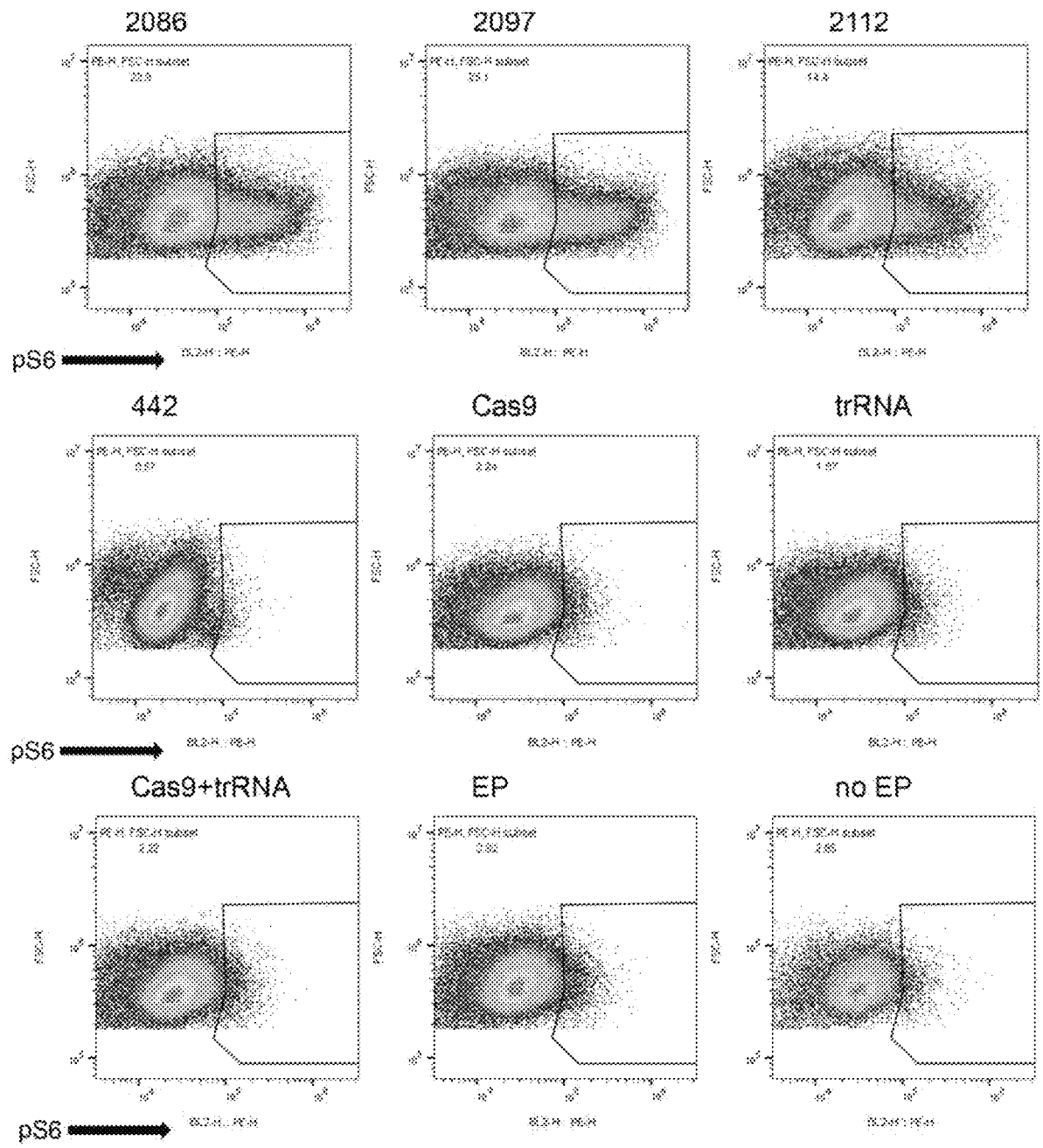
FIG. 54: T cells were edited with RNPs containing gRNAs comprising targeting domains to FKBP1A (CR002086, CR002097, CR002122; indicated as 2086, 2097, and 2112, respectively) or with negative controls: 442 (an irrelevant guide CR00442 targeting B2M); Cas9 (Cas9 alone with no trRNA or crRNA); trRNA (tracer RNA, but no crRNA or Cas9 protein); Cas9+trRNA (Cas9 and tracer RNA but no crRNA); EP (cells only with electroporation); no EP (cells only with no electroporation). After electroporation cells were treated with 2.5 nM RAD001 (FIG. 54A) or left untreated (FIG. 54B) and the impact on mTOR pathway inhibition was evaluated by analyzing S6 phosphorylation (pS6) by flow cytometry. The Y-axis indicates forward scatter (FSC) and the X-axis indicates the level of pS6. Positive staining for pS6 (shown in the gating trace) was determined by gating above the fluorescence level seen in a control stained with isotype antibody (not shown). Quantitation of S6 phosphorylation from the flow cytometry data is shown in the graph in the lower panel (FIG. 54C).
Figure 54B:
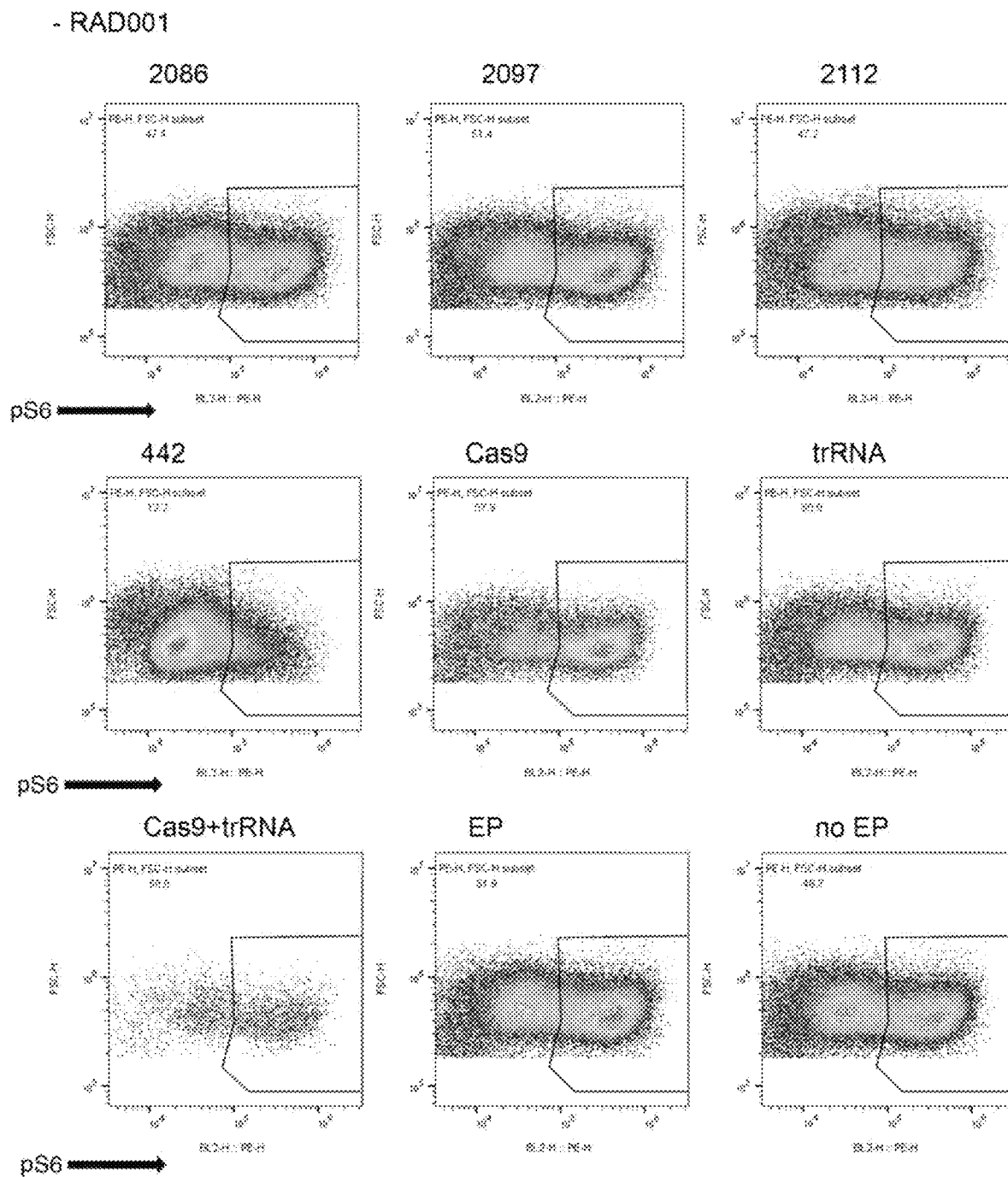
Figure 54C:
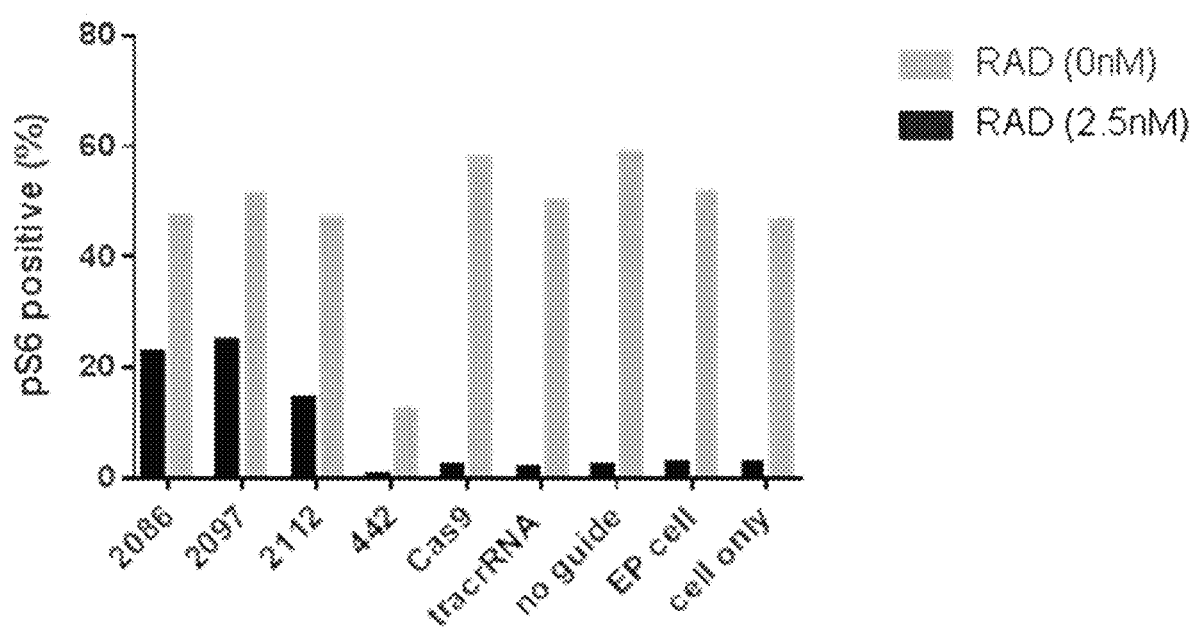

FIG. 54 shows the results of S6 phosphorylation in the presence or absence of mTor inhibitor RAD001 after exposure to gRNA targeted towards FKBP1A. T cells were edited with RNPs containing guide sequences targeting FKBP1A (CR002086, CR002097, CR002122; indicated as 2086, 2097, and 2112, respectively) or with negative controls: 442 (an irrelevant guide CR00442 targeting B2M); Cas9 (Cas9 alone with no trRNA or crRNA); trRNA (tracer RNA, but no crRNA or Cas9 protein); Cas9+trRNA (Cas9 and tracer RNA but no crRNA); EP (cells only with electroporation); no EP (cells only with no electroporation). After electroporation cells were treated with 2.5 nM RAD001 (upper panel) or left untreated (lower panel) and the impact on mTOR pathway inhibition was evaluated by analyzing S6 phosphorylation (pS6) by flow cytometry. The Y-axis indicates forward scatter (FSC) and the X-axis indicates the level of pS6. Positive staining for pS6 (shown in the gating trace) was determined by gating above the fluorescence level seen in a control stained with isotype antibody (not shown). Quantitation of S6 phosphorylation from the flow cytometry data is shown in the graph in the lower panel. These data demonstrate that editing of FKBP1A (and subsequence loss of FKBP12 protein) renders primary T cells refractory to the inhibitory effects of the rapalog RAD001.

Next, CART cells were generated which are TCR negative and FKBP12 negative, and their function evaluated. Briefly, PBMC were isolated from human blood by using centrifugation method using Ficoll. Total T cells were isolated from these PBMC's using human Pan T Cell Isolation Kit (Miltenyi Biotec #130-096-535). These cells were aliquoted and frozen. These frozen cell aliquots were then thawed and activated using CD3/CD28 beads (DynaBeads Invitrogen Cat #111.41D) at bead to cell ratio of 3:1. Day 1 post activation, CAR BCMA-10 or CAR-CD19 (CTL019) virus was used to transduce these cells at MOI of 5. UTD (untransduced cells) were not treated with virus. Day 4 post activation, either CAR BCMA-10 or CAR-CD19 or untransduced T cells were then electroporated with RNP with the indicated guide RNAs or without guide RNA (no guide) as indicated using Neon electroporator. RNP were prepared as described above. For TRAC editing, CR000961 was used (indicated as 961) alone or with guides targeting FKBP1A as indicated. For FKBP1A editing CR0002097 (indicated as 2097) or CR002097 and CR002086 together (indicated as 2097+2086) was used. The RNP (or RNPs) was then mixed with 100 ul of cells at a cell count of 2 million cells per ml of T buffer (Invitrogen; Cat #: MPK1096). 100 ul of cells mixed with RNP was transferred to the Neon pipette tip and electroporated at 1600V, 10 ms, 3 pulses. The RNP was at a final concentration of 3.3 uM as a measure of Cas9 protein. After electroporation, cells were then transferred into a 6-well plate with 2 ml of T cell media with beads at a 3:1 bead to cell ratio. Fresh media was added every other day. Five days after electroporation, 500,000 cells (for phosphor-S6 staining) or 50,000 cells for cell surface marker staining (eg CD3) were removed from culture and analyzed by flow cytometry (BD Fortessa) using FlowJo software. Expression of TCR was detected by using anti-CD3-PercpCy5.5 (Ebiosciences 45-0037-42). Cell surface expression of CAR was evaluated by staining with Biotinylated Protein L followed by Streptavidin-PE (016-110-084 Jackson Immuno Research). T cells were detected by staining CD4 using anti-CD4-V450 (48-0047-42 Ebiosciences) or CD8 using anti-CD8-APC (17-0087-42 eBiosciences).

To determine the functional effects of FKBP1A editing, on day 4 after electroporation, cells were debeaded and re-plated at a density of 0.5 million per well in a 96-well plate with 100 ul of T cell media and fresh beads were added at a bead to cell ratio of 1:1 for 2 hours. Cells were then treated with or without 2.5 nM RAD001 (as indicated) for 3 hours. The phosphorylation of S6 was detected by flow cytometry. For preparation of samples for flow cytometry, cells were spun down and washed with FACS buffer (MACS running buffer+0.5% sBSA), the stained with Dead/live stain (Zombie violet fixable viability kit, Biolegend, Catalog #423114) for 10 minutes. Cells were then washed with FACS buffer and fixed overnight with Cytofix/Cytoperm solution (Becton Dickenson, Catalog #554714). Cells were then washed twice with PBS and permeabilized with Cytofix/Cytoperm solution (Becton Dickenson, Catalog #554714) for 20 minutes. Cells were then washed twice with PBS and incubated with PE conjugated anti-phospho-S6 antibody (phospho-S6 ribosomal protein Ser240/244 (D68F8) Rabbit mAb, Cell Signaling Technologies, Catalog #14236) for 1 hour at 4 degrees. Cells were then washed twice with PBS and analyzed by flow cytometry on the Becton Dickenson LSR Fortessa using FloJo-V10 software.

To test the cytokine release from edited CART cells, effector cells (edited/unedited CART or untransduced cells) were thawed in media (RPMI, 5% FCS, 10 mM Hepes, 1× Pen/Strep, 1× Glutamine) on the day of the assay and counted on Cellometer (Nexelcom). These cells were then co-cultured with target cells expressing BCMA (KMS11, RPM18226) or cells expressing CD19 (Nalm6) at Effector: Target ratio of 1:1. 100 ul of co-culture supernatant was harvested after 20 hours. These supernatants were then used measure the cytokines IL-2 and IFN-gamma released using Meso Scale Discovery, Proinflammatory Panel 1 catalog #N05049A-1 system according to the manufacturer's protocol.

To measure the cytolytic capacity of effector cells (edited/unedited CART or untransduced cells), cells were thawed in media (RPMI, 5% FCS, 10 mM Hepes, 1× Pen/Strep, 1× Glutamine) on the day of the assay and counted on Cellometer (Nexelcom). These cells were then co-cultured for 20 hours with 30,000 target cells stably expressing the luciferase reporter gene and expressing BCMA (KMS11, RPMI8226) or cells expressing CD19 (Nalm6) at Effector: Target ratio of 1:1 in a 96 well assay plate black with clear bottom (Costar, cat #3904). Luciferase signal was measured using Bright-Glo substrate (Promega, Ref #E263B) on the EnVision multiple plate reader instrument from Perkin Elmer. Cell killing was inferred from the decrease in luciferase signal and was calculated as follows:

$$\text{Target cell killing (\%)}=100-(\text{sample luminescence}/\text{average maximal luminescence})*100$$

For the T cell proliferation assay, cells prepared as above were thawed and co-cultured with target cells expressing BCMA (KMS11, RPMI8226) or cells expressing CD19 (Nalm6). Irradiated target tumor cells were co-cultured with edited or unedited CART cells at an effector to target ratio of 1:1 for 4 days followed sample staining for CD4, CD8, and CAR as above and flow cytometry analysis Becton Dickenson LSR Fortessa and analyzed with FloJo-V10 software. The number of T-cells (stained with anti-CD4-V450 and anti-CD8-APC) was determined by the number of CD4+ plus CD8+ cells relative to 3000 counting beads (Life technology, Catalog #C36950). The number of CAR+ T cells was determined by gating the CAR+ cell population (stained with Biotinylated Protein L followed by Streptavidin-PE).

Figure 55A:
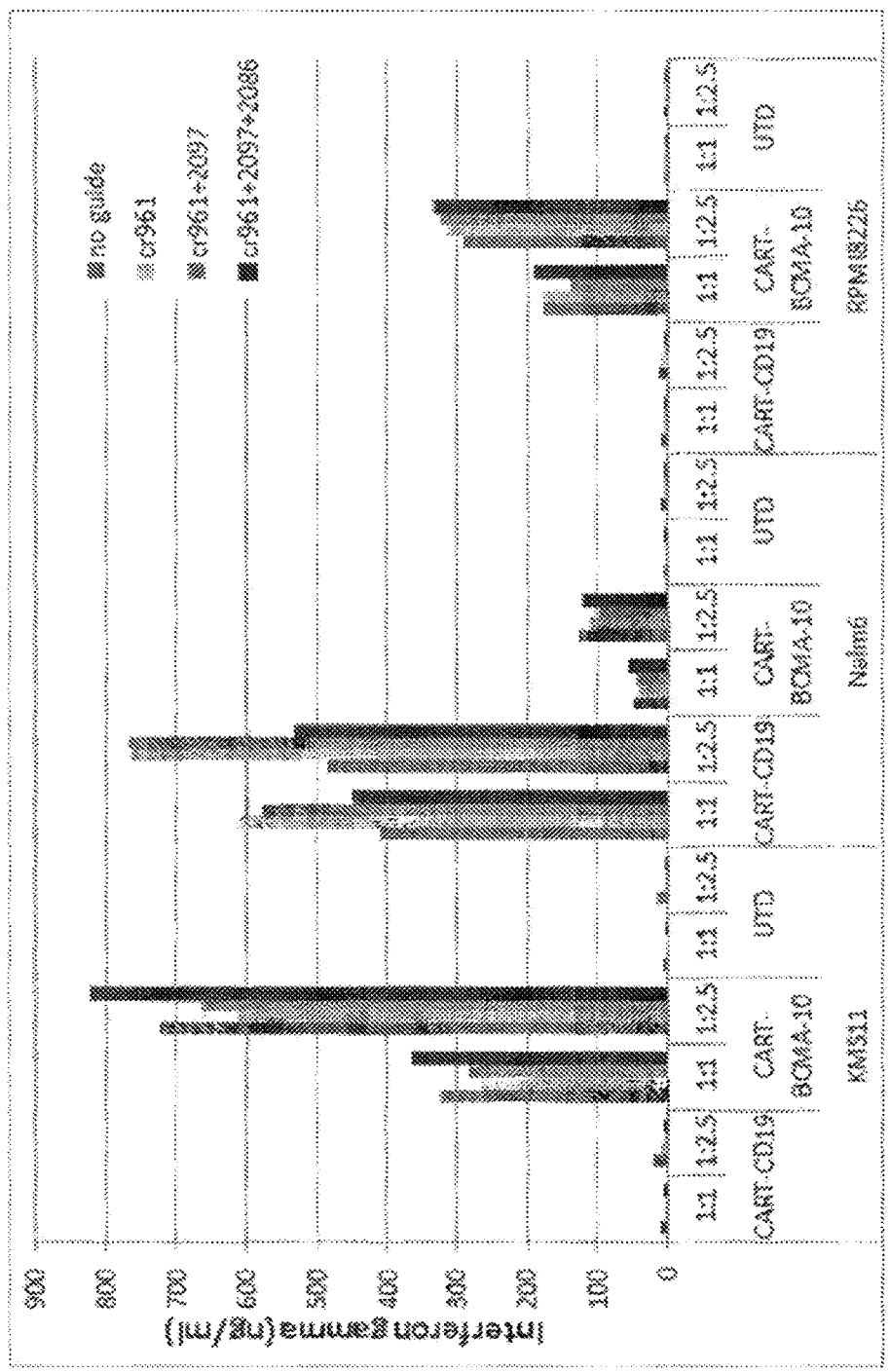
FIGS. 55A and 55B: Cytokine production by edited CART cells in response to antigen exposure. Gene editing was performed on CART cells using the CR000961 guide to target the TRAC locus and/or the CR002097 and CR002086 guides to target the FKBP1A locus (as indicated by cr961, 2097, and 2086, respectively). CART cells electroporated with an RNP containing no guide RNA were prepared as a negative control. CART cells expressing either CART-CD19, CART-BCMA-10, or untransduced (UTD) (as indicated) were mixed with the indicated cancer cell (KMS11 (BCMA positive), Nalm6 (CD19 positive), or RPMI8226 (BCMA positive)) at an effector to target ratio of either 1:1 or 1:2.5 (as indicated). Cell culture supernatants were collected and interferon gamma was measured (Figure A) or IL-2 was measured (Figure B).
Figure 55B:
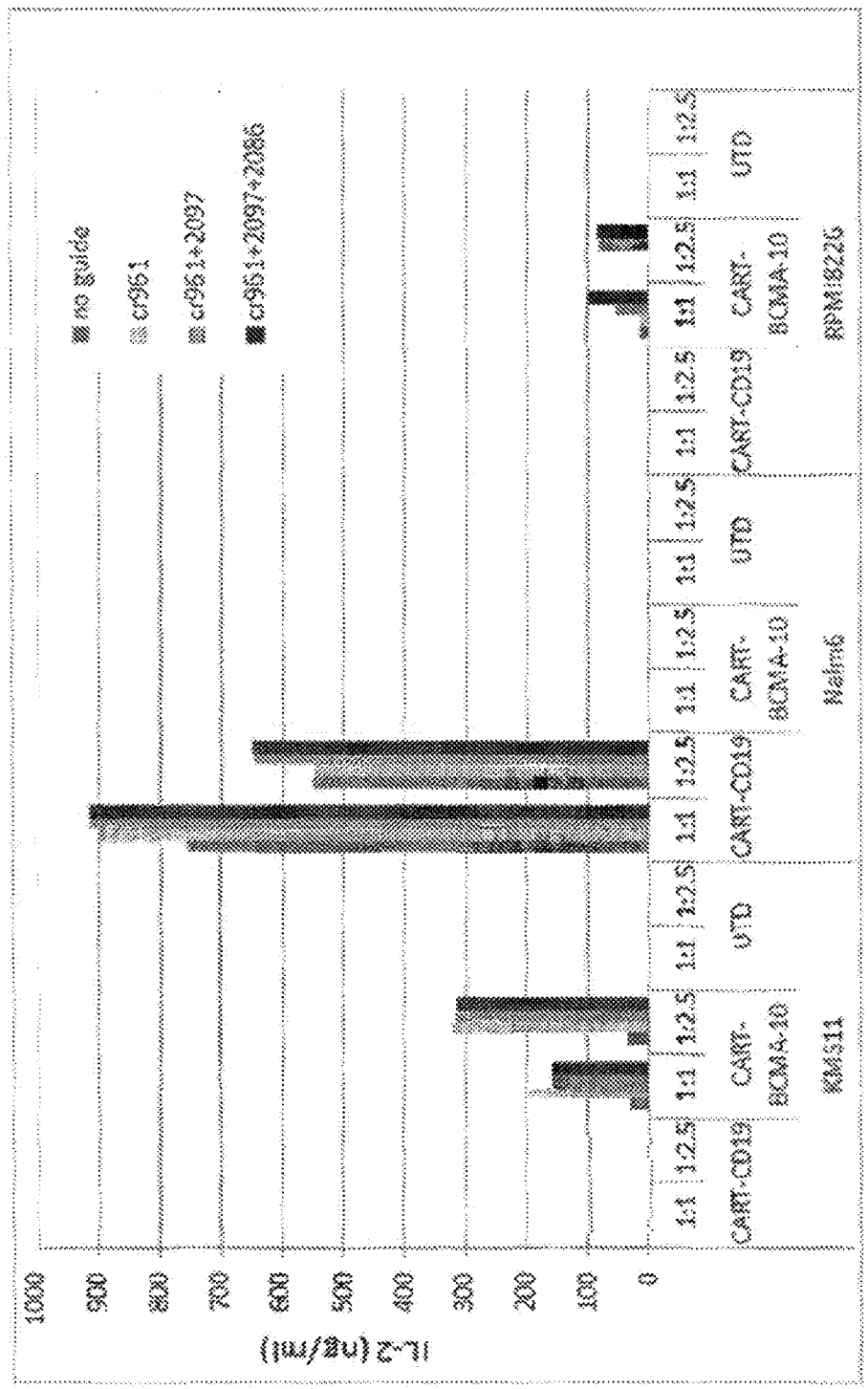
Figure 56:
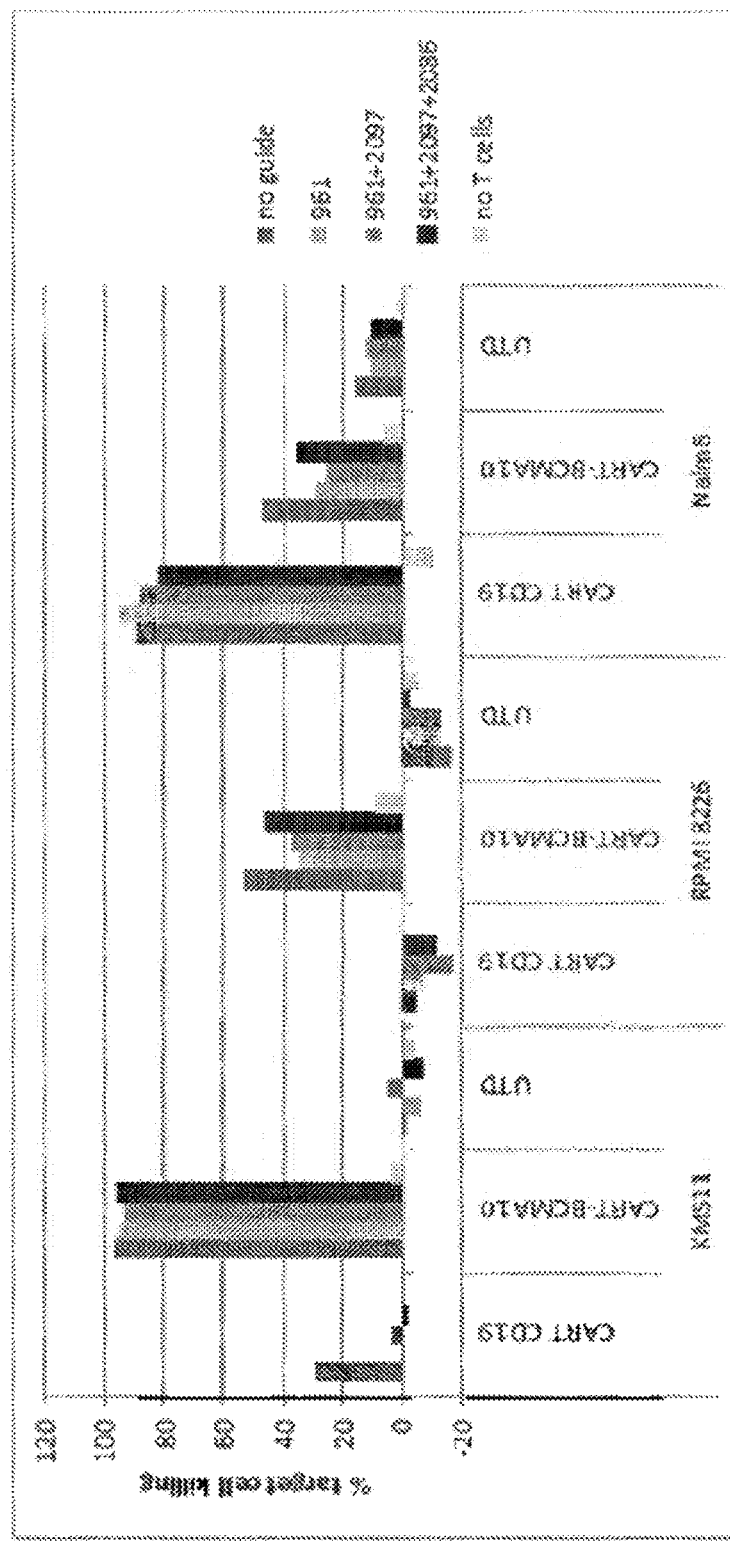
FIG. 56: Killing of antigen positive cancer cell lines by edited CART cells. Gene editing was performed on CART cells using the CR000961 guide to target the TRAC locus and/or the CR002097 and CR002086 guides to target the FKBP1A locus (as indicated by cr961, 2097, and 2086, respectively). CART cells electroporated with an RNP containing no guide RNA were prepared as a negative control. CART cells expressing either CART-CD19, CART-BCMA-10, or untransduced (UTD) (as indicated) were mixed with the indicated cancer cell lines that stable express the luciferase reporter (KMS11 (BCMA positive), Nalm6 (CD19 positive), or RPMI8226 (BCMA positive)) at an effector to target ratio of 1:1. Luciferase signal was measured and cell killing was determined as a loss of luciferase activity.
Figure 57:
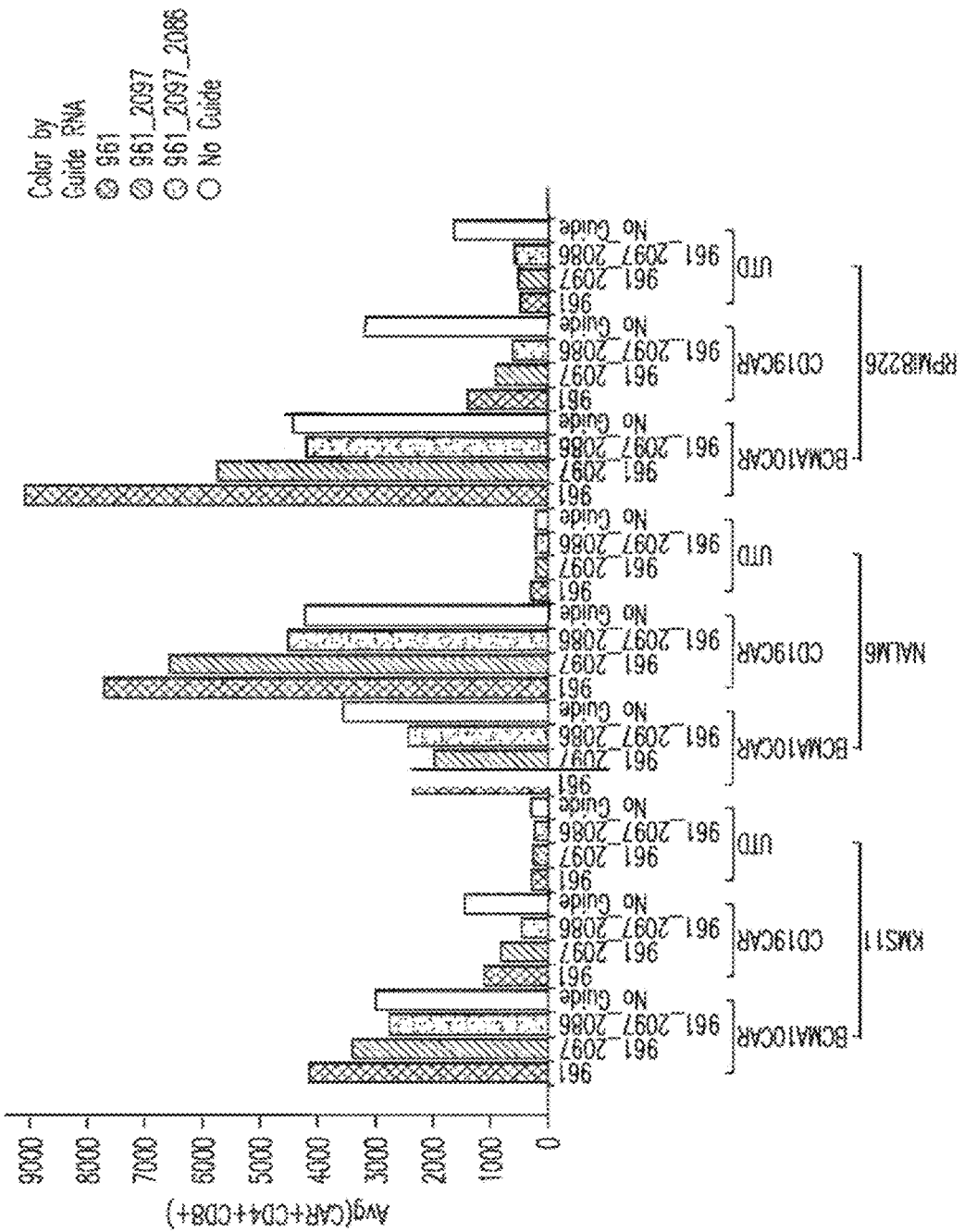
FIG. 57: Proliferation of edited CART cells in response to antigen exposure. Gene editing was performed on CART cells using the CR000961 guide to target the TRAC locus and/or the CR002097 and CR002086 guides to target the FKBP1A locus (as indicated by 961, 2097, and 2086, respectively). CART cells electroporated with an RNP containing no guide RNA were prepared as a negative control. CART cells expressing either CART-CD19 (labeled CD19CAR), CART-BCMA-10 (labeled BCMA10CAR), or untransduced (UTD) (as indicated) were mixed with the indicated cancer cell lines (KMS11 (BCMA positive), Nalm6 (CD19 positive), or RPMI8226 (BCMA positive)) at an effector to target ratio of 1:1. Proliferation was measured by counting the sum of CD4+ and CD8+ cells that are CAR+ relative to a fixed number of counting beads.
Figures 1, 58A:
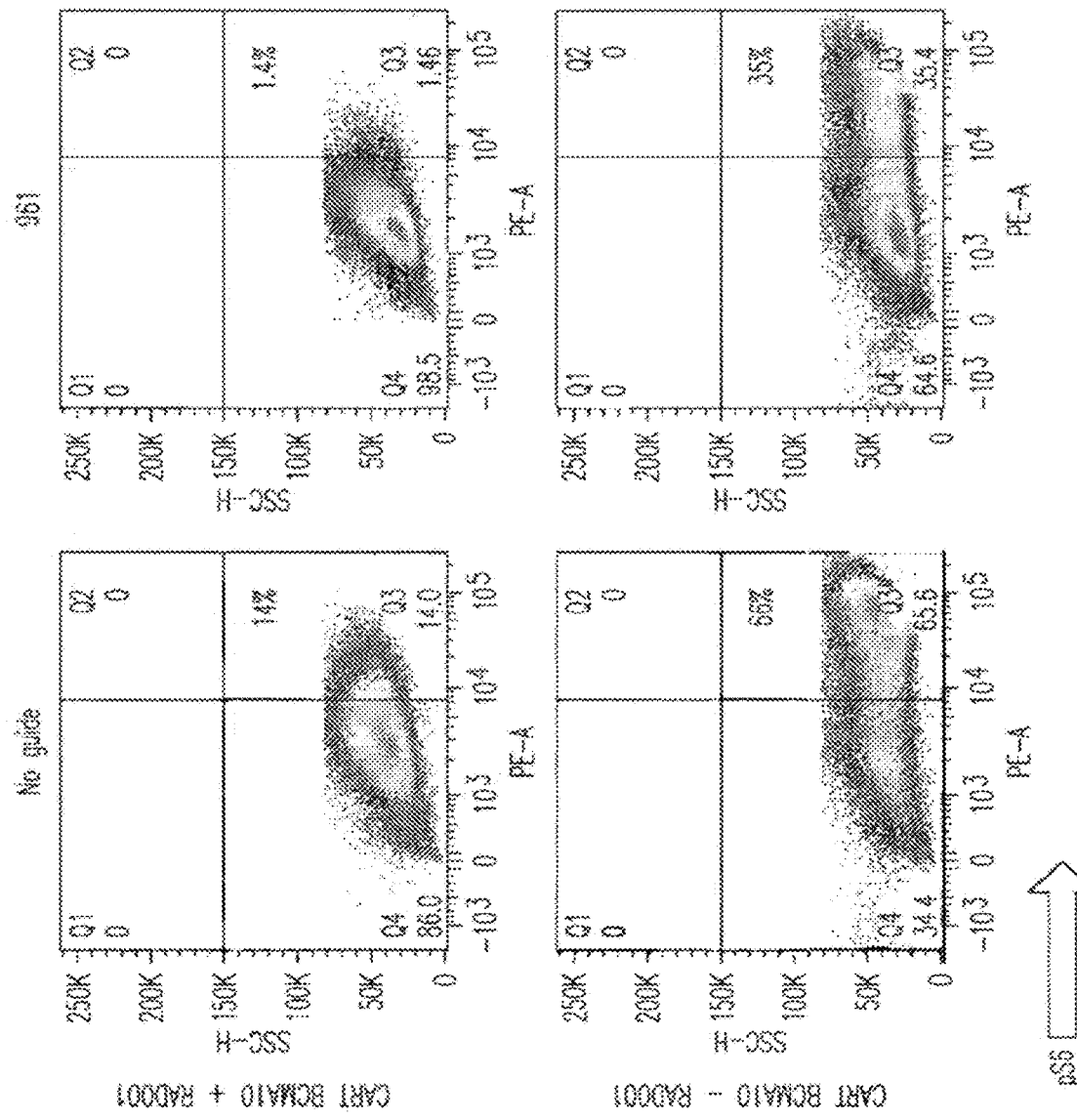
Figures 2, 58A:
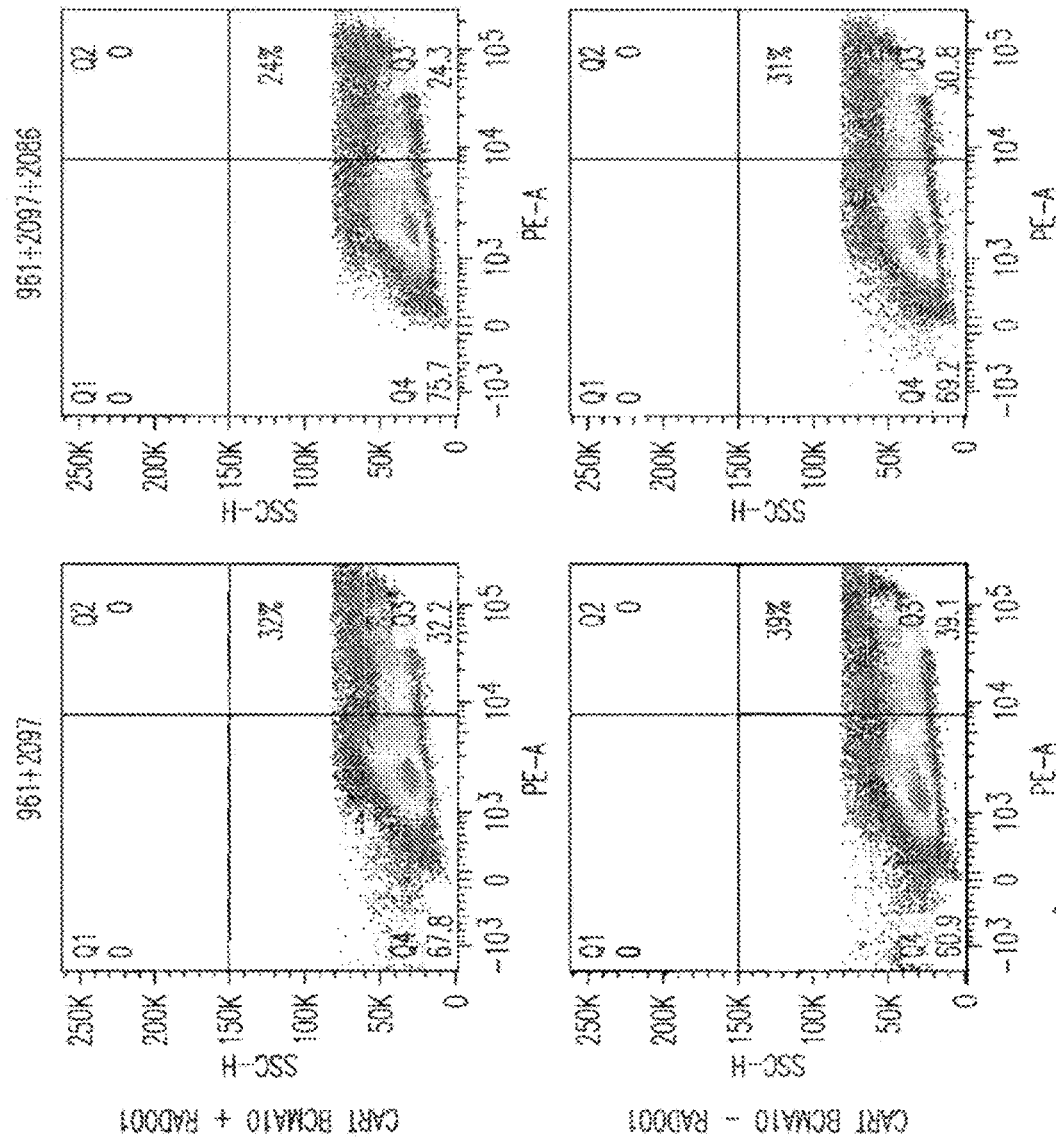
Figures 3, 58A:
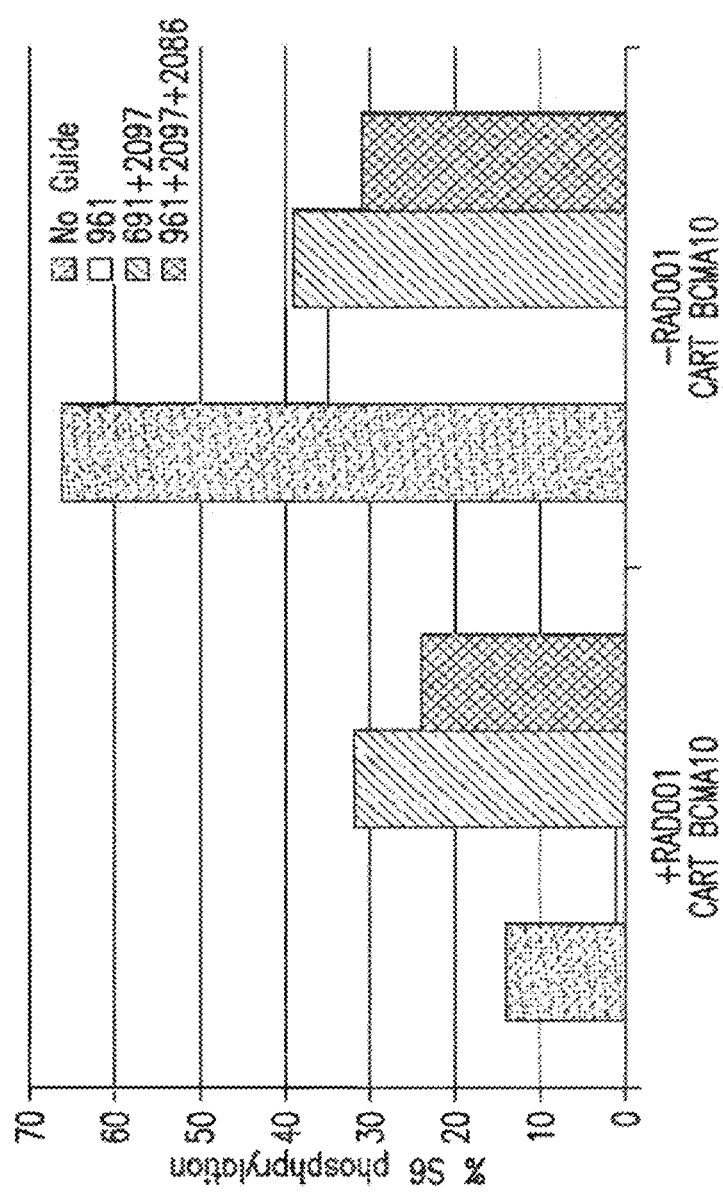
Figures 1, 58B:
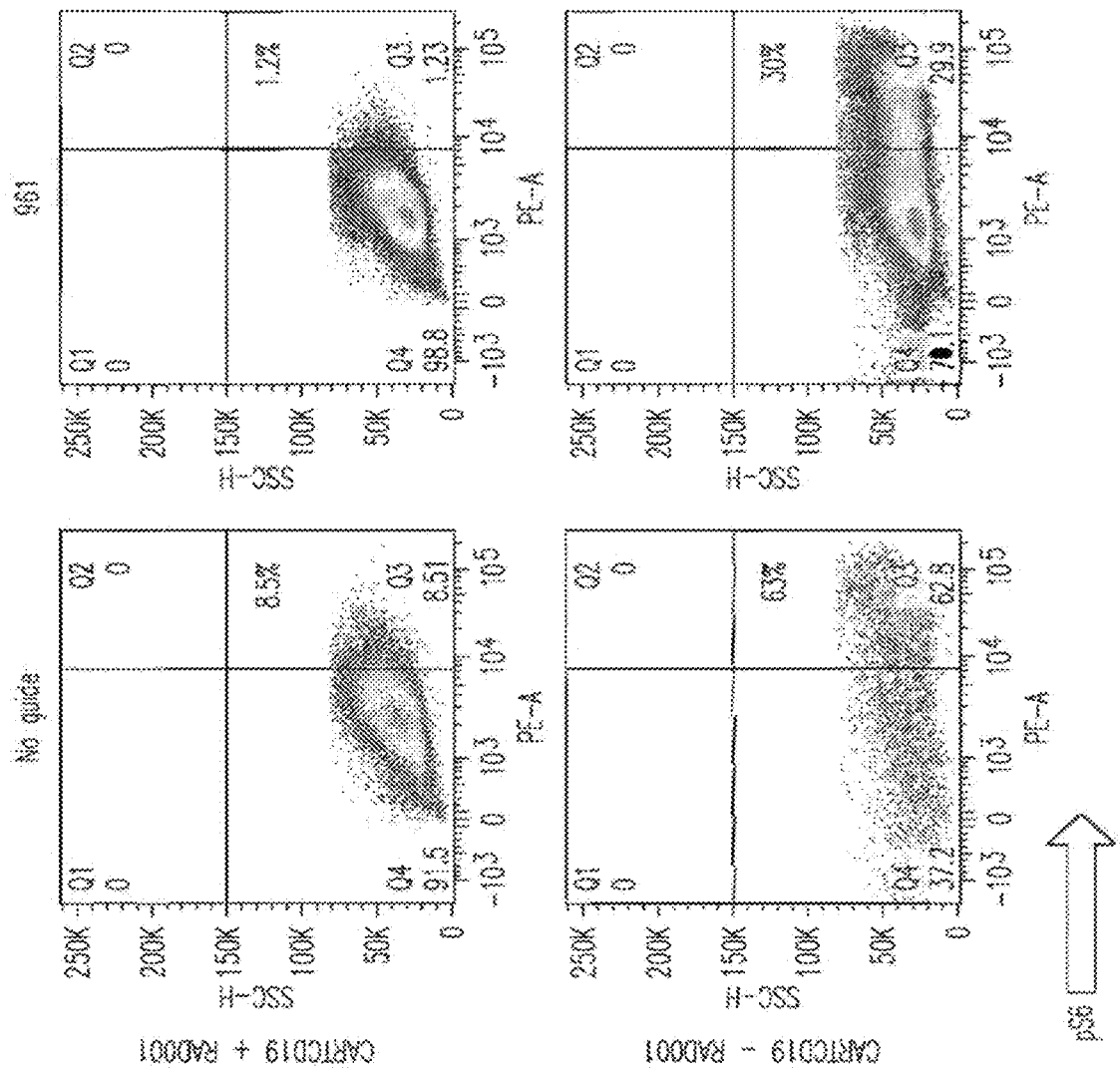
Figures 2, 58B:
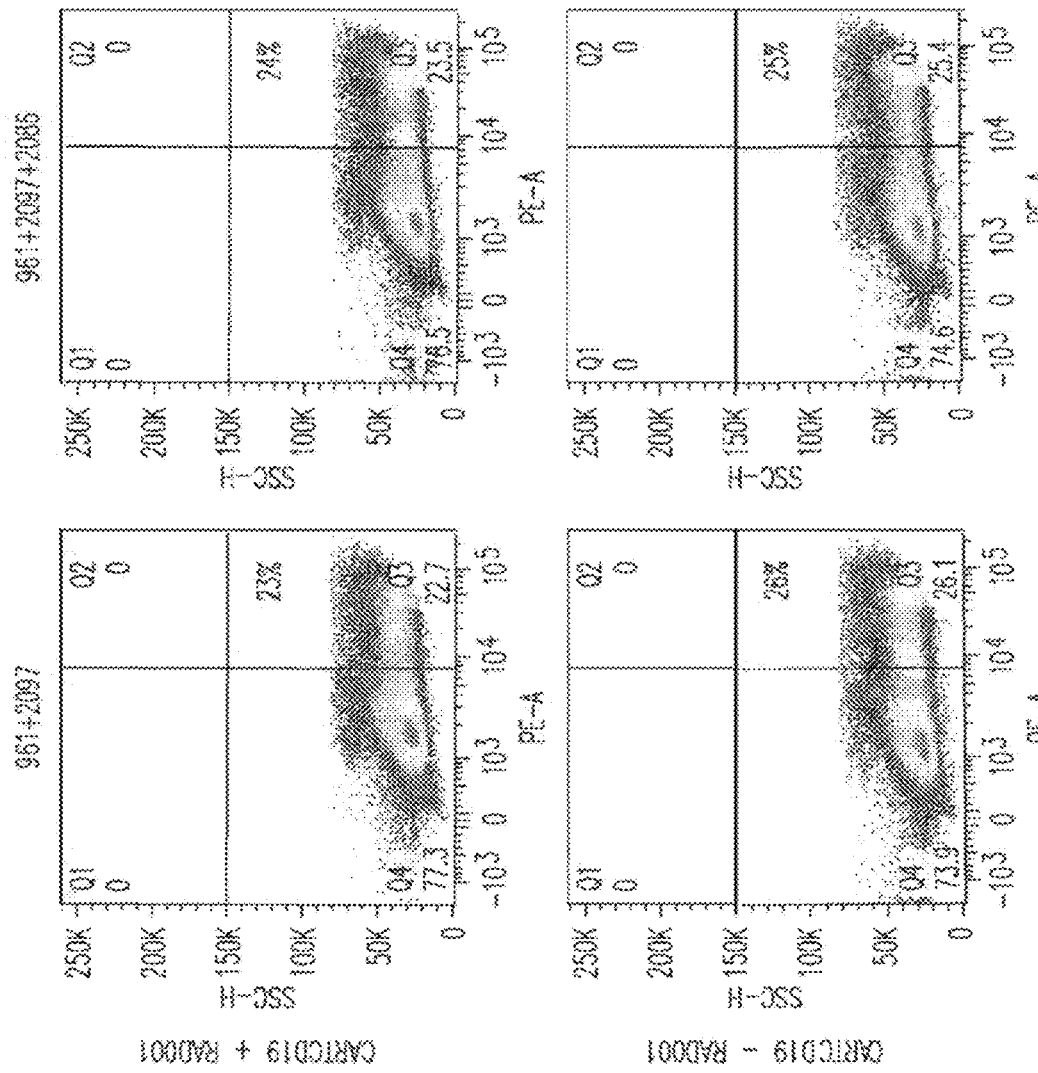
Figures 3, 58B:
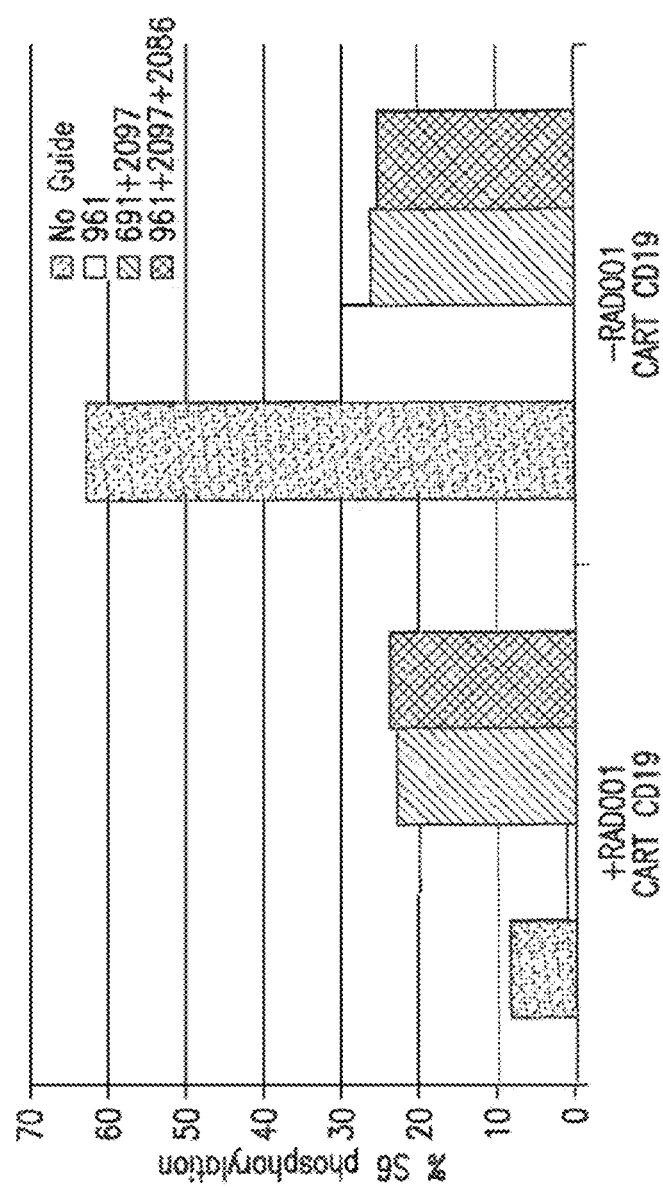
Figures 1, 58C:
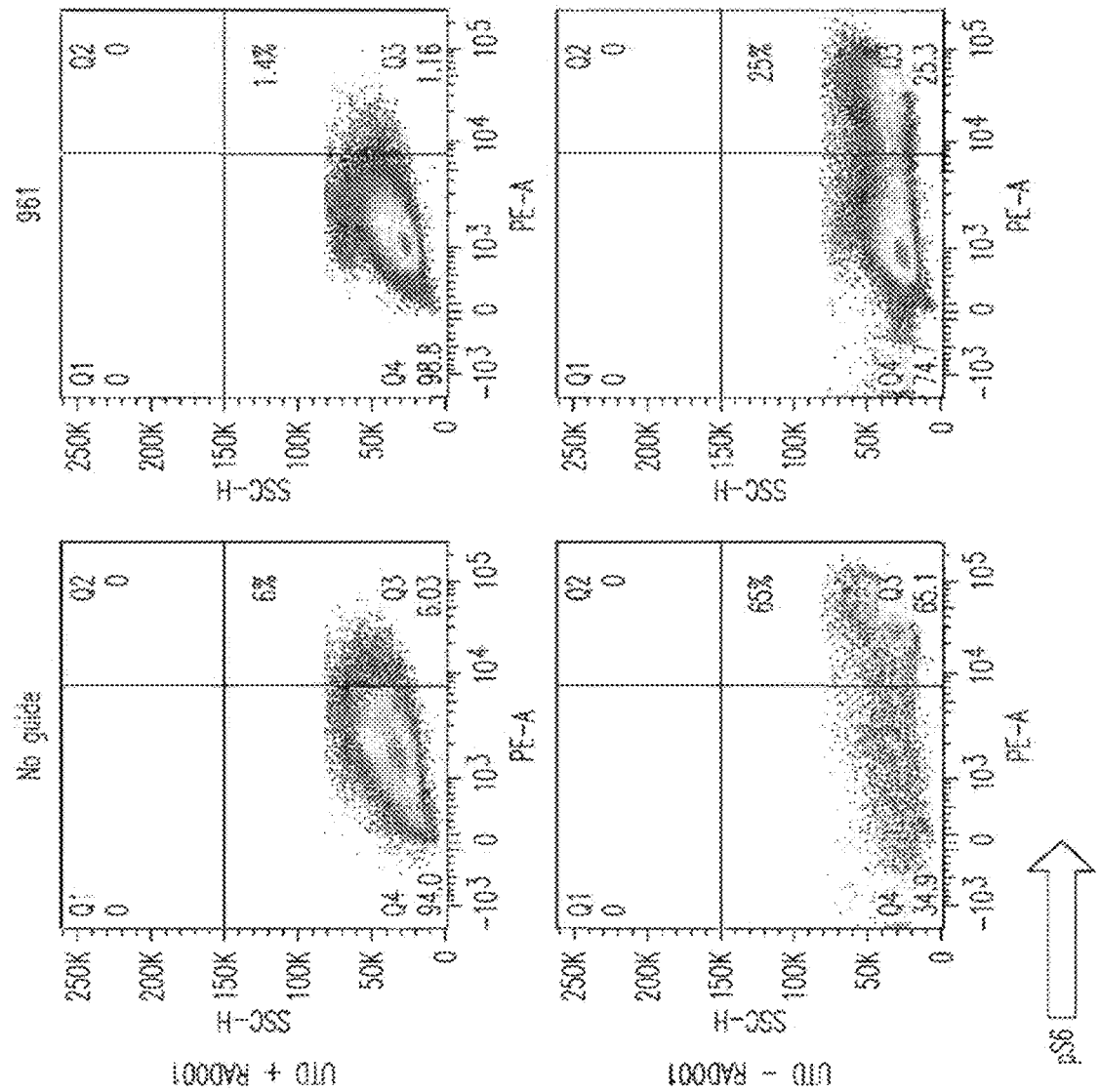
Figure 58C:
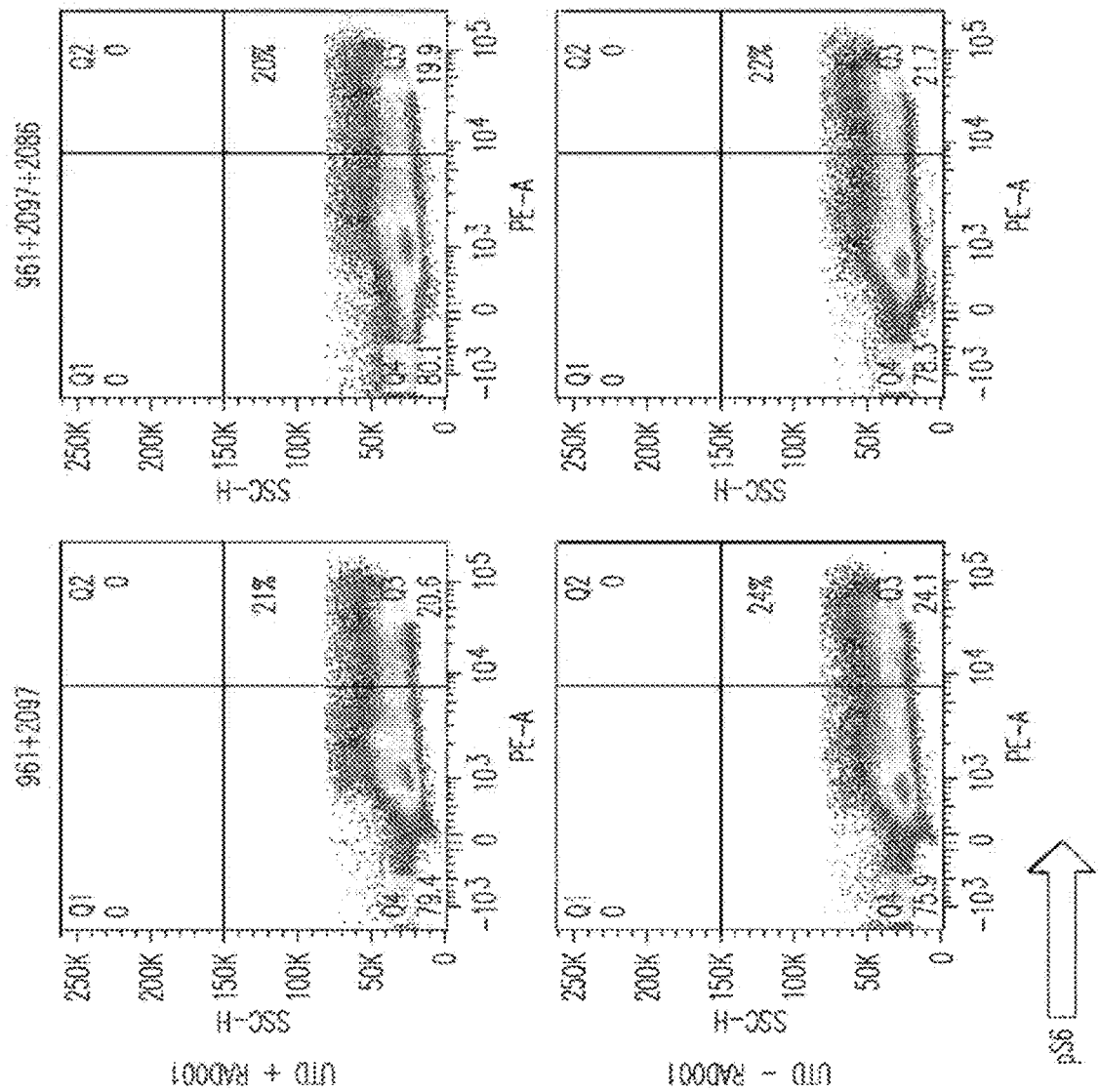
Figure 2:
Figures 3, 58C:
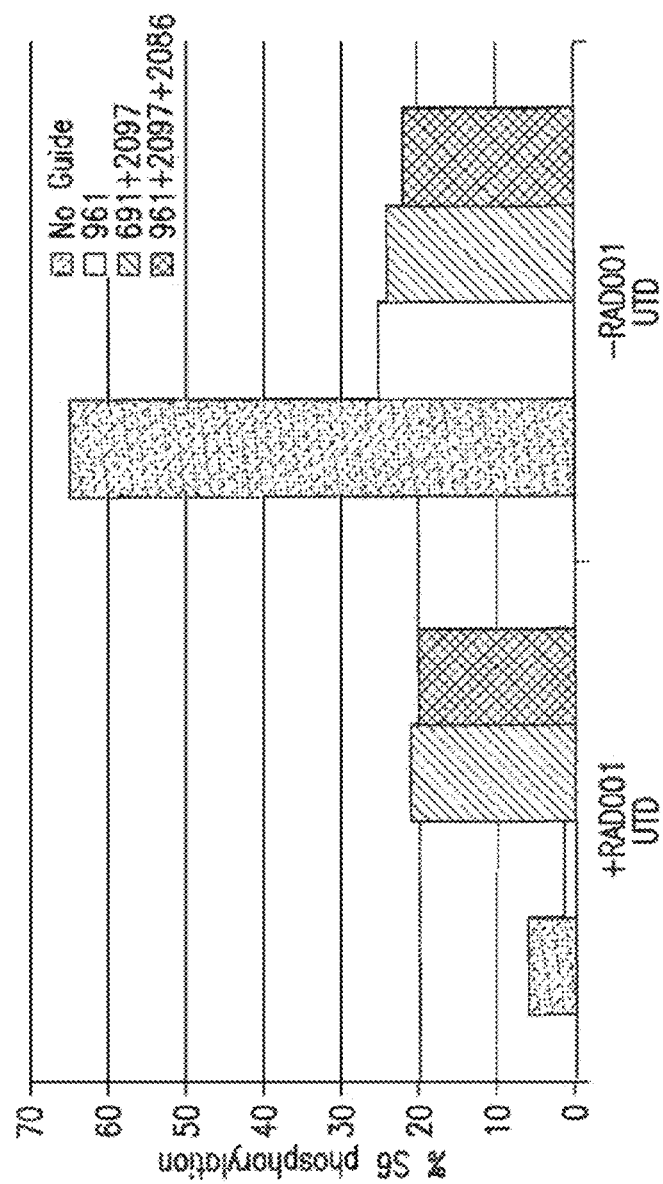

Results:

Cytokine production by CART cells in response to antigen exposure was determined. Gene editing was performed on CART cells using the CR000961 guide to target the TRAC locus and/or the CR002097 and CR002086 guides to target the FKBP1A locus (as indicated by cr961, 2097, and 2086, respectively). FIGS. 55A and 55B show interferon gamma release and IL-2 release, respectively, from edited/unedited CART cells. These data indicate that loss of FKBP12 and/or TCR through gene editing does not impair cytokine production in activated CART cells. FIG. 56 shows the killing of antigen positive cancer cell lines by edited and unedited CART cells. These data indicate that loss of FKBP12 and/or TCR through gene editing does not impair the target cell killing capacity of CART cells. FIG. 57 shows proliferation of edited and unedited CART cells in response to antigen exposure. These data indicate that loss of FKBP12 through gene editing does not impair the proliferation capacity of CART cells relative to cells treated with no guide. Finally, edited CART cells were investigated for their ability to resist immunosuppression by the rapalog RAD001. The results are shown in FIG. 58. These data indicate that editing of FKBP1A (and subsequence loss of FKBP12 protein) renders CART cells refractory to the inhibitory effects of the rapalog RAD001.

Example 14: Expression of HLA-G:B2M Fusion Protein

Without being bound by theory, it is believed that a cell that has been rendered TCR-B2M-/CIITA- may be recognized as foreign by NK cells and targeted for destruction. Thus, an otherwise unmodified TCR-/B2M-/CIITA- allogeneic CART cell may be at risk for attack when administered to, for example, a cancer patient. Again, without being bound by theory, it is believed that expression of HLA-G on said cells should suppress any NK cell activity against that cell. Because some forms of HLA-G require B2M, for cells in which expression of B2M has been reduced or eliminated, we investigated expression of a HLA-G:B2M fusion molecule.

The HLA-G/B2M fusion protein was synthesized as follows. β2 microglobulin and HLA-G amino acid sequences were obtained from databases. It is known that the HLA-G1 isoform of HLA-G forms a complex with B2M at the cell surface. In order to reconstitute this complex, for example, in a B2M- cell, the β2 microglobulin N terminal fusion polypeptide was linked to HLA-G1. Furthermore, B2M is linked to HLA-G1 through a glycine/serine (G4S)n linker (SEQ ID NO: 6629). The amino acid sequence was designed in the following order to create the fusion protein: B2M sequence—(G4S)3—HLA—G1 ("(G4S)3" disclosed as SEQ ID NO: 6594). The fusion protein nucleotide sequence was codon optimized by GeneArt® GeneOptimizer® process (Thermo Fisher Scientific Inc) for mammalian cell expression. Optimized DNA was synthesized by Genescript. Synthesized DNA was amplified by PCR (NEB, Q5® Hot Start High-Fidelity DNA Polymerase, Catalog number: M0493L) and subcloned to pELPS vector by Gibson Assembly (NEB, Catalog number: E2611L). Subclone sequence was further verified by genewiz sequencing.

HLA-G-B2M Virus or HLA-G virus was generated using LentiX-293T cells. The cells were transfected with HLA-G-B2M or HLA-G lentiviral DNA plasmid along with packaging plasmid DNA (pRSV.REV (Rev expression plasmid), pMDLg/p.RRE (Gag/Pol expression plasmid), pVSV-G (VSV glycoprotein expression plasmid)) using Lipofectamine 2000 (Invitrogen). Media was changed after 12 hours post transfection. Fresh media was added to the cells and supernatants were harvested 30 hours post media change. Using LentiX concentrator, the virus was concentrated and aliquoted to be frozen. Virus was tittered using supT1 cells. Serial dilution of supernatant containing virus was incubated with 20,000 SupT1 cells for 3 days. Fresh media was added 24 hr after transduction. Cells were harvested and washed with FACS buffer and incubated with anti HLA-G-PE antibody. (335906 Biolegend) and cells were analyzed using BD Fortessa and flowJo Software.

Figure 59:
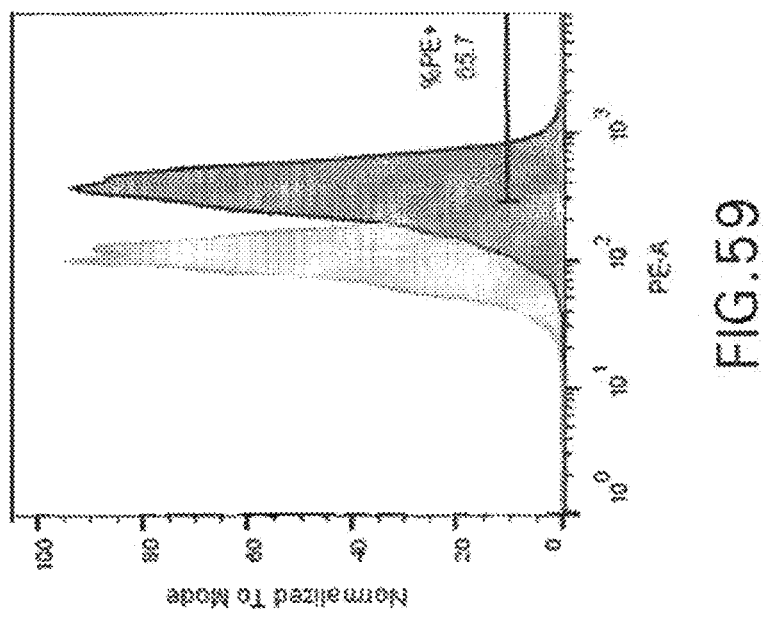
FIG. 59: Expression of HLA-G/B2M fusion protein in SupT1 cells, as detected by HLA-G flow cytometry. The light gray histogram indicates the background fluorescence in the PE channel in untransduced cells. The dark gray histogram indicates fluorescence in the PE channel from cells transduced with HLA-G/B2M.

FIG. 59 shows the results of transduction of SupT1 cells with nucleic acid encoding the HLA-G:B2M fusion described above. The HLA-G/B2M fusion protein was introduced into SupT1 cells by lentiviral transduction. Cells surface expression of HLA-G was detected by flow cytometry. The light gray histogram indicates the background fluorescence in the PE channel in untransduced cells. The dark gray histogram indicates fluorescence in the PE channel from cells transduced with HLA-G/B2M. This indicates successful expression and surface location of HLA-G:B2M fusion protein in T cells.

Example 15: Editing of CD3-Epsilon (CD3E) in HEK-293 (Cas9) Cells dgRNA molecules comprising the indicated targeting domain were chemically synthesized, and editing assessed in HEK-293 cells by NGS as described in Example 1. The results of the editing experiments are shown in Table 28. This Example shows gRNA molecules targeting CD3E are capable of editing the target locus when delivered as RNP at frequencies ranging from 3% to over 75%. Several gRNA molecules were able to edit more than 50% of the cells, including producing a frameshift mutation in more than 50% of the cells.

TABLE 28

% Edit and % Frameshift Edit with dgRNA to CD3E in HEK-293(Cas9) Cells

| Targeting Domain ID | Avg. % Edit (any indel) | Std. Dev. % Edit | Avg. Frameshift % | Std. Dev. Frameshift |
| --- | --- | --- | --- | --- |
| CR002275 | 76.01 | 5.72 | 15.70 | 0.95 |
| CR002282 | 67.86 | 4.87 | 49.37 | 3.04 |
| CR002272 | 64.58 | 4.15 | 46.13 | 2.53 |
| CR002317 | 64.37 | 8.01 | 52.67 | 7.38 |
| CR002242 | 62.63 | 14.18 | 60.27 | 13.41 |
| CR002254 | 60.61 | 11.17 | 57.40 | 10.85 |
| CR002253 | 60.56 | 12.93 | 57.47 | 12.22 |
| CR002238 | 59.48 | 9.56 | 47.73 | 8.60 |
| CR002316 | 58.02 | 6.94 | 33.73 | 1.04 |
| CR002244 | 57.67 | 8.32 | 55.70 | 7.45 |
| CR002273 | 56.67 | 14.54 | 41.70 | 12.21 |
| CR002269 | 55.71 | 9.82 | 39.57 | 6.98 |
| CR002234 | 53.46 | 5.59 | 48.40 | 4.19 |
| CR002306 | 52.44 | 2.86 | 39.37 | 2.12 |
| CR002294 | 50.53 | 2.60 | 43.10 | 2.51 |
| CR002239 | 49.40 | 10.43 | 41.43 | 9.15 |
| CR002263 | 49.02 | 10.60 | 46.10 | 9.98 |

TABLE 28-continued

% Edit and % Frameshift Edit with dgRNA to CD3E in HEK-293(Cas9) Cells

| Targeting Domain ID | Avg. % Edit (any indel) | Std. Dev. % Edit | Avg. Frameshift % | Std. Dev. Frameshift |
|---|---|---|---|---|
| CR002257 | 48.84 | 4.53 | 27.40 | 1.85 |
| CR002312 | 48.83 | 5.89 | 41.00 | 6.08 |
| CR002292 | 48.53 | 2.67 | 26.27 | 0.91 |
| CR002262 | 46.30 | 9.31 | 40.53 | 7.39 |
| CR002248 | 44.72 | 11.44 | 29.47 | 7.17 |
| CR002243 | 43.63 | 5.20 | 42.90 | 5.22 |
| CR002276 | 43.24 | 8.71 | 24.47 | 5.10 |
| CR002286 | 42.49 | 12.84 | 34.50 | 8.76 |
| CR002313 | 42.09 | 16.14 | 32.37 | 11.91 |
| CR002280 | 41.57 | 6.24 | 35.23 | 4.77 |
| CR002305 | 41.32 | 4.80 | 29.00 | 2.55 |
| CR002293 | 40.95 | 13.91 | 33.93 | 10.96 |
| CR002250 | 40.13 | 8.00 | 29.93 | 5.62 |
| CR002274 | 39.19 | 4.25 | 21.20 | 4.16 |
| CR002270 | 39.10 | 9.71 | 20.90 | 4.78 |
| CR002287 | 38.67 | 4.82 | 31.63 | 3.42 |
| CR002237 | 38.48 | 8.58 | 33.90 | 7.32 |
| CR002233 | 37.97 | 16.11 | 30.65 | 13.22 |
| CR002240 | 37.60 | 8.12 | 27.67 | 5.78 |
| CR002268 | 37.55 | 6.09 | 33.63 | 5.30 |
| CR002309 | 36.78 | 11.88 | 25.40 | 6.76 |
| CR002235 | 35.81 | 13.86 | 31.33 | 11.72 |
| CR002304 | 35.42 | 4.37 | 31.63 | 3.45 |
| CR002258 | 34.45 | 3.18 | 28.67 | 2.30 |
| CR002266 | 34.31 | 8.23 | 28.87 | 7.65 |
| CR002308 | 33.64 | 6.64 | 25.73 | 6.48 |
| CR002281 | 33.35 | 4.23 | 26.00 | 4.04 |
| CR002310 | 31.16 | 12.69 | 20.73 | 8.20 |
| CR002256 | 31.04 | 5.30 | 27.83 | 4.20 |
| CR002271 | 30.93 | 10.56 | 21.93 | 7.31 |
| CR002288 | 30.39 | 6.64 | 20.43 | 4.56 |
| CR002236 | 29.27 | 12.38 | 25.90 | 10.78 |
| CR002289 | 29.10 | 7.53 | 20.63 | 4.28 |
| CR002307 | 29.04 | 5.90 | 22.00 | 4.74 |
| CR002284 | 29.02 | 7.03 | 24.33 | 6.11 |
| CR002279 | 28.69 | 2.73 | 27.30 | 2.63 |
| CR002291 | 28.24 | 5.73 | 24.50 | 4.72 |
| CR002241 | 27.78 | 8.43 | 24.37 | 7.27 |
| CR002277 | 27.37 | 6.06 | 20.43 | 3.67 |
| CR002260 | 26.89 | 7.90 | 21.93 | 5.79 |
| CR002245 | 26.47 | 5.52 | 22.97 | 4.95 |
| CR002303 | 26.17 | 6.27 | 22.43 | 5.61 |
| CR002267 | 26.14 | 6.26 | 23.83 | 5.66 |
| CR002249 | 25.67 | 12.15 | 15.37 | 7.09 |
| CR002299 | 25.37 | 3.62 | 15.03 | 3.63 |
| CR002283 | 24.47 | 6.84 | 19.07 | 5.75 |
| CR002297 | 24.19 | 3.09 | 13.80 | 1.90 |
| CR002252 | 22.37 | 4.23 | 12.57 | 1.43 |
| CR002290 | 21.69 | 7.77 | 16.60 | 5.82 |
| CR002285 | 21.07 | 10.10 | 15.70 | 7.20 |
| CR002298 | 20.74 | 6.51 | 19.13 | 6.60 |
| CR002230 | 20.64 | 10.21 | 20.10 | 10.02 |
| CR002232 | 20.62 | 5.79 | 20.30 | 5.63 |
| CR002311 | 20.48 | 3.46 | 12.73 | 1.10 |
| CR002300 | 19.46 | 11.73 | 15.07 | 9.41 |
| CR002259 | 19.23 | 6.38 | 15.27 | 5.03 |
| CR002296 | 18.26 | 2.92 | 17.33 | 2.61 |
| CR002261 | 17.11 | 3.65 | 15.50 | 3.08 |
| CR002251 | 16.52 | 2.59 | 13.03 | 2.44 |
| CR002302 | 14.54 | 3.42 | 12.93 | 3.02 |
| CR002231 | 13.83 | 4.08 | 12.37 | 3.70 |
| CR002295 | 13.11 | 9.91 | 5.20 | 3.90 |
| CR002246 | 12.89 | 5.72 | 12.07 | 5.35 |
| CR002265 | 12.38 | 4.56 | 10.20 | 3.46 |
| CR002278 | 11.66 | 4.48 | 7.47 | 3.23 |
| CR002301 | 10.91 | 1.00 | 4.70 | 0.26 |
| CR002255 | 7.38 | 2.00 | 6.43 | 1.85 |
| CR002315 | 5.97 | 0.49 | 5.63 | 0.47 |
| CR002264 | 5.96 | 1.05 | 5.57 | 0.83 |
| CR002247 | 3.92 | 1.09 | 3.43 | 0.96 |
| CR002314 | 3.43 | 0.99 | 3.40 | 0.95 |

Example 16: Evaluation of Cas9 Variants

Evaluation in CD34+ Hematopoietic Stem Cells

Figure 60:
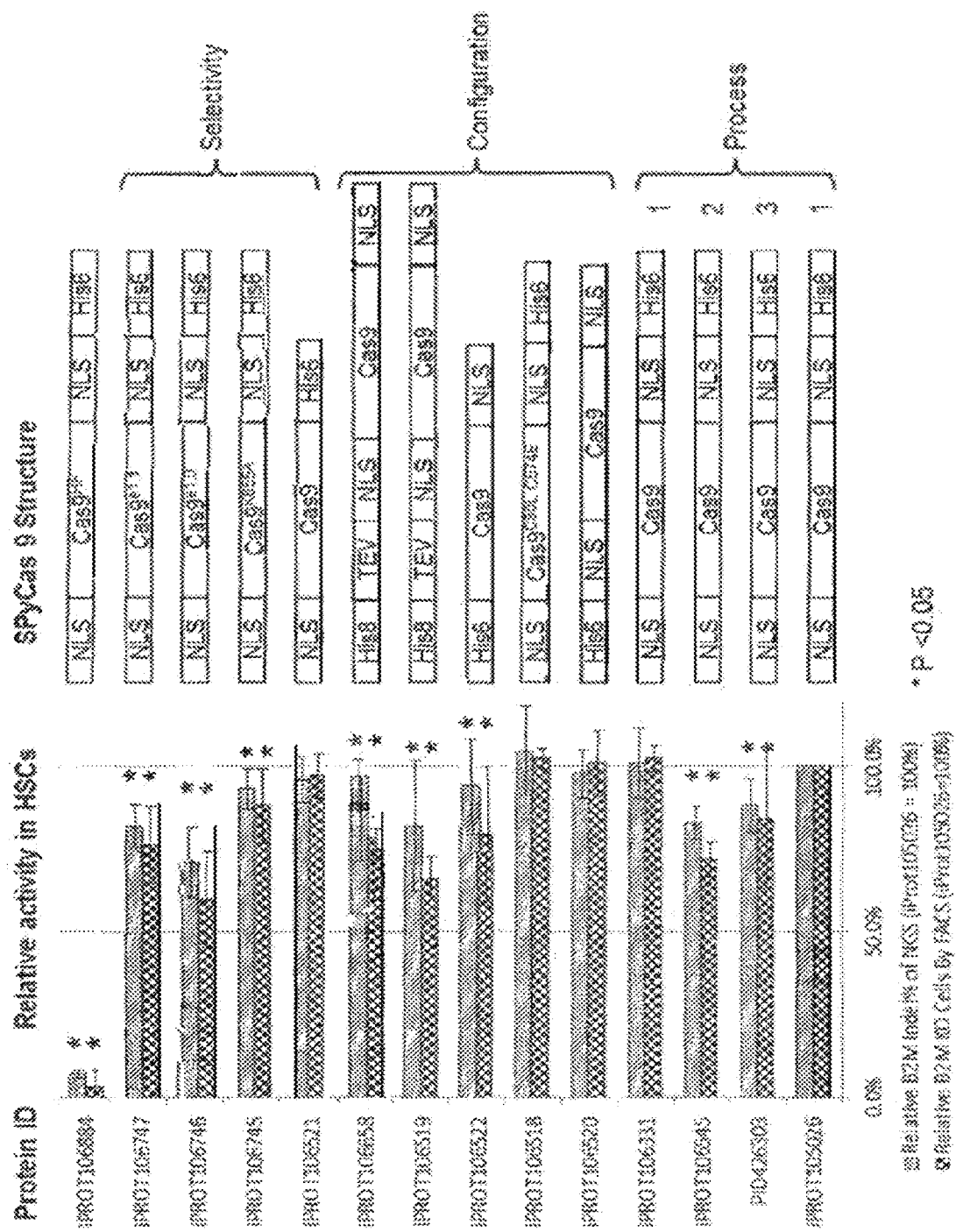
FIG. 60: Editing efficiency at targeted B2M locus in CD34+ hematopoietic stem cells by different Cas9 variants, as evaluated by NGS and Flow cytometry. NLS=SV40 NLS; His6 (SEQ ID NO: 10795) or His8 (SEQ ID NO: 10796) refers to 6 or 8 histidine residues, respectively; TEV=tobacco etch virus cleavage site; Cas9=wild type *S. pyogenes* Cas9-mutations or variants are as indicated).

We evaluated 14 purified *Streptococcus pyogenes* Cas9 (SPyCas9) proteins by measuring their efficiency of knocking out the beta-2-microglobulin (B2M) gene in primary human hematopoietic stem cells (HSCs). These proteins were divided into 3 groups: the first group consisted of SPyCas9 variants with improved selectivity (Slaymaker et al. 2015, Science 351: 84 (e1.0, e1.1 and K855A); Kleinstiver et al. 2016, Nature 529: 490 (HF)). The second group consisted of wild type SPyCas9 with different numbers and/or positions of the SV40 nuclear localization signal (NLS) and the 6× Histidine (His6) (SEQ ID NO: 10795) or 8× Histidine (His8) (SEQ ID NO: 10796) tag with or without a cleavable TEV site, and a SPyCas9 protein with two cysteine substitutions (C80L, C574E), which have been reported to stabilize Cas9 for structural studies (Nishimasu et al. 2014, Cell 156:935). The third group consisted of the same recombinant SPyCas9 produced by different processes (FIG. 60). B2M knockout was determined by FACS and next generation sequencing (NGS).

Methods

Materials

1. Neon electroporation instrument (Invitrogen, MPK5000)
2. Neon electroporation kit (Invitrogen, MPK1025)
3. crRNA (targeting domain of CR00441 (SEQ ID NO: 5495) fused to SEQ ID NO: 6607)
4. tracrRNA (SEQ ID NO: 6660)
5. Cas9 storage buffer: 20 mM Tris-C1, pH 8.0, 200 mM KCl, 10 mM $MgCl_2$
6. Bone marrow derived CD34+HSCs (Lonza, 2M-101C)
7. Cell culture media (Stemcell Technologies, StemSpam SFEM II with StemSpam CC-100)
8. FACS wash buffer: 2% FCS in PBS
9. FACS block buffer: per mL PBS, add 0.5 ug mouse IgG, 150 ug Fc block, 20 uL FCS
10. Chelex suspension: 10% Chelex 100 (bioRad, Cat #142-1253) in $H_2O$
11. Anti-B2M antibody: Biolegend, cat #316304

Process

Thaw and grow the cells following Lonza's recommendations, add media every 2-3 days. On day 5, pellet the cells at 200×g for 15 min, wash once with PBS, resuspend the cells with T-buffer from NEON kit at $2\times10^4$/uL, put on ice. Dilute Cas 9 protein with Cas9 storage buffer to 5 mg/ml. Reconstitute crRNA and tracrRNA to 100 uM with $H_2O$. The ribonucleoprotein (RNP) complex is made by mixing 0.8 uL each of CAS 9 protein, crRNA and tracrRNA with 0.6 uL of Cas9 storage buffer, incubate at room temperature for 10 min. Mix 7 uL of HSCs with RNP complex for two minutes and transfer the entire 10 uL into a Neon pipette tip, electroporate at 1700v, 20 ms and 1 pulse. After electroporation, immediately transfer cells into a well of 24-well plate containing 1 ml media pre-calibrated at 37° C., 5% $CO_2$. Harvest cells 72 hrs post-electroporation for FACS and NGS analysis.

FACS: take 250 uL of the cells from each well of 24-well plate, to wells of 96-well U-bottom plate and pellet the cells. Wash once with 2% FCS (fetal calf serum)-PBS. Add 50 uL FACS block buffer to the cells and incubate on ice for 10 minutes, add 1 uL FITC labeled B2M antibody and incubate for 30 minutes. Wash with 150 uL FACS wash buffer once followed by once more with 200 uL FACS wash buffer once. Cells were resuspended in 200 uL FACS buffer FACS analysis.

NGS sample prep: transfer 250 uL of cell suspension from each well of the 24-well plate to a 1.5 ml Eppendorf tube, add 1 mL PBS and pellet the cells. Add 100 uL of Chelex suspension, incubate at 99° C. for 8 minutes and vortex 10 seconds followed by incubating at 99° C. for 8 minutes, vortex 10 seconds. Pellet down the resin by centrifuging at 10,000×g for 3 minutes and the supernatant lysate is used for PCR. Take 4 uL lysate and do PCR reaction with the b2m primers (b2mg67F: CAGACAGCAAACTCACCCAGT (SEQ ID NO: 10807), b2mg67R: CTGACGCTTATCGACGCCCT (SEQ ID NO: 10808)) using Titanium kit (Clonetech, cat #639208) and follow the manufacturer's instruction. The following PCR conditions are used: 5 minutes at 98° C. for 1 cycle; 15 seconds at 95° C., 15 seconds at 62° C., and 1 minute at 72° C. for 30 cycles; and finally 3 minutes at 72° C. for 1 cycle. The PCR product was used for NGS.

Statistics: The percentage of B2M KO cells by FACS and the percentage of indels by NGS are used to evaluate the CAS 9 cleavage efficiency. The experiment was designed with Cas9 as fixed effect. Each experiment is nested within donors, as nested random effects. Therefore, the mixed linear model was applied for the analysis of FACS and NGS data.

Results

In order to normalize the experimental and donor variations, we graphed the relative activity of each protein to iProt105026, the original design with two SV40 NLS flanking the wild type SPyCas9 and the His6 tag (SEQ ID NO: 10795) at the C-terminal of the protein (FIG. 60). The statistical analysis shows that compared with the reference Cas9 protein iProt105026, iProt106331, iProt106518, iProt106520 and iProt106521 are not significantly different in knocking out B2M in HSCs, while the other variants tested (PID426303, iProt106519, iProt106522, iProt106545, iProt106658, iProt106745, iProt106746, iProt106747, iProt106884) are highly significantly different from the reference iProt105026 in knocking out B2M in HSCs. We found that moving the His6 tag (SEQ ID NO: 10795) from the C-terminal to N-terminal (iProt106520) did not affect the activity of the protein (FIG. 60). One NLS was sufficient to maintain activity only when it was placed at the C-terminal of the protein (iProt106521 vs. iProt106522, FIG. 60). Proteins purified from process 1 had consistent higher knockout efficiency than those from processes 2 and 3 (iProt106331 vs. iProt106545 & PID426303, FIG. 60). In general, the SPyCas9 variants with a reported improved selectivity were not as active as the wild type SPyCas9 (iProt106745, iProt106746 and iProt106747, FIG. 60). Interestingly iProt106884 did not cut the targeting site. This is consistent with the report by Kleinstiver et al that this variant failed to cut up to 20% of the legitimate targeting sites in mammalian cells (Kleinstiver et al. 2016, Nature 529: 490). Finally, the Cas9 variant with two cysteine substitutions (iProt106518) maintained high levels of enzymatic activity (FIG. 60).

Evaluation in T Cells

Methods

The different S Pyogenes Cas9 variants shown in Table 29 were used in these experiments. The structures are also shown in FIG. 60.

TABLE 29

Cas9 variants (NLS = SV40 NLS; Cas9 = S. Pyogenes Cas9 wild type, with any mutations indicated in parenthesis; Cas9e1.1 (as described in

| iprot | CAS9 (His6 disclosed as SEQ ID NO: 10795) | Size (Daltons) | Conc (ug/ml) | Molar conc. [uM] |
|---|---|---|---|---|
| 106520 | His6-GGS-NLS-CAS9-NLS | 161696.22 | 6.2 | 38.34 |
| 106518 | NLS-CAS9(C80L, C574E)-NLS-His6 | 161531.04 | 6.5 | 40.24 |
| 106521 | NLS-CAS9-His6 | 160629.9 | 6 | 37.12 |
| 106745 | NLS-CAS9(K855A)-NLS-His6 | 161437.94 | 5.9 | 36.55 |
| 106747 | NLS-CAS9e1.1-NLS-His6 | 161295.74 | 6.5 | 40.3 |
| 106154 (also referred to as 105026) | NLS-CAS9-NLS-His6 | 161495.04 | 5.9 | 36.54 |

PBMC were isolated from human blood (obtained from Hemacare/ALL Cells) by using centrifugation method using Ficoll (GE Healthcare catalog #17-1440-03). Total T cells were isolated from these PBMC's using human Pan T Cell Isolation Kit (Miltenyi Biotec #130-096-535). These cells were aliquoted, frozen using CRYOSTOR CS10 media (Biolife Solution-210102), and stored in liquid nitrogen. These frozen cell aliquots were then thawed in a 37 degree C. water bath for 20 secs and then transferred to a 50 ml conical tube in 10 ml of pre-warmed T cell media and centrifuged at 300 rpm for 5-10 mins at 24 degrees C. to remove the freezing media and resuspended with prewarmed T cell media. These are then activated by using CD3/CD28 beads (DynaBeads Invitrogen Cat #111.41D) at a bead to cell ratio of 3:1 at keeping the cell concentration at 0.5 million/ml and activated using CD3/CD28 beads (DynaBeads Invitrogen Cat #111.41D) at bead to cell ratio of 3:1 at 0.5 million/ml concentration of cells.

On Day 3 post bead activation, the 200,000 cells are used per electroporation. RNP complex used for T cell genome editing was formed using a 1:2 molar ratio of Cas9 protein to RNA (crRNA and tracRNA). 100 μM crRNA ([targeting domain]-[SEQ ID NO: 6607]) and 100 μM tracrRNA (SEQ ID NO: 6660) were denatured separately at 95° C. for 2 min and cooled to room temperature. In a final volume of 5 μL, 1.4 μL of Cas9 proteins at a concentration of 5.9 μg/μL was mixed with 1.6 μL of reaction buffer (20 mM Tris, pH8.0; 200 mM KCL, 10 mM MgCl2) and mixed with 1 μL of 100 μM tracrRNA at room temperature. Next 1 μL of 100 μM crRNA was added, mixed and incubated for 10 min at 37° C. The targeting domain for B2M was CR000442, and for TRAC was CR000961. These RNP's at higher concentrations were used to generate samples of RNP serial dilutions. These RNP dilutions were then used to mix with 200,000 cells in 10 ul of T Buffer (neon transfection system 10 ul Kit). Electroporation was performed by Neon electroporator using Neon® Transfection System 10 μL Kit (MPK1096) at 1600V, 10 ms, 3 pulses. Cells were cultured in T cell media without antibiotics. Cells were taken from each sample pipetted to dissociate them from beads and beads were removed by using 96 welled plate magnet and centrifuged with 100 ul of FACS buffer (Miltenyi MACS buffer catalog

130-092-987 with 0.5% BSA (Miltenyi-catalog #130-091-376) to wash the cells. Cells were then incubated with different antibodies diluted in 100 ul FACS buffer for 30 mins on ice. Cells were then washed two times with 200 ul of FACS buffer. Cells are then resuspended in 150 ul of FACS buffer and run on BD 5 laser Fortessa. Expression of TCR was detected by using anti-CD3-PercpCy5.5 (Ebiosciences 45-0037-42) and expression of B2M was detected by using anti-B2M-APC (316312 Biolegend). Flow cytometry data was analyzed using FlowJo Software.

Results

Figure 61:
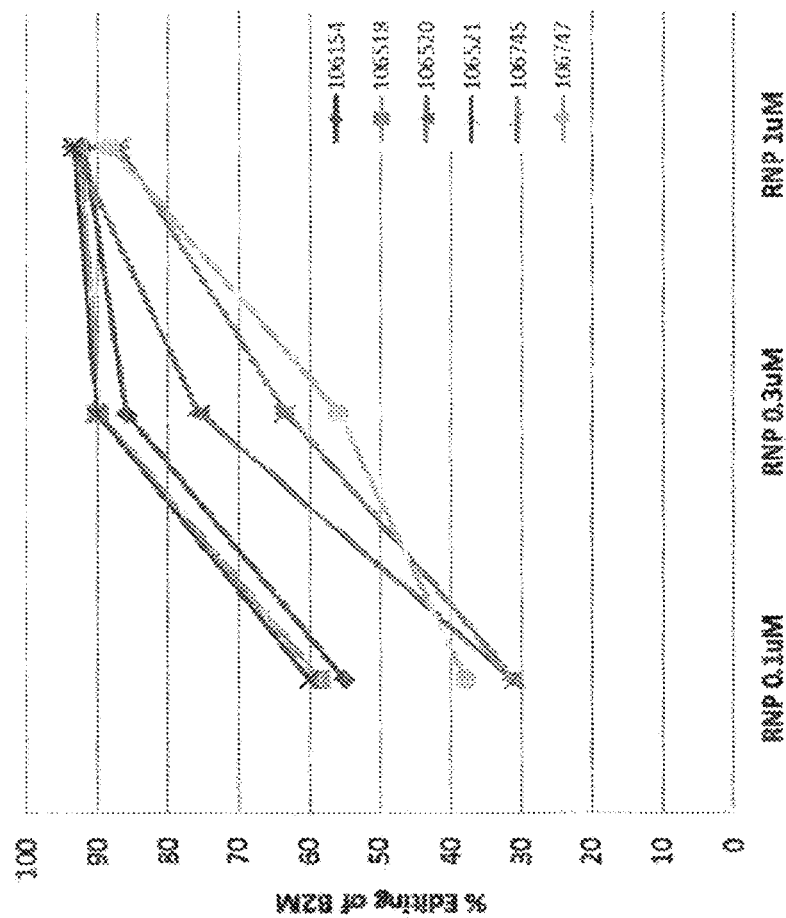
FIG. 61: Editing efficiency at targeted B2M locus in primary human T cells by different Cas9 variants and a range of concentrations, as measured by flow cytometry.
Figure 62:
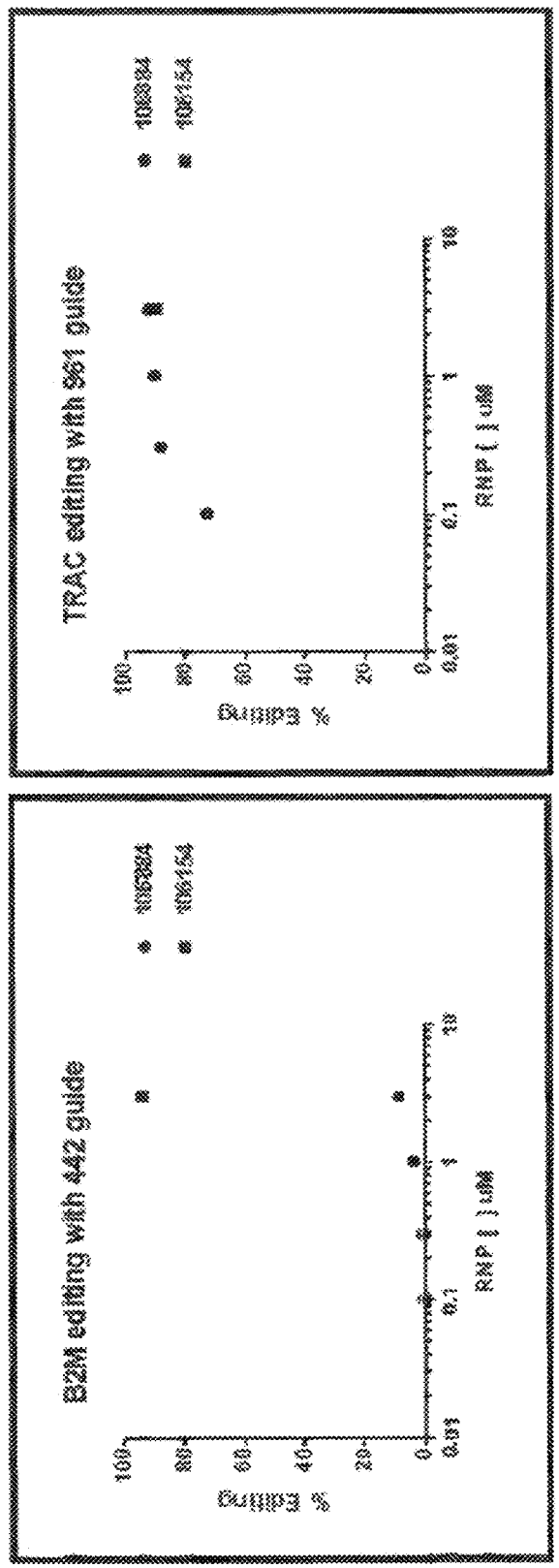
FIG. 62: Editing efficiency of two different Cas9 variants, at various concentrations, in primary human T cells using two different gRNAs targeting either B2M (left panel) or TRAC (right panel). Editing efficiency (% editing) was measured by flow cytometry by measuring the loss of cell surface expression of B2M (left panel) or TCR (right panel).

Generation of low concentrations of RNP, and highest editing efficiency, proceeded well when RNP was generated at high concentration, and then diluted to the desired concentrations. 6 different Cas9 proteins were tested for efficiency of editing using the B2M guide CR00442 in primary T cells. Editing efficiency was measured using cell surface detection by flow cytometry of the B2M protein and the results are shown in FIG. 61 (Y-axis; % Editing of B2M) 3 days after RNP electroporation at the indicated concentrations of RNP (X-axis). The different Cas9 proteins tested are indicated by their "iprot" ID numbers (see FIG. 60 and Table. The results are shown in FIG. 61. These data indicate that all of these variants of Cas9 are active, but Cas9 proteins 106521, 106518, and 106154 (also referred to as 105026) show higher activity in T cells, as evidenced by their greater activity at lower concentrations of RNP. Next, two different Cas9 proteins, 106884 or 106154 (also referred to as 105026), as indicated, were tested for editing efficiency using the B2M targeting guide CR00442 (FIG. 62, left panel) or the TRAC targeting guide CR000961 (FIG. 62, right panel) by using different concentrations of RNP as indicated on the X-axis. Editing efficiency (% editing) was measured by flow cytometry by measuring the loss of cell surface expression of B2M (FIG. 62, left panel) or TCR using CD3 epsilon antibody (FIG. 62, right panel).

Example 17: Off-Target Evaluation

T Cell Culture and CRISPR/Cas9 Genome Editing

Peripheral blood mononuclear cells (PBMC) were isolated from human blood (HemaCare, Cat #PB000) using standard Ficoll density gradient centrifugation methods. Total T cells were isolated from PBMC using the Pan T Cell Isolation Kit for human cells (Miltenyi Biotec, Cat #130-096-535) following manufacturer's recommendations and stored at −80° C. T cells were thawed and activated using Dynabeads Human T-Activator CD3/CD28 for T Cell Expansion and Activation (Thermo Fisher Scientific, Cat #11131D) at a 3:1 bead to cell number ratio following manufacturer's recommendations. T cells were cultured in antibiotic-free complete T cell medium (RPMI 1640 with L-glutamine, Lonza, Cat #12-702F; 10% FBS, GE HyClone, Cat #SH30071; 200 mM L-glutamine, GE HyClone, Cat #SH30034.01; 10 mM non-essential amino acids, GE HyClone, Cat #13-114E; 100 mM sodium pyruvate, Invitrogen, Cat #11360-070; 1 M HEPES buffer, GE HyClone, Cat #17-737E and 55 mM 2-mercaptoethanol, Invitrogen, Cat #21985-023) at 37° C., 5% $CO_2$ for 3 days prior to genome editing.

RNP complex used for T cell genome editing was formed using a 1:2 molar ratio of Cas9 protein to gRNA (crRNA and tracRNA). Chemically synthesized crRNA at a concentration of 100 µM ([targeting domain]-[SEQ ID NO: 6607]) and tracr (SEQ ID NO: 6660) at a concentration of 100 µM were denatured separately at 95° C. for 2 mM and cooled to room temperature. In a final volume of 5µ buffer (20 mM Tris, pH8.0; 200 mM KCL, 10 mM $MgCl_2$), Cas9 protein (NLS-Cas9-NLS-His6 ("His6" disclosed as SEQ ID NO: 10795); iPROT105026; NLS=SV40 NLS; Cas9=wt S. Py Cas9) was first mixed with tracrRNA at room temperature and then mixed with crRNA and incubated for 5 min at 37° C. Final concentrations of Cas9 protein, tracrRNA and crRNA used were 10 µM, 20 µM and 20 µM respectively. Bead activated T cells were collected by centrifugation and resuspended in the Neon electroporation kit T buffer (Invitrogen; Cat #MPK1096) at a cell density of $20 \times 10^6$/mL. 5 µL of RNP was mixed with 10 µl of T cells by gentle pipetting and incubated at room temperature for 5 min. The RNP T cell mixture was transferred into a 10 µL Neon electroporation tip probe. Electroporation was performed using the Neon transfection system (Invitrogen; MPK5000S) using the following conditions: 3 pulses of 1600 volts/10 milliseconds. Duplicate 10 µL electroporation reactions were performed. Electroporated T cells were then immediately transferred into 200 µL pre-warmed antibiotics-free complete T cell medium in a 96 well plate and incubated at 37° C., 5% $CO_2$ for 2 days. T cells were then diluted at 1:1 volume using antibiotics-free complete T cell medium and transferred to a 24 well plate and cultured an additional 4-7 days at 37° C., 5% $CO_2$. In parallel activated T cells without RNP treatment were similarly cultured to serve as untreated control samples. T cells were then collected by centrifugation and genomic DNA was isolated from 1-2 million cells using the DNeasy Blood & Tissue Kit (Qiagen, Cat #69506) following the manufacturer's recommendations. Genome editing was performed for gRNAs comprising the targeting domain sequences of CR00442, CR00444, CR000961 and CR000984 generating two treated and one untreated replicate per gRNA.

In Silico Identification of Potential gRNA Off-Target Loci

For gRNAs CR00442, CR00444, CR000961 and CR000984, potential off-target loci were identified by aligning the 20 nucleotide gRNA protospacer sequence to the human genome reference sequence (build GRCh38) using the BFAST sequence aligner (version 0.6.4f, Homer et al, PLoS One, 2009, 4(11), e7767, PMID: 19907642) using standard parameters allowing up to 5 nucleotide mismatches. Loci identified were filtered to only contain sites that are 5' adjacent to the Cas9 canonical 5'-NGG-3' PAM sequence (i.e. 5'-off-target locus-PAM-3'). Using the BEDTools script (version 2.11.2, Quinlan and Hall, Bioinformatics, 2010 26(6):841-2, PMID: 20110278) sites with 5 nucleotide mismatches were further filtered against RefSeq gene annotations (Pruitt et al, Nucleic Acids Res., 2014 42 (Database issue):D756-63, PMID: 24259432) to only contain loci annotated as exons. Counts of the potential off-target loci identified for each gRNA are shown in Table 30.

TABLE 30

Counts of in silico off-target loci identified for gRNAs CR00442, CR00444, CR000961 and CR00098 with 0, 1, 2, 3 and 4 nucleotide mismatches and 5 nucleotide mismatches within RefSeq exons are shown.

| Gene | gRNA name | Number of off-targets with N mismatches | | | | | 5 RefSeq exons | Total |
|---|---|---|---|---|---|---|---|---|
| | | 0 | 1 | 2 | 3 | 4 | | |
| B2M | CR00442 | 0 | 0 | 0 | 7 | 72 | 71 | 150 |
| | CR00444 | 0 | 0 | 0 | 2 | 24 | 33 | 59 |
| TRAC | CR000961 | 0 | 0 | 2 | 23 | 224 | 63 | 312 |
| | CR000984 | 0 | 0 | 0 | 3 | 40 | 15 | 58 |

PCR Primer Design for Targeted Amplification of Potential Off-Target Sites

PCR amplicons targeting potential off-target loci (and the on-target locus) identified for gRNAs CR00442, CR00444, CR000961 and CR00098 were design using Primer3 (version 2.3.6, Untergasser et al, Nucleic Acids Res., 2012 40(15):e115, PMID: 22730293) using default parameters aiming for an amplicon size range of approximately 160-300 bp in length with the gRNA protospacer sequence located in the center of the amplicon. Resulting PCR primer pairs and amplicon sequences were checked for uniqueness by BLAST searching (version 2.2.19, Altschul et al, J Mol Biol., 1990, 215(3):403-10, PMID: 2231712) sequences against the human genome reference sequence (build GRCh38). Primer pairs resulting in more than one amplicon sequence were discarded and redesigned. Table 31 provides a count of successful primer pairs designed for each gRNA.

Illumina Sequencing Library Preparation, Quantification and Sequencing

Genomic DNA from RNP treated (2 replicates per gRNA) and untreated (1 replicate per gRNA) T-cell samples was quantified using the Quant-iT PicoGreen dsDNA kit (Thermo Fisher, Cat #P7581) using manufacture's recommendations. Illumina sequencing libraries targeting individual off-target loci (and the on-target locus) were generated for each sample using two sequential PCR reactions. The first PCR amplified the target locus using target specific PCR primers (designed above) that were tailed with universal Illumina sequencing compatible sequences. The second PCR added additional Illumina sequencing compatible sequences to the first PCR amplicon, including sample barcodes to enable multiplexing during sequencing. PCR 1 was performed in a final volume of 10 µL with each reaction containing 6 ng of gDNA (equivalent to approximately 1000 cells), PCR 1 primer pairs (Integrated DNA Technologies) at a final concentration of 0.25 uM and 1× final concentration of Q5 Hot Start Master Mix (New England BioLabs, Cat #102500-140). PCR 1 left primers were 5' tailed (i.e. 5'-tail-target specific left primer-3') with sequence 5'-TCGTCGGCAGCGTCAGATGTGTATAAGAGACAG-3' (SEQ ID NO: 10810) and right primers were 5' tailed (i.e. 5'-tail-target specific right primer-3') with sequence 5'-GTCTCGTGGGCTCGGAGATGTGTATAAGA-GACAG-3' (SEQ ID NO: 10811). PCR 1 was performed on a thermocycler using the following cycling conditions: 1 cycle of 98° C. for 1 min; 25 cycles of 98° C. for 10 sec, 63° C. for 20 sec, and 72° C. for 30 sec; 1 cycle at 72° C. for 2 min. PCR 1 was then diluted 1 in 100 using nuclease free water (Ambion, Cat #AM9932) and used as input into PCR 2. PCR 2 was performed in a final volume of 10 pit with each reaction containing 2 µL of diluted PCR 1 product, PCR 2 primer pairs (Integrated DNA Technologies) at a final concentration of 0.5 µM and 1× final concentration of Q5 Hot Start Master Mix (New England BioLabs, Cat #102500-140). PCR 2 left primer sequence used was 5'-AATGA-TACGGCGACCACCGAGATCTA-CACTCGTCGGCAGCGTC-3' (SEQ ID NO: 10812) and PCR 2 right primer sequence used was 5'-CAAGCAGAA-GACGGCAT-ACGAGATNNNNNNNNGTCTCGTGGGCTCGG-3' (SEQ ID NO: 10813) where the NNNNNNNN denote an 8 nucleotide barcode sequence used for sample multiplexing as part of the standard Illumina sequencing process. PCR 2 was performed on a thermocycler using the following cycling conditions: 1 cycle of 72° C. for 3 min; 1 cycle of 98° C. for 2 min; 15 cycles of 98° C. for 10 sec, 63° C. for 30 sec, and 72° C. for 2 min. PCR 2 amplicons, now viable Illumina sequencing libraries, were cleaned up using Agencourt AMPure XP beads (Beckman Coulter, Cat #A63882) following the manufacture's recommendations. The cleaned Illumina sequencing libraries were then quantified using standard qPCR quantification methods using Power SYBR Green PCR master mix (Life Technologies, Cat #4367660) and primers specific to the Illumina sequencing library ends (forward primer sequence 5'-CAAGCAGAAGACGGCAT-ACGA-3' (SEQ ID NO: 10814) and reverse primer sequence 5'-AATGATACGGCGACCACCGAGA-3' (SEQ ID NO: 10815)). Illumina sequencing libraries were then pooled equimolar and subjected to Illumina sequencing on a MiSeq instrument (Illumina, Cat #SY-410-1003) with 300 base paired-end reads using a MiSeq Reagent Kit v3 (Illumina, Cat #MS-102-3003) following the manufacture's recommendations. A minimum of 1000-fold sequence coverage was generated for each locus. PCR, cleanup, pooling and sequencing of treated and untreated samples were performed separately to avoid any possibility of cross contamination between treated and untreated samples or PCR amplicons generated therefrom.

Illumina Sequencing Data QC and Variant Analysis

Using default parameters, the Illumina MiSeq analysis software (MiSeq reporter, version 2.6.2, Illumina) was used to generate amplicon specific FASTQ sequencing data files (Cock et al, Nucleic Acids Res. 2010, 38(6):1767-71, PMID: 20015970). FASTQ files were then processed through an internally developed variant analysis pipeline consisting of a series of public domain software packages joined together using a standard Pert script wrapper. The workflow used was divided into five stages.

Stage 1, PCR primer and on- and off-target sequence QC: For both on- and off-target sites the 20 nucleotide gRNA protospacer sequence plus PAM sequence and target specific PCR primer sequences (left and right without the additional Illumina sequenced) were aligned to the human genome reference sequence (build GRCh38) using a BLAST search (version 2.2.29+, Altschul et al, J Mol Biol., 1990, 215(3): 403-10, PMID: 2231712). On- and off-target sites with multiple genomic locations were flagged.

Stage 2, sequencer file decompression: Illumina sequencer generated FASTQ.GZ files were decompressed to FASTQ files using the gzip script (version 1.3.12) and number of reads per file was calculated. Files with no reads were excluded from further analysis.

Stage 3, sequence read alignment and quality trimming: Sequencing reads in FASTQ files were aligned to the human genome reference sequence (build GRCh38) using the BWA-MEM aligner (version Li and Durbin, Bioinformatics, 2009, 25(14):1754-60, PMID: 19451168) using 'hard-clipping' to trim 3' ends of reads of Illumina sequences and low quality bases. Resulting aligned reads, in the BAM file format (Li et al, Bioinformatics, 2009 25(16):2078-9, PMID: 19505943), were converted to FASTQ files using the SAMtools script (version 0.1.19-44428cd, Li et al, Bioinformatics, 2009 25(16):2078-9, PMID: 19505943). FASTQ files were then aligned again to the human genome reference sequence (build GRCh38) using the BWA-MEM aligner, this time without 'hard-clipping'.

Stage 4, variant (SNP and INDEL) analysis: BAM files of aligned reads were processed using the VarDict variant caller (version 1.0 'Cas9 aware' modified by developer ZhangWu Lia, Lai et al, Nucleic Acids Res., 2016, 44(11): e108, PMID: 27060149) with allele frequency detection limit set at >=0.0001 to identify variants (SNPs and INDELs). The Cas9 aware VarDict caller is based on a public domain package but able to move ambiguous variant calls, generated due to repetitive sequences in the alignment region of the variant events, toward the potential Cas9 nuclease cut site in the gRNA protospacer sequence located 3 bases 5' of the PAM sequence. The SAMtools script was used to calculate read coverage per sample amplicon to determine whether the on- and off-target sites were covered at >1000-fold sequence coverage. Sites with <1000-fold sequence coverage were flagged and more sequencing data was generated.

Stage 5, dbSNP filtering and treated/untreated differential analysis: Variants identified were filtered for known variants (SNPs and INDELs) found in dbSNP (build 142, Shery et al, Nucleic Acids Res. 2001, 29(1):308-11, PMID: 11125122). Variants in the treated samples were further filtered to exclude: 1) variants identified in the untreated control samples; 2) variants with a VarDict strand bias of 2:1 (where forward and reverse read counts supporting the reference sequence are balanced but imbalanced for the non-reference variant call); 3) variants located outside a 100 bp window around the potential Cas9 cut site; 4) single nucleotide variants within a 100 bp window around the potential Cas9 cut site. Finally only sites with a combined INDEL frequency of >2% (editing in more than approximately 20 cells) in a 100 bp window of the potential Cas9 cut site were considered. Potential active editing sites were further examined at the read alignment level using the Integrative Genome Viewer (IGV version 2.3, Robinson et al, Nat Biotechnol. 2011, 9(1):24-6, PMID: 21221095) that allows for visual inspection of read alignments to the genome reference sequence. Sites identified to have potential off-target activity were reworked a second time through the entire laboratory (starting with PCR) and analysis process.

On- and Off-Target Analysis Results

On-target sites for gRNA CR00442, CR00444, CR000961 and CR000984 all showed robust editing at the intended Cas9 cut site in both treated biological replicates with an average variant frequency of 96%, 84%, 81%, and 98% respectively. No editing was observed in any of the untreated control samples. Table 31 shows number of off-target sites identified and characterized. Uncharacterized sites either failed in PCR primer design or PCR amplification and are currently still under investigation.

gRNA CR00442: The on-target site for gRNA CR00442 showed robust editing at the intended Cas9 cut site in both treated biological replicates with an average INDEL frequency of 96%. No editing was observed in the untreated control sample. Table 31 shows the number of off-target sites characterized. Uncharacterized sites failed in PCR primer design or PCR amplification and are currently still under investigation. Characterization of potential off-target sites identified two weak off-target sites for gRNA CR00442 with average INDEL frequencies of 3.7% and 4.4% in the 100 bp window around the proposed Cas9 cut site. One site has 3 mismatches relative to the on-target gRNA protospacer sequence (5'-GGCaACaGAGCGAGACAaCT-PAM-3', PAM=GGG (SEQ ID NO: 10816)) and is located in intron 1 of the zinc finger protein 440 gene (ZNF440) on chromosome 19 at base pair position 11,815,253-11,815,275, approximately 0.9 kb away from exon 1. The second site also has 3 mismatches relative to the on-target gRNA protospacer sequence (5'-GGCgACaGAaCGAGACATCT-PAM-3', PAM=CGG (SEQ ID NO: 10817)) and is located in intron 9 of the epithelial cell-transforming sequence 2 oncogene-like gene (ECT2L) on chromosome 6 at base pair position 138,856,234-138,856,256, approximately 2 kb away from exon 9. Manual inspection of both sites showed typical INDEL patterns surrounding the proposed Cas9 cut sites typical of Cas9 mediated double stranded break non homologous end joining DNA repair. Reamplification and sequencing of both sites gave similar results. It is unclear whether editing at either site identified has any detrimental effect on gene expression or cell viability, further analysis is required.

gRNA CR00444: The on-target site for gRNA CR00444 showed robust editing at the intended Cas9 cut site in both treated biological replicates with an average INDEL frequency of 84%. No editing was observed in the untreated control sample. Table 31 shows the number of off-target sites successfully characterized. Uncharacterized sites failed in PCR primer design or PCR amplification and are currently still under investigation. To date no significant off-target activity was observed for gRNA CR00444 at sites examined. However, as Table 31 shows, there are still two sites that have not yet been characterized, one with 4 mismatches located in an intergenic region and another with 5 mismatches located in exon 4 of the non-coding dynamin 1 pseudogene 46 gene (DNM1P46). Based on the high number of mismatches in these sites it is expected that these sites will likely not show any significant editing, however further analysis is required to confirm this.

gRNA CR000961: The on-target site for gRNA CR000961 showed robust editing at the intended Cas9 cut site in both treated biological replicates with an average INDEL frequency of 81%. No editing was observed in the untreated control sample. Table 31 shows the number of off-target sites successfully characterized. Uncharacterized sites failed in PCR primer design or PCR amplification and are currently still under investigation. Characterization of potential off-target sites identified one weak off-target site for gRNA CR000961 with an average INDEL frequency of 5.5% in the 100 bp window around the proposed Cas9 cut site. The site has 3 mismatches relative to the gRNA protospacer sequence (5'-AaAGTCaCaCAGCTGGTACA-PAM-3', PAM=TGG (SEQ ID NO: 10818)) and is located in intron 12 of the doublecortin domain-containing protein 1 gene (DCDC1) on chromosome 11 at base pair position 31,102,920-31,102,942, approximately 0.6 kb away from exon 13. Manual inspection of the site showed typical INDEL patterns surrounding the proposed Cas9 cut sites typical of Cas9 mediated double stranded break non homologous end joining DNA repair. Reamplification and sequencing of the site gave similar results. It is unclear whether editing at this site has any detrimental effect on gene expression or cell viability, however further analysis is required.

gRNA CR000984: The on-target site for gRNA CR000984 showed robust editing at the intended Cas9 cut site in both treated biological replicates with an average INDEL frequency of 98%. No editing was observed in the untreated control sample. Table 31 the shows the number of off-target sites successfully characterized. Uncharacterized sites failed in PCR primer design or PCR amplification and are currently still under investigation. Characterization of off-target sites identified no significant off-target activity for gRNA CR000984 at sites examined. However, as Table 31 shows, there is still one site that has not yet been characterized. The site has 5 mismatches and is located in an exon of an uncharacterized long non-coding RNA (LOC440896). Based on the high number of mismatches it is expected that this site will likely not show any significant editing, however further analysis is required to confirm this.

TABLE 31

Counts of total number of potential off-target sites, number of successfully characterized off-target sites and number of active off-target sites identified for gRNAs CR00442, CR00444, CR000961 and CR000984 are shown.

| Gene | Targeting domain gRNA name | Total number of off-target sites | Number of off-target sites characterized | Number of active off-target sites identified |
|---|---|---|---|---|
| B2M | CR00442 | 150 | 147 (98%) | 2 |
|  | CR00444 | 59 | 57 (97%) | 0 |
| TRAC | CR000961 | 312 | 306 (98%) | 1 |
|  | CR000984 | 58 | 57 (98%) | 0 |

GUIDE-Seq Hit Validation Results

Potential off-target loci identified using the GUIDE-seq method (Tsai et al, Nat Biotechnol. 2015, 33(2):187-97, PMID: 25513782) were characterized in RNP treated and untreated T cells using the same methods described for in silico identified sites. GUIDE-Seq identified 2 potential sites for gRNA CR00442, 1 potential site for CR00444 and 1 potential site for gRNA CR000984. No active sites were identified for gRNA CR000961. Target sequencing analysis of all potential GUIDE-seq sites showed no significant activity in RNP treated T cells tested.

Off-Target Editing Assessment by Insertional Analysis

Figure 63:
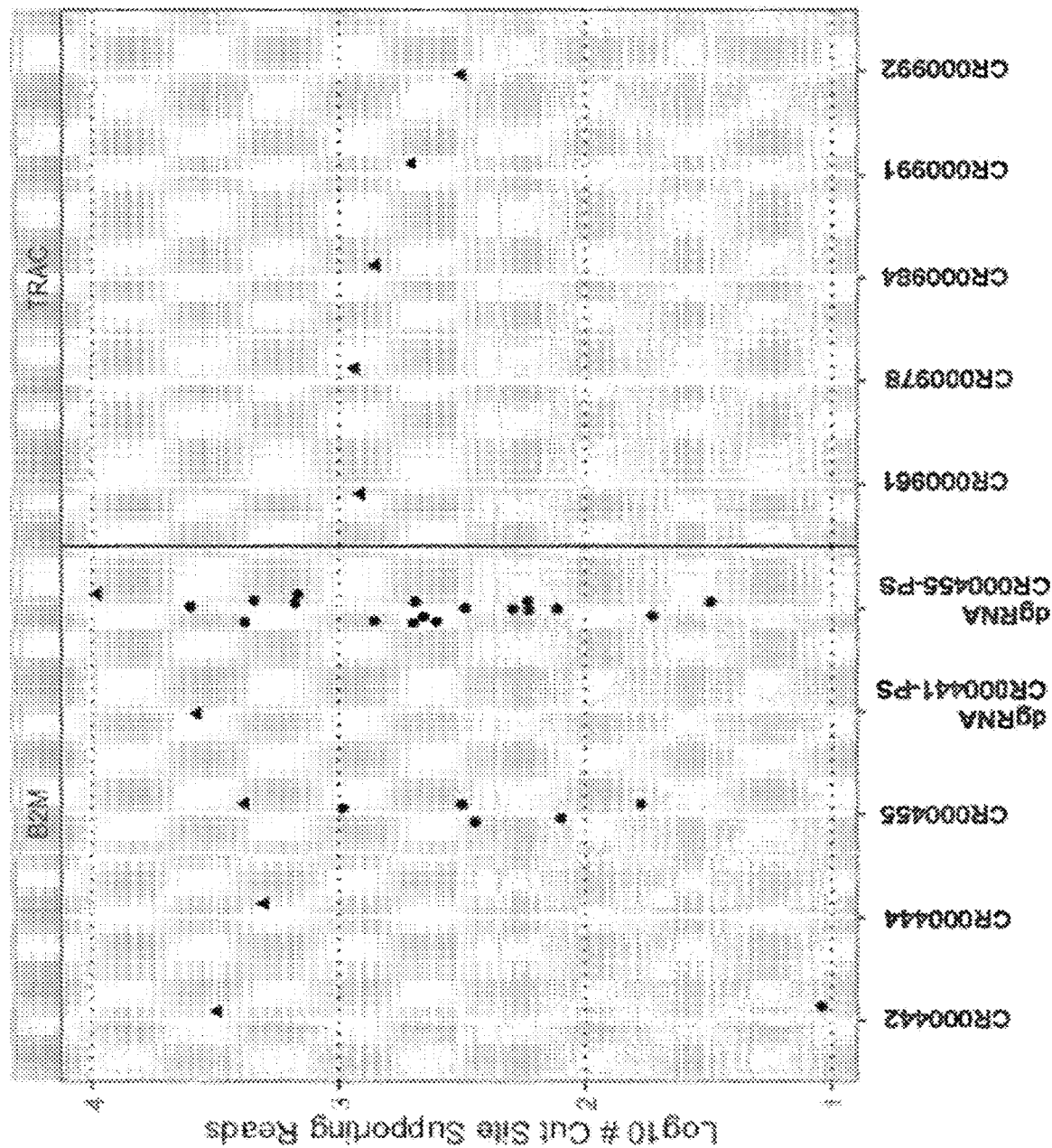
FIG. 63: Off-target activity for TRAC and B2M guides was assessed using an dsDNA oligo-insertion method in Cas9 overexpressing HEK-293 cells. The on-target site (triangle) and the potential off-target sites (circles) detected are indicated; y-axis indicates frequency of detection. All gRNAs were tested in dgRNA format with the targeting domain indicated by the CRxxxxx identifier. Where indicated, each gRNA was modified such that the 5' three internucleotide bonds and the 3' three internucleotide bonds are phosphorothioate bonds ("PS").
Figure 64:
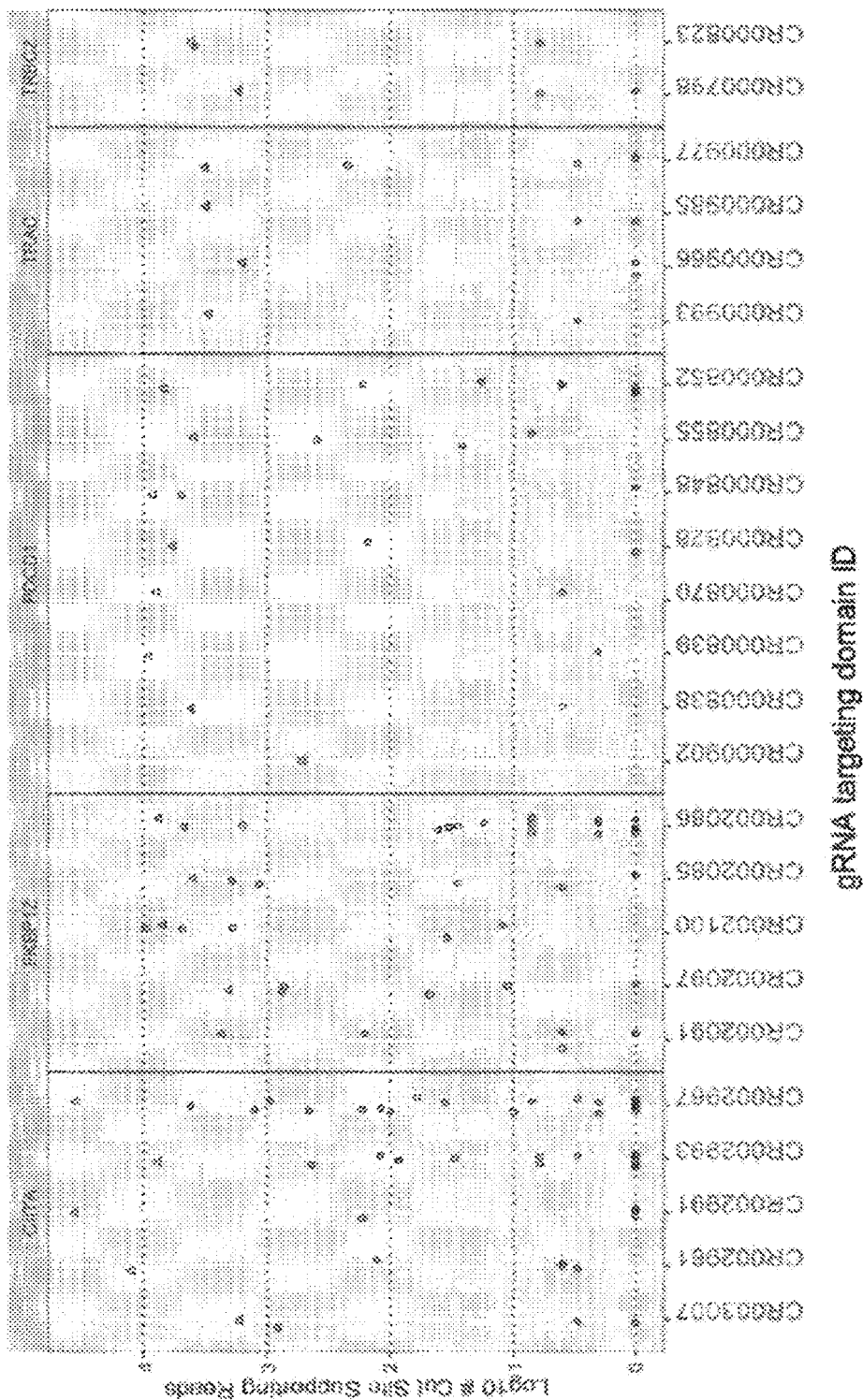
FIG. 64: Off-target activity for CIITA-, FKBP1A-, PDCD1-, TRAC- and TRBC2-targeting guide RNA molecules was assessed using an dsDNA oligo-insertion method in Cas9 overexpressing HEK-293 cells. The on-target site (triangle) and the potential off-target sites (circles) detected are indicated; y-axis indicates frequency of detection. All gRNAs were tested in dgRNA format with the targeting domain indicated by the CRxxxxx identifier.

An oligo insertion based assay (See, e.g., Tsai et al., *Nature Biotechnology*. 33, 187-197; 2015) was used to determine potential off-target genomic sites cleaved by Cas9 targeting B2M TRAC, TRBC2, PDCD1, CIITA, and FKBP1A. A total of 34 guideRNAs (dual guide RNAs comprising the indicated targeting domain, modified or unmodified, as indicated) targeting B2M (5), TRAC (9), TRBC2 (2), PDCD1 (8), FKBP1A (5), or CIITA (5) were screened in the Cas9-expressing HEK293 cells described above in Example 1, and the results are plotted in FIG. 63 and FIG. 64. The assay detected high-efficiency editing at the expected target sequences. No off-target editing was observed for the B2M-targeting gRNA comprising the targeting domain of CR00444 or the targeting domain of CR00441, and only a single very low-efficiency off-target edit was detected using the B2M-targeting gRNA comprising the targeting domain of CR00442. The results show that for gRNAs targeting TRAC comprising the targeting domain of CR00961, CR00978, CR00984, CR00991 and CR00992, each resulted in high-efficiency editing of the target sequence without editing at any off-target location. As well, no off-target editing was detected for the PDCD1-targeting gRNA comprising the targeting domain of CR00902. With respect to gRNA molecules which demonstrated potential off-target editing in this assay, deep sequencing will be used to determine whether the potential sites are bona fide off-target sites cleaved by Cas9. As well, any potential off-target edit will be assessed for presence and frequency in T-cells.

Example 18: Editing of CD3 Delta and CD3 Gamma in Primary Human CD3+ Cells

Editing of CRISPR systems containing dgRNA molecules comprising targeting domains to sequences of CD3 delta and CD3 gamma were tested for editing in primary CD3+ T cells (gRNA/Cas9 RNP delivered by electroporation) according to the methods described herein. Surface expression of CD3 after editing was assayed by flow cytometry. Briefly, edited CD3+ cells were stained with antibodies against CD3 (OKT3, BioLegend) at day 7 post-electroporation. Expression of CD3 in live cells (identified using 7AAD exclusion) relative to the un-edited controls was used to determine frequency of RNP editing. The results are reported in FIG. 65 and FIG. 66, which include flow cytometry data showing the % editing in primary human CD3+ T cells as measured by loss of surface expression of CD3. Notably, the dgRNA comprising the targeting domain of CR005334 resulted in 98% loss of CD3.

The present invention is not to be limited in scope by the exemplified constructs, since the exemplified embodiments are intended to illustrate only certain aspects of the invention and any constructs that are functionally equivalent are within the scope of this invention. Various modifications of the invention in addition to those shown and described herein will become apparent to those skilled in the art from the foregoing description and fall within the scope of the appended claims.

It is understood that the application of the teachings of the present invention to a specific problem or situation will be within the capabilities of one having ordinary skill in the art in light of the teachings contained herein.

The disclosures of each and every citation in the specification are expressly incorporated herein by reference.

This application is being filed with a sequence listing. To the extent there are any discrepancies between the sequence listing and any sequence recited in the specification, the sequence recited in the specification should be considered the correct sequence. Unless otherwise indicated, all genomic locations are according to hg38.

LENGTHY TABLES

The patent contains a lengthy table section. A copy of the table is available in electronic form from the USPTO web site (https://seqdata.uspto.gov/?pageRequest=docDetail&DocID=US12037583B2). An electronic copy of the table will also be available from the USPTO upon request and payment of the fee set forth in 37 CFR 1.19(b)(3).

SEQUENCE LISTING

The patent contains a lengthy sequence listing. A copy of the sequence listing is available in electronic form from the USPTO web site (https://seqdata.uspto.gov/?pageRequest=docDetail&DocID=US12037583B2). An electronic copy of the sequence listing will also be available from the USPTO upon request and payment of the fee set forth in 37 CFR 1.19(b)(3).

The invention claimed is:

1. A gRNA molecule comprising a tracr and a crRNA, wherein the crRNA comprises a targeting domain that is complementary to a target sequence of B2M, wherein the targeting domain comprises at least 19 consecutive nucleotides of a sequence selected from SEQ ID NO: 5498, SEQ ID NO: 5496, SEQ ID NO: 5499, or SEQ ID NO: 5509.

2. The gRNA molecule of claim 1, wherein the targeting domain comprises SEQ ID NO: 5498, SEQ ID NO: 5496, SEQ ID NO: 5499, or SEQ ID NO: 5509.

3. The gRNA molecule of claim 1, wherein the gRNA molecule comprises SEQ ID NO: 7858 or SEQ ID NO: 7853.

4. The gRNA molecule of claim 1, wherein the targeting domain comprises SEQ ID NO: 5498.

5. The gRNA molecule of claim 1, wherein the targeting domain and the tracr are disposed on separate nucleic acid molecules, and wherein the nucleic acid molecule comprising the targeting domain comprises SEQ ID NO: 6607, disposed immediately 3' to the targeting domain, and wherein the nucleic acid molecule comprising the tracr comprises SEQ ID NO: 6660.

6. The gRNA molecule of claim 1, wherein the gRNA molecule comprises one or more nucleic acid molecules comprising:
   a) one or more phosphorothioate modification(s) at the 3' end of said nucleic acid molecule or molecules;
   b) one or more phosphorothioate modification(s) at the 5' end of said nucleic acid molecule or molecules;
   c) one or more 2'-O-methyl modification(s) at the 3' end of said nucleic acid molecule or molecules;
   d) one or more 2'-O-methyl modification(s) at the 5' end of said nucleic acid molecule or molecules;
   e) one or more 2' O-methyl modification at each of the 4th-to-terminal, 3rd-to-terminal, and 2nd-to-terminal 3' residues of said nucleic acid molecule or molecules; or
   f) any combination thereof.

7. A nucleic acid comprising a sequence that encodes the gRNA molecule of claim 1.

8. A vector comprising the nucleic acid of claim 7.

9. The vector of claim 8, wherein the vector is selected from the group consisting of a lentiviral vector, an adenoviral vector, an adeno-associated viral (AAV) vector, a herpes simplex virus (HSV) vector, a plasmid, a minicircle, a nanoplasmid, and an RNA vector.

10. A composition comprising: (i) a gRNA molecule of claim 1 or nucleic acid comprising a sequence that encodes the gRNA molecule of claim 1; and (ii) a Cas9 molecule or a nucleic acid encoding a Cas9 molecule.

11. The composition of claim 10, wherein the Cas9 molecule comprises any one of SEQ ID NO: 6611 or SEQ ID NO: 7821 to SEQ ID NO: 7831, or a sequence having at least 95% homology thereto.

12. The composition of claim 10, wherein the gRNA molecule and Cas9 molecule are present in a ribonuclear protein complex (RNP).

13. The composition of claim 10, further comprising a second gRNA molecule; a second gRNA molecule and a third gRNA molecule; or a second gRNA molecule, a third gRNA molecule, and a fourth gRNA molecule, wherein the second gRNA molecule, third gRNA molecule, and fourth gRNA molecule are each complementary to a different target sequence.

14. A composition comprising:
   a) a first gRNA molecule comprising the gRNA molecule of claim 1; and
   b) a second gRNA molecule comprising a tracr and a crRNA, wherein the crRNA of said second gRNA molecule comprises a targeting domain selected from any one of SEQ ID NO: 5528 to SEQ ID NO: 5623, SEQ ID NO: 5816 to SEQ ID NO: 5965, SEQ ID NO: 5624 to SEQ ID NO: 5643, SEQ ID NO: 5966 to SEQ ID NO: 6097, SEQ ID NO: 5644 to SEQ ID NO: 5719, SEQ ID NO: 6098 to SEQ ID NO: 6226, SEQ ID NO: 84 to SEQ ID NO: 392, SEQ ID NO: 393 to SEQ ID NO: 532, SEQ ID NO: 10780 to SEQ ID NO: 10794, SEQ ID NO: 533 to SEQ ID NO: 839, SEQ ID NO: 10677 to SEQ ID NO: 10764, SEQ ID NO: 840 to SEQ ID NO: 968, and SEQ ID NO: 10765 to SEQ ID NO: 10779.

15. The composition of claim 14, wherein the targeting domain of said second gRNA molecule is selected from any one of SEQ ID NO: 5624 to SEQ ID NO: 5643 and SEQ ID NO: 5966 to SEQ ID NO: 6097.

16. The composition of claim 14, further comprising a third gRNA molecule comprising a tracr and a crRNA, wherein the crRNA of said third gRNA molecule comprises a targeting domain selected from any one of SEQ ID NO: 6325 to SEQ ID NO: 6583, SEQ ID NO: 6662 to SEQ ID NO: 6749, SEQ ID NO: 6750 to SEQ ID NO: 7716, SEQ ID NO: 7717 to SEQ ID NO: 7804, and SEQ ID NO: 8622 to SEQ ID NO: 10089.

17. The composition of claim 16, wherein the targeting domain of said third gRNA molecule is selected from any one of SEQ ID NO: 6750 to SEQ ID NO: 7716 and SEQ ID NO: 7717 to SEQ ID NO: 7804.

18. The composition of claim 16, further comprising a fourth gRNA molecule comprising a tracr and a crRNA, wherein the crRNA of said fourth gRNA molecule comprises a targeting domain that is complementary to a target sequence of a target of an NK inhibitory molecule.

19. The composition of claim 18, wherein the target of an NK inhibitory molecule is LILRB1.

20. The composition of claim 18, wherein the targeting domain of said fourth gRNA molecule consists of:
    a) any one of SEQ ID NO: 10090 to SEQ ID NO: 10673;
    b) 17, 18, 19, 20, 21, 22, 23, or 24 consecutive nucleotides of any one of SEQ ID NO: 10090 to SEQ ID NO: 10673;
    c) the 5' 17, 18, 19, 20, 21, 22, 23 or 24 nucleotides, preferably 20 nucleotides, of any one of SEQ ID NO: 10090 to SEQ ID NO: 10673; or
    d) the 3' 17, 18, 19, 20, 21, 22, 23 or 24 nucleotides, preferably 20 nucleotides, of any one of SEQ ID NO: 10090 to SEQ ID NO: 10673.

21. The composition of claim 10, formulated in a medium suitable for electroporation.

22. The composition of claim 10, further comprising a template nucleic acid.

23. The composition of claim 22, wherein the template nucleic acid is in a vector.

24. The composition of claim 22, wherein the template nucleic acid comprises a nucleic acid encoding a chimeric antigen receptor (CAR).

25. The composition of claim 24, wherein the CAR is:
    (a) a CD19 CAR;
    (b) a BCMA CAR;
    (c) a CD20 CAR;
    (d) a CD22 CAR;
    (e) a CD123 CAR;
    (f) an EGFRvIII CAR; or
    (g) a mesothelin CAR.

26. The composition of claim 22, wherein the template nucleic acid comprises a nucleic acid encoding an NK inhibitory molecule.

27. A method of altering a target sequence of a cell, comprising contacting said cell with:
    a) a gRNA molecule of claim 1, and a Cas9 molecule;
    b) a gRNA molecule of claim 1, and a nucleic acid encoding a Cas9 molecule;
    c) a nucleic acid encoding a gRNA molecule of claim 1 and a Cas9 molecule;
    d) a nucleic acid encoding a gRNA molecule of claim 1, and a nucleic acid encoding a Cas9 molecule;
    e) any of a) to d), above, and a template nucleic acid; or
    f) any of a) to d) above, and a nucleic acid comprising sequence encoding a template nucleic acid; and
    (g) any one of a) to f), above, and one or more additional gRNA molecules.

28. The method of claim 27, wherein the gRNA molecule or the nucleic acid encoding the gRNA molecule, and the Cas9 molecule or the nucleic acid encoding the Cas9 molecule, are formulated in more than one composition.

29. The method of claim 27, wherein the gRNA molecule or the nucleic acid encoding the gRNA molecule, the Cas9 molecule or the nucleic acid encoding the Cas9 molecule, and, if present, the one or more additional gRNA molecule(s) and template nucleic acid are introduced into the cell by electroporation.

30. The method of claim 27, wherein the cell is a mammalian, primate, or human cell.

31. The method of claim 27, wherein the cell is an immune effector cell.

32. The method of claim 31, wherein the immune effector cell is a T cell or NK cell.

33. The method of claim 31, wherein the immune effector cell is a T cell, wherein the T cell is a CD4+ T cell, a CD8+ T cell, or a combination thereof.

34. The method of claim 27, wherein the cell is autologous or allogeneic with respect to a patient to be administered said cell.

35. The method of claim 27, wherein contacting the cell comprises introducing a nucleic acid sequence encoding a chimeric antigen receptor (CAR).

36. The method of claim 35, wherein the nucleic acid sequence encoding the CAR is in a vector.

37. The method of claim 35, wherein the CAR is:
    (a) a CD19 CAR;
    (b) a BCMA CAR;
    (c) a CD20 CAR;
    (d) a CD22 CAR;
    (e) a CD123 CAR;
    (f) an EGFRvIII CAR; or
    (g) a mesothelin CAR.

38. The method of claim 37, wherein:
    (a) the CAR is a CD19 CAR comprising an antigen binding domain comprising any one of SEQ ID NO: 7883 to SEQ ID NO: 7898;
    (b) the CAR is a CD19 CAR and comprises any one of SEQ ID NO: 7908 to SEQ ID NO: 7920;
    (c) the CAR is a BCMA CAR comprising an antigen binding domain comprising any one of SEQ ID NO: 7939 to SEQ ID NO: 8112;
    (d) the CAR is a BCMA CAR and comprises any one of SEQ ID NO: 8549 to SEQ ID NO: 8621; or
    (e) the CAR is a CD123 CAR and comprises any one of SEQ ID NO: 7812-7818.

39. A cell, altered by the method of claim 27.

40. A cell, comprising the gRNA molecule of claim 1 or an indel at or near a target sequence that is complementary to the targeting domain of the gRNA molecule of claim 1.

41. The cell of claim 40, wherein the gRNA molecule comprises SEQ ID NO: 7858 or SEQ ID NO: 7853.

42. The cell of claim 40, wherein the cell comprises a nucleic acid sequence encoding a chimeric antigen receptor (CAR).

43. The cell of claim 40, wherein the cell comprises a second gRNA molecule, or a nucleic acid encoding a second gRNA molecule, or an indel at or near a target sequence that is complementary to the targeting domain of a second gRNA molecule, wherein the first gRNA molecule and second gRNA molecule comprise nonidentical targeting domains.

44. The cell of claim 43, wherein the second gRNA molecule comprises a targeting domain complementary with a target sequence of an inhibitory molecule or downstream effector of signaling through an inhibitory molecule, wherein the inhibitory molecule or downstream effector of signaling through an inhibitory molecule is CD274, HAVCR2, LAG3, PDCD1, PD-L2, CTLA4, CEACAM, VISTA, BTLA, TIGIT, LAIR1, CD160, 2B4, CD80, CD86, B7-H3 (CD113), B7-H4 (VTCN1), HVEM (TNFRSF14 or CD107), KIR, A2aR, MHC class I, MHC class II, GAL9, adenosine, TGF beta, or PTPN11.

45. The cell of claim 43, wherein the second gRNA molecule is selected from:
   (a) a gRNA molecule that comprises a targeting domain complementary to a target sequence of NLRC5; and
   (b) a gRNA molecule that comprises a targeting domain complementary to a target sequence of B2M, HLA-A, HLA-B or HLA-C.

46. The cell of claim 43, wherein the cell further comprises a third gRNA molecule, or a nucleic acid encoding a third gRNA molecule, wherein the first gRNA molecule, the second gRNA molecule and the third gRNA molecule comprise nonidentical targeting domains.

47. The cell of claim 46, wherein the third gRNA molecule comprises a targeting domain complementary to a target sequence of CIITA, RFXANK, RFX5, or RFXAP.

48. The cell of claim 47, wherein the third gRNA molecule comprises a targeting domain complementary to a target sequence of CIITA comprising any one of SEQ ID NO: 7717 to SEQ ID NO: 7804, SEQ ID NO: 7769, SEQ ID NO: 7771, or SEQ ID NO: 7785.

49. The cell of claim 43, wherein:
   (1) the second guide RNA molecule comprises a targeting domain selected from the group consisting of SEQ ID NO: 1 to SEQ ID NO: 83 and SEQ ID NO: 5492 to SEQ ID NO: 5527;
   (2) the second guide RNA molecule comprises a targeting domain selected from the group consisting of SEQ ID NO: 969 to SEQ ID NO: 1345;
   (3) the second guide RNA molecule comprises a targeting domain selected from the group consisting of SEQ ID NO: 1346 to SEQ ID NO: 1698;
   (4) the second guide RNA molecule comprises a targeting domain selected from the group consisting of SEQ ID NO: 1699 to SEQ ID NO: 2068;
   (5) the second guide RNA molecule comprises a targeting domain selected from the group consisting of SEQ ID NO: 2069 to SEQ ID NO: 2941;
   (6) the second guide RNA molecule comprises a targeting domain selected from the group consisting of SEQ ID NO: 5278 to SEQ ID NO: 5491;
   (7) the second guide RNA molecule comprises a targeting domain selected from the group consisting of SEQ ID NO: 6227 to SEQ ID NO: 6324; and
   (8) the second guide RNA molecule comprises a targeting domain selected from the group consisting of SEQ ID NO: 6325 to SEQ ID NO: 6583.

50. The cell of claim 43, wherein:
   (1) the second guide RNA molecule comprises a targeting domain selected from the group consisting of SEQ ID NO: 2942 to SEQ ID NO: 3270;
   (2) the second guide RNA molecule comprises a targeting domain selected from the group consisting of SEQ ID NO: 3271 to SEQ ID NO: 3541;
   (3) the second guide RNA molecule comprises a targeting domain selected from the group consisting of SEQ ID NO: 3542 to SEQ ID NO: 4032;
   (4) the second guide RNA molecule comprises a targeting domain selected from the group consisting of SEQ ID NO: 4033 to SEQ ID NO: 4589 and SEQ ID NO: 5720 to SEQ ID NO: 5815; and
   (5) the second guide RNA molecule comprises a targeting domain selected from the group consisting of SEQ ID NO: 4590 to SEQ ID NO: 5277.

51. A population of cells, wherein at least about 30% of the population is a cell of claim 40.

52. A method of preparing cells for immunotherapy comprising: (a) modifying cells by reducing or eliminating expression of a component of a T-cell receptor (TCR) comprising introducing into said cells a gRNA molecule comprising a targeting domain which comprises any one of SEQ ID NO: 5528 to SEQ ID NO: 5623 or SEQ ID NO: 5816 to SEQ ID NO: 5965; (b) modifying cells by reducing or eliminating expression of B2M comprising introducing into said cells a gRNA molecule of claim 1; and (c) expanding said cells.

53. The method of claim 52, further comprising modifying said cells by reducing or eliminating expression of CIITA comprising introducing into said cells a gRNA molecule comprising a targeting domain which comprises any one of SEQ ID NO: 6750 to SEQ ID NO: 7716 or SEQ ID NO: 7717 to SEQ ID NO: 7804, wherein said modifying takes place before the step of expanding said cells.

54. The gRNA molecule of claim 1, wherein the targeting domain and the tracr are disposed on a single nucleic acid molecule.

55. The gRNA molecule of claim 54, wherein the single nucleic acid molecule is an sgRNA molecule.

* * * * *